US012036266B2

(12) United States Patent
Winston et al.

(10) Patent No.: US 12,036,266 B2
(45) **Date of Patent: *Jul. 16, 2024**

(54) ACTIVATABLE CYTOKINE POLYPEPTIDES AND METHODS OF USE THEREOF

(71) Applicant: Werewolf Therapeutics, Inc., Cambridge, MA (US)

(72) Inventors: William Winston, West Newton, MA (US); Daniel Hicklin, Boston, MA (US); Jose Andres Salemeron-Garcia, Acton, MA (US); Heather Brodkin, West Newton, MA (US); Cynthia Seidel-Dugan, Belmont, MA (US)

(73) Assignee: Werewolf Therapeutics, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/934,811

(22) Filed: Sep. 23, 2022

(65) Prior Publication Data

US 2023/0056051 A1 Feb. 23, 2023

Related U.S. Application Data

(63) Continuation of application No. 17/741,275, filed on May 10, 2022, which is a continuation of application No. PCT/US2020/060624, filed on Nov. 14, 2020.

(60) Provisional application No. 62/935,605, filed on Nov. 14, 2019.

(51) Int. Cl.

| | |
|---|---|
| ***C07K 14/715*** | (2006.01) |
| ***A61K 35/17*** | (2015.01) |
| ***A61K 38/17*** | (2006.01) |
| ***A61K 38/20*** | (2006.01) |
| ***A61K 38/21*** | (2006.01) |
| ***A61K 47/64*** | (2017.01) |
| ***A61K 47/65*** | (2017.01) |
| ***A61K 47/68*** | (2017.01) |
| ***A61P 31/12*** | (2006.01) |
| ***A61P 35/00*** | (2006.01) |
| ***C12N 15/63*** | (2006.01) |

(52) U.S. Cl.

CPC .......... *A61K 38/2013* (2013.01); *A61K 35/17* (2013.01); *A61K 38/1774* (2013.01); *A61K 38/208* (2013.01); *A61K 38/212* (2013.01); *A61K 38/215* (2013.01); *A61K 38/217* (2013.01); *A61K 47/6425* (2017.08); *A61K 47/65* (2017.08); *A61K 47/6813* (2017.08); *A61K 47/6845* (2017.08); *A61P 31/12* (2018.01); *A61P 35/00* (2018.01); *C12N 15/63* (2013.01)

(58) Field of Classification Search

None

See application file for complete search history.

(56) References Cited

U.S. PATENT DOCUMENTS

| | | | |
|---|---|---|---|
| 4,419,446 | A | 12/1983 | Howley et al. |
| 4,560,655 | A | 12/1985 | Baker |
| 4,601,978 | A | 7/1986 | Karin |
| 4,657,866 | A | 4/1987 | Kumar |
| 4,676,980 | A | 6/1987 | Segal et al. |
| 4,767,704 | A | 8/1988 | Cleveland |
| 4,816,567 | A | 3/1989 | Cabilly et al. |
| 4,927,762 | A | 5/1990 | Darfler |
| 4,965,199 | A | 10/1990 | Capon et al. |
| 5,089,261 | A | 2/1992 | Nitecki et al. |
| 5,122,464 | A | 6/1992 | Wilson et al. |
| 5,122,469 | A | 6/1992 | Mather et al. |
| 5,208,020 | A | 5/1993 | Chari et al. |
| 5,264,365 | A | 11/1993 | Georgiou |
| 5,416,064 | A | 5/1995 | Chari et al. |
| 5,508,192 | A | 4/1996 | Georgiou et al. |
| 5,571,894 | A | 11/1996 | Weis et al. |
| 5,587,458 | A | 12/1996 | King et al. |
| 5,624,821 | A | 4/1997 | Winter et al. |
| 5,635,483 | A | 6/1997 | Pettit et al. |
| 5,639,635 | A | 6/1997 | Joly et al. |

(Continued)

FOREIGN PATENT DOCUMENTS

| | | | |
|---|---|---|---|
| DE | 19701141 | C1 | 4/1998 |
| EP | 547163 | B1 | 2/2002 |

(Continued)

OTHER PUBLICATIONS

Desnoyers et al., Tumor-Specific Activation of an EGFR-Targeting Probody Enhances Therapeutic Index, Science Translational Medicine, Oct. 16, 2013, , vol. 5, Issue 207, American Association for the Advancement of Science, USA.

Halin et al., Synergistic Therapeutic Effects of a Tumor Targeting Antibody Fragment, Fused to Interleukin 12 and to Tumor Necrosis Factor α, Cancer Research, Jun. 2003, 3202-3210, vol. 63, Issue 12, AACR, USA.

Helguera, et al "Antibody-Cytokine fusion proteins: Harnessing the combined power of cytokines and antibodies for cancer therapy" Clinical immunology 105 (3) Dec. 2002, 233-246.

(Continued)

*Primary Examiner* — Michail A Belyavskyi

(74) *Attorney, Agent, or Firm* — Hogan Lovells US LLP

(57) ABSTRACT

The disclosure features fusion proteins that are conditionally active variants of a cytokine of interest. In one aspect, the full-length polypeptides of the invention have reduced or minimal cytokine-receptor activating activity even though they contain a functional cytokine polypeptide. Upon activation, e.g., by cleavage of a linker that joins a blocking moiety, e.g. a steric blocking polypeptide, in sequence to the active cytokine, the cytokine can bind its receptor and effect signaling. Typically, the fusion proteins further comprise an in vivo half-life extension element, which may be cleaved from the cytokine in the tumor microenvironment.

19 Claims, 223 Drawing Sheets

Specification includes a Sequence Listing.

(56) References Cited

U.S. PATENT DOCUMENTS

| | | | |
|---|---|---|---|
| 5,641,870 | A | 6/1997 | Rinderknecht et al. |
| 5,648,237 | A | 7/1997 | Carter et al. |
| 5,648,260 | A | 7/1997 | Winter et al. |
| 5,712,374 | A | 1/1998 | Kunstmann et al. |
| 5,714,586 | A | 2/1998 | Kunstmann et al. |
| 5,739,277 | A | 4/1998 | Presta et al. |
| 5,767,285 | A | 6/1998 | Hamann et al. |
| 5,770,701 | A | 6/1998 | McGahren et al. |
| 5,770,710 | A | 6/1998 | McGahren et al. |
| 5,773,001 | A | 6/1998 | Hamann et al. |
| 5,780,588 | A | 7/1998 | Pettit et al. |
| 5,834,597 | A | 11/1998 | Tso et al. |
| 5,869,046 | A | 2/1999 | Presta et al. |
| 5,877,296 | A | 3/1999 | Hamann et al. |
| 5,891,693 | A | 4/1999 | Bebbington et al. |
| 5,939,598 | A | 8/1999 | Kucherlapati et al. |
| 6,027,888 | A | 2/2000 | Georgiou et al. |
| 6,075,181 | A | 6/2000 | Kucherlapati et al. |
| 6,083,715 | A | 7/2000 | Georgiou et al. |
| 6,114,598 | A | 9/2000 | Kucherlapati et al. |
| 6,150,584 | A | 11/2000 | Kucherlapati et al. |
| 6,162,963 | A | 12/2000 | Kucherlapati et al. |
| 6,165,745 | A | 12/2000 | Ward et al. |
| 6,248,516 | B1 | 6/2001 | Winter et al. |
| 6,602,684 | B1 | 8/2003 | Umana et al. |
| 6,630,579 | B2 | 10/2003 | Chari et al. |
| 6,670,147 | B1 | 12/2003 | Heidtman et al. |
| 6,821,505 | B2 | 11/2004 | Ward et al. |
| 6,942,853 | B2 | 9/2005 | Chernajovsky et al. |
| 7,498,298 | B2 | 3/2009 | Doronina et al. |
| 7,514,073 | B2 | 4/2009 | Epstein et al. |
| 8,399,219 | B2 | 3/2013 | Stagliano et al. |
| 8,563,269 | B2 | 10/2013 | Stagliano et al. |
| 8,734,774 | B2 | 5/2014 | Frelinger et al. |
| 8,809,504 | B2 | 8/2014 | Lauermann et al. |
| 8,969,538 | B2 | 3/2015 | Rosen et al. |
| 8,993,266 | B2 | 3/2015 | Stagliano et al. |
| 9,206,243 | B2 | 12/2015 | Leon Monzon et al. |
| 9,309,510 | B2 | 4/2016 | Porte et al. |
| 9,453,078 | B2 | 9/2016 | Stagliano et al. |
| 9,487,590 | B2 | 11/2016 | West et al. |
| 9,517,276 | B2 | 12/2016 | Lowman et al. |
| 9,540,440 | B2 | 1/2017 | Lowman et al. |
| 9,644,016 | B2 | 5/2017 | Stagliano et al. |
| 9,708,412 | B2 | 7/2017 | Baeuerle et al. |
| 9,775,913 | B2 | 10/2017 | Lauermann |
| 9,856,314 | B2 | 1/2018 | Lowman et al. |
| 9,861,705 | B2 | 1/2018 | Bossard et al. |
| 9,889,211 | B2 | 2/2018 | Lowman et al. |
| 10,059,762 | B2 | 8/2018 | Stagliano et al. |
| 10,077,300 | B2 | 9/2018 | Daugherty et al. |
| 10,100,106 | B2 | 10/2018 | Dubridge et al. |
| 10,138,272 | B2 | 11/2018 | Moore et al. |
| 10,179,817 | B2 | 1/2019 | Sagert et al. |
| 10,233,244 | B2 | 3/2019 | Sagert et al. |
| 10,301,380 | B2 | 3/2019 | West et al. |
| 10,261,083 | B2 | 4/2019 | Vasiljeva et al. |
| 10,513,549 | B2 | 12/2019 | Stagliano et al. |
| 2002/0164328 | A1 | 11/2002 | Shinkawa et al. |
| 2003/0139575 | A1 | 7/2003 | Gillies et al. |
| 2003/0157108 | A1 | 8/2003 | Presta et al. |
| 2003/0190311 | A1 | 10/2003 | Dall'Acqua et al. |
| 2004/0014652 | A1 | 1/2004 | Trouet et al. |
| 2004/0093621 | A1 | 5/2004 | Shitara et al. |
| 2004/0109865 | A1 | 6/2004 | Niwa et al. |
| 2004/0110282 | A1 | 6/2004 | Kanda et al. |
| 2004/0110682 | A1 | 6/2004 | Heidtmann et al. |
| 2004/0132140 | A1 | 7/2004 | Satoh et al. |
| 2004/0136952 | A1 | 7/2004 | Bhaskaran et al. |
| 2005/0014934 | A1 | 1/2005 | Hinton et al. |
| 2006/0166329 | A1 | 7/2006 | Rosen et al. |
| 2006/0205926 | A1 | 9/2006 | Ross et al. |
| 2006/0236411 | A1 | 10/2006 | Dreher et al. |
| 2007/0048282 | A1 | 3/2007 | Rosen et al. |
| 2007/0269422 | A1 | 11/2007 | Beimnaert et al. |
| 2010/0254944 | A1 | 10/2010 | Subramanian et al. |
| 2011/0190209 | A1 | 8/2011 | Culbertson et al. |
| 2013/0064788 | A1 | 3/2013 | Barnes et al. |
| 2013/0089516 | A1 | 11/2013 | Frelinger et al. |
| 2015/0079088 | A1 | 3/2015 | Lowman et al. |
| 2015/0087810 | A1 | 3/2015 | Moore et al. |
| 2016/0152686 | A1 | 6/2016 | Camphausen et al. |
| 2016/0194399 | A1 | 7/2016 | Irving et al. |
| 2016/0289324 | A1 | 10/2016 | Moore et al. |
| 2016/0311903 | A1 | 10/2016 | West et al. |
| 2016/0354472 | A1 | 12/2016 | Merchant et al. |
| 2016/0355587 | A1 | 12/2016 | West et al. |
| 2017/0044259 | A1 | 2/2017 | Tipton et al. |
| 2017/0096472 | A1 | 4/2017 | Rosen et al. |
| 2017/0240608 | A1 | 8/2017 | Stagliano et al. |
| 2018/0016316 | A1 | 1/2018 | Garcia et al. |
| 2018/0119128 | A1 | 5/2018 | Metzner et al. |
| 2018/0134789 | A1 | 5/2018 | Baeuerle et al. |
| 2018/0200346 | A1 | 7/2018 | Ballance et al. |
| 2018/0303952 | A1 | 10/2018 | Sagert |
| 2018/0344810 | A1 | 12/2018 | Addepalli et al. |
| 2019/0008978 | A1 | 1/2019 | Huang et al. |
| 2019/0016814 | A1 | 1/2019 | Humphrey et al. |
| 2019/0117789 | A1 | 4/2019 | Carman et al. |
| 2019/0135943 | A1 | 5/2019 | Boustany et al. |
| 2019/0225702 | A1 | 7/2019 | Baeuerle et al. |
| 2019/0367576 | A1* | 12/2019 | Winston ............. C07K 16/2887 |
| 2020/0044052 | A1* | 2/2020 | Bao ................. H01L 21/823842 |
| 2022/0339193 | A1* | 10/2022 | Xiao ...................... A61K 35/17 |

FOREIGN PATENT DOCUMENTS

| | | | |
|---|---|---|---|
| EP | 1867660 | A1 | 12/2007 |
| EP | 2639241 | A2 | 9/2013 |
| EP | 3134102 | A4 | 11/2017 |
| EP | 3792277 | A1 | 3/2021 |
| WO | 1987/00195 | | 1/1987 |
| WO | 1990/03430 | | 4/1990 |
| WO | 1991/01743 | | 2/1991 |
| WO | 1993/08829 | | 5/1993 |
| WO | 1993/16185 | | 8/1993 |
| WO | 1994/11026 | | 5/1994 |
| WO | 199429351 | | 12/1994 |
| WO | 1996027011 | | 9/1996 |
| WO | 1997/30087 | | 8/1997 |
| WO | 1998/58964 | | 12/1998 |
| WO | 199858964 | | 12/1998 |
| WO | 1999/22764 | | 5/1999 |
| WO | 1999/51642 | | 10/1999 |
| WO | 2000/61739 | | 10/2000 |
| WO | 200130460 | A1 | 5/2001 |
| WO | 2001/079271 | A1 | 10/2001 |
| WO | 2002022833 | A1 | 3/2002 |
| WO | 2002/43478 | | 6/2002 |
| WO | 2002055098 | A2 | 7/2002 |
| WO | 2002076489 | | 10/2002 |
| WO | 2003/011878 | | 2/2003 |
| WO | 2003/59934 | A2 | 7/2003 |
| WO | 2003/084570 | | 10/2003 |
| WO | 2003/085119 | | 10/2003 |
| WO | 2003/106381 | A2 | 12/2003 |
| WO | 2004/041865 | | 5/2004 |
| WO | 2004/056312 | | 7/2004 |
| WO | 2005/035586 | | 4/2005 |
| WO | 2005/035778 | | 4/2005 |
| WO | 2005/053742 | | 6/2005 |
| WO | 2006/0166329 | A1 | 7/2006 |
| WO | 20060166329 | A1 | 7/2006 |
| WO | 2006/106905 | A1 | 10/2006 |
| WO | 2006110728 | A2 | 10/2006 |
| WO | 2008147530 | A1 | 12/2008 |
| WO | 2009/025846 | A2 | 2/2009 |
| WO | 2009103965 | A1 | 8/2009 |
| WO | 2010020766 | A2 | 2/2010 |
| WO | 2011011797 | A2 | 1/2011 |
| WO | 2011/124718 | | 10/2011 |
| WO | 2011123683 | A2 | 10/2011 |
| WO | 2012/059486 | | 5/2012 |
| WO | 2013163631 | A2 | 10/2013 |

(56) References Cited

FOREIGN PATENT DOCUMENTS

| | | | |
|---|---|---|---|
| WO | 2013/177187 | A2 | 11/2013 |
| WO | 2013177187 | A2 | 11/2013 |
| WO | 2014100014 | A1 | 6/2014 |
| WO | 2014120555 | A1 | 8/2014 |
| WO | 2015066279 | A2 | 5/2015 |
| WO | 2016/200645 | A1 | 12/2016 |
| WO | 2017156178 | A1 | 9/2017 |
| WO | 2018/071918 | | 4/2018 |
| WO | 2018071777 | A1 | 4/2018 |
| WO | 2018136725 | A1 | 4/2018 |
| WO | 2018160754 | A2 | 9/2018 |
| WO | 2018160877 | A1 | 9/2018 |
| WO | 201808555 | A1 | 11/2018 |
| WO | 2018204528 | A1 | 11/2018 |
| WO | 2018204717 | A1 | 11/2018 |
| WO | 2018213341 | A1 | 11/2018 |
| WO | 2018236701 | A1 | 12/2018 |
| WO | 2019014586 | A1 | 1/2019 |
| WO | 2019018828 | A1 | 1/2019 |
| WO | 2019036031 | A2 | 2/2019 |
| WO | 2019094396 | A1 | 5/2019 |
| WO | WO2019136305 | * | 7/2019 |
| WO | 2019/173832 | A2 | 9/2019 |
| WO | 2019/214757 | A1 | 11/2019 |
| WO | 2019/222294 | A1 | 11/2019 |
| WO | 2019/222295 | A1 | 11/2019 |
| WO | 2019222295 | A1 | 11/2019 |
| WO | 2019/246392 | | 12/2019 |
| WO | 2020069398 | A1 | 2/2020 |
| WO | 2020/069398 | A1 | 4/2020 |
| WO | 2020232305 | A1 | 11/2020 |
| WO | 2020/252264 | A1 | 12/2020 |
| WO | 2021/016599 | A1 | 1/2021 |
| WO | 2021/030483 | A1 | 2/2021 |
| WO | 2021062406 | A1 | 4/2021 |
| WO | 2021202673 | A1 | 7/2021 |
| WO | 2021202675 | A1 | 7/2021 |
| WO | 2021/202678 | A1 | 10/2021 |
| WO | 2021202678 | A1 | 10/2021 |
| WO | 2002022833 | A1 | 3/2022 |

OTHER PUBLICATIONS

Hemar et al "Endocytosis of Interleukin 2 receptors in human T lymphocytes: distinct intracellular localization and fate of the receptor alpha, beta, and gamma chains." J. Cell Biol. 1995; 129(1): 55-64.

Hoos et al., CCR 20th Anniversary Commentary: Immune-Related Response Criteria—Capturing Clinical Activity in Immuno-Oncology, Clin Cancer Res. Nov. 15, 2015, 4989-4991, vol. 21, Issue 22, American Association of Cancer Research, USA.

Irving et al., A Clue to Antigen Receptor Tails, J Immunol, May 1, 2014, 4013-4014, vol. 192, Issue 9, The American Association of Immunologists, Inc., USA.

Jabaiah et al., Identification of protease exosite-interacting peptides that enhance substrate cleavage kinetics, Biol Chem., Sep. 2012, 933-941, vol. 393, Issue 9, ASBMB Publications, USA.

Jana et al "Interleukin-12 (IL-12), but not IL-23, induces the expression of IL-7 in microglia and macrophages: Implications for multiple sclerosis." Immunology 2013; 141: 549-563.

Kaspar et al., The antibody-mediated targeted delivery of interleukin-15 and GM-CSF to the tumor neovasculature Inhibits tumor growth and metastasis, Cancer Res, May 15, 2007, 4940-4098, vol. 67 Issue 10, AACR. USA.

Kim et al., Novel immunocytokine IL 12-SS1 (Fv) inhibits mesothelioma tumor growth in nude mice, PLoS One, Nov. 15, 2013, 1-11, vol. 8, Issue 11, PLOS.

Klatzmann, D and Abbas, A.K. "The promise of low-dose interleukin-2 therapy for autoimmune and inflammatory diseases." Nat. Rev. Immunol. 2015; 15: 283-294.Oh et al "IL-15 as a mediator of CD4+ help for CD8+ T cell longevity and avoidance of TRAIL-mediated apoptosis." PNAS 2008; 105(13): 5201-5206.

Koreth et al "Interleukin-2 and Regulatory T Cells in Graft-versus-host disease." N. Engl. J. Med. 2011; 365(22): 2055-2066.

Lasek et al "Interleukin 12: still a promising candidate for tumor immunotherapy?" Cancer Immunol Immunother (2014) 63:419-435.

Lebeau et al., Imaging a functional tumorigenic biomarker in the transformed epithelium, PNAS, Jan. 2, 2013, 93-98, vol. 110, Issue 1, National Academy of Sciences, USA.

Lin et al., Targeting Drug Conjugates to the Tumor Microenvironment: Probody Drug Conjugates, Innovations for Next-Generation Antibody-Drug Conjugates, 2018, 281-298, Humana Press, USA.

Malek, T.R. and Castro, I. Interleukin-2 receptor signaling: at the interface between tolerance and immunity. Immunity 2010 33(2): 153-165.

Manuale L. Penichet, "Antibody-cytokine fusion proteins for the therapy of cancer", Immunology, 2001, pp. 91-101.

Marks-Konczalik et al "IL-2-induced cell death is inhibited in IL-15 transgenic mice." PNAS 2000; 97(21): 11445-11450.

Mitsiades et al., Matrix Metalloproteinase-7-mediated Cleavage of Fas Ligand Protects Tumor Cells from Chemotherapeutic Drug Cytotoxicity, Cancer Research, Jan. 15, 2001, 577-581, vol. 61, AACR, USA.

Montepaone et al."Profile of ustekinumab and its potential in the treatment of active psoriatic arthritis" Open Access Rheumatol. 2014; 6: 7-13.

Oh et al "IL-15 as a mediator of CD4+ help for CD8+ T cell longevity and avoidance of TRAIL-mediated apoptosis." PNAS 2008; 105(13): 5201-5206.

Osorio et al., Understanding and quantifying the immune microenvironment in hepatocellular carcinoma, Transl Gastroenterol Hepatol. Dec. 24, 2018, 3:107, AME Publishing Company.

Pandya et al., PKCα Attenuates Jagged-1-Mediated Notch Signaling in ErbB-2-Positive Breast Cancer to Reverse Trastuzumab Resistance, Clin Cancer Res, 175-186, Jan. 1, 2016, vol. 22 Issue 1, AACR, USA.

Pedretti et al., Combination of temozolomide with immunocytokine F16-IL2 for the treatment of glioblastoma, Br J Cancer, Sep. 7, 2010, 827-836, vol. 103, Issue 6, SpringerNature, UK.

Polu et al., Probody therapeutics for targeting antibodies to diseased tissue, May 20, 2014, Expert Opinion on Biological Therapy, 1049-1053, vol. 14, Issue 8, Taylor & Francis Online.

Puskas et al., "Development of an attenuated interleukin-2 fusion protein that can be activated by tumour-expressed proteases," Immunology, Mar. 23, 2011 (Mar. 23, 2011), vol. 133, pp. 206-220.

Rice et al., Bacterial display using circularly permuted outer membrane protein OmpX yields high affinity peptide ligands, Protein Sci., 825-836, Apr. 2006, vol. 15, Issue 4, Wiley.

Rochman et al. "New insights into the regulation of T cells by gamma-c family cytokines." Nat Rev Immunol 2009; 9 (7): 480.

Rodrigo Vazquez-Lombardi et al., Molecular Engineering of Therapeutic Cytokines, Antibodies, vol. 2 No. 3, Jul. 3, 2013, pp. 426-451.

Saadoun, et al. "Regulatory T-Cell Responses to Low-Dose Interleukin-2 in HCV-Induced Vasculitis." N. Engl. J. Med. 2011; 365(22): 2067-2077.

Sadlack et al "Ulcerative colitis-like disease in mice with a disrupted interleukin 2 gene." Cell 1993; 75: 253-261.

Smith, T.F. and Waterman, M.S. "Comparison of biosequences." Advances in applied mathematics 1981; 2: 482-489.

Suzuki et al. "Deregulated T cell activation and autoimmunity in Mice lacking interleukin-2 Receptor Beta." Science 1995; 268: 1472-1476.

Trinchieri et al "The IL-2 family of heterodimeric cytokines: new players in the regulation of T cell responses." Immunity 2003; 19: 641-644.

Uhland, Matriptase and its putative role in cancer, Cell Mol Life Sci., Dec. 2006, 2968-2978, vol. 63, Issue 24.

Ulisse et al., The urokinase plasminogen activator system: a target for anti-cancer therapy, Curr Cancer Drug Targets, Feb. 2009, 32-71, vol. 9, Issue 1, Bentham Science.

Vartak et al. Matrix metalloproteases: underutilized targets for drug delivery, J Drug Target, Jan. 2007, 1-20, vol. 15, Issue 1.

(56) References Cited

OTHER PUBLICATIONS

Vasiljeva et al., The multifaceted roles of tumor-associated proteases and harnessing their activity for prodrug activation, Biological Chemistry, Apr. 22, 2019, Walter de Gruyter GmbH, (abstract only).

Wang et al Structure of the Quaternary Complex of Interleukin-2 with its alpha, beta, and gamma-c receptors. Science Nov. 18, 2005 vol. 310, 1159-1163.

Willerford, et al "Interleukin-2 receptor alpha chain regulates the size and content of the peripheral lymphoid compartment." Immunity 1995; 3: 521-530.

William R. Strohl, Fusion Proteins for Half-Life Extension of Biologics as a Strategy to Make Biobetters, Biodrugs, vol. 29, No. 4, Jul. 16, 2015, pp. 215-239.

Wong et al., In vivo imaging of protease activity by Probody therapeutic activation, Biochimie, Nov. 4, 2015, 62-67, vol. 122, Elsevier, USA.

Yu, A and Malek, T.R. "The Proteosome regulates receptor-mediated endocytosis of interleukin-2" The Journal of Biological Chemistry 2001; 276(1): 381-385.

Zavrsnik et al., Cystatin C deficiency suppresses tumor growth in a breast cancer model through decreased proliferation of tumor cells, Oncotarget, Apr. 24, 2017, 73793-73809, vol. 8, Issue 43, Impact Journals, LLC.

Zhao et al., FGFR1β is a driver isoform of FGFR1 alternative splicing in breast cancer cells, Oncotarget, Jan. 1, 2019, 30-44, vol. 10, Issue 1, Impact Journals, LLC.

Shinkawa et al., The absence of fucose but not the presence of galactose or bisecting N-acetylglucosamine of human IgG1 complex-type oligosaccharides shows the critical role of enhancing antibody-dependent cellular cytotoxicity, J. Biol. Chem., 278(5):3466-73 (2003).

Sola et al., "Effects of Glycosylation on the Stability of Protein Pharmaceuticals," J. Pharm. Sci., 98(4): 1223-1245 (2009).

Keunok Jung et al., "Heterodimeric Fc-fused IL12 shows potent antitumor activity by generating memory CD8+ T cells", Oncoimmunology, vol. 7, No. 7, Mar. 6, 2018, pp. e1438800, XP055653232.

Germa N L. Rosano et al., "Recombinant protein expression in *Escherichia coli*: advances and challenges", Frontiers in Microbiology, vol. 5, Apr. 17, 2014 (Apr. 17, 2014), XP055474138.

Lebeau et al., Imaging Active Urokinase Plasminogen Activator in Prostate Cancer, Cancer Res, 1225-1235, vol. 75, Issue 7, AACR, USA (2015).

Giesen et al., 8089Zr-labeled anti-PD-L1 CX-072 PET imaging in human xenograft and syngeneic tumors, Annals of Oncology, Feb. 27, 2019, vol. 30, Issue Supplement 1, Oxford Academic.

Gillies, et al "Improved circulating half-life and efficacy of an antibody-interleukin 2 immunocytokine based on reduced intracellular proteolysis" Clinical Cancer Research, the American Association for Cancer Research, US, 8(1) Jan. 2002, 210-216.

Gerber et al Preferential attachment of peritoneal tumor metastases to omental immune aggregates and possible role of a unique vascular microenvironment in metastatic survival and growth. Am J Pathol 169(5): 1739-1752.

Geletu et al., Effect of Caveolin-1 upon Stat3-ptyr705 levels in breast and lung carcinoma cells., Biochem Cell Biol., Apr. 15, 2019, 1-19, Canadian Science Publishing.

Gao et al "High-throughput screening using patient-derived tumor xenografts to predict clinical trial drug response." Nature Medicine 2015; 21(11): 1318-1325.

Fercher et al., Evolution of the magic bullet: Single chain antibody fragments for the targeted delivery of Immunomodulatory proteins, Exp Biol Med, Jan. 2018, 166-183, vol. 243, Issue 2, Sage Journals.

Erster et al., Site-specific targeting of antibody activity in vivo mediated by disease-associated proteases, Journal of Controlled Release, Aug. 10, 2012, 804-812, vol. 161, Issue 3, Elsevier, USA.

Drag et al., Emerging principles in protease-based drug discovery, Nat Rev Drug Discov., Nov. 5, 2010, 690-701, vol. 9, Issue 9, Springer Nature, USA.

Desbois et al IL-15 Trans-signaling with the superagonist RLI Promotes Effector/Memory CD8+ T cell responses and enhances antitumor activity of PD-1 antagonists. 2016 J Immunol 1-11.

Denise Skrombolas et al., Challenges and developing solutions for increasing the benefits of IL-2 treatment in tumor therapy, Expert Review of Clinical Immunology, vol. 10, No. 2, Feb. 1, 2014, pp. 207-217.

Deluca et al., Potentiation of PD-L1 blockade with a potency-matched dual cytokine-antibody fusion protein leads to cancer eradication in BALB/c-derived tumors but not in other mouse strains, Cancer Immunol Immunother, Sep. 6, 2018, 1381-1391, vol. 67, Issue 9, Springer.

Declerck et al., Proteases, extracellular matrix, and cancer: a workshop of the path B study section, Am J Pathol., Apr. 2004, 1131-1139, vol. 164, Issue 4, Elsevier, USA.

De Luca et al., Potency-matched Dual Cytokine-Antibody Fusion Proteins for Cancer Therapy. Mol Cancer Ther, Nov. 2017, 2442-2451, vol. 16, Issue 11, AACR, USA.

Darragh et al., Specific targeting of proteolytic activity for tumor detection in vivo, Cancer Res., Feb. 15, 2010, 1505-1512, vol. 70, Issue 5, AACR, USA.

Conlon et al "Redistribution, hyperproliferation, activation of natural killer cells and CD8 T cells, and cytokine production during first-in-human clinical trial of recombinant human interleukin-15 in patients with cancer." J Clin Oncol 2015; 33(1): 74-82.

Boulware et al., Protease specificity determination by using cellular libraries of peptide substrates (CLiPS), PNAS, May 16, 2006, 7583-7588, vol. 103, Issue 20, National Academy of Sciences, USA.

Boulware et al., Evolutionary optimization of peptide substrates for proteases that exhibit rapid hydrolysis kinetics, Biotechnol Bioeng., Jun. 15, 2010, 339-46, vol. 106, Issue 3, Wiley, USA.

Bessard et al High antitumor activity of RLI, an interleukin-15 (IL-15)-IL-15 receptor alpha fusion protein, in metastatic melanoma and colorectal cancer. Mol Cancer Ther 2009; 8(9): 2736-2745.

Berger et al "An Operational definition of epigenetics." Genes Dev 2009; 23: 781-783.

Agard et al., Methods for the proteomic identification of protease substrates, Curr Opin Chem Biol., Dec. 2009, 503-509, vol. 12, Issue 5-6, Elsevier, USA.

Afonina et al., Proteolytic Processing of Interleukin-1 Family Cytokines: Variations on a Common Theme, Immunity Review16 Jun. 2015, 991-1004, vol. 42, Issue 6, Elsevier, USA.

Adusumilli et al., New Cancer Immunotherapy Agents in Development: a report from an associated program of the 31stAnnual Meeting of the Society for Immunotherapy of Cancer, 2016, J Immunother Cancer, Jun. 20, 2017, 1-9, vol. 5, Issue 50, BioMed Central, USA.

Skrombolas, etl al. "Development of an Interleukin-12 Fusion Protein That Is Activated by Cleavage with Matrix Metalloproteinase 9," Journal of Interferon & Cytokine Research, 39(4):233-245 (2019).

Berger et al "Safety and immunologic effects of IL-15 administration in nonhuman primates." Blood 2009; 114(12): 2417-2426.

Skrombolas, et al. "Development of Protease Activated Interleukin-12 Cytokine Fusion Proteins for Tumor Immunotherapy (TUM7P. 946)," The Journal of Immunology; 203:28, 192 (1 Supplement) (2014).

Skrombolas, et al. "Development of an Interleukin-12 Fusion Protein That Is Activated by Cleavage with Matrix Metalloproteinase 9," Journal of Interferon & Cytokine Research, 39(4):233-245 (2019).

Zapata et al., "Engineering linear F(ab')2 fragments for efficient production in *Escherichia coli* and enhanced antiproliferative activity," Protein Eng., 8(10):1057-1062 (1995).

Yeung et al., "Engineering Human IgG1 Affinity to Human Neonatal Fe Receptor: Impact of Affinity Improvement on Pharmacokinetics in Primates," J. Immunol., 182:7667-7671 (2009).

Yaniv, "Enhancing elements for activation of eukaryotic promoters," Nature 297:17-18 (1982).

Yamane-Ohnuki et al., "Production of therapeutic antibodies with controlled fucosylation," MAbs, 1 (3):230-236 (2009).

(56) References Cited

OTHER PUBLICATIONS

Yamane-Ohnuki et al., "Establishment of FUT8 knockout Chinese hamster ovary cells: an ideal host cell line for producing completely defucosylated antibodies with enhanced antibody-dependent cellular cytotoxicity," Biotech. Bioeng., 87:614-22 (2004).
Vitetta et al., "Redesigning nature's poisons to create anti-tumor reagents," Science, 238:1098-1104 (1987).
Verhoeven et al., "Reshaping human antibodies: grafting an antilysozyme activity," Science, 239:1534-1536. (1988).
Urlaub et al., "Isolation of Chinese hamster cell mutants deficient in dihydrofolate reductase activity," Proc. Natl. Acad. Sci. USA, 77:4216-4220 (1980).
Traunecker et al., "Bispecific single chain molecules (Janusins) target cytotoxic lymphocytes on HIV infected cells," EMBO J., 10:3655-365 (1991).
Torgov et al., "Generation of an Intensely Potent Anthracycline by a Monoclonal Antibody-[3-Galactosidase Conjugate," Bioconj. Chem., 16:717-721 (2005).
Tomizuka et al., "Double trans-chromosomic mice: Maintenance of two individual human chromosome fragments containing Ig heavy and K loci and expression of fully human antibodies," Proc. Natl. Acad. Sci. USA, 97:722-727 (2000).
Suresh et al., "Bispecific monoclonal antibodies from hybrid hybridomas," Methods in Enzymology, 121:210-228 (1986).
Sties et al. (eds), Basic and Clinical Immunology, 8th Edition, Appleton & Lange, Nmwalk, CT,p. 71 and Chapter 6 (1994).
Sola et al., "Modulation of protein biophysical properties by chemical glycosylation: biochemical insights and biomedical implications," Cell. Mol. Life Sci., 64(16):2133-2152 (2007).
Simmons et al., "Expression of full-length immunoglobulins in *Escherichia coli*: rapid and efficient production of aglycosylated antibodies," J. Immunol. Methods, 263:133-147 (2002).
Shields et al., "Lack of fucose on human IgG1 N-linked oligosaccharide improves binding to human Fcgamma Rlii and antibody-dependent cellular toxicity," J. Biol. Chem., 277(30):26733-40 (2002).
Shields et al, "High resolution mapping of the binding site on human IgG1 for Fe gamma Rl, Fe gamma RII, Fe gamma Rlii, and FcRn and design of IgG1 variants with improved binding to the Fe gamma R," J. Biol. Chem., 276:6591-6604 (2001).
Schlapschy et al., "PASylation: a biological alternative to PEGylation for extending the plasma half-life of pharmaceutically active proteins," Protein Eng. Des. Sel., 26(8):489-501 (2013).
Sali et al. "Characterization of a Novel Human-Specific STING Agonist that Elicits Antiviral Activity Against Emerging Alphaviruses," PloS Pathog., 11(12):e1005324, 30 pages (2015).
Lehninger, in Biochemistry, second ed., pp. 73-75, Worth Publishers, New York (1975).
Lindmark et al., "Binding of immunoglobulins to protein A and immunoglobulin levels in mammalian sera," J. Immunol. Meth., 62:1-13 (1983).
Lode et al., "Targeted Therapy with a Novel Enediyene Antibiotic Calicheamicin -al 1 Effectively Suppresses Growth and Dissemination of Liver Metastases in a Syngeneic Model of Murine Neuroblastoma," Cancer Res., 58:2925-2928 (1998).
Lonberg, et al., "Antigen-specific human antibodies from mice comprising four distinct genetic modifications," Nature 368:856-859 (1994).
Mather et al., "Culture of testicular cells in hormone-supplemented serum-free medium," Annals N.Y. Acad. Sci., 383:44-68 (1982).
Mather, "Establishment and characterization of two distinct mouse testicular epithelial cell lines," Biol. Reprod. 23:243-251 (1980).
Merchant et al., "An efficient route to human bispecific IgG," Nat. Biotechnol., 16(7):677-681 (1998).
Milstein et al.,. "Hybrid hybridomas and their use in immunohistochemistry," Nature, 305:537 (1983).
Moore et al., "A novel bispecific antibody format enables simultaneous bivalent and monovalent co-engagement of distinct target antigens," MAbs., 3(6): 546-557 (2011).
Mori et al., "Engineering Chinese hamster ovary cells to maximize effector function of produced antibodies using FUT8 siRNA," Biotechnol. Bioeng. 88(7):901-908 (2004).
Morimoto et al., "Single-step purification of F(ab12 fragments of mouse monoclonal antibodies (immunoglobulins G1) by hydrophobic interaction high performance liquid chromatography using TSKgel Phenyl-5PW," Journal of Biochemical and Biophysical Methods, 24:107-117 (1992).
Nagy et al., "Stability of cytotoxic luteinizing hormone-releasing hormone conjugate (AN-152) containing doxorubicin 14-O-hemiglutarate in mouse and human serum in vitro: Implications for the design of preclinical studies," Proc. Natl. Acad. Sci. USA, 97:829-834 (2000).
Nilvebrant et al., "The albumin-binding domain as a scaffold for protein engineering," Comput. Struct. Biotechol. J., 6:e201303009, 8 pages (2013).
Nygren et al., "Analysis and use of the serum albumin binding domains of streptococcal protein G," J. Mal. Recogn., 1 (2):69-74 (1988).
Okazaki et al., "Fucose depletion from human IgG1 oligosaccharide enhances binding enthalpy and association rate between IgG1 and FcgammaRlIIa," J. Mal. Biol., 336:1239-1249 (2004).
Omasa et al., "Decrease in antithrombin Ill fucosylation by expressing GDP-fucose transporter siRNA in Chinese hamster ovary cells," J. Biosci. Bioeng., 106(2):168-173 (2008).
Podust et al., "Extension of in vivo half-life of biologically active molecules by XTEN protein polymers," J. Controlled Release, 240:52-66 (2016).
Proba et al., "Functional antibody single-chain fragments from the cytoplasm of *Escherichia coli*: influence of thioredoxin reductase (TrxB)," Gene, 159:203-7 (1995).
Ramm et al., "The periplasmic *Escherichia coli* peptidylprolyl cis, trans-isomerase FkpA II. Isomerase-independent chaperone activity in vitro," J. Biol. Chem., 275:17106-17113 (2000).
Reyes et al., "Expression of human 13-interferon cDNA under the control of a thymidine kinase promoter from herpes simplex virus," Nature, 297:598-601 (1982).
Riechmann et al., "Reshaping human antibodies for therapy," Nature, 332:323-327 (1988).
Ridgway et al., "Knobs-into-holes' engineering of antibody CH3 domains for heavy chain heterodimerization," Protein Eng., 9(7):617-621 (1996).
Ripka et al., "Two chinese hamster ovary glycosylation mutants affected in the conversion of GDP-man nose to GDP- fucose," Arch. Biochem. Biophys., 249:533-545 (1986).
Roux et al., "Comparisons of the ability of human IgG3 hinge mutants, IgM, IgE, and IgA2, to form small immune complexes: a role for flexibility and geometry," J Immunol, 161 :4083-90 (1998).
Cao, et al., "Next generation of tumor-activating type I IFN enhances anti-tumor immune responses to overcome therapy resistance", Nature Communications, 12:5866, pp. 1-11 (2021).
Puskas et al., "Development of an attenuated interleukin-2 fusion protein that can be activated by tumour-expressed proteases," Immunology, 133:206-220 (2011).
Dubowchik et al., "Doxorubicin Immunoconjugates Containing Bivalent, Lysosomally-Cleavable Dipeptide Linkages," Bioorg. & Med. Chem. Letters 12:1529-1532 (2002).
Xue et al., "A tumor-specific pro-IL-12 activates preexisting cytotoxic T cells to control established tumors" Science Immunology, vol. 7, Jan. 7, 2022, pp. 1-14.
Xue et al., "Supplementary Materials for A tumor-specific pro-IL-12 activates preexisting cytotoxic T cells to control established tumors" Science Immunology, vol. 7, (2022), pp. 1-26.
Arie et al. "Chaperone function of FkpA, a heat shock prolyl isomerase, in the periplasm of *Escherichia coli*,", Mol. Micro biol. 39:199-210 (2001).
Atwell et al., "Stable heterodimers from remodeling the domain interface of a homodimer using a phage display library," J. Mol. Biol., 270(1):26-35 (1997).
Bachmann, Cellular and Molecular Biology, vol. 2 (Washington, D.C.: American Society for Microbiology), pp. 1190-1219 (1987).
Barnes et al., "Methods for growth of cultured cells in serum-free medium," Anal. Biochem. 102:255 (1980).

(56) References Cited

OTHER PUBLICATIONS

Bass et al., "Hormone phage: an enrichment method for variant proteins with altered binding properties," Proteins, 8:309-314 (1990).
Bernett et al., "Potency-reduced IL 15/IL 15Ra heterodimeric Fe-fusions display enhanced in vivo activity through Increased exposure," Xencor, AACR (2018) Abstract #5565.
Boerner et al., "Production of antigen-specific human monoclonal antibodies from in vitro-primed human splenocytes," J. Immunol., 147: 86 (1991).
Bothmann and Pluckthun. "Improving Expression of scFv Fragments by Coexpression of Periplasmic Chaperones," J. Biol. Chem. 275:17100-17105 (2000).
Brennan et al., "Preparation of bispecific antibodies by chemical recombination of monoclonal immunoglobulin G1 fragments," Science, 229:81 (1985).
Brodeur et al., Monoclonal Antibody Production Techniques and Applications, pp. 51-63 Marcel Dekker, Inc., New York, (1987).
Caescu et al., "Active site determinants of substrate recognition by the metalloproteinases TACE and ADAM10," Biochem. J., 424(1):79-88 (2010).
Carter et al., "High level *Escherichia coli* expression and production of a bivalent humanized antibody fragment," BiofTechnology 10: 163-167 (1992).
Carter et al., "Bispecific human IgG by design," J. Immunol. Methods, 248: 7-15 (2001).
Chapman et al. "Therapeutic antibody fragments with prolonged in vivo half-lives," Nature Biotechnol., 17:780-783 (1999).
Chari et al., "Immunoconjugates containing novel maytansinoids: promising anticancer drugs," Cancer Res. 52:127-131 (1992).
Chen et al., "Chaperone activity of DsbC," J. Biol. Chem. 274:19601-19605 (1999).
Choe et al. , "Fe-Binding Ligands of Immunoglobulin G: An Overview of High Affinity Proteins and Peptides," Materials 9(12): 994 (2016).
Cunningham and Wells ,"High-resolution epitope mapping of hGH-receptor interactions by alanine-scanning mutagenesis," Science, 244:1081-1085 (1989).
Davies et al., "Antibody-antigen complexes," Annual Rev Biochem. 59:439-473, (1990).
Dennis et al., "Albumin binding as a general strategy for improving the pharmacokinetics of proteins," JBC 277(38): 35035-35043 (2002).
Duncan and Winter, "The binding site for C1q on IgG," Nature 322:738-40 (1988).
Damodaran, "Protein PEGylation: An overview of chemistry and process considerations," European Pharmaceutical Review, 15(1): 18-26 (2010).
Firan, M., et al., "The MHC class I-related receptor, FcRn, plays an essential role in the maternofetal transfer of y-globulin in humans," Int. Immunol. 13: 993-1002 (2001).
Fishwild, D. et al., "High-avidity human IgG kappa monoclonal antibodies from a novel strain of minilocus transgenic mice," Nature Biotechnology 14: 845-851 (1996).
Graham et al., "Characteristics of a human cell line transformed by DNA from human adenovirus type 5," J. Gen Virol. 36:59 (1977).
Gunasekaran et al., "Enhancing antibody Fe heterodimer formation through electrostatic steering effects: applications to bispecific molecules and monovalent IgG," J Biol Chem., 285(25): 19637-19646 (2010).
Guss et al., "Structure of the IgG-binding regions of streptococcal protein G.," EMBO J. 5:15671575 (1986).
Guyer et al., "Immunoglobulin Binding by Mouse Intestinal Epithelial Cell Receptors," J. Immunol. 117:587 (1976).
Ham et al., "Media and Growth Requirements," Meth. Enz. 58:44 (1979).
Hara et al., "Overproduction of Penicillin-Binding Protein 7 Suppresses Thermosensitive Growth Defect at Low Osmolarity due to an spr Mutation of *Escherichia coli*," Microbial Drug Resistance, 2:63-72 (1996).
Hinman et al., "Preparation and characterization of monoclonal antibody conjugates of the calicheamicins: a novel and potent family of antitumor antibiotics," Cancer Res. 53:3336-3342 (1993).
Hudson et al., "Engineered antibodies," Nat. Med., 9:129-134 (2003).
Idusogie et al., "Mapping of the C1q Binding Site on Rituxan, a Chimeric Antibody with a Human IgG1 Fe," J. Immunol., 164:4178-4184, (2000).
Imai-Nishiya et al., "Double knockdown of a1 ,6-fucosyltransferase (FUT8) and GDP-mannose 4,6-dehydratase (GMD) in antibody-producing cells: a new strategy for generating fully non-fucosylated therapeutic antibodies with enhanced ADCC," BMC Biotechnol., 7:84, 13 pages (2007).
Jefferis et al., "Human immunoglobulin allotypes: Possible implications for immunogenicity," mAbs, 1 (4):332-8 (2009).
Jeffrey et al., "Dipeptide-based highly potent doxorubicin antibody conjugates," Bioorganic & Med. Chem. Letters, 16:358-362 (2006).
Jones et al., "Replacing the complementarity-determining regions in a human antibody with those from a mouse," Nature, 321 :522-525 (1986).
Kim et al., "Localization of the site of the murine IgG1 molecule that is involved in binding to the murine intestinal Fe receptor'," European Journal of Immunology, 24:2429-2434 (1994).
King et al., "Monoclonal Antibody Conjugates of Doxorubicin Prepared with Branched Peptide Linkers: Inhibition of Aggregation by Methoxytriethyleneglycol Chains," J. Med. Chem., 45:4336-4343 (2002).
Klein et al., "Progress in overcoming the chain association issue in bispecific heterodimeric IgG antibodies," MAbs, 4 (6):653-663 (2012).
Kontermann et al., "Bispecific antibodies," Drug Discovery Today, 20(7) :838-84 7 (2015).
Kozbor et al., "A human hybrid myeloma for production of human monoclonal antibodies," J. Immunol., 133:3001-5 (1984).
Kratz et al., "Prodrugs of anthracyclines in cancer chemotherapy," Current Med. Chem. 13:477-523 (2006).
Krieg et al., "Improved IL-2 immunotherapy by selective stimulation of IL-2 receptors on lymphocytes and endothelial cells," PNAS, 107(26):11906-11911 (2010).
Chen, et al., "Fusion protein linkers: Property, design and functionality", Advanced Drug Delivery Reviews, vol. 65, No. 10, (Sep. 1, 2012), pp. 1357-1369.
International Search Report and Written Opinion of PCT/US2020/060624 mailed May 20, 2021.

* cited by examiner

| | EC50 |
|---|---|
| WW0548/556 intact | 2.524 |
| WW0548/556 cleaved | 0.02542 |

| | EC50 |
|---|---|
| WW0735/523 intact | 0.4315 |
| WW0735/523 cleaved | 0.004755 |

| | EC50 |
|---|---|
| Human IL-2 | 0.006989 |
| WW0621/523 intact | 0.5104 |
| WW0621/523 cleaved | 0.005443 |

| | EC50 |
|---|---|
| Human IL-2 | 0.005379 |
| WW0729/523 | 1.181 |
| WW0729/523+MMP9 | 0.6798 |

| | EC50 |
|---|---|
| Human IL-2 | 0.006770 |
| WW0317 intact | 1.133 |
| WW0317 cleaved | 0.03572 |

| | EC50 |
|---|---|
| Human IL-2 | 0.004964 |
| WW0520/WW0523 intact | 0.3057 |
| WW0520/WW0523 cleaved | 0.004593 |

| | EC50 |
|---|---|
| Human IL-2 | 0.006014 |
| WW0621/WW0523 intact | ~ 0.2867 |
| WW0621/WW0523 cleaved | 0.01808 |

| | EC50 |
|---|---|
| Human IL-2 | 0.006313 |
| WW0048 intact | 7.505 |
| WW0048 cleaved | 0.08367 |

| | Human IL-2 | Intact | Cut |
|---|---|---|---|
| IC50 | 0.03912 | 1.230 | 0.4793 |

| | EC50 |
|---|---|
| Human IL-2 | 0.07770 |
| WW0520/524 intact | 2.824e+020 |
| WW0520/524 cleaved | 0.2341 |

| | Human IL-2 | Intact | Cut |
|---|---|---|---|
| IC50 | 0.04292 | 1.983 | 0.1162 |

| | EC50 |
|---|---|
| WW0295 (chimeric IL-12) | 0.02130 |
| WW0667 (uncleaved) | 4.805 |
| WW0667 (cleaved) | 0.04966 |

| | EC50 |
|---|---|
| WW0295 (chimeric IL-12) | 0.02016 |
| WW0665 (uncleaved) | 3.381 |
| WW0665 (cleaved) | 0.05049 |

| | EC50 |
|---|---|
| WW0295 (chimeric IL-12) | 0.02001 |
| WW0669 (uncleaved) | 1.983 |
| WW0669 (cleaved) | 0.03294 |

| | EC50 |
|---|---|
| rhIL-12 | 0.01355 |
| WW0671 (uncleaved) | 1.303 |
| WW0671 (cleaved) | 0.02322 |

| | EC50 |
|---|---|
| WW0295 (chimeric IL-12) | 0.01383 |
| WW0673 (uncleaved) | 2.355 |
| WW0673 (cleaved) | 0.03338 |

| | EC50 |
|---|---|
| WW0295 (chimeric IL-12) | 0.01240 |
| WW0675 (uncleaved) | 6.451 |
| WW0675 (cleaved) | 0.04843 |

| | IL-12 | Intact | Cut |
|---|---|---|---|
| IC50 | 0.0009438 | 0.3993 | 0.006594 |

| | IL-12 | Intact | Cut |
|---|---|---|---|
| IC50 | 0.005183 | 1.734 | 0.01196 |

| | IL-12 | Intact | Cut |
|---|---|---|---|
| IC50 | 0.0009899 | 0.4738 | 0.002594 |

| | IL-12 | Intact | Cut |
|---|---|---|---|
| IC50 | 0.002393 | 0.1033 | 0.002373 |

| | EC50 |
|---|---|
| mIFNa1 (R&D Systems) | 42.09 |
| WW0609 intact | 3581 |
| WW0609 cleaved | 3.408 |

| | EC50 |
|---|---|
| WW0126_Mouse_IFNA1 | 3.231 |
| WW0610 Intact | 477.5 |
| WW0610 cleaved | 0.3708 |

B16-Blue mIFNa/b Reporter Assay Using WW0643

| | EC50 |
|---|---|
| WW0647 lot2 | 0.9197 |
| WW0643 intact | 16.23 |
| WW0643 cleaved | 0.01595 |

B16-Blue mIFNa/b Reporter Assay Using WW0644

| | EC50 |
|---|---|
| WW0647 Mouse IFNa11 | 0.08700 |
| WW0644 intact | 3.000 |
| WW0644 cleaved | 0.004277 |

B16 Blue mIFNa/b Reporter assay with WW0815

| | EC50 |
|---|---|
| WW0126_Mouse_IFNA1 | 2.161 |
| WW0815 Intact | 189.4 |
| WW0815 Cleaved | 0.7231 |

B16 Blue mIFNa/b Reporter assay with WW0816

| | EC50 |
|---|---|
| WW0647_Mouse_IFNA11 | 0.1089 |
| WW0816 Intact | 3.432 |
| WW0816 Cleaved | 0.01356 |

| | EC50 |
| --- | --- |
| WW0126 Mouse IFNA1 | 2.265 |
| WW0817 Intact | 10.69 |
| WW0817 Cleaved | 0.1334 |

| | EC50 |
| --- | --- |
| WW0126 Mouse IFNa1 | 2.383 |
| WW0819 Intact | 24.72 |
| WW0819 Cleaved | 0.1559 |

| | EC50 |
|---|---|
| WW0647_Mouse_IFNA11 | 0.07948 |
| WW0818 Intact | 0.3053 |
| WW0818 Cleaved | 0.007163 |

| | EC50 |
|---|---|
| WW0647_Mouse_IFNA11 | 0.06983 |
| WW0820 Intact | 0.7076 |
| WW0820 Cleaved | 0.01457 |

ACP36 - HSA

ACP36 + HSA

ACP37 - HSA

ACP37 + HSA

| | ACP01 uncut + HSA | ACP01 cut +HSA |
|---|---|---|
| EC50 | 147.0 | 0.4295 |

| | ACP02 uncut +HSA | ACP02 cut +HSA |
|---|---|---|
| EC50 | 3.234 | 0.05013 |

| | ACP03 uncut +HSA | ACP03 cut +HSA |
|---|---|---|
| EC50 | 2.587 | 0.04462 |

| | ACP01 uncut - HSA | ACP01 cut -HSA |
|---|---|---|
| EC50 | 0.2730 | 0.2869 |

| | ACP02 uncut -HSA | ACP02 cut -HSA |
|---|---|---|
| EC50 | 0.05001 | 0.03578 |

| | ACP03 uncut -HSA | ACP3 cut-HSA |
|---|---|---|
| EC50 | 0.04556 | 0.04677 |

ACP02+HSA

ACP30+HSA

| | ACP31 uncut | ACP31 cut |
|---|---|---|
| EC50 | ~ 4.134 | 3.069 |

| | ACP33 uncut | ACP33 cut |
|---|---|---|
| EC50 | 100.6 | 7.239 |

| | ACP51 uncut | ACP51 Preactivated MMP9 |
|---|---|---|
| EC50 | 343.2 | 0.5649 |

| | ACP52 uncut | ACP52 Preactivated MMP9 |
|---|---|---|
| EC50 | | ~ 9.475 |

| | ACP53 uncut | ACP53 Preactivated MMP9 |
|---|---|---|
| EC50 | 283.5 | 0.164 |

| | ACP54 uncut | ACP54 Preactivated MMP9 | ACP54 Catalytic domain MMP9 |
|---|---|---|---|
| EC50 | 3.03 | 0.05893 | 0.1647 |

| | EC50 |
|---|---|
| ACP133 (- alb) | 0.03946 |
| ACP132 (- alb) | 0.02814 |
| ACP133 (+ alb) | 0.04565 |
| ACP132(+ alb) | 0.02589 |

| | EC50 |
|---|---|
| ACP16 | ~ 77.45 |
| ACP16 +MMP9 | 0.4789 |

| | ACP16 uncut+ HSA | ACP16 cut + HSA |
|---|---|---|
| EC50 | 1.214 | 0.03146 |

| | ACP124 + HSA uncut | ACP124+ HSA cut |
|---|---|---|
| EC50 | 3.066 | 2.865 |

| | ACP11 uncut | ACP11 + MMP9 |
|---|---|---|
| EC50 | ~ 212.2 | 1.349 |

| | ACP91 uncut | ACP91 + MMP9 |
|---|---|---|
| EC50 | 255.9 | 288.2 |

| | ACP136 uncut | ACP136 + MMP9 |
|---|---|---|
| EC50 | 261.8 | 2.598 |

| | ACP31 uncut + HSA | ACP31 cut + HSA |
|---|---|---|
| EC50 | 460.3 | 3.028 |

| | ACP125 + HSA uncut | ACP125 + HSA cut |
|---|---|---|
| EC50 | 35.65 | 3.175 |

| | ACP126 uncut + HSA | ACP126 cut + HSA |
|---|---|---|
| EC50 | 156.6 | 2.352 |

| | ACP127 uncut | ACP127 cut |
|---|---|---|
| EC50 | 183.5 | 1.245 |

| | ACP128 uncut | ACP128 cut |
|---|---|---|
| EC50 | 30.71 | 1.563 |

| | ACP129 uncut | ACP129 cut |
|---|---|---|
| EC50 | 40.93 | 1.638 |

| | ACP56 uncut | ACP56 cut |
|---|---|---|
| EC50 | 137.2 | 0.3401 |

| | ACP57 uncut | ACP57 cut |
|---|---|---|
| EC50 | 308.7 | 0.1636 |

| | ACP58 uncut | ACP58 cut |
|---|---|---|
| EC50 | 3.360 | 0.2114 |

| | ACP59 uncut | ACP59 cut |
|---|---|---|
| EC50 | 5.263 | 0.1355 |

| | ACP60 uncut | ACP60 cut |
|---|---|---|
| EC50 | 10.05 | 0.07688 |

| | ACP61 uncut | ACP61 cut |
|---|---|---|
| EC50 | ~ 211.2 | ~ 4.226 |

| | ACP30 uncut + HSA | ACP30 cut + HSA |
|---|---|---|
| EC50 | 66.26 | 0.04456 |

| | ACP73 uncut | ACP73 cut |
|---|---|---|
| EC50 | 67.24 | 0.02719 |

| | ACP70 +HSA uncut | ACP70 +HSA cut |
|---|---|---|
| EC50 | 10.83 | 0.03898 |

| | ACP71 uncut | ACP71 cut |
|---|---|---|
| EC50 | 3.028 | 0.02914 |

| | ACP72 uncut | ACP72 cut |
|---|---|---|
| EC50 | 1.567 | 0.03718 |

| | ACP73 uncut | ACP73 cut |
|---|---|---|
| EC50 | 92.99 | 0.03993 |

| | ACP74 uncut | ACP74 cut |
|---|---|---|
| EC50 | 54.09 | 0.03094 |

| | ACP75 uncut | ACP75 cut |
|---|---|---|
| EC50 | 34.31 | 0.03035 |

| | EC50 |
|---|---|
| WW0635 (hIFNa2b) | 0.001066 |
| hIFNa2b (R&D) | 0.002892 |
| hIFNa2b (Invivogen) | 0.003408 |
| WW0612 intact | 1.254 |
| WW0612 cleaved | 0.001798 |

| | EC50 |
|---|---|
| WW0635 (hIFNa2b) | 0.002171 |
| hIFNa2b (R&D) | 0.003637 |
| hIFNa2b (Invivogen) | 0.004893 |
| WW0613 intact | 1.342 |
| WW0613 cleaved | 0.001599 |

HEK-Blue hIFNa/b Reporter Assay Using WW0821

| | EC50 |
|---|---|
| WW0635 (hIFNa2b) | 0.007553 |
| WW0821 intact | 3.183 |
| WW0821 cleaved | 5.519e-005 |

HEK-Blue hIFNa/b Reporter Assay Using WW0822

| | EC50 |
|---|---|
| rhIFNa14 (Invivogen) | 0.01530 |
| WW0822 intact | 0.4337 |
| WW0822 cleaved | 1.595e-005 |
| WW0822 CTSL cleaved | 0.001199 |

| | EC50 |
|---|---|
| IFNa8 (Sino Biological) | 0.008269 |
| WW0831 intact | 0.6960 |
| WW0831 cut | 0.002336 |

| | EC50 |
|---|---|
| IFNa8 (Sino Biological) | 0.01286 |
| WW0833 intact | 2.737 |
| WW0833 cut | 0.002759 |

| | EC50 |
|---|---|
| hIFNbeta (Sino Biol.) | 0.0004100 |
| WW0741 intact | 0.6854 |
| WW0741 cleaved | 0.008059 |

| | EC50 |
|---|---|
| hIFNbeta (Sino Biol.) | 0.0004189 |
| WW0743 intact | 0.2435 |
| WW0743 cleaved | 0.0007304 |

| | WW0635 | Intact WW0612 | Cut WW0612 |
|---|---|---|---|
| EC50 | 0.5252 | 21.63 | 0.5189 |

| | WW0635 | Intact WW0613 | Cut WW0613 |
|---|---|---|---|
| EC50 | 0.9388 | 63.63 | 0.7485 |

| | WW0648 | Intact WW0645 | Cut WW0645 |
|---|---|---|---|
| EC50 | 1.438 | 39.00 | 0.2899 |

| Treatment | Dead | Day |
|---|---|---|
| 610 (369 µg, x4) | | |
| 610 (553 µg, x4) | 1 | 15 |
| 610 (830 µg, x4) | | |
| 610 (1,245 µg, x4) | 1 | 22 |

| Treatment | Dead | Day |
|---|---|---|
| 815 (1,231 µg, x4) | | |
| 815 (1,845 µg, x4) | | |
| 815 (2,770 µg, x4) | 1 | 8 |
| 815 (4,154 µg, x4) | 3 | 4, 22, 22 |

FIG. 42A
B16-Blue IFNg Reporter Assay Using ACP211
OD (620nm)
Log nM
mIFNg
ACP211 intact
ACP211 cleaved
B16-Blue IFNa/b Reporter Assay Using ACP211
OD (620nm)
Log nM
mIFNa1
ACP211 intact
ACP211 cleaved
uncut cut
IFNγ
IFNα
Anti-HSA

| Mouse Serum Albumin | KD (nM) | kon(1/Ms) | kdis(1/s) |
|---|---|---|---|
| ACP16 | 2.6 | 4.3E+4 | 1.1E-4 |
| ACP10 | 0.38 | 2.5E+5 | 9.7E-5 |
| ACP11 | No binding | No binding | No binding |

| Human Serum Albumin | KD (nM) | kon(1/Ms) | kdis(1/s) |
|---|---|---|---|
| ACP16 | 4.3 | 3.4E+5 | 1.5E-3 |
| ACP10 | 4.4 | 2.8E+5 | 1.2E-3 |
| ACP11 | 79 | 3.1E+4 | 2.5E-3 |

FIG. 43

| | EC50 |
|---|---|
| mIFNa1 R&D Systems + albumin | 9.002 |
| WW609 intact + albumin | 532.5 |
| WW609 cleaved + albumin | 2.211 |

| | EC50 |
|---|---|
| mIFNa1 R&D Systems no albumin | 2.136 |
| WW609 intact no albumin | 6.652 |
| WW609 cleaved no albumin | 8.896 |

| | EC50 |
|---|---|
| WW0647_Mouse_IFNA11 +albumin | 0.2994 |
| WW0643 intact +albumin | 165.7 |
| WW0643 cleaved +albumin | 0.07501 |

| | EC50 |
|---|---|
| WW0647_Mouse_IFNA11 no albumin | 0.6224 |
| WW0643 intact no albumin | 0.3660 |
| WW0643 cleaved no albumin | 0.1622 |

SEQUENCE LISTING

```
Sequence total quantity: 647
SEQ ID NO: 1            moltype = AA  length = 153
FEATURE                 Location/Qualifiers
source                  1..153
                        mol_type = protein
                        organism = Homo sapiens
SEQUENCE: 1
MYRMQLLSCI ALSLALVTNS APTSSSTKKT QLQLEHLLLD LQMILNGINN YKNPKLTRML  60
TFKFYMPKKA TELKHLQCLE EELKPLEEVL NLAQSKNFHL RPRDLISNIN VIVLELKGSE  120
TTFMCEYADE TATIVEFLNR WITFCQSIIS TLT                              153

SEQ ID NO: 2            moltype = AA  length = 609
FEATURE                 Location/Qualifiers
source                  1..609
                        mol_type = protein
                        organism = Homo sapiens
SEQUENCE: 2
MKWVTFISLL FLFSSAYSRG VFRRDAHKSE VAHRFKDLGE ENFKALVLIA FAQYLQQCPF  60
EDHVKLVNEV TEFAKTCVAD ESAENCDKSL HTLFGDKLCT VATLRETYGE MADCCAKQEP  120
ERNECFLQHK DDNPNLPRLV RPEVDVMCTA FHDNEETFLK KYLYEIARRH PYFYAPELLF  180
FAKRYKAAFT ECCQAADKAA CLLPKLDELR DEGKASSAKQ GLKCASLQKF GERAFKAWAV  240
ARLSQRFPKA EFAEVSKLVT DLTKVHTECC HGDLLECADD RADLAKYICE NQDSISSKLK  300
ECCEKPLLEK SHCIAEVEND EMPADLPSLA ADFVGSKDVC KNYAEAKDVF LGMFLYEYAR  360
RHPDYSVVLL LRLAKTYETT LEKCCAAADP HECYAKVFDE FKPLVEEPQN LIKQNCELFE  420
QLGEYKFQNA LLVRYTKKVP QVSTPTLVEV SRNLGKVGSK CCKHPEAKRM PCAEDCLSVF  480
LNQLCVLHEK TPVSDRVTKC CTESLVNGRP CFSALEVDET YVPKEFNAET FTFHADICTL  540
SEKERQIKKQ TALVELVKHK PKATKEQLKA VMDDFAAFVE KCCKADDKET CFAEEGKKLV  600
AASQAALGL                                                         609

SEQ ID NO: 3            moltype = AA  length = 8
FEATURE                 Location/Qualifiers
REGION                  1..8
                        note = MMP7 cleavage domain sequence
source                  1..8
                        mol_type = protein
                        organism = unidentified
SEQUENCE: 3
KRALGLPG                                                          8

SEQ ID NO: 4            moltype = AA  length = 40
FEATURE                 Location/Qualifiers
REGION                  1..40
                        note = MMP7 cleavage domain sequence
source                  1..40
```

```
                         mol_type = protein
                         organism = unidentified
SEQUENCE: 4
DEDEDEDEDE DEDEDERPLA LWRSDRDRDR DRDRDRDRDR                          40

SEQ ID NO: 5             moltype = AA  length = 5
FEATURE                  Location/Qualifiers
VARIANT                  3
                         note = S or T
VARIANT                  4
                         note = L or I
VARIANT                  5
                         note = S or T
REGION                   1..5
                         note = MMP9 cleavage domain sequence
source                   1..5
                         mol_type = protein
                         organism = unidentified
SEQUENCE: 5
PRSLS                                                                5

SEQ ID NO: 6             moltype = AA  length = 5
FEATURE                  Location/Qualifiers
REGION                   1..5
                         note = MMP9 cleavage domain sequence
source                   1..5
                         mol_type = protein
                         organism = unidentified
SEQUENCE: 6
LEATA                                                                5

SEQ ID NO: 7             moltype = AA  length = 10
FEATURE                  Location/Qualifiers
REGION                   1..10
                         note = MMP11 cleavage domain sequence
source                   1..10
                         mol_type = protein
                         organism = unidentified
SEQUENCE: 7
GGAANLVRGG                                                           10

SEQ ID NO: 8             moltype = AA  length = 10
FEATURE                  Location/Qualifiers
REGION                   1..10
                         note = MMP14 cleavage domain sequence
source                   1..10
                         mol_type = protein
                         organism = unidentified
SEQUENCE: 8
SGRIGFLRTA                                                           10

SEQ ID NO: 9             moltype = AA  length = 6
FEATURE                  Location/Qualifiers
REGION                   1..6
                         note = MMP cleavage domain sequence
source                   1..6
                         mol_type = protein
                         organism = unidentified
SEQUENCE: 9
PLGLAG                                                               6

SEQ ID NO: 10            moltype = AA  length = 6
FEATURE                  Location/Qualifiers
REGION                   1..6
                         note = MMP cleavage domain sequence
source                   1..6
                         mol_type = protein
                         organism = unidentified
SEQUENCE: 10
PLGLAX                                                               6

SEQ ID NO: 11            moltype = AA  length = 6
FEATURE                  Location/Qualifiers
MOD_RES                  4
                         note = Cysteine(me)
REGION                   1..6
                         note = MMP cleavage domain sequence
source                   1..6
                         mol_type = protein
```

```
                        organism = unidentified
SEQUENCE: 11
PLGXAG                                                                    6

SEQ ID NO: 12           moltype = AA  length = 8
FEATURE                 Location/Qualifiers
REGION                  1..8
                        note = MMP cleavage domain sequence
source                  1..8
                        mol_type = protein
                        organism = unidentified
SEQUENCE: 12
ESPAYYTA                                                                  8

SEQ ID NO: 13           moltype = AA  length = 6
FEATURE                 Location/Qualifiers
REGION                  1..6
                        note = MMP cleavage domain sequence
source                  1..6
                        mol_type = protein
                        organism = unidentified
SEQUENCE: 13
RLQLKL                                                                    6

SEQ ID NO: 14           moltype = AA  length = 7
FEATURE                 Location/Qualifiers
REGION                  1..7
                        note = MMP cleavage domain sequence
source                  1..7
                        mol_type = protein
                        organism = unidentified
SEQUENCE: 14
RLQLKAC                                                                   7

SEQ ID NO: 15           moltype = AA  length = 7
FEATURE                 Location/Qualifiers
MOD_RES                 3
                        note = Citrulline
MOD_RES                 5
                        note = Homo-Phenylalanine
REGION                  1..7
                        note = MMP2, MMP9, MMP14 cleavage domain sequence
source                  1..7
                        mol_type = protein
                        organism = unidentified
SEQUENCE: 15
EPXGXYL                                                                   7

SEQ ID NO: 16           moltype = AA  length = 5
FEATURE                 Location/Qualifiers
REGION                  1..5
                        note = Urokinase plasminogen activator (uPA) cleavage
                         domainsequence
source                  1..5
                        mol_type = protein
                        organism = unidentified
SEQUENCE: 16
SGRSA                                                                     5

SEQ ID NO: 17           moltype = AA  length = 4
FEATURE                 Location/Qualifiers
REGION                  1..4
                        note = Urokinase plasminogen activator (uPA) cleavage
                         domainsequence
source                  1..4
                        mol_type = protein
                        organism = unidentified
SEQUENCE: 17
DAFK                                                                      4

SEQ ID NO: 18           moltype = AA  length = 5
FEATURE                 Location/Qualifiers
REGION                  1..5
                        note = Urokinase plasminogen activator (uPA) cleavage
                         domainsequence
source                  1..5
                        mol_type = protein
                        organism = unidentified
SEQUENCE: 18
```

```
GGGRR                                                 5

SEQ ID NO: 19         moltype = AA  length = 4
FEATURE               Location/Qualifiers
REGION                1..4
                      note = Lysosomal Enzyme cleavage domain sequence
source                1..4
                      mol_type = protein
                      organism = unidentified
SEQUENCE: 19
GFLG                                                  4

SEQ ID NO: 20         moltype = AA  length = 4
FEATURE               Location/Qualifiers
REGION                1..4
                      note = Lysosomal Enzyme cleavage domain sequence
source                1..4
                      mol_type = protein
                      organism = unidentified
SEQUENCE: 20
ALAL                                                  4

SEQ ID NO: 21         moltype =   length =
SEQUENCE: 21
000

SEQ ID NO: 22         moltype =   length =
SEQUENCE: 22
000

SEQ ID NO: 23         moltype = AA  length = 5
FEATURE               Location/Qualifiers
MOD_RES               3
                      note = Cysteine(Et)
REGION                1..5
                      note = Cathepsin D cleavage domain sequence
source                1..5
                      mol_type = protein
                      organism = unidentified
SEQUENCE: 23
PIXFF                                                 5

SEQ ID NO: 24         moltype = AA  length = 8
FEATURE               Location/Qualifiers
REGION                1..8
                      note = Cathepsin K cleavage domain sequence
source                1..8
                      mol_type = protein
                      organism = unidentified
SEQUENCE: 24
GGPRGLPG                                              8

SEQ ID NO: 25         moltype = AA  length = 6
FEATURE               Location/Qualifiers
REGION                1..6
                      note = Prostate Specific Antigen cleavage domain sequence
source                1..6
                      mol_type = protein
                      organism = unidentified
SEQUENCE: 25
HSSKLQ                                                6

SEQ ID NO: 26         moltype = AA  length = 7
FEATURE               Location/Qualifiers
REGION                1..7
                      note = Prostate Specific Antigen cleavage domain sequence
source                1..7
                      mol_type = protein
                      organism = unidentified
SEQUENCE: 26
HSSKLQL                                               7

SEQ ID NO: 27         moltype = AA  length = 9
FEATURE               Location/Qualifiers
REGION                1..9
                      note = Prostate Specific Antigen cleavage domain sequence
source                1..9
                      mol_type = protein
                      organism = unidentified
```

```
SEQUENCE: 27
HSSKLQEDA                                                     9

SEQ ID NO: 28          moltype = AA  length = 10
FEATURE                Location/Qualifiers
REGION                 1..10
                       note = Herpes Simplex Virus Protease cleavage domainsequence
source                 1..10
                       mol_type = protein
                       organism = unidentified
SEQUENCE: 28
LVLASSSFGY                                                    10

SEQ ID NO: 29          moltype = AA  length = 10
FEATURE                Location/Qualifiers
REGION                 1..10
                       note = HIV Protease cleavage domain sequence
source                 1..10
                       mol_type = protein
                       organism = unidentified
SEQUENCE: 29
GVSQNYPIVG                                                    10

SEQ ID NO: 30          moltype = AA  length = 10
FEATURE                Location/Qualifiers
REGION                 1..10
                       note = CMV Protease cleavage domain sequence
source                 1..10
                       mol_type = protein
                       organism = unidentified
SEQUENCE: 30
GVVQASCRLA                                                    10

SEQ ID NO: 31          moltype =   length =
SEQUENCE: 31
000

SEQ ID NO: 32          moltype = AA  length = 6
FEATURE                Location/Qualifiers
REGION                 1..6
                       note = Thrombin cleavage domain sequence
source                 1..6
                       mol_type = protein
                       organism = unidentified
SEQUENCE: 32
DPRSFL                                                        6

SEQ ID NO: 33          moltype = AA  length = 6
FEATURE                Location/Qualifiers
REGION                 1..6
                       note = Thrombin cleavage domain sequence
source                 1..6
                       mol_type = protein
                       organism = unidentified
SEQUENCE: 33
PPRSFL                                                        6

SEQ ID NO: 34          moltype = AA  length = 4
FEATURE                Location/Qualifiers
REGION                 1..4
                       note = Caspase-3 cleavage domain sequence
source                 1..4
                       mol_type = protein
                       organism = unidentified
SEQUENCE: 34
DEVD                                                          4

SEQ ID NO: 35          moltype = AA  length = 5
FEATURE                Location/Qualifiers
REGION                 1..5
                       note = Caspase-3 cleavage domain sequence
source                 1..5
                       mol_type = protein
                       organism = unidentified
SEQUENCE: 35
DEVDP                                                         5

SEQ ID NO: 36          moltype = AA  length = 8
FEATURE                Location/Qualifiers
```

```
REGION                  1..8
                        note = Caspase-3 cleavage domain sequence
source                  1..8
                        mol_type = protein
                        organism = unidentified
SEQUENCE: 36
KGSGDVEG                                                                  8

SEQ ID NO: 37           moltype = AA  length = 6
FEATURE                 Location/Qualifiers
REGION                  1..6
                        note = Interleukin 1-beta converting enzyme cleavage
                         domainsequence
source                  1..6
                        mol_type = protein
                        organism = unidentified
SEQUENCE: 37
GWEHDG                                                                    6

SEQ ID NO: 38           moltype = AA  length = 7
FEATURE                 Location/Qualifiers
REGION                  1..7
                        note = Enterokinase cleavage domain sequence
source                  1..7
                        mol_type = protein
                        organism = unidentified
SEQUENCE: 38
EDDDDKA                                                                   7

SEQ ID NO: 39           moltype = AA  length = 9
FEATURE                 Location/Qualifiers
REGION                  1..9
                        note = FAP cleavage domain sequence
source                  1..9
                        mol_type = protein
                        organism = unidentified
SEQUENCE: 39
KQEQNPGST                                                                 9

SEQ ID NO: 40           moltype = AA  length = 6
FEATURE                 Location/Qualifiers
REGION                  1..6
                        note = Kallikrein 2 cleavage domain sequence
source                  1..6
                        mol_type = protein
                        organism = unidentified
SEQUENCE: 40
GKAFRR                                                                    6

SEQ ID NO: 41           moltype = AA  length = 4
FEATURE                 Location/Qualifiers
REGION                  1..4
                        note = Plasmin cleavage domain sequence
source                  1..4
                        mol_type = protein
                        organism = unidentified
SEQUENCE: 41
DAFK                                                                      4

SEQ ID NO: 42           moltype = AA  length = 4
FEATURE                 Location/Qualifiers
REGION                  1..4
                        note = Plasmin cleavage domain sequence
source                  1..4
                        mol_type = protein
                        organism = unidentified
SEQUENCE: 42
DVLK                                                                      4

SEQ ID NO: 43           moltype = AA  length = 4
FEATURE                 Location/Qualifiers
REGION                  1..4
                        note = Plasmin cleavage domain sequence
source                  1..4
                        mol_type = protein
                        organism = unidentified
SEQUENCE: 43
DAFK                                                                      4
```

-continued

```
SEQ ID NO: 44          moltype = AA  length = 7
FEATURE                Location/Qualifiers
REGION                 1..7
                       note = TOP cleavage domain sequence
source                 1..7
                       mol_type = protein
                       organism = unidentified
SEQUENCE: 44
ALLLALL                                                           7

SEQ ID NO: 45          moltype = AA  length = 652
FEATURE                Location/Qualifiers
source                 1..652
                       mol_type = protein
                       organism = synthetic construct
SEQUENCE: 45
QVQLQESGGG LVQAGGSLRL SCAASGRIFS IDIMSWYRQA PGKQRELVAR ITRGGTISYD  60
DSVKGRFTIS RDNAKNTVYL QMNSLKPEDT GVYYCNALYG TDYWGKGTQV TVSSGGGGSG  120
GGGSGGGGSA PTSSSTKKTQ LQLEHLLLDL QMILNGINNY KNPKLTRMLT FKFYMPKKAT  180
ELKHLQCLEE ELKPLEEVLN LAQSKNFHLR PRDLISNINV IVLELKGSET TFMCEYADET  240
ATIVEFLNRW ITFCQSIIST LTSGGPGPAG MKGLPGSEVQ LVESGGGLVQ PGNSLRLSCA  300
ASGFTFSKFG MSWVRQAPGK GLEWVSSISG SGRDTLYAES VKGRFTISRD NAKTTLYLQM  360
NSLRPEDTAV YYCTIGGSLS VSSQGTLVTV SSGGGGSGGG GSGGGGSEVQ LVESGGGLVQ  420
PGGSLRLSCA ASGFTFSSYT LAWVRQAPGK GLEWVAAIDS SSYTYSPDTV RGRFTISRDN  480
AKNSLYLQMN SLRAEDTAVY YCARDSNWDA LDYWGQGTTV TVSSGGGGSG GGGSGGGGSD  540
IQMTQSPSSL SASVGDRVTI TCKASQNVGT NVGWYQQKPG KAPKALIYSA SFRYSGVPSR  600
FSGSGSGTDF TLTISSLQPE DFATYYCQQY YTYPYTFGGG TKVEIKHHHH HH          652

SEQ ID NO: 46          moltype = AA  length = 652
FEATURE                Location/Qualifiers
source                 1..652
                       mol_type = protein
                       organism = synthetic construct
SEQUENCE: 46
QVQLQESGGG LVQAGGSLRL SCAASGRIFS IDIMSWYRQA PGKQRELVAR ITRGGTISYD  60
DSVKGRFTIS RDNAKNTVYL QMNSLKPEDT GVYYCNALYG TDYWGKGTQV TVSSGGGGSG  120
GGGSGGGGSE VQLVESGGGL VQPGGSLRLS CAASGFTFSS YTLAWVRQAP GKGLEWVAAI  180
DSSSYTYSPD TVRGRFTISR DNAKNSLYLQ MNSLRAEDTA VYYCARDSNW DALDYWGQGT  240
TVTVSSGGGG SGGGGSGGGG SDIQMTQSPS SLSASVGDRV TITCKASQNV GTNVGWYQQK  300
PGKAPKALIY SASFRYSGVP SRFSGSGSGT DFTLTISSLQ PEDFATYYCQ QYYTYPYTFG  360
GGTKVEIKGG GGSGGGGSGG GGSEVQLVES GGGLVQPGNS LRLSCAASGF TFSKFGMSWV  420
RQAPGKGLEW VSSISGSGRD TLYAESVKGR FTISRDNAKT TLYLQMNSLR PEDTAVYYCT  480
IGGSLSVSSQ GTLVTVSSSG GPGPAGMKGL PGSAPTSSST KKTQLQLEHL LLDLQMILNG  540
INNYKNPKLT RMLTFKFYMP KKATELKHLQ CLEEELKPLE EVLNLAQSKN FHLRPRDLIS  600
NINVIVLELK GSETTFMCEY ADETATIVEF LNRWITFCQS IISTLTHHHH HH          652

SEQ ID NO: 47          moltype = AA  length = 553
FEATURE                Location/Qualifiers
source                 1..553
                       mol_type = protein
                       organism = synthetic construct
SEQUENCE: 47
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSGGG  120
GSGGGGSGGG GSDIQMTQSP SSLSASVGDR VTITCKASQN VGTNVGWYQQ KPGKAPKALI  180
YSASFRYSGV PSRFSGSGSG TDFTLTISSL QPEDFATYYC QQYYTYPYTF GGGTKVEIKG  240
GGGSGGGGSG GGGSGGGGSG GGGSGGGGSS GGPGPAGMKG LPGSAPTSSS TKKTQLQLEH  300
LLLDLQMILN GINNYKNPKL TRMLTFKFYM PKKATELKHL QCLEEELKPL EEVLNLAQSK  360
NFHLRPRDLI SNINVIVLEL KGSETTFMCE YADETATIVE FLNRWITFCQ SIISTLTSGG  420
PGPAGMKGLP GSEVQLVESG GGLVQPGNSL RLSCAASGFT FSKFGMSWVR QAPGKGLEWV  480
SSISGSGRDT LYAESVKGRF TISRDNAKTT LYLQMNSLRP EDTAVYYCTI GGSLSVSSQG  540
TLVTVSSHHH HHH                                                    553

SEQ ID NO: 48          moltype = AA  length = 553
FEATURE                Location/Qualifiers
source                 1..553
                       mol_type = protein
                       organism = synthetic construct
SEQUENCE: 48
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSGGG  120
GSGGGGSGGG GSDIQMTQSP SSLSASVGDR VTITCKASQN VGTNVGWYQQ KPGKAPKALI  180
YSASFRYSGV PSRFSGSGSG TDFTLTISSL QPEDFATYYC QQYYTYPYTF GGGTKVEIKG  240
GGGSGGGGSG GGGSGGGGSG GGGSGGGGSE VQLVESGGGL VQPGNSLRLS CAASGFTFSK  300
FGMSWVRQAP GKGLEWVSSI SGSGRDTLYA ESVKGRFTIS RDNAKTTLYL QMNSLRPEDT  360
AVYYCTIGGS LSVSSQGTLV TVSSGGGGSG GGGSGGGGSS GGPGPAGMKG LPGSAPTSSS  420
TKKTQLQLEH LLLDLQMILN GINNYKNPKL TRMLTFKFYM PKKATELKHL QCLEEELKPL  480
EEVLNLAQSK NFHLRPRDLI SNINVIVLEL KGSETTFMCE YADETATIVE FLNRWITFCQ  540
SIISTLTHHH HHH                                                    553
```

```
SEQ ID NO: 49          moltype = AA  length = 553
FEATURE                Location/Qualifiers
source                 1..553
                       mol_type = protein
                       organism = synthetic construct
SEQUENCE: 49
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GMKGLPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKASQNVG TNVGWYQQKP  480
GKAPKALIYS ASFRYSGVPS RFSGSGSGTD FTLTISSLQP EDFATYYCQQ YYTYPYTFGG  540
GTKVEIKHHH HHH                                                     553

SEQ ID NO: 50          moltype = AA  length = 682
FEATURE                Location/Qualifiers
source                 1..682
                       mol_type = protein
                       organism = synthetic construct
SEQUENCE: 50
QVQLQESGGG LVQAGGSLRL SCAASGRIFS IDIMSWYRQA PGKQRELVAR ITRGGTISYD  60
DSVKGRFTIS RDNAKNTVYL QMNSLKPEDT GVYYCNALYG TDYWGKGTQV TVSSGGGGSG  120
GGGSGGGGSA PTSSSTKKTQ LQLEHLLLDL QMILNGINNY KNPKLTRMLT FKFYMPKKAT  180
ELKHLQCLEE ELKPLEEVLN LAQSKNFHLR PRDLISNINV IVLELKGSET TFMCEYADET  240
ATIVEFLNRW ITFCQSIIST LTSGGPGPAG MKGLPGSEVQ LVESGGGLVQ PGNSLRLSCA  300
ASGFTFSKFG MSWVRQAPGK GLEWVSSISG SGRDTLYAES VKGRFTISRD NAKTTLYLQM  360
NSLRPEDTAV YYCTIGGSLS VSSQGTLVTV SSGGGGSGGG GSGGGGSGGG GSGGGGSGGG  420
GSSGGPGPAG MKGLPGSEVQ LVESGGGLVQ PGGSLRLSCA ASGFTFSSYT LAWVRQAPGK  480
GLEWVAAIDS SSYTYSPDTV RGRFTISRDN AKNSLYLQMN SLRAEDTAVY YCARDSNWDA  540
LDYWGQGTTV TVSSGGGGSG GGGSGGGGSD IQMTQSPSSL SASVGDRVTI TCKASQNVGT  600
NVGWYQQKPG KAPKALIYSA SFRYSGVPSR FSGSGSGTDF TLTISSLQPE DFATYYCQQY  660
YTYPYTFGGG TKVEIKHHHH HH                                           682

SEQ ID NO: 51          moltype = AA  length = 667
FEATURE                Location/Qualifiers
source                 1..667
                       mol_type = protein
                       organism = synthetic construct
SEQUENCE: 51
QVQLQESGGG LVQAGGSLRL SCAASGRIFS IDIMSWYRQA PGKQRELVAR ITRGGTISYD  60
DSVKGRFTIS RDNAKNTVYL QMNSLKPEDT GVYYCNALYG TDYWGKGTQV TVSSGGGGSG  120
GGGSGGGGSA PTSSSTKKTQ LQLEHLLLDL QMILNGINNY KNPKLTRMLT FKFYMPKKAT  180
ELKHLQCLEE ELKPLEEVLN LAQSKNFHLR PRDLISNINV IVLELKGSET TFMCEYADET  240
ATIVEFLNRW ITFCQSIIST LTSGGPGPAG MKGLPGSEVQ LVESGGGLVQ PGNSLRLSCA  300
ASGFTFSKFG MSWVRQAPGK GLEWVSSISG SGRDTLYAES VKGRFTISRD NAKTTLYLQM  360
NSLRPEDTAV YYCTIGGSLS VSSQGTLVTV SSGGGGSGGG GSGGGGSGGG GSGGGGSGGG  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG QGTTVTVSSS  540
GGPGPAGMKG LPGSDIQMTQ SPSSLSASVG DRVTITCKAS QNVGTNVGWY QQKPGKAPKA  600
LIYSASFRYS GVPSRFSGSG SGTDFTLTIS SLQPEDFATY YCQQYYTYPY TFGGGTKVEI  660
KHHHHHH                                                            667

SEQ ID NO: 52          moltype = AA  length = 682
FEATURE                Location/Qualifiers
source                 1..682
                       mol_type = protein
                       organism = synthetic construct
SEQUENCE: 52
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSGG GGSGGGGSGG GGSGGGGSGG GGSGGGGSEV  180
QLVESGGGLV QPGGSLRLSC AASGFTFSSY TLAWVRQAPG KGLEWVAAID SSSYTYSPDT  240
VRGRFTISRD NAKNSLYLQM NSLRAEDTAV YYCARDSNWD ALDYWGQGTT VTVSSGGGGS  300
GGGGSGGGGS DIQMTQSPSS LSASVGDRVT ITCKASQNVG TNVGWYQQKP GKAPKALIYS  360
ASFRYSGVPS RFSGSGSGTD FTLTISSLQP EDFATYYCQQ YYTYPYTFGG GTKVEIKGGG  420
GSGGGGSGGG GSEVQLVESG GGLVQPGNSL RLSCAASGFT FSKFGMSWVR QAPGKGLEWV  480
SSISGSGRDT LYAESVKGRF TISRDNAKTT LYLQMNSLRP EDTAVYYCTI GGSLSVSSQG  540
TLVTVSSGGG GSGGGGSGGG GSQVQLQESG GGLVQAGGSL RLSCAASGRI FSIDIMSWYR  600
QAPGKQRELV ARITRGGTIS YDDSVKGRFT ISRDNAKNTV YLQMNSLKPE DTGVYYCNAL  660
YGTDYWGKGT QVTVSSHHHH HH                                           682

SEQ ID NO: 53          moltype = AA  length = 393
FEATURE                Location/Qualifiers
source                 1..393
                       mol_type = protein
```

```
                         organism = synthetic construct
SEQUENCE: 53
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGGSLRLSC AASGFTFSSY  180
TLAWVRQAPG KGLEWVAAID SSSYTYSPDT VRGRFTISRD NAKNSLYLQM NSLRAEDTAV  240
YYCARDSNWD ALDYWGQGTT VTVSSGGGGS GGGGSGGGGS DIQMTQSPSS LSASVGDRVT  300
ITCKASQNVG TNVGWYQQKP GKAPKALIYS ASFRYSGVPS RFSGSGSGTD FTLTISSLQP  360
EDFATYYCQQ YYTYPYTFGG GTKVEIKHHH HHH                                393

SEQ ID NO: 54            moltype = AA  length = 423
FEATURE                  Location/Qualifiers
source                   1..423
                         mol_type = protein
                         organism = synthetic construct
SEQUENCE: 54
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSGG GGSGGGGSGG GGSGGGGSGG GGSGGGGSEV  180
QLVESGGGLV QPGGSLRLSC AASGFTFSSY TLAWVRQAPG KGLEWVAAID SSSYTYSPDT  240
VRGRFTISRD NAKNSLYLQM NSLRAEDTAV YYCARDSNWD ALDYWGQGTT VTVSSGGGGS  300
GGGGSGGGGS DIQMTQSPSS LSASVGDRVT ITCKASQNVG TNVGWYQQKP GKAPKALIYS  360
ASFRYSGVPS RFSGSGSGTD FTLTISSLQP EDFATYYCQQ YYTYPYTFGG GTKVEIKHHH  420
HHH                                                                 423

SEQ ID NO: 55            moltype = AA  length = 682
FEATURE                  Location/Qualifiers
source                   1..682
                         mol_type = protein
                         organism = synthetic construct
SEQUENCE: 55
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSGG GGSGGGGSGG GGSGGGGSGG GGSGGGGSEV  180
QLVESGGGLV QPGGSLRLSC AASGFTFSSY TLAWVRQAPG KGLEWVAAID SSSYTYSPDT  240
VRGRFTISRD NAKNSLYLQM NSLRAEDTAV YYCARDSNWD ALDYWGQGTT VTVSSGGGGS  300
GGGGSGGGGS DIQMTQSPSS LSASVGDRVT ITCKASQNVG TNVGWYQQKP GKAPKALIYS  360
ASFRYSGVPS RFSGSGSGTD FTLTISSLQP EDFATYYCQQ YYTYPYTFGG GTKVEIKSGG  420
PGPAGMKGLP GSEVQLVESG GGLVQPGNSL RLSCAASGFT FSKFGMSWVR QAPGKGLEWV  480
SSISGSGRDT LYAESVKGRF TISRDNAKTT LYLQMNSLRP EDTAVYYCTI GGSLSVSSQG  540
TLVTVSSGGG GSGGGGSGGG GSQVQLQESG GGLVQAGGSL RLSCAASGRI FSIDIMSWYR  600
QAPGKQRELV ARITRGGTIS YDDSVKGRFT ISRDNAKNTV YLQMNSLKPE DTGVYYCNAL  660
YGTDYWGKGT QVTVSSHHHH HH                                             682

SEQ ID NO: 56            moltype = AA  length = 682
FEATURE                  Location/Qualifiers
source                   1..682
                         mol_type = protein
                         organism = synthetic construct
SEQUENCE: 56
QVQLQESGGG LAQAGGSLSL SCAASGFTVS NSVMAWYRQT PGKQREFVAI INSVGSTNYA  60
DSVKGRFTIS RDNAKNTVYL QMNNLKPEDT AVYVCNRNFD RIYWGQGTQV TVSSSGGPGP  120
AGMKGLPGSE VQLVESGGGL VQPGGSLRLS CAASGFTFSS YTLAWVRQAP GKGLEWVAAI  180
DSSSYTYSPD TVRGRFTISR DNAKNSLYLQ MNSLRAEDTA VYYCARDSNW DALDYWGQGT  240
TVTVSSGGGG SGGGGSGGGG SDIQMTQSPS SLSASVGDRV TITCKASQNV GTNVGWYQQK  300
PGKAPKALIY SASFRYSGVP SRFSGSGSGT DFTLTISSLQ PEDFATYYCQ QYYTYPYTFG  360
GGTKVEIKGG GGSGGGGSGG GGSGGGGSGG GGSGGGGSSG GPGPAGMKGL PGSEVQLVES  420
GGGLVQPGNS LRLSCAASGF TFSKFGMSWV RQAPGKGLEW VSSISGSGRD TLYAESVKGR  480
FTISRDNAKT TLYLQMNSLR PEDTAVYYCT IGGSLSVSSQ GTLVTVSSSG GPGPAGMKGL  540
PGSAPTSSST KKTQLQLEHL LLDLQMILNG INNYKNPKLT RMLTFKFYMP KKATELKHLQ  600
CLEEELKPLE EVLNLAQSKN FHLRPRDLIS NINVIVLELK GSETTFMCEY ADETATIVEF  660
LNRWITFCQS IISTLTHHHH HH                                             682

SEQ ID NO: 57            moltype = AA  length = 393
FEATURE                  Location/Qualifiers
source                   1..393
                         mol_type = protein
                         organism = synthetic construct
SEQUENCE: 57
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSGGG  120
GSGGGGSGGG GSDIQMTQSP SSLSASVGDR VTITCKASQN VGTNVGWYQQ KPGKAPKALI  180
YSASFRYSGV PSRFSGSGSG TDFTLTISSL QPEDFATYYC QQYYTYPYTF GGGTKVEIKS  240
GGPGPAGMKG LPGSAPTSSS TKKTQLQLEH LLLDLQMILN GINNYKNPKL TRMLTFKFYM  300
PKKATELKHL QCLEEELKPL EEVLNLAQSK NFHLRPRDLI SNINVIVLEL KGSETTFMCE  360
YADETATIVE FLNRWITFCQ SIISTLTHHH HHH                                393

SEQ ID NO: 58            moltype = AA  length = 423
FEATURE                  Location/Qualifiers
```

```
source                 1..423
                       mol_type = protein
                       organism = synthetic construct
SEQUENCE: 58
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSGGG  120
GSGGGGSGGG GSDIQMTQSP SSLSASVGDR VTITCKASQN VGTNVGWYQQ KPGKAPKALI  180
YSASFRYSGV PSRFSGSGSG TDFTLTISSL QPEDFATYYC QQYYTYPYTF GGGTKVEIKG  240
GGGSGGGGSG GGGSGGGGSG GGGSGGGGSS GGPGPAGMKG LPGSAPTSSS TKKTQLQLEH  300
LLLDLQMILN GINNYKNPKL TRMLTFKFYM PKKATELKHL QCLEEELKPL EEVLNLAQSK  360
NFHLRPRDLI SNINVIVLEL KGSETTFMCE YADETATIVE FLNRWITFCQ SIISTLTHHH  420
HHH                                                                423

SEQ ID NO: 59          moltype = AA  length = 669
FEATURE                Location/Qualifiers
source                 1..669
                       mol_type = protein
                       organism = synthetic construct
SEQUENCE: 59
QVQLQESGGG LVQAGGSLRL SCAASGRIFS IDIMSWYRQA PGKQRELVAR ITRGGTISYD  60
DSVKGRFTIS RDNAKNTVYL QMNSLKPEDT GVYYCNALYG TDYWGKGTQV TVSSGGGGSG  120
GGGSGGGGSA PTSSSTKKTQ LQLEHLLLDL QMILNGINNY KNPKLTRMLT FKFYMPKKAT  180
ELKHLQCLEE ELKPLEEVLN LAQSKNFHLR PRDLISNINV IVLELKGSET TFMCEYADET  240
ATIVEFLNRW ITFCQSIIST LTSGGPGPAG MKGLPGSEVQ LVESGGGLVQ PGNSLRLSCA  300
ASGFTFSKFG MSWVRQAPGK GLEWVSSISG SGRDTLYAES VKGRFTISRD NAKTTLYLQM  360
NSLRPEDTAV YYCTIGGSLS VSSQGTLVTV SSGGGGSGGG GSGGGGSGGG GSQVQLQQSG  420
AELVRPGTSV KVSCKASGYA FTNYLIEWVK QRPGQGLEWI GVINPGSGGT NYNEKFKGKA  480
TLTADKSSST AYMQLSSLTS DDSAVYFCAR WRGDGYYAYF DVWGAGTTVT VSSGGGGSGG  540
GGSGGGGSDI VLTQSPASLA VSLGQRATIS CKASQSVDYD GDSYMNWYQQ KPGQPPKLLI  600
YAASNLESGI PARFSGSGSG TDFTLNIHPV EEEDAATYYC QQSNEDPYTF GGGTKLEIKH  660
HHHHHEPEA                                                          669

SEQ ID NO: 60          moltype = AA  length = 669
FEATURE                Location/Qualifiers
source                 1..669
                       mol_type = protein
                       organism = synthetic construct
SEQUENCE: 60
QVQLQESGGG LVQAGGSLRL SCAASGRIFS IDIMSWYRQA PGKQRELVAR ITRGGTISYD  60
DSVKGRFTIS RDNAKNTVYL QMNSLKPEDT GVYYCNALYG TDYWGKGTQV TVSSGGGGSG  120
GGGSGGGGSA PTSSSTKKTQ LQLEHLLLDL QMILNGINNY KNPKLTRMLT FKFYMPKKAT  180
ELKHLQCLEE ELKPLEEVLN LAQSKNFHLR PRDLISNINV IVLELKGSET TFMCEYADET  240
ATIVEFLNRW ITFCQSIIST LTSGGPGPAG MKGLPGSEVQ LVESGGGLVQ PGNSLRLSCA  300
ASGFTFSKFG MSWVRQAPGK GLEWVSSISG SGRDTLYAES VKGRFTISRD NAKTTLYLQM  360
NSLRPEDTAV YYCTIGGSLS VSSQGTLVTV SSGGGGSGGG GSGGGGSGGG GSDIVLTQSP  420
ASLAVSLGQR ATISCKASQS VDYDGDSYMN WYQQKPGQPP KLLIYAASNL ESGIPARFSG  480
SGSGTDFTLN IHPVEEEDAA TYYCQQSNED PYTFGGGTKL EIKGGGGSGG GGSGGGGSQV  540
QLQQSGAELV RPGTSVKVSC KASGYAFTNY LIEWVKQRPG QGLEWIGVIN PGSGGTNYNE  600
KFKGKATLTA DKSSSTAYMQ LSSLTSDDSA VYFCARWRGD GYYAYFDVWG AGTTVTVSSH  660
HHHHHEPEA                                                          669

SEQ ID NO: 61          moltype = AA  length = 689
FEATURE                Location/Qualifiers
source                 1..689
                       mol_type = protein
                       organism = synthetic construct
SEQUENCE: 61
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSGG GGSGGGGSGG GGSGGGGSGG GGSQVQLQQS  180
GAELVRPGTS VKVSCKASGY AFTNYLIEWV KQRPGQGLEW IGVINPGSGG TNYNEKFKGK  240
ATLTADKSSS TAYMQLSSLT SDDSAVYFCA RWRGDGYYAY FDVWGAGTTV TVSSGGGGSG  300
GGGSGGGGSD IVLTQSPASL AVSLGQRATI SCKASQSVDY DGDSYMNWYQ QKPGQPPKLL  360
IYAASNLESG IPARFSGSGS GTDFTLNIHP VEEEDAATYY CQQSNEDPYT FGGGTKLEIK  420
GGGGSGGGGS GGGGSEVQLV ESGGGLVQPG NSLRLSCAAS GFTFSKFGMS WVRQAPGKGL  480
EWVSSISGSG RDTLYAESVK GRFTISRDNA KTTLYLQMNS LRPEDTAVYY CTIGGSLSVS  540
SQGTLVTVSS GGGGSGGGGS GGGGSQVQLQ ESGGGLVQAG GSLRLSCAAS GRIFSIDIMS  600
WYRQAPGKQR ELVARITRGG TISYDDSVKG RFTISRDNAK NTVYLQMNSL KPEDTGVYYC  660
NALYGTDYWG KGTQVTVSSH HHHHHEPEA                                    689

SEQ ID NO: 62          moltype = AA  length = 689
FEATURE                Location/Qualifiers
source                 1..689
                       mol_type = protein
                       organism = synthetic construct
SEQUENCE: 62
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSGG GGSGGGGSGG GGSGGGGSGG GGSDIVLTQS  180
```

```
PASLAVSLGQ RATISCKASQ SVDYDGDSYM NWYQQKPGQP PKLLIYAASN LESGIPARFS  240
GSGSGTDFTL NIHPVEEEDA ATYYCQQSNE DPYTFGGGTK LEIKGGGGSG GGGSGGGGSQ  300
VQLQQSGAEL VRPGTSVKVS CKASGYAFTN YLIEWVKQRP GQGLEWIGVI NPGSGGTNYN  360
EKFKGKATLT ADKSSSTAYM QLSSLTSDDS AVYFCARWRG DGYYAYFDVW GAGTTVTVSS  420
GGGGSGGGGS GGGGSEVQLV ESGGGLVQPG NSLRLSCAAS GFTFSKFGMS WVRQAPGKGL  480
EWVSSISGSG RDTLYAESVK GRFTISRDNA KTTLYLQMNS LRPEDTAVYY CTIGGSLSVS  540
SQGTLVTVSS GGGGSGGGGS GGGGSQVQLQ ESGGGLVQAG GSLRLSCAAS GRIFSIDIMS  600
WYRQAPGKQR ELVARITRGG TISYDDSVKG RFTISRDNAK NTVYLQMNSL KPEDTGVYYC  660
NALYGTDYWG KGTQVTVSSH HHHHHEPEA                                    689

SEQ ID NO: 63           moltype = AA  length = 272
FEATURE                 Location/Qualifiers
source                  1..272
                        mol_type = protein
                        organism = unidentified
SEQUENCE: 63
MDSYLLMWGL LTFIMVPGCQ AELCDDDPPE IPHATFKAMA YKEGTMLNCE CKRGFRRIKS  60
GSLYMLCTGN SSHSSWDNQC QCTSSATRNT TKQVTPQPEE QKERKTTEMQ SPMQPVDQAS  120
LPGHCREPPP WENEATERIY HFVVGQMVYY QCVQGYRALH RGPAESVCKM THGKTRWTQP  180
QLICTGEMET SQFPGEEKPQ ASPEGRPESE TSCLVTTTDF QIQTEMAATM ETSIFTTEYQ  240
VAVAGCVFLL ISVLLLSGLT WQRRQRKSRR TI                                272

SEQ ID NO: 64           moltype = AA  length = 551
FEATURE                 Location/Qualifiers
REGION                  1..551
                        note = IL2Rb sequence
source                  1..551
                        mol_type = protein
                        organism = unidentified
SEQUENCE: 64
MAAPALSWRL PLLILLLPLA TSWASAAVNG TSQFTCFYNS RANISCVWSQ DGALQDTSCQ  60
VHAWPDRRRW NQTCELLPVS QASWACNLIL GAPDSQKLTT VDIVTLRVLC REGVRWRVMA  120
IQDFKPFENL RLMAPISLQV VHVETHRCNI SWEISQASHY FERHLEFEAR TLSPGHTWEE  180
APLLTLKQKQ EWICLETLTP DTQYEFQVRV KPLQGEFTTW SPWSQPLAFR TKPAALGKDT  240
IPWLGHLLVG LSGAFGFIIL VYLLINCRNT GPWLKKVLKC NTPDPSKFFS QLSSEHGGDV  300
QKWLSSPFPS SSFSPGGLAP EISPLEVLER DKVTQLLLQQ DKVPEPASLS SNHSLTSCFT  360
NQGYFFFHLP DALEIEACQV YFTYDPYSEE DPDEGVAGAP TGSSPQPLQP LSGEDDAYCT  420
FPSRDDLLLF SPSLLGGPSP PSTAPGGSGA GEERMPPSLQ ERVPRDWDPQ PLGPPTPGVP  480
DLVDFQPPPE LVLREAGEEV PDAGPREGVS FPWSRPPGQG EFRALNARLP LNTDAYLSLQ  540
ELQGQDPTHL V                                                       551

SEQ ID NO: 65           moltype = AA  length = 369
FEATURE                 Location/Qualifiers
REGION                  1..369
                        note = IL2Rg sequence
source                  1..369
                        mol_type = protein
                        organism = unidentified
SEQUENCE: 65
MLKPSLPFTS LLFLQLPLLG VGLNTTILTP NGNEDTTADF FLTTMPTDSL SVSTLPLPEV  60
QCFVFNVEYM NCTWNSSSEP QPTNLTLHYW YKNSDNDKVQ KCSHYLFSEE ITSGCQLQKK  120
EIHLYQTFVV QLQDPREPRR QATQMLKLQN LVIPWAPENL TLHKLSESQL ELNWNNRFLN  180
HCLEHLVQYR TDWDHSWTEQ SVDYRHKFSL PSVDGQKRYT FRVRSRFNPL CGSAQHWSEW  240
SHPIHWGSNT SKENPFLFAL EAVVISVGSM GLIISLLCVY FWLERTMPRI PTLKNLEDLV  300
TEYHGNFSAW SGVSKGLAES LQPDYSERLC LVSEIPPKGG ALGEGPGASP CNQHSPYWAP  360
PCYTLKPET                                                          369

SEQ ID NO: 66           moltype = AA  length = 520
FEATURE                 Location/Qualifiers
source                  1..520
                        mol_type = protein
                        organism = synthetic construct
SEQUENCE: 66
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRVIPVSGPA RCLSQSRNLL KTTDDMVKTA REKLKHYSCT  360
AEDIDHEDIT RDQTSTLKTC LPLELHKNES CLATRETSST TRGSCLPPQK TSLMMTLCLG  420
SIYEDLKMYQ TEFQAINAAL QNHNHQQIIL DKGMLVAIDE LMQSLNHNGE TLRQKPPVGE  480
ADPYRVKMKL CILLHAFSTR VVTINRVMGY LSSAHHHHHH                        520

SEQ ID NO: 67           moltype = AA  length = 524
FEATURE                 Location/Qualifiers
source                  1..524
                        mol_type = protein
                        organism = synthetic construct
SEQUENCE: 67
```

-continued

```
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRNLPVATPD PGMFPCLHHS QNLLRAVSNM LQKARQTLEF  360
YPCTSEEIDH EDITKDKTST VEACLPLELT KNESCLNSRE TSFITNGSCL ASRKTSFMMA  420
LCLSSIYEDL KMYQVEFKTM NAKLLMDPKR QIFLDQNMLA VIDELMQALN FNSETVPQKS  480
SLEEPDFYKT KIKLCILLHA FRIRAVTIDR VMSYLNASHH HHHH                  524

SEQ ID NO: 68           moltype = AA  length = 940
FEATURE                 Location/Qualifiers
source                  1..940
                        mol_type = protein
                        organism = synthetic construct
SEQUENCE: 68
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SGGGGSGGGG SGGGGSGGGG SGGGGSGGGG SSGGPGPAGM KGLPGSIWEL KKDVYVVELD  300
WYPDAPGEMV VLTCDTPEED GITWTLDQSS EVLGSGKTLT IQVKEFGDAG QYTCHKGGEV  360
LSHSLLLLHK KEDGIWSTDI LKDQKEPKNK TFLRCEAKNY SGRFTCWWLT TISTDLTFSV  420
KSSRGSSDPQ GVTCGAATLS AERVRGDNKE YEYSVECQED SACPAAEESL PIEVMVDAVH  480
KLKYENYTSS FFIRDIIKPD PPKNLQLKPL KNSRQVEVSW EYPDTWSTPH SYFSLTFCVQ  540
VQGKSKREKK DRVFTDKTSA TVICRKNASI SVRAQDRYYS SSWSEWASVP CSGGGGSGGG  600
GSGGGGSRVI PVSGPARCLS QSRNLLKTTD DMVKTAREKL KHYSCTAEDI DHEDITRDQT  660
STLKTCLPLE LHKNESCLAT RETSSTTRGS CLPPQKTSLM MTLCLGSIYE DLKMYQTEFQ  720
AINAALQNHN HQQIILDKGM LVAIDELMQS LNHNGETLRQ KPPVGEADPY RVKMKLCILL  780
HAFSTRVVTI NRVMGYLSSA SGGPGPAGMK GLPGSEVQLV ESGGGLVQPG NSLRLSCAAS  840
GFTFSKFGMS WVRQAPGKGL EWVSSISGSG RDTLYAESVK GRFTISRDNA KTTLYLQMNS  900
LRPEDTAVYY CTIGGSLSVS SQGTLVTVSS HHHHHHEPEA                        940

SEQ ID NO: 69           moltype = AA  length = 1069
FEATURE                 Location/Qualifiers
source                  1..1069
                        mol_type = protein
                        organism = synthetic construct
SEQUENCE: 69
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SGGGGSGGGG SGGGGSGGGG SGGGGSGGGG SSGGPGPAGM KGLPGSIWEL KKDVYVVELD  300
WYPDAPGEMV VLTCDTPEED GITWTLDQSS EVLGSGKTLT IQVKEFGDAG QYTCHKGGEV  360
LSHSLLLLHK KEDGIWSTDI LKDQKEPKNK TFLRCEAKNY SGRFTCWWLT TISTDLTFSV  420
KSSRGSSDPQ GVTCGAATLS AERVRGDNKE YEYSVECQED SACPAAEESL PIEVMVDAVH  480
KLKYENYTSS FFIRDIIKPD PPKNLQLKPL KNSRQVEVSW EYPDTWSTPH SYFSLTFCVQ  540
VQGKSKREKK DRVFTDKTSA TVICRKNASI SVRAQDRYYS SSWSEWASVP CSGGGGSGGG  600
GSGGGGSRVI PVSGPARCLS QSRNLLKTTD DMVKTAREKL KHYSCTAEDI DHEDITRDQT  660
STLKTCLPLE LHKNESCLAT RETSSTTRGS CLPPQKTSLM MTLCLGSIYE DLKMYQTEFQ  720
AINAALQNHN HQQIILDKGM LVAIDELMQS LNHNGETLRQ KPPVGEADPY RVKMKLCILL  780
HAFSTRVVTI NRVMGYLSSA SGGPGPAGMK GLPGSEVQLV ESGGGLVQPG NSLRLSCAAS  840
GFTFSKFGMS WVRQAPGKGL EWVSSISGSG RDTLYAESVK GRFTISRDNA KTTLYLQMNS  900
LRPEDTAVYY CTIGGSLSVS SQGTLVTVSS GGGGSGGGGS GGGGSQVQLQ ESGGGLAQAG  960
GSLSLSCAAS GFTVSNSVMA WYRQTPGKQR EFVAIINSVG STNYADSVKG RFTISRDNAK  1020
NTVYLQMNNL KPEDTAVYVC NRNFDRIYWG QGTQVTVSSH HHHHHEPEA              1069

SEQ ID NO: 70           moltype = AA  length = 1069
FEATURE                 Location/Qualifiers
source                  1..1069
                        mol_type = protein
                        organism = synthetic construct
SEQUENCE: 70
QVQLQESGGG LAQAGGSLSL SCAASGFTVS NSVMAWYRQT PGKQREFVAI INSVGSTNYA  60
DSVKGRFTIS RDNAKNTVYL QMNNLKPEDT AVYVCNRNFD RIYWGQGTQV TVSSGGGGSG  120
GGGSGGGGSQ SVLTQPPSVS GAPGQRVTIS CSGSRSNIGS NTVKWYQQLP GTAPKLLIYY  180
NDQRPSGVPD RFSGSKSGTS ASLAITGLQA EDEADYYCQS YDRYTHPALL FGTGTKVTVL  240
GGGGSGGGGS GGGGSQVQLV ESGGGVVQPG RSLRLSCAAS GFTFSSYGMH WVRQAPGKGL  300
EWVAFIRYDG SNKYYADSVK GRFTISRDNS KNTLYLQMNS LRAEDTAVYY CKTHGSHDNW  360
GQGTMVTVSS GGGGSGGGGS GGGGSGGGGS GGGGSGGGGS SGGPGPAGMK GLPGSIWELK  420
KDVYVVELDW YPDAPGEMVV LTCDTPEEDG ITWTLDQSSE VLGSGKTLTI QVKEFGDAGQ  480
YTCHKGGEVL SHSLLLLHKK EDGIWSTDIL KDQKEPKNKT FLRCEAKNYS GRFTCWWLTT  540
ISTDLTFSVK SSRGSSDPQG VTCGAATLSA ERVRGDNKEY EYSVECQEDS ACPAAEESLP  600
IEVMVDAVHK LKYENYTSSF FIRDIIKPDP PKNLQLKPLK NSRQVEVSWE YPDTWSTPHS  660
YFSLTFCVQV QGKSKREKKD RVFTDKTSAT VICRKNASIS VRAQDRYYSS SWSEWASVPC  720
SGGGGSGGGG SGGGGSRVIP VSGPARCLSQ SRNLLKTTDD MVKTAREKLK HYSCTAEDID  780
HEDITRDQTS TLKTCLPLEL HKNESCLATR ETSSTTRGSC LPPQKTSLMM TLCLGSIYED  840
LKMYQTEFQA INAALQNHNH QQIILDKGML VAIDELMQSL NHNGETLRQK PPVGEADPYR  900
```

-continued

```
VKMKLCILLH AFSTRVVTIN RVMGYLSSAS GGPGPAGMKG LPGSEVQLVE SGGGLVQPGN  960
SLRLSCAASG FTFSKFGMSW VRQAPGKGLE WVSSISGSGR DTLYAESVKG RFTISRDNAK  1020
TTLYLQMNSL RPEDTAVYYC TIGGSLSVSS QGTLVTVSSH HHHHHEPEA             1069

SEQ ID NO: 71          moltype = AA  length = 940
FEATURE                Location/Qualifiers
source                 1..940
                       mol_type = protein
                       organism = synthetic construct
SEQUENCE: 71
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSGGGGS  120
GGGGSGGGGS QSVLTQPPSV SGAPGQRVTI SCSGSRSNIG SNTVKWYQQL PGTAPKLLIY  180
YNDQRPSGVP DRFSGSKSGT SASLAITGLQ AEDEADYYCQ SYDRYTHPAL LFGTGTKVTV  240
LGGGGSGGGG SGGGGSQVQL VESGGGVVQP GRSLRLSCAA SGFTFSSYGM HWVRQAPGKG  300
LEWVAFIRYD GSNKYYADSV KGRFTISRDN SKNTLYLQMN SLRAEDTAVY YCKTHGSHDN  360
WGQGTMVTVS SGGGGSGGGG SGGGGSGGGG SGGGGSGGGG SSGGPGPAGM KGLPGSIWEL  420
KKDVYVVELD WYPDAPGEMV VLTCDTPEED GITWTLDQSS EVLGSGKTLT IQVKEFGDAG  480
QYTCHKGGEV LSHSLLLLHK KEDGIWSTDI LKDQKEPKNK TFLRCEAKNY SGRFTCWWLT  540
TISTDLTFSV KSSRGSSDPQ GVTCGAATLS AERVRGDNKE YEYSVECQED SACPAAEESL  600
PIEVMVDAVH KLKYENYTSS FFIRDIIKPD PPKNLQLKPL KNSRQVEVSW EYPDTWSTPH  660
SYFSLTFCVQ VQGKSKREKK DRVFTDKTSA TVICRKNASI SVRAQDRYYS SSWSEWASVP  720
CSGGGGSGGG GSGGGGSRVI PVSGPARCLS QSRNLLKTTD DMVKTAREKL KHYSCTAEDI  780
DHEDITRDQT STLKTCLPLE LHKNESCLAT RETSSTTRGS CLPPQKTSLM MTLCLGSIYE  840
DLKMYQTEFQ AINAALQNHN HQQIILDKGM LVAIDELMQS LNHNGETLRQ KPPVGEADPY  900
RVKMKLCILL HAFSTRVVTI NRVMGYLSSA HHHHHHEPEA                       940

SEQ ID NO: 72          moltype = AA  length = 940
FEATURE                Location/Qualifiers
source                 1..940
                       mol_type = protein
                       organism = synthetic construct
SEQUENCE: 72
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGMKGLPGSG  660
GGGSGGGGSG GGGSGGGGSG GGGSGGGGSQ SVLTQPPSVS GAPGQRVTIS CSGSRSNIGS  720
NTVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYDG SNKYYADSVK GRFTISRDNS KNTLYLQMNS  900
LRAEDTAVYY CKTHGSHDNW GQGTMVTVSS HHHHHHEPEA                       940

SEQ ID NO: 73          moltype = AA  length = 940
FEATURE                Location/Qualifiers
source                 1..940
                       mol_type = protein
                       organism = synthetic construct
SEQUENCE: 73
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRVIPVSGPA RCLSQSRNLL KTTDDMVKTA REKLKHYSCT  360
AEDIDHEDIT RDQTSTLKTC LPLELHKNES CLATRETSST TRGSCLPPQK TSLMMTLCLG  420
SIYEDLKMYQ TEFQAINAAL QNHNHQQIIL DKGMLVAIDE LMQSLNHNGE TLRQKPPVGE  480
ADPYRVKMKL CILLHAFSTR VVTINRVMGY LSSASGGPGP AGMKGLPGSG GGGSGGGGSG  540
GGGSGGGGSG GGGSGGGGSQ SVLTQPPSVS GAPGQRVTIS CSGSRSNIGS NTVKWYQQLP  600
GTAPKLLIYY NDQRPSGVPD RFSGSKSGTS ASLAITGLQA EDEADYYCQS YDRYTHPALL  660
FGTGTKVTVL GGGGSGGGGS GGGGSQVQLV ESGGGVVQPG RSLRLSCAAS GFTFSSYGMH  720
WVRQAPGKGL EWVAFIRYDG SNKYYADSVK GRFTISRDNS KNTLYLQMNS LRAEDTAVYY  780
CKTHGSHDNW GQGTMVTVSS GGGGSGGGGS GGGGSEVQLV ESGGGLVQPG NSLRLSCAAS  840
GFTFSKFGMS WVRQAPGKGL EWVSSISGSG RDTLYAESVK GRFTISRDNA KTTLYLQMNS  900
LRPEDTAVYY CTIGGSLSVS SQGTLVTVSS HHHHHHEPEA                       940

SEQ ID NO: 74          moltype = AA  length = 328
FEATURE                Location/Qualifiers
source                 1..328
                       mol_type = protein
                       organism = Homo sapiens
SEQUENCE: 74
```

```
MCHQQLVISW FSLVFLASPL VAIWELKKDV YVVELDWYPD APGEMVVLTC DTPEEDGITW  60
TLDQSSEVLG SGKTLTIQVK EFGDAGQYTC HKGGEVLSHS LLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCS                                    328

SEQ ID NO: 75          moltype = AA  length = 215
FEATURE                Location/Qualifiers
source                 1..215
                       mol_type = protein
                       organism = Mus musculus
SEQUENCE: 75
MCQSRYLLFL ATLALLNHLS LARVIPVSGP ARCLSQSRNL LKTTDDMVKT AREKLKHYSC  60
TAEDIDHEDI TRDQTSTLKT CLPLELHKNE SCLATRETSS TTRGSCLPPQ KTSLMMTLCL  120
GSIYEDLKMY QTEFQAINAA LQNHNHQQII LDKGMLVAID ELMQSLNHNG ETLRQKPPVG  180
EADPYRVKMK LCILLHAFST RVVTINRVMG YLSSA                            215

SEQ ID NO: 76          moltype = AA  length = 862
FEATURE                Location/Qualifiers
REGION                 1..862
                       note = IL12Rb-2 sequence
source                 1..862
                       mol_type = protein
                       organism = unidentified
SEQUENCE: 76
MAHTFRGCSL AFMFIITWLL IKAKIDACKR GDVTVKPSHV ILLGSTVNIT CSLKPRQGCF  60
HYSRRNKLIL YKFDRRINFH HGHSLNSQVT GLPLGTTLFV CKLACINSDE IQICGAEIFV  120
GVAPEQPQNL SCIQKGEQGT VACTWERGRD THLYTEYTLQ LSGPKNLTWQ KQCKDIYCDY  180
LDFGINLTPE SPESNFTAKV TAVNSLGSSS SLPSTFTFLD IVRPLPPWDI RIKFQKASVS  240
RCTLYWRDEG LVLLNRLRYR PSNSRLWNMV NVTKAKGRHD LLDLKPFTEY EFQISSKLHL  300
YKGSWSDWSE SLRAQTPEEE PTGMLDVWYM KRHIDYSRQQ ISLFWKNLSV SEARGKILHY  360
QVTLQELTGG KAMTQNITGH TSWTTVIPRT GNWAVAVSAA NSKGSSLPTR INIMNLCEAG  420
LLAPRQVSAN SEGMDNILVT WQPPRKDPSA VQEYVVEWRE LHPGGDTQVP LNWLRSRPYN  480
VSALISENIK SYICYEIRVY ALSGDQGGCS SILGNSKHKA PLSGPHINAI TEEKGSILIS  540
WNSIPVQEQM GCLLHYRIYW KERDSNSQPQ LCEIPYRVSQ NSHPINSLQP RVTYVLWMTA  600
LTAAGESSHG NEREFCLQGK ANWMAFVAPS ICIAIIMVGI FSTHYFQQKV FVLLAALRPQ  660
WCSREIPDPA NSTCAKKYPI AEEKTQLPLD RLLIDWPTPE DPEPLVISEV LHQVTPVFRH  720
PPCSNWPQRE KGIQGHQASE KDMMHSASSP PPPRALQAES RQLVDLYKVL ESRGSDPKPE  780
NPACPWTVLP AGDLPTHDGY LPSNIDDLPS HEAPLADSLE ELEPQHISLS VFPSSSLHPL  840
TFSCGDKLTL DQLKMRCDSL ML                                          862

SEQ ID NO: 77          moltype = AA  length = 662
FEATURE                Location/Qualifiers
REGION                 1..662
                       note = IL12Rb-1 sequence
source                 1..662
                       mol_type = protein
                       organism = unidentified
SEQUENCE: 77
MEPLVTWVVP LLFLFLLSRQ GAACRTSECC FQDPPYPDAD SGSASGPRDL RCYRISSDRY  60
ECSWQYEGPT AGVSHFLRCC LSSGRCCYFA AGSATRLQFS DQAGVSVLYT VTLWVESWAR  120
NQTEKSPEVT LQLYNSVKYE PPLGDIKVSK LAGQLRMEWE TPDNQVGAEV QFRHRTPSSP  180
WKLGDCGPQD DDTESCLCPL EMNVAQEFQL RRRQLGSQGS SWSKWSSPVC VPPENPPQPQ  240
VRFSVEQLGQ DGRRRLTLKE QPTQLELPEG CQGLAPGTEV TYRLQLHMLS CPCKAKATRT  300
LHLGKMPYLS GAAYNVAVIS SNQFGPGLNQ TWHIPADTHT EPVALNISVG TNGTTMYWPA  360
RAQSMTYCIE WQPVGQDGGL ATCSLTAPQD PDPAGMATYS WSRESGAMGQ EKCYYITIFA  420
SAHPEKLTLW STVLSTYHFG GNASAAGTPH HVSVKNHSLD SVSVDWAPSL LSTCPGVLKE  480
YVVRCRDEDS KQVSEHPVQP TETQVTLSGL RAGVAYTVQV RADTAWLRGV WSQPQRFSIE  540
VQVSDWLIFF ASLGSFLSIL LVGVLGYLGL NRAARHLCPP LPTPCASSAI EFPGGKETWQ  600
WINPVDFQEE ASLQEALVVE MSWDKGERTE PLEKTELPEG APELALDTEL SLEDGDRCKA  660
KM                                                                662

SEQ ID NO: 78          moltype = AA  length = 328
FEATURE                Location/Qualifiers
source                 1..328
                       mol_type = protein
                       organism = Homo sapiens
SEQUENCE: 78
MCHQQLVISW FSLVFLASPL VAIWELKKDV YVVELDWYPD APGEMVVLTC DTPEEDGITW  60
TLDQSSEVLG SGKTLTIQVK EFGDAGQYTC HKGGEVLSHS LLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCS                                    328

SEQ ID NO: 79          moltype = AA  length = 335
FEATURE                Location/Qualifiers
source                 1..335
```

```
                          mol_type = protein
                          organism = Mus musculus
SEQUENCE: 79
MCPQKLTISW FAIVLLVSPL MAMWELEKDV YVVEVDWTPD APGETVNLTC DTPEEDDITW  60
TSDQRHGVIG SGKTLTITVK EFLDAGQYTC HKGGETLSHS HLLLHKKENG IWSTEILKNF  120
KNKTFLKCEA PNYSGRFTCS WLVQRNMDLK FNIKSSSSSP DSRAVTCGMA SLSAEKVTLD  180
QRDYEKYSVS CQEDVTCPTA EETLPIELAL EARQQNKYEN YSTSFFIRDI IKPDPPKNLQ  240
MKPLKNSQVE VSWEYPDSWS TPHSYFSLKF FVRIQRKKEK MKETEEGCNQ KGAFLVEKTS  300
TEVQCKGGNV CVQAQDRYYN SSCSKWACVP CRVRS                            335

SEQ ID NO: 80             moltype = AA  length = 399
FEATURE                   Location/Qualifiers
source                    1..399
                          mol_type = protein
                          organism = synthetic construct
SEQUENCE: 80
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS HGTVIESLES LNNYFNSSGI DVEEKSLFLD IWRNWQKDGD MKILQSQIIS  180
FYLRLFEVLK DNQAISNNIS VIESHLITTF FSNSKAKKDA FMSIAKFEVN NPQVQRQAFN  240
ELIRVVHQLL PESSLRKRKR SRCSGGPGPA GMKGLPGSEV QLVESGGGLV QPGNSLRLSC  300
AASGFTFSKF GMSWVRQAPG KGLEWVSSIS GSGRDTLYAE SVKGRFTISR DNAKTTLYLQ  360
MNSLRPEDTA VYYCTIGGSL SVSSQGTLVT VSSHHHHHH                        399

SEQ ID NO: 81             moltype = AA  length = 547
FEATURE                   Location/Qualifiers
source                    1..547
                          mol_type = protein
                          organism = synthetic construct
SEQUENCE: 81
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS HGTVIESLES LNNYFNSSGI DVEEKSLFLD IWRNWQKDGD MKILQSQIIS  180
FYLRLFEVLK DNQAISNNIS VIESHLITTF FSNSKAKKDA FMSIAKFEVN NPQVQRQAFN  240
ELIRVVHQLL PESSLRKRKR SRCSGGPGPA GMKGLPGSHG TVIESLESLN NYFNSSGIDV  300
EEKSLFLDIW RNWQKDGDMK ILQSQIISFY LRLFEVLKDN QAISNNISVI ESHLITTFFS  360
NSKAKKDAFM SIAKFEVNNP QVQRQAFNEL IRVVHQLLPE SSLRKRKRSR CSGGPGPAGM  420
KGLPGSEVQL VESGGGLVQP GNSLRLSCAA SGFTFSKFGM SWVRQAPGKG LEWVSSISGS  480
GRDTLYAESV KGRFTISRDN AKTTLYLQMN SLRPEDTAVY YCTIGGSLSV SSQGTLVTVS  540
SHHHHHH                                                           547

SEQ ID NO: 82             moltype = AA  length = 547
FEATURE                   Location/Qualifiers
source                    1..547
                          mol_type = protein
                          organism = synthetic construct
SEQUENCE: 82
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS HGTVIESLES LNNYFNSSGI DVEEKSLFLD IWRNWQKDGD MKILQSQIIS  180
FYLRLFEVLK DNQAISNNIS VIESHLITTF FSNSKAKKDA FMSIAKFEVN NPQVQRQAFN  240
ELIRVVHQLL PESSLRKRKR SRCGGGGSGG GGSGGGGSHG TVIESLESLN NYFNSSGIDV  300
EEKSLFLDIW RNWQKDGDMK ILQSQIISFY LRLFEVLKDN QAISNNISVI ESHLITTFFS  360
NSKAKKDAFM SIAKFEVNNP QVQRQAFNEL IRVVHQLLPE SSLRKRKRSR CSGGPGPAGM  420
KGLPGSEVQL VESGGGLVQP GNSLRLSCAA SGFTFSKFGM SWVRQAPGKG LEWVSSISGS  480
GRDTLYAESV KGRFTISRDN AKTTLYLQMN SLRPEDTAVY YCTIGGSLSV SSQGTLVTVS  540
SHHHHHH                                                           547

SEQ ID NO: 83             moltype = AA  length = 166
FEATURE                   Location/Qualifiers
source                    1..166
                          mol_type = protein
                          organism = Homo sapiens
SEQUENCE: 83
MKYTSYILAF QLCIVLGSLG CYCQDPYVKE AENLKKYFNA GHSDVADNGT LFLGILKNWK  60
EESDRKIMQS QIVSFYFKLF KNFKDDQSIQ KSVETIKEDM NVKFFNSNKK KRDDFEKLTN  120
YSVTDLNVQR KAIHELIQVM AELSPAAKTG KRKRSQMLFR GRRASQ                166

SEQ ID NO: 84             moltype = AA  length = 155
FEATURE                   Location/Qualifiers
source                    1..155
                          mol_type = protein
                          organism = Mus musculus
SEQUENCE: 84
MNATHCILAL QLFLMAVSGC YCHGTVIESL ESLNNYFNSS GIDVEEKSLF LDIWRNWQKD  60
GDMKILQSQI ISFYLRLFEV LKDNQAISNN ISVIESHLIT TFFSNSKAKK DAFMSIAKFE  120
VNNPQVQRQA FNELIRVVHQ LLPESSLRKR KRSRC                            155

SEQ ID NO: 85             moltype = AA  length = 699
```

```
FEATURE                Location/Qualifiers
source                 1..699
                       mol_type = protein
                       organism = synthetic construct
SEQUENCE: 85
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSHGTVIESL ESLNNYFNSS GIDVEEKSLF  180
LDIWRNWQKD GDMKILQSQI ISFYLRLFEV LKDNQAISNN ISVIESHLIT TFFSNSKAKK  240
DAFMSIAKFE VNNPQVQRQA FNELIRVVHQ LLPESSLRKR KRSRCSGGPG PAGMKGLPGS  300
EVQLVESGGG LVQPGNSLRL SCAASGFTFS KFGMSWVRQA PGKGLEWVSS ISGSGRDTLY  360
AESVKGRFTI SRDNAKTTLY LQMNSLRPED TAVYYCTIGG SLSVSSQGTL VTVSSSGGPG  420
PAGMKGLPGS HGTVIESLES LNNYFNSSGI DVEEKSLFLD IWRNWQKDGD MKILQSQIIS  480
FYLRLFEVLK DNQAISNNIS VIESHLITTF FSNSKAKKDA FMSIAKFEVN NPQVQRQAFN  540
ELIRVVHQLL PESSLRKRKR SRCSGGPGPA GMKGLPGSEV QLVESGGGLV QPGNSLRLSC  600
AASGFTFSKF GMSWVRQAPG KGLEWVSSIS GSGRDTLYAE SVKGRFTISR DNAKTTLYLQ  660
MNSLRPEDTA VYYCTIGGSL SVSSQGTLVT VSSHHHHHH                         699

SEQ ID NO: 86          moltype = AA  length = 436
FEATURE                Location/Qualifiers
source                 1..436
                       mol_type = protein
                       organism = synthetic construct
SEQUENCE: 86
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS CDLPQTHNLR NKRALTLLVQ MRRLSPLSCL KDRKDFGFPQ EKVDAQQIKK  180
AQAIPVLSEL TQQILNIFTS KDSSAAWNTT LLDSFCNDLH QQLNDLQGCL MQQVGVQEFP  240
LTQEDALLAV RKYFHRITVY LREKKHSPCA WEVVRAEVWR ALSSSANVLG RLREEKSGGP  300
GPAGMKGLPG SEVQLVESGG GLVQPGNSLR LSCAASGFTF SKFGMSWVRQ APGKGLEWVS  360
SISGSGRDTL YAESVKGRFT ISRDNAKTTL YLQMNSLRPE DTAVYYCTIG GSLSVSSQGT  420
LVTVSSHHHH HHEPEA                                                  436

SEQ ID NO: 87          moltype = AA  length = 428
FEATURE                Location/Qualifiers
source                 1..428
                       mol_type = protein
                       organism = synthetic construct
SEQUENCE: 87
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS CDLPQTHNLR NKRALTLLVQ MRRLSPLSCL KDRKDFGFPQ EKVDAQQIKK  180
AQAIPVLSEL TQQILNIFTS KDSSAAWNTT LLDSFCNDLH QQLNDLQGCL MQQVGVQEFP  240
LTQEDALLAV RKYFHRITVY LREKKHSPCA WEVVRAEVWR ALSSSANVSG GPGPAGMKGL  300
PGSEVQLVES GGGLVQPGNS LRLSCAASGF TFSKFGMSWV RQAPGKGLEW VSSISGSGRD  360
TLYAESVKGR FTISRDNAKT TLYLQMNSLR PEDTAVYYCT IGGSLSVSSQ GTLVTVSSHH  420
HHHHEPEA                                                           428

SEQ ID NO: 88          moltype = AA  length = 489
FEATURE                Location/Qualifiers
REGION                 1..489
                       note = IFNgR1 sequence
source                 1..489
                       mol_type = protein
                       organism = unidentified
SEQUENCE: 88
MALLFLLPLV MQGVSRAEMG TADLGPSSVP TPTNVTIESY NMNPIVYWEY QIMPQVPVFT  60
VEVKNYGVKN SEWIDACINI SHHYCNISDH VGDPSNSLWV RVKARVGQKE SAYAKSEEFA  120
VCRDGKIGPP KLDIRKEEKQ IMIDIFHPSV FVNGDEQEVD YDPETTCYIR VYNVYVRMNG  180
SEIQYKILTQ KEDDCDEIQC QLAIPVSSLN SQYCVSAEGV LHVWGVTTEK SKEVCITIFN  240
SSIKGSLWIP VVAALLLFLV LSLVFICFYI KKINPLKEKS IILPKSLISV VRSATLETKP  300
ESKYVSLITS YQPFSLEKEV VCEEPLSPAT VPGMHTEDNP GKVEHTEELS SITEVVTTEE  360
NIPDVVPGSH LTPIERESSS PLSSNQSEPG SIALNSYHSR NCSESDHSRN GFDTDSSCLE  420
SHSSLSDSEF PPNNKGEIKT EGQELITVIK APTSFGYDKP HVLVDLLVDD SGKESLIGYR  480
PTEDSKEFS                                                          489

SEQ ID NO: 89          moltype = AA  length = 337
FEATURE                Location/Qualifiers
REGION                 1..337
                       note = IFNgR2 sequence
source                 1..337
                       mol_type = protein
                       organism = unidentified
SEQUENCE: 89
MRPTLLWSLL LLLGVFAAAA AAPPDPLSQL PAPQHPKIRL YNAEQVLSWE PVALSNSTRP  60
VVYQVQFKYT DSKWFTADIM SIGVNCTQIT ATECDFTAAS PSAGFPMDFN VTLRLRAELG  120
ALHSAWVTMP WFQHYRNVTV GPPENIEVTP GEGSLIIRFS SPFDIADTST AFFCYYVHYW  180
EKGGIQQVKG PFRSNSISLD NLKPSRVYCL QVQAQLLWNK SNIFRVGHLS NISCYETMAD  240
ASTELQQVIL ISVGTFSLLS VLAGACFFLV LKYRGLIKYW FHTPPSIPLQ IEEYLKDPTQ  300
```

```
PILEALDKDS SPKDDVWDSV SIISFPEKEQ EDVLQTL                          337

SEQ ID NO: 90          moltype = AA  length = 528
FEATURE                Location/Qualifiers
source                 1..528
                       mol_type = protein
                       organism = synthetic construct
SEQUENCE: 90
QVQLQESGGG LVQAGGSLRL SCAASGRIFS IDIMSWYRQA PGKQRELVAR ITRGGTISYD  60
DSVKGRFTIS RDNAKNTVYL QMNSLKPEDT GVYYCNALYG TDYWGKGTQV TVSSGGGGSG  120
GGGSGGGGSE VQLVESGGGL VQPGNSLRLS CAASGFTFSK FGMSWVRQAP GKGLEWVSSI  180
SGSGRDTLYA ESVKGRFTIS RDNAKTTLYL QMNSLRPEDT AVYYCTIGGS LSVSSQGTLV  240
TVSSSGGPGP AGMKGLPGSH GTVIESLESL NNYFNSSGID VEEKSLFLDI WRNWQKDGDM  300
KILQSQIISF YLRLFEVLKD NQAISNNISV IESHLITTFF SNSKAKKDAF MSIAKFEVNN  360
PQVQRQAFNE LIRVVHQLLP ESSLRKRKRS RCSGGPGPAG MKGLPGSEVQ LVESGGGLVQ  420
PGNSLRLSCA ASGFTFSKFG MSWVRQAPGK GLEWVSSISG SGRDTLYAES VKGRFTISRD  480
NAKTTLYLQM NSLRPEDTAV YYCTIGGSLS VSSQGTLVTV SSHHHHHH              528

SEQ ID NO: 91          moltype = AA  length = 658
FEATURE                Location/Qualifiers
source                 1..658
                       mol_type = protein
                       organism = synthetic construct
SEQUENCE: 91
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS HGTVIESLES LNNYFNSSGI DVEEKSLFLD IWRNWQKDGD MKILQSQIIS  180
FYLRLFEVLK DNQAISNNIS VIESHLITTF FSNSKAKKDA FMSIAKFEVN NPQVQRQAFN  240
ELIRVVHQLL PESSLRKRKR SRCSGGPGPA GMKGLPGSEV QLVESGGGLV QPGNSLRLSC  300
AASGFTFSKF GMSWVRQAPG KGLEWVSSIS GSGRDTLYAE SVKGRFTISR DNAKTTLYLQ  360
MNSLRPEDTA VYYCTIGGSL SVSSQGTLVT VSSSGGPGPA GMKGLPGSEV QLVESGGGLV  420
QPGNSLRLSC AASGFTFSKF GMSWVRQAPG KGLEWVSSIS GSGRDTLYAE SVKGRFTISR  480
DNAKTTLYLQ MNSLRPEDTA VYYCTIGGSL SVSSQGTLVT VSSGGGGSGG GGSGGGGSQV  540
QLQESGGGLV QAGGSLRLSC AASGRIFSID IMSWYRQAPG KQRELVARIT RGGTISYDDS  600
VKGRFTISRD NAKNTVYLQM NSLKPEDTGV YYCNALYGTD YWGKGTQVTV SSHHHHHH    658

SEQ ID NO: 92          moltype = AA  length = 1337
FEATURE                Location/Qualifiers
source                 1..1337
                       mol_type = protein
                       organism = synthetic construct
SEQUENCE: 92
EAHKSEIAHR YNDLGEQHFK GLVLIAFSQY LQKCSYDEHA KLVQEVTDFA KTCVADESAA  60
NCDKSLHTLF GDKLCAIPNL RENYGELADC CTKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQRMKC SSMQKFGERA FKAWAVARLS QTFPNADFAE ITKLATDLTK  240
VNKECCHGDL LECADDRAEL AKYMCENQAT ISSKLQTCCD KPLLKKAHCL SEVEHDTMPA  300
DLPAIAADFV EDQEVCKNYA EAKDVFLGTF LYEYSRRHPD YSVSLLLRLA KKYEATLEKC  360
CAEANPPACY GTVLAEFQPL VEEPKNLVKT NCDLYEKLGE YGFQNAILVR YTQKAPQVST  420
PTLVEAARNL GRVGTKCCTL PEDQRLPCVE DYLSAILNRV CLLHEKTPVS EHVTKCCSGS  480
LVERRPCFSA LTVDETYVPK EFKAETFTFH SDICTLPEKE KQIKKQTALA ELVKHKPKAT  540
AEQLKTVMDD FAQFLDTCCK AADKDTCFST EGPNLVTRCK DALASGGPGP AGMKGLPGSH  600
GTVIESLESL NNYFNSSGID VEEKSLFLDI WRNWQKDGDM KILQSQIISF YLRLFEVLKD  660
NQAISNNISV IESHLITTFF SNSKAKKDAF MSIAKFEVNN PQVQRQAFNE LIRVVHQLLP  720
ESSLRKRKRS RCSGGPGPAG MKGLPGSEAH KSEIAHRYND LGEQHFKGLV LIAFSQYLQK  780
CSYDEHAKLV QEVTDFAKTC VADESAANCD KSLHTLFGDK LCAIPNLREN YGELADCCTK  840
QEPERNECFL QHKDDNPSLP PFERPEAEAM CTSFKENPTT FMGHYLHEVA RRHPYFYAPE  900
LLYYAEQYNE ILTQCCAEAD KESCLTPKLD GVKEKALVSS VRQRMKCSSM QKFGERAFKA  960
WAVARLSQTF PNADFAEITK LATDLTKVNK ECCHGDLLEC ADDRAELAKY MCENQATISS  1020
KLQTCCDKPL LKKAHCLSEV EHDTMPADLP AIAADFVEDQ EVCKNYAEAK DVFLGTFLYE  1080
YSRRHPDYSV SLLLRLAKKY EATLEKCCAE ANPPACYGTV LAEFQPLVEE PKNLVKTNCD  1140
LYEKLGEYGF QNAILVRYTQ KAPQVSTPTL VEAARNLGRV GTKCCTLPED QRLPCVEDYL  1200
SAILNRVCLL HEKTPVSEHV TKCCSGSLVE RRPCFSALTV DETYVPKEFK AETFTFHSDI  1260
CTLPEKEKQI KKQTALAELV KHKPKATAEQ LKTVMDDFAQ FLDTCCKAAD KDTCFSTEGP  1320
NLVTRCKDAL AHHHHHH                                                1337

SEQ ID NO: 93          moltype = AA  length = 1485
FEATURE                Location/Qualifiers
source                 1..1485
                       mol_type = protein
                       organism = synthetic construct
SEQUENCE: 93
EAHKSEIAHR YNDLGEQHFK GLVLIAFSQY LQKCSYDEHA KLVQEVTDFA KTCVADESAA  60
NCDKSLHTLF GDKLCAIPNL RENYGELADC CTKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQRMKC SSMQKFGERA FKAWAVARLS QTFPNADFAE ITKLATDLTK  240
VNKECCHGDL LECADDRAEL AKYMCENQAT ISSKLQTCCD KPLLKKAHCL SEVEHDTMPA  300
DLPAIAADFV EDQEVCKNYA EAKDVFLGTF LYEYSRRHPD YSVSLLLRLA KKYEATLEKC  360
CAEANPPACY GTVLAEFQPL VEEPKNLVKT NCDLYEKLGE YGFQNAILVR YTQKAPQVST  420
```

-continued

```
PTLVEAARNL GRVGTKCCTL PEDQRLPCVE DYLSAILNRV CLLHEKTPVS EHVTKCCSGS  480
LVERRPCFSA LTVDETYVPK EFKAETFTFH SDICTLPEKE KQIKKQTALA ELVKHKPKAT  540
AEQLKTVMDD FAQFLDTCCK AADKDTCFST EGPNLVTRCK DALASGGPGP AGMKGLPGSH  600
GTVIESLESL NNYFNSSGID VEEKSLFLDI WRNWQKDGDM KILQSQIISF YLRLFEVLKD  660
NQAISNNISV IESHLITTFF SNSKAKKDAF MSIAKFEVNN PQVQRQAFNE LIRVVHQLLP  720
ESSLRKRKRS RCGGGGSGGG GSGGGGSHGT VIESLESLNN YFNSSGIDVE EKSLFLDIWR  780
NWQKDGDMKI LQSQIISFYL RLFEVLKDNQ AISNNISVIE SHLITTFFSN SKAKKDAFMS  840
IAKFEVNNPQ VQRQAFNELI RVVHQLLPES SLRKRKRSRC SGGPGPAGMK GLPGSEAHKS  900
EIAHRYNDLG EQHFKGLVLI AFSQYLQKCS YDEHAKLVQE VTDFAKTCVA DESAANCDKS  960
LHTLFGDKLC AIPNLRENYG ELADCCTKQE PERNECFLQH KDDNPSLPPF ERPEAEAMCT  1020
SFKENPTTFM GHYLHEVARR HPYFYAPELL YYAEQYNEIL TQCCAEADKE SCLTPKLDGV  1080
KEKALVSSVR QRMKCSSMQK FGERAFKAWA VARLSQTFPN ADFAEITKLA TDLTKVNKEC  1140
CHGDLLECAD DRAELAKYMC ENQATISSKL QTCCDKPLLK KAHCLSEVEH DTMPADLPAI  1200
AADFVEDQEV CKNYAEAKDV FLGTFLYEYS RRHPDYSVSL LLRLAKKYEA TLEKCCAEAN  1260
PPACYGTVLA EFQPLVEEPK NLVKTNCDLY EKLGEYGFQN AILVRYTQKA PQVSTPTLVE  1320
AARNLGRVGT KCCTLPEDQR LPCVEDYLSA ILNRVCLLHE KTPVSEHVTK CCSGSLVERR  1380
PCFSALTVDE TYVPKEFKAE TFTFHSDICT LPEKEKQIKK QTALAELVKH KPKATAEQLK  1440
TVMDDFAQFL DTCCKAADKD TCFSTEGPNL VTRCKDALAH HHHHH                1485

SEQ ID NO: 94          moltype = AA  length = 698
FEATURE                Location/Qualifiers
source                 1..698
                       mol_type = protein
                       organism = synthetic construct
SEQUENCE: 94
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGGGG SGGGGSGGGG SEVQLVESGG GLVQPGNSLR LSCAASGFTF  180
SKFGMSWVRQ APGKGLEWVS SISGSGRDTL YAESVKGRFT ISRDNAKTTL YLQMNSLRPE  240
DTAVYYCTIG GSLSVSSQGT LVTVSSSGGP GPAGMKGLPG SHGTVIESLE SLNNYFNSSG  300
IDVEEKSLFL DIWRNWQKDG DMKILQSQII SFYLRLFEVL KDNQAISNNI SVIESHLITT  360
FFSNSKAKKD AFMSIAKFEV NNPQVQRQAF NELIRVVHQL LPESSLRKRK RSRCGGGGSG  420
GGGSGGGGSH GTVIESLESL NNYFNSSGID VEEKSLFLDI WRNWQKDGDM KILQSQIISF  480
YLRLFEVLKD NQAISNNISV IESHLITTFF SNSKAKKDAF MSIAKFEVNN PQVQRQAFNE  540
LIRVVHQLLP ESSLRKRKRS RCSGGPGPAG MKGLPGSEVQ LVESGGGLVQ PGNSLRLSCA  600
ASGFTFSKFG MSWVRQAPGK GLEWVSSISG SGRDTLYAES VKGRFTISRD NAKTTLYLQM  660
NSLRPEDTAV YYCTIGGSLS VSSQGTLVTV SSHHHHHH                         698

SEQ ID NO: 95          moltype = AA  length = 699
FEATURE                Location/Qualifiers
source                 1..699
                       mol_type = protein
                       organism = synthetic construct
SEQUENCE: 95
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSHGTVIESL ESLNNYFNSS GIDVEEKSLF  180
LDIWRNWQKD GDMKILQSQI ISFYLRLFEV LKDNQAISNN ISVIESHLIT TFFSNSKAKK  240
DAFMSIAKFE VNNPQVQRQA FNELIRVVHQ LLPESSLRKR KRSRCSGGPG PAGMKGLPGS  300
EVQLVESGGG LVQPGNSLRL SCAASGFTFS KFGMSWVRQA PGKGLEWVSS ISGSGRDTLY  360
AESVKGRFTI SRDNAKTTLY LQMNSLRPED TAVYYCTIGG SLSVSSQGTL VTVSSSGGPG  420
PAGMKGLPGS HGTVIESLES LNNYFNSSGI DVEEKSLFLD IWRNWQKDGD MKILQSQIIS  480
FYLRLFEVLK DNQAISNNIS VIESHLITTF FSNSKAKKDA FMSIAKFEVN NPQVQRQAFN  540
ELIRVVHQLL PESSLRKRKR SRCSGGPGPA GMKGLPGSEV QLVESGGGLV QPGNSLRLSC  600
AASGFTFSKF GMSWVRQAPG KGLEWVSSIS GSGRDTLYAE SVKGRFTISR DNAKTTLYLQ  660
MNSLRPEDTA VYYCTIGGSL SVSSQGTLVT VSSHHHHHH                        699

SEQ ID NO: 96          moltype = AA  length = 554
FEATURE                Location/Qualifiers
source                 1..554
                       mol_type = protein
                       organism = synthetic construct
SEQUENCE: 96
MDMRVPAQLL GLLLLWLRGA RCQVQLQESG GGLAQAGGSL SLSCAASGFT VSNSVMAWYR  60
QTPGKQREFV AIINSVGSTN YADSVKGRFT ISRDNAKNTV YLQMNNLKPE DTAVYVCNRN  120
FDRIYWGQGT QVTVSSGGGG SGGGGSGGGG SEVQLVESGG GLVQPGNSLR LSCAASGFTF  180
SKFGMSWVRQ APGKGLEWVS SISGSGRDTL YAESVKGRFT ISRDNAKTTL YLQMNSLRPE  240
DTAVYYCTIG GSLSVSSQGT LVTVSSSGGP GPAGMKGLPG SHGTVIESLE SLNNYFNSSG  300
IDVEEKSLFL DIWRNWQKDG DMKILQSQII SFYLRLFEVL KDNQAISNNI SVIESHLITT  360
FFSNSKAKKD AFMSIAKFEV NNPQVQRQAF NELIRVVHQL LPESSLRKRK RSRCSGGPGP  420
AGMKGLPGSE VQLVESGGGL VQPGNSLRLS CAASGFTFSK FGMSWVRQAP GKGLEWVSSI  480
SGSGRDTLYA ESVKGRFTIS RDNAKTTLYL QMNSLRPEDT AVYYCTIGGS LSVSSQGTLV  540
TVSSHHHHHH EPEA                                                   554

SEQ ID NO: 97          moltype = AA  length = 554
FEATURE                Location/Qualifiers
source                 1..554
                       mol_type = protein
                       organism = synthetic construct
```

```
SEQUENCE: 97
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSHGTVIESL ESLNNYFNSS GIDVEEKSLF  180
LDIWRNWQKD GDMKILQSQI ISFYLRLFEV LKDNQAISNN ISVIESHLIT TFFSNSKAKK  240
DAFMSIAKFE VNNPQVQRQA FNELIRVVHQ LLPESSLRKR KRSRCSGGPG PAGMKGLPGS  300
EVQLVESGGG LVQPGNSLRL SCAASGFTFS KFGMSWVRQA PGKGLEWVSS ISGSGRDTLY  360
AESVKGRFTI SRDNAKTTLY LQMNSLRPED TAVYYCTIGG SLSVSSQGTL VTVSSGGGGS  420
GGGGSGGGGS QVQLQESGGG LAQAGGSLSL SCAASGFTVS NSVMAWYRQT PGKQREFVAI  480
INSVGSTNYA DSVKGRFTIS RDNAKNTVYL QMNNLKPEDT AVYVCNRNFD RIYWGQGTQV  540
TVSSHHHHHH EPEA                                                  554

SEQ ID NO: 98          moltype = AA  length = 702
FEATURE                Location/Qualifiers
source                 1..702
                       mol_type = protein
                       organism = synthetic construct
SEQUENCE: 98
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSHGTVIESL ESLNNYFNSS GIDVEEKSLF  180
LDIWRNWQKD GDMKILQSQI ISFYLRLFEV LKDNQAISNN ISVIESHLIT TFFSNSKAKK  240
DAFMSIAKFE VNNPQVQRQA FNELIRVVHQ LLPESSLRKR KRSRCSGGPG PAGMKGLPGS  300
HGTVIESLES LNNYFNSSGI DVEEKSLFLD IWRNWQKDGD MKILQSQIIS FYLRLFEVLK  360
DNQAISNNIS VIESHLITTF FSNSKAKKDA FMSIAKFEVN NPQVQRQAFN ELIRVVHQLL  420
PESSLRKRKR SRCSGGPGPA GMKGLPGSEV QLVESGGGLV QPGNSLRLSC AASGFTFSKF  480
GMSWVRQAPG KGLEWVSSIS GSGRDTLYAE SVKGRFTISR DNAKTTLYLQ MNSLRPEDTA  540
VYYCTIGGSL SVSSQGTLVT VSSGGGGSGG GGSGGGGSQV QLQESGGGLV QAGGSLRLSC  600
AASGRIFSID IMSWYRQAPG KQRELVARIT RGGTISYDDS VKGRFTISRD NAKNTVYLQM  660
NSLKPEDTGV YYCNALYGTD YWGKGTQVTV SSHHHHHHEP EA                   702

SEQ ID NO: 99          moltype = AA  length = 702
FEATURE                Location/Qualifiers
source                 1..702
                       mol_type = protein
                       organism = synthetic construct
SEQUENCE: 99
MDMRVPAQLL GLLLLWLRGA RCQVQLQESG GGLAQAGGSL SLSCAASGFT VSNSVMAWYR  60
QTPGKQREFV AIINSVGSTN YADSVKGRFT ISRDNAKNTV YLQMNNLKPE DTAVYVCNRN  120
FDRIYWGQGT QVTVSSGGGG SGGGGSGGGG SEVQLVESGG GLVQPGNSLR LSCAASGFTF  180
SKFGMSWVRQ APGKGLEWVS SISGSGRDTL YAESVKGRFT ISRDNAKTTL YLQMNSLRPE  240
DTAVYYCTIG GSLSVSSQGT LVTVSSSGGP GPAGMKGLPG SHGTVIESLE SLNNYFNSSG  300
IDVEEKSLFL DIWRNWQKDG DMKILQSQII SFYLRLFEVL KDNQAISNNI SVIESHLITT  360
FFSNSKAKKD AFMSIAKFEV NNPQVQRQAF NELIRVVHQL LPESSLRKRK RSRCSGGPGP  420
AGMKGLPGSH GTVIESLESL NNYFNSSGID VEEKSLFLDI WRNWQKDGDM KILQSQIISF  480
YLRLFEVLKD NQAISNNISV IESHLITTFF SNSKAKKDAF MSIAKFEVNN PQVQRQAFNE  540
LIRVVHQLLP ESSLRKRKRS RCSGGPGPAG MKGLPGSEVQ LVESGGGLVQ PGNSLRLSCA  600
ASGFTFSKFG MSWVRQAPGK GLEWVSSISG SGRDTLYAES VKGRFTISRD NAKTTLYLQM  660
NSLRPEDTAV YYCTIGGSLS VSSQGTLVTV SSHHHHHHEP EA                   702

SEQ ID NO: 100         moltype = AA  length = 702
FEATURE                Location/Qualifiers
source                 1..702
                       mol_type = protein
                       organism = synthetic construct
SEQUENCE: 100
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSHGTVIESL ESLNNYFNSS GIDVEEKSLF  180
LDIWRNWQKD GDMKILQSQI ISFYLRLFEV LKDNQAISNN ISVIESHLIT TFFSNSKAKK  240
DAFMSIAKFE VNNPQVQRQA FNELIRVVHQ LLPESSLRKR KRSRCSGGPG PAGMKGLPGS  300
HGTVIESLES LNNYFNSSGI DVEEKSLFLD IWRNWQKDGD MKILQSQIIS FYLRLFEVLK  360
DNQAISNNIS VIESHLITTF FSNSKAKKDA FMSIAKFEVN NPQVQRQAFN ELIRVVHQLL  420
PESSLRKRKR SRCSGGPGPA GMKGLPGSEV QLVESGGGLV QPGNSLRLSC AASGFTFSKF  480
GMSWVRQAPG KGLEWVSSIS GSGRDTLYAE SVKGRFTISR DNAKTTLYLQ MNSLRPEDTA  540
VYYCTIGGSL SVSSQGTLVT VSSGGGGSGG GGSGGGGSQV QLQESGGGLA QAGGSLSLSC  600
AASGFTVSNS VMAWYRQTPG KQREFVAIIN SVGSTNYADS VKGRFTISRD NAKNTVYLQM  660
NNLKPEDTAV YVCNRNFDRI YWGQGTQVTV SSHHHHHHEP EA                   702

SEQ ID NO: 101         moltype = AA  length = 832
FEATURE                Location/Qualifiers
source                 1..832
                       mol_type = protein
                       organism = synthetic construct
SEQUENCE: 101
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSHGTVIESL ESLNNYFNSS GIDVEEKSLF  180
LDIWRNWQKD GDMKILQSQI ISFYLRLFEV LKDNQAISNN ISVIESHLIT TFFSNSKAKK  240
```

```
DAFMSIAKFE VNNPQVQRQA FNELIRVVHQ LLPESSLRKR KRSRCSGGPG PAGMKGLPGS  300
HGTVIESLES LNNYFNSSGI DVEEKSLFLD IWRNWQKDGD MKILQSQIIS FYLRLFEVLK  360
DNQAISNNIS VIESHLITTF FSNSKAKKDA FMSIAKFEVN NPQVQRQAFN ELIRVVHQLL  420
PESSLRKRKR SRCSGGPGPA GMKGLPGSEV QLVESGGGLV QPGNSLRLSC AASGFTFSKF  480
GMSWVRQAPG KGLEWVSSIS GSGRDTLYAE SVKGRFTISR DNAKTTLYLQ MNSLRPEDTA  540
VYYCTIGGSL SVSSQGTLVT VSSGGGGSGG GGSGGGGSEV QLVESGGGLV QPGGSLRLSC  600
AASGFTFSSY AMSWVRQAPG KGLEWVSAIS GSGGSTYYAD SVKGRFTISR DNSKNTLYLQ  660
MNSLRAEDTA VYYCARGVGA FRPYRKHEWG QGTLVTVSRG GGGSGGGGSG GGGSSSELTQ  720
DPAVSVALGQ TVRITCQGDS LRSYYASWYQ QKPGQAPVLV IYGKNNRPSG IPDRFSGSSS  780
GNTASLTTTG AQAEDEADYY CNSSPFEHNL VVFGGGTKLT VLHHHHHHEP EA          832

SEQ ID NO: 102         moltype = AA  length = 276
FEATURE                Location/Qualifiers
source                 1..276
                       mol_type = protein
                       organism = synthetic construct
SEQUENCE: 102
MDMRVPAQLL GLLLLWLRGA RCEVQLVESG GGLVQPGGSL RLSCAASGFT FSSYAMSWVR  60
QAPGKGLEWV SAISGSGGST YYADSVKGRF TISRDNSKNT LYLQMNSLRA EDTAVYYCAR  120
GVGAFRPYRK HEWGQGTLVT VSRGGGGSGG GGSGGGGSSS ELTQDPAVSV ALGQTVRITC  180
QGDSLRSYYA SWYQQKPGQA PVLVIYGKNN RPSGIPDRFS GSSSGNTASL TTTGAQAEDE  240
ADYYCNSSPF EHNLVVFGGG TKLTVLHHHH HHEPEA                            276

SEQ ID NO: 103         moltype = AA  length = 573
FEATURE                Location/Qualifiers
source                 1..573
                       mol_type = protein
                       organism = synthetic construct
SEQUENCE: 103
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSHGTVIESL ESLNNYFNSS GIDVEEKSLF  180
LDIWRNWQKD GDMKILQSQI ISFYLRLFEV LKDNQAISNN ISVIESHLIT TFFSNSKAKK  240
DAFMSIAKFE VNNPQVQRQA FNELIRVVHQ LLPESSLRKR KRSRCSGGPG PAGMKGLPGS  300
EVQLVESGGG LVQPGNSLRL SCAASGFTFS KFGMSWVRQA PGKGLEWVSS ISGSGRDTLY  360
AESVKGRFTI SRDNAKTTLY LQMNSLRPED TAVYYCTIGG SLSVSSQGTL VTVSSSGGPG  420
PAGMKGLPGS HGTVIESLES LNNYFNSSGI DVEEKSLFLD IWRNWQKDGD MKILQSQIIS  480
FYLRLFEVLK DNQAISNNIS VIESHLITTF FSNSKAKKDA FMSIAKFEVN NPQVQRQAFN  540
ELIRVVHQLL PESSLRKRKR SRCHHHHHHE PEA                               573

SEQ ID NO: 104         moltype = AA  length = 573
FEATURE                Location/Qualifiers
source                 1..573
                       mol_type = protein
                       organism = synthetic construct
SEQUENCE: 104
MDMRVPAQLL GLLLLWLRGA RCHGTVIESL ESLNNYFNSS GIDVEEKSLF LDIWRNWQKD  60
GDMKILQSQI ISFYLRLFEV LKDNQAISNN ISVIESHLIT TFFSNSKAKK DAFMSIAKFE  120
VNNPQVQRQA FNELIRVVHQ LLPESSLRKR KRSRCSGGPG PAGMKGLPGS EVQLVESGGG  180
LVQPGNSLRL SCAASGFTFS KFGMSWVRQA PGKGLEWVSS ISGSGRDTLY AESVKGRFTI  240
SRDNAKTTLY LQMNSLRPED TAVYYCTIGG SLSVSSQGTL VTVSSSGGPG PAGMKGLPGS  300
HGTVIESLES LNNYFNSSGI DVEEKSLFLD IWRNWQKDGD MKILQSQIIS FYLRLFEVLK  360
DNQAISNNIS VIESHLITTF FSNSKAKKDA FMSIAKFEVN NPQVQRQAFN ELIRVVHQLL  420
PESSLRKRKR SRCSGGPGPA GMKGLPGSEV QLVESGGGLV QPGNSLRLSC AASGFTFSKF  480
GMSWVRQAPG KGLEWVSSIS GSGRDTLYAE SVKGRFTISR DNAKTTLYLQ MNSLRPEDTA  540
VYYCTIGGSL SVSSQGTLVT VSSHHHHHHE PEA                               573

SEQ ID NO: 105         moltype = AA  length = 1511
FEATURE                Location/Qualifiers
source                 1..1511
                       mol_type = protein
                       organism = synthetic construct
SEQUENCE: 105
MDMRVPAQLL GLLLLWLRGA RCHGTVIESL ESLNNYFNSS GIDVEEKSLF LDIWRNWQKD  60
GDMKILQSQI ISFYLRLFEV LKDNQAISNN ISVIESHLIT TFFSNSKAKK DAFMSIAKFE  120
VNNPQVQRQA FNELIRVVHQ LLPESSLRKR KRSRCSGGPG PAGMKGLPGS EAHKSEIAHR  180
YNDLGEQHFK GLVLIAFSQY LQKCSYDEHA KLVQEVTDFA KTCVADESAA NCDKSLHTLF  240
GDKLCAIPNL RENYGELADC CTKQEPERNE CFLQHKDDNP SLPPFERPEA EAMCTSFKEN  300
PTTFMGHYLH EVARRHPYFY APELLYYAEQ YNEILTQCCA EADKESCLTP KLDGVKEKAL  360
VSSVRQRMKC SSMQKFGERA FKAWAVARLS QTFPNADFAE ITKLATDLTK VNKECCHGDL  420
LECADDRAEL AKYMCENQAT ISSKLQTCCD KPLLKKAHCL SEVEHDTMPA DLPAIAADFV  480
EDQEVCKNYA EAKDVFLGTF LYEYSRRHPD YSVSLLLRLA KKYEATLEKC CAEANPPACY  540
GTVLAEFQPL VEEPKNLVKT NCDLYEKLGE YGFQNAILVR YTQKAPQVST PTLVEAARNL  600
GRVGTKCCTL PEDQRLPCVE DYLSAILNRV CLLHEKTPVS EHVTKCCSGS LVERRPCFSA  660
LTVDETYVPK EFKAETFTFH SDICTLPEKE KQIKKQTALA ELVKHKPKAT AEQLKTVMDD  720
FAQFLDTCCK AADKDTCFST EGPNLVTRCK DALASGGPGP AGMKGLPGSH GTVIESLESL  780
NNYFNSSGID VEEKSLFLDI WRNWQKDGDM KILQSQIISF YLRLFEVLKD NQAISNNISV  840
IESHLITTFF SNSKAKKDAF MSIAKFEVNN PQVQRQAFNE LIRVVHQLLP ESSLRKRKRS  900
RCSGGPGPAG MKGLPGSEAH KSEIAHRYND LGEQHFKGLV LIAFSQYLQK CSYDEHAKLV  960
```

-continued

```
QEVTDFAKTC VADESAANCD KSLHTLFGDK LCAIPNLREN YGELADCCTK QEPERNECFL  1020
QHKDDNPSLP PFERPEAEAM CTSFKENPTT FMGHYLHEVA RRHPYFYAPE LLYYAEQYNE  1080
ILTQCCAEAD KESCLTPKLD GVKEKALVSS VRQRMKCSSM QKFGERAFKA WAVARLSQTF  1140
PNADFAEITK LATDLTKVNK ECCHGDLLEC ADDRAELAKY MCENQATISS KLQTCCDKPL  1200
LKKAHCLSEV EHDTMPADLP AIAADFVEDQ EVCKNYAEAK DVFLGTFLYE YSRRHPDYSV  1260
SLLLRLAKKY EATLEKCCAE ANPPACYGTV LAEFQPLVEE PKNLVKTNCD LYEKLGEYGF  1320
QNAILVRYTQ KAPQVSTPTL VEAARNLGRV GTKCCTLPED QRLPCVEDYL SAILNRVCLL  1380
HEKTPVSEHV TKCCSGSLVE RRPCFSALTV DETYVPKEFK AETFTFHSDI CTLPEKEKQI  1440
KKQTALAELV KHKPKATAEQ LKTVMDDFAQ FLDTCCKAAD KDTCFSTEGP NLVTRCKDAL  1500
AHHHHHHEPE A                                                       1511

SEQ ID NO: 106          moltype = AA  length = 1511
FEATURE                 Location/Qualifiers
source                  1..1511
                        mol_type = protein
                        organism = synthetic construct
SEQUENCE: 106
MDMRVPAQLL GLLLLWLRGA RCEAHKSEIA HRYNDLGEQH FKGLVLIAFS QYLQKCSYDE  60
HAKLVQEVTD FAKTCVADES AANCDKSLHT LFGDKLCAIP NLRENYGELA DCCTKQEPER  120
NECFLQHKDD NPSLPPFERP EAEAMCTSFK ENPTTFMGHY LHEVARRHPY FYAPELLYYA  180
EQYNEILTQC CAEADKESCL TPKLDGVKEK ALVSSVRQRM KCSSMQKFGE RAFKAWAVAR  240
LSQTFPNADF AEITKLATDL TKVNKECCHG DLLECADDRA ELAKYMCENQ ATISSKLQTC  300
CDKPLLKKAH CLSEVEHDTM PADLPAIAAD FVEDQEVCKN YAEAKDVFLG TFLYEYSRRH  360
PDYSVSLLLR LAKKYEATLE KCCAEANPPA CYGTVLAEFQ PLVEEPKNLV KTNCDLYEKL  420
GEYGFQNAIL VRYTQKAPQV STPTLVEAAR NLGRVGTKCC TLPEDQRLPC VEDYLSAILN  480
RVCLLHEKTP VSEHVTKCCS GSLVERRPCF SALTVDETYV PKEFKAETFT FHSDICTLPE  540
KEKQIKKQTA LAELVKHKPK ATAEQLKTVM DDFAQFLDTC CKAADKDTCF STEGPNLVTR  600
CKDALASGGP GPAGMKGLPG SHGTVIESLE SLNNYFNSSG IDVEEKSLFL DIWRNWQKDG  660
DMKILQSQII SFYLRLFEVL KDNQAISNNI SVIESHLITT FFSNSKAKKD AFMSIAKFEV  720
NNPQVQRQAF NELIRVVHQL LPESSLRKRK RSRCSGGPGP AGMKGLPGSE AHKSEIAHRY  780
NDLGEQHFKG LVLIAFSQYL QKCSYDEHAK LVQEVTDFAK TCVADESAAN CDKSLHTLFG  840
DKLCAIPNLR ENYGELADCC TKQEPERNEC FLQHKDDNPS LPPFERPEAE AMCTSFKENP  900
TTFMGHYLHE VARRHPYFYA PELLYYAEQY NEILTQCCAE ADKESCLTPK LDGVKEKALV  960
SSVRQRMKCS SMQKFGERAF KAWAVARLSQ TFPNADFAEI TKLATDLTKV NKECCHGDLL  1020
ECADDRAELA KYMCENQATI SSKLQTCCDK PLLKKAHCLS EVEHDTMPAD LPAIAADFVE  1080
DQEVCKNYAE AKDVFLGTFL YEYSRRHPDY SVSLLLRLAK KYEATLEKCC AEANPPACYG  1140
TVLAEFQPLV EEPKNLVKTN CDLYEKLGEY GFQNAILVRY TQKAPQVSTP TLVEAARNLG  1200
RVGTKCCTLP EDQRLPCVED YLSAILNRVC LLHEKTPVSE HVTKCCSGSL VERRPCFSAL  1260
TVDETYVPKE FKAETFTFHS DICTLPEKEK QIKKQTALAE LVKHKPKATA EQLKTVMDDF  1320
AQFLDTCCKA ADKDTCFSTE GPNLVTRCKD ALASGGPGPA GMKGLPGSHG TVIESLESLN  1380
NYFNSSGIDV EEKSLFLDIW RNWQKDGDMK ILQSQIISFY LRLFEVLKDN QAISNNISVI  1440
ESHLITTFFS NSKAKKDAFM SIAKFEVNNP QVQRQAFNEL IRVVHQLLPE SSLRKRKRSR  1500
CHHHHHHEPE A                                                       1511

SEQ ID NO: 107          moltype = AA  length = 2110
FEATURE                 Location/Qualifiers
source                  1..2110
                        mol_type = protein
                        organism = synthetic construct
SEQUENCE: 107
MDMRVPAQLL GLLLLWLRGA RCEAHKSEIA HRYNDLGEQH FKGLVLIAFS QYLQKCSYDE  60
HAKLVQEVTD FAKTCVADES AANCDKSLHT LFGDKLCAIP NLRENYGELA DCCTKQEPER  120
NECFLQHKDD NPSLPPFERP EAEAMCTSFK ENPTTFMGHY LHEVARRHPY FYAPELLYYA  180
EQYNEILTQC CAEADKESCL TPKLDGVKEK ALVSSVRQRM KCSSMQKFGE RAFKAWAVAR  240
LSQTFPNADF AEITKLATDL TKVNKECCHG DLLECADDRA ELAKYMCENQ ATISSKLQTC  300
CDKPLLKKAH CLSEVEHDTM PADLPAIAAD FVEDQEVCKN YAEAKDVFLG TFLYEYSRRH  360
PDYSVSLLLR LAKKYEATLE KCCAEANPPA CYGTVLAEFQ PLVEEPKNLV KTNCDLYEKL  420
GEYGFQNAIL VRYTQKAPQV STPTLVEAAR NLGRVGTKCC TLPEDQRLPC VEDYLSAILN  480
RVCLLHEKTP VSEHVTKCCS GSLVERRPCF SALTVDETYV PKEFKAETFT FHSDICTLPE  540
KEKQIKKQTA LAELVKHKPK ATAEQLKTVM DDFAQFLDTC CKAADKDTCF STEGPNLVTR  600
CKDALASGGP GPAGMKGLPG SHGTVIESLE SLNNYFNSSG IDVEEKSLFL DIWRNWQKDG  660
DMKILQSQII SFYLRLFEVL KDNQAISNNI SVIESHLITT FFSNSKAKKD AFMSIAKFEV  720
NNPQVQRQAF NELIRVVHQL LPESSLRKRK RSRCSGGPGP AGMKGLPGSE AHKSEIAHRY  780
NDLGEQHFKG LVLIAFSQYL QKCSYDEHAK LVQEVTDFAK TCVADESAAN CDKSLHTLFG  840
DKLCAIPNLR ENYGELADCC TKQEPERNEC FLQHKDDNPS LPPFERPEAE AMCTSFKENP  900
TTFMGHYLHE VARRHPYFYA PELLYYAEQY NEILTQCCAE ADKESCLTPK LDGVKEKALV  960
SSVRQRMKCS SMQKFGERAF KAWAVARLSQ TFPNADFAEI TKLATDLTKV NKECCHGDLL  1020
ECADDRAELA KYMCENQATI SSKLQTCCDK PLLKKAHCLS EVEHDTMPAD LPAIAADFVE  1080
DQEVCKNYAE AKDVFLGTFL YEYSRRHPDY SVSLLLRLAK KYEATLEKCC AEANPPACYG  1140
TVLAEFQPLV EEPKNLVKTN CDLYEKLGEY GFQNAILVRY TQKAPQVSTP TLVEAARNLG  1200
RVGTKCCTLP EDQRLPCVED YLSAILNRVC LLHEKTPVSE HVTKCCSGSL VERRPCFSAL  1260
TVDETYVPKE FKAETFTFHS DICTLPEKEK QIKKQTALAE LVKHKPKATA EQLKTVMDDF  1320
AQFLDTCCKA ADKDTCFSTE GPNLVTRCKD ALASGGPGPA GMKGLPGSHG TVIESLESLN  1380
NYFNSSGIDV EEKSLFLDIW RNWQKDGDMK ILQSQIISFY LRLFEVLKDN QAISNNISVI  1440
ESHLITTFFS NSKAKKDAFM SIAKFEVNNP QVQRQAFNEL IRVVHQLLPE SSLRKRKRSR  1500
CSGGPGPAGM KGLPGSEAHK SEIAHRYNDL GEQHFKGLVL IAFSQYLQKC SYDEHAKLVQ  1560
EVTDFAKTCV ADESAANCDK SLHTLFGDKL CAIPNLRENY GELADCCTKQ EPERNECFLQ  1620
HKDDNPSLPP FERPEAEAMC TSFKENPTTF MGHYLHEVAR RHPYFYAPEL LYYAEQYNEI  1680
LTQCCAEADK ESCLTPKLDG VKEKALVSSV RQRMKCSSMQ KFGERAFKAW AVARLSQTFP  1740
```

```
NADFAEITKL ATDLTKVNKE CCHGDLLECA DDRAELAKYM CENQATISSK LQTCCDKPLL  1800
KKAHCLSEVE HDTMPADLPA IAADFVEDQE VCKNYAEAKD VFLGTFLYEY SRRHPDYSVS  1860
LLLRLAKKYE ATLEKCCAEA NPPACYGTVL AEFQPLVEEP KNLVKTNCDL YEKLGEYGFQ  1920
NAILVRYTQK APQVSTPTLV EAARNLGRVG TKCCTLPEDQ RLPCVEDYLS AILNRVCLLH  1980
EKTPVSEHVT KCCSGSLVER RPCFSALTVD ETYVPKEFKA ETFTFHSDIC TLPEKEKQIK  2040
KQTALAELVK HKPKATAEQL KTVMDDFAQF LDTCCKAADK DTCFSTEGPN LVTRCKDALA  2100
HHHHHHEPEA                                                         2110

SEQ ID NO: 108         moltype = AA  length = 2120
FEATURE                Location/Qualifiers
source                 1..2120
                       mol_type = protein
                       organism = synthetic construct
SEQUENCE: 108
MDMRVPAQLL GLLLLWLRGA RCEAHKSEIA HRYNDLGEQH FKGLVLIAFS QYLQKCSYDE  60
HAKLVQEVTD FAKTCVADES AANCDKSLHT LFGDKLCAIP NLRENYGELA DCCTKQEPER  120
NECFLQHKDD NPSLPPFERP EAEAMCTSFK ENPTTFMGHY LHEVARRHPY FYAPELLYYA  180
EQYNEILTQC CAEADKESCL TPKLDGVKEK ALVSSVRQRM KCSSMQKFGE RAFKAWAVAR  240
LSQTFPNADF AEITKLATDL TKVNKECCHG DLLECADDRA ELAKYMCENQ ATISSKLQTC  300
CDKPLLKKAH CLSEVEHDTM PADLPAIAAD FVEDQEVCKN YAEAKDVFLG TFLYEYSRRH  360
PDYSVSLLLR LAKKYEATLE KCCAEANPPA CYGTVLAEFQ PLVEEPKNLV KTNCDLYEKL  420
GEYGFQNAIL VRYTQKAPQV STPTLVEAAR NLGRVGTKCC TLPEDQRLPC VEDYLSAILN  480
RVCLLHEKTP VSEHVTKCCS GSLVERRPCF SALTVDETYV PKEFKAETFT FHSDICTLPE  540
KEKQIKKQTA LAELVKHKPK ATAEQLKTVM DDFAQFLDTC CKAADKDTCF STEGPNLVTR  600
CKDALASGGP GPAGMKGLPG SHGTVIESLE SLNNYFNSSG IDVEEKSLFL DIWRNWQKDG  660
DMKILQSQII SFYLRLFEVL KDNQAISNNI SVIESHLITT FFSNSKAKKD AFMSIAKFEV  720
NNPQVQRQAF NELIRVVHQL LPESSLRKRK RSRCSGGPGP AGMKGLPGSG GGGSEAHKSE  780
IAHRYNDLGE QHFKGLVLIA FSQYLQKCSY DEHAKLVQEV TDFAKTCVAD ESAANCDKSL  840
HTLFGDKLCA IPNLRENYGE LADCCTKQEP ERNECFLQHK DDNPSLPPFE RPEAEAMCTS  900
FKENPTTFMG HYLHEVARRH PYFYAPELLY YAEQYNEILT QCCAEADKES CLTPKLDGVK  960
EKALVSSVRQ RMKCSSMQKF GERAFKAWAV ARLSQTFPNA DFAEITKLAT DLTKVNKECC  1020
HGDLLECADD RAELAKYMCE NQATISSKLQ TCCDKPLLKK AHCLSEVEHD TMPADLPAIA  1080
ADFVEDQEVC KNYAEAKDVF LGTFLYEYSR RHPDYSVSLL LRLAKKYEAT LEKCCAEANP  1140
PACYGTVLAE FQPLVEEPKN LVKTNCDLYE KLGEYGFQNA ILVRYTQKAP QVSTPTLVEA  1200
ARNLGRVGTK CCTLPEDQRL PCVEDYLSAI LNRVCLLHEK TPVSEHVTKC CSGSLVERRP  1260
CFSALTVDET YVPKEFKAET FTFHSDICTL PEKEKQIKKQ TALAELVKHK PKATAEQLKT  1320
VMDDFAQFLD TCCKAADKDT CFSTEGPNLV TRCKDALAGG GGSSGGPGPA GMKGLPGSHG  1380
TVIESLESLN NYFNSSGIDV EEKSLFLDIW RNWQKDGDMK ILQSQIISFY LRLFEVLKDN  1440
QAISNNISVI ESHLITTFFS NSKAKKDAFM SIAKFEVNNP QVQRQAFNEL IRVVHQLLPE  1500
SSLRKRKRSR CSGGPGPAGM KGLPGSEAHK SEIAHRYNDL GEQHFKGLVL IAFSQYLQKC  1560
SYDEHAKLVQ EVTDFAKTCV ADESAANCDK SLHTLFGDKL CAIPNLRENY GELADCCTKQ  1620
EPERNECFLQ HKDDNPSLPP FERPEAEAMC TSFKENPTTF MGHYLHEVAR RHPYFYAPEL  1680
LYYAEQYNEI LTQCCAEADK ESCLTPKLDG VKEKALVSSV RQRMKCSSMQ KFGERAFKAW  1740
AVARLSQTFP NADFAEITKL ATDLTKVNKE CCHGDLLECA DDRAELAKYM CENQATISSK  1800
LQTCCDKPLL KKAHCLSEVE HDTMPADLPA IAADFVEDQE VCKNYAEAKD VFLGTFLYEY  1860
SRRHPDYSVS LLLRLAKKYE ATLEKCCAEA NPPACYGTVL AEFQPLVEEP KNLVKTNCDL  1920
YEKLGEYGFQ NAILVRYTQK APQVSTPTLV EAARNLGRVG TKCCTLPEDQ RLPCVEDYLS  1980
AILNRVCLLH EKTPVSEHVT KCCSGSLVER RPCFSALTVD ETYVPKEFKA ETFTFHSDIC  2040
TLPEKEKQIK KQTALAELVK HKPKATAEQL KTVMDDFAQF LDTCCKAADK DTCFSTEGPN  2100
LVTRCKDALA HHHHHHEPEA                                              2120

SEQ ID NO: 109         moltype = AA  length = 2130
FEATURE                Location/Qualifiers
source                 1..2130
                       mol_type = protein
                       organism = synthetic construct
SEQUENCE: 109
MDMRVPAQLL GLLLLWLRGA RCEAHKSEIA HRYNDLGEQH FKGLVLIAFS QYLQKCSYDE  60
HAKLVQEVTD FAKTCVADES AANCDKSLHT LFGDKLCAIP NLRENYGELA DCCTKQEPER  120
NECFLQHKDD NPSLPPFERP EAEAMCTSFK ENPTTFMGHY LHEVARRHPY FYAPELLYYA  180
EQYNEILTQC CAEADKESCL TPKLDGVKEK ALVSSVRQRM KCSSMQKFGE RAFKAWAVAR  240
LSQTFPNADF AEITKLATDL TKVNKECCHG DLLECADDRA ELAKYMCENQ ATISSKLQTC  300
CDKPLLKKAH CLSEVEHDTM PADLPAIAAD FVEDQEVCKN YAEAKDVFLG TFLYEYSRRH  360
PDYSVSLLLR LAKKYEATLE KCCAEANPPA CYGTVLAEFQ PLVEEPKNLV KTNCDLYEKL  420
GEYGFQNAIL VRYTQKAPQV STPTLVEAAR NLGRVGTKCC TLPEDQRLPC VEDYLSAILN  480
RVCLLHEKTP VSEHVTKCCS GSLVERRPCF SALTVDETYV PKEFKAETFT FHSDICTLPE  540
KEKQIKKQTA LAELVKHKPK ATAEQLKTVM DDFAQFLDTC CKAADKDTCF STEGPNLVTR  600
CKDALASGGP GPAGMKGLPG SHGTVIESLE SLNNYFNSSG IDVEEKSLFL DIWRNWQKDG  660
DMKILQSQII SFYLRLFEVL KDNQAISNNI SVIESHLITT FFSNSKAKKD AFMSIAKFEV  720
NNPQVQRQAF NELIRVVHQL LPESSLRKRK RSRCSGGPGP AGMKGLPGSG GGSGGGGSE  780
AHKSEIAHRY NDLGEQHFKG LVLIAFSQYL QKCSYDEHAK LVQEVTDFAK TCVADESAAN  840
CDKSLHTLFG DKLCAIPNLR ENYGELADCC TKQEPERNEC FLQHKDDNPS LPPFERPEAE  900
AMCTSFKENP TTFMGHYLHE VARRHPYFYA PELLYYAEQY NEILTQCCAE ADKESCLTPK  960
LDGVKEKALV SSVRQRMKCS SMQKFGERAF KAWAVARLSQ TFPNADFAEI TKLATDLTKV  1020
NKECCHGDLL ECADDRAELA KYMCENQATI SSKLQTCCDK PLLKKAHCLS EVEHDTMPAD  1080
LPAIAADFVE DQEVCKNYAE AKDVFLGTFL YEYSRRHPDY SVSLLLRLAK KYEATLEKCC  1140
AEANPPACYG TVLAEFQPLV EEPKNLVKTN CDLYEKLGEY GFQNAILVRY TQKAPQVSTP  1200
TLVEAARNLG RVGTKCCTLP EDQRLPCVED YLSAILNRVC LLHEKTPVSE HVTKCCSGSL  1260
VERRPCFSAL TVDETYVPKE FKAETFTFHS DICTLPEKEK QIKKQTALAE LVKHKPKATA  1320
```

```
EQLKTVMDDF AQFLDTCCKA ADKDTCFSTE GPNLVTRCKD ALAGGGGSGG GGSSGGPGPA  1380
GMKGLPGSHG TVIESLESLN NYFNSSGIDV EEKSLFLDIW RNWQKDGDMK ILQSQIISFY  1440
LRLFEVLKDN QAISNNISVI ESHLITTFFS NSKAKKDAFM SIAKFEVNNP QVQRQAFNEL  1500
IRVVHQLLPE SSLRKRKRSR CSGGPGPAGM KGLPGSEAHK SEIAHRYNDL GEQHFKGLVL  1560
IAFSQYLQKC SYDEHAKLVQ EVTDFAKTCV ADESAANCDK SLHTLFGDKL CAIPNLRENY  1620
GELADCCTKQ EPERNECFLQ HKDDNPSLPP FERPEAEAMC TSFKENPTTF MGHYLHEVAR  1680
RHPYFYAPEL LYYAEQYNEI LTQCCAEADK ESCLTPKLDG VKEKALVSSV RQRMKCSSMQ  1740
KFGERAFKAW AVARLSQTFP NADFAEITKL ATDLTKVNKE CCHGDLLECA DDRAELAKYM  1800
CENQATISSK LQTCCDKPLL KKAHCLSEVE HDTMPADLPA IAADFVEDQE VCKNYAEAKD  1860
VFLGTFLYEY SRRHPDYSVS LLLRLAKKYE ATLEKCCAEA NPPACYGTVL AEFQPLVEEP  1920
KNLVKTNCDL YEKLGEYGFQ NAILVRYTQK APQVSTPTLV EAARNLGRVG TKCCTLPEDQ  1980
RLPCVEDYLS AILNRVCLLH EKTPVSEHVT KCCSGSLVER RPCFSALTVD ETYVPKEFKA  2040
ETFTFHSDIC TLPEKEKQIK KQTALAELVK HKPKATAEQL KTVMDDFAQF LDTCCKAADK  2100
DTCFSTEGPN LVTRCKDALA HHHHHHEPEA                                   2130

SEQ ID NO: 110         moltype = AA  length = 703
FEATURE                Location/Qualifiers
source                 1..703
                       mol_type = protein
                       organism = synthetic construct
SEQUENCE: 110
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSGGG GSGGGGSGGG GSHGTVIESL ESLNNYFNSS GIDVEEKSLF  180
LDIWRNWQKD GDMKILQSQI ISFYLRLFEV LKDNQAISNN ISVIESHLIT TFFSNSKAKK  240
DAFMSIAKFE VNNPQVQRQA FNELIRVVHQ LLPESSLRKR KRSRCGGGGS GGGGSGGGGS  300
EVQLVESGGG LVQPGNSLRL SCAASGFTFS KFGMSWVRQA PGKGLEWVSS ISGSGRDTLY  360
AESVKGRFTI SRDNAKTTLY LQMNSLRPED TAVYYCTIGG SLSVSSQGTL VTVSSGGGGS  420
GGGGSGGGGS HGTVIESLES LNNYFNSSGI DVEEKSLFLD IWRNWQKDGD MKILQSQIIS  480
FYLRLFEVLK DNQAISNNIS VIESHLITTF FSNSKAKKDA FMSIAKFEVN NPQVQRQAFN  540
ELIRVVHQLL PESSLRKRKR SRCGGGGSGG GGSGGGGSEV QLVESGGGLV QPGNSLRLSC  600
AASGFTFSKF GMSWVRQAPG KGLEWVSSIS GSGRDTLYAE SVKGRFTISR DNAKTTLYLQ  660
MNSLRPEDTA VYYCTIGGSL SVSSQGTLVT VSSHHHHHHE PEA                    703

SEQ ID NO: 111         moltype = AA  length = 832
FEATURE                Location/Qualifiers
source                 1..832
                       mol_type = protein
                       organism = synthetic construct
SEQUENCE: 111
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSHGTVIESL ESLNNYFNSS GIDVEEKSLF  180
LDIWRNWQKD GDMKILQSQI ISFYLRLFEV LKDNQAISNN ISVIESHLIT TFFSNSKAKK  240
DAFMSIAKFE VNNPQVQRQA FNELIRVVHQ LLPESSLRKR KRSRCSGGPG PAGMKGLPGS  300
EVQLVESGGG LVQPGNSLRL SCAASGFTFS KFGMSWVRQA PGKGLEWVSS ISGSGRDTLY  360
AESVKGRFTI SRDNAKTTLY LQMNSLRPED TAVYYCTIGG SLSVSSQGTL VTVSSSGGPG  420
PAGMKGLPGS HGTVIESLES LNNYFNSSGI DVEEKSLFLD IWRNWQKDGD MKILQSQIIS  480
FYLRLFEVLK DNQAISNNIS VIESHLITTF FSNSKAKKDA FMSIAKFEVN NPQVQRQAFN  540
ELIRVVHQLL PESSLRKRKR SRCSGGPGPA GMKGLPGSEV QLVESGGGLV QPGNSLRLSC  600
AASGFTFSKF GMSWVRQAPG KGLEWVSSIS GSGRDTLYAE SVKGRFTISR DNAKTTLYLQ  660
MNSLRPEDTA VYYCTIGGSL SVSSQGTLVT VSSGGGGSGG GGSGGGGSQV QLQESGGGLA  720
QAGGSLSLSC AASGFTVSNS VMAWYRQTPG KQREFVAIIN SVGSTNYADS VKGRFTISRD  780
NAKNTVYLQM NNLKPEDTAV YYCNRNFDRI YWGQGTQVTV SSHHHHHHEP EA          832

SEQ ID NO: 112         moltype = AA  length = 832
FEATURE                Location/Qualifiers
source                 1..832
                       mol_type = protein
                       organism = synthetic construct
SEQUENCE: 112
MDMRVPAQLL GLLLLWLRGA RCQVQLQESG GGLAQAGGSL SLSCAASGFT VSNSVMAWYR  60
QTPGKQREFV AIINSVGSTN YADSVKGRFT ISRDNAKNTV YLQMNNLKPE DTAVYVCNRN  120
FDRIYWGQGT QVTVSSGGGG SGGGGSGGGG SEVQLVESGG GLVQPGNSLR LSCAASGFTF  180
SKFGMSWVRQ APGKGLEWVS SISGSGRDTL YAESVKGRFT ISRDNAKTTL YLQMNSLRPE  240
DTAVYYCTIG GSLSVSSQGT LVTVSSSGGP GPAGMKGLPG SHGTVIESLE SLNNYFNSSG  300
IDVEEKSLFL DIWRNWQKDG DMKILQSQII SFYLRLFEVL KDNQAISNNI SVIESHLITT  360
FFSNSKAKKD AFMSIAKFEV NNPQVQRQAF NELIRVVHQL LPESSLRKRK RSRCSGGPGP  420
AGMKGLPGSE VQLVESGGGL VQPGNSLRLS CAASGFTFSK FGMSWVRQAP GKGLEWVSSI  480
SGSGRDTLYA ESVKGRFTIS RDNAKTTLYL QMNSLRPEDT AVYYCTIGGS LSVSSQGTLV  540
TVSSSGGPGP AGMKGLPGSH GTVIESLESL NNYFNSSGID VEEKSLFLDI WRNWQKDGDM  600
KILQSQIISF YLRLFEVLKD NQAISNNISV IESHLITTFF SNSKAKKDAF MSIAKFEVNN  660
PQVQRQAFNE LIRVVHQLLP ESSLRKRKRS RCSGGPGPAG MKGLPGSEVQ LVESGGGLVQ  720
PGNSLRLSCA ASGFTFSKFG MSWVRQAPGK GLEWVSSISG SGRDTLYAES VKGRFTISRD  780
NAKTTLYLQM NSLRPEDTAV YYCTIGGSLS VSSQGTLVTV SSHHHHHHEP EA          832

SEQ ID NO: 113         moltype = AA  length = 549
FEATURE                Location/Qualifiers
source                 1..549
```

```
                         mol_type = protein
                         organism = synthetic construct
SEQUENCE: 113
MDMRVPAQLL GLLLLWLRGA RCRVIPVSGP ARCLSQSRNL LKTTDDMVKT AREKLKHYSC  60
TAEDIDHEDI TRDQTSTLKT CLPLELHKNE SCLATRETSS TTRGSCLPPQ KTSLMMTLCL  120
GSIYEDLKMY QTEFQAINAA LQNHNHQQII LDKGMLVAID ELMQSLNHNG ETLRQKPPVG  180
EADPYRVKMK LCILLHAFST RVVTINRVMG YLSSASGGPG PAGMKGLPGS MWELEKDVYV  240
VEVDWTPDAP GETVNLTCDT PEEDDITWTS DQRHGVIGSG KTLTITVKEF LDAGQYTCHK  300
GGETLSHSHL LLHKKENGIW STEILKNFKN KTFLKCEAPN YSGRFTCSWL VQRNMDLKFN  360
IKSSSSSPDS RAVTCGMASL SAEKVTLDQR DYEKYSVSCQ EDVTCPTAEE TLPIELALEA  420
RQQNKYENYS TSFFIRDIIK PDPPKNLQMK PLKNSQVEVS WEYPDSWSTP HSYFSLKFFV  480
RIQRKKEKMK ETEEGCNQKG AFLVEKTSTE VQCKGGNVCV QAQDRYYNSS CSKWACVPCR  540
VRSHHHHHH                                                         549

SEQ ID NO: 114           moltype = AA  length = 579
FEATURE                  Location/Qualifiers
source                   1..579
                         mol_type = protein
                         organism = synthetic construct
SEQUENCE: 114
MDMRVPAQLL GLLLLWLRGA RCRVIPVSGP ARCLSQSRNL LKTTDDMVKT AREKLKHYSC  60
TAEDIDHEDI TRDQTSTLKT CLPLELHKNE SCLATRETSS TTRGSCLPPQ KTSLMMTLCL  120
GSIYEDLKMY QTEFQAINAA LQNHNHQQII LDKGMLVAID ELMQSLNHNG ETLRQKPPVG  180
EADPYRVKMK LCILLHAFST RVVTINRVMG YLSSAGGGGS GGGGSGGGGS SGGPGPAGMK  240
GLPGSGGGGS GGGGSGGGGS MWELEKDVYV VEVDWTPDAP GETVNLTCDT PEEDDITWTS  300
DQRHGVIGSG KTLTITVKEF LDAGQYTCHK GGETLSHSHL LLHKKENGIW STEILKNFKN  360
KTFLKCEAPN YSGRFTCSWL VQRNMDLKFN IKSSSSSPDS RAVTCGMASL SAEKVTLDQR  420
DYEKYSVSCQ EDVTCPTAEE TLPIELALEA RQQNKYENYS TSFFIRDIIK PDPPKNLQMK  480
PLKNSQVEVS WEYPDSWSTP HSYFSLKFFV RIQRKKEKMK ETEEGCNQKG AFLVEKTSTE  540
VQCKGGNVCV QAQDRYYNSS CSKWACVPCR VRSHHHHHH                         579

SEQ ID NO: 115           moltype = AA  length = 809
FEATURE                  Location/Qualifiers
source                   1..809
                         mol_type = protein
                         organism = synthetic construct
SEQUENCE: 115
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSMWELEKDV YVVEVDWTPD APGETVNLTC  180
DTPEEDDITW TSDQRHGVIG SGKTLTITVK EFLDAGQYTC HKGGETLSHS HLLLHKKENG  240
IWSTEILKNF KNKTFLKCEA PNYSGRFTCS WLVQRNMDLK FNIKSSSSSP DSRAVTCGMA  300
SLSAEKVTLD QRDYEKYSVS CQEDVTCPTA EETLPIELAL EARQQNKYEN YSTSFFIRDI  360
IKPDPPKNLQ MKPLKNSQVE VSWEYPDSWS TPHSYFSLKF FVRIQRKKEK MKETEEGCNQ  420
KGAFLVEKTS TEVQCKGGNV CVQAQDRYYN SSCSKWACVP CRVRSGGGGS GGGGSGGGGS  480
RVIPVSGPAR CLSQSRNLLK TTDDMVKTAR EKLKHYSCTA EDIDHEDITR DQTSTLKTCL  540
PLELHKNESC LATRETSSTT RGSCLPPQKT SLMMTLCLGS IYEDLKMYQT EFQAINAALQ  600
NHNHQQIILD KGMLVAIDEL MQSLNHNGET LRQKPPVGEA DPYRVKMKLC ILLHAFSTRV  660
VTINRVMGYL SSASGGPGPA GMKGLPGSEV QLVESGGGLV QPGNSLRLSC AASGFTFSKF  720
GMSWVRQAPG KGLEWVSSIS GSGRDTLYAE SVKGRFTISR DNAKTTLYLQ MNSLRPEDTA  780
VYYCTIGGSL SVSSQGTLVT VSSHHHHHH                                   809

SEQ ID NO: 116           moltype = AA  length = 938
FEATURE                  Location/Qualifiers
source                   1..938
                         mol_type = protein
                         organism = synthetic construct
SEQUENCE: 116
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGGGG SGGGGSGGGG SEVQLVESGG GLVQPGNSLR LSCAASGFTF  180
SKFGMSWVRQ APGKGLEWVS SISGSGRDTL YAESVKGRFT ISRDNAKTTL YLQMNSLRPE  240
DTAVYYCTIG GSLSVSSQGT LVTVSSSGGP GPAGMKGLPG SMWELEKDVY VVEVDWTPDA  300
PGETVNLTCD TPEEDDITWT SDQRHGVIGS GKTLTITVKE FLDAGQYTCH KGGETLSHSH  360
LLLHKKENGI WSTEILKNFK NKTFLKCEAP NYSGRFTCSW LVQRNMDLKF NIKSSSSSPD  420
SRAVTCGMAS LSAEKVTLDQ RDYEKYSVSC QEDVTCPTAE ETLPIELALE ARQQNKYENY  480
STSFFIRDII KPDPPKNLQM KPLKNSQVEV SWEYPDSWST PHSYFSLKFF VRIQRKKEKM  540
KETEEGCNQK GAFLVEKTST EVQCKGGNVC VQAQDRYYNS SCSKWACVPC RVRSGGGGSG  600
GGGSGGGGSR VIPVSGPARC LSQSRNLLKT TDDMVKTARE KLKHYSCTAE DIDHEDITRD  660
QTSTLKTCLP LELHKNESCL ATRETSSTTR GSCLPPQKTS LMMTLCLGSI YEDLKMYQTE  720
FQAINAALQN HNHQQIILDK GMLVAIDELM QSLNHNGETL RQKPPVGEAD PYRVKMKLCI  780
LLHAFSTRVV TINRVMGYLS SASGGPGPAG MKGLPGSEVQ LVESGGGLVQ PGNSLRLSCA  840
ASGFTFSKFG MSWVRQAPGK GLEWVSSISG SGRDTLYAES VKGRFTISRD NAKTTLYLQM  900
NSLRPEDTAV YYCTIGGSLS VSSQGTLVTV SSHHHHHH                          938

SEQ ID NO: 117           moltype = AA  length = 938
FEATURE                  Location/Qualifiers
source                   1..938
                         mol_type = protein
```

```
                         organism = synthetic construct
SEQUENCE: 117
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGGGG SGGGGSGGGG SEVQLVESGG GLVQPGNSLR LSCAASGFTF  180
SKFGMSWVRQ APGKGLEWVS SISGSGRDTL YAESVKGRFT ISRDNAKTTL YLQMNSLRPE  240
DTAVYYCTIG GSLSVSSQGT LVTVSSGGGP GPAGMKGLPG SMWELEKDVY VVEVDWTPDA  300
PGETVNLTCD TPEEDDITWT SDQRHGVIGS GKTLTITVKE FLDAGQYTCH KGGETLSHSH  360
LLLHKKENGI WSTEILKNFK NKTFLKCEAP NYSGRFTCSW LVQRNMDLKF NIKSSSSSPD  420
SRAVTCGMAS LSAEKVTLDQ RDYEKYSVSC QEDVTCPTAE ETLPIELALE ARQQNKYENY  480
STSFFIRDII KPDPPKNLQM KPLKNSQVEV SWEYPDSWST PHSYFSLKFF VRIQRKKEKM  540
KETEEGCNQK GAFLVEKTST EVQCKGGNVC VQAQDRYYNS SCSKWACVPC RVRSGGGGSG  600
GGGSGGGGSR VIPVSGPARC LSQSRNLLKT TDDMVKTARE KLKHYSCTAE DIDHEDITRD  660
QTSTLKTCLP LELHKNESCL ATRETSSTTR GSCLPPQKTS LMMTLCLGSI YEDLKMYQTE  720
FQAINAALQN HNHQQIILDK GMLVAIDELM QSLNHNGETL RQKPPVGEAD PYRVKMKLCI  780
LLHAFSTRVV TINRVMGYLS SASGGPGPAG MKGLPGSEVQ LVESGGGLVQ PGNSLRLSCA  840
ASGFTFSKFG MSWVRQAPGK GLEWVSSISG SGRDTLYAES VKGRFTISRD NAKTTLYLQM  900
NSLRPEDTAV YYCTIGGSLS VSSQGTLVTV SSHHHHHH                        938

SEQ ID NO: 118           moltype = AA  length = 938
FEATURE                  Location/Qualifiers
source                   1..938
                         mol_type = protein
                         organism = synthetic construct
SEQUENCE: 118
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSMWELEKDV YVVEVDWTPD APGETVNLTC  180
DTPEEDDITW TSDQRHGVIG SGKTLTITVK EFLDAGQYTC HKGGETLSHS HLLLHKKENG  240
IWSTEILKNF KNKTFLKCEA PNYSGRFTCS WLVQRNMDLK FNIKSSSSSP DSRAVTCGMA  300
SLSAEKVTLD QRDYEKYSVS CQEDVTCPTA EETLPIELAL EARQQNKYEN YSTSFFIRDI  360
IKPDPPKNLQ MKPLKNSQVE VSWEYPDSWS TPHSYFSLKF FVRIQRKKEK MKETEEGCNQ  420
KGAFLVEKTS TEVQCKGGNV CVQAQDRYYN SSCSKWACVP CRVRSGGGGS GGGGSGGGGS  480
RVIPVSGPAR CLSQSRNLLK TTDDMVKTAR EKLKHYSCTA EDIDHEDITR DQTSTLKTCL  540
PLELHKNESC LATRETSSTT RGSCLPPQKT SLMMTLCLGS IYEDLKMYQT EFQAINAALQ  600
NHNHQQIILD KGMLVAIDEL MQSLNHNGET LRQKPPVGEA DPYRVKMKLC ILLHAFSTRV  660
VTINRVMGYL SSASGGPGPA GMKGLPGSEV QLVESGGGLV QPGNSLRLSC AASGFTFSKF  720
GMSWVRQAPG KGLEWVSSIS GSGRDTLYAE SVKGRFTISR DNAKTTLYLQ MNSLRPEDTA  780
VYYCTIGGSL SVSSQGTLVT VSSGGGGSGG GGSGGGGSQV QLQESGGGLV QAGGSLRLSC  840
AASGRIFSID IMSWYRQAPG KQRELVARIT RGGTISYDDS VKGRFTISRD NAKNTVYLQM  900
NSLKPEDTGV YYCNALYGTD YWGKGTQVTV SSHHHHHH                        938

SEQ ID NO: 119           moltype = AA  length = 962
FEATURE                  Location/Qualifiers
source                   1..962
                         mol_type = protein
                         organism = synthetic construct
SEQUENCE: 119
MDMRVPAQLL GLLLLWLRGA RCIWELKKDV YVVELDWYPD APGEMVVLTC DTPEEDGITW  60
TLDQSSEVLG SGKTLTIQVK EFGDAGQYTC HKGGEVLSHS LLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCSGG GGSGGGGSGG GGSRVIPVSG PARCLSQSRN  360
LLKTTDDMVK TAREKLKHYS CTAEDIDHED ITRDQTSTLK TCLPLELHKN ESCLATRETS  420
STTRGSCLPP QKTSLMMTLC LGSIYEDLKM YQTEFQAINA ALQNHNHQQI ILDKGMLVAI  480
DELMQSLNHN GETLRQKPPV GEADPYRVKM KLCILLHAFS TRVVTINRVM GYLSSAGGGG  540
SGGGGSGGGG SGGGGSGGGG SGGGGSGGGG SGGGGSGGGG SQSVLTQPPS VSGAPGQRVT  600
ISCSGSRSNI GSNTVKWYQQ LPGTAPKLLI YYNDQRPSGV PDRFSGSKSG TSASLAITGL  660
QAEDEADYYC QSYDRYTHPA LLFGTGTKVT VLGGGGSGGG GSGGGGSQVQ LVESGGGVVQ  720
PGRSLRLSCA ASGFTFSSYG MHWVRQAPGK GLEWVAFIRY DGSNKYYADS VKGRFTISRD  780
NSKNTLYLQM NSLRAEDTAV YYCKTHGSHD NWGQGTMVTV SSGGGGSGGG GSGGGGSEVQ  840
LVESGGGLVQ PGNSLRLSCA ASGFTFSKFG MSWVRQAPGK GLEWVSSISG SGRDTLYAES  900
VKGRFTISRD NAKTTLYLQM NSLRPEDTAV YYCTIGGSLS VSSQGTLVTV SSHHHHHHEP  960
EA                                                                962

SEQ ID NO: 120           moltype = AA  length = 832
FEATURE                  Location/Qualifiers
source                   1..832
                         mol_type = protein
                         organism = synthetic construct
SEQUENCE: 120
MDMRVPAQLL GLLLLWLRGA RCIWELKKDV YVVELDWYPD APGEMVVLTC DTPEEDGITW  60
TLDQSSEVLG SGKTLTIQVK EFGDAGQYTC HKGGEVLSHS LLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCSGG GGSGGGGSGG GGSRVIPVSG PARCLSQSRN  360
LLKTTDDMVK TAREKLKHYS CTAEDIDHED ITRDQTSTLK TCLPLELHKN ESCLATRETS  420
```

```
STTRGSCLPP QKTSLMMTLC LGSIYEDLKM YQTEFQAINA ALQNHNHQQI ILDKGMLVAI  480
DELMQSLNHN GETLRQKPPV GEADPYRVKM KLCILLHAFS TRVVTINRVM GYLSSASGGP  540
GPAGMKGLPG SGGGGSGGGG SGGGGSGGGG SGGGGSGGGG SQSVLTQPPS VSGAPGQRVT  600
ISCSGSRSNI GSNTVKWYQQ LPGTAPKLLI YYNDQRPSGV PDRFSGSKSG TSASLAITGL  660
QAEDEADYYC QSYDRYTHPA LLFGTGTKVT VLGGGGSGGG GSGGGGSQVQ LVESGGGVVQ  720
PGRSLRLSCA ASGFTFSSYG MHWVRQAPGK GLEWVAFIRY DGSNKYYADS VKGRFTISRD  780
NSKNTLYLQM NSLRAEDTAV YYCKTHGSHD NWGQGTMVTV SSHHHHHHEP EA          832

SEQ ID NO: 121         moltype = AA  length = 1091
FEATURE                Location/Qualifiers
source                 1..1091
                       mol_type = protein
                       organism = synthetic construct
SEQUENCE: 121
MDMRVPAQLL GLLLLWLRGA RCIWELKKDV YVVELDWYPD APGEMVVLTC DTPEEDGITW  60
TLDQSSEVLG SGKTLTIQVK EFGDAGQYTC HKGGEVLSHS LLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCSGG GGSGGGGSGG GGSRVIPVSG PARCLSQSRN  360
LLKTTDDMVK TAREKLKHYS CTAEDIDHED ITRDQTSTLK TCLPLELHKN ESCLATRETS  420
STTRGSCLPP QKTSLMMTLC LGSIYEDLKM YQTEFQAINA ALQNHNHQQI ILDKGMLVAI  480
DELMQSLNHN GETLRQKPPV GEADPYRVKM KLCILLHAFS TRVVTINRVM GYLSSASGGP  540
GPAGMKGLPG SGGGGSGGGG SGGGGSGGGG SGGGGSGGGG SQSVLTQPPS VSGAPGQRVT  600
ISCSGSRSNI GSNTVKWYQQ LPGTAPKLLI YYNDQRPSGV PDRFSGSKSG TSASLAITGL  660
QAEDEADYYC QSYDRYTHPA LLFGTGTKVT VLGGGGSGGG GSGGGGSQVQ LVESGGGVVQ  720
PGRSLRLSCA ASGFTFSSYG MHWVRQAPGK GLEWVAFIRY DGSNKYYADS VKGRFTISRD  780
NSKNTLYLQM NSLRAEDTAV YYCKTHGSHD NWGQGTMVTV SSGGGGSGGG GSGGGGSEVQ  840
LVESGGGLVQ PGNSLRLSCA ASGFTFSKFG MSWVRQAPGK GLEWVSSISG SGRDTLYAES  900
VKGRFTISRD NAKTTLYLQM NSLRPEDTAV YYCTIGGSLS VSSQGTLVTV SSGGGGSGGG  960
GSGGGGSQVQ LQESGGGLAQ AGGSLSLSCA ASGFTVSNSV MAWYRQTPGK QREFVAIINS  1020
VGSTNYADSV KGRFTISRDN AKNTVYLQMN NLKPEDTAVY VCNRNFDRIY WGQGTQVTVS  1080
SHHHHHHEPE A                                                       1091

SEQ ID NO: 122         moltype = AA  length = 1091
FEATURE                Location/Qualifiers
source                 1..1091
                       mol_type = protein
                       organism = synthetic construct
SEQUENCE: 122
MDMRVPAQLL GLLLLWLRGA RCQVQLQESG GGLAQAGGSL SLSCAASGFT VSNSVMAWYR  60
QTPGKQREFV AIINSVGSTN YADSVKGRFT ISRDNAKNTV YLQMNNLKPE DTAVYVCNRN  120
FDRIYWGQGT QVTVSSGGGG SGGGGSGGGG SIWELKKDVY VVELDWYPDA PGEMVVLTCD  180
TPEEDGITWT LDQSSEVLGS GKTLTIQVKE FGDAGQYTCH KGGEVLSHSL LLLHKKEDGI  240
WSTDILKDQK EPKNKTFLRC EAKNYSGRFT CWWLTTISTD LTFSVKSSRG SSDPQGVTCG  300
AATLSAERVR GDNKEYEYSV ECQEDSACPA AEESLPIEVM VDAVHKLKYE NYTSSFFIRD  360
IIKPDPPKNL QLKPLKNSRQ VEVSWEYPDT WSTPHSYFSL TFCVQVQGKS KREKKDRVFT  420
DKTSATVICR KNASISVRAQ DRYYSSSWSE WASVPCSGGG GSGGGGSGGG GSRVIPVSGP  480
ARCLSQSRNL LKTTDDMVKT AREKLKHYSC TAEDIDHEDI TRDQTSTLKT CLPLELHKNE  540
SCLATRETSS TTRGSCLPPQ KTSLMMTLCL GSIYEDLKMY QTEFQAINAA LQNHNHQQII  600
LDKGMLVAID ELMQSLNHNG ETLRQKPPVG EADPYRVKMK LCILLHAFST RVVTINRVMG  660
YLSSASGGPG PAGMKGLPGS GGGGSGGGGS GGGGSGGGGS GGGGSGGGGS QSVLTQPPSV  720
SGAPGQRVTI SCSGSRSNIG SNTVKWYQQL PGTAPKLLIY YNDQRPSGVP DRFSGSKSGT  780
SASLAITGLQ AEDEADYYCQ SYDRYTHPAL LFGTGTKVTV LGGGGSGGGG SGGGGSQVQL  840
VESGGGVVQP GRSLRLSCAA SGFTFSSYGM HWVRQAPGKG LEWVAFIRYD GSNKYYADSV  900
KGRFTISRDN SKNTLYLQMN SLRAEDTAVY YCKTHGSHDN WGQGTMVTVS SGGGGSGGGG  960
SGGGGSEVQL VESGGGLVQP GNSLRLSCAA SGFTFSKFGM SWVRQAPGKG LEWVSSISGS  1020
GRDTLYAESV KGRFTISRDN AKTTLYLQMN SLRPEDTAVY YCTIGGSLSV SSQGTLVTVS  1080
SHHHHHHEPE A                                                       1091

SEQ ID NO: 123         moltype = AA  length = 1091
FEATURE                Location/Qualifiers
source                 1..1091
                       mol_type = protein
                       organism = synthetic construct
SEQUENCE: 123
MDMRVPAQLL GLLLLWLRGA RCQVQLQESG GGLAQAGGSL SLSCAASGFT VSNSVMAWYR  60
QTPGKQREFV AIINSVGSTN YADSVKGRFT ISRDNAKNTV YLQMNNLKPE DTAVYVCNRN  120
FDRIYWGQGT QVTVSSSGGP GPAGMKGLPG SIWELKKDVY VVELDWYPDA PGEMVVLTCD  180
TPEEDGITWT LDQSSEVLGS GKTLTIQVKE FGDAGQYTCH KGGEVLSHSL LLLHKKEDGI  240
WSTDILKDQK EPKNKTFLRC EAKNYSGRFT CWWLTTISTD LTFSVKSSRG SSDPQGVTCG  300
AATLSAERVR GDNKEYEYSV ECQEDSACPA AEESLPIEVM VDAVHKLKYE NYTSSFFIRD  360
IIKPDPPKNL QLKPLKNSRQ VEVSWEYPDT WSTPHSYFSL TFCVQVQGKS KREKKDRVFT  420
DKTSATVICR KNASISVRAQ DRYYSSSWSE WASVPCSGGG GSGGGGSGGG GSRVIPVSGP  480
ARCLSQSRNL LKTTDDMVKT AREKLKHYSC TAEDIDHEDI TRDQTSTLKT CLPLELHKNE  540
SCLATRETSS TTRGSCLPPQ KTSLMMTLCL GSIYEDLKMY QTEFQAINAA LQNHNHQQII  600
LDKGMLVAID ELMQSLNHNG ETLRQKPPVG EADPYRVKMK LCILLHAFST RVVTINRVMG  660
YLSSASGGPG PAGMKGLPGS GGGGSGGGGS GGGGSGGGGS GGGGSGGGGS QSVLTQPPSV  720
SGAPGQRVTI SCSGSRSNIG SNTVKWYQQL PGTAPKLLIY YNDQRPSGVP DRFSGSKSGT  780
```

```
SASLAITGLQ AEDEADYYCQ SYDRYTHPAL LFGTGTKVTV LGGGGSGGGG SGGGGSQVQL  840
VESGGGVVQP GRSLRLSCAA SGFTFSSYGM HWVRQAPGKG LEWVAFIRYD GSNKYYADSV  900
KGRFTISRDN SKNTLYLQMN SLRAEDTAVY YCKTHGSHDN WGQGTMVTVS SGGGGSGGGG  960
SGGGGSEVQL VESGGGLVQP GNSLRLSCAA SGFTFSKFGM SWVRQAPGKG LEWVSSISGS  1020
GRDTLYAESV KGRFTISRDN AKTTLYLQMN SLRPEDTAVY YCTIGGSLSV SSQGTLVTVS  1080
SHHHHHHEPE A                                                       1091

SEQ ID NO: 124          moltype = AA  length = 674
FEATURE                 Location/Qualifiers
source                  1..674
                        mol_type = protein
                        organism = synthetic construct
SEQUENCE: 124
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGMKGLPGS EVQLVESGGG  180
LVQPGGSLRL SCAASGFTFS SYTLAWVRQA PGKGLEWVAA IDSSSYTYSP DTVRGRFTIS  240
RDNAKNSLYL QMNSLRAEDT AVYYCARDSN WDALDYWGQG TTVTVSSGGG GSGGGGSGGG  300
GSDIQMTQSP SSLSASVGDR VTITCKASQN VGTNVGWYQQ KPGKAPKALI YSASFRYSGV  360
PSRFSGSGSG TDFTLTISSL QPEDFATYYC QQYYTYPYTF GGGTKVEIKG GGGSGGGGSG  420
GGGSEVQLVE SGGGLVQPGN SLRLSCAASG FTFSKFGMSW VRQAPGKGLE WVSSISGSGR  480
DTLYAESVKG RFTISRDNAK TTLYLQMNSL RPEDTAVYYC TIGGSLSVSS QGTLVTVSSG  540
GGGSGGGGSG GGGSQVQLQE SGGGLVQAGG SLRLSCAASG RIFSIDIMSW YRQAPGKQRE  600
LVARITRGGT ISYDDSVKGR FTISRDNAKN TVYLQMNSLK PEDTGVYYCN ALYGTDYWGK  660
GTQVTVSSHH HHHH                                                    674

SEQ ID NO: 125          moltype = AA  length = 674
FEATURE                 Location/Qualifiers
source                  1..674
                        mol_type = protein
                        organism = synthetic construct
SEQUENCE: 125
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSSGGP GPAGMKGLPG SEVQLVESGG GLVQPGNSLR LSCAASGFTF  180
SKFGMSWVRQ APGKGLEWVS SISGSGRDTL YAESVKGRFT ISRDNAKTTL YLQMNSLRPE  240
DTAVYYCTIG GSLSVSSQGT LVTVSSSGGP GPAGMKGLPG SEVQLVESGG GLVQPGGSLR  300
LSCAASGFTF SSYTLAWVRQ APGKGLEWVA AIDSSSYTYS PDTVRGRFTI SRDNAKNSLY  360
LQMNSLRAED TAVYYCARDS NWDALDYWGQ GTTVTVSSGG GGSGGGGSGG GGSDIQMTQS  420
PSSLSASVGD RVTITCKASQ NVGTNVGWYQ QKPGKAPKAL IYSASFRYSG VPSRFSGSGS  480
GTDFTLTISS LQPEDFATYY CQQYYTYPYT FGGGTKVEIK SGGPGPAGMK GLPGSAPTSS  540
STKKTQLQLE HLLLDLQMIL NGINNYKNPK LTRMLTFKFY MPKKATELKH LQCLEEELKP  600
LEEVLNLAQS KNFHLRPRDL ISNINVIVLE LKGSETTFMC EYADETATIV EFLNRWITFC  660
QSIISTLTHH HHHH                                                    674

SEQ ID NO: 126          moltype = AA  length = 425
FEATURE                 Location/Qualifiers
source                  1..425
                        mol_type = protein
                        organism = synthetic construct
SEQUENCE: 126
MDMRVPAQLL GLLLLWLRGA RCELCDDDPP EIPHATFKAM AYKEGTMLNC ECKRGFRRIK  60
SGSLYMLCTG NSSHSSWDNQ CQCTSSATRN TTKQVTPQPE EQKERKTTEM QSPMQPVDQA  120
SLPGHCREPP PWENEATERI YHFVVGQMVY YQCVQGYRAL HRGPAESVCK MTHGKTRWTQ  180
PQLICTGEME TSQFPGEEKP QASPEGRPES ETSCLVTTTD FQIQTEMAAT METSIFTTEY  240
QGGGGSGGGG SGGGGSGGGG SGGGGSGGGG SSGGPGPAGM KGLPGSAPTS SSTKKTQLQL  300
EHLLLDLQMI LNGINNYKNP KLTRMLTFKF YMPKKATELK HLQCLEEELK PLEEVLNLAQ  360
SKNFHLRPRD LISNINVIVL ELKGSETTFM CEYADETATI VEFLNRWITF CQSIISTLTH  420
HHHHH                                                              425

SEQ ID NO: 127          moltype = AA  length = 425
FEATURE                 Location/Qualifiers
source                  1..425
                        mol_type = protein
                        organism = synthetic construct
SEQUENCE: 127
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGMKGLPGS GGGGSGGGGS  180
GGGGSGGGGS GGGGSGGGGS ELCDDDPPEI PHATFKAMAY KEGTMLNCEC KRGFRRIKSG  240
SLYMLCTGNS SHSSWDNQCQ CTSSATRNTT KQVTPQPEEQ KERKTTEMQS PMQPVDQASL  300
PGHCREPPPW ENEATERIYH FVVGQMVYYQ CVQGYRALHR GPAESVCKMT HGKTRWTQPQ  360
LICTGEMETS QFPGEEKPQA SPEGRPESET SCLVTTTDFQ IQTEMAATME TSIFTTEYQH  420
HHHHH                                                              425

SEQ ID NO: 128          moltype = AA  length = 555
FEATURE                 Location/Qualifiers
source                  1..555
                        mol_type = protein
```

```
                         organism = synthetic construct
SEQUENCE: 128
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSGGG GSGGGGSGGG GSELCDDDPP EIPHATFKAM AYKEGTMLNC  180
ECKRGFRRIK SGSLYMLCTG NSSHSSWDNQ CQCTSSATRN TTKQVTPQPE EQKERKTTEM  240
QSPMQPVDQA SLPGHCREPP PWENEATERI YHFVVGQMVY YQCVQGYRAL HRGPAESVCK  300
MTHGKTRWTQ PQLICTGEME TSQFPGEEKP QASPEGRPES ETSCLVTTTD FQIQTEMAAT  360
METSIFTTEY QGGGGSGGGG SGGGGSGGGG SGGGGSGGGG SSGGPGPAGM KGLPGSAPTS  420
SSTKKTQLQL EHLLLDLQMI LNGINNYKNP KLTRMLTFKF YMPKKATELK HLQCLEEELK  480
PLEEVLNLAQ SKNFHLRPRD LISNINVIVL ELKGSETTFM CEYADETATI VEFLNRWITF  540
CQSIISTLTH HHHHH                                                 555

SEQ ID NO: 129           moltype = AA  length = 555
FEATURE                  Location/Qualifiers
source                   1..555
                         mol_type = protein
                         organism = synthetic construct
SEQUENCE: 129
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGMKGLPGS GGGGSGGGGS  180
GGGGSGGGGS GGGGSGGGGS ELCDDDPPEI PHATFKAMAY KEGTMLNCEC KRGFRRIKSG  240
SLYMLCTGNS SHSSWDNQCQ CTSSATRNTT KQVTPQPEEQ KERKTTEMQS PMQPVDQASL  300
PGHCREPPPW ENEATERIYH FVVGQMVYYQ CVQGYRALHR GPAESVCKMT HGKTRWTQPQ  360
LICTGEMETS QFPGEEKPQA SPEGRPESET SCLVTTTDFQ IQTEMAATME TSIFTTEYQG  420
GGGSGGGGSG GGGSEVQLVE SGGGLVQPGN SLRLSCAASG FTFSKFGMSW VRQAPGKGLE  480
WVSSISGSGR DTLYAESVKG RFTISRDNAK TTLYLQMNSL RPEDTAVYYC TIGGSLSVSS  540
QGTLVTVSSH HHHHH                                                 555

SEQ ID NO: 130           moltype = AA  length = 555
FEATURE                  Location/Qualifiers
source                   1..555
                         mol_type = protein
                         organism = synthetic construct
SEQUENCE: 130
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGMKGLPGS GGGGSGGGGS  180
GGGGSGGGGS GGGGSGGGGS ELCDDDPPEI PHATFKAMAY KEGTMLNCEC KRGFRRIKSG  240
SLYMLCTGNS SHSSWDNQCQ CTSSATRNTT KQVTPQPEEQ KERKTTEMQS PMQPVDQASL  300
PGHCREPPPW ENEATERIYH FVVGQMVYYQ CVQGYRALHR GPAESVCKMT HGKTRWTQPQ  360
LICTGEMETS QFPGEEKPQA SPEGRPESET SCLVTTTDFQ IQTEMAATME TSIFTTEYQS  420
GGPGPAGMKG LPGSEVQLVE SGGGLVQPGN SLRLSCAASG FTFSKFGMSW VRQAPGKGLE  480
WVSSISGSGR DTLYAESVKG RFTISRDNAK TTLYLQMNSL RPEDTAVYYC TIGGSLSVSS  540
QGTLVTVSSH HHHHH                                                 555

SEQ ID NO: 131           moltype = AA  length = 575
FEATURE                  Location/Qualifiers
source                   1..575
                         mol_type = protein
                         organism = synthetic construct
SEQUENCE: 131
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSEVQLVESG GGLVQPGGSL RLSCAASGFT  180
FSSYTLAWVR QAPGKGLEWV AAIDSSSYTY SPDTVRGRFT ISRDNAKNSL YLQMNSLRAE  240
DTAVYYCARD SNWDALDYWG QGTTVTVSSG GGGSGGGGSG GGGSDIQMTQ SPSSLSASVG  300
DRVTITCKAS QNVGTNVGWY QQKPGKAPKA LIYSASFRYS GVPSRFSGSG SGTDFTLTIS  360
SLQPEDFATY YCQQYYTYPY TFGGGTKVEI KGGGGSGGGG SGGGGSGGGG SGGGGSGGGG  420
SSGGPGPAGM KGLPGSAPTS SSTKKTQLQL EHLLLDLQMI LNGINNYKNP KLTRMLTFKF  480
YMPKKATELK HLQCLEEELK PLEEVLNLAQ SKNFHLRPRD LISNINVIVL ELKGSETTFM  540
CEYADETATI VEFLNRWITF CQSIISTLTH HHHHH                           575

SEQ ID NO: 132           moltype = AA  length = 704
FEATURE                  Location/Qualifiers
source                   1..704
                         mol_type = protein
                         organism = synthetic construct
SEQUENCE: 132
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGMKGLPGS GGGGSGGGGS  180
GGGGSGGGGS GGGGSGGGGS EVQLVESGGG LVQPGGSLRL SCAASGFTFS SYTLAWVRQA  240
PGKGLEWVAA IDSSSYTYSP DTVRGRFTIS RDNAKNSLYL QMNSLRAEDT AVYYCARDSN  300
WDALDYWGQG TTVTVSSSGG PGPAGMKGLP GSDIQMTQSP SSLSASVGDR VTITCKASQN  360
VGTNVGWYQQ KPGKAPKALI YSASFRYSGV PSRFSGSGSG TDFTLTISSL QPEDFATYYC  420
QQYYTYPYTF GGGTKVEIKG GGGSGGGGSG GGGSEVQLVE SGGGLVQPGN SLRLSCAASG  480
FTFSKFGMSW VRQAPGKGLE WVSSISGSGR DTLYAESVKG RFTISRDNAK TTLYLQMNSL  540
```

-continued

```
RPEDTAVYYC TIGGSLSVSS QGTLVTVSSG GGGSGGGGSG GGGSQVQLQE SGGGLVQAGG  600
SLRLSCAASG RIFSIDIMSW YRQAPGKQRE LVARITRGGT ISYDDSVKGR FTISRDNAKN  660
TVYLQMNSLK PEDTGVYYCN ALYGTDYWGK GTQVTVSSHH HHHH                   704

SEQ ID NO: 133         moltype = AA  length = 689
FEATURE                Location/Qualifiers
source                 1..689
                       mol_type = protein
                       organism = synthetic construct
SEQUENCE: 133
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGGGG SGGGGSGGGG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NVIVLELKGS ETTFMCEYAD ETATIVEFLN RWITFCQSII STLTSGGPGP AGMKGLPGSE  300
VQLVESGGGL VQPGNSLRLS CAASGFTFSK FGMSWVRQAP GKGLEWVSSI SGSGRDTLYA  360
ESVKGRFTIS RDNAKTTLYL QMNSLRPEDT AVYYCTIGGS LSVSSQGTLV TVSSGGGGSG  420
GGGSGGGGSG GGGSGGGGSG GGGSEVQLVE SGGGLVQPGG SLRLSCAASG FTFSSYTLAW  480
VRQAPGKGLE WVAAIDSSSY TYSPDTVRGR FTISRDNAKN SLYLQMNSLR AEDTAVYYCA  540
RDSNWDALDY WGQGTTVTVS SGGGGSGGGG SGGGGSDIQM TQSPSSLSAS VGDRVTITCK  600
ASQNVGTNVG WYQQKPGKAP KALIYSASFR YSGVPSRFSG SGSGTDFTLT ISSLQPEDFA  660
TYYCQQYYTY PYTFGGGTKV EIKHHHHHH                                    689

SEQ ID NO: 134         moltype = AA  length = 545
FEATURE                Location/Qualifiers
source                 1..545
                       mol_type = protein
                       organism = synthetic construct
SEQUENCE: 134
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGMKGLPGS EVQLVESGGG  180
LVQPGGSLRL SCAASGFTFS SYTLAWVRQA PGKGLEWVAA IDSSSYTYSP DTVRGRFTIS  240
RDNAKNSLYL QMNSLRAEDT AVYYCARDSN WDALDYWGQG TTVTVSSGGG GSGGGGSGGG  300
GSDIQMTQSP SSLSASVGDR VTITCKASQN VGTNVGWYQQ KPGKAPKALI YSASFRYSGV  360
PSRFSGSGSG TDFTLTISSL QPEDFATYYC QQYYTYPYTF GGGTKVEIKG GGGSGGGGSG  420
GGGSEVQLVE SGGGLVQPGN SLRLSCAASG FTFSKFGMSW VRQAPGKGLE WVSSISGSGR  480
DTLYAESVKG RFTISRDNAK TTLYLQMNSL RPEDTAVYYC TIGGSLSVSS QGTLVTVSSH  540
HHHHH                                                              545

SEQ ID NO: 135         moltype = AA  length = 575
FEATURE                Location/Qualifiers
source                 1..575
                       mol_type = protein
                       organism = synthetic construct
SEQUENCE: 135
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGMKGLPGS GGGGSGGGGS  180
GGGGSGGGGS GGGGSGGGGS EVQLVESGGG LVQPGGSLRL SCAASGFTFS SYTLAWVRQA  240
PGKGLEWVAA IDSSSYTYSP DTVRGRFTIS RDNAKNSLYL QMNSLRAEDT AVYYCARDSN  300
WDALDYWGQG TTVTVSSGGG GSGGGGSGGG GSDIQMTQSP SSLSASVGDR VTITCKASQN  360
VGTNVGWYQQ KPGKAPKALI YSASFRYSGV PSRFSGSGSG TDFTLTISSL QPEDFATYYC  420
QQYYTYPYTF GGGTKVEIKG GGGSGGGGSG GGGSEVQLVE SGGGLVQPGN SLRLSCAASG  480
FTFSKFGMSW VRQAPGKGLE WVSSISGSGR DTLYAESVKG RFTISRDNAK TTLYLQMNSL  540
RPEDTAVYYC TIGGSLSVSS QGTLVTVSSH HHHHH                             575

SEQ ID NO: 136         moltype = AA  length = 421
FEATURE                Location/Qualifiers
source                 1..421
                       mol_type = protein
                       organism = synthetic construct
SEQUENCE: 136
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSAPTSSSTK KTQLQLEHLL LDLQMILNGI  180
NNYKNPKLTR MLTFKFYMPK KATELKHLQC LEEELKPLEE VLNLAQSKNF HLRPRDLISN  240
INVIVLELKG SETTFMCEYA DETATIVEFL NRWITFCQSI ISTLTSGGPG PAGMKGLPGS  300
EVQLVESGGG LVQPGNSLRL SCAASGFTFS KFGMSWVRQA PGKGLEWVSS ISGSGRDTLY  360
AESVKGRFTI SRDNAKTTLY LQMNSLRPED TAVYYCTIGG SLSVSSQGTL VTVSSHHHHH  420
H                                                                  421

SEQ ID NO: 137         moltype = AA  length = 806
FEATURE                Location/Qualifiers
source                 1..806
                       mol_type = protein
                       organism = synthetic construct
SEQUENCE: 137
MDMRVPAQLL GLLLLWLRGA RCQVQLQESG GGLVQAGGSL RLSCAASGRI FSIDIMSWYR  60
```

-continued

```
QAPGKQRELV ARITRGGTIS YDDSVKGRFT ISRDNAKNTV YLQMNSLKPE DTGVYYCNAL  120
YGTDYWGKGT QVTVSSGSGS GSGSGSGSGS GSEVQLVESG GGLVQPGNSL RLSCAASGFT  180
FSKFGMSWVR QAPGKGLEWV SSISGSGRDT LYAESVKGRF TISRDNAKTT LYLQMNSLRP  240
EDTAVYYCTI GGSLSVSSQG TLVTVSSGSG SGSGSGSGSG SGSQVQLQES GGGLVQAGGS  300
LRLSCAASGR IFSIDIMSWY RQAPGKQREL VARITRGGTI SYDDSVKGRF TISRDNAKNT  360
VYLQMNSLKP EDTGVYYCNA LYGTDYWGKG TQVTVSSGSG SGSGSGSGSG SGSEVQLVES  420
GGGLVQPGGS LRLSCAASGF TFSSYTLAWV RQAPGKGLEW VAAIDSSSYT YSPDTVRGRF  480
TISRDNAKNS LYLQMNSLRA EDTAVYYCAR DSNWDALDYW GQGTTVTVSS GGGGSGGGGS  540
GGGGSDIQMT QSPSSLSASV GDRVTITCKA SQNVGTNVGW YQQKPGKAPK ALIYSASFRY  600
SGVPSRFSGS GSGTDFTLTI SSLQPEDFAT YYCQQYYTYP YTFGGGTKVE IKSGGPGPAG  660
MKGLPGSAPT SSSTKKTQLQ LEHLLLDLQM ILNGINNYKN PKLTRMLTFK FYMPKKATEL  720
KHLQCLEEEL KPLEEVLNLA QSKNFHLRPR DLISNINVIV LELKGSETTF MCEYADETAT  780
IVEFLNRWIT FCQSIISTLT HHHHHH                                       806

SEQ ID NO: 138         moltype = AA  length = 676
FEATURE                Location/Qualifiers
source                 1..676
                       mol_type = protein
                       organism = synthetic construct
SEQUENCE: 138
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGSGS GSGSGSGSGS GSEVQLVESG GGLVQPGNSL RLSCAASGFT  180
FSKFGMSWVR QAPGKGLEWV SSISGSGRDT LYAESVKGRF TISRDNAKTT LYLQMNSLRP  240
EDTAVYYCTI GGSLSVSSQG TLVTVSSGSG SGSGSGSGSG SGSEVQLVES GGGLVQPGGS  300
LRLSCAASGF TFSSYTLAWV RQAPGKGLEW VAAIDSSSYT YSPDTVRGRF TISRDNAKNS  360
LYLQMNSLRA EDTAVYYCAR DSNWDALDYW GQGTTVTVSS GGGGSGGGGS GGGGSDIQMT  420
QSPSSLSASV GDRVTITCKA SQNVGTNVGW YQQKPGKAPK ALIYSASFRY SGVPSRFSGS  480
GSGTDFTLTI SSLQPEDFAT YYCQQYYTYP YTFGGGTKVE IKSGGPGPAG MKGLPGSAPT  540
SSSTKKTQLQ LEHLLLDLQM ILNGINNYKN PKLTRMLTFK FYMPKKATEL KHLQCLEEEL  600
KPLEEVLNLA QSKNFHLRPR DLISNINVIV LELKGSETTF MCEYADETAT IVEFLNRWIT  660
FCQSIISTLT HHHHHH                                                  676

SEQ ID NO: 139         moltype = AA  length = 421
FEATURE                Location/Qualifiers
source                 1..421
                       mol_type = protein
                       organism = synthetic construct
SEQUENCE: 139
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGSGS GSGSGSGSGS GSEVQLVESG GGLVQPGNSL RLSCAASGFT  180
FSKFGMSWVR QAPGKGLEWV SSISGSGRDT LYAESVKGRF TISRDNAKTT LYLQMNSLRP  240
EDTAVYYCTI GGSLSVSSQG TLVTVSSSGG PGPAGMKGLP GSAPTSSSTK KTQLQLEHLL  300
LDLQMILNGI NNYKNPKLTR MLTFKFYMPK KATELKHLQC LEEELKPLEE VLNLAQSKNF  360
HLRPRDLISN INVIVLELKG SETTFMCEYA DETATIVEFL NRWITFCQSI ISTLTHHHHH  420
H                                                                  421

SEQ ID NO: 140         moltype = AA  length = 420
FEATURE                Location/Qualifiers
source                 1..420
                       mol_type = protein
                       organism = synthetic construct
SEQUENCE: 140
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSSGGP GPAGMKGLPG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NVIVLELKGS ETTFMCEYAD ETATIVEFLN RWITFCQSII STLTSGGPGP AGMKGLPGSE  300
VQLVESGGGL VQPGNSLRLS CAASGFTFSK FGMSWVRQAP GKGLEWVSSI SGSGRDTLYA  360
ESVKGRFTIS RDNAKTTLYL QMNSLRPEDT AVYYCTIGGS LSVSSQGTLV TVSSHHHHHH  420

SEQ ID NO: 141         moltype = AA  length = 550
FEATURE                Location/Qualifiers
source                 1..550
                       mol_type = protein
                       organism = synthetic construct
SEQUENCE: 141
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGGGG SGGGGSGGGG SEVQLVESGG GLVQPGNSLR LSCAASGFTF  180
SKFGMSWVRQ APGKGLEWVS SISGSGRDTL YAESVKGRFT ISRDNAKTTL YLQMNSLRPE  240
DTAVYYCTIG GSLSVSSQGT LVTVSSSGGP GPAGMKGLPG SAPTSSSTKK TQLQLEHLLL  300
DLQMILNGIN NYKNPKLTRM LTFKFYMPKK ATELKHLQCL EEELKPLEEV LNLAQSKNFH  360
LRPRDLISNI NVIVLELKGS ETTFMCEYAD ETATIVEFLN RWITFCQSII STLTSGGPGP  420
AGMKGLPGSE VQLVESGGGL VQPGNSLRLS CAASGFTFSK FGMSWVRQAP GKGLEWVSSI  480
SGSGRDTLYA ESVKGRFTIS RDNAKTTLYL QMNSLRPEDT AVYYCTIGGS LSVSSQGTLV  540
TVSSHHHHHH                                                         550
```

-continued

```
SEQ ID NO: 142          moltype = AA  length = 420
FEATURE                 Location/Qualifiers
source                  1..420
                        mol_type = protein
                        organism = synthetic construct
SEQUENCE: 142
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGGGG SGGGGSGGGG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NVIVLELKGS ETTFMCEYAD ETATIVEFLN RWITFCQSII STLTSGGPGP AGMKGLPGSE  300
VQLVESGGGL VQPGNSLRLS CAASGFTFSK FGMSWVRQAP GKGLEWVSSI SGSGRDTLYA  360
ESVKGRFTIS RDNAKTTLYL QMNSLRPEDT AVYYCTIGGS LSVSSQGTLV TVSSHHHHHH  420

SEQ ID NO: 143          moltype = AA  length = 290
FEATURE                 Location/Qualifiers
source                  1..290
                        mol_type = protein
                        organism = synthetic construct
SEQUENCE: 143
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGGGG SGGGGSGGGG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NVIVLELKGS ETTFMCEYAD ETATIVEFLN RWITFCQSII STLTHHHHHH             290

SEQ ID NO: 144          moltype = AA  length = 291
FEATURE                 Location/Qualifiers
source                  1..291
                        mol_type = protein
                        organism = synthetic construct
SEQUENCE: 144
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGMKGLPGS EVQLVESGGG  180
LVQPGNSLRL SCAASGFTFS KFGMSWVRQA PGKGLEWVSS ISGSGRDTLY AESVKGRFTI  240
SRDNAKTTLY LQMNSLRPED TAVYYCTIGG SLSVSSQGTL VTVSSHHHHH H           291

SEQ ID NO: 145          moltype = AA  length = 689
FEATURE                 Location/Qualifiers
source                  1..689
                        mol_type = protein
                        organism = synthetic construct
SEQUENCE: 145
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSSGGP GPAGMKGLPG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NVIVLELKGS ETTFMCEYAD ETATIVEFLN RWITFCQSII STLTSGGPGP AGMKGLPGSE  300
VQLVESGGGL VQPGNSLRLS CAASGFTFSK FGMSWVRQAP GKGLEWVSSI SGSGRDTLYA  360
ESVKGRFTIS RDNAKTTLYL QMNSLRPEDT AVYYCTIGGS LSVSSQGTLV TVSSGGGGSG  420
GGGSGGGGSG GGGSGGGGSG GGGSEVQLVE SGGGLVQPGG SLRLSCAASG FTFSSYTLAW  480
VRQAPGKGLE WVAAIDSSSY TYSPDTVRGR FTISRDNAKN SLYLQMNSLR AEDTAVYYCA  540
RDSNWDALDY WGQGTTVTVS SGGGGSGGGG SGGGGSDIQM TQSPSSLSAS VGDRVTITCK  600
ASQNVGTNVG WYQQKPGKAP KALIYSASFR YSGVPSRFSG SGSGTDFTLT ISSLQPEDFA  660
TYYCQQYYTY PYTFGGGTKV EIKHHHHHH                                    689

SEQ ID NO: 146          moltype = AA  length = 704
FEATURE                 Location/Qualifiers
source                  1..704
                        mol_type = protein
                        organism = synthetic construct
SEQUENCE: 146
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGMKGLPGS GGGGSGGGGS  180
GGGGSGGGGS GGGGSGGGGS EVQLVESGGG LVQPGGSLRL SCAASGFTFS SYTLAWVRQA  240
PGKGLEWVAA IDSSSYTYSP DTVRGRFTIS RDNAKNSLYL QMNSLRAEDT AVYYCARDSN  300
WDALDYWGQG TTVTVSSGGG GSGGGGSGGG GSDIQMTQSP SSLSASVGDR VTITCKASQN  360
VGTNVGWYQQ KPGKAPKALI YSASFRYSGV PSRFSGSGSG TDFTLTISSL QPEDFATYYC  420
QQYYTYPYTF GGGTKVEIKG GGGSGGGGSG GGGSEVQLVE SGGGLVQPGN SLRLSCAASG  480
FTFSKFGMSW VRQAPGKGLE WVSSISGSGR DTLYAESVKG RFTISRDNAK TTLYLQMNSL  540
RPEDTAVYYC TIGGSLSVSS QGTLVTVSSG GGGSGGGGSG GGGSQVQLQE SGGGLAQAGG  600
SLSLSCAASG FTVSNSVMAW YRQTPGKQRE FVAIINSVGS TNYADSVKGR FTISRDNAKN  660
TVYLQMNNLK PEDTAVYVCN RNFDRIYWGQ GTQVTVSSHH HHHH                   704

SEQ ID NO: 147          moltype = AA  length = 674
FEATURE                 Location/Qualifiers
source                  1..674
```

```
                         mol_type = protein
                         organism = synthetic construct
SEQUENCE: 147
MDMRVPAQLL GLLLLWLRGA RCQVQLQESG GGLAQAGGSL SLSCAASGFT VSNSVMAWYR  60
QTPGKQREFV AIINSVGSTN YADSVKGRFT ISRDNAKNTV YLQMNNLKPE DTAVYVCNRN  120
FDRIYWGQGT QVTVSSAPTS SSTKKTQLQL EHLLLDLQMI LNGINNYKNP KLTRMLTFKF  180
YMPKKATELK HLQCLEEELK PLEEVLNLAQ SKNFHLRPRD LISNINVIVL ELKGSETTFM  240
CEYADETATI VEFLNRWITF CQSIISTLTS GGPGPAGMKG LPGSEVQLVE SGGGLVQPGN  300
SLRLSCAASG FTFSKFGMSW VRQAPGKGLE WVSSISGSGR DTLYAESVKG RFTISRDNAK  360
TTLYLQMNSL RPEDTAVYYC TIGGSLSVSS QGTLVTVSSG GGGSGGGGSG GGGSGGGGSG  420
GGGSGGGGSE VQLVESGGGL VQPGGSLRLS CAASGFTFSS YTLAWVRQAP GKGLEWVAAI  480
DSSSYTYSPD TVRGRFTISR DNAKNSLYLQ MNSLRAEDTA VYYCARDSNW DALDYWGQGT  540
TVTVSSGGGG SGGGGSGGGG SDIQMTQSPS SLSASVGDRV TITCKASQNV GTNVGWYQQK  600
PGKAPKALIY SASFRYSGVP SRFSGSGSGT DFTLTISSLQ PEDFATYYCQ QYYTYPYTFG  660
GGTKVEIKHH HHHH                                                    674

SEQ ID NO: 148           moltype = AA  length = 704
FEATURE                  Location/Qualifiers
source                   1..704
                         mol_type = protein
                         organism = synthetic construct
SEQUENCE: 148
MDMRVPAQLL GLLLLWLRGA RCEVQLVESG GGLVQPGGSL RLSCAASGFT FSSYTLAWVR  60
QAPGKGLEWV AAIDSSSYTY SPDTVRGRFT ISRDNAKNSL YLQMNSLRAE DTAVYYCARD  120
SNWDALDYWG QGTTVTVSSG GGGSGGGGSG GGGSDIQMTQ SPSSLSASVG DRVTITCKAS  180
QNVGTNVGWY QQKPGKAPKA LIYSASFRYS GVPSRFSGSG SGTDFTLTIS SLQPEDFATY  240
YCQQYYTYPY TFGGGTKVEI KGGGGSGGGG SGGGGSGGGG SGGGGSGGGG SSGGPGPAGM  300
KGLPGSAPTS SSTKKTQLQL EHLLLDLQMI LNGINNYKNP KLTRMLTFKF YMPKKATELK  360
HLQCLEEELK PLEEVLNLAQ SKNFHLRPRD LISNINVIVL ELKGSETTFM CEYADETATI  420
VEFLNRWITF CQSIISTLTS GGPGPAGMKG LPGSEVQLVE SGGGLVQPGN SLRLSCAASG  480
FTFSKFGMSW VRQAPGKGLE WVSSISGSGR DTLYAESVKG RFTISRDNAK TTLYLQMNSL  540
RPEDTAVYYC TIGGSLSVSS QGTLVTVSSG GGGSGGGGSG GGGSQVQLQE SGGGLAQAGG  600
SLSLSCAASG FTVSNSVMAW YRQTPGKQRE FVAIINSVGS TNYADSVKGR FTISRDNAKN  660
TVYLQMNNLK PEDTAVYVCN RNFDRIYWGQ GTQVTVSSHH HHHH                  704

SEQ ID NO: 149           moltype = AA  length = 704
FEATURE                  Location/Qualifiers
source                   1..704
                         mol_type = protein
                         organism = synthetic construct
SEQUENCE: 149
MDMRVPAQLL GLLLLWLRGA RCQVQLQESG GGLAQAGGSL SLSCAASGFT VSNSVMAWYR  60
QTPGKQREFV AIINSVGSTN YADSVKGRFT ISRDNAKNTV YLQMNNLKPE DTAVYVCNRN  120
FDRIYWGQGT QVTVSSGGGG SGGGGSGGGG SEVQLVESGG GLVQPGNSLR LSCAASGFTF  180
SKFGMSWVRQ APGKGLEWVS SISGSGRDTL YAESVKGRFT ISRDNAKTTL YLQMNSLRPE  240
DTAVYYCTIG GSLSVSSQGT LVTVSSSGGP GPAGMKGLPG SEVQLVESGG GLVQPGGSLR  300
LSCAASGFTF SSYTLAWVRQ APGKGLEWVA AIDSSSYTYS PDTVRGRFTI SRDNAKNSLY  360
LQMNSLRAED TAVYYCARDS NWDALDYWGQ GTTVTVSSGG GGSGGGGSGG GGSDIQMTQS  420
PSSLSASVGD RVTITCKASQ NVGTNVGWYQ QKPGKAPKAL IYSASFRYSG VPSRFSGSGS  480
GTDFTLTISS LQPEDFATYY CQQYYTYPYT FGGGTKVEIK GGGGSGGGGS GGGGSGGGGS  540
GGGGSGGGGS SGGPGPAGMK GLPGSAPTSS STKKTQLQLE HLLLDLQMIL NGINNYKNPK  600
LTRMLTFKFY MPKKATELKH LQCLEEELKP LEEVLNLAQS KNFHLRPRDL ISNINVIVLE  660
LKGSETTFMC EYADETATIV EFLNRWITFC QSIISTLTHH HHHH                  704

SEQ ID NO: 150           moltype = AA  length = 689
FEATURE                  Location/Qualifiers
source                   1..689
                         mol_type = protein
                         organism = synthetic construct
SEQUENCE: 150
MDMRVPAQLL GLLLLWLRGA RCEVQLVESG GGLVQPGGSL RLSCAASGFT FSSYTLAWVR  60
QAPGKGLEWV AAIDSSSYTY SPDTVRGRFT ISRDNAKNSL YLQMNSLRAE DTAVYYCARD  120
SNWDALDYWG QGTTVTVSSG GGGSGGGGSG GGGSDIQMTQ SPSSLSASVG DRVTITCKAS  180
QNVGTNVGWY QQKPGKAPKA LIYSASFRYS GVPSRFSGSG SGTDFTLTIS SLQPEDFATY  240
YCQQYYTYPY TFGGGTKVEI KGGGGSGGGG SGGGGSGGGG SGGGGSGGGG SEVQLVESGG  300
GLVQPGNSLR LSCAASGFTF SKFGMSWVRQ APGKGLEWVS SISGSGRDTL YAESVKGRFT  360
ISRDNAKTTL YLQMNSLRPE DTAVYYCTIG GSLSVSSQGT LVTVSSSGGP GPAGMKGLPG  420
SAPTSSSTKK TQLQLEHLLL DLQMILNGIN NYKNPKLTRM LTFKFYMPKK ATELKHLQCL  480
EEELKPLEEV LNLAQSKNFH LRPRDLISNI NVIVLELKGS ETTFMCEYAD ETATIVEFLN  540
RWITFCQSII STLTGGGGSG GGGSGGGGSQ VQLQESGGGL AQAGGSLSLS CAASGFTVSN  600
SVMAWYRQTP GKQREFVAII NSVGSTNYAD SVKGRFTISR DNAKNTVYLQ MNNLKPEDTA  660
VYVCNRNFDR IYWGQGTQVT VSSHHHHHH                                   689

SEQ ID NO: 151           moltype = AA  length = 700
FEATURE                  Location/Qualifiers
source                   1..700
                         mol_type = protein
                         organism = synthetic construct
SEQUENCE: 151
```

-continued

```
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGGGG SGGGGSGGGG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NVIVLELKGS ETTFMCEYAD ETATIVEFLN RWITFCQSII STLTSGGPGP AGMKGLPGSR  300
GETGPAAPGS EVQLVESGGG LVQPGNSLRL SCAASGFTFS KFGMSWVRQA PGKGLEWVSS  360
ISGSGRDTLY AESVKGRFTI SRDNAKTTLY LQMNSLRPED TAVYYCTIGG SLSVSSQGTL  420
VTVSSGGGGS GGGGSGGGGS GGGGSGGGGS GGGGSEVQLV ESGGGLVQPG GSLRLSCAAS  480
GFTFSSYTLA WVRQAPGKGL EWVAAIDSSS YTYSPDTVRG RFTISRDNAK NSLYLQMNSL  540
RAEDTAVYYC ARDSNWDALD YWGQGTTVTV SSGGGGSGGG GSGGGGSDIQ MTQSPSSLSA  600
SVGDRVTITC KASQNVGTNV GWYQQKPGKA PKALIYSASF RYSGVPSRFS GSGSGTDFTL  660
TISSLQPEDF ATYYCQQYYT YPYTFGGGTK VEIKHHHHHH                       700

SEQ ID NO: 152         moltype = AA  length = 276
FEATURE                Location/Qualifiers
source                 1..276
                       mol_type = protein
                       organism = synthetic construct
SEQUENCE: 152
MDMRVPAQLL GLLLLWLRGA RCEVQLVESG GGLVQPGGSL RLSCAASGFT FSSYAMSWVR  60
QAPGKGLEWV SAISGSGGST YYADSVKGRF TISRDNSKNT LYLQMNSLRA EDTAVYYCAR  120
GVGAFRPYRK HEWGQGTLVT VSRGGGGSGG GGSGGGGSSS ELTQDPAVSV ALGQTVRITC  180
QGDSLRSYYA SWYQQKPGQA PVLVIYGKNN RPSGIPDRFS GSSSGNTASL TTTGAQAEDE  240
ADYYCNSSPF EHNLVVFGGG TKLTVLHHHH HHEPEA                           276

SEQ ID NO: 153         moltype = AA  length = 279
FEATURE                Location/Qualifiers
source                 1..279
                       mol_type = protein
                       organism = synthetic construct
SEQUENCE: 153
MDMRVPAQLL GLLLLWLRGA RCQVQLQQSG AELVRPGTSV KVSCKASGYA FTNYLIEWVK  60
QRPGQGLEWI GVINPGSGGT NYNEKFKGKA TLTADKSSST AYMQLSSLTS DDSAVYFCAR  120
WRGDGYYAYF DVWGAGTTVT VSSGGGGSGG GGSGGGGSDI VLTQSPASLA VSLGQRATIS  180
CKASQSVDYD GDSYMNWYQQ KPGQPPKLLI YAASNLESGI PARFSGSGSG TDFTLNIHPV  240
EEEDAATYYC QQSNEDPYTF GGGTKLEIKH HHHHHEPEA                        279

SEQ ID NO: 154         moltype = AA  length = 279
FEATURE                Location/Qualifiers
source                 1..279
                       mol_type = protein
                       organism = synthetic construct
SEQUENCE: 154
MDMRVPAQLL GLLLLWLRGA RCQVQLQQSG AELVRPGTSV KVSCKASGYA FTNYLIEWVK  60
QRPGQGLEWI GVINPGSGGT NYNEKFKGKA TLTADKSSST AYMQLSSLTS DDSAVYFCAR  120
WRGDGYYAYF DVWGAGTTVT VSSSGGPGPA GMKGLPGSDI VLTQSPASLA VSLGQRATIS  180
CKASQSVDYD GDSYMNWYQQ KPGQPPKLLI YAASNLESGI PARFSGSGSG TDFTLNIHPV  240
EEEDAATYYC QQSNEDPYTF GGGTKLEIKH HHHHHEPEA                        279

SEQ ID NO: 155         moltype = AA  length = 279
FEATURE                Location/Qualifiers
source                 1..279
                       mol_type = protein
                       organism = synthetic construct
SEQUENCE: 155
MDMRVPAQLL GLLLLWLRGA RCDIVLTQSP ASLAVSLGQR ATISCKASQS VDYDGDSYMN  60
WYQQKPGQPP KLLIYAASNL ESGIPARFSG SGSGTDFTLN IHPVEEEDAA TYYCQQSNED  120
PYTFGGGTKL EIKGGGGSGG GGSGGGGSQV QLQQSGAELV RPGTSVKVSC KASGYAFTNY  180
LIEWVKQRPG QGLEWIGVIN PGSGGTNYNE KFKGKATLTA DKSSSTAYMQ LSSLTSDDSA  240
VYFCARWRGD GYYAYFDVWG AGTTVTVSSH HHHHHEPEA                        279

SEQ ID NO: 156         moltype = AA  length = 279
FEATURE                Location/Qualifiers
source                 1..279
                       mol_type = protein
                       organism = synthetic construct
SEQUENCE: 156
MDMRVPAQLL GLLLLWLRGA RCDIVLTQSP ASLAVSLGQR ATISCKASQS VDYDGDSYMN  60
WYQQKPGQPP KLLIYAASNL ESGIPARFSG SGSGTDFTLN IHPVEEEDAA TYYCQQSNED  120
PYTFGGGTKL EIKSGGPGPA GMKGLPGSQV QLQQSGAELV RPGTSVKVSC KASGYAFTNY  180
LIEWVKQRPG QGLEWIGVIN PGSGGTNYNE KFKGKATLTA DKSSSTAYMQ LSSLTSDDSA  240
VYFCARWRGD GYYAYFDVWG AGTTVTVSSH HHHHHEPEA                        279

SEQ ID NO: 157         moltype = AA  length = 295
FEATURE                Location/Qualifiers
source                 1..295
                       mol_type = protein
                       organism = synthetic construct
SEQUENCE: 157
```

```
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTGGGGS GGGGSGGGGS EVQLVESGGG  180
LVQPGNSLRL SCAASGFTFS KFGMSWVRQA PGKGLEWVSS ISGSGRDTLY AESVKGRFTI  240
SRDNAKTTLY LQMNSLRPED TAVYYCTIGG SLSVSSQGTL VTVSSHHHHH HEPEA       295

SEQ ID NO: 158         moltype = AA  length = 765
FEATURE                Location/Qualifiers
source                 1..765
                       mol_type = protein
                       organism = synthetic construct
SEQUENCE: 158
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTGGGGS GGGGSGGGGS DAHKSEVAHR  180
FKDLGEENFK ALVLIAFAQY LQQCPFEDHV KLVNEVTEFA KTCVADESAE NCDKSLHTLF  240
GDKLCTVATL RETYGEMADC CAKQEPERNE CFLQHKDDNP NLPRLVRPEV DVMCTAFHDN  300
EETFLKKYLY EIARRHPYFY APELLFFAKR YKAAFTECCQ AADKAACLLP KLDELRDEGK  360
ASSAKQRLKC ASLQKFGERA FKAWAVARLS QRFPKAEFAE VSKLVTDLTK VHTECCHGDL  420
LECADDRADL AKYICENQDS ISSKLKECCE KPLLEKSHCI AEVENDEMPA DLPSLAADFV  480
ESKDVCKNYA EAKDVFLGMF LYEYARRHPD YSVVLLLRLA KTYETTLEKC CAAADPHECY  540
AKVFDEFKPL VEEPQNLIKQ NCELFEQLGE YKFQNALLVR YTKKVPQVST PTLVEVSRNL  600
GKVGSKCCKH PEAKRMPCAE DYLSVVLNQL CVLHEKTPVS DRVTKCCTES LVNRRPCFSA  660
LEVDETYVPK EFNAETFTFH ADICTLSEKE RQIKKQTALV ELVKHKPKAT KEQLKAVMDD  720
FAAFVEKCCK ADDKETCFAE EGKKLVAASQ AALGLHHHHH HEPEA                  765

SEQ ID NO: 159         moltype = AA  length = 765
FEATURE                Location/Qualifiers
source                 1..765
                       mol_type = protein
                       organism = synthetic construct
SEQUENCE: 159
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTGGGGS GGGGSGGGGS DAHKSEVAHR  180
FKDLGEENFK ALVLIAFAQY LQQCPFEDHV KLVNEVTEFA KTCVADESAE NCDKSLHTLF  240
GDKLCTVATL RETYGEMADC CAKQEPERNE CFLQHKDDNP NLPRLVRPEV DVMCTAFHDN  300
EETFLKKYLY EIARRHPYFY APELLFFAKR YKAAFTECCQ AADKAACLLP KLDELRDEGK  360
ASSAKQRLKC ASLQKFGERA FKAWAVARLS QRFPKAEFAE VSKLVTDLTK VHTECCHGDL  420
LECADDRADL AKYICENQDS ISSKLKECCE KPLLEKSHCI AEVENDEMPA DLPSLAADFV  480
ESKDVCKNYA EAKDVFLGMF LYEYARRHPD YSVVLLLRLA KTYETTLEKC CAAADPHECY  540
AKVFDEFKPL VEEPQNLIKQ NCELFEQLGE YKFQNALLVR YTKKVPQVST PTLVEVSRNL  600
GKVGSKCCKH PEAKRMPCAE DYLSVVLNQL CVLHEKTPVS DRVTKCCTES LVNRRPCFSA  660
LEVDETYVPK EFNAETFTFH ADICTLSEKE RQIKKQTALV ELVKHKPKAT KEQLKAVMDD  720
FAAFVEKCCK ADDKETCFAE EGKKLVAASQ AALGLHHHHH HEPEA                  765

SEQ ID NO: 160         moltype = AA  length = 765
FEATURE                Location/Qualifiers
source                 1..765
                       mol_type = protein
                       organism = synthetic construct
SEQUENCE: 160
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGMKGLPGS DAHKSEVAHR  180
FKDLGEENFK ALVLIAFAQY LQQCPFEDHV KLVNEVTEFA KTCVADESAE NCDKSLHTLF  240
GDKLCTVATL RETYGEMADC CAKQEPERNE CFLQHKDDNP NLPRLVRPEV DVMCTAFHDN  300
EETFLKKYLY EIARRHPYFY APELLFFAKR YKAAFTECCQ AADKAACLLP KLDELRDEGK  360
ASSAKQRLKC ASLQKFGERA FKAWAVARLS QRFPKAEFAE VSKLVTDLTK VHTECCHGDL  420
LECADDRADL AKYICENQDS ISSKLKECCE KPLLEKSHCI AEVENDEMPA DLPSLAADFV  480
ESKDVCKNYA EAKDVFLGMF LYEYARRHPD YSVVLLLRLA KTYETTLEKC CAAADPHECY  540
AKVFDEFKPL VEEPQNLIKQ NCELFEQLGE YKFQNALLVR YTKKVPQVST PTLVEVSRNL  600
GKVGSKCCKH PEAKRMPCAE DYLSVVLNQL CVLHEKTPVS DRVTKCCTES LVNRRPCFSA  660
LEVDETYVPK EFNAETFTFH ADICTLSEKE RQIKKQTALV ELVKHKPKAT KEQLKAVMDD  720
FAAFVEKCCK ADDKETCFAE EGKKLVAASQ AALGLHHHHH HEPEA                  765

SEQ ID NO: 161         moltype = AA  length = 708
FEATURE                Location/Qualifiers
source                 1..708
                       mol_type = protein
                       organism = synthetic construct
SEQUENCE: 161
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGMKGLPGS EVQLVESGGG  180
LVQPGNSLRL SCAASGFTFS KFGMSWVRQA PGKGLEWVSS ISGSGRDTLY AESVKGRFTI  240
SRDNAKTTLY LQMNSLRPED TAVYYCTIGG SLSVSSQGTL VTVSSGGGGS GGGGSGGGGS  300
GGGGSGGGGS GGGGSSGGPG PAGMKGLPGS EVQLVESGGG LVQPGGSLRL SCAASGFTFS  360
SYTLAWVRQA PGKGLEWVAA IDSSSYTYSP DTVRGRFTIS RDNAKNSLYL QMNSLRAEDT  420
```

-continued

```
AVYYCARDSN WDALDYWGQG TTVTVSSGGG GSGGGGSGGG GSDIQMTQSP SSLSASVGDR  480
VTITCKASQN VGTNVGWYQQ KPGKAPKALI YSASFRYSGV PSRFSGSGSG TDFTLTISSL  540
QPEDFATYYC QQYYTYPYTF GGGTKVEIKG GGGSGGGGSG GGGSQVQLQE SGGGLAQAGG  600
SLSLSCAASG FTVSNSVMAW YRQTPGKQRE FVAIINSVGS TNYADSVKGR FTISRDNAKN  660
TVYLQMNNLK PEDTAVYVCN RNFDRIYWGQ GTQVTVSSHH HHHHEPEA              708

SEQ ID NO: 162          moltype = AA  length = 708
FEATURE                 Location/Qualifiers
source                  1..708
                        mol_type = protein
                        organism = synthetic construct
SEQUENCE: 162
MDMRVPAQLL GLLLLWLRGA RCQVQLQESG GGLAQAGGSL SLSCAASGFT VSNSVMAWYR  60
QTPGKQREFV AIINSVGSTN YADSVKGRFT ISRDNAKNTV YLQMNNLKPE DTAVYVCNRN  120
FDRIYWGQGT QVTVSSGGGG SGGGGSGGGG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NVIVLELKGS ETTFMCEYAD ETATIVEFLN RWITFCQSII STLTSGGPGP AGMKGLPGSE  300
VQLVESGGGL VQPGNSLRLS CAASGFTFSK FGMSWVRQAP GKGLEWVSSI SGSGRDTLYA  360
ESVKGRFTIS RDNAKTTLYL QMNSLRPEDT AVYYCTIGGS LSVSSQGTLV TVSSGGGGSG  420
GGGSGGGGSG GGGSGGGGSG GGGSSGGPGP AGMKGLPGSE VQLVESGGGL VQPGGSLRLS  480
CAASGFTFSS YTLAWVRQAP GKGLEWVAAI DSSSYTYSPD TVRGRFTISR DNAKNSLYLQ  540
MNSLRAEDTA VYYCARDSNW DALDYWGQGT TVTVSSGGGG SGGGGSGGGG SDIQMTQSPS  600
SLSASVGDRV TITCKASQNV GTNVGWYQQK PGKAPKALIY SASFRYSGVP SRFSGSGSGT  660
DFTLTISSLQ PEDFATYYCQ QYYTYPYTFG GGTKVEIKHH HHHHEPEA              708

SEQ ID NO: 163          moltype = AA  length = 708
FEATURE                 Location/Qualifiers
source                  1..708
                        mol_type = protein
                        organism = synthetic construct
SEQUENCE: 163
MDMRVPAQLL GLLLLWLRGA RCQVQLQESG GGLAQAGGSL SLSCAASGFT VSNSVMAWYR  60
QTPGKQREFV AIINSVGSTN YADSVKGRFT ISRDNAKNTV YLQMNNLKPE DTAVYVCNRN  120
FDRIYWGQGT QVTVSSSGGP GPAGMKGLPG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NVIVLELKGS ETTFMCEYAD ETATIVEFLN RWITFCQSII STLTSGGPGP AGMKGLPGSE  300
VQLVESGGGL VQPGNSLRLS CAASGFTFSK FGMSWVRQAP GKGLEWVSSI SGSGRDTLYA  360
ESVKGRFTIS RDNAKTTLYL QMNSLRPEDT AVYYCTIGGS LSVSSQGTLV TVSSGGGGSG  420
GGGSGGGGSG GGGSGGGGSG GGGSSGGPGP AGMKGLPGSE VQLVESGGGL VQPGGSLRLS  480
CAASGFTFSS YTLAWVRQAP GKGLEWVAAI DSSSYTYSPD TVRGRFTISR DNAKNSLYLQ  540
MNSLRAEDTA VYYCARDSNW DALDYWGQGT TVTVSSGGGG SGGGGSGGGG SDIQMTQSPS  600
SLSASVGDRV TITCKASQNV GTNVGWYQQK PGKAPKALIY SASFRYSGVP SRFSGSGSGT  660
DFTLTISSLQ PEDFATYYCQ QYYTYPYTFG GGTKVEIKHH HHHHEPEA              708

SEQ ID NO: 164          moltype = AA  length = 161
FEATURE                 Location/Qualifiers
source                  1..161
                        mol_type = protein
                        organism = synthetic construct
SEQUENCE: 164
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTHHHHH H                     161

SEQ ID NO: 165          moltype = AA  length = 708
FEATURE                 Location/Qualifiers
source                  1..708
                        mol_type = protein
                        organism = synthetic construct
SEQUENCE: 165
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGMKGLPGS EVQLVESGGG  180
LVQPGNSLRL SCAASGFTFS KFGMSWVRQA PGKGLEWVSS ISGSGRDTLY AESVKGRFTI  240
SRDNAKTTLY LQMNSLRPED TAVYYCTIGG SLSVSSQGTL VTVSSGGGGS GGGGSGGGGS  300
GGGGSGGGGS GGGGSSGGPG PAGMKGLPGS EVQLVESGGG LVQPGGSLRL SCAASGFTFS  360
SYTLAWVRQA PGKGLEWVAA IDSSSYTYSP DTVRGRFTIS RDNAKNSLYL QMNSLRAEDT  420
AVYYCARDSN WDALDYWGQG TTVTVSSGGG GSGGGGSGGG GSDIQMTQSP SSLSASVGDR  480
VTITCKASQN VGTNVGWYQQ KPGKAPKALI YSASFRYSGV PSRFSGSGSG TDFTLTISSL  540
QPEDFATYYC QQYYTYPYTF GGGTKVEIKG GGGSGGGGSG GGGSQVQLQE SGGGLVQAGG  600
SLRLSCAASG RIFSIDIMSW YRQAPGKQRE LVARITRGGT ISYDDSVKGR FTISRDNAKN  660
TVYLQMNSLK PEDTGVYYCN ALYGTDYWGK GTQVTVSSHH HHHHEPEA              708

SEQ ID NO: 166          moltype = AA  length = 708
FEATURE                 Location/Qualifiers
source                  1..708
                        mol_type = protein
                        organism = synthetic construct
SEQUENCE: 166
```

```
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGGGG SGGGGSGGGG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NVIVLELKGS ETTFMCEYAD ETATIVEFLN RWITFCQSII STLTSGGPGP AGMKGLPGSE  300
VQLVESGGGL VQPGNSLRLS CAASGFTFSK FGMSWVRQAP GKGLEWVSSI SGSGRDTLYA  360
ESVKGRFTIS RDNAKTTLYL QMNSLRPEDT AVYYCTIGGS LSVSSQGTLV TVSSGGGGSG  420
GGGSGGGGSG GGGSGGGGSG GGGSSGGPGP AGMKGLPGSE VQLVESGGGL VQPGGSLRLS  480
CAASGFTFSS YTLAWVRQAP GKGLEWVAAI DSSSYTYSPD TVRGRFTISR DNAKNSLYLQ  540
MNSLRAEDTA VYYCARDSNW DALDYWGQGT TVTVSSGGGG SGGGGSGGGG SDIQMTQSPS  600
SLSASVGDRV TITCKASQNV GTNVGWYQQK PGKAPKALIY SASFRYSGVP SRFSGSGSGT  660
DFTLTISSLQ PEDFATYYCQ QYYTYPYTFG GGTKVEIKHH HHHHEPEA                708

SEQ ID NO: 167          moltype = AA  length = 708
FEATURE                 Location/Qualifiers
source                  1..708
                        mol_type = protein
                        organism = synthetic construct
SEQUENCE: 167
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSSGGP GPAGMKGLPG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NVIVLELKGS ETTFMCEYAD ETATIVEFLN RWITFCQSII STLTSGGPGP AGMKGLPGSE  300
VQLVESGGGL VQPGNSLRLS CAASGFTFSK FGMSWVRQAP GKGLEWVSSI SGSGRDTLYA  360
ESVKGRFTIS RDNAKTTLYL QMNSLRPEDT AVYYCTIGGS LSVSSQGTLV TVSSGGGGSG  420
GGGSGGGGSG GGGSGGGGSG GGGSSGGPGP AGMKGLPGSE VQLVESGGGL VQPGGSLRLS  480
CAASGFTFSS YTLAWVRQAP GKGLEWVAAI DSSSYTYSPD TVRGRFTISR DNAKNSLYLQ  540
MNSLRAEDTA VYYCARDSNW DALDYWGQGT TVTVSSGGGG SGGGGSGGGG SDIQMTQSPS  600
SLSASVGDRV TITCKASQNV GTNVGWYQQK PGKAPKALIY SASFRYSGVP SRFSGSGSGT  660
DFTLTISSLQ PEDFATYYCQ QYYTYPYTFG GGTKVEIKHH HHHHEPEA                708

SEQ ID NO: 168          moltype = AA  length = 450
FEATURE                 Location/Qualifiers
source                  1..450
                        mol_type = protein
                        organism = synthetic construct
SEQUENCE: 168
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSCDLPQTHN LRNKRALTLL VQMRRLSPLS  180
CLKDRKDFGF PQEKVDAQQI KKAQAIPVLS ELTQQILNIF TSKDSSAAWN TTLLDSFCND  240
LHQQLNDLQG CLMQQVGVQE FPLTQEDALL AVRKYFHRIT VYLREKKHSP CAWEVVRAEV  300
WRALSSSANV SGGPGPAGMK GLPGSEVQLV ESGGGLVQPG NSLRLSCAAS GFTFSKFGMS  360
WVRQAPGKGL EWVSSISGSG RDTLYAESVK GRFTISRDNA KTTLYLQMNS LRPEDTAVYY  420
CTIGGSLSVS SQGTLVTVSS HHHHHHEPEA                                    450

SEQ ID NO: 169          moltype = AA  length = 198
FEATURE                 Location/Qualifiers
source                  1..198
                        mol_type = protein
                        organism = synthetic construct
SEQUENCE: 169
MDMRVPAQLL GLLLLWLRGA RCCDLPQTHN LRNKRALTLL VQMRRLSPLS CLKDRKDFGF  60
PQEKVDAQQI KKAQAIPVLS ELTQQILNIF TSKDSSAAWN TTLLDSFCND LHQQLNDLQG  120
CLMQQVGVQE FPLTQEDALL AVRKYFHRIT VYLREKKHSP CAWEVVRAEV WRALSSSANV  180
LGRLREEKHH HHHHEPEA                                                 198

SEQ ID NO: 170          moltype = AA  length = 328
FEATURE                 Location/Qualifiers
source                  1..328
                        mol_type = protein
                        organism = synthetic construct
SEQUENCE: 170
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSCDLPQTHN LRNKRALTLL VQMRRLSPLS  180
CLKDRKDFGF PQEKVDAQQI KKAQAIPVLS ELTQQILNIF TSKDSSAAWN TTLLDSFCND  240
LHQQLNDLQG CLMQQVGVQE FPLTQEDALL AVRKYFHRIT VYLREKKHSP CAWEVVRAEV  300
WRALSSSANV LGRLREEKHH HHHHEPEA                                      328

SEQ ID NO: 171          moltype = AA  length = 328
FEATURE                 Location/Qualifiers
source                  1..328
                        mol_type = protein
                        organism = synthetic construct
SEQUENCE: 171
MDMRVPAQLL GLLLLWLRGA RCCDLPQTHN LRNKRALTLL VQMRRLSPLS CLKDRKDFGF  60
PQEKVDAQQI KKAQAIPVLS ELTQQILNIF TSKDSSAAWN TTLLDSFCND LHQQLNDLQG  120
```

-continued

```
CLMQQVGVQE FPLTQEDALL AVRKYFHRIT VYLREKKHSP CAWEVVRAEV WRALSSSANV  180
LGRLREEKSG GPGPAGMKGL PGSEVQLVES GGGLVQPGNS LRLSCAASGF TFSKFGMSWV  240
RQAPGKGLEW VSSISGSGRD TLYAESVKGR FTISRDNAKT TLYLQMNSLR PEDTAVYYCT  300
IGGSLSVSSQ GTLVTVSSHH HHHHEPEA                                     328

SEQ ID NO: 172          moltype = AA  length = 1396
FEATURE                 Location/Qualifiers
source                  1..1396
                        mol_type = protein
                        organism = synthetic construct
SEQUENCE: 172
MDMRVPAQLL GLLLLWLRGA RCEAHKSEIA HRYNDLGEQH FKGLVLIAFS QYLQKCSYDE  60
HAKLVQEVTD FAKTCVADES AANCDKSLHT LFGDKLCAIP NLRENYGELA DCCTKQEPER  120
NECFLQHKDD NPSLPPFERP EAEAMCTSFK ENPTTFMGHY LHEVARRHPY FYAPELLYYA  180
EQYNEILTQC CAEADKESCL TPKLDGVKEK ALVSSVRQRM KCSSMQKFGE RAFKAWAVAR  240
LSQTFPNADF AEITKLATDL TKVNKECCHG DLLECADDRA ELAKYMCENQ ATISSKLQTC  300
CDKPLLKKAH CLSEVEHDTM PADLPAIAAD FVEDQEVCKN YAEAKDVFLG TFLYEYSRRH  360
PDYSVSLLLR LAKKYEATLE KCCAEANPPA CYGTVLAEFQ PLVEEPKNLV KTNCDLYEKL  420
GEYGFQNAIL VRYTQKAPQV STPTLVEAAR NLGRVGTKCC TLPEDQRLPC VEDYLSAILN  480
RVCLLHEKTP VSEHVTKCCS GSLVERRPCF SALTVDETYV PKEFKAETFT FHSDICTLPE  540
KEKQIKKQTA LAELVKHKPK ATAEQLKTVM DDFAQFLDTC CKAADKDTCF STEGPNLVTR  600
CKDALASGGP GPAGMKGLPG SCDLPQTHNL RNKRALTLLV QMRRLSPLSC LKDRKDFGFP  660
QEKVDAQQIK KAQAIPVLSE LTQQILNIFT SKDSSAAWNT TLLDSFCNDL HQQLNDLQGC  720
LMQQVGVQEF PLTQEDALLA VRKYFHRITV YLREKKHSPC AWEVVRAEVW RALSSSANVL  780
GRLREEKSGG PGPAGMKGLP GSEAHKSEIA HRYNDLGEQH FKGLVLIAFS QYLQKCSYDE  840
HAKLVQEVTD FAKTCVADES AANCDKSLHT LFGDKLCAIP NLRENYGELA DCCTKQEPER  900
NECFLQHKDD NPSLPPFERP EAEAMCTSFK ENPTTFMGHY LHEVARRHPY FYAPELLYYA  960
EQYNEILTQC CAEADKESCL TPKLDGVKEK ALVSSVRQRM KCSSMQKFGE RAFKAWAVAR  1020
LSQTFPNADF AEITKLATDL TKVNKECCHG DLLECADDRA ELAKYMCENQ ATISSKLQTC  1080
CDKPLLKKAH CLSEVEHDTM PADLPAIAAD FVEDQEVCKN YAEAKDVFLG TFLYEYSRRH  1140
PDYSVSLLLR LAKKYEATLE KCCAEANPPA CYGTVLAEFQ PLVEEPKNLV KTNCDLYEKL  1200
GEYGFQNAIL VRYTQKAPQV STPTLVEAAR NLGRVGTKCC TLPEDQRLPC VEDYLSAILN  1260
RVCLLHEKTP VSEHVTKCCS GSLVERRPCF SALTVDETYV PKEFKAETFT FHSDICTLPE  1320
KEKQIKKQTA LAELVKHKPK ATAEQLKTVM DDFAQFLDTC CKAADKDTCF STEGPNLVTR  1380
CKDALAHHHH HHEPEA                                                  1396

SEQ ID NO: 173          moltype = AA  length = 797
FEATURE                 Location/Qualifiers
source                  1..797
                        mol_type = protein
                        organism = synthetic construct
SEQUENCE: 173
MDMRVPAQLL GLLLLWLRGA RCEAHKSEIA HRYNDLGEQH FKGLVLIAFS QYLQKCSYDE  60
HAKLVQEVTD FAKTCVADES AANCDKSLHT LFGDKLCAIP NLRENYGELA DCCTKQEPER  120
NECFLQHKDD NPSLPPFERP EAEAMCTSFK ENPTTFMGHY LHEVARRHPY FYAPELLYYA  180
EQYNEILTQC CAEADKESCL TPKLDGVKEK ALVSSVRQRM KCSSMQKFGE RAFKAWAVAR  240
LSQTFPNADF AEITKLATDL TKVNKECCHG DLLECADDRA ELAKYMCENQ ATISSKLQTC  300
CDKPLLKKAH CLSEVEHDTM PADLPAIAAD FVEDQEVCKN YAEAKDVFLG TFLYEYSRRH  360
PDYSVSLLLR LAKKYEATLE KCCAEANPPA CYGTVLAEFQ PLVEEPKNLV KTNCDLYEKL  420
GEYGFQNAIL VRYTQKAPQV STPTLVEAAR NLGRVGTKCC TLPEDQRLPC VEDYLSAILN  480
RVCLLHEKTP VSEHVTKCCS GSLVERRPCF SALTVDETYV PKEFKAETFT FHSDICTLPE  540
KEKQIKKQTA LAELVKHKPK ATAEQLKTVM DDFAQFLDTC CKAADKDTCF STEGPNLVTR  600
CKDALASGGP GPAGMKGLPG SCDLPQTHNL RNKRALTLLV QMRRLSPLSC LKDRKDFGFP  660
QEKVDAQQIK KAQAIPVLSE LTQQILNIFT SKDSSAAWNT TLLDSFCNDL HQQLNDLQGC  720
LMQQVGVQEF PLTQEDALLA VRKYFHRITV YLREKKHSPC AWEVVRAEVW RALSSSANVL  780
GRLREEKHHH HHHEPEA                                                 797

SEQ ID NO: 174          moltype = AA  length = 797
FEATURE                 Location/Qualifiers
source                  1..797
                        mol_type = protein
                        organism = synthetic construct
SEQUENCE: 174
MDMRVPAQLL GLLLLWLRGA RCCDLPQTHN LRNKRALTLL VQMRRLSPLS CLKDRKDFGF  60
PQEKVDAQQI KKAQAIPVLS ELTQQILNIF TSKDSSAAWN TTLLDSFCND LHQQLNDLQG  120
CLMQQVGVQE FPLTQEDALL AVRKYFHRIT VYLREKKHSP CAWEVVRAEV WRALSSSANV  180
LGRLREEKSG GPGPAGMKGL PGSEAHKSEI AHRYNDLGEQ HFKGLVLIAF SQYLQKCSYD  240
EHAKLVQEVT DFAKTCVADE SAANCDKSLH TLFGDKLCAI PNLRENYGEL ADCCTKQEPE  300
RNECFLQHKD DNPSLPPFER PEAEAMCTSF KENPTTFMGH YLHEVARRHP YFYAPELLYY  360
AEQYNEILTQ CCAEADKESC LTPKLDGVKE KALVSSVRQR MKCSSMQKFG ERAFKAWAVA  420
RLSQTFPNAD FAEITKLATD LTKVNKECCH GDLLECADDR AELAKYMCEN QATISSKLQT  480
CCDKPLLKKA HCLSEVEHDT MPADLPAIAA DFVEDQEVCK NYAEAKDVFL GTFLYEYSRR  540
HPDYSVSLLL RLAKKYEATL EKCCAEANPP ACYGTVLAEF QPLVEEPKNL VKTNCDLYEK  600
LGEYGFQNAI LVRYTQKAPQ VSTPTLVEAA RNLGRVGTKC CTLPEDQRLP CVEDYLSAIL  660
NRVCLLHEKT PVSEHVTKCC SGSLVERRPC FSALTVDETY VPKEFKAETF TFHSDICTLP  720
EKEKQIKKQT ALAELVKHKP KATAEQLKTV MDDFAQFLDT CCKAADKDTC FSTEGPNLVT  780
RCKDALAHHH HHHEPEA                                                 797

SEQ ID NO: 175          moltype = AA  length = 587
```

```
FEATURE                Location/Qualifiers
source                 1..587
                       mol_type = protein
                       organism = synthetic construct
SEQUENCE: 175
MDMRVPAQLL GLLLLWLRGA RCQVQLQESG GGLAQAGGSL SLSCAASGFT VSNSVMAWYR  60
QTPGKQREFV AIINSVGSTN YADSVKGRFT ISRDNAKNTV YLQMNNLKPE DTAVYVCNRN  120
FDRIYWGQGT QVTVSSGGGG SGGGGSGGGG SEVQLVESGG GLVQPGNSLR LSCAASGFTF  180
SKFGMSWVRQ APGKGLEWVS SISGSGRDTL YAESVKGRFT ISRDNAKTTL YLQMNSLRPE  240
DTAVYYCTIG GSLSVSSQGT LVTVSSSGGP GPAGMKGLPG SCDLPQTHNL RNKRALTLLV  300
QMRRLSPLSC LKDRKDFGFP QEKVDAQQIK KAQAIPVLSE LTQQILNIFT SKDSSAAWNT  360
TLLDSFCNDL HQQLNDLQGC LMQQVGVQEF PLTQEDALLA VRKYFHRITV YLREKKHSPC  420
AWEVVRAEVW RALSSSANVL GRLREEKSGG PGPAGMKGLP GSEVQLVESG GGLVQPGNSL  480
RLSCAASGFT FSKFGMSWVR QAPGKGLEWV SSISGSGRDT LYAESVKGRF TISRDNAKTT  540
LYLQMNSLRP EDTAVYYCTI GGSLSVSSQG TLVTVSSHHH HHHEPEA              587

SEQ ID NO: 176         moltype = AA  length = 587
FEATURE                Location/Qualifiers
source                 1..587
                       mol_type = protein
                       organism = synthetic construct
SEQUENCE: 176
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSCDLPQTHN LRNKRALTLL VQMRRLSPLS  180
CLKDRKDFGF PQEKVDAQQI KKAQAIPVLS ELTQQILNIF TSKDSSAAWN TTLLDSFCND  240
LHQQLNDLQG CLMQQVGVQE FPLTQEDALL AVRKYFHRIT VYLREKKHSP CAWEVVRAEV  300
WRALSSSANV LGRLREEKSG GPGPAGMKGL PGSEVQLVES GGGLVQPGNS LRLSCAASGF  360
TFSKFGMSWV RQAPGKGLEW VSSISGSGRD TLYAESVKGR FTISRDNAKT TLYLQMNSLR  420
PEDTAVYYCT IGGSLSVSSQ GTLVTVSSGG GGSGGGGSGG GGSQVQLQES GGGLAQAGGS  480
LSLSCAASGF TVSNSVMAWY RQTPGKQREF VAIINSVGST NYADSVKGRF TISRDNAKNT  540
VYLQMNNLKP EDTAVYVCNR NFDRIYWGQG TQVTVSSHHH HHHEPEA              587

SEQ ID NO: 177         moltype = AA  length = 458
FEATURE                Location/Qualifiers
source                 1..458
                       mol_type = protein
                       organism = synthetic construct
SEQUENCE: 177
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSGGG GSGGGGSGGG GSCDLPQTHN LRNKRALTLL VQMRRLSPLS  180
CLKDRKDFGF PQEKVDAQQI KKAQAIPVLS ELTQQILNIF TSKDSSAAWN TTLLDSFCND  240
LHQQLNDLQG CLMQQVGVQE FPLTQEDALL AVRKYFHRIT VYLREKKHSP CAWEVVRAEV  300
WRALSSSANV LGRLREEKGG GGSGGGGSGG GGSEVQLVES GGGLVQPGNS LRLSCAASGF  360
TFSKFGMSWV RQAPGKGLEW VSSISGSGRD TLYAESVKGR FTISRDNAKT TLYLQMNSLR  420
PEDTAVYYCT IGGSLSVSSQ GTLVTVSSHH HHHHEPEA                        458

SEQ ID NO: 178         moltype = AA  length = 579
FEATURE                Location/Qualifiers
source                 1..579
                       mol_type = protein
                       organism = synthetic construct
SEQUENCE: 178
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGLYAQPGS EVQLVESGGG  180
LVQPGNSLRL SCAASGFTFS KFGMSWVRQA PGKGLEWVSS ISGSGRDTLY AESVKGRFTI  240
SRDNAKTTLY LQMNSLRPED TAVYYCTIGG SLSVSSQGTL VTVSSGGGGS GGGGSGGGGS  300
GGGGSGGGGS GGGGSSGGPG PAGLYAQPGS EVQLVESGGG LVQPGGSLRL SCAASGFTFS  360
SYTLAWVRQA PGKGLEWVAA IDSSSYTYSP DTVRGRFTIS RDNAKNSLYL QMNSLRAEDT  420
AVYYCARDSN WDALDYWGQG TTVTVSSGGG GSGGGGSGGG GSDIQMTQSP SSLSASVGDR  480
VTITCKASQN VGTNVGWYQQ KPGKAPKALI YSASFRYSGV PSRFSGSGSG TDFTLTISSL  540
QPEDFATYYC QQYYTYPYTF GGGTKVEIKH HHHHHEPEA                       579

SEQ ID NO: 179         moltype = AA  length = 579
FEATURE                Location/Qualifiers
source                 1..579
                       mol_type = protein
                       organism = synthetic construct
SEQUENCE: 179
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPP GGPAGIGPGS EVQLVESGGG  180
LVQPGNSLRL SCAASGFTFS KFGMSWVRQA PGKGLEWVSS ISGSGRDTLY AESVKGRFTI  240
SRDNAKTTLY LQMNSLRPED TAVYYCTIGG SLSVSSQGTL VTVSSGGGGS GGGGSGGGGS  300
GGGGSGGGGS GGGGSSGGPP GGPAGIGPGS EVQLVESGGG LVQPGGSLRL SCAASGFTFS  360
SYTLAWVRQA PGKGLEWVAA IDSSSYTYSP DTVRGRFTIS RDNAKNSLYL QMNSLRAEDT  420
AVYYCARDSN WDALDYWGQG TTVTVSSGGG GSGGGGSGGG GSDIQMTQSP SSLSASVGDR  480
```

-continued

```
VTITCKASQN VGTNVGWYQQ KPGKAPKALI YSASFRYSGV PSRFSGSGSG TDFTLTISSL  540
QPEDFATYYC QQYYTYPYTF GGGTKVEIKH HHHHHEPEA                         579

SEQ ID NO: 180         moltype = AA  length = 579
FEATURE                Location/Qualifiers
source                 1..579
                       mol_type = protein
                       organism = synthetic construct
SEQUENCE: 180
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPA LFKSSFPPGS EVQLVESGGG  180
LVQPGNSLRL SCAASGFTFS KFGMSWVRQA PGKGLEWVSS ISGSGRDTLY AESVKGRFTI  240
SRDNAKTTLY LQMNSLRPED TAVYYCTIGG SLSVSSQGTL VTVSSGGGGS GGGGSGGGGS  300
GGGGSGGGGS GGGGSSGGPA LFKSSFPPGS EVQLVESGGG LVQPGGSLRL SCAASGFTFS  360
SYTLAWVRQA PGKGLEWVAA IDSSSYTYSP DTVRGRFTIS RDNAKNSLYL QMNSLRAEDT  420
AVYYCARDSN WDALDYWGQG TTVTVSSGGG GSGGGGSGGG GSDIQMTQSP SSLSASVGDR  480
VTITCKASQN VGTNVGWYQQ KPGKAPKALI YSASFRYSGV PSRFSGSGSG TDFTLTISSL  540
QPEDFATYYC QQYYTYPYTF GGGTKVEIKH HHHHHEPEA                         579

SEQ ID NO: 181         moltype = AA  length = 581
FEATURE                Location/Qualifiers
source                 1..581
                       mol_type = protein
                       organism = synthetic construct
SEQUENCE: 181
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPP LAQKLKSSPG SEVQLVESGG  180
GLVQPGNSLR LSCAASGFTF SKFGMSWVRQ APGKGLEWVS SISGSGRDTL YAESVKGRFT  240
ISRDNAKTTL YLQMNSLRPE DTAVYYCTIG GSLSVSSQGT LVTVSSGGGG SGGGGSGGGG  300
SGGGGSGGGG SGGGGSSGGP PLAQKLKSSP GSEVQLVESG GGLVQPGGSL RLSCAASGFT  360
FSSYTLAWVR QAPGKGLEWV AAIDSSSYTY SPDTVRGRFT ISRDNAKNSL YLQMNSLRAE  420
DTAVYYCARD SNWDALDYWG QGTTVTVSSG GGGSGGGGSG GGGSDIQMTQ SPSSLSASVG  480
DRVTITCKAS QNVGTNVGWY QQKPGKAPKA LIYSASFRYS GVPSRFSGSG SGTDFTLTIS  540
SLQPEDFATY YCQQYYTYPY TFGGGTKVEI KHHHHHHEPE A                      581

SEQ ID NO: 182         moltype = AA  length = 613
FEATURE                Location/Qualifiers
source                 1..613
                       mol_type = protein
                       organism = synthetic construct
SEQUENCE: 182
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPP GGPAGIGALF KSSFPPLAQK  180
LKSSPGSEVQ LVESGGGLVQ PGNSLRLSCA ASGFTFSKFG MSWVRQAPGK GLEWVSSISG  240
SGRDTLYAES VKGRFTISRD NAKTTLYLQM NSLRPEDTAV YYCTIGGSLS VSSQGTLVTV  300
SSGGGGSGGG GSGGGGSGGG GSGGGGSGGG GSSGGPPGGP AGIGALFKSS FPPLAQKLKS  360
SPGSEVQLVE SGGGLVQPGG SLRLSCAASG FTFSSYTLAW VRQAPGKGLE WVAAIDSSSY  420
TYSPDTVRGR FTISRDNAKN SLYLQMNSLR AEDTAVYYCA RDSNWDALDY WGQGTTVTVS  480
SGGGGSGGGG SGGGGSDIQM TQSPSSLSAS VGDRVTITCK ASQNVGTNVG WYQQKPGKAP  540
KALIYSASFR YSGVPSRFSG SGSGTDFTLT ISSLQPEDFA TYYCQQYYTY PYTFGGGTKV  600
EIKHHHHHHE PEA                                                     613

SEQ ID NO: 183         moltype =   length =
SEQUENCE: 183
000

SEQ ID NO: 184         moltype =   length =
SEQUENCE: 184
000

SEQ ID NO: 185         moltype =   length =
SEQUENCE: 185
000

SEQ ID NO: 186         moltype =   length =
SEQUENCE: 186
000

SEQ ID NO: 187         moltype =   length =
SEQUENCE: 187
000

SEQ ID NO: 188         moltype =   length =
SEQUENCE: 188
000
```

-continued

```
SEQ ID NO: 189         moltype =   length =
SEQUENCE: 189
000

SEQ ID NO: 190         moltype =   length =
SEQUENCE: 190
000

SEQ ID NO: 191         moltype = AA  length = 267
FEATURE                Location/Qualifiers
source                 1..267
                       mol_type = protein
                       organism = synthetic construct
SEQUENCE: 191
MDMRVPAQLL GLLLLWLRGA RCEVQLVESG GGLVQPGGSL RLSCAASGFT FSSYTLAWVR  60
QAPGKGLEWV AAIDSSSYTY SPDTVRGRFT ISRDNAKNSL YLQMNSLRAE DTAVYYCARD  120
SNWDALDYWG QGTTVTVSSG GGGSGGGGSG GGGSDIQMTQ SPSSLSASVG DRVTITCKAS  180
QNVGTNVGWY QQKPGKAPKA LIYSASFRYS GVPSRFSGSG SGTDFTLTIS SLQPEDFATY  240
YCQQYYTYPY TFGGGTKVEI KHHHHHH                                      267

SEQ ID NO: 192         moltype = AA  length = 269
FEATURE                Location/Qualifiers
source                 1..269
                       mol_type = protein
                       organism = synthetic construct
SEQUENCE: 192
MDMRVPAQLL GLLLLWLRGA RCQSVLTQPP SVSGAPGQRV TISCSGSRSN IGSNTVKWYQ  60
QLPGTAPKLL IYYNDQRPSG VPDRFSGSKS GTSASLAITG LQAEDEADYY CQSYDRYTHP  120
ALLFGTGTKV TVLGGGGSGG GGSGGGGSQV QLVESGGGVV QPGRSLRLSC AASGFTFSSY  180
GMHWVRQAPG KGLEWVAFIR YDGSNKYYAD SVKGRFTISR DNSKNTLYLQ MNSLRAEDTA  240
VYYCKTHGSH DNWGQGTMVT VSSHHHHHH                                    269

SEQ ID NO: 193         moltype = AA  length = 171
FEATURE                Location/Qualifiers
source                 1..171
                       mol_type = protein
                       organism = synthetic construct
SEQUENCE: 193
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKEHHHHH H            171

SEQ ID NO: 194         moltype = AA  length = 520
FEATURE                Location/Qualifiers
source                 1..520
                       mol_type = protein
                       organism = synthetic construct
SEQUENCE: 194
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRVIPVSGPA RCLSQSRNLL KTTDDMVKTA REKLKHYSCT  360
AEDIDHEDIT RDQTSTLKTC LPLELHKNES CLATRETSST TRGSCLPPQK TSLMMTLCLG  420
SIYEDLKMYQ TEFQAINAAL QNHNHQQIIL DKGMLVAIDE LMQSLNHNGE TLRQKPPVGE  480
ADPYRVKMKL CILLHAFSTR VVTINRVMGY LSSAHHHHHH                        520

SEQ ID NO: 195         moltype = AA  length = 141
FEATURE                Location/Qualifiers
source                 1..141
                       mol_type = protein
                       organism = synthetic construct
SEQUENCE: 195
QVQLQESGGG LVQAGGSLRL SCAASGRTFS SVYDMGWFRQ APGKDREFVA RITESARNTR  60
YADSVRGRFT ISRDNAKNTV YLQMNNLELE DAAVYYCAAD PQTVVVGTPD YWGQGTQVTV  120
SSAAAYPYDV PDYGSHHHHH H                                            141

SEQ ID NO: 196         moltype = AA  length = 247
FEATURE                Location/Qualifiers
source                 1..247
                       mol_type = protein
                       organism = synthetic construct
SEQUENCE: 196
QSVLTQPPSV SGAPGQRVTI SCTGSSSNIG SNTVKWYQQL PGTAPKLLIY GNDQRPSGVP  60
DRFSGSKSGT SASLAITGLQ AEDEADYYCQ SYDRYTHPAY VFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247
```

```
SEQ ID NO: 197          moltype = AA  length = 247
FEATURE                 Location/Qualifiers
source                  1..247
                        mol_type = protein
                        organism = synthetic construct
SEQUENCE: 197
QSVLTQPPSV SGAPGQRVTI SCTGSSSNIG SNTVKWYQQL PGTAPKLLIY YNDQRPSGVP  60
DRFSGSKSGT SASLAITGLQ AEDEADYYCQ SYDRYTHPAY VFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 198          moltype = AA  length = 247
FEATURE                 Location/Qualifiers
source                  1..247
                        mol_type = protein
                        organism = synthetic construct
SEQUENCE: 198
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYAM HWVRQAPGKG LEWVAVISYD  180
GSNKYYADSV KGRFTISRDN SKNTLYLQMN SLRAEDTAVY YCARHGSHDN WGQGTMVTVS  240
SHHHHHH                                                            247

SEQ ID NO: 199          moltype = AA  length = 247
FEATURE                 Location/Qualifiers
source                  1..247
                        mol_type = protein
                        organism = synthetic construct
SEQUENCE: 199
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYE  180
GSNKYYADSV KGRFTISRDN SKNTLYLQMN SLRAEDTAVY YCKTHGSHDN WGQGTMVTVS  240
SHHHHHH                                                            247

SEQ ID NO: 200          moltype = AA  length = 247
FEATURE                 Location/Qualifiers
source                  1..247
                        mol_type = protein
                        organism = synthetic construct
SEQUENCE: 200
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYAESV KGRFTISRDN SKNTLYLQMN SLRAEDTAVY YCKTHGSHDN WGQGTMVTVS  240
SHHHHHH                                                            247

SEQ ID NO: 201          moltype = AA  length = 247
FEATURE                 Location/Qualifiers
source                  1..247
                        mol_type = protein
                        organism = synthetic construct
SEQUENCE: 201
QSVLTQPPSV SGAPGQRVTI SCSGSRSNIG SQTVKWYQQL PGTAPKLLIY YNDQRPSGVP  60
DRFSGSKSGT SASLAITGLQ AEDEADYYCQ SYERYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 202          moltype = AA  length = 247
FEATURE                 Location/Qualifiers
source                  1..247
                        mol_type = protein
                        organism = synthetic construct
SEQUENCE: 202
QSVLTQPPSV SGAPGQRVTI SCSGSRSNIG SQTVKWYQQL PGTAPKLLIY YNDQRPSGVP  60
DRFSGSKSGT SASLAITGLQ AEDEADYYCQ SYSRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 203          moltype = AA  length = 247
FEATURE                 Location/Qualifiers
source                  1..247
                        mol_type = protein
                        organism = synthetic construct
SEQUENCE: 203
```

-continued

```
QSVLTQPPSV SGAPGQRVTI SCSGSESNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 204          moltype = AA  length = 247
FEATURE                 Location/Qualifiers
source                  1..247
                        mol_type = protein
                        organism = synthetic construct
SEQUENCE: 204
QSVLTQPPSV SGAPGQRVTI SCSGSSSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 205          moltype = AA  length = 247
FEATURE                 Location/Qualifiers
source                  1..247
                        mol_type = protein
                        organism = synthetic construct
SEQUENCE: 205
QSVLTQPPSV SGAPGQRVTI SCSGSRSNIG DNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 206          moltype = AA  length = 247
FEATURE                 Location/Qualifiers
source                  1..247
                        mol_type = protein
                        organism = synthetic construct
SEQUENCE: 206
QSVLTQPPSV SGAPGQRVTI SCSGSRSNIG ENTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 207          moltype = AA  length = 247
FEATURE                 Location/Qualifiers
source                  1..247
                        mol_type = protein
                        organism = synthetic construct
SEQUENCE: 207
QSVLTQPPSV SGAPGQRVTI SCSGSRSNIG SDTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 208          moltype = AA  length = 247
FEATURE                 Location/Qualifiers
source                  1..247
                        mol_type = protein
                        organism = synthetic construct
SEQUENCE: 208
QSVLTQPPSV SGAPGQRVTI SCSGSRSNIG SETVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 209          moltype = AA  length = 247
FEATURE                 Location/Qualifiers
source                  1..247
                        mol_type = protein
                        organism = synthetic construct
SEQUENCE: 209
QSVLTQPPSV SGAPGQRVTI SCSGSRSNIG SNDVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 210          moltype = AA  length = 247
```

-continued

```
FEATURE                Location/Qualifiers
source                 1..247
                       mol_type = protein
                       organism = synthetic construct
SEQUENCE: 210
QSVLTQPPSV SGAPGQRVTI SCSGSRSNIG SNTVDWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 211         moltype = AA  length = 247
FEATURE                Location/Qualifiers
source                 1..247
                       mol_type = protein
                       organism = synthetic construct
SEQUENCE: 211
QSVLTQPPSV SGAPGQRVTI SCSGSRSNIG SNTVEWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 212         moltype = AA  length = 247
FEATURE                Location/Qualifiers
source                 1..247
                       mol_type = protein
                       organism = synthetic construct
SEQUENCE: 212
QSVLTQPPSV SGAPGQRVTI SCSGSRSNIG SNTVKWYQQL PGTAPKLLIY YNDQDPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 213         moltype = AA  length = 247
FEATURE                Location/Qualifiers
source                 1..247
                       mol_type = protein
                       organism = synthetic construct
SEQUENCE: 213
QSVLTQPPSV SGAPGQRVTI SCSGSRSNIG SNTVKWYQQL PGTAPKLLIY YNDQEPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 214         moltype = AA  length = 247
FEATURE                Location/Qualifiers
source                 1..247
                       mol_type = protein
                       organism = synthetic construct
SEQUENCE: 214
QSVLTQPPSV SGAPGQRVTI SCSGSRSNIG SNTVKWYQQL PGTAPKLLIY YNDQRPDGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 215         moltype = AA  length = 247
FEATURE                Location/Qualifiers
source                 1..247
                       mol_type = protein
                       organism = synthetic construct
SEQUENCE: 215
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDEYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 216         moltype = AA  length = 247
FEATURE                Location/Qualifiers
source                 1..247
                       mol_type = protein
                       organism = synthetic construct
SEQUENCE: 216
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTDPAL LFGTGTKVTV LGGGGSGGGG  120
```

```
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 217         moltype = AA  length = 247
FEATURE                Location/Qualifiers
source                 1..247
                       mol_type = protein
                       organism = synthetic construct
SEQUENCE: 217
QSVLTQPPSV SGAPGQRVTI SCSGSESNIG SNTVKWYQQL PGTAPKLLIY YNDQEPSGVP  60
DRFSGSKSGT SASLAITGLQ AEDEADYYCQ SYDEYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 218         moltype = AA  length = 247
FEATURE                Location/Qualifiers
source                 1..247
                       mol_type = protein
                       organism = synthetic construct
SEQUENCE: 218
QSVLTQPPSV SGAPGQRVTI SCSGSESNIG SNDVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 219         moltype = AA  length = 247
FEATURE                Location/Qualifiers
source                 1..247
                       mol_type = protein
                       organism = synthetic construct
SEQUENCE: 219
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFESYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 220         moltype = AA  length = 247
FEATURE                Location/Qualifiers
source                 1..247
                       mol_type = protein
                       organism = synthetic construct
SEQUENCE: 220
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSEYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 221         moltype = AA  length = 247
FEATURE                Location/Qualifiers
source                 1..247
                       mol_type = protein
                       organism = synthetic construct
SEQUENCE: 221
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSDYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 222         moltype = AA  length = 247
FEATURE                Location/Qualifiers
source                 1..247
                       mol_type = protein
                       organism = synthetic construct
SEQUENCE: 222
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIEYD  180
GSNKYYADSV KGRFTISRDN SKNTLYLQMN SLRAEDTAVY YCKTHGSHDN WGQGTMVTVS  240
SHHHHHH                                                            247

SEQ ID NO: 223         moltype = AA  length = 247
FEATURE                Location/Qualifiers
source                 1..247
```

```
                         mol_type = protein
                         organism = synthetic construct
SEQUENCE: 223
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIDYD  180
GSNKYYADSV KGRFTISRDN SKNTLYLQMN SLRAEDTAVY YCKTHGSHDN WGQGTMVTVS  240
SHHHHHH                                                            247

SEQ ID NO: 224           moltype = AA  length = 247
FEATURE                  Location/Qualifiers
source                   1..247
                         mol_type = protein
                         organism = synthetic construct
SEQUENCE: 224
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNDYYADSV KGRFTISRDN SKNTLYLQMN SLRAEDTAVY YCKTHGSHDN WGQGTMVTVS  240
SHHHHHH                                                            247

SEQ ID NO: 225           moltype = AA  length = 247
FEATURE                  Location/Qualifiers
source                   1..247
                         mol_type = protein
                         organism = synthetic construct
SEQUENCE: 225
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNEYYADSV KGRFTISRDN SKNTLYLQMN SLRAEDTAVY YCKTHGSHDN WGQGTMVTVS  240
SHHHHHH                                                            247

SEQ ID NO: 226           moltype = AA  length = 247
FEATURE                  Location/Qualifiers
source                   1..247
                         mol_type = protein
                         organism = synthetic construct
SEQUENCE: 226
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV EGRFTISRDN SKNTLYLQMN SLRAEDTAVY YCKTHGSHDN WGQGTMVTVS  240
SHHHHHH                                                            247

SEQ ID NO: 227           moltype = AA  length = 247
FEATURE                  Location/Qualifiers
source                   1..247
                         mol_type = protein
                         organism = synthetic construct
SEQUENCE: 227
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSEDN WGQGTMVTVS  240
SHHHHHH                                                            247

SEQ ID NO: 228           moltype = AA  length = 247
FEATURE                  Location/Qualifiers
source                   1..247
                         mol_type = protein
                         organism = synthetic construct
SEQUENCE: 228
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIEYD  180
GSNKYYADSV EGRFTISRDN SKNTLYLQMN SLRAEDTAVY YCKTHGSHDN WGQGTMVTVS  240
SHHHHHH                                                            247

SEQ ID NO: 229           moltype = AA  length = 247
FEATURE                  Location/Qualifiers
source                   1..247
                         mol_type = protein
                         organism = synthetic construct
SEQUENCE: 229
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIEYD  180
GSNKYYADSV EGRFTISRDN SKNTLYLQMN SLRAEDTAVY YCKTHGSEDN WGQGTMVTVS  240
```

```
SHHHHHH                                                           247

SEQ ID NO: 230         moltype = AA  length = 247
FEATURE                Location/Qualifiers
source                 1..247
                       mol_type = protein
                       organism = synthetic construct
SEQUENCE: 230
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                           247

SEQ ID NO: 231         moltype = AA  length = 306
FEATURE                Location/Qualifiers
source                 1..306
                       mol_type = protein
                       organism = synthetic construct
SEQUENCE: 231
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCS                                                            306

SEQ ID NO: 232         moltype = AA  length = 137
FEATURE                Location/Qualifiers
source                 1..137
                       mol_type = protein
                       organism = synthetic construct
SEQUENCE: 232
QVQLQESGGG LVQTGGSLRL SCTTSGTIFS GYTMGWYRQA PGEQRELVAV ISGGGDTNYA  60
DSVKGRFTIS RDNTKDTMYL QMNSLKPEDT AVYYCYSREV TPPWKLYWGQ GTQVTVSSAA  120
AYPYDVPDYG SHHHHHH                                                137

SEQ ID NO: 233         moltype = AA  length = 137
FEATURE                Location/Qualifiers
source                 1..137
                       mol_type = protein
                       organism = synthetic construct
SEQUENCE: 233
QVQLQESGGG LVQEGGSLRL SCAASERIFS TDVMGWYRQA AEKQRELVAV VSARGTTNYL  60
DAVKGRFTIS RDNARNTLTL QMNDLKPEDT ASYYCYVRET TSPWRIYWGQ GTQVTVSSAA  120
AYPYDVPDYG SHHHHHH                                                137

SEQ ID NO: 234         moltype = AA  length = 138
FEATURE                Location/Qualifiers
source                 1..138
                       mol_type = protein
                       organism = synthetic construct
SEQUENCE: 234
QVQLQESGGG LVQAGGSLRL SCAASGSIFS ANAMGWYRQA PGKQRELVAV ISSGGSTNYA  60
DSVKGRFTIS RDNAKNTVYL QMNSLKPEDT AVYYCMYSGS YYYTPNDYWG QGTQVTVSSA  120
AAYPYDVPDY GSHHHHHH                                               138

SEQ ID NO: 235         moltype = AA  length = 245
FEATURE                Location/Qualifiers
source                 1..245
                       mol_type = protein
                       organism = synthetic construct
SEQUENCE: 235
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSGGG  120
GSGGGGSGGG GSDIQMTQSP SSLSASVGDR VTITCKASQN VGTNVGWYQQ KPGKAPKALI  180
YSASFRYSGV PSRFSGSGSG TDFTLTISSL QPEDFATYYC QQYYTYPYTF GGGTKVEIKH  240
HHHHH                                                             245

SEQ ID NO: 236         moltype = AA  length = 138
FEATURE                Location/Qualifiers
source                 1..138
                       mol_type = protein
                       organism = synthetic construct
SEQUENCE: 236
EVQLLESGGG LVQPGGSLRL SCAASGSIFS ANAMGWYRQA PGKQRELVAV ISSGGSTNYA  60
DSVKGRFTIS RDNSKNTVYL QMNSLRAEDT AVYYCMYSGS YYYTPNDYWG QGTLVTVSSA  120
AAYPYDVPDY GSHHHHHH                                               138
```

-continued

```
SEQ ID NO: 237         moltype = AA  length = 138
FEATURE                Location/Qualifiers
source                 1..138
                       mol_type = protein
                       organism = synthetic construct
SEQUENCE: 237
EVQLLESGGG LVQPGGSLRL SCAASGSIFS ANAMGWYRQA PGKGLELVAV ISSGGSTNYA  60
DSVKGRFTIS RDNSKNTVYL QMNSLRAEDT AVYYCMYSGS YYYTPNDYWG QGTLVTVSSA  120
AAYPYDVPDY GSHHHHHH                                                138

SEQ ID NO: 238         moltype = AA  length = 138
FEATURE                Location/Qualifiers
source                 1..138
                       mol_type = protein
                       organism = synthetic construct
SEQUENCE: 238
EVQLLESGGG LVQPGGSLRL SCAASGSIFS ANAMGWVRQA PGKGLEWVSV ISSGGSTNYA  60
DSVKGRFTIS RDNSKNTLYL QMNSLRAEDT AVYYCMYSGS YYYTPNDYWG QGTLVTVSSA  120
AAYPYDVPDY GSHHHHHH                                                138

SEQ ID NO: 239         moltype = AA  length = 138
FEATURE                Location/Qualifiers
source                 1..138
                       mol_type = protein
                       organism = synthetic construct
SEQUENCE: 239
QVQLLESGGG LVQPGGSLRL SCAASGSIFS ANAMGWYRQA PGKQRELVAV ISSGGSTNYA  60
DSVKGRFTIS RDNSKNTVYL QMNSLRAEDT AVYYCMYSGS YYYTPNDYWG QGTLVTVSSA  120
AAYPYDVPDY GSHHHHHH                                                138

SEQ ID NO: 240         moltype = AA  length = 138
FEATURE                Location/Qualifiers
source                 1..138
                       mol_type = protein
                       organism = synthetic construct
SEQUENCE: 240
EVQLLESGGG LVQPGGSLRL SCAASGSIFS ANAMGWYRQA PGKGRELVAV ISSGGSTNYA  60
DSVKGRFTIS RDNSKNTVYL QMNSLRAEDT AVYYCMYSGS YYYTPNDYWG QGTLVTVSSA  120
AAYPYDVPDY GSHHHHHH                                                138

SEQ ID NO: 241         moltype = AA  length = 138
FEATURE                Location/Qualifiers
source                 1..138
                       mol_type = protein
                       organism = synthetic construct
SEQUENCE: 241
QVQLLESGGG LVQAGGSLRL SCAASGSIFS ANAMGWYRQA PGKQRELVAV ISSGGSTNYA  60
DSVKGRFTIS RDNSKNTVYL QMNSLRAEDT AVYYCMYSGS YYYTPNDYWG QGTLVTVSSA  120
AAYPYDVPDY GSHHHHHH                                                138

SEQ ID NO: 242         moltype = AA  length = 137
FEATURE                Location/Qualifiers
source                 1..137
                       mol_type = protein
                       organism = synthetic construct
SEQUENCE: 242
EVQLLESGGG LVQPGGSLRL SCAASERIFS TDVMGWYRQA PGKQRELVAV VSARGTTNYL  60
DAVKGRFTIS RDNSKNTLYL QMNSLRAEDT AVYYCYVRET TSPWRIYWGQ GTLVTVSSAA  120
AYPYDVPDYG SHHHHHH                                                 137

SEQ ID NO: 243         moltype = AA  length = 137
FEATURE                Location/Qualifiers
source                 1..137
                       mol_type = protein
                       organism = synthetic construct
SEQUENCE: 243
EVQLLESGGG LVQPGGSLRL SCAASERIFS TDVMGWYRQA PGKGLELVAV VSARGTTNYL  60
DAVKGRFTIS RDNSKNTLYL QMNSLRAEDT AVYYCYVRET TSPWRIYWGQ GTLVTVSSAA  120
AYPYDVPDYG SHHHHHH                                                 137

SEQ ID NO: 244         moltype = AA  length = 137
FEATURE                Location/Qualifiers
source                 1..137
                       mol_type = protein
                       organism = synthetic construct
SEQUENCE: 244
EVQLLESGGG LVQPGGSLRL SCAASERIFS TDVMGWVRQA PGKGLEWVSV VSARGTTNYL  60
DAVKGRFTIS RDNSKNTLYL QMNSLRAEDT AVYYCYVRET TSPWRIYWGQ GTLVTVSSAA  120
AYPYDVPDYG SHHHHHH                                                 137
```

```
SEQ ID NO: 245         moltype = AA  length = 137
FEATURE                Location/Qualifiers
source                 1..137
                       mol_type = protein
                       organism = synthetic construct
SEQUENCE: 245
QVQLLESGGG LVQPGGSLRL SCAASERIFS TDVMGWYRQA PGKQRELVAV VSARGTTNYL  60
DAVKGRFTIS RDNSKNTLYL QMNSLRAEDT AVYYCYVRET TSPWRIYWGQ GTLVTVSSAA  120
AYPYDVPDYG SHHHHHH                                                137

SEQ ID NO: 246         moltype = AA  length = 137
FEATURE                Location/Qualifiers
source                 1..137
                       mol_type = protein
                       organism = synthetic construct
SEQUENCE: 246
EVQLLESGGG LVQPGGSLRL SCAASERIFS TDVMGWYRQA PGKGRELVAV VSARGTTNYL  60
DSVKGRFTIS RDNSKNTLYL QMNSLRAEDT AVYYCYVRET TSPWRIYWGQ GTLVTVSSAA  120
AYPYDVPDYG SHHHHHH                                                137

SEQ ID NO: 247         moltype = AA  length = 137
FEATURE                Location/Qualifiers
source                 1..137
                       mol_type = protein
                       organism = synthetic construct
SEQUENCE: 247
QVQLLESGGG LVQEGGSLRL SCAASERIFS TDVMGWYRQA AGKQRELVAV VSARGTTNYL  60
DAVKGRFTIS RDNSKNTLYL QMNSLRAEDT ASYYCYVRET TSPWRIYWGQ GTLVTVSSAA  120
AYPYDVPDYG SHHHHHH                                                137

SEQ ID NO: 248         moltype = AA  length = 137
FEATURE                Location/Qualifiers
source                 1..137
                       mol_type = protein
                       organism = synthetic construct
SEQUENCE: 248
EVQLLESGGG LVQPGGSLRL SCAASERIFS TDVMGWYRQA PGKGLELVAV VSARGTTNYL  60
DSVKGRFTIS RDNSKNTLYL QMNSLRAEDT AVYYCYVRET TSPWRIYWGQ GTLVTVSSAA  120
AYPYDVPDYG SHHHHHH                                                137

SEQ ID NO: 249         moltype = AA  length = 137
FEATURE                Location/Qualifiers
source                 1..137
                       mol_type = protein
                       organism = synthetic construct
SEQUENCE: 249
EVQLLESGGG LVQPGGSLRL SCATSGTIFS GYTMGWYRQA PGKQRELVAV ISGGGDTNYA  60
DSVKGRFTIS RDNSKDTMYL QMNSLRAEDT AVYYCYSREV TPPWKLYWGQ GTLVTVSSAA  120
AYPYDVPDYG SHHHHHH                                                137

SEQ ID NO: 250         moltype = AA  length = 137
FEATURE                Location/Qualifiers
source                 1..137
                       mol_type = protein
                       organism = synthetic construct
SEQUENCE: 250
EVQLLESGGG LVQPGGSLRL SCATSGTIFS GYTMGWYRQA PGKGLELVAV ISGGGDTNYA  60
DSVKGRFTIS RDNSKDTMYL QMNSLRAEDT AVYYCYSREV TPPWKLYWGQ GTLVTVSSAA  120
AYPYDVPDYG SHHHHHH                                                137

SEQ ID NO: 251         moltype = AA  length = 137
FEATURE                Location/Qualifiers
source                 1..137
                       mol_type = protein
                       organism = synthetic construct
SEQUENCE: 251
EVQLLESGGG LVQPGGSLRL SCAASGTIFS GYTMGWVRQA PGKGLEWVSV ISGGGDTNYA  60
DSVKGRFTIS RDNSKNTLYL QMNSLRAEDT AVYYCYSREV TPPWKLYWGQ GTLVTVSSAA  120
AYPYDVPDYG SHHHHHH                                                137

SEQ ID NO: 252         moltype = AA  length = 137
FEATURE                Location/Qualifiers
source                 1..137
                       mol_type = protein
                       organism = synthetic construct
SEQUENCE: 252
QVQLLESGGG LVQPGGSLRL SCATSGTIFS GYTMGWYRQA PGKQRELVAV ISGGGDTNYA  60
DSVKGRFTIS RDNSKDTMYL QMNSLRAEDT AVYYCYSREV TPPWKLYWGQ GTLVTVSSAA  120
```

```
AYPYDVPDYG SHHHHHH                                          137

SEQ ID NO: 253         moltype = AA  length = 137
FEATURE                Location/Qualifiers
source                 1..137
                       mol_type = protein
                       organism = synthetic construct
SEQUENCE: 253
EVQLLESGGG LVQPGGSLRL SCATSGTIFS GYTMGWYRQA PGKQRELVAV ISGGGDTNYA  60
DSVKGRFTIS RDNSKNTMYL QMNSLRAEDT AVYYCYSREV TPPWKLYWGQ GTLVTVSSAA  120
AYPYDVPDYG SHHHHHH                                          137

SEQ ID NO: 254         moltype = AA  length = 137
FEATURE                Location/Qualifiers
source                 1..137
                       mol_type = protein
                       organism = synthetic construct
SEQUENCE: 254
EVQLLESGGG LVQPGGSLRL SCATSGTIFS GYTMGWYRQA PGKGRELVAV ISGGGDTNYA  60
DSVKGRFTIS RDNSKNTMYL QMNSLRAEDT AVYYCYSREV TPPWKLYWGQ GTLVTVSSAA  120
AYPYDVPDYG SHHHHHH                                          137

SEQ ID NO: 255         moltype = AA  length = 137
FEATURE                Location/Qualifiers
source                 1..137
                       mol_type = protein
                       organism = synthetic construct
SEQUENCE: 255
QVQLLESGGG LVQTGGSLRL SCATSGTIFS GYTMGWYRQA PGKQRELVAV ISGGGDTNYA  60
DSVKGRFTIS RDNSKDTMYL QMNSLRAEDT AVYYCYSREV TPPWKLYWGQ GTLVTVSSAA  120
AYPYDVPDYG SHHHHHH                                          137

SEQ ID NO: 256         moltype = AA  length = 137
FEATURE                Location/Qualifiers
source                 1..137
                       mol_type = protein
                       organism = synthetic construct
SEQUENCE: 256
EVQLLESGGG LVQPGGSLRL SCATSGTIFS GYTMGWYRQA PGKGLELVAV ISGGGDTNYA  60
DSVKGRFTIS RDNSKNTMYL QMNSLRAEDT AVYYCYSREV TPPWKLYWGQ GTLVTVSSAA  120
AYPYDVPDYG SHHHHHH                                          137

SEQ ID NO: 257         moltype = AA  length = 245
FEATURE                Location/Qualifiers
source                 1..245
                       mol_type = protein
                       organism = synthetic construct
SEQUENCE: 257
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSGGG  120
GSGGGGSGGG GSDIQMTQSP SSLSASVGDR VTITCKAREK LWSAVAWYQQ KPGKAPKALI  180
YSASFRYSGV PSRFSGSGSG TDFTLTISSL QPEDFATYYC QQYYTYPYTF GGGTKVEIKH  240
HHHHH                                                       245

SEQ ID NO: 258         moltype = AA  length = 245
FEATURE                Location/Qualifiers
source                 1..245
                       mol_type = protein
                       organism = synthetic construct
SEQUENCE: 258
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSGGG  120
GSGGGGSGGG GSDIQMTQSP SSLSASVGDR VTITCKAREK LWSAVAWYQQ KPGKAPKSLI  180
YSASFRYSGV PSRFSGSGSG TDFTLTISSL QPEDFATYYC QQYYTYPYTF GGGTKVEIKH  240
HHHHH                                                       245

SEQ ID NO: 259         moltype = AA  length = 245
FEATURE                Location/Qualifiers
source                 1..245
                       mol_type = protein
                       organism = synthetic construct
SEQUENCE: 259
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSGGG  120
GSGGGGSGGG GSDIQMTQSP SSLSASVGDR VTITCKVTEK VWGNVAWYQQ KPGKAPISLI  180
YSPSLRKSGV PSRFSGSGSG TDFTLTISSL QPEDFATYYC QQYYTYPYTF GGGTKVEIKH  240
HHHHH                                                       245

SEQ ID NO: 260         moltype = AA  length = 245
```

```
FEATURE                 Location/Qualifiers
source                  1..245
                        mol_type = protein
                        organism = synthetic construct
SEQUENCE: 260
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSGGG  120
GSGGGGSGGG GSDIQMTQSP SSLSASVGDR VTITCKSSEK LWANVAWYQQ KPGKAPKALI  180
YSASFRYSGV PSRFSGSGSG TDFTLTISSL QPEDFATYYC QQYYTYPYTF GGGTKVEIKH  240
HHHHH                                                              245

SEQ ID NO: 261          moltype = AA  length = 245
FEATURE                 Location/Qualifiers
source                  1..245
                        mol_type = protein
                        organism = synthetic construct
SEQUENCE: 261
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSGGG  120
GSGGGGSGGG GSDIQMTQSP SSLSASVGDR VTITCKSSEK LWANVAWYQQ KPGKAPKSLI  180
YSASFRYSGV PSRFSGSGSG TDFTLTISSL QPEDFATYYC QQYYTYPYTF GGGTKVEIKH  240
HHHHH                                                              245

SEQ ID NO: 262          moltype = AA  length = 214
FEATURE                 Location/Qualifiers
source                  1..214
                        mol_type = protein
                        organism = synthetic construct
SEQUENCE: 262
DIQMTQSPSS LSASVGDRVT ITCKASQNVG TNVGWYQQKP GKAPKALIYS ASFRYSGVPS  60
RFSGSGSGTD FTLTISSLQP EDFATYYCQQ YYTYPYTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 263          moltype = AA  length = 214
FEATURE                 Location/Qualifiers
source                  1..214
                        mol_type = protein
                        organism = synthetic construct
SEQUENCE: 263
DIQMTQSPSS LSASVGDRVT ITCKAREKLW SAVAWYQQKP GKAPKSLIYS ASFRYSGVPS  60
RFSGSGSGTD FTLTISSLQP EDFATYYCQQ YYTYPYTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 264          moltype = AA  length = 214
FEATURE                 Location/Qualifiers
source                  1..214
                        mol_type = protein
                        organism = synthetic construct
SEQUENCE: 264
DIQMTQSPSS LSASVGDRVT ITCKVTEKVW GNVAWYQQKP GKAPISLIYS PSLRKSGVPS  60
RFSGSGSGTD FTLTISSLQP EDFATYYCQQ YYTYPYTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 265          moltype = AA  length = 363
FEATURE                 Location/Qualifiers
source                  1..363
                        mol_type = protein
                        organism = synthetic construct
SEQUENCE: 265
DIQMTQSPSS LSASVGDRVT ITCKAREKLW SAVAWYQQKP GKAPKSLIYS ASFRYSGVPS  60
RFSGSGSGTD FTLTISSLQP EDFATYYCQQ YYTYPYTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECGGGGSG GGGSGGGGSG GGGSGGGGSG  240
GGGSEVQLLE SGGGLVQPGG SLRLSCAASG SIFSANAMGW YRQAPGKQRE LVAVISSGGS  300
TNYADSVKGR FTISRDNSKN TVYLQMNSLR AEDTAVYYCM YSGSYYYTPN DYWGQGTLVT  360
VSS                                                                363

SEQ ID NO: 266          moltype = AA  length = 363
FEATURE                 Location/Qualifiers
source                  1..363
                        mol_type = protein
                        organism = synthetic construct
SEQUENCE: 266
DIQMTQSPSS LSASVGDRVT ITCKAREKLW SAVAWYQQKP GKAPKSLIYS ASFRYSGVPS  60
RFSGSGSGTD FTLTISSLQP EDFATYYCQQ YYTYPYTFGG GTKVEIKRTV AAPSVFIFPP  120
SDEQLKSGTA SVVCLLNNFY PREAKVQWKV DNALQSGNSQ ESVTEQDSKD STYSLSSTLT  180
```

-continued

```
LSKADYEKHK VYACEVTHQG LSSPVTKSFN RGECGGGGSG GGGSGGGGSG GGGSGGGGSG  240
GGGSEVQLLE SGGGLVQPGG SLRLSCAASG SIFSANAMGW YRQAPGKGLE LVAVISSGGS  300
TNYADSVKGR FTISRDNSKN TVYLQMNSLR AEDTAVYYCM YSGSYYYTPN DYWGQGTLVT  360
VSS                                                                363

SEQ ID NO: 267          moltype = AA  length = 363
FEATURE                 Location/Qualifiers
source                  1..363
                        mol_type = protein
                        organism = synthetic construct
SEQUENCE: 267
DIQMTQSPSS LSASVGDRVT ITCKVTEKVW GNVAWYQQKP GKAPISLIYS PSLRKSGVPS  60
RFSGSGSGTD FTLTISSLQP EDFATYYCQQ YYTYPYTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECGGGGSG GGGSGGGGSG GGGSGGGGSG  240
GGGSEVQLLE SGGGLVQPGG SLRLSCAASG SIFSANAMGW YRQAPGKQRE LVAVISSGGS  300
TNYADSVKGR FTISRDNSKN TVYLQMNSLR AEDTAVYYCM YSGSYYYTPN DYWGQGTLVT  360
VSS                                                                363

SEQ ID NO: 268          moltype = AA  length = 363
FEATURE                 Location/Qualifiers
source                  1..363
                        mol_type = protein
                        organism = synthetic construct
SEQUENCE: 268
DIQMTQSPSS LSASVGDRVT ITCKVTEKVW GNVAWYQQKP GKAPISLIYS PSLRKSGVPS  60
RFSGSGSGTD FTLTISSLQP EDFATYYCQQ YYTYPYTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECGGGGSG GGGSGGGGSG GGGSGGGGSG  240
GGGSEVQLLE SGGGLVQPGG SLRLSCAASG SIFSANAMGW YRQAPGKGLE LVAVISSGGS  300
TNYADSVKGR FTISRDNSKN TVYLQMNSLR AEDTAVYYCM YSGSYYYTPN DYWGQGTLVT  360
VSS                                                                363

SEQ ID NO: 269          moltype = AA  length = 214
FEATURE                 Location/Qualifiers
source                  1..214
                        mol_type = protein
                        organism = synthetic construct
SEQUENCE: 269
DIQMTQSPSS LSASVGDRVT ITCKSSEKLW ANVAWYQQKP GKAPKSLIYS ASFRYSGVPS  60
RFSGSGSGTD FTLTISSLQP EDFATYYCQQ YYTYPYTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 270          moltype = AA  length = 214
FEATURE                 Location/Qualifiers
source                  1..214
                        mol_type = protein
                        organism = synthetic construct
SEQUENCE: 270
DIQMTQSPSS LSASVGDRVT ITCKSSEKLW ANVAWYQQKP GKAPKLLIYS ASFRYSGVPS  60
RFSGSGSGTD FTLTISSLQP EDFATYYCQQ YYTYPYTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 271          moltype = AA  length = 214
FEATURE                 Location/Qualifiers
source                  1..214
                        mol_type = protein
                        organism = synthetic construct
SEQUENCE: 271
DIQMTQSPSS LSASVGDRVT ITCKAREKLW SAVAWYQQKP GKAPKLLIYS ASFRYSGVPS  60
RFSGSGSGTD FTLTISSLQP EDFATYYCQQ YYTYPYTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 272          moltype = AA  length = 547
FEATURE                 Location/Qualifiers
source                  1..547
                        mol_type = protein
                        organism = synthetic construct
SEQUENCE: 272
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
```

-continued

```
VTVSSGGGGS GGGGSGGGGS DIQMTQSPSS LSASVGDRVT ITCKSSEKLW ANVAWYQQKP  480
GKAPKALIYS ASFRYSGVPS RFSGSGSGTD FTLTISSLQP EDFATYYCQQ YYTYPYTFGG  540
GTKVEIK                                                            547

SEQ ID NO: 273         moltype = AA  length = 547
FEATURE                Location/Qualifiers
source                 1..547
                       mol_type = protein
                       organism = synthetic construct
SEQUENCE: 273
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKSSEKLW ANVAWYQQKP  480
GKAPKSLIYS ASFRYSGVPS RFSGSGSGTD FTLTISSLQP EDFATYYCQQ YYTYPYTFGG  540
GTKVEIK                                                            547

SEQ ID NO: 274         moltype = AA  length = 547
FEATURE                Location/Qualifiers
source                 1..547
                       mol_type = protein
                       organism = synthetic construct
SEQUENCE: 274
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKSSEKLW ANVAWYQQKP  480
GKAPKLLIYS ASFRYSGVPS RFSGSGSGTD FTLTISSLQP EDFATYYCQQ YYTYPYTFGG  540
GTKVEIK                                                            547

SEQ ID NO: 275         moltype = AA  length = 547
FEATURE                Location/Qualifiers
source                 1..547
                       mol_type = protein
                       organism = synthetic construct
SEQUENCE: 275
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KCLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKSSEKLW ANVAWYQQKP  480
GKAPKSLIYS ASFRYSGVPS RFSGSGSGTD FTLTISSLQP EDFATYYCQQ YYTYPYTFGC  540
GTKVEIK                                                            547

SEQ ID NO: 276         moltype = AA  length = 547
FEATURE                Location/Qualifiers
source                 1..547
                       mol_type = protein
                       organism = synthetic construct
SEQUENCE: 276
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KCLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKSSEKLW ANVAWYQQKP  480
GKAPKLLIYS ASFRYSGVPS RFSGSGSGTD FTLTISSLQP EDFATYYCQQ YYTYPYTFGC  540
GTKVEIK                                                            547

SEQ ID NO: 277         moltype = AA  length = 547
FEATURE                Location/Qualifiers
source                 1..547
                       mol_type = protein
                       organism = synthetic construct
SEQUENCE: 277
APTSSSTKKT QLQLEHLLLD LQMILNGINN YKNPKLTRML TFKFYMPKKA TELKHLQCLE  60
```

```
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGCGTT  420
VTVSSGGGGS GGGGSGGGGS DIQMTQSPSS LSASVGDRVT ITCKSSEKLW ANVAWYQQKP  480
GKCPKALIYS ASFRYSGVPS RFSGSGSGTD FTLTISSLQP EDFATYYCQQ YYTYPYTFGG  540
GTKVEIK                                                           547

SEQ ID NO: 278          moltype = AA  length = 547
FEATURE                 Location/Qualifiers
source                  1..547
                        mol_type = protein
                        organism = synthetic construct
SEQUENCE: 278
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSSGGPG PAGLYAQPGS DIQMTQSPSS LSASVGDRVT ITCKAREKLW SAVAWYQQKP  480
GKAPKLLIYS ASFRYSGVPS RFSGSGSGTD FTLTISSLQP EDFATYYCQQ YYTYPYTFGG  540
GTKVEIK                                                           547

SEQ ID NO: 279          moltype = AA  length = 547
FEATURE                 Location/Qualifiers
source                  1..547
                        mol_type = protein
                        organism = synthetic construct
SEQUENCE: 279
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKAREKLW SAVAWYQQKP  480
GKAPKLLIYS ASFRYSGVPS RFSGSGSGTD FTLTISSLQP EDFATYYCQQ YYTYPYTFGG  540
GTKVEIK                                                           547

SEQ ID NO: 280          moltype = AA  length = 547
FEATURE                 Location/Qualifiers
source                  1..547
                        mol_type = protein
                        organism = synthetic construct
SEQUENCE: 280
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KCLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKAREKLW SAVAWYQQKP  480
GKAPKLLIYS ASFRYSGVPS RFSGSGSGTD FTLTISSLQP EDFATYYCQQ YYTYPYTFGC  540
GTKVEIK                                                           547

SEQ ID NO: 281          moltype = AA  length = 547
FEATURE                 Location/Qualifiers
source                  1..547
                        mol_type = protein
                        organism = synthetic construct
SEQUENCE: 281
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPALF KSSFPPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPALF  300
KSSFPPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKAREKLW SAVAWYQQKP  480
GKAPKSLIYS ASFRYSGVPS RFSGSGSGTD FTLTISSLQP EDFATYYCQQ YYTYPYTFGG  540
GTKVEIK                                                           547

SEQ ID NO: 282          moltype = AA  length = 547
```

```
FEATURE                Location/Qualifiers
source                 1..547
                       mol_type = protein
                       organism = synthetic construct
SEQUENCE: 282
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPALF KSSFPPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPALF  300
KSSFPPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKVTEKVW GNVAWYQQKP  480
GKAPISLIYS PSLRKSGVPS RFSGSGSGTD FTLTISSLQP EDFATYYCQQ YYTYPYTFGG  540
GTKVEIK                                                          547

SEQ ID NO: 283         moltype = AA  length = 547
FEATURE                Location/Qualifiers
source                 1..547
                       mol_type = protein
                       organism = synthetic construct
SEQUENCE: 283
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPALF KSSFPPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPALF  300
KSSFPPGSEV QLVESGGGLV QPGGSLRLSC AASGFTFSSY TLAWVRQAPG KCLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKAREKLW SAVAWYQQKP  480
GKAPKSLIYS ASFRYSGVPS RFSGSGSGTD FTLTISSLQP EDFATYYCQQ YYTYPYTFGC  540
GTKVEIK                                                          547

SEQ ID NO: 284         moltype = AA  length = 547
FEATURE                Location/Qualifiers
source                 1..547
                       mol_type = protein
                       organism = synthetic construct
SEQUENCE: 284
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPALF KSSFPPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPALF  300
KSSFPPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGCGTT  420
VTVSSGGGGS GGGGSGGGGS DIQMTQSPSS LSASVGDRVT ITCKAREKLW SAVAWYQQKP  480
GKCPKALIYS ASFRYSGVPS RFSGSGSGTD FTLTISSLQP EDFATYYCQQ YYTYPYTFGG  540
GTKVEIK                                                          547

SEQ ID NO: 285         moltype = AA  length = 547
FEATURE                Location/Qualifiers
source                 1..547
                       mol_type = protein
                       organism = synthetic construct
SEQUENCE: 285
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPALF KSSFPPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPALF  300
KSSFPPGSEV QLVESGGGLV QPGGSLRLSC AASGFTFSSY TLAWVRQAPG KCLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKVTEKVW GNVAWYQQKP  480
GKAPISLIYS PSLRKSGVPS RFSGSGSGTD FTLTISSLQP EDFATYYCQQ YYTYPYTFGC  540
GTKVEIK                                                          547

SEQ ID NO: 286         moltype = AA  length = 528
FEATURE                Location/Qualifiers
source                 1..528
                       mol_type = protein
                       organism = synthetic construct
SEQUENCE: 286
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPALF KSSFPPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPALF  300
KSSFPPGSEV QLVESGGGLV QPGGSLRLSC AASGFTFSSY TLAWVRQAPG KGLEWVAAID  360
```

```
SSSYTYSPDT VRGRFTISRD NAKNSLYLQM NSLRAEDTAV YYCARDSNWD ALDYWGQGTT  420
VTVSSASTKG PSVFPLAPSS KSTSGGTAAL GCLVKDYFPE PVTVSWNSGA LTSGVHTFPA  480
VLQSSGLYSL SSVVTVPSSS LGTQTYICNV NHKPSNTKVD KRVEPKSC              528

SEQ ID NO: 287         moltype = AA  length = 642
FEATURE                Location/Qualifiers
source                 1..642
                       mol_type = protein
                       organism = synthetic construct
SEQUENCE: 287
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPALFKSSF  240
PPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PALFKSSFPP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG QGTTVTVSSA  540
STKGPSVFPL APSSKSTSGG TAALGCLVKD YFPEPVTVSW NSGALTSGVH TFPAVLQSSG  600
LYSLSSVVTV PSSSLGTQTY ICNVNHKPSN TKVDKRVEPK SC                    642

SEQ ID NO: 288         moltype = AA  length = 661
FEATURE                Location/Qualifiers
source                 1..661
                       mol_type = protein
                       organism = synthetic construct
SEQUENCE: 288
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPALFKSSF  240
PPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PALFKSSFPP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG QGTTVTVSSG  540
GGGSGGGGSG GGGSDIQMTQ SPSSLSASVG DRVTITCKAR EKLWSAVAWY QQKPGKAPKS  600
LIYSASFRYS GVPSRFSGSG SGTDFTLTIS SLQPEDFATY YCQQYYTYPY TFGGGTKVEI  660
K                                                                 661

SEQ ID NO: 289         moltype = AA  length = 661
FEATURE                Location/Qualifiers
source                 1..661
                       mol_type = protein
                       organism = synthetic construct
SEQUENCE: 289
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPALFKSSF  240
PPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PALFKSSFPP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG QGTTVTVSSG  540
GGGSGGGGSG GGGSDIQMTQ SPSSLSASVG DRVTITCKVT EKVWGNVAWY QQKPGKAPIS  600
LIYSPSLRKS GVPSRFSGSG SGTDFTLTIS SLQPEDFATY YCQQYYTYPY TFGGGTKVEI  660
K                                                                 661

SEQ ID NO: 290         moltype = AA  length = 661
FEATURE                Location/Qualifiers
source                 1..661
                       mol_type = protein
                       organism = synthetic construct
SEQUENCE: 290
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPALFKSSF  240
PPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PALFKSSFPP  420
GSEVQLVESG GGLVQPGGSL RLSCAASGFT FSSYTLAWVR QAPGKCLEWV AAIDSSSYTY  480
SPDTVRGRFT ISRDNAKNSL YLQMNSLRAE DTAVYYCARD SNWDALDYWG QGTTVTVSSG  540
GGGSGGGGSG GGGSDIQMTQ SPSSLSASVG DRVTITCKAR EKLWSAVAWY QQKPGKAPKS  600
LIYSASFRYS GVPSRFSGSG SGTDFTLTIS SLQPEDFATY YCQQYYTYPY TFGCGTKVEI  660
K                                                                 661
```

-continued

```
SEQ ID NO: 291         moltype = AA  length = 661
FEATURE                Location/Qualifiers
source                 1..661
                       mol_type = protein
                       organism = synthetic construct
SEQUENCE: 291
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPALFKSSF  240
PPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PALFKSSFPP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG CGTTVTVSSG  540
GGGSGGGGSG GGGSDIQMTQ SPSSLSASVG DRVTITCKAR EKLWSAVAWY QQKPGKCPKA  600
LIYSASFRYS GVPSRFSGSG SGTDFTLTIS SLQPEDFATY YCQQYYTYPY TFGGGTKVEI  660
K                                                                 661

SEQ ID NO: 292         moltype = AA  length = 661
FEATURE                Location/Qualifiers
source                 1..661
                       mol_type = protein
                       organism = synthetic construct
SEQUENCE: 292
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPALFKSSF  240
PPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PALFKSSFPP  420
GSEVQLVESG GGLVQPGGSL RLSCAASGFT FSSYTLAWVR QAPGKCLEWV AAIDSSSYTY  480
SPDTVRGRFT ISRDNAKNSL YLQMNSLRAE DTAVYYCARD SNWDALDYWG QGTTVTVSSG  540
GGGSGGGGSG GGGSDIQMTQ SPSSLSASVG DRVTITCKVT EKVWGNVAWY QQKPGKAPIS  600
LIYSPSLRKS GVPSRFSGSG SGTDFTLTIS SLQPEDFATY YCQQYYTYPY TFGCGTKVEI  660
K                                                                 661

SEQ ID NO: 293         moltype = AA  length = 661
FEATURE                Location/Qualifiers
source                 1..661
                       mol_type = protein
                       organism = synthetic construct
SEQUENCE: 293
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPALFKSSF  240
PPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PALFKSSFPP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG CGTTVTVSSG  540
GGGSGGGGSG GGGSDIQMTQ SPSSLSASVG DRVTITCKVT EKVWGNVAWY QQKPGKCPIS  600
LIYSPSLRKS GVPSRFSGSG SGTDFTLTIS SLQPEDFATY YCQQYYTYPY TFGGGTKVEI  660
K                                                                 661

SEQ ID NO: 294         moltype = AA  length = 659
FEATURE                Location/Qualifiers
source                 1..659
                       mol_type = protein
                       organism = synthetic construct
SEQUENCE: 294
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PALFKSSFPP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPA LFKSSFPPGS  420
EVQLVESGGG LVQPGGSLRL SCAASGFTFS SYTLAWVRQA PGKGLEWVAA IDSSSYTYSP  480
DTVRGRFTIS RDNAKNSLYL QMNSLRAEDT AVYYCARDSN WDALDYWGQG TTVTVSSGGG  540
GSGGGGSGGG GSDIQMTQSP SSLSASVGDR VTITCKAREK LWSAVAWYQQ KPGKAPKSLI  600
YSASFRYSGV PSRFSGSGSG TDFTLTISSL QPEDFATYYC QQYYTYPYTF GGGTKVEIK   659

SEQ ID NO: 295         moltype = AA  length = 659
FEATURE                Location/Qualifiers
source                 1..659
                       mol_type = protein
```

```
                         organism = synthetic construct
SEQUENCE: 295
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PALFKSSFPP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPA LFKSSFPPGS  420
EVQLVESGGG LVQPGGSLRL SCAASGFTFS SYTLAWVRQA PGKGLEWVAA IDSSSYTYSP  480
DTVRGRFTIS RDNAKNSLYL QMNSLRAEDT AVYYCARDSN WDALDYWGQG TTVTVSSGGG  540
GSGGGGSGGG GSDIQMTQSP SSLSASVGDR VTITCKVTEK VWGNVAWYQQ KPGKAPISLI  600
YSPSLRKSGV PSRFSGSGSG TDFTLTISSL QPEDFATYYC QQYYTYPYTF GGGTKVEIK   659

SEQ ID NO: 296           moltype = AA  length = 659
FEATURE                  Location/Qualifiers
source                   1..659
                         mol_type = protein
                         organism = synthetic construct
SEQUENCE: 296
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PALFKSSFPP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPA LFKSSFPPGS  420
EVQLVESGGG LVQPGGSLRL SCAASGFTFS SYTLAWVRQA PGKCLEWVAA IDSSSYTYSP  480
DTVRGRFTIS RDNAKNSLYL QMNSLRAEDT AVYYCARDSN WDALDYWGQG TTVTVSSGGG  540
GSGGGGSGGG GSDIQMTQSP SSLSASVGDR VTITCKAREK LWSAVAWYQQ KPGKAPKSLI  600
YSASFRYSGV PSRFSGSGSG TDFTLTISSL QPEDFATYYC QQYYTYPYTF GCGTKVEIK   659

SEQ ID NO: 297           moltype = AA  length = 659
FEATURE                  Location/Qualifiers
source                   1..659
                         mol_type = protein
                         organism = synthetic construct
SEQUENCE: 297
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PALFKSSFPP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPA LFKSSFPPGS  420
EVQLVESGGG LVQPGGSLRL SCAASGFTFS SYTLAWVRQA PGKGLEWVAA IDSSSYTYSP  480
DTVRGRFTIS RDNAKNSLYL QMNSLRAEDT AVYYCARDSN WDALDYWGCG TTVTVSSGGG  540
GSGGGGSGGG GSDIQMTQSP SSLSASVGDR VTITCKAREK LWSAVAWYQQ KPGKCPKALI  600
YSASFRYSGV PSRFSGSGSG TDFTLTISSL QPEDFATYYC QQYYTYPYTF GGGTKVEIK   659

SEQ ID NO: 298           moltype = AA  length = 659
FEATURE                  Location/Qualifiers
source                   1..659
                         mol_type = protein
                         organism = synthetic construct
SEQUENCE: 298
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PALFKSSFPP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPA LFKSSFPPGS  420
EVQLVESGGG LVQPGGSLRL SCAASGFTFS SYTLAWVRQA PGKCLEWVAA IDSSSYTYSP  480
DTVRGRFTIS RDNAKNSLYL QMNSLRAEDT AVYYCARDSN WDALDYWGQG TTVTVSSGGG  540
GSGGGGSGGG GSDIQMTQSP SSLSASVGDR VTITCKVTEK VWGNVAWYQQ KPGKAPISLI  600
YSPSLRKSGV PSRFSGSGSG TDFTLTISSL QPEDFATYYC QQYYTYPYTF GCGTKVEIK   659

SEQ ID NO: 299           moltype = AA  length = 659
FEATURE                  Location/Qualifiers
source                   1..659
                         mol_type = protein
                         organism = synthetic construct
SEQUENCE: 299
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PALFKSSFPP  240
GSAPTSSSTK KTQLQLEHLL LDLQMILNGI NNYKNPKLTR MLTFKFYMPK KATELKHLQC  300
```

-continued

```
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPA LFKSSFPPGS  420
EVQLVESGGG LVQPGGSLRL SCAASGFTFS SYTLAWVRQA PGKGLEWVAA IDSSSYTYSP  480
DTVRGRFTIS RDNAKNSLYL QMNSLRAEDT AVYYCARDSN WDALDYWGCG TTVTVSSGGG  540
GSGGGGSGGG GSDIQMTQSP SSLSASVGDR VTITCKVTEK VWGNVAWYQQ KPGKCPISLI  600
YSPSLRKSGV PSRFSGSGSG TDFTLTISSL QPEDFATYYC QQYYTYPYTF GGGTKVEIK   659

SEQ ID NO: 300         moltype = AA  length = 662
FEATURE                Location/Qualifiers
source                 1..662
                       mol_type = protein
                       organism = synthetic construct
SEQUENCE: 300
MDMRVPAQLL GLLLLWLRGA RCVPRDCGCK PCICTVPEVS SVFIFPPKPK DVLTITLTPK  60
VTCVVVDISK DDPEVQFSWF VDDVEVHTAQ TQPREEQFNS TFRSVSELPI MHQDWLNGKE  120
FKCRVNSAAF PAPIEKTISK TKGRPKAPQV YTIPPPKEQM AKDKVSLTCM ITDFFPEDIT  180
VEWQWNGQPA ENYKNTQPIM DTDGSYFVYS KLNVQKSNWE AGNTFTCSVL HEGLHNHHTE  240
KSLSHSPGKS GGPALFKSSF PPGSAPTSSS TKKTQLQLEH LLLDLQMILN GINNYKNPKL  300
TRMLTFKFYM PKKATELKHL QCLEEELKPL EEVLNLAQSK NFHLRPRDLI SNINVIVLEL  360
KGSETTFMCE YADETATIVE FLNRWITFCQ SIISTLTGGG GSGGGGSGGG GSGGGGSGGG  420
GSGGGGSSGG PALFKSSFPP GSEVQLVESG GGLVQPGGSL RLSCAASGFT FSSYTLAWVR  480
QAPGKGLEWV AAIDSSSYTY SPDTVRGRFT ISRDNAKNSL YLQMNSLRAE DTAVYYCARD  540
SNWDALDYWG QGTTVTVSSA STKGPSVFPL APSSKSTSGG TAALGCLVKD YFPEPVTVSW  600
NSGALTSGVH TFPAVLQSSG LYSLSSVVTV PSSSLGTQTY ICNVNHKPSN TKVDKRVEPK  660
SC                                                                662

SEQ ID NO: 301         moltype = AA  length = 214
FEATURE                Location/Qualifiers
source                 1..214
                       mol_type = protein
                       organism = synthetic construct
SEQUENCE: 301
DIQMTQSPSS LSASVGDRVT ITCKVTEKVW GNVAWYQQKP GKAPISLIYS PSLRKSGVPS  60
RFSGSGSGTD FTLTISSLQP EDFATYYCQQ YYTYPYTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 302         moltype = AA  length = 661
FEATURE                Location/Qualifiers
source                 1..661
                       mol_type = protein
                       organism = synthetic construct
SEQUENCE: 302
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLVESG GGLVQPGGSL RLSCAASGFT FSSYTLAWVR QAPGKCLEWV AAIDSSSYTY  480
SPDTVRGRFT ISRDNAKNSL YLQMNSLRAE DTAVYYCARD SNWDALDYWG QGTTVTVSSG  540
GGGSGGGGSG GGGSDIQMTQ SPSSLSASVG DRVTITCKAS QNVGTNVGWY QQKPGKAPKA  600
LIYSASFRYS GVPSRFSGSG SGTDFTLTIS SLQPEDFATY YCQQYYTYPY TFGCGTKVEI  660
K                                                                 661

SEQ ID NO: 303         moltype = AA  length = 661
FEATURE                Location/Qualifiers
source                 1..661
                       mol_type = protein
                       organism = synthetic construct
SEQUENCE: 303
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG CGTTVTVSSG  540
GGGSGGGGSG GGGSDIQMTQ SPSSLSASVG DRVTITCKAS QNVGTNVGWY QQKPGKCPKA  600
LIYSASFRYS GVPSRFSGSG SGTDFTLTIS SLQPEDFATY YCQQYYTYPY TFGGGTKVEI  660
K                                                                 661

SEQ ID NO: 304         moltype = AA  length = 661
FEATURE                Location/Qualifiers
source                 1..661
                       mol_type = protein
```

```
                          organism = synthetic construct
SEQUENCE: 304
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLVESG GGLVQPGGSL RLSCAASGFT FSSYTLAWVR QAPGKCLEWV AAIDSSSYTY  480
SPDTVRGRFT ISRDNAKNSL YLQMNSLRAE DTAVYYCARD SNWDALDYWG QGTTVTVSSG  540
GGGSGGGGSG GGGSDIQMTQ SPSSLSASVG DRVTITCKAR EKLWSAVAWY QQKPGKAPKA  600
LIYSASFRYS GVPSRFSGSG SGTDFTLTIS SLQPEDFATY YCQQYYTYPY TFGCGTKVEI  660
K                                                                 661

SEQ ID NO: 305            moltype = AA  length = 661
FEATURE                   Location/Qualifiers
source                    1..661
                          mol_type = protein
                          organism = synthetic construct
SEQUENCE: 305
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG CGTTVTVSSG  540
GGGSGGGGSG GGGSDIQMTQ SPSSLSASVG DRVTITCKAR EKLWSAVAWY QQKPGKCPKA  600
LIYSASFRYS GVPSRFSGSG SGTDFTLTIS SLQPEDFATY YCQQYYTYPY TFGGGTKVEI  660
K                                                                 661

SEQ ID NO: 306            moltype = AA  length = 661
FEATURE                   Location/Qualifiers
source                    1..661
                          mol_type = protein
                          organism = synthetic construct
SEQUENCE: 306
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLVESG GGLVQPGGSL RLSCAASGFT FSSYTLAWVR QAPGKCLEWV AAIDSSSYTY  480
SPDTVRGRFT ISRDNAKNSL YLQMNSLRAE DTAVYYCARD SNWDALDYWG QGTTVTVSSG  540
GGGSGGGGSG GGGSDIQMTQ SPSSLSASVG DRVTITCKVT EKVWGNVAWY QQKPGKAPIS  600
LIYSPSLRKS GVPSRFSGSG SGTDFTLTIS SLQPEDFATY YCQQYYTYPY TFGCGTKVEI  660
K                                                                 661

SEQ ID NO: 307            moltype = AA  length = 661
FEATURE                   Location/Qualifiers
source                    1..661
                          mol_type = protein
                          organism = synthetic construct
SEQUENCE: 307
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG CGTTVTVSSG  540
GGGSGGGGSG GGGSDIQMTQ SPSSLSASVG DRVTITCKVT EKVWGNVAWY QQKPGKCPIS  600
LIYSPSLRKS GVPSRFSGSG SGTDFTLTIS SLQPEDFATY YCQQYYTYPY TFGGGTKVEI  660
K                                                                 661

SEQ ID NO: 308            moltype = AA  length = 541
FEATURE                   Location/Qualifiers
source                    1..541
                          mol_type = protein
                          organism = synthetic construct
SEQUENCE: 308
ESKYGPPCPP CPAPEFLGGP SVFLFPPKPK DTLMISRTPE VTCVVVDVSQ EDPEVQFNWY  60
```

```
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLLESG GGLVQPGGSL RLSCAASGSI FSANAMGWYR QAPGKQRELV AVISSGGSTN  480
YADSVKGRFT ISRDNSKNTV YLQMNSLRAE DTAVYYCMYS GSYYYTPNDY WGQGTLVTVS  540
S                                                                 541

SEQ ID NO: 309         moltype = AA  length = 547
FEATURE                Location/Qualifiers
source                 1..547
                       mol_type = protein
                       organism = synthetic construct
SEQUENCE: 309
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KCLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKAREKLW SAVAWYQQKP  480
GKAPKSLIYS ASFRYSGVPS RFSGSGSGTD FTLTISSLQP EDFATYYCQQ YYTYPYTFGC  540
GTKVEIK                                                           547

SEQ ID NO: 310         moltype = AA  length = 661
FEATURE                Location/Qualifiers
source                 1..661
                       mol_type = protein
                       organism = synthetic construct
SEQUENCE: 310
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLVESG GGLVQPGGSL RLSCAASGFT FSSYTLAWVR QAPGKCLEWV AAIDSSSYTY  480
SPDTVRGRFT ISRDNAKNSL YLQMNSLRAE DTAVYYCARD SNWDALDYWG QGTTVTVSSG  540
GGGSGGGGSG GGGSDIQMTQ SPSSLSASVG DRVTITCKAR EKLWSAVAWY QQKPGKAPKS  600
LIYSASFRYS GVPSRFSGSG SGTDFTLTIS SLQPEDFATY YCQQYYTYPY TFGCGTKVEI  660
K                                                                 661

SEQ ID NO: 311         moltype = AA  length = 811
FEATURE                Location/Qualifiers
source                 1..811
                       mol_type = protein
                       organism = synthetic construct
SEQUENCE: 311
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSGG GGSGGGGSEL  180
CDDDPPEIPH ATFKAMAYKE GTMLNCECKR GFRRIKSGSL YMLCTGNSSH SSWDNQCQCT  240
SSATRNTTKQ VTPQPEEQKE RKTTEMQSPM QPVDQASLPG HCREPPPWEN EATERIYHFV  300
VGQMVYYQCV QGYRALHRGP AESVCKMTHG KTRWTQPQLI CTGEMETSQF PGEEKPQASP  360
EGRPESETSS LVTTTDFQIQ TEMAATMETS IFTTEYQSGG PGPAGLYAQP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGLYAQP GSEVQLVESG GGLVQPGGSL RLSCAASGFT  600
FSSYTLAWVR QAPGKCLEWV AAIDSSSYTY SPDTVRGRFT ISRDNAKNSL YLQMNSLRAE  660
DTAVYYCARD SNWDALDYWG QGTTVTVSSG GGGSGGGGSG GGGSDIQMTQ SPSSLSASVG  720
DRVTITCKAR EKLWSAVAWY QQKPGKAPKS LIYSASFRYS GVPSRFSGSG SGTDFTLTIS  780
SLQPEDFATY YCQQYYTYPY TFGCGTKVEI K                                811

SEQ ID NO: 312         moltype = AA  length = 811
FEATURE                Location/Qualifiers
source                 1..811
                       mol_type = protein
                       organism = synthetic construct
SEQUENCE: 312
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSGG GGSGGGGSEL  180
CDDDPPEIPH ATFKAMAYKE GTMLNCECKR GFRRIKSGSL YMLCTGNSSH SSWDNQCQCT  240
SSATRNTTKQ VTPQPEEQKE RKTTEMQSPM QPVDQASLPG HCREPPPWEN EATERIYHFV  300
VGQMVYYQCV QGYRALHRGP AESVCKMTHG KTRWTQPQLI CTGEMETSQF PGEEKPQASP  360
```

```
EGRPESETSS LVTTTDFQIQ TEMAATMETS IFTTEYQSGG PGPAGLYAQP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGLYAQP GSEVQLVESG GGLVQPGGSL RLSCAASGFT  600
FSSYTLAWVR QAPGKGLEWV AAIDSSSYTY SPDTVRGRFT ISRDNAKNSL YLQMNSLRAE  660
DTAVYYCARD SNWDALDYWG CGTTVTVSSG GGGSGGGGSG GGGSDIQMTQ SPSSLSASVG  720
DRVTITCKAR EKLWSAVAWY QQKPGKCPKA LIYSASFRYS GVPSRFSGSG SGTDFTLTIS  780
SLQPEDFATY YCQQYYTYPY TFGGGTKVEI K                                 811

SEQ ID NO: 313         moltype = AA  length = 811
FEATURE                Location/Qualifiers
source                 1..811
                       mol_type = protein
                       organism = synthetic construct
SEQUENCE: 313
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSGG GGSGGGGSEL  180
CDDDPPEIPH ATFKAMAYKE GTMLNCECKR GFRRIKSGSL YMLCTGNSSH SSWDNQCQCT  240
SSATRNTTKQ VTPQPEEQKE RKTTEMQSPM QPVDQASLPG HCREPPPWEN EATERIYHFV  300
VGQMVYYQCV QGYRALHRGP AESVCKMTHG KTRWTQPQLI CTGEMETSQF PGEEKPQASP  360
EGRPESETSS LVTTTDFQIQ TEMAATMETS IFTTEYQSGG PGPAGLYAQP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGLYAQP GSEVQLVESG GGLVQPGGSL RLSCAASGFT  600
FSSYTLAWVR QAPGKCLEWV AAIDSSSYTY SPDTVRGRFT ISRDNAKNSL YLQMNSLRAE  660
DTAVYYCARD SNWDALDYWG QGTTVTVSSG GGGSGGGGSG GGGSDIQMTQ SPSSLSASVG  720
DRVTITCKVT EKVWGNVAWY QQKPGKAPIS LIYSPSLRKS GVPSRFSGSG SGTDFTLTIS  780
SLQPEDFATY YCQQYYTYPY TFGCGTKVEI K                                 811

SEQ ID NO: 314         moltype = AA  length = 811
FEATURE                Location/Qualifiers
source                 1..811
                       mol_type = protein
                       organism = synthetic construct
SEQUENCE: 314
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSGG GGSGGGGSEL  180
CDDDPPEIPH ATFKAMAYKE GTMLNCECKR GFRRIKSGSL YMLCTGNSSH SSWDNQCQCT  240
SSATRNTTKQ VTPQPEEQKE RKTTEMQSPM QPVDQASLPG HCREPPPWEN EATERIYHFV  300
VGQMVYYQCV QGYRALHRGP AESVCKMTHG KTRWTQPQLI CTGEMETSQF PGEEKPQASP  360
EGRPESETSS LVTTTDFQIQ TEMAATMETS IFTTEYQSGG PGPAGLYAQP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGLYAQP GSEVQLVESG GGLVQPGGSL RLSCAASGFT  600
FSSYTLAWVR QAPGKGLEWV AAIDSSSYTY SPDTVRGRFT ISRDNAKNSL YLQMNSLRAE  660
DTAVYYCARD SNWDALDYWG CGTTVTVSSG GGGSGGGGSG GGGSDIQMTQ SPSSLSASVG  720
DRVTITCKVT EKVWGNVAWY QQKPGKCPIS LIYSPSLRKS GVPSRFSGSG SGTDFTLTIS  780
SLQPEDFATY YCQQYYTYPY TFGGGTKVEI K                                 811

SEQ ID NO: 315         moltype = AA  length = 691
FEATURE                Location/Qualifiers
source                 1..691
                       mol_type = protein
                       organism = synthetic construct
SEQUENCE: 315
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSGG GGSGGGGSEL  180
CDDDPPEIPH ATFKAMAYKE GTMLNCECKR GFRRIKSGSL YMLCTGNSSH SSWDNQCQCT  240
SSATRNTTKQ VTPQPEEQKE RKTTEMQSPM QPVDQASLPG HCREPPPWEN EATERIYHFV  300
VGQMVYYQCV QGYRALHRGP AESVCKMTHG KTRWTQPQLI CTGEMETSQF PGEEKPQASP  360
EGRPESETSS LVTTTDFQIQ TEMAATMETS IFTTEYQSGG PGPAGLYAQP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGLYAQP GSEVQLLESG GGLVQPGGSL RLSCAASGSI  600
FSANAMGWYR QAPGKQRELV AVISSGGSTN YADSVKGRFT ISRDNSKNTV YLQMNSLRAE  660
DTAVYYCMYS GSYYYTPNDY WGQGTLVTVS S                                 691

SEQ ID NO: 316         moltype = AA  length = 691
FEATURE                Location/Qualifiers
source                 1..691
                       mol_type = protein
                       organism = synthetic construct
SEQUENCE: 316
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSGG GGSGGGGSEL  180
```

```
CDDDPPEIPH ATFKAMAYKE GTMLNCECKR GFRRIKSGSL YMLCTGNSSH SSWDNQCQCT  240
SSATRNTTKQ VTPQPEEQKE RKTTEMQSPM QPVDQASLPG HCREPPPWEN EATERIYHFV  300
VGQMVYYQCV QGYRALHRGP AESVCKMTHG KTRWTQPQLI CTGEMETSQF PGEEKPQASP  360
EGRPESETSS LVTTTDFQIQ TEMAATMETS IFTTEYQSGG PGPAGLYAQP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGLYAQP GSEVQLLESG GGLVQPGGSL RLSCAASGSI  600
FSANAMGWYR QAPGKGLELV AVISSGGSTN YADSVKGRFT ISRDNSKNTV YLQMNSLRAE  660
DTAVYYCMYS GSYYYTPNDY WGQGTLVTVS S                                691

SEQ ID NO: 317         moltype = AA  length = 792
FEATURE                Location/Qualifiers
source                 1..792
                       mol_type = protein
                       organism = synthetic construct
SEQUENCE: 317
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSGG GGSGGGGSEL  180
CDDDPPEIPH ATFKAMAYKE GTMLNCECKR GFRRIKSGSL YMLCTGNSSH SSWDNQCQCT  240
SSATRNTTKQ VTPQPEEQKE RKTTEMQSPM QPVDQASLPG HCREPPPWEN EATERIYHFV  300
VGQMVYYQCV QGYRALHRGP AESVCKMTHG KTRWTQPQLI CTGEMETSQF PGEEKPQASP  360
EGRPESETSS LVTTTDFQIQ TEMAATMETS IFTTEYQSGG PGPAGLYAQP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGLYAQP GSEVQLVESG GGLVQPGGSL RLSCAASGFT  600
FSSYTLAWVR QAPGKGLEWV AAIDSSSYTY SPDTVRGRFT ISRDNAKNSL YLQMNSLRAE  660
DTAVYYCARD SNWDALDYWG QGTTVTVSSA STKGPSVFPL APSSKSTSGG TAALGCLVKD  720
YFPEPVTVSW NSGALTSGVH TFPAVLQSSG LYSLSSVVTV PSSSLGTQTY ICNVNHKPSN  780
TKVDKRVEPK SC                                                     792

SEQ ID NO: 318         moltype = AA  length = 676
FEATURE                Location/Qualifiers
source                 1..676
                       mol_type = protein
                       organism = synthetic construct
SEQUENCE: 318
EVQLVESGGG LVQPGGSLRL SCAASGFTFS SYTLAWVRQA PGKCLEWVAA IDSSSYTYSP  60
DTVRGRFTIS RDNAKNSLYL QMNSLRAEDT AVYYCARDSN WDALDYWGQG TTVTVSSGGG  120
GSGGGGSGGG GSDIQMTQSP SSLSASVGDR VTITCKAREK LWSAVAWYQQ KPGKAPKSLI  180
YSASFRYSGV PSRFSGSGSG TDFTLTISSL QPEDFATYYC QQYYTYPYTF GCGTKVEIKS  240
GGPGPAGLYA QPGSGGGGSG GGGSGGGGSG GGGSGGGGSG GGGSEVQLVE SGGGLVQPGN  300
SLRLSCAASG FTFSKFGMSW VRQAPGKGLE WVSSISGSGR DTLYAESVKG RFTISRDNAK  360
TTLYLQMNSL RPEDTAVYYC TIGGSLSVSS QGTLVTVSSS GGPGPAGLYA QPGSTFKFYM  420
PKKATELKHL QCLEEELKPL EEVLNLAQSK NFHLRPRDLI SNINVIVLEL KGSETTFMCE  480
YADETATIVE FLNRWITFCQ SIISTLTGGS SSTKKTQLQL EHLLLDLQMI LNGINNYKNP  540
KLTRMLSGGP GPAGLYAQPG SEVQLVESGG GLVQPGNSLR LSCAASGFTF SKFGMSWVRQ  600
APGKGLEWVS SISGSGRDTL YAESVKGRFT ISRDNAKTTL YLQMNSLRPE DTAVYYCTIG  660
GSLSVSSQGT LVTVSS                                                 676

SEQ ID NO: 319         moltype = AA  length = 676
FEATURE                Location/Qualifiers
source                 1..676
                       mol_type = protein
                       organism = synthetic construct
SEQUENCE: 319
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGCG TTVTVSSGGG  120
GSGGGGSGGG GSDIQMTQSP SSLSASVGDR VTITCKAREK LWSAVAWYQQ KPGKCPKALI  180
YSASFRYSGV PSRFSGSGSG TDFTLTISSL QPEDFATYYC QQYYTYPYTF GGGTKVEIKS  240
GGPGPAGLYA QPGSGGGGSG GGGSGGGGSG GGGSGGGGSG GGGSEVQLVE SGGGLVQPGN  300
SLRLSCAASG FTFSKFGMSW VRQAPGKGLE WVSSISGSGR DTLYAESVKG RFTISRDNAK  360
TTLYLQMNSL RPEDTAVYYC TIGGSLSVSS QGTLVTVSSS GGPGPAGLYA QPGSTFKFYM  420
PKKATELKHL QCLEEELKPL EEVLNLAQSK NFHLRPRDLI SNINVIVLEL KGSETTFMCE  480
YADETATIVE FLNRWITFCQ SIISTLTGGS SSTKKTQLQL EHLLLDLQMI LNGINNYKNP  540
KLTRMLSGGP GPAGLYAQPG SEVQLVESGG GLVQPGNSLR LSCAASGFTF SKFGMSWVRQ  600
APGKGLEWVS SISGSGRDTL YAESVKGRFT ISRDNAKTTL YLQMNSLRPE DTAVYYCTIG  660
GSLSVSSQGT LVTVSS                                                 676

SEQ ID NO: 320         moltype = AA  length = 676
FEATURE                Location/Qualifiers
source                 1..676
                       mol_type = protein
                       organism = synthetic construct
SEQUENCE: 320
EVQLVESGGG LVQPGGSLRL SCAASGFTFS SYTLAWVRQA PGKCLEWVAA IDSSSYTYSP  60
DTVRGRFTIS RDNAKNSLYL QMNSLRAEDT AVYYCARDSN WDALDYWGQG TTVTVSSGGG  120
GSGGGGSGGG GSDIQMTQSP SSLSASVGDR VTITCKVTEK VWGNVAWYQQ KPGKAPISLI  180
YSPSLRKSGV PSRFSGSGSG TDFTLTISSL QPEDFATYYC QQYYTYPYTF GCGTKVEIKS  240
```

-continued

```
GGPGPAGLYA QPGSGGGGSG GGGSGGGGSG GGGSGGGGSG GGGSEVQLVE SGGGLVQPGN  300
SLRLSCAASG FTFSKFGMSW VRQAPGKGLE WVSSISGSGR DTLYAESVKG RFTISRDNAK  360
TTLYLQMNSL RPEDTAVYYC TIGGSLSVSS QGTLVTVSSS GGPGPAGLYA QPGSTFKFYM  420
PKKATELKHL QCLEEELKPL EEVLNLAQSK NFHLRPRDLI SNINVIVLEL KGSETTFMCE  480
YADETATIVE FLNRWITFCQ SIISTLTGGS SSTKKTQLQL EHLLLDLQMI LNGINNYKNP  540
KLTRMLSGGP GPAGLYAQPG SEVQLVESGG GLVQPGNSLR LSCAASGFTF SKFGMSWVRQ  600
APGKGLEWVS SISGSGRDTL YAESVKGRFT ISRDNAKTTL YLQMNSLRPE DTAVYYCTIG  660
GSLSVSSQGT LVTVSS                                                  676

SEQ ID NO: 321         moltype = AA  length = 676
FEATURE                Location/Qualifiers
source                 1..676
                       mol_type = protein
                       organism = synthetic construct
SEQUENCE: 321
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGCG TTVTVSSGGG  120
GSGGGGSGGG GSDIQMTQSP SSLSASVGDR VTITCKVTEK VWGNVAWYQQ KPGKCPISLI  180
YSPSLRKSGV PSRFSGSGSG TDFTLTISSL QPEDFATYYC QQYYTYPYTF GGGTKVEIKS  240
GGPGPAGLYA QPGSGGGGSG GGGSGGGGSG GGGSGGGGSG GGGSEVQLVE SGGGLVQPGN  300
SLRLSCAASG FTFSKFGMSW VRQAPGKGLE WVSSISGSGR DTLYAESVKG RFTISRDNAK  360
TTLYLQMNSL RPEDTAVYYC TIGGSLSVSS QGTLVTVSSS GGPGPAGLYA QPGSTFKFYM  420
PKKATELKHL QCLEEELKPL EEVLNLAQSK NFHLRPRDLI SNINVIVLEL KGSETTFMCE  480
YADETATIVE FLNRWITFCQ SIISTLTGGS SSTKKTQLQL EHLLLDLQMI LNGINNYKNP  540
KLTRMLSGGP GPAGLYAQPG SEVQLVESGG GLVQPGNSLR LSCAASGFTF SKFGMSWVRQ  600
APGKGLEWVS SISGSGRDTL YAESVKGRFT ISRDNAKTTL YLQMNSLRPE DTAVYYCTIG  660
GSLSVSSQGT LVTVSS                                                  676

SEQ ID NO: 322         moltype = AA  length = 556
FEATURE                Location/Qualifiers
source                 1..556
                       mol_type = protein
                       organism = synthetic construct
SEQUENCE: 322
EVQLLESGGG LVQPGGSLRL SCAASGSIFS ANAMGWYRQA PGKQRELVAV ISSGGSTNYA  60
DSVKGRFTIS RDNSKNTVYL QMNSLRAEDT AVYYCMYSGS YYYTPNDYWG QGTLVTVSSS  120
GGPGPAGLYA QPGSGGGGSG GGGSGGGGSG GGGSGGGGSG GGGSEVQLVE SGGGLVQPGN  180
SLRLSCAASG FTFSKFGMSW VRQAPGKGLE WVSSISGSGR DTLYAESVKG RFTISRDNAK  240
TTLYLQMNSL RPEDTAVYYC TIGGSLSVSS QGTLVTVSSS GGPGPAGLYA QPGSTFKFYM  300
PKKATELKHL QCLEEELKPL EEVLNLAQSK NFHLRPRDLI SNINVIVLEL KGSETTFMCE  360
YADETATIVE FLNRWITFCQ SIISTLTGGS SSTKKTQLQL EHLLLDLQMI LNGINNYKNP  420
KLTRMLSGGP GPAGLYAQPG SEVQLVESGG GLVQPGNSLR LSCAASGFTF SKFGMSWVRQ  480
APGKGLEWVS SISGSGRDTL YAESVKGRFT ISRDNAKTTL YLQMNSLRPE DTAVYYCTIG  540
GSLSVSSQGT LVTVSS                                                  556

SEQ ID NO: 323         moltype = AA  length = 556
FEATURE                Location/Qualifiers
source                 1..556
                       mol_type = protein
                       organism = synthetic construct
SEQUENCE: 323
EVQLLESGGG LVQPGGSLRL SCAASGSIFS ANAMGWYRQA PGKGLELVAV ISSGGSTNYA  60
DSVKGRFTIS RDNSKNTVYL QMNSLRAEDT AVYYCMYSGS YYYTPNDYWG QGTLVTVSSS  120
GGPGPAGLYA QPGSGGGGSG GGGSGGGGSG GGGSGGGGSG GGGSEVQLVE SGGGLVQPGN  180
SLRLSCAASG FTFSKFGMSW VRQAPGKGLE WVSSISGSGR DTLYAESVKG RFTISRDNAK  240
TTLYLQMNSL RPEDTAVYYC TIGGSLSVSS QGTLVTVSSS GGPGPAGLYA QPGSTFKFYM  300
PKKATELKHL QCLEEELKPL EEVLNLAQSK NFHLRPRDLI SNINVIVLEL KGSETTFMCE  360
YADETATIVE FLNRWITFCQ SIISTLTGGS SSTKKTQLQL EHLLLDLQMI LNGINNYKNP  420
KLTRMLSGGP GPAGLYAQPG SEVQLVESGG GLVQPGNSLR LSCAASGFTF SKFGMSWVRQ  480
APGKGLEWVS SISGSGRDTL YAESVKGRFT ISRDNAKTTL YLQMNSLRPE DTAVYYCTIG  540
GSLSVSSQGT LVTVSS                                                  556

SEQ ID NO: 324         moltype = AA  length = 657
FEATURE                Location/Qualifiers
source                 1..657
                       mol_type = protein
                       organism = synthetic construct
SEQUENCE: 324
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKRVEPKSC SGGPGPAGLY AQPGSGGGGS  240
GGGGSGGGGS GGGGSGGGGS GGGGSEVQLV ESGGGLVQPG NSLRLSCAAS GFTFSKFGMS  300
WVRQAPGKGL EWVSSISGSG RDTLYAESVK GRFTISRDNA KTTLYLQMNS LRPEDTAVYY  360
CTIGGSLSVS SQGTLVTVSS SGGPGPAGLY AQPGSTFKFY MPKKATELKH LQCLEEELKP  420
LEEVLNLAQS KNFHLRPRDL ISNINVIVLE LKGSETTFMC EYADETATIV EFLNRWITFC  480
QSIISTLTGG SSSTKKTQLQ LEHLLLDLQM ILNGINNYKN PKLTRMLSGG PGPAGLYAQP  540
GSEVQLVESG GGLVQPGNSL RLSCAASGFT FSKFGMSWVR QAPGKGLEWV SSISGSGRDT  600
LYAESVKGRF TISRDNAKTT LYLQMNSLRP EDTAVYYCTI GGSLSVSSQG TLVTVSS     657
```

```
SEQ ID NO: 325          moltype = AA  length = 640
FEATURE                 Location/Qualifiers
source                  1..640
                        mol_type = protein
                        organism = synthetic construct
SEQUENCE: 325
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGLYAQP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGLYAQPGS  420
EVQLVESGGG LVQPGGSLRL SCAASGFTFS SYTLAWVRQA PGKGLEWVAA IDSSSYTYSP  480
DTVRGRFTIS RDNAKNSLYL QMNSLRAEDT AVYYCARDSN WDALDYWGQG TTVTVSSAST  540
KGPSVFPLAP SSKSTSGGTA ALGCLVKDYF PEPVTVSWNS GALTSGVHTF PAVLQSSGLY  600
SLSSVVTVPS SSLGTQTYIC NVNHKPSNTK VDKRVEPKSC                        640

SEQ ID NO: 326          moltype = AA  length = 659
FEATURE                 Location/Qualifiers
source                  1..659
                        mol_type = protein
                        organism = synthetic construct
SEQUENCE: 326
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGLYAQP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGLYAQPGS  420
EVQLVESGGG LVQPGGSLRL SCAASGFTFS SYTLAWVRQA PGKCLEWVAA IDSSSYTYSP  480
DTVRGRFTIS RDNAKNSLYL QMNSLRAEDT AVYYCARDSN WDALDYWGQG TTVTVSSGGG  540
GSGGGGSGGG GSDIQMTQSP SSLSASVGDR VTITCKAREK LWSAVAWYQQ KPGKAPKALI  600
YSASFRYSGV PSRFSGSGSG TDFTLTISSL QPEDFATYYC QQYYTYPYTF GCGTKVEIK   659

SEQ ID NO: 327          moltype = AA  length = 659
FEATURE                 Location/Qualifiers
source                  1..659
                        mol_type = protein
                        organism = synthetic construct
SEQUENCE: 327
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGLYAQP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGLYAQPGS  420
EVQLVESGGG LVQPGGSLRL SCAASGFTFS SYTLAWVRQA PGKCLEWVAA IDSSSYTYSP  480
DTVRGRFTIS RDNAKNSLYL QMNSLRAEDT AVYYCARDSN WDALDYWGQG TTVTVSSGGG  540
GSGGGGSGGG GSDIQMTQSP SSLSASVGDR VTITCKAREK LWSAVAWYQQ KPGKAPKSLI  600
YSASFRYSGV PSRFSGSGSG TDFTLTISSL QPEDFATYYC QQYYTYPYTF GCGTKVEIK   659

SEQ ID NO: 328          moltype = AA  length = 659
FEATURE                 Location/Qualifiers
source                  1..659
                        mol_type = protein
                        organism = synthetic construct
SEQUENCE: 328
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGLYAQP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGLYAQPGS  420
EVQLVESGGG LVQPGGSLRL SCAASGFTFS SYTLAWVRQA PGKGLEWVAA IDSSSYTYSP  480
DTVRGRFTIS RDNAKNSLYL QMNSLRAEDT AVYYCARDSN WDALDYWGCG TTVTVSSGGG  540
GSGGGGSGGG GSDIQMTQSP SSLSASVGDR VTITCKAREK LWSAVAWYQQ KPGKCPKALI  600
YSASFRYSGV PSRFSGSGSG TDFTLTISSL QPEDFATYYC QQYYTYPYTF GGGTKVEIK   659

SEQ ID NO: 329          moltype = AA  length = 659
FEATURE                 Location/Qualifiers
source                  1..659
                        mol_type = protein
                        organism = synthetic construct
SEQUENCE: 329
```

-continued

```
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGLYAQP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGLYAQPGS  420
EVQLVESGGG LVQPGGSLRL SCAASGFTFS SYTLAWVRQA PGKCLEWVAA IDSSSYTYSP  480
DTVRGRFTIS RDNAKNSLYL QMNSLRAEDT AVYYCARDSN WDALDYWGQG TTVTVSSGGG  540
GSGGGGSGGG GSDIQMTQSP SSLSASVGDR VTITCKVTEK VWGNVAWYQQ KPGKAPISLI  600
YSPSLRKSGV PSRFSGSGSG TDFTLTISSL QPEDFATYYC QQYYTYPYTF GCGTKVEIK   659

SEQ ID NO: 330         moltype = AA  length = 659
FEATURE                Location/Qualifiers
source                 1..659
                       mol_type = protein
                       organism = synthetic construct
SEQUENCE: 330
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGLYAQP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGLYAQPGS  420
EVQLVESGGG LVQPGGSLRL SCAASGFTFS SYTLAWVRQA PGKGLEWVAA IDSSSYTYSP  480
DTVRGRFTIS RDNAKNSLYL QMNSLRAEDT AVYYCARDSN WDALDYWGCG TTVTVSSGGG  540
GSGGGGSGGG GSDIQMTQSP SSLSASVGDR VTITCKVTEK VWGNVAWYQQ KPGKCPISLI  600
YSPSLRKSGV PSRFSGSGSG TDFTLTISSL QPEDFATYYC QQYYTYPYTF GGGTKVEIK   659

SEQ ID NO: 331         moltype = AA  length = 539
FEATURE                Location/Qualifiers
source                 1..539
                       mol_type = protein
                       organism = synthetic construct
SEQUENCE: 331
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGLYAQP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGLYAQPGS  420
EVQLLESGGG LVQPGGSLRL SCAASGSIFS ANAMGWYRQA PGKQRELVAV ISSGGSTNYA  480
DSVKGRFTIS RDNSKNTVYL QMNSLRAEDT AVYYCMYSGS YYYTPNDYWG QGTLVTVSS   539

SEQ ID NO: 332         moltype = AA  length = 463
FEATURE                Location/Qualifiers
source                 1..463
                       mol_type = protein
                       organism = synthetic construct
SEQUENCE: 332
ELCDDDPPEI PHATFKAMAY KEGTMLNCEC KRGFRRIKSG SLYMLCTGNS SHSSWDNQCQ  60
CTSSATRNTT KQVTPQPEEQ KERKTTEMQS PMQPVDQASL PGHCREPPPW ENEATERIYH  120
FVVGQMVYYQ CVQGYRALHR GPAESVCKMT HGKTRWTQPQ LICTGEMETS QFPGEEKPQA  180
SPEGRPESET SSLVTTTDFQ IQTEMAATME TSIFTTEYQG GGGSGGGGSG GGGSGGGGSG  240
GGGSGGGGSD IQMTQSPSSL SASVGDRVTI TCKAREKLWS AVAWYQQKPG KAPKSLIYSA  300
SFRYSGVPSR FSGSGSGTDF TLTISSLQPE DFATYYCQQY YTYPYTFGGG TKVEIKRTVA  360
APSVFIFPPS DEQLKSGTAS VVCLLNNFYP REAKVQWKVD NALQSGNSQE SVTEQDSKDS  420
TYSLSSTLTL SKADYEKHKV YACEVTHQGL SSPVTKSFNR GEC                   463

SEQ ID NO: 333         moltype = AA  length = 463
FEATURE                Location/Qualifiers
source                 1..463
                       mol_type = protein
                       organism = synthetic construct
SEQUENCE: 333
ELCDDDPPEI PHATFKAMAY KEGTMLNCEC KRGFRRIKSG SLYMLCTGNS SHSSWDNQCQ  60
CTSSATRNTT KQVTPQPEEQ KERKTTEMQS PMQPVDQASL PGHCREPPPW ENEATERIYH  120
FVVGQMVYYQ CVQGYRALHR GPAESVCKMT HGKTRWTQPQ LICTGEMETS QFPGEEKPQA  180
SPEGRPESET SSLVTTTDFQ IQTEMAATME TSIFTTEYQG GGGSGGGGSG GGGSGGGGSG  240
GGGSGGGGSD IQMTQSPSSL SASVGDRVTI TCKVTEKVWG NVAWYQQKPG KAPISLIYSP  300
SLRKSGVPSR FSGSGSGTDF TLTISSLQPE DFATYYCQQY YTYPYTFGGG TKVEIKRTVA  360
APSVFIFPPS DEQLKSGTAS VVCLLNNFYP REAKVQWKVD NALQSGNSQE SVTEQDSKDS  420
TYSLSSTLTL SKADYEKHKV YACEVTHQGL SSPVTKSFNR GEC                   463

SEQ ID NO: 334         moltype = AA  length = 811
FEATURE                Location/Qualifiers
source                 1..811
```

```
                         mol_type = protein
                         organism = synthetic construct
SEQUENCE: 334
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSGG GGSGGGGSEV  180
QLVESGGGLV QPGGSLRLSC AASGFTFSSY TLAWVRQAPG KCLEWVAAID SSSYTYSPDT  240
VRGRFTISRD NAKNSLYLQM NSLRAEDTAV YYCARDSNWD ALDYWGQGTT VTVSSGGGGS  300
GGGGSGGGGS DIQMTQSPSS LSASVGDRVT ITCKAREKLW SAVAWYQQKP GKAPKSLIYS  360
ASFRYSGVPS RFSGSGSGTD FTLTISSLQP EDFATYYCQQ YYTYPYTFGC GTKVEIKGGG  420
GSGGGGSGGG GSGGGGSGGG GSGGGGSGGG GSGGGGSGGG GSELCDDDPP EIPHATFKAM  480
AYKEGTMLNC ECKRGFRRIK SGSLYMLCTG NSSHSSWDNQ CQCTSSATRN TTKQVTPQPE  540
EQKERKTTEM QSPMQPVDQA SLPGHCREPP PWENEATERI YHFVVGQMVY YQCVQGYRAL  600
HRGPAESVCK MTHGKTRWTQ PQLICTGEME TSQFPGEEKP QASPEGRPES ETSSLVTTTD  660
FQIQTEMAAT METSIFTTEY QSGGPGPAGL YAQPGSEVQL VESGGGLVQP GNSLRLSCAA  720
SGFTFSKFGM SWVRQAPGKG LEWVSSISGS GRDTLYAESV KGRFTISRDN AKTTLYLQMN  780
SLRPEDTAVY YCTIGGSLSV SSQGTLVTVS S                                811

SEQ ID NO: 335           moltype = AA  length = 811
FEATURE                  Location/Qualifiers
source                   1..811
                         mol_type = protein
                         organism = synthetic construct
SEQUENCE: 335
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSGG GGSGGGGSEV  180
QLVESGGGLV QPGGSLRLSC AASGFTFSSY TLAWVRQAPG KGLEWVAAID SSSYTYSPDT  240
VRGRFTISRD NAKNSLYLQM NSLRAEDTAV YYCARDSNWD ALDYWGCGTT VTVSSGGGGS  300
GGGGSGGGGS DIQMTQSPSS LSASVGDRVT ITCKAREKLW SAVAWYQQKP GKCPKALIYS  360
ASFRYSGVPS RFSGSGSGTD FTLTISSLQP EDFATYYCQQ YYTYPYTFGG GTKVEIKGGG  420
GSGGGGSGGG GSGGGGSGGG GSGGGGSGGG GSGGGGSGGG GSELCDDDPP EIPHATFKAM  480
AYKEGTMLNC ECKRGFRRIK SGSLYMLCTG NSSHSSWDNQ CQCTSSATRN TTKQVTPQPE  540
EQKERKTTEM QSPMQPVDQA SLPGHCREPP PWENEATERI YHFVVGQMVY YQCVQGYRAL  600
HRGPAESVCK MTHGKTRWTQ PQLICTGEME TSQFPGEEKP QASPEGRPES ETSSLVTTTD  660
FQIQTEMAAT METSIFTTEY QSGGPGPAGL YAQPGSEVQL VESGGGLVQP GNSLRLSCAA  720
SGFTFSKFGM SWVRQAPGKG LEWVSSISGS GRDTLYAESV KGRFTISRDN AKTTLYLQMN  780
SLRPEDTAVY YCTIGGSLSV SSQGTLVTVS S                                811

SEQ ID NO: 336           moltype = AA  length = 811
FEATURE                  Location/Qualifiers
source                   1..811
                         mol_type = protein
                         organism = synthetic construct
SEQUENCE: 336
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSGG GGSGGGGSEV  180
QLVESGGGLV QPGGSLRLSC AASGFTFSSY TLAWVRQAPG KCLEWVAAID SSSYTYSPDT  240
VRGRFTISRD NAKNSLYLQM NSLRAEDTAV YYCARDSNWD ALDYWGQGTT VTVSSGGGGS  300
GGGGSGGGGS DIQMTQSPSS LSASVGDRVT ITCKVTEKVW GNVAWYQQKP GKAPISLIYS  360
PSLRKSGVPS RFSGSGSGTD FTLTISSLQP EDFATYYCQQ YYTYPYTFGC GTKVEIKGGG  420
GSGGGGSGGG GSGGGGSGGG GSGGGGSGGG GSGGGGSGGG GSELCDDDPP EIPHATFKAM  480
AYKEGTMLNC ECKRGFRRIK SGSLYMLCTG NSSHSSWDNQ CQCTSSATRN TTKQVTPQPE  540
EQKERKTTEM QSPMQPVDQA SLPGHCREPP PWENEATERI YHFVVGQMVY YQCVQGYRAL  600
HRGPAESVCK MTHGKTRWTQ PQLICTGEME TSQFPGEEKP QASPEGRPES ETSSLVTTTD  660
FQIQTEMAAT METSIFTTEY QSGGPGPAGL YAQPGSEVQL VESGGGLVQP GNSLRLSCAA  720
SGFTFSKFGM SWVRQAPGKG LEWVSSISGS GRDTLYAESV KGRFTISRDN AKTTLYLQMN  780
SLRPEDTAVY YCTIGGSLSV SSQGTLVTVS S                                811

SEQ ID NO: 337           moltype = AA  length = 811
FEATURE                  Location/Qualifiers
source                   1..811
                         mol_type = protein
                         organism = synthetic construct
SEQUENCE: 337
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSGG GGSGGGGSEV  180
QLVESGGGLV QPGGSLRLSC AASGFTFSSY TLAWVRQAPG KGLEWVAAID SSSYTYSPDT  240
VRGRFTISRD NAKNSLYLQM NSLRAEDTAV YYCARDSNWD ALDYWGCGTT VTVSSGGGGS  300
GGGGSGGGGS DIQMTQSPSS LSASVGDRVT ITCKVTEKVW GNVAWYQQKP GKCPISLIYS  360
PSLRKSGVPS RFSGSGSGTD FTLTISSLQP EDFATYYCQQ YYTYPYTFGG GTKVEIKGGG  420
GSGGGGSGGG GSGGGGSGGG GSGGGGSGGG GSGGGGSGGG GSELCDDDPP EIPHATFKAM  480
AYKEGTMLNC ECKRGFRRIK SGSLYMLCTG NSSHSSWDNQ CQCTSSATRN TTKQVTPQPE  540
EQKERKTTEM QSPMQPVDQA SLPGHCREPP PWENEATERI YHFVVGQMVY YQCVQGYRAL  600
HRGPAESVCK MTHGKTRWTQ PQLICTGEME TSQFPGEEKP QASPEGRPES ETSSLVTTTD  660
FQIQTEMAAT METSIFTTEY QSGGPGPAGL YAQPGSEVQL VESGGGLVQP GNSLRLSCAA  720
SGFTFSKFGM SWVRQAPGKG LEWVSSISGS GRDTLYAESV KGRFTISRDN AKTTLYLQMN  780
```

-continued

```
SLRPEDTAVY YCTIGGSLSV SSQGTLVTVS S                          811

SEQ ID NO: 338          moltype = AA  length = 691
FEATURE                 Location/Qualifiers
source                  1..691
                        mol_type = protein
                        organism = synthetic construct
SEQUENCE: 338
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSGG GGSGGGGSEV  180
QLLESGGGLV QPGGSLRLSC AASGSIFSAN AMGWYRQAPG KQRELVAVIS SGGSTNYADS  240
VKGRFTISRD NSKNTVYLQM NSLRAEDTAV YYCMYSGSYY YTPNDYWGQG TLVTVSSGGG  300
GSGGGGSGGG GSGGGGSGGG GSGGGGSGGG GSGGGGSGGG GSELCDDDPP EIPHATFKAM  360
AYKEGTMLNC ECKRGFRRIK SGSLYMLCTG NSSHSSWDNQ CQCTSSATRN TTKQVTPQPE  420
EQKERKTTEM QSPMQPVDQA SLPGHCREPP PWENEATERI YHFVVGQMVY YQCVQGYRAL  480
HRGPAESVCK MTHGKTRWTQ PQLICTGEME TSQFPGEEKP QASPEGRPES ETSSLVTTTD  540
FQIQTEMAAT METSIFTTEY QSGGPGPAGL YAQPGSEVQL VESGGGLVQP GNSLRLSCAA  600
SGFTFSKFGM SWVRQAPGKG LEWVSSISGS GRDTLYAESV KGRFTISRDN AKTTLYLQMN  660
SLRPEDTAVY YCTIGGSLSV SSQGTLVTVS S                          691

SEQ ID NO: 339          moltype = AA  length = 691
FEATURE                 Location/Qualifiers
source                  1..691
                        mol_type = protein
                        organism = synthetic construct
SEQUENCE: 339
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSGG GGSGGGGSEV  180
QLLESGGGLV QPGGSLRLSC AASGSIFSAN AMGWYRQAPG KGLELVAVIS SGGSTNYADS  240
VKGRFTISRD NSKNTVYLQM NSLRAEDTAV YYCMYSGSYY YTPNDYWGQG TLVTVSSGGG  300
GSGGGGSGGG GSGGGGSGGG GSGGGGSGGG GSGGGGSGGG GSELCDDDPP EIPHATFKAM  360
AYKEGTMLNC ECKRGFRRIK SGSLYMLCTG NSSHSSWDNQ CQCTSSATRN TTKQVTPQPE  420
EQKERKTTEM QSPMQPVDQA SLPGHCREPP PWENEATERI YHFVVGQMVY YQCVQGYRAL  480
HRGPAESVCK MTHGKTRWTQ PQLICTGEME TSQFPGEEKP QASPEGRPES ETSSLVTTTD  540
FQIQTEMAAT METSIFTTEY QSGGPGPAGL YAQPGSEVQL VESGGGLVQP GNSLRLSCAA  600
SGFTFSKFGM SWVRQAPGKG LEWVSSISGS GRDTLYAESV KGRFTISRDN AKTTLYLQMN  660
SLRPEDTAVY YCTIGGSLSV SSQGTLVTVS S                          691

SEQ ID NO: 340          moltype = AA  length = 811
FEATURE                 Location/Qualifiers
source                  1..811
                        mol_type = protein
                        organism = synthetic construct
SEQUENCE: 340
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS EVQLVESGGG LVQPGGSLRL SCAASGFTFS SYTLAWVRQA PGKCLEWVAA  180
IDSSSYTYSP DTVRGRFTIS RDNAKNSLYL QMNSLRAEDT AVYYCARDSN WDALDYWGQG  240
TTVTVSSGGG GSGGGGSGGG GSDIQMTQSP SSLSASVGDR VTITCKAREK LWSAVAWYQQ  300
KPGKAPKSLI YSASFRYSGV PSRFSGSGSG TDFTLTISSL QPEDFATYYC QQYYTYPYTF  360
GCGTKVEIKG GGGSGGGGSG GGGSGGGGSG GGGSGGGGSG GGGSGGGGSG GGGSELCDDD  420
PPEIPHATFK AMAYKEGTML NCECKRGFRR IKSGSLYMLC TGNSSHSSWD NQCQCTSSAT  480
RNTTKQVTPQ PEEQKERKTT EMQSPMQPVD QASLPGHCRE PPPWENEATE RIYHFVVGQM  540
VYYQCVQGYR ALHRGPAESV CKMTHGKTRW TQPQLICTGE METSQFPGEE KPQASPEGRP  600
ESETSSLVTT TDFQIQTEMA ATMETSIFTT EYQGGGGSGG GGSGGGGSGG GGSGGGGSGG  660
GGSSGGPGPA GLYAQPGSAP TSSSTKKTQL QLEHLLLDLQ MILNGINNYK NPKLTRMLTF  720
KFYMPKKATE LKHLQCLEEE LKPLEEVLNL AQSKNFHLRP RDLISNINVI VLELKGSETT  780
FMCEYADETA TIVEFLNRWI TFCQSIISTL T                          811

SEQ ID NO: 341          moltype = AA  length = 811
FEATURE                 Location/Qualifiers
source                  1..811
                        mol_type = protein
                        organism = synthetic construct
SEQUENCE: 341
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS EVQLVESGGG LVQPGGSLRL SCAASGFTFS SYTLAWVRQA PGKGLEWVAA  180
IDSSSYTYSP DTVRGRFTIS RDNAKNSLYL QMNSLRAEDT AVYYCARDSN WDALDYWGCG  240
TTVTVSSGGG GSGGGGSGGG GSDIQMTQSP SSLSASVGDR VTITCKAREK LWSAVAWYQQ  300
KPGKCPKALI YSASFRYSGV PSRFSGSGSG TDFTLTISSL QPEDFATYYC QQYYTYPYTF  360
GGGTKVEIKG GGGSGGGGSG GGGSGGGGSG GGGSGGGGSG GGGSGGGGSG GGGSELCDDD  420
PPEIPHATFK AMAYKEGTML NCECKRGFRR IKSGSLYMLC TGNSSHSSWD NQCQCTSSAT  480
RNTTKQVTPQ PEEQKERKTT EMQSPMQPVD QASLPGHCRE PPPWENEATE RIYHFVVGQM  540
VYYQCVQGYR ALHRGPAESV CKMTHGKTRW TQPQLICTGE METSQFPGEE KPQASPEGRP  600
ESETSSLVTT TDFQIQTEMA ATMETSIFTT EYQGGGGSGG GGSGGGGSGG GGSGGGGSGG  660
GGSSGGPGPA GLYAQPGSAP TSSSTKKTQL QLEHLLLDLQ MILNGINNYK NPKLTRMLTF  720
```

-continued

```
KFYMPKKATE LKHLQCLEEE LKPLEEVLNL AQSKNFHLRP RDLISNINVI VLELKGSETT  780
FMCEYADETA TIVEFLNRWI TFCQSIISTL T                                 811

SEQ ID NO: 342          moltype = AA  length = 811
FEATURE                 Location/Qualifiers
source                  1..811
                        mol_type = protein
                        organism = synthetic construct
SEQUENCE: 342
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS EVQLVESGGG LVQPGGSLRL SCAASGFTFS SYTLAWVRQA PGKCLEWVAA  180
IDSSSYTYSP DTVRGRFTIS RDNAKNSLYL QMNSLRAEDT AVYYCARDSN WDALDYWGQG  240
TTVTVSSGGG GSGGGGSGGG GSDIQMTQSP SSLSASVGDR VTITCKVTEK VWGNVAWYQQ  300
KPGKAPISLI YSPSLRKSGV PSRFSGSGSG TDFTLTISSL QPEDFATYYC QQYYTYPYTF  360
GCGTKVEIKG GGGSGGGGSG GGGSGGGGSG GGGSGGGGSG GGGSGGGGSG GGGSELCDDD  420
PPEIPHATFK AMAYKEGTML NCECKRGFRR IKSGSLYMLC TGNSSHSSWD NQCQCTSSAT  480
RNTTKQVTPQ PEEQKERKTT EMQSPMQPVD QASLPGHCRE PPPWENEATE RIYHFVVGQM  540
VYYQCVQGYR ALHRGPAESV CKMTHGKTRW TQPQLICTGE METSQFPGEE KPQASPEGRP  600
ESETSSLVTT TDFQIQTEMA ATMETSIFTT EYQGGGGSGG GGSGGGGSGG GGSGGGGSGG  660
GGSSGGPGPA GLYAQPGSAP TSSSTKKTQL QLEHLLLDLQ MILNGINNYK NPKLTRMLTF  720
KFYMPKKATE LKHLQCLEEE LKPLEEVLNL AQSKNFHLRP RDLISNINVI VLELKGSETT  780
FMCEYADETA TIVEFLNRWI TFCQSIISTL T                                 811

SEQ ID NO: 343          moltype = AA  length = 811
FEATURE                 Location/Qualifiers
source                  1..811
                        mol_type = protein
                        organism = synthetic construct
SEQUENCE: 343
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS EVQLVESGGG LVQPGGSLRL SCAASGFTFS SYTLAWVRQA PGKGLEWVAA  180
IDSSSYTYSP DTVRGRFTIS RDNAKNSLYL QMNSLRAEDT AVYYCARDSN WDALDYWGCG  240
TTVTVSSGGG GSGGGGSGGG GSDIQMTQSP SSLSASVGDR VTITCKVTEK VWGNVAWYQQ  300
KPGKCPISLI YSPSLRKSGV PSRFSGSGSG TDFTLTISSL QPEDFATYYC QQYYTYPYTF  360
GGGTKVEIKG GGGSGGGGSG GGGSGGGGSG GGGSGGGGSG GGGSGGGGSG GGGSELCDDD  420
PPEIPHATFK AMAYKEGTML NCECKRGFRR IKSGSLYMLC TGNSSHSSWD NQCQCTSSAT  480
RNTTKQVTPQ PEEQKERKTT EMQSPMQPVD QASLPGHCRE PPPWENEATE RIYHFVVGQM  540
VYYQCVQGYR ALHRGPAESV CKMTHGKTRW TQPQLICTGE METSQFPGEE KPQASPEGRP  600
ESETSSLVTT TDFQIQTEMA ATMETSIFTT EYQGGGGSGG GGSGGGGSGG GGSGGGGSGG  660
GGSSGGPGPA GLYAQPGSAP TSSSTKKTQL QLEHLLLDLQ MILNGINNYK NPKLTRMLTF  720
KFYMPKKATE LKHLQCLEEE LKPLEEVLNL AQSKNFHLRP RDLISNINVI VLELKGSETT  780
FMCEYADETA TIVEFLNRWI TFCQSIISTL T                                 811

SEQ ID NO: 344          moltype = AA  length = 691
FEATURE                 Location/Qualifiers
source                  1..691
                        mol_type = protein
                        organism = synthetic construct
SEQUENCE: 344
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS EVQLLESGGG LVQPGGSLRL SCAASGSIFS ANAMGWYRQA PGKQRELVAV  180
ISSGGSTNYA DSVKGRFTIS RDNSKNTVYL QMNSLRAEDT AVYYCMYSGS YYYTPNDYWG  240
QGTLVTVSSG GGGSGGGGSG GGGSGGGGSG GGGSGGGGSG GGGSGGGGSG GGGSELCDDD  300
PPEIPHATFK AMAYKEGTML NCECKRGFRR IKSGSLYMLC TGNSSHSSWD NQCQCTSSAT  360
RNTTKQVTPQ PEEQKERKTT EMQSPMQPVD QASLPGHCRE PPPWENEATE RIYHFVVGQM  420
VYYQCVQGYR ALHRGPAESV CKMTHGKTRW TQPQLICTGE METSQFPGEE KPQASPEGRP  480
ESETSSLVTT TDFQIQTEMA ATMETSIFTT EYQGGGGSGG GGSGGGGSGG GGSGGGGSGG  540
GGSSGGPGPA GLYAQPGSAP TSSSTKKTQL QLEHLLLDLQ MILNGINNYK NPKLTRMLTF  600
KFYMPKKATE LKHLQCLEEE LKPLEEVLNL AQSKNFHLRP RDLISNINVI VLELKGSETT  660
FMCEYADETA TIVEFLNRWI TFCQSIISTL T                                 691

SEQ ID NO: 345          moltype = AA  length = 691
FEATURE                 Location/Qualifiers
source                  1..691
                        mol_type = protein
                        organism = synthetic construct
SEQUENCE: 345
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS EVQLLESGGG LVQPGGSLRL SCAASGSIFS ANAMGWYRQA PGKGLELVAV  180
ISSGGSTNYA DSVKGRFTIS RDNSKNTVYL QMNSLRAEDT AVYYCMYSGS YYYTPNDYWG  240
QGTLVTVSSG GGGSGGGGSG GGGSGGGGSG GGGSGGGGSG GGGSGGGGSG GGGSELCDDD  300
PPEIPHATFK AMAYKEGTML NCECKRGFRR IKSGSLYMLC TGNSSHSSWD NQCQCTSSAT  360
RNTTKQVTPQ PEEQKERKTT EMQSPMQPVD QASLPGHCRE PPPWENEATE RIYHFVVGQM  420
VYYQCVQGYR ALHRGPAESV CKMTHGKTRW TQPQLICTGE METSQFPGEE KPQASPEGRP  480
ESETSSLVTT TDFQIQTEMA ATMETSIFTT EYQGGGGSGG GGSGGGGSGG GGSGGGGSGG  540
```

-continued

```
GGSSGGPGPA GLYAQPGSAP TSSSTKKTQL QLEHLLLDLQ MILNGINNYK NPKLTRMLTF  600
KFYMPKKATE LKHLQCLEEE LKPLEEVLNL AQSKNFHLRP RDLISNINVI VLELKGSETT  660
FMCEYADETA TIVEFLNRWI TFCQSIISTL T                                 691

SEQ ID NO: 346          moltype = AA  length = 696
FEATURE                 Location/Qualifiers
source                  1..696
                        mol_type = protein
                        organism = synthetic construct
SEQUENCE: 346
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KCLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKAREKLW SAVAWYQQKP  480
GKAPKSLIYS ASFRYSGVPS RFSGSGSGTD FTLTISSLQP EDFATYYCQQ YYTYPYTFGC  540
GTKVEIKGGG GSGGGGSGGG GSGGGGSGGG GSGGGGSEVQ LLESGGGLVQ PGGSLRLSCA  600
ASGSIFSANA MGWYRQAPGK QRELVAVISS GGSTNYADSV KGRFTISRDN SKNTVYLQMN  660
SLRAEDTAVY YCMYSGSYYY TPNDYWGQGT LVTVSS                            696

SEQ ID NO: 347          moltype = AA  length = 696
FEATURE                 Location/Qualifiers
source                  1..696
                        mol_type = protein
                        organism = synthetic construct
SEQUENCE: 347
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGCGTT  420
VTVSSGGGGS GGGGSGGGGS DIQMTQSPSS LSASVGDRVT ITCKAREKLW SAVAWYQQKP  480
GKCPKALIYS ASFRYSGVPS RFSGSGSGTD FTLTISSLQP EDFATYYCQQ YYTYPYTFGG  540
GTKVEIKGGG GSGGGGSGGG GSGGGGSGGG GSGGGGSEVQ LLESGGGLVQ PGGSLRLSCA  600
ASGSIFSANA MGWYRQAPGK QRELVAVISS GGSTNYADSV KGRFTISRDN SKNTVYLQMN  660
SLRAEDTAVY YCMYSGSYYY TPNDYWGQGT LVTVSS                            696

SEQ ID NO: 348          moltype = AA  length = 696
FEATURE                 Location/Qualifiers
source                  1..696
                        mol_type = protein
                        organism = synthetic construct
SEQUENCE: 348
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KCLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKVTEKVW GNVAWYQQKP  480
GKAPISLIYS PSLRKSGVPS RFSGSGSGTD FTLTISSLQP EDFATYYCQQ YYTYPYTFGC  540
GTKVEIKGGG GSGGGGSGGG GSGGGGSGGG GSGGGGSEVQ LLESGGGLVQ PGGSLRLSCA  600
ASGSIFSANA MGWYRQAPGK QRELVAVISS GGSTNYADSV KGRFTISRDN SKNTVYLQMN  660
SLRAEDTAVY YCMYSGSYYY TPNDYWGQGT LVTVSS                            696

SEQ ID NO: 349          moltype = AA  length = 696
FEATURE                 Location/Qualifiers
source                  1..696
                        mol_type = protein
                        organism = synthetic construct
SEQUENCE: 349
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGCGTT  420
VTVSSGGGGS GGGGSGGGGS DIQMTQSPSS LSASVGDRVT ITCKVTEKVW GNVAWYQQKP  480
GKCPISLIYS PSLRKSGVPS RFSGSGSGTD FTLTISSLQP EDFATYYCQQ YYTYPYTFGG  540
GTKVEIKGGG GSGGGGSGGG GSGGGGSGGG GSGGGGSEVQ LLESGGGLVQ PGGSLRLSCA  600
ASGSIFSANA MGWYRQAPGK QRELVAVISS GGSTNYADSV KGRFTISRDN SKNTVYLQMN  660
SLRAEDTAVY YCMYSGSYYY TPNDYWGQGT LVTVSS                            696
```

```
SEQ ID NO: 350          moltype = AA  length = 696
FEATURE                 Location/Qualifiers
source                  1..696
                        mol_type = protein
                        organism = synthetic construct
SEQUENCE: 350
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KCLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKAREKLW SAVAWYQQKP  480
GKAPKSLIYS ASFRYSGVPS RFSGSGSGTD FTLTISSLQP EDFATYYCQQ YYTYPYTFGC  540
GTKVEIKGGG GSGGGGSGGG GSGGGGSGGG GSGGGGSEVQ LLESGGGLVQ PGGSLRLSCA  600
ASGSIFSANA MGWYRQAPGK GLELVAVISS GGSTNYADSV KGRFTISRDN SKNTVYLQMN  660
SLRAEDTAVY YCMYSGSYYY TPNDYWGQGT LVTVSS                           696

SEQ ID NO: 351          moltype = AA  length = 696
FEATURE                 Location/Qualifiers
source                  1..696
                        mol_type = protein
                        organism = synthetic construct
SEQUENCE: 351
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGCGTT  420
VTVSSGGGGS GGGGSGGGGS DIQMTQSPSS LSASVGDRVT ITCKAREKLW SAVAWYQQKP  480
GKCPKALIYS ASFRYSGVPS RFSGSGSGTD FTLTISSLQP EDFATYYCQQ YYTYPYTFGG  540
GTKVEIKGGG GSGGGGSGGG GSGGGGSGGG GSGGGGSEVQ LLESGGGLVQ PGGSLRLSCA  600
ASGSIFSANA MGWYRQAPGK GLELVAVISS GGSTNYADSV KGRFTISRDN SKNTVYLQMN  660
SLRAEDTAVY YCMYSGSYYY TPNDYWGQGT LVTVSS                           696

SEQ ID NO: 352          moltype = AA  length = 696
FEATURE                 Location/Qualifiers
source                  1..696
                        mol_type = protein
                        organism = synthetic construct
SEQUENCE: 352
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KCLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKVTEKVW GNVAWYQQKP  480
GKAPISLIYS PSLRKSGVPS RFSGSGSGTD FTLTISSLQP EDFATYYCQQ YYTYPYTFGC  540
GTKVEIKGGG GSGGGGSGGG GSGGGGSGGG GSGGGGSEVQ LLESGGGLVQ PGGSLRLSCA  600
ASGSIFSANA MGWYRQAPGK GLELVAVISS GGSTNYADSV KGRFTISRDN SKNTVYLQMN  660
SLRAEDTAVY YCMYSGSYYY TPNDYWGQGT LVTVSS                           696

SEQ ID NO: 353          moltype = AA  length = 696
FEATURE                 Location/Qualifiers
source                  1..696
                        mol_type = protein
                        organism = synthetic construct
SEQUENCE: 353
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGCGTT  420
VTVSSGGGGS GGGGSGGGGS DIQMTQSPSS LSASVGDRVT ITCKVTEKVW GNVAWYQQKP  480
GKCPISLIYS PSLRKSGVPS RFSGSGSGTD FTLTISSLQP EDFATYYCQQ YYTYPYTFGG  540
GTKVEIKGGG GSGGGGSGGG GSGGGGSGGG GSGGGGSEVQ LLESGGGLVQ PGGSLRLSCA  600
ASGSIFSANA MGWYRQAPGK GLELVAVISS GGSTNYADSV KGRFTISRDN SKNTVYLQMN  660
SLRAEDTAVY YCMYSGSYYY TPNDYWGQGT LVTVSS                           696

SEQ ID NO: 354          moltype = AA  length = 6
FEATURE                 Location/Qualifiers
```

```
source                  1..6
                        mol_type = protein
                        organism = synthetic construct
SEQUENCE: 354
HHHHHH                                                             6

SEQ ID NO: 355          moltype = AA  length = 547
FEATURE                 Location/Qualifiers
source                  1..547
                        mol_type = protein
                        organism = synthetic construct
SEQUENCE: 355
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KCLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKASQNVG TNVGWYQQKP  480
GKAPKALIYS ASFRYSGVPS RFSGSGSGTD FTLTISSLQP EDFATYYCQQ YYTYPYTFGC  540
GTKVEIK                                                            547

SEQ ID NO: 356          moltype = AA  length = 547
FEATURE                 Location/Qualifiers
source                  1..547
                        mol_type = protein
                        organism = synthetic construct
SEQUENCE: 356
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGCGTT  420
VTVSSGGGGS GGGGSGGGGS DIQMTQSPSS LSASVGDRVT ITCKASQNVG TNVGWYQQKP  480
GKCPKALIYS ASFRYSGVPS RFSGSGSGTD FTLTISSLQP EDFATYYCQQ YYTYPYTFGG  540
GTKVEIK                                                            547

SEQ ID NO: 357          moltype = AA  length = 547
FEATURE                 Location/Qualifiers
source                  1..547
                        mol_type = protein
                        organism = synthetic construct
SEQUENCE: 357
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KCLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKAREKLW SAVAWYQQKP  480
GKAPKALIYS ASFRYSGVPS RFSGSGSGTD FTLTISSLQP EDFATYYCQQ YYTYPYTFGC  540
GTKVEIK                                                            547

SEQ ID NO: 358          moltype = AA  length = 547
FEATURE                 Location/Qualifiers
source                  1..547
                        mol_type = protein
                        organism = synthetic construct
SEQUENCE: 358
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGCGTT  420
VTVSSGGGGS GGGGSGGGGS DIQMTQSPSS LSASVGDRVT ITCKAREKLW SAVAWYQQKP  480
GKCPKALIYS ASFRYSGVPS RFSGSGSGTD FTLTISSLQP EDFATYYCQQ YYTYPYTFGG  540
GTKVEIK                                                            547

SEQ ID NO: 359          moltype = AA  length = 547
FEATURE                 Location/Qualifiers
source                  1..547
                        mol_type = protein
                        organism = synthetic construct
```

```
SEQUENCE: 359
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KCLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKVTEKVW GNVAWYQQKP  480
GKAPISLIYS PSLRKSGVPS RFSGSGSGTD FTLTISSLQP EDFATYYCQQ YYTYPYTFGC  540
GTKVEIK                                                            547

SEQ ID NO: 360         moltype = AA  length = 547
FEATURE                Location/Qualifiers
source                 1..547
                       mol_type = protein
                       organism = synthetic construct
SEQUENCE: 360
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGCGTT  420
VTVSSGGGGS GGGGSGGGGS DIQMTQSPSS LSASVGDRVT ITCKVTEKVW GNVAWYQQKP  480
GKCPISLIYS PSLRKSGVPS RFSGSGSGTD FTLTISSLQP EDFATYYCQQ YYTYPYTFGG  540
GTKVEIK                                                            547

SEQ ID NO: 361         moltype = AA  length = 427
FEATURE                Location/Qualifiers
source                 1..427
                       mol_type = protein
                       organism = synthetic construct
SEQUENCE: 361
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLLESGGGLV QPGGSLRLSC AASGSIFSAN AMGWYRQAPG KQRELVAVIS  360
SGGSTNYADS VKGRFTISRD NSKNTVYLQM NSLRAEDTAV YYCMYSGSYY YTPNDYWGQG  420
TLVTVSS                                                            427

SEQ ID NO: 362         moltype = AA  length = 528
FEATURE                Location/Qualifiers
source                 1..528
                       mol_type = protein
                       organism = synthetic construct
SEQUENCE: 362
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSASTKG PSVFPLAPSS KSTSGGTAAL GCLVKDYFPE PVTVSWNSGA LTSGVHTFPA  480
VLQSSGLYSL SSVVTVPSSS LGTQTYICNV NHKPSNTKVD KRVEPKSC               528

SEQ ID NO: 363         moltype = AA  length = 642
FEATURE                Location/Qualifiers
source                 1..642
                       mol_type = protein
                       organism = synthetic construct
SEQUENCE: 363
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG QGTTVTVSSA  540
STKGPSVFPL APSSKSTSGG TAALGCLVKD YFPEPVTVSW NSGALTSGVH TFPAVLQSSG  600
LYSLSSVVTV PSSSLGTQTY ICNVNHKPSN TKVDKRVEPK SC                     642

SEQ ID NO: 364         moltype = AA  length = 245
```

-continued

```
FEATURE               Location/Qualifiers
source                1..245
                      mol_type = protein
                      organism = synthetic construct
SEQUENCE: 364
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSSGG  120
PGPAGLYAQP GSDIQMTQSP SSLSASVGDR VTITCKVTEK VWGNVAWYQQ KPGKAPISLI  180
YSPSLRKSGV PSRFSGSGSG TDFTLTISSL QPEDFATYYC QQYYTYPYTF GGGTKVEIKH  240
HHHHH                                                          245

SEQ ID NO: 365        moltype = AA  length = 245
FEATURE               Location/Qualifiers
source                1..245
                      mol_type = protein
                      organism = synthetic construct
SEQUENCE: 365
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSSGG  120
PGPAGLYAQP GSDIQMTQSP SSLSASVGDR VTITCKAREK LWSAVAWYQQ KPGKAPKALI  180
YSASFRYSGV PSRFSGSGSG TDFTLTISSL QPEDFATYYC QQYYTYPYTF GGGTKVEIKH  240
HHHHH                                                          245

SEQ ID NO: 366        moltype = AA  length = 245
FEATURE               Location/Qualifiers
source                1..245
                      mol_type = protein
                      organism = synthetic construct
SEQUENCE: 366
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSSGG  120
PGPAGLYAQP GSDIQMTQSP SSLSASVGDR VTITCKAREK LWSAVAWYQQ KPGKAPKSLI  180
YSASFRYSGV PSRFSGSGSG TDFTLTISSL QPEDFATYYC QQYYTYPYTF GGGTKVEIKH  240
HHHHH                                                          245

SEQ ID NO: 367        moltype = AA  length = 609
FEATURE               Location/Qualifiers
source                1..609
                      mol_type = protein
                      organism = synthetic construct
SEQUENCE: 367
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS RVIPVSGPAR CLSQSRNLLK TTDDMVKTAR EKLKHYSCTA EDIDHEDITR  180
DQTSTLKTCL PLELHKNESC LATRETSSTT RGSCLPPQKT SLMMTLCLGS IYEDLKMYQT  240
EFQAINAALQ NHNHQQIILD KGMLVAIDEL MQSLNHNGET LRQKPPVGEA DPYRVKMKLC  300
ILLHAFSTRV VTINRVMGYL SSASGGPGPA GMKGLPGSGG GGSGGGGSGG GGSGGGGSGG  360
GGSGGGGSQS VLTQPPSVSG APGQRVTISC SGSRSNIGSN TVKWYQQLPG TAPKLLIYYN  420
DQRPSGVPDR FSGSKSGTSA SLAITGLQAE DEADYYCQSY DRYTHPALLF GTGTKVTVLG  480
GGGSGGGGSG GGGSQVQLVE SGGGVVQPGR SLRLSCAASG FTFSSYGMHW VRQAPGKGLE  540
WVAFIRYDGS NKYYADSVKG RFTISRDNSK NTLYLQMNSL RAEDTAVYYC KTHGSHDNWG  600
QGTMVTVSS                                                      609

SEQ ID NO: 368        moltype = AA  length = 930
FEATURE               Location/Qualifiers
source                1..930
                      mol_type = protein
                      organism = synthetic construct
SEQUENCE: 368
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSASPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES SLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGMKGLPGSG  660
GGGSGGGGSG GGGSGGGGSG GGGSGGGGSQ SVLTQPPSVS GAPGQRVTIS CSGSRSNIGS  720
NTVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYDG SNKYYADSVK GRFTISRDNS KNTLYLQMNS  900
LRAEDTAVYY CKTHGSHDNW GQGTMVTVSS                                930

SEQ ID NO: 369        moltype = AA  length = 935
FEATURE               Location/Qualifiers
source                1..935
```

```
                        mol_type = protein
                        organism = synthetic construct
SEQUENCE: 369
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SGGGGSRVIP VSGPARCLSQ SRNLLKTTDD  480
MVKTAREKLK HYSCTAEDID HEDITRDQTS TLKTCLPLEL HKNESCLATR ETSSTTRGSC  540
LPPQKTSLMM TLCLGSIYED LKMYQTEFQA INAALQNHNH QQIILDKGML VAIDELMQSL  600
NHNGETLRQK PPVGEADPYR VKMKLCILLH AFSTRVVTIN RVMGYLSSAS GGPGPAGMKG  660
LPGSGGGGSG GGGSGGGGSG GGGSGGGGSG GGGSQSVLTQ PPSVSGAPGQ RVTISCSGSR  720
SNIGSNTVKW YQQLPGTAPK LLIYYNDQRP SGVPDRFSGS KSGTSASLAI TGLQAEDEAD  780
YYCQSYDRYT HPALLFGTGT KVTVLGGGGS GGGGSGGGGS QVQLVESGGG VVQPGRSLRL  840
SCAASGFTFS SYGMHWVRQA PGKGLEWVAF IRYDGSNKYY ADSVKGRFTI SRDNSKNTLY  900
LQMNSLRAED TAVYYCKTHG SHDNWGQGTM VTVSS                            935

SEQ ID NO: 370          moltype = AA  length = 930
FEATURE                 Location/Qualifiers
source                  1..930
                        mol_type = protein
                        organism = synthetic construct
SEQUENCE: 370
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGMKGLPGSG  660
GGGSGGGGSG GGGSGGGGSG GGGSGGGGSQ SVLTQPPSVS GAPGQRVTIS CSGSRSNIGS  720
NTVKWYQQLP GTAPKLLIYY NDQRPSGVPD RFSGSKSGTS ASLAITGLQA EDEADYYCQS  780
YDRYTHPALL FGCGTKVTVL GGGGSGGGGS GGGGSQVQLV ESGGGVVQPG RSLRLSCAAS  840
GFTFSSYGMH WVRQAPGKCL EWVAFIRYDG SNKYYADSVK GRFTISRDNS KNTLYLQMNS  900
LRAEDTAVYY CKTHGSHDNW GQGTMVTVSS                                  930

SEQ ID NO: 371          moltype = AA  length = 930
FEATURE                 Location/Qualifiers
source                  1..930
                        mol_type = protein
                        organism = synthetic construct
SEQUENCE: 371
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGMKGLPGSG  660
GGGSGGGGSG GGGSGGGGSG GGGSGGGGSQ SVLTQPPSVS GAPGQRVTIS CSGSRSNIGS  720
NTVKWYQQLP GTCPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYDG SNKYYADSVK GRFTISRDNS KNTLYLQMNS  900
LRAEDTAVYY CKTHGSHDNW GCGTMVTVSS                                  930

SEQ ID NO: 372          moltype = AA  length = 553
FEATURE                 Location/Qualifiers
source                  1..553
                        mol_type = protein
                        organism = synthetic construct
SEQUENCE: 372
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GMKGLPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
```

-continued

```
VTVSSGGGGS GGGGSGGGGS DIQMTQSPSS LSASVGDRVT ITCKASQNVG TNVGWYQQKP  480
GKAPKALIYS ASFRYSGVPS RFSGSGSGTD FTLTISSLQP EDFATYYCQQ YYTYPYTFGG  540
GTKVEIKHHH HHH                                                     553

SEQ ID NO: 373          moltype = AA  length = 444
FEATURE                 Location/Qualifiers
source                  1..444
                        mol_type = protein
                        organism = synthetic construct
SEQUENCE: 373
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GMKGLPGQVQ LQESGGGLVQ TGGSLRLSCT TSGTIFSGYT MGWYRQAPGE QRELVAVISG  360
GGDTNYADSV KGRFTISRDN TKDTMYLQMN SLKPEDTAVY YCYSREVTPP WKLYWGQGTQ  420
VTVSSAAAYP YDVPDYGSHH HHHH                                         444

SEQ ID NO: 374          moltype = AA  length = 444
FEATURE                 Location/Qualifiers
source                  1..444
                        mol_type = protein
                        organism = synthetic construct
SEQUENCE: 374
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GMKGLPGQVQ LQESGGGLVQ EGGSLRLSCA ASERIFSTDV MGWYRQAAEK QRELVAVVSA  360
RGTTNYLDAV KGRFTISRDN ARNTLTLQMN DLKPEDTASY YCYVRETTSP WRIYWGQGTQ  420
VTVSSAAAYP YDVPDYGSHH HHHH                                         444

SEQ ID NO: 375          moltype = AA  length = 445
FEATURE                 Location/Qualifiers
source                  1..445
                        mol_type = protein
                        organism = synthetic construct
SEQUENCE: 375
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GMKGLPGQVQ LQESGGGLVQ AGGSLRLSCA ASGSIFSANA MGWYRQAPGK QRELVAVISS  360
GGSTNYADSV KGRFTISRDN AKNTVYLQMN SLKPEDTAVY YCMYSGSYYY TPNDYWGQGT  420
QVTVSSAAAY PYDVPDYGSH HHHHH                                        445

SEQ ID NO: 376          moltype = AA  length = 557
FEATURE                 Location/Qualifiers
source                  1..557
                        mol_type = protein
                        organism = synthetic construct
SEQUENCE: 376
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GMKGLPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSSGGPG PAGMKGLPGS DIQMTQSPSS LSASVGDRVT ITCKASQNVG TNVGWYQQKP  480
GKAPKALIYS ASFRYSGVPS RFSGSGSGTD FTLTISSLQP EDFATYYCQQ YYTYPYTFGG  540
GTKVEIKHHH HHHEPEA                                                 557

SEQ ID NO: 377          moltype = AA  length = 557
FEATURE                 Location/Qualifiers
source                  1..557
                        mol_type = protein
                        organism = synthetic construct
SEQUENCE: 377
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GMKGLPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
```

```
VTVSSGGGGS GGGGSGGGGS DIQMTQSPSS LSASVGDRVT ITCKASQNVG TNVGWYQQKP  480
GKAPKLLIYS ASFRYSGVPS RFSGSGSGTD FTLTISSLQP EDFATYYCQQ YYTYPYTFGG  540
GTKVEIKHHH HHHEPEA                                                557

SEQ ID NO: 378         moltype = AA  length = 557
FEATURE                Location/Qualifiers
source                 1..557
                       mol_type = protein
                       organism = synthetic construct
SEQUENCE: 378
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GMKGLPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKASQNVG TNVGWYQQKP  480
GKAPKGLIYS ASFRYSGVPS RFSGSGSGTD FTLTISSLQP EDFATYYCQQ YYTYPYTFGG  540
GTKVEIKHHH HHHEPEA                                                557

SEQ ID NO: 379         moltype = AA  length = 557
FEATURE                Location/Qualifiers
source                 1..557
                       mol_type = protein
                       organism = synthetic construct
SEQUENCE: 379
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFSQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GMKGLPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKASQNVG TNVGWYQQKP  480
GKAPKALIYS ASFRYSGVPS RFSGSGSGTD FTLTISSLQP EDFATYYCQQ YYTYPYTFGG  540
GTKVEIKHHH HHHEPEA                                                557

SEQ ID NO: 380         moltype = AA  length = 1027
FEATURE                Location/Qualifiers
source                 1..1027
                       mol_type = protein
                       organism = synthetic construct
SEQUENCE: 380
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSDA HKSEVAHRFK DLGEENFKAL VLIAFAQYLQ  180
QCPFEDHVKL VNEVTEFAKT CVADESAENC DKSLHTLFGD KLCTVATLRE TYGEMADCCA  240
KQEPERNECF LQHKDDNPNL PRLVRPEVDV MCTAFHDNEE TFLKKYLYEI ARRHPYFYAP  300
ELLFFAKRYK AAFTECCQAA DKAACLLPKL DELRDEGKAS SAKQRLKCAS LQKFGERAFK  360
AWAVARLSQR FPKAEFAEVS KLVTDLTKVH TECCHGDLLE CADDRADLAK YICENQDSIS  420
SKLKECCEKP LLEKSHCIAE VENDEMPADL PSLAADFVES KDVCKNYAEA KDVFLGMFLY  480
EYARRHPDYS VVLLLRLAKT YETTLEKCCA AADPHECYAK VFDEFKPLVE EPQNLIKQNC  540
ELFEQLGEYK FQNALLVRYT KKVPQVSTPT LVEVSRNLGK VGSKCCKHPE AKRMPCAEDY  600
LSVVLNQLCV LHEKTPVSDR VTKCCTESLV NRRPCFSALE VDETYVPKEF NAETFTFHAD  660
ICTLSEKERQ IKKQTALVEL VKHKPKATKE QLKAVMDDFA AFVEKCCKAD DKETCFAEEG  720
KKLVAASQAA LGLGGGGSGG GGSGGGGSGG GGSGGGGSGG GGSSGGPGPA GMKGLPGSEV  780
QLVESGGGLV QPGGSLRLSC AASGFTFSSY TLAWVRQAPG KGLEWVAAID SSSYTYSPDT  840
VRGRFTISRD NAKNSLYLQM NSLRAEDTAV YYCARDSNWD ALDYWGQGTT VTVSSGGGGS  900
GGGGSGGGGS DIQMTQSPSS LSASVGDRVT ITCKASQNVG TNVGWYQQKP GKAPKALIYS  960
ASFRYSGVPS RFSGSGSGTD FTLTISSLQP EDFATYYCQQ YYTYPYTFGG GTKVEIKHHH  1020
HHHEPEA                                                           1027

SEQ ID NO: 381         moltype = AA  length = 1022
FEATURE                Location/Qualifiers
source                 1..1022
                       mol_type = protein
                       organism = synthetic construct
SEQUENCE: 381
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEA HKSEIAHRYN DLGEQHFKGL VLIAFSQYLQ  180
KCSYDEHAKL VQEVTDFAKT CVADESAANC DKSLHTLFGD KLCAIPNLRE NYGELADCCT  240
KQEPERNECF LQHKDDNPSL PPFERPEAEA MCTSFKENPT TFMGHYLHEV ARRHPYFYAP  300
ELLYYAEQYN EILTQCCAEA DKESCLTPKL DGVKEKALVS SVRQRMKCSS MQKFGERAFK  360
AWAVARLSQT FPNADFAEIT KLATDLTKVN KECCHGDLLE CADDRAELAK YMCENQATIS  420
SKLQTCCDKP LLKKAHCLSE VEHDTMPADL PAIAADFVED QEVCKNYAEA KDVFLGTFLY  480
EYSRRHPDYS VSLLLRLAKK YEATLEKCCA EANPPACYGT VLAEFQPLVE EPKNLVKTNC  540
DLYEKLGEYG FQNAILVRYT QKAPQVSTPT LVEAARNLGR VGTKCCTLPE DQRLPCVEDY  600
```

```
LSAILNRVCL LHEKTPVSEH VTKCCSGSLV ERRPCFSALT VDETYVPKEF KAETFTFHSD  660
ICTLPEKEKQ IKKQTALAEL VKHKPKATAE QLKTVMDDFA QFLDTCCKAA DKDTCFSTEG  720
PNLVTRCKDA LAGGGGSGGG GSGGGGSGGG GSGGGGSGGG GSSGGPGPAG MKGLPGSEVQ  780
LVESGGGLVQ PGGSLRLSCA ASGFTFSSYT LAWVRQAPGK GLEWVAAIDS SSYTYSPDTV  840
RGRFTISRDN AKNSLYLQMN SLRAEDTAVY YCARDSNWDA LDYWGQGTTV TVSSGGGGSG  900
GGGSGGGGSD IQMTQSPSSL SASVGDRVTI TCKASQNVGT NVGWYQQKPG KAPKALIYSA  960
SFRYSGVPSR FSGSGSGTDF TLTISSLQPE DFATYYCQQY YTYPYTFGGG TKVEIKHHHH  1020
HH                                                                1022

SEQ ID NO: 382          moltype = AA  length = 1336
FEATURE                 Location/Qualifiers
source                  1..1336
                        mol_type = protein
                        organism = synthetic construct
SEQUENCE: 382
EAHKSEIAHR YNDLGEQHFK GLVLIAFSQY LQKCSYDEHA KLVQEVTDFA KTCVADESAA  60
NCDKSLHTLF GDKLCAIPNL RENYGELADC CTKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQRMKC SSMQKFGERA FKAWAVARLS QTFPNADFAE ITKLATDLTK  240
VNKECCHGDL LECADDRAEL AKYMCENQAT ISSKLQTCCD KPLLKKAHCL SEVEHDTMPA  300
DLPAIAADFV EDQEVCKNYA EAKDVFLGTF LYEYSRRHPD YSVSLLLRLA KKYEATLEKC  360
CAEANPPACY GTVLAEFQPL VEEPKNLVKT NCDLYEKLGE YGFQNAILVR YTQKAPQVST  420
PTLVEAARNL GRVGTKCCTL PEDQRLPCVE DYLSAILNRV CLLHEKTPVS EHVTKCCSGS  480
LVERRPCFSA LTVDETYVPK EFKAETFTFH SDICTLPEKE KQIKKQTALA ELVKHKPKAT  540
AEQLKTVMDD FAQFLDTCCK AADKDTCFST EGPNLVTRCK DALASGGPGP AGMKGLPGST  600
FKFYMPKKAT ELKHLQCLEE ELKPLEEVLN LAQSKNFHLR PRDLISNINV IVLELKGSET  660
TFMCEYADET ATIVEFLNRW ITFCQSIIST LTGGSSSTKK TQLQLEHLLL DLQMILNGIN  720
NYKNPKLTRM LSGGPGPAGM KGLPGSEAHK SEIAHRYNDL GEQHFKGLVL IAFSQYLQKC  780
SYDEHAKLVQ EVTDFAKTCV ADESAANCDK SLHTLFGDKL CAIPNLRENY GELADCCTKQ  840
EPERNECFLQ HKDDNPSLPP FERPEAEAMC TSFKENPTTF MGHYLHEVAR RHPYFYAPEL  900
LYYAEQYNEI LTQCCAEADK ESCLTPKLDG VKEKALVSSV RQRMKCSSMQ KFGERAFKAW  960
AVARLSQTFP NADFAEITKL ATDLTKVNKE CCHGDLLECA DDRAELAKYM CENQATISSK  1020
LQTCCDKPLL KKAHCLSEVE HDTMPADLPA IAADFVEDQE VCKNYAEAKD VFLGTFLYEY  1080
SRRHPDYSVS LLLRLAKKYE ATLEKCCAEA NPPACYGTVL AEFQPLVEEP KNLVKTNCDL  1140
YEKLGEYGFQ NAILVRYTQK APQVSTPTLV EAARNLGRVG TKCCTLPEDQ RLPCVEDYLS  1200
AILNRVCLLH EKTPVSEHVT KCCSGSLVER RPCFSALTVD ETYVPKEFKA ETFTFHSDIC  1260
TLPEKEKQIK KQTALAELVK HKPKATAEQL KTVMDDFAQF LDTCCKAADK DTCFSTEGPN  1320
LVTRCKDALA HHHHHH                                                 1336

SEQ ID NO: 383          moltype = AA  length = 817
FEATURE                 Location/Qualifiers
source                  1..817
                        mol_type = protein
                        organism = synthetic construct
SEQUENCE: 383
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GMKGLPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKASQNVG TNVGWYQQKP  480
GKAPKALIYS ASFRYSGVPS RFSGSGSGTD FTLTISSLQP EDFATYYCQQ YYTYPYTFGG  540
GTKVEIKSGG PGPAGMKGLP GSGGGGSGGG GSGGGGSGGG GSGGGGSGGG GSELCDDDPP  600
EIPHATFKAM AYKEGTMLNC ECKRGFRRIK SGSLYMLCTG NSSHSSWDNQ CQCTSSATRN  660
TTKQVTPQPE EQKERKTTEM QSPMQPVDQA SLPGHCREPP PWENEATERI YHFVVGQMVY  720
YQCVQGYRAL HRGPAESVCK MTHGKTRWTQ PQLICTGEME TSQFPGEEKP QASPEGRPES  780
ETSCLVTTTD FQIQTEMAAT METSIFTTEY QHHHHHH                          817

SEQ ID NO: 384          moltype = AA  length = 817
FEATURE                 Location/Qualifiers
source                  1..817
                        mol_type = protein
                        organism = synthetic construct
SEQUENCE: 384
ELCDDDPPEI PHATFKAMAY KEGTMLNCEC KRGFRRIKSG SLYMLCTGNS SHSSWDNQCQ  60
CTSSATRNTT KQVTPQPEEQ KERKTTEMQS PMQPVDQASL PGHCREPPPW ENEATERIYH  120
FVVGQMVYYQ CVQGYRALHR GPAESVCKMT HGKTRWTQPQ LICTGEMETS QFPGEEKPQA  180
SPEGRPESET SCLVTTTDFQ IQTEMAATME TSIFTTEYQG GGGSGGGGSG GGGSGGGGSG  240
GGGSGGGGSS GGPGPAGMKG LPGSAPTSSS TKKTQLQLEH LLLDLQMILN GINNYKNPKL  300
TRMLTFKFYM PKKATELKHL QCLEEELKPL EEVLNLAQSK NFHLRPRDLI SNINVIVLEL  360
KGSETTFMCE YADETATIVE FLNRWITFCQ SIISTLTSGG PGPAGMKGLP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGMKGLP GSEVQLVESG GGLVQPGGSL RLSCAASGFT  600
FSSYTLAWVR QAPGKGLEWV AAIDSSSYTY SPDTVRGRFT ISRDNAKNSL YLQMNSLRAE  660
DTAVYYCARD SNWDALDYWG QGTTVTVSSG GGGSGGGGSG GGGSDIQMTQ SPSSLSASVG  720
DRVTITCKAS QNVGTNVGWY QQKPGKAPKA LIYSASFRYS GVPSRFSGSG SGTDFTLTIS  780
```

```
SLQPEDFATY YCQQYYTYPY TFGGGTKVEI KHHHHHH                      817

SEQ ID NO: 385          moltype = AA  length = 817
FEATURE                 Location/Qualifiers
source                  1..817
                        mol_type = protein
                        organism = synthetic construct
SEQUENCE: 385
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSGG GGSGGGGSGG GGSGGGGSGG GGSGGGGSEL  180
CDDDPPEIPH ATFKAMAYKE GTMLNCECKR GFRRIKSGSL YMLCTGNSSH SSWDNQCQCT  240
SSATRNTTKQ VTPQPEEQKE RKTTEMQSPM QPVDQASLPG HCREPPPWEN EATERIYHFV  300
VGQMVYYQCV QGYRALHRGP AESVCKMTHG KTRWTQPQLI CTGEMETSQF PGEEKPQASP  360
EGRPESETSC LVTTTDFQIQ TEMAATMETS IFTTEYQSGG PGPAGMKGLP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGMKGLP GSEVQLVESG GGLVQPGGSL RLSCAASGFT  600
FSSYTLAWVR QAPGKGLEWV AAIDSSSYTY SPDTVRGRFT ISRDNAKNSL YLQMNSLRAE  660
DTAVYYCARD SNWDALDYWG QGTTVTVSSG GGGSGGGGSG GGGSDIQMTQ SPSSLSASVG  720
DRVTITCKAS QNVGTNVGWY QQKPGKAPKA LIYSASFRYS GVPSRFSGSG SGTDFTLTIS  780
SLQPEDFATY YCQQYYTYPY TFGGGTKVEI KHHHHHH                      817

SEQ ID NO: 386          moltype = AA  length = 682
FEATURE                 Location/Qualifiers
source                  1..682
                        mol_type = protein
                        organism = synthetic construct
SEQUENCE: 386
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS TFKFYMPKKA TELKHLQCLE EELKPLEEVL NLAQSKNFHL RPRDLISNIN  180
VIVLELKGSE TTFMCEYADE TATIVEFLNR WITFCQSIIS TLTGGSSSTK KTQLQLEHLL  240
LDLQMILNGI NNYKNPKLTR MLSGGPGPAG MKGLPGSEVQ LVESGGGLVQ PGNSLRLSCA  300
ASGFTFSKFG MSWVRQAPGK GLEWVSSISG SGRDTLYAES VKGRFTISRD NAKTTLYLQM  360
NSLRPEDTAV YYCTIGGSLS VSSQGTLVTV SSGGGGSGGG GSGGGGSGGG GSGGGGSGGG  420
GSSGGPGPAG MKGLPGSEVQ LVESGGGLVQ PGGSLRLSCA ASGFTFSSYT LAWVRQAPGK  480
GLEWVAAIDS SSYTYSPDTV RGRFTISRDN AKNSLYLQMN SLRAEDTAVY YCARDSNWDA  540
LDYWGQGTTV TVSSGGGGSG GGGSGGGGSD IQMTQSPSSL SASVGDRVTI TCKASQNVGT  600
NVGWYQQKPG KAPKALIYSA SFRYSGVPSR FSGSGSGTDF TLTISSLQPE DFATYYCQQY  660
YTYPYTFGGG TKVEIKHHHH HH                                      682

SEQ ID NO: 387          moltype = AA  length = 682
FEATURE                 Location/Qualifiers
source                  1..682
                        mol_type = protein
                        organism = synthetic construct
SEQUENCE: 387
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSGGG  120
GSGGGGSGGG GSDIQMTQSP SSLSASVGDR VTITCKASQN VGTNVGWYQQ KPGKAPKALI  180
YSASFRYSGV PSRFSGSGSG TDFTLTISSL QPEDFATYYC QQYYTYPYTF GGGTKVEIKS  240
GGPGPAGMKG LPGSGGGGSG GGGSGGGGSG GGGSGGGGSG GGGSEVQLVE SGGGLVQPGN  300
SLRLSCAASG FTFSKFGMSW VRQAPGKGLE WVSSISGSGR DTLYAESVKG RFTISRDNAK  360
TTLYLQMNSL RPEDTAVYYC TIGGSLSVSS QGTLVTVSSS GGPGPAGMKG LPGSTFKFYM  420
PKKATELKHL QCLEEELKPL EEVLNLAQSK NFHLRPRDLI SNINVIVLEL KGSETTFMCE  480
YADETATIVE FLNRWITFCQ SIISTLTGGS SSTKKTQLQL EHLLLDLQMI LNGINNYKNP  540
KLTRMLSGGP GPAGMKGLPG SEVQLVESGG GLVQPGNSLR LSCAASGFTF SKFGMSWVRQ  600
APGKGLEWVS SISGSGRDTL YAESVKGRFT ISRDNAKTTL YLQMNSLRPE DTAVYYCTIG  660
GSLSVSSQGT LVTVSSHHHH HH                                      682

SEQ ID NO: 388          moltype = AA  length = 553
FEATURE                 Location/Qualifiers
source                  1..553
                        mol_type = protein
                        organism = synthetic construct
SEQUENCE: 388
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GMKGLPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKASQNVG TNVGWYQQKP  480
GKAPKSLIYS ASFRYSGVPS RFSGSGSGTD FTLTISSLQP EDFATYYCQQ YYTYPYTFGG  540
GTKVEIKHHH HHH                                                553

SEQ ID NO: 389          moltype = AA  length = 553
```

```
FEATURE                Location/Qualifiers
source                 1..553
                       mol_type = protein
                       organism = synthetic construct
SEQUENCE: 389
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GMKGLPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKASQNVG TNVGWYQQKP  480
GQAPRLLIYS ASFRYSGVPS RFSGSGSGTD FTLTISSLQP EDFATYYCQQ YYTYPYTFGG  540
GTKVEIKHHH HHH                                                   553

SEQ ID NO: 390         moltype = AA  length = 667
FEATURE                Location/Qualifiers
source                 1..667
                       mol_type = protein
                       organism = synthetic construct
SEQUENCE: 390
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSES KYGPPCPPCP APEFLGGPSV FLFPPKPKDT  180
LMISRTPEVT CVVVDVSQED PEVQFNWYVD GVEVHNAKTK PREEQFNSTY RVVSVLTVLH  240
QDWLNGKEYK CKVSNKGLPS SIEKTISKAK GQPREPQVYT LPPSQEEMTK NQVSLTCLVK  300
GFYPSDIAVE WESNGQPENN YKTTPPVLDS DGSFFLYSRL TVDKSRWQEG NVFSCSVMHE  360
ALHNHYTQKS LSLSLGKGGG GSGGGGSGGG GSGGGGSGGG GSGGGGSSGG PGPAGMKGLP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG QGTTVTVSSG  540
GGGSGGGGSG GGGSDIQMTQ SPSSLSASVG DRVTITCKAS QNVGTNVGWY QQKPGKAPKA  600
LIYSASFRYS GVPSRFSGSG SGTDFTLTIS SLQPEDFATY YCQQYYTYPY TFGGGTKVEI  660
KHHHHHH                                                          667

SEQ ID NO: 391         moltype = AA  length = 667
FEATURE                Location/Qualifiers
source                 1..667
                       mol_type = protein
                       organism = synthetic construct
SEQUENCE: 391
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGMKG  240
LPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGMKGLP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG QGTTVTVSSG  540
GGGSGGGGSG GGGSDIQMTQ SPSSLSASVG DRVTITCKAS QNVGTNVGWY QQKPGKAPKA  600
LIYSASFRYS GVPSRFSGSG SGTDFTLTIS SLQPEDFATY YCQQYYTYPY TFGGGTKVEI  660
KHHHHHH                                                          667

SEQ ID NO: 392         moltype = AA  length = 667
FEATURE                Location/Qualifiers
source                 1..667
                       mol_type = protein
                       organism = synthetic construct
SEQUENCE: 392
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSGG GGSGGGGSGG GGSGGGGSGG GGSGGGGSEV  180
QLVESGGGLV QPGGSLRLSC AASGFTFSSY TLAWVRQAPG KGLEWVAAID SSSYTYSPDT  240
VRGRFTISRD NAKNSLYLQM NSLRAEDTAV YYCARDSNWD ALDYWGQGTT VTVSSGGGGS  300
GGGGSGGGGS DIQMTQSPSS LSASVGDRVT ITCKASQNVG TNVGWYQQKP GKAPKALIYS  360
ASFRYSGVPS RFSGSGSGTD FTLTISSLQP EDFATYYCQQ YYTYPYTFGG GTKVEIKSGG  420
PGPAGMKGLP GSESKYGPPC PPCPAPEFLG GPSVFLFPPK PKDTLMISRT PEVTCVVVDV  480
SQEDPEVQFN WYVDGVEVHN AKTKPREEQF NSTYRVVSVL TVLHQDWLNG KEYKCKVSNK  540
GLPSSIEKTI SKAKGQPREP QVYTLPPSQE EMTKNQVSLT CLVKGFYPSD IAVEWESNGQ  600
PENNYKTTPP VLDSDGSFFL YSRLTVDKSR WQEGNVFSCS VMHEALHNHY TQKSLSLSLG  660
KHHHHHH                                                          667

SEQ ID NO: 393         moltype = AA  length = 665
FEATURE                Location/Qualifiers
source                 1..665
                       mol_type = protein
                       organism = synthetic construct
SEQUENCE: 393
```

-continued

```
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGMKGLP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGMKGLPGS  420
EVQLVESGGG LVQPGGSLRL SCAASGFTFS SYTLAWVRQA PGKGLEWVAA IDSSSYTYSP  480
DTVRGRFTIS RDNAKNSLYL QMNSLRAEDT AVYYCARDSN WDALDYWGQG TTVTVSSGGG  540
GSGGGGSGGG GSDIQMTQSP SSLSASVGDR VTITCKASQN VGTNVGWYQQ KPGKAPKALI  600
YSASFRYSGV PSRFSGSGSG TDFTLTISSL QPEDFATYYC QQYYTYPYTF GGGTKVEIKH  660
HHHHH                                                            665

SEQ ID NO: 394          moltype = AA  length = 547
FEATURE                 Location/Qualifiers
source                  1..547
                        mol_type = protein
                        organism = synthetic construct
SEQUENCE: 394
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSSGGPG PAGLYAQPGS DIQMTQSPSS LSASVGDRVT ITCKAREKLW SAVAWYQQKP  480
GKAPKSLIYS ASFRYSGVPS RFSGSGSGTD FTLTISSLQP EDFATYYCQQ YYTYPYTFGG  540
GTKVEIK                                                          547

SEQ ID NO: 395          moltype = AA  length = 547
FEATURE                 Location/Qualifiers
source                  1..547
                        mol_type = protein
                        organism = synthetic construct
SEQUENCE: 395
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKAREKLW SAVAWYQQKP  480
GKAPKSLIYS ASFRYSGVPS RFSGSGSGTD FTLTISSLQP EDFATYYCQQ YYTYPYTFGG  540
GTKVEIK                                                          547

SEQ ID NO: 396          moltype = AA  length = 547
FEATURE                 Location/Qualifiers
source                  1..547
                        mol_type = protein
                        organism = synthetic construct
SEQUENCE: 396
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSSGGPG PAGLYAQPGS DIQMTQSPSS LSASVGDRVT ITCKVTEKVW GNVAWYQQKP  480
GKAPISLIYS PSLRKSGVPS RFSGSGSGTD FTLTISSLQP EDFATYYCQQ YYTYPYTFGG  540
GTKVEIK                                                          547

SEQ ID NO: 397          moltype = AA  length = 547
FEATURE                 Location/Qualifiers
source                  1..547
                        mol_type = protein
                        organism = synthetic construct
SEQUENCE: 397
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKVTEKVW GNVAWYQQKP  480
GKAPISLIYS PSLRKSGVPS RFSGSGSGTD FTLTISSLQP EDFATYYCQQ YYTYPYTFGG  540
```

```
GTKVEIK                                                         547

SEQ ID NO: 398          moltype = AA  length = 427
FEATURE                 Location/Qualifiers
source                  1..427
                        mol_type = protein
                        organism = synthetic construct
SEQUENCE: 398
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLLESGGGLV QPGGSLRLSC AASGSIFSAN AMGWYRQAPG KGLELVAVIS  360
SGGSTNYADS VKGRFTISRD NSKNTVYLQM NSLRAEDTAV YYCMYSGSYY YTPNDYWGQG  420
TLVTVSS                                                         427

SEQ ID NO: 399          moltype = AA  length = 426
FEATURE                 Location/Qualifiers
source                  1..426
                        mol_type = protein
                        organism = synthetic construct
SEQUENCE: 399
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGPA  300
GLYAQPGSEV QLLESGGGLV QPGGSLRLSC AASERIFSTD VMGWYRQAPG KQRELVAVVS  360
ARGTTNYLDA VKGRFTISRD NSKNTLYLQM NSLRAEDTAV YYCYVRETTS PWRIYWGQGT  420
LVTVSS                                                          426

SEQ ID NO: 400          moltype = AA  length = 811
FEATURE                 Location/Qualifiers
source                  1..811
                        mol_type = protein
                        organism = synthetic construct
SEQUENCE: 400
ELCDDDPPEI PHATFKAMAY KEGTMLNCEC KRGFRRIKSG SLYMLCTGNS SHSSWDNQCQ  60
CTSSATRNTT KQVTPQPEEQ KERKTTEMQS PMQPVDQASL PGHCREPPPW ENEATERIYH  120
FVVGQMVYYQ CVQGYRALHR GPAESVCKMT HGKTRWTQPQ LICTGEMETS QFPGEEKPQA  180
SPEGRPESET SSLVTTTDFQ IQTEMAATME TSIFTTEYQG GGGSGGGGSG GGGSGGGGSG  240
GGGSGGGGSS GGPGPAGLYA QPGSAPTSSS TKKTQLQLEH LLLDLQMILN GINNYKNPKL  300
TRMLTFKFYM PKKATELKHL QCLEEELKPL EEVLNLAQSK NFHLRPRDLI SNINVIVLEL  360
KGSETTFMCE YADETATIVE FLNRWITFCQ SIISTLTSGG PGPAGLYAQP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGLYAQP GSEVQLVESG GGLVQPGGSL RLSCAASGFT  600
FSSYTLAWVR QAPGKGLEWV AAIDSSSYTY SPDTVRGRFT ISRDNAKNSL YLQMNSLRAE  660
DTAVYYCARD SNWDALDYWG QGTTVTVSSS GGPGPAGLYA QPGSDIQMTQ SPSSLSASVG  720
DRVTITCKAR EKLWSAVAWY QQKPGKAPKS LIYSASFRYS GVPSRFSGSG SGTDFTLTIS  780
SLQPEDFATY YCQQYYTYPY TFGGGTKVEI K                              811

SEQ ID NO: 401          moltype = AA  length = 811
FEATURE                 Location/Qualifiers
source                  1..811
                        mol_type = protein
                        organism = synthetic construct
SEQUENCE: 401
ELCDDDPPEI PHATFKAMAY KEGTMLNCEC KRGFRRIKSG SLYMLCTGNS SHSSWDNQCQ  60
CTSSATRNTT KQVTPQPEEQ KERKTTEMQS PMQPVDQASL PGHCREPPPW ENEATERIYH  120
FVVGQMVYYQ CVQGYRALHR GPAESVCKMT HGKTRWTQPQ LICTGEMETS QFPGEEKPQA  180
SPEGRPESET SSLVTTTDFQ IQTEMAATME TSIFTTEYQG GGGSGGGGSG GGGSGGGGSG  240
GGGSGGGGSS GGPGPAGLYA QPGSAPTSSS TKKTQLQLEH LLLDLQMILN GINNYKNPKL  300
TRMLTFKFYM PKKATELKHL QCLEEELKPL EEVLNLAQSK NFHLRPRDLI SNINVIVLEL  360
KGSETTFMCE YADETATIVE FLNRWITFCQ SIISTLTSGG PGPAGLYAQP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGLYAQP GSEVQLVESG GGLVQPGGSL RLSCAASGFT  600
FSSYTLAWVR QAPGKGLEWV AAIDSSSYTY SPDTVRGRFT ISRDNAKNSL YLQMNSLRAE  660
DTAVYYCARD SNWDALDYWG QGTTVTVSSG GGGSGGGGSG GGGSDIQMTQ SPSSLSASVG  720
DRVTITCKAR EKLWSAVAWY QQKPGKAPKS LIYSASFRYS GVPSRFSGSG SGTDFTLTIS  780
SLQPEDFATY YCQQYYTYPY TFGGGTKVEI K                              811

SEQ ID NO: 402          moltype = AA  length = 811
FEATURE                 Location/Qualifiers
source                  1..811
                        mol_type = protein
                        organism = synthetic construct
```

```
SEQUENCE: 402
ELCDDDPPEI PHATFKAMAY KEGTMLNCEC KRGFRRIKSG SLYMLCTGNS SHSSWDNQCQ  60
CTSSATRNTT KQVTPQPEEQ KERKTTEMQS PMQPVDQASL PGHCREPPPW ENEATERIYH  120
FVVGQMVYYQ CVQGYRALHR GPAESVCKMT HGKTRWTQPQ LICTGEMETS QFPGEEKPQA  180
SPEGRPESET SSLVTTTDFQ IQTEMAATME TSIFTTEYQG GGGSGGGGSG GGGSGGGGSG  240
GGGSGGGGSS GGPGPAGLYA QPGSAPTSSS TKKTQLQLEH LLLDLQMILN GINNYKNPKL  300
TRMLTFKFYM PKKATELKHL QCLEEELKPL EEVLNLAQSK NFHLRPRDLI SNINVIVLEL  360
KGSETTFMCE YADETATIVE FLNRWITFCQ SIISTLTSGG PGPAGLYAQP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGLYAQP GSEVQLVESG GGLVQPGGSL RLSCAASGFT  600
FSSYTLAWVR QAPGKGLEWV AAIDSSSYTY SPDTVRGRFT ISRDNAKNSL YLQMNSLRAE  660
DTAVYYCARD SNWDALDYWG QGTTVTVSSS GGPGPAGLYA QPGSDIQMTQ SPSSLSASVG  720
DRVTITCKVT EKVWGNVAWY QQKPGKAPIS LIYSPSLRKS GVPSRFSGSG SGTDFTLTIS  780
SLQPEDFATY YCQQYYTYPY TFGGGTKVEI K                                811

SEQ ID NO: 403          moltype = AA  length = 811
FEATURE                 Location/Qualifiers
source                  1..811
                        mol_type = protein
                        organism = synthetic construct
SEQUENCE: 403
ELCDDDPPEI PHATFKAMAY KEGTMLNCEC KRGFRRIKSG SLYMLCTGNS SHSSWDNQCQ  60
CTSSATRNTT KQVTPQPEEQ KERKTTEMQS PMQPVDQASL PGHCREPPPW ENEATERIYH  120
FVVGQMVYYQ CVQGYRALHR GPAESVCKMT HGKTRWTQPQ LICTGEMETS QFPGEEKPQA  180
SPEGRPESET SSLVTTTDFQ IQTEMAATME TSIFTTEYQG GGGSGGGGSG GGGSGGGGSG  240
GGGSGGGGSS GGPGPAGLYA QPGSAPTSSS TKKTQLQLEH LLLDLQMILN GINNYKNPKL  300
TRMLTFKFYM PKKATELKHL QCLEEELKPL EEVLNLAQSK NFHLRPRDLI SNINVIVLEL  360
KGSETTFMCE YADETATIVE FLNRWITFCQ SIISTLTSGG PGPAGLYAQP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGLYAQP GSEVQLVESG GGLVQPGGSL RLSCAASGFT  600
FSSYTLAWVR QAPGKGLEWV AAIDSSSYTY SPDTVRGRFT ISRDNAKNSL YLQMNSLRAE  660
DTAVYYCARD SNWDALDYWG QGTTVTVSSG GGGSGGGGSG GGGSDIQMTQ SPSSLSASVG  720
DRVTITCKVT EKVWGNVAWY QQKPGKAPIS LIYSPSLRKS GVPSRFSGSG SGTDFTLTIS  780
SLQPEDFATY YCQQYYTYPY TFGGGTKVEI K                                811

SEQ ID NO: 404          moltype = AA  length = 691
FEATURE                 Location/Qualifiers
source                  1..691
                        mol_type = protein
                        organism = synthetic construct
SEQUENCE: 404
ELCDDDPPEI PHATFKAMAY KEGTMLNCEC KRGFRRIKSG SLYMLCTGNS SHSSWDNQCQ  60
CTSSATRNTT KQVTPQPEEQ KERKTTEMQS PMQPVDQASL PGHCREPPPW ENEATERIYH  120
FVVGQMVYYQ CVQGYRALHR GPAESVCKMT HGKTRWTQPQ LICTGEMETS QFPGEEKPQA  180
SPEGRPESET SSLVTTTDFQ IQTEMAATME TSIFTTEYQG GGGSGGGGSG GGGSGGGGSG  240
GGGSGGGGSS GGPGPAGLYA QPGSAPTSSS TKKTQLQLEH LLLDLQMILN GINNYKNPKL  300
TRMLTFKFYM PKKATELKHL QCLEEELKPL EEVLNLAQSK NFHLRPRDLI SNINVIVLEL  360
KGSETTFMCE YADETATIVE FLNRWITFCQ SIISTLTSGG PGPAGLYAQP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGLYAQP GSEVQLLESG GGLVQPGGSL RLSCAASGSI  600
FSANAMGWYR QAPGKGLELV AVISSGGSTN YADSVKGRFT ISRDNSKNTV YLQMNSLRAE  660
DTAVYYCMYS GSYYYTPNDY WGQGTLVTVS S                                691

SEQ ID NO: 405          moltype = AA  length = 690
FEATURE                 Location/Qualifiers
source                  1..690
                        mol_type = protein
                        organism = synthetic construct
SEQUENCE: 405
ELCDDDPPEI PHATFKAMAY KEGTMLNCEC KRGFRRIKSG SLYMLCTGNS SHSSWDNQCQ  60
CTSSATRNTT KQVTPQPEEQ KERKTTEMQS PMQPVDQASL PGHCREPPPW ENEATERIYH  120
FVVGQMVYYQ CVQGYRALHR GPAESVCKMT HGKTRWTQPQ LICTGEMETS QFPGEEKPQA  180
SPEGRPESET SSLVTTTDFQ IQTEMAATME TSIFTTEYQG GGGSGGGGSG GGGSGGGGSG  240
GGGSGGGGSS GGPGPAGLYA QPGSAPTSSS TKKTQLQLEH LLLDLQMILN GINNYKNPKL  300
TRMLTFKFYM PKKATELKHL QCLEEELKPL EEVLNLAQSK NFHLRPRDLI SNINVIVLEL  360
KGSETTFMCE YADETATIVE FLNRWITFCQ SIISTLTSGG PGPAGLYAQP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGLYAQP GSEVQLLESG GGLVQPGGSL RLSCAASERI  600
FSTDVMGWYR QAPGKQRELV AVVSARGTTN YLDAVKGRFT ISRDNSKNTL YLQMNSLRAE  660
DTAVYYCYVR ETTSPWRIYW GQGTLVTVSS                                  690

SEQ ID NO: 406          moltype = AA  length = 661
FEATURE                 Location/Qualifiers
source                  1..661
                        mol_type = protein
```

```
                         organism = synthetic construct
SEQUENCE: 406
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG QGTTVTVSSS  540
GGPGPAGLYA QPGSDIQMTQ SPSSLSASVG DRVTITCKAR EKLWSAVAWY QQKPGKAPKS  600
LIYSASFRYS GVPSRFSGSG SGTDFTLTIS SLQPEDFATY YCQQYYTYPY TFGGGTKVEI  660
K                                                                 661

SEQ ID NO: 407           moltype = AA  length = 661
FEATURE                  Location/Qualifiers
source                   1..661
                         mol_type = protein
                         organism = synthetic construct
SEQUENCE: 407
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG QGTTVTVSSG  540
GGGSGGGGSG GGGSDIQMTQ SPSSLSASVG DRVTITCKAR EKLWSAVAWY QQKPGKAPKS  600
LIYSASFRYS GVPSRFSGSG SGTDFTLTIS SLQPEDFATY YCQQYYTYPY TFGGGTKVEI  660
K                                                                 661

SEQ ID NO: 408           moltype = AA  length = 661
FEATURE                  Location/Qualifiers
source                   1..661
                         mol_type = protein
                         organism = synthetic construct
SEQUENCE: 408
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG QGTTVTVSSS  540
GGPGPAGLYA QPGSDIQMTQ SPSSLSASVG DRVTITCKVT EKVWGNVAWY QQKPGKAPIS  600
LIYSPSLRKS GVPSRFSGSG SGTDFTLTIS SLQPEDFATY YCQQYYTYPY TFGGGTKVEI  660
K                                                                 661

SEQ ID NO: 409           moltype = AA  length = 661
FEATURE                  Location/Qualifiers
source                   1..661
                         mol_type = protein
                         organism = synthetic construct
SEQUENCE: 409
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG QGTTVTVSSG  540
GGGSGGGGSG GGGSDIQMTQ SPSSLSASVG DRVTITCKVT EKVWGNVAWY QQKPGKAPIS  600
LIYSPSLRKS GVPSRFSGSG SGTDFTLTIS SLQPEDFATY YCQQYYTYPY TFGGGTKVEI  660
K                                                                 661

SEQ ID NO: 410           moltype = AA  length = 541
FEATURE                  Location/Qualifiers
source                   1..541
                         mol_type = protein
                         organism = synthetic construct
SEQUENCE: 410
ESKYGPPCPP CPAPEFLGGP SVFLFPPKPK DTLMISRTPE VTCVVVDVSQ EDPEVQFNWY  60
```

```
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLLESG GGLVQPGGSL RLSCAASGSI FSANAMGWYR QAPGKGLELV AVISSGGSTN  480
YADSVKGRFT ISRDNSKNTV YLQMNSLRAE DTAVYYCMYS GSYYYTPNDY WGQGTLVTVS  540
S                                                                 541

SEQ ID NO: 411         moltype = AA  length = 540
FEATURE                Location/Qualifiers
source                 1..540
                       mol_type = protein
                       organism = synthetic construct
SEQUENCE: 411
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLLESG GGLVQPGGSL RLSCAASERI FSTDVMGWYR QAPGKQRELV AVVSARGTTN  480
YLDAVKGRFT ISRDNSKNTL YLQMNSLRAE DTAVYYCYVR ETTSPWRIYW GQGTLVTVSS  540

SEQ ID NO: 412         moltype = AA  length = 925
FEATURE                Location/Qualifiers
source                 1..925
                       mol_type = protein
                       organism = synthetic construct
SEQUENCE: 412
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSELCDDD PPEIPHATFK AMAYKEGTML NCECKRGFRR IKSGSLYMLC TGNSSHSSWD  300
NQCQCTSSAT RNTTKQVTPQ PEEQKERKTT EMQSPMQPVD QASLPGHCRE PPPWENEATE  360
RIYHFVVGQM VYYQCVQGYR ALHRGPAESV CKMTHGKTRW TQPQLICTGE METSQFPGEE  420
KPQASPEGRP ESETSSLVTT TDFQIQTEMA ATMETSIFTT EYQGGGGSGG GGSGGGGSGG  480
GGSGGGGSGG GGSSGGPGPA GLYAQPGSAP TSSSTKKTQL QLEHLLLDLQ MILNGINNYK  540
NPKLTRMLTF KFYMPKKATE LKHLQCLEEE LKPLEEVLNL AQSKNFHLRP RDLISNINVI  600
VLELKGSETT FMCEYADETA TIVEFLNRWI TFCQSIISTL TGGGGSGGGG SGGGGSGGGG  660
SGGGGSGGGG SSGGPGPAGL YAQPGSEVQL VESGGGLVQP GGSLRLSCAA SGFTFSSYTL  720
AWVRQAPGKG LEWVAAIDSS SYTYSPDTVR GRFTISRDNA KNSLYLQMNS LRAEDTAVYY  780
CARDSNWDAL DYWGQGTTVT VSSSGGPGPA GLYAQPGSDI QMTQSPSSLS ASVGDRVTIT  840
CKAREKLWSA VAWYQQKPGK APKSLIYSAS FRYSGVPSRF SGSGSGTDFT LTISSLQPED  900
FATYYCQQYY TYPYTFGGGT KVEIK                                       925

SEQ ID NO: 413         moltype = AA  length = 925
FEATURE                Location/Qualifiers
source                 1..925
                       mol_type = protein
                       organism = synthetic construct
SEQUENCE: 413
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSELCDDD PPEIPHATFK AMAYKEGTML NCECKRGFRR IKSGSLYMLC TGNSSHSSWD  300
NQCQCTSSAT RNTTKQVTPQ PEEQKERKTT EMQSPMQPVD QASLPGHCRE PPPWENEATE  360
RIYHFVVGQM VYYQCVQGYR ALHRGPAESV CKMTHGKTRW TQPQLICTGE METSQFPGEE  420
KPQASPEGRP ESETSSLVTT TDFQIQTEMA ATMETSIFTT EYQGGGGSGG GGSGGGGSGG  480
GGSGGGGSGG GGSSGGPGPA GLYAQPGSAP TSSSTKKTQL QLEHLLLDLQ MILNGINNYK  540
NPKLTRMLTF KFYMPKKATE LKHLQCLEEE LKPLEEVLNL AQSKNFHLRP RDLISNINVI  600
VLELKGSETT FMCEYADETA TIVEFLNRWI TFCQSIISTL TGGGGSGGGG SGGGGSGGGG  660
SGGGGSGGGG SSGGPGPAGL YAQPGSEVQL VESGGGLVQP GGSLRLSCAA SGFTFSSYTL  720
AWVRQAPGKG LEWVAAIDSS SYTYSPDTVR GRFTISRDNA KNSLYLQMNS LRAEDTAVYY  780
CARDSNWDAL DYWGQGTTVT VSSGGGGSGG GGSGGGGSDI QMTQSPSSLS ASVGDRVTIT  840
CKAREKLWSA VAWYQQKPGK APKSLIYSAS FRYSGVPSRF SGSGSGTDFT LTISSLQPED  900
FATYYCQQYY TYPYTFGGGT KVEIK                                       925

SEQ ID NO: 414         moltype = AA  length = 925
FEATURE                Location/Qualifiers
source                 1..925
                       mol_type = protein
                       organism = synthetic construct
SEQUENCE: 414
ESKYGPPCPP CPAPEFLGGP SVFLFPPKPK DTLMISRTPE VTCVVVDVSQ EDPEVQFNWY  60
```

-continued

```
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSELCDDD PPEIPHATFK AMAYKEGTML NCECKRGFRR IKSGSLYMLC TGNSSHSSWD  300
NQCQCTSSAT RNTTKQVTPQ PEEQKERKTT EMQSPMQPVD QASLPGHCRE PPPWENEATE  360
RIYHFVVGQM VYYQCVQGYR ALHRGPAESV CKMTHGKTRW TQPQLICTGE METSQFPGEE  420
KPQASPEGRP ESETSSLVTT TDFQIQTEMA ATMETSIFTT EYQGGGGSGG GGSGGGGSGG  480
GGSGGGGSGG GGSSGGPGPA GLYAQPGSAP TSSSTKKTQL QLEHLLLDLQ MILNGINNYK  540
NPKLTRMLTF KFYMPKKATE LKHLQCLEEE LKPLEEVLNL AQSKNFHLRP RDLISNINVI  600
VLELKGSETT FMCEYADETA TIVEFLNRWI TFCQSIISTL TGGGGSGGGG SGGGGSGGGG  660
SGGGGSGGGG SSGGPGPAGL YAQPGSEVQL VESGGGLVQP GGSLRLSCAA SGFTFSSYTL  720
AWVRQAPGKG LEWVAAIDSS SYTYSPDTVR GRFTISRDNA KNSLYLQMNS LRAEDTAVYY  780
CARDSNWDAL DYWGQGTTVT VSSSGGPGPA GLYAQPGSDI QMTQSPSSLS ASVGDRVTIT  840
CKVTEKVWGN VAWYQQKPGK APISLIYSPS LRKSGVPSRF SGSGSGTDFT LTISSLQPED  900
FATYYCQQYY TYPYTFGGGT KVEIK                                       925

SEQ ID NO: 415          moltype = AA  length = 925
FEATURE                 Location/Qualifiers
source                  1..925
                        mol_type = protein
                        organism = synthetic construct
SEQUENCE: 415
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSELCDDD PPEIPHATFK AMAYKEGTML NCECKRGFRR IKSGSLYMLC TGNSSHSSWD  300
NQCQCTSSAT RNTTKQVTPQ PEEQKERKTT EMQSPMQPVD QASLPGHCRE PPPWENEATE  360
RIYHFVVGQM VYYQCVQGYR ALHRGPAESV CKMTHGKTRW TQPQLICTGE METSQFPGEE  420
KPQASPEGRP ESETSSLVTT TDFQIQTEMA ATMETSIFTT EYQGGGGSGG GGSGGGGSGG  480
GGSGGGGSGG GGSSGGPGPA GLYAQPGSAP TSSSTKKTQL QLEHLLLDLQ MILNGINNYK  540
NPKLTRMLTF KFYMPKKATE LKHLQCLEEE LKPLEEVLNL AQSKNFHLRP RDLISNINVI  600
VLELKGSETT FMCEYADETA TIVEFLNRWI TFCQSIISTL TGGGGSGGGG SGGGGSGGGG  660
SGGGGSGGGG SSGGPGPAGL YAQPGSEVQL VESGGGLVQP GGSLRLSCAA SGFTFSSYTL  720
AWVRQAPGKG LEWVAAIDSS SYTYSPDTVR GRFTISRDNA KNSLYLQMNS LRAEDTAVYY  780
CARDSNWDAL DYWGQGTTVT VSSGGGGSGG GGSGGGGSDI QMTQSPSSLS ASVGDRVTIT  840
CKVTEKVWGN VAWYQQKPGK APISLIYSPS LRKSGVPSRF SGSGSGTDFT LTISSLQPED  900
FATYYCQQYY TYPYTFGGGT KVEIK                                       925

SEQ ID NO: 416          moltype = AA  length = 805
FEATURE                 Location/Qualifiers
source                  1..805
                        mol_type = protein
                        organism = synthetic construct
SEQUENCE: 416
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSELCDDD PPEIPHATFK AMAYKEGTML NCECKRGFRR IKSGSLYMLC TGNSSHSSWD  300
NQCQCTSSAT RNTTKQVTPQ PEEQKERKTT EMQSPMQPVD QASLPGHCRE PPPWENEATE  360
RIYHFVVGQM VYYQCVQGYR ALHRGPAESV CKMTHGKTRW TQPQLICTGE METSQFPGEE  420
KPQASPEGRP ESETSSLVTT TDFQIQTEMA ATMETSIFTT EYQGGGGSGG GGSGGGGSGG  480
GGSGGGGSGG GGSSGGPGPA GLYAQPGSAP TSSSTKKTQL QLEHLLLDLQ MILNGINNYK  540
NPKLTRMLTF KFYMPKKATE LKHLQCLEEE LKPLEEVLNL AQSKNFHLRP RDLISNINVI  600
VLELKGSETT FMCEYADETA TIVEFLNRWI TFCQSIISTL TGGGGSGGGG SGGGGSGGGG  660
SGGGGSGGGG SSGGPGPAGL YAQPGSEVQL LESGGGLVQP GGSLRLSCAA SGSIFSANAM  720
GWYRQAPGKG LELVAVISSG GSTNYADSVK GRFTISRDNS KNTVYLQMNS LRAEDTAVYY  780
CMYSGSYYYT PNDYWGQGTL VTVSS                                       805

SEQ ID NO: 417          moltype = AA  length = 804
FEATURE                 Location/Qualifiers
source                  1..804
                        mol_type = protein
                        organism = synthetic construct
SEQUENCE: 417
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSELCDDD PPEIPHATFK AMAYKEGTML NCECKRGFRR IKSGSLYMLC TGNSSHSSWD  300
NQCQCTSSAT RNTTKQVTPQ PEEQKERKTT EMQSPMQPVD QASLPGHCRE PPPWENEATE  360
RIYHFVVGQM VYYQCVQGYR ALHRGPAESV CKMTHGKTRW TQPQLICTGE METSQFPGEE  420
KPQASPEGRP ESETSSLVTT TDFQIQTEMA ATMETSIFTT EYQGGGGSGG GGSGGGGSGG  480
GGSGGGGSGG GGSSGGPGPA GLYAQPGSAP TSSSTKKTQL QLEHLLLDLQ MILNGINNYK  540
NPKLTRMLTF KFYMPKKATE LKHLQCLEEE LKPLEEVLNL AQSKNFHLRP RDLISNINVI  600
VLELKGSETT FMCEYADETA TIVEFLNRWI TFCQSIISTL TGGGGSGGGG SGGGGSGGGG  660
SGGGGSGGGG SSGGPGPAGL YAQPGSEVQL LESGGGLVQP GGSLRLSCAA SERIFSTDVM  720
GWYRQAPGKQ RELVAVVSAR GTTNYLDAVK GRFTISRDNS KNTLYLQMNS LRAEDTAVYY  780
```

```
CYVRETTSPW RIYWGQGTLV TVSS                                    804

SEQ ID NO: 418         moltype = AA  length = 245
FEATURE                Location/Qualifiers
source                 1..245
                       mol_type = protein
                       organism = synthetic construct
SEQUENCE: 418
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSGGG  120
GSGGGGSGGG GSDIQMTQSP SSLSASVGDR VTITCKASQN VGTNVGWYQQ KPGKAPKSLI  180
YSASFRYSGV PSRFSGSGSG TDFTLTISSL QPEDFATYYC QQYYTYPYTF GGGTKVEIKH  240
HHHHH                                                         245

SEQ ID NO: 419         moltype = AA  length = 245
FEATURE                Location/Qualifiers
source                 1..245
                       mol_type = protein
                       organism = synthetic construct
SEQUENCE: 419
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSSGG  120
PGPAGLYAQP GSDIQMTQSP SSLSASVGDR VTITCKASQN VGTNVGWYQQ KPGKAPKALI  180
YSASFRYSGV PSRFSGSGSG TDFTLTISSL QPEDFATYYC QQYYTYPYTF GGGTKVEIKH  240
HHHHH                                                         245

SEQ ID NO: 420         moltype = AA  length = 245
FEATURE                Location/Qualifiers
source                 1..245
                       mol_type = protein
                       organism = synthetic construct
SEQUENCE: 420
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSSGG  120
PGPAGLYAQP GSDIQMTQSP SSLSASVGDR VTITCKASQN VGTNVGWYQQ KPGKAPKSLI  180
YSASFRYSGV PSRFSGSGSG TDFTLTISSL QPEDFATYYC QQYYTYPYTF GGGTKVEIKH  240
HHHHH                                                         245

SEQ ID NO: 421         moltype = AA  length = 612
FEATURE                Location/Qualifiers
source                 1..612
                       mol_type = protein
                       organism = synthetic construct
SEQUENCE: 421
LVEEPKNLVK TNCDLYEKLG EYGFQNAILV RYTQKAPQVS TPTLVEAARN LGRVGTKCCT  60
LPEDQRLPCV EDYLSAILNR VCLLHEKTPV SEHVTKCCSG SLVERRPCFS ALTVDETYVP  120
KEFKAETFTF HSDICTLPEK EKQIKKQTAL AELVKHKPKA TAEQLKTVMD DFAQFLDTCC  180
KAADKDTCFS TEGPNLVTRC KDALASGGPG PAGMKGLPGS CDLPQTHNLR NKRALTLLVQ  240
MRRLSPLSCL KDRKDFGFPQ EKVDAQQIKK AQAIPVLSEL TQQILNIFTS KDSSAAWNTT  300
LLDSFCNDLH QQLNDLQGCL MQQVGVQEFP LTQEDALLAV RKYFHRITVY LREKKHSPCA  360
WEVVRAEVWR ALSSSANVLG RLREEKSGGP GPAGMKGLPG SLVEEPKNLV KTNCDLYEKL  420
GEYGFQNAIL VRYTQKAPQV STPTLVEAAR NLGRVGTKCC TLPEDQRLPC VEDYLSAILN  480
RVCLLHEKTP VSEHVTKCCS GSLVERRPCF SALTVDETYV PKEFKAETFT FHSDICTLPE  540
KEKQIKKQTA LAELVKHKPK ATAEQLKTVM DDFAQFLDTC CKAADKDTCF STEGPNLVTR  600
CKDALAHHHH HH                                                 612

SEQ ID NO: 422         moltype = AA  length = 1030
FEATURE                Location/Qualifiers
source                 1..1030
                       mol_type = protein
                       organism = synthetic construct
SEQUENCE: 422
EAHKSEIAHR YNDLGEQHFK GLVLIAFSQY LQKCSYDEHA KLVQEVTDFA KTCVADESAA  60
NCDKSLHTLF GDKLCAIPNL RENYGELADC CTKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQGGGG SGGGGSGGSL VEEPKNLVKT NCDLYEKLGE YGFQNAILVR  240
YTQKAPQVST PTLVEAARNL GRVGTKCCTL PEDQRLPCVE DYLSAILNRV CLLHEKTPVS  300
EHVTKCCSGS LVERRPCFSA LTVDETYVPK EFKAETFTFH SDICTLPEKE KQIKKQTALA  360
ELVKHKPKAT AEQLKTVMDD FAQFLDTCCK AADKDTCFST EGPNLVTRCK DALASGGPGP  420
AGMKGLPGSC DLPQTHNLRN KRALTLLVQM RRLSPLSCLK DRKDFGFPQE KVDAQQIKKA  480
QAIPVLSELT QQILNIFTSK DSSAAWNTTL LDSFCNDLHQ QLNDLQGCLM QQVGVQEFPL  540
TQEDALLAVR KYFHRITVYL REKKHSPCAW EVVRAEVWRA LSSSANVLGR LREEKSGGPG  600
PAGMKGLPGS EAHKSEIAHR YNDLGEQHFK GLVLIAFSQY LQKCSYDEHA KLVQEVTDFA  660
KTCVADESAA NCDKSLHTLF GDKLCAIPNL RENYGELADC CTKQEPERNE CFLQHKDDNP  720
SLPPFERPEA EAMCTSFKEN PTTFMGHYLH EVARRHPYFY APELLYYAEQ YNEILTQCCA  780
EADKESCLTP KLDGVKEKAL VSSVRQGGGG SGGGGSGGSL VEEPKNLVKT NCDLYEKLGE  840
YGFQNAILVR YTQKAPQVST PTLVEAARNL GRVGTKCCTL PEDQRLPCVE DYLSAILNRV  900
CLLHEKTPVS EHVTKCCSGS LVERRPCFSA LTVDETYVPK EFKAETFTFH SDICTLPEKE  960
KQIKKQTALA ELVKHKPKAT AEQLKTVMDD FAQFLDTCCK AADKDTCFST EGPNLVTRCK  1020
```

-continued

```
DALAHHHHHH                                                  1030

SEQ ID NO: 423          moltype = AA  length = 466
FEATURE                 Location/Qualifiers
source                  1..466
                        mol_type = protein
                        organism = synthetic construct
SEQUENCE: 423
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSGGGGS  120
GGGSGGPGPA GMKGLPGSGG GGSGGGSCDL PQTHNLRNKR ALTLLVQMRR LSPLSCLKDR  180
KDFGFPQEKV DAQQIKKAQA IPVLSELTQQ ILNIFTSKDS SAAWNTTLLD SFCNDLHQQL  240
NDLQGCLMQQ VGVQEFPLTQ EDALLAVRKY FHRITVYLRE KKHSPCAWEV VRAEVWRALS  300
SSANVLGRLR EEKGGGGSGG GSGGPGPAGM KGLPGSGGGG SGGGSEVQLV ESGGGLVQPG  360
NSLRLSCAAS GFTFSKFGMS WVRQAPGKGL EWVSSISGSG RDTLYAESVK GRFTISRDNA  420
KTTLYLQMNS LRPEDTAVYY CTIGGSLSVS SQGTLVTVSS HHHHHH                466

SEQ ID NO: 424          moltype = AA  length = 426
FEATURE                 Location/Qualifiers
source                  1..426
                        mol_type = protein
                        organism = synthetic construct
SEQUENCE: 424
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS CDLPQTHNLR NKRALTLLVQ MRRLSPLSCL KDRKDFGFPQ EKVDAQQIKK  180
AQAIPVLSEL TQQILNIFTS KDSSAAWNTT LLDSFCNDLH QQLNDLQGCL MQQVGVQEFP  240
LTQEDALLAV RKYFHRITVY LREKKHSPCA WEVVRAEVWR ALSSSANVLG RLREEKSGGP  300
GPAGLYAQPG SEVQLVESGG GLVQPGNSLR LSCAASGFTF SKFGMSWVRQ APGKGLEWVS  360
SISGSGRDTL YAESVKGRFT ISRDNAKTTL YLQMNSLRPE DTAVYYCTIG GSLSVSSQGT  420
LVTVSS                                                            426

SEQ ID NO: 425          moltype = AA  length = 426
FEATURE                 Location/Qualifiers
source                  1..426
                        mol_type = protein
                        organism = synthetic construct
SEQUENCE: 425
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS CDLPQTHNLR NKRALTLLVQ MRRLSPLSCL KDRKDFGFPQ EKVDAQQIKK  180
AQAIPVLSEL TQQILNIFTS KDSSAAWNTT LLDSFCNDLH QQLNDLQGCL MQQVGVQEFP  240
LTQEDALLAV RKYFHRITVY LREKKHSPCA WEVVRAEVWR ALSSSANVLG RLREEKSGGP  300
ALFKSSFPPG SEVQLVESGG GLVQPGNSLR LSCAASGFTF SKFGMSWVRQ APGKGLEWVS  360
SISGSGRDTL YAESVKGRFT ISRDNAKTTL YLQMNSLRPE DTAVYYCTIG GSLSVSSQGT  420
LVTVSS                                                            426

SEQ ID NO: 426          moltype = AA  length = 428
FEATURE                 Location/Qualifiers
source                  1..428
                        mol_type = protein
                        organism = synthetic construct
SEQUENCE: 426
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPP  120
LAQKLKSSPG SCDLPQTHNL RNKRALTLLV QMRRLSPLSC LKDRKDFGFP QEKVDAQQIK  180
KAQAIPVLSE LTQQILNIFT SKDSSAAWNT TLLDSFCNDL HQQLNDLQGC LMQQVGVQEF  240
PLTQEDALLA VRKYFHRITV YLREKKHSPC AWEVVRAEVW RALSSSANVL GRLREEKSGG  300
PPLAQKLKSS PGSEVQLVES GGGLVQPGNS LRLSCAASGF TFSKFGMSWV RQAPGKGLEW  360
VSSISGSGRD TLYAESVKGR FTISRDNAKT TLYLQMNSLR PEDTAVYYCT IGGSLSVSSQ  420
GTLVTVSS                                                          428

SEQ ID NO: 427          moltype = AA  length = 425
FEATURE                 Location/Qualifiers
source                  1..425
                        mol_type = protein
                        organism = synthetic construct
SEQUENCE: 427
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS CDLPQTHSLG SRRTLMLLAQ MRRISLFSCL KDRHDFGFPQ EEFGNQFQKA  180
ETIPVLHEMI QQIFNLFSTK DSSAAWDETL LDKFYTELYQ QLNDLEACVI QGVGVTETPL  240
MKEDSILAVR KYFQRITLYL KEKKYSPCAW EVVRAEIMRS FSLSTNLQES LRSKESGGPG  300
PAGLYAQPGS EVQLVESGGG LVQPGNSLRL SCAASGFTFS KFGMSWVRQA PGKGLEWVSS  360
ISGSGRDTLY AESVKGRFTI SRDNAKTTLY LQMNSLRPED TAVYYCTIGG SLSVSSQGTL  420
VTVSS                                                             425

SEQ ID NO: 428          moltype = AA  length = 425
FEATURE                 Location/Qualifiers
```

```
source                1..425
                      mol_type = protein
                      organism = synthetic construct
SEQUENCE: 428
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS CDLPQTHSLG SRRTLMLLAQ MRRISLFSCL KDRHDFGFPQ EEFGNQFQKA  180
ETIPVLHEMI QQIFNLFSTK DSSAAWDETL LDKFYTELYQ QLNDLEACVI QGVGVTETPL  240
MKEDSILAVR KYFQRITLYL KEKKYSPCAW EVVRAEIMRS FSLSTNLQES LRSKESGGPA  300
LFKSSFPPGS EVQLVESGGG LVQPGNSLRL SCAASGFTFS KFGMSWVRQA PGKGLEWVSS  360
ISGSGRDTLY AESVKGRFTI SRDNAKTTLY LQMNSLRPED TAVYYCTIGG SLSVSSQGTL  420
VTVSS                                                              425

SEQ ID NO: 429        moltype = AA  length = 427
FEATURE               Location/Qualifiers
source                1..427
                      mol_type = protein
                      organism = synthetic construct
SEQUENCE: 429
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPP  120
LAQKLKSSPG SCDLPQTHSL GSRRTLMLLA QMRRISLFSC LKDRHDFGFP QEEFGNQFQK  180
AETIPVLHEM IQQIFNLFST KDSSAAWDET LLDKFYTELY QQLNDLEACV IQGVGVTETP  240
LMKEDSILAV RKYFQRITLY LKEKKYSPCA WEVVRAEIMR SFSLSTNLQE SLRSKESGGP  300
PLAQKLKSSP GSEVQLVESG GGLVQPGNSL RLSCAASGFT FSKFGMSWVR QAPGKGLEWV  360
SSISGSGRDT LYAESVKGRF TISRDNAKTT LYLQMNSLRP EDTAVYYCTI GGSLSVSSQG  420
TLVTVSS                                                            427

SEQ ID NO: 430        moltype = AA  length = 728
FEATURE               Location/Qualifiers
source                1..728
                      mol_type = protein
                      organism = synthetic construct
SEQUENCE: 430
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS HGTVIESLES LNNYFNSSGI DVEEKSLFLD IWRNWQKDGD MKILQSQIIS  180
FYLRLFEVLK DNQAISNNIS VIESHLITTF FSNSKAKKDA FMSIAKFEVN NPQVQRQAFN  240
ELIRVVHQLL PESSLRKRKR SRCSGGPGPA GMKGLPGSCD LPQTHNLRNK RALTLLVQMR  300
RLSPLSCLKD RKDFGFPQEK VDAQQIKKAQ AIPVLSELTQ QILNIFTSKD SSAAWNTTLL  360
DSFCNDLHQQ LNDLQGCLMQ QVGVQEFPLT QEDALLAVRK YFHRITVYLR EKKHSPCAWE  420
VVRAEVWRAL SSSANVLGRL REEKSGGPGP AGMKGLPGSH GTVIESLESL NNYFNSSGID  480
VEEKSLFLDI WRNWQKDGDM KILQSQIISF YLRLFEVLKD NQAISNNISV IESHLITTFF  540
SNSKAKKDAF MSIAKFEVNN PQVQRQAFNE LIRVVHQLLP ESSLRKRKRS RCSGGPGPAG  600
MKGLPGSEVQ LVESGGGLVQ PGNSLRLSCA ASGFTFSKFG MSWVRQAPGK GLEWVSSISG  660
SGRDTLYAES VKGRFTISRD NAKTTLYLQM NSLRPEDTAV YYCTIGGSLS VSSQGTLVTV  720
SSHHHHHH                                                           728

SEQ ID NO: 431        moltype = AA  length = 947
FEATURE               Location/Qualifiers
source                1..947
                      mol_type = protein
                      organism = synthetic construct
SEQUENCE: 431
LVEEPKNLVK TNCDLYEKLG EYGFQNAILV RYTQKAPQVS TPTLVEAARN LGRVGTKCCT  60
LPEDQRLPCV EDYLSAILNR VCLLHEKTPV SEHVTKCCSG SLVERRPCFS ALTVDETYVP  120
KEFKAETFTF HSDICTLPEK EKQIKKQTAL AELVKHKPKA TAEQLKTVMD DFAQFLDTCC  180
KAADKDTCFS TEGPNLVTRC KDALASGGPG PAGMKGLPGS HGTVIESLES LNNYFNSSGI  240
DVEEKSLFLD IWRNWQKDGD MKILQSQIIS FYLRLFEVLK DNQAISNNIS VIESHLITTF  300
FSNSKAKKDA FMSIAKFEVN NPQVQRQAFN ELIRVVHQLL PESSLRKRKR SRCSGGPGPA  360
GMKGLPGSLV EEPKNLVKTN CDLYEKLGEY GFQNAILVRY TQKAPQVSTP TLVEAARNLG  420
RVGTKCCTLP EDQRLPCVED YLSAILNRVC LLHEKTPVSE HVTKCCSGSL VERRPCFSAL  480
TVDETYVPKE FKAETFTFHS DICTLPEKEK QIKKQTALAE LVKHKPKATA EQLKTVMDDF  540
AQFLDTCCKA ADKDTCFSTE GPNLVTRCKD ALASGGPGPA GMKGLPGSHG TVIESLESLN  600
NYFNSSGIDV EEKSLFLDIW RNWQKDGDMK ILQSQIISFY LRLFEVLKDN QAISNNISVI  660
ESHLITTFFS NSKAKKDAFM SIAKFEVNNP QVQRQAFNEL IRVVHQLLPE SSLRKRKRSR  720
CSGGPGPAGM KGLPGSLVEE PKNLVKTNCD LYEKLGEYGF QNAILVRYTQ KAPQVSTPTL  780
VEAARNLGRV GTKCCTLPED QRLPCVEDYL SAILNRVCLL HEKTPVSEHV TKCCSGSLVE  840
RRPCFSALTV DETYVPKEFK AETFTFHSDI CTLPEKEKQI KKQTALAELV KHKPKATAEQ  900
LKTVMDDFAQ FLDTCCKAAD KDTCFSTEGP NLVTRCKDAL AHHHHHH                947

SEQ ID NO: 432        moltype = AA  length = 1574
FEATURE               Location/Qualifiers
source                1..1574
                      mol_type = protein
                      organism = synthetic construct
SEQUENCE: 432
EAHKSEIAHR YNDLGEQHFK GLVLIAFSQY LQKCSYDEHA KLVQEVTDFA KTCVADESAA  60
NCDKSLHTLF GDKLCAIPNL RENYGELADC CTKQEPERNE CFLQHKDDNP SLPPFERPEA  120
```

```
EAMCTSFKEN PTTFMGHYLH EVARRHPYFY APELLYYAEQ YNEILTQCCA EADKESCLTP  180
KLDGVKEKAL VSSVRQGGGG SGGGGSGGSL VEEPKNLVKT NCDLYEKLGE YGFQNAILVR  240
YTQKAPQVST PTLVEAARNL GRVGTKCCTL PEDQRLPCVE DYLSAILNRV CLLHEKTPVS  300
EHVTKCCSGS LVERRPCFSA LTVDETYVPK EFKAETFTFH SDICTLPEKE KQIKKQTALA  360
ELVKHKPKAT AEQLKTVMDD FAQFLDTCCK AADKDTCFST EGPNLVTRCK DALASGGPGP  420
AGMKGLPGSH GTVIESLESL NNYFNSSGID VEEKSLFLDI WRNWQKDGDM KILQSQIISF  480
YLRLFEVLKD NQAISNNISV IESHLITTFF SNSKAKKDAF MSIAKFEVNN PQVQRQAFNE  540
LIRVVHQLLP ESSLRKRKRS RCSGGPGPAG MKGLPGSEAH KSEIAHRYND LGEQHFKGLV  600
LIAFSQYLQK CSYDEHAKLV QEVTDFAKTC VADESAANCD KSLHTLFGDK LCAIPNLREN  660
YGELADCCTK QEPERNECFL QHKDDNPSLP PFERPEAEAM CTSFKENPTT FMGHYLHEVA  720
RRHPYFYAPE LLYYAEQYNE ILTQCCAEAD KESCLTPKLD GVKEKALVSS VRQGGGGSGG  780
GGSGGSLVEE PKNLVKTNCD LYEKLGEYGF QNAILVRYTQ KAPQVSTPTL VEAARNLGRV  840
GTKCCTLPED QRLPCVEDYL SAILNRVCLL HEKTPVSEHV TKCCSGSLVE RRPCFSALTV  900
DETYVPKEFK AETFTFHSDI CTLPEKEKQI KKQTALAELV KHKPKATAEQ LKTVMDDFAQ  960
FLDTCCKAAD KDTCFSTEGP NLVTRCKDAL ASGGPGPAGM KGLPGSHGTV IESLESLNNY  1020
FNSSGIDVEE KSLFLDIWRN WQKDGDMKIL QSQIISFYLR LFEVLKDNQA ISNNISVIES  1080
HLITTFFSNS KAKKDAFMSI AKFEVNNPQV QRQAFNELIR VVHQLLPESS LRKRKRSRCS  1140
GGPGPAGMKG LPGSEAHKSE IAHRYNDLGE QHFKGLVLIA FSQYLQKCSY DEHAKLVQEV  1200
TDFAKTCVAD ESAANCDKSL HTLFGDKLCA IPNLRENYGE LADCCTKQEP ERNECFLQHK  1260
DDNPSLPPFE RPEAEAMCTS FKENPTTFMG HYLHEVARRH PYFYAPELLY YAEQYNEILT  1320
QCCAEADKES CLTPKLDGVK EKALVSSVRQ GGGGSGGGGS GGSLVEEPKN LVKTNCDLYE  1380
KLGEYGFQNA ILVRYTQKAP QVSTPTLVEA ARNLGRVGTK CCTLPEDQRL PCVEDYLSAI  1440
LNRVCLLHEK TPVSEHVTKC CSGSLVERRP CFSALTVDET YVPKEFKAET FTFHSDICTL  1500
PEKEKQIKKQ TALAELVKHK PKATAEQLKT VMDDFAQFLD TCCKAADKDT CFSTEGPNLV  1560
TRCKDALAHH HHHH                                                    1574

SEQ ID NO: 433         moltype = AA  length = 745
FEATURE                Location/Qualifiers
source                 1..745
                       mol_type = protein
                       organism = synthetic construct
SEQUENCE: 433
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSGGGGS  120
GGGSGGPGPA GMKGLPGSGG GGSGGGSHGT VIESLESLNN YFNSSGIDVE EKSLFLDIWR  180
NWQKDGDMKI LQSQIISFYL RLFEVLKDNQ AISNNISVIE SHLITTFFSN SKAKKDAFMS  240
IAKFEVNNPQ VQRQAFNELI RVVHQLLPES SLRKRKRSRC GGGGSGGGSG GPGPAGMKGL  300
PGSGGGGSGG GSEVQLVESG GGLVQPGNSL RLSCAASGFT FSKFGMSWVR QAPGKGLEWV  360
SSISGSGRDT LYAESVKGRF TISRDNAKTT LYLQMNSLRP EDTAVYYCTI GGSLSVSSQG  420
TLVTVSSGGG GSGGGSGGPG PAGMKGLPGS GGGGSGGGSH GTVIESLESL NNYFNSSGID  480
VEEKSLFLDI WRNWQKDGDM KILQSQIISF YLRLFEVLKD NQAISNNISV IESHLITTFF  540
SNSKAKKDAF MSIAKFEVNN PQVQRQAFNE LIRVVHQLLP ESSLRKRKRS RCGGGGSGGG  600
SGGPGPAGMK GLPGSGGGGS GGGSEVQLVE SGGGLVQPGN SLRLSCAASG FTFSKFGMSW  660
VRQAPGKGLE WVSSISGSGR DTLYAESVKG RFTISRDNAK TTLYLQMNSL RPEDTAVYYC  720
TIGGSLSVSS QGTLVTVSSH HHHHH                                        745

SEQ ID NO: 434         moltype = AA  length = 936
FEATURE                Location/Qualifiers
source                 1..936
                       mol_type = protein
                       organism = synthetic construct
SEQUENCE: 434
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSGGGGS  120
GGGGSGGGGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSAGGGGSG GGGSGGGGSG  660
GGGSGGGGSG GGGSGGGGSG GGGSGGGGSQ SVLTQPPSVS GAPGQRVTIS CSGSRSNIGS  720
NTVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYDG SNKYYADSVK GRFTISRDNS KNTLYLQMNS  900
LRAEDTAVYY CKTHGSHDNW GQGTMVTVSS HHHHHH                             936

SEQ ID NO: 435         moltype = AA  length = 1405
FEATURE                Location/Qualifiers
source                 1..1405
                       mol_type = protein
                       organism = synthetic construct
SEQUENCE: 435
EAHKSEIAHR YNDLGEQHFK GLVLIAFSQY LQKCSYDEHA KLVQEVTDFA KTCVADESAA  60
NCDKSLHTLF GDKLCAIPNL RENYGELADC CTKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQRMKC SSMQKFGERA FKAWAVARLS QTFPNADFAE ITKLATDLTK  240
```

```
VNKECCHGDL LECADDRAEL AKYMCENQAT ISSKLQTCCD KPLLKKAHCL SEVEHDTMPA  300
DLPAIAADFV EDQEVCKNYA EAKDVFLGTF LYEYSRRHPD YSVSLLLRLA KKYEATLEKC  360
CAEANPPACY GTVLAEFQPL VEEPKNLVKT NCDLYEKLGE YGFQNAILVR YTQKAPQVST  420
PTLVEAARNL GRVGTKCCTL PEDQRLPCVE DYLSAILNRV CLLHEKTPVS EHVTKCCSGS  480
LVERRPCFSA LTVDETYVPK EFKAETFTFH SDICTLPEKE KQIKKQTALA ELVKHKPKAT  540
AEQLKTVMDD FAQFLDTCCK AADKDTCFST EGPNLVTRCK DALASGGPGP AGMKGLPGSI  600
WELKKDVYVV ELDWYPDAPG EMVVLTCDTP EEDGITWTLD QSSEVLGSGK TLTIQVKEFG  660
DAGQYTCHKG GEVLSHSLLL LHKKEDGIWS TDILKDQKEP KNKTFLRCEA KNYSGRFTCW  720
WLTTISTDLT FSVKSSRGSS DPQGVTCGAA TLSAERVRGD NKEYEYSVEC QEDSACPAAE  780
ESLPIEVMVD AVHKLKYENY TSSFFIRDII KPDPPKNLQL KPLKNSRQVE VSWEYPDTWS  840
TPHSYFSLTF CVQVQGKSKR EKKDRVFTDK TSATVICRKN ASISVRAQDR YYSSSWSEWA  900
SVPCSGGGGS GGGGSGGGGS RVIPCSGPAR CLSQSRNLLK TTDDMVKTAR EKLKHYSCTA  960
EDIDHEDITR DQTSTLKTCL PLELHKNESC LATRETSSTT RGSCLPPQKT SLMMTLCLGS  1020
IYEDLKMYQT EFQAINAALQ NHNHQQIILD KGMLVAIDEL MQSLNHNGET LRQKPPVGEA  1080
DPYRVKMKLC ILLHAFSTRV VTINRVMGYL SSASGGPGPA GMKGLPGSGG GGSGGGGSGG  1140
GGSGGGGSGG GGSGGGGSQS VLTQPPSVSG APGQRVTISC SGSRSNIGSN TVKWYQQLPG  1200
TAPKLLIYYN DQRPSGVPDR FSGSKSGTSA SLAITGLQAE DEADYYCQSY DRYTHPALLF  1260
GTGTKVTVLG GGGSGGGGSG GGGSQVQLVE SGGGVVQPGR SLRLSCAASG FTFSSYGMHW  1320
VRQAPGKGLE WVAFIRYDGS NKYYADSVKG RFTISRDNSK NTLYLQMNSL RAEDTAVYYC  1380
KTHGSHDNWG QGTMVTVSSH HHHHH                                        1405

SEQ ID NO: 436         moltype = AA  length = 1405
FEATURE                Location/Qualifiers
source                 1..1405
                       mol_type = protein
                       organism = synthetic construct
SEQUENCE: 436
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRVIPVSGPA RCLSQSRNLL KTTDDMVKTA REKLKHYSCT  360
AEDIDHEDIT RDQTSTLKTC LPLELHKNES CLATRETSST TRGSCLPPQK TSLMMTLCLG  420
SIYEDLKMYQ TEFQAINAAL QNHNHQQIIL DKGMLVAIDE LMQSLNHNGE TLRQKPPVGE  480
ADPYRVKMKL CILLHAFSTR VVTINRVMGY LSSASGGPGP AGMKGLPGSG GGGSGGGGSG  540
GGGSGGGGSG GGGSGGGGSQ SVLTQPPSVS GAPGQRVTIS CSGSRSNIGS NTVKWYQQLP  600
GTAPKLLIYY NDQRPSGVPD RFSGSKSGTS ASLAITGLQA EDEADYYCQS YDRYTHPALL  660
FGTGTKVTVL GGGGSGGGGS GGGGSQVQLV ESGGGVVQPG RSLRLSCAAS GFTFSSYGMH  720
WVRQAPGKGL EWVAFIRYDG SNKYYADSVK GRFTISRDNS KNTLYLQMNS LRAEDTAVYY  780
CKTHGSHDNW GQGTMVTVSS SGGPGPAGMK GLPGSEAHKS EIAHRYNDLG EQHFKGLVLI  840
AFSQYLQKCS YDEHAKLVQE VTDFAKTCVA DESAANCDKS LHTLFGDKLC AIPNLRENYG  900
ELADCCTKQE PERNECFLQH KDDNPSLPPF ERPEAEAMCT SFKENPTTFM GHYLHEVARR  960
HPYFYAPELL YYAEQYNEIL TQCCAEADKE SCLTPKLDGV KEKALVSSVR QRMKCSSMQK  1020
FGERAFKAWA VARLSQTFPN ADFAEITKLA TDLTKVNKEC CHGDLLECAD DRAELAKYMC  1080
ENQATISSKL QTCCDKPLLK KAHCLSEVEH DTMPADLPAI AADFVEDQEV CKNYAEAKDV  1140
FLGTFLYEYS RRHPDYSVSL LLRLAKKYEA TLEKCCAEAN PPACYGTVLA EFQPLVEEPK  1200
NLVKTNCDLY EKLGEYGFQN AILVRYTQKA PQVSTPTLVE AARNLGRVGT KCCTLPEDQR  1260
LPCVEDYLSA ILNRVCLLHE KTPVSEHVTK CCSGSLVERR PCFSALTVDE TYVPKEFKAE  1320
TFTFHSDICT LPEKEKQIKK QTALAELVKH KPKATAEQLK TVMDDFAQFL DTCCKAADKD  1380
TCFSTEGPNL VTRCKDALAH HHHHH                                        1405

SEQ ID NO: 437         moltype = AA  length = 1048
FEATURE                Location/Qualifiers
source                 1..1048
                       mol_type = protein
                       organism = synthetic construct
SEQUENCE: 437
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGMKGLP  240
GSIWELKKDV YVVELDWYPD APGEMVVLTC DTPEEDGITW TLDQSSEVLG SGKTLTIQVK  300
EFGDAGQYTC HKGGEVLSHS LLLLHKKEDG IWSTDILKDQ KEPKNKTFLR CEAKNYSGRF  360
TCWWLTTIST DLTFSVKSSR GSSDPQGVTC GAATLSAERV RGDNKEYEYS VECQEDSACP  420
AAEESLPIEV MVDAVHKLKY ENYTSSFFIR DIIKPDPPKN LQLKPLKNSR QVEVSWEYPD  480
TWSTPHSYFS LTFCVQVQGK SKREKKDRVF TDKTSATVIC RKNASISVRA QDRYYSSSWS  540
EWASVPCSGG GGSGGGGSGG GGSRVIPVSG PARCLSQSRN LLKTTDDMVK TAREKLKHYS  600
CTAEDIDHED ITRDQTSTLK TCLPLELHKN ESCLATRETS STTRGSCLPP QKTSLMMTLC  660
LGSIYEDLKM YQTEFQAINA ALQNHNHQQI ILDKGMLVAI DELMQSLNHN GETLRQKPPV  720
GEADPYRVKM KLCILLHAFS TRVVTINRVM GYLSSASGGP GPAGMKGLPG SGGGGSGGGG  780
SGGGGSGGGG SGGGGSGGGG SQSVLTQPPS VSGAPGQRVT ISCSGSRSNI GSNTVKWYQQ  840
LPGTAPKLLI YYNDQRPSGV PDRFSGSKSG TSASLAITGL QAEDEADYYC QSYDRYTHPA  900
LLFGTGTKVT VLGGGGSGGG GSGGGGSQVQ LVESGGGVVQ PGRSLRLSCA ASGFTFSSYG  960
MHWVRQAPGK GLEWVAFIRY DGSNKYYADS VKGRFTISRD NSKNTLYLQM NSLRAEDTAV  1020
YYCKTHGSHD NWGQGTMVTV SSHHHHHH                                     1048

SEQ ID NO: 438         moltype = AA  length = 1048
FEATURE                Location/Qualifiers
```

```
source                  1..1048
                        mol_type = protein
                        organism = synthetic construct
SEQUENCE: 438
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRVIPVSGPA RCLSQSRNLL KTTDDMVKTA REKLKHYSCT  360
AEDIDHEDIT RDQTSTLKTC LPLELHKNES CLATRETSST TRGSCLPPQK TSLMMTLCLG  420
SIYEDLKMYQ TEFQAINAAL QNHNHQQIIL DKGMLVAIDE LMQSLNHNGE TLRQKPPVGE  480
ADPYRVKMKL CILLHAFSTR VVTINRVMGY LSSASGGPGP AGMKGLPGSG GGGSGGGGSG  540
GGGSGGGGSG GGGSGGGGSQ SVLTQPPSVS GAPGQRVTIS CSGSRSNIGS NTVKWYQQLP  600
GTAPKLLIYY NDQRPSGVPD RFSGSKSGTS ASLAITGLQA EDEADYYCQS YDRYTHPALL  660
FGTGTKVTVL GGGGSGGGGS GGGGSQVQLV ESGGGVVQPG RSLRLSCAAS GFTFSSYGMH  720
WVRQAPGKGL EWVAFIRYDG SNKYYADSVK GRFTISRDNS KNTLYLQMNS LRAEDTAVYY  780
CKTHGSHDNW GQGTMVTVSS SGGPGPAGMK GLPGSVPRDC GCKPCICTVP EVSSVFIFPP  840
KPKDVLTITL TPKVTCVVVD ISKDDPEVQF SWFVDDVEVH TAQTQPREEQ FNSTFRSVSE  900
LPIMHQDWLN GKEFKCRVNS AAFPAPIEKT ISKTKGRPKA PQVYTIPPPK EQMAKDKVSL  960
TCMITDFFPE DITVEWQWNG QPAENYKNTQ PIMDTDGSYF VYSKLNVQKS NWEAGNTFTC  1020
SVLHEGLHNH HTEKSLSHSP GKHHHHHH                                   1048

SEQ ID NO: 439          moltype = AA  length = 936
FEATURE                 Location/Qualifiers
source                  1..936
                        mol_type = protein
                        organism = synthetic construct
SEQUENCE: 439
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGMKGLPGSG  660
GGGSGGGGSG GGGSGGGGSG GGGSGGGGSQ SVLTQPPSVS GAPGQRVTIS CSGSRSNIGS  720
NTVKWYQQLP GTAPKLLIYY NDQRPSGVPD RFSGSKSGTS ASLAITGLQA EDEADYYCQS  780
YDRYTHPALL FGTGTKVTVL SGGPGPAGMK GLPGSQVQLV ESGGGVVQPG RSLRLSCAAS  840
GFTFSSYGMH WVRQAPGKGL EWVAFIRYDG SNKYYADSVK GRFTISRDNS KNTLYLQMNS  900
LRAEDTAVYY CKTHGSHDNW GQGTMVTVSS HHHHHH                           936

SEQ ID NO: 440          moltype = AA  length = 817
FEATURE                 Location/Qualifiers
source                  1..817
                        mol_type = protein
                        organism = synthetic construct
SEQUENCE: 440
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGMKGLPGSG  660
GGGSGGGGSG GGGSGGGGSG GGGSGGGGSQ VQLQESGGGL VQAGGSLRLS CAASGRTFSS  720
VYDMGWFRQA PGKDREFVAR ITESARNTRY ADSVRGRFTI SRDNAKNTVY LQMNNLELED  780
AAVYYCAADP QTVVVGTPDY WGQGTQVTVS SHHHHHH                           817

SEQ ID NO: 441          moltype = AA  length = 547
FEATURE                 Location/Qualifiers
source                  1..547
                        mol_type = protein
                        organism = synthetic construct
SEQUENCE: 441
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPALF KSSFPPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPALF  300
KSSFPPGSEV QLVESGGGLV QPGGSLRLSC AASGFTFSSY TLAWVRQAPG KGLEWVAAID  360
```

```
SSSYTYSPDT VRGRFTISRD NAKNSLYLQM NSLRAEDTAV YYCARDSNWD ALDYWGCGTT  420
VTVSSGGGGS GGGGSGGGGS DIQMTQSPSS LSASVGDRVT ITCKVTEKVW GNVAWYQQKP  480
GKCPISLIYS PSLRKSGVPS RFSGSGSGTD FTLTISSLQP EDFATYYCQQ YYTYPYTFGG  540
GTKVEIK                                                            547

SEQ ID NO: 442          moltype = AA  length = 5
FEATURE                 Location/Qualifiers
REGION                  1..5
                        note = Sortase A cleavage site
source                  1..5
                        mol_type = protein
                        organism = unidentified
SEQUENCE: 442
LPXTG                                                              5

SEQ ID NO: 443          moltype = AA  length = 25
FEATURE                 Location/Qualifiers
SITE                    1..25
                        note = This sequence may encompass 1-5 'Gly Gly Gly Gly
                         Ser'repeating units
source                  1..25
                        mol_type = protein
                        organism = synthetic construct
SEQUENCE: 443
GGGGSGGGGS GGGGSGGGGS GGGGS                                        25

SEQ ID NO: 444          moltype = AA  length = 20
FEATURE                 Location/Qualifiers
SITE                    1..20
                        note = This sequence may encompass 1-5 'Gly Gly Gly
                         Ser'repeating units
source                  1..20
                        mol_type = protein
                        organism = synthetic construct
SEQUENCE: 444
GGGSGGGSGG GSGGGSGGGS                                              20

SEQ ID NO: 445          moltype = AA  length = 7
FEATURE                 Location/Qualifiers
REGION                  1..7
                        note = protease-cleavable sequence
source                  1..7
                        mol_type = protein
                        organism = unidentified
SEQUENCE: 445
GPLGVRG                                                            7

SEQ ID NO: 446          moltype = AA  length = 8
FEATURE                 Location/Qualifiers
REGION                  1..8
                        note = protease-cleavable sequence
source                  1..8
                        mol_type = protein
                        organism = unidentified
SEQUENCE: 446
IPVSLRSG                                                           8

SEQ ID NO: 447          moltype = AA  length = 8
FEATURE                 Location/Qualifiers
REGION                  1..8
                        note = protease-cleavable sequence
source                  1..8
                        mol_type = protein
                        organism = unidentified
SEQUENCE: 447
VPLSLYSG                                                           8

SEQ ID NO: 448          moltype = AA  length = 10
FEATURE                 Location/Qualifiers
REGION                  1..10
                        note = protease-cleavable sequence
source                  1..10
                        mol_type = protein
                        organism = unidentified
SEQUENCE: 448
SGESPAYYTA                                                         10

SEQ ID NO: 449          moltype = AA  length = 5
FEATURE                 Location/Qualifiers
```

```
source                  1..5
                        mol_type = protein
                        organism = synthetic construct
SEQUENCE: 449
GGGGS                                                                     5

SEQ ID NO: 450          moltype = AA  length = 6
FEATURE                 Location/Qualifiers
source                  1..6
                        mol_type = protein
                        organism = synthetic construct
SEQUENCE: 450
GSGSGS                                                                    6

SEQ ID NO: 451          moltype = AA  length = 13
FEATURE                 Location/Qualifiers
source                  1..13
                        mol_type = protein
                        organism = synthetic construct
SEQUENCE: 451
GSGGGSGGGS GGT                                                            13

SEQ ID NO: 452          moltype = AA  length = 15
FEATURE                 Location/Qualifiers
source                  1..15
                        mol_type = protein
                        organism = synthetic construct
SEQUENCE: 452
GGGGSGGGGS GGGGS                                                          15

SEQ ID NO: 453          moltype = AA  length = 20
FEATURE                 Location/Qualifiers
source                  1..20
                        mol_type = protein
                        organism = synthetic construct
SEQUENCE: 453
GGGGSGGGGS GGGGSGGGGS                                                     20

SEQ ID NO: 454          moltype = AA  length = 934
FEATURE                 Location/Qualifiers
source                  1..934
                        mol_type = protein
                        organism = synthetic construct
SEQUENCE: 454
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPGPAGLYAQ  660
PGSGGGGSGG GGSGGGGSGG GGSGGGGSGG GGSQSVLTQP PSVSGAPGQR VTISCSGSRS  720
NIGSNTVKWY QQLPGTAPKL LIYYNDQRPS GVPDRFSGSK SGTSASLAIT GLQAEDEADY  780
YCQSYDRYTH PALLFGTGTK VTVLGGGGSG GGGSGGGGSQ VQLVESGGGV VQPGRSLRLS  840
CAASGFTFSS YGMHWVRQAP GKGLEWVAFI RYDGSNKYYA DSVKGRFTIS RDNSKNTLYL  900
QMNSLRAEDT AVYYCKTHGS HDNWGQGTMV TVSS                              934

SEQ ID NO: 455          moltype = AA  length = 930
FEATURE                 Location/Qualifiers
source                  1..930
                        mol_type = protein
                        organism = synthetic construct
SEQUENCE: 455
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPAL FKSSFPPGSG  660
GGGSGGGGSG GGGSGGGGSG GGGSGGGGSQ SVLTQPPSVS GAPGQRVTIS CSGSRSNIGS  720
```

```
NTVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYDG SNKYYADSVK GRFTISRDNS KNTLYLQMNS  900
LRAEDTAVYY CKTHGSHDNW GQGTMVTVSS                                   930

SEQ ID NO: 456         moltype = AA  length = 934
FEATURE                Location/Qualifiers
source                 1..934
                       mol_type = protein
                       organism = synthetic construct
SEQUENCE: 456
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPALFKSSFP  660
PGSGGGGSGG GGSGGGGSGG GGSGGGGSGG GGSQSVLTQP PSVSGAPGQR VTISCSGSRS  720
NIGSNTVKWY QQLPGTAPKL LIYYNDQRPS GVPDRFSGSK SGTSASLAIT GLQAEDEADY  780
YCQSYDRYTH PALLFGTGTK VTVLGGGGSG GGGSGGGGSQ VQLVESGGGV VQPGRSLRLS  840
CAASGFTFSS YGMHWVRQAP GKGLEWVAFI RYDGSNKYYA DSVKGRFTIS RDNSKNTLYL  900
QMNSLRAEDT AVYYCKTHGS HDNWGQGTMV TVSS                              934

SEQ ID NO: 457         moltype = AA  length = 930
FEATURE                Location/Qualifiers
source                 1..930
                       mol_type = protein
                       organism = synthetic construct
SEQUENCE: 457
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGLYAQPGSG  660
GGGSGGGGSG GGGSGGGGSG GGGSGGGGSQ SVLTQPPSVS GAPGQRVTIS CSGSRSNIGS  720
NTVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYEG SNKYYAESVK GRFTISRDNS KNTLYLQMNS  900
LRAEDTAVYY CKTHGSHDNW GQGTMVTVSS                                   930

SEQ ID NO: 458         moltype = AA  length = 934
FEATURE                Location/Qualifiers
source                 1..934
                       mol_type = protein
                       organism = synthetic construct
SEQUENCE: 458
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPGPAGLYAQ  660
PGSGGGGSGG GGSGGGGSGG GGSGGGGSGG GGSQSVLTQP PSVSGAPGQR VTISCSGSRS  720
NIGSNTVKWY QQLPGTAPKL LIYYNDQRPS GVPDRFSGSK SGTSASLAIT GLQAEDEADY  780
YCQSYDRYTH PALLFGTGTK VTVLGGGGSG GGGSGGGGSQ VQLVESGGGV VQPGRSLRLS  840
CAASGFTFSS YGMHWVRQAP GKGLEWVAFI RYEGSNKYYA ESVKGRFTIS RDNSKNTLYL  900
QMNSLRAEDT AVYYCKTHGS HDNWGQGTMV TVSS                              934

SEQ ID NO: 459         moltype = AA  length = 930
FEATURE                Location/Qualifiers
source                 1..930
                       mol_type = protein
                       organism = synthetic construct
```

-continued

```
SEQUENCE: 459
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG 120
PAGLYAQPGS IWELKKDVYV VELDWYPDAP GEMVVLTCDT PEEDGITWTL DQSSEVLGSG 180
KTLTIQVKEF GDAGQYTCHK GGEVLSHSLL LLHKKEDGIW STDILKDQKE PKNKTFLRCE 240
AKNYSGRFTC WWLTTISTDL TFSVKSSRGS SDPQGVTCGA ATLSAERVRG DNKEYEYSVE 300
CQEDSACPAA EESLPIEVMV DAVHKLKYEN YTSSFFIRDI IKPDPPKNLQ LKPLKNSRQV 360
EVSWEYPDTW STPHSYFSLT FCVQVQGKSK REKKDRVFTD KTSATVICRK NASISVRAQD 420
RYYSSSWSEW ASVPCSGGGG SGGGGSGGGG SRVIPVSGPA RCLSQSRNLL KTTDDMVKTA 480
REKLKHYSCT AEDIDHEDIT RDQTSTLKTC LPLELHKNES CLATRETSST TRGSCLPPQK 540
TSLMMTLCLG SIYEDLKMYQ TEFQAINAAL QNHNHQQIIL DKGMLVAIDE LMQSLNHNGE 600
TLRQKPPVGE ADPYRVKMKL CILLHAFSTR VVTINRVMGY LSSASGGPGP AGLYAQPGSG 660
GGGSGGGGSG GGGSGGGGSG GGGSGGGGSQ SVLTQPPSVS GAPGQRVTIS CSGSRSNIGS 720
ETVKWYQQLP GTAPKLLIYY NDQRPSGVPD RFSGSKSGTS ASLAITGLQA EDEADYYCQS 780
YDRYTHPALL FGTGTKVTVL GGGGSGGGGS GGGGSQVQLV ESGGGVVQPG RSLRLSCAAS 840
GFTFSSYGMH WVRQAPGKGL EWVAFIRYEG SNKYYAESVK GRFTISRDNS KNTLYLQMNS 900
LRAEDTAVYY CKTHGSHDNW GQGTMVTVSS                                  930

SEQ ID NO: 460          moltype = AA  length = 934
FEATURE                 Location/Qualifiers
source                  1..934
                        mol_type = protein
                        organism = synthetic construct
SEQUENCE: 460
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG 120
PAGLYAQPGS IWELKKDVYV VELDWYPDAP GEMVVLTCDT PEEDGITWTL DQSSEVLGSG 180
KTLTIQVKEF GDAGQYTCHK GGEVLSHSLL LLHKKEDGIW STDILKDQKE PKNKTFLRCE 240
AKNYSGRFTC WWLTTISTDL TFSVKSSRGS SDPQGVTCGA ATLSAERVRG DNKEYEYSVE 300
CQEDSACPAA EESLPIEVMV DAVHKLKYEN YTSSFFIRDI IKPDPPKNLQ LKPLKNSRQV 360
EVSWEYPDTW STPHSYFSLT FCVQVQGKSK REKKDRVFTD KTSATVICRK NASISVRAQD 420
RYYSSSWSEW ASVPCSGGGG SGGGGSGGGG SRNLPVATPD PGMFPCLHHS QNLLRAVSNM 480
LQKARQTLEF YPCTSEEIDH EDITKDKTST VEACLPLELT KNESCLNSRE TSFITNGSCL 540
ASRKTSFMMA LCLSSIYEDL KMYQVEFKTM NAKLLMDPKR QIFLDQNMLA VIDELMQALN 600
FNSETVPQKS SLEEPDFYKT KIKLCILLHA FRIRAVTIDR VMSYLNASSG GPGPAGLYAQ 660
PGSGGGGSGG GGSGGGGSGG GGSGGGGSGG GGSQSVLTQP PSVSGAPGQR VTISCSGSRS 720
NIGSETVKWY QQLPGTAPKL LIYYNDQRPS GVPDRFSGSK SGTSASLAIT GLQAEDEADY 780
YCQSYDRYTH PALLFGTGTK VTVLGGGGSG GGGSGGGGSQ VQLVESGGGV VQPGRSLRLS 840
CAASGFTFSS YGMHWVRQAP GKGLEWVAFI RYEGSNKYYA ESVKGRFTIS RDNSKNTLYL 900
QMNSLRAEDT AVYYCKTHGS HDNWGQGTMV TVSS                              934

SEQ ID NO: 461          moltype = AA  length = 930
FEATURE                 Location/Qualifiers
source                  1..930
                        mol_type = protein
                        organism = synthetic construct
SEQUENCE: 461
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG 120
PAGLYAQPGS IWELKKDVYV VELDWYPDAP GEMVVLTCDT PEEDGITWTL DQSSEVLGSG 180
KTLTIQVKEF GDAGQYTCHK GGEVLSHSLL LLHKKEDGIW STDILKDQKE PKNKTFLRCE 240
AKNYSGRFTC WWLTTISTDL TFSVKSSRGS SDPQGVTCGA ATLSAERVRG DNKEYEYSVE 300
CQEDSACPAA EESLPIEVMV DAVHKLKYEN YTSSFFIRDI IKPDPPKNLQ LKPLKNSRQV 360
EVSWEYPDTW STPHSYFSLT FCVQVQGKSK REKKDRVFTD KTSATVICRK NASISVRAQD 420
RYYSSSWSEW ASVPCSGGGG SGGGGSGGGG SRVIPVSGPA RCLSQSRNLL KTTDDMVKTA 480
REKLKHYSCT AEDIDHEDIT RDQTSTLKTC LPLELHKNES CLATRETSST TRGSCLPPQK 540
TSLMMTLCLG SIYEDLKMYQ TEFQAINAAL QNHNHQQIIL DKGMLVAIDE LMQSLNHNGE 600
TLRQKPPVGE ADPYRVKMKL CILLHAFSTR VVTINRVMGY LSSASGGPGP AGLYAQPGSG 660
GGGSGGGGSG GGGSGGGGSG GGGSGGGGSQ SVLTQPPSVS GAPGQRVTIS CSGSRSNIGD 720
NTVKWYQQLP GTAPKLLIYY NDQRPSGVPD RFSGSKSGTS ASLAITGLQA EDEADYYCQS 780
YDRYTHPALL FGTGTKVTVL GGGGSGGGGS GGGGSQVQLV ESGGGVVQPG RSLRLSCAAS 840
GFTFSSYGMH WVRQAPGKGL EWVAFIRYEG SNKYYAESVK GRFTISRDNS KNTLYLQMNS 900
LRAEDTAVYY CKTHGSHDNW GQGTMVTVSS                                  930

SEQ ID NO: 462          moltype = AA  length = 934
FEATURE                 Location/Qualifiers
source                  1..934
                        mol_type = protein
                        organism = synthetic construct
SEQUENCE: 462
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG 120
PAGLYAQPGS IWELKKDVYV VELDWYPDAP GEMVVLTCDT PEEDGITWTL DQSSEVLGSG 180
KTLTIQVKEF GDAGQYTCHK GGEVLSHSLL LLHKKEDGIW STDILKDQKE PKNKTFLRCE 240
AKNYSGRFTC WWLTTISTDL TFSVKSSRGS SDPQGVTCGA ATLSAERVRG DNKEYEYSVE 300
CQEDSACPAA EESLPIEVMV DAVHKLKYEN YTSSFFIRDI IKPDPPKNLQ LKPLKNSRQV 360
EVSWEYPDTW STPHSYFSLT FCVQVQGKSK REKKDRVFTD KTSATVICRK NASISVRAQD 420
RYYSSSWSEW ASVPCSGGGG SGGGGSGGGG SRNLPVATPD PGMFPCLHHS QNLLRAVSNM 480
LQKARQTLEF YPCTSEEIDH EDITKDKTST VEACLPLELT KNESCLNSRE TSFITNGSCL 540
```

```
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPGPAGLYAQ  660
PGSGGGGSGG GGSGGGGSGG GGSGGGGSGG GGSQSVLTQP PSVSGAPGQR VTISCSGSRS  720
NIGDNTVKWY QQLPGTAPKL LIYYNDQRPS GVPDRFSGSK SGTSASLAIT GLQAEDEADY  780
YCQSYDRYTH PALLFGTGTK VTVLGGGGSG GGGSGGGGSQ VQLVESGGGV VQPGRSLRLS  840
CAASGFTFSS YGMHWVRQAP GKGLEWVAFI RYEGSNKYYA ESVKGRFTIS RDNSKNTLYL  900
QMNSLRAEDT AVYYCKTHGS HDNWGQGTMV TVSS                             934

SEQ ID NO: 463          moltype = AA  length = 930
FEATURE                 Location/Qualifiers
source                  1..930
                        mol_type = protein
                        organism = synthetic construct
SEQUENCE: 463
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGLYAQPGSG  660
GGGSGGGGSG GGGSGGGGSG GGGSGGGGSQ SVLTQPPSVS GAPGQRVTIS CSGSRSNIGD  720
ETVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYDG SNKYYADSVK GRFTISRDNS KNTLYLQMNS  900
LRAEDTAVYY CKTHGSHDNW GQGTMVTVSS                                  930

SEQ ID NO: 464          moltype = AA  length = 934
FEATURE                 Location/Qualifiers
source                  1..934
                        mol_type = protein
                        organism = synthetic construct
SEQUENCE: 464
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPGPAGLYAQ  660
PGSGGGGSGG GGSGGGGSGG GGSGGGGSGG GGSQSVLTQP PSVSGAPGQR VTISCSGSRS  720
NIGDETVKWY QQLPGTAPKL LIYYNDQRPS GVPDRFSGSK SGTSASLAIT GLQAEDEADY  780
YCQSYDRYTH PALLFGTGTK VTVLGGGGSG GGGSGGGGSQ VQLVESGGGV VQPGRSLRLS  840
CAASGFTFSS YGMHWVRQAP GKGLEWVAFI RYDGSNKYYA DSVKGRFTIS RDNSKNTLYL  900
QMNSLRAEDT AVYYCKTHGS HDNWGQGTMV TVSS                             934

SEQ ID NO: 465          moltype = AA  length = 930
FEATURE                 Location/Qualifiers
source                  1..930
                        mol_type = protein
                        organism = synthetic construct
SEQUENCE: 465
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGLYAQPGSG  660
GGGSGGGGSG GGGSGGGGSG GGGSGGGGSQ SVLTQPPSVS GAPGQRVTIS CSGSRSNIGD  720
ETVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYEG SNKYYAESVK GRFTISRDNS KNTLYLQMNS  900
LRAEDTAVYY CKTHGSHDNW GQGTMVTVSS                                  930

SEQ ID NO: 466          moltype = AA  length = 934
FEATURE                 Location/Qualifiers
```

-continued

```
source                  1..934
                        mol_type = protein
                        organism = synthetic construct
SEQUENCE: 466
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPGPAGLYAQ  660
PGSGGGGSGG GGSGGGGSGG GGSGGGGSGG GGSQSVLTQP PSVSGAPGQR VTISCSGSRS  720
NIGDETVKWY QQLPGTAPKL LIYYNDQRPS GVPDRFSGSK SGTSASLAIT GLQAEDEADY  780
YCQSYDRYTH PALLFGTGTK VTVLGGGGSG GGGSGGGGSQ VQLVESGGGV VQPGRSLRLS  840
CAASGFTFSS YGMHWVRQAP GKGLEWVAFI RYEGSNKYYA ESVKGRFTIS RDNSKNTLYL  900
QMNSLRAEDT AVYYCKTHGS HDNWGQGTMV TVSS                             934

SEQ ID NO: 467          moltype = AA  length = 930
FEATURE                 Location/Qualifiers
source                  1..930
                        mol_type = protein
                        organism = synthetic construct
SEQUENCE: 467
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGLYAQPGSG  660
GGGSGGGGSG GGGSGGGGSG GGGSGGGGSQ SVLTQPPSVS GAPGQRVTIS CSGSESNIGS  720
NDVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYDG SNKYYADSVK GRFTISRDNS KNTLYLQMNS  900
LRAEDTAVYY CKTHGSHDNW GQGTMVTVSS                                  930

SEQ ID NO: 468          moltype = AA  length = 934
FEATURE                 Location/Qualifiers
source                  1..934
                        mol_type = protein
                        organism = synthetic construct
SEQUENCE: 468
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPGPAGLYAQ  660
PGSGGGGSGG GGSGGGGSGG GGSGGGGSGG GGSQSVLTQP PSVSGAPGQR VTISCSGSES  720
NIGSNDVKWY QQLPGTAPKL LIYYNDQRPS GVPDRFSGSK SGTSASLAIT GLQAEDEADY  780
YCQSYDRYTH PALLFGTGTK VTVLGGGGSG GGGSGGGGSQ VQLVESGGGV VQPGRSLRLS  840
CAASGFTFSS YGMHWVRQAP GKGLEWVAFI RYDGSNKYYA DSVKGRFTIS RDNSKNTLYL  900
QMNSLRAEDT AVYYCKTHGS HDNWGQGTMV TVSS                             934

SEQ ID NO: 469          moltype = AA  length = 930
FEATURE                 Location/Qualifiers
source                  1..930
                        mol_type = protein
                        organism = synthetic construct
SEQUENCE: 469
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
```

-continued

```
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGLYAQPGSG  660
GGGSGGGGSG GGGSGGGGSG GGGSGGGGSQ SVLTQPPSVS GAPGQRVTIS CSGSRSNIGE  720
NTVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYEG SNKYYAESVK GRFTISRDNS KNTLYLQMNS  900
LRAEDTAVYY CKTHGSHDNW GQGTMVTVSS                                   930

SEQ ID NO: 470         moltype = AA  length = 934
FEATURE                Location/Qualifiers
source                 1..934
                       mol_type = protein
                       organism = synthetic construct
SEQUENCE: 470
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPGPAGLYAQ  660
PGSGGGGSGG GGSGGGGSGG GGSGGGGSGG GGSQSVLTQP PSVSGAPGQR VTISCSGSRS  720
NIGENTVKWY QQLPGTAPKL LIYYNDQRPS GVPDRFSGSK SGTSASLAIT GLQAEDEADY  780
YCQSYDRYTH PALLFGTGTK VTVLGGGGSG GGGSGGGGSQ VQLVESGGGV VQPGRSLRLS  840
CAASGFTFSS YGMHWVRQAP GKGLEWVAFI RYEGSNKYYA ESVKGRFTIS RDNSKNTLYL  900
QMNSLRAEDT AVYYCKTHGS HDNWGQGTMV TVSS                              934

SEQ ID NO: 471         moltype = AA  length = 930
FEATURE                Location/Qualifiers
source                 1..930
                       mol_type = protein
                       organism = synthetic construct
SEQUENCE: 471
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGLYAQPGSG  660
GGGSGGGGSG GGGSGGGGSG GGGSGGGGSQ SVLTQPPSVS GAPGQRVTIS CSGSRSNIGE  720
ETVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYDG SNKYYADSVK GRFTISRDNS KNTLYLQMNS  900
LRAEDTAVYY CKTHGSHDNW GQGTMVTVSS                                   930

SEQ ID NO: 472         moltype = AA  length = 934
FEATURE                Location/Qualifiers
source                 1..934
                       mol_type = protein
                       organism = synthetic construct
SEQUENCE: 472
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPGPAGLYAQ  660
PGSGGGGSGG GGSGGGGSGG GGSGGGGSGG GGSQSVLTQP PSVSGAPGQR VTISCSGSRS  720
NIGEETVKWY QQLPGTAPKL LIYYNDQRPS GVPDRFSGSK SGTSASLAIT GLQAEDEADY  780
YCQSYDRYTH PALLFGTGTK VTVLGGGGSG GGGSGGGGSQ VQLVESGGGV VQPGRSLRLS  840
CAASGFTFSS YGMHWVRQAP GKGLEWVAFI RYDGSNKYYA DSVKGRFTIS RDNSKNTLYL  900
QMNSLRAEDT AVYYCKTHGS HDNWGQGTMV TVSS                              934
```

```
SEQ ID NO: 473          moltype = AA  length = 930
FEATURE                 Location/Qualifiers
source                  1..930
                        mol_type = protein
                        organism = synthetic construct
SEQUENCE: 473
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGLYAQPGSG  660
GGGSGGGGSG GGGSGGGGSG GGGSGGGGSQ SVLTQPPSVS GAPGQRVTIS CSGSRSNIGS  720
ETVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYEG SNKYYADSVK GRFTISRDNS KNTLYLQMNS  900
LRAEDTAVYY CKTHGSHDNW GQGTMVTVSS                                 930

SEQ ID NO: 474          moltype = AA  length = 934
FEATURE                 Location/Qualifiers
source                  1..934
                        mol_type = protein
                        organism = synthetic construct
SEQUENCE: 474
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPGPAGLYAQ  660
PGSGGGGSGG GGSGGGGSGG GGSGGGGSGG GGSQSVLTQP PSVSGAPGQR VTISCSGSRS  720
NIGSETVKWY QQLPGTAPKL LIYYNDQRPS GVPDRFSGSK SGTSASLAIT GLQAEDEADY  780
YCQSYDRYTH PALLFGTGTK VTVLGGGGSG GGGSGGGGSQ VQLVESGGGV VQPGRSLRLS  840
CAASGFTFSS YGMHWVRQAP GKGLEWVAFI RYEGSNKYYA DSVKGRFTIS RDNSKNTLYL  900
QMNSLRAEDT AVYYCKTHGS HDNWGQGTMV TVSS                            934

SEQ ID NO: 475          moltype = AA  length = 930
FEATURE                 Location/Qualifiers
source                  1..930
                        mol_type = protein
                        organism = synthetic construct
SEQUENCE: 475
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPAL FKSSFPPGSG  660
GGGSGGGGSG GGGSGGGGSG GGGSGGGGSQ SVLTQPPSVS GAPGQRVTIS CSGSRSNIGS  720
NTVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYEG SNKYYAESVK GRFTISRDNS KNTLYLQMNS  900
LRAEDTAVYY CKTHGSHDNW GQGTMVTVSS                                 930

SEQ ID NO: 476          moltype = AA  length = 934
FEATURE                 Location/Qualifiers
source                  1..934
                        mol_type = protein
                        organism = synthetic construct
SEQUENCE: 476
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
```

```
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPALFKSSFP  660
PGSGGGGSGG GGSGGGGSGG GGSGGGGSGG GGSQSVLTQP PSVSGAPGQR VTISCSGSRS  720
NIGSNTVKWY QQLPGTAPKL LIYYNDQRPS GVPDRFSGSK SGTSASLAIT GLQAEDEADY  780
YCQSYDRYTH PALLFGTGTK VTVLGGGGSG GGGSGGGGSQ VQLVESGGGV VQPGRSLRLS  840
CAASGFTFSS YGMHWVRQAP GKGLEWVAFI RYEGSNKYYA ESVKGRFTIS RDNSKNTLYL  900
QMNSLRAEDT AVYYCKTHGS HDNWGQGTMV TVSS                              934

SEQ ID NO: 477         moltype = AA  length = 930
FEATURE                Location/Qualifiers
source                 1..930
                       mol_type = protein
                       organism = synthetic construct
SEQUENCE: 477
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPAL FKSSFPPGSG  660
GGGSGGGGSG GGGSGGGGSG GGGSGGGGSQ SVLTQPPSVS GAPGQRVTIS CSGSRSNIGS  720
ETVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYEG SNKYYAESVK GRFTISRDNS KNTLYLQMNS  900
LRAEDTAVYY CKTHGSHDNW GQGTMVTVSS                                   930

SEQ ID NO: 478         moltype = AA  length = 930
FEATURE                Location/Qualifiers
source                 1..930
                       mol_type = protein
                       organism = synthetic construct
SEQUENCE: 478
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPAL FKSSFPPGSG  660
GGGSGGGGSG GGGSGGGGSG GGGSGGGGSQ SVLTQPPSVS GAPGQRVTIS CSGSRSNIGD  720
NTVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYEG SNKYYAESVK GRFTISRDNS KNTLYLQMNS  900
LRAEDTAVYY CKTHGSHDNW GQGTMVTVSS                                   930

SEQ ID NO: 479         moltype = AA  length = 934
FEATURE                Location/Qualifiers
source                 1..934
                       mol_type = protein
                       organism = synthetic construct
SEQUENCE: 479
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPALFKSSFP  660
PGSGGGGSGG GGSGGGGSGG GGSGGGGSGG GGSQSVLTQP PSVSGAPGQR VTISCSGSRS  720
NIGDNTVKWY QQLPGTAPKL LIYYNDQRPS GVPDRFSGSK SGTSASLAIT GLQAEDEADY  780
```

```
YCQSYDRYTH PALLFGTGTK VTVLGGGGSG GGGSGGGGSQ VQLVESGGGV VQPGRSLRLS  840
CAASGFTFSS YGMHWVRQAP GKGLEWVAFI RYEGSNKYYA ESVKGRFTIS RDNSKNTLYL  900
QMNSLRAEDT AVYYCKTHGS HDNWGQGTMV TVSS                              934

SEQ ID NO: 480         moltype = AA  length = 930
FEATURE                Location/Qualifiers
source                 1..930
                       mol_type = protein
                       organism = synthetic construct
SEQUENCE: 480
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPAL FKSSFPPGSG  660
GGGSGGGGSG GGGSGGGGSG GGGSGGGGSQ SVLTQPPSVS GAPGQRVTIS CSGSRSNIGD  720
ETVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYDG SNKYYADSVK GRFTISRDNS KNTLYLQMNS  900
LRAEDTAVYY CKTHGSHDNW GQGTMVTVSS                                   930

SEQ ID NO: 481         moltype = AA  length = 934
FEATURE                Location/Qualifiers
source                 1..934
                       mol_type = protein
                       organism = synthetic construct
SEQUENCE: 481
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPALFKSSFP  660
PGSGGGGSGG GGSGGGGSGG GGSGGGGSGG GGSQSVLTQP PSVSGAPGQR VTISCSGSRS  720
NIGDETVKWY QQLPGTAPKL LIYYNDQRPS GVPDRFSGSK SGTSASLAIT GLQAEDEADY  780
YCQSYDRYTH PALLFGTGTK VTVLGGGGSG GGGSGGGGSQ VQLVESGGGV VQPGRSLRLS  840
CAASGFTFSS YGMHWVRQAP GKGLEWVAFI RYDGSNKYYA DSVKGRFTIS RDNSKNTLYL  900
QMNSLRAEDT AVYYCKTHGS HDNWGQGTMV TVSS                              934

SEQ ID NO: 482         moltype = AA  length = 930
FEATURE                Location/Qualifiers
source                 1..930
                       mol_type = protein
                       organism = synthetic construct
SEQUENCE: 482
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPAL FKSSFPPGSG  660
GGGSGGGGSG GGGSGGGGSG GGGSGGGGSQ SVLTQPPSVS GAPGQRVTIS CSGSRSNIGD  720
ETVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYEG SNKYYAESVK GRFTISRDNS KNTLYLQMNS  900
LRAEDTAVYY CKTHGSHDNW GQGTMVTVSS                                   930

SEQ ID NO: 483         moltype = AA  length = 934
FEATURE                Location/Qualifiers
source                 1..934
                       mol_type = protein
                       organism = synthetic construct
SEQUENCE: 483
```

```
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPALFKSSFP  660
PGSGGGGSGG GGSGGGGSGG GGSGGGGSGG GGSQSVLTQP PSVSGAPGQR VTISCSGSRS  720
NIGDETVKWY QQLPGTAPKL LIYYNDQRPS GVPDRFSGSK SGTSASLAIT GLQAEDEADY  780
YCQSYDRYTH PALLFGTGTK VTVLGGGGSG GGGSGGGGSQ VQLVESGGGV VQPGRSLRLS  840
CAASGFTFSS YGMHWVRQAP GKGLEWVAFI RYEGSNKYYA ESVKGRFTIS RDNSKNTLYL  900
QMNSLRAEDT AVYYCKTHGS HDNWGQGTMV TVSS                             934

SEQ ID NO: 484         moltype = AA  length = 930
FEATURE                Location/Qualifiers
source                 1..930
                       mol_type = protein
                       organism = synthetic construct
SEQUENCE: 484
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPAL FKSSFPPGSG  660
GGGSGGGGSG GGGSGGGGSG GGGSGGGGSQ SVLTQPPSVS GAPGQRVTIS CSGSESNIGS  720
NDVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYDG SNKYYADSVK GRFTISRDNS KNTLYLQMNS  900
LRAEDTAVYY CKTHGSHDNW GQGTMVTVSS                                  930

SEQ ID NO: 485         moltype = AA  length = 934
FEATURE                Location/Qualifiers
source                 1..934
                       mol_type = protein
                       organism = synthetic construct
SEQUENCE: 485
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPALFKSSFP  660
PGSGGGGSGG GGSGGGGSGG GGSGGGGSGG GGSQSVLTQP PSVSGAPGQR VTISCSGSES  720
NIGSNDVKWY QQLPGTAPKL LIYYNDQRPS GVPDRFSGSK SGTSASLAIT GLQAEDEADY  780
YCQSYDRYTH PALLFGTGTK VTVLGGGGSG GGGSGGGGSQ VQLVESGGGV VQPGRSLRLS  840
CAASGFTFSS YGMHWVRQAP GKGLEWVAFI RYDGSNKYYA DSVKGRFTIS RDNSKNTLYL  900
QMNSLRAEDT AVYYCKTHGS HDNWGQGTMV TVSS                             934

SEQ ID NO: 486         moltype = AA  length = 930
FEATURE                Location/Qualifiers
source                 1..930
                       mol_type = protein
                       organism = synthetic construct
SEQUENCE: 486
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
```

```
TLRQKPPVGE ADPYRVKMKL CILLHAFSTR VVTINRVMGY LSSASGGPAL FKSSFPPGSG  660
GGGSGGGGSG GGGSGGGGSG GGGSGGGGSQ SVLTQPPSVS GAPGQRVTIS CSGSRSNIGE  720
NTVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYEG SNKYYAESVK GRFTISRDNS KNTLYLQMNS  900
LRAEDTAVYY CKTHGSHDNW GQGTMVTVSS                                   930

SEQ ID NO: 487          moltype = AA  length = 934
FEATURE                 Location/Qualifiers
source                  1..934
                        mol_type = protein
                        organism = synthetic construct
SEQUENCE: 487
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPALFKSSFP  660
PGSGGGGSGG GGSGGGGSGG GGSGGGGSGG GGSQSVLTQP PSVSGAPGQR VTISCSGSRS  720
NIGENTVKWY QQLPGTAPKL LIYYNDQRPS GVPDRFSGSK SGTSASLAIT GLQAEDEADY  780
YCQSYDRYTH PALLFGTGTK VTVLGGGGSG GGGSGGGGSQ VQLVESGGGV VQPGRSLRLS  840
CAASGFTFSS YGMHWVRQAP GKGLEWVAFI RYEGSNKYYA ESVKGRFTIS RDNSKNTLYL  900
QMNSLRAEDT AVYYCKTHGS HDNWGQGTMV TVSS                              934

SEQ ID NO: 488          moltype = AA  length = 930
FEATURE                 Location/Qualifiers
source                  1..930
                        mol_type = protein
                        organism = synthetic construct
SEQUENCE: 488
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPAL FKSSFPPGSG  660
GGGSGGGGSG GGGSGGGGSG GGGSGGGGSQ SVLTQPPSVS GAPGQRVTIS CSGSRSNIGE  720
ETVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYDG SNKYYADSVK GRFTISRDNS KNTLYLQMNS  900
LRAEDTAVYY CKTHGSHDNW GQGTMVTVSS                                   930

SEQ ID NO: 489          moltype = AA  length = 934
FEATURE                 Location/Qualifiers
source                  1..934
                        mol_type = protein
                        organism = synthetic construct
SEQUENCE: 489
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPALFKSSFP  660
PGSGGGGSGG GGSGGGGSGG GGSGGGGSGG GGSQSVLTQP PSVSGAPGQR VTISCSGSRS  720
NIGEETVKWY QQLPGTAPKL LIYYNDQRPS GVPDRFSGSK SGTSASLAIT GLQAEDEADY  780
YCQSYDRYTH PALLFGTGTK VTVLGGGGSG GGGSGGGGSQ VQLVESGGGV VQPGRSLRLS  840
CAASGFTFSS YGMHWVRQAP GKGLEWVAFI RYDGSNKYYA DSVKGRFTIS RDNSKNTLYL  900
QMNSLRAEDT AVYYCKTHGS HDNWGQGTMV TVSS                              934

SEQ ID NO: 490          moltype = AA  length = 930
FEATURE                 Location/Qualifiers
source                  1..930
```

```
                         mol_type = protein
                         organism = synthetic construct
SEQUENCE: 490
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPAL FKSSFPPGSG  660
GGGSGGGGSG GGGSGGGGSG GGGSGGGGSQ SVLTQPPSVS GAPGQRVTIS CSGSRSNIGS  720
ETVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYEG SNKYYADSVK GRFTISRDNS KNTLYLQMNS  900
LRAEDTAVYY CKTHGSHDNW GQGTMVTVSS                                  930

SEQ ID NO: 491           moltype = AA  length = 934
FEATURE                  Location/Qualifiers
source                   1..934
                         mol_type = protein
                         organism = synthetic construct
SEQUENCE: 491
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPALFKSSFP  660
PGSGGGGSGG GGSGGGGSGG GGSGGGGSGG GGSQSVLTQP PSVSGAPGQR VTISCSGSRS  720
NIGSETVKWY QQLPGTAPKL LIYYNDQRPS GVPDRFSGSK SGTSASLAIT GLQAEDEADY  780
YCQSYDRYTH PALLFGTGTK VTVLGGGGSG GGGSGGGGSQ VQLVESGGGV VQPGRSLRLS  840
CAASGFTFSS YGMHWVRQAP GKGLEWVAFI RYEGSNKYYA DSVKGRFTIS RDNSKNTLYL  900
QMNSLRAEDT AVYYCKTHGS HDNWGQGTMV TVSS                             934

SEQ ID NO: 492           moltype = AA  length = 906
FEATURE                  Location/Qualifiers
source                   1..906
                         mol_type = protein
                         organism = synthetic construct
SEQUENCE: 492
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGLYAQPGSG  660
GGGSGGGGSG GGGSGGGGSG GGGSGGGGSQ SVLTQPPSVS GAPGQRVTIS CSGSRSNIGS  720
NTVKWYQQLP GTAPKLLIYY NDQRPSGVPD RFSGSKSGTS ASLAITGLQA EDEADYYCQS  780
YDRYTHPALL FGTGTKVTVL GQPKAAPSVT LFPPSSEELQ ANKATLVCLI SDFYPGAVTV  840
AWKADSSPVK AGVETTTPSK QSNNKYAASS YLSLTPEQWK SHRSYSCQVT HEGSTVEKTV  900
APTECS                                                            906

SEQ ID NO: 493           moltype = AA  length = 910
FEATURE                  Location/Qualifiers
source                   1..910
                         mol_type = protein
                         organism = synthetic construct
SEQUENCE: 493
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
```

-continued

```
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPGPAGLYAQ  660
PGSGGGGSGG GGSGGGGSGG GGSGGGGSGG GGSQSVLTQP PSVSGAPGQR VTISCSGSRS  720
NIGSNTVKWY QQLPGTAPKL LIYYNDQRPS GVPDRFSGSK SGTSASLAIT GLQAEDEADY  780
YCQSYDRYTH PALLFGTGTK VTVLGQPKAA PSVTLFPPSS EELQANKATL VCLISDFYPG  840
AVTVAWKADS SPVKAGVETT TPSKQSNNKY AASSYLSLTP EQWKSHRSYS CQVTHEGSTV  900
EKTVAPTECS                                                         910

SEQ ID NO: 494          moltype = AA  length = 906
FEATURE                 Location/Qualifiers
source                  1..906
                        mol_type = protein
                        organism = synthetic construct
SEQUENCE: 494
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGLYAQPGSG  660
GGGSGGGGSG GGGSGGGGSG GGGSGGGGSQ SVLTQPPSVS GAPGQRVTIS CSGSRSNIGS  720
ETVKWYQQLP GTAPKLLIYY NDQRPSGVPD RFSGSKSGTS ASLAITGLQA EDEADYYCQS  780
YDRYTHPALL FGTGTKVTVL GQPKAAPSVT LFPPSSEELQ ANKATLVCLI SDFYPGAVTV  840
AWKADSSPVK AGVETTTPSK QSNNKYAASS YLSLTPEQWK SHRSYSCQVT HEGSTVEKTV  900
APTECS                                                             906

SEQ ID NO: 495          moltype = AA  length = 910
FEATURE                 Location/Qualifiers
source                  1..910
                        mol_type = protein
                        organism = synthetic construct
SEQUENCE: 495
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPGPAGLYAQ  660
PGSGGGGSGG GGSGGGGSGG GGSGGGGSGG GGSQSVLTQP PSVSGAPGQR VTISCSGSRS  720
NIGSETVKWY QQLPGTAPKL LIYYNDQRPS GVPDRFSGSK SGTSASLAIT GLQAEDEADY  780
YCQSYDRYTH PALLFGTGTK VTVLGQPKAA PSVTLFPPSS EELQANKATL VCLISDFYPG  840
AVTVAWKADS SPVKAGVETT TPSKQSNNKY AASSYLSLTP EQWKSHRSYS CQVTHEGSTV  900
EKTVAPTECS                                                         910

SEQ ID NO: 496          moltype = AA  length = 906
FEATURE                 Location/Qualifiers
source                  1..906
                        mol_type = protein
                        organism = synthetic construct
SEQUENCE: 496
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGLYAQPGSG  660
GGGSGGGGSG GGGSGGGGSG GGGSGGGGSQ SVLTQPPSVS GAPGQRVTIS CSGSRSNIGD  720
NTVKWYQQLP GTAPKLLIYY NDQRPSGVPD RFSGSKSGTS ASLAITGLQA EDEADYYCQS  780
YDRYTHPALL FGTGTKVTVL GQPKAAPSVT LFPPSSEELQ ANKATLVCLI SDFYPGAVTV  840
AWKADSSPVK AGVETTTPSK QSNNKYAASS YLSLTPEQWK SHRSYSCQVT HEGSTVEKTV  900
APTECS                                                             906
```

```
SEQ ID NO: 497         moltype = AA  length = 910
FEATURE                Location/Qualifiers
source                 1..910
                       mol_type = protein
                       organism = synthetic construct
SEQUENCE: 497
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPGPAGLYAQ  660
PGSGGGGSGG GGSGGGGSGG GGSGGGGSGG GGSQSVLTQP PSVSGAPGQR VTISCSGSRS  720
NIGDNTVKWY QQLPGTAPKL LIYYNDQRPS GVPDRFSGSK SGTSASLAIT GLQAEDEADY  780
YCQSYDRYTH PALLFGTGTK VTVLGQPKAA PSVTLFPPSS EELQANKATL VCLISDFYPG  840
AVTVAWKADS SPVKAGVETT TPSKQSNNKY AASSYLSLTP EQWKSHRSYS CQVTHEGSTV  900
EKTVAPTECS                                                     910

SEQ ID NO: 498         moltype = AA  length = 906
FEATURE                Location/Qualifiers
source                 1..906
                       mol_type = protein
                       organism = synthetic construct
SEQUENCE: 498
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGLYAQPGSG  660
GGGSGGGGSG GGGSGGGGSG GGGSGGGGSQ SVLTQPPSVS GAPGQRVTIS CSGSRSNIGD  720
ETVKWYQQLP GTAPKLLIYY NDQRPSGVPD RFSGSKSGTS ASLAITGLQA EDEADYYCQS  780
YDRYTHPALL FGTGTKVTVL GQPKAAPSVT LFPPSSEELQ ANKATLVCLI SDFYPGAVTV  840
AWKADSSPVK AGVETTTPSK QSNNKYAASS YLSLTPEQWK SHRSYSCQVT HEGSTVEKTV  900
APTECS                                                         906

SEQ ID NO: 499         moltype = AA  length = 910
FEATURE                Location/Qualifiers
source                 1..910
                       mol_type = protein
                       organism = synthetic construct
SEQUENCE: 499
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPGPAGLYAQ  660
PGSGGGGSGG GGSGGGGSGG GGSGGGGSGG GGSQSVLTQP PSVSGAPGQR VTISCSGSRS  720
NIGDETVKWY QQLPGTAPKL LIYYNDQRPS GVPDRFSGSK SGTSASLAIT GLQAEDEADY  780
YCQSYDRYTH PALLFGTGTK VTVLGQPKAA PSVTLFPPSS EELQANKATL VCLISDFYPG  840
AVTVAWKADS SPVKAGVETT TPSKQSNNKY AASSYLSLTP EQWKSHRSYS CQVTHEGSTV  900
EKTVAPTECS                                                     910

SEQ ID NO: 500         moltype = AA  length = 906
FEATURE                Location/Qualifiers
source                 1..906
                       mol_type = protein
                       organism = synthetic construct
SEQUENCE: 500
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
```

-continued

```
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGLYAQPGSG  660
GGGSGGGGSG GGGSGGGGSG GGGSGGGGSQ SVLTQPPSVS GAPGQRVTIS CSGSESNIGS  720
NDVKWYQQLP GTAPKLLIYY NDQRPSGVPD RFSGSKSGTS ASLAITGLQA EDEADYYCQS  780
YDRYTHPALL FGTGTKVTVL GQPKAAPSVT LFPPSSEELQ ANKATLVCLI SDFYPGAVTV  840
AWKADSSPVK AGVETTTPSK QSNNKYAASS YLSLTPEQWK SHRSYSCQVT HEGSTVEKTV  900
APTECS                                                            906

SEQ ID NO: 501          moltype = AA  length = 910
FEATURE                 Location/Qualifiers
source                  1..910
                        mol_type = protein
                        organism = synthetic construct
SEQUENCE: 501
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPGPAGLYAQ  660
PGSGGGGSGG GGSGGGGSGG GGSGGGGSGG GGSQSVLTQP PSVSGAPGQR VTISCSGSES  720
NIGSNDVKWY QQLPGTAPKL LIYYNDQRPS GVPDRFSGSK SGTSASLAIT GLQAEDEADY  780
YCQSYDRYTH PALLFGTGTK VTVLGQPKAA PSVTLFPPSS EELQANKATL VCLISDFYPG  840
AVTVAWKADS SPVKAGVETT TPSKQSNNKY AASSYLSLTP EQWKSHRSYS CQVTHEGSTV  900
EKTVAPTECS                                                        910

SEQ ID NO: 502          moltype = AA  length = 906
FEATURE                 Location/Qualifiers
source                  1..906
                        mol_type = protein
                        organism = synthetic construct
SEQUENCE: 502
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGLYAQPGSG  660
GGGSGGGGSG GGGSGGGGSG GGGSGGGGSQ SVLTQPPSVS GAPGQRVTIS CSGSRSNIGE  720
NTVKWYQQLP GTAPKLLIYY NDQRPSGVPD RFSGSKSGTS ASLAITGLQA EDEADYYCQS  780
YDRYTHPALL FGTGTKVTVL GQPKAAPSVT LFPPSSEELQ ANKATLVCLI SDFYPGAVTV  840
AWKADSSPVK AGVETTTPSK QSNNKYAASS YLSLTPEQWK SHRSYSCQVT HEGSTVEKTV  900
APTECS                                                            906

SEQ ID NO: 503          moltype = AA  length = 910
FEATURE                 Location/Qualifiers
source                  1..910
                        mol_type = protein
                        organism = synthetic construct
SEQUENCE: 503
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPGPAGLYAQ  660
PGSGGGGSGG GGSGGGGSGG GGSGGGGSGG GGSQSVLTQP PSVSGAPGQR VTISCSGSRS  720
NIGENTVKWY QQLPGTAPKL LIYYNDQRPS GVPDRFSGSK SGTSASLAIT GLQAEDEADY  780
YCQSYDRYTH PALLFGTGTK VTVLGQPKAA PSVTLFPPSS EELQANKATL VCLISDFYPG  840
```

```
AVTVAWKADS SPVKAGVETT TPSKQSNNKY AASSYLSLTP EQWKSHRSYS CQVTHEGSTV  900
EKTVAPTECS                                                         910

SEQ ID NO: 504          moltype = AA  length = 906
FEATURE                 Location/Qualifiers
source                  1..906
                        mol_type = protein
                        organism = synthetic construct
SEQUENCE: 504
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGLYAQPGSG  660
GGGSGGGGSG GGGSGGGGSG GGGSGGGGSQ SVLTQPPSVS GAPGQRVTIS CSGSRSNIGE  720
ETVKWYQQLP GTAPKLLIYY NDQRPSGVPD RFSGSKSGTS ASLAITGLQA EDEADYYCQS  780
YDRYTHPALL FGTGTKVTVL GQPKAAPSVT LFPPSSEELQ ANKATLVCLI SDFYPGAVTV  840
AWKADSSPVK AGVETTTPSK QSNNKYAASS YLSLTPEQWK SHRSYSCQVT HEGSTVEKTV  900
APTECS                                                             906

SEQ ID NO: 505          moltype = AA  length = 910
FEATURE                 Location/Qualifiers
source                  1..910
                        mol_type = protein
                        organism = synthetic construct
SEQUENCE: 505
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPGPAGLYAQ  660
PGSGGGGSGG GGSGGGGSGG GGSGGGGSGG GGSQSVLTQP PSVSGAPGQR VTISCSGSRS  720
NIGEETVKWY QQLPGTAPKL LIYYNDQRPS GVPDRFSGSK SGTSASLAIT GLQAEDEADY  780
YCQSYDRYTH PALLFGTGTK VTVLGQPKAA PSVTLFPPSS EELQANKATL VCLISDFYPG  840
AVTVAWKADS SPVKAGVETT TPSKQSNNKY AASSYLSLTP EQWKSHRSYS CQVTHEGSTV  900
EKTVAPTECS                                                         910

SEQ ID NO: 506          moltype = AA  length = 906
FEATURE                 Location/Qualifiers
source                  1..906
                        mol_type = protein
                        organism = synthetic construct
SEQUENCE: 506
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPAL FKSSFPPGSG  660
GGGSGGGGSG GGGSGGGGSG GGGSGGGGSQ SVLTQPPSVS GAPGQRVTIS CSGSRSNIGS  720
NTVKWYQQLP GTAPKLLIYY NDQRPSGVPD RFSGSKSGTS ASLAITGLQA EDEADYYCQS  780
YDRYTHPALL FGTGTKVTVL GQPKAAPSVT LFPPSSEELQ ANKATLVCLI SDFYPGAVTV  840
AWKADSSPVK AGVETTTPSK QSNNKYAASS YLSLTPEQWK SHRSYSCQVT HEGSTVEKTV  900
APTECS                                                             906

SEQ ID NO: 507          moltype = AA  length = 910
FEATURE                 Location/Qualifiers
source                  1..910
                        mol_type = protein
                        organism = synthetic construct
SEQUENCE: 507
EVQLVESGGG LVQPGNSLRL SCAASGFTFS KFGMSWVRQA PGKGLEWVSS ISGSGRDTLY  60
```

-continued

```
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPALFKSSFP  660
PGSGGGGSGG GGSGGGGSGG GGSGGGGSGG GGSQSVLTQP PSVSGAPGQR VTISCSGSRS  720
NIGSNTVKWY QQLPGTAPKL LIYYNDQRPS GVPDRFSGSK SGTSASLAIT GLQAEDEADY  780
YCQSYDRYTH PALLFGTGTK VTVLGQPKAA PSVTLFPPSS EELQANKATL VCLISDFYPG  840
AVTVAWKADS SPVKAGVETT TPSKQSNNKY AASSYLSLTP EQWKSHRSYS CQVTHEGSTV  900
EKTVAPTECS                                                        910

SEQ ID NO: 508          moltype = AA  length = 906
FEATURE                 Location/Qualifiers
source                  1..906
                        mol_type = protein
                        organism = synthetic construct
SEQUENCE: 508
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPAL FKSSFPPGSG  660
GGGSGGGGSG GGGSGGGGSG GGGSGGGGSQ SVLTQPPSVS GAPGQRVTIS CSGSRSNIGS  720
ETVKWYQQLP GTAPKLLIYY NDQRPSGVPD RFSGSKSGTS ASLAITGLQA EDEADYYCQS  780
YDRYTHPALL FGTGTKVTVL GQPKAAPSVT LFPPSSEELQ ANKATLVCLI SDFYPGAVTV  840
AWKADSSPVK AGVETTTPSK QSNNKYAASS YLSLTPEQWK SHRSYSCQVT HEGSTVEKTV  900
APTECS                                                            906

SEQ ID NO: 509          moltype = AA  length = 910
FEATURE                 Location/Qualifiers
source                  1..910
                        mol_type = protein
                        organism = synthetic construct
SEQUENCE: 509
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPALFKSSFP  660
PGSGGGGSGG GGSGGGGSGG GGSGGGGSGG GGSQSVLTQP PSVSGAPGQR VTISCSGSRS  720
NIGSETVKWY QQLPGTAPKL LIYYNDQRPS GVPDRFSGSK SGTSASLAIT GLQAEDEADY  780
YCQSYDRYTH PALLFGTGTK VTVLGQPKAA PSVTLFPPSS EELQANKATL VCLISDFYPG  840
AVTVAWKADS SPVKAGVETT TPSKQSNNKY AASSYLSLTP EQWKSHRSYS CQVTHEGSTV  900
EKTVAPTECS                                                        910

SEQ ID NO: 510          moltype = AA  length = 906
FEATURE                 Location/Qualifiers
source                  1..906
                        mol_type = protein
                        organism = synthetic construct
SEQUENCE: 510
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPAL FKSSFPPGSG  660
```

-continued

```
GGGSGGGGSG GGGSGGGGSG GGGSGGGGSQ SVLTQPPSVS GAPGQRVTIS CSGSRSNIGD  720
NTVKWYQQLP GTAPKLLIYY NDQRPSGVPD RFSGSKSGTS ASLAITGLQA EDEADYYCQS  780
YDRYTHPALL FGTGTKVTVL GQPKAAPSVT LFPPSSEELQ ANKATLVCLI SDFYPGAVTV  840
AWKADSSPVK AGVETTTPSK QSNNKYAASS YLSLTPEQWK SHRSYSCQVT HEGSTVEKTV  900
APTECS                                                             906

SEQ ID NO: 511         moltype = AA  length = 910
FEATURE                Location/Qualifiers
source                 1..910
                       mol_type = protein
                       organism = synthetic construct
SEQUENCE: 511
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPALFKSSFP  660
PGSGGGGSGG GGSGGGGSGG GGSGGGGSGG GGSQSVLTQP PSVSGAPGQR VTISCSGSRS  720
NIGDNTVKWY QQLPGTAPKL LIYYNDQRPS GVPDRFSGSK SGTSASLAIT GLQAEDEADY  780
YCQSYDRYTH PALLFGTGTK VTVLGQPKAA PSVTLFPPSS EELQANKATL VCLISDFYPG  840
AVTVAWKADS SPVKAGVETT TPSKQSNNKY AASSYLSLTP EQWKSHRSYS CQVTHEGSTV  900
EKTVAPTECS                                                         910

SEQ ID NO: 512         moltype = AA  length = 906
FEATURE                Location/Qualifiers
source                 1..906
                       mol_type = protein
                       organism = synthetic construct
SEQUENCE: 512
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPAL FKSSFPPGSG  660
GGGSGGGGSG GGGSGGGGSG GGGSGGGGSQ SVLTQPPSVS GAPGQRVTIS CSGSRSNIGD  720
ETVKWYQQLP GTAPKLLIYY NDQRPSGVPD RFSGSKSGTS ASLAITGLQA EDEADYYCQS  780
YDRYTHPALL FGTGTKVTVL GQPKAAPSVT LFPPSSEELQ ANKATLVCLI SDFYPGAVTV  840
AWKADSSPVK AGVETTTPSK QSNNKYAASS YLSLTPEQWK SHRSYSCQVT HEGSTVEKTV  900
APTECS                                                             906

SEQ ID NO: 513         moltype = AA  length = 910
FEATURE                Location/Qualifiers
source                 1..910
                       mol_type = protein
                       organism = synthetic construct
SEQUENCE: 513
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPALFKSSFP  660
PGSGGGGSGG GGSGGGGSGG GGSGGGGSGG GGSQSVLTQP PSVSGAPGQR VTISCSGSRS  720
NIGDETVKWY QQLPGTAPKL LIYYNDQRPS GVPDRFSGSK SGTSASLAIT GLQAEDEADY  780
YCQSYDRYTH PALLFGTGTK VTVLGQPKAA PSVTLFPPSS EELQANKATL VCLISDFYPG  840
AVTVAWKADS SPVKAGVETT TPSKQSNNKY AASSYLSLTP EQWKSHRSYS CQVTHEGSTV  900
EKTVAPTECS                                                         910

SEQ ID NO: 514         moltype = AA  length = 906
FEATURE                Location/Qualifiers
source                 1..906
                       mol_type = protein
```

```
                         organism = synthetic construct
SEQUENCE: 514
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPAL FKSSFPPGSG  660
GGGSGGGGSG GGGSGGGGSG GGGSGGGGSQ SVLTQPPSVS GAPGQRVTIS CSGSESNIGS  720
NDVKWYQQLP GTAPKLLIYY NDQRPSGVPD RFSGSKSGTS ASLAITGLQA EDEADYYCQS  780
YDRYTHPALL FGTGTKVTVL GQPKAAPSVT LFPPSSEELQ ANKATLVCLI SDFYPGAVTV  840
AWKADSSPVK AGVETTTPSK QSNNKYAASS YLSLTPEQWK SHRSYSCQVT HEGSTVEKTV  900
APTECS                                                             906

SEQ ID NO: 515           moltype = AA  length = 910
FEATURE                  Location/Qualifiers
source                   1..910
                         mol_type = protein
                         organism = synthetic construct
SEQUENCE: 515
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPALFKSSFP  660
PGSGGGGSGG GGSGGGGSGG GGSGGGGSGG GGSQSVLTQP PSVSGAPGQR VTISCSGSES  720
NIGSNDVKWY QQLPGTAPKL LIYYNDQRPS GVPDRFSGSK SGTSASLAIT GLQAEDEADY  780
YCQSYDRYTH PALLFGTGTK VTVLGQPKAA PSVTLFPPSS EELQANKATL VCLISDFYPG  840
AVTVAWKADS SPVKAGVETT TPSKQSNNKY AASSYLSLTP EQWKSHRSYS CQVTHEGSTV  900
EKTVAPTECS                                                         910

SEQ ID NO: 516           moltype = AA  length = 906
FEATURE                  Location/Qualifiers
source                   1..906
                         mol_type = protein
                         organism = synthetic construct
SEQUENCE: 516
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPAL FKSSFPPGSG  660
GGGSGGGGSG GGGSGGGGSG GGGSGGGGSQ SVLTQPPSVS GAPGQRVTIS CSGSRSNIGE  720
NTVKWYQQLP GTAPKLLIYY NDQRPSGVPD RFSGSKSGTS ASLAITGLQA EDEADYYCQS  780
YDRYTHPALL FGTGTKVTVL GQPKAAPSVT LFPPSSEELQ ANKATLVCLI SDFYPGAVTV  840
AWKADSSPVK AGVETTTPSK QSNNKYAASS YLSLTPEQWK SHRSYSCQVT HEGSTVEKTV  900
APTECS                                                             906

SEQ ID NO: 517           moltype = AA  length = 910
FEATURE                  Location/Qualifiers
source                   1..910
                         mol_type = protein
                         organism = synthetic construct
SEQUENCE: 517
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
```

-continued

```
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPALFKSSFP  660
PGSGGGGSGG GGSGGGGSGG GGSGGGGSGG GGSQSVLTQP PSVSGAPGQR VTISCSGSRS  720
NIGENTVKWY QQLPGTAPKL LIYYNDQRPS GVPDRFSGSK SGTSASLAIT GLQAEDEADY  780
YCQSYDRYTH PALLFGTGTK VTVLGQPKAA PSVTLFPPSS EELQANKATL VCLISDFYPG  840
AVTVAWKADS SPVKAGVETT TPSKQSNNKY AASSYLSLTP EQWKSHRSYS CQVTHEGSTV  900
EKTVAPTECS                                                         910

SEQ ID NO: 518         moltype = AA  length = 906
FEATURE                Location/Qualifiers
source                 1..906
                       mol_type = protein
                       organism = synthetic construct
SEQUENCE: 518
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPAL FKSSFPPGSG  660
GGGSGGGGSG GGGSGGGGSG GGGSGGGGSQ SVLTQPPSVS GAPGQRVTIS CSGSRSNIGE  720
ETVKWYQQLP GTAPKLLIYY NDQRPSGVPD RFSGSKSGTS ASLAITGLQA EDEADYYCQS  780
YDRYTHPALL FGTGTKVTVL GQPKAAPSVT LFPPSSEELQ ANKATLVCLI SDFYPGAVTV  840
AWKADSSPVK AGVETTTPSK QSNNKYAASS YLSLTPEQWK SHRSYSCQVT HEGSTVEKTV  900
APTECS                                                             906

SEQ ID NO: 519         moltype = AA  length = 910
FEATURE                Location/Qualifiers
source                 1..910
                       mol_type = protein
                       organism = synthetic construct
SEQUENCE: 519
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPALFKSSFP  660
PGSGGGGSGG GGSGGGGSGG GGSGGGGSGG GGSQSVLTQP PSVSGAPGQR VTISCSGSRS  720
NIGEETVKWY QQLPGTAPKL LIYYNDQRPS GVPDRFSGSK SGTSASLAIT GLQAEDEADY  780
YCQSYDRYTH PALLFGTGTK VTVLGQPKAA PSVTLFPPSS EELQANKATL VCLISDFYPG  840
AVTVAWKADS SPVKAGVETT TPSKQSNNKY AASSYLSLTP EQWKSHRSYS CQVTHEGSTV  900
EKTVAPTECS                                                         910

SEQ ID NO: 520         moltype = AA  length = 218
FEATURE                Location/Qualifiers
source                 1..218
                       mol_type = protein
                       organism = synthetic construct
SEQUENCE: 520
QVQLVESGGG VVQPGRSLRL SCAASGFTFS SYGMHWVRQA PGKGLEWVAF IRYDGSNKYY  60
ADSVKGRFTI SRDNSKNTLY LQMNSLRAED TAVYYCKTHG SHDNWGQGTM VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSC                          218

SEQ ID NO: 521         moltype = AA  length = 218
FEATURE                Location/Qualifiers
source                 1..218
                       mol_type = protein
                       organism = synthetic construct
SEQUENCE: 521
QVQLVESGGG VVQPGRSLRL SCAASGFTFS SYGMHWVRQA PGKGLEWVAF IRYEGSNKYY  60
AESVKGRFTI SRDNSKNTLY LQMNSLRAED TAVYYCKTHG SHDNWGQGTM VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSC                          218

SEQ ID NO: 522         moltype = AA  length = 218
FEATURE                Location/Qualifiers
```

-continued

```
source                  1..218
                        mol_type = protein
                        organism = synthetic construct
SEQUENCE: 522
QVQLVESGGG VVQPGRSLRL SCAASGFTFS SYGMHWVRQA PGKGLEWVAF IRYEGSNKYY  60
ADSVKGRFTI SRDNSKNTLY LQMNSLRAED TAVYYCKTHG SHDNWGQGTM VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSC                         218

SEQ ID NO: 523          moltype = AA  length = 915
FEATURE                 Location/Qualifiers
source                  1..915
                        mol_type = protein
                        organism = synthetic construct
SEQUENCE: 523
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRVIPVSGPA RCLSQSRNLL KTTDDMVKTA REKLKHYSCT  360
AEDIDHEDIT RDQTSTLKTC LPLELHKNES CLATRETSST TRGSCLPPQK TSLMMTLCLG  420
SIYEDLKMYQ TEFQAINAAL QNHNHQQIIL DKGMLVAIDE LMQSLNHNGE TLRQKPPVGE  480
ADPYRVKMKL CILLHAFSTR VVTINRVMGY LSSASGGPGP AGLYAQPGSE VQLVESGGGL  540
VQPGNSLRLS CAASGFTFSK FGMSWVRQAP GKGLEWVSSI SGSGRDTLYA ESVKGRFTIS  600
RDNAKTTLYL QMNSLRPEDT AVYYCTIGGS LSVSSQGTLV TVSSGGGGSG GGGSGGGGSG  660
GGGSGGGGSG GGGSQSVLTQ PPSVSGAPGQ RVTISCSGSR SNIGSNTVKW YQQLPGTAPK  720
LLIYYNDQRP SGVPDRFSGS KSGTSASLAI TGLQAEDEAD YYCQSYDRYT HPALLFGTGT  780
KVTVLGGGGS GGGGSGGGGS QVQLVESGGG VVQPGRSLRL SCAASGFTFS SYGMHWVRQA  840
PGKGLEWVAF IRYEGSNKYY AESVKGRFTI SRDNSKNTLY LQMNSLRAED TAVYYCKTHG  900
SHDNWGQGTM VTVSS                                                  915

SEQ ID NO: 524          moltype = AA  length = 919
FEATURE                 Location/Qualifiers
source                  1..919
                        mol_type = protein
                        organism = synthetic construct
SEQUENCE: 524
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRNLPVATPD PGMFPCLHHS QNLLRAVSNM LQKARQTLEF  360
YPCTSEEIDH EDITKDKTST VEACLPLELT KNESCLNSRE TSFITNGSCL ASRKTSFMMA  420
LCLSSIYEDL KMYQVEFKTM NAKLLMDPKR QIFLDQNMLA VIDELMQALN FNSETVPQKS  480
SLEEPDFYKT KIKLCILLHA FRIRAVTIDR VMSYLNASSG GPGPAGLYAQ PGSEVQLVES  540
GGGLVQPGNS LRLSCAASGF TFSKFGMSWV RQAPGKGLEW VSSISGSGRD TLYAESVKGR  600
FTISRDNAKT TLYLQMNSLR PEDTAVYYCT IGGSLSVSSQ GTLVTVSSGG GGSGGGGSGG  660
GGSGGGGSGG GGSGGGGSQS VLTQPPSVSG APGQRVTISC SGSRSNIGSN TVKWYQQLPG  720
TAPKLLIYYN DQRPSGVPDR FSGSKSGTSA SLAITGLQAE DEADYYCQSY DRYTHPALLF  780
GTGTKVTVLG GGGSGGGGSG GGGSQVQLVE SGGGVVQPGR SLRLSCAASG FTFSSYGMHW  840
VRQAPGKGLE WVAFIRYEGS NKYYAESVKG RFTISRDNSK NTLYLQMNSL RAEDTAVYYC  900
KTHGSHDNWG QGTMVTVSS                                              919

SEQ ID NO: 525          moltype = AA  length = 915
FEATURE                 Location/Qualifiers
source                  1..915
                        mol_type = protein
                        organism = synthetic construct
SEQUENCE: 525
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRVIPVSGPA RCLSQSRNLL KTTDDMVKTA REKLKHYSCT  360
AEDIDHEDIT RDQTSTLKTC LPLELHKNES CLATRETSST TRGSCLPPQK TSLMMTLCLG  420
SIYEDLKMYQ TEFQAINAAL QNHNHQQIIL DKGMLVAIDE LMQSLNHNGE TLRQKPPVGE  480
ADPYRVKMKL CILLHAFSTR VVTINRVMGY LSSASGGPGP AGLYAQPGSE VQLVESGGGL  540
VQPGNSLRLS CAASGFTFSK FGMSWVRQAP GKGLEWVSSI SGSGRDTLYA ESVKGRFTIS  600
RDNAKTTLYL QMNSLRPEDT AVYYCTIGGS LSVSSQGTLV TVSSGGGGSG GGGSGGGGSG  660
GGGSGGGGSG GGGSQSVLTQ PPSVSGAPGQ RVTISCSGSR SNIGDETVKW YQQLPGTAPK  720
LLIYYNDQRP SGVPDRFSGS KSGTSASLAI TGLQAEDEAD YYCQSYDRYT HPALLFGTGT  780
KVTVLGGGGS GGGGSGGGGS QVQLVESGGG VVQPGRSLRL SCAASGFTFS SYGMHWVRQA  840
PGKGLEWVAF IRYEGSNKYY AESVKGRFTI SRDNSKNTLY LQMNSLRAED TAVYYCKTHG  900
SHDNWGQGTM VTVSS                                                  915

SEQ ID NO: 526          moltype = AA  length = 919
```

-continued

```
FEATURE                Location/Qualifiers
source                 1..919
                       mol_type = protein
                       organism = synthetic construct
SEQUENCE: 526
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRNLPVATPD PGMFPCLHHS QNLLRAVSNM LQKARQTLEF  360
YPCTSEEIDH EDITKDKTST VEACLPLELT KNESCLNSRE TSFITNGSCL ASRKTSFMMA  420
LCLSSIYEDL KMYQVEFKTM NAKLLMDPKR QIFLDQNMLA VIDELMQALN FNSETVPQKS  480
SLEEPDFYKT KIKLCILLHA FRIRAVTIDR VMSYLNASSG GPGPAGLYAQ PGSEVQLVES  540
GGGLVQPGNS LRLSCAASGF TFSKFGMSWV RQAPGKGLEW VSSISGSGRD TLYAESVKGR  600
FTISRDNAKT TLYLQMNSLR PEDTAVYYCT IGGSLSVSSQ GTLVTVSSGG GGSGGGGSGG  660
GGSGGGGSGG GGSGGGGSQS VLTQPPSVSG APGQRVTISC SGSRSNIGDE TVKWYQQLPG  720
TAPKLLIYYN DQRPSGVPDR FSGSKSGTSA SLAITGLQAE DEADYYCQSY DRYTHPALLF  780
GTGTKVTVLG GGGSGGGGSG GGGSQVQLVE SGGGVVQPGR SLRLSCAASG FTFSSYGMHW  840
VRQAPGKGLE WVAFIRYEGS NKYYAESVKG RFTISRDNSK NTLYLQMNSL RAEDTAVYYC  900
KTHGSHDNWG QGTMVTVSS                                               919

SEQ ID NO: 527         moltype = AA  length = 891
FEATURE                Location/Qualifiers
source                 1..891
                       mol_type = protein
                       organism = synthetic construct
SEQUENCE: 527
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRVIPVSGPA RCLSQSRNLL KTTDDMVKTA REKLKHYSCT  360
AEDIDHEDIT RDQTSTLKTC LPLELHKNES CLATRETSST TRGSCLPPQK TSLMMTLCLG  420
SIYEDLKMYQ TEFQAINAAL QNHNHQQIIL DKGMLVAIDE LMQSLNHNGE TLRQKPPVGE  480
ADPYRVKMKL CILLHAFSTR VVTINRVMGY LSSASGGPGP AGLYAQPGSE VQLVESGGGL  540
VQPGNSLRLS CAASGFTFSK FGMSWVRQAP GKGLEWVSSI SGSGRDTLYA ESVKGRFTIS  600
RDNAKTTLYL QMNSLRPEDT AVYYCTIGGS LSVSSQGTLV TVSSGGGGSG GGGSGGGGSG  660
GGGSGGGGSG GGGSQSVLTQ PPSVSGAPGQ RVTISCSGSR SNIGSNTVKW YQQLPGTAPK  720
LLIYYNDQRP SGVPDRFSGS KSGTSASLAI TGLQAEDEAD YYCQSYDRYT HPALLFGTGT  780
KVTVLGQPKA APSVTLFPPS SEELQANKAT LVCLISDFYP GAVTVAWKAD SSPVKAGVET  840
TTPSKQSNNK YAASSYLSLT PEQWKSHRSY SCQVTHEGST VEKTVAPTEC S           891

SEQ ID NO: 528         moltype = AA  length = 895
FEATURE                Location/Qualifiers
source                 1..895
                       mol_type = protein
                       organism = synthetic construct
SEQUENCE: 528
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRNLPVATPD PGMFPCLHHS QNLLRAVSNM LQKARQTLEF  360
YPCTSEEIDH EDITKDKTST VEACLPLELT KNESCLNSRE TSFITNGSCL ASRKTSFMMA  420
LCLSSIYEDL KMYQVEFKTM NAKLLMDPKR QIFLDQNMLA VIDELMQALN FNSETVPQKS  480
SLEEPDFYKT KIKLCILLHA FRIRAVTIDR VMSYLNASSG GPGPAGLYAQ PGSEVQLVES  540
GGGLVQPGNS LRLSCAASGF TFSKFGMSWV RQAPGKGLEW VSSISGSGRD TLYAESVKGR  600
FTISRDNAKT TLYLQMNSLR PEDTAVYYCT IGGSLSVSSQ GTLVTVSSGG GGSGGGGSGG  660
GGSGGGGSGG GGSGGGGSQS VLTQPPSVSG APGQRVTISC SGSRSNIGSN TVKWYQQLPG  720
TAPKLLIYYN DQRPSGVPDR FSGSKSGTSA SLAITGLQAE DEADYYCQSY DRYTHPALLF  780
GTGTKVTVLG QPKAAPSVTL FPPSSEELQA NKATLVCLIS DFYPGAVTVA WKADSSPVKA  840
GVETTTPSKQ SNNKYAASSY LSLTPEQWKS HRSYSCQVTH EGSTVEKTVA PTECS       895

SEQ ID NO: 529         moltype = AA  length = 891
FEATURE                Location/Qualifiers
source                 1..891
                       mol_type = protein
                       organism = synthetic construct
SEQUENCE: 529
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRVIPVSGPA RCLSQSRNLL KTTDDMVKTA REKLKHYSCT  360
AEDIDHEDIT RDQTSTLKTC LPLELHKNES CLATRETSST TRGSCLPPQK TSLMMTLCLG  420
```

-continued

```
SIYEDLKMYQ TEFQAINAAL QNHNHQQIIL DKGMLVAIDE LMQSLNHNGE TLRQKPPVGE  480
ADPYRVKMKL CILLHAFSTR VVTINRVMGY LSSASGGPGP AGLYAQPGSE VQLVESGGGL  540
VQPGNSLRLS CAASGFTFSK FGMSWVRQAP GKGLEWVSSI SGSGRDTLYA ESVKGRFTIS  600
RDNAKTTLYL QMNSLRPEDT AVYYCTIGGS LSVSSQGTLV TVSSGGGGSG GGGSGGGGSG  660
GGGSGGGGSG GGGSQSVLTQ PPSVSGAPGQ RVTISCSGSR SNIGDETVKW YQQLPGTAPK  720
LLIYYNDQRP SGVPDRFSGS KSGTSASLAI TGLQAEDEAD YYCQSYDRYT HPALLFGTGT  780
KVTVLGQPKA APSVTLFPPS SEELQANKAT LVCLISDFYP GAVTVAWKAD SSPVKAGVET  840
TTPSKQSNNK YAASSYLSLT PEQWKSHRSY SCQVTHEGST VEKTVAPTEC S          891

SEQ ID NO: 530         moltype = AA  length = 895
FEATURE                Location/Qualifiers
source                 1..895
                       mol_type = protein
                       organism = synthetic construct
SEQUENCE: 530
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRNLPVATPD PGMFPCLHHS QNLLRAVSNM LQKARQTLEF  360
YPCTSEEIDH EDITKDKTST VEACLPLELT KNESCLNSRE TSFITNGSCL ASRKTSFMMA  420
LCLSSIYEDL KMYQVEFKTM NAKLLMDPKR QIFLDQNMLA VIDELMQALN FNSETVPQKS  480
SLEEPDFYKT KIKLCILLHA FRIRAVTIDR VMSYLNASSG GPGPAGLYAQ PGSEVQLVES  540
GGGLVQPGNS LRLSCAASGF TFSKFGMSWV RQAPGKGLEW VSSISGSGRD TLYAESVKGR  600
FTISRDNAKT TLYLQMNSLR PEDTAVYYCT IGGSLSVSSQ GTLVTVSSGG GGSGGGGSGG  660
GGSGGGGSGG GGSGGGGSQS VLTQPPSVSG APGQRVTISC SGSRSNIGDE TVKWYQQLPG  720
TAPKLLIYYN DQRPSGVPDR FSGSKSGTSA SLAITGLQAE DEADYYCQSY DRYTHPALLF  780
GTGTKVTVLG QPKAAPSVTL FPPSSEELQA NKATLVCLIS DFYPGAVTVA WKADSSPVKA  840
GVETTTPSKQ SNNKYAASSY LSLTPEQWKS HRSYSCQVTH EGSTVEKTVA PTECS       895

SEQ ID NO: 531         moltype = AA  length = 915
FEATURE                Location/Qualifiers
source                 1..915
                       mol_type = protein
                       organism = synthetic construct
SEQUENCE: 531
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRVIPVSGPA RCLSQSRNLL KTTDDMVKTA REKLKHYSCT  360
AEDIDHEDIT RDQTSTLKTC LPLELHKNES CLATRETSST TRGSCLPPQK TSLMMTLCLG  420
SIYEDLKMYQ TEFQAINAAL QNHNHQQIIL DKGMLVAIDE LMQSLNHNGE TLRQKPPVGE  480
ADPYRVKMKL CILLHAFSTR VVTINRVMGY LSSASGGPAL FKSSFPPGSE VQLVESGGGL  540
VQPGNSLRLS CAASGFTFSK FGMSWVRQAP GKGLEWVSSI SGSGRDTLYA ESVKGRFTIS  600
RDNAKTTLYL QMNSLRPEDT AVYYCTIGGS LSVSSQGTLV TVSSGGGGSG GGGSGGGGSG  660
GGGSGGGGSG GGGSQSVLTQ PPSVSGAPGQ RVTISCSGSR SNIGSNTVKW YQQLPGTAPK  720
LLIYYNDQRP SGVPDRFSGS KSGTSASLAI TGLQAEDEAD YYCQSYDRYT HPALLFGTGT  780
KVTVLGGGGS GGGGSGGGGS QVQLVESGGG VVQPGRSLRL SCAASGFTFS SYGMHWVRQA  840
PGKGLEWVAF IRYEGSNKYY AESVKGRFTI SRDNSKNTLY LQMNSLRAED TAVYYCKTHG  900
SHDNWGQGTM VTVSS                                                   915

SEQ ID NO: 532         moltype = AA  length = 919
FEATURE                Location/Qualifiers
source                 1..919
                       mol_type = protein
                       organism = synthetic construct
SEQUENCE: 532
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRNLPVATPD PGMFPCLHHS QNLLRAVSNM LQKARQTLEF  360
YPCTSEEIDH EDITKDKTST VEACLPLELT KNESCLNSRE TSFITNGSCL ASRKTSFMMA  420
LCLSSIYEDL KMYQVEFKTM NAKLLMDPKR QIFLDQNMLA VIDELMQALN FNSETVPQKS  480
SLEEPDFYKT KIKLCILLHA FRIRAVTIDR VMSYLNASSG GPALFKSSFP PGSEVQLVES  540
GGGLVQPGNS LRLSCAASGF TFSKFGMSWV RQAPGKGLEW VSSISGSGRD TLYAESVKGR  600
FTISRDNAKT TLYLQMNSLR PEDTAVYYCT IGGSLSVSSQ GTLVTVSSGG GGSGGGGSGG  660
GGSGGGGSGG GGSGGGGSQS VLTQPPSVSG APGQRVTISC SGSRSNIGSN TVKWYQQLPG  720
TAPKLLIYYN DQRPSGVPDR FSGSKSGTSA SLAITGLQAE DEADYYCQSY DRYTHPALLF  780
GTGTKVTVLG GGGSGGGGSG GGGSQVQLVE SGGGVVQPGR SLRLSCAASG FTFSSYGMHW  840
VRQAPGKGLE WVAFIRYEGS NKYYAESVKG RFTISRDNSK NTLYLQMNSL RAEDTAVYYC  900
KTHGSHDNWG QGTMVTVSS                                               919

SEQ ID NO: 533         moltype = AA  length = 915
FEATURE                Location/Qualifiers
```

```
source                1..915
                      mol_type = protein
                      organism = synthetic construct
SEQUENCE: 533
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRVIPVSGPA RCLSQSRNLL KTTDDMVKTA REKLKHYSCT  360
AEDIDHEDIT RDQTSTLKTC LPLELHKNES CLATRETSST TRGSCLPPQK TSLMMTLCLG  420
SIYEDLKMYQ TEFQAINAAL QNHNHQQIIL DKGMLVAIDE LMQSLNHNGE TLRQKPPVGE  480
ADPYRVKMKL CILLHAFSTR VVTINRVMGY LSSASGGPAL FKSSFPPGSE VQLVESGGGL  540
VQPGNSLRLS CAASGFTFSK FGMSWVRQAP GKGLEWVSSI SGSGRDTLYA ESVKGRFTIS  600
RDNAKTTLYL QMNSLRPEDT AVYYCTIGGS LSVSSQGTLV TVSSGGGGSG GGGSGGGGSG  660
GGGSGGGGSG GGGSQSVLTQ PPSVSGAPGQ RVTISCSGSR SNIGDETVKW YQQLPGTAPK  720
LLIYYNDQRP SGVPDRFSGS KSGTSASLAI TGLQAEDEAD YYCQSYDRYT HPALLFGTGT  780
KVTVLGGGGS GGGGSGGGGS QVQLVESGGG VVQPGRSLRL SCAASGFTFS SYGMHWVRQA  840
PGKGLEWVAF IRYEGSNKYY AESVKGRFTI SRDNSKNTLY LQMNSLRAED TAVYYCKTHG  900
SHDNWGQGTM VTVSS                                                  915

SEQ ID NO: 534        moltype = AA  length = 919
FEATURE               Location/Qualifiers
source                1..919
                      mol_type = protein
                      organism = synthetic construct
SEQUENCE: 534
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRNLPVATPD PGMFPCLHHS QNLLRAVSNM LQKARQTLEF  360
YPCTSEEIDH EDITKDKTST VEACLPLELT KNESCLNSRE TSFITNGSCL ASRKTSFMMA  420
LCLSSIYEDL KMYQVEFKTM NAKLLMDPKR QIFLDQNMLA VIDELMQALN FNSETVPQKS  480
SLEEPDFYKT KIKLCILLHA FRIRAVTIDR VMSYLNASSG GPALFKSSFP PGSEVQLVES  540
GGGLVQPGNS LRLSCAASGF TFSKFGMSWV RQAPGKGLEW VSSISGSGRD TLYAESVKGR  600
FTISRDNAKT TLYLQMNSLR PEDTAVYYCT IGGSLSVSSQ GTLVTVSSGG GGSGGGGSGG  660
GGSGGGGSGG GGSGGGGSQS VLTQPPSVSG APGQRVTISC SGSRSNIGDE TVKWYQQLPG  720
TAPKLLIYYN DQRPSGVPDR FSGSKSGTSA SLAITGLQAE DEADYYCQSY DRYTHPALLF  780
GTGTKVTVLG GGGSGGGGSG GGGSQVQLVE SGGGVVQPGR SLRLSCAASG FTFSSYGMHW  840
VRQAPGKGLE WVAFIRYEGS NKYYAESVKG RFTISRDNSK NTLYLQMNSL RAEDTAVYYC  900
KTHGSHDNWG QGTMVTVSS                                              919

SEQ ID NO: 535        moltype = AA  length = 891
FEATURE               Location/Qualifiers
source                1..891
                      mol_type = protein
                      organism = synthetic construct
SEQUENCE: 535
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRVIPVSGPA RCLSQSRNLL KTTDDMVKTA REKLKHYSCT  360
AEDIDHEDIT RDQTSTLKTC LPLELHKNES CLATRETSST TRGSCLPPQK TSLMMTLCLG  420
SIYEDLKMYQ TEFQAINAAL QNHNHQQIIL DKGMLVAIDE LMQSLNHNGE TLRQKPPVGE  480
ADPYRVKMKL CILLHAFSTR VVTINRVMGY LSSASGGPAL FKSSFPPGSE VQLVESGGGL  540
VQPGNSLRLS CAASGFTFSK FGMSWVRQAP GKGLEWVSSI SGSGRDTLYA ESVKGRFTIS  600
RDNAKTTLYL QMNSLRPEDT AVYYCTIGGS LSVSSQGTLV TVSSGGGGSG GGGSGGGGSG  660
GGGSGGGGSG GGGSQSVLTQ PPSVSGAPGQ RVTISCSGSR SNIGSNTVKW YQQLPGTAPK  720
LLIYYNDQRP SGVPDRFSGS KSGTSASLAI TGLQAEDEAD YYCQSYDRYT HPALLFGTGT  780
KVTVLGQPKA APSVTLFPPS SEELQANKAT LVCLISDFYP GAVTVAWKAD SSPVKAGVET  840
TTPSKQSNNK YAASSYLSLT PEQWKSHRSY SCQVTHEGST VEKTVAPTEC S          891

SEQ ID NO: 536        moltype = AA  length = 895
FEATURE               Location/Qualifiers
source                1..895
                      mol_type = protein
                      organism = synthetic construct
SEQUENCE: 536
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRNLPVATPD PGMFPCLHHS QNLLRAVSNM LQKARQTLEF  360
YPCTSEEIDH EDITKDKTST VEACLPLELT KNESCLNSRE TSFITNGSCL ASRKTSFMMA  420
```

-continued

```
LCLSSIYEDL KMYQVEFKTM NAKLLMDPKR QIFLDQNMLA VIDELMQALN FNSETVPQKS  480
SLEEPDFYKT KIKLCILLHA FRIRAVTIDR VMSYLNASSG GPALFKSSFP PGSEVQLVES  540
GGGLVQPGNS LRLSCAASGF TFSKFGMSWV RQAPGKGLEW VSSISGSGRD TLYAESVKGR  600
FTISRDNAKT TLYLQMNSLR PEDTAVYYCT IGGSLSVSSQ GTLVTVSSGG GGSGGGGSGG  660
GGSGGGGSGG GGSGGGGSQS VLTQPPSVSG APGQRVTISC SGSRSNIGSN TVKWYQQLPG  720
TAPKLLIYYN DQRPSGVPDR FSGSKSGTSA SLAITGLQAE DEADYYCQSY DRYTHPALLF  780
GTGTKVTVLG QPKAAPSVTL FPPSSEELQA NKATLVCLIS DFYPGAVTVA WKADSSPVKA  840
GVETTTPSKQ SNNKYAASSY LSLTPEQWKS HRSYSCQVTH EGSTVEKTVA PTECS       895

SEQ ID NO: 537         moltype = AA  length = 891
FEATURE                Location/Qualifiers
source                 1..891
                       mol_type = protein
                       organism = synthetic construct
SEQUENCE: 537
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRVIPVSGPA RCLSQSRNLL KTTDDMVKTA REKLKHYSCT  360
AEDIDHEDIT RDQTSTLKTC LPLELHKNES CLATRETSST TRGSCLPPQK TSLMMTLCLG  420
SIYEDLKMYQ TEFQAINAAL QNHNHQQIIL DKGMLVAIDE LMQSLNHNGE TLRQKPPVGE  480
ADPYRVKMKL CILLHAFSTR VVTINRVMGY LSSASGGPAL FKSSFPPGSE VQLVESGGGL  540
VQPGNSLRLS CAASGFTFSK FGMSWVRQAP GKGLEWVSSI SGSGRDTLYA ESVKGRFTIS  600
RDNAKTTLYL QMNSLRPEDT AVYYCTIGGS LSVSSQGTLV TVSSGGGGSG GGGSGGGGSG  660
GGGSGGGGSG GGGSQSVLTQ PPSVSGAPGQ RVTISCSGSR SNIGDETVKW YQQLPGTAPK  720
LLIYYNDQRP SGVPDRFSGS KSGTSASLAI TGLQAEDEAD YYCQSYDRYT HPALLFGTGT  780
KVTVLGQPKA APSVTLFPPS SEELQANKAT LVCLISDFYP GAVTVAWKAD SSPVKAGVET  840
TTPSKQSNNK YAASSYLSLT PEQWKSHRSY SCQVTHEGST VEKTVAPTEC S           891

SEQ ID NO: 538         moltype = AA  length = 895
FEATURE                Location/Qualifiers
source                 1..895
                       mol_type = protein
                       organism = synthetic construct
SEQUENCE: 538
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRNLPVATPD PGMFPCLHHS QNLLRAVSNM LQKARQTLEF  360
YPCTSEEIDH EDITKDKTST VEACLPLELT KNESCLNSRE TSFITNGSCL ASRKTSFMMA  420
LCLSSIYEDL KMYQVEFKTM NAKLLMDPKR QIFLDQNMLA VIDELMQALN FNSETVPQKS  480
SLEEPDFYKT KIKLCILLHA FRIRAVTIDR VMSYLNASSG GPALFKSSFP PGSEVQLVES  540
GGGLVQPGNS LRLSCAASGF TFSKFGMSWV RQAPGKGLEW VSSISGSGRD TLYAESVKGR  600
FTISRDNAKT TLYLQMNSLR PEDTAVYYCT IGGSLSVSSQ GTLVTVSSGG GGSGGGGSGG  660
GGSGGGGSGG GGSGGGGSQS VLTQPPSVSG APGQRVTISC SGSRSNIGDE TVKWYQQLPG  720
TAPKLLIYYN DQRPSGVPDR FSGSKSGTSA SLAITGLQAE DEADYYCQSY DRYTHPALLF  780
GTGTKVTVLG QPKAAPSVTL FPPSSEELQA NKATLVCLIS DFYPGAVTVA WKADSSPVKA  840
GVETTTPSKQ SNNKYAASSY LSLTPEQWKS HRSYSCQVTH EGSTVEKTVA PTECS       895

SEQ ID NO: 539         moltype = AA  length = 427
FEATURE                Location/Qualifiers
source                 1..427
                       mol_type = protein
                       organism = synthetic construct
SEQUENCE: 539
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS CDLPHTYNLR NKRALKVLAQ MRRLTPLSCL KDRKDFGFPL EKVDAQQIQK  180
AQSIPVLRDL TQQILNLFAS KDSSAAWNAT LLDSFCNDLH QQLNDLQGCL MQQVGVQESP  240
LTQEDSLLAV RIYFHRITVF LREKKHSPCA WEVVRAEVWR ALSSSANVLG RLREEKASGG  300
PGPAGLYAQP GSEVQLVESG GGLVQPGNSL RLSCAASGFT FSKFGMSWVR QAPGKGLEWV  360
SSISGSGRDT LYAESVKGRF TISRDNAKTT LYLQMNSLRP EDTAVYYCTI GGSLSVSSQG  420
TLVTVSS                                                            427

SEQ ID NO: 540         moltype = AA  length = 427
FEATURE                Location/Qualifiers
source                 1..427
                       mol_type = protein
                       organism = synthetic construct
SEQUENCE: 540
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS CDLPHTYNLR NKRALKVLAQ MRRLTPLSCL KDRKDFGFPL EKVDAQQIQK  180
AQSIPVLRDL TQQILNLFAS KDSSAAWNAT LLDSFCNDLH QQLNDLQGCL MQQVGVQESP  240
LTQEDSLLAV RIYFHRITVF LREKKHSPCA WEVVRAEVWR ALSSSANVLG RLREEKASGG  300
```

-continued

```
PALFKSSFPP GSEVQLVESG GGLVQPGNSL RLSCAASGFT FSKFGMSWVR QAPGKGLEWV  360
SSISGSGRDT LYAESVKGRF TISRDNAKTT LYLQMNSLRP EDTAVYYCTI GGSLSVSSQG  420
TLVTVSS                                                          427

SEQ ID NO: 541          moltype = AA  length = 426
FEATURE                 Location/Qualifiers
source                  1..426
                        mol_type = protein
                        organism = synthetic construct
SEQUENCE: 541
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS CNLSQTHSLN NRRTLMLMAQ MRRISPFSCL KDRHDFEFPQ EEFDGNQFQK  180
AQAISVLHEM MQQTFNLFST KNSSAAWDET LLEKFYIELF QQMNDLEACV IQEVGVEETP  240
LMNEDSILAV KKYFQRITLY LMEKKYSPCA WEVVRAEIMR SLSFSTNLQK RLRRKDSGGP  300
GPAGLYAQPG SEVQLVESGG GLVQPGNSLR LSCAASGFTF SKFGMSWVRQ APGKGLEWVS  360
SISGSGRDTL YAESVKGRFT ISRDNAKTTL YLQMNSLRPE DTAVYYCTIG GSLSVSSQGT  420
LVTVSS                                                           426

SEQ ID NO: 542          moltype = AA  length = 426
FEATURE                 Location/Qualifiers
source                  1..426
                        mol_type = protein
                        organism = synthetic construct
SEQUENCE: 542
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS CNLSQTHSLN NRRTLMLMAQ MRRISPFSCL KDRHDFEFPQ EEFDGNQFQK  180
AQAISVLHEM MQQTFNLFST KNSSAAWDET LLEKFYIELF QQMNDLEACV IQEVGVEETP  240
LMNEDSILAV KKYFQRITLY LMEKKYSPCA WEVVRAEIMR SLSFSTNLQK RLRRKDSGGP  300
ALFKSSFPPG SEVQLVESGG GLVQPGNSLR LSCAASGFTF SKFGMSWVRQ APGKGLEWVS  360
SISGSGRDTL YAESVKGRFT ISRDNAKTTL YLQMNSLRPE DTAVYYCTIG GSLSVSSQGT  420
LVTVSS                                                           426

SEQ ID NO: 543          moltype = AA  length = 173
FEATURE                 Location/Qualifiers
source                  1..173
                        mol_type = protein
                        organism = synthetic construct
SEQUENCE: 543
CDLPHTYNLR NKRALKVLAQ MRRLTPLSCL KDRKDFGFPL EKVDAQQIQK AQSIPVLRDL  60
TQQILNLFAS KDSSAAWNAT LLDSFCNDLH QQLNDLQGCL MQQVGVQESP LTQEDSLLAV  120
RIYFHRITVF LREKKHSPCA WEVVRAEVWR ALSSSANVLG RLREEKAHHH HHH        173

SEQ ID NO: 544          moltype = AA  length = 172
FEATURE                 Location/Qualifiers
source                  1..172
                        mol_type = protein
                        organism = synthetic construct
SEQUENCE: 544
CNLSQTHSLN NRRTLMLMAQ MRRISPFSCL KDRHDFEFPQ EEFDGNQFQK AQAISVLHEM  60
MQQTFNLFST KNSSAAWDET LLEKFYIELF QQMNDLEACV IQEVGVEETP LMNEDSILAV  120
KKYFQRITLY LMEKKYSPCA WEVVRAEIMR SLSFSTNLQK RLRRKDHHHH HH         172

SEQ ID NO: 545          moltype = AA  length = 425
FEATURE                 Location/Qualifiers
source                  1..425
                        mol_type = protein
                        organism = synthetic construct
SEQUENCE: 545
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS CDLPQTHSLG SRRTLMLLAQ MRRISLFSCL KDRHDFGFPQ EEFGNQFQKA  180
ETIPVLHEMI QQIFNLFSTK DSSAAWDETL LDKFYTELYQ QLNDLEACVI QGVGVEETPL  240
MKEDSILAVR KYFQRITLYL KEKKYSPCAW EVVRAEIMRS FSLSTNLQES LRSKESGGPG  300
PAGLYAQPGS EVQLVESGGG LVQPGNSLRL SCAASGFTFS KFGMSWVRQA PGKGLEWVSS  360
ISGSGRDTLY AESVKGRFTI SRDNAKTTLY LQMNSLRPED TAVYYCTIGG SLSVSSQGTL  420
VTVSS                                                            425

SEQ ID NO: 546          moltype = AA  length = 426
FEATURE                 Location/Qualifiers
source                  1..426
                        mol_type = protein
                        organism = synthetic construct
SEQUENCE: 546
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS CNLSQTHSLN NRRTLMLMAQ MRRISPFSCL KDRHDFEFPQ EEFDGNQFQK  180
AQAISVLHEM MQQTFNLFST KDSSAAWDET LLEKFYIELF QQMNDLEACV IQEVGVEETP  240
```

```
LMNEDSILAV KKYFQRITLY LMEKKYSPCA WEVVRAEIMR SLSFSTNLQK RLRRKDSGGP  300
GPAGLYAQPG SEVQLVESGG GLVQPGNSLR LSCAASGFTF SKFGMSWVRQ APGKGLEWVS  360
SISGSGRDTL YAESVKGRFT ISRDNAKTTL YLQMNSLRPE DTAVYYCTIG GSLSVSSQGT  420
LVTVSS                                                            426

SEQ ID NO: 547         moltype = AA  length = 426
FEATURE                Location/Qualifiers
source                 1..426
                       mol_type = protein
                       organism = synthetic construct
SEQUENCE: 547
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS CDLPQTHSLN NRRTLMLMAQ MRRISPFSCL KDRHDFEFPQ EEFDGNQFQK  180
AQAISVLHEM MQQTFNLFST KDSSAAWDET LLEKFYIELF QQMNDLEACV IQEVGVEETP  240
LMNEDSILAV KKYFQRITLY LMEKKYSPCA WEVVRAEIMR SLSFSTNLQK RLRRKDSGGP  300
GPAGLYAQPG SEVQLVESGG GLVQPGNSLR LSCAASGFTF SKFGMSWVRQ APGKGLEWVS  360
SISGSGRDTL YAESVKGRFT ISRDNAKTTL YLQMNSLRPE DTAVYYCTIG GSLSVSSQGT  420
LVTVSS                                                            426

SEQ ID NO: 548         moltype = AA  length = 171
FEATURE                Location/Qualifiers
source                 1..171
                       mol_type = protein
                       organism = synthetic construct
SEQUENCE: 548
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVEETPL MKEDSILAVR  120
KYFQRITLYL KEKKYSPCAW EVVRAEIMRS FSLSTNLQES LRSKEHHHHH H          171

SEQ ID NO: 549         moltype = AA  length = 172
FEATURE                Location/Qualifiers
source                 1..172
                       mol_type = protein
                       organism = synthetic construct
SEQUENCE: 549
CNLSQTHSLN NRRTLMLMAQ MRRISPFSCL KDRHDFEFPQ EEFDGNQFQK AQAISVLHEM  60
MQQTFNLFST KDSSAAWDET LLEKFYIELF QQMNDLEACV IQEVGVEETP LMNEDSILAV  120
KKYFQRITLY LMEKKYSPCA WEVVRAEIMR SLSFSTNLQK RLRRKDHHHH HH         172

SEQ ID NO: 550         moltype = AA  length = 172
FEATURE                Location/Qualifiers
source                 1..172
                       mol_type = protein
                       organism = synthetic construct
SEQUENCE: 550
CDLPQTHSLN NRRTLMLMAQ MRRISPFSCL KDRHDFEFPQ EEFDGNQFQK AQAISVLHEM  60
MQQTFNLFST KDSSAAWDET LLEKFYIELF QQMNDLEACV IQEVGVEETP LMNEDSILAV  120
KKYFQRITLY LMEKKYSPCA WEVVRAEIMR SLSFSTNLQK RLRRKDHHHH HH         172

SEQ ID NO: 551         moltype = AA  length = 1370
FEATURE                Location/Qualifiers
source                 1..1370
                       mol_type = protein
                       organism = synthetic construct
SEQUENCE: 551
EAHKSEIAHR YNDLGEQHFK GLVLIAFSQY LQKCSYDEHA KLVQEVTDFA KTCVADESAA  60
NCDKSLHTLF GDKLCAIPNL RENYGELADC CTKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQRMKC SSMQKFGERA FKAWAVARLS QTFPNADFAE ITKLATDLTK  240
VNKECCHGDL LECADDRAEL AKYMCENQAT ISSKLQTCCD KPLLKKAHCL SEVEHDTMPA  300
DLPAIAADFV EDQEVCKNYA EAKDVFLGTF LYEYSRRHPD YSVSLLLRLA KKYEATLEKC  360
CAEANPPACY GTVLAEFQPL VEEPKNLVKT NCDLYEKLGE YGFQNAILVR YTQKAPQVST  420
PTLVEAARNL GRVGTKCCTL PEDQRLPCVE DYLSAILNRV CLLHEKTPVS EHVTKCCSGS  480
LVERRPCFSA LTVDETYVPK EFKAETFTFH SDICTLPEKE KQIKKQTALA ELVKHKPKAT  540
AEQLKTVMDD FAQFLDTCCK AADKDTCFST EGPNLVTRCK DALASGGPAL FKSSFPPGSC  600
DLPQTHNLRN KRALTLLVQM RRLSPLSCLK DRKDFGFPQE KVDAQQIKKA QAIPVLSELT  660
QQILNIFTSK DSSAAWNTTL LDSFCNDLHQ QLNDLQGCLM QQVGVQEFPL TQEDALLAVR  720
KYFHRITVYL REKKHSPCAW EVVRAEVWRA LSSSANVLGR LREEKSGGPA LFKSSFPPGS  780
EAHKSEIAHR YNDLGEQHFK GLVLIAFSQY LQKCSYDEHA KLVQEVTDFA KTCVADESAA  840
NCDKSLHTLF GDKLCAIPNL RENYGELADC CTKQEPERNE CFLQHKDDNP SLPPFERPEA  900
EAMCTSFKEN PTTFMGHYLH EVARRHPYFY APELLYYAEQ YNEILTQCCA EADKESCLTP  960
KLDGVKEKAL VSSVRQRMKC SSMQKFGERA FKAWAVARLS QTFPNADFAE ITKLATDLTK  1020
VNKECCHGDL LECADDRAEL AKYMCENQAT ISSKLQTCCD KPLLKKAHCL SEVEHDTMPA  1080
DLPAIAADFV EDQEVCKNYA EAKDVFLGTF LYEYSRRHPD YSVSLLLRLA KKYEATLEKC  1140
CAEANPPACY GTVLAEFQPL VEEPKNLVKT NCDLYEKLGE YGFQNAILVR YTQKAPQVST  1200
PTLVEAARNL GRVGTKCCTL PEDQRLPCVE DYLSAILNRV CLLHEKTPVS EHVTKCCSGS  1260
LVERRPCFSA LTVDETYVPK EFKAETFTFH SDICTLPEKE KQIKKQTALA ELVKHKPKAT  1320
AEQLKTVMDD FAQFLDTCCK AADKDTCFST EGPNLVTRCK DALAHHHHHH            1370
```

```
SEQ ID NO: 552          moltype = AA  length = 1371
FEATURE                 Location/Qualifiers
source                  1..1371
                        mol_type = protein
                        organism = synthetic construct
SEQUENCE: 552
EAHKSEIAHR YNDLGEQHFK GLVLIAFSQY LQKCSYDEHA KLVQEVTDFA KTCVADESAA  60
NCDKSLHTLF GDKLCAIPNL RENYGELADC CTKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQRMKC SSMQKFGERA FKAWAVARLS QTFPNADFAE ITKLATDLTK  240
VNKECCHGDL LECADDRAEL AKYMCENQAT ISSKLQTCCD KPLLKKAHCL SEVEHDTMPA  300
DLPAIAADFV EDQEVCKNYA EAKDVFLGTF LYEYSRRHPD YSVSLLLRLA KKYEATLEKC  360
CAEANPPACY GTVLAEFQPL VEEPKNLVKT NCDLYEKLGE YGFQNAILVR YTQKAPQVST  420
PTLVEAARNL GRVGTKCCTL PEDQRLPCVE DYLSAILNRV CLLHEKTPVS EHVTKCCSGS  480
LVERRPCFSA LTVDETYVPK EFKAETFTFH SDICTLPEKE KQIKKQTALA ELVKHKPKAT  540
AEQLKTVMDD FAQFLDTCCK AADKDTCFST EGPNLVTRCK DALASGGPAL FKSSFPPGSC  600
DLPHTYNLRN KRALKVLAQM RRLTPLSCLK DRKDFGFPLE KVDAQQIQKA QSIPVLRDLT  660
QQILNLFASK DSSAAWNATL LDSFCNDLHQ QLNDLQGCLM QQVGVQESPL TQEDSLLAVR  720
IYFHRITVFL REKKHSPCAW EVVRAEVWRA LSSSANVLGR LREEKASGGP ALFKSSFPPG  780
SEAHKSEIAH RYNDLGEQHF KGLVLIAFSQ YLQKCSYDEH AKLVQEVTDF AKTCVADESA  840
ANCDKSLHTL FGDKLCAIPN LRENYGELAD CCTKQEPERN ECFLQHKDDN PSLPPFERPE  900
AEAMCTSFKE NPTTFMGHYL HEVARRHPYF YAPELLYYAE QYNEILTQCC AEADKESCLT  960
PKLDGVKEKA LVSSVRQRMK CSSMQKFGER AFKAWAVARL SQTFPNADFA EITKLATDLT  1020
KVNKECCHGD LLECADDRAE LAKYMCENQA TISSKLQTCC DKPLLKKAHC LSEVEHDTMP  1080
ADLPAIAADF VEDQEVCKNY AEAKDVFLGT FLYEYSRRHP DYSVSLLLRL AKKYEATLEK  1140
CCAEANPPAC YGTVLAEFQP LVEEPKNLVK TNCDLYEKLG EYGFQNAILV RYTQKAPQVS  1200
TPTLVEAARN LGRVGTKCCT LPEDQRLPCV EDYLSAILNR VCLLHEKTPV SEHVTKCCSG  1260
SLVERRPCFS ALTVDETYVP KEFKAETFTF HSDICTLPEK EKQIKKQTAL AELVKHKPKA  1320
TAEQLKTVMD DFAQFLDTCC KAADKDTCFS TEGPNLVTRC KDALAHHHHH H           1371

SEQ ID NO: 553          moltype = AA  length = 901
FEATURE                 Location/Qualifiers
source                  1..901
                        mol_type = protein
                        organism = synthetic construct
SEQUENCE: 553
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS CDLPQTHNLR NKRALTLLVQ MRRLSPLSCL KDRKDFGFPQ EKVDAQQIKK  180
AQAIPVLSEL TQQILNIFTS KDSSAAWNTT LLDSFCNDLH QQLNDLQGCL MQQVGVQEFP  240
LTQEDALLAV RKYFHRITVY LREKKHSPCA WEVVRAEVWR ALSSSANVLG RLREEKSGGP  300
ALFKSSFPPG SEAHKSEIAH RYNDLGEQHF KGLVLIAFSQ YLQKCSYDEH AKLVQEVTDF  360
AKTCVADESA ANCDKSLHTL FGDKLCAIPN LRENYGELAD CCTKQEPERN ECFLQHKDDN  420
PSLPPFERPE AEAMCTSFKE NPTTFMGHYL HEVARRHPYF YAPELLYYAE QYNEILTQCC  480
AEADKESCLT PKLDGVKEKA LVSSVRQRMK CSSMQKFGER AFKAWAVARL SQTFPNADFA  540
EITKLATDLT KVNKECCHGD LLECADDRAE LAKYMCENQA TISSKLQTCC DKPLLKKAHC  600
LSEVEHDTMP ADLPAIAADF VEDQEVCKNY AEAKDVFLGT FLYEYSRRHP DYSVSLLLRL  660
AKKYEATLEK CCAEANPPAC YGTVLAEFQP LVEEPKNLVK TNCDLYEKLG EYGFQNAILV  720
RYTQKAPQVS TPTLVEAARN LGRVGTKCCT LPEDQRLPCV EDYLSAILNR VCLLHEKTPV  780
SEHVTKCCSG SLVERRPCFS ALTVDETYVP KEFKAETFTF HSDICTLPEK EKQIKKQTAL  840
AELVKHKPKA TAEQLKTVMD DFAQFLDTCC KAADKDTCFS TEGPNLVTRC KDALAHHHHH  900
H                                                                 901

SEQ ID NO: 554          moltype = AA  length = 902
FEATURE                 Location/Qualifiers
source                  1..902
                        mol_type = protein
                        organism = synthetic construct
SEQUENCE: 554
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS CDLPHTYNLR NKRALKVLAQ MRRLTPLSCL KDRKDFGFPL EKVDAQQIQK  180
AQSIPVLRDL TQQILNLFAS KDSSAAWNAT LLDSFCNDLH QQLNDLQGCL MQQVGVQESP  240
LTQEDSLLAV RIYFHRITVF LREKKHSPCA WEVVRAEVWR ALSSSANVLG RLREEKASGG  300
PALFKSSFPP GSEAHKSEIA HRYNDLGEQH FKGLVLIAFS QYLQKCSYDE HAKLVQEVTD  360
FAKTCVADES AANCDKSLHT LFGDKLCAIP NLRENYGELA DCCTKQEPER NECFLQHKDD  420
NPSLPPFERP EAEAMCTSFK ENPTTFMGHY LHEVARRHPY FYAPELLYYA EQYNEILTQC  480
CAEADKESCL TPKLDGVKEK ALVSSVRQRM KCSSMQKFGE RAFKAWAVAR LSQTFPNADF  540
AEITKLATDL TKVNKECCHG DLLECADDRA ELAKYMCENQ ATISSKLQTC CDKPLLKKAH  600
CLSEVEHDTM PADLPAIAAD FVEDQEVCKN YAEAKDVFLG TFLYEYSRRH PDYSVSLLLR  660
LAKKYEATLE KCCAEANPPA CYGTVLAEFQ PLVEEPKNLV KTNCDLYEKL GEYGFQNAIL  720
VRYTQKAPQV STPTLVEAAR NLGRVGTKCC TLPEDQRLPC VEDYLSAILN RVCLLHEKTP  780
VSEHVTKCCS GSLVERRPCF SALTVDETYV PKEFKAETFT FHSDICTLPE KEKQIKKQTA  840
LAELVKHKPK ATAEQLKTVM DDFAQFLDTC CKAADKDTCF STEGPNLVTR CKDALAHHHH  900
HH                                                                902

SEQ ID NO: 555          moltype = AA  length = 901
FEATURE                 Location/Qualifiers
```

```
source                  1..901
                        mol_type = protein
                        organism = synthetic construct
SEQUENCE: 555
EAHKSEIAHR YNDLGEQHFK GLVLIAFSQY LQKCSYDEHA KLVQEVTDFA KTCVADESAA  60
NCDKSLHTLF GDKLCAIPNL RENYGELADC CTKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQRMKC SSMQKFGERA FKAWAVARLS QTFPNADFAE ITKLATDLTK  240
VNKECCHGDL LECADDRAEL AKYMCENQAT ISSKLQTCCD KPLLKKAHCL SEVEHDTMPA  300
DLPAIAADFV EDQEVCKNYA EAKDVFLGTF LYEYSRRHPD YSVSLLLRLA KKYEATLEKC  360
CAEANPPACY GTVLAEFQPL VEEPKNLVKT NCDLYEKLGE YGFQNAILVR YTQKAPQVST  420
PTLVEAARNL GRVGTKCCTL PEDQRLPCVE DYLSAILNRV CLLHEKTPVS EHVTKCCSGS  480
LVERRPCFSA LTVDETYVPK EFKAETFTFH SDICTLPEKE KQIKKQTALA ELVKHKPKAT  540
AEQLKTVMDD FAQFLDTCCK AADKDTCFST EGPNLVTRCK DALASGGPAL FKSSFPPGSC  600
DLPQTHNLRN KRALTLLVQM RRLSPLSCLK DRKDFGFPQE KVDAQQIKKA QAIPVLSELT  660
QQILNIFTSK DSSAAWNTTL LDSFCNDLHQ QLNDLQGCLM QQVGVQEFPL TQEDALLAVR  720
KYFHRITVYL REKKHSPCAW EVVRAEVWRA LSSSANVLGR LREEKSGGPA LFKSSFPPGS  780
EVQLVESGGG LVQPGNSLRL SCAASGFTFS KFGMSWVRQA PGKGLEWVSS ISGSGRDTLY  840
AESVKGRFTI SRDNAKTTLY LQMNSLRPED TAVYYCTIGG SLSVSSQGTL VTVSSHHHHH  900
H                                                                 901

SEQ ID NO: 556          moltype = AA  length = 902
FEATURE                 Location/Qualifiers
source                  1..902
                        mol_type = protein
                        organism = synthetic construct
SEQUENCE: 556
EAHKSEIAHR YNDLGEQHFK GLVLIAFSQY LQKCSYDEHA KLVQEVTDFA KTCVADESAA  60
NCDKSLHTLF GDKLCAIPNL RENYGELADC CTKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQRMKC SSMQKFGERA FKAWAVARLS QTFPNADFAE ITKLATDLTK  240
VNKECCHGDL LECADDRAEL AKYMCENQAT ISSKLQTCCD KPLLKKAHCL SEVEHDTMPA  300
DLPAIAADFV EDQEVCKNYA EAKDVFLGTF LYEYSRRHPD YSVSLLLRLA KKYEATLEKC  360
CAEANPPACY GTVLAEFQPL VEEPKNLVKT NCDLYEKLGE YGFQNAILVR YTQKAPQVST  420
PTLVEAARNL GRVGTKCCTL PEDQRLPCVE DYLSAILNRV CLLHEKTPVS EHVTKCCSGS  480
LVERRPCFSA LTVDETYVPK EFKAETFTFH SDICTLPEKE KQIKKQTALA ELVKHKPKAT  540
AEQLKTVMDD FAQFLDTCCK AADKDTCFST EGPNLVTRCK DALASGGPAL FKSSFPPGSC  600
DLPHTYNLRN KRALKVLAQM RRLTPLSCLK DRKDFGFPLE KVDAQQIQKA QSIPVLRDLT  660
QQILNLFASK DSSAAWNATL LDSFCNDLHQ QLNDLQGCLM QQVGVQESPL TQEDSLLAVR  720
IYFHRITVFL REKKHSPCAW EVVRAEVWRA LSSSANVLGR LREEKASGGP ALFKSSFPPG  780
SEVQLVESGG GLVQPGNSLR LSCAASGFTF SKFGMSWVRQ APGKGLEWVS SISGSGRDTL  840
YAESVKGRFT ISRDNAKTTL YLQMNSLRPE DTAVYYCTIG GSLSVSSQGT LVTVSSHHHH  900
HH                                                                902

SEQ ID NO: 557          moltype = AA  length = 1365
FEATURE                 Location/Qualifiers
source                  1..1365
                        mol_type = protein
                        organism = synthetic construct
SEQUENCE: 557
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGKKLVAASQ AALGLSGGPA LFKSSFPPGS  600
CDLPQTHSLG SRRTLMLLAQ MRRISLFSCL KDRHDFGFPQ EEFGNQFQKA ETIPVLHEMI  660
QQIFNLFSTK DSSAAWDETL LDKFYTELYQ QLNDLEACVI QGVGVTETPL MKEDSILAVR  720
KYFQRITLYL KEKKYSPCAW EVVRAEIMRS FSLSTNLQES LRSKESGGPA LFKSSFPPGS  780
DAHKSEVAHR FKDLGEENFK ALVLIAFAQY LQQCPFEDHV KLVNEVTEFA KTCVADESAE  840
NCDKSLHTLF GDKLCTVATL RETYGEMADC CAKQEPERNE CFLQHKDDNP NLPRLVRPEV  900
DVMCTAFHDN EETFLKKYLY EIARRHPYFY APELLFFAKR YKAAFTECCQ AADKAACLLP  960
KLDELRDEGK ASSAKQRLKC ASLQKFGERA FKAWAVARLS QRFPKAEFAE VSKLVTDLTK  1020
VHTECCHGDL LECADDRADL AKYICENQDS ISSKLKECCE KPLLEKSHCI AEVENDEMPA  1080
DLPSLAADFV ESKDVCKNYA EAKDVFLGMF LYEYARRHPD YSVVLLLRLA KTYETTLEKC  1140
CAAADPHECY AKVFDEFKPL VEEPQNLIKQ NCELFEQLGE YKFQNALLVR YTKKVPQVST  1200
PTLVEVSRNL GKVGSKCCKH PEAKRMPCAE DYLSVVLNQL CVLHEKTPVS DRVTKCCTES  1260
LVNRRPCFSA LEVDETYVPK EFNAETFTFH ADICTLSEKE RQIKKQTALV ELVKHKPKAT  1320
KEQLKAVMDD FAAFVEKCCK ADDKETCFAE EGKKLVAASQ AALGL                 1365

SEQ ID NO: 558          moltype = AA  length = 1366
FEATURE                 Location/Qualifiers
source                  1..1366
                        mol_type = protein
                        organism = synthetic construct
```

-continued

SEQUENCE: 558
DAHKSEVAHR FKDLGEENFK ALVLIAFAQY LQQCPFEDHV KLVNEVTEFA KTCVADESAE 60
NCDKSLHTLF GDKLCTVATL RETYGEMADC CAKQEPERNE CFLQHKDDNP NLPRLVRPEV 120
DVMCTAFHDN EETFLKKYLY EIARRHPYFY APELLFFAKR YKAAFTECCQ AADKAACLLP 180
KLDELRDEGK ASSAKQRLKC ASLQKFGERA FKAWAVARLS QRFPKAEFAE VSKLVTDLTK 240
VHTECCHGDL LECADDRADL AKYICENQDS ISSKLKECCE KPLLEKSHCI AEVENDEMPA 300
DLPSLAADFV ESKDVCKNYA EAKDVFLGMF LYEYARRHPD YSVVLLLRLA KTYETTLEKC 360
CAAADPHECY AKVFDEFKPL VEEPQNLIKQ NCELFEQLGE YKFQNALLVR YTKKVPQVST 420
PTLVEVSRNL GKVGSKCCKH PEAKRMPCAE DYLSVVLNQL CVLHEKTPVS DRVTKCCTES 480
LVNRRPCFSA LEVDETYVPK EFNAETFTFH ADICTLSEKE RQIKKQTALV ELVKHKPKAT 540
KEQLKAVMDD FAAFVEKCCK ADDKETCFAE EGKKLVAASQ AALGLSGGPA LFKSSFPPGS 600
CNLSQTHSLN NRRTLMLMAQ MRRISPFSCL KDRHDFEFPQ EEFDGNQFQK AQAISVLHEM 660
MQQTFNLFST KNSSAAWDET LLEKFYIELF QQMNDLEACV IQEVGVEETP LMNEDSILAV 720
KKYFQRITLY LMEKKYSPCA WEVVRAEIMR SLSFSTNLQK RLRRKDSGGP ALFKSSFPPG 780
SDAHKSEVAH RFKDLGEENF KALVLIAFAQ YLQQCPFEDH VKLVNEVTEF AKTCVADESA 840
ENCDKSLHTL FGDKLCTVAT LRETYGEMAD CCAKQEPERN ECFLQHKDDN PNLPRLVRPE 900
VDVMCTAFHD NEETFLKKYL YEIARRHPYF YAPELLFFAK RYKAAFTECC QAADKAACLL 960
PKLDELRDEG KASSAKQRLK CASLQKFGER AFKAWAVARL SQRFPKAEFA EVSKLVTDLT 1020
KVHTECCHGD LLECADDRAD LAKYICENQD SISSKLKECC EKPLLEKSHC IAEVENDEMP 1080
ADLPSLAADF VESKDVCKNY AEAKDVFLGM FLYEYARRHP DYSVVLLLRL AKTYETTLEK 1140
CCAAADPHEC YAKVFDEFKP LVEEPQNLIK QNCELFEQLG EYKFQNALLV RYTKKVPQVS 1200
TPTLVEVSRN LGKVGSKCCK HPEAKRMPCA EDYLSVVLNQ LCVLHEKTPV SDRVTKCCTE 1260
SLVNRRPCFS ALEVDETYVP KEFNAETFTF HADICTLSEK ERQIKKQTAL VELVKHKPKA 1320
TKEQLKAVMD DFAAFVEKCC KADDKETCFA EEGKKLVAAS QAALGL 1366

SEQ ID NO: 559 moltype = AA length = 1366
FEATURE Location/Qualifiers
source 1..1366
mol_type = protein
organism = synthetic construct
SEQUENCE: 559
DAHKSEVAHR FKDLGEENFK ALVLIAFAQY LQQCPFEDHV KLVNEVTEFA KTCVADESAE 60
NCDKSLHTLF GDKLCTVATL RETYGEMADC CAKQEPERNE CFLQHKDDNP NLPRLVRPEV 120
DVMCTAFHDN EETFLKKYLY EIARRHPYFY APELLFFAKR YKAAFTECCQ AADKAACLLP 180
KLDELRDEGK ASSAKQRLKC ASLQKFGERA FKAWAVARLS QRFPKAEFAE VSKLVTDLTK 240
VHTECCHGDL LECADDRADL AKYICENQDS ISSKLKECCE KPLLEKSHCI AEVENDEMPA 300
DLPSLAADFV ESKDVCKNYA EAKDVFLGMF LYEYARRHPD YSVVLLLRLA KTYETTLEKC 360
CAAADPHECY AKVFDEFKPL VEEPQNLIKQ NCELFEQLGE YKFQNALLVR YTKKVPQVST 420
PTLVEVSRNL GKVGSKCCKH PEAKRMPCAE DYLSVVLNQL CVLHEKTPVS DRVTKCCTES 480
LVNRRPCFSA LEVDETYVPK EFNAETFTFH ADICTLSEKE RQIKKQTALV ELVKHKPKAT 540
KEQLKAVMDD FAAFVEKCCK ADDKETCFAE EGKKLVAASQ AALGLSGGPA LFKSSFPPGS 600
CDLPQTHSLG NRRALILLAQ MRRISPFSCL KDRHDFEFPQ EEFDDKQFQK AQAISVLHEM 660
IQQTFNLFST KDSSAALDET LLDEFYIELD QQLNDLESCV MQEVGVIESP LMYEDSILAV 720
RKYFQRITLY LTEKKYSSCA WEVVRAEIMR SFSLSINLQK RLKSKESGGP ALFKSSFPPG 780
SDAHKSEVAH RFKDLGEENF KALVLIAFAQ YLQQCPFEDH VKLVNEVTEF AKTCVADESA 840
ENCDKSLHTL FGDKLCTVAT LRETYGEMAD CCAKQEPERN ECFLQHKDDN PNLPRLVRPE 900
VDVMCTAFHD NEETFLKKYL YEIARRHPYF YAPELLFFAK RYKAAFTECC QAADKAACLL 960
PKLDELRDEG KASSAKQRLK CASLQKFGER AFKAWAVARL SQRFPKAEFA EVSKLVTDLT 1020
KVHTECCHGD LLECADDRAD LAKYICENQD SISSKLKECC EKPLLEKSHC IAEVENDEMP 1080
ADLPSLAADF VESKDVCKNY AEAKDVFLGM FLYEYARRHP DYSVVLLLRL AKTYETTLEK 1140
CCAAADPHEC YAKVFDEFKP LVEEPQNLIK QNCELFEQLG EYKFQNALLV RYTKKVPQVS 1200
TPTLVEVSRN LGKVGSKCCK HPEAKRMPCA EDYLSVVLNQ LCVLHEKTPV SDRVTKCCTE 1260
SLVNRRPCFS ALEVDETYVP KEFNAETFTF HADICTLSEK ERQIKKQTAL VELVKHKPKA 1320
TKEQLKAVMD DFAAFVEKCC KADDKETCFA EEGKKLVAAS QAALGL 1366

SEQ ID NO: 560 moltype = AA length = 1366
FEATURE Location/Qualifiers
source 1..1366
mol_type = protein
organism = synthetic construct
SEQUENCE: 560
DAHKSEVAHR FKDLGEENFK ALVLIAFAQY LQQCPFEDHV KLVNEVTEFA KTCVADESAE 60
NCDKSLHTLF GDKLCTVATL RETYGEMADC CAKQEPERNE CFLQHKDDNP NLPRLVRPEV 120
DVMCTAFHDN EETFLKKYLY EIARRHPYFY APELLFFAKR YKAAFTECCQ AADKAACLLP 180
KLDELRDEGK ASSAKQRLKC ASLQKFGERA FKAWAVARLS QRFPKAEFAE VSKLVTDLTK 240
VHTECCHGDL LECADDRADL AKYICENQDS ISSKLKECCE KPLLEKSHCI AEVENDEMPA 300
DLPSLAADFV ESKDVCKNYA EAKDVFLGMF LYEYARRHPD YSVVLLLRLA KTYETTLEKC 360
CAAADPHECY AKVFDEFKPL VEEPQNLIKQ NCELFEQLGE YKFQNALLVR YTKKVPQVST 420
PTLVEVSRNL GKVGSKCCKH PEAKRMPCAE DYLSVVLNQL CVLHEKTPVS DRVTKCCTES 480
LVNRRPCFSA LEVDETYVPK EFNAETFTFH ADICTLSEKE RQIKKQTALV ELVKHKPKAT 540
KEQLKAVMDD FAAFVEKCCK ADDKETCFAE EGKKLVAASQ AALGLSGGPA LFKSSFPPGS 600
CDLPQTHSLG NRRALILLAQ MGRISHFSCL KDRYDFGFPQ EVFDGNQFQK AQAISAFHEM 660
IQQTFNLFST KDSSAAWDET LLDKFYIELF QQLNDLEACV TQEVGVEEIA LMNEDSILAV 720
RKYFQRITLY LMGKKYSPCA WEVVRAEIMR SFSFSTNLQK GLRRKDSGGP ALFKSSFPPG 780
SDAHKSEVAH RFKDLGEENF KALVLIAFAQ YLQQCPFEDH VKLVNEVTEF AKTCVADESA 840
ENCDKSLHTL FGDKLCTVAT LRETYGEMAD CCAKQEPERN ECFLQHKDDN PNLPRLVRPE 900
VDVMCTAFHD NEETFLKKYL YEIARRHPYF YAPELLFFAK RYKAAFTECC QAADKAACLL 960
PKLDELRDEG KASSAKQRLK CASLQKFGER AFKAWAVARL SQRFPKAEFA EVSKLVTDLT 1020
KVHTECCHGD LLECADDRAD LAKYICENQD SISSKLKECC EKPLLEKSHC IAEVENDEMP 1080

-continued

```
ADLPSLAADF VESKDVCKNY AEAKDVFLGM FLYEYARRHP DYSVVLLLRL AKTYETTLEK  1140
CCAAADPHEC YAKVFDEFKP LVEEPQNLIK QNCELFEQLG EYKFQNALLV RYTKKVPQVS  1200
TPTLVEVSRN LGKVGSKCCK HPEAKRMPCA EDYLSVVLNQ LCVLHEKTPV SDRVTKCCTE  1260
SLVNRRPCFS ALEVDETYVP KEFNAETFTF HADICTLSEK ERQIKKQTAL VELVKHKPKA  1320
TKEQLKAVMD DFAAFVEKCC KADDKETCFA EEGKKLVAAS QAALGL                 1366

SEQ ID NO: 561         moltype = AA  length = 426
FEATURE                Location/Qualifiers
source                 1..426
                       mol_type = protein
                       organism = synthetic construct
SEQUENCE: 561
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS CDLPQTHSLG NRRALILLAQ MRRISPFSCL KDRHDFEFPQ EEFDDKQFQK  180
AQAISVLHEM IQQTFNLFST KDSSAALDET LLDEFYIELD QQLNDLESCV MQEVGVIESP  240
LMYEDSILAV RKYFQRITLY LTEKKYSSCA WEVVRAEIMR SFSLSINLQK RLKSKESGGP  300
ALFKSSFPPG SEVQLVESGG GLVQPGNSLR LSCAASGFTF SKFGMSWVRQ APGKGLEWVS  360
SISGSGRDTL YAESVKGRFT ISRDNAKTTL YLQMNSLRPE DTAVYYCTIG GSLSVSSQGT  420
LVTVSS                                                             426

SEQ ID NO: 562         moltype = AA  length = 426
FEATURE                Location/Qualifiers
source                 1..426
                       mol_type = protein
                       organism = synthetic construct
SEQUENCE: 562
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS CDLPQTHSLG NRRALILLAQ MGRISHFSCL KDRYDFGFPQ EVFDGNQFQK  180
AQAISAFHEM IQQTFNLFST KDSSAAWDET LLDKFYIELF QQLNDLEACV TQEVGVEEIA  240
LMNEDSILAV RKYFQRITLY LMGKKYSPCA WEVVRAEIMR SFSFSTNLQK GLRRKDSGGP  300
ALFKSSFPPG SEVQLVESGG GLVQPGNSLR LSCAASGFTF SKFGMSWVRQ APGKGLEWVS  360
SISGSGRDTL YAESVKGRFT ISRDNAKTTL YLQMNSLRPE DTAVYYCTIG GSLSVSSQGT  420
LVTVSS                                                             426

SEQ ID NO: 563         moltype = AA  length = 421
FEATURE                Location/Qualifiers
source                 1..421
                       mol_type = protein
                       organism = synthetic construct
SEQUENCE: 563
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS INYKQLQLQE RTNIRKCQEL LEQLNGKINL TYRADFKIPM EMTEKMQKSY  180
TAFAIQEMLQ NVFLVFRNNF SSTGWNETIV VRLLDELHQQ TVFLKTVLEE KQEERLTWEM  240
SSTALHLKSY YWRVQRYLKL MKYNSYAWMV VRAEIFRNFL IIRRLTRNFQ NSGGPGPAGL  300
YAQPGSEVQL VESGGGLVQP GNSLRLSCAA SGFTFSKFGM SWVRQAPGKG LEWVSSISGS  360
GRDTLYAESV KGRFTISRDN AKTTLYLQMN SLRPEDTAVY YCTIGGSLSV SSQGTLVTVS  420
S                                                                  421

SEQ ID NO: 564         moltype = AA  length = 421
FEATURE                Location/Qualifiers
source                 1..421
                       mol_type = protein
                       organism = synthetic construct
SEQUENCE: 564
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS INYKQLQLQE RTNIRKCQEL LEQLNGKINL TYRADFKIPM EMTEKMQKSY  180
TAFAIQEMLQ NVFLVFRNNF SSTGWNETIV VRLLDELHQQ TVFLKTVLEE KQEERLTWEM  240
SSTALHLKSY YWRVQRYLKL MKYNSYAWMV VRAEIFRNFL IIRRLTRNFQ NSGGPALFKS  300
SFPPGSEVQL VESGGGLVQP GNSLRLSCAA SGFTFSKFGM SWVRQAPGKG LEWVSSISGS  360
GRDTLYAESV KGRFTISRDN AKTTLYLQMN SLRPEDTAVY YCTIGGSLSV SSQGTLVTVS  420
S                                                                  421

SEQ ID NO: 565         moltype = AA  length = 421
FEATURE                Location/Qualifiers
source                 1..421
                       mol_type = protein
                       organism = synthetic construct
SEQUENCE: 565
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS INYKQLQLQE RTNIRKSQEL LEQLNGKINL TYRADFKIPM EMTEKMQKSY  180
TAFAIQEMLQ NVFLVFRNNF SSTGWNETIV VRLLDELHQQ TVFLKTVLEE KQEERLTWEM  240
SSTALHLKSY YWRVQRYLKL MKYNSYAWMV VRAEIFRNFL IIRRLTRNFQ NSGGPGPAGL  300
YAQPGSEVQL VESGGGLVQP GNSLRLSCAA SGFTFSKFGM SWVRQAPGKG LEWVSSISGS  360
GRDTLYAESV KGRFTISRDN AKTTLYLQMN SLRPEDTAVY YCTIGGSLSV SSQGTLVTVS  420
```

```
S                                                                421

SEQ ID NO: 566         moltype = AA  length = 421
FEATURE                Location/Qualifiers
source                 1..421
                       mol_type = protein
                       organism = synthetic construct
SEQUENCE: 566
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS INYKQLQLQE RTNIRKSQEL LEQLNGKINL TYRADFKIPM EMTEKMQKSY  180
TAFAIQEMLQ NVFLVFRNNF SSTGWNETIV VRLLDELHQQ TVFLKTVLEE KQEERLTWEM  240
SSTALHLKSY YWRVQRYLKL MKYNSYAWMV VRAEIFRNFL IIRRLTRNFQ NSGGPALFKS  300
SFPPGSEVQL VESGGGLVQP GNSLRLSCAA SGFTFSKFGM SWVRQAPGKG LEWVSSISGS  360
GRDTLYAESV KGRFTISRDN AKTTLYLQMN SLRPEDTAVY YCTIGGSLSV SSQGTLVTVS  420
S                                                                421

SEQ ID NO: 567         moltype = AA  length = 426
FEATURE                Location/Qualifiers
source                 1..426
                       mol_type = protein
                       organism = synthetic construct
SEQUENCE: 567
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS MSYNLLGFLQ RSSNFQCQKL LWQLNGRLEY CLKDRMNFDI PEEIKQLQQF  180
QKEDAALTIY EMLQNIFAIF RQDSSSTGWN ETIVENLLAN VYHQINHLKT VLEEKLEKED  240
FTRGKLMSSL HLKRYYGRIL HYLKAKEYSH CAWTIVRVEI LRNFYFINRL TGYLRNSGGP  300
GPAGLYAQPG SEVQLVESGG GLVQPGNSLR LSCAASGFTF SKFGMSWVRQ APGKGLEWVS  360
SISGSGRDTL YAESVKGRFT ISRDNAKTTL YLQMNSLRPE DTAVYYCTIG GSLSVSSQGT  420
LVTVSS                                                           426

SEQ ID NO: 568         moltype = AA  length = 426
FEATURE                Location/Qualifiers
source                 1..426
                       mol_type = protein
                       organism = synthetic construct
SEQUENCE: 568
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS MSYNLLGFLQ RSSNFQCQKL LWQLNGRLEY CLKDRMNFDI PEEIKQLQQF  180
QKEDAALTIY EMLQNIFAIF RQDSSSTGWN ETIVENLLAN VYHQINHLKT VLEEKLEKED  240
FTRGKLMSSL HLKRYYGRIL HYLKAKEYSH CAWTIVRVEI LRNFYFINRL TGYLRNSGGP  300
ALFKSSFPPG SEVQLVESGG GLVQPGNSLR LSCAASGFTF SKFGMSWVRQ APGKGLEWVS  360
SISGSGRDTL YAESVKGRFT ISRDNAKTTL YLQMNSLRPE DTAVYYCTIG GSLSVSSQGT  420
LVTVSS                                                           426

SEQ ID NO: 569         moltype = AA  length = 426
FEATURE                Location/Qualifiers
source                 1..426
                       mol_type = protein
                       organism = synthetic construct
SEQUENCE: 569
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS MSYNLLGFLQ RSSNFQSQKL LWQLNGRLEY CLKDRMNFDI PEEIKQLQQF  180
QKEDAALTIY EMLQNIFAIF RQDSSSTGWN ETIVENLLAN VYHQINHLKT VLEEKLEKED  240
FTRGKLMSSL HLKRYYGRIL HYLKAKEYSH CAWTIVRVEI LRNFYFINRL TGYLRNSGGP  300
GPAGLYAQPG SEVQLVESGG GLVQPGNSLR LSCAASGFTF SKFGMSWVRQ APGKGLEWVS  360
SISGSGRDTL YAESVKGRFT ISRDNAKTTL YLQMNSLRPE DTAVYYCTIG GSLSVSSQGT  420
LVTVSS                                                           426

SEQ ID NO: 570         moltype = AA  length = 426
FEATURE                Location/Qualifiers
source                 1..426
                       mol_type = protein
                       organism = synthetic construct
SEQUENCE: 570
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS MSYNLLGFLQ RSSNFQSQKL LWQLNGRLEY CLKDRMNFDI PEEIKQLQQF  180
QKEDAALTIY EMLQNIFAIF RQDSSSTGWN ETIVENLLAN VYHQINHLKT VLEEKLEKED  240
FTRGKLMSSL HLKRYYGRIL HYLKAKEYSH CAWTIVRVEI LRNFYFINRL TGYLRNSGGP  300
ALFKSSFPPG SEVQLVESGG GLVQPGNSLR LSCAASGFTF SKFGMSWVRQ APGKGLEWVS  360
SISGSGRDTL YAESVKGRFT ISRDNAKTTL YLQMNSLRPE DTAVYYCTIG GSLSVSSQGT  420
LVTVSS                                                           426

SEQ ID NO: 571         moltype = AA  length = 167
FEATURE                Location/Qualifiers
```

```
source                  1..167
                        mol_type = protein
                        organism = synthetic construct
SEQUENCE: 571
INYKQLQLQE RTNIRKCQEL LEQLNGKINL TYRADFKIPM EMTEKMQKSY TAFAIQEMLQ  60
NVFLVFRNNF SSTGWNETIV VRLLDELHQQ TVFLKTVLEE KQEERLTWEM SSTALHLKSY  120
YWRVQRYLKL MKYNSYAWMV VRAEIFRNFL IIRRLTRNFQ NHHHHHH                167

SEQ ID NO: 572          moltype = AA  length = 167
FEATURE                 Location/Qualifiers
source                  1..167
                        mol_type = protein
                        organism = synthetic construct
SEQUENCE: 572
INYKQLQLQE RTNIRKSQEL LEQLNGKINL TYRADFKIPM EMTEKMQKSY TAFAIQEMLQ  60
NVFLVFRNNF SSTGWNETIV VRLLDELHQQ TVFLKTVLEE KQEERLTWEM SSTALHLKSY  120
YWRVQRYLKL MKYNSYAWMV VRAEIFRNFL IIRRLTRNFQ NHHHHHH                167

SEQ ID NO: 573          moltype = AA  length = 172
FEATURE                 Location/Qualifiers
source                  1..172
                        mol_type = protein
                        organism = synthetic construct
SEQUENCE: 573
MSYNLLGFLQ RSSNFQCQKL LWQLNGRLEY CLKDRMNFDI PEEIKQLQQF QKEDAALTIY  60
EMLQNIFAIF RQDSSSTGWN ETIVENLLAN VYHQINHLKT VLEEKLEKED FTRGKLMSSL  120
HLKRYYGRIL HYLKAKEYSH CAWTIVRVEI LRNFYFINRL TGYLRNHHHH HH          172

SEQ ID NO: 574          moltype = AA  length = 172
FEATURE                 Location/Qualifiers
source                  1..172
                        mol_type = protein
                        organism = synthetic construct
SEQUENCE: 574
MSYNLLGFLQ RSSNFQSQKL LWQLNGRLEY CLKDRMNFDI PEEIKQLQQF QKEDAALTIY  60
EMLQNIFAIF RQDSSSTGWN ETIVENLLAN VYHQINHLKT VLEEKLEKED FTRGKLMSSL  120
HLKRYYGRIL HYLKAKEYSH CAWTIVRVEI LRNFYFINRL TGYLRNHHHH HH          172

SEQ ID NO: 575          moltype = AA  length = 426
FEATURE                 Location/Qualifiers
source                  1..426
                        mol_type = protein
                        organism = synthetic construct
SEQUENCE: 575
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS MSYNLLGFLQ RSSNFQCQKL LWQLNGRLEY CLKDRMNFDI PEEIKQLQQF  180
QKEDAALTIY EMLQNIFAIF RQDSSSTGWQ ETIVENLLAN VYHQINHLKT VLEEKLEKED  240
FTRGKLMSSL HLKRYYGRIL HYLKAKEYSH CAWTIVRVEI LRNFYFINRL TGYLRNSGGP  300
GPAGLYAQPG SEVQLVESGG GLVQPGNSLR LSCAASGFTF SKFGMSWVRQ APGKGLEWVS  360
SISGSGRDTL YAESVKGRFT ISRDNAKTTL YLQMNSLRPE DTAVYYCTIG GSLSVSSQGT  420
LVTVSS                                                             426

SEQ ID NO: 576          moltype = AA  length = 426
FEATURE                 Location/Qualifiers
source                  1..426
                        mol_type = protein
                        organism = synthetic construct
SEQUENCE: 576
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS MSYNLLGFLQ RSSNFQSQKL LWQLNGRLEY CLKDRMNFDI PEEIKQLQQF  180
QKEDAALTIY EMLQNIFAIF RQDSSSTGWQ ETIVENLLAN VYHQINHLKT VLEEKLEKED  240
FTRGKLMSSL HLKRYYGRIL HYLKAKEYSH CAWTIVRVEI LRNFYFINRL TGYLRNSGGP  300
GPAGLYAQPG SEVQLVESGG GLVQPGNSLR LSCAASGFTF SKFGMSWVRQ APGKGLEWVS  360
SISGSGRDTL YAESVKGRFT ISRDNAKTTL YLQMNSLRPE DTAVYYCTIG GSLSVSSQGT  420
LVTVSS                                                             426

SEQ ID NO: 577          moltype = AA  length = 172
FEATURE                 Location/Qualifiers
source                  1..172
                        mol_type = protein
                        organism = synthetic construct
SEQUENCE: 577
MSYNLLGFLQ RSSNFQCQKL LWQLNGRLEY CLKDRMNFDI PEEIKQLQQF QKEDAALTIY  60
EMLQNIFAIF RQDSSSTGWQ ETIVENLLAN VYHQINHLKT VLEEKLEKED FTRGKLMSSL  120
HLKRYYGRIL HYLKAKEYSH CAWTIVRVEI LRNFYFINRL TGYLRNHHHH HH          172

SEQ ID NO: 578          moltype = AA  length = 172
```

```
FEATURE                Location/Qualifiers
source                 1..172
                       mol_type = protein
                       organism = synthetic construct
SEQUENCE: 578
MSYNLLGFLQ RSSNFQSQKL LWQLNGRLEY CLKDRMNFDI PEEIKQLQQF QKEDAALTIY  60
EMLQNIFAIF RQDSSSTGWQ ETIVENLLAN VYHQINHLKT VLEEKLEKED FTRGKLMSSL  120
HLKRYYGRIL HYLKAKEYSH CAWTIVRVEI LRNFYFINRL TGYLRNHHHH HH          172

SEQ ID NO: 579         moltype = AA  length = 528
FEATURE                Location/Qualifiers
source                 1..528
                       mol_type = protein
                       organism = synthetic construct
SEQUENCE: 579
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGGG GSGGGPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPGGG  300
GSGGGPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSASTKG PSVFPLAPSS KSTSGGTAAL GCLVKDYFPE PVTVSWNSGA LTSGVHTFPA  480
VLQSSGLYSL SSVVTVPSSS LGTQTYICNV NHKPSNTKVD KRVEPKSC              528

SEQ ID NO: 580         moltype = AA  length = 528
FEATURE                Location/Qualifiers
source                 1..528
                       mol_type = protein
                       organism = synthetic construct
SEQUENCE: 580
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSGGGGSGG  300
GGSGGGGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSASTKG PSVFPLAPSS KSTSGGTAAL GCLVKDYFPE PVTVSWNSGA LTSGVHTFPA  480
VLQSSGLYSL SSVVTVPSSS LGTQTYICNV NHKPSNTKVD KRVEPKSC              528

SEQ ID NO: 581         moltype = AA  length = 528
FEATURE                Location/Qualifiers
source                 1..528
                       mol_type = protein
                       organism = synthetic construct
SEQUENCE: 581
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSGGGGSGG  300
GGSGGGGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSASTKG PSVFPLAPSS KSTSGGTAAL GCLVKDYFPE PVTVSWNSGA LTSGVHTFPA  480
VLQSSGLYSL SSVVTVPSSS LGTQTYICNV NHKPSNTKVD KRVEPKSC              528

SEQ ID NO: 582         moltype = AA  length = 528
FEATURE                Location/Qualifiers
source                 1..528
                       mol_type = protein
                       organism = synthetic construct
SEQUENCE: 582
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPALF KSSFPPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSGGGGSGG  300
GGSGGGGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSASTKG PSVFPLAPSS KSTSGGTAAL GCLVKDYFPE PVTVSWNSGA LTSGVHTFPA  480
VLQSSGLYSL SSVVTVPSSS LGTQTYICNV NHKPSNTKVD KRVEPKSC              528

SEQ ID NO: 583         moltype = AA  length = 226
FEATURE                Location/Qualifiers
source                 1..226
                       mol_type = protein
                       organism = synthetic construct
SEQUENCE: 583
```

```
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGQG TTVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKRVEPKSC HHHHHH                226

SEQ ID NO: 584         moltype = AA  length = 269
FEATURE                Location/Qualifiers
source                 1..269
                       mol_type = protein
                       organism = synthetic construct
SEQUENCE: 584
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSHHHHHH                                   269

SEQ ID NO: 585         moltype = AA  length = 137
FEATURE                Location/Qualifiers
source                 1..137
                       mol_type = protein
                       organism = synthetic construct
SEQUENCE: 585
QVQLQESGGG LVQTGGSLRL SCTTSGTIFS GYTMGWYRQA PGEQRELVAV ISGGGDTNYA  60
DSVKGRFTIS RDNTKDTMYL QMNSLKPEDT AVYYCYSREV TPPWKLYWGQ GTQVTVSSAA  120
AYPYDVPDYG SHHHHHH                                                137

SEQ ID NO: 586         moltype = AA  length = 137
FEATURE                Location/Qualifiers
source                 1..137
                       mol_type = protein
                       organism = synthetic construct
SEQUENCE: 586
QVQLQESGGG LVQEGGSLRL SCAASERIFS TDVMGWYRQA AEKQRELVAV VSARGTTNYL  60
DAVKGRFTIS RDNARNTLTL QMNDLKPEDT ASYYCYVRET TSPWRIYWGQ GTQVTVSSAA  120
AYPYDVPDYG SHHHHHH                                                137

SEQ ID NO: 587         moltype = AA  length = 138
FEATURE                Location/Qualifiers
source                 1..138
                       mol_type = protein
                       organism = synthetic construct
SEQUENCE: 587
QVQLQESGGG LVQAGGSLRL SCAASGSIFS ANAMGWYRQA PGKQRELVAV ISSGGSTNYA  60
DSVKGRFTIS RDNAKNTVYL QMNSLKPEDT AVYYCMYSGS YYYTPNDYWG QGTQVTVSSA  120
AAYPYDVPDY GSHHHHHH                                               138

SEQ ID NO: 588         moltype = AA  length = 138
FEATURE                Location/Qualifiers
source                 1..138
                       mol_type = protein
                       organism = synthetic construct
SEQUENCE: 588
EVQLLESGGG LVQPGGSLRL SCAASGSIFS ANAMGWYRQA PGKQRELVAV ISSGGSTNYA  60
DSVKGRFTIS RDNSKNTVYL QMNSLRAEDT AVYYCMYSGS YYYTPNDYWG QGTLVTVSSA  120
AAYPYDVPDY GSHHHHHH                                               138

SEQ ID NO: 589         moltype = AA  length = 138
FEATURE                Location/Qualifiers
source                 1..138
                       mol_type = protein
                       organism = synthetic construct
SEQUENCE: 589
EVQLLESGGG LVQPGGSLRL SCAASGSIFS ANAMGWYRQA PGKGLELVAV ISSGGSTNYA  60
DSVKGRFTIS RDNSKNTVYL QMNSLRAEDT AVYYCMYSGS YYYTPNDYWG QGTLVTVSSA  120
AAYPYDVPDY GSHHHHHH                                               138

SEQ ID NO: 590         moltype = AA  length = 138
FEATURE                Location/Qualifiers
source                 1..138
                       mol_type = protein
                       organism = synthetic construct
SEQUENCE: 590
EVQLLESGGG LVQPGGSLRL SCAASGSIFS ANAMGWVRQA PGKGLEWVSV ISSGGSTNYA  60
DSVKGRFTIS RDNSKNTLYL QMNSLRAEDT AVYYCMYSGS YYYTPNDYWG QGTLVTVSSA  120
AAYPYDVPDY GSHHHHHH                                               138

SEQ ID NO: 591         moltype = AA  length = 138
FEATURE                Location/Qualifiers
```

```
source                  1..138
                        mol_type = protein
                        organism = synthetic construct
SEQUENCE: 591
QVQLLESGGG LVQPGGSLRL SCAASGSIFS ANAMGWYRQA PGKQRELVAV ISSGGSTNYA  60
DSVKGRFTIS RDNSKNTVYL QMNSLRAEDT AVYYCMYSGS YYYTPNDYWG QGTLVTVSSA  120
AAYPYDVPDY GSHHHHHH                                                138

SEQ ID NO: 592          moltype = AA  length = 138
FEATURE                 Location/Qualifiers
source                  1..138
                        mol_type = protein
                        organism = synthetic construct
SEQUENCE: 592
EVQLLESGGG LVQPGGSLRL SCAASGSIFS ANAMGWYRQA PGKGRELVAV ISSGGSTNYA  60
DSVKGRFTIS RDNSKNTVYL QMNSLRAEDT AVYYCMYSGS YYYTPNDYWG QGTLVTVSSA  120
AAYPYDVPDY GSHHHHHH                                                138

SEQ ID NO: 593          moltype = AA  length = 138
FEATURE                 Location/Qualifiers
source                  1..138
                        mol_type = protein
                        organism = synthetic construct
SEQUENCE: 593
QVQLLESGGG LVQAGGSLRL SCAASGSIFS ANAMGWYRQA PGKQRELVAV ISSGGSTNYA  60
DSVKGRFTIS RDNSKNTVYL QMNSLRAEDT AVYYCMYSGS YYYTPNDYWG QGTLVTVSSA  120
AAYPYDVPDY GSHHHHHH                                                138

SEQ ID NO: 594          moltype = AA  length = 137
FEATURE                 Location/Qualifiers
source                  1..137
                        mol_type = protein
                        organism = synthetic construct
SEQUENCE: 594
EVQLLESGGG LVQPGGSLRL SCAASERIFS TDVMGWYRQA PGKQRELVAV VSARGTTNYL  60
DAVKGRFTIS RDNSKNTLYL QMNSLRAEDT AVYYCYVRET TSPWRIYWGQ GTLVTVSSAA  120
AYPYDVPDYG SHHHHHH                                                 137

SEQ ID NO: 595          moltype = AA  length = 137
FEATURE                 Location/Qualifiers
source                  1..137
                        mol_type = protein
                        organism = synthetic construct
SEQUENCE: 595
EVQLLESGGG LVQPGGSLRL SCAASERIFS TDVMGWYRQA PGKGLELVAV VSARGTTNYL  60
DAVKGRFTIS RDNSKNTLYL QMNSLRAEDT AVYYCYVRET TSPWRIYWGQ GTLVTVSSAA  120
AYPYDVPDYG SHHHHHH                                                 137

SEQ ID NO: 596          moltype = AA  length = 137
FEATURE                 Location/Qualifiers
source                  1..137
                        mol_type = protein
                        organism = synthetic construct
SEQUENCE: 596
EVQLLESGGG LVQPGGSLRL SCAASERIFS TDVMGWVRQA PGKGLEWVSV VSARGTTNYL  60
DAVKGRFTIS RDNSKNTLYL QMNSLRAEDT AVYYCYVRET TSPWRIYWGQ GTLVTVSSAA  120
AYPYDVPDYG SHHHHHH                                                 137

SEQ ID NO: 597          moltype = AA  length = 137
FEATURE                 Location/Qualifiers
source                  1..137
                        mol_type = protein
                        organism = synthetic construct
SEQUENCE: 597
QVQLLESGGG LVQPGGSLRL SCAASERIFS TDVMGWYRQA PGKQRELVAV VSARGTTNYL  60
DAVKGRFTIS RDNSKNTLYL QMNSLRAEDT AVYYCYVRET TSPWRIYWGQ GTLVTVSSAA  120
AYPYDVPDYG SHHHHHH                                                 137

SEQ ID NO: 598          moltype = AA  length = 137
FEATURE                 Location/Qualifiers
source                  1..137
                        mol_type = protein
                        organism = synthetic construct
SEQUENCE: 598
EVQLLESGGG LVQPGGSLRL SCAASERIFS TDVMGWYRQA PGKGRELVAV VSARGTTNYL  60
DSVKGRFTIS RDNSKNTLYL QMNSLRAEDT AVYYCYVRET TSPWRIYWGQ GTLVTVSSAA  120
AYPYDVPDYG SHHHHHH                                                 137

SEQ ID NO: 599          moltype = AA  length = 137
```

-continued

```
FEATURE                 Location/Qualifiers
source                  1..137
                        mol_type = protein
                        organism = synthetic construct
SEQUENCE: 599
QVQLLESGGG LVQEGGSLRL SCAASERIFS TDVMGWYRQA AGKQRELVAV VSARGTTNYL  60
DAVKGRFTIS RDNSKNTLYL QMNSLRAEDT ASYYCYVRET TSPWRIYWGQ GTLVTVSSAA  120
AYPYDVPDYG SHHHHHH                                                 137

SEQ ID NO: 600          moltype = AA  length = 137
FEATURE                 Location/Qualifiers
source                  1..137
                        mol_type = protein
                        organism = synthetic construct
SEQUENCE: 600
EVQLLESGGG LVQPGGSLRL SCAASERIFS TDVMGWYRQA PGKGLELVAV VSARGTTNYL  60
DSVKGRFTIS RDNSKNTLYL QMNSLRAEDT AVYYCYVRET TSPWRIYWGQ GTLVTVSSAA  120
AYPYDVPDYG SHHHHHH                                                 137

SEQ ID NO: 601          moltype = AA  length = 137
FEATURE                 Location/Qualifiers
source                  1..137
                        mol_type = protein
                        organism = synthetic construct
SEQUENCE: 601
EVQLLESGGG LVQPGGSLRL SCATSGTIFS GYTMGWYRQA PGKQRELVAV ISGGGDTNYA  60
DSVKGRFTIS RDNSKDTMYL QMNSLRAEDT AVYYCYSREV TPPWKLYWGQ GTLVTVSSAA  120
AYPYDVPDYG SHHHHHH                                                 137

SEQ ID NO: 602          moltype = AA  length = 137
FEATURE                 Location/Qualifiers
source                  1..137
                        mol_type = protein
                        organism = synthetic construct
SEQUENCE: 602
EVQLLESGGG LVQPGGSLRL SCATSGTIFS GYTMGWYRQA PGKGLELVAV ISGGGDTNYA  60
DSVKGRFTIS RDNSKDTMYL QMNSLRAEDT AVYYCYSREV TPPWKLYWGQ GTLVTVSSAA  120
AYPYDVPDYG SHHHHHH                                                 137

SEQ ID NO: 603          moltype = AA  length = 137
FEATURE                 Location/Qualifiers
source                  1..137
                        mol_type = protein
                        organism = synthetic construct
SEQUENCE: 603
EVQLLESGGG LVQPGGSLRL SCAASGTIFS GYTMGWVRQA PGKGLEWVSV ISGGGDTNYA  60
DSVKGRFTIS RDNSKNTLYL QMNSLRAEDT AVYYCYSREV TPPWKLYWGQ GTLVTVSSAA  120
AYPYDVPDYG SHHHHHH                                                 137

SEQ ID NO: 604          moltype = AA  length = 137
FEATURE                 Location/Qualifiers
source                  1..137
                        mol_type = protein
                        organism = synthetic construct
SEQUENCE: 604
QVQLLESGGG LVQPGGSLRL SCATSGTIFS GYTMGWYRQA PGKQRELVAV ISGGGDTNYA  60
DSVKGRFTIS RDNSKDTMYL QMNSLRAEDT AVYYCYSREV TPPWKLYWGQ GTLVTVSSAA  120
AYPYDVPDYG SHHHHHH                                                 137

SEQ ID NO: 605          moltype = AA  length = 137
FEATURE                 Location/Qualifiers
source                  1..137
                        mol_type = protein
                        organism = synthetic construct
SEQUENCE: 605
EVQLLESGGG LVQPGGSLRL SCATSGTIFS GYTMGWYRQA PGKQRELVAV ISGGGDTNYA  60
DSVKGRFTIS RDNSKNTMYL QMNSLRAEDT AVYYCYSREV TPPWKLYWGQ GTLVTVSSAA  120
AYPYDVPDYG SHHHHHH                                                 137

SEQ ID NO: 606          moltype = AA  length = 137
FEATURE                 Location/Qualifiers
source                  1..137
                        mol_type = protein
                        organism = synthetic construct
SEQUENCE: 606
EVQLLESGGG LVQPGGSLRL SCATSGTIFS GYTMGWYRQA PGKGRELVAV ISGGGDTNYA  60
DSVKGRFTIS RDNSKNTMYL QMNSLRAEDT AVYYCYSREV TPPWKLYWGQ GTLVTVSSAA  120
AYPYDVPDYG SHHHHHH                                                 137
```

```
SEQ ID NO: 607          moltype = AA  length = 137
FEATURE                 Location/Qualifiers
source                  1..137
                        mol_type = protein
                        organism = synthetic construct
SEQUENCE: 607
QVQLLESGGG LVQTGGSLRL SCATSGTIFS GYTMGWYRQA PGKQRELVAV ISGGGDTNYA  60
DSVKGRFTIS RDNSKDTMYL QMNSLRAEDT AVYYCYSREV TPPWKLYWGQ GTLVTVSSAA  120
AYPYDVPDYG SHHHHHH                                                 137

SEQ ID NO: 608          moltype = AA  length = 137
FEATURE                 Location/Qualifiers
source                  1..137
                        mol_type = protein
                        organism = synthetic construct
SEQUENCE: 608
EVQLLESGGG LVQPGGSLRL SCATSGTIFS GYTMGWYRQA PGKGLELVAV ISGGGDTNYA  60
DSVKGRFTIS RDNSKNTMYL QMNSLRAEDT AVYYCYSREV TPPWKLYWGQ GTLVTVSSAA  120
AYPYDVPDYG SHHHHHH                                                 137

SEQ ID NO: 609          moltype = AA  length = 8
FEATURE                 Location/Qualifiers
source                  1..8
                        mol_type = protein
                        organism = synthetic construct
SEQUENCE: 609
GPAGLYAQ                                                           8

SEQ ID NO: 610          moltype = AA  length = 8
FEATURE                 Location/Qualifiers
source                  1..8
                        mol_type = protein
                        organism = synthetic construct
SEQUENCE: 610
GPAGMKGL                                                           8

SEQ ID NO: 611          moltype = AA  length = 8
FEATURE                 Location/Qualifiers
source                  1..8
                        mol_type = protein
                        organism = synthetic construct
SEQUENCE: 611
PGGPAGIG                                                           8

SEQ ID NO: 612          moltype = AA  length = 8
FEATURE                 Location/Qualifiers
source                  1..8
                        mol_type = protein
                        organism = synthetic construct
SEQUENCE: 612
ALFKSSFP                                                           8

SEQ ID NO: 613          moltype = AA  length = 8
FEATURE                 Location/Qualifiers
source                  1..8
                        mol_type = protein
                        organism = synthetic construct
SEQUENCE: 613
ALFFSSPP                                                           8

SEQ ID NO: 614          moltype = AA  length = 8
FEATURE                 Location/Qualifiers
source                  1..8
                        mol_type = protein
                        organism = synthetic construct
SEQUENCE: 614
LAQRLRSS                                                           8

SEQ ID NO: 615          moltype = AA  length = 8
FEATURE                 Location/Qualifiers
source                  1..8
                        mol_type = protein
                        organism = synthetic construct
SEQUENCE: 615
LAQKLKSS                                                           8

SEQ ID NO: 616          moltype = AA  length = 30
FEATURE                 Location/Qualifiers
source                  1..30
```

```
                        mol_type = protein
                        organism = synthetic construct
SEQUENCE: 616
GALFKSSFPS GGGPAGLYAQ GGSGKGGSGK                                      30

SEQ ID NO: 617          moltype = AA  length = 30
FEATURE                 Location/Qualifiers
source                  1..30
                        mol_type = protein
                        organism = synthetic construct
SEQUENCE: 617
RGSGGGPAGL YAQGSGGGPA GLYAQGGSGK                                      30

SEQ ID NO: 618          moltype = AA  length = 30
FEATURE                 Location/Qualifiers
source                  1..30
                        mol_type = protein
                        organism = synthetic construct
SEQUENCE: 618
KGGGPAGLYA QGPAGLYAQG PAGLYAQGSR                                      30

SEQ ID NO: 619          moltype = AA  length = 30
FEATURE                 Location/Qualifiers
source                  1..30
                        mol_type = protein
                        organism = synthetic construct
SEQUENCE: 619
RGGPAGLYAQ GGPAGLYAQG GGPAGLYAQK                                      30

SEQ ID NO: 620          moltype = AA  length = 30
FEATURE                 Location/Qualifiers
source                  1..30
                        mol_type = protein
                        organism = synthetic construct
SEQUENCE: 620
KGGALFKSSF PGGPAGIGPL AQKLKSSGGS                                      30

SEQ ID NO: 621          moltype = AA  length = 30
FEATURE                 Location/Qualifiers
source                  1..30
                        mol_type = protein
                        organism = synthetic construct
SEQUENCE: 621
SGGPGGPAGI GALFKSSFPL AQKLKSSGGG                                      30

SEQ ID NO: 622          moltype = AA  length = 30
FEATURE                 Location/Qualifiers
source                  1..30
                        mol_type = protein
                        organism = synthetic construct
SEQUENCE: 622
RGPLAQKLKS SALFKSSFPG GPAGIGGGGK                                      30

SEQ ID NO: 623          moltype = AA  length = 30
FEATURE                 Location/Qualifiers
source                  1..30
                        mol_type = protein
                        organism = synthetic construct
SEQUENCE: 623
GGGALFKSSF PLAQKLKSSP GGPAGIGGGR                                      30

SEQ ID NO: 624          moltype = AA  length = 30
FEATURE                 Location/Qualifiers
source                  1..30
                        mol_type = protein
                        organism = synthetic construct
SEQUENCE: 624
RGPGGPAGIG PLAQKLKSSA LFKSSFPGGG                                      30

SEQ ID NO: 625          moltype = AA  length = 30
FEATURE                 Location/Qualifiers
source                  1..30
                        mol_type = protein
                        organism = synthetic construct
SEQUENCE: 625
RGGPLAQKLK SSPGGPAGIG ALFKSSFPGK                                      30

SEQ ID NO: 626          moltype = AA  length = 30
FEATURE                 Location/Qualifiers
```

```
source                  1..30
                        mol_type = protein
                        organism = synthetic construct
SEQUENCE: 626
RSGGPAGLYA QALFKSSFPL AQKLKSSGGG                                  30

SEQ ID NO: 627          moltype = AA  length = 30
FEATURE                 Location/Qualifiers
source                  1..30
                        mol_type = protein
                        organism = synthetic construct
SEQUENCE: 627
GGPLAQKLKS SALFKSSFPG PAGLYAQGGR                                  30

SEQ ID NO: 628          moltype = AA  length = 30
FEATURE                 Location/Qualifiers
source                  1..30
                        mol_type = protein
                        organism = synthetic construct
SEQUENCE: 628
GGALFKSSFP GPAGLYAQPL AQKLKSSGGK                                  30

SEQ ID NO: 629          moltype = AA  length = 30
FEATURE                 Location/Qualifiers
source                  1..30
                        mol_type = protein
                        organism = synthetic construct
SEQUENCE: 629
RGGALFKSSF PLAQKLKSSG PAGLYAQGGK                                  30

SEQ ID NO: 630          moltype = AA  length = 30
FEATURE                 Location/Qualifiers
source                  1..30
                        mol_type = protein
                        organism = synthetic construct
SEQUENCE: 630
RGGGPAGLYA QPLAQKLKSS ALFKSSFPGG                                  30

SEQ ID NO: 631          moltype = AA  length = 30
FEATURE                 Location/Qualifiers
source                  1..30
                        mol_type = protein
                        organism = synthetic construct
SEQUENCE: 631
SGPLAQKLKS SGPAGLYAQA LFKSSFPGSK                                  30

SEQ ID NO: 632          moltype = AA  length = 30
FEATURE                 Location/Qualifiers
source                  1..30
                        mol_type = protein
                        organism = synthetic construct
SEQUENCE: 632
KGGPGGPAGI GPLAQRLRSS ALFKSSFPGR                                  30

SEQ ID NO: 633          moltype = AA  length = 30
FEATURE                 Location/Qualifiers
source                  1..30
                        mol_type = protein
                        organism = synthetic construct
SEQUENCE: 633
KSGPGGPAGI GALFFSSPPL AQKLKSSGGR                                  30

SEQ ID NO: 634          moltype = AA  length = 30
FEATURE                 Location/Qualifiers
source                  1..30
                        mol_type = protein
                        organism = synthetic construct
SEQUENCE: 634
SGGFPRSGGS FNPRTFGSKR KRRGSRGGGG                                  30

SEQ ID NO: 635          moltype = AA  length = 934
FEATURE                 Location/Qualifiers
source                  1..934
                        mol_type = protein
                        organism = synthetic construct
SEQUENCE: 635
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPA  120
LFKSSFPPGS IWELKKDVYV VELDWYPDAP GEMVVLTCDT PEEDGITWTL DQSSEVLGSG  180
```

```
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRNLPVATPD PGMFPCLHHS QNLLRAVSNM  480
LQKARQTLEF YPCTSEEIDH EDITKDKTST VEACLPLELT KNESCLNSRE TSFITNGSCL  540
ASRKTSFMMA LCLSSIYEDL KMYQVEFKTM NAKLLMDPKR QIFLDQNMLA VIDELMQALN  600
FNSETVPQKS SLEEPDFYKT KIKLCILLHA FRIRAVTIDR VMSYLNASSG GPALFKSSFP  660
PGSGGGGSGG GGSGGGGSGG GGSGGGGSGG GGSQSVLTQP PSVSGAPGQR VTISCSGSRS  720
NIGSETVKWY QQLPGTAPKL LIYYNDQRPS GVPDRFSGSK SGTSASLAIT GLQAEDEADY  780
YCQSYDRYTH PALLFGTGTK VTVLGGGGSG GGGSGGGGSQ VQLVESGGGV VQPGRSLRLS  840
CAASGFTFSS YGMHWVRQAP GKGLEWVAFI RYEGSNKYYA ESVKGRFTIS RDNSKNTLYL  900
QMNSLRAEDT AVYYCKTHGS HDNWGQGTMV TVSS                              934

SEQ ID NO: 636          moltype = AA  length = 553
FEATURE                 Location/Qualifiers
source                  1..553
                        mol_type = protein
                        organism = synthetic construct
SEQUENCE: 636
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSGGGGSGG  300
GGSGGGGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKASQNVG TNVGWYQQKP  480
GKAPKALIYS ASFRYSGVPS RFSGSGSGTD FTLTISSLQP EDFATYYCQQ YYTYPYTFGG  540
GTKVEIKHHH HHH                                                     553

SEQ ID NO: 637          moltype = AA  length = 665
FEATURE                 Location/Qualifiers
source                  1..665
                        mol_type = protein
                        organism = synthetic construct
SEQUENCE: 637
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSVP RDCGCKPCIC TVPEVSSVFI FPPKPKDVLT  180
ITLTPKVTCV VVDISKDDPE VQFSWFVDDV EVHTAQTQPR EEQFNSTFRS VSELPIMHQD  240
WLNGKEFKCR VNSAAFPAPI EKTISKTKGR PKAPQVYTIP PPKEQMAKDK VSLTCMITDF  300
FPEDITVEWQ WNGQPAENYK NTQPIMDTDG SYFVYSKLNV QKSNWEAGNT FTCSVLHEGL  360
HNHHTEKSLS HSPGKGGGGS GGGGSGGGGS GGGGSGGGGS GGGGSSGGPG PAGMKGLPGS  420
EVQLVESGGG LVQPGGSLRL SCAASGFTFS SYTLAWVRQA PGKGLEWVAA IDSSSYTYSP  480
DTVRGRFTIS RDNAKNSLYL QMNSLRAEDT AVYYCARDSN WDALDYWGQG TTVTVSSGGG  540
GSGGGGSGGG GSDIQMTQSP SSLSASVGDR VTITCKASQN VGTNVGWYQQ KPGKAPKALI  600
YSASFRYSGV PSRFSGSGSG TDFTLTISSL QPEDFATYYC QQYYTYPYTF GGGTKVEIKH  660
HHHHH                                                              665

SEQ ID NO: 638          moltype = AA  length = 665
FEATURE                 Location/Qualifiers
source                  1..665
                        mol_type = protein
                        organism = synthetic construct
SEQUENCE: 638
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSGG GGSGGGGSGG GGSGGGGSGG GGSGGGGSEV  180
QLVESGGGLV QPGGSLRLSC AASGFTFSSY TLAWVRQAPG KGLEWVAAID SSSYTYSPDT  240
VRGRFTISRD NAKNSLYLQM NSLRAEDTAV YYCARDSNWD ALDYWGQGTT VTVSSGGGGS  300
GGGGSGGGGS DIQMTQSPSS LSASVGDRVT ITCKASQNVG TNVGWYQQKP GKAPKALIYS  360
ASFRYSGVPS RFSGSGSGTD FTLTISSLQP EDFATYYCQQ YYTYPYTFGG GTKVEIKSGG  420
PGPAGMKGLP GSVPRDCGCK PCICTVPEVS SVFIFPPKPK DVLTITLTPK VTCVVVDISK  480
DDPEVQFSWF VDDVEVHTAQ TQPREEQFNS TFRSVSELPI MHQDWLNGKE FKCRVNSAAF  540
PAPIEKTISK TKGRPKAPQV YTIPPPKEQM AKDKVSLTCM ITDFFPEDIT VEWQWNGQPA  600
ENYKNTQPIM DTDGSYFVYS KLNVQKSNWE AGNTFTCSVL HEGLHNHHTE KSLSHSPGKH  660
HHHHH                                                              665

SEQ ID NO: 639          moltype = AA  length = 558
FEATURE                 Location/Qualifiers
source                  1..558
                        mol_type = protein
                        organism = synthetic construct
SEQUENCE: 639
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTGGGSGGG SGGGSGGGSE VQLVESGGGL VQPGNSLRLS CAASGFTFSK  180
FGMSWVRQAP GKGLEWVSSI SGSGRDTLYA ESVKGRFTIS RDNAKTTLYL QMNSLRPEDT  240
```

-continued

```
AVYYCTIGGS LSVSSQGTLV TVSSGGGGSG GGGSGGGGSG GGGSGGGGSG GGGSSGGPGP  300
AGMKGLPGSE VQLVESGGGL VQPGGSLRLS CAASGFTFSS YTLAWVRQAP GKGLEWVAAI  360
DSSSYTYSPD TVRGRFTISR DNAKNSLYLQ MNSLRAEDTA VYYCARDSNW DALDYWGQGT  420
TVTVSSGGGG SGGGGSGGGG SDIQMTQSPS SLSASVGDRV TITCKASQNV GTNVGWYQQK  480
PGKAPKALIY SASFRYSGVP SRFSGSGSGT DFTLTISSLQ PEDFATYYCQ QYYTYPYTFG  540
GGTKVEIKHH HHHHEPEA                                                558

SEQ ID NO: 640         moltype = AA  length = 273
FEATURE                Location/Qualifiers
source                 1..273
                       mol_type = protein
                       organism = synthetic construct
SEQUENCE: 640
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GMKGLPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSHHHHHHE PEA                               273

SEQ ID NO: 641         moltype = AA  length = 659
FEATURE                Location/Qualifiers
source                 1..659
                       mol_type = protein
                       organism = synthetic construct
SEQUENCE: 641
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGLYAQP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGLYAQPGS  420
EVQLVESGGG LVQPGGSLRL SCAASGFTFS SYTLAWVRQA PGKGLEWVAA IDSSSYTYSP  480
DTVRGRFTIS RDNAKNSLYL QMNSLRAEDT AVYYCARDSN WDALDYWGQG TTVTVSSSGG  540
PGPAGLYAQP GSDIQMTQSP SSLSASVGDR VTITCKAREK LWSAVAWYQQ KPGKAPKSLI  600
YSASFRYSGV PSRFSGSGSG TDFTLTISSL QPEDFATYYC QQYYTYPYTF GGGTKVEIK   659

SEQ ID NO: 642         moltype = AA  length = 659
FEATURE                Location/Qualifiers
source                 1..659
                       mol_type = protein
                       organism = synthetic construct
SEQUENCE: 642
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGLYAQP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGLYAQPGS  420
EVQLVESGGG LVQPGGSLRL SCAASGFTFS SYTLAWVRQA PGKGLEWVAA IDSSSYTYSP  480
DTVRGRFTIS RDNAKNSLYL QMNSLRAEDT AVYYCARDSN WDALDYWGQG TTVTVSSGGG  540
GSGGGGSGGG GSDIQMTQSP SSLSASVGDR VTITCKAREK LWSAVAWYQQ KPGKAPKSLI  600
YSASFRYSGV PSRFSGSGSG TDFTLTISSL QPEDFATYYC QQYYTYPYTF GGGTKVEIK   659

SEQ ID NO: 643         moltype = AA  length = 659
FEATURE                Location/Qualifiers
source                 1..659
                       mol_type = protein
                       organism = synthetic construct
SEQUENCE: 643
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGLYAQP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGLYAQPGS  420
EVQLVESGGG LVQPGGSLRL SCAASGFTFS SYTLAWVRQA PGKGLEWVAA IDSSSYTYSP  480
DTVRGRFTIS RDNAKNSLYL QMNSLRAEDT AVYYCARDSN WDALDYWGQG TTVTVSSSGG  540
PGPAGLYAQP GSDIQMTQSP SSLSASVGDR VTITCKVTEK VWGNVAWYQQ KPGKAPISLI  600
YSPSLRKSGV PSRFSGSGSG TDFTLTISSL QPEDFATYYC QQYYTYPYTF GGGTKVEIK   659

SEQ ID NO: 644         moltype = AA  length = 659
FEATURE                Location/Qualifiers
source                 1..659
                       mol_type = protein
                       organism = synthetic construct
SEQUENCE: 644
```

-continued

```
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGLYAQP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGLYAQPGS  420
EVQLVESGGG LVQPGGSLRL SCAASGFTFS SYTLAWVRQA PGKGLEWVAA IDSSSYTYSP  480
DTVRGRFTIS RDNAKNSLYL QMNSLRAEDT AVYYCARDSN WDALDYWGQG TTVTVSSGGG  540
GSGGGGSGGG GSDIQMTQSP SSLSASVGDR VTITCKVTEK VWGNVAWYQQ KPGKAPISLI  600
YSPSLRKSGV PSRFSGSGSG TDFTLTISSL QPEDFATYYC QQYYTYPYTF GGGTKVEIK   659

SEQ ID NO: 645         moltype = AA  length = 539
FEATURE                Location/Qualifiers
source                 1..539
                       mol_type = protein
                       organism = synthetic construct
SEQUENCE: 645
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGLYAQP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGLYAQPGS  420
EVQLLESGGG LVQPGGSLRL SCAASGSIFS ANAMGWYRQA PGKGLELVAV ISSGGSTNYA  480
DSVKGRFTIS RDNSKNTVYL QMNSLRAEDT AVYYCMYSGS YYYTPNDYWG QGTLVTVSS   539

SEQ ID NO: 646         moltype = AA  length = 538
FEATURE                Location/Qualifiers
source                 1..538
                       mol_type = protein
                       organism = synthetic construct
SEQUENCE: 646
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PGPAGLYAQP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPG PAGLYAQPGS  420
EVQLLESGGG LVQPGGSLRL SCAASERIFS TDVMGWYRQA PGKQRELVAV VSARGTTNYL  480
DAVKGRFTIS RDNSKNTLYL QMNSLRAEDT AVYYCYVRET TSPWRIYWGQ GTLVTVSS    538

SEQ ID NO: 647         moltype = AA  length = 930
FEATURE                Location/Qualifiers
source                 1..930
                       mol_type = protein
                       organism = synthetic construct
SEQUENCE: 647
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS IWELKKDVYV VELDWYPDAP GEMVVLTCDT PEEDGITWTL DQSSEVLGSG  180
KTLTIQVKEF GDAGQYTCHK GGEVLSHSLL LLHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGLYAQPGSG  660
GGGSGGGGSG GGGSGGGGSG GGGSGGGGSQ SVLTQPPSVS GAPGQRVTIS CSGSRSNIGS  720
NTVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYDG SNKYYADSVK GRFTISRDNS KNTLYLQMNS  900
LRAEDTAVYY CKTHGSHDNW GQGTMVTVSS                                   930
```

ACTIVATABLE CYTOKINE POLYPEPTIDES AND METHODS OF USE THEREOF

This application is a continuation of U.S. patent application Ser. No. 17/741,275, filed on May 10, 2022, which is a continuation of International Patent Application No. PCT/US2020/060624, filed on Nov. 14, 2020, which claims the benefit of U.S. Provisional Application No. 62/935,605, filed on Nov. 14, 2019, each of which are incorporated herein by reference.

SEQUENCE LISTING

The instant application contains a Sequence Listing which has been submitted electronically in XML format and is hereby incorporated by reference in its entirety. Said XML file, created on Sep. 20, 2022, is named 761146_300011_SL.xml and is 908,507 bytes in size.

BACKGROUND

The development of mature immunocompetent lymphoid cells from less-committed precursors, their subsequent antigen-driven immune responses, and the suppression of these and unwanted autoreactive responses are highly dependent and regulated by cytokines (including interleukin-2 [IL-2], IL-4, IL-7, IL-9, IL-15, and IL-21) that utilize receptors in the common γ-chain (γc) family (Rochman et al., 2009) and family members including IL-12, 18 and 23. IL-2 is essential for thymic development of Treg cells and critically regulates several key aspects of mature peripheral Treg and antigen-activated conventional T cells. Because of its potent T cell growth factor activity in vitro, IL-2 has been extensively studied in part because this activity offered a potential means to directly boost immunity, e.g., in cancer and AIDS-HIV patients, or a target to antagonize unwanted responses, e.g., transplantation rejection and autoimmune diseases. Although in vitro studies with IL-2 provided a strong rationale for these studies, the function of IL-2 in vivo is clearly much more complex as first illustrated in IL-2-deficient mice, where a rapid lethal autoimmune syndrome, not lack of immunity, was observed (Sadlack et al., 1993, 1995). Similar observations were later made when the gene encoding IL-2Rα (Il2ra) and IL-2Rβ (Il2rb) were individually ablated (Suzuki et al., 1995; Willerford et al., 1995).

The present invention refers to conditionally active and/or targeted cytokines for use in the treatment of cancer and other diseases dependent on immune up or down regulation. For example, the antitumoral activity of some cytokines is well known and described and some cytokines have already been used therapeutically in humans. Cytokines such as interleukin-2 (IL-2) and interferon α (IFNα) have shown positive antitumoral activity in patients with different types of tumors, such as kidney metastatic carcinoma, hairy cell leukemia, Kaposi sarcoma, melanoma, multiple myeloma, and the like. Other cytokines like IFNβ, the Tumor Necrosis Factor (TNF) α, TNFβ, IL-1, 4, 6, 12, 15 and the CSFs have shown a certain antitumoral activity on some types of tumors and therefore are the object of further studies.

SUMMARY

Provided herein are therapeutic proteins, nucleic acids (e.g., DNA, RNA, mRNA) that encode the proteins, and compositions and methods of using the proteins and nucleic acids for the treatment of a disease or disorder, such as proliferative disease, a tumorous disease, an inflammatory disease, an immunological disorder, an autoimmune disease, an infectious disease, a viral disease, an allergic reaction, a parasitic reaction, graft-versus-host disease and the like. In certain embodiments, the fusion protein the amino acid sequence of any one of SEQ ID NOs.: 193-271. Certain fusion proteins disclosed herein are referred to as ACP200-208, ACP211, ACP213-ACP215, ACP240-ACP245, ACP247, ACP284-ACP292, ACP296-ACP300, ACP302-ACP306, ACP309-ACP314, ACP336-ACP359, ACP371-ACP379, ACP383-ACP434, ACP439-ACP447, or ACP451-ACP471. This disclosure also relates to nucleic acids (e.g., DNA, RNA, mRNA) that encode the fusion proteins, methods of making fusion proteins, compositions comprising a fusion protein, as well as methods of using the fusion proteins to treat cancer including combination of two or more fusion proteins and one or more fusion protein in combination with another therapeutic agent.

The invention features fusion proteins that are conditionally active variants of a cytokine of interest. Cytokines of particular interest include IL-2, IL-12, and IFN. In one aspect, the full-length polypeptides of the invention have reduced or minimal cytokine-receptor activating activity even though they contain a functional cytokine polypeptide. Upon activation, e.g., by cleavage of a linker that joins a blocking moiety, e.g. a steric blocking polypeptide, in sequence to the active cytokine, the cytokine, e.g., IL-2, IL-7, IL-12, IL-15, IL-18, IL-21, IL-23, IFNalpha, IFNbeta, IFNgamma, TNFalpha, lymphotoxin, TGF-beta1, TGF-beta2, TGFbeta3, GM-CSF, CXCL10, CCL19, CCL20, CCL21 or functional fragment or mutein or functional variant or a subunit of any of the foregoing, can bind its receptor and effect signaling. If desired, the full-length polypeptides can include a blocking polypeptide moiety that also provides additional advantageous properties. For example, the full-length polypeptide can contain a blocking polypeptide moiety that also extends the serum half-life and/or targets the full-length polypeptide to a desired site of cytokine activity. Alternatively, the full-length fusion polypeptides can contain a serum half-life extension element and/or targeting domain that are distinct from the blocking polypeptide moiety. Preferably, the fusion protein contains at least one element or domain capable of extending in vivo circulating half-life. Preferably, this element is removed enzymatically in the desired body location (e.g. protease cleavage in the tumor microenvironment), restoring pharmacokinetic properties to the payload molecule (e.g. IL2, IL-12, IFNb or IFNa) substantially similar to the naturally occurring payload molecule. The fusion proteins may be targeted to a desired cell or tissue.

The fusion polypeptides typically comprise a cytokine polypeptide [A], a blocking moiety [D], optionally a half-life extension moiety [H], and a protease-cleavable polypeptide linker. The cytokine polypeptide and the blocking moiety and the optional half-life extension element when present are operably linked by the protease-cleavable polypeptide linker and the fusion polypeptide has attenuated cytokine receptor activating activity, e.g., the cytokine-receptor activating activity of the fusion polypeptide is at least about 10× less than the cytokine receptor activating activity of the polypeptide that contains the cytokine polypeptide that is produced by cleavage of the protease cleavable linker. Some preferred fusion polypeptides are of one of formula (I)-(VI):

[A]-[L1]-[H]-[L2]-[D] (I);

[D]-[L2]-[H]-[L1]-[A] (II);

[A]-[L1]-[D]-[L2]-[H] (III);

[H]-[L2]-[D]-[L1]-[A] (IV);

[H]-[L1]-[A]-[L2']-[D] (V);

[D]-[L1]-[A]-[L2']-[H] (VI);

wherein A is a cytokine polypeptide, D is a blocking moiety, H is a half-life extension moiety, L1 is a protease-cleavable polypeptide linker, L2 is an polypeptide linker that is optionally protease-cleavable, and L2' is a protease-cleavable polypeptide linker. L1 and L2 or L1 and L2' can be have the same or different amino acid sequence and or protease-cleavage site (when L2 is protease-cleavable) as desired.

In some aspects, the fusion proteins described herein are conditionally active variants of IL-12, IL-2, or IFN. In embodiments, the fusion protein can contain an IL-2 polypeptide. The fusion protein containing an IL-2 polypeptide can comprise or consist of the amino acid sequence of SEQ ID NOs. 257-300, 302-317, 325-353, 355-365, 366, 372-381, 383-385, 388-420, 579-608, and 636-646. The fusion proteins disclosed as SEQ ID NOs. 257-300, 302-317, 325-353, 355-365, 366, 372-381, 383-385, 388420, 579-608, 636-646 are referred to herein as ACP289-ACP292, ACP296-ACP302, WW0301, ACP304-ACP306, ACP309-ACP313, WW0353, ACP414, ACP336-ACP398, WW0472-WW0477, ACP406-ACP426, ACP439-ACP447, ACP451-ACP471, WW0729, WW0734-WW0792, ACP101, ACP293-ACP295, ACP316-ACP335, ACP427-ACP438, and ACP448-ACP450. For example, the fusion protein can comprise the amino acid sequence of SEQ ID NO: 272. The fusion protein can comprise the amino acid sequence of SEQ ID NO: 286. The fusion protein can comprise the amino acid sequence of SEQ ID NO:362. The fusion protein can comprise the amino acid sequence of SEQ ID NO:336. The fusion protein can comprise the amino acid sequence of SEQ ID NO: 348. The fusion protein can comprise the amino acid sequence of SEQ ID NO: 363. The fusion protein can comprise the amino acid sequence of SEQ ID NO: 580.

In embodiments, the fusion protein can contain IL-12. The fusion protein containing an IL-12 polypeptide can comprise or consist of the amino acid sequence of any one of SEQ ID NOs. 368-371, 434-440, 453-519, or 523-538. The fusion proteins disclosed as SEQ ID NOs. 368-371, 434-440, 453-519, or 523-538 are referred to herein as ACP240-ACP245, ACP247, ACP285-ACP288, WW0641, WW0649-WW0652, WW0662-WW0725, WW0765-WW0772, and WW0796-WW0803. For example, the fusion protein can comprise the amino acid sequence of SEQ ID NO: 424. For example, the fusion protein can comprise the amino acid sequence of SEQ ID NO: 428. For example, the fusion protein can comprise the amino acid sequence of SEQ ID NO: 541. For example, the fusion protein can comprise the amino acid sequence of SEQ ID NO: 556. For example, the fusion protein can comprise the amino acid sequence of SEQ ID NO: 560. For example, the fusion protein can comprise the amino acid sequence of SEQ ID NO: 568. For example, the fusion protein can comprise the amino acid sequence of SEQ ID NO: 573.

In embodiments, the fusion protein contains IFN. The fusion protein containing an IFN polypeptide can comprise or consist of the amino acid sequence of any one of SEQ ID NOs. 421-430, and 539-578. The fusion proteins disclosed as SEQ ID NOs. 421-430, and 539-578 can be referred to herein as ACP200-ACP209, WW0644-WW0648, WW0781-WW0786, WW0815-WW0822, WW0831-WW0834, WW0737-WW0748, and WW0787-WW0790.

In some aspects, the fusion polypeptide disclosed herein can be covalently or non-covalently bonded to a second polypeptide chain. For example, a fusion polypeptide can dimerize (i.e. form a dimer) or a portion of a fusion polypeptide may associate with another polypeptide, for example, to form a functional binding site for a cytokine polypeptide or serum albumin. In certain embodiments, the second polypeptide chain and the blocking moiety on the fusion polypeptide are complementary and together form a functional binding site that has specificity for the cytokine polypeptide contained in the fusion polypeptide. Exemplary functional binding sites that can be formed by the blocking moiety of the fusion polypeptide and a complimentary second polypeptide include antigen binding sites of antibodies, such as a Fab fragment of an antibody or a portion thereof. For example, one chain of a Fab that binds the cytokine can be the blocking moiety of the fusion polypeptide, e.g., a VH-CH1, and the complementary VL-CL can be part of the second polypeptide. In such situations, the blocking moiety of the fusion protein i.e., VH-CH1 and the second polypeptide that comprises the complementary VL-CL, can associate to form a functional binding site with specificity for the cytokine polypeptide contained within the fusion protein (e.g., IL-2, IL-12, IFNalpha, IFNbeta) and attenuate cytokine polypeptide activity.

In embodiments, the fusion protein containing an IL-2 cytokine polypeptide can be bonded covalently or noncovalently to a second polypeptide chain. The second polypeptide chain can contain an antibody light chain VL-CL that comprises or consists of the amino acid sequence of SEQ ID NO: 263, 264, or 333. Such a second polypeptide can bond with a complimentary VH-CH1 polypeptide contained within the fusion protein, e.g., as contained within SEQ ID NOS: 362, 363, 325, 286, 579, 581, or 582. The second polypeptide chain disclosed as SEQ ID NOs. 263, 264, and 333 can be referred herein as WW0523 (ACP381), WW0524 (ACP382), or WW0556 (ACP414).

In embodiments, the fusion polypeptide can comprise or consist of the amino acid sequence of SEQ ID NOs. 362, 363, 325, 286, 579, 581, or 582 and the second polypeptide chain can comprise or consist of the amino acid sequence of SEQ ID NOs: 263, 264, or 333. The fusion polypeptide disclosed as SEQ ID NOs. 362, 363, 325, 286, 579, 581, or 582 can be referred to as WW0520 (ACP378), WW0521 (ACP379), WW0548 (ACP406), WW0621 (ACP457), WW0729, WW0735, or WW0736, and the second polypeptide chain disclosed as SEQ ID NOs. 263, 264, and 333 can be referred herein as WW0523 (ACP381), WW0524 (ACP382), or WW0556 (ACP414). For example, the fusion protein can comprise or consist the amino acid sequence of SEQ ID NO: 362 and the second polypeptide chain can comprise or consist the amino acid sequence of SEQ ID NO: 263. For example, the fusion protein can comprise or consist the amino acid sequence of SEQ ID NO: 362 and the second polypeptide chain can comprise or consist the amino acid sequence of SEQ ID NO: 264. For example, the fusion protein can comprise or consist the amino acid sequence of SEQ ID NO: 362 and the second polypeptide chain can comprise or consist the amino acid sequence of SEQ ID NO: 333. For example, the fusion protein can comprise or consist of an amino acid sequence of SEQ ID NO: 363 and the second polypeptide chain can comprise or consist of an amino acid sequence of SEQ ID NO: 263. For example, the fusion protein can comprise or consist of an amino acid sequence of SEQ ID No. 363 and the second polypeptide chain can comprise or consist of an amino acid sequence of SEQ ID NO: 264. For example, the fusion protein can comprise or consist of an amino acid sequence of SEQ ID NO: 363 and the second polypeptide chain can comprise or consist of an amino acid sequence of SEQ ID NO: 333. For example, the fusion protein can comprise or consist of an amino acid sequence of SEQ ID NO: 325 and the second polypeptide chain can comprise or consist of an amino acid sequence of SEQ ID NO: 264. For example, the fusion protein can comprise or consist of an amino acid sequence of SEQ ID NO: 325 and the second polypeptide chain can comprise or consist of an amino acid sequence of SEQ ID NO: 333. For example, the fusion protein can comprise or consist of an amino acid sequence of SEQ ID NO: 325 and the second polypeptide chain can comprise or consist of an amino acid sequence of SEQ ID NO: 263. For example, the fusion protein can comprise or consist of an amino acid sequence of SEQ ID NO: 286 and the second polypeptide chain can comprise or consist of an amino acid sequence of SEQ ID NO: 263. For example, the fusion protein can comprise or consist of an amino acid sequence of SEQ ID NO: 286 and the second polypeptide chain can comprise or consist of an amino acid sequence of SEQ ID NO: 264. For example, the fusion protein can comprise or consist of an amino acid sequence of SEQ ID NO: 286, and the second polypeptide can comprise or consist of an amino acid sequence of SEW ID NO: 333. For example, the fusion protein can comprise or consist of an amino acid sequence of SEQ ID NO: 579 and the second polypeptide chain can comprise or consist of an amino acid sequence of SEQ ID NO: 263. For example, the fusion protein can comprise or consist of an amino acid sequence of SEQ ID NO: 579 and the second polypeptide chain can comprise or consist of an amino acid sequence of SEQ ID NO: 264. For example, the fusion protein can comprise or consist of an amino acid sequence of SEQ ID NO: 579 and the second polypeptide chain can comprise or consist of an amino acid sequence of SEQ ID NO: 233. For example, the fusion protein can comprise or consist of SEQ ID NO: 581 and the second polypeptide chain can comprise or consist of SEQ ID NO.: 263. For example, the fusion protein can comprise or consist of SEQ ID NO: 581 and the second polypeptide chain can comprise or consist of SEQ ID NO.: 264. For example, the fusion protein can comprise or consist of SEQ ID NO: 581 and the second polypeptide chain can comprise or consist of SEQ ID NO.: 333. For example, the fusion protein can comprise or consist of SEQ ID NO: 582 and the second polypeptide chain can comprise or consist of SEQ ID NO: 263. For example, the fusion protein can comprise or consist of SEQ ID NO: 582 and the second polypeptide chain can comprise or consist of SEQ ID NO: 264. For example, the fusion protein can comprise or consist of SEQ ID NO: 582 and the second polypeptide chain can comprise or consist of SEQ ID NO: 333.

As described herein targeting is accomplished through the action of a blocking polypeptide moiety that also binds to a desired target, or through a targeting domain. The domain that recognizes a target antigen on a preferred target (for example a tumor-specific antigen), may be attached to the cytokine via a cleavable or non-cleavable linker. If attached by a non-cleavable linker, the targeting domain may further aid in retaining the cytokine in the tumor, and it may be considered a retention domain. The targeting domain does not necessarily need to be directly linked to the payload molecule, and it may be linked directly to another element of the fusion protein. This is especially true if the targeting domain is attached via a cleavable linker.

In one aspect is provided a fusion polypeptide comprising a cytokine polypeptide, or functional fragment, a mutein thereof, a functional variant thereof or a subunit thereof, and a blocking moiety, e.g. a steric blocking domain. The blocking moiety is fused to the cytokine polypeptide, directly or through a linker, and can be separated from the cytokine polypeptide by cleavage (e.g., protease mediated cleavage) of the fusion polypeptide at or near the fusion site or linker or in the blocking moiety. For example, when the cytokine polypeptide is fused to a blocking moiety through a linker that contains a protease cleavage site, the cytokine polypeptide is released from the blocking moiety and can bind its receptor, upon protease mediated cleavage of the linker. The linker is designed to be cleaved at the site of desired cytokine activity, for example in the tumor microenvironment, avoiding off-target cytokine activity and reducing overall toxicity of cytokine therapy.

The blocking moiety can also function as a serum half-life extension element. In some embodiments, the fusion polypeptide further comprises a separate serum half-life extension element. In some embodiments, the fusion polypeptide further comprises a targeting domain. In various embodiments, the serum half-life extension element is a water-soluble polypeptide such as optionally branched or multi-armed polyethylene glycol (PEG), full length human serum albumin (HSA) or a fragment that preserves binding to FcRn, an Fc fragment, or a nanobody that binds to FcRn directly or to human serum albumin.

In addition to serum half-life extension elements, the pharmaceutical compositions described herein preferably comprise at least one, or more targeting domains that bind to one or more target antigens or one or more regions on a single target antigen. It is contemplated herein that a polypeptide construct of the invention is cleaved, for example, in a disease-specific microenvironment or in the blood of a subject at the protease cleavage site and that the targeting domain(s) will bind to a target antigen on a target cell. At least one target antigen is involved in and/or associated with a disease, disorder or condition. Exemplary target antigens include those associated with a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

In some embodiments, a target antigen is a cell surface molecule such as a protein, lipid or polysaccharide. In some embodiments, a target antigen is a on a tumor cell, virally infected cell, bacterially infected cell, damaged red blood cell, arterial plaque cell, or fibrotic tissue cell.

Target antigens, in some cases, are expressed on the surface of a diseased cell or tissue, for example a tumor or a cancer cell. Target antigens for tumors include but are not limited to Fibroblast activation protein alpha (FAPa), Trophoblast glycoprotein (5T4), Tumor-associated calcium signal transducer 2 (Trop2), Fibronectin EDB (EDB-FN), fibronectin EIIIB domain, CGS-2, EpCAM, EGFR, HER-2, HER-3, c-Met, FOLR1, FAP, and CEA. Pharmaceutical compositions disclosed herein, also include proteins comprising two antigen binding domains that bind to two different target antigens known to be expressed on a diseased cell or tissue. Exemplary pairs of antigen binding domains include but are not limited to EGFR/CEA, EpCAM/CEA, and HER-2/HER-3.

In some embodiments, the targeting polypeptides independently comprise a scFv, a VH domain, a VL domain, a non-Ig domain, or a ligand that specifically binds to the target antigen. In some embodiments, the targeting polypeptides specifically bind to a cell surface molecule. In some embodiments, the targeting polypeptides specifically bind to a tumor antigen. In some embodiments, the targeting polypeptides specifically and independently bind to a tumor antigen selected from at least one of EpCAM, EGFR, HER-2, HER-3, cMet, CEA, and FOLR1. In some embodiments, the targeting polypeptides specifically and independently bind to two different antigens, wherein at least one of the antigens is a tumor antigen selected from EpCAM, EGFR, HER-2, HER-3, cMet, CEA, and FOLR1. In some embodiments, the targeting polypeptide serves as a retention domain and is attached to the cytokine via a non-cleavable linker.

As described herein, the cytokine blocking moiety can bind to the cytokine and thereby block activation of the cognate receptor of the cytokine.

This disclosure also related to nucleic acids, e.g., DNA, RNA, mRNA, that encode the conditionally active proteins described herein, as well as vectors and host cells that contain such nucleic acids.

This disclosure also relates to pharmaceutical compositions that contain a conditionally active protein, nucleic acid that encodes the conditionally active protein, and vectors and host cells that contain such nucleic acids. Typically, the pharmaceutical composition contains one or more physiologically acceptable carriers and/or excipients.

The disclosure also relates to therapeutic methods that include administering to a subject in need thereof an effective amount of a conditionally active protein, nucleic acid that encodes the conditionally active protein, vector or host cells that contain such a nucleic acid, and pharmaceutical compositions of any of the foregoing. Typically, the subject has, or is at risk of developing, a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

The disclosure also relates to the use of a conditionally active protein, nucleic acid that encodes the conditionally active protein, vector or host cells that contain such a nucleic acid, and pharmaceutical compositions of any of the foregoing, for treating a subject in need thereof. Typically, the subject has, or is at risk of developing, a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

The disclosure also relates to the use of a conditionally active protein, nucleic acid that encodes the conditionally active protein, vector or host cells that contain such a nucleic acid for the manufacture of a medicament for treating a disease, such as a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

BRIEF DESCRIPTION OF THE DRAWINGS

FIGS. 1A-IE also depict results of the protein cleavage assay for each IL-2 polypeptide. Constructs tested and depicted include WW0475 (FIG. 1A), WW0517 (FIG. 1B), WW0548/556 (FIG. 1C), WW0735/523 (FIG. 1D), and WW0621/523 (FIG. 1E). FIG. 1F also depicts results of a protein cleavage assay for the non-cleavable control.

In FIGS. 3B, 3D, 3J squares and in FIGS. 3A, 3C, 3E, 3I triangles depict activity of the uncut IL-2 polypeptide (intact), and in FIGS. 3B, 3D, 3J triangles, and in FIGS. 3A, 3C and 3E-3I upside down triangles depict the activity of the cut polypeptide (cleaved). Circles (FIGS. 3B, 3D, 3J) or squares (FIGS. 3A, 3C, 3E-3I) depict activity of the control human IL-2. EC50 values for each are shown in the table. Constructs tests and depicted include WW0317 (FIG. 3A), WW0516 (FIG. 3B), WW0354 (FIG. 3C), WW0517 (FIG. 3D), WW0621/0523 (FIG. 3E), WW0521/524 (FIG. 3F), WW0520/0523 (FIG. 3G), WW0729/523 (FIG. 3H), and WW0735/523 (FIG. 3I), WW0520/524 (FIG. 3J).

FIG. 5A contains the data corresponding to vehicle treatment and fusion proteins WW0517 and WW0520/523. FIG. 5B contains the data corresponding to treatment with fusion proteins WW0548/0524, WW0548/0556, and WW0475. FIG. 5C contains the data corresponding to treatment with fusion proteins WW0619 and WW0621/0523.

FIG. 6A contains the data corresponding to vehicle treatment and fusion proteins WW0517 and WW0520/523. FIG. 6B contains the data corresponding to treatment with fusion proteins WW0548/0524, WW0548/0556, and WW0475. FIG. 6C contains the data corresponding to treatment with fusion proteins WW0619 and WW0621/0523.

7A-7Q depict IL-12/STAT4 activation in a comparison of human p40/murine p35 IL-12 or human IL-12 fusion proteins to chimeric IL-12 (mouse p35/human $p^{40}$) or recombinant human IL-12 (control). Squares depict activity of the uncut IL-12 polypeptide (intact) and triangles depict the activity of the cut IL-12 polypeptide (cleaved). Circles depict activity of the control. EC50 values for each are shown in the table.

FIGS. 8A-8D are a series of graphs showing activity of fusion proteins in an IL12 T-Blast assay. FIGS. 8A-8D depicts activation of IL-12 signaling in a comparison of a human p40/murine p35 IL12 or human IL12 fusion protein to control, chimeric IL-12 (human p40/murine p35 IL12) or recombinant human IL12. Squares depict activity of the uncut IL-12 polypeptide (intact) and triangles depict the activity of the cut IL-12 polypeptide (cleaved). Circles depict activity of the control chimeric IL-12 or recombinant human IL-12. EC50 values for each are shown in the table.

Figure 9A:
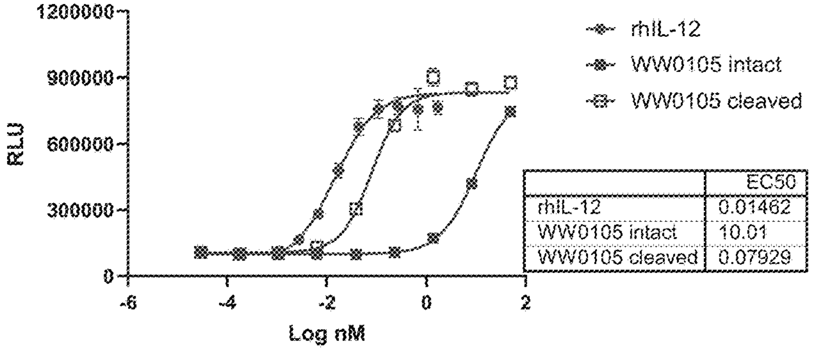
Figure 9B:
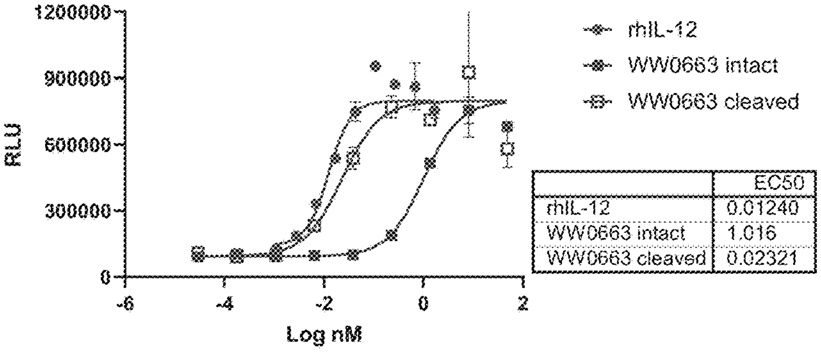
Figure 9C:
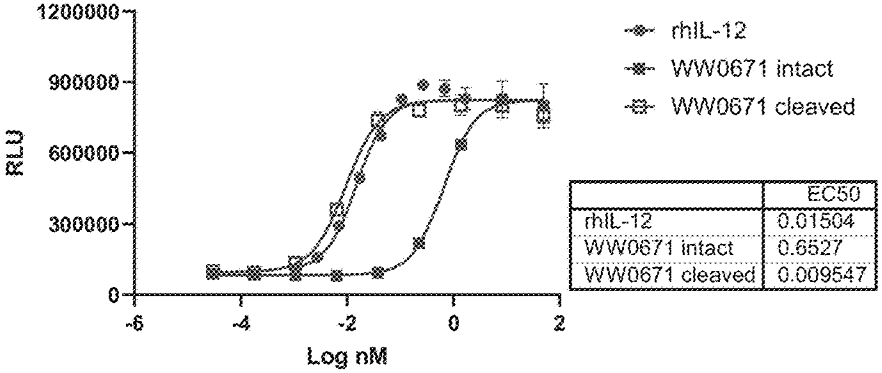
Figure 10A:
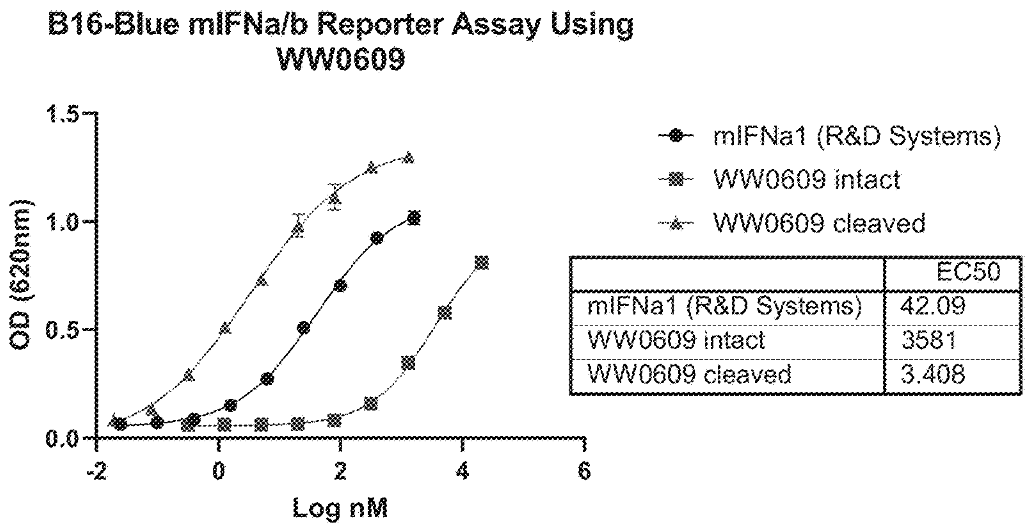
Figure 10A:
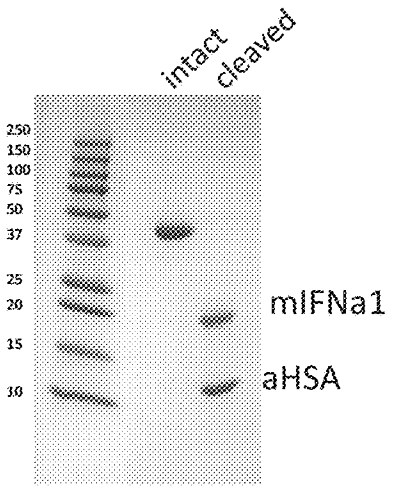
Figure 10B:
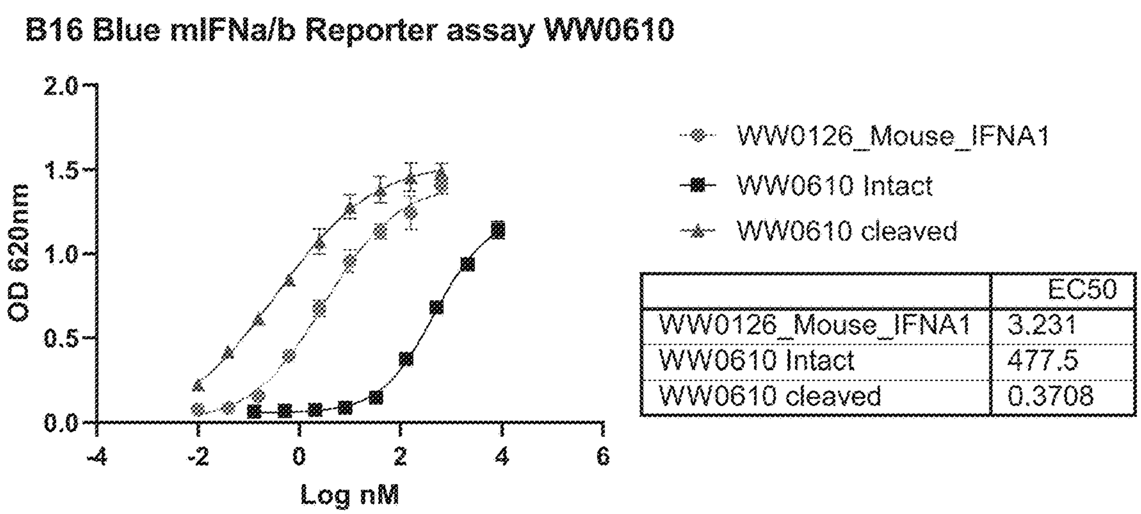
Figure 10B:
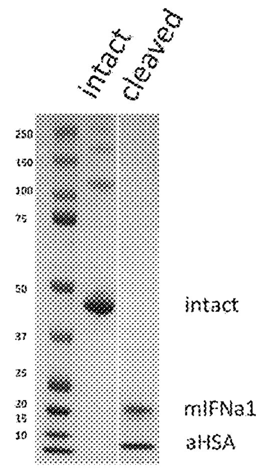
Figure 10C:
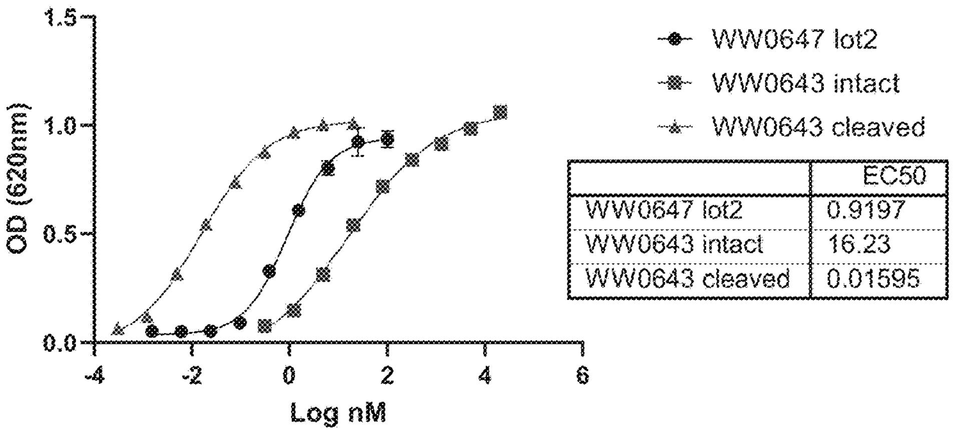
Figure 10C:
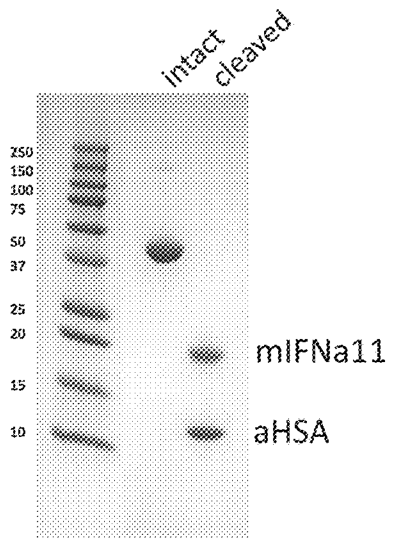
Figure 10D:
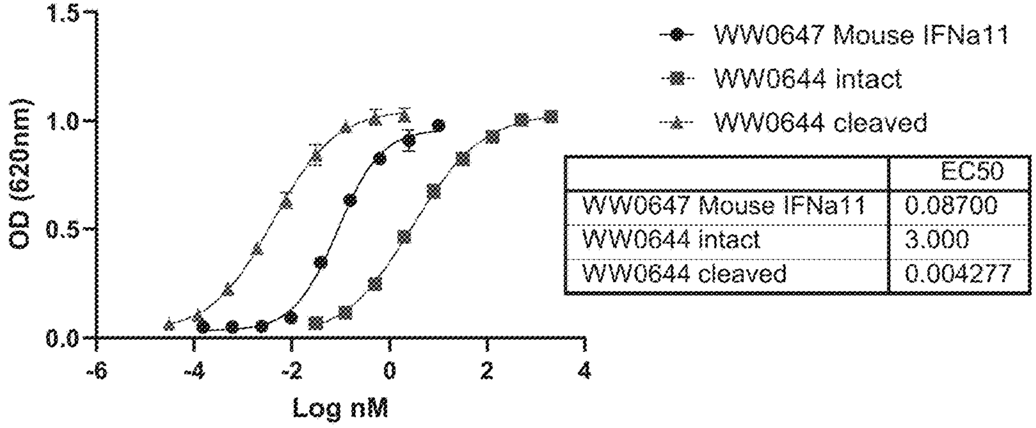
Figure 10D:
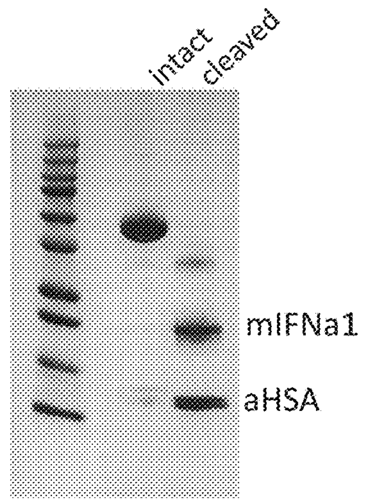
Figure 10E:
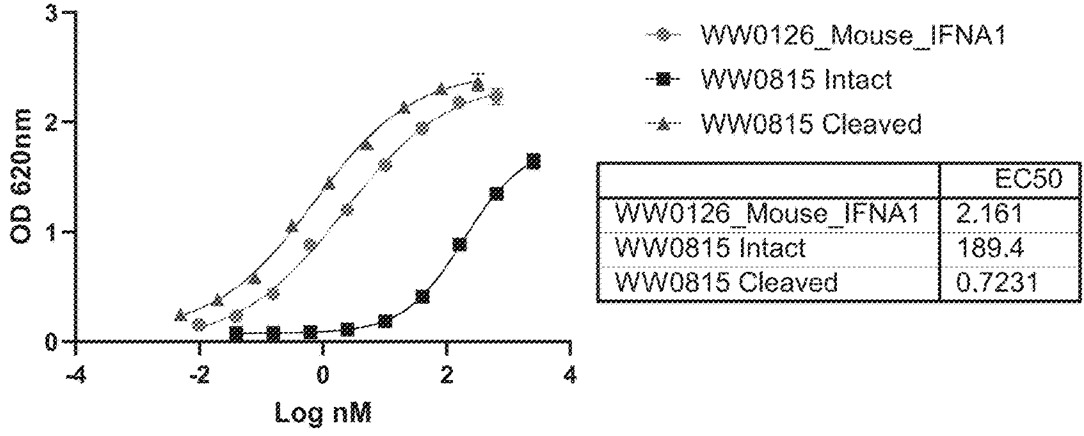
Figure 10E:
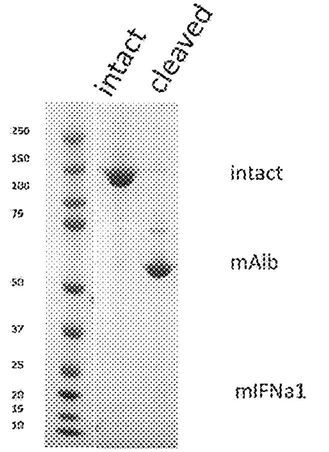
Figure 10F:
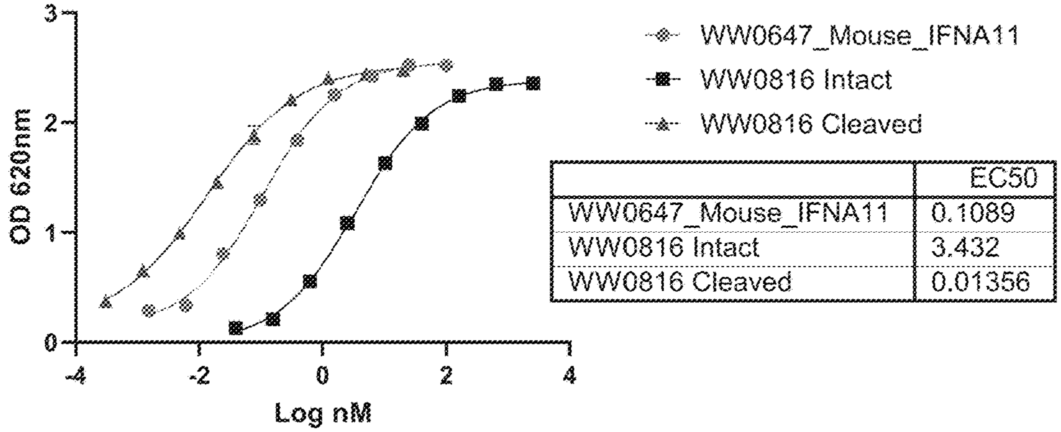
Figure 10F:
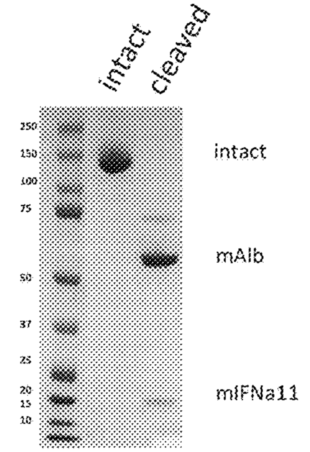
Figure 10G:
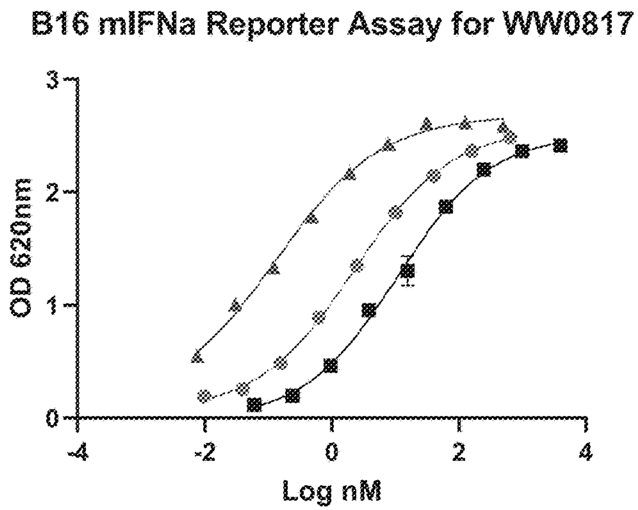
Figure 10G:
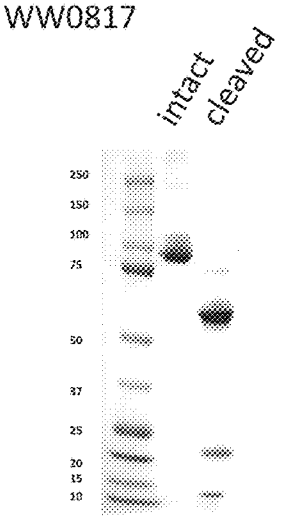
Figure 10H:
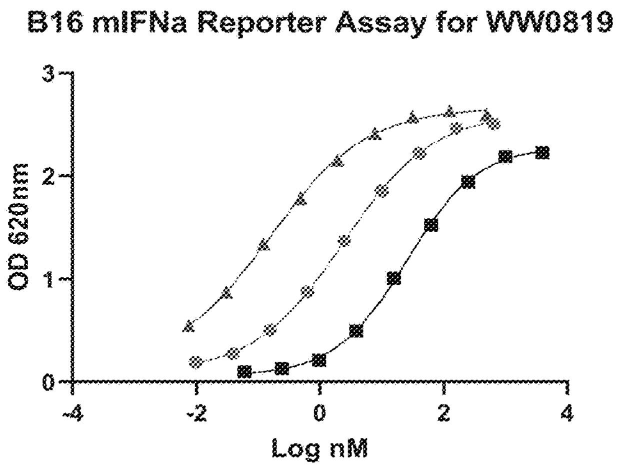
Figure 10H:
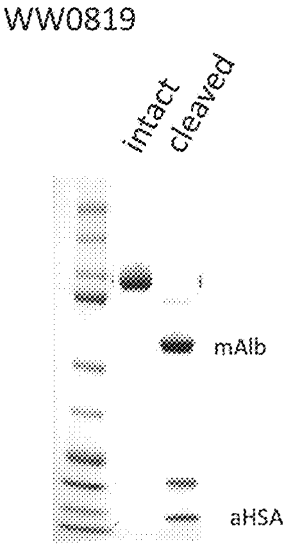
Figure 10I:
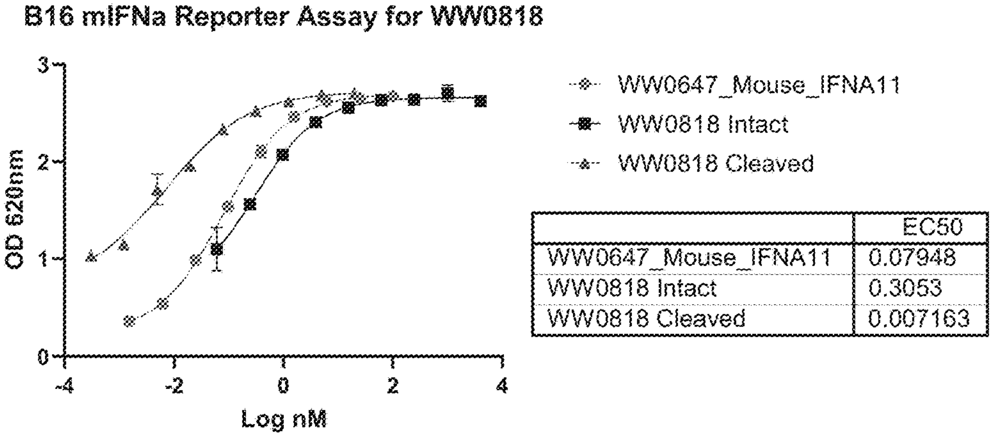
Figure 10I:
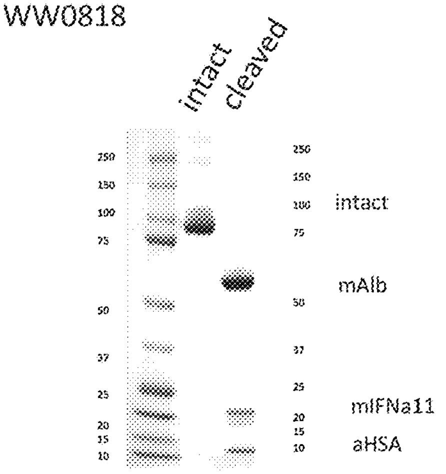
Figure 10J:
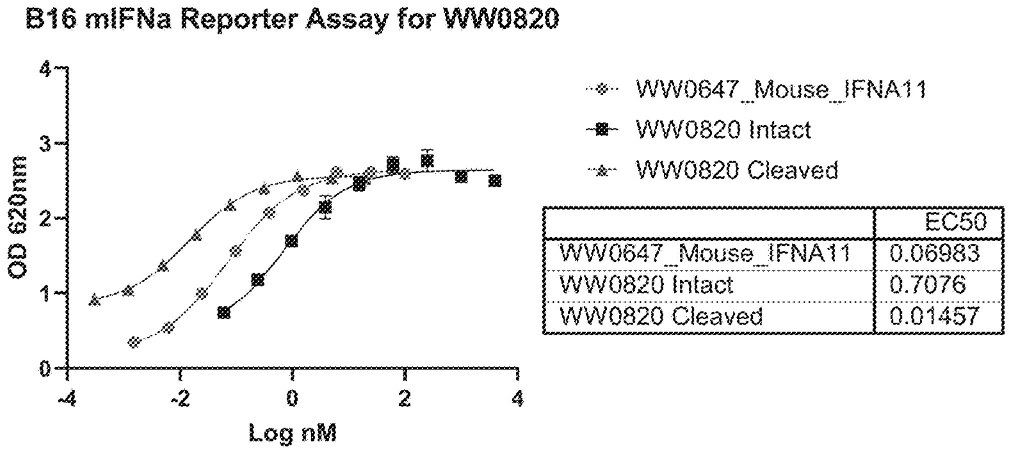
Figure 10J:
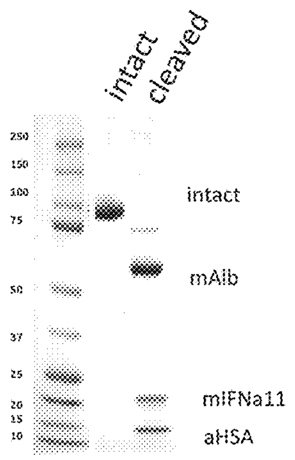

FIGS. 9A-9C are a series of graphs showing activity of fusion proteins in an IL-12 luciferase reporter assay. FIGS. 9A-9B depict activation of IL-12 signaling in a comparison of a human p40/murine p35 IL-12 fusion protein to recombinant human IL-12 (control). FIG. 9C depicts activation of IL-12 signaling in comparison of a human IL-12 (human p40/human p35 IL-12) fusion protein to recombinant human IL12. Closed squares depict activity of the uncut IL-12 polypeptide (intact) and open squares depict the activity of the cut polypeptide (cleaved). Circles depict activity of the control. EC50 values for each are shown in the table.

FIGS. 10A-10J are a series of graphs showing activity of fusion proteins in the B16-Blue IFN-α/β reporter assay. FIGS. 10A-10J depict activation of the IFN-α/β pathway in a comparison of mouse IFNα fusion protein to mouse IFNα (control). Squares depict activity of the uncut IFNα polypeptide (intact) and triangles depict the activity of the cut IFNα polypeptide (cleaved). Circles depict activity of the control (mouse IFNα). EC50 values for each are shown in the table. FIGS. 10A-10J also depict results of the protein cleavage assay for each IFNα fusion protein. Each IFNα fusion protein was run on an SDS-PAGE gel in both cleaved and uncleaved form. As can be seen in the gel, cleavage was complete.

Figure 11A:
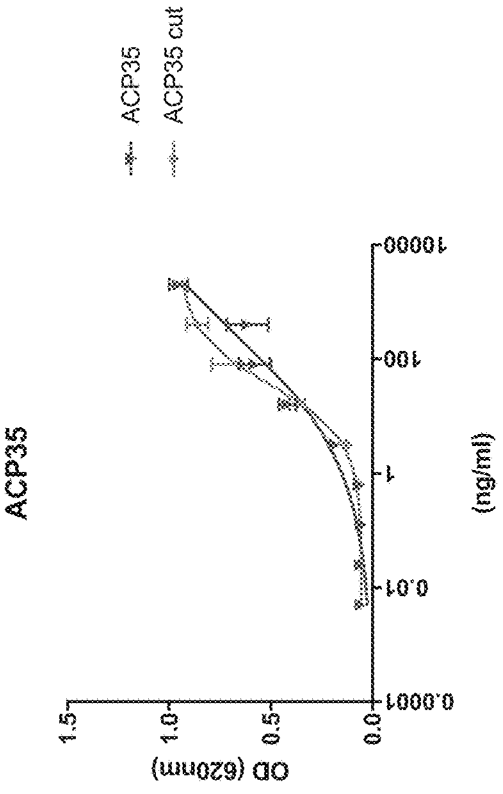
Figure 11B:
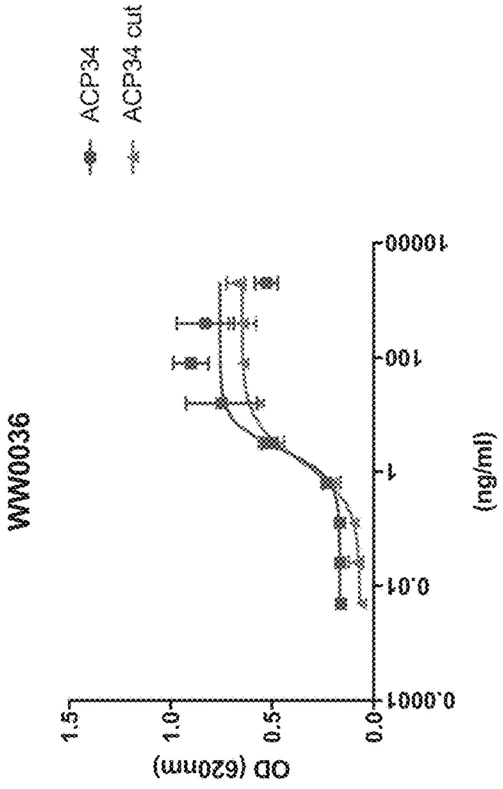

FIGS. 11A-11B are graphs depicting results from a HEK-Blue IL-12 reporter assay performed on human p40/murine p35 IL12 fusion proteins before and after protease cleavage. Constructs ACP35 (FIG. 11A) and ACP34 (FIG. 11B) were tested. Analysis was performed based on quantification of Secreted Alkaline Phosphatase (SEAP) activity using the reagent QUANTI-Blue® (InvivoGen). Results confirm that IL12 protein fusion proteins are active.

Figure 12A:
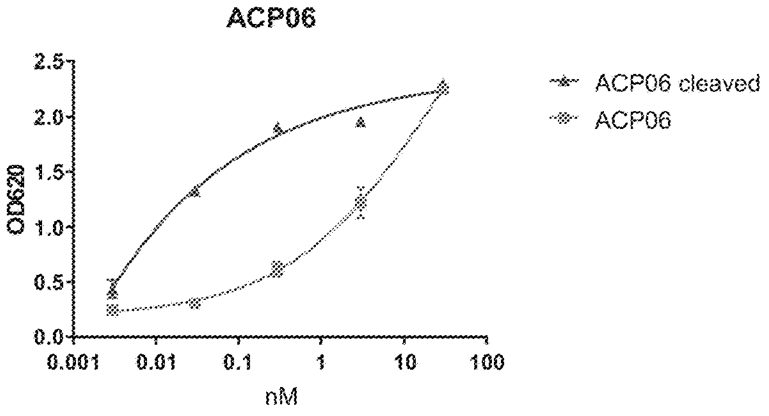
Figure 12B:
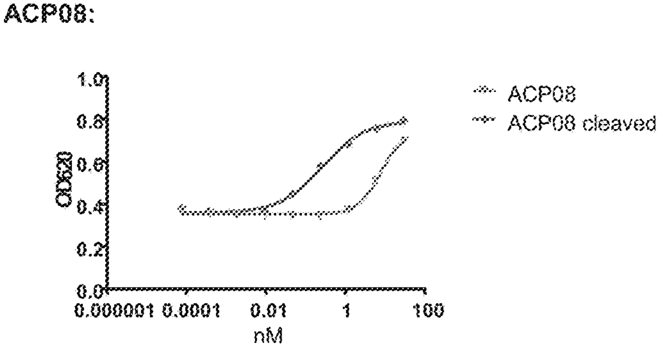
Figure 12C:
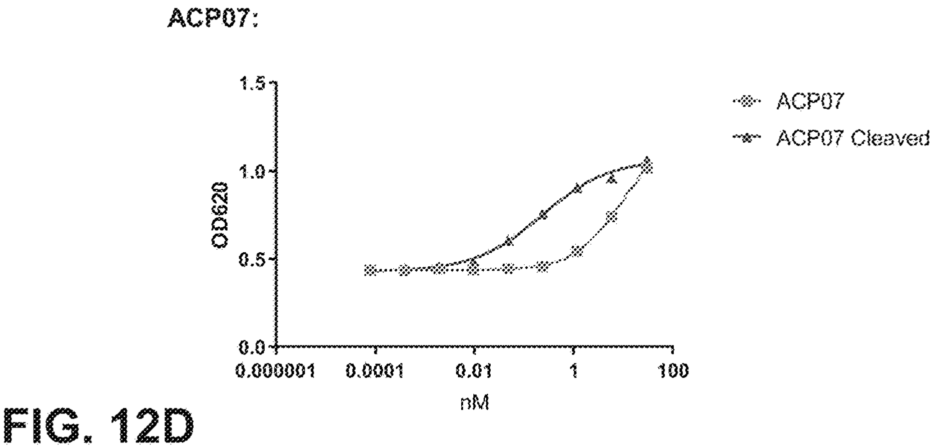
Figure 12D:
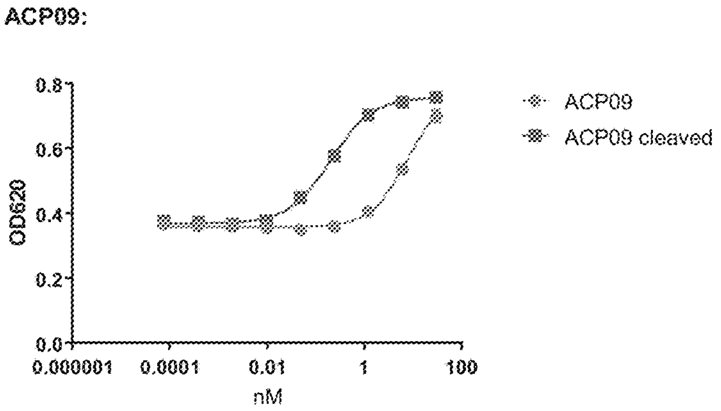
Figure 12E:
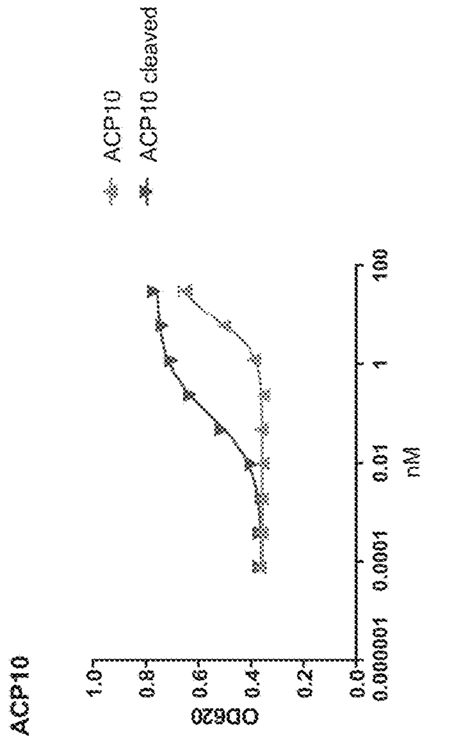
Figure 12F:
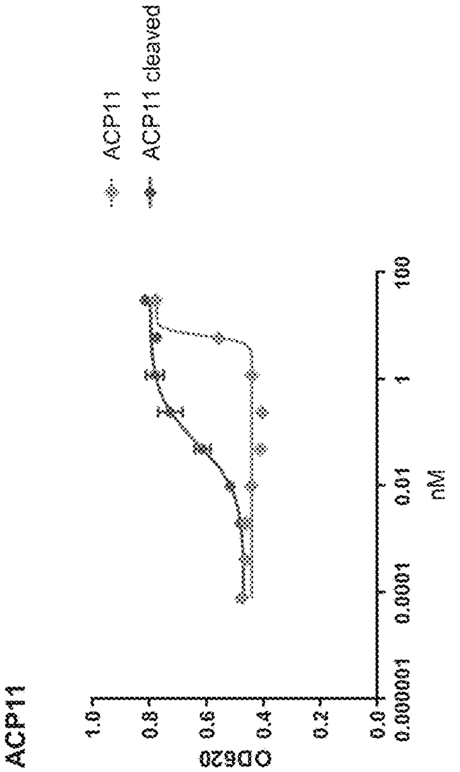

FIGS. 12A-12F show a series of graphs depicting the results of HEK-blue assay of four IL-12 fusion proteins, before and after cleavage by MMP9. Analysis was performed based on quantification of Secreted Alkaline Phosphatase (SEAP) activity using the reagent QUANTI-Blue (InvivoGen). The data show greater activity in the cleaved IL12 than in the full fusion protein. Constructs tested were ACP06 (FIG. 12A), ACP07 (FIG. 12C), ACP08 (FIG. 12B), ACP09 (FIG. 12D), ACP10 (FIG. 12E), ACP11 (FIG. 12F).

Figure 13:
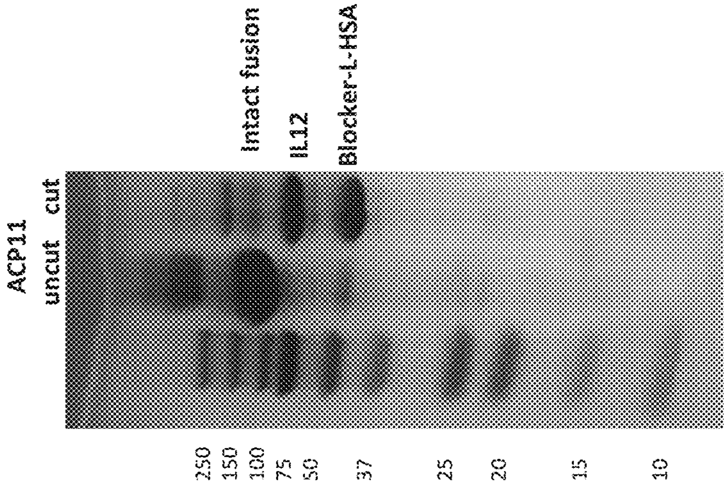

FIG. 13 shows results of protein cleavage assay. Fusion protein ACP11 was run on an SDS-PAGE gel in both cleaved and uncleaved form. As can be seen in the gel, cleavage was complete.

Figure 14:
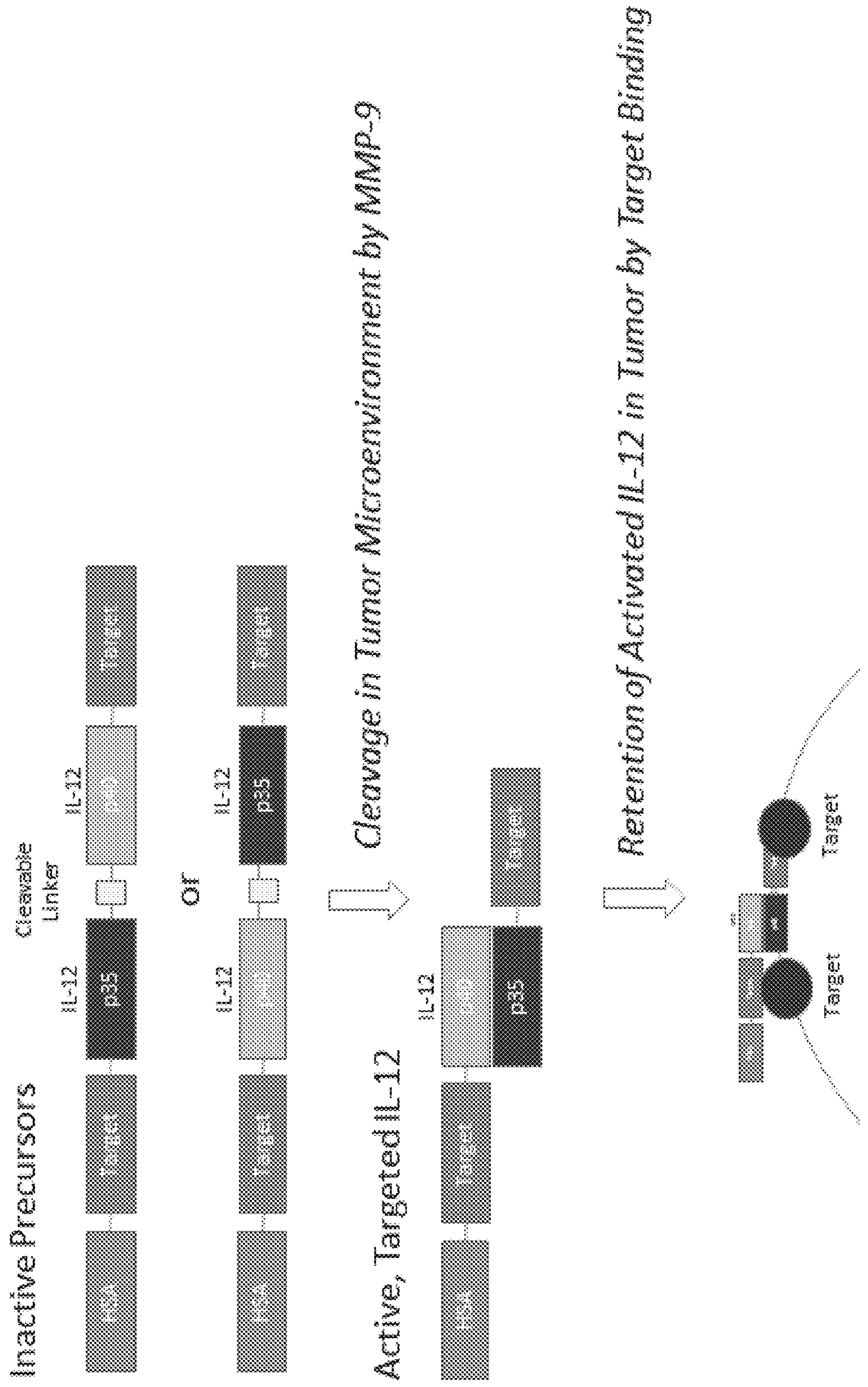
Figure 15A:
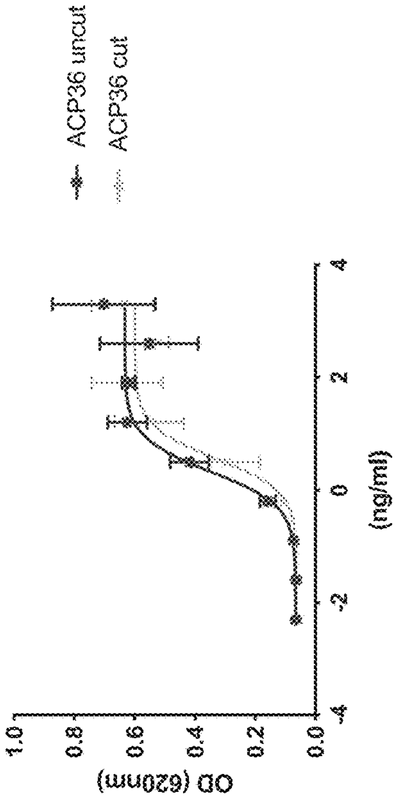
Figure 15B:
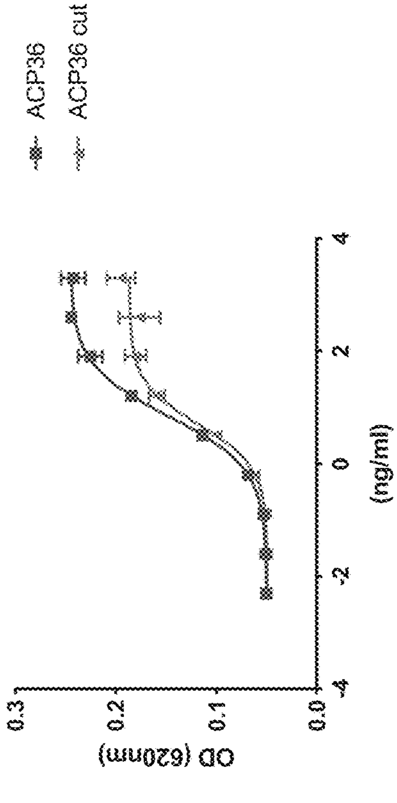
Figure 15C:
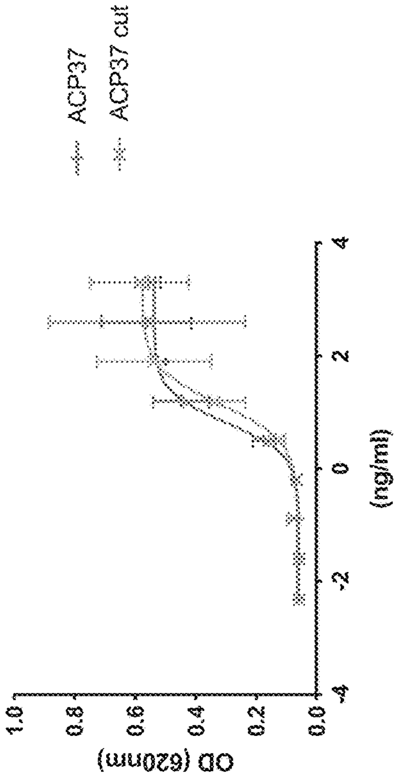
Figure 15D:
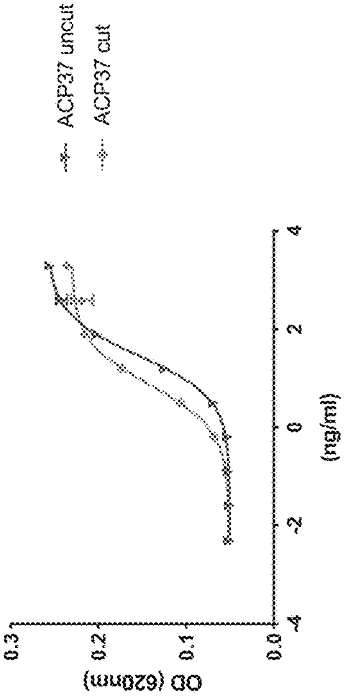
Figure 16A:
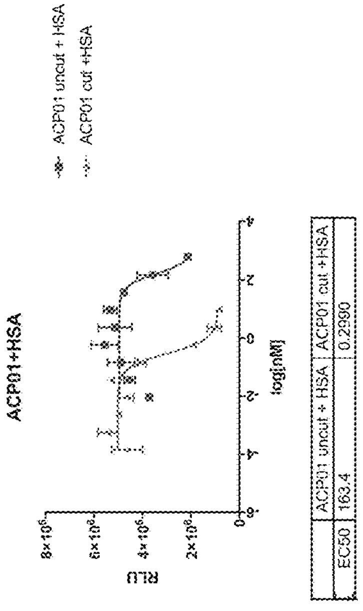
Figure 16B:
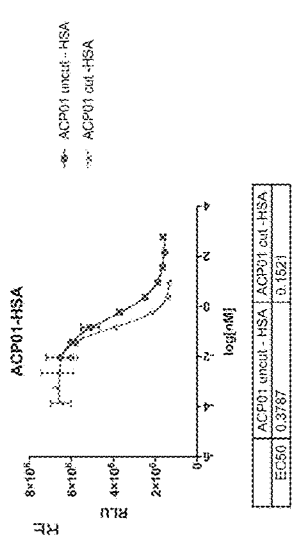
Figure 16C:
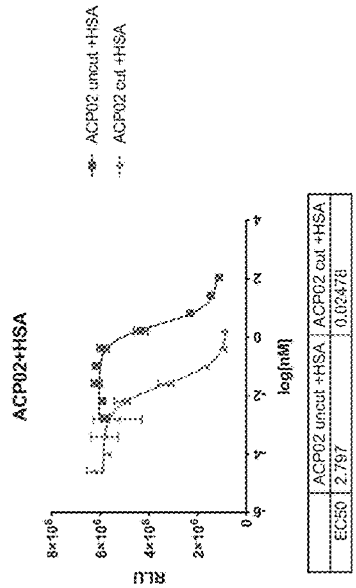
Figure 16D:
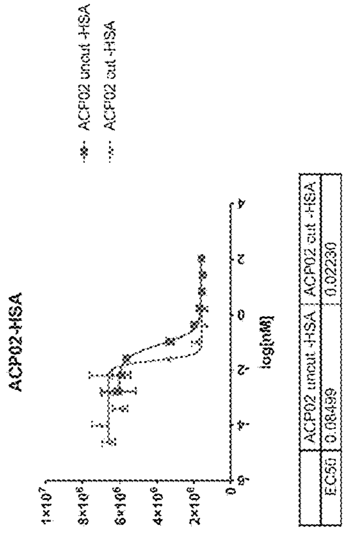
Figure 16E:
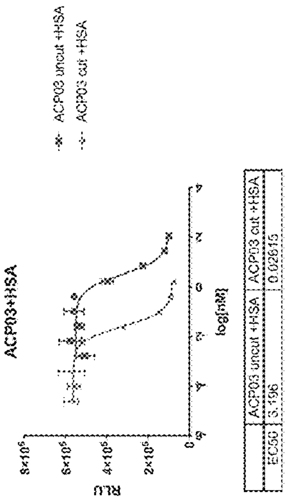
Figure 16F:
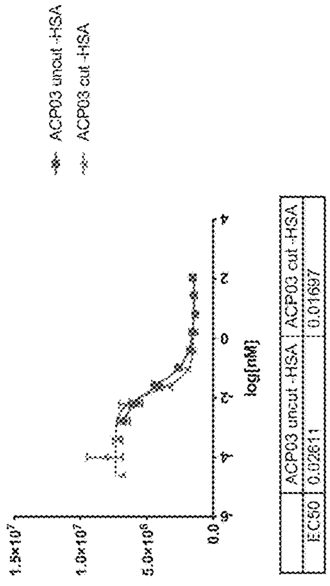
Figure 17A:
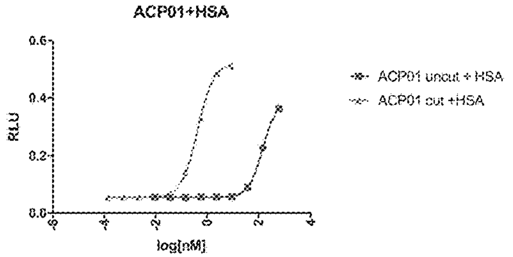
Figure 17C:
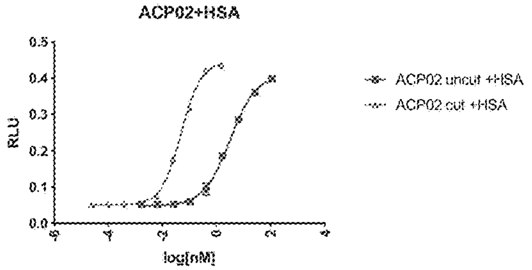
Figure 17E:
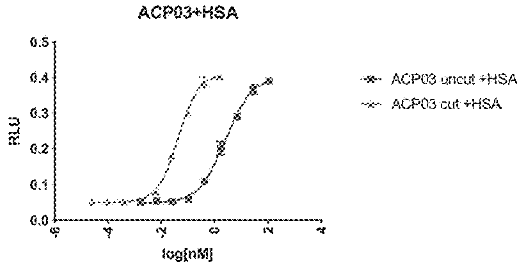
Figure 17B:
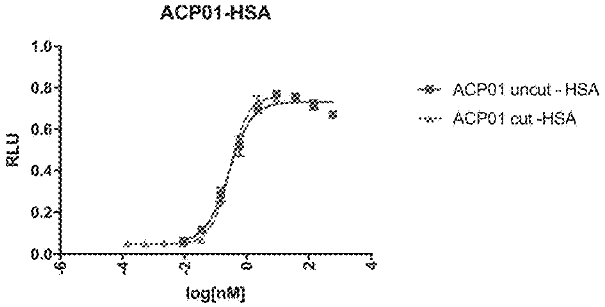
Figure 17D:
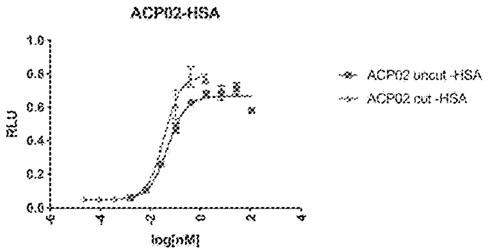
Figure 17F:
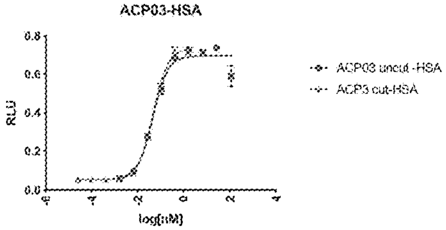

FIG. 14 is a schematic which depicts a non-limiting example of an inducible cytokine protein, wherein the construct is activated upon protease cleavage of a linker attached between two subunits of the cytokine.

FIGS. 15A-15D are graphs depicting results from a HEK-Blue assay performed on human p40/murine p35 IL12 fusion proteins before and after protease cleavage. Results confirm that IL12 protein fusion proteins are active. Each proliferation assay was performed with HSA or without HSA.

FIGS. 16A-16F are a series of graphs showing activity of exemplary IFNγ fusion proteins compared to activity of mouse IFNγ control using WEHI 279 cell survival assay. Each assay was performed with medium containing HSA (+HSA) or not containing HSA (-HSA). Each fusion protein comprises an anti-HSA binder, and both uncleaved and MMP9 protease cleaved versions of the fusion protein were used in each assay.

FIGS. 17A-17F are a series of graphs showing activity of exemplary IFNγ fusion proteins compared to activity of mouse IFNγ control using B16 reporter assay. Each assay was performed with medium containing HSA (+HSA) or not containing HSA (-HSA). Each fusion protein comprises an anti-HSA binder, and both uncleaved and MMP9 protease cleaved versions of the fusion protein were used in each assay.

Figure 18B:
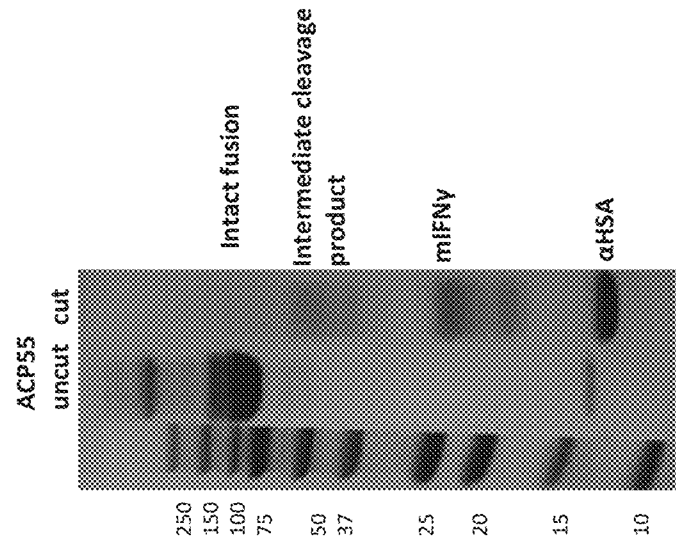
Figure 18A:
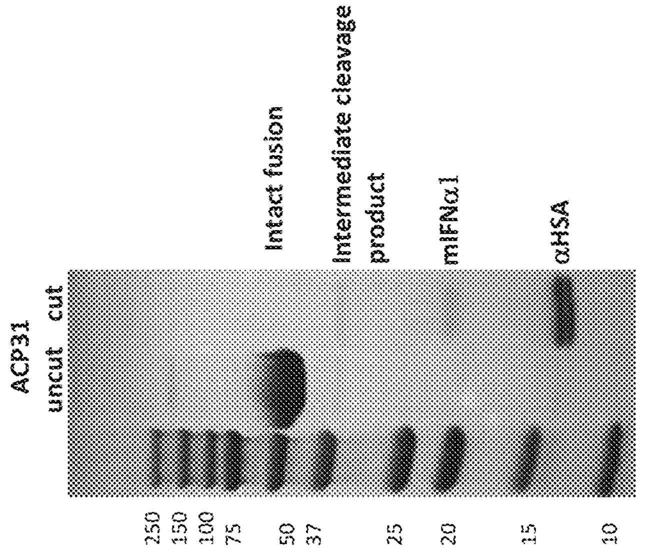

FIGS. 18A-18B show results of protein cleavage assay, as described in Example 2. Two constructs, ACP31 (IFN-α fusion protein; FIG. 18A) and ACP55 (IFN-γ fusion protein; 18B), were run on an SDS-PAGE gel in both cleaved and uncleaved form. As can be seen in the gel, cleavage was complete.

Figure 19B:
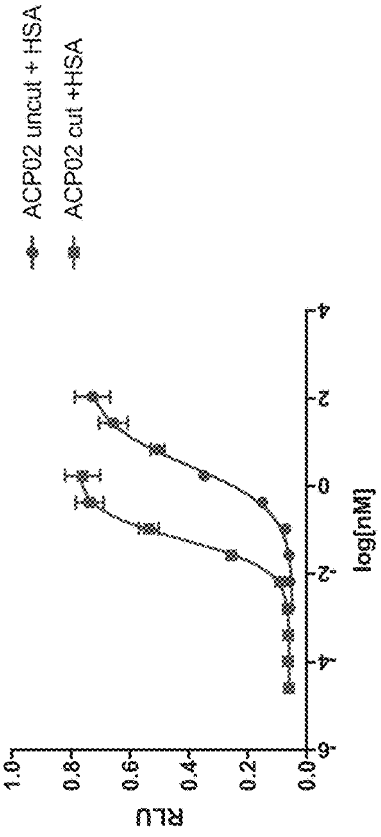
Figure 19A:
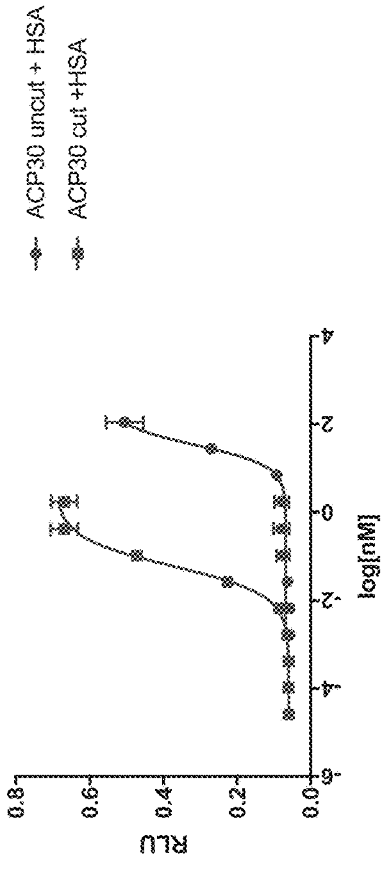

FIGS. 19A-19B are a series of graphs (FIGS. 19A and 19B) showing activity of exemplary IFNγ fusion proteins before and after protease cleavage using B16 reporter assay. Each assay was performed with culture medium containing HSA, and each fusion protein comprises an anti-HSA binder. Both uncleaved and MMP9 protease cleaved versions of the fusion protein were used in each assay.

Figure 20A:
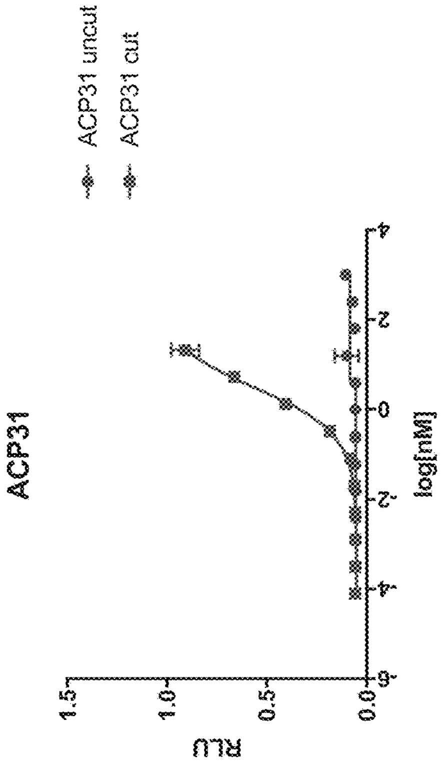
Figure 20B:
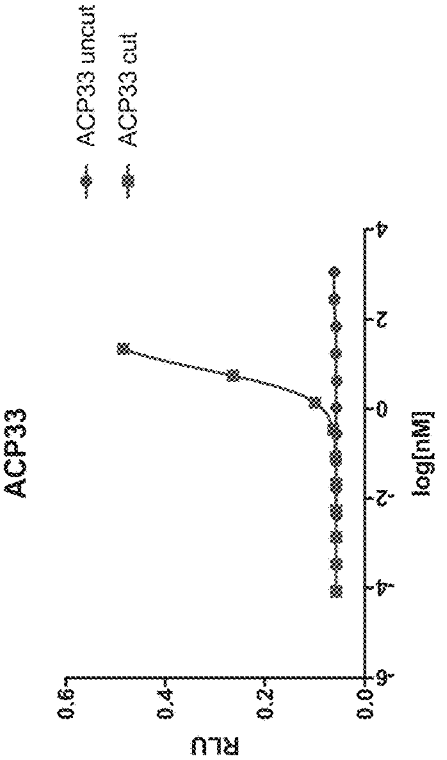

FIGS. 20A-20B are a series of graphs (FIG. 20A and FIG. 20B) showing activity of exemplary IFNα fusion proteins before and after cleavage using a B16 reporter assay. Each assay was performed with medium containing HSA, and each fusion protein comprises an anti-HSA binder. Both uncleaved and MMP9 protease cleaved versions of the fusion protein were used in each assay.

Figure 21A:
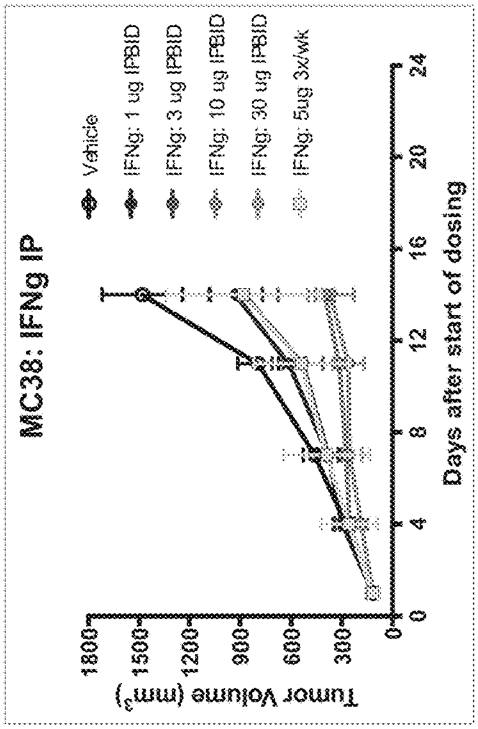
Figure 21B:
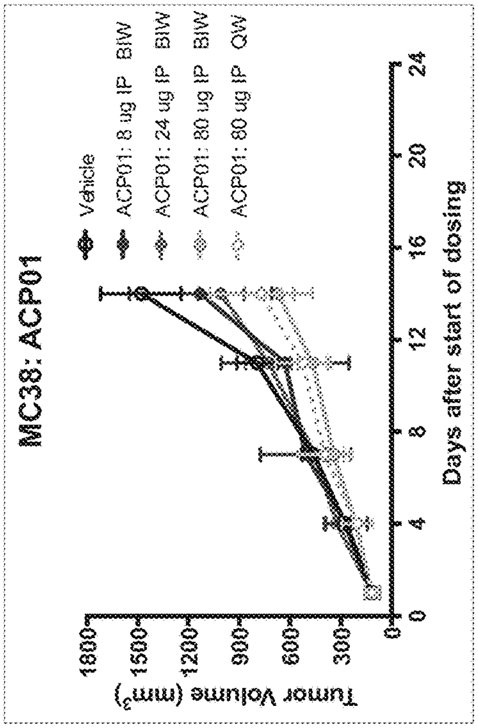
Figure 21C:
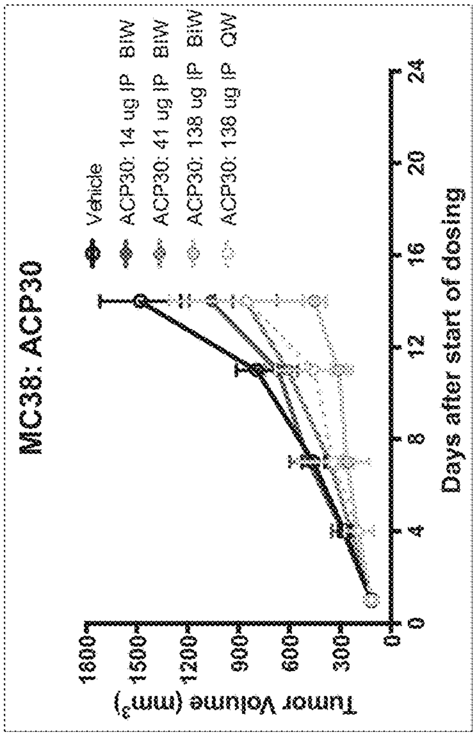
Figure 21D:
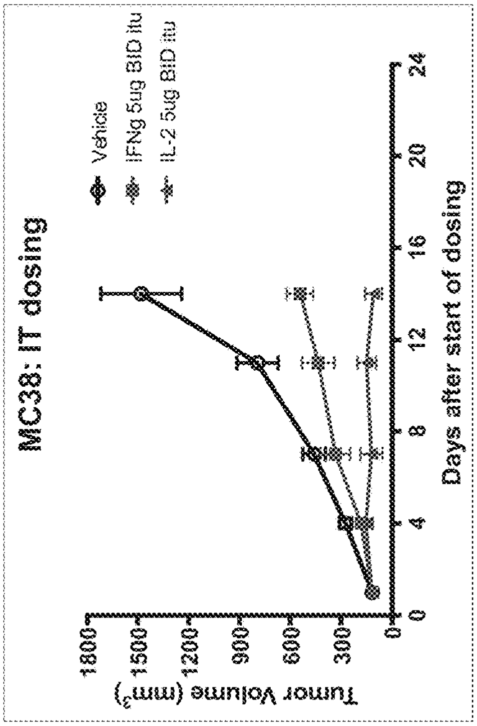

FIGS. 21A-21D are a series of graphs depicting the results of tumor growth studies using the MC38 cell line. FIG. 21A-C show the effect of IFNγ and IFNγ fusion proteins on tumor growth when injected intraperitoneally (IP) using different dosing levels and schedules (ug=micrograms, BID=twice daily, BIW=twice weekly, QW=weekly). FIG. 21D shows the effect of intratumoral (IT) injection of IFNγ and IL-2 on tumor growth.

Figure 22A:
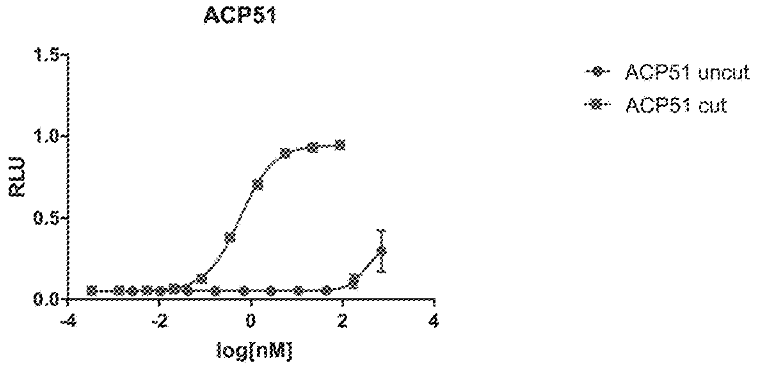
Figure 22B:
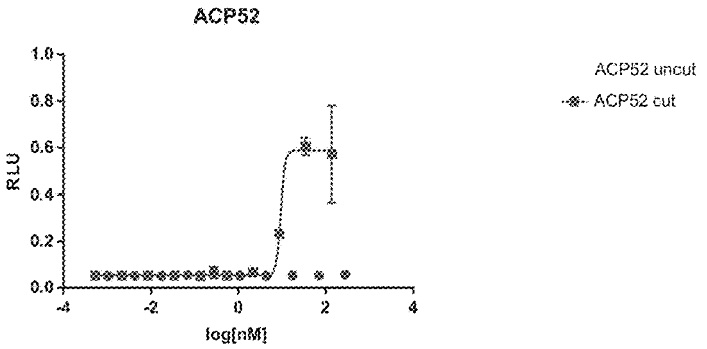

FIGS. 22A-22B are a series of graphs showing activity of exemplary IFNγ fusion proteins (ACP51 (FIG. 22A), and ACP52 (FIG. 22B)) cleaved by MMP9 protease compared to activity of uncleaved fusion proteins using B16 reporter assay. Each fusion protein comprises an anti-HSA binder and a tumor targeting domain.

Figure 23A:
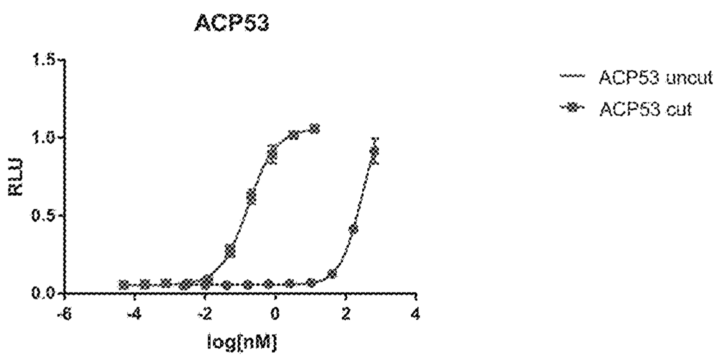
Figure 23B:
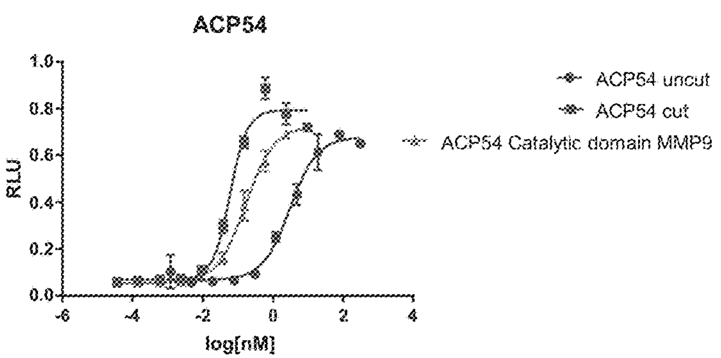

FIGS. 23A-23B are a series of graphs showing activity of exemplary IFNγ fusion proteins (ACP53 and ACP54) cleaved by MMP9 protease compared to activity of uncleaved fusion proteins using B16 reporter assay. Each fusion protein comprises IFNγ directly fused to albumin.

Figure 24A:
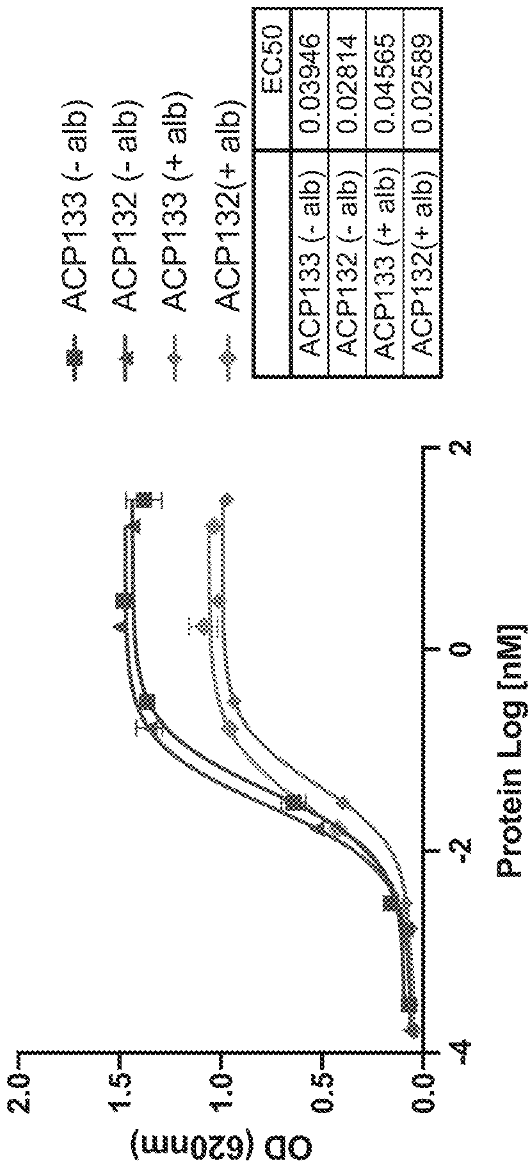
Figure 24B:
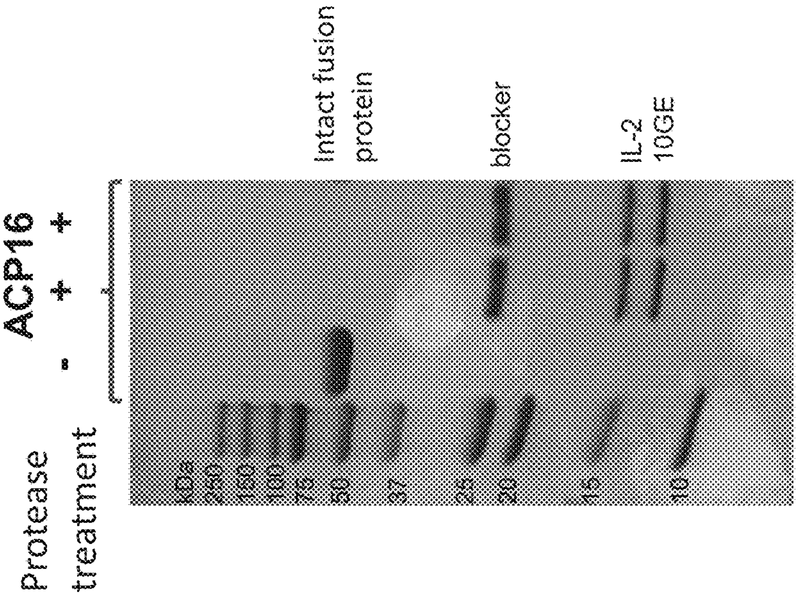
Figure 24B:
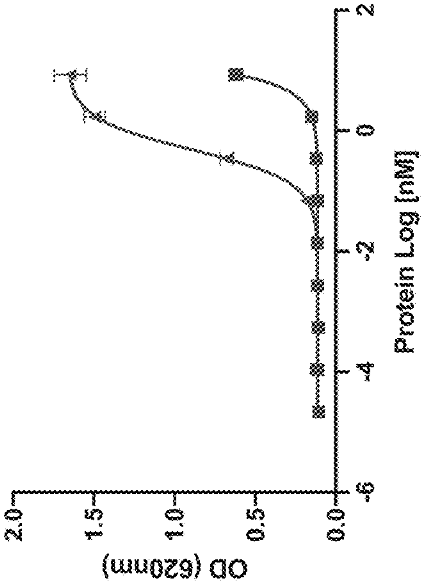
Figure 24C:
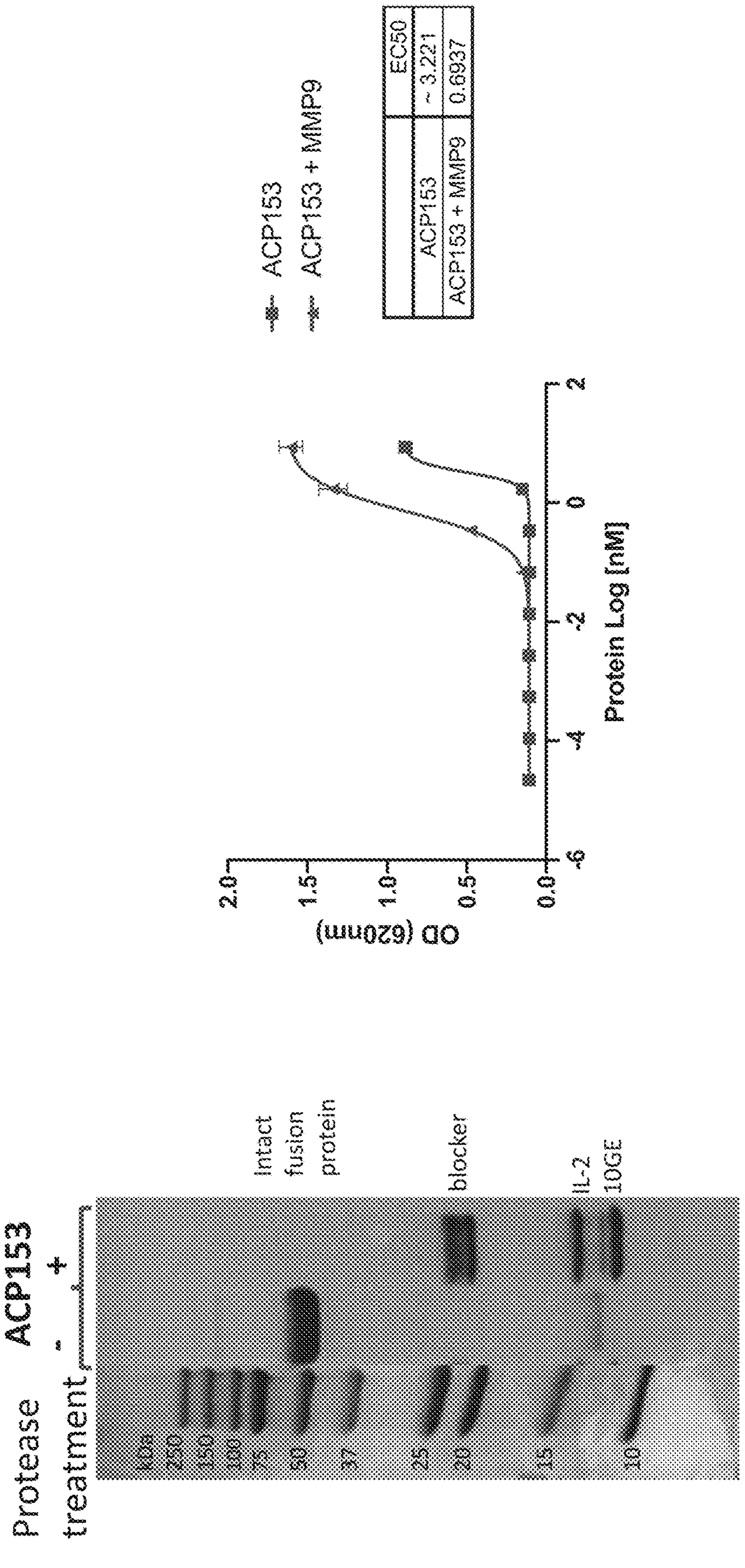
Figure 24D:
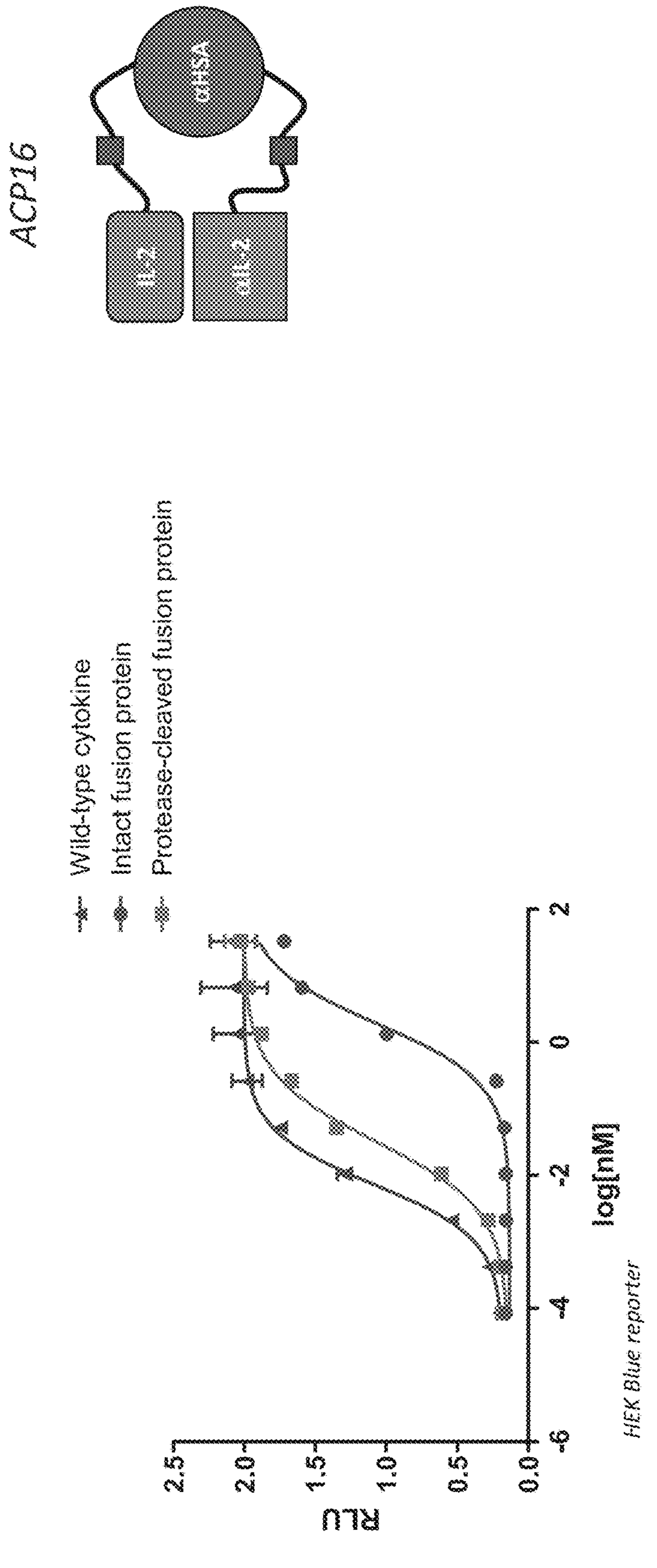

FIGS. 24A-24D are graphs depicting results from a HEK-Blue IL-2 reporter assay performed on IL-2 fusion proteins and recombinant human IL2 (Rec hIL-2). Analysis was performed based on quantification of Secreted Alkaline Phosphatase (SEAP) activity using the reagent QUANTI-Blue (InvivoGen). FIG. 24A shows results of IL-2 constructs ACP132 and ACP 133 with and without albumin. FIG. 24B shows results of IL-2 construct ACP16 cleaved and uncleaved. Results of a protein cleavage assay of ACP16 in cleaved and uncleaved forms is also depicted. FIG. 24C shows results of IL-2 construct ACP153 in cleaved and uncleaved forms. Results of a protein cleavage assay are also depicted. FIG. 24D illustrates the results from a HEK-Blue IL-2 assay using wild-type cytokine, intact fusion protein, and protease-cleaved fusion protein.

Figure 25A:
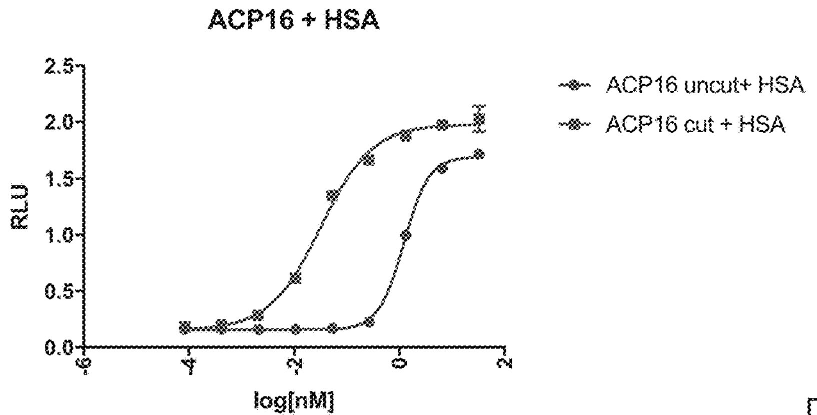
Figure 25B:
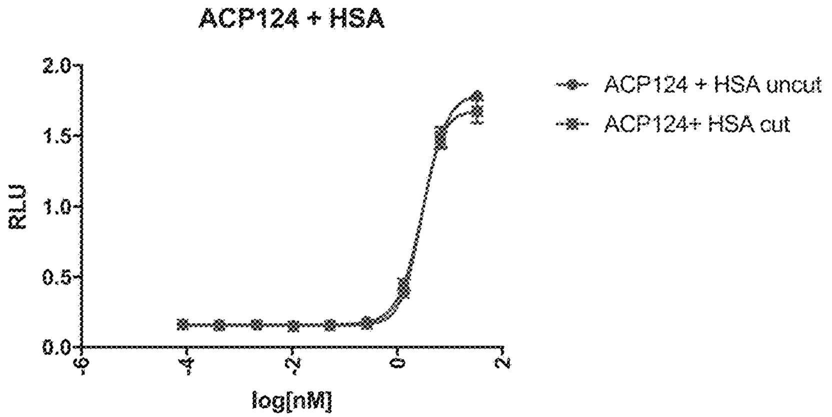
Figure 25C:
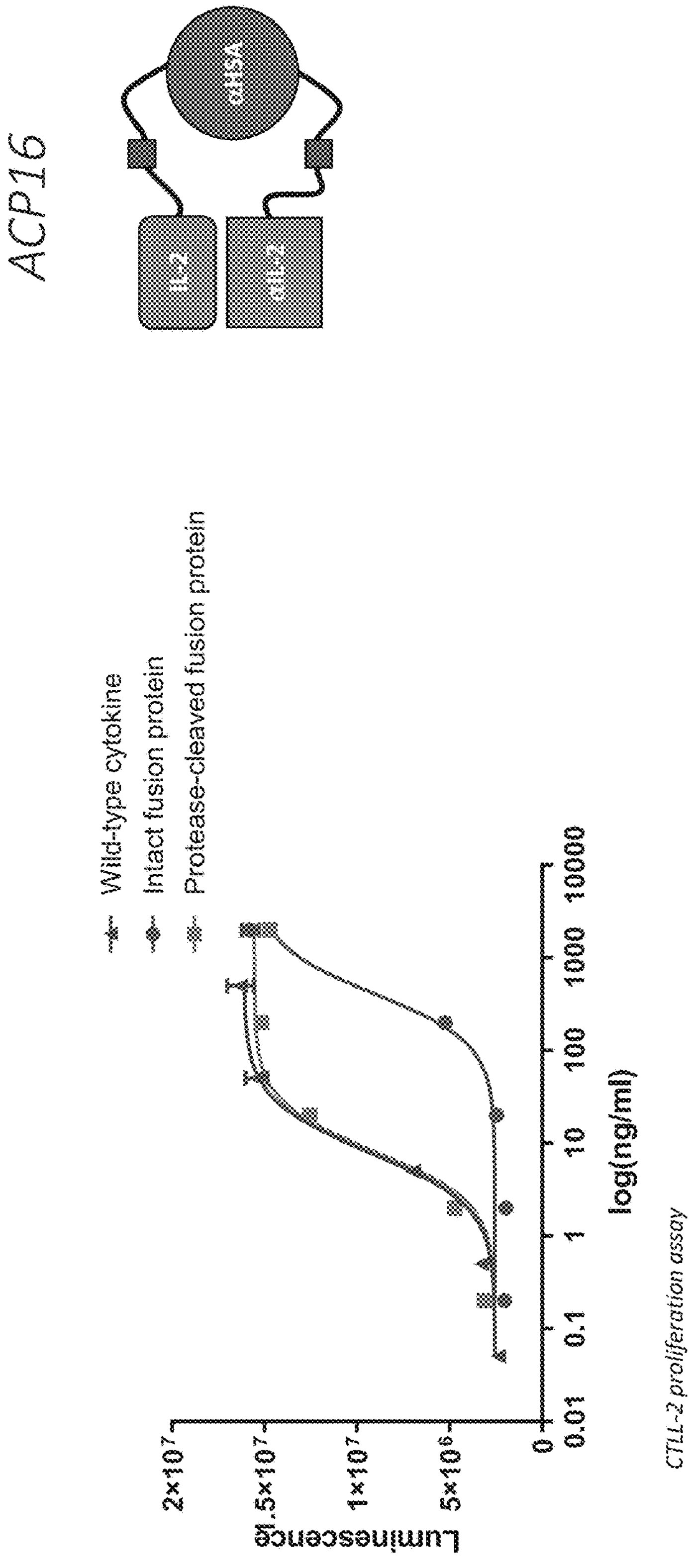

FIGS. 25A and 25B are two graphs showing analysis of ACP16 (FIG. 25A) and ACP124 (FIG. 25B) in a HEKBlue IL-2 reporter assay in the presence of HSA. Circles depict the activity of the uncut polypeptide; squares depict activity of the cut polypeptide. FIG. 25C is a graph showing results of a CTLL-2 proliferation assay. CTLL2 cells (ATCC) were plated in suspension at a concentration of 500,000 cells/well in culture media with or without 40 mg/ml human serum albumin (HSA) and stimulated with a dilution series of activatable hIL2 for 72 hours at 37° C. and 5% $CO_2$. Activity of uncleaved and cleaved activatable ACP16 was tested. Cleaved activatable hIL2 was generated by incubation with active MMP9. Cell activity was assessed using a CellTiter-Glo (Promega) luminescence-based cell viability assay. Circles depict intact fusion protein, and squares depict protease-cleaved fusion protein.

Figure 26A:
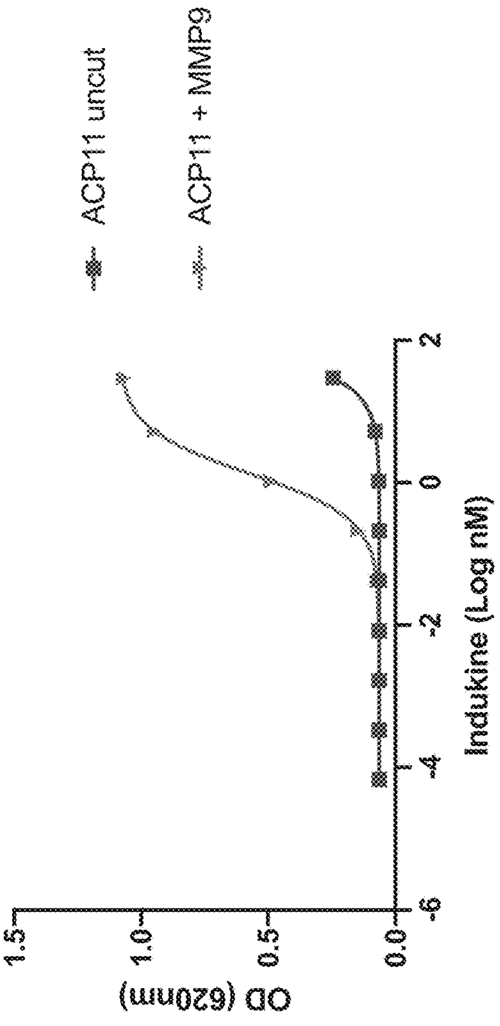
Figure 26B:
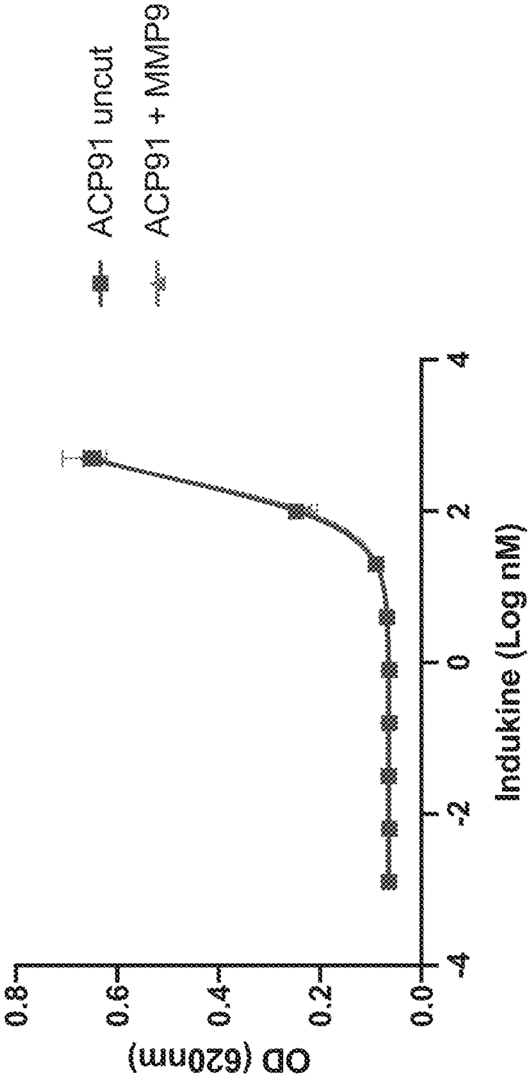
Figure 26C:
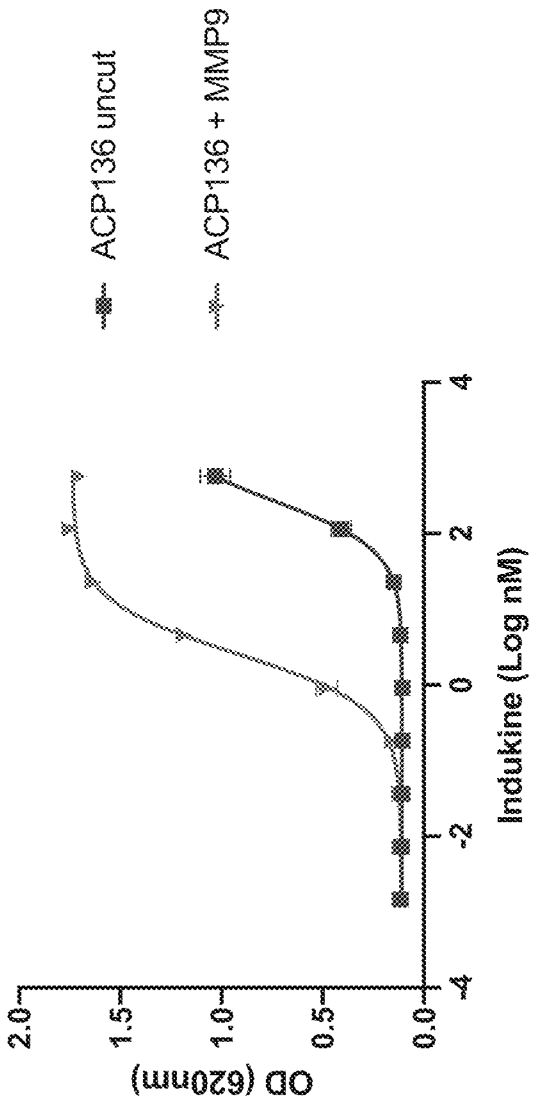
Figure 27A:
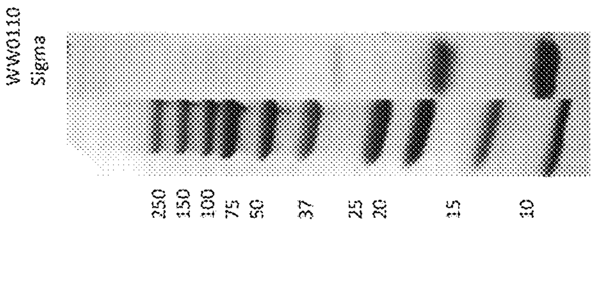
Figure 27A:
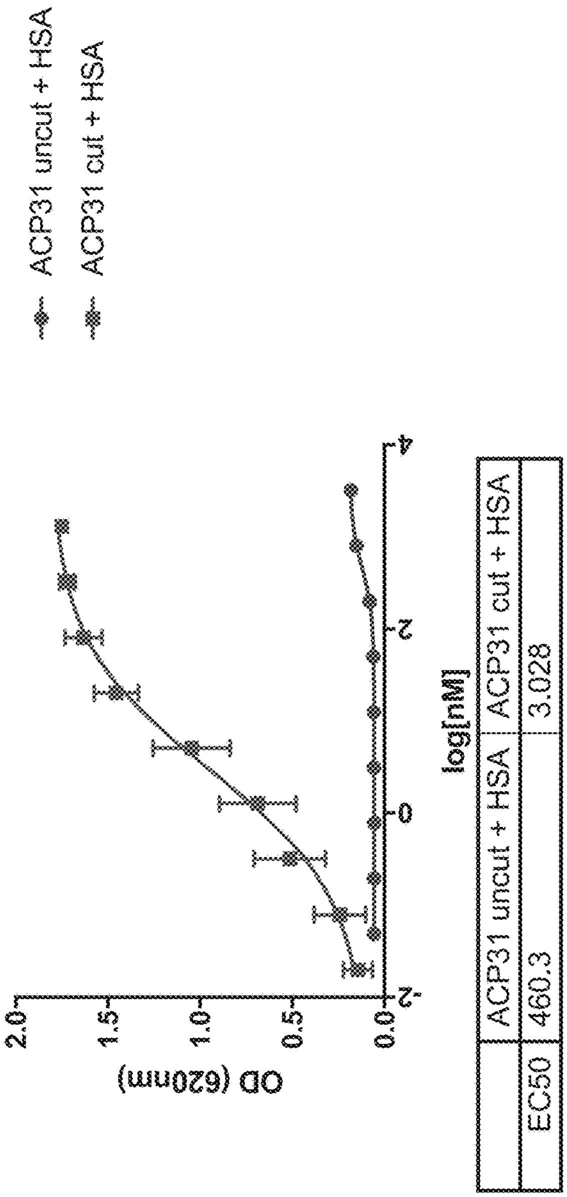
Figure 27B:
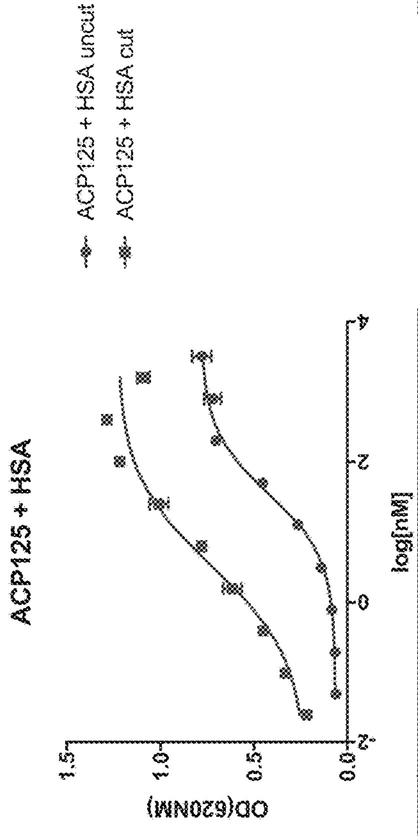
Figure 27C:
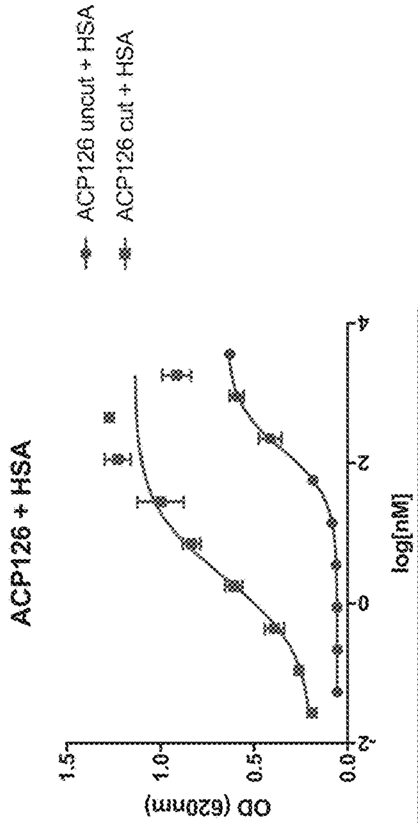
Figure 27D:
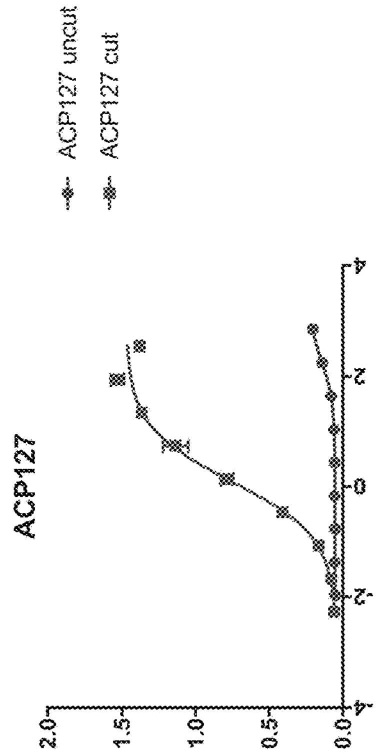
Figure 27E:
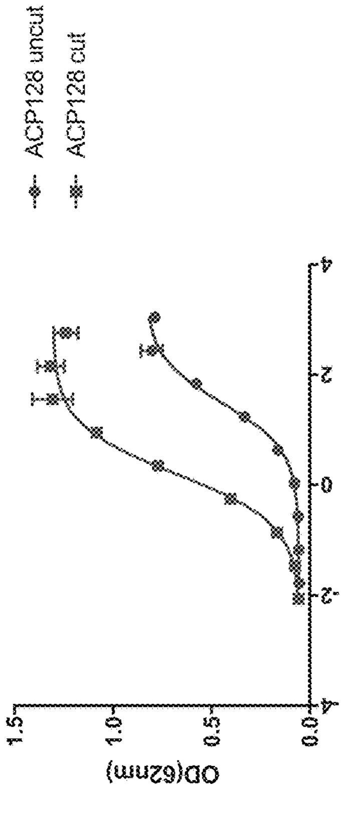
Figure 27F:
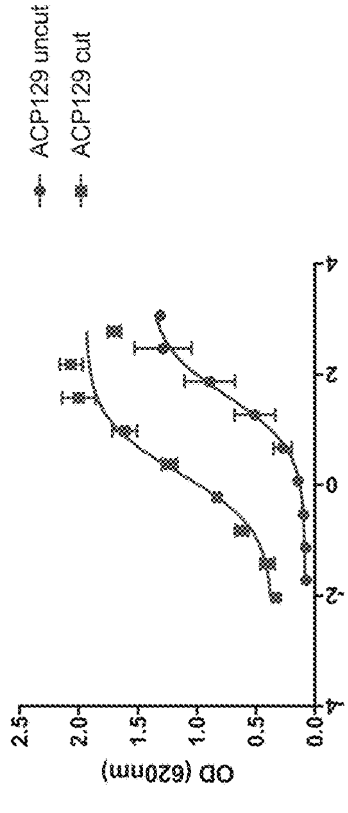

FIGS. 26A-26C are a series of graphs showing activity of fusion proteins in an HEKBlue IL-12 reporter assay. FIG. 26A depicts IL-12/STAT4 activation in a comparison of ACP11 (a human p40/murine p35 IL12 fusion protein) to ACP04 (negative control). FIG. 26B is a graph showing analysis of ACP91 (a chimeric IL-12 fusion protein). Squares depict activity of the uncut ACP91 polypeptide, and triangles depict the activity of the cut polypeptide (ACP91+MMP9). EC50 values for each are shown in the table. FIG. 26C is a graph showing analysis of ACP136 (a chimeric IL-12 fusion protein). Squares depict activity of the uncut ACP136 polypeptide, and triangles depict the activity of the cut polypeptide (ACP136+MMP9). EC50 values for each are shown in the table insert.

FIGS. 27A-27F are a series of graphs showing that cleaved mouse IFNα1 polypeptides ACP31 (FIG. 27A), ACP125 (FIG. 27B), ACP126 (FIG. 27C), ACP127 (FIG. 27D), APC128 (FIG. 27E), and APC129 (FIG. 27F) are active in an B16-Blue IFN-α/p reporter assay.

Figure 28A:
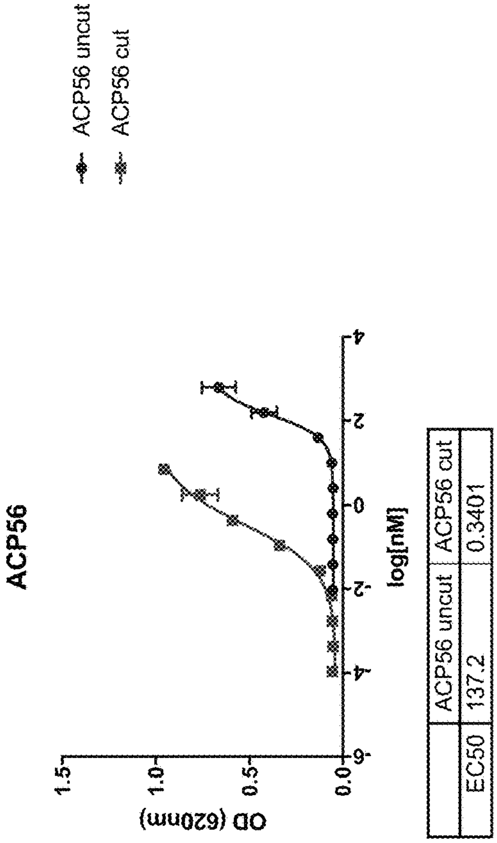
Figure 28B:
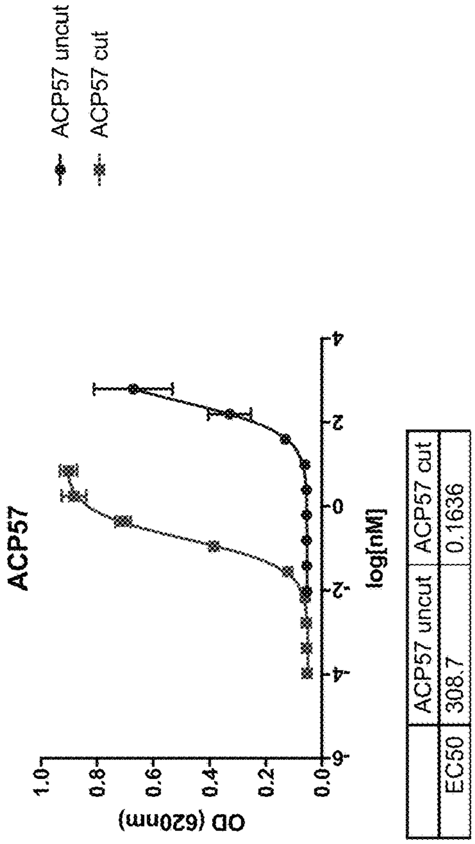
Figure 28C:
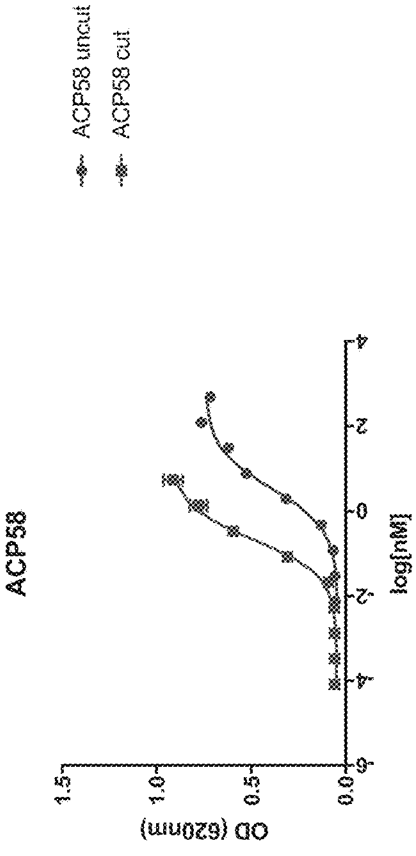
Figure 28D:
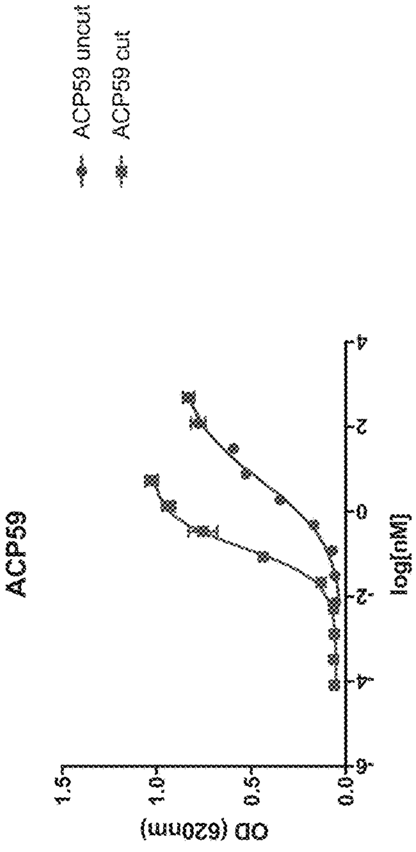
Figure 28E:
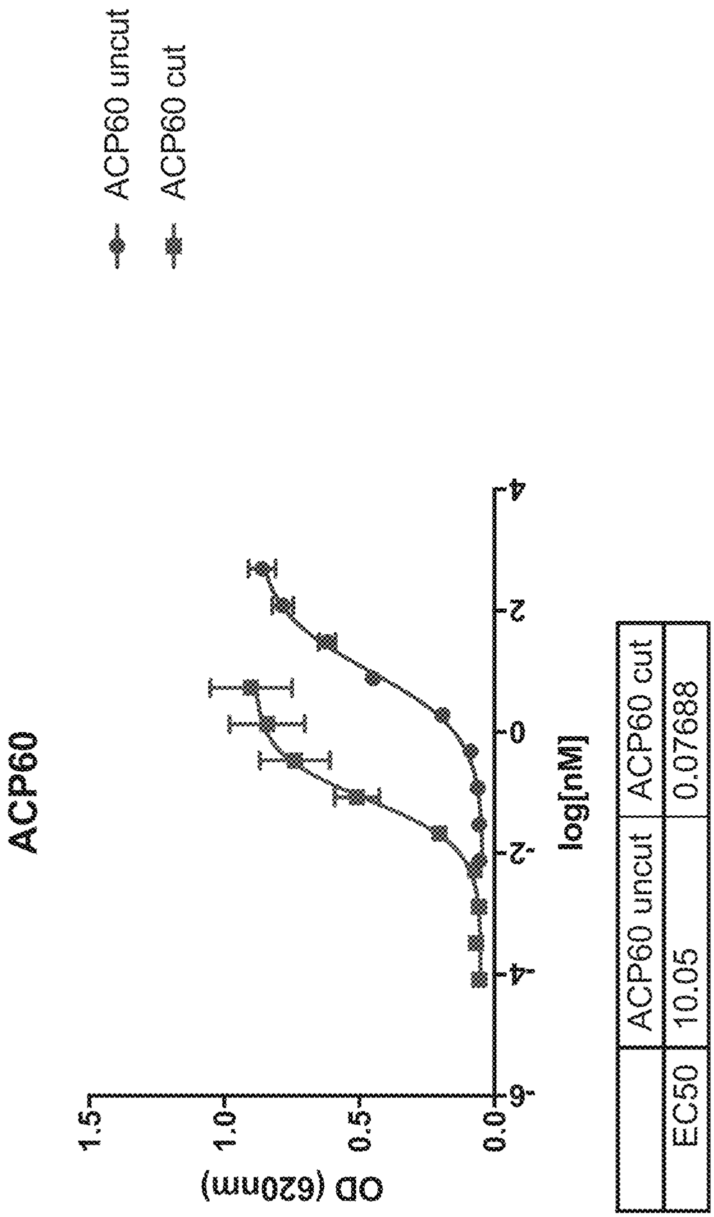
Figure 28F:
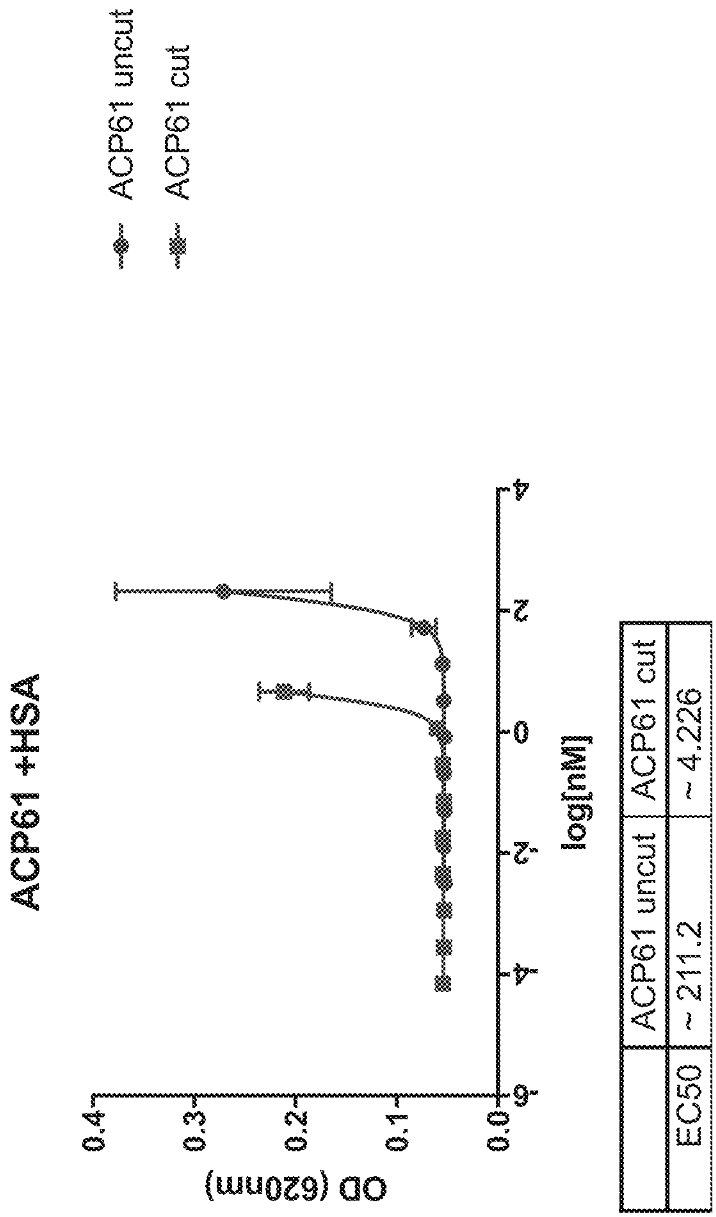
Figure 28G:
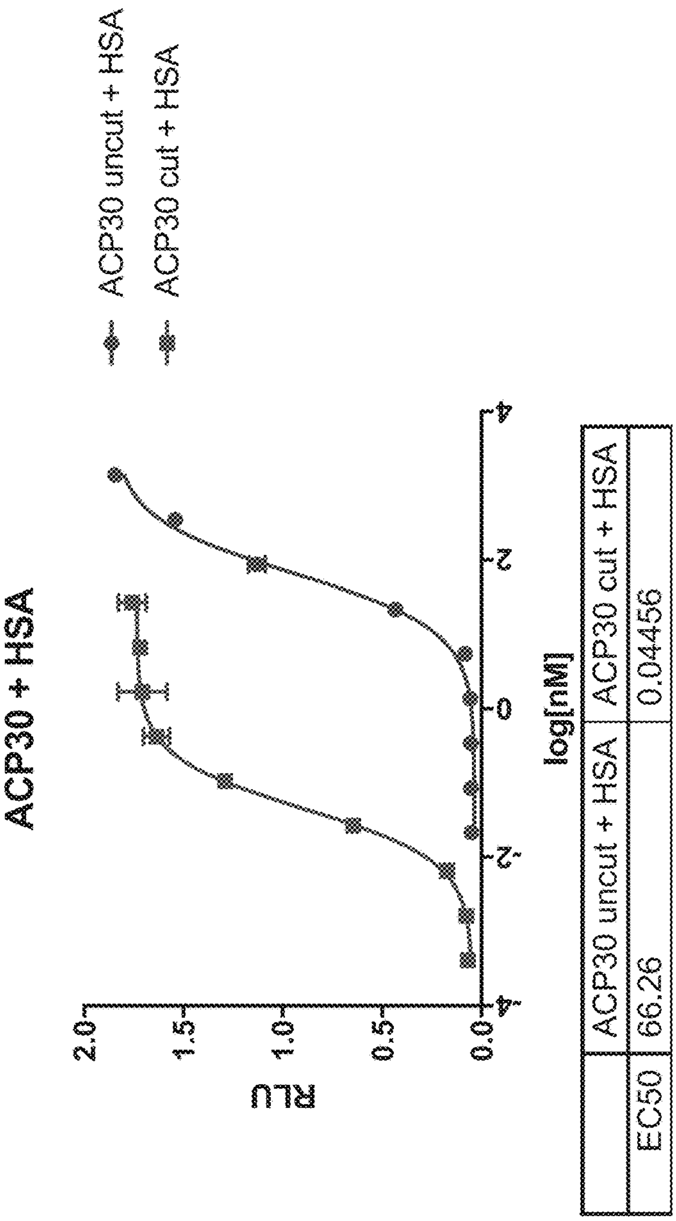
Figure 28H:
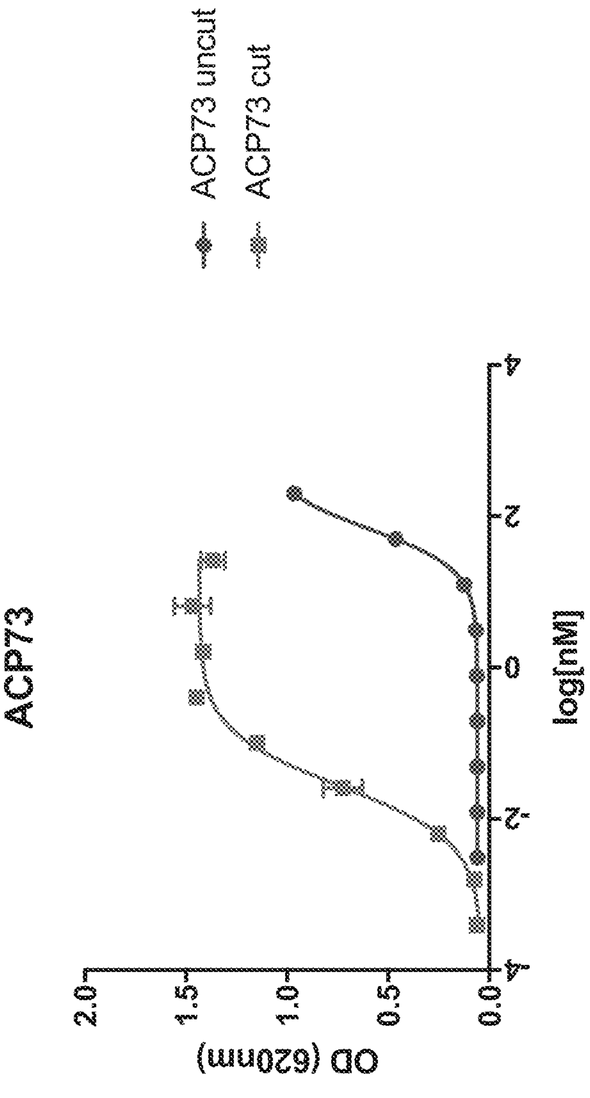
Figure 28I:
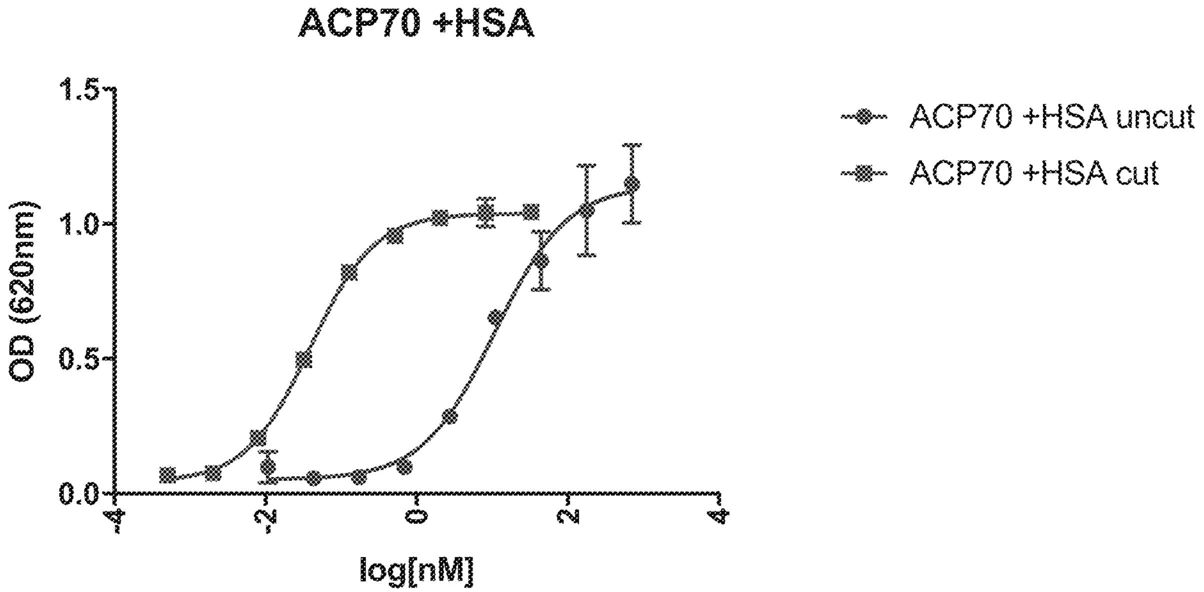
Figure 28J:
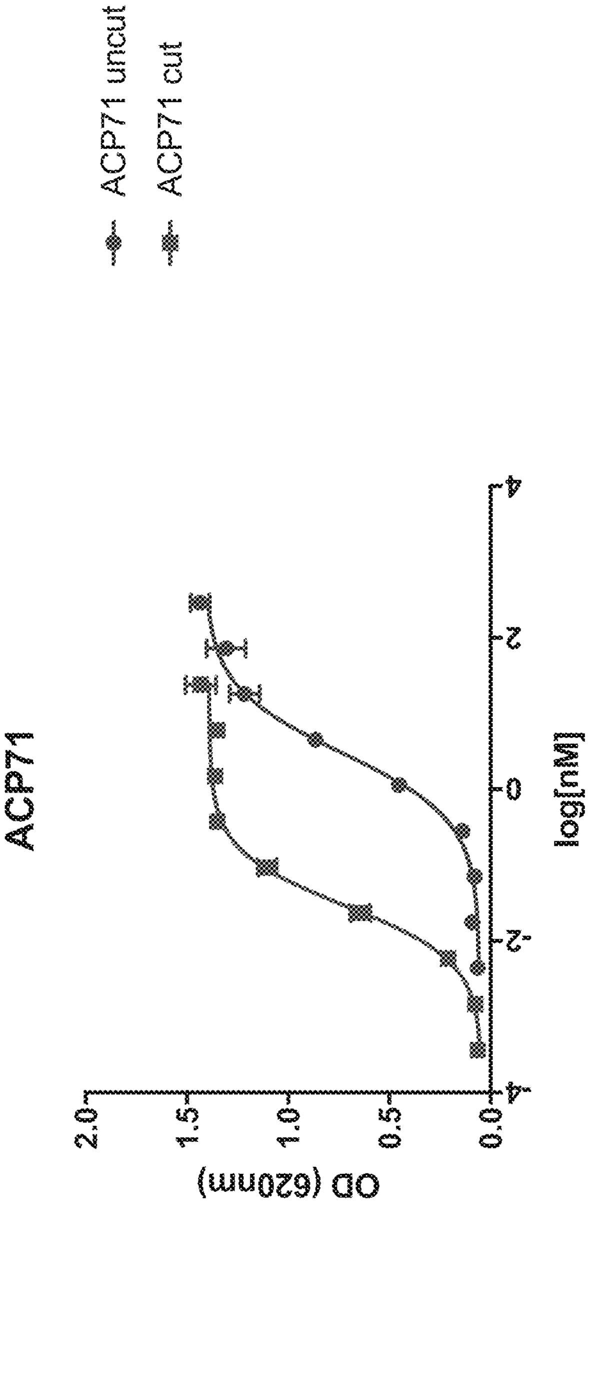
Figure 28K:
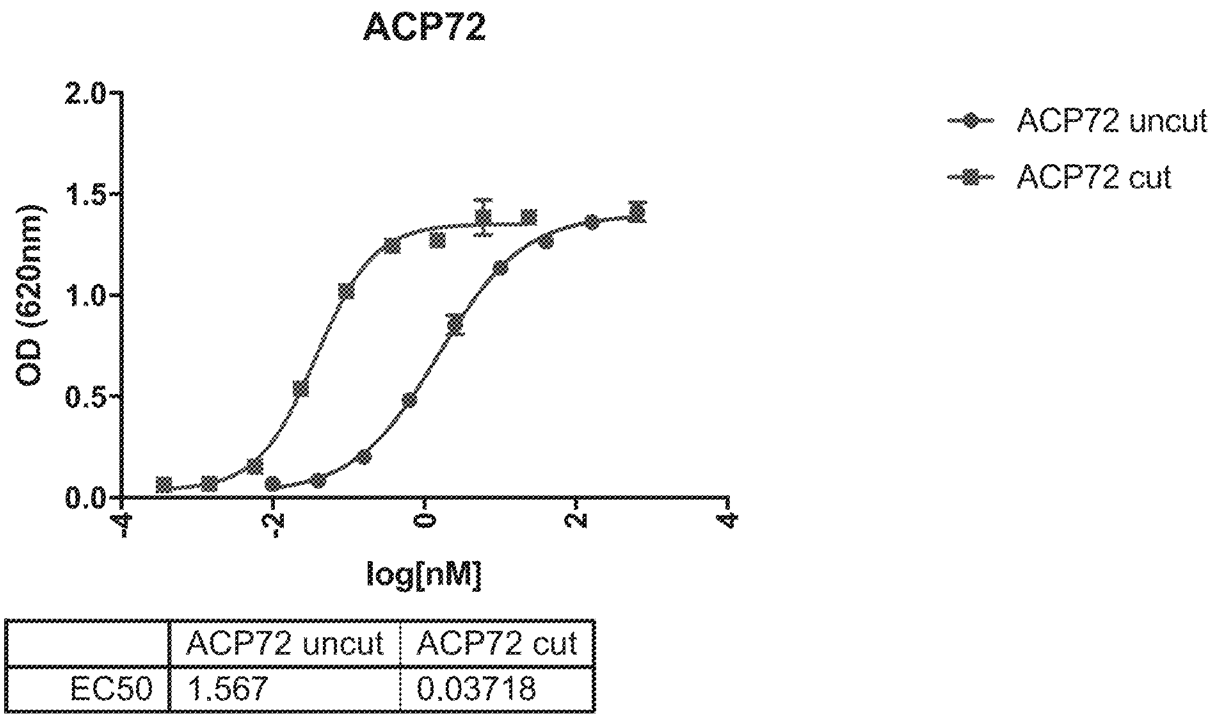
Figure 28L:
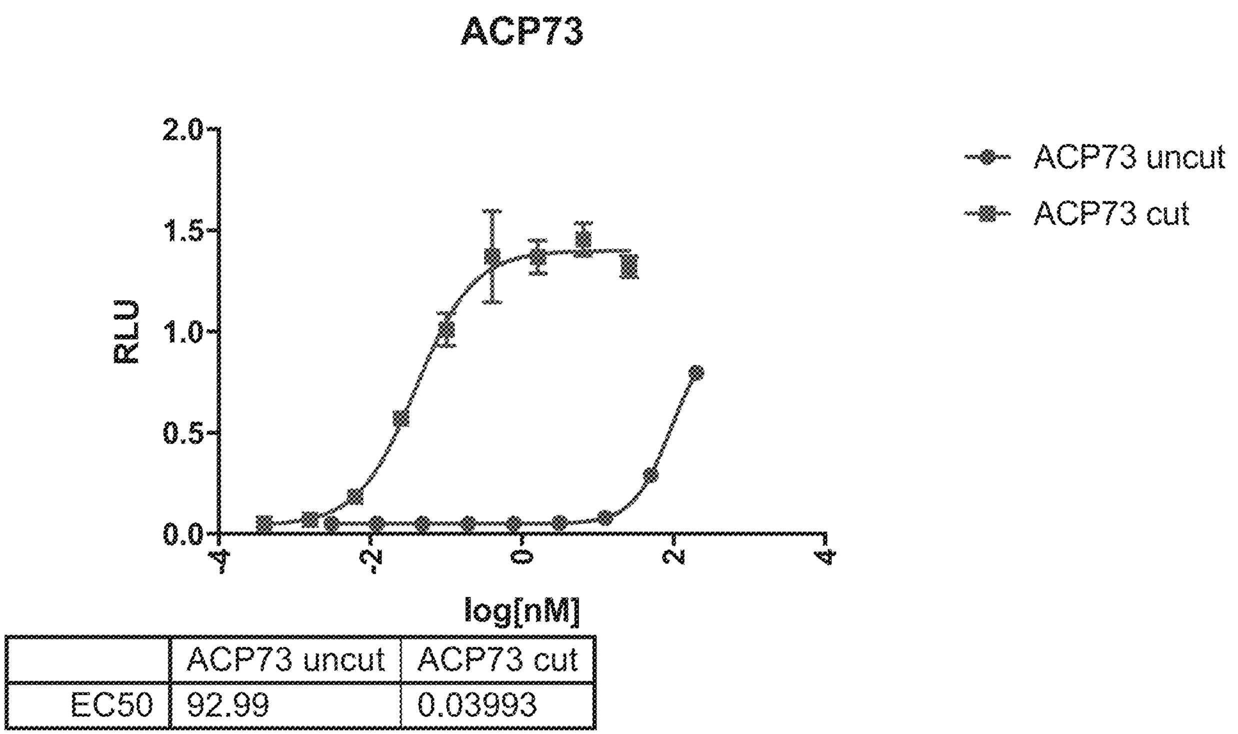
Figure 28M:
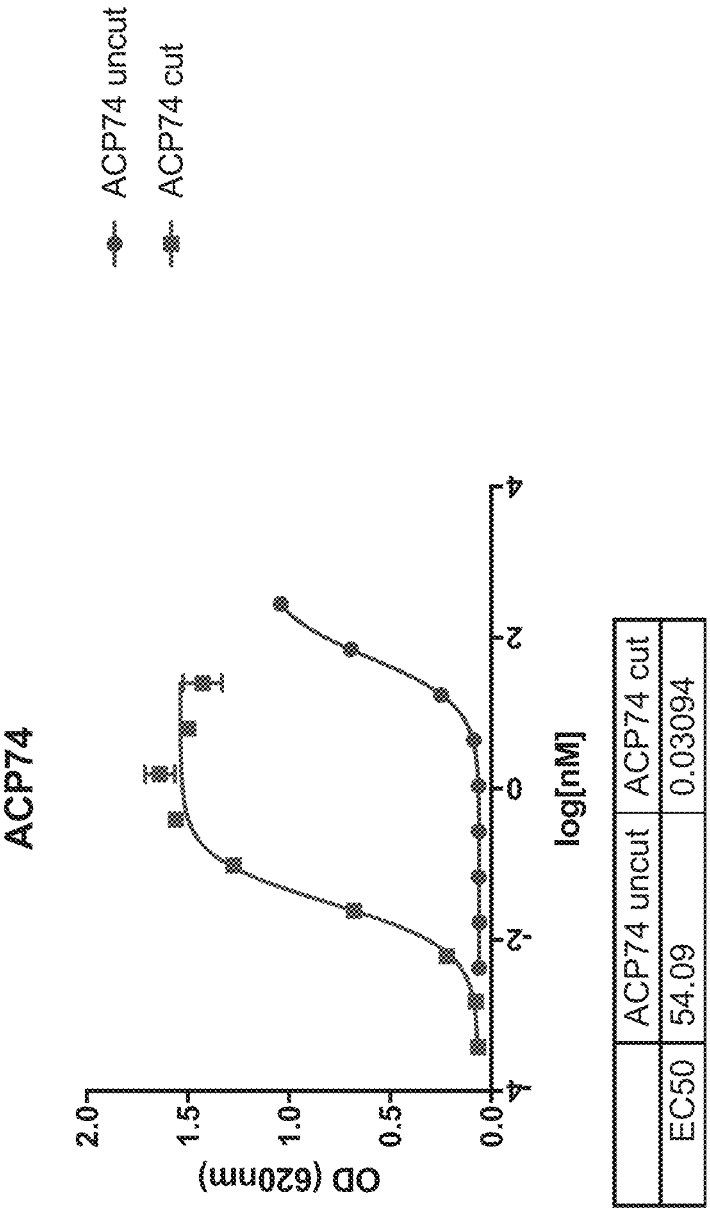
Figure 28N:
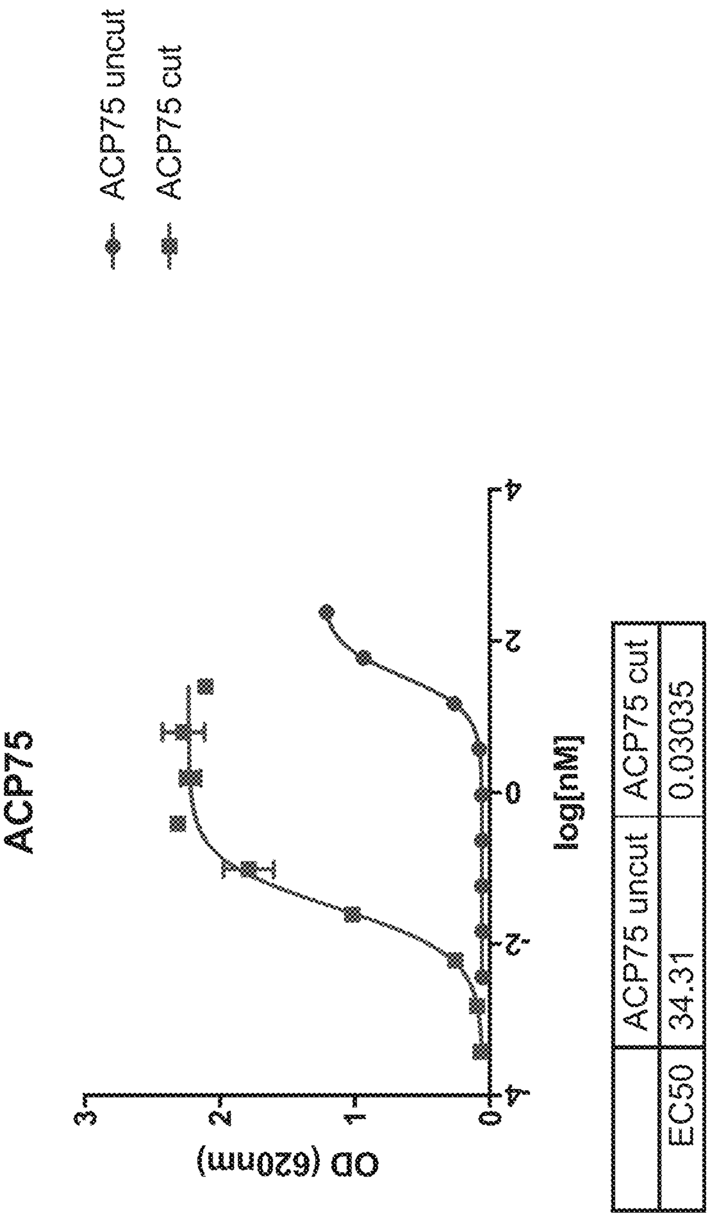

FIGS. 28A-28N are a series of graphs depicting the activity of ACP56 (FIG. 28A), ACP57 (FIG. 28B) ACP58 (FIG. 28C), ACP59 (FIG. 28D), ACP60 (FIG. 28E), ACP61+HSA (FIG. 28F), ACP30+HSA (FIG. 28G), ACP73 (FIG. 28H), ACP70+HSA (FIG. 28I), ACP71 (FIG. 28J), ACP72 (FIG. 28K), ACP 73 (FIG. 28L), ACP74 (FIG. 28M), and ACP75 (FIG. 28N) in a B16 IFNγ reporter assay. Each fusion was tested for its activity when cut (squares) and uncut (circles).

Figure 29A:
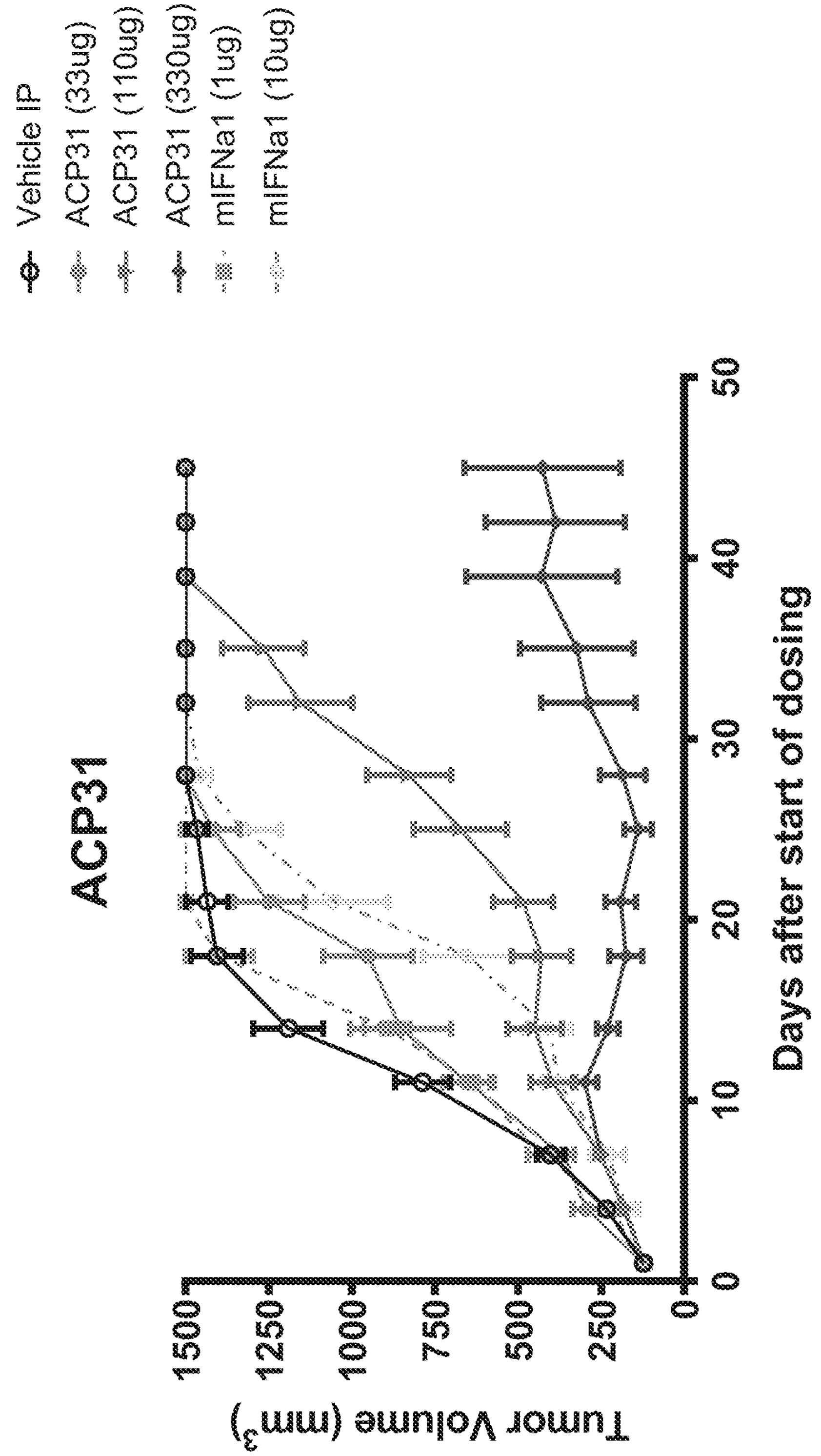
Figure 29B:
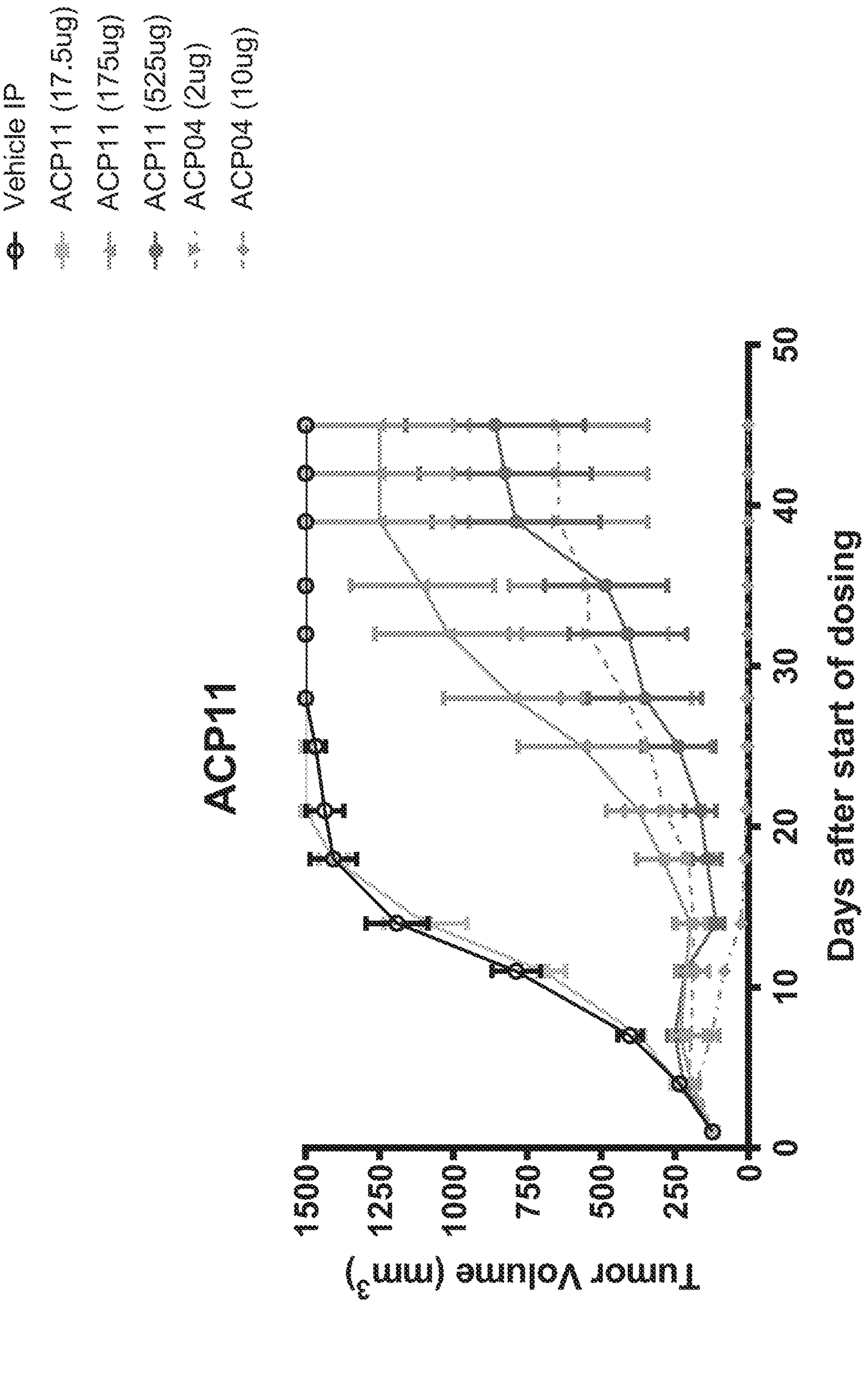

FIGS. 29A-29B are two graphs showing results of analyzing ACP31 (mouse IFNα1 fusion protein) and ACP11 (a human p40/murine p35 IL12 fusion protein) in a tumor xenograft model. FIG. 29A shows tumor volume over time in mice treated with 33 μg ACP31 (circles), 110 μg ACP31 (triangles), 330 μg ACP31 (diamonds), and as controls 1p g murine wild type IFNα1 (dashed line, squares) and 10 μg mIFNα1 (dashed line, small circles). Vehicle alone is indicated by large open circles. The data show tumor volume decreasing over time in a dose-dependent manner in mice treated with ACP31. FIG. 29B shows tumor volume over time in mice treated with 17.5 μg ACP11 (squares), 175 μg ACP11 (triangles), 525 μg ACP11 (circles), and as controls 2 μg ACP04 (dashed line, triangles) and 10 μg ACP04 (dashed line, diamonds). Vehicle alone is indicated by large open circles. The data show tumor volume decreasing over time in a dose-dependent manner in mice treated with both ACP11 and ACP04 (a human p40/murine p35 IL12 fusion protein).

Figure 30A:
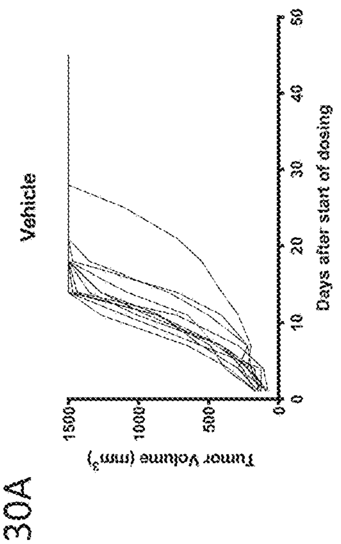
Figure 30B:
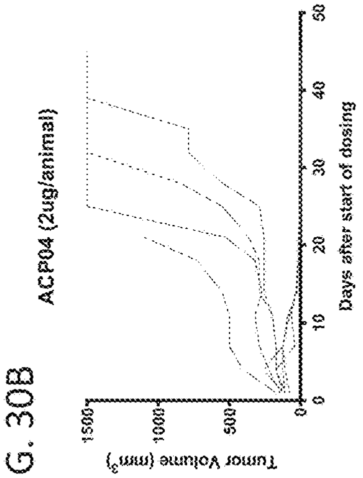
Figure 30C:
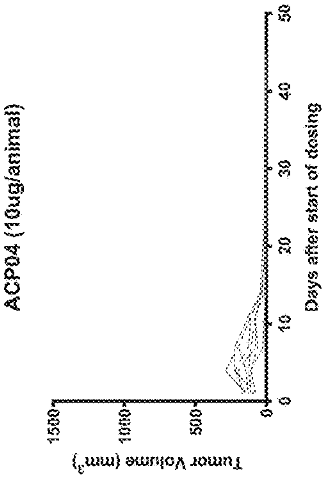
Figure 30D:
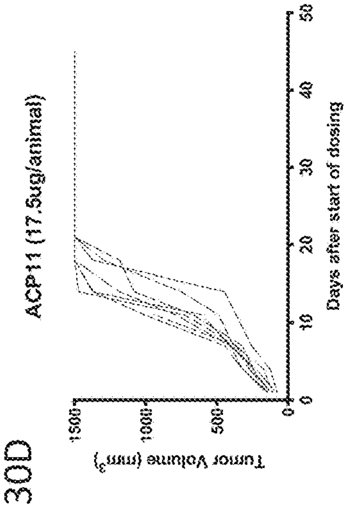
Figure 30E:
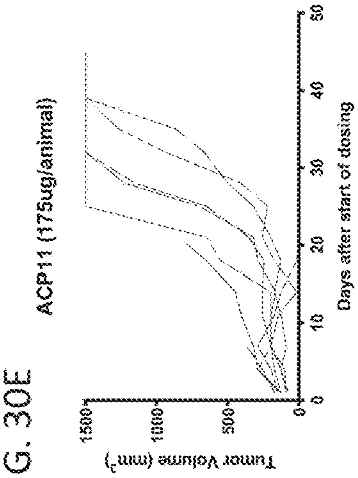
Figure 30F:
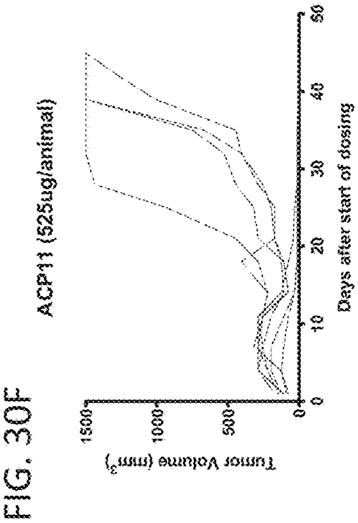

FIGS. 30A-30F are a series of spaghetti plots showing tumor volume over time in a mouse xenograft tumor model in mice each treated with vehicle alone (FIG. 30A), 2 μg ACP04 (FIG. 30B), 10 μg ACP04 (FIG. 30C), 17.5 μg ACP11 (FIG. 30D), 175 μg ACP11 (FIG. 30E), and 525 μg ACP11 (FIG. 30F). Each line represents a single mouse.

Figure 31A:
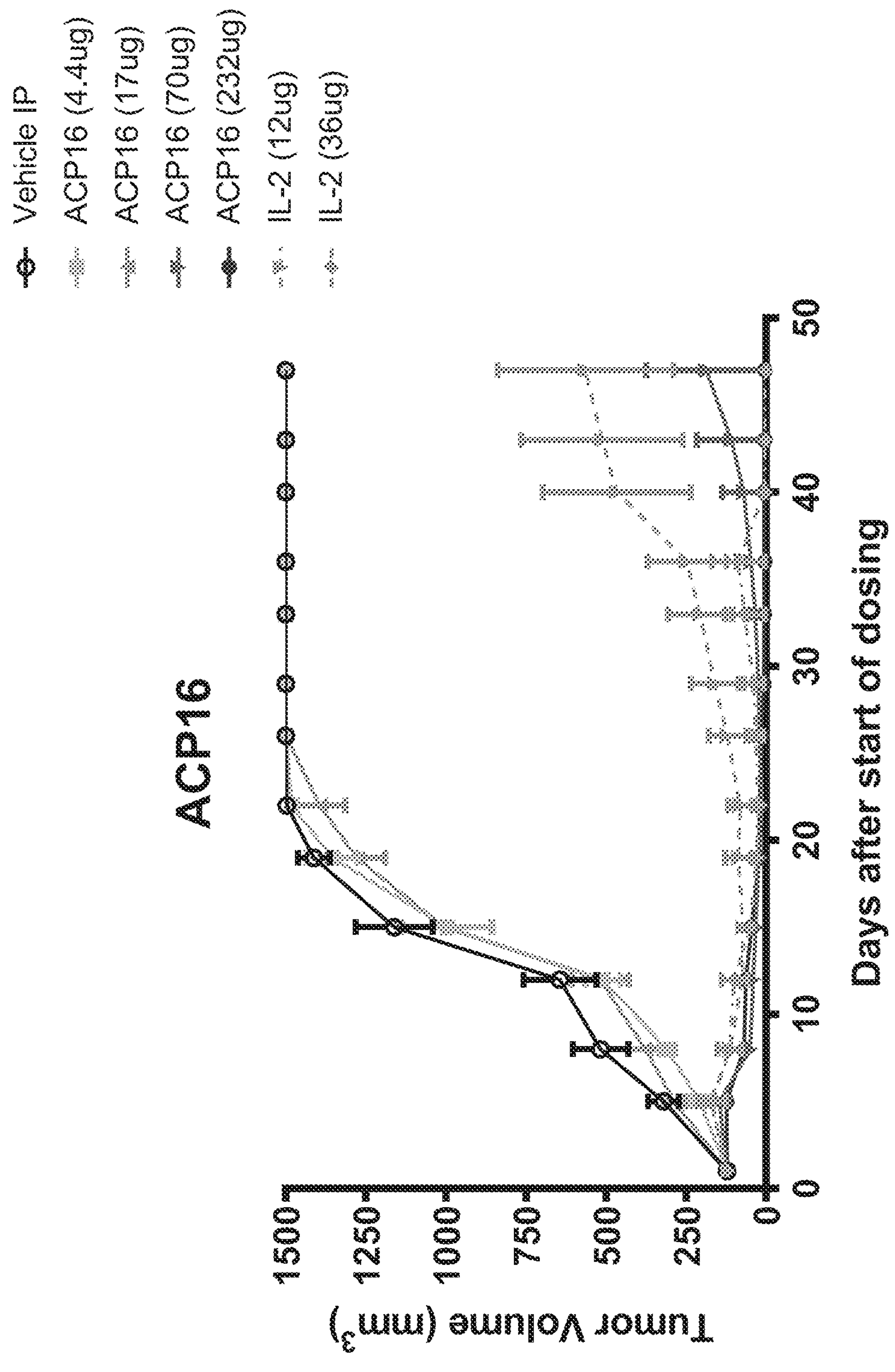
Figure 31B:
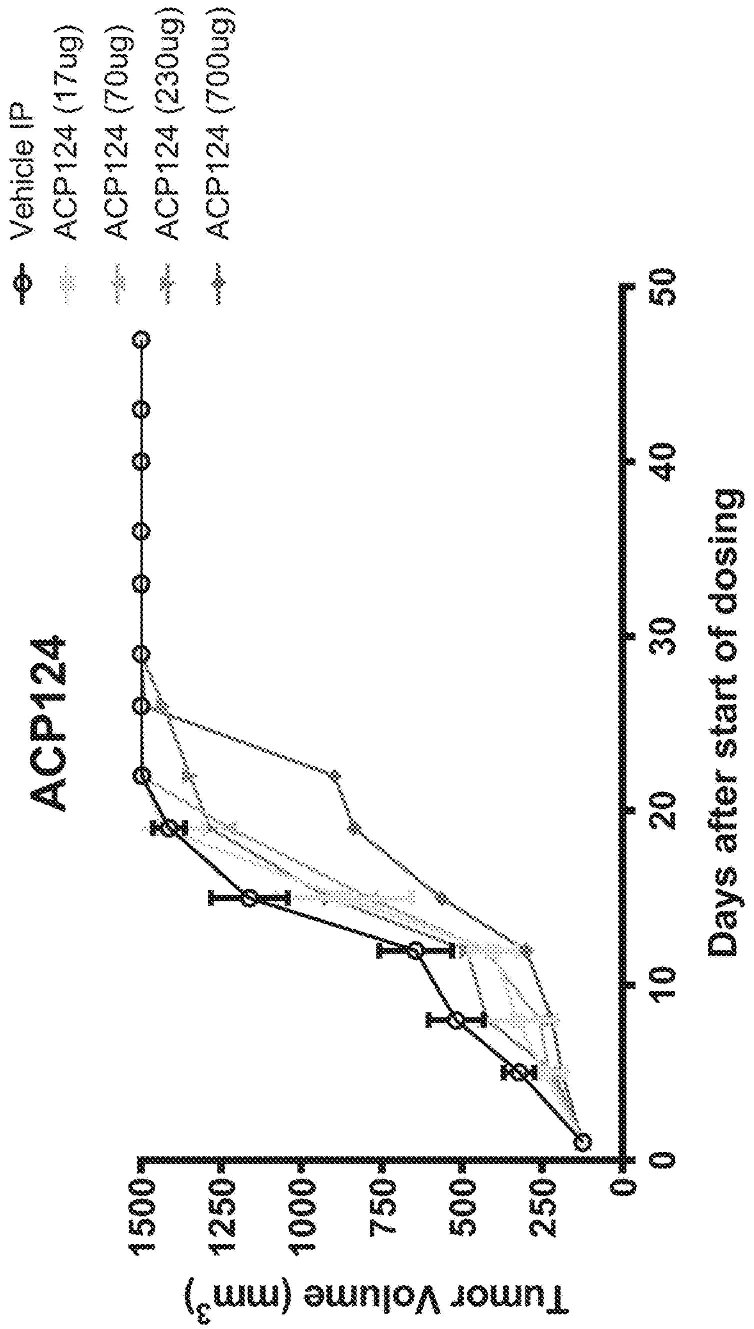
Figure 31C:
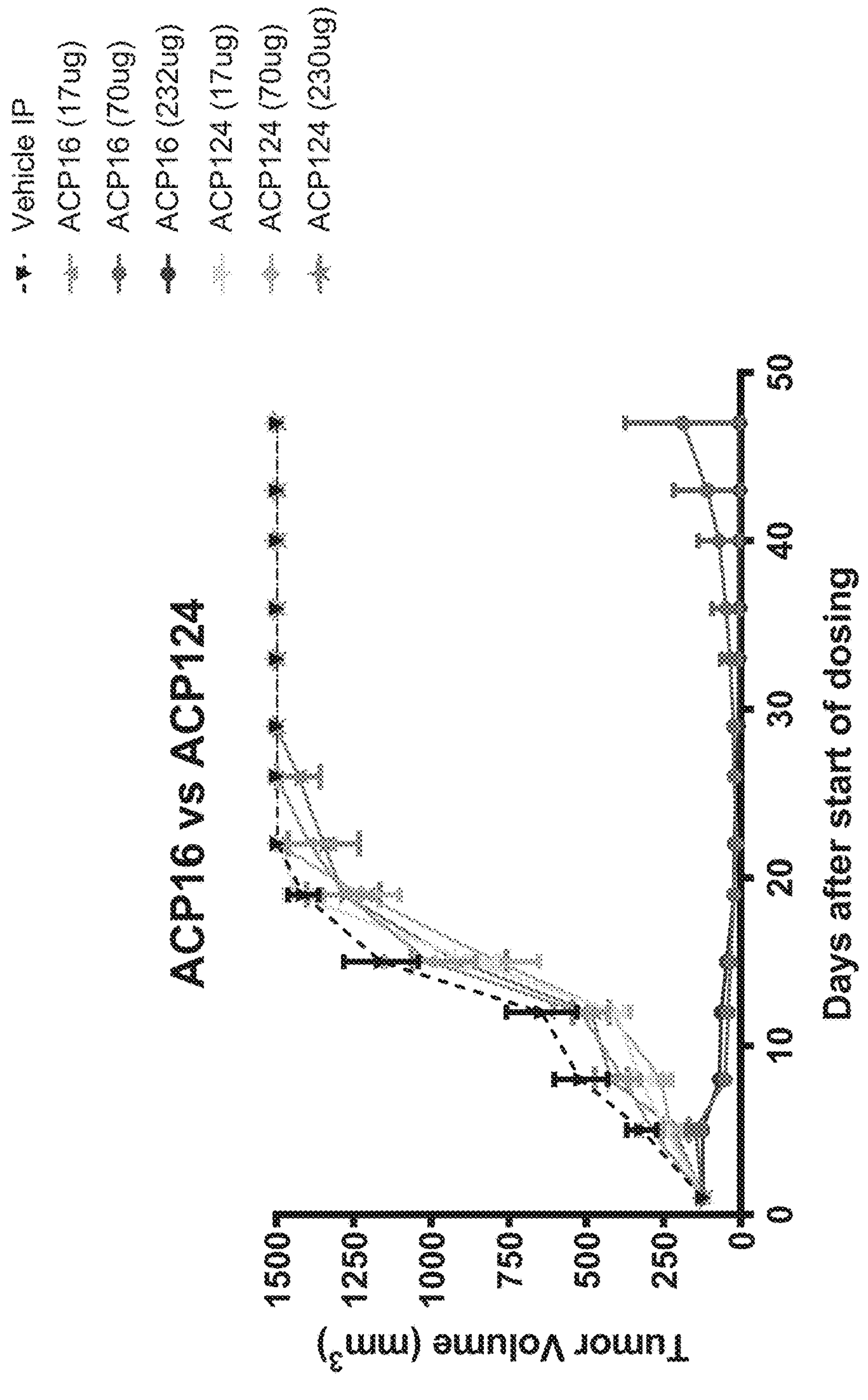

FIG. 31A-31C are three graphs showing results of analyzing ACP16 and ACP124 in a tumor xenograft model. FIG. 31A shows tumor volume over time in mice treated with 4.4 μg ACP16 (squares), 17 μg ACP16 (triangles), 70 μg ACP16 (downward triangles), 232 μg ACP16 (dark circles), and as a comparator 12 μg wild type IL-2 (dashed line, triangles) and 36 μg wild type IL-2 (dashed line, diamonds. Vehicle alone is indicated by large open circles. The data show tumor volume decreasing over time in a dose-dependent manner in mice treated with ACP16 at higher concentrations. FIG. 31B shows tumor volume over time in mice treated with 17 μg ACP124 (squares), 70 μg ACP124 (triangles), 230 μg ACP124 (downward triangles), and 700 μg ACP124. Vehicle alone is indicated by large open circles. FIG. 31C shows tumor volume over time in mice treated with 17 μg ACP16 (triangles), 70 μg ACP16 (circles), 232 μg ACP16 (dark circles), and as a comparator 17 μg ACP124 (dashed line, triangles) 70 μg ACP124 (dashed line, diamonds), 230 μg ACP124 (dashed line, stars). Vehicle alone is indicated by dark downward triangles. The data show tumor volume decreasing over time in a dose-dependent manner in mice treated with ACP16, but not ACP124.

Figure 32A:
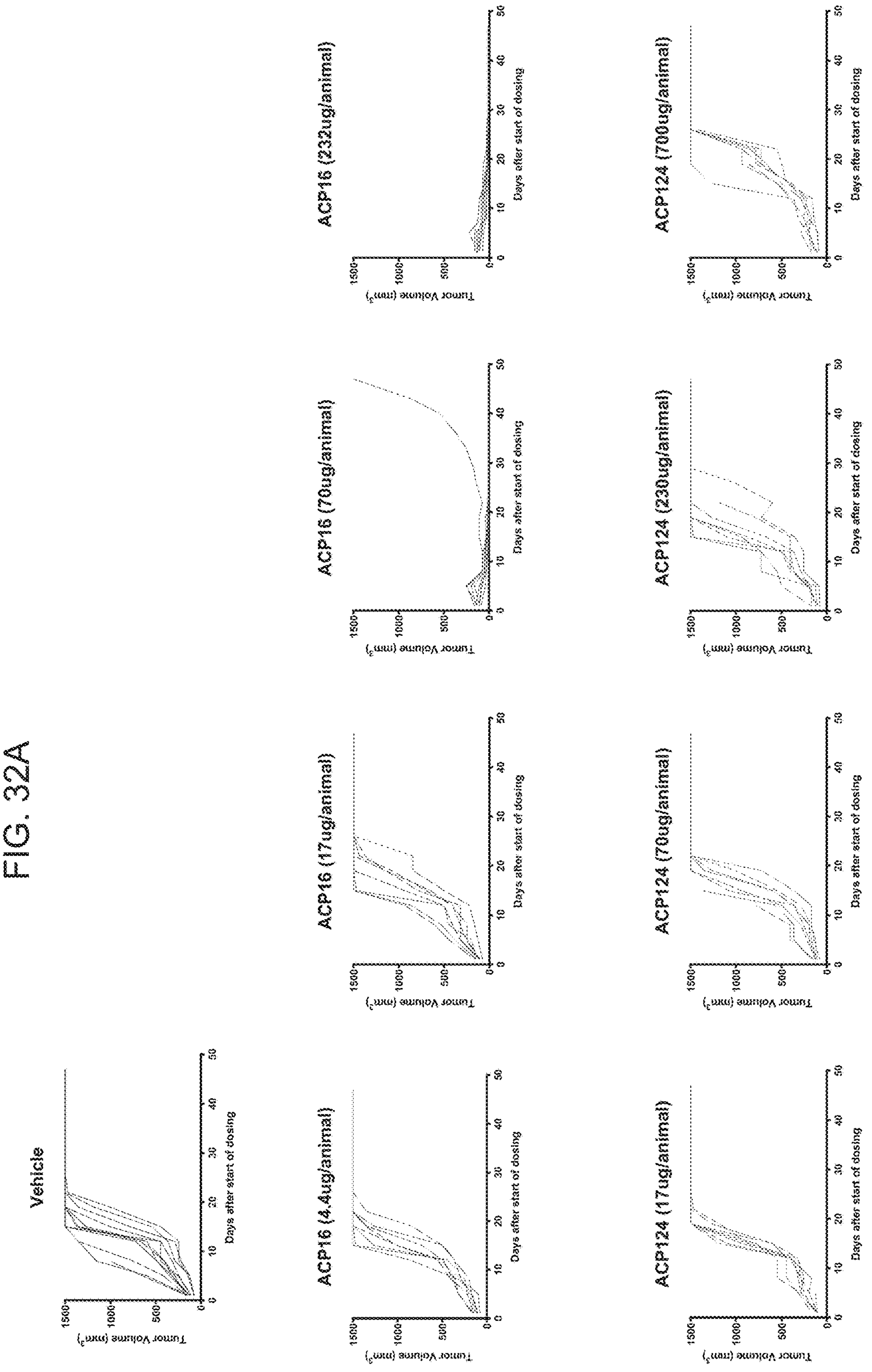
Figure 32B:
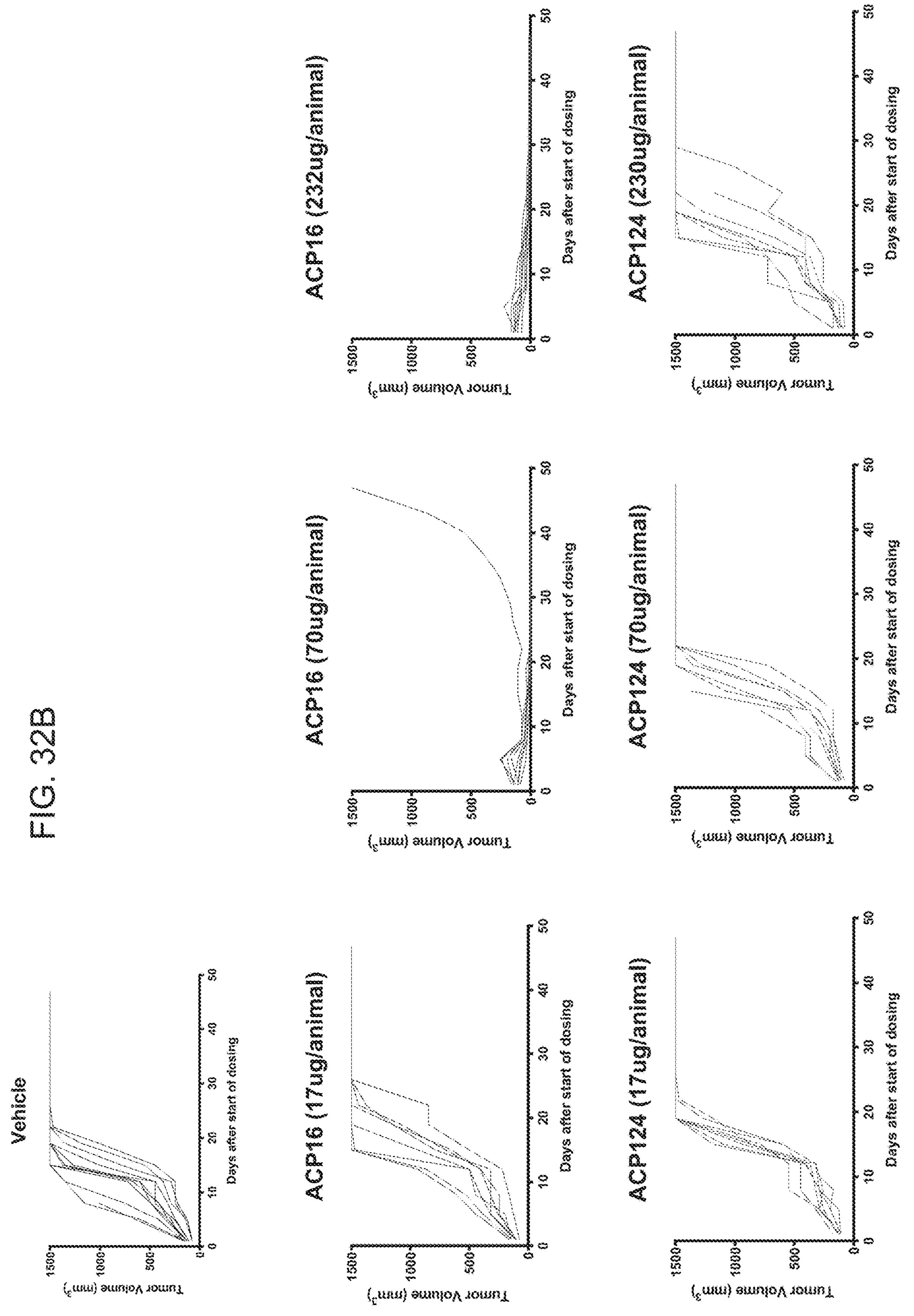

FIG. 32A-32B are a series of spaghetti plots showing activity of fusion proteins in an MC38 mouse xenograft model corresponding to the data shown in FIG. 31A-31C. Each line in the plots is a single mouse.

Figure 33:
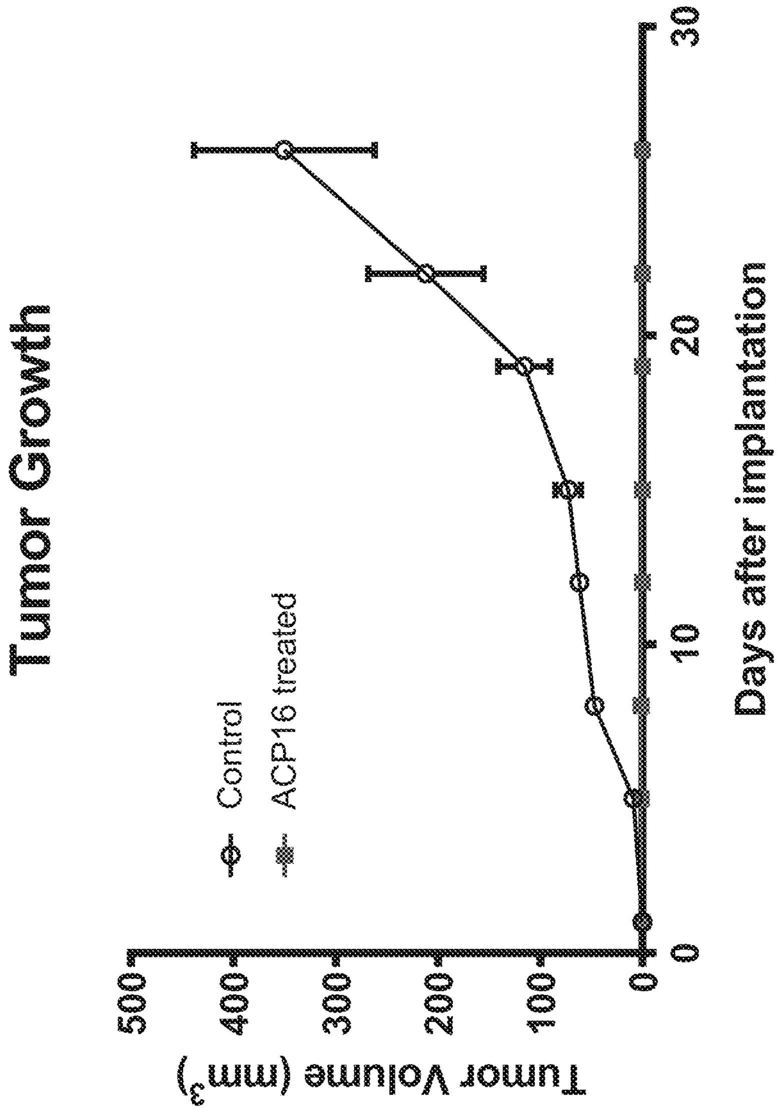

FIG. 33 is a graph showing tumor volume over time in a mouse xenograft model showing tumor growth in control mice (open circles) and AP16-treated mice (squares).

Figure 34A:
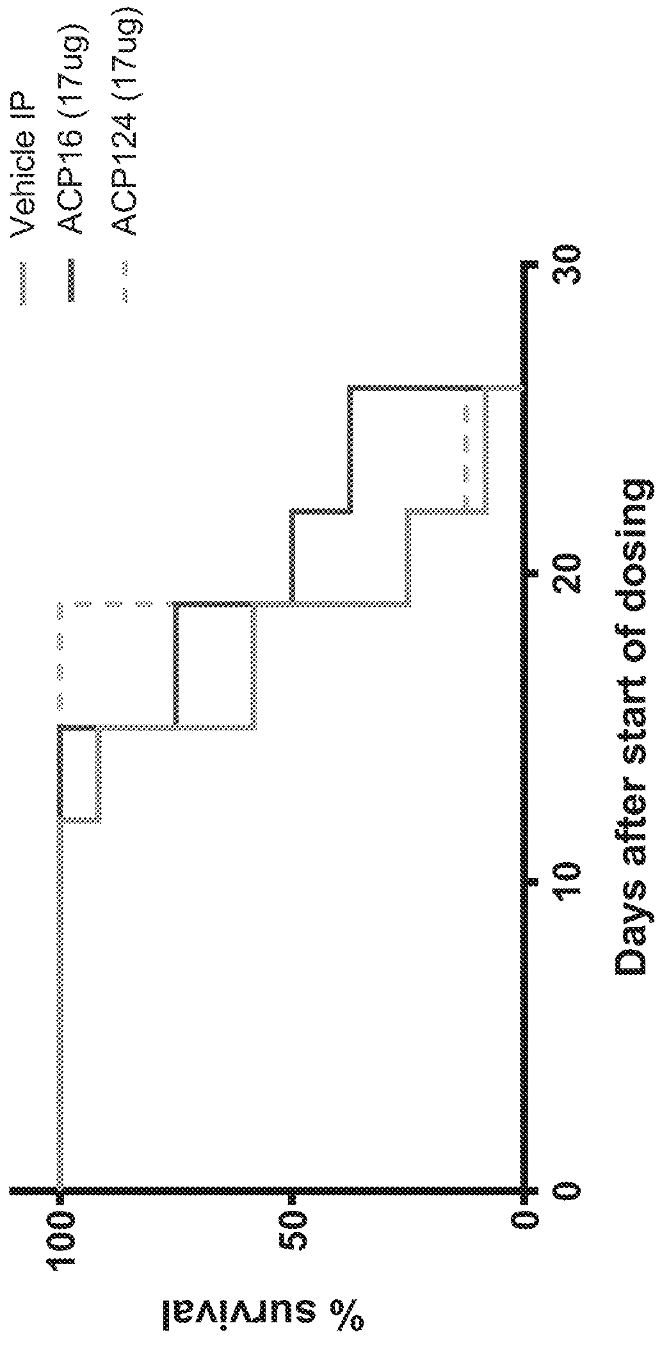
Figure 34B:
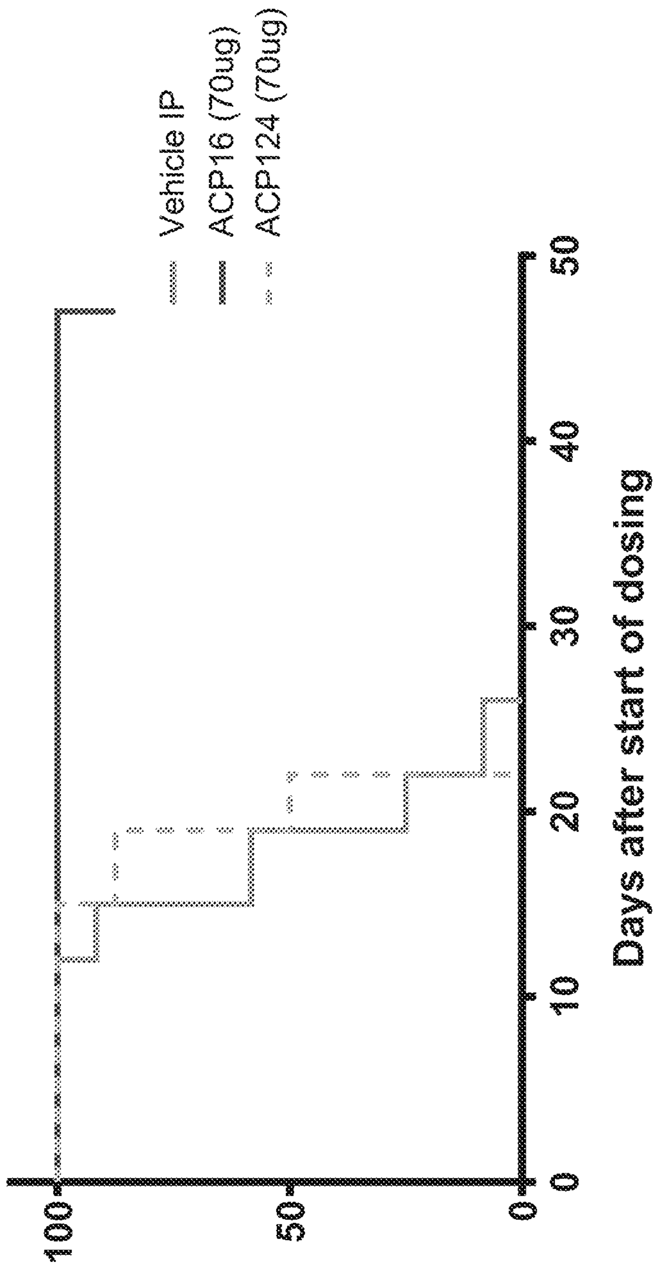
Figure 34C:
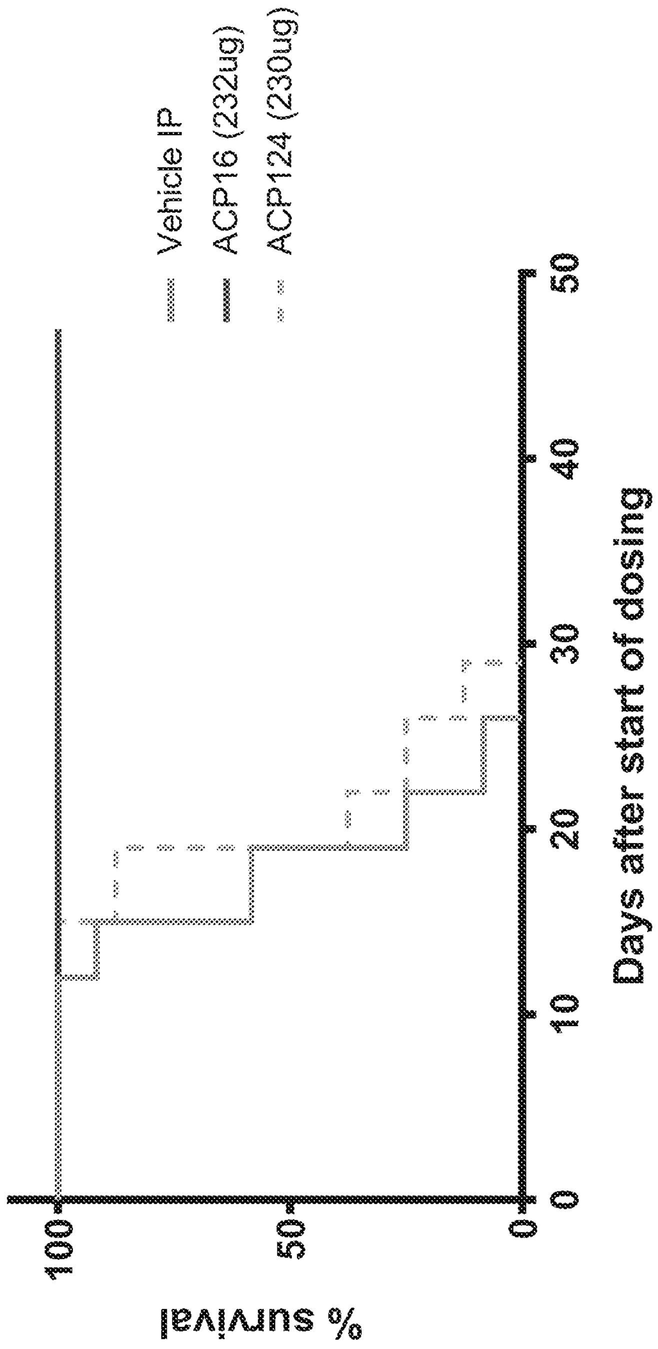
Figure 34D:
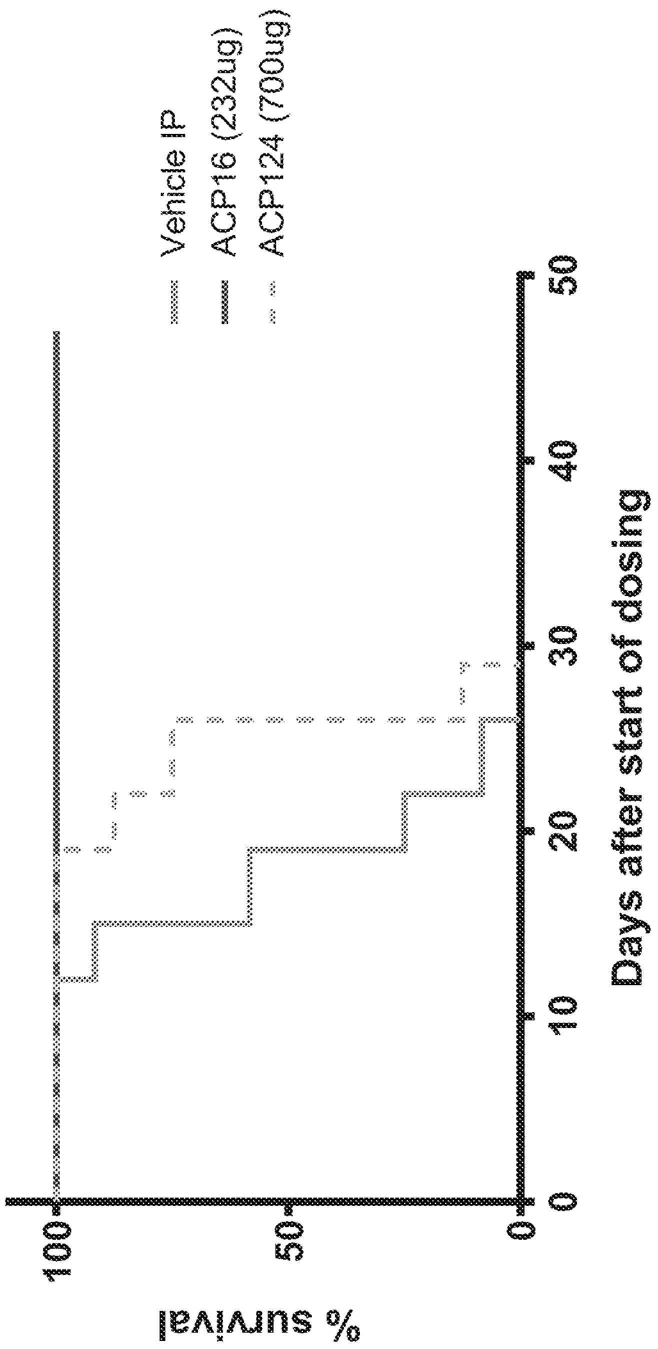

FIGS. 34A-34D are a series of survival plots showing survival of mice over time after treatment with cleavable fusion proteins. FIG. 34A shows data for mice treated with vehicle alone (gray line), 17 μg ACP16 (dark line), and 17 μg ACP124 (dashed line). FIG. 34B shows data for mice treated with vehicle alone (gray line), 70 μg ACP16 (dark line), and 70 μg ACP124 (dashed line). FIG. 34C shows data for mice treated with vehicle alone (gray line), 232 μg ACP16 (dark line), and 230 μg ACP124 (dashed line). FIG. 34D shows data for mice treated with vehicle alone (gray line), 232 μg ACP16 (dark line), and 700 μg ACP124 (dashed line).

Figure 35:
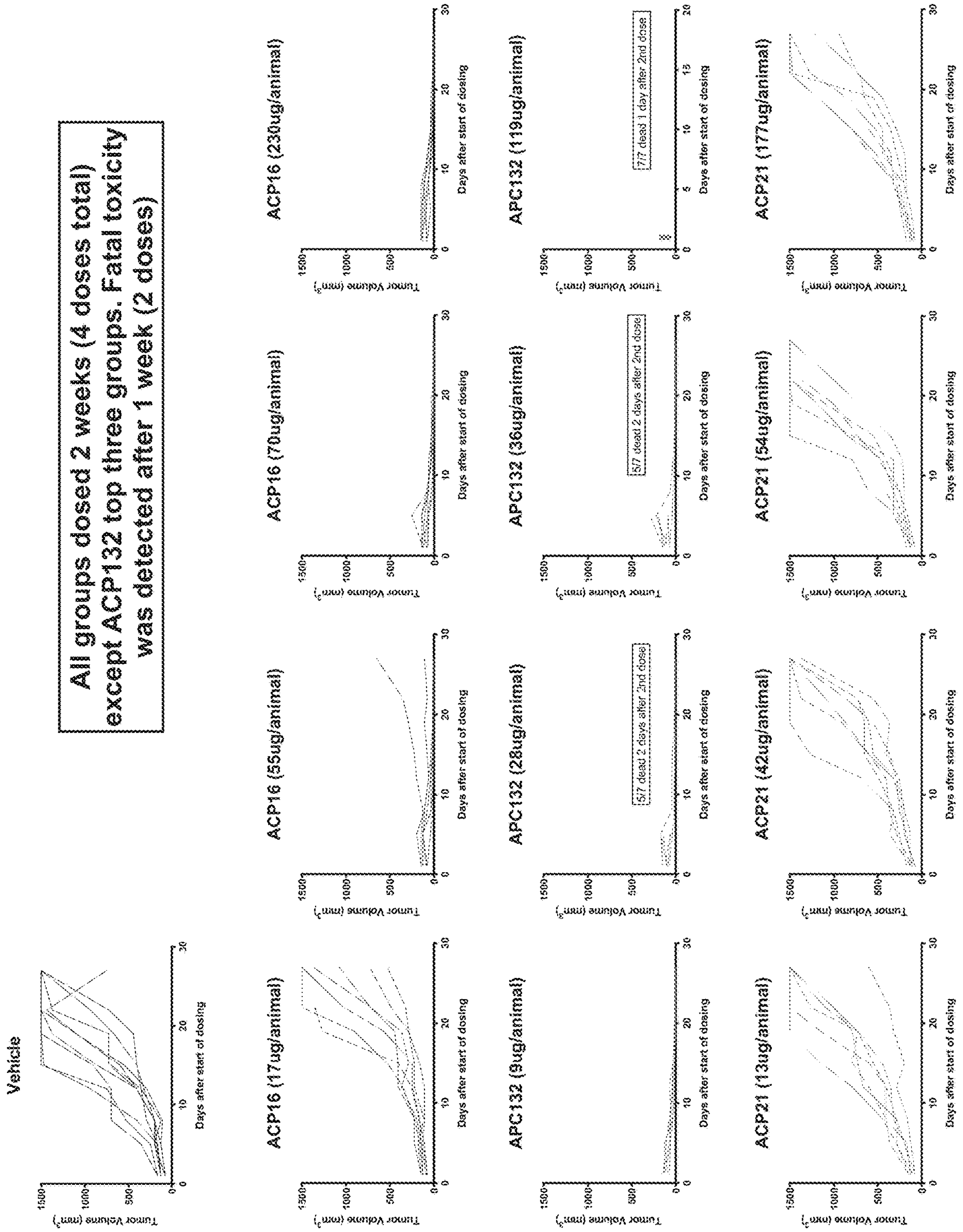
Figure 36A:
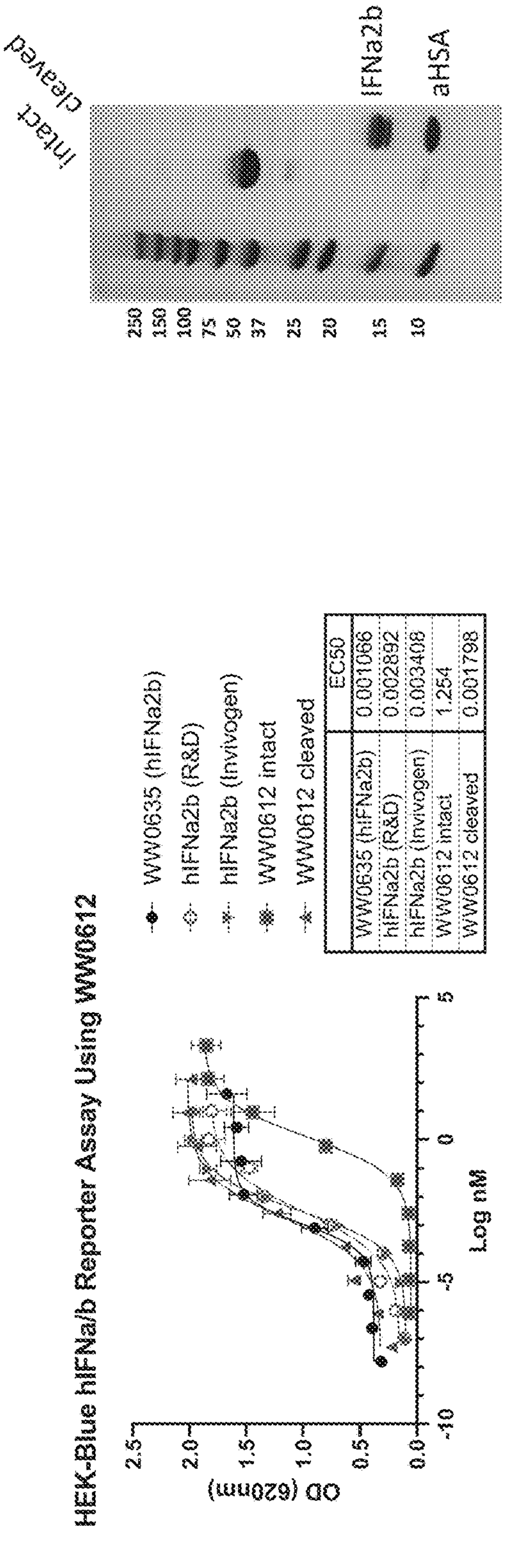
Figure 36B:
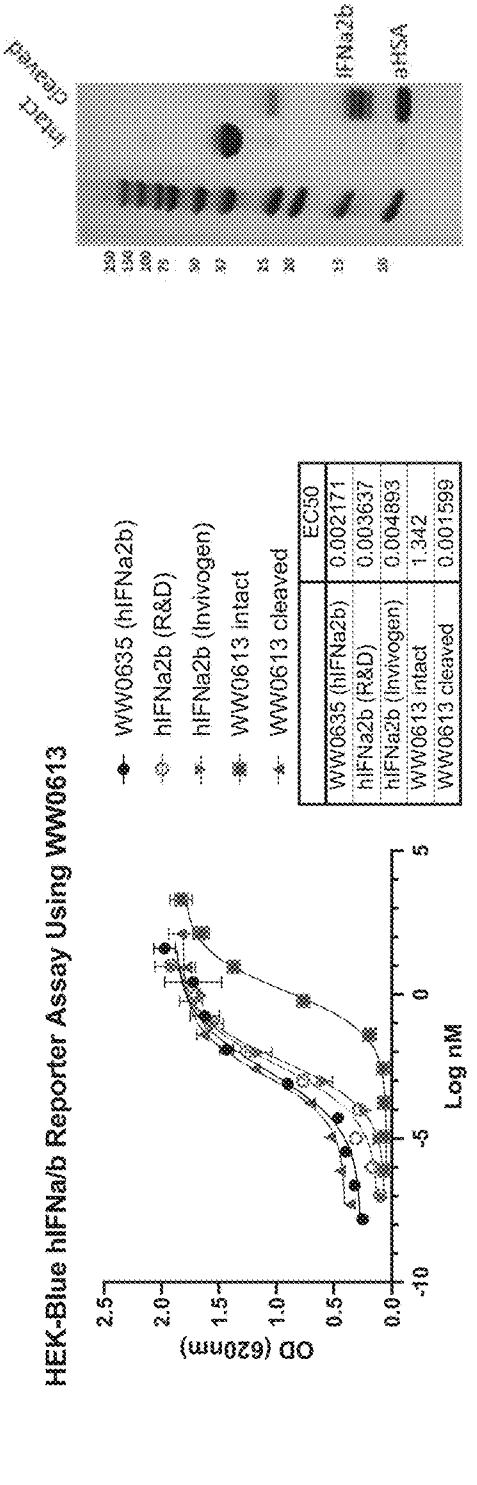
Figure 36C:
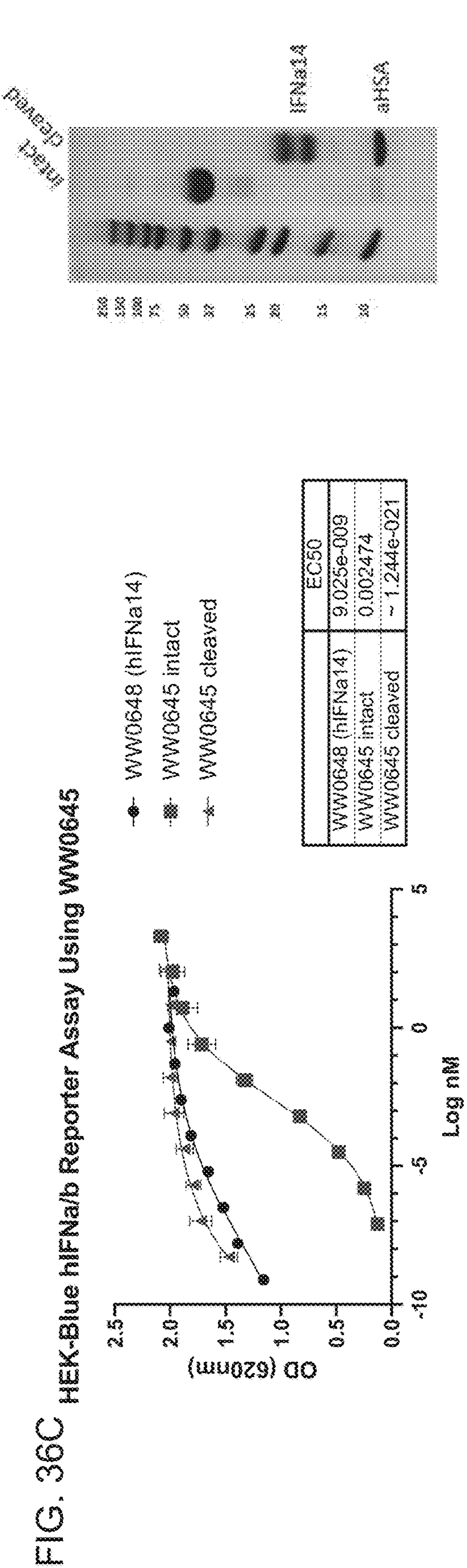
Figure 36D:
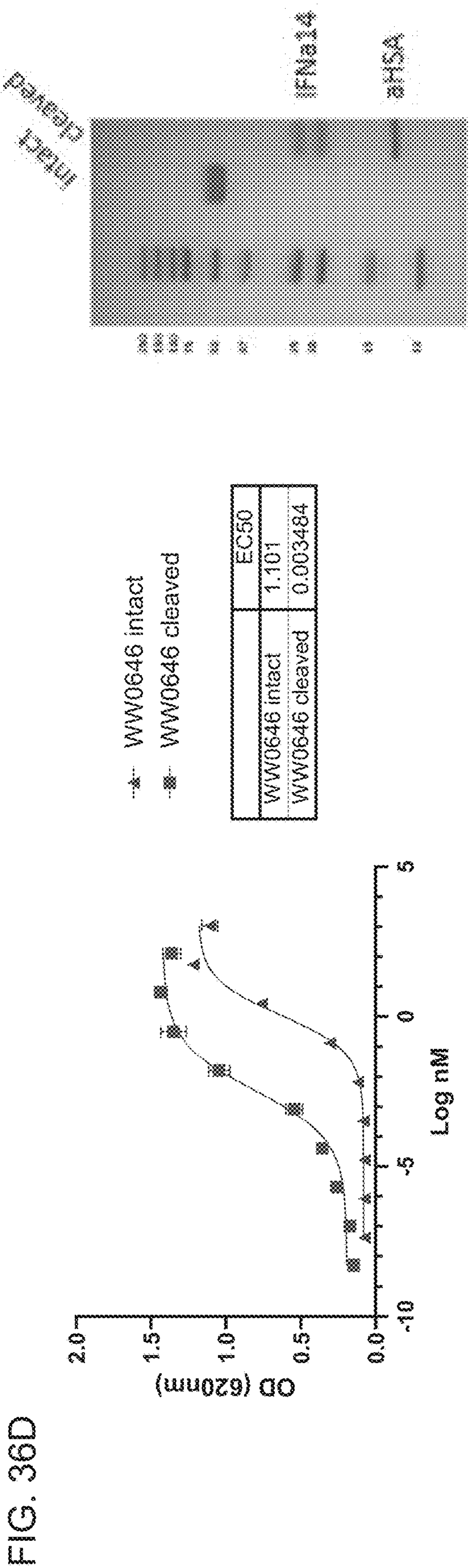
Figure 36E:
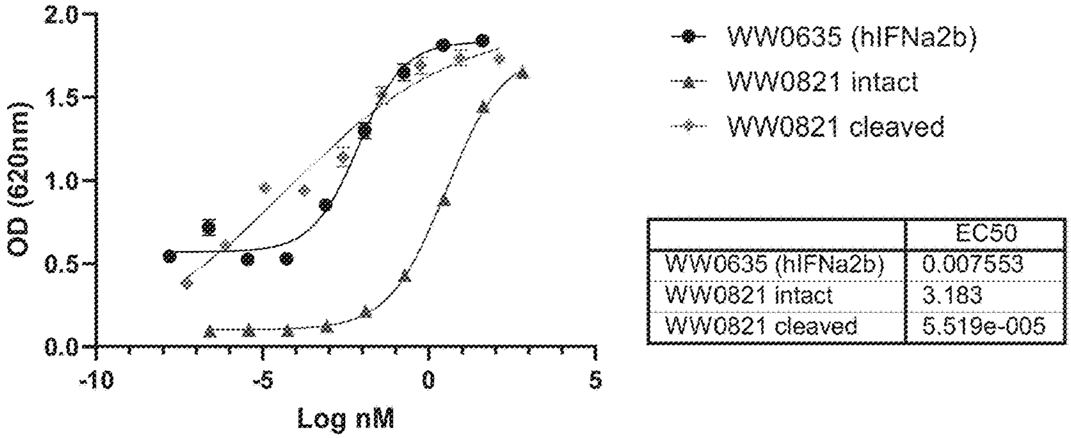
Figure 36E:
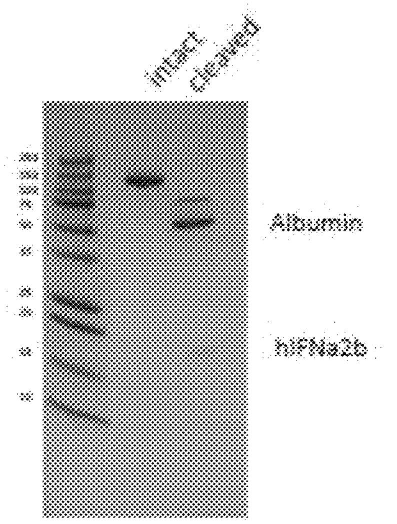
Figure 36F:
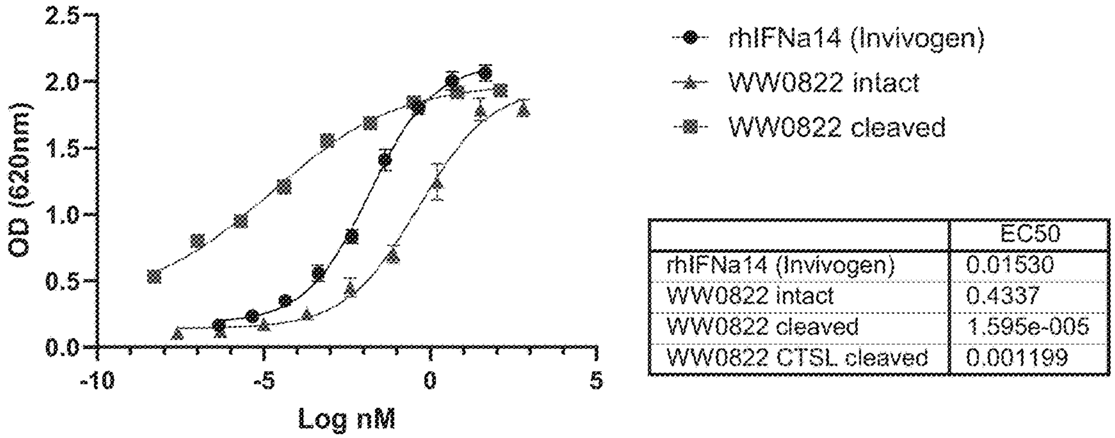
Figure 36F:
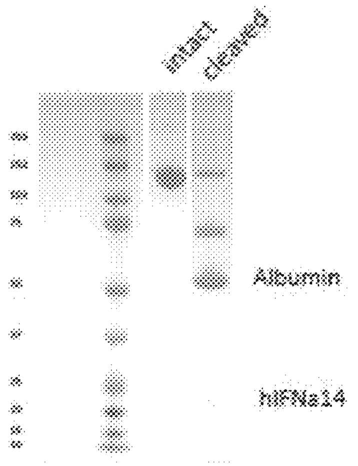
Figure 36G:
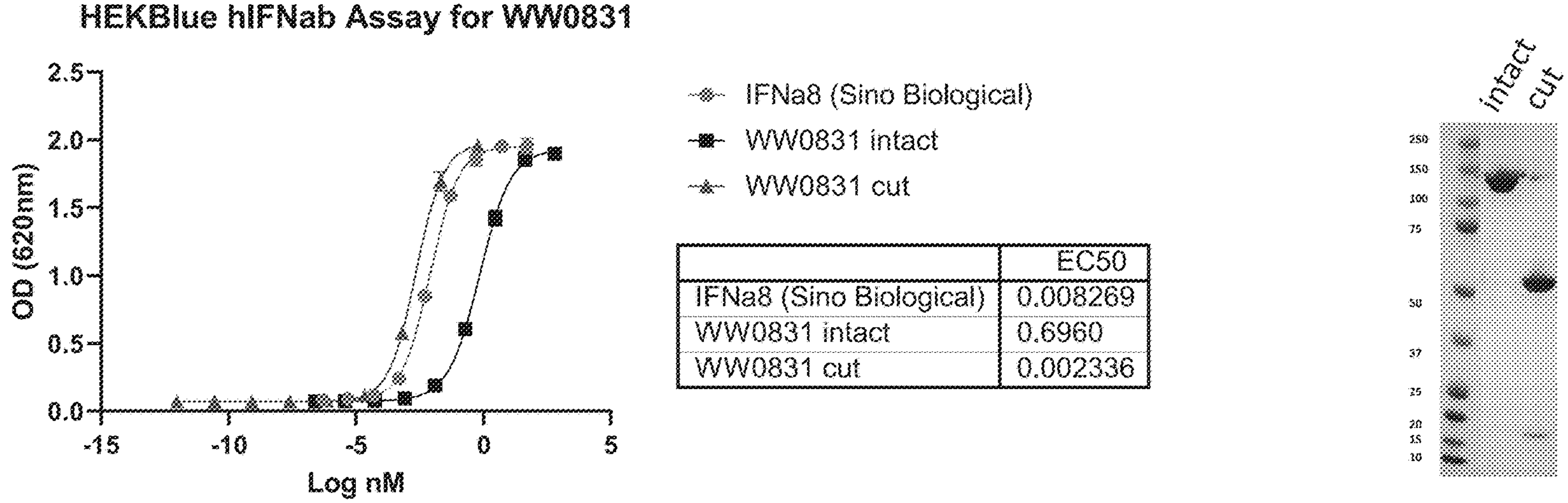
Figure 36H:
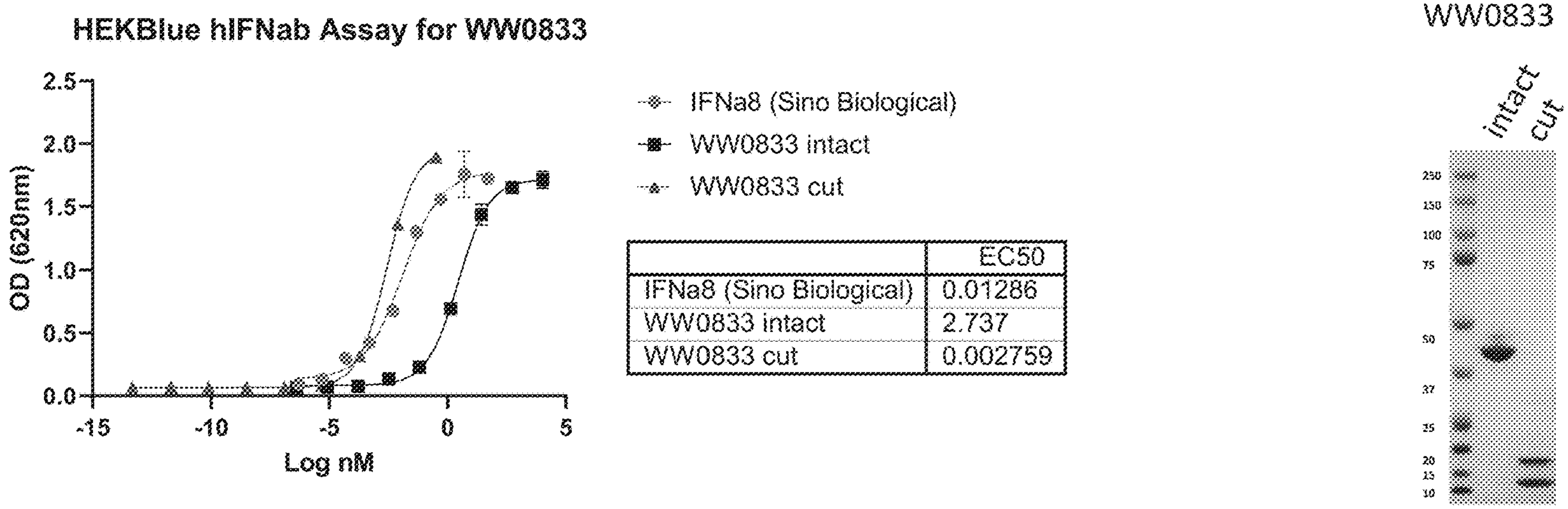

FIG. 35 a series of spaghetti plots showing activity of fusion proteins in an MC38 mouse xenograft model. All mouse groups were given four doses total except for the highest three doses of APC132, wherein fatal toxicity was detected after 1 week/2 doses. Shown are vehicle alone (top), 17, 55, 70, and 230 μg ACP16 (top full row), 9, 28, 36, and 119 μg ACP132 (middle full row), and 13, 42, 54, and 177 μg ACP21 (bottom full row). Each line in the plots represents an individual animal.

FIGS. 36A-36H are a series of graphs showing activity of fusion proteins in the HEK-Blue IFN-α/p reporter assay. FIGS. 36A-36H depict activation of the IFN-α/β pathway in a comparison of human IFNα fusion protein) to control (human IFNα). Squares depict activity of the uncut IFNα polypeptide (intact) and triangles depict the activity of the cut IFNα polypeptide (cleaved). Circles depict activity of the control (human IFNα). EC50 values for each are shown in the table. Results confirm that the IFNα fusion proteins are active and inducible. FIGS. 36A-36H also depict results of the protein cleavage assay for each IFNα fusion protein. Each IFNα fusion protein was run on an SDS-PAGE gel in both cleaved and uncleaved form. As can be seen in the gel, cleavage was complete.

Figure 37A:
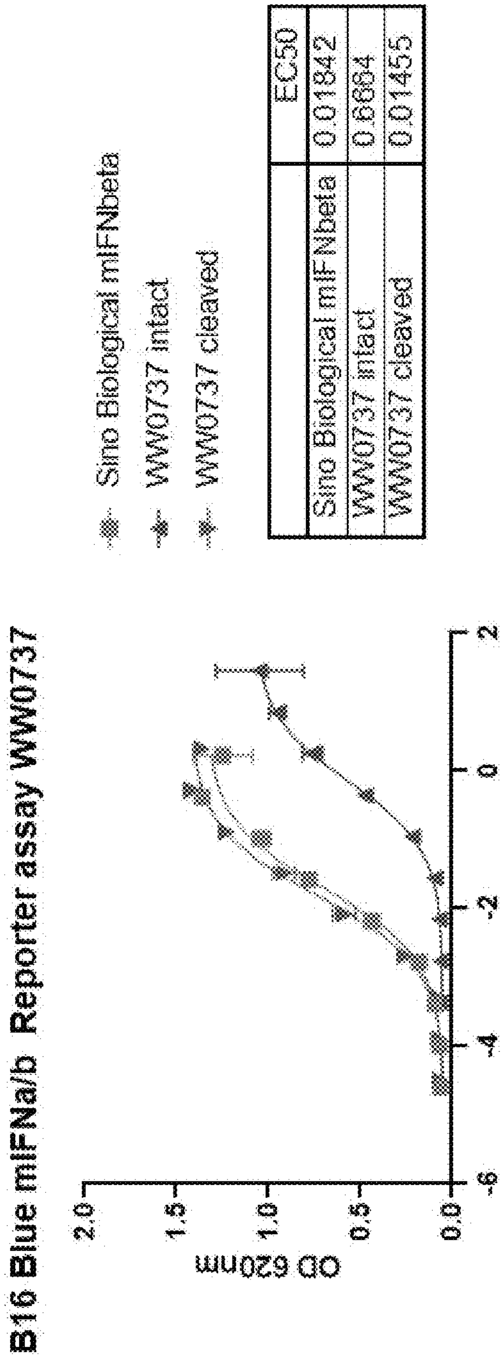
Figure 37B:
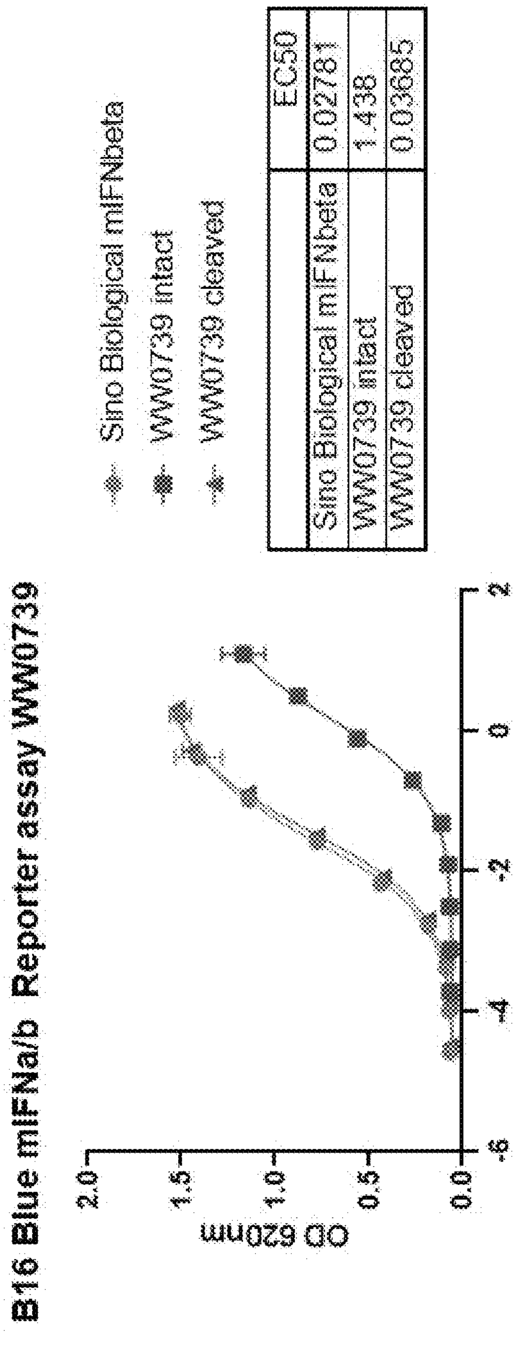
Figure 37C:
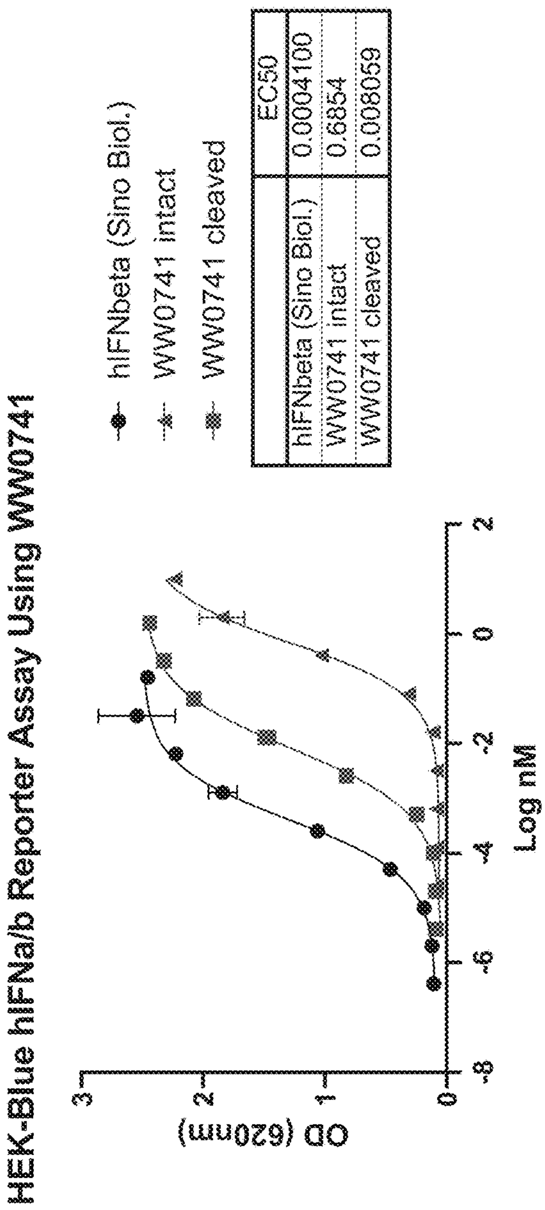
Figure 37D:
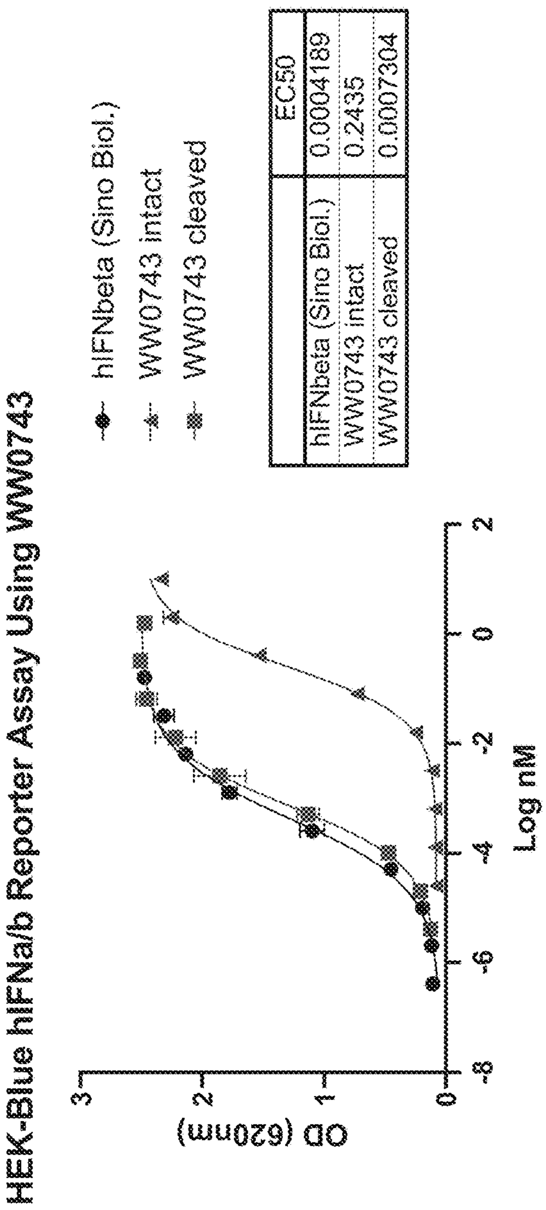

FIGS. 37A-37D are a series of graphs showing activity of fusion proteins in the HEK-Blue IFN-α/p reporter assay. FIGS. 37A-37B depict activation of the IFN-α/β pathway in a comparison of a mouse IFNβ fusion protein to control (mouse IFNβ). FIGS. 37C-37D depict activation of the IFN-α/β pathway in a comparison of a human IFNβ fusion protein to control (human IFNβ). Squares depict activity of the uncut IFNβ polypeptide (intact) and triangles depict the activity of the cut IFNβ polypeptide (cleaved). Circles depict activity of the control. EC50 values for each are shown in the table. Results confirm that the IFNβ fusion proteins are active and inducible.

Figure 38A:
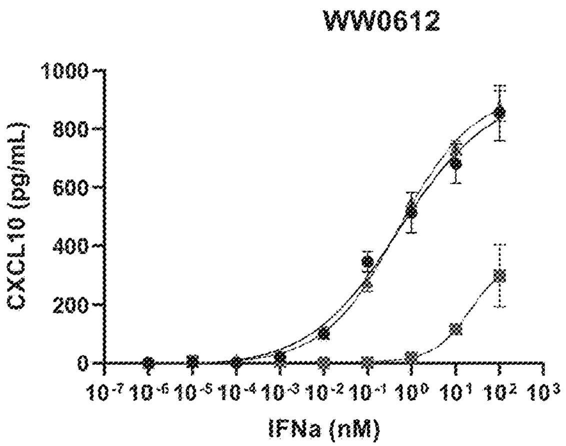
Figure 38B:
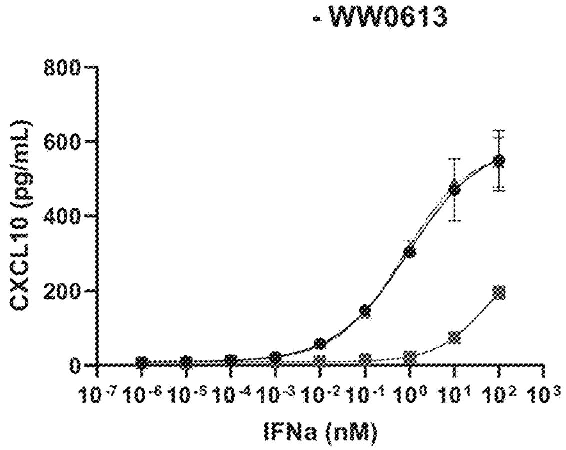
Figure 38C:
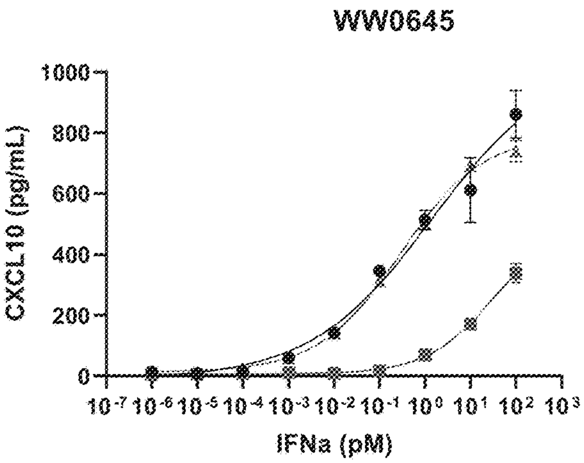

FIGS. 38A-38C are a series of graphs showing activity of fusion proteins in the human PBMCs assay. FIGS. 38A-38C depict activation of the IFNα pathway in a comparison of human IFNα fusion protein to control (human IFNα). Squares depict activity of the uncut IFNα polypeptide (intact) and triangles depict the activity of the cut IFNα polypeptide (cleaved). Circles depict activity of the control human IFNα. EC50 values for each are shown in the table. Analysis was performed based on quantification of CXCL-10 (IP-10). Results confirm that the IFNα fusion proteins are active and inducible.

Figure 39B:
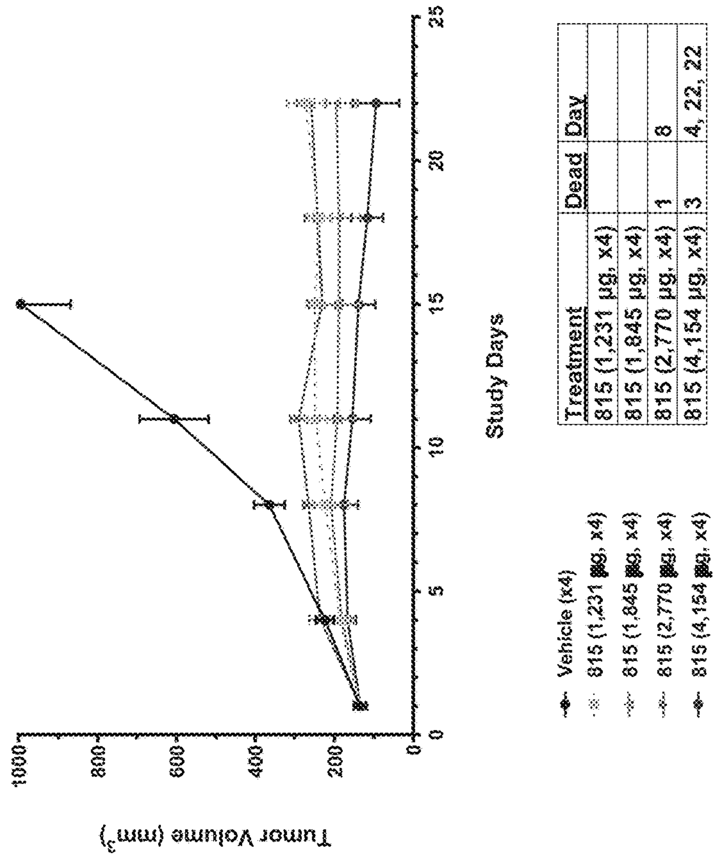
Figure 39A:
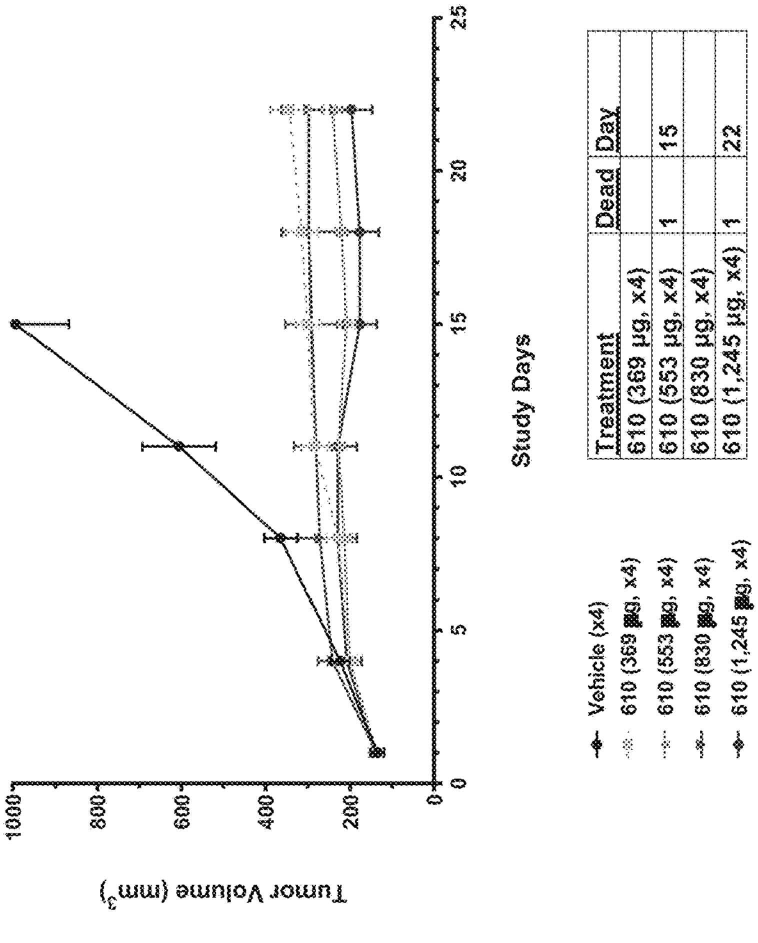
Figure 39D:
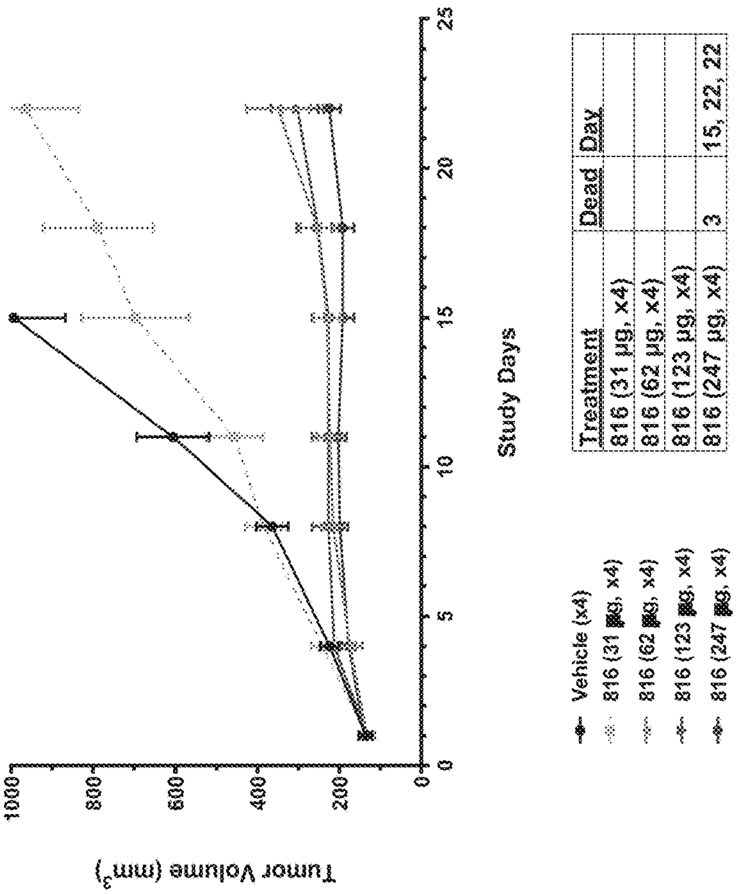
Figure 39C:
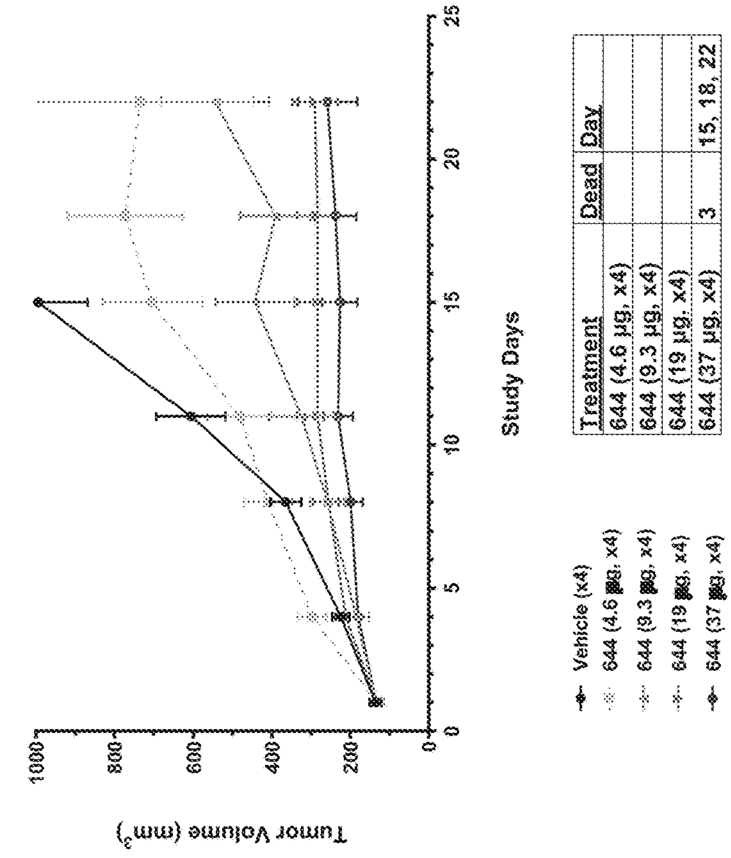
Figure 39F:
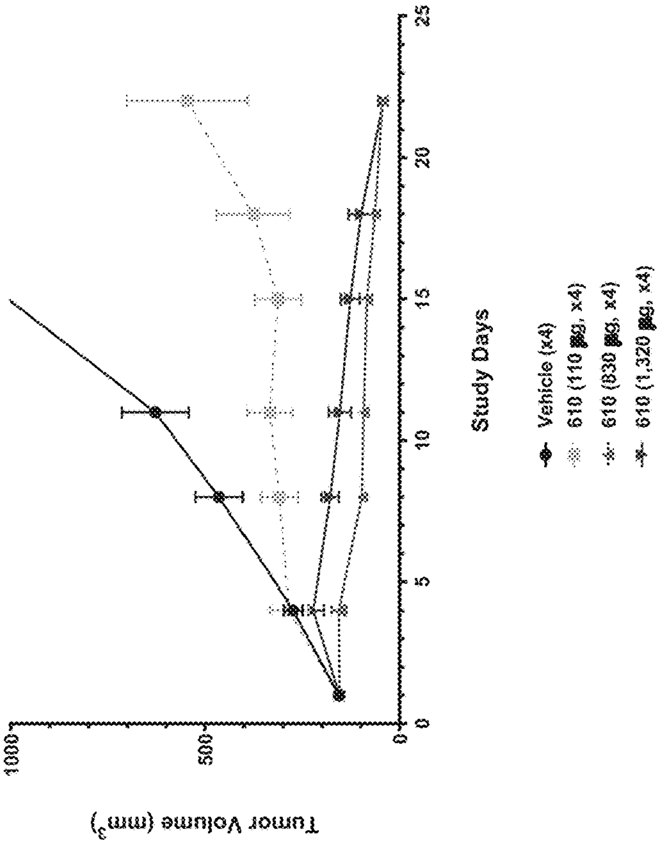
Figure 39E:
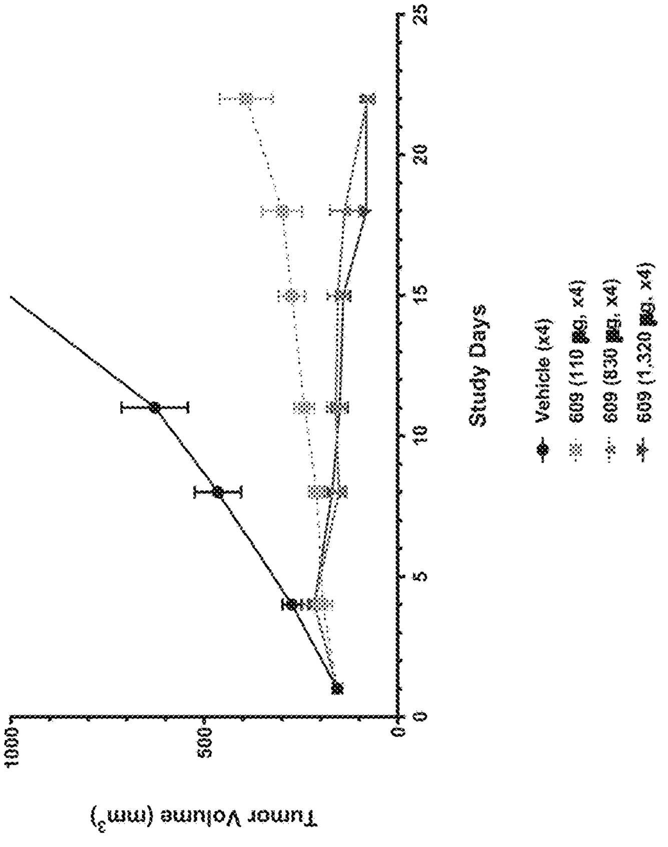
Figure 39G:
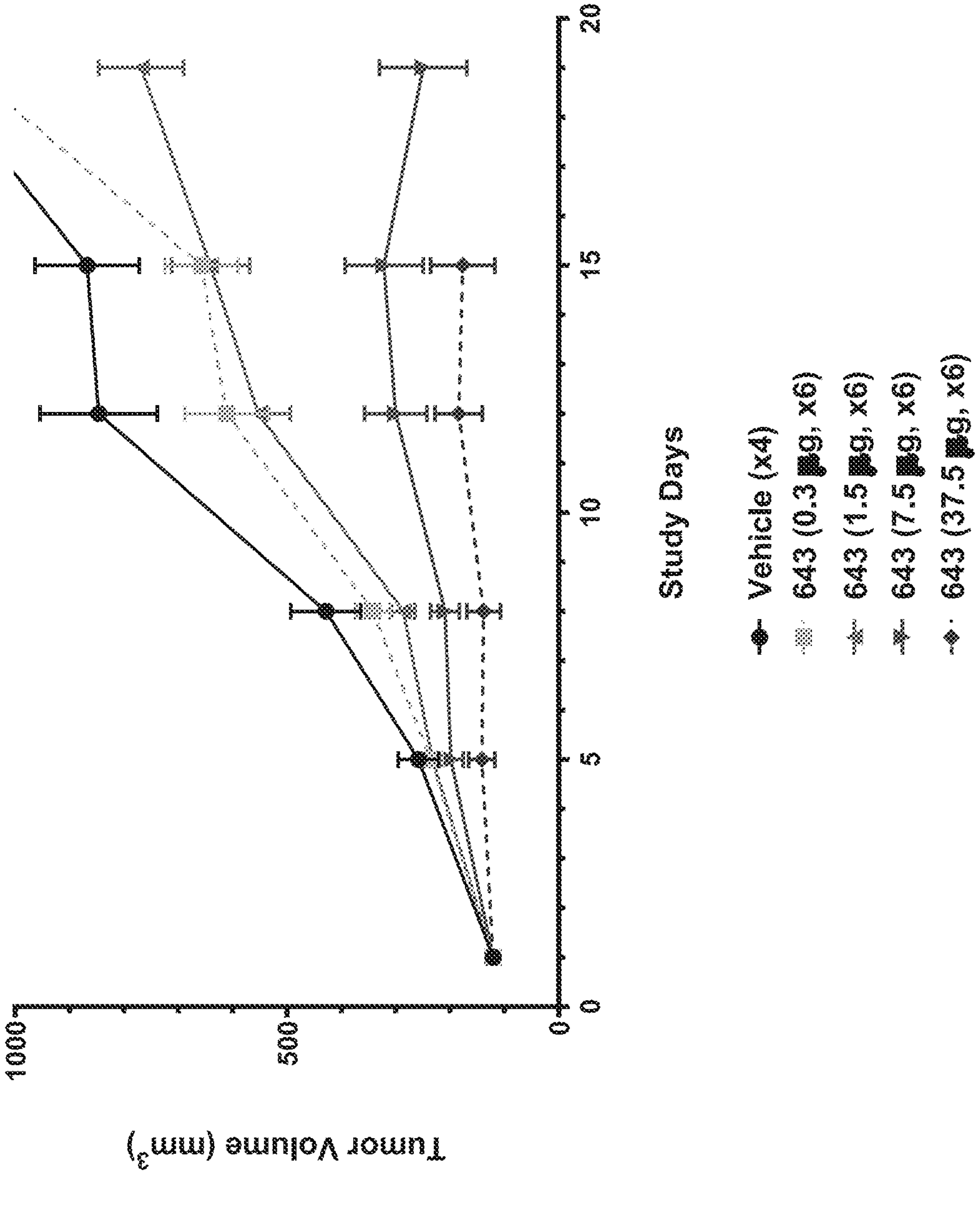
Figure 40A:
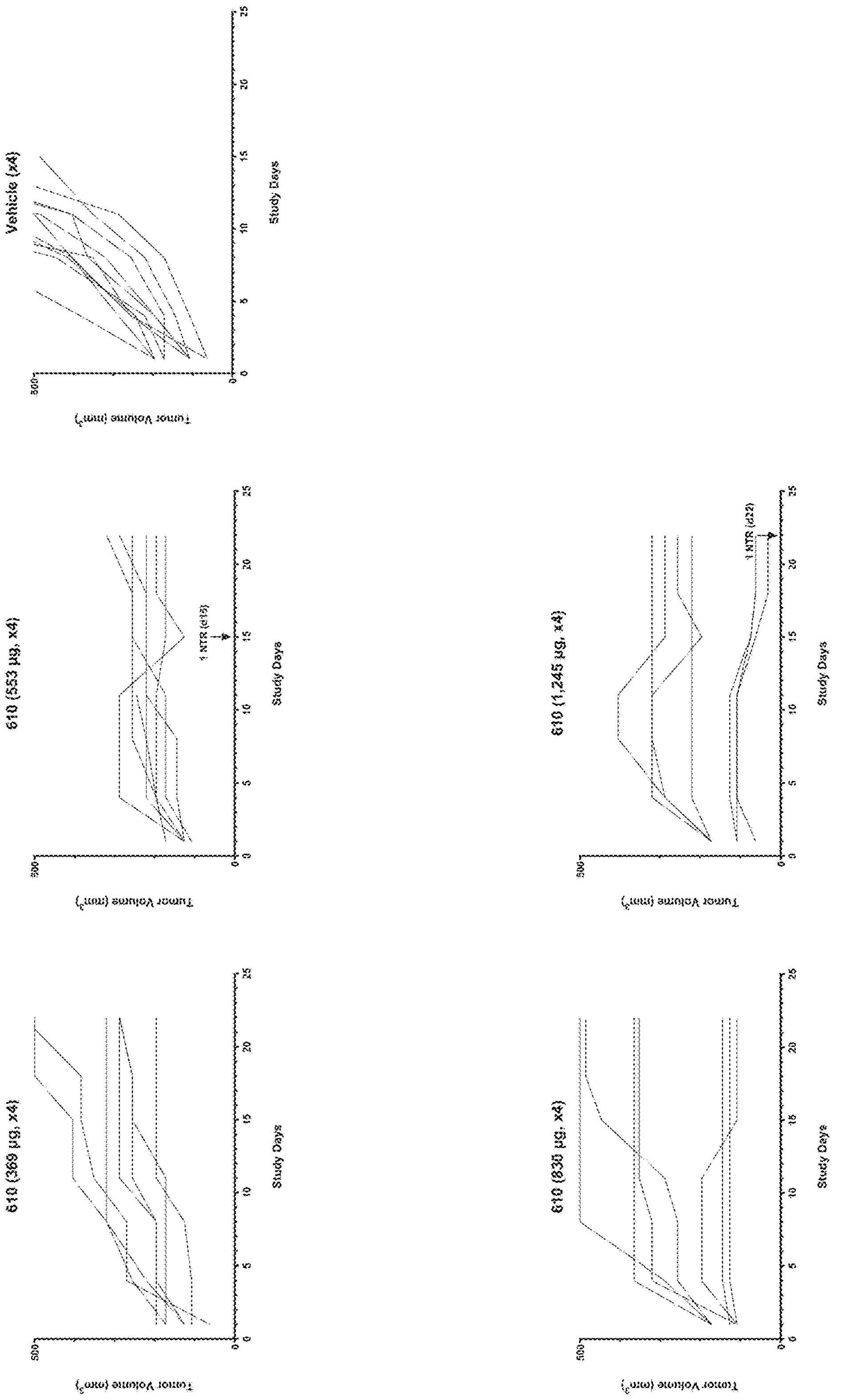
Figure 40B:
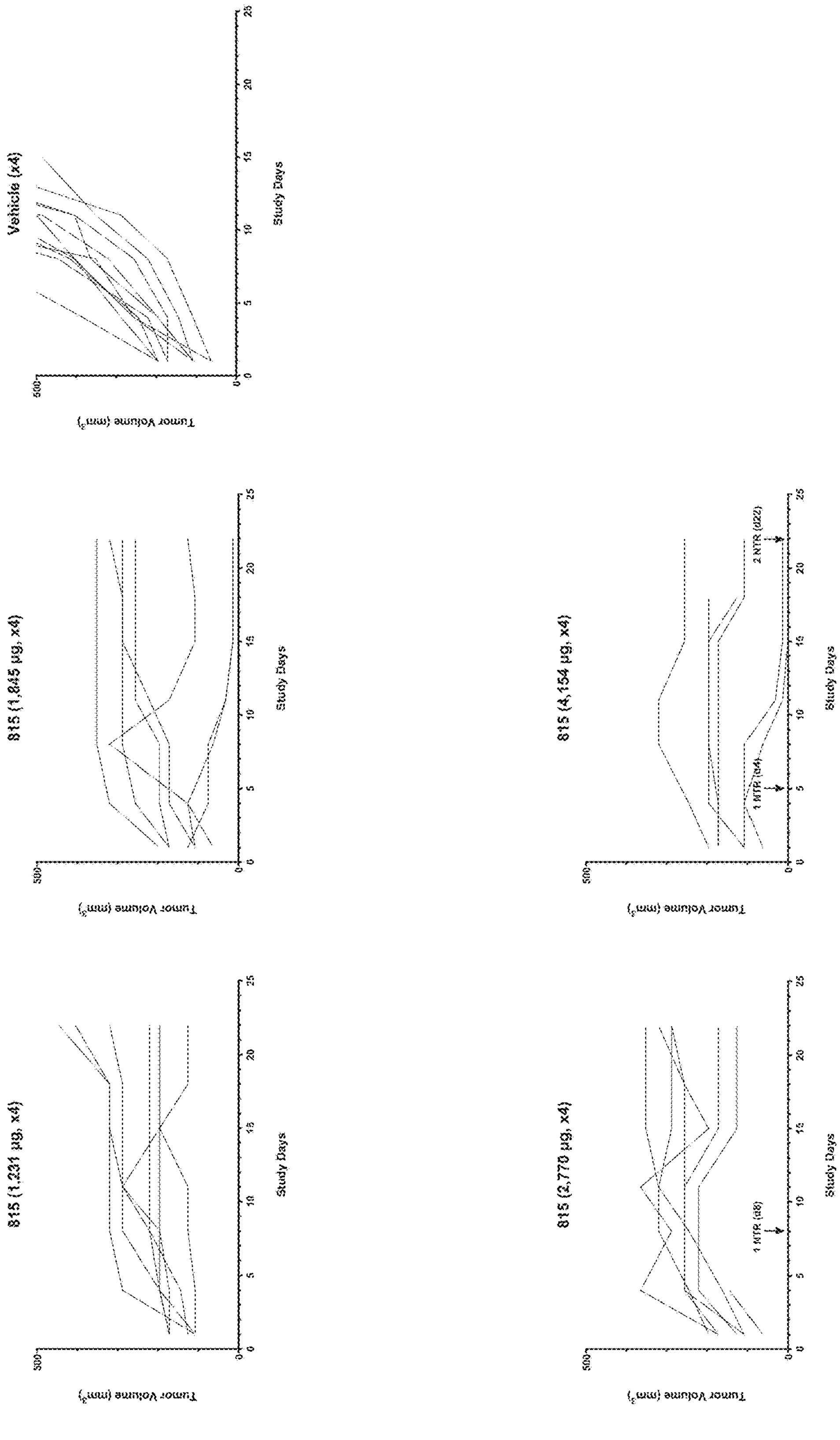
Figure 40C:
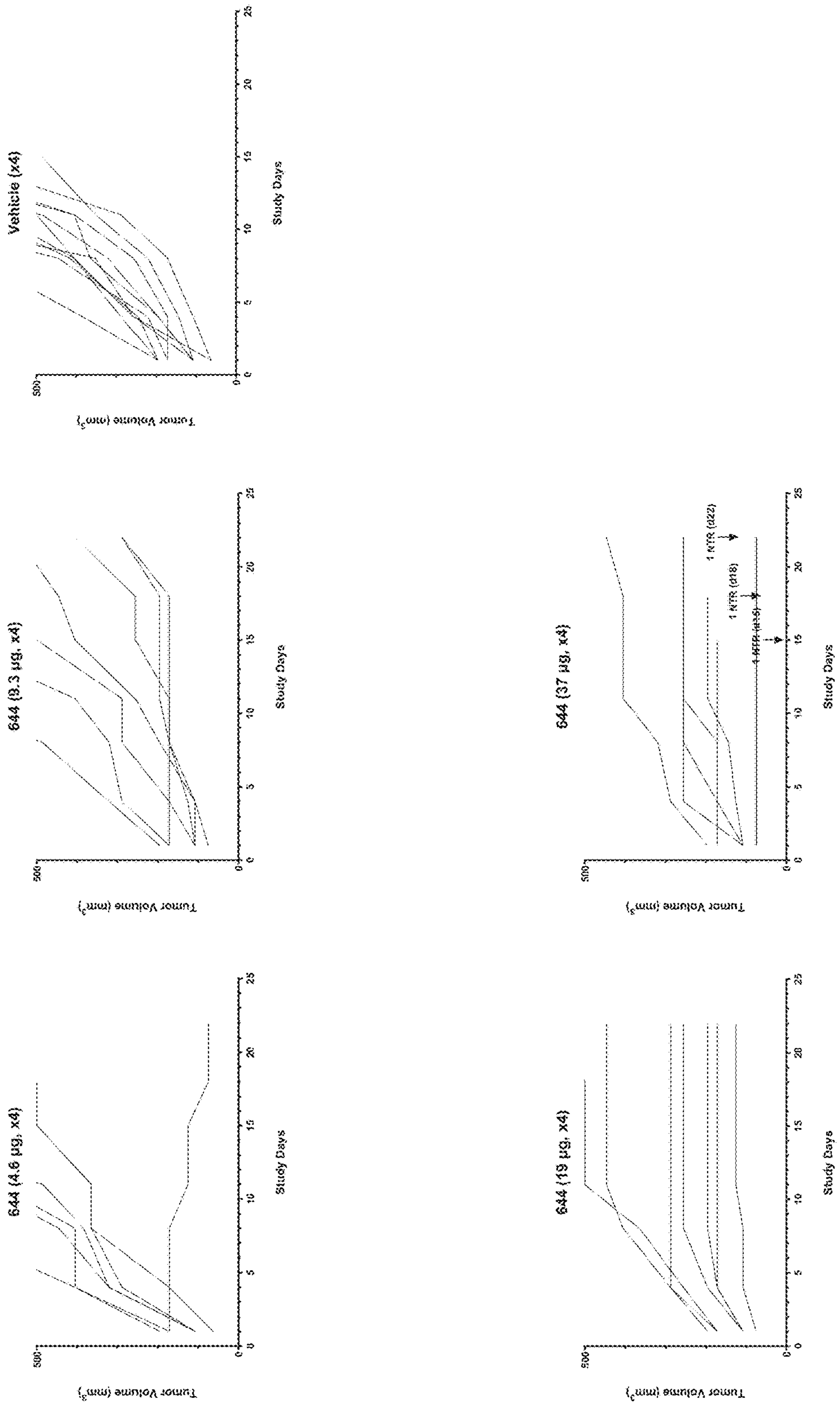
Figure 40D:
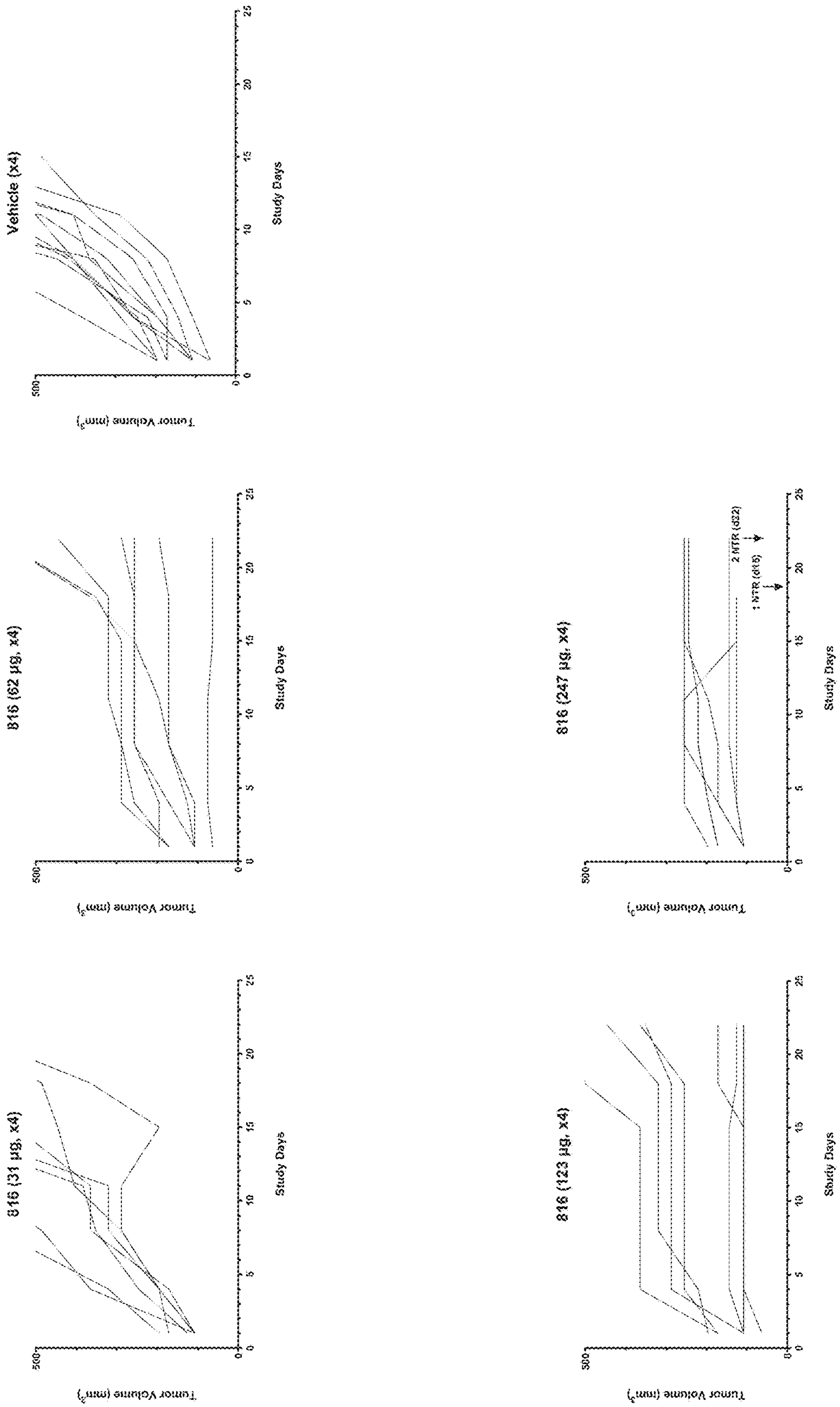
Figure 40E:
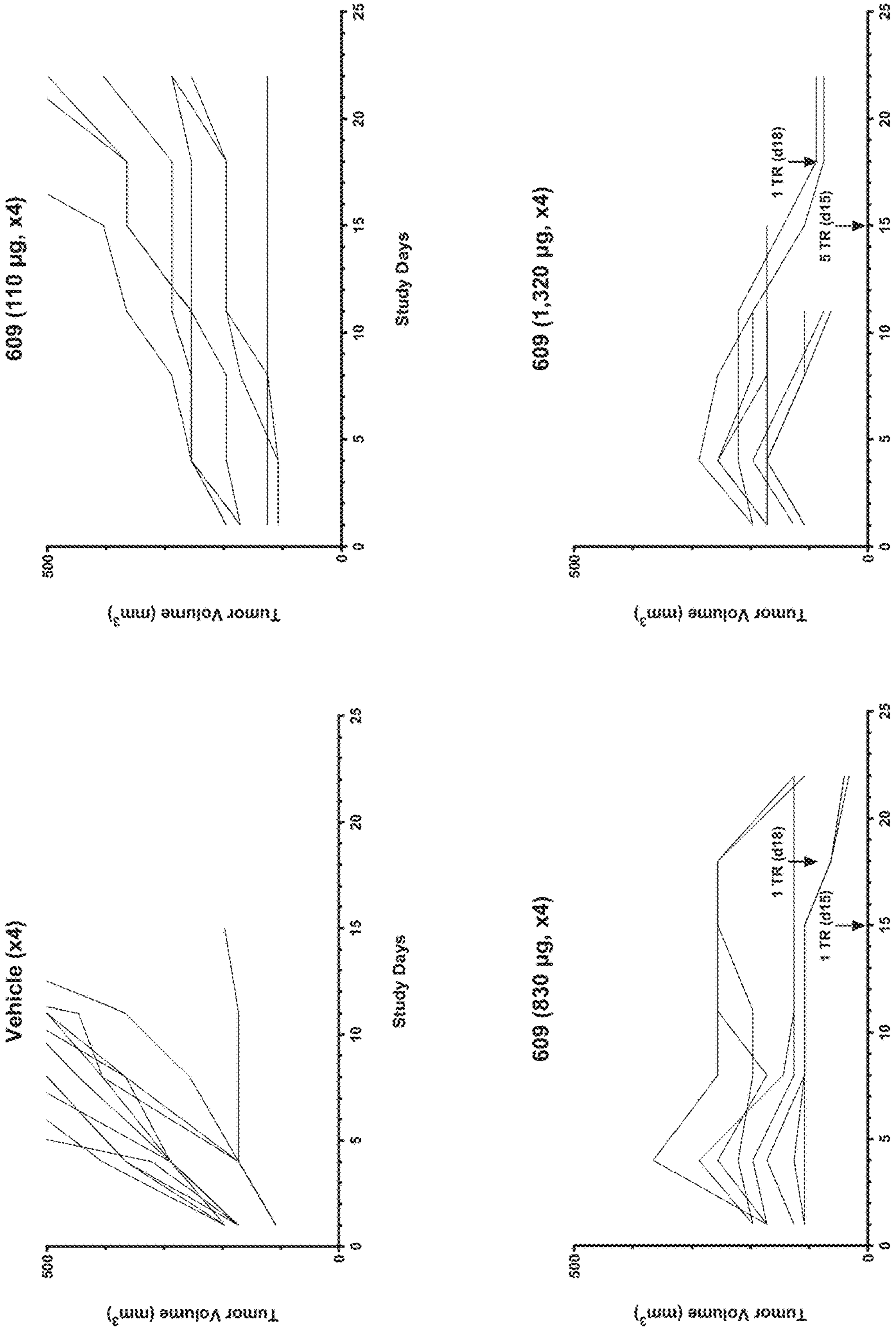
Figure 40F:
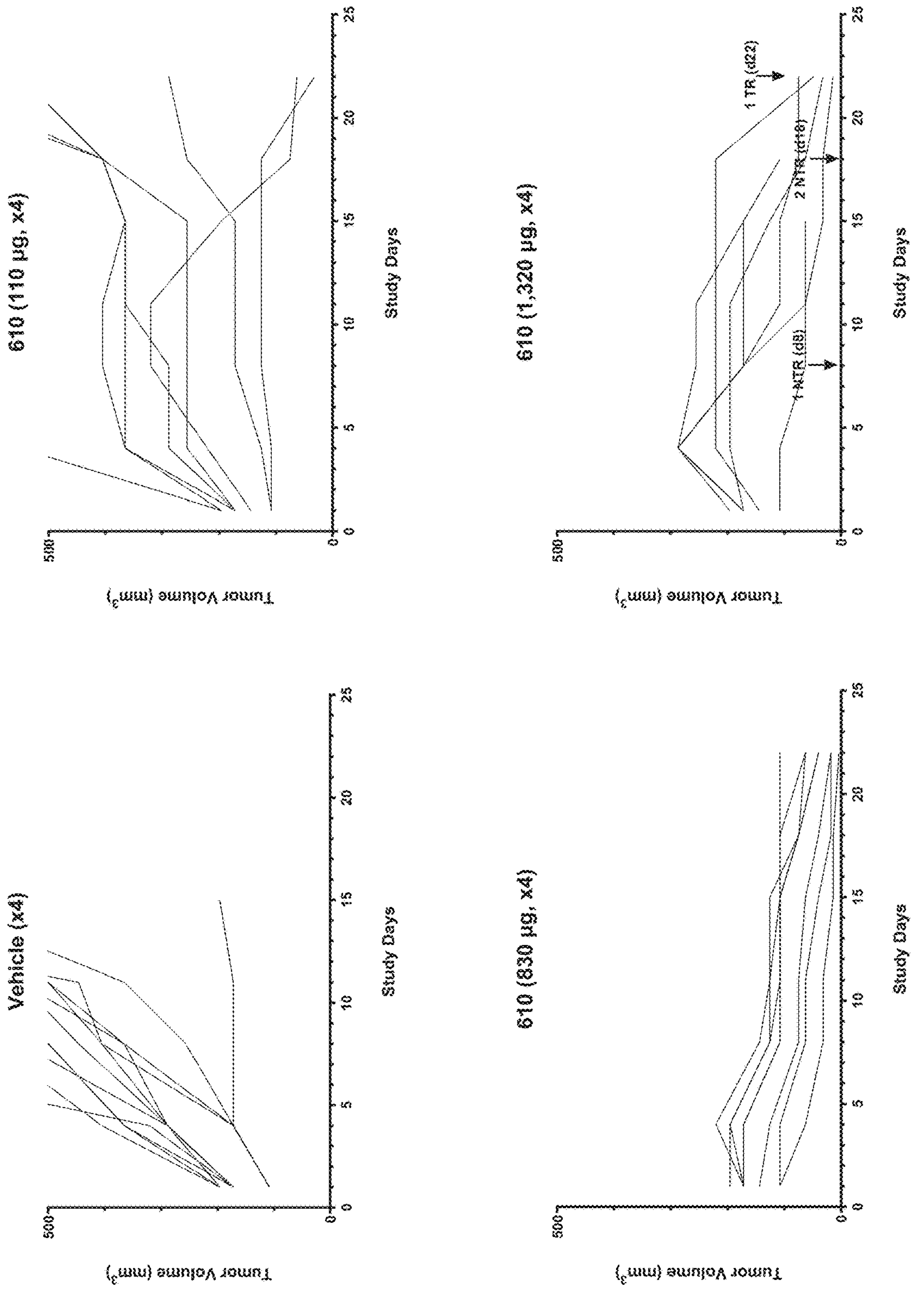
Figure 40G:
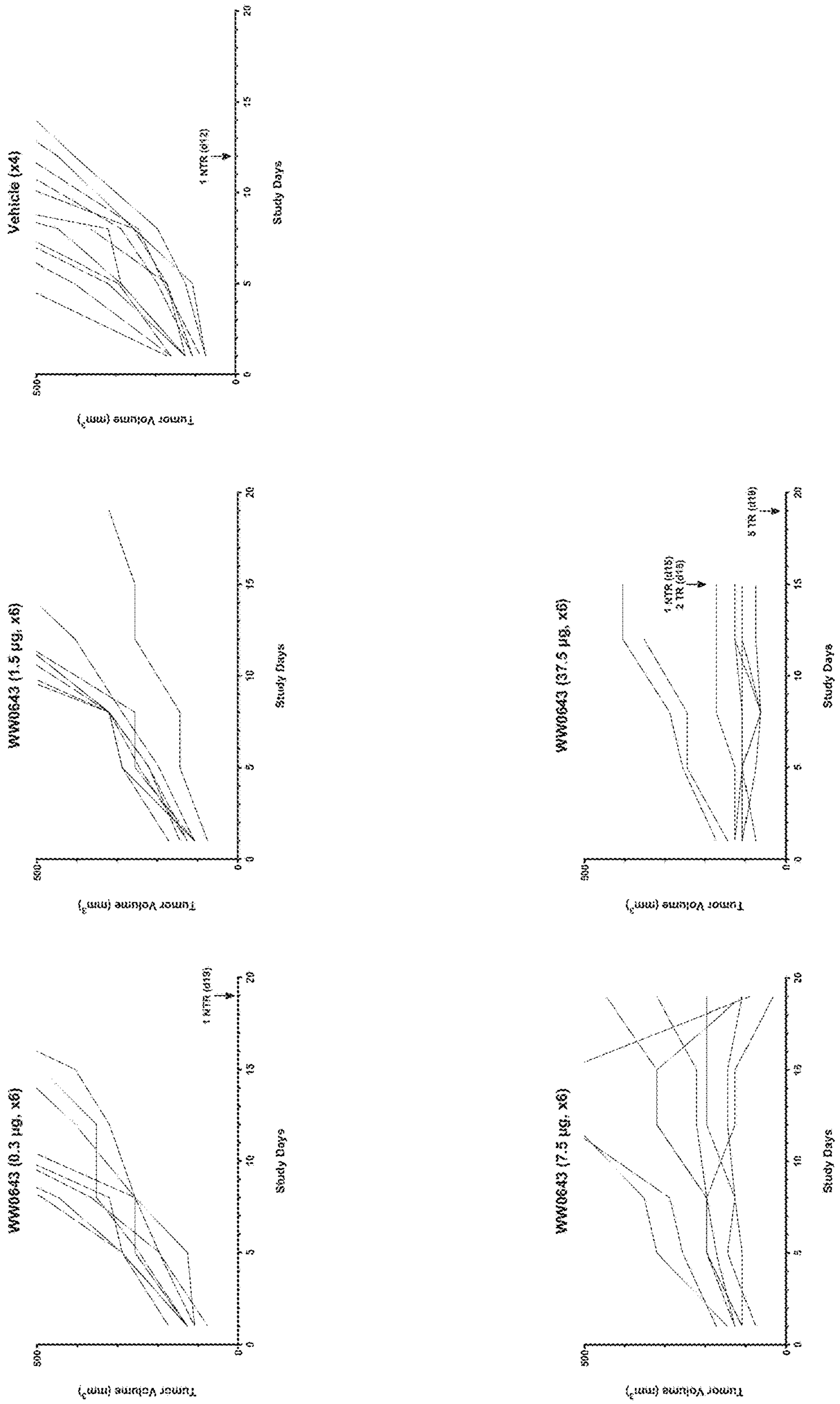
Figure 41A:
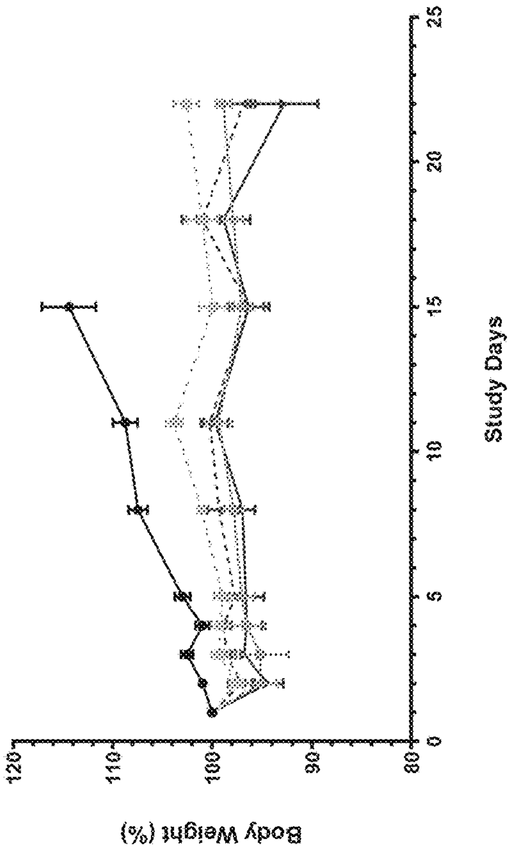
Figure 41B:
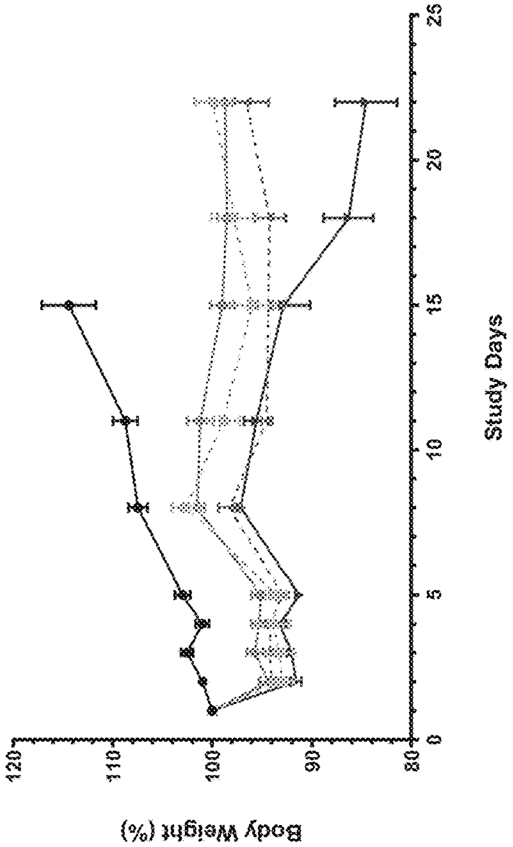
Figure 41D:
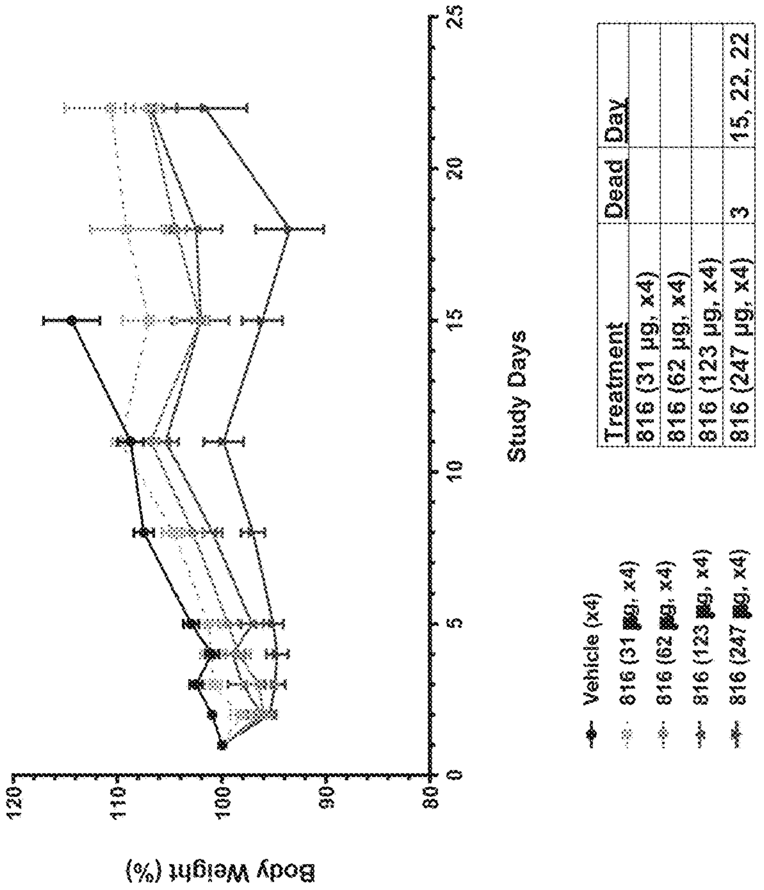
Figure 41C:
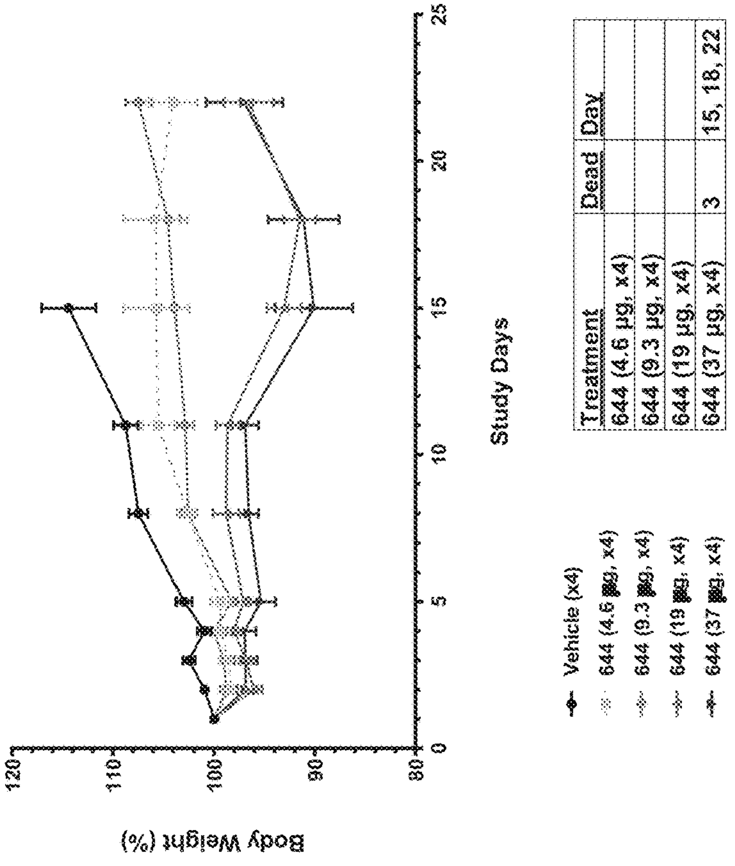
Figure 41E:
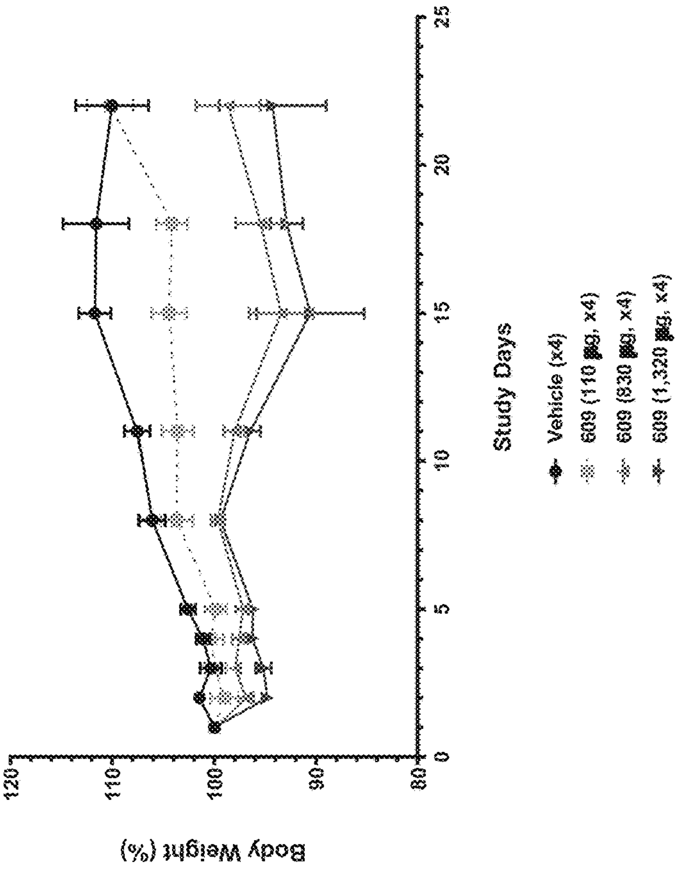
Figure 41F:
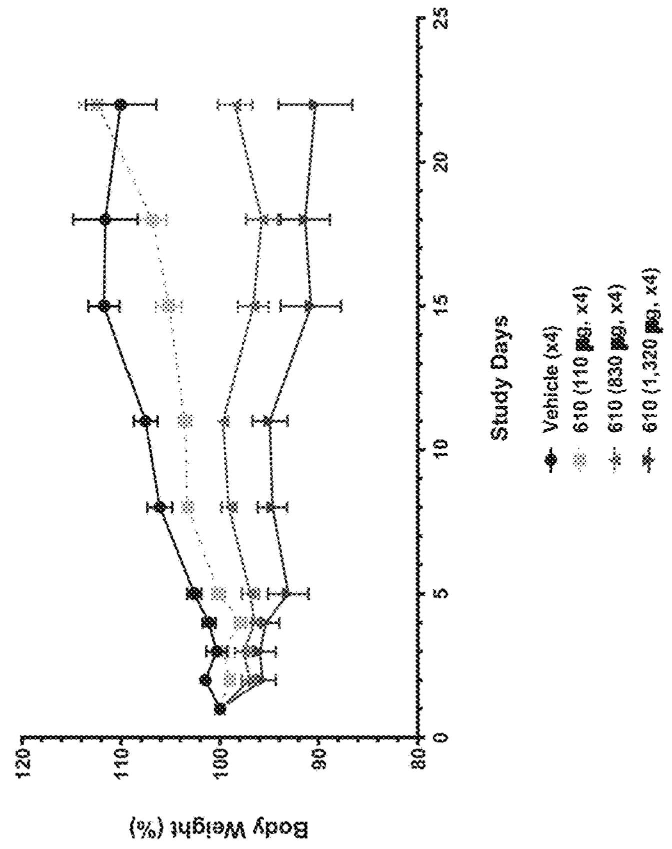
Figure 41G:
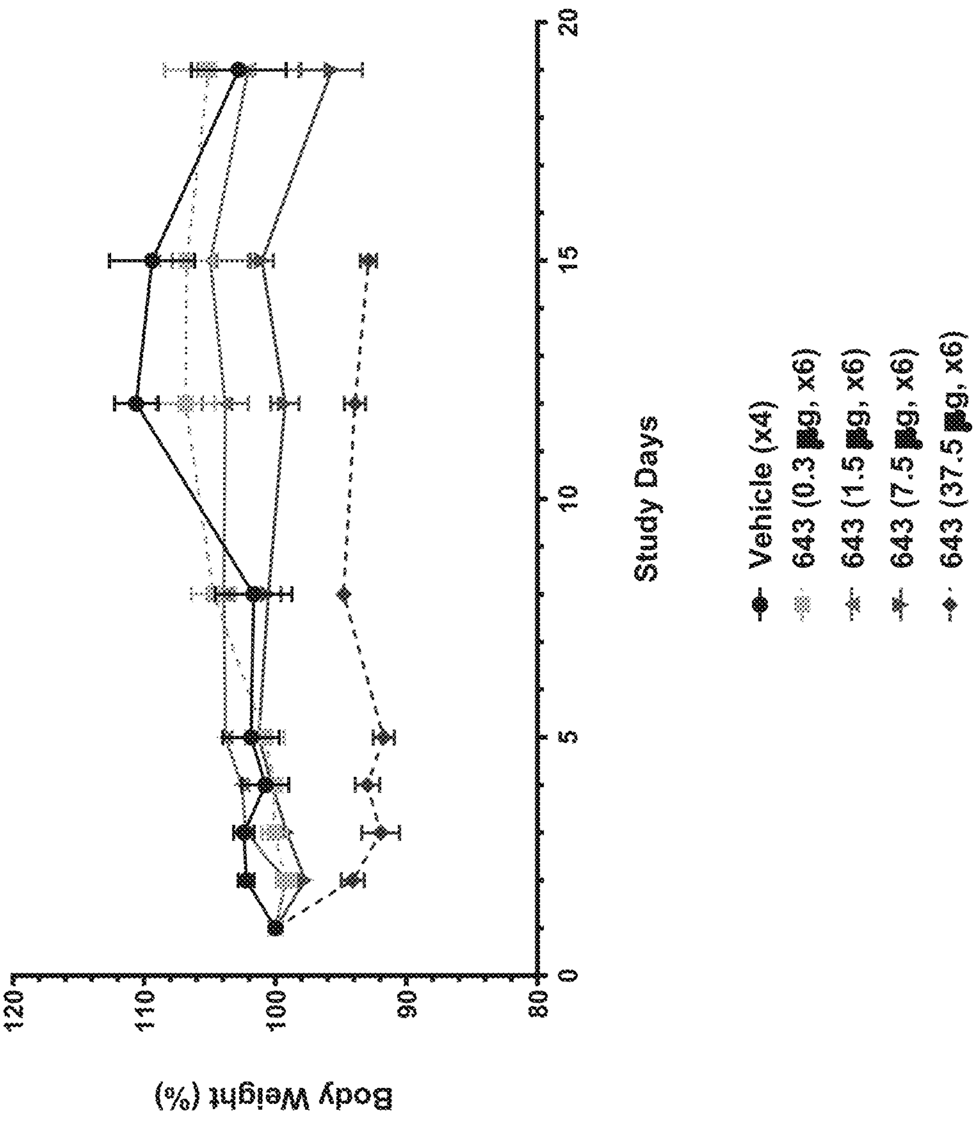
Figure 42A:
Figure 42B:
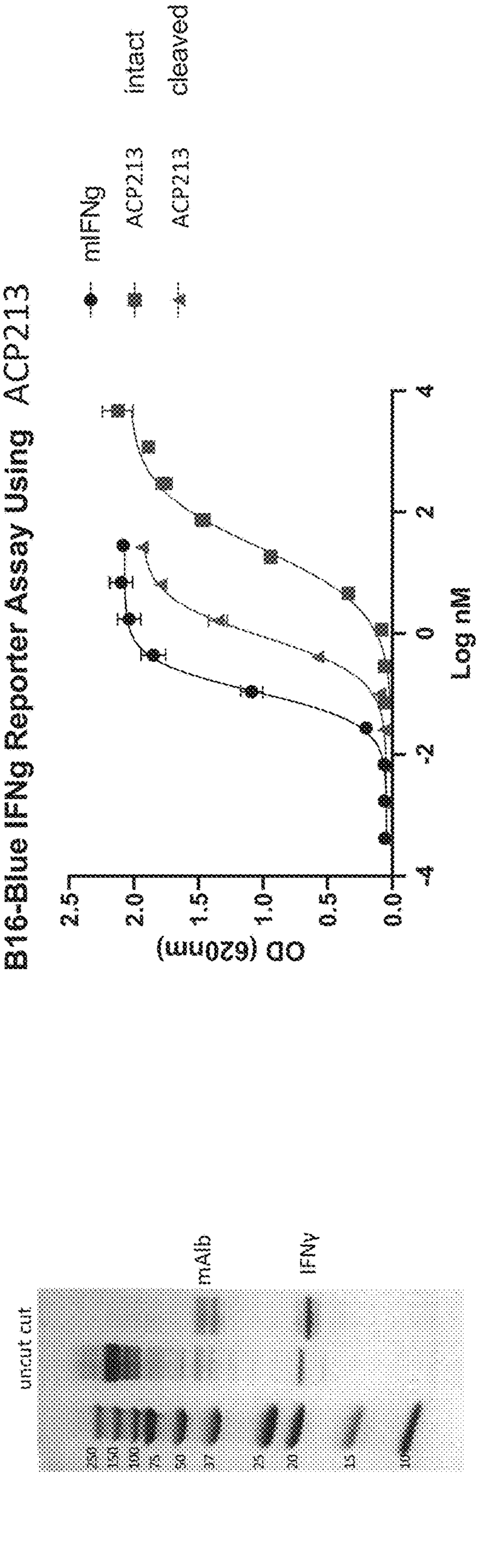
Figure 42C:
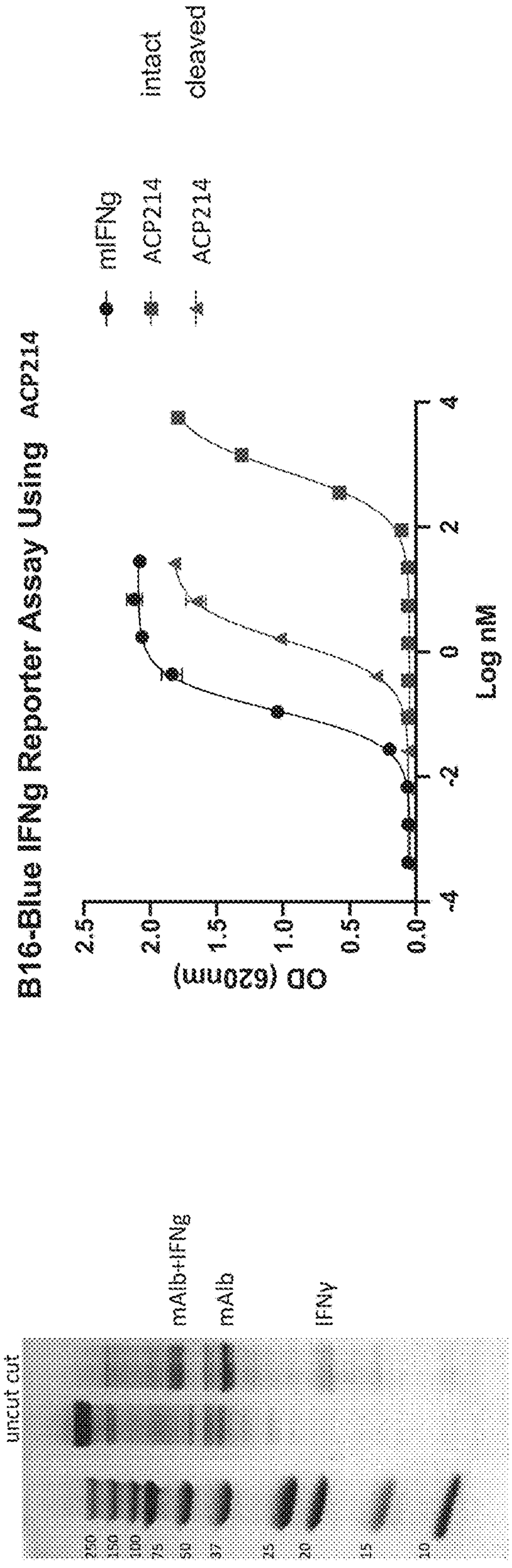
Figure 42D:
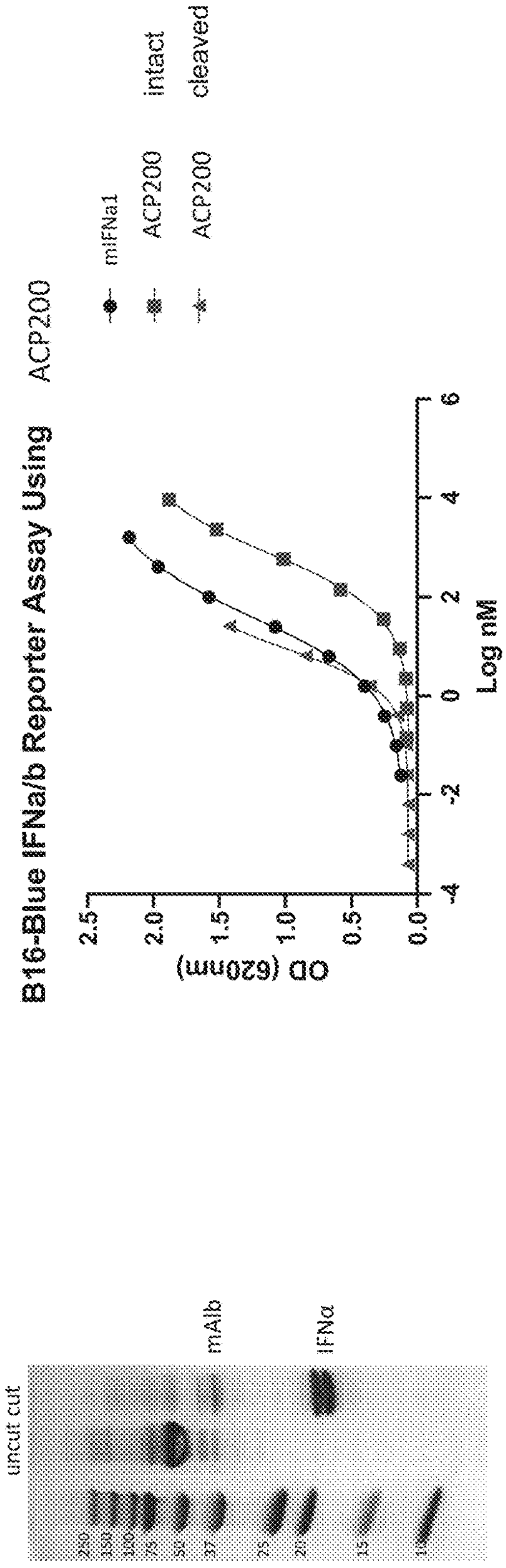
Figure 42E:
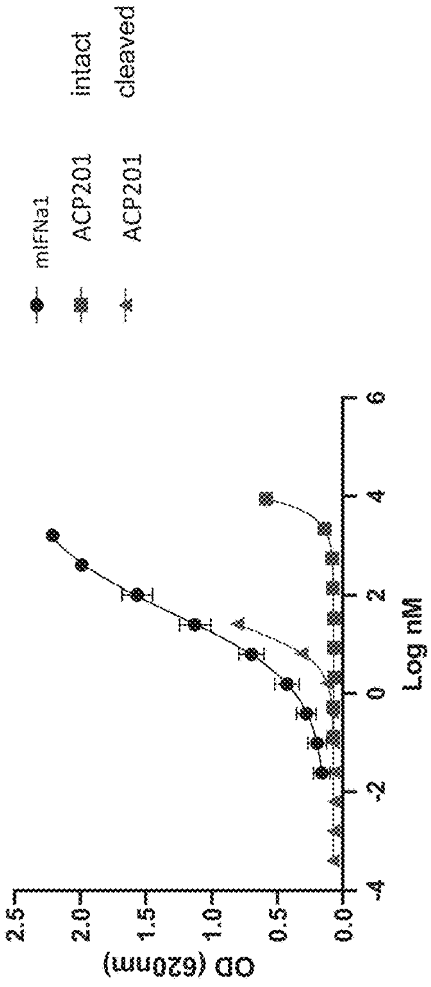
Figure 42E:
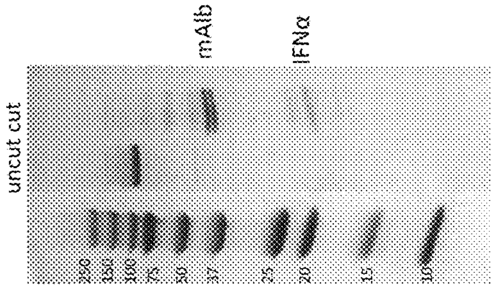
Figure 44A:
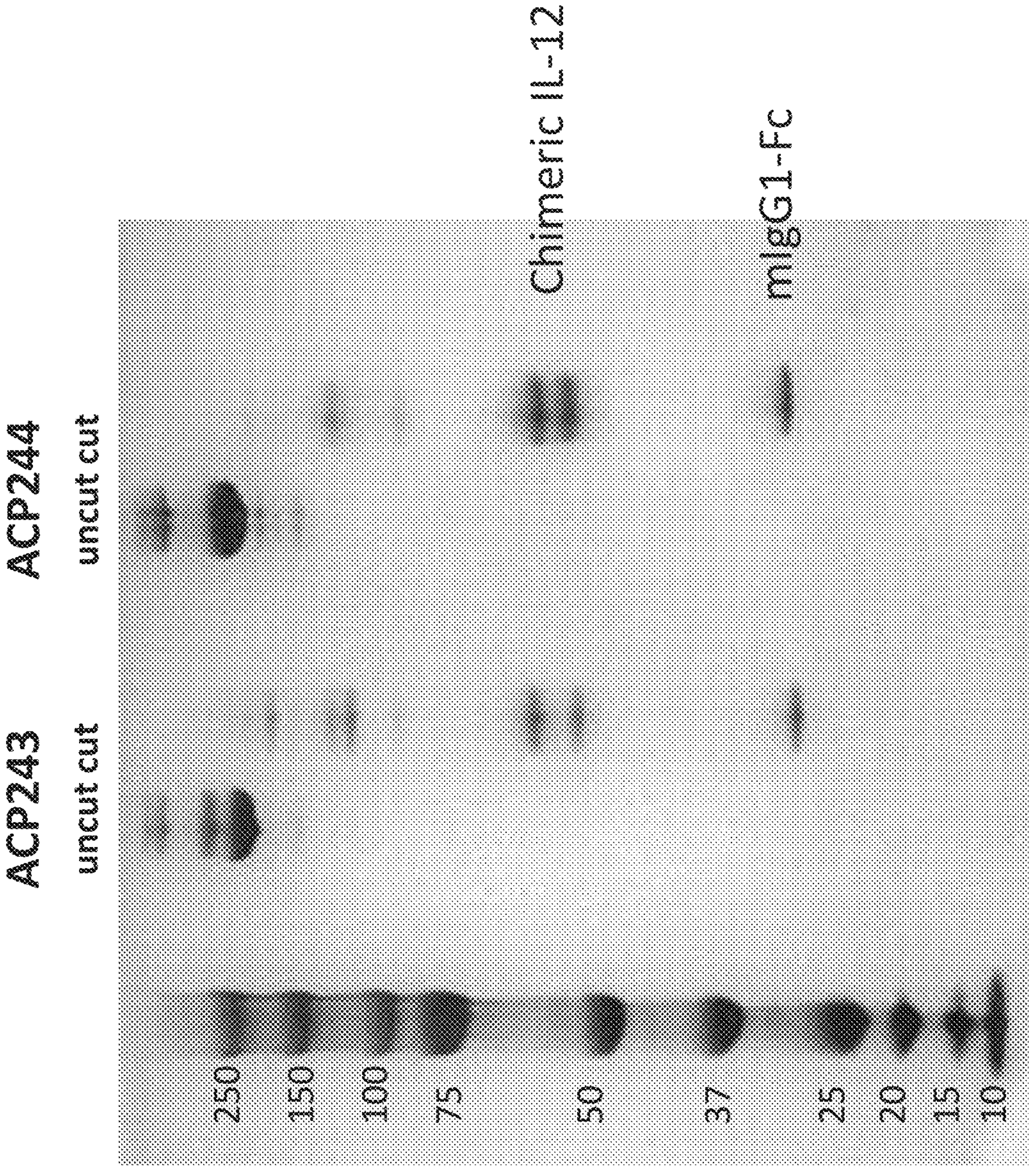
Figure 44B:
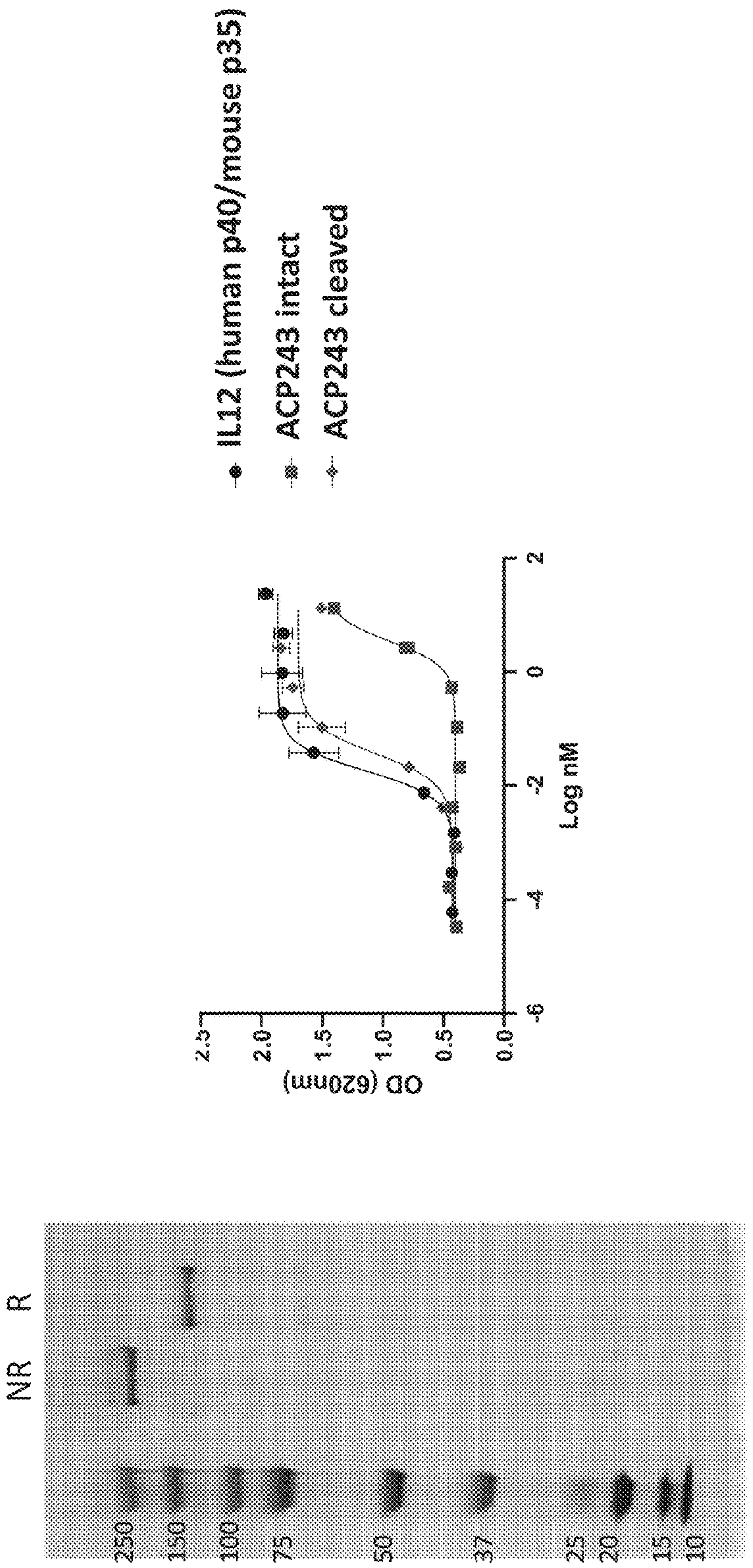
Figure 44C:
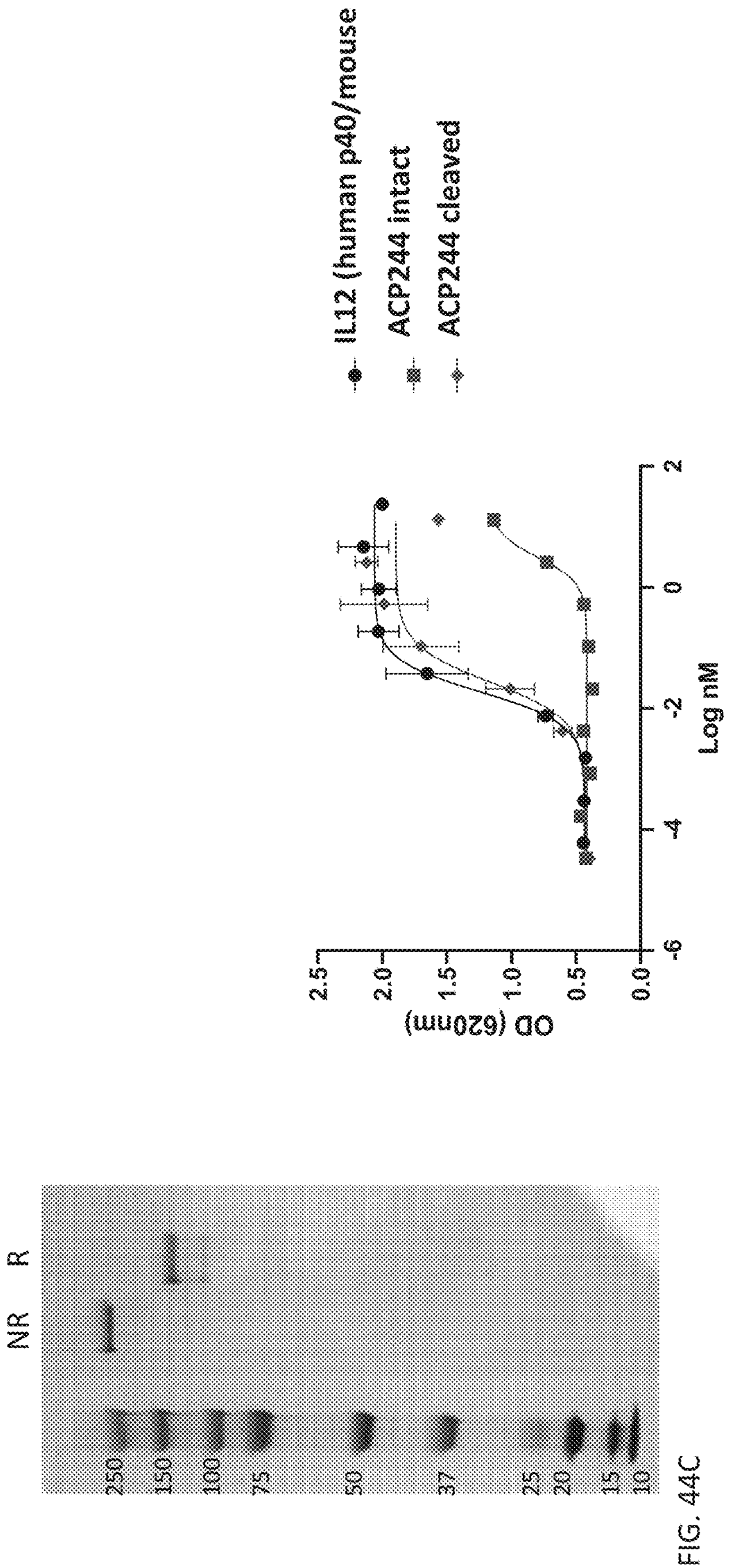
Figure 44D:
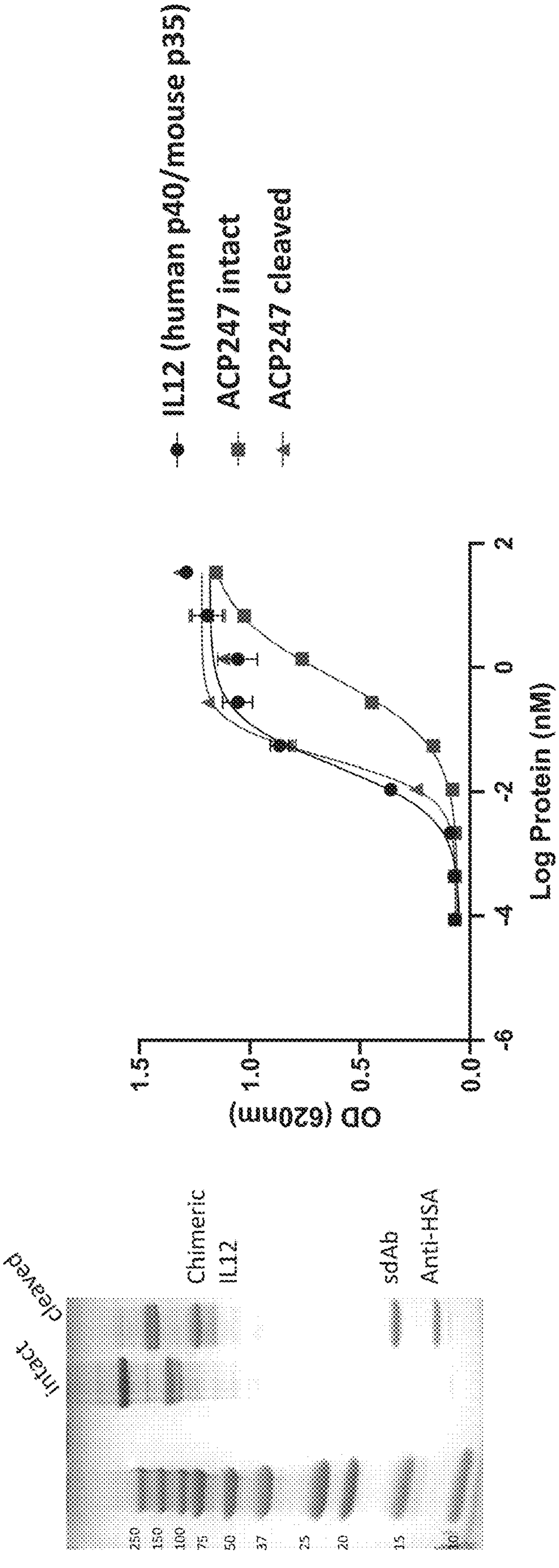

FIGS. 39A-39G show are results of analyzing IFN fusion proteins in syngeneic MC38 mouse tumor model. FIG. 39A shows average tumor volume over time in mice treated with 369 μg WW0610 (square), 553 μg WW0610 (down triangle), 830 μg WW0610 (up triangle), and 1,245 μg WW0610 (circle). Vehicle alone is indicated by a black circle. FIG. 39B shows average tumor volume over time in mice treated with 1,231 μg WW0815 (square), 1,845 μg WW0815 (down triangle), 2,770 μg WW0815 (up triangle), and 4,154 μg WW0815 (circle). Vehicle alone is indicated by a black circle. FIG. 39C shows average tumor volume over time in mice treated with 4.6 μg WW0644 (square), 9.3 μg WW0644 (down triangle), 19 μg WW0644 (up triangle), and 37 μg WW0644 (circle). Vehicle alone is indicated by a black circle. FIG. 39D shows average tumor volume over time in mice treated with 31 μg WW0816 (square), 62 μg WW0816 (down triangle), 123 μg WW0816 (up triangle), and 247 μg WW0816 (circle). Vehicle alone is indicated by a black circle. FIG. 39E shows average tumor volume over time in mice treated with 110 μg WW0609 (square), 830 μg WW0609 (down triangle), and 1,320 μg WW0609 (up triangle). FIG. 39F shows average tumor volume over time in mice treated with 110 μg WW0610 (square), 830 μg WW0610 (down triangle), and 1,320 μg WW0610 (up triangle). FIG. 39G shows average tumor volume over time in mice treated with 0.3 μg WW0643 (square), 1.5 μg WW0643 (down triangle), 7.5 μg WW0643 (up triangle), and 37.5 μg WW0643 (diamond). Vehicle alone is indicated by a black circle.

FIG. 40A-40G shows a series of spider plots showing activity of fusion proteins in an MC38 xenograft model corresponding to data in FIGS. 39A-39G. Each line in the plots is the tumor volume over time for a single mouse.

FIG. 41A-41G show average percent body weight over time in mice treated with the IFN fusion proteins in FIGS. 39A-39G.

FIGS. 42A-42E shows the results of B16 IFN reporter assays. Inducible interferon constructs of interest were tested before and after cleavage. The relevant wildtype IFN was tested as a control.

FIG. 43 shows binding data of ACP16, ACP10, ACP11

FIGS. 44A-44D depict the activity of cytokine fusion proteins constructs ACP243, ACP244, ACP243, ACP244, and ACP247.

Figure 45:
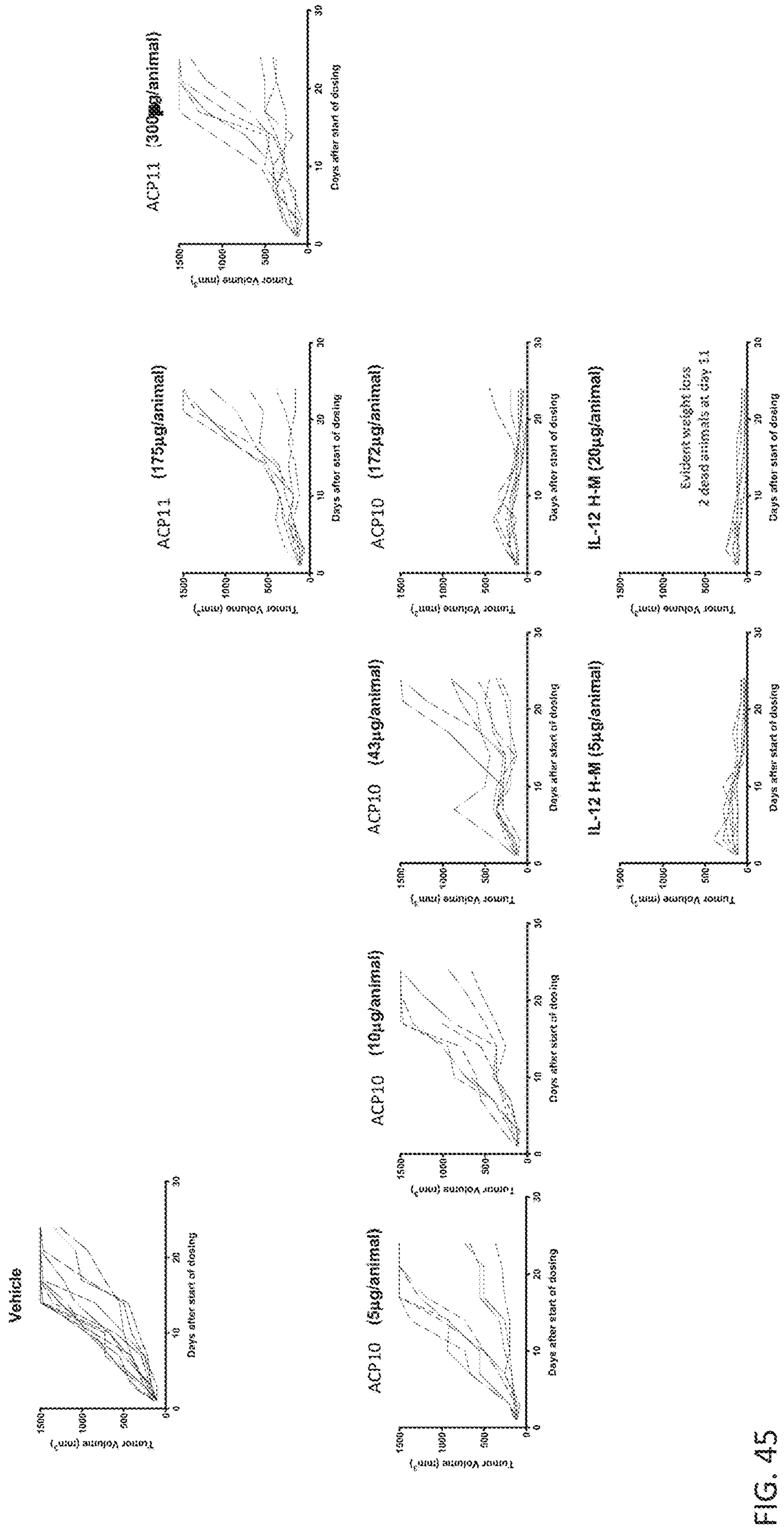
Figure 46A:
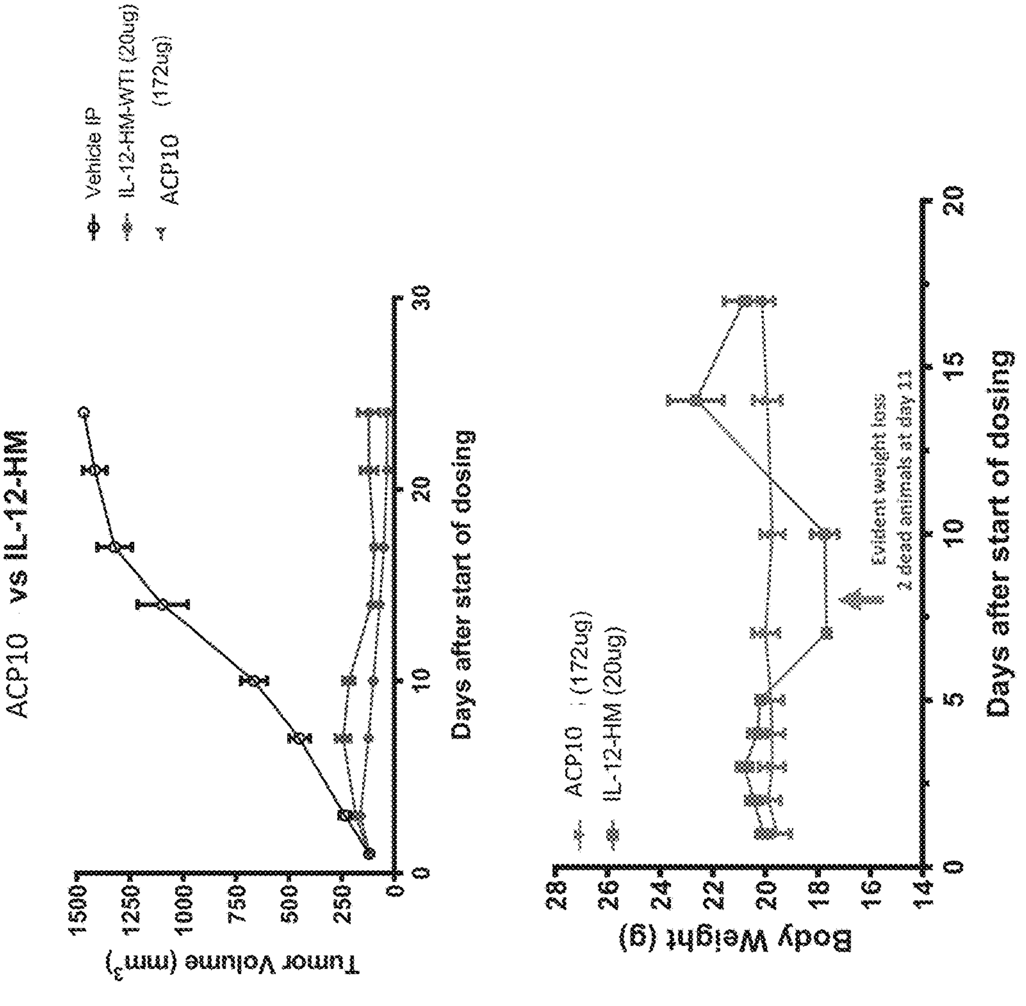
Figure 46B:
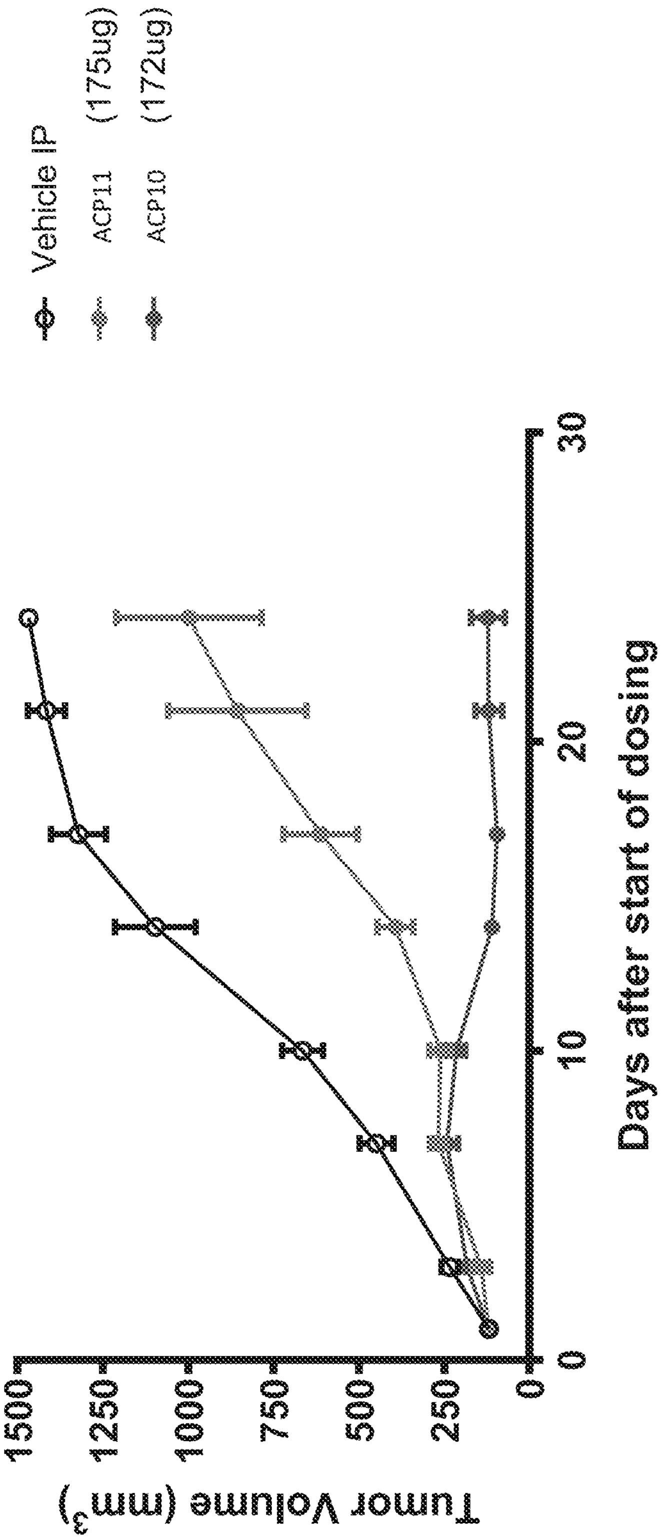
Figure 46C:
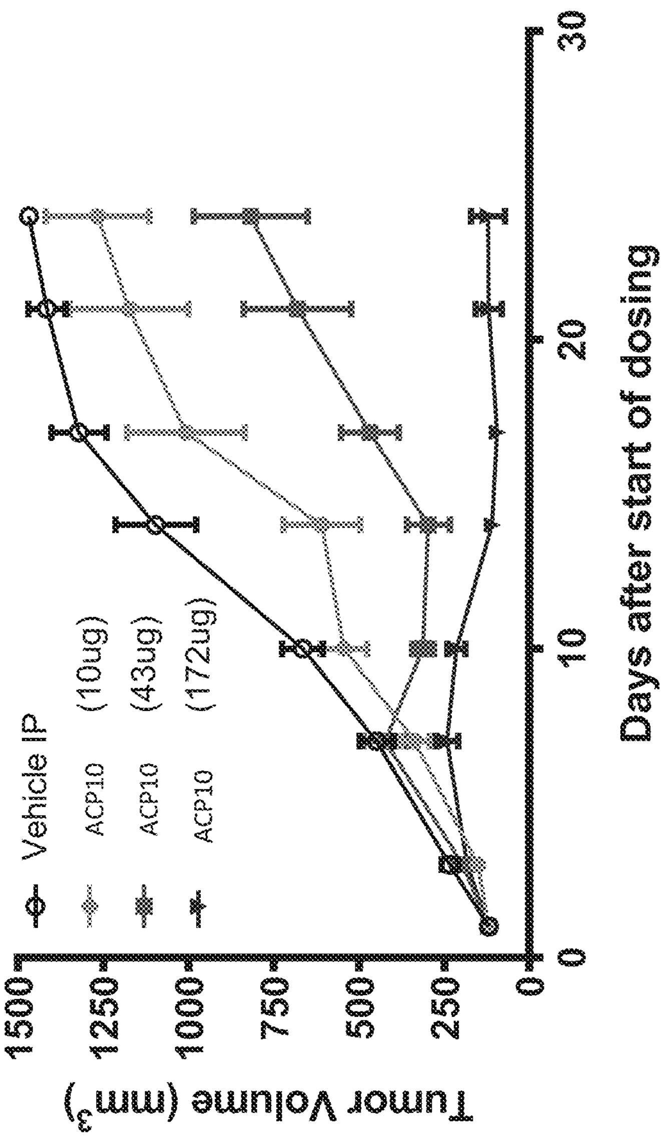
Figure 46D:
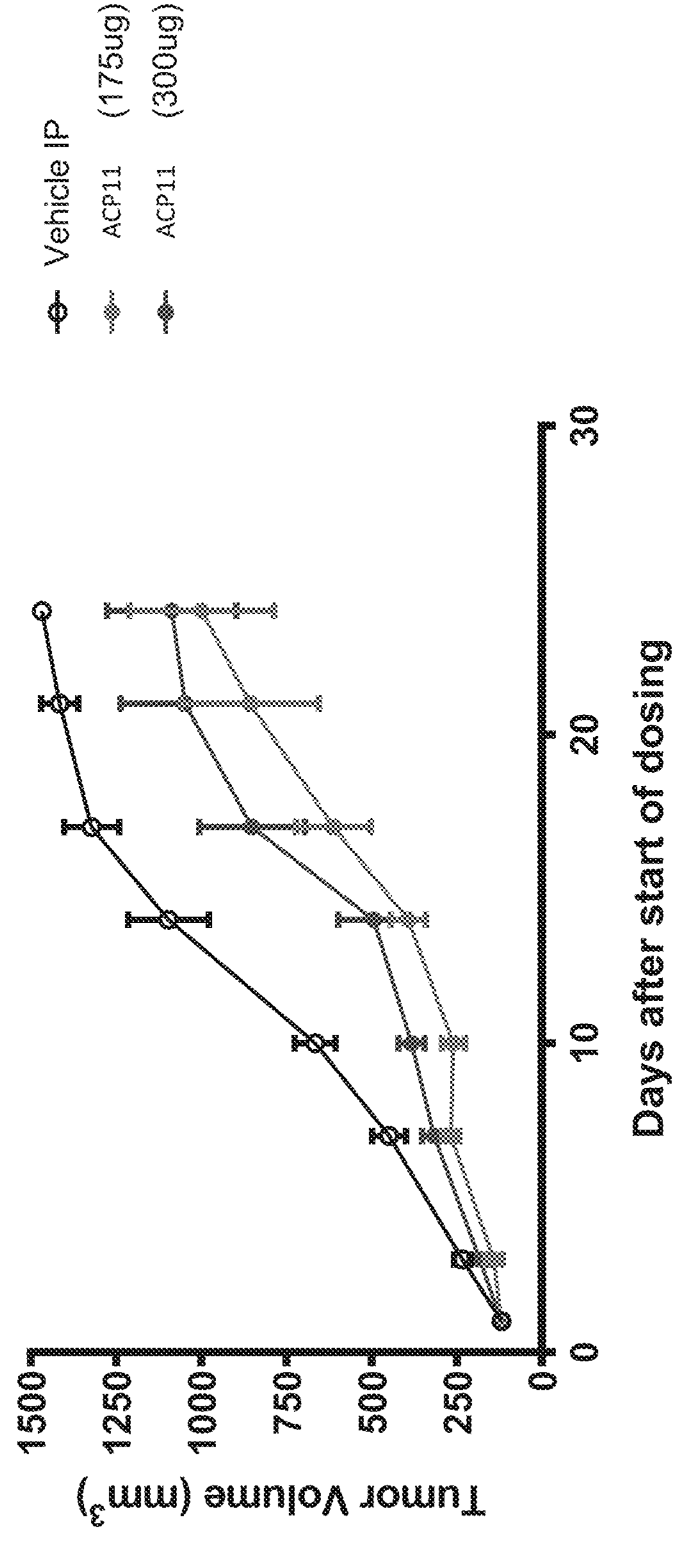
Figure 47A:
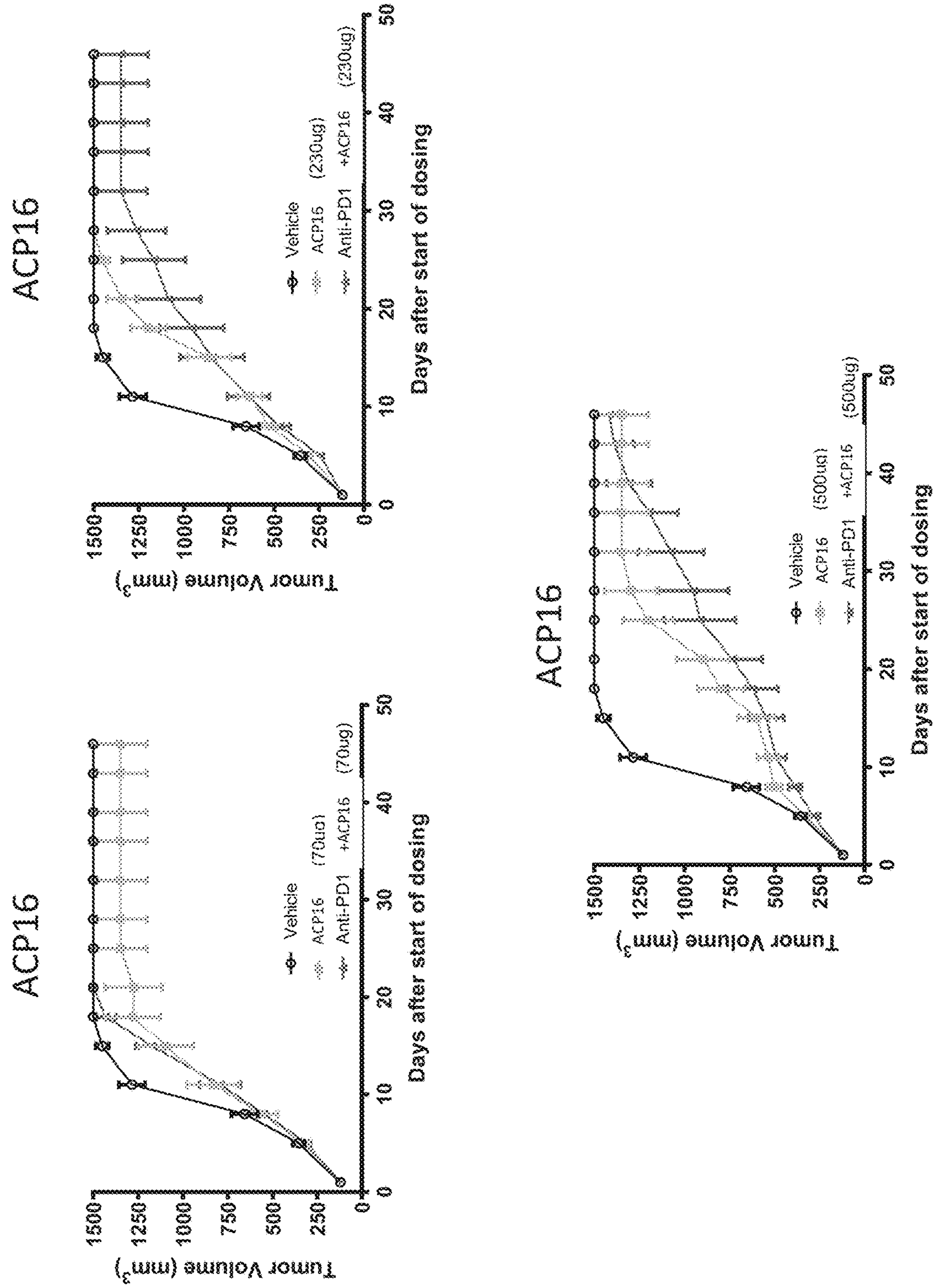
Figure 47B:
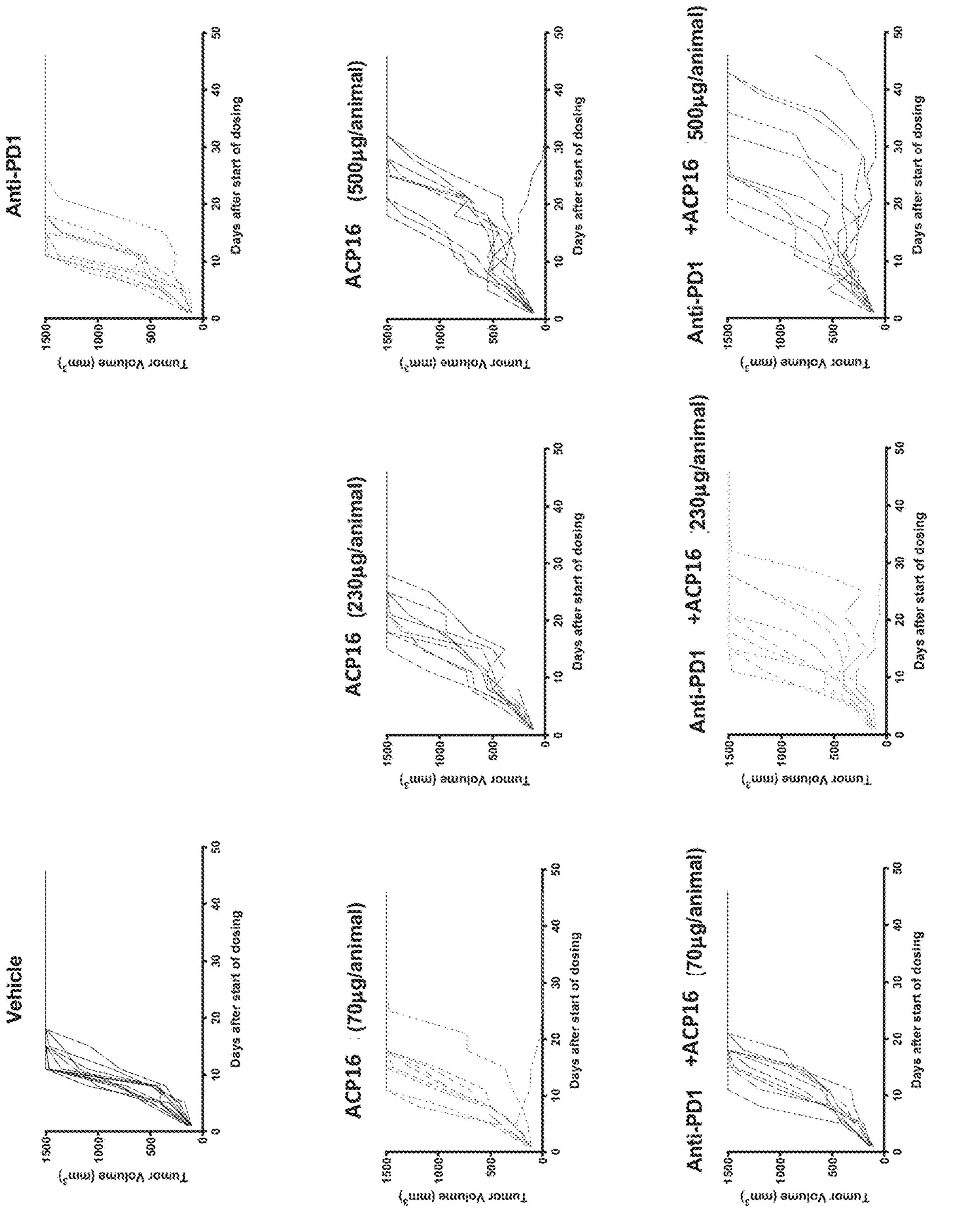
Figure 47C:
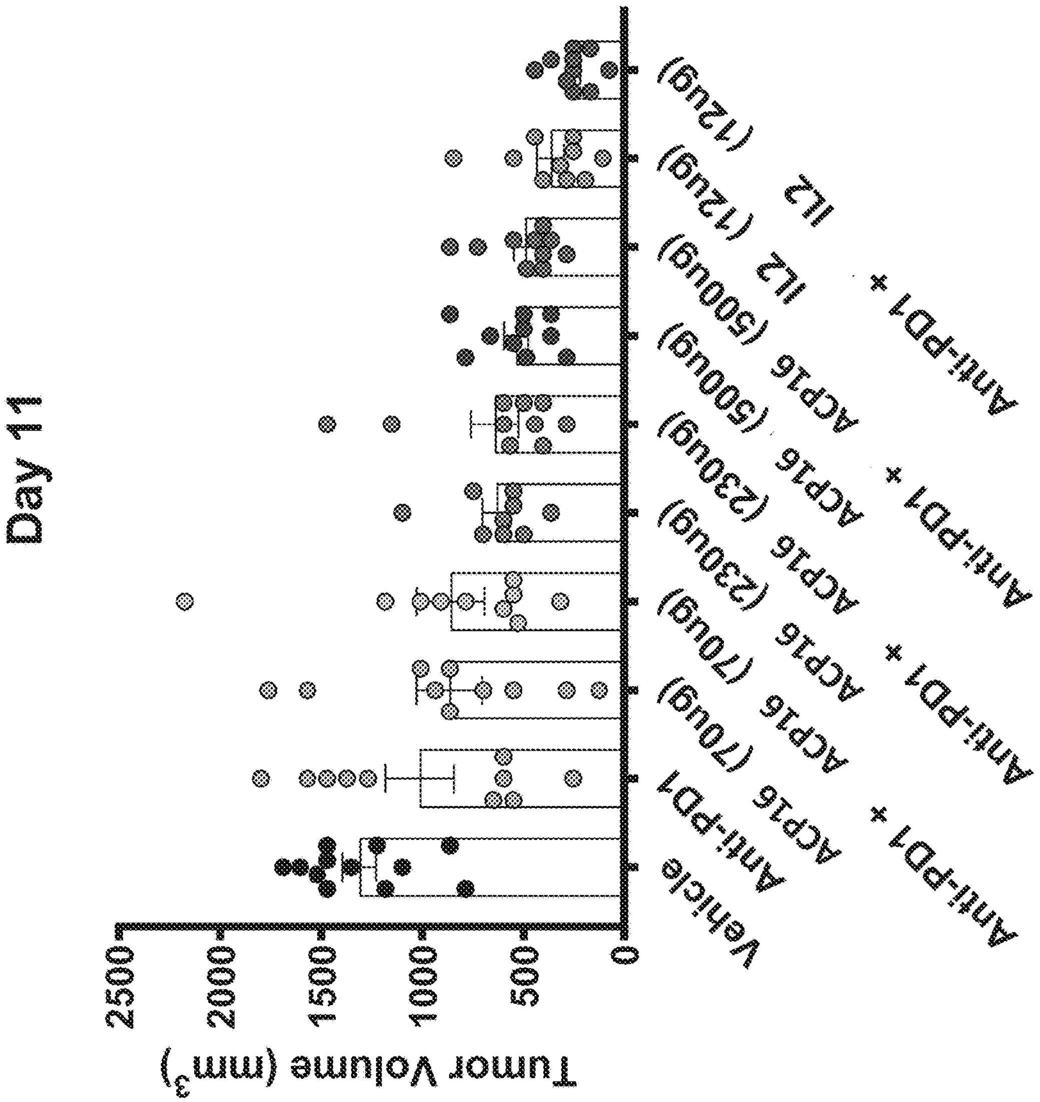
Figure 47D:
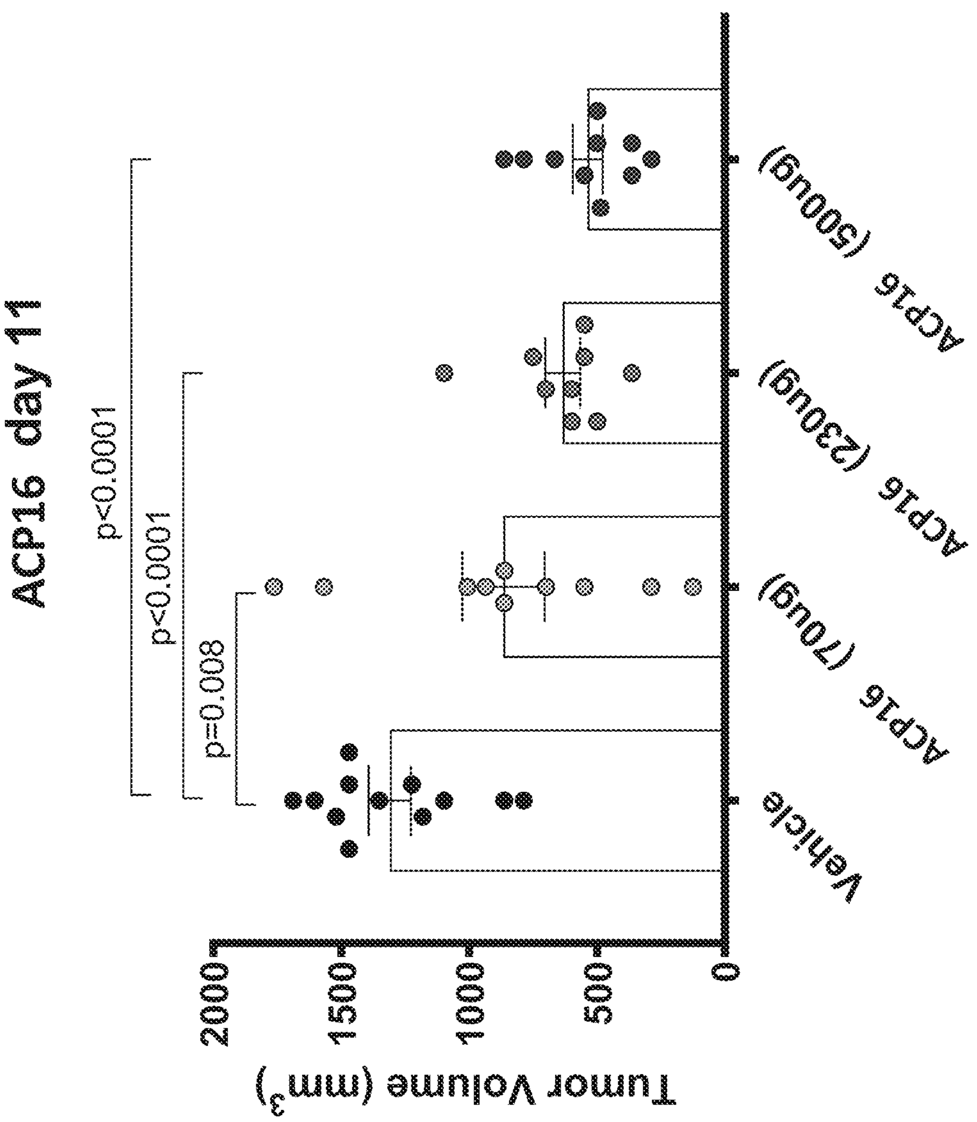
Figure 48A:
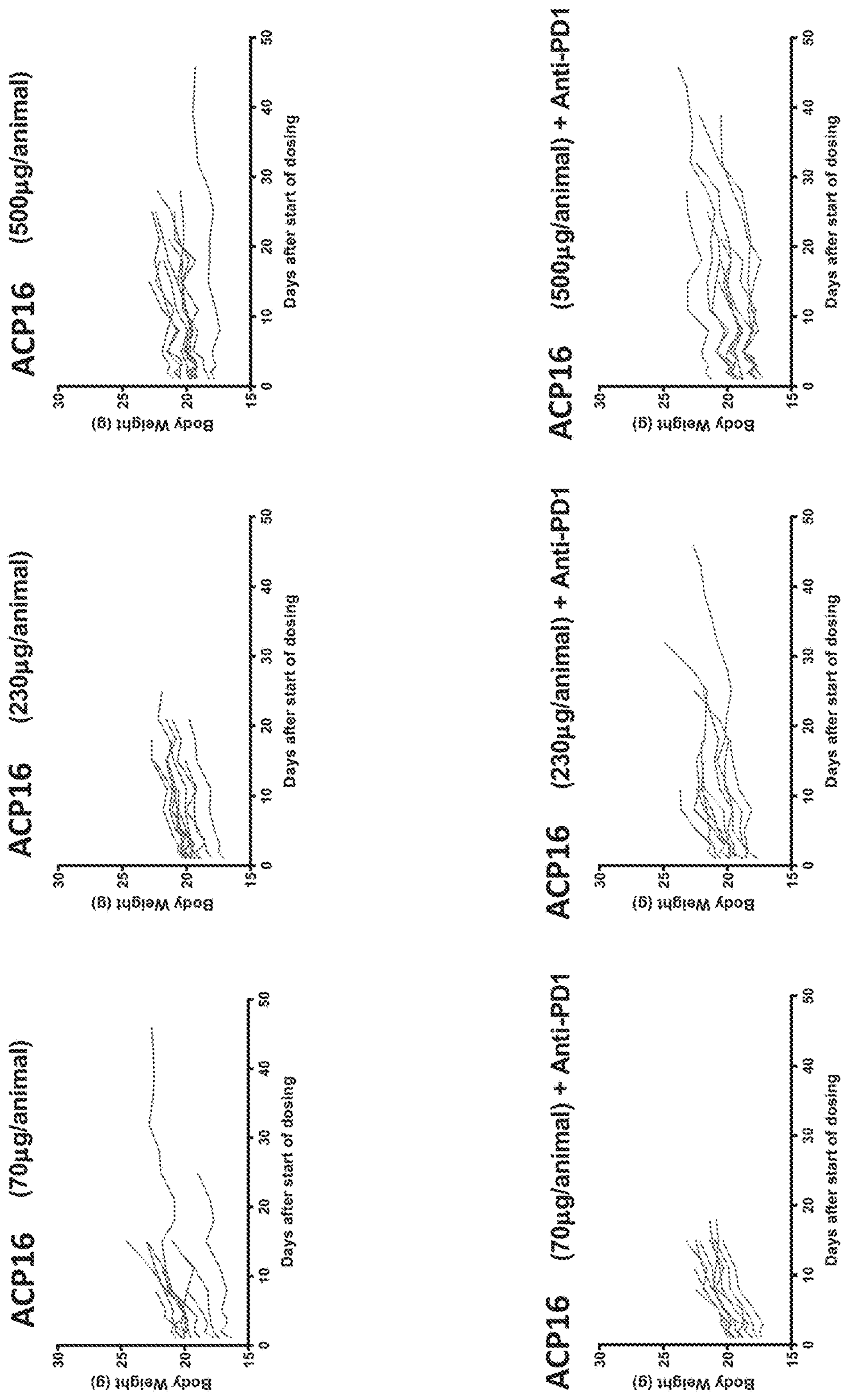
Figure 48B:
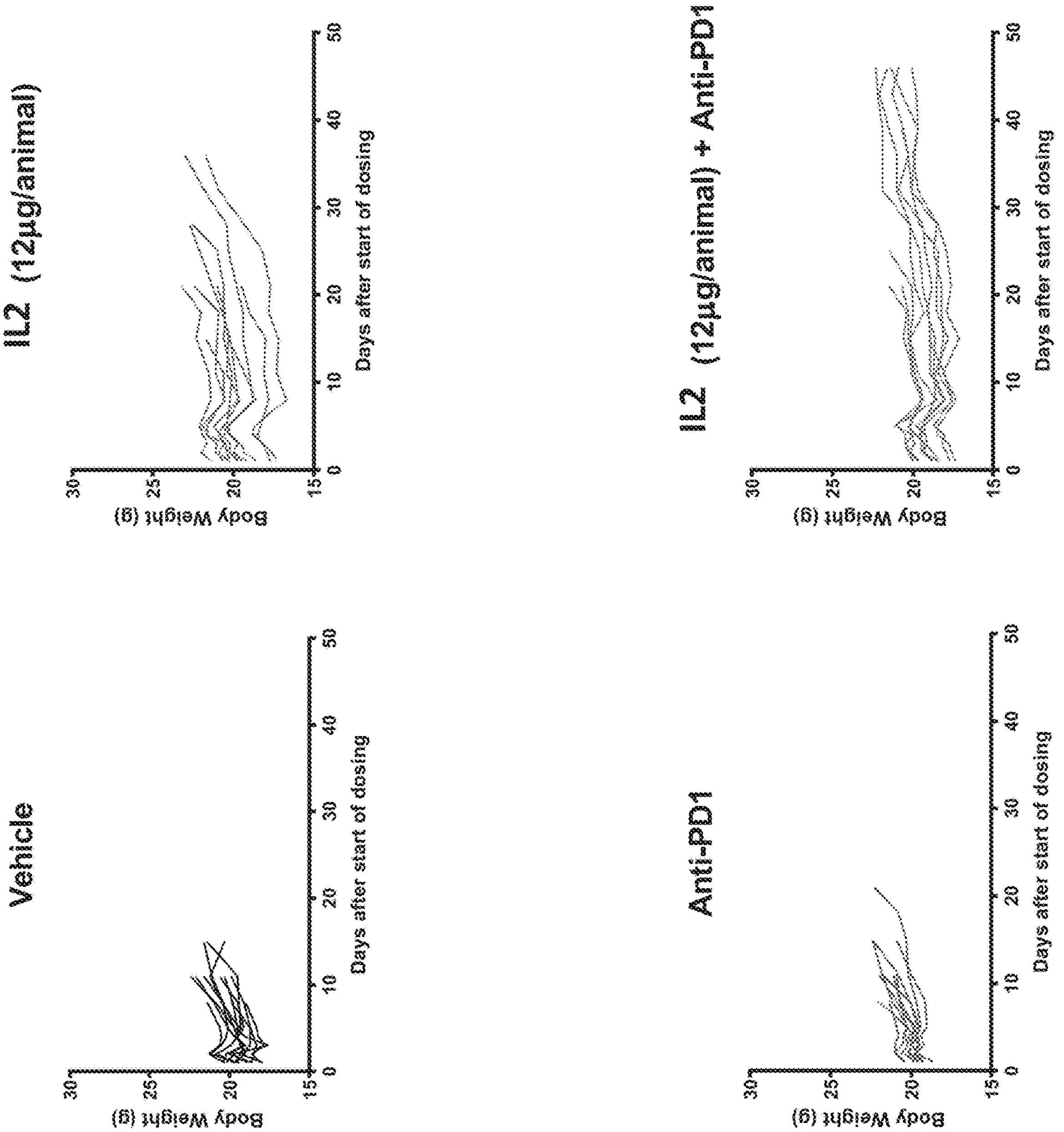
Figure 49A:
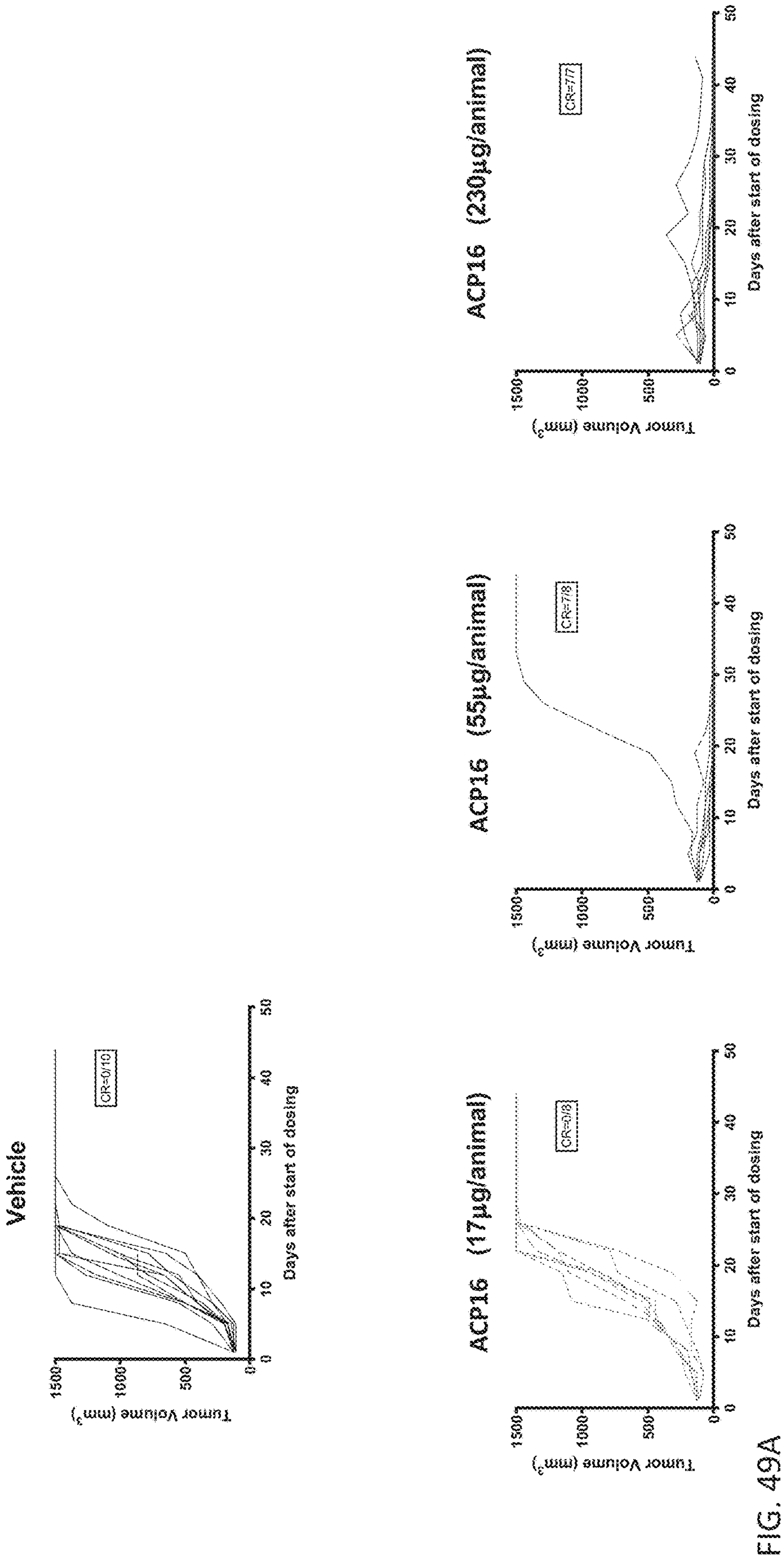
Figure 49B:
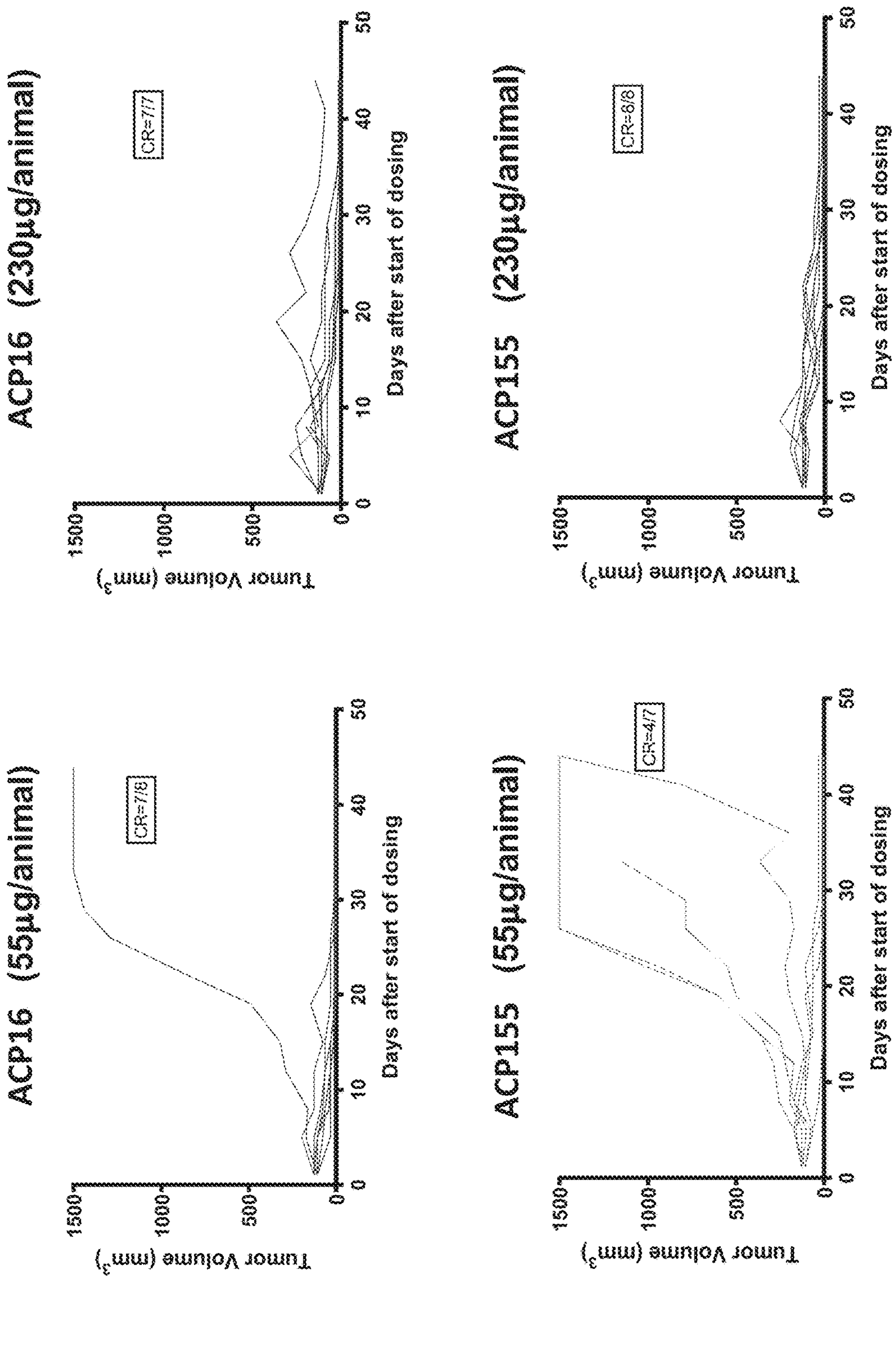
Figure 49C:
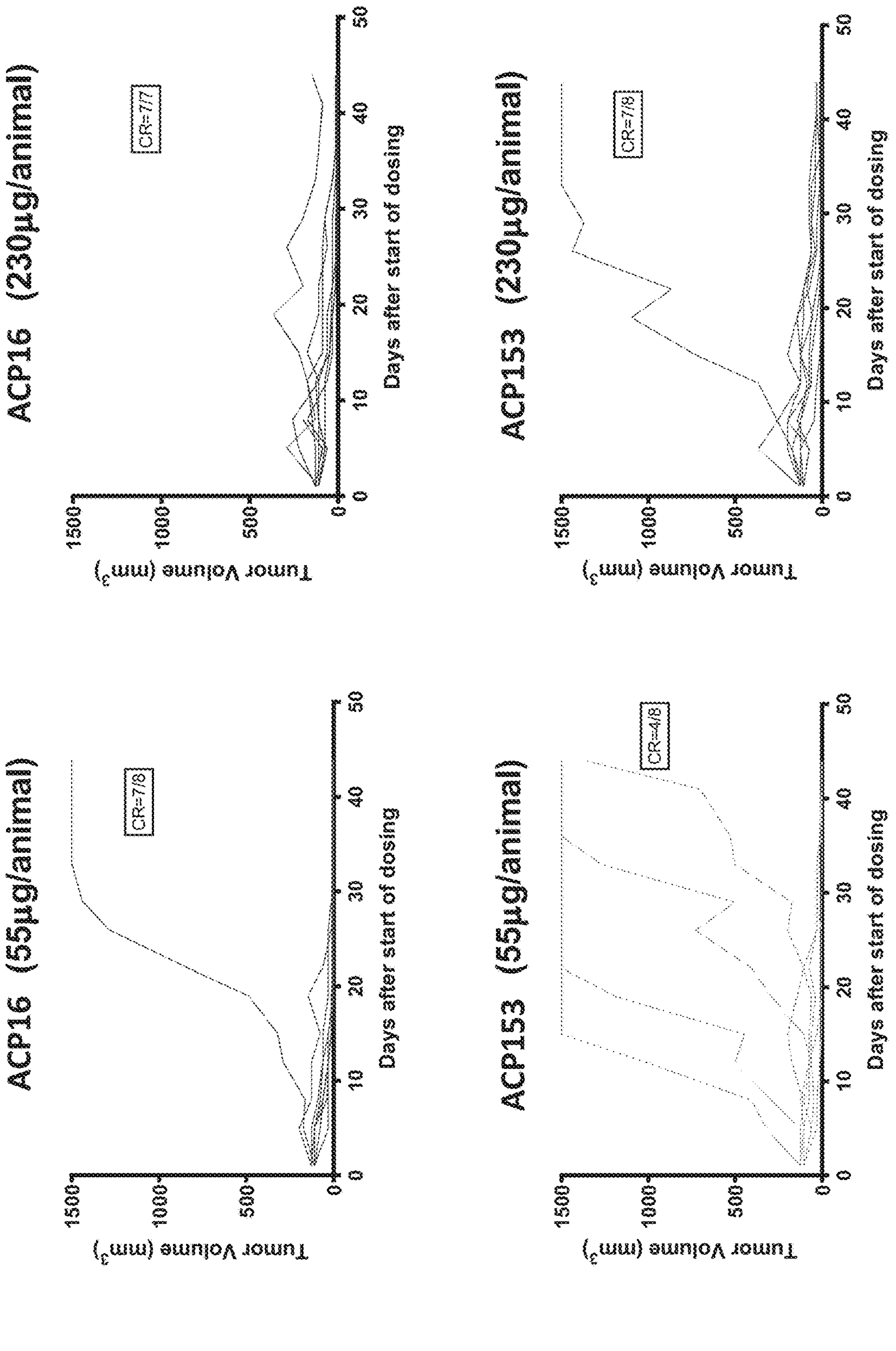
Figure 49D:
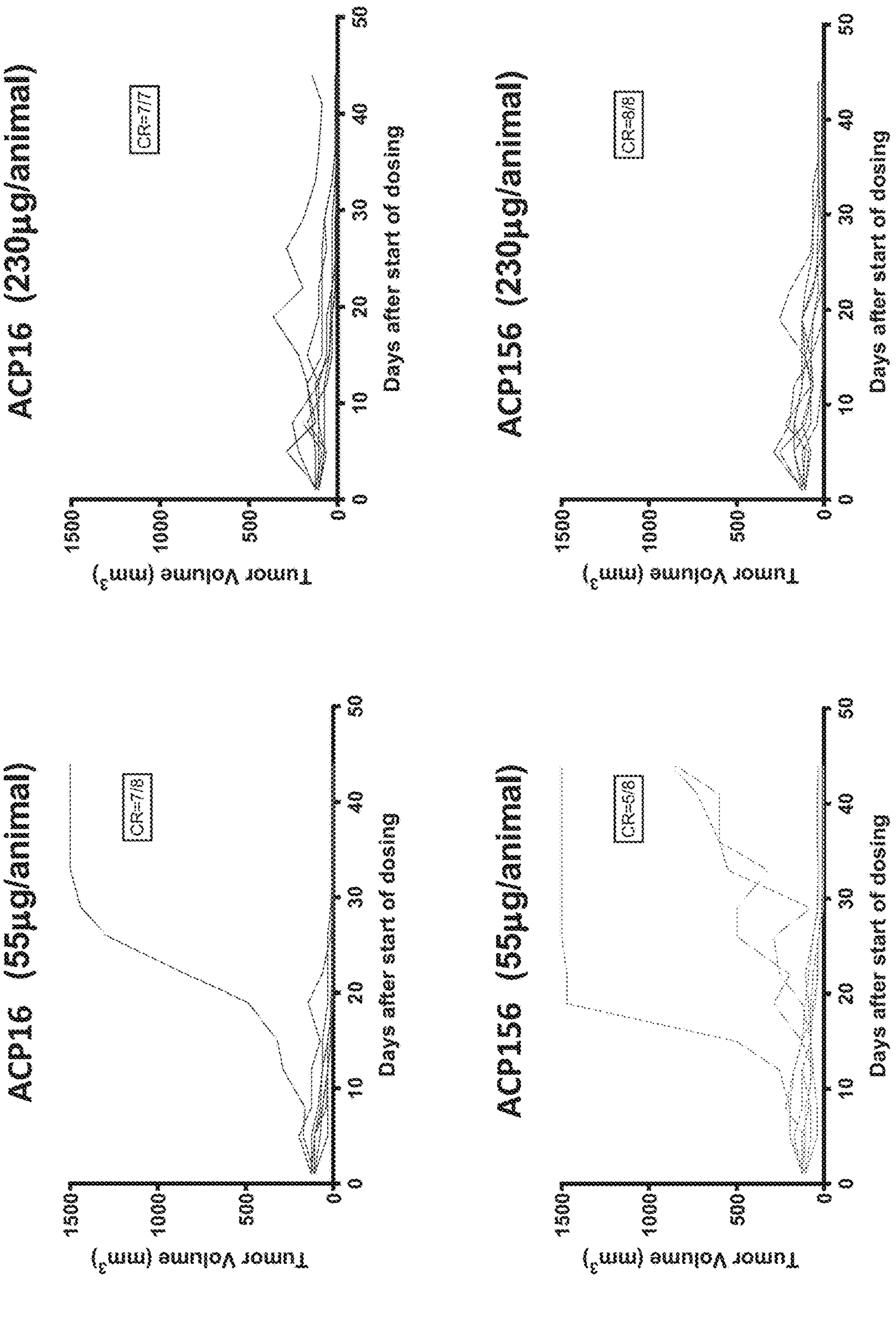
Figure 49E:
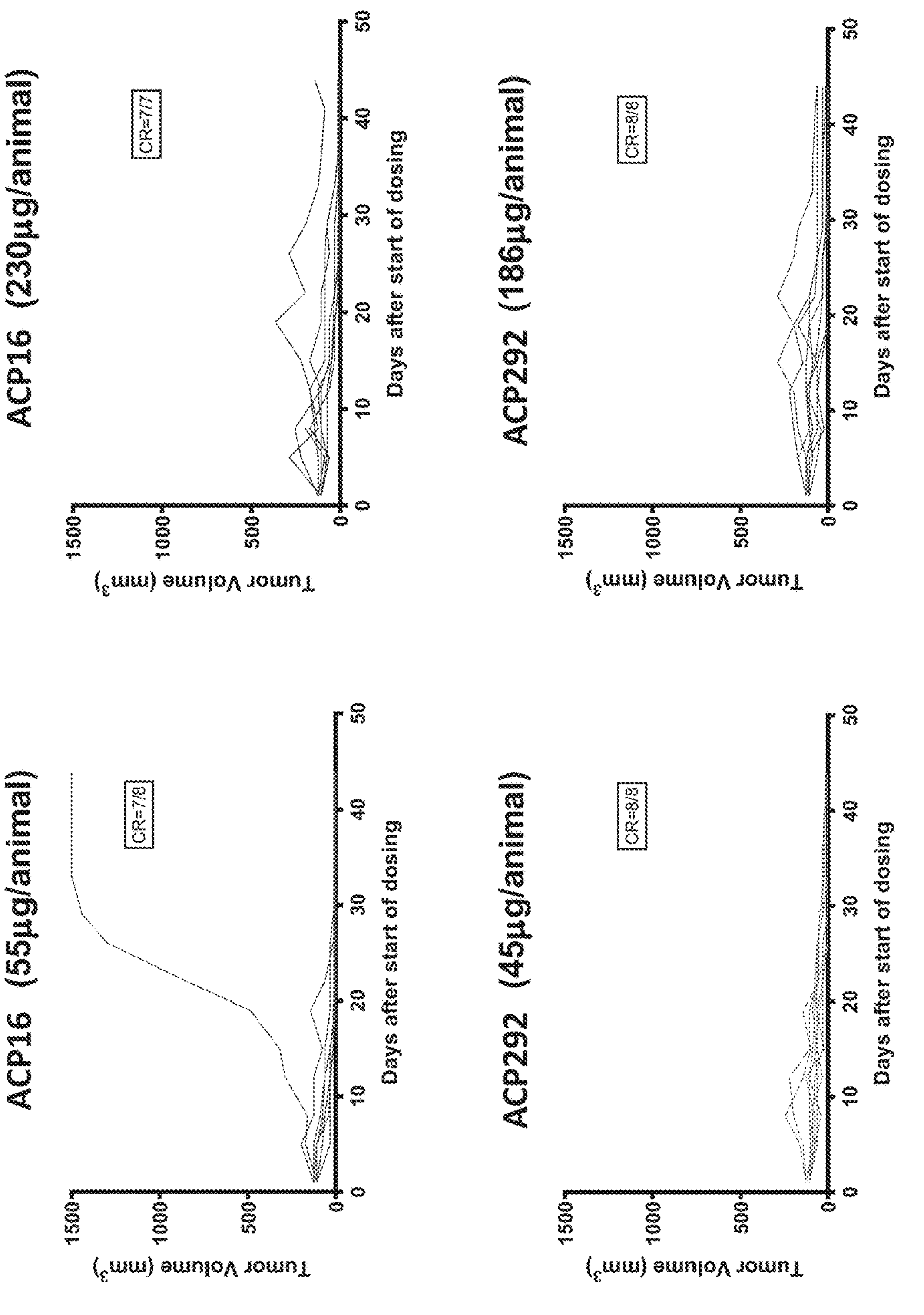
Figure 49F:
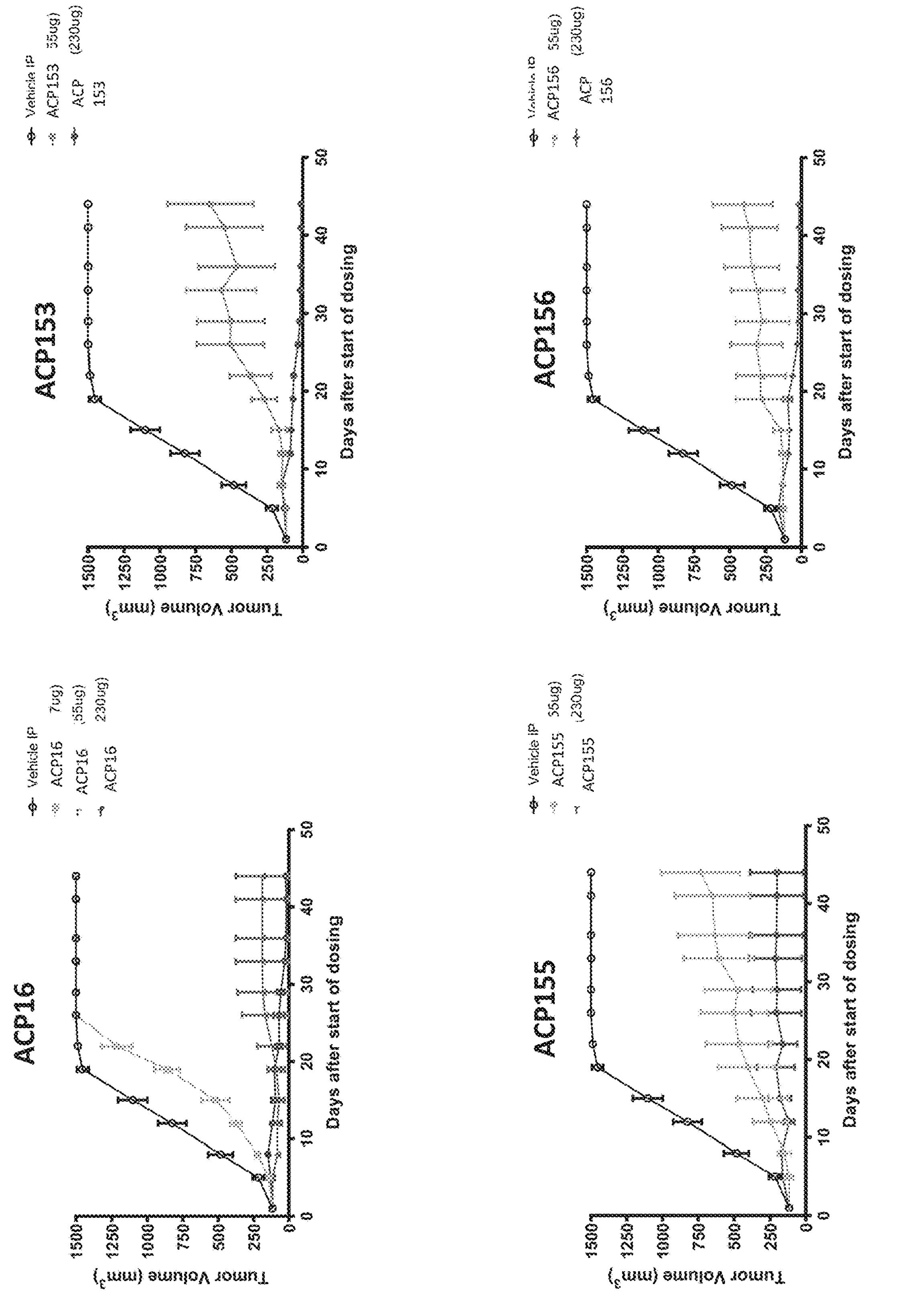
Figure 49G:
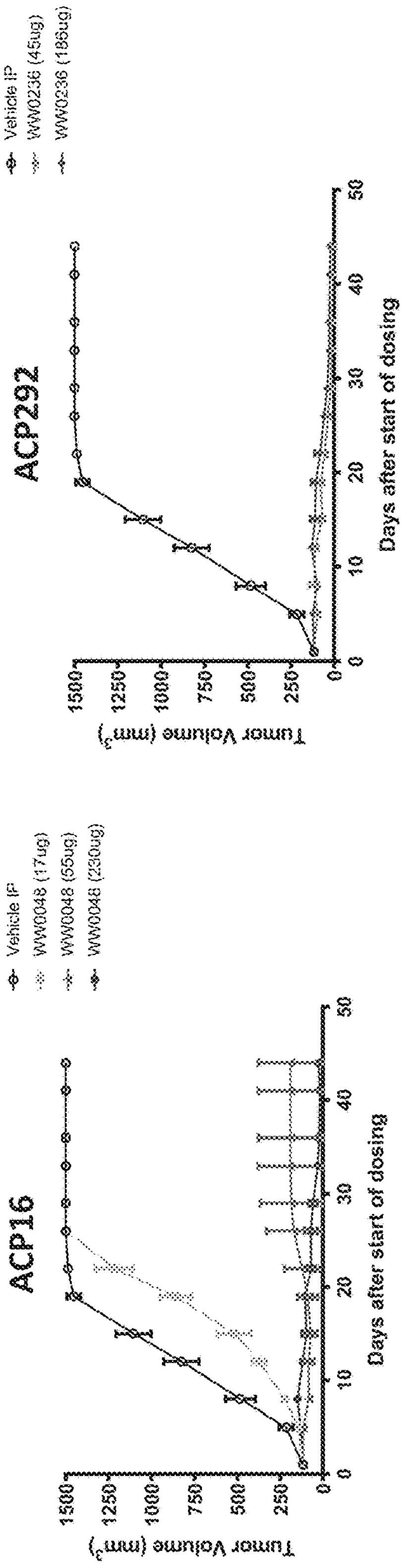
Figure 49H:
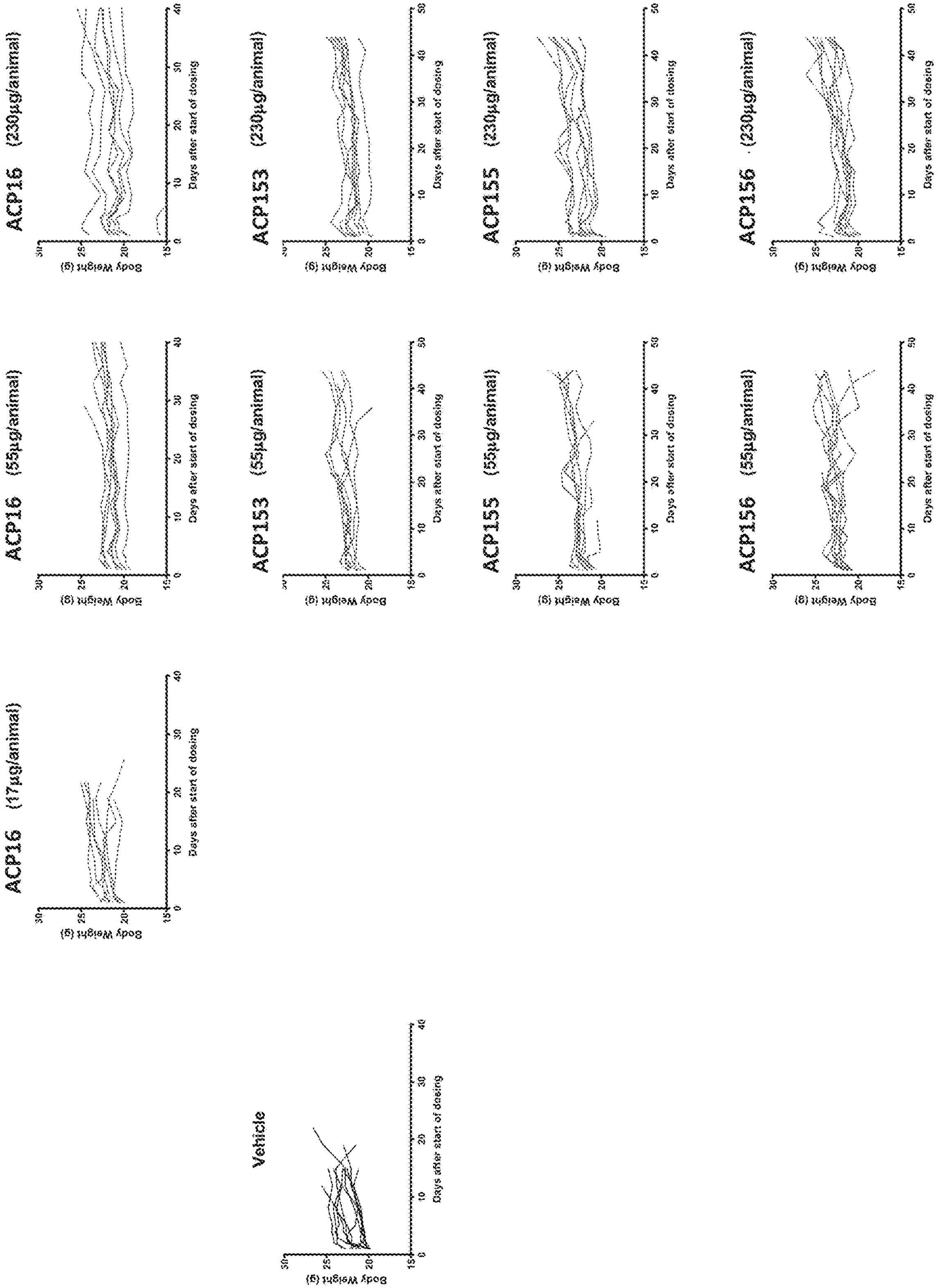
Figure 49I:
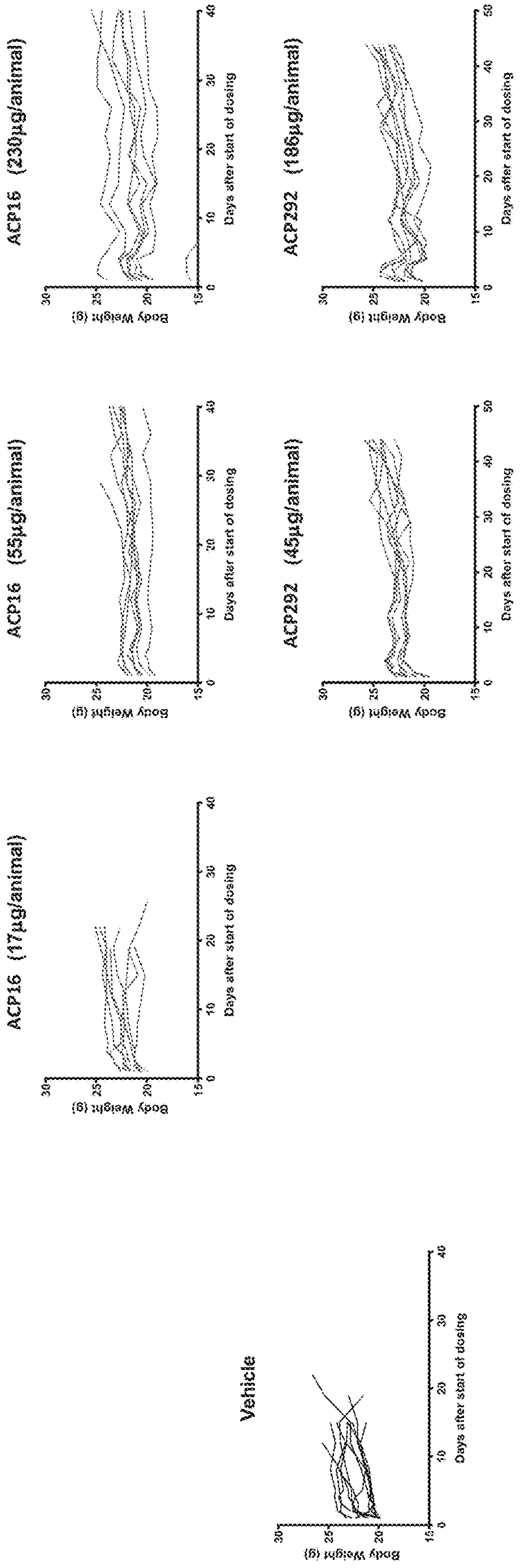

FIG. 45 shows a series of spider plots showing tumor volume over time during treatment with vehicle, IL-12, ACP11 or ACP10.

FIGS. 46A-46D, 47A-47D, 48A, 48B, 49A-49I, 50A, 50B, and 51A-51C shows data (tumor volume and/or body weight) for mice treated with cytokine fusion proteins constructs.

FIGS. 52A-52N, 53A, and 53B depict the activity of cytokine fusion proteins constructs.

Figure 54A:
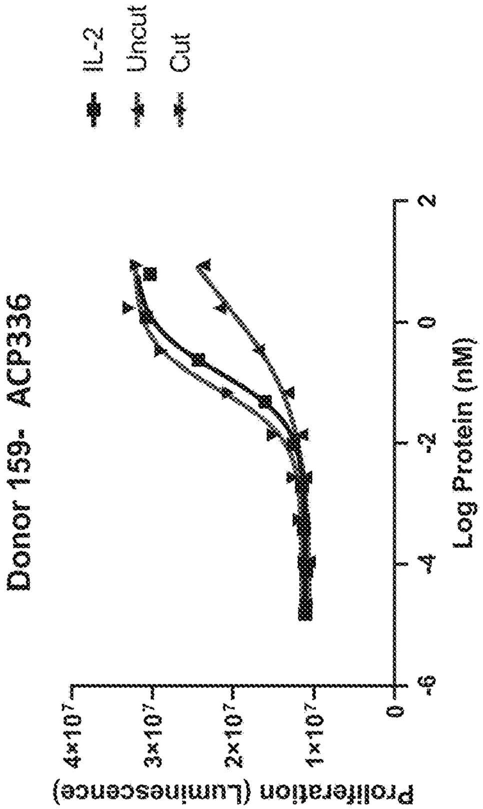
Figure 54A:
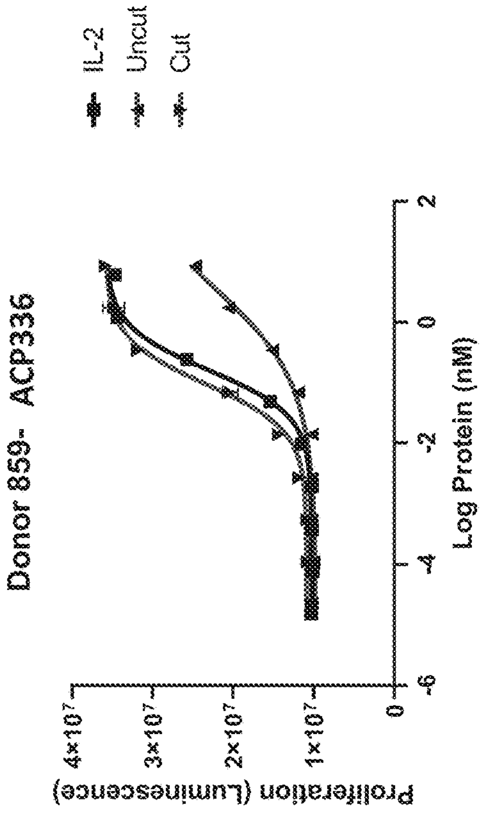
Figure 54B:
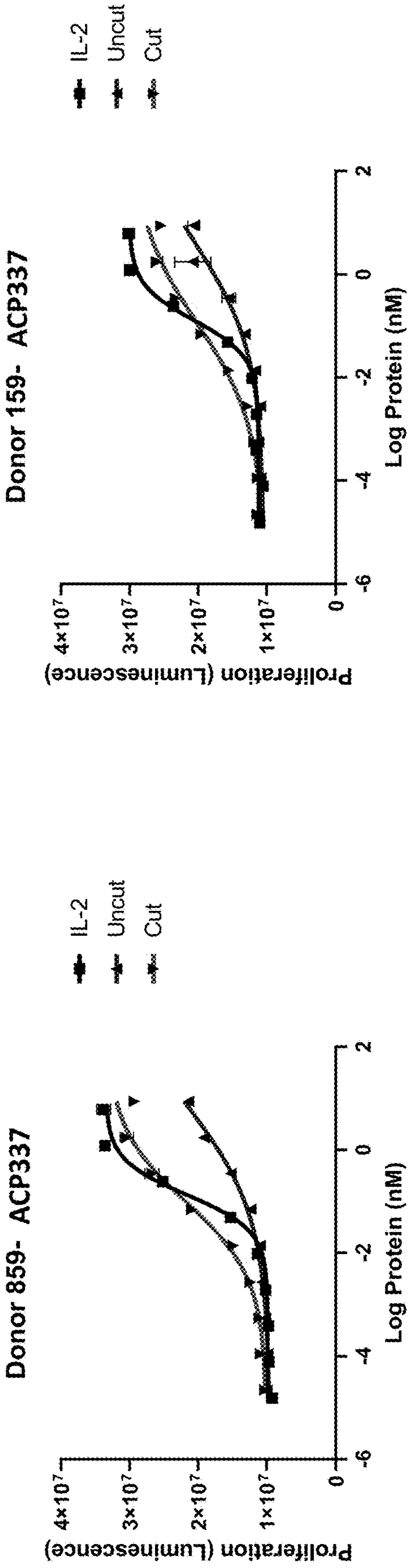
Figure 54C:
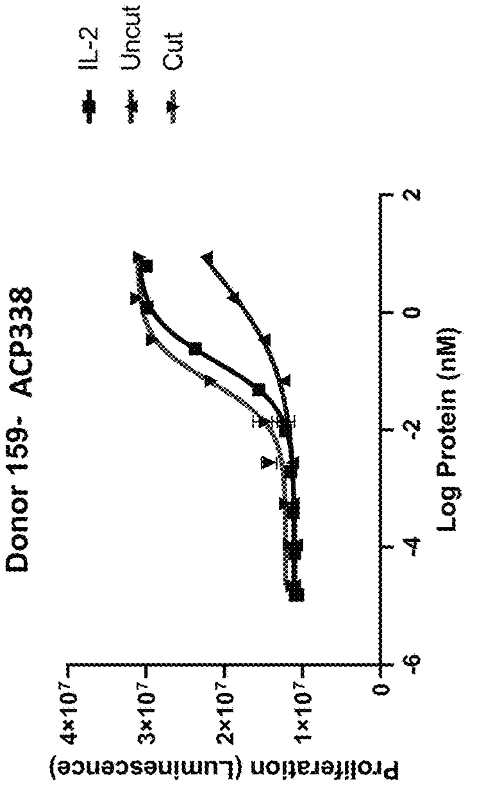
Figure 54C:
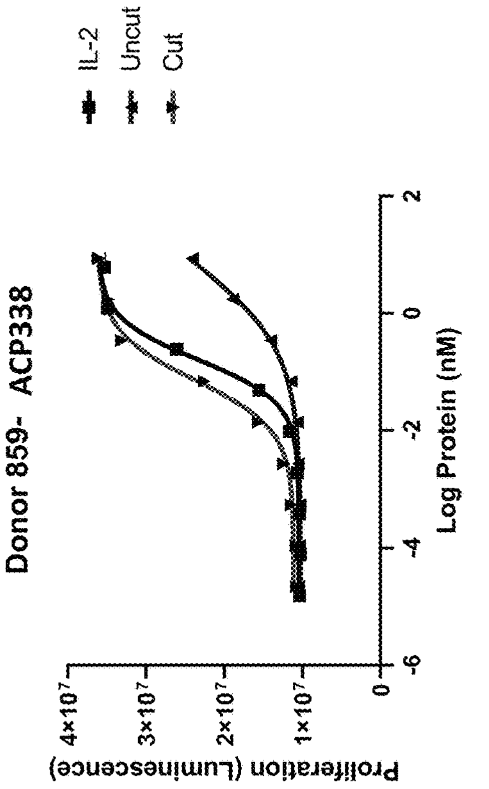
Figure 54D:
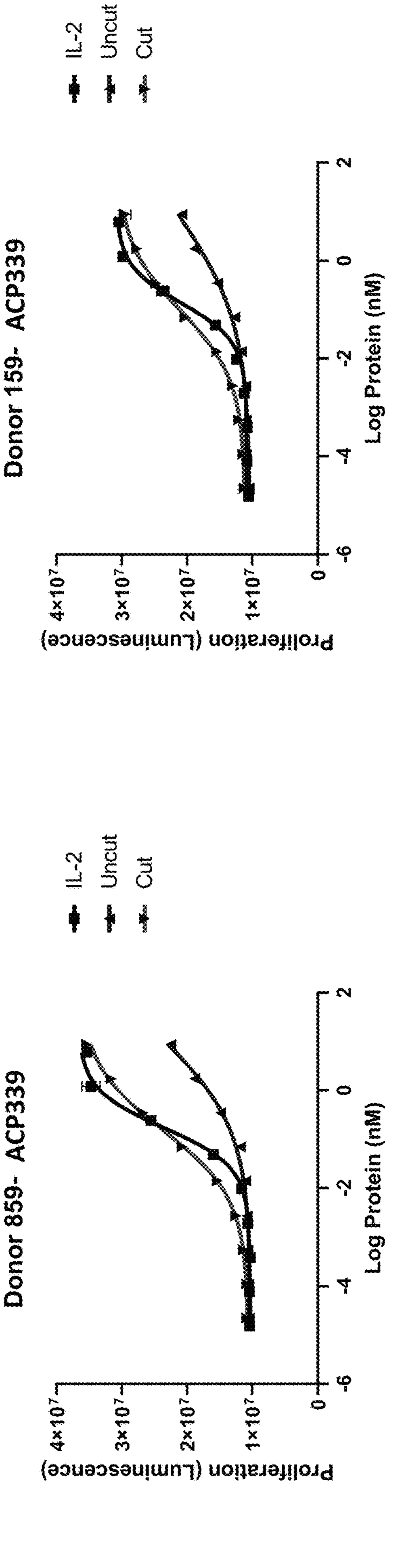
Figure 54E:
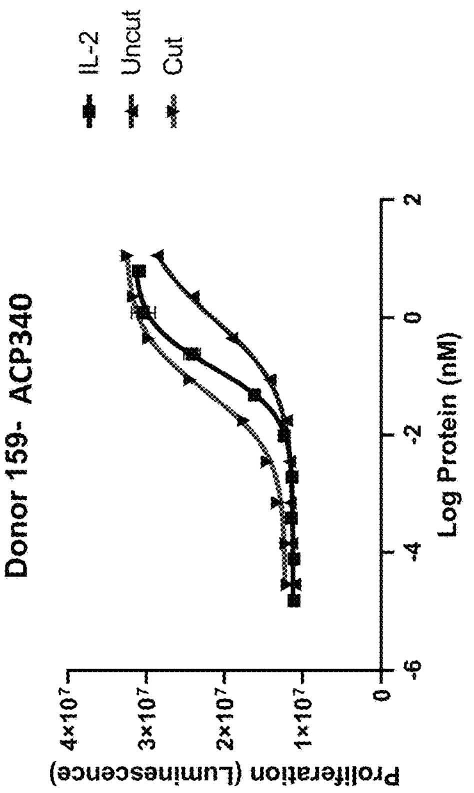
Figure 54E:
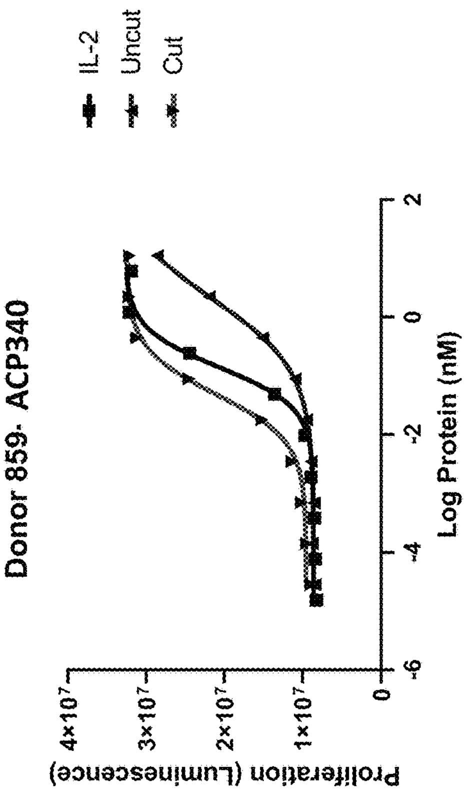
Figure 54F:
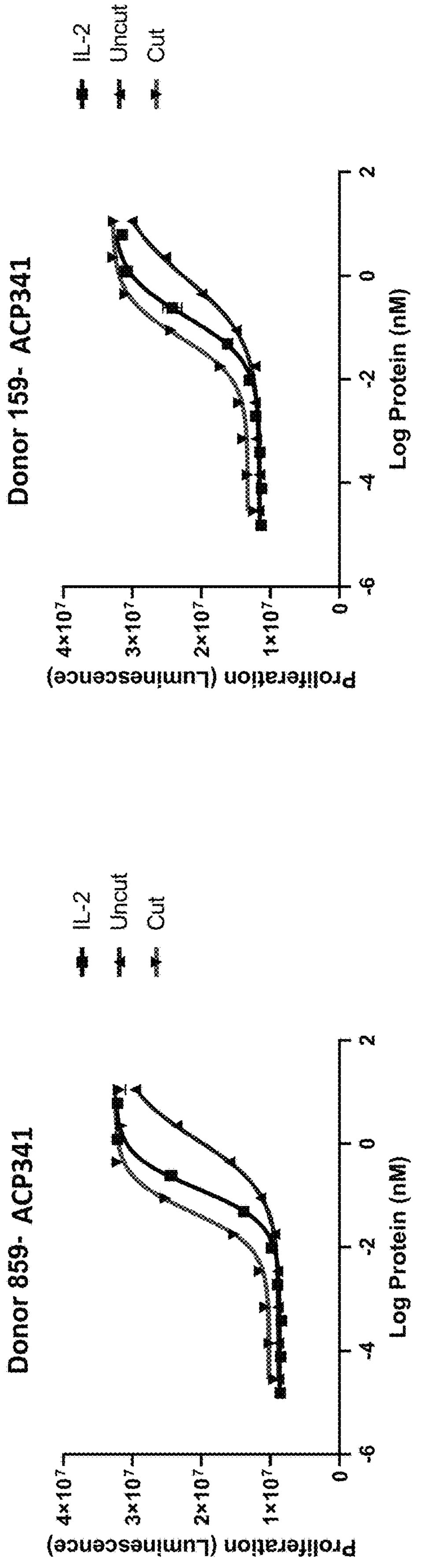
Figure 54G:
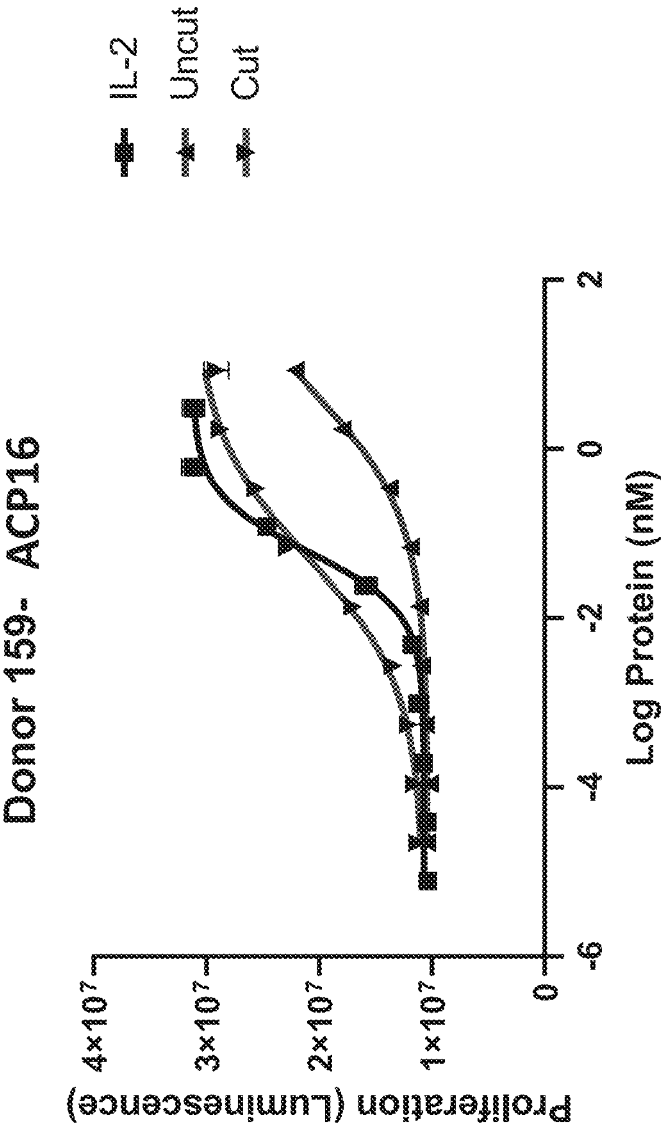
Figure 54H:
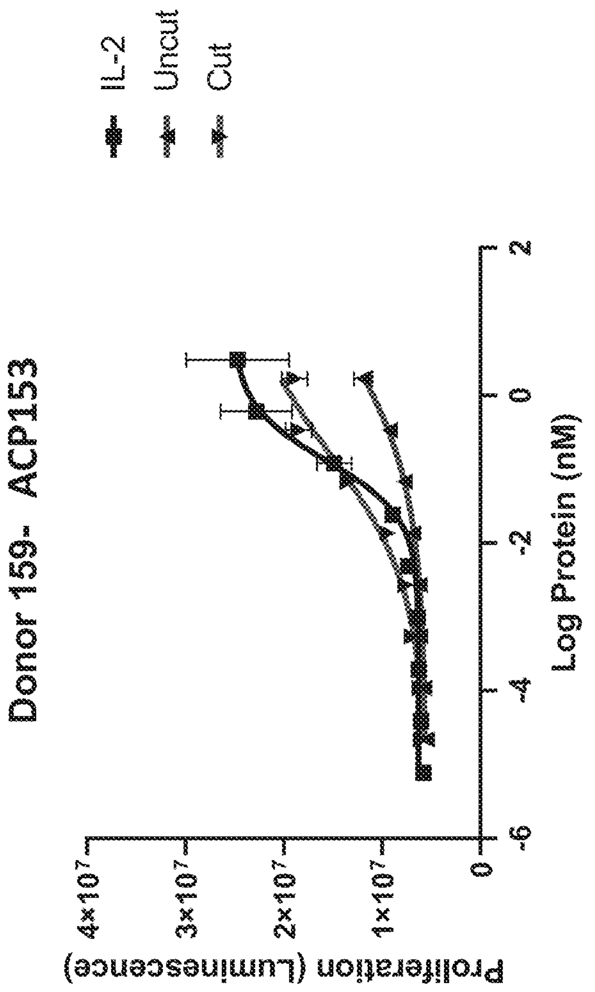
Figure 54I:
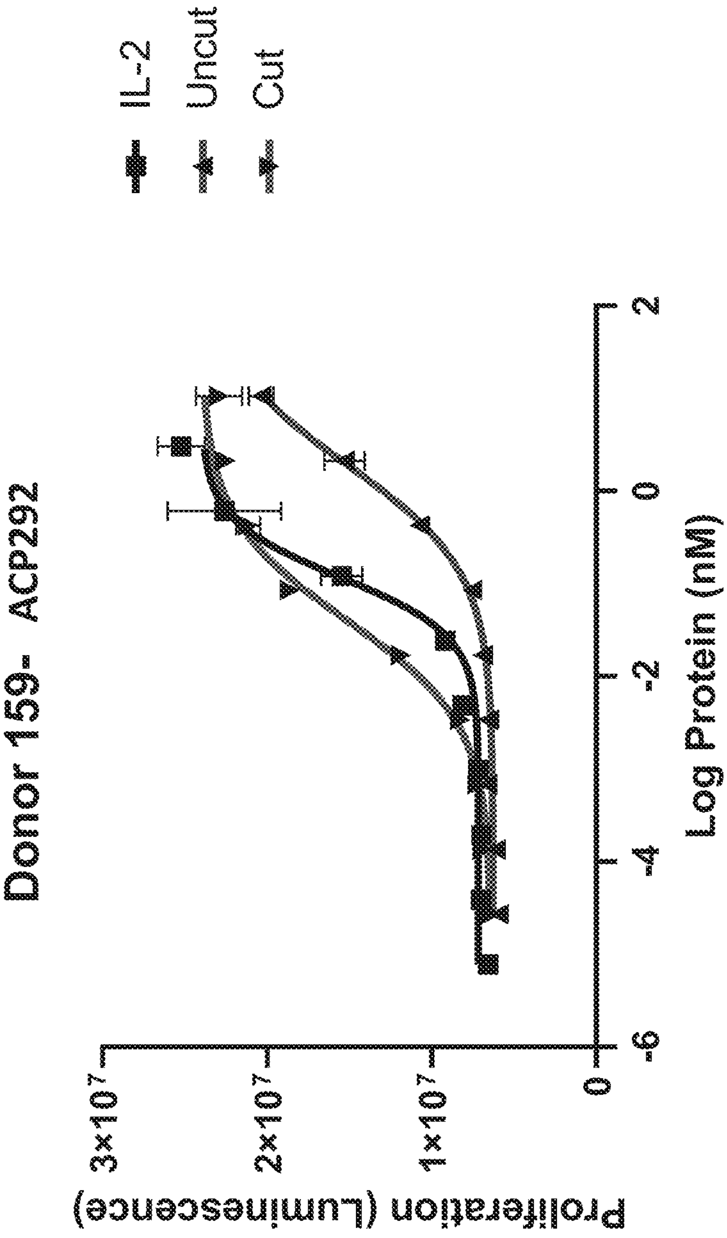
Figure 54J:
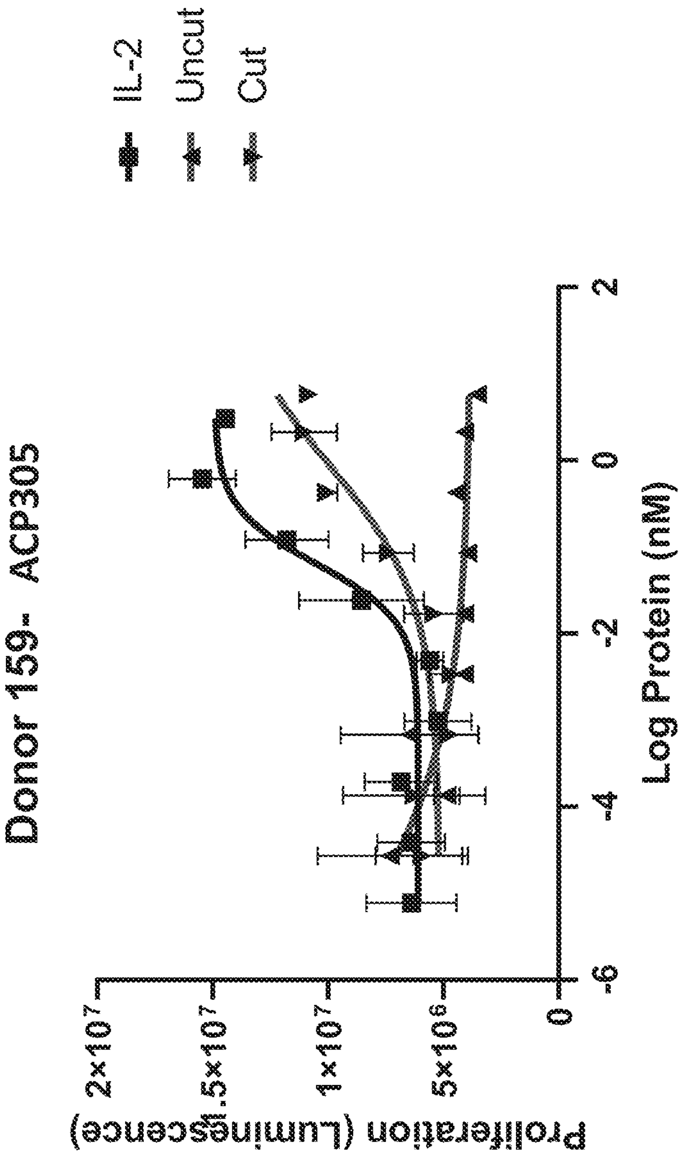
Figure 54K:
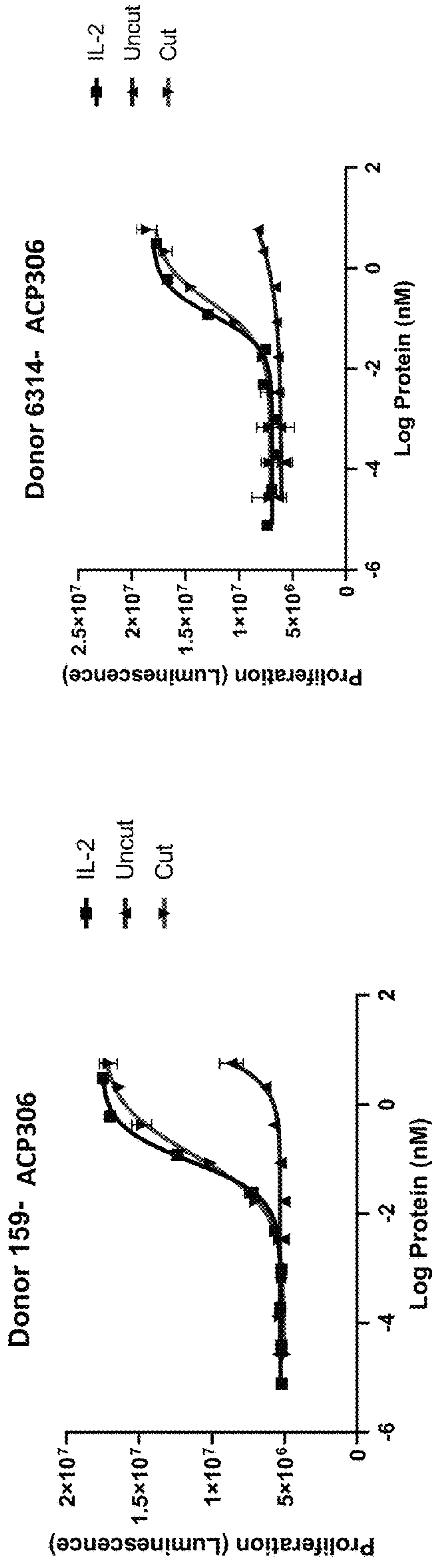
Figure 54L:
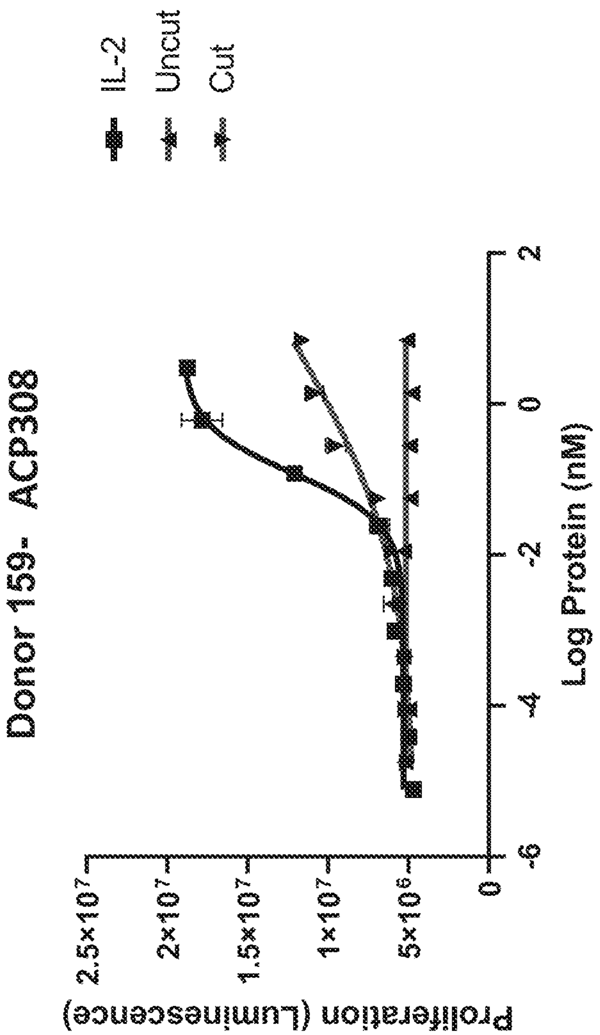
Figure 54M:
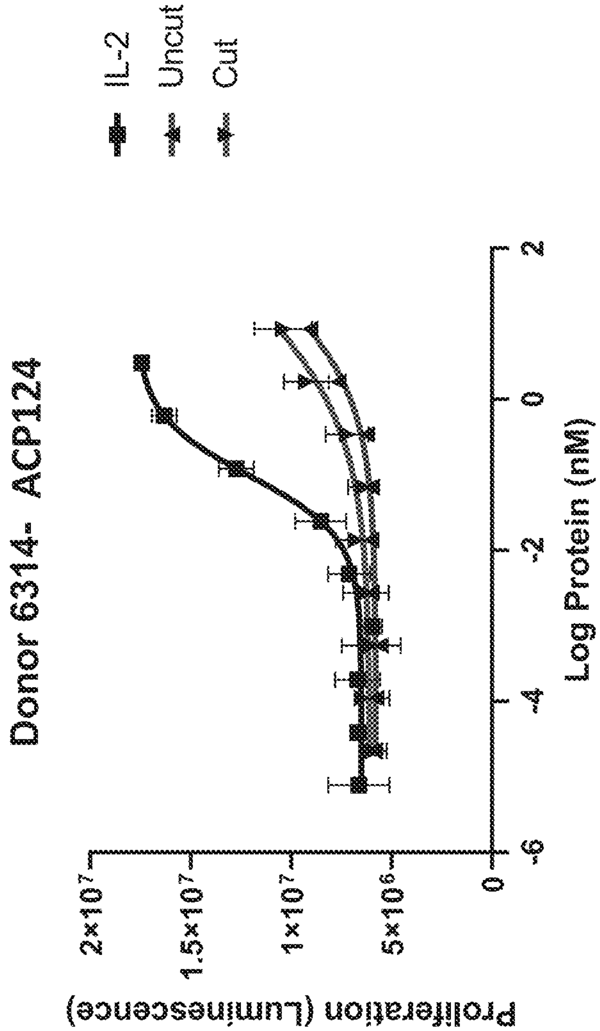
Figure 54N:
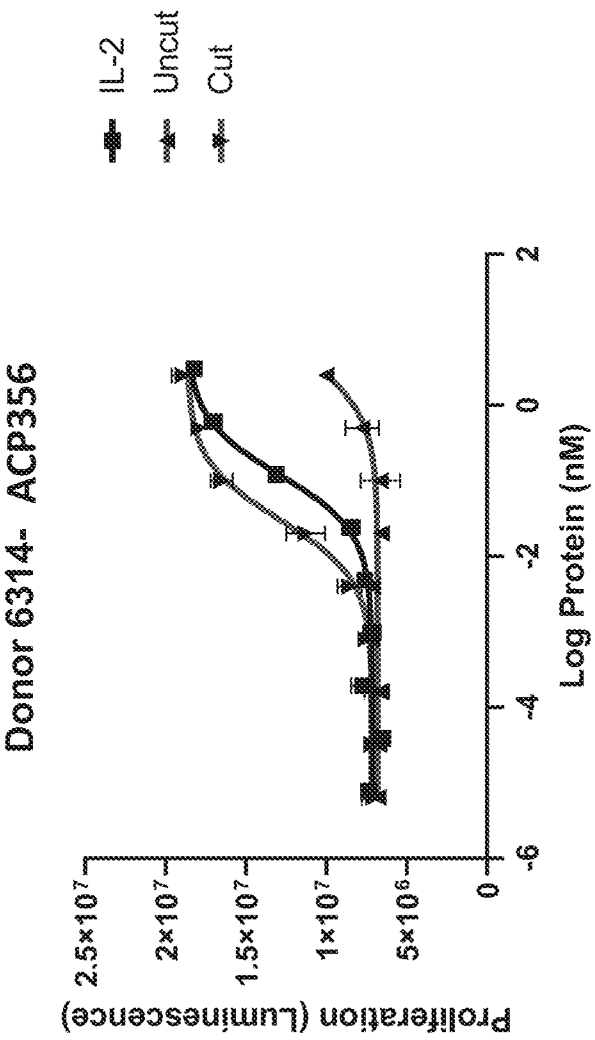

FIG. 54A-54N shows the results of proliferation assays comparing cut protein, uncut protein, and IL2 as a control.

Figure 55A:
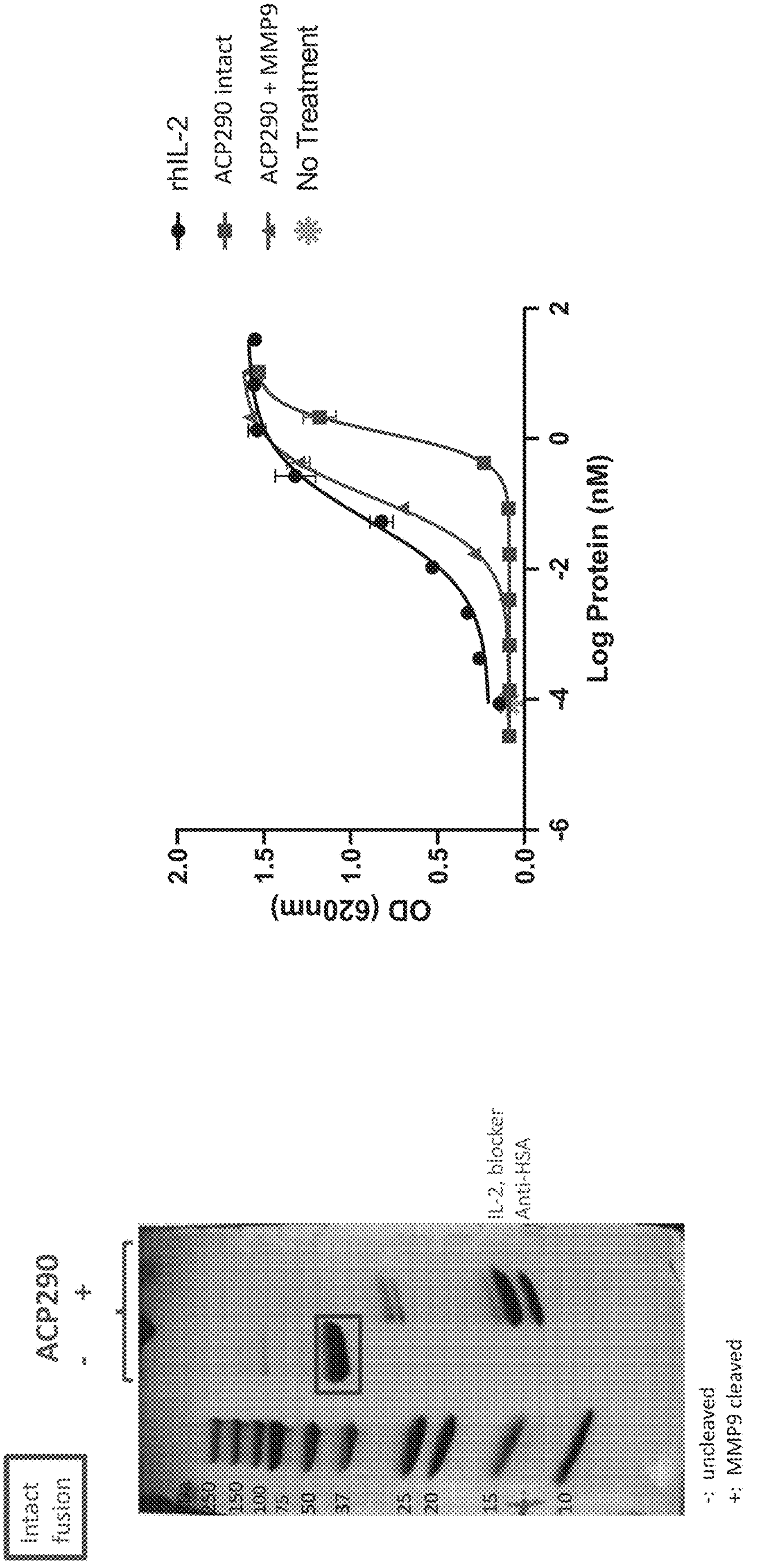
Figure 55B:
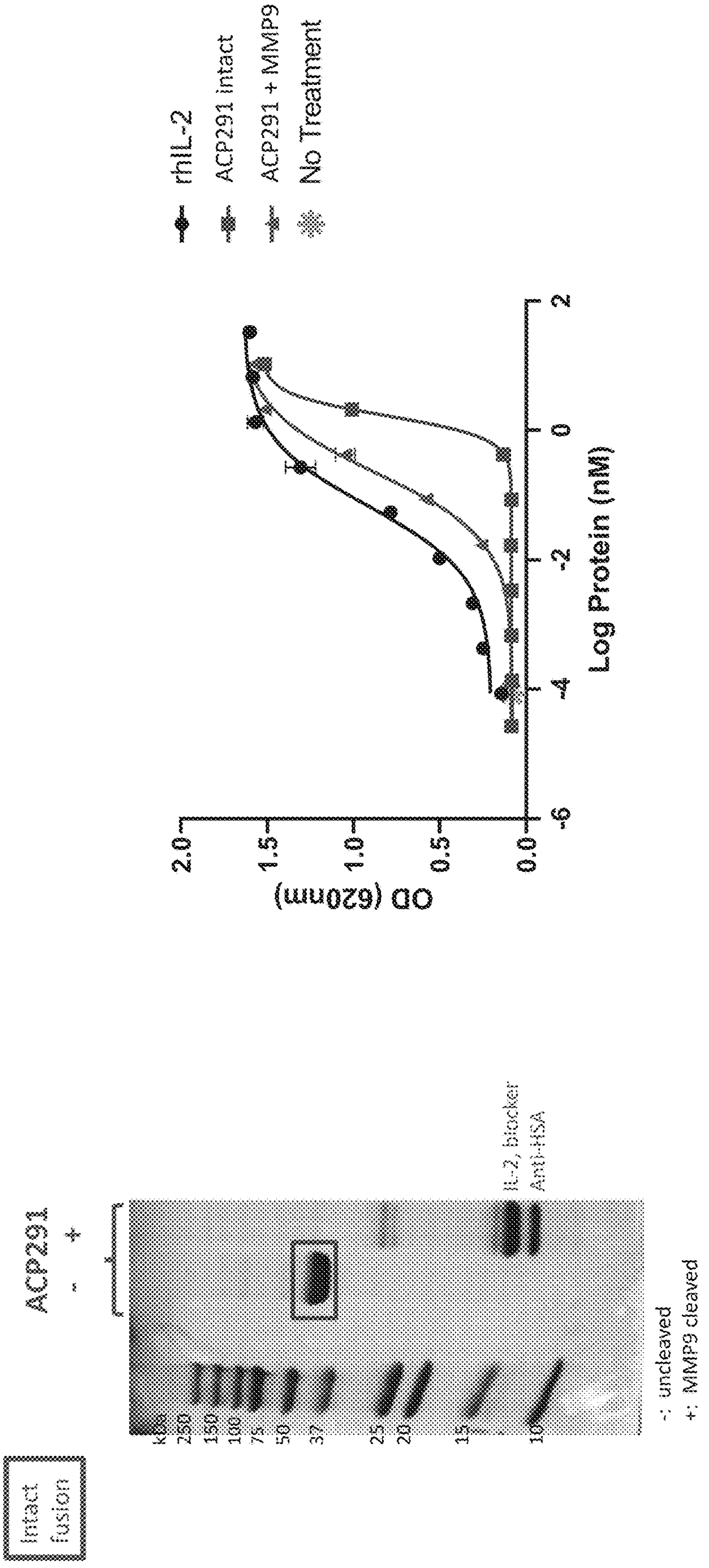
Figure 55C:
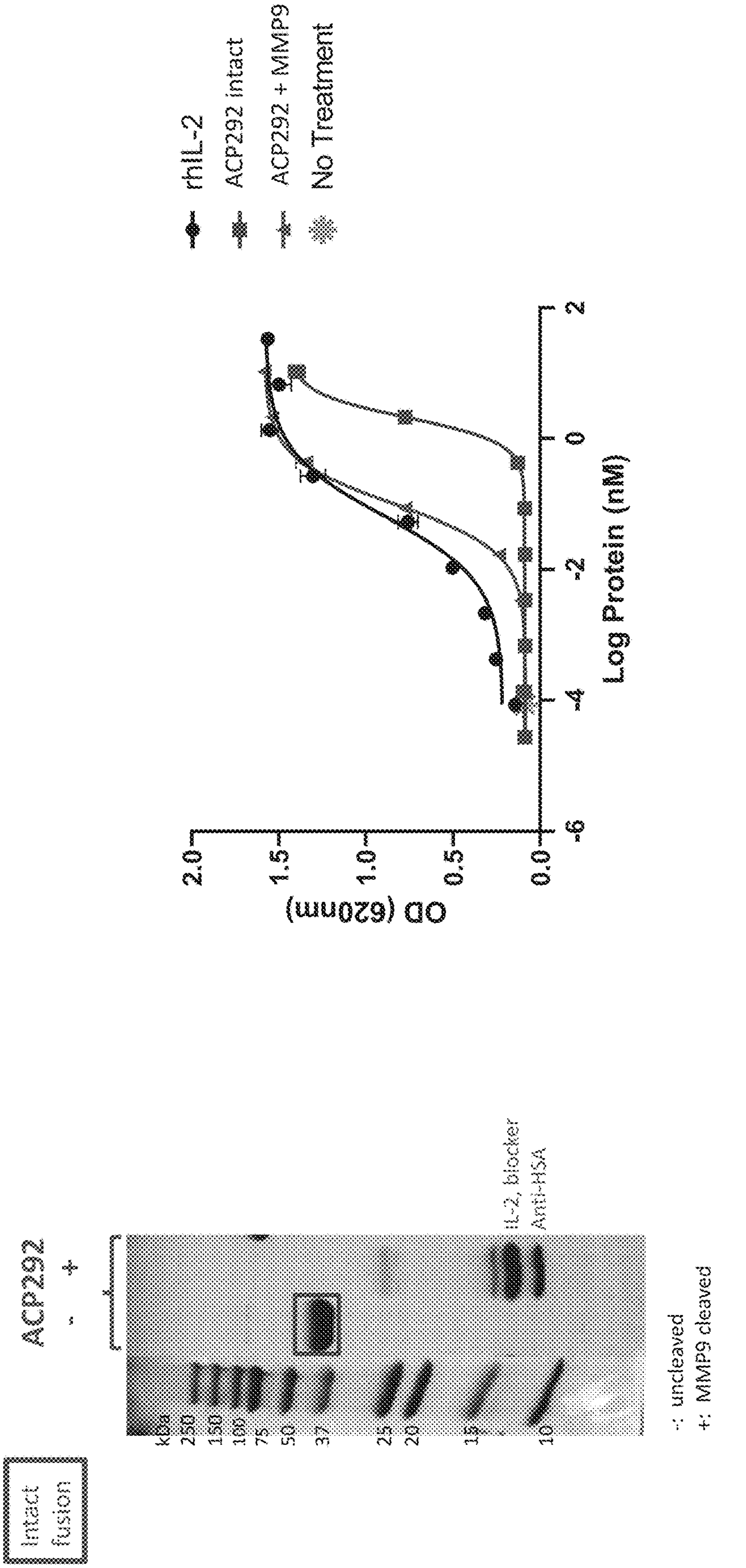
Figure 55D:
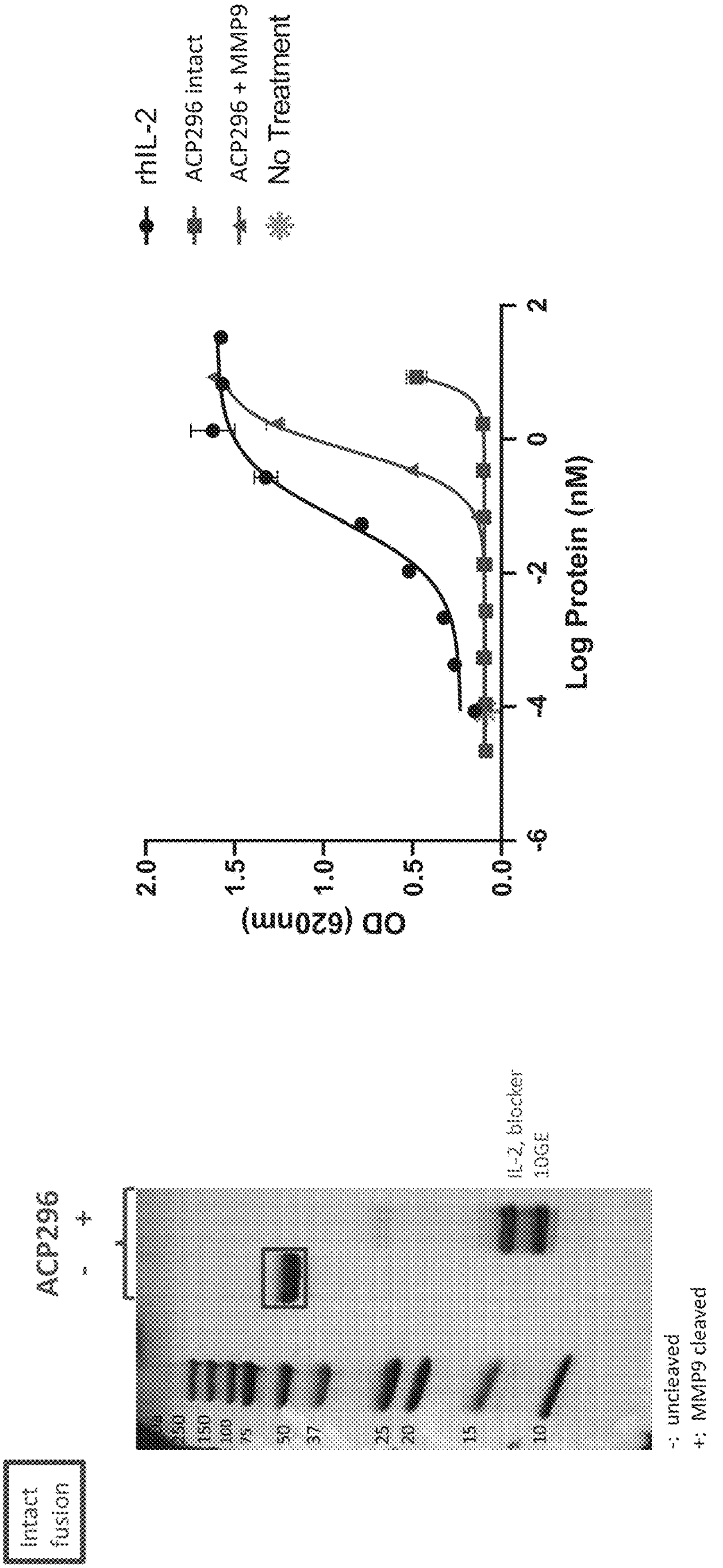
Figure 55E:
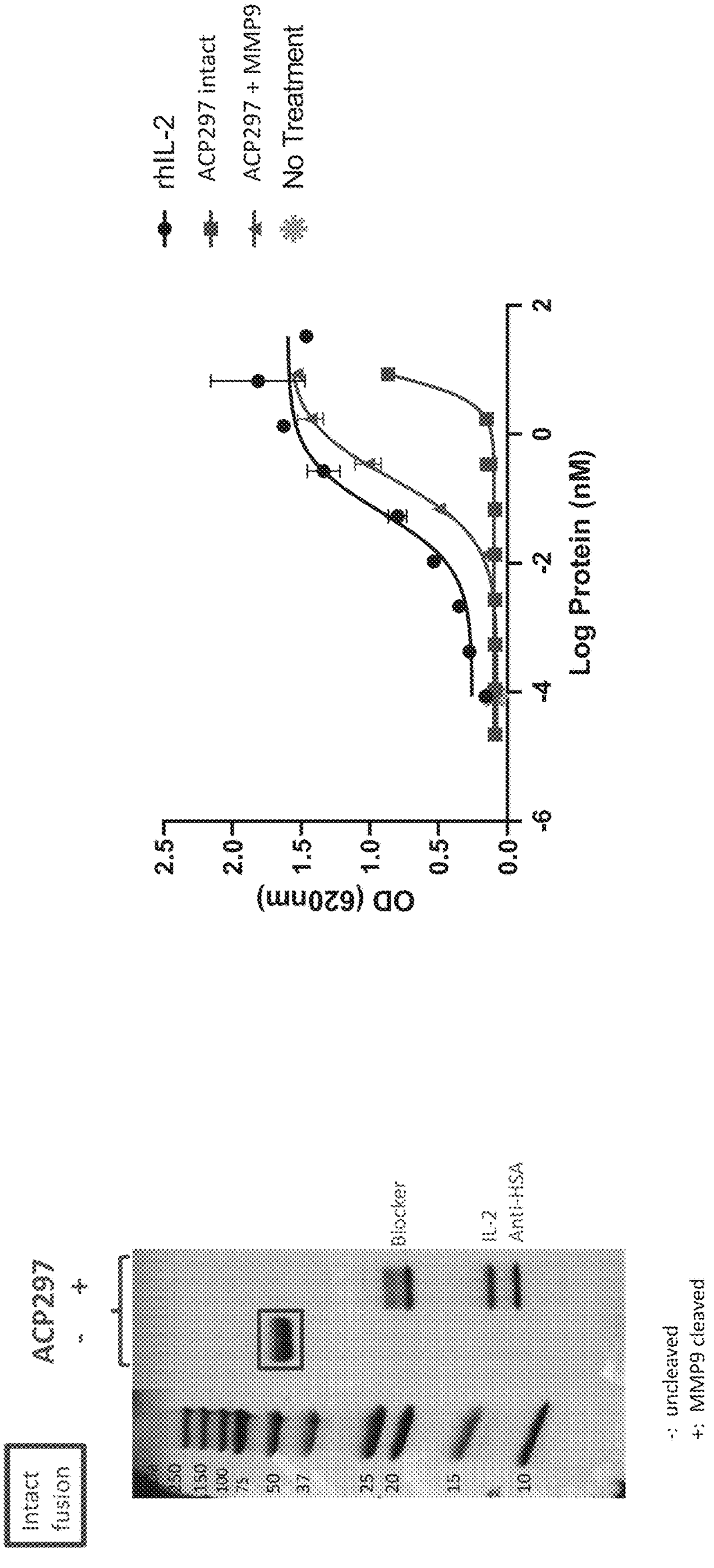
Figure 55F:
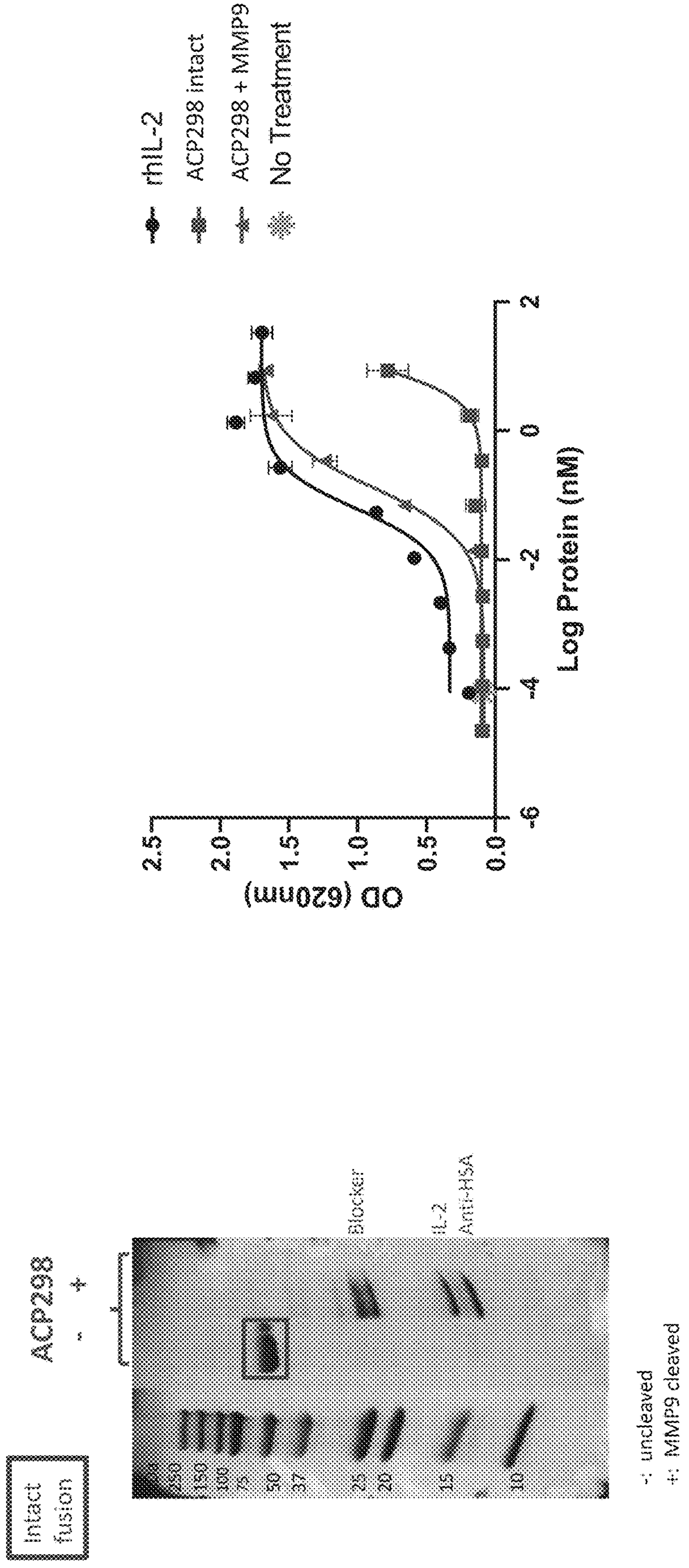
Figure 55G:
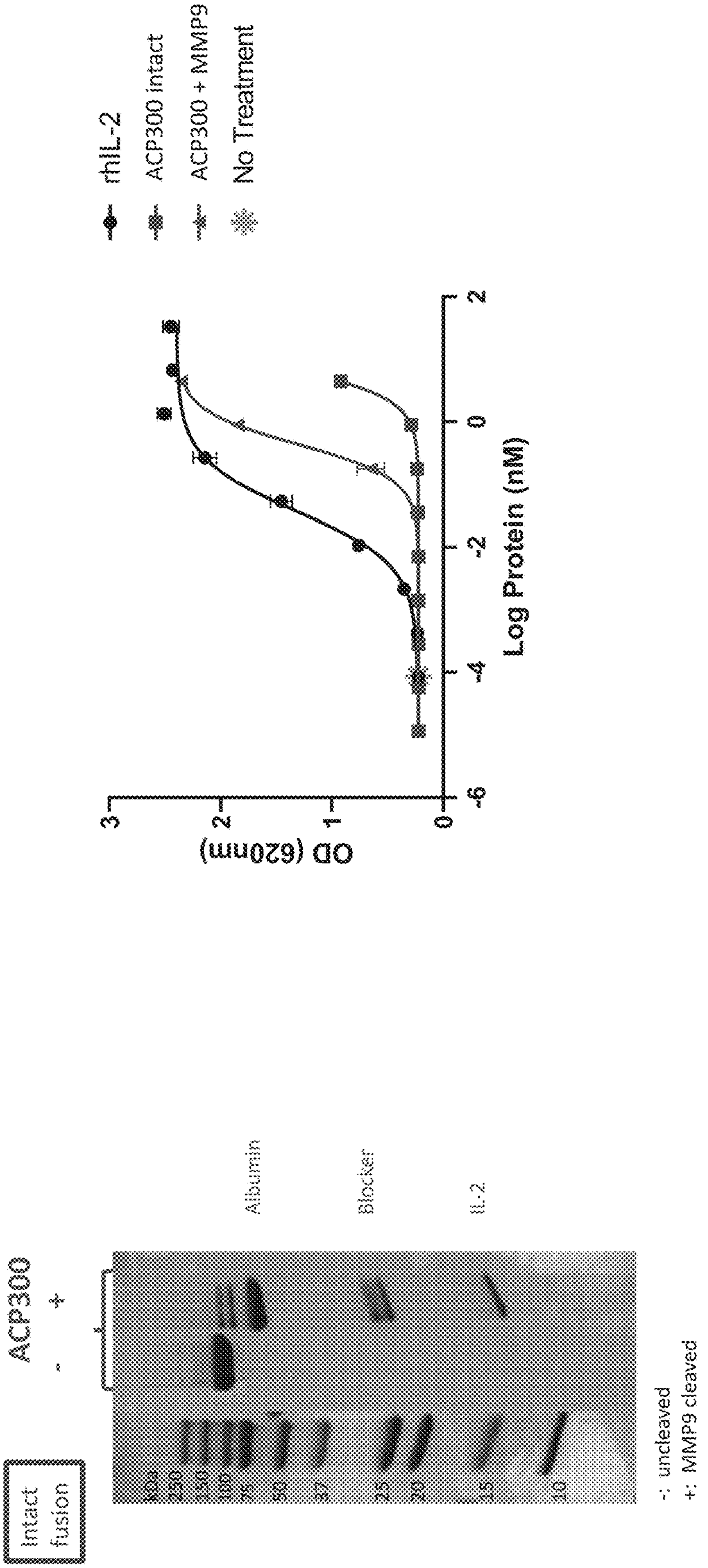
Figure 55H:
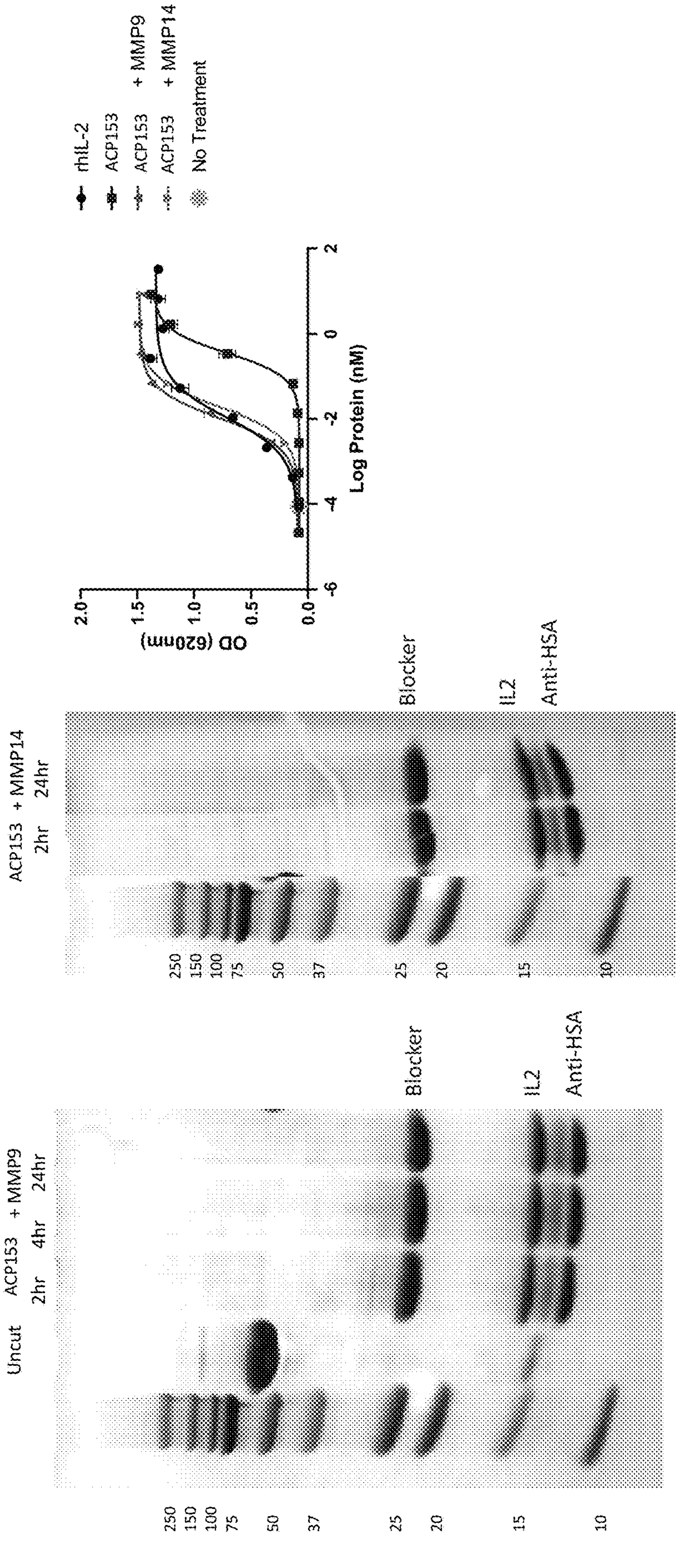
Figure 55I:
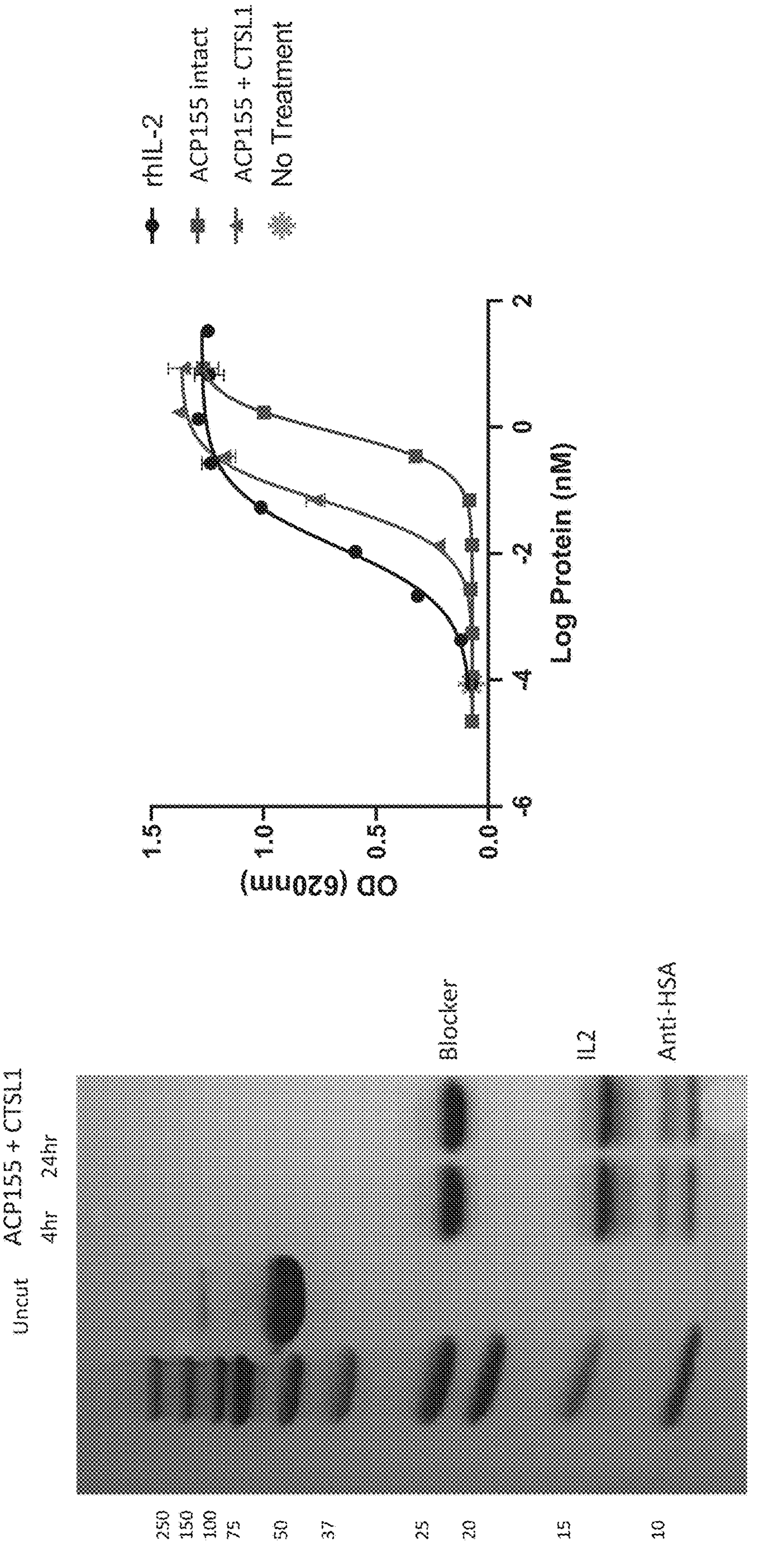
Figure 55J:
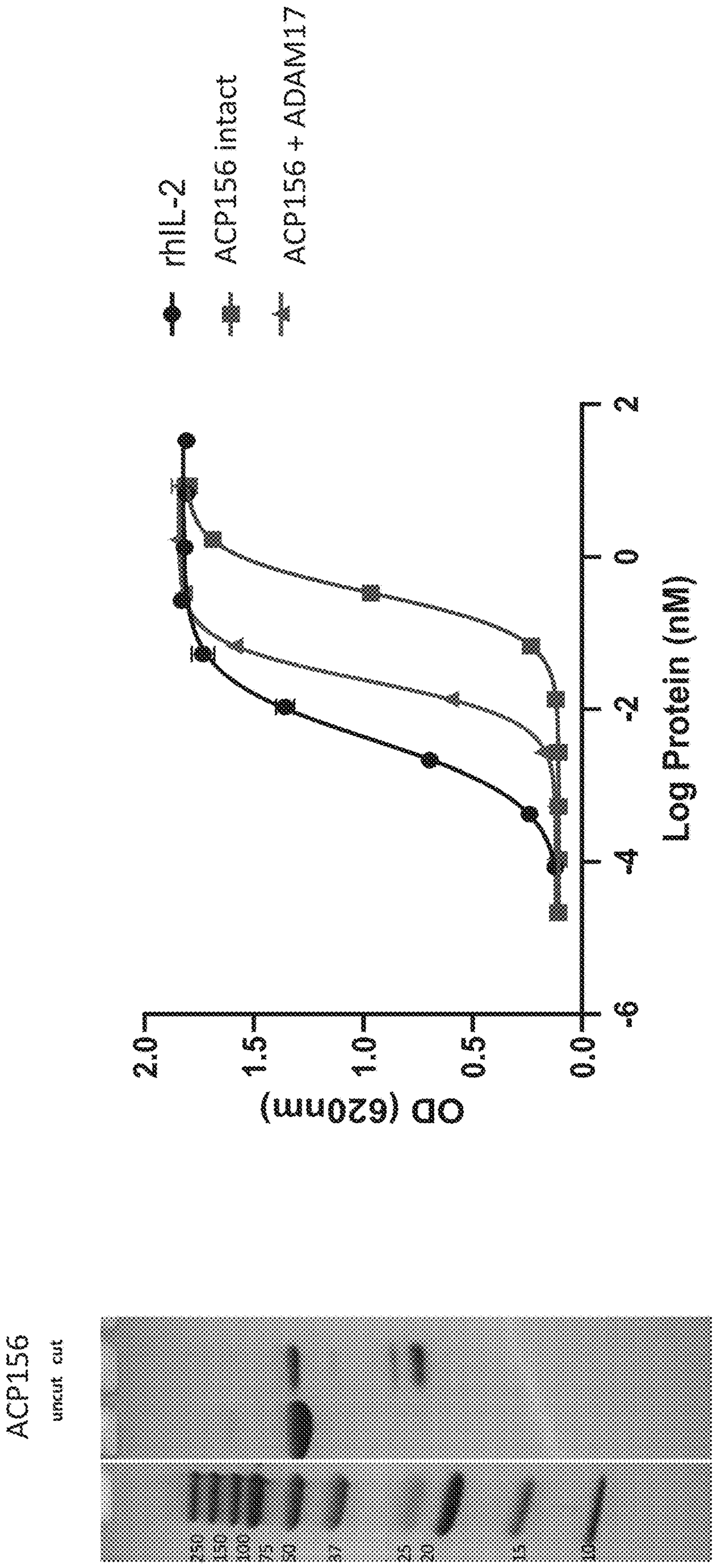
Figure 55K:
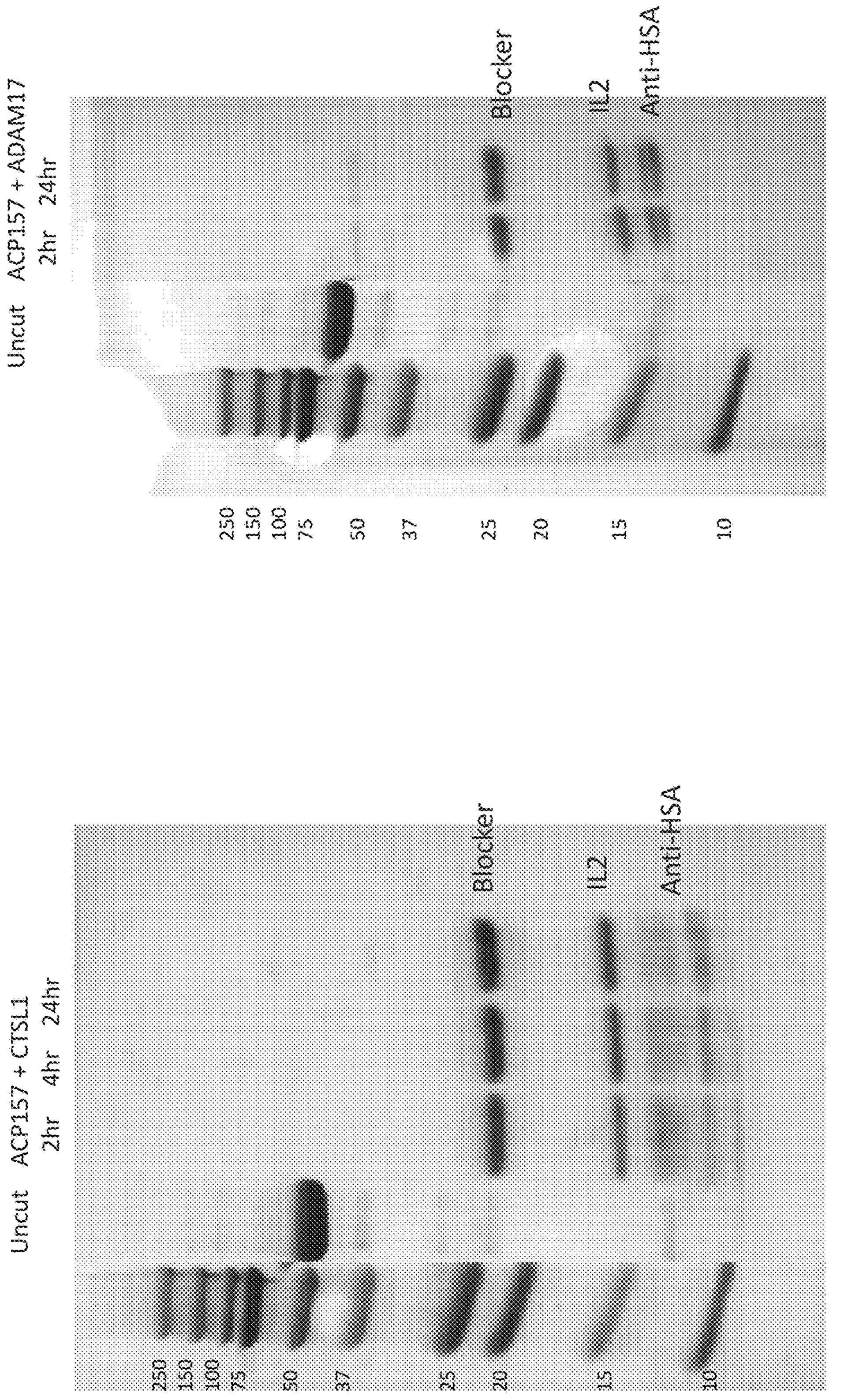
Figure 55L:
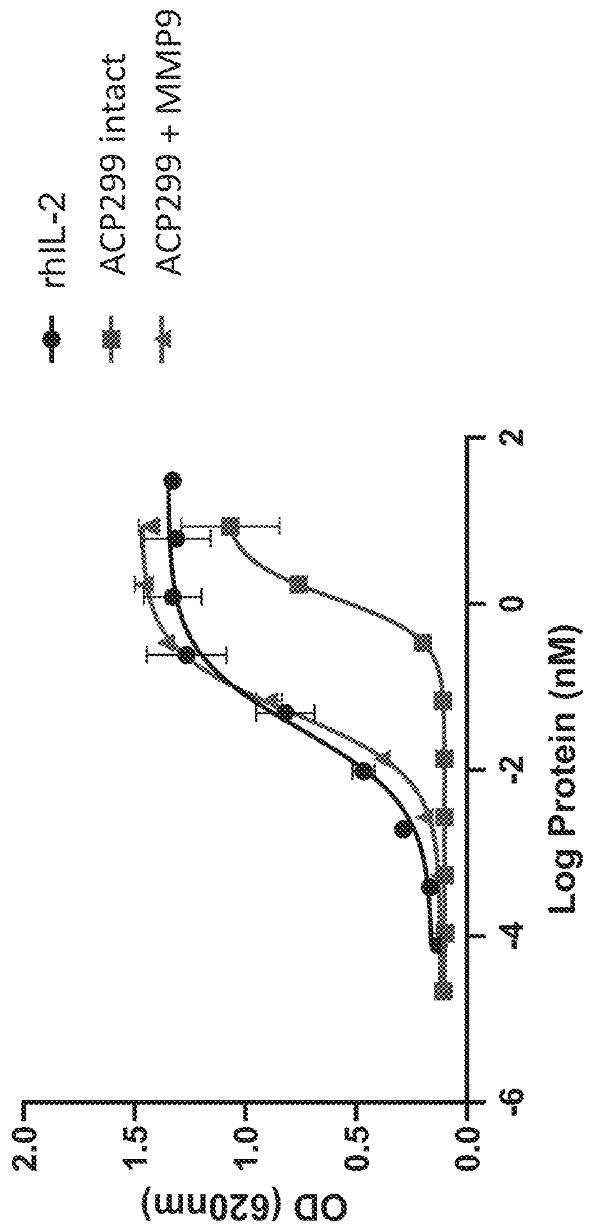
Figure 55M:
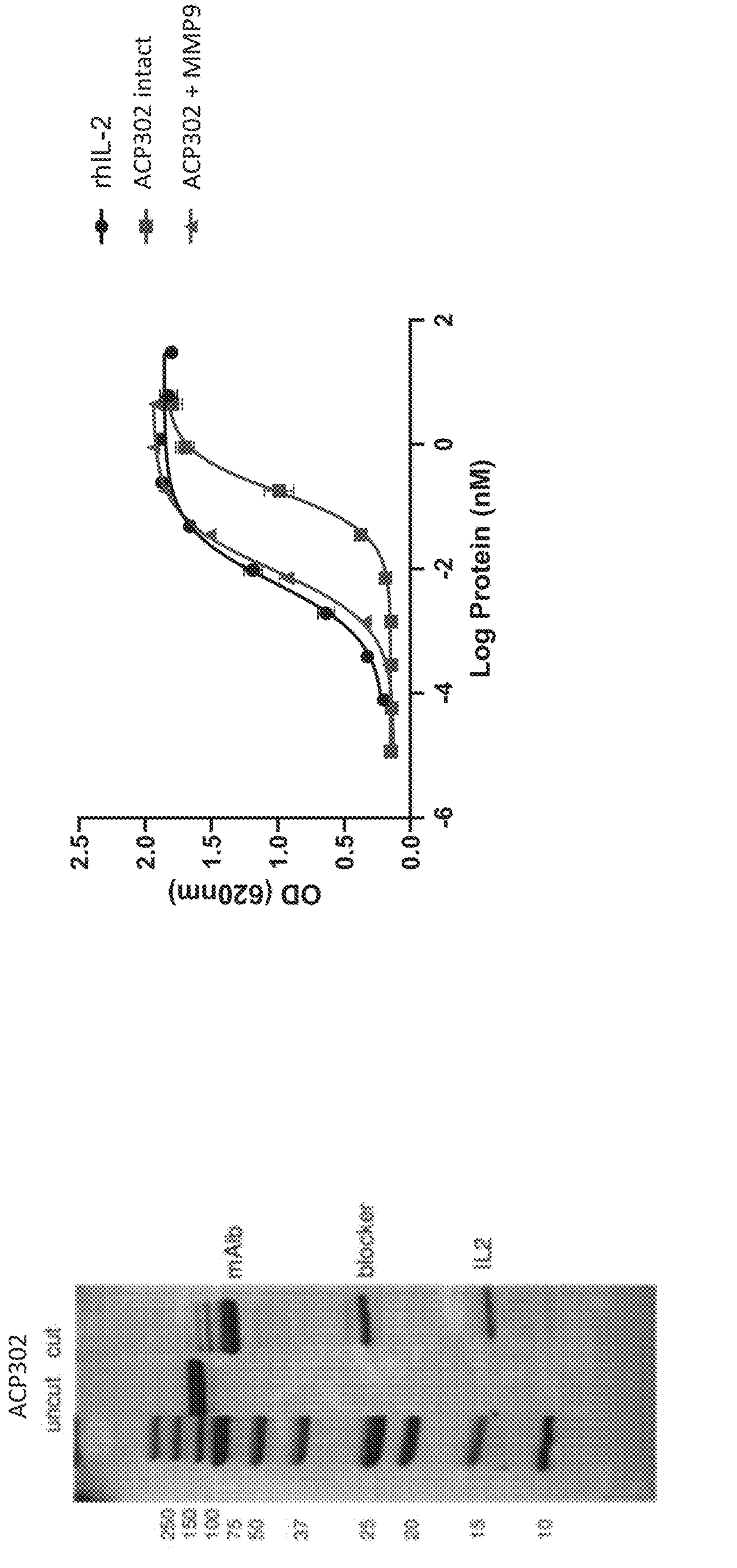
Figure 55N:
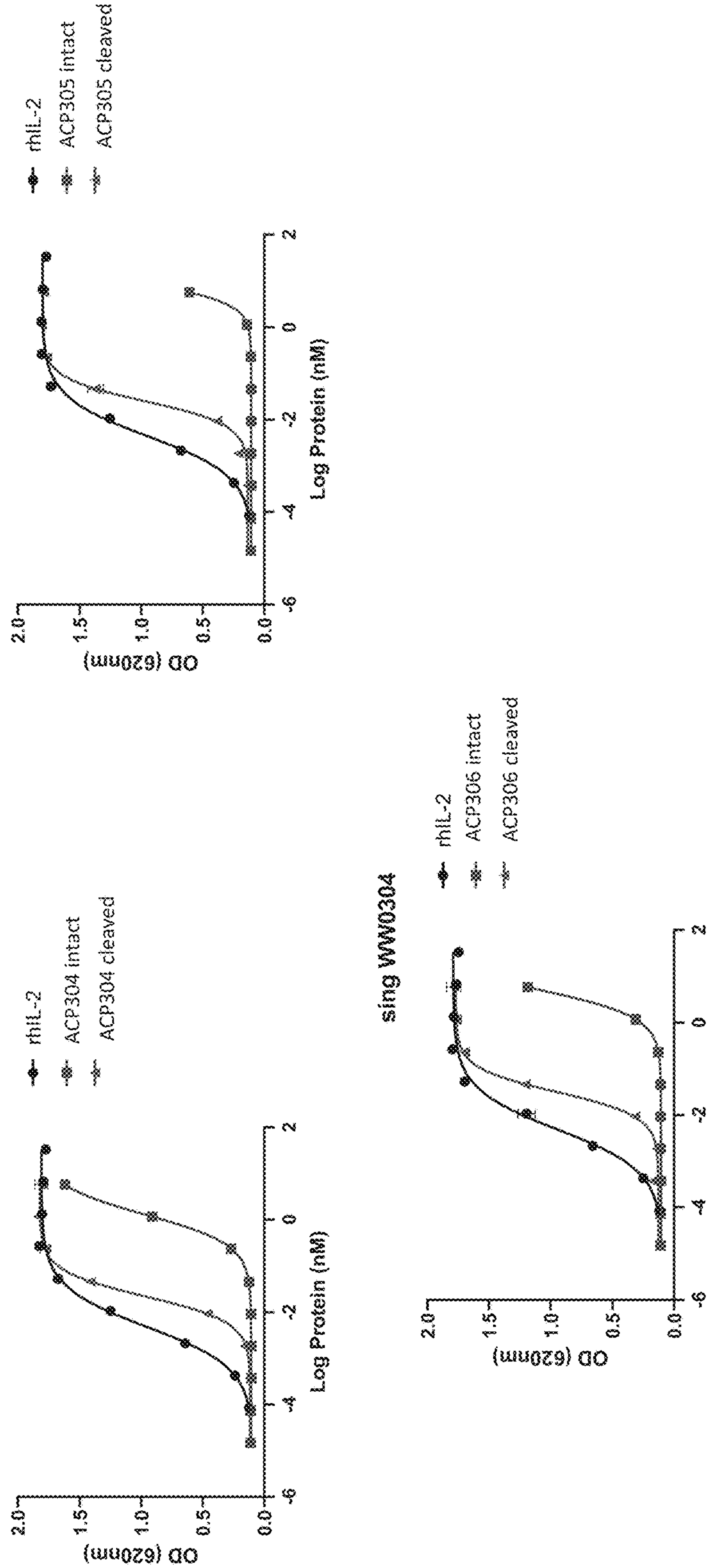
Figure 56:
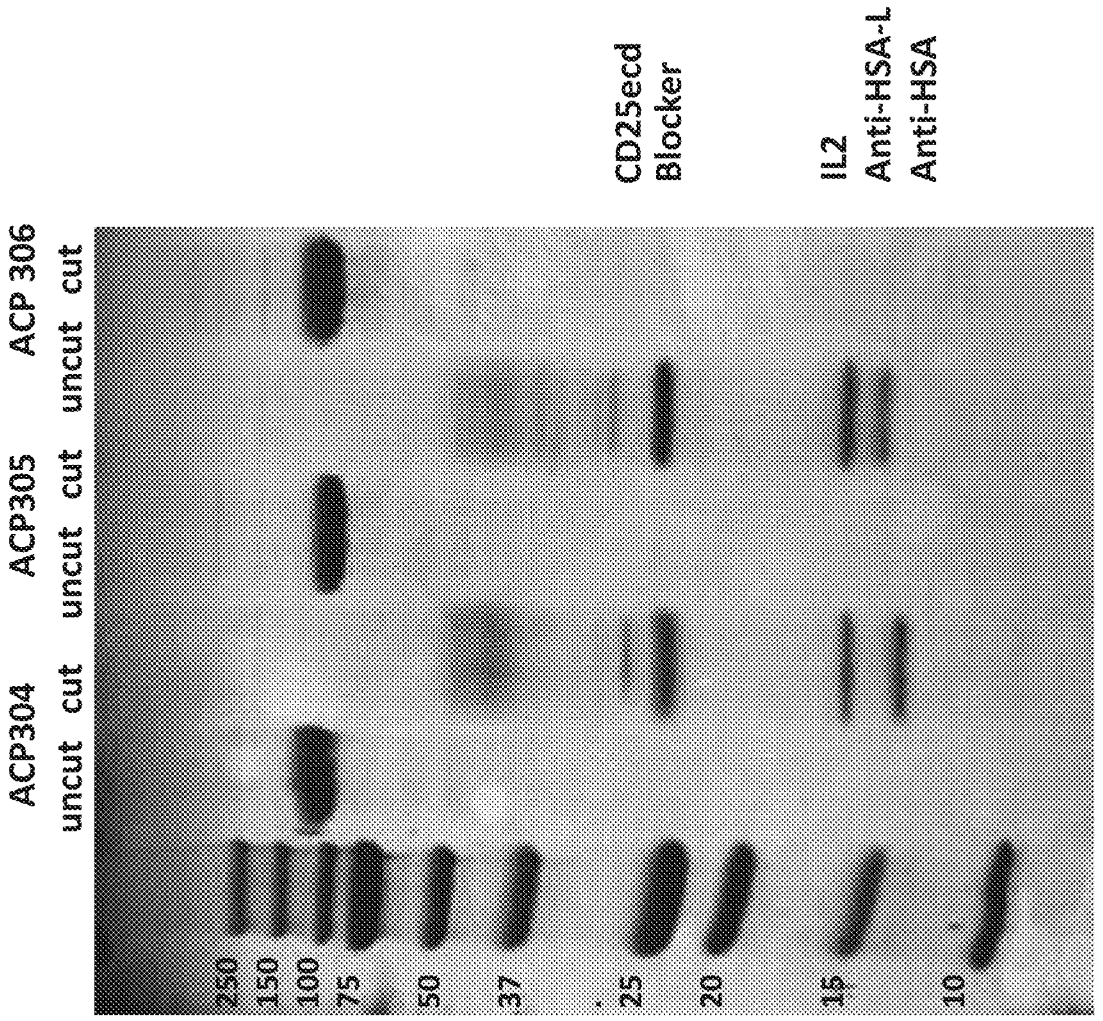
Figure 57A:
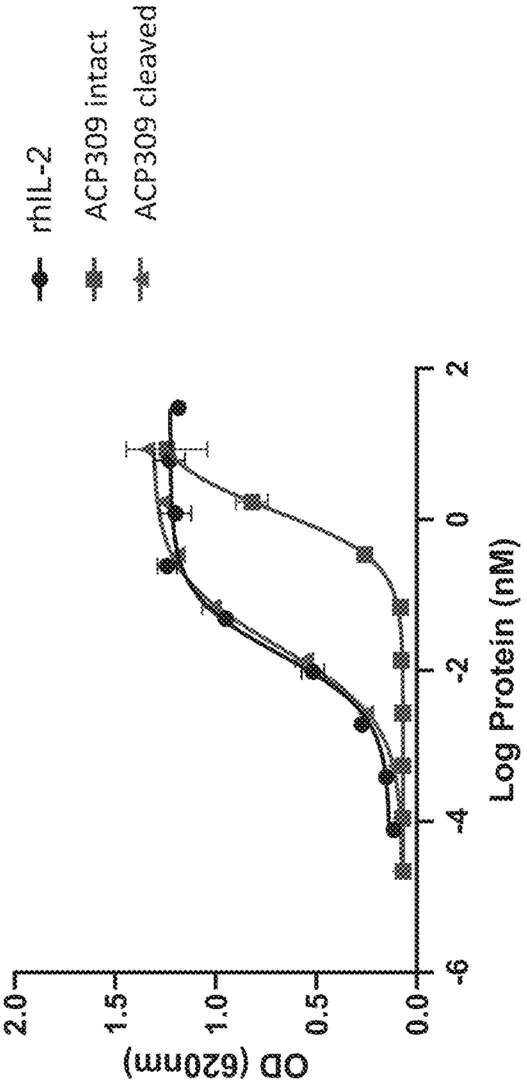
Figure 57B:
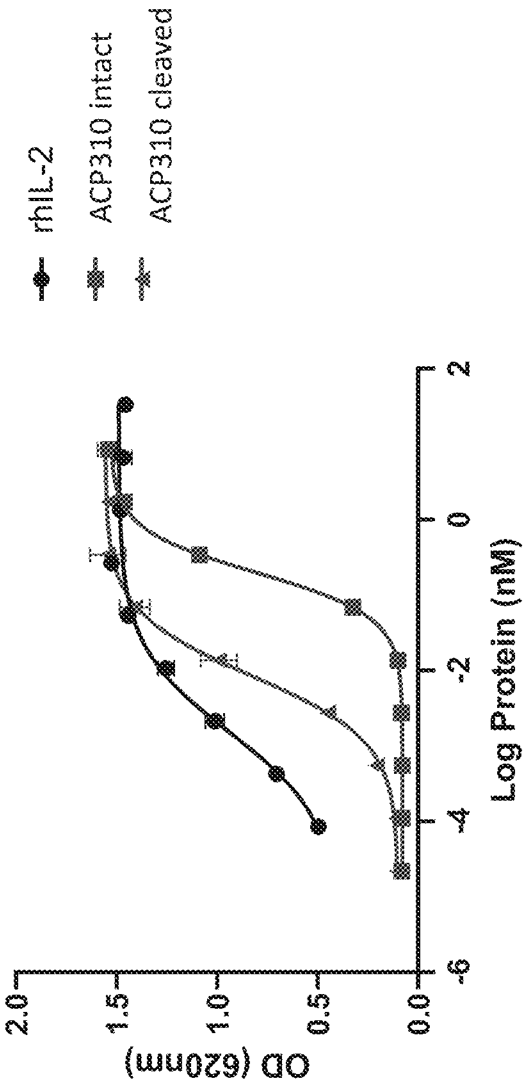
Figure 57C:
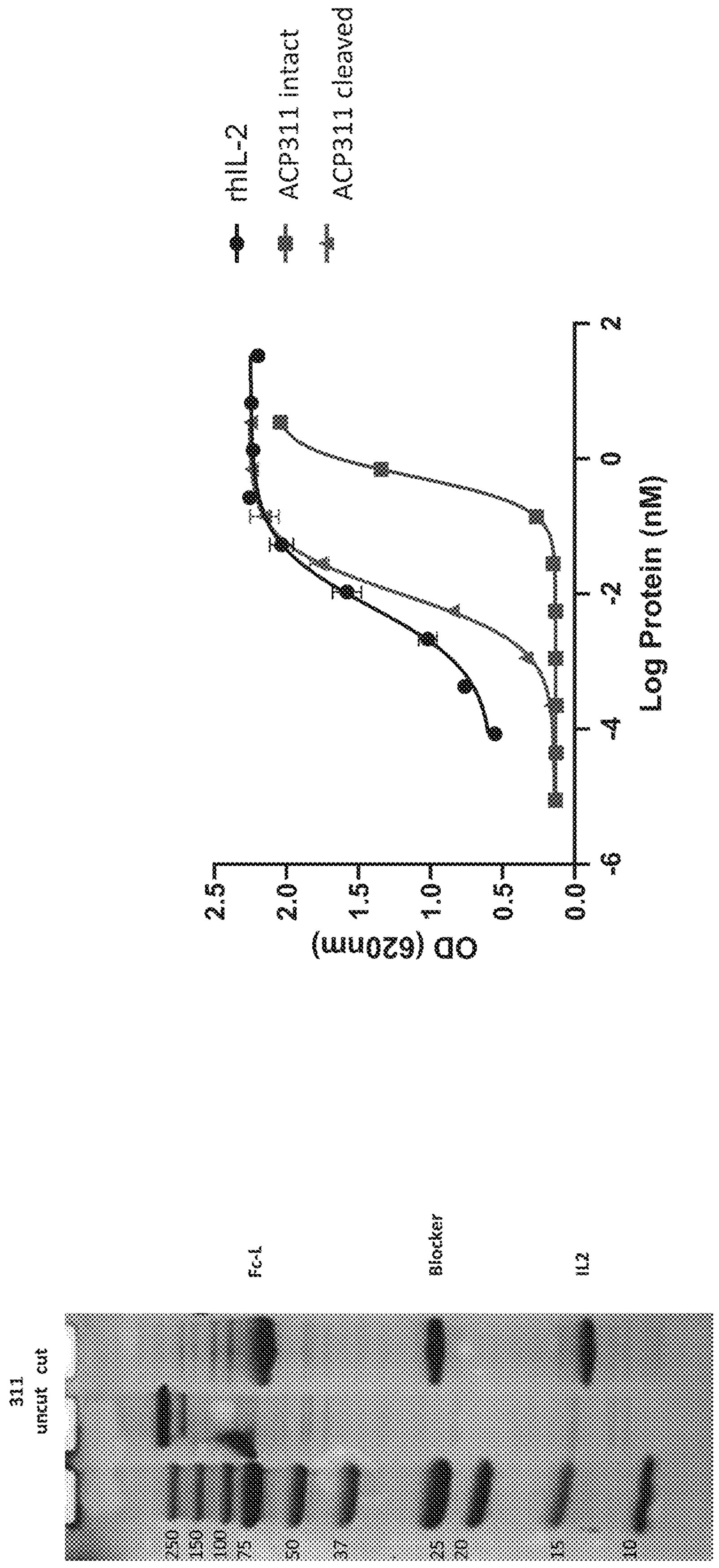
Figure 57D:
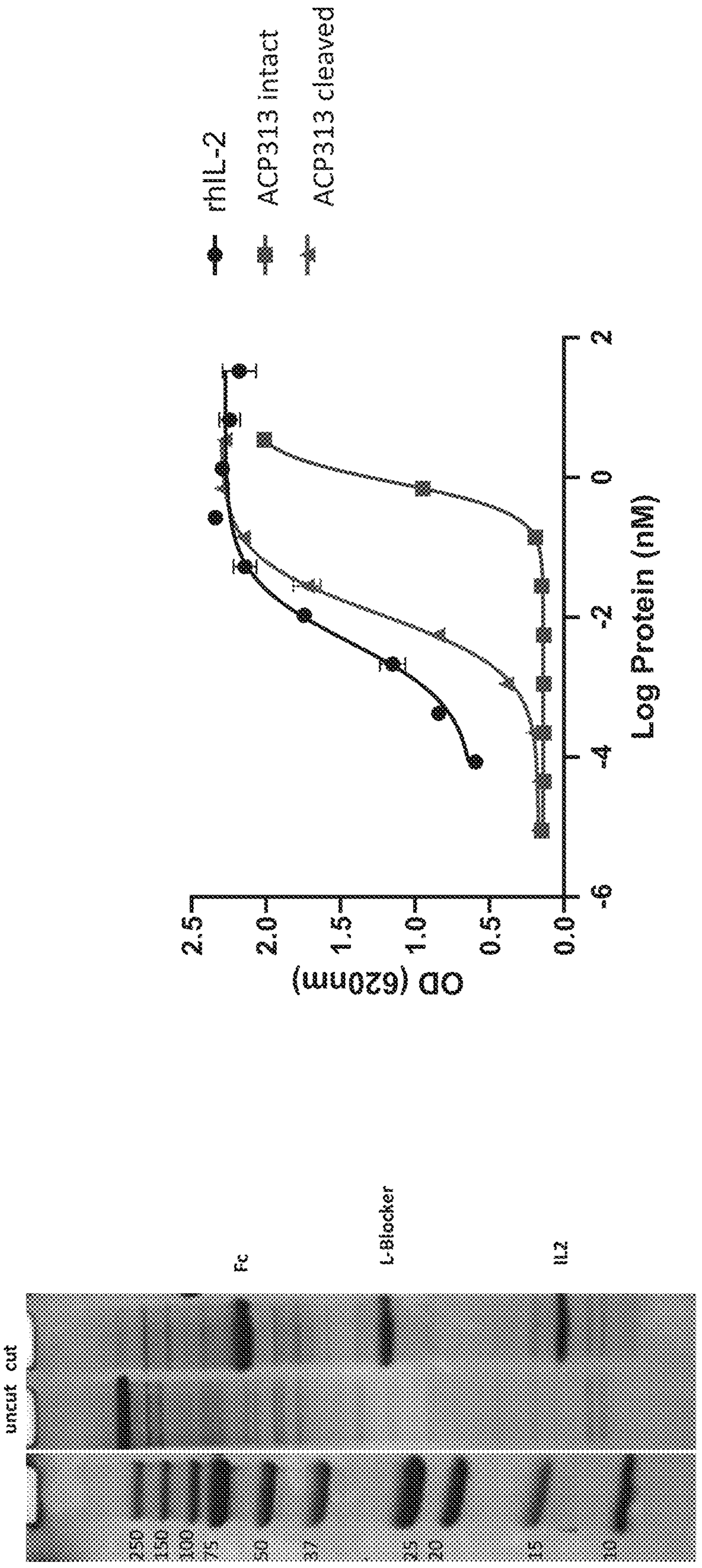
Figure 58:
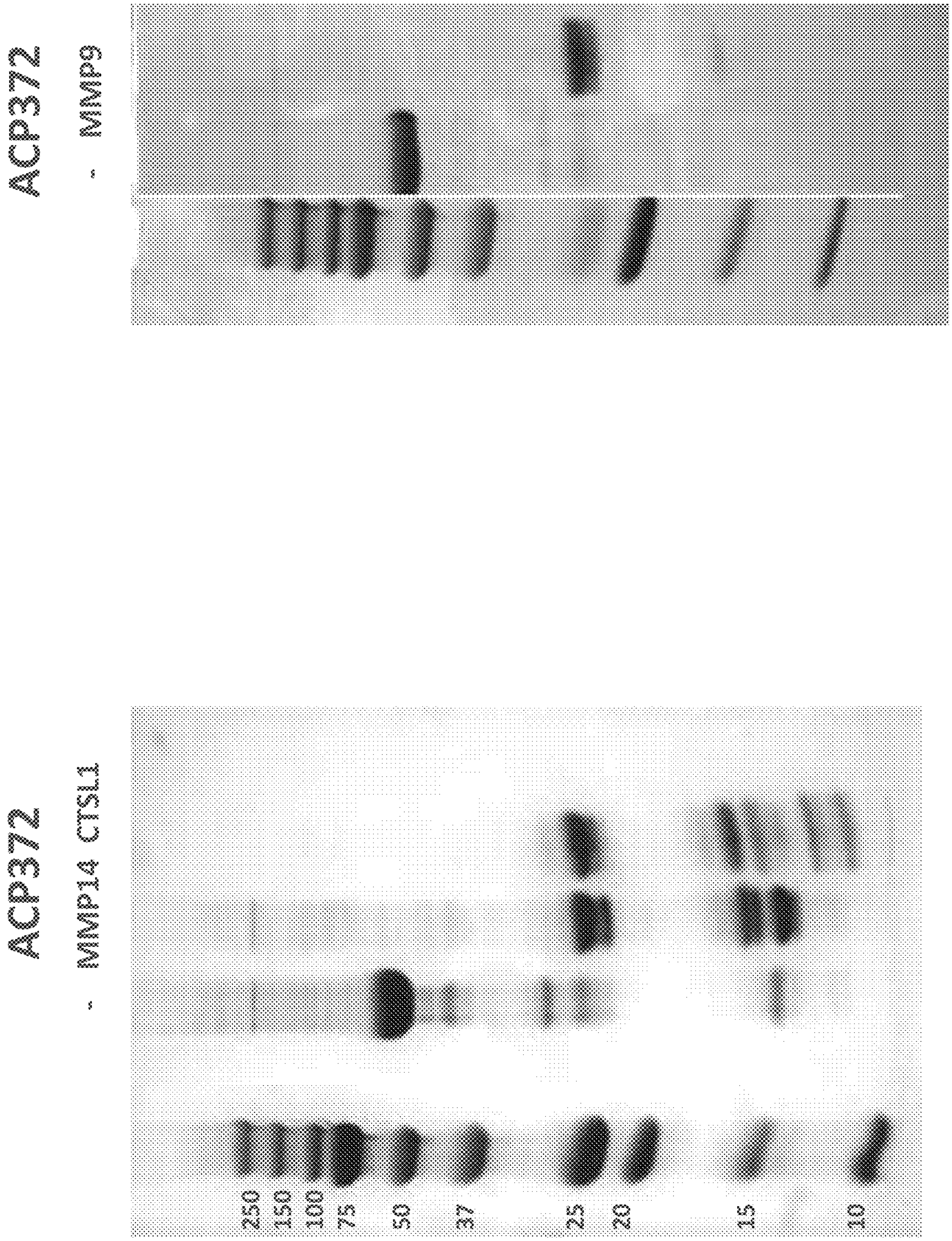
Figure 59A:
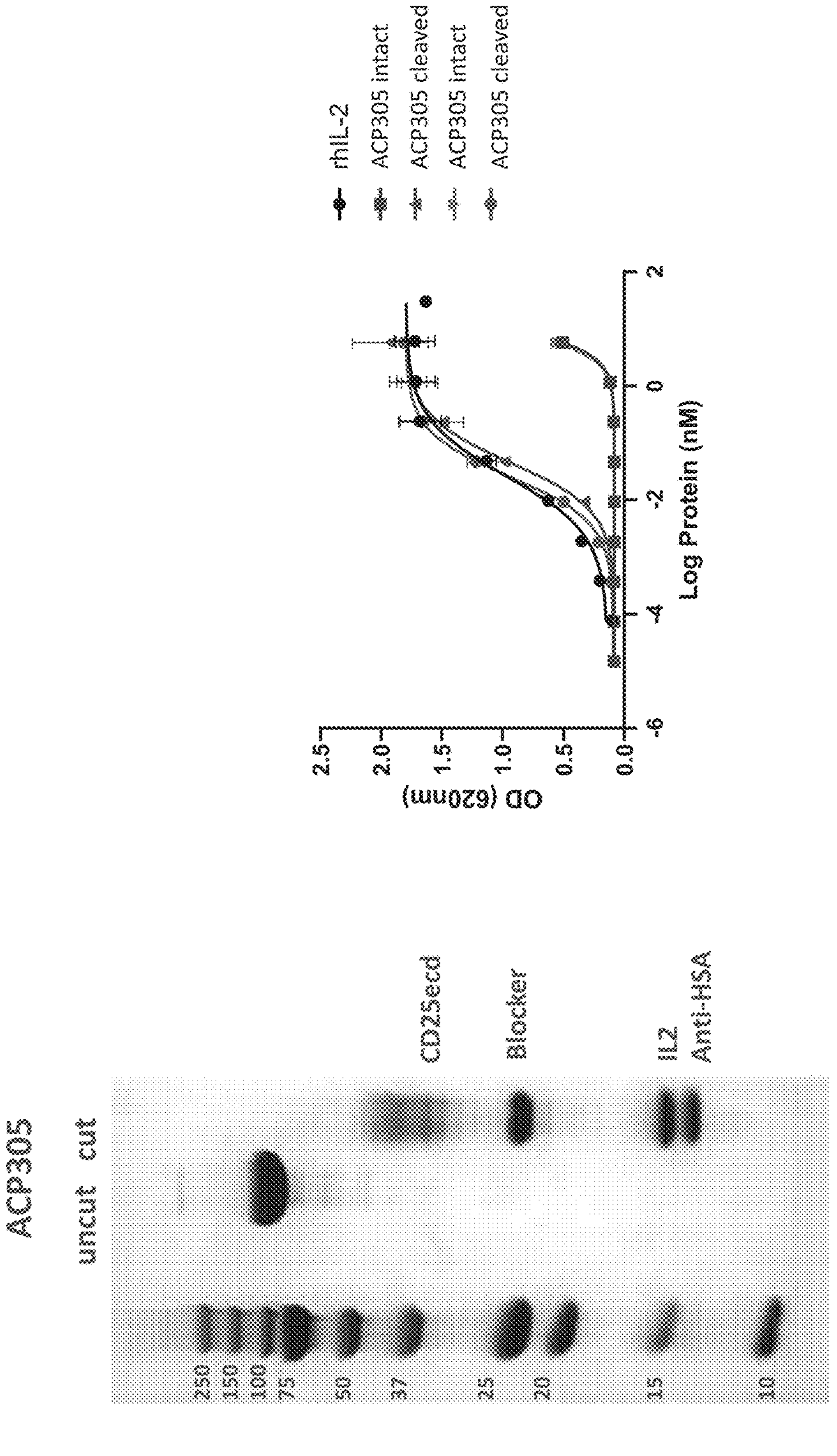
Figure 59B:
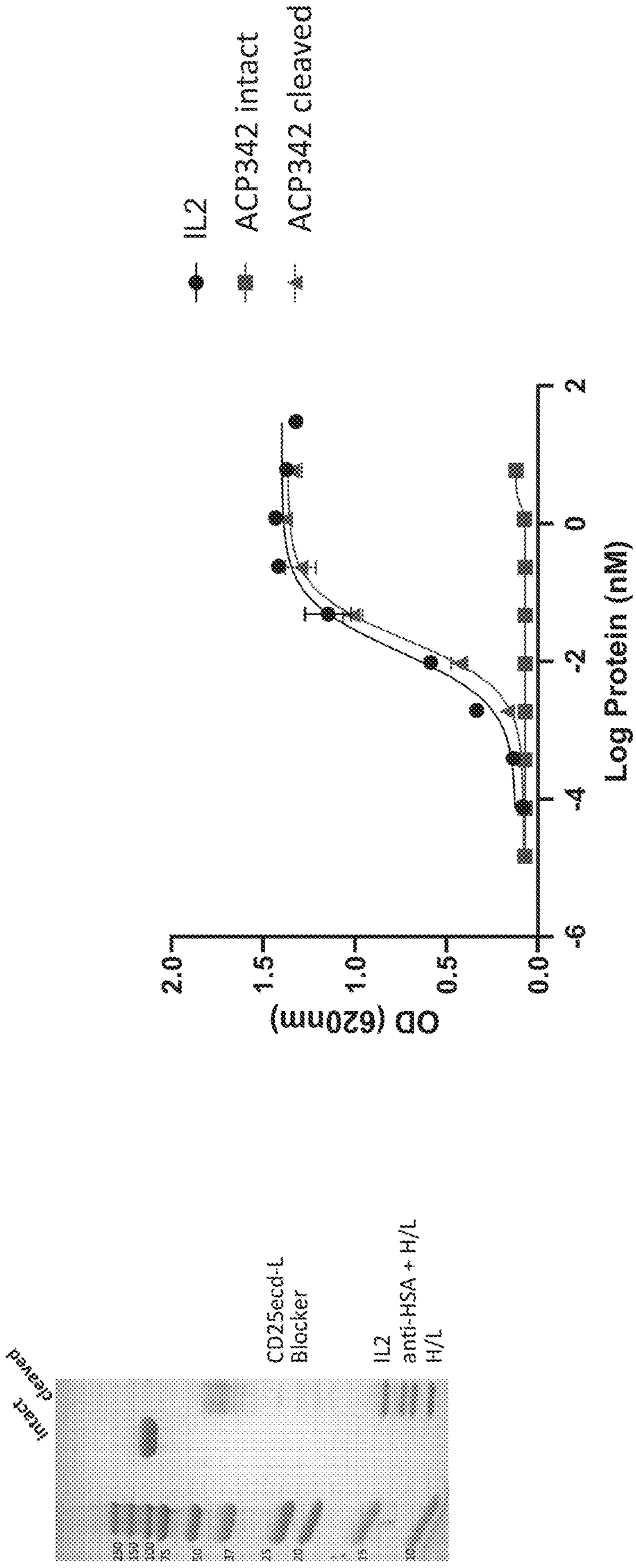
Figure 59C:
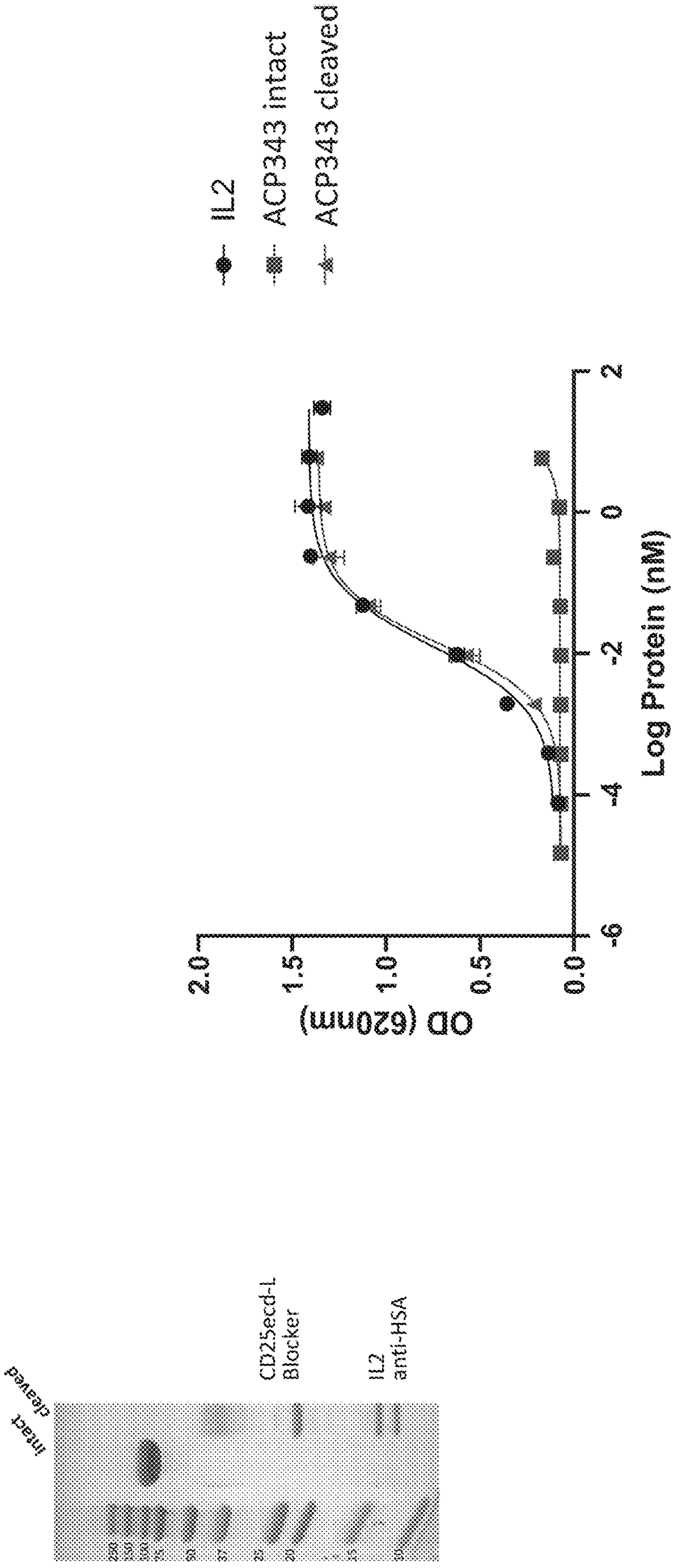
Figure 59D:
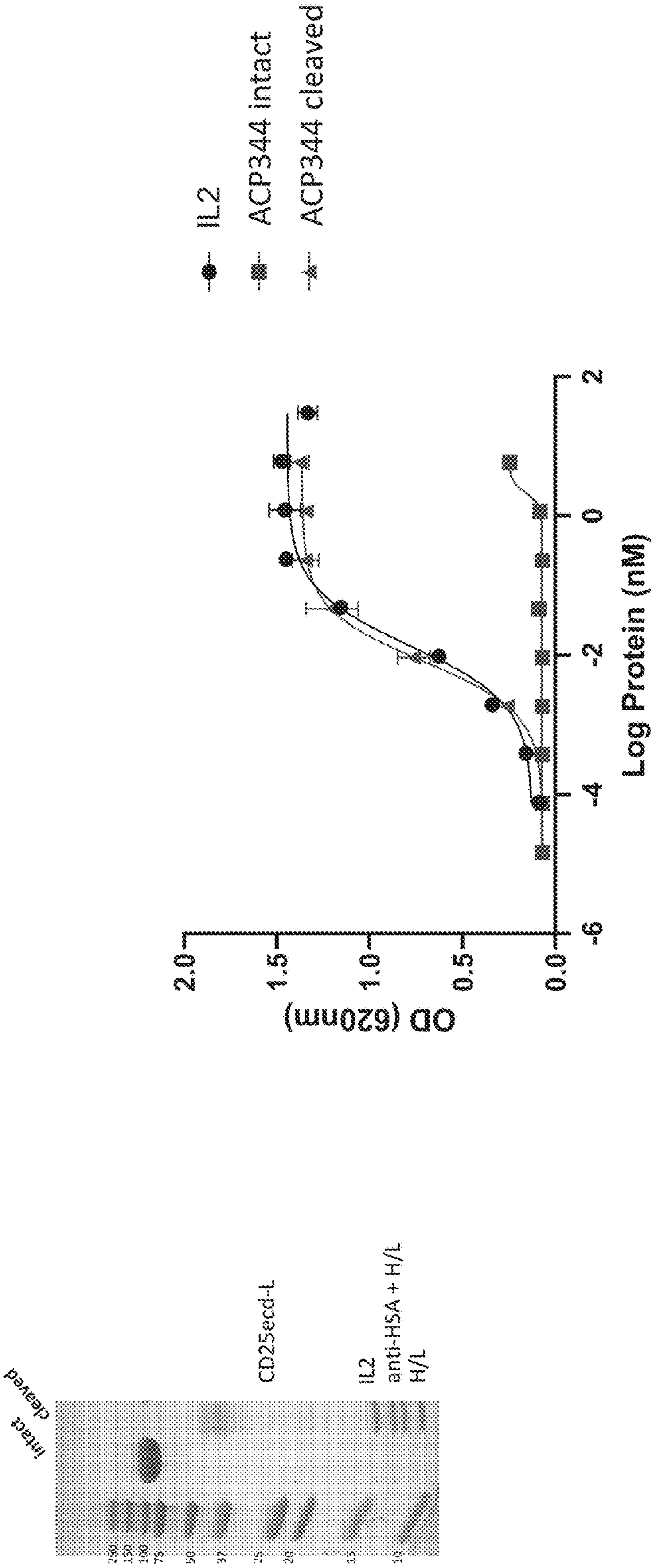
Figure 59E:
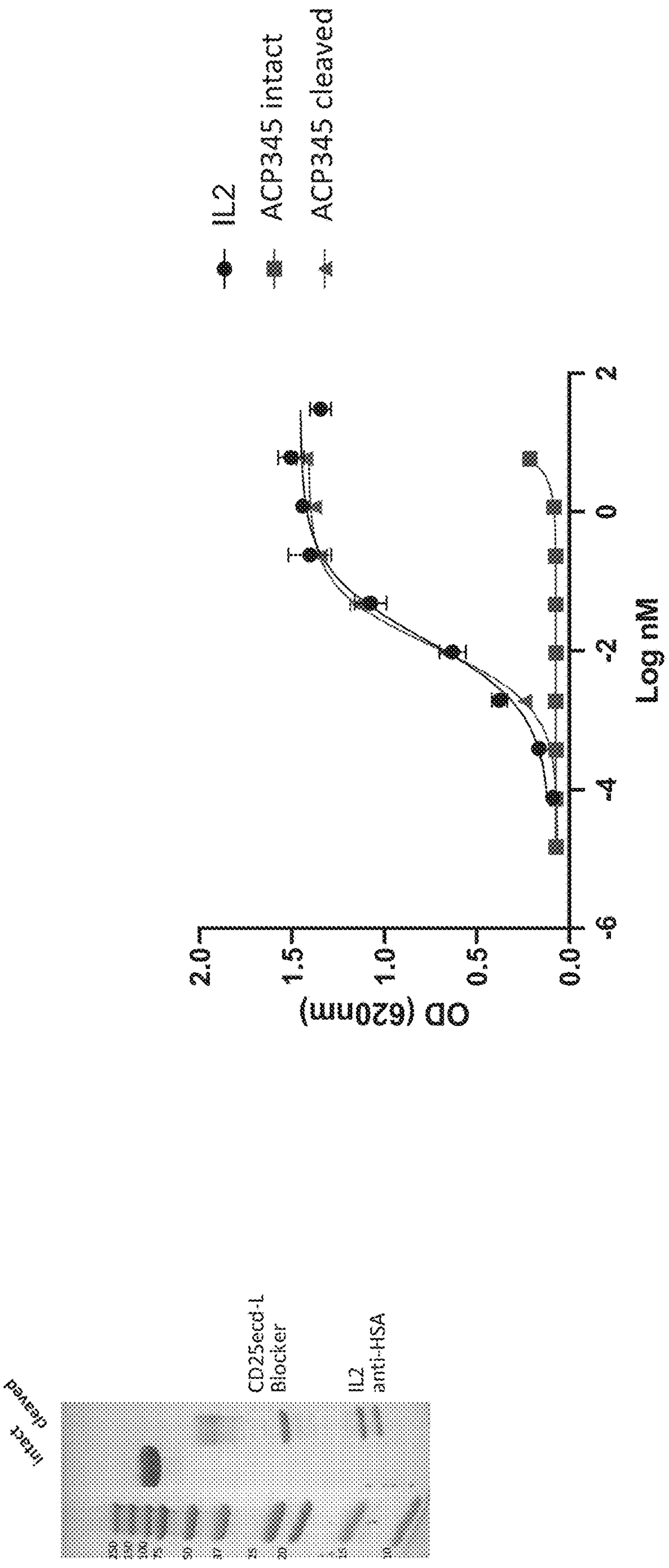
Figure 59F:
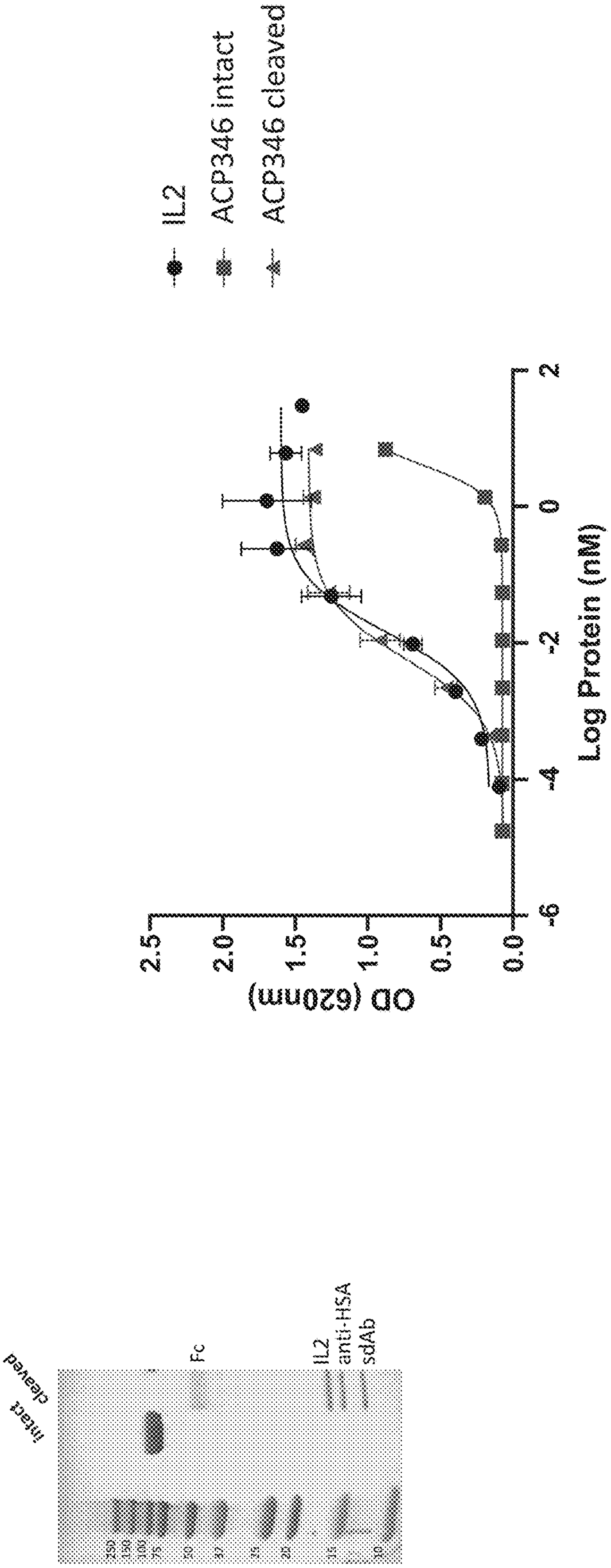
Figure 59G:
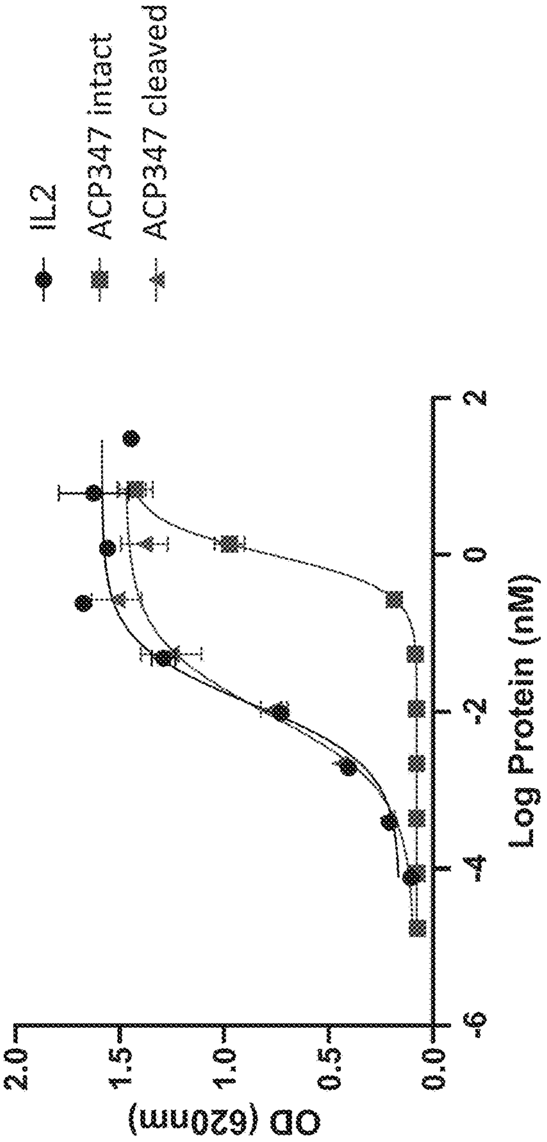
Figure 59G:
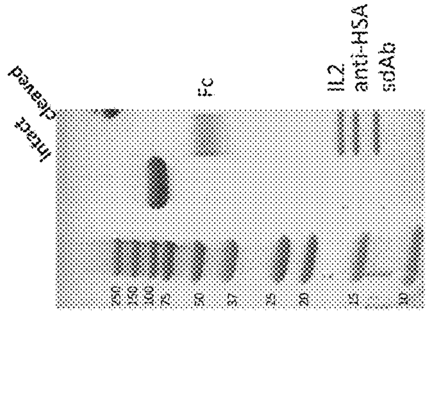
Figure 59H:
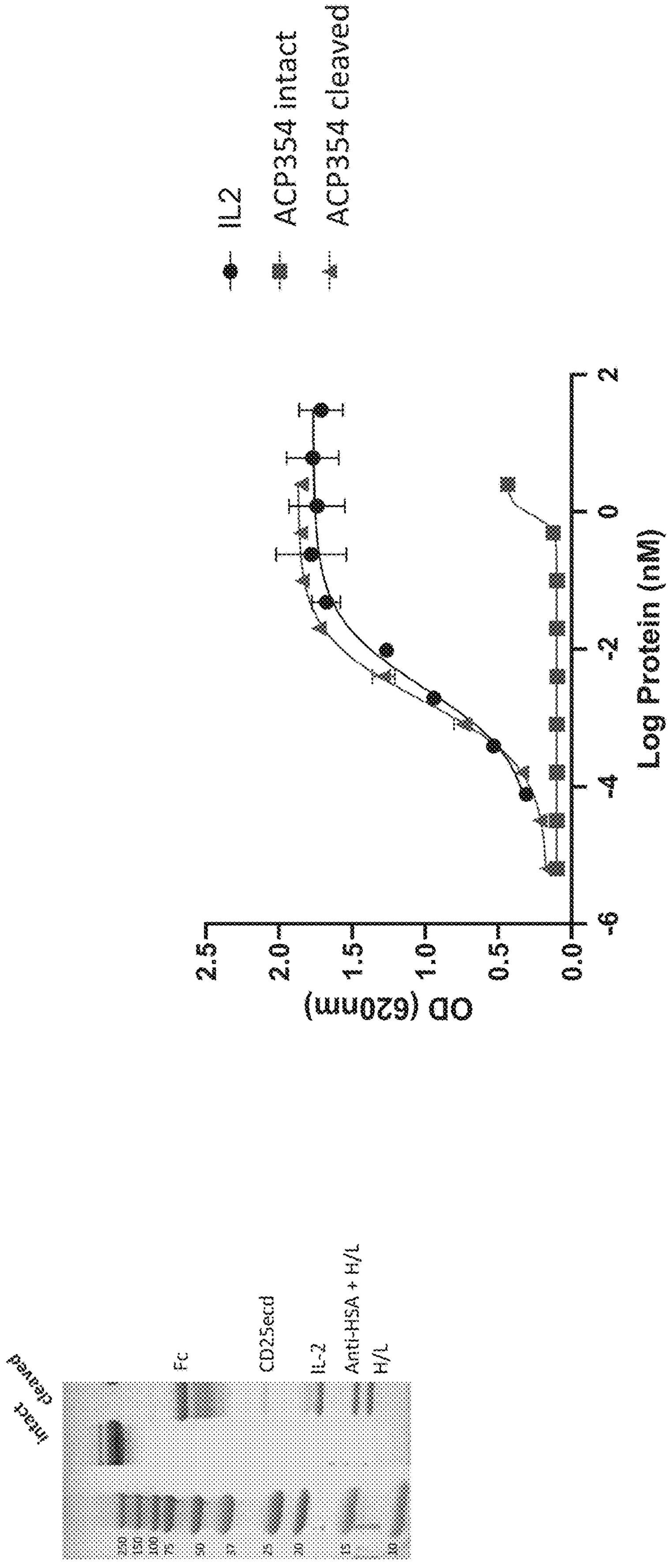
Figure 59I:
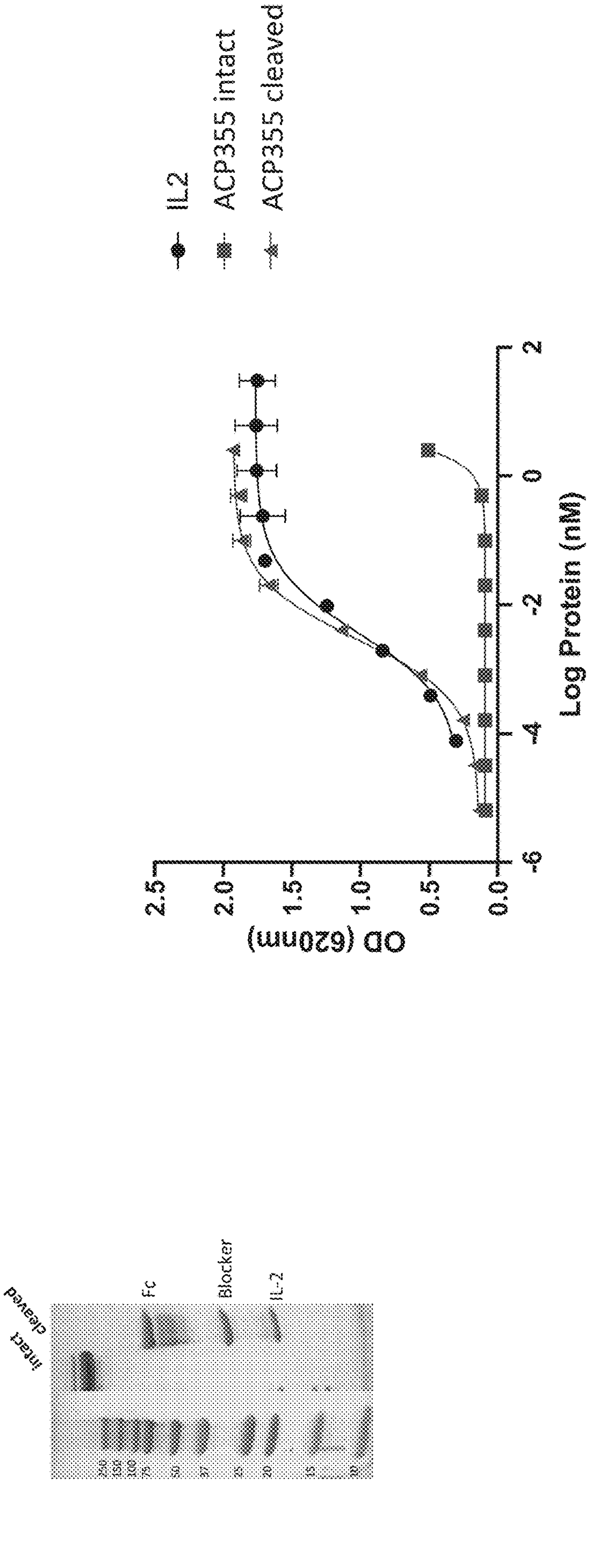
Figure 59J:
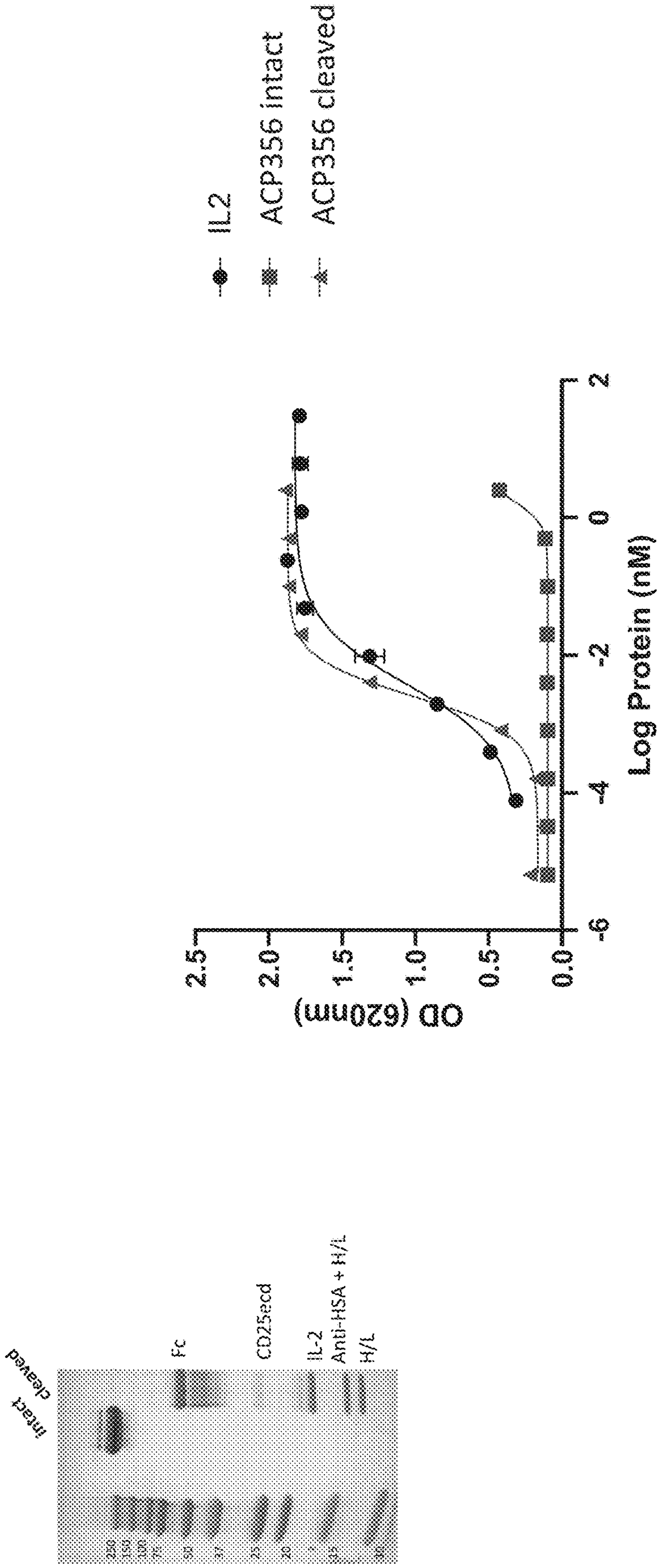
Figure 59K:
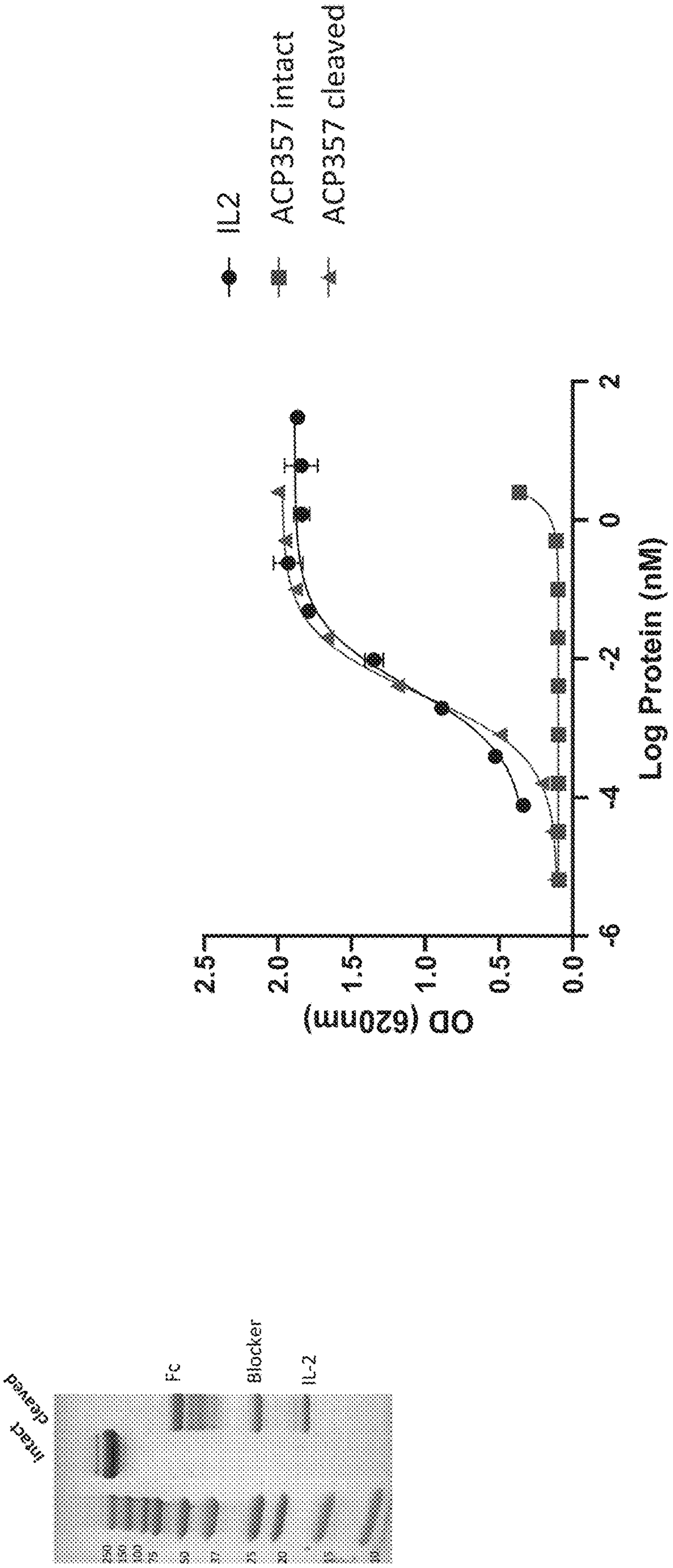
Figure 59L:
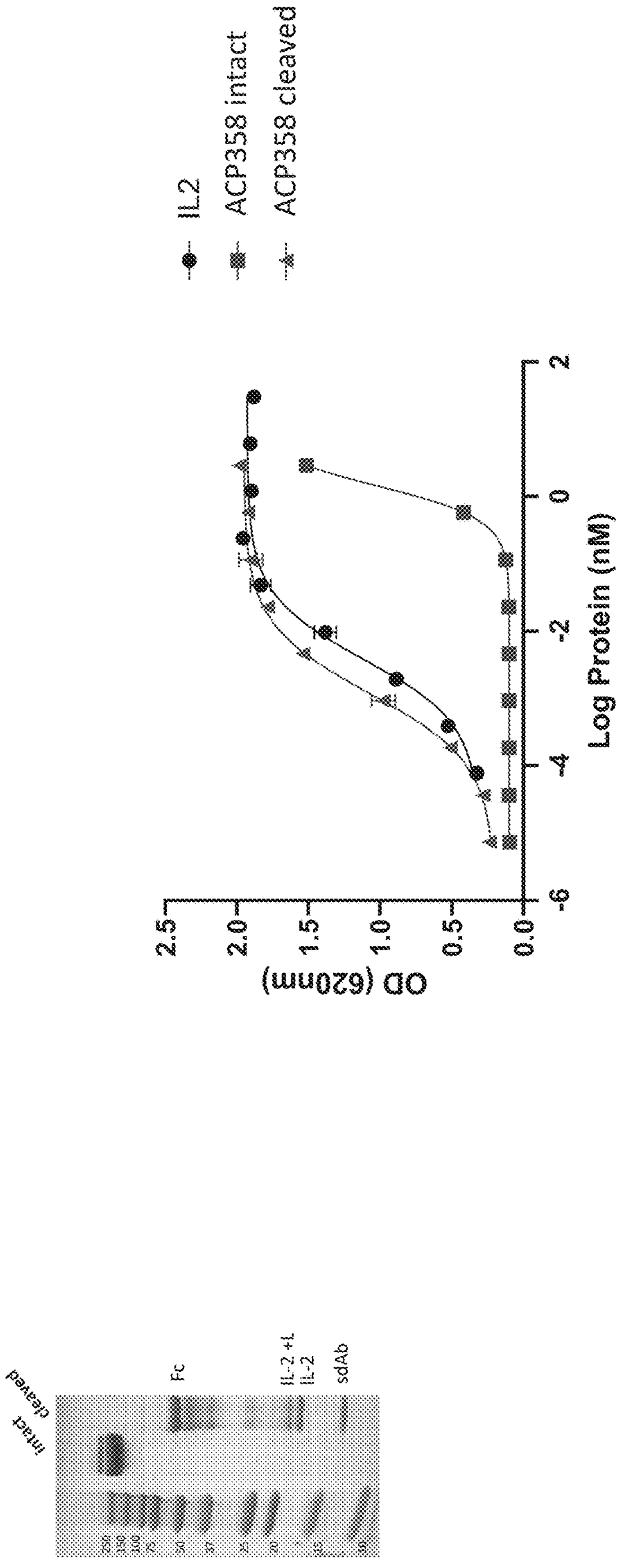
Figure 59M:
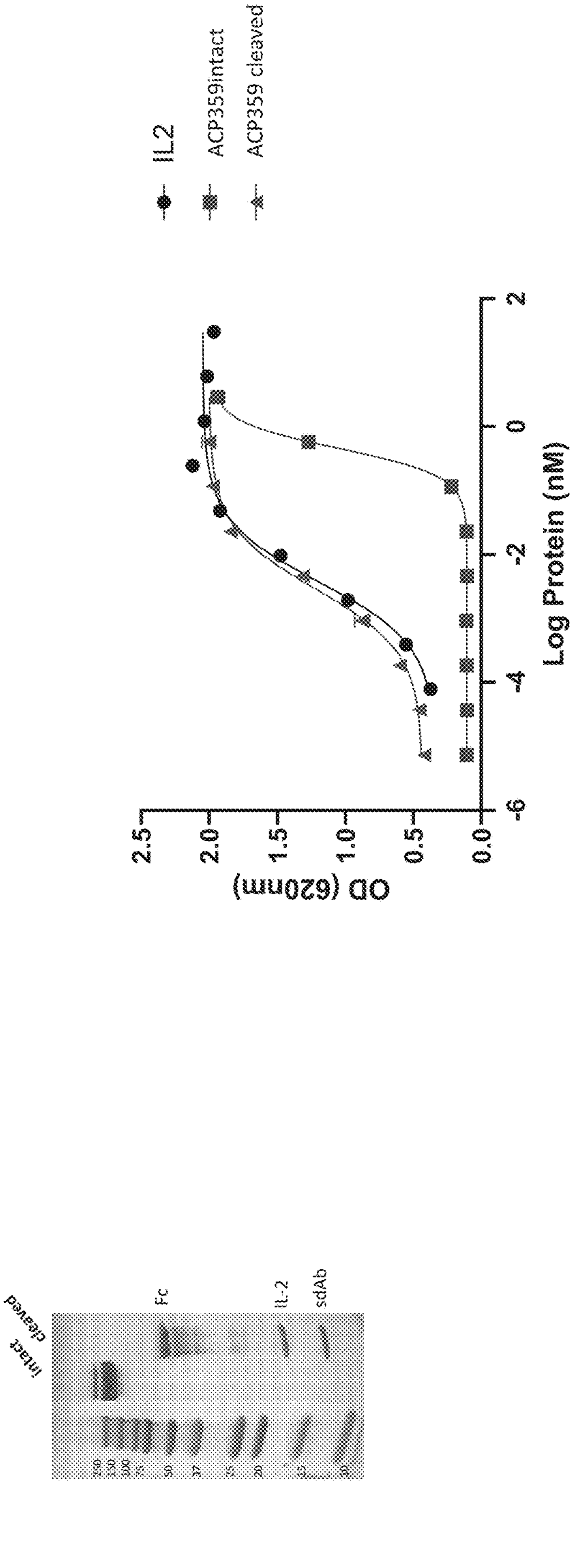
Figure 59N:
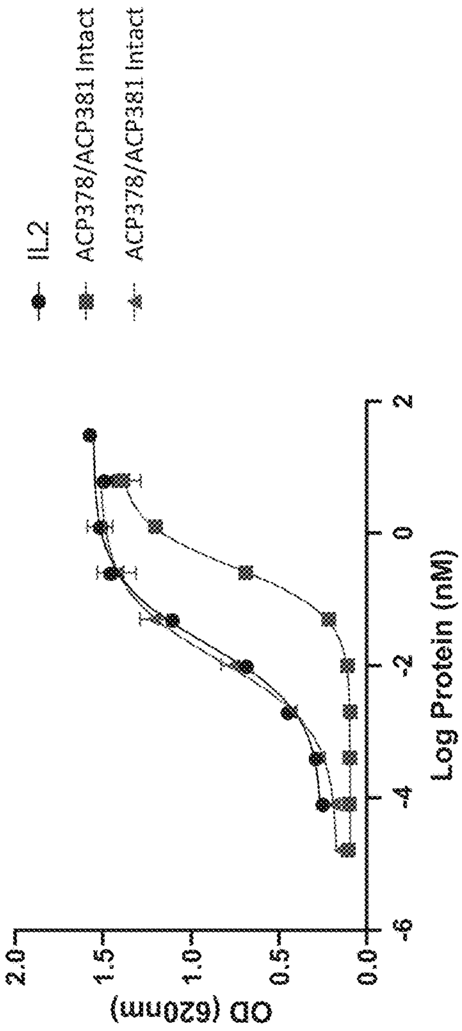
Figure 59N:
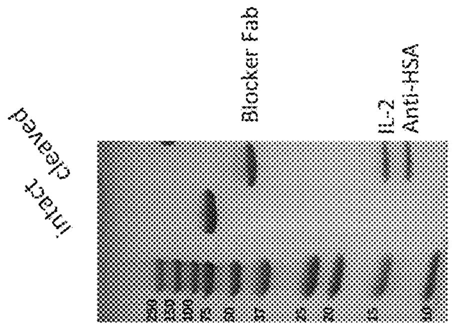
Figure 59O:
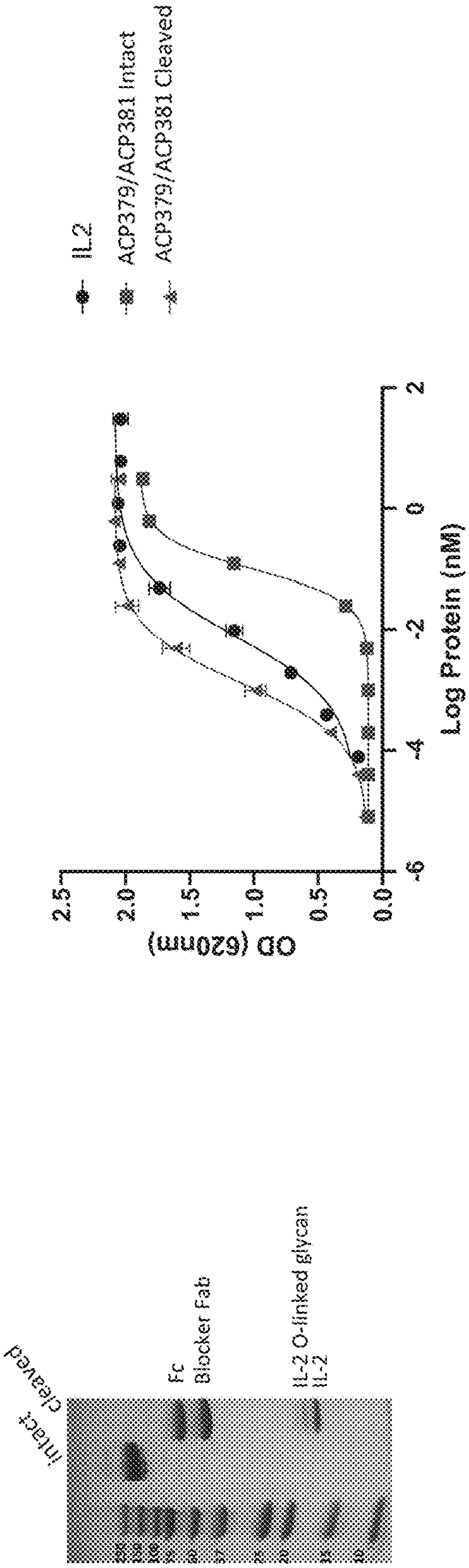
Figure 59P:
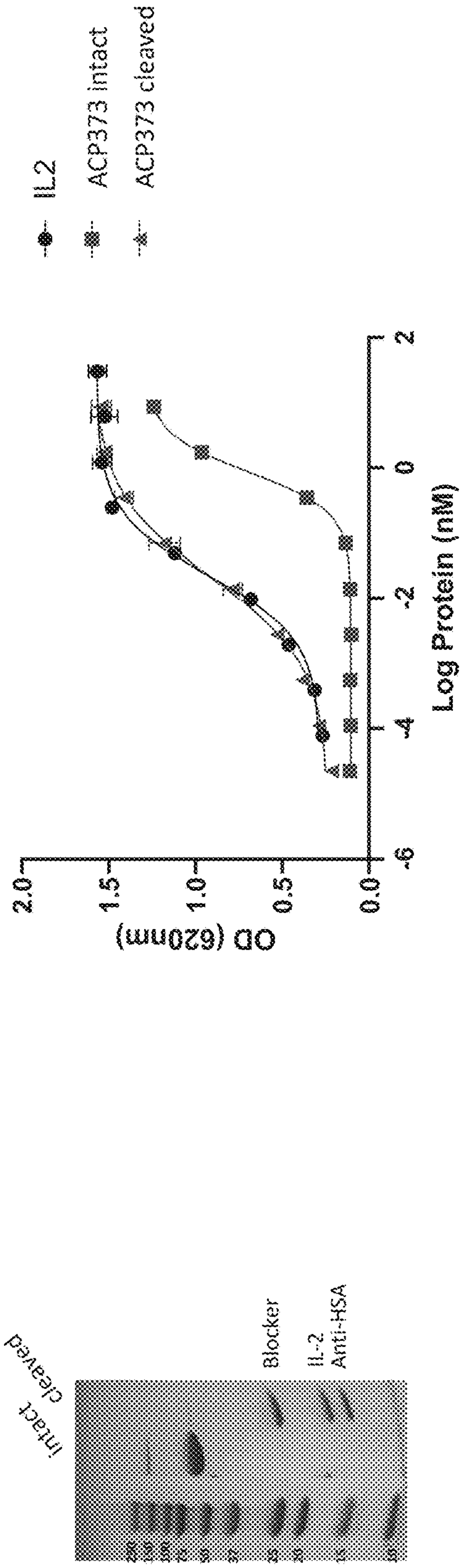
Figure 59Q:
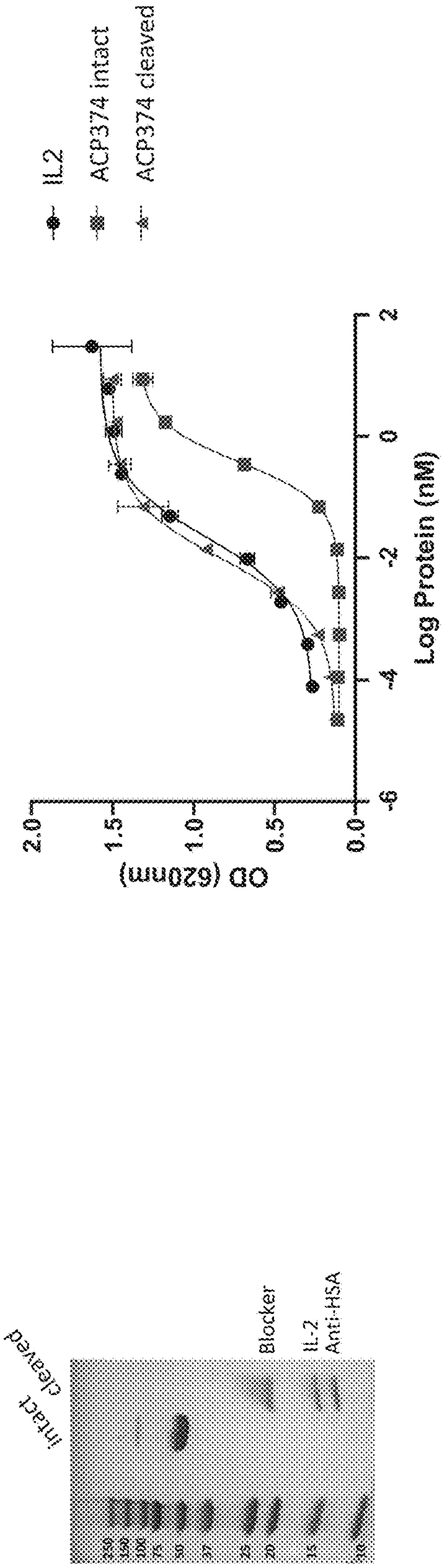
Figure 59R:
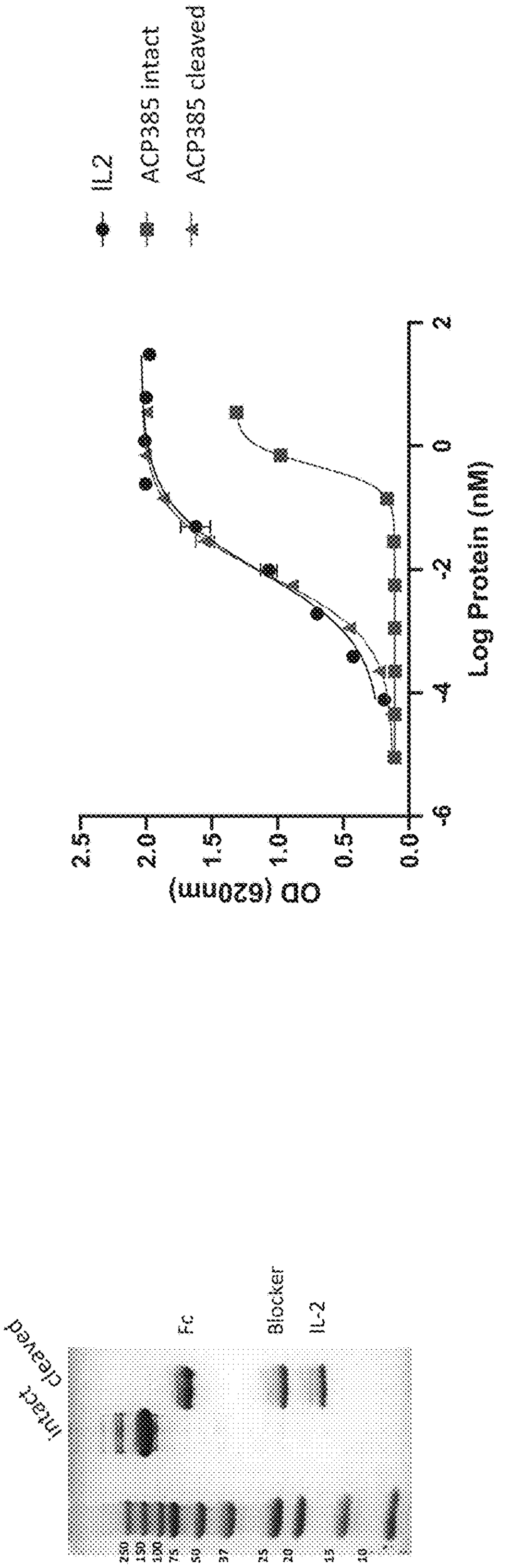
Figure 59S:
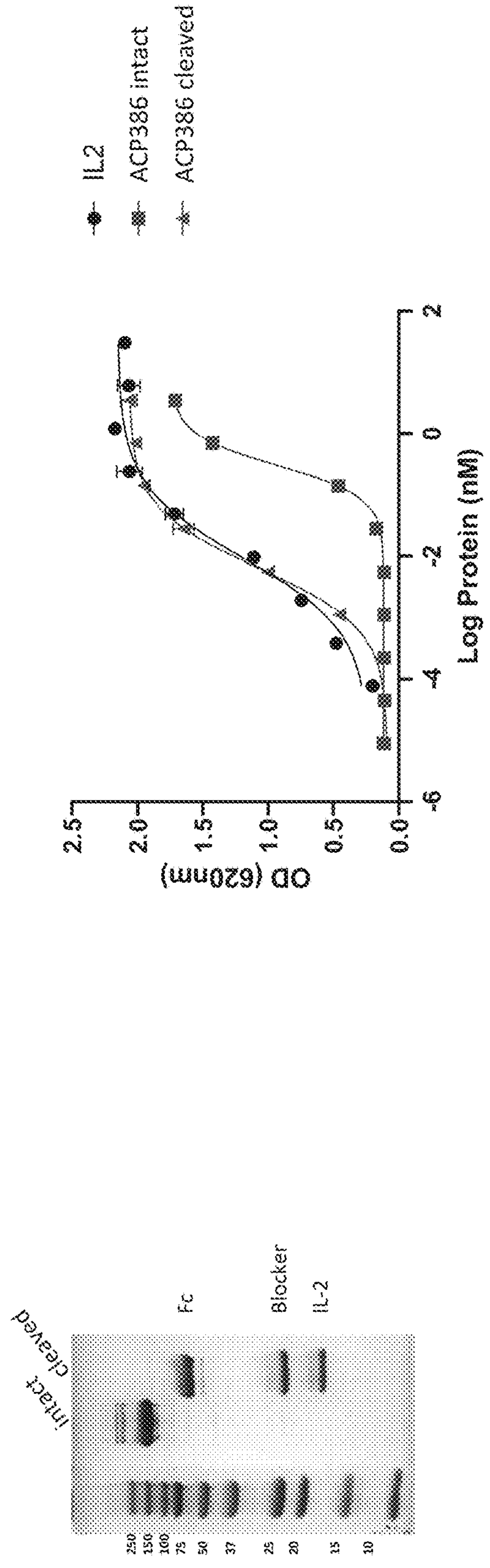
Figure 59T:
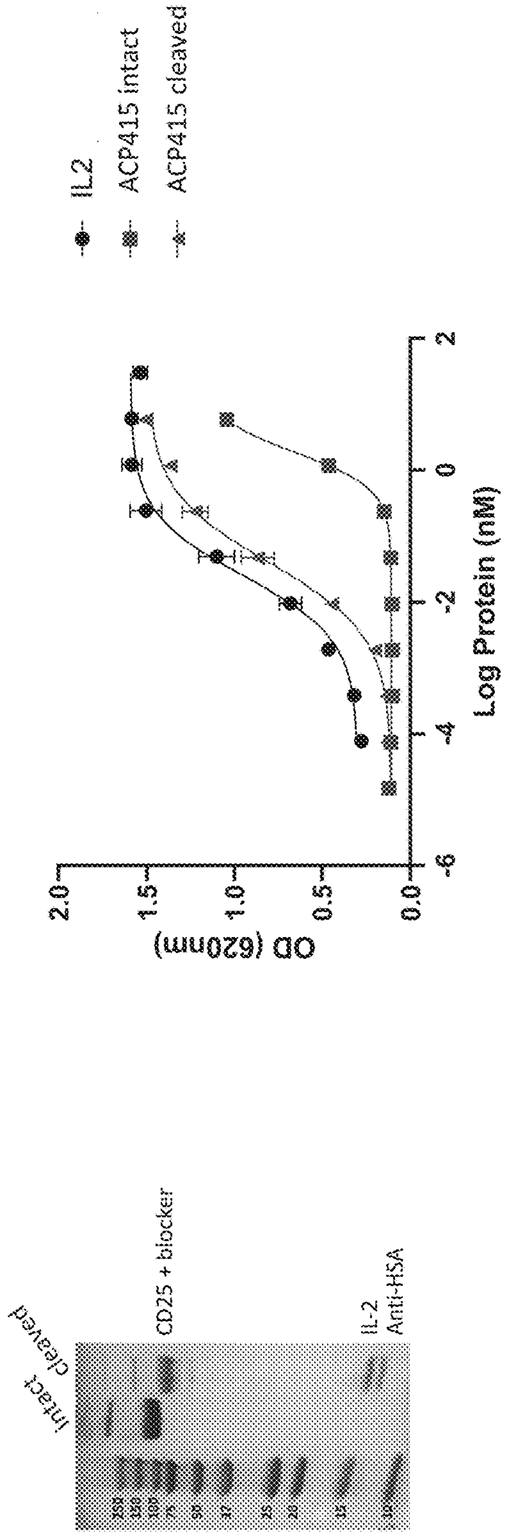
Figure 59U:
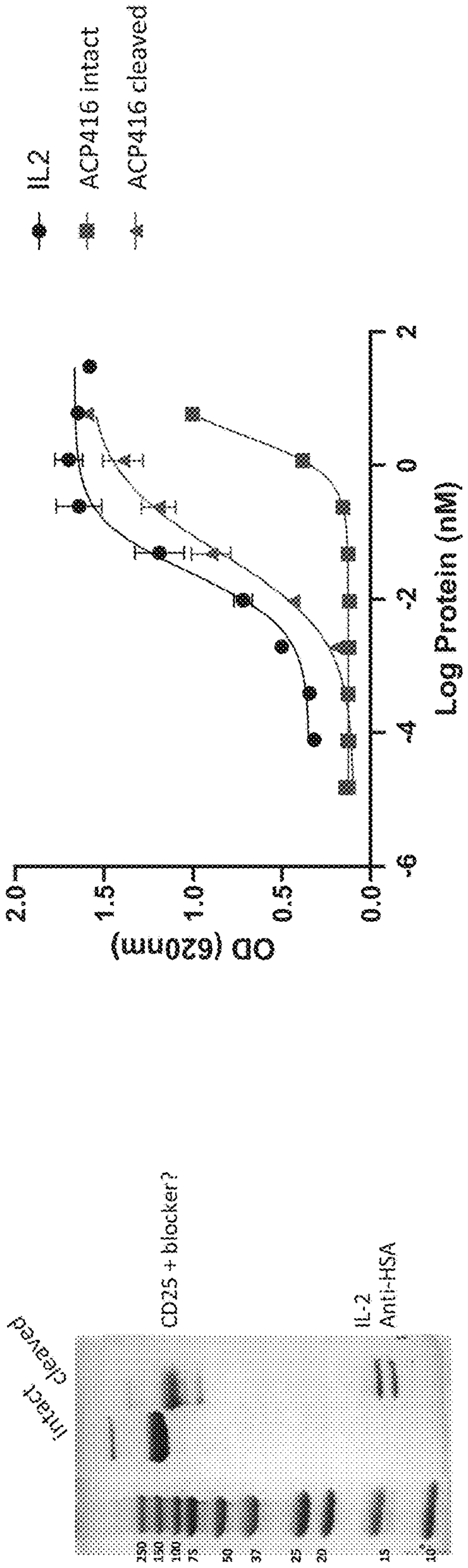
Figure 59V:
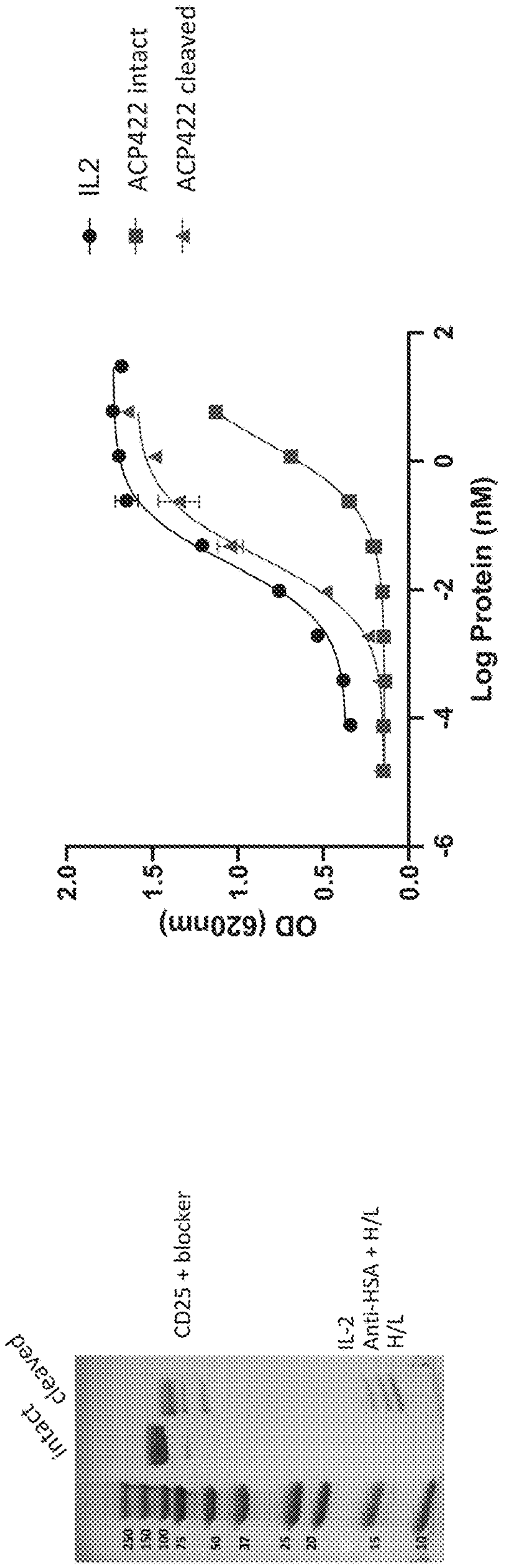
Figure 59W:
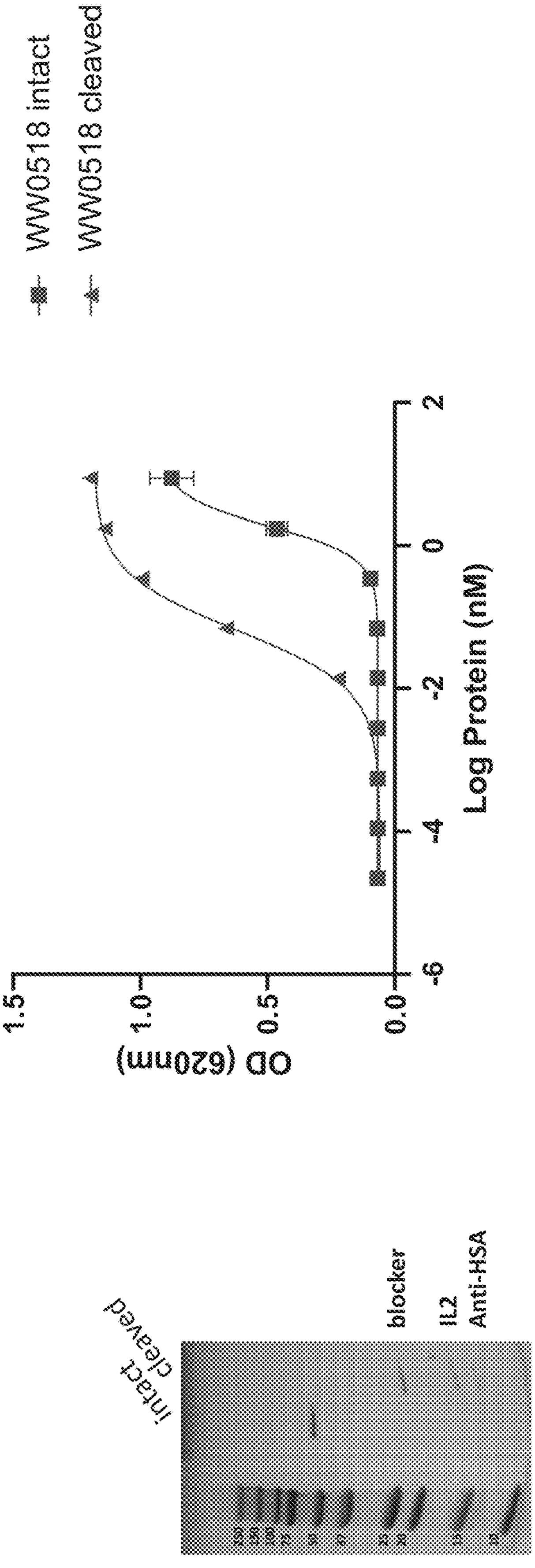
Figure 59X:
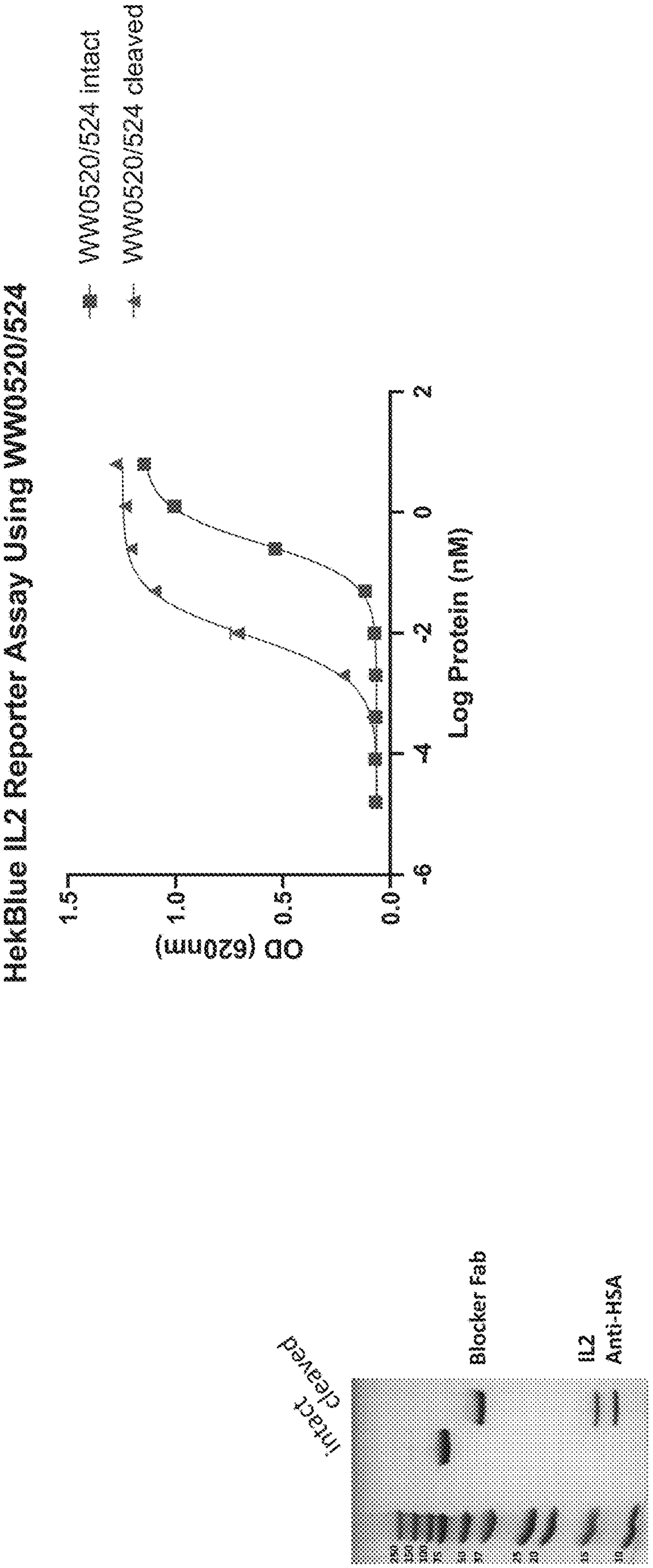
Figure 59Y:
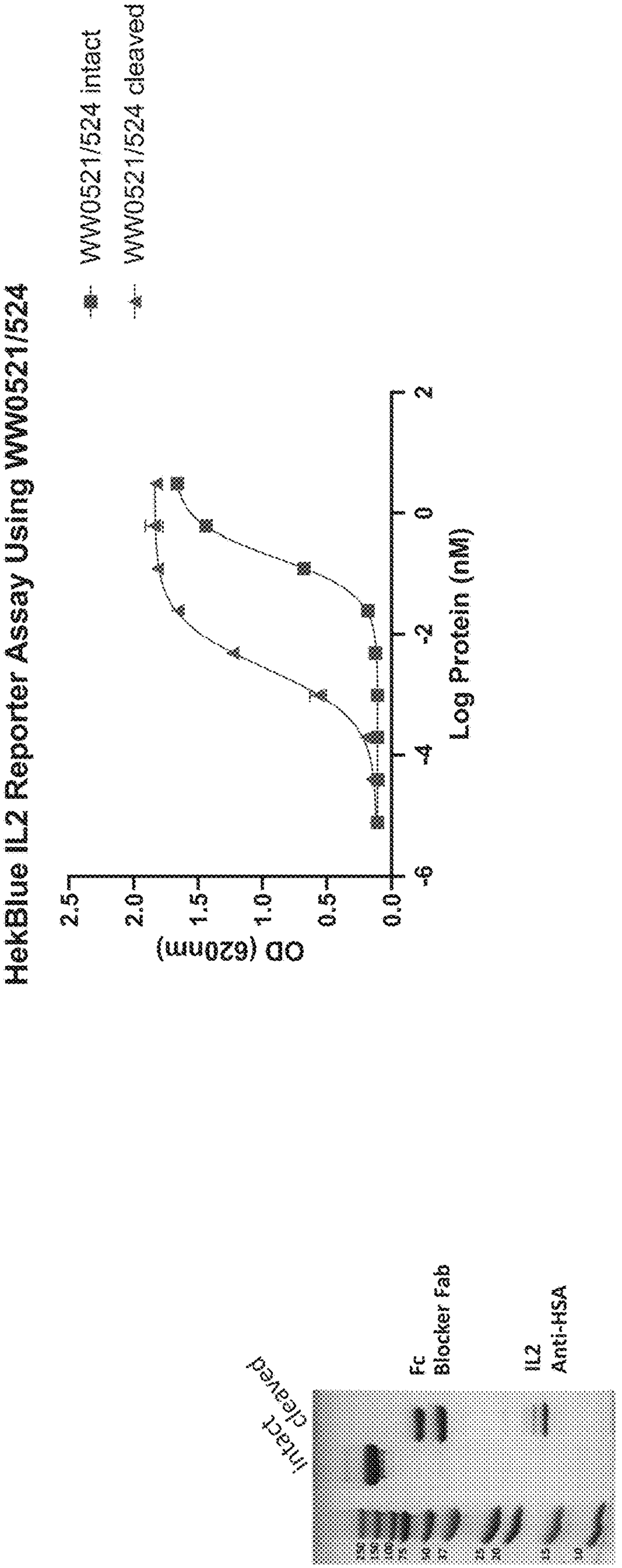
Figure 59Z:
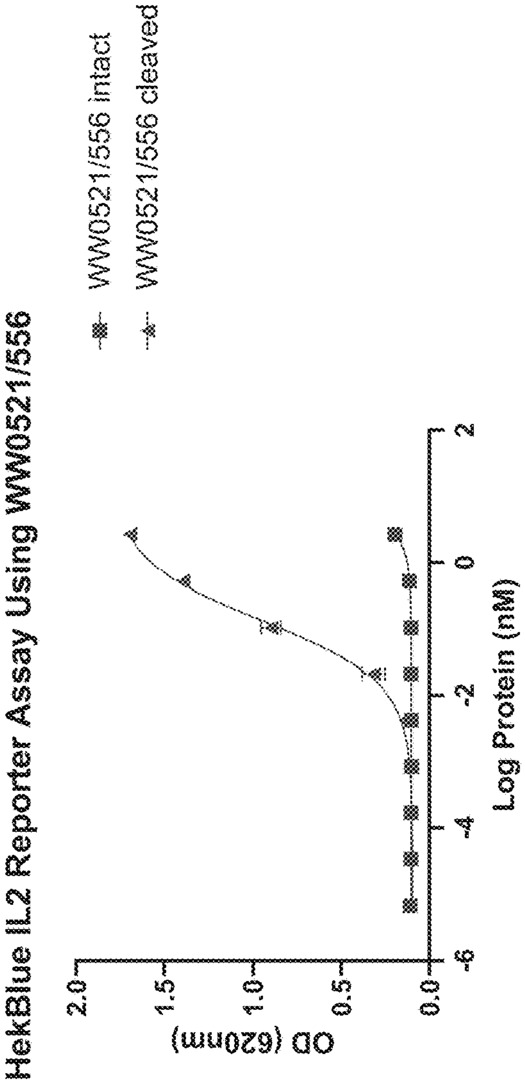
Figure 59Z:
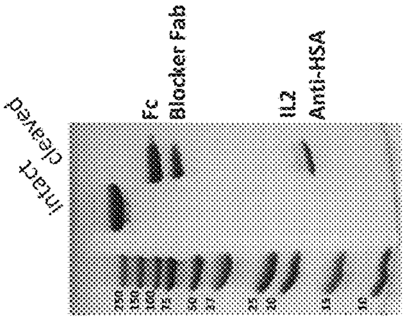
Figure 60A:
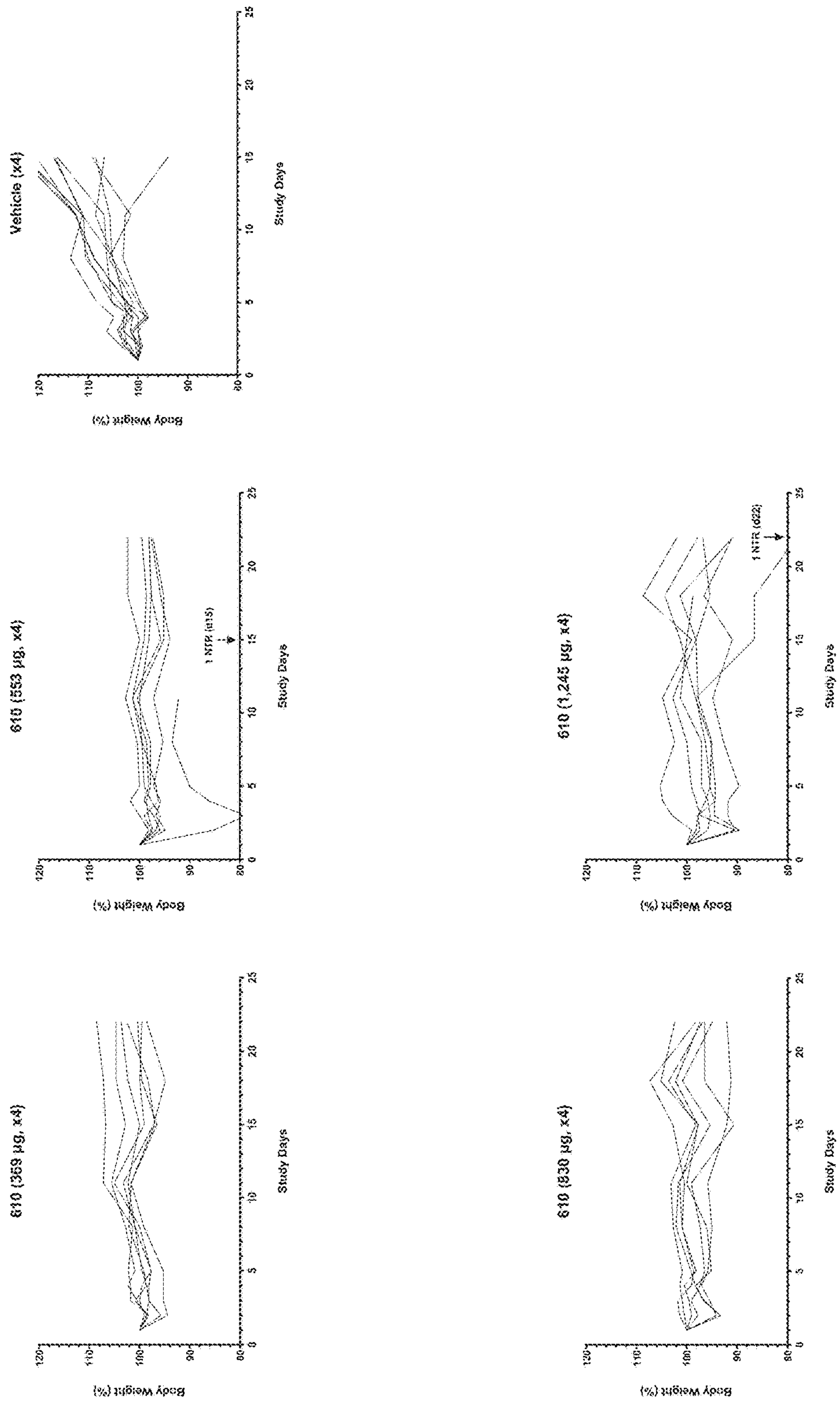
Figure 60B:
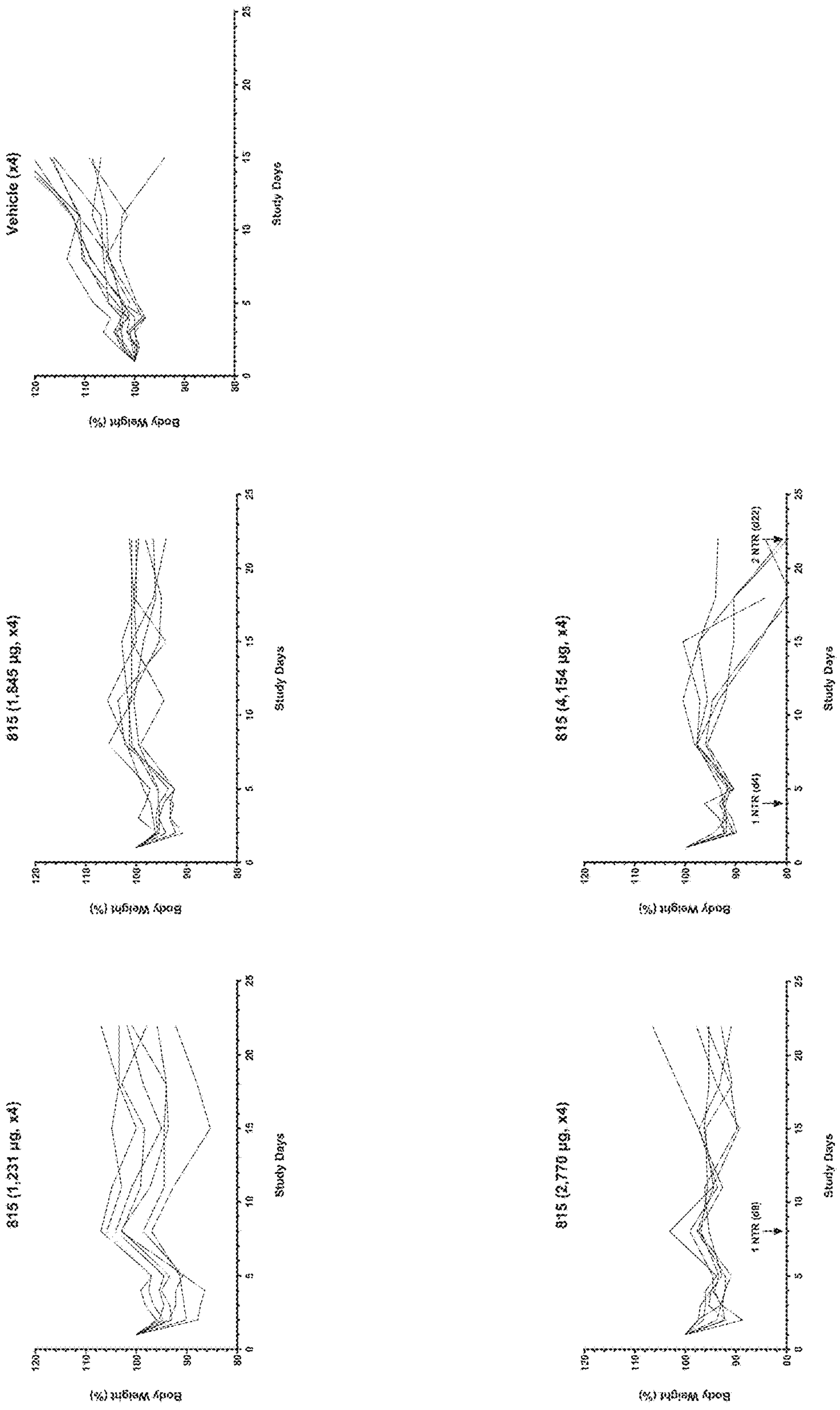
Figure 60C:
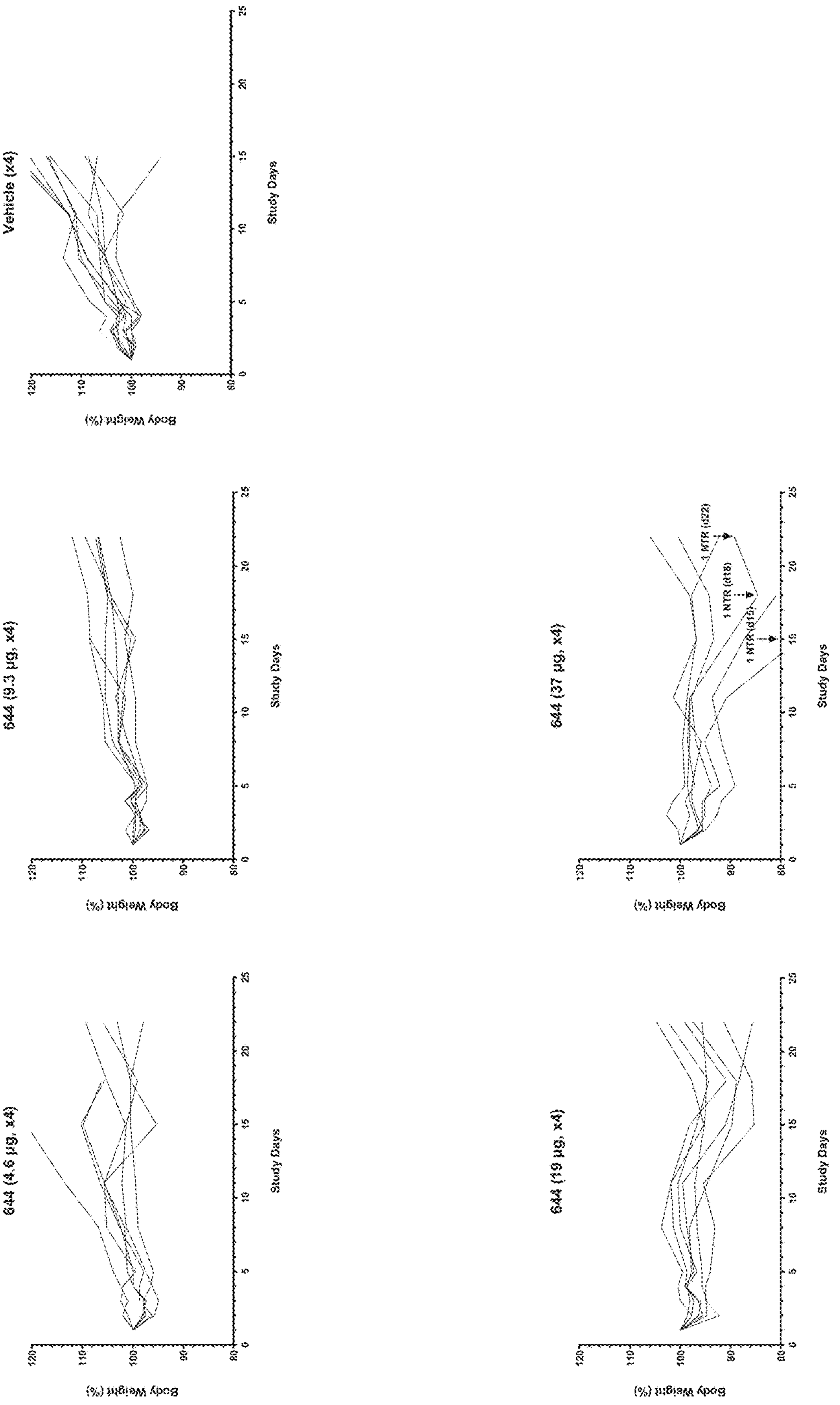
Figure 60D:
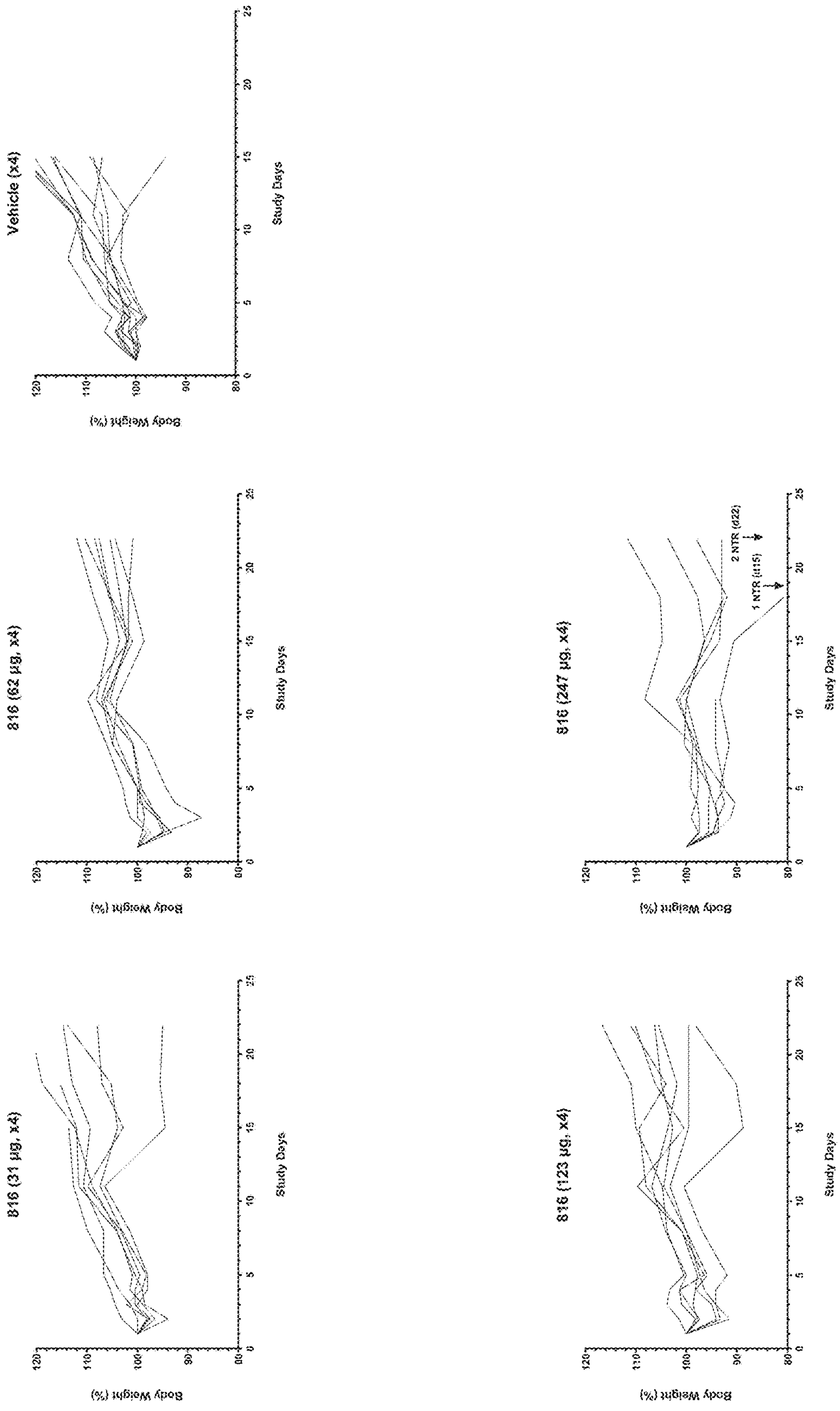
Figure 60E:
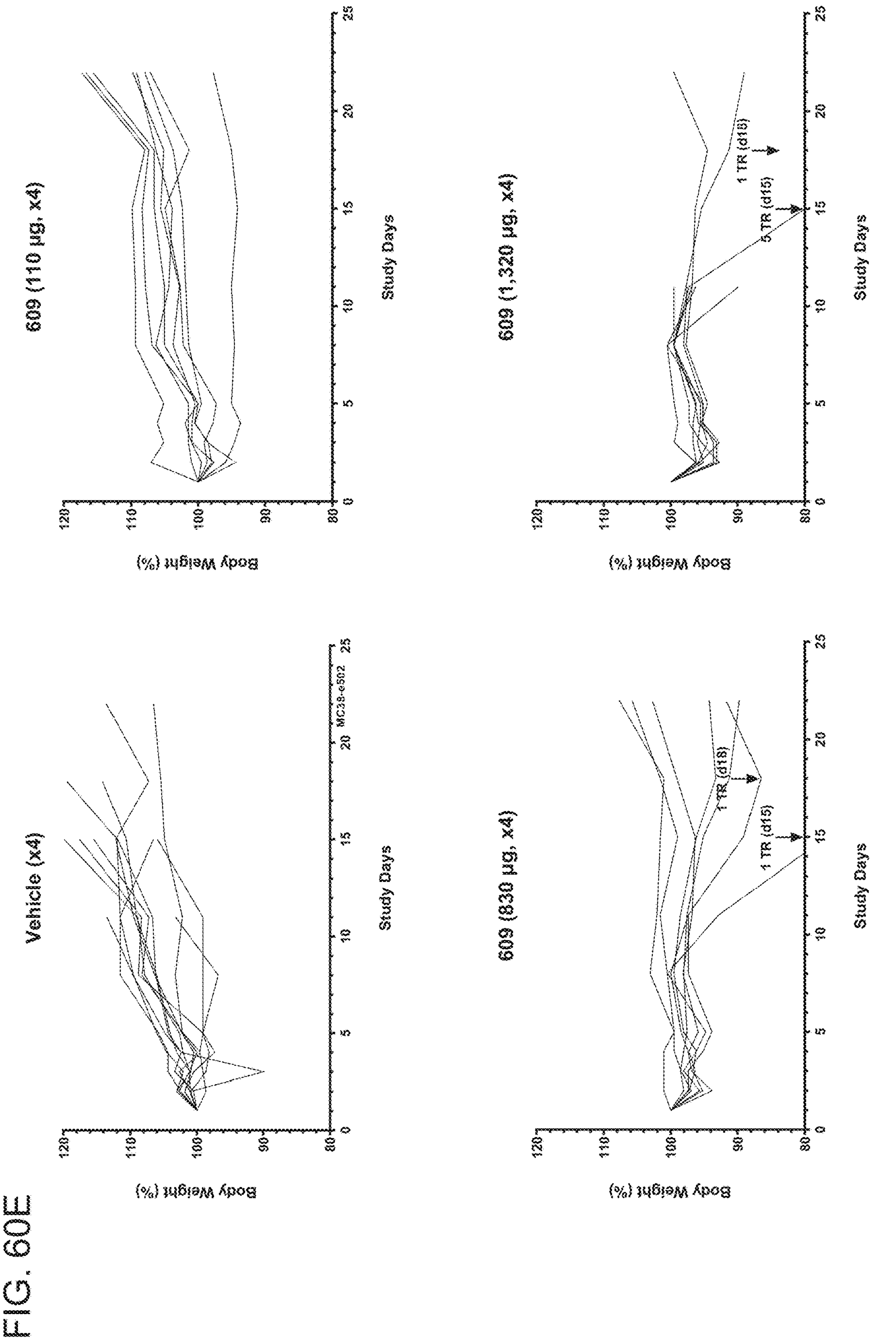
Figure 60F:
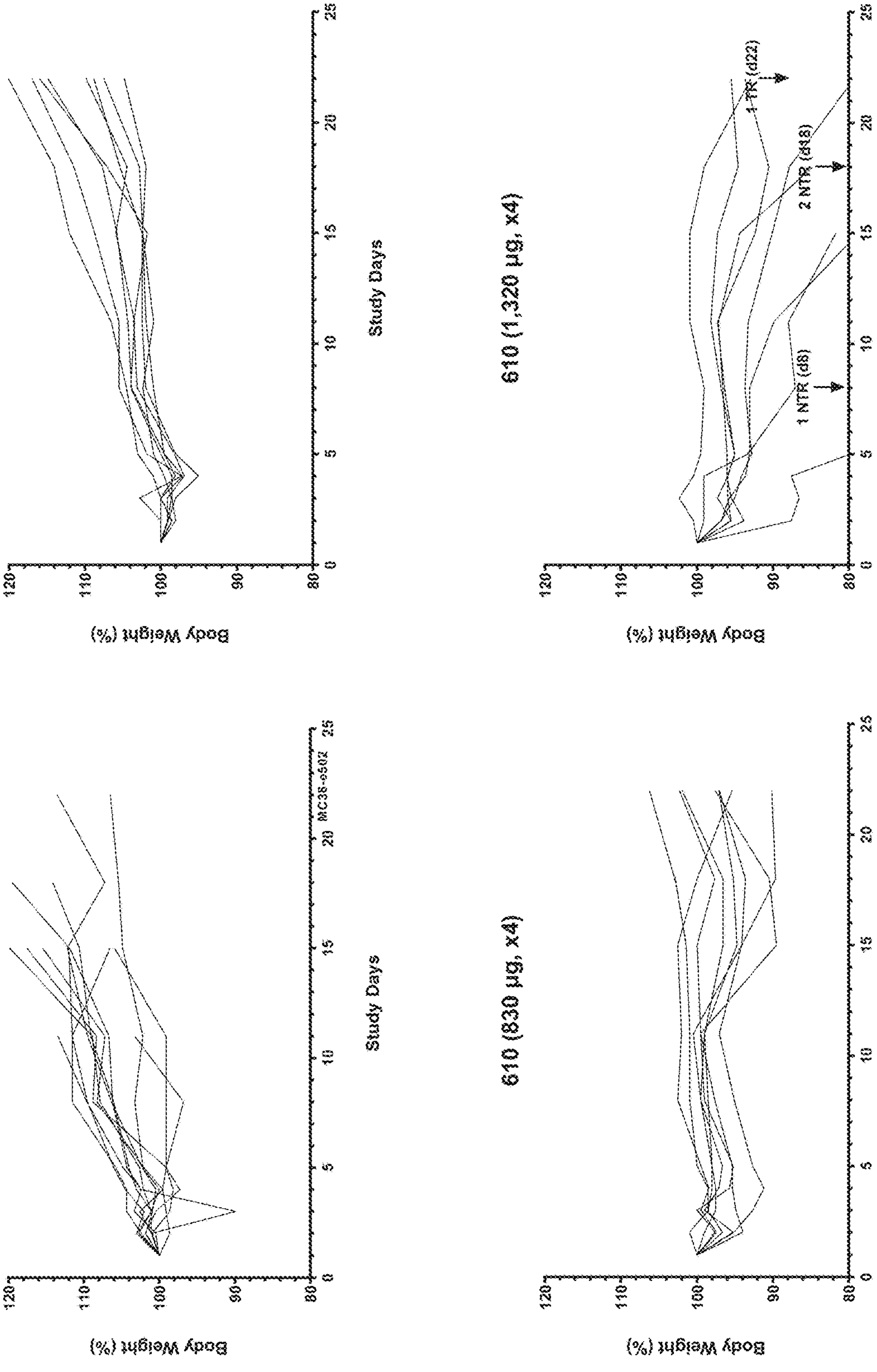
Figure 60G:
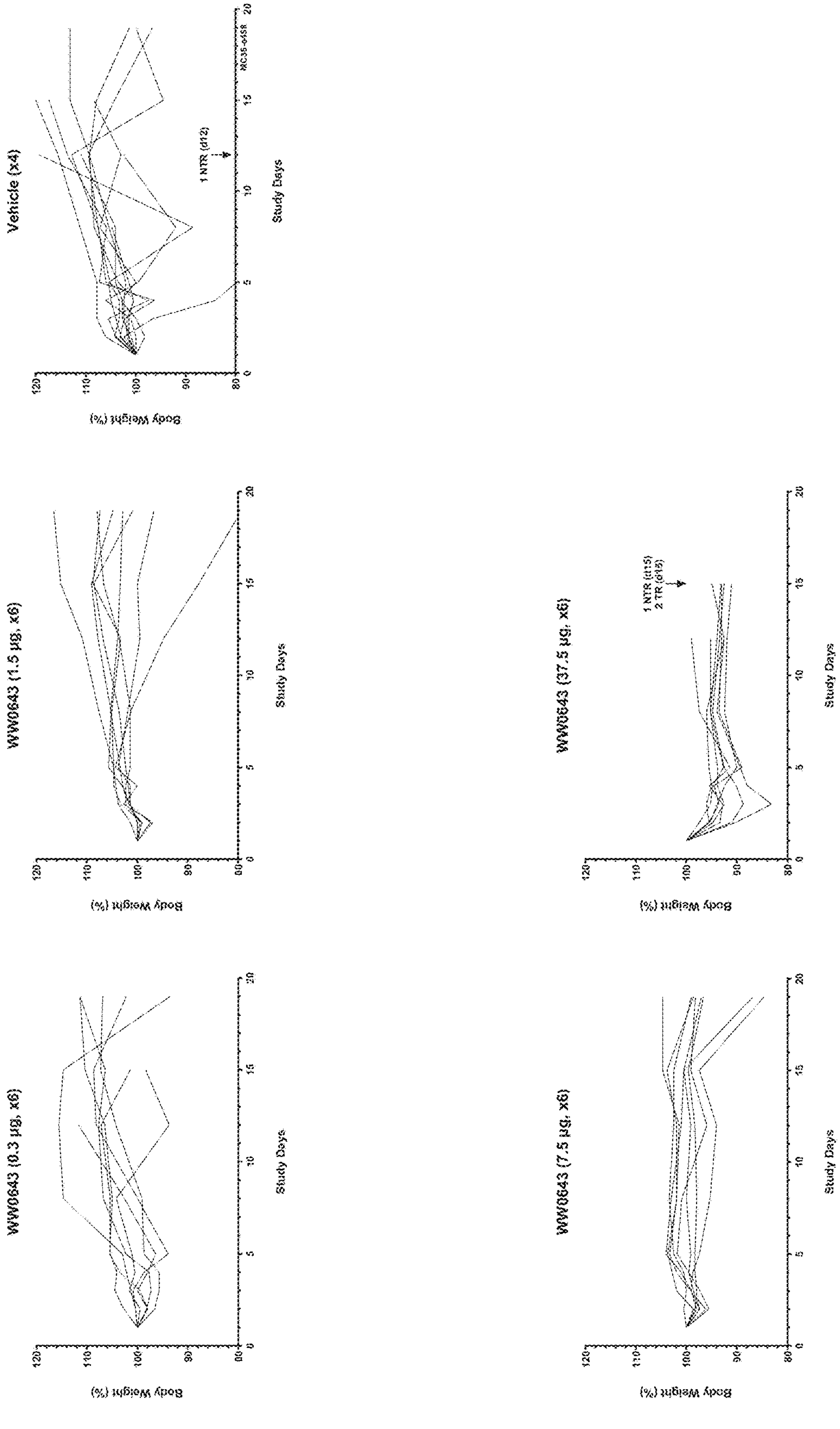

FIGS. 55A-55N shows the results of HekBlue IL2 reporter assays comparing activity of constructs with and without protease cleavage; IL-2 is included as a control.

FIGS. 56, 57A-57D, 58, 59A-59Z depict the activity of cytokine fusion proteins constructs.

FIGS. 60A-60G shows a series of spider plots showing the impact of IFN fusion proteins on body weight in an MC38 mouse xenograft model corresponding to the data shown in FIGS. 41A-41G. Each line in the plots is the body weight over time for a single mouse.

Figure 61A:
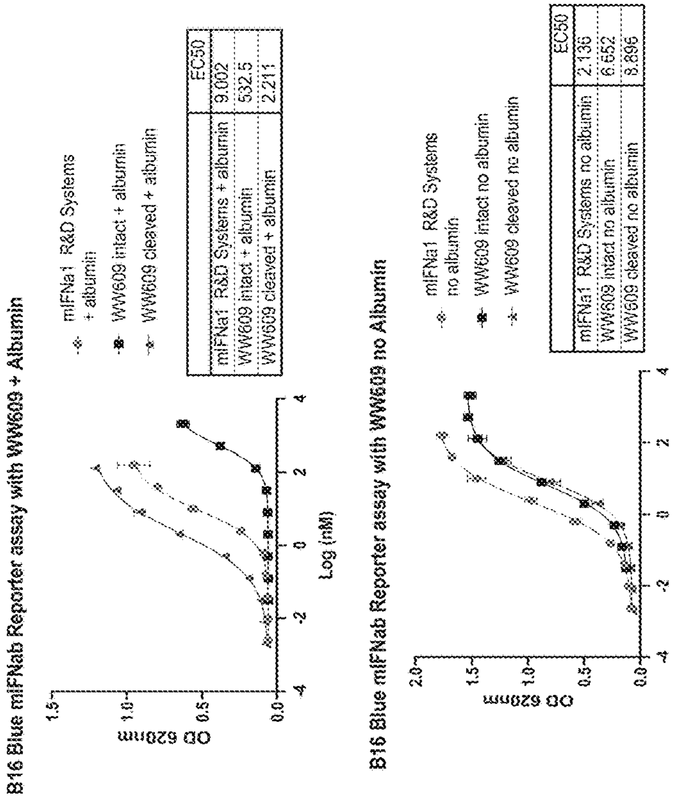
Figure 61B:
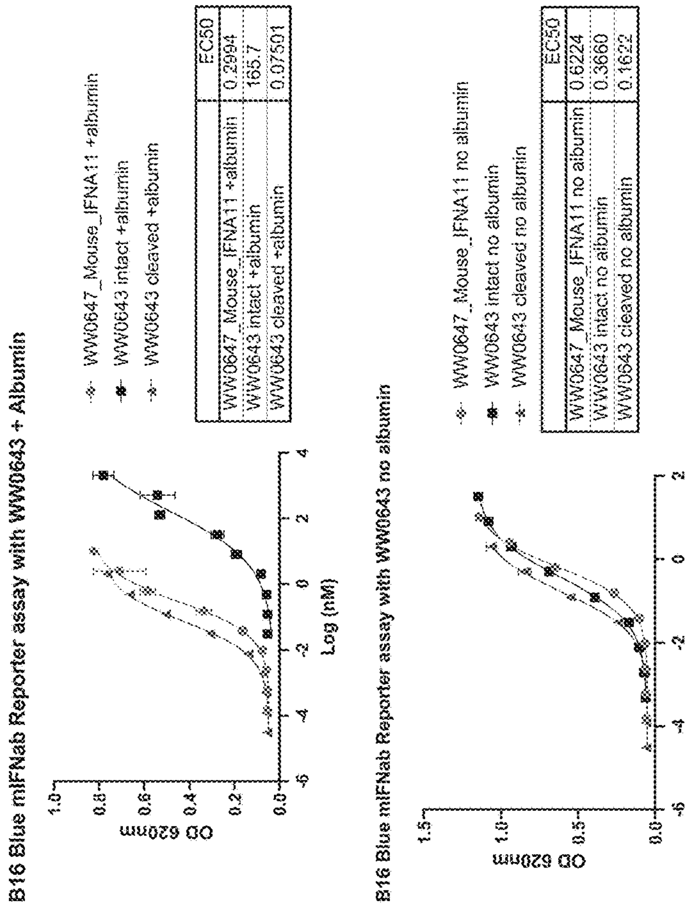

FIGS. 61A-61B are a series of graphs showing activity of fusion proteins in the B16-Blue IFN-α/β reporter assay. FIG. 61A depicts activation of the IFN-α/β pathway for construct WW0609 in the presence and absence of albumin. FIG. 61B depicts activation of the IFN-α/β pathway for construct WW0643 in the presence and absence of albumin. Squares depict activity of the uncut IFNα polypeptide (intact) and triangles depict the activity of the cut IFNα polypeptide (cleaved). Circles depict activity of the control (mouse IFNα). EC50 values for each are shown in the table.

DETAILED DESCRIPTION

Disclosed herein are methods and compositions to engineer and use constructs comprising inducible cytokines. Cytokines are potent immune agonists, which lead to them being considered promising therapeutic agents for oncology. However, cytokines proved to have a very narrow therapeutic window. Cytokines have short serum half-lives and are also considered to be highly potent. Consequently, therapeutic administration of cytokines produced undesirable systemic effects and toxicities. These were exacerbated by the need to administer large quantities of cytokine in order to achieve the desired levels of cytokine at the intended site of cytokine action (e.g., a tumor). Unfortunately, due to the biology of cytokines and inability to effectively target and control their activity, cytokines did not achieve the hoped-for clinical advantages in the treatment of tumors.

Disclosed herein are fusion proteins that overcome the toxicity and short half-life problems that have severely limited the clinical use of cytokines in oncology. The fusion proteins contain cytokine polypeptides that have receptor agonist activity. But in the context of the fusion protein, the cytokine receptor agonist activity is attenuated, and the circulating half-life is extended. The fusion proteins include protease cleave sites, which are cleaved by proteases that are associated with a desired site of cytokine activity (e.g., a tumor), and are typically enriched or selectively present at the site of desired activity. Thus, the fusion proteins are preferentially (or selectively) and efficiently cleaved at the desired site of activity to limit cytokine activity substantially to the desired site of activity, such as the tumor microenvironment. Protease cleavage at the desired site of activity, such as in a tumor microenvironment, releases a form of the cytokine from the fusion protein that is much more active as a cytokine receptor agonist than the fusion protein (typically at least about 100× more active than the fusion protein). The form of the cytokine that is released upon cleavage of the fusion protein typically has a short half-life, which is often substantially similar to the half-life of the naturally occurring cytokine, further restricting cytokine activity to the tumor microenvironment. Even though the half-life of the fusion protein is extended, toxicity is dramatically reduced or eliminated because the circulating fusion protein is attenuated, and active cytokine is targeted to the tumor microenvironment. The fusion proteins described herein, for the first time, enable the administration of an effective therapeutic dose of a cytokine to treat tumors with the activity of the cytokine substantially limited to the tumor microenvironment, and dramatically reduces or eliminates unwanted systemic effects and toxicity of the cytokine.

The fusion proteins disclosed herein typically comprise a cytokine polypeptide [A], a blocking moiety [D], optionally a half-life extension moiety [H], and a protease-cleavable polypeptide linker. The cytokine polypeptide and the blocking moiety and the optional half-life extension element when present are operably linked by the protease-cleavable polypeptide linker and the fusion polypeptide has attenuated cytokine receptor activating activity, e.g., the cytokine-receptor activating activity of the fusion polypeptide is at least about 10× less than the cytokine receptor activating activity of the polypeptide that contains the cytokine polypeptide that is produced by cleavage of the protease cleavable linker. Some preferred fusion polypeptides are of one of formula (I)-(VI):

[A]-[L1]-[H]-[L2]-[D] (I);

[D]-[L2]-[H]-[L1]-[A] (II);

[A]-[L1]-[D]-[L2]-[H] (III);

[H]-[L2]-[D]-[L1]-[A] (IV);

[H]-[L1]-[A]-[L2']-[D] (V);

[D]-[L1]-[A]-[L2']-[H] (VI);

wherein [A] is a cytokine polypeptide, [D] is a blocking moiety, [H] is a half-life extension moiety, [L1] is a protease-cleavable polypeptide linker, [L2] is an polypeptide linker that is optionally protease-cleavable, and [L2'] is a protease-cleavable polypeptide linker. [L1] and [L2] or [L1] and [L2'] can be have the same or different amino acid sequence and or protease-cleavage site (when L2 is protease-cleavable) as desired.

This disclosure further relates to pharmaceutical compositions that contain the inducible fusion protein and an additional therapeutic agent, as well as nucleic acids that encode the polypeptides, and recombinant expression vectors and host sells for making such fusion proteins. Also provided herein are methods of using the disclosed fusion proteins in the treatment of diseases, conditions, and disorders.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 4th ed. (2012) Cold Spring Harbor Laboratory Press, Cold Spring Harbor, NY. As appropriate, procedures involving the use of commercially available kits and reagents are generally carried out in accordance with manufacturer-defined protocols and conditions unless otherwise noted.

"Cytokine" is a well-known term of art that refers to any of a class of immunoregulatory proteins (such as interleukin or interferon) that are secreted by cells especially of the immune system and that are modulators of the immune system. Cytokine polypeptides that can be used in the fusion proteins disclosed herein include, but are not limited to transforming growth factors, such as TGF-α and TGF-β (e.g., TGFbeta1, TGFbeta2, TGFbeta3); interferons, such as interferon-α, interferon-β, interferon-γ, interferon-kappa and interferon-omega; interleukins, such as IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21 and IL-25; tumor necrosis factors, such as tumor necrosis factor alpha and lymphotoxin; chemokines (e.g., C-X-C motifchemokine 10 (CXCL10), CCL19, CCL20, CCL21), and granulocyte macrophage-colony stimulating factor (GM-CS), as well as fragments of such polypeptides that active the cognate receptors for the cytokine (i.e., functional fragments of the foregoing). "Chemokine" is a term of art that refers to any of a family of small cytokines with the ability to induce directed chemotaxis in nearby responsive cells.

Cytokines are well-known to have short serum half-lives that frequently are only a few minutes or hours. Even forms of cytokines that have altered amino acid sequences intended to extend the serum half-life yet retain receptor agonist activity typically also have short serum half-lives. As used herein, a "short-half-life cytokine" refers to a cytokine that has a substantially brief half-life circulating in the serum of a subject, such as a serum half-life that is less than 10, less than 15, less than 30, less than 60, less than 90, less than 120, less than 240, or less than 480 minutes. As used herein, a short half-life cytokine includes cytokines which have not been modified in their sequence to achieve a longer than usual half-life in the body of a subject and polypeptides that have altered amino acid sequences intended to extend the serum half-life yet retain receptor agonist activity. This latter case is not meant to include the addition of heterologous protein domains, such as a bona fide half-life extension element, such as serum albumin.

"Sortases" are transpeptidases that modify proteins by recognizing and cleaving a carboxyl-terminal sorting signal embedded in or terminally attached to a target protein or peptide. Sortase A catalyzes the cleavage of the LPXTG motif (SEQ ID NO.: 442) (where X is any standard amino acid) between the Thr and Gly residue on the target protein, with transient attachment of the Thr residue to the active site Cys residue on the enzyme, forming an enzyme-thioacyl intermediate. To complete transpeptidation and create the peptide-monomer conjugate, a biomolecule with an N-terminal nucleophilic group, typically an oligoglycine motif, attacks the intermediate, displacing Sortase A and joining the two molecules.

As used herein, the term "steric blocker" refers to a polypeptide or polypeptide moiety that can be covalently bonded to a cytokine polypeptide directly or indirectly through other moieties such as linkers, for example in the form of a chimeric polypeptide (fusion protein), but otherwise does not covalently bond to the cytokine polypeptide. A steric blocker can non-covalently bond to the cytokine polypeptide, for example though electrostatic, hydrophobic, ionic or hydrogen bonding. A steric blocker typically inhibits or blocks the activity of the cytokine moiety due to its proximity to the cytokine moiety and comparative size. A steric blocker may also block by virtue of recruitment of a large protein binding partner. An example of this is an antibody which binds to serum albumin; while the antibody itself may or may not be large enough to block activation or binding on its own, recruitment of albumin allows for sufficient steric blocking.

As used and described herein, a "half-life extension element" is a part of the chimeric polypeptide that increases the serum half-life and improve pK, for example, by altering its size (e.g., to be above the kidney filtration cutoff), shape, hydrodynamic radius, charge, or parameters of absorption, biodistribution, metabolism, and elimination.

As used herein, the terms "activatable," "activate," "induce," and "inducible" refer to the ability of a protein, i.e. a cytokine, that is part of a fusion protein, to bind its receptor and effectuate activity upon cleavage of additional elements from the fusion protein.

As used herein, "plasmids" or "viral vectors" are agents that transport the disclosed nucleic acids into the cell without degradation and include a promoter yielding expression of the nucleic acid molecule and/or polypeptide in the cells into which it is delivered.

As used herein, the terms "peptide", "polypeptide", or "protein" are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more.

As used throughout, "subject" can be a vertebrate, more specifically a mammal (e.g. a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered.

As used herein, "patient" or "subject" may be used interchangeably and can refer to a subject with a disease or disorder (e.g. cancer). The term patient or subject includes human and veterinary subjects.

As used herein the terms "treatment", "treat", or "treating" refers to a method of reducing the effects of a disease or condition or symptom of the disease or condition. Thus, in the disclosed method, treatment can refer to at least about 10%, at least about 20%, at least about 30%, at least about 40%, at least about 50%, at least about 60%, at least about 70%, at least about 80%, at least about 90%, or substantially complete reduction in the severity of an established disease or condition or symptom of the disease or condition. For example, a method for treating a disease is considered to be a treatment if there is a 10% reduction in one or more symptoms of the disease in a subject as compared to a control. Thus, the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms "prevent", "preventing", and "prevention" of a disease or disorder refers to an action, for example, administration of the chimeric polypeptide or nucleic acid sequence encoding the chimeric polypeptide, that occurs before or at about the same time a subject begins to show one or more symptoms of the disease or disorder, which inhibits or delays onset or exacerbation of one or more symptoms of the disease or disorder.

As used herein, references to "decreasing", "reducing", or "inhibiting" include a change of at least about 10%, of at least about 20%, of at least about 30%, of at least about 40%, of at least about 50%, of at least about 60%, of at least about 70%, of at least about 80%, of at least about 90% or greater as compared to a suitable control level. Such terms can include but do not necessarily include complete elimination of a function or property, such as agonist activity.

An "attenuated cytokine receptor agonist" is a cytokine receptor agonist that has decreased receptor agonist activity as compared to the cytokine receptor's naturally occurring agonist. An attenuated cytokine agonist may have at least about 10×, at least about 50×, at least about 100×, at least about 250×, at least about 500×, at least about 1000× or less agonist activity as compared to the receptor's naturally occurring agonist. When a fusion protein that contains a cytokine polypeptide as described herein is described as "attenuated" or having "attenuated activity", it is meant that the fusion protein is an attenuated cytokine receptor agonist.

An "intact fusion protein" is a fusion protein in which no domain has been removed, for example by protease cleavage. A domain may be removable by protease cleavage or other enzymatic activity, but when the fusion protein is "intact", this has not occurred.

As used herein "moiety" refers to a portion of a molecule that has a distinct function within that molecule, and that function may be performed by that moiety in the context of another molecule. A moiety may be a chemical entity with a particular function, or a portion of a biological molecule with a particular function. For example, a "blocking moiety" within a fusion protein is a portion of the fusion protein which is capable of blocking the activity of some or all of the fusion polypeptide. This may be a protein domain, such as serum albumin. Blocking may be accomplished by a steric blocker or a specific blocker. A steric blocker blocks by virtue of size and position and not based upon specific binding; an examples is serum albumin. A specific blocker blocks by virtue of specific interactions with the moiety to be blocked. A specific blocker must be tailored to the particular cytokine or active domain; a steric blocker can be used regardless of the payload, as long as it is large enough. If desired a blocking moiety that is incorporated into a fusion proteins described herein can associate with another polypeptide to create a specific binding domain. For example, if a cytokine binding fragment of an antibody is used as the blocking moiety, the fusion polypeptide can include an scFv that is specific for the cytokine as the blocking moiety or the fusion polypeptide can comprise half of a Fab, for example VH-CH1 or VL-CL as the blocking moity, which can associate with a complementary chain VL-CL or VH-CH1, respectively, to form an Fab fragment that specifically binds the cytokine. As further described herein, the blocking moiety may block activity of the fusion protein directly or when the blocking moiety associates with another polypeptide. For example, when an anti-HSA scFv binds HSA or when a VH-CH1 polypeptide associates with a complementary VL-CL polypeptide and then binds the cytokine polypeptide.

In general, the therapeutic use of cytokines is strongly limited by their systemic toxicity. TNF, for example, was originally discovered for its capacity of inducing the hemorrhagic necrosis of some tumors, and for its in vitro cytotoxic effect on different tumoral lines, but it subsequently proved to have strong pro-inflammatory activity, which can, in case of overproduction conditions, dangerously affect the human body. As the systemic toxicity is a fundamental problem with the use of pharmacologically active amounts of cytokines in humans, novel derivatives and therapeutic strategies are now under evaluation, aimed at reducing the toxic effects of this class of biological effectors while keeping their therapeutic efficacy.

IL-2 exerts both stimulatory and regulatory functions in the immune system and is, along with other members of the common γ chain (γc) cytokine family, central to immune homeostasis. IL-2 mediates its action by binding to IL-2 receptors (IL-2R), consisting of either trimeric receptors made of IL-2Rα (CD25), IL-2Rβ (CD122), and IL-2Rγ (γc, CD132) chains or dimeric βγ IL-2Rs (1, 3). Both IL-2R variants are able to transmit signal upon IL-2 binding. However, trimeric αβγ IL-2Rs have a roughly 10-100 times higher affinity for IL-2 than dimeric βγ IL-2Rs (3), implicating that CD25 confers high-affinity binding of IL-2 to its receptor but is not crucial for signal transduction. Trimeric IL-2Rs are found on activated T cells and CD4+ forkhead box P3 (FoxP3)+ T regulatory cells (Treg), which are sensitive to IL-2 in vitro and in vivo. Conversely, antigen-experienced (memory) CD8+, CD44 high memory-phenotype (MP) CD8+, and natural killer (NK) cells are endowed with high levels of dimeric βγ IL-2Rs, and these cells also respond vigorously to IL-2 in vitro and in vivo.

Expression of the high-affinity IL-2R is critical for endowing T cells to respond to low concentrations of IL-2 that is transiently available in vivo. IL-2Rα expression is absent on naive and memory T cells but is induced after antigen activation. IL-2Rβ is constitutively expressed by NK, NKT, and memory CD8+ T cells but is also induced on naive T cells after antigen activation. γc is much less stringently regulated and is constitutively expressed by all lymphoid cells. Once the high-affinity IL-2R is induced by antigen, IL-2R signaling upregulates the expression of IL-2Rα in part through Stat5-dependent regulation of Il2ra transcription (Kim et al., 2001). This process represents a mechanism to maintain expression of the high-affinity IL-2R and sustain IL-2 signaling while there remains a source of IL-2.

IL-2 is captured by IL-2Rα through a large hydrophobic binding surface surrounded by a polar periphery that results in a relatively weak interaction (Kd 10-8 M) with rapid on-off binding kinetics. However, the IL-2Rα-IL-2 binary complex leads to a very small conformational change in IL-2 that promotes association with IL-2Rβ through a distinct polar interaction between IL-2 and IL-2Rβ. The pseudo-high affinity of the IL2/α/β trimeric complex (i.e. Kd ~300 μM) clearly indicates that the trimeric complex is more stable than either IL2 bound to the α chain alone (Kd=10 nM) or to the 0 chain alone (Kd=450 nM) as shown by Ciardelli's data. In any event, the IL2/α/β trimer then recruits the γ chain into the quaternary complex capable of signaling, which is facilitated by the large composite binding site on the IL2-bound β chain for the γ chain.

In other words, the ternary IL-2Rα-IL-2Rβ-IL-2 complex then recruits γc through a weak interaction with IL-2 and a stronger interaction with IL-2Rβ to produce a stable quaternary high-affinity IL-2R (Kd 10-11 M which is 10 pM). The formation of the high-affinity quaternary IL-2-IL-2R complex leads to signal transduction through the tyrosine kinases Jak1 and Jak3, which are associated with IL-2Rβ and γc, respectively (Nelson and Willerford, 1998). The quaternary IL-2-IL-2R complex is rapidly internalized, where IL-2, IL-2Rβ, and γc are rapidly degraded, but IL-2Rα is recycled to the cell surface (Hémar et al., 1995; Yu and Malek, 2001). Thus, those functional activities that require sustained IL-2R signaling require a continued source of IL-2 to engage IL-2Rα and form additional IL-2-IL-2R signaling complexes.

Interleukin-15 (IL-15), another member of the 4-alpha-helix bundle family of cytokines, has also emerged as an immunomodulator for the treatment of cancer. IL-15 is initially captured via IL-15Rα, which is expressed on antigen-presenting dendritic cells, monocytes and macrophages. IL-15 exhibits broad activity and induces the differentiation and proliferation of T, B and natural killer (NK) cells via signaling through the IL-15/IL-2-R-β (CD122) and the common γ chain (CD132). It also enhances cytolytic activity of $CD8^+$ T cells and induces long-lasting antigen-experienced $CD8^+$CD44 memory T cells. IL-15 stimulates differentiation and immunoglobulin synthesis by B cells and induces maturation of dendritic cells. It does not stimulate immunosuppressive T regulatory cells (Tregs). Thus, boosting IL-15 activity selectively in the tumor micro-environment could enhance innate and specific immunity and fight tumors (Waldmann et al., 2012). IL-15 was initially identified for its ability to stimulate T cell proliferation in an IL-2-like manner through common receptor components (IL-2R/15Rβ-γc) and signaling through JAK1/JAK3 and STAT3/STAT5. Like IL-2, IL-15 has been shown to stimulate proliferation of activated CD4−CD8−, CD4+CD8+, CD4+ and CD8+ T cells as well as facilitate the induction of cytotoxic T-lymphocytes, and the generation, proliferation and activation of NK cells (Waldmann et al., 1999). However, unlike IL-2 which is required to maintain forkhead box P3 (FOXP3)-expressing CD4+CD25+ Treg cells and for the retention of these cells in the periphery, IL-15 has little effect on Tregs (Berger et al., 2009). This is important as FOXP3-expressing CD4+CD25+ Tregs inhibit effector T cells, thereby inhibiting immune responses including those directed against the tumor. IL-2 also has a crucial role in initiating activation induced cell death (AICD), a process that leads to the elimination of self-reactive T cells, whereas IL-15 is an anti-apoptotic factor for T cells (Marks-Konczalik et al., 2000). IL-15 co-delivered with HIV peptide vaccines has been shown to overcome CD4+ T cell deficiency by promoting longevity of antigen-specific CD8+ T cells and blocking TRAIL-mediated apoptosis (Oh et al., 2008). Furthermore, IL-15 promotes the long-term maintenance of CD8+CD44hi memory T cells (Kanegane et al., 1996).

The importance of IL-15 and IL-15Rα to T and NK cell development is further highlighted by the phenotype of IL-15$Rα^{+/+}$ and IL-$15^{-/-}$ mice. Knockout mice demonstrate decreased numbers of total CD8+ T cells, and are deficient in memory-phenotype CD8+ T cells, NK cells, NK/T cells and some subsets of intestinal intraepithelial lymphocytes, indicating that IL-15 provides essential positive homeostatic functions for these subsets of cells (Lodolce et al., 1996;

Kennedy et al., 1998). The similarities in the phenotypes of these two strains of knockout mice suggest the importance of IL-15Rα in maintaining physiologically relevant IL-15 signals.

IL-15 is presented in trans by the IL-15 receptor alpha-chain to the IL-15Rβγc complex displayed on the surface of T cells and natural killer (NK) cells (Han et al., 2011). The IL-15Ra-chain plays a role of chaperone protein, stabilizes, and increases IL-15 activity (Desbois et al., 2016). It has been shown that exogenous IL-15 may have a limited impact on patients with cancer due to its dependency on IL-15Ra frequently downregulated in cancer patients. Therefore, the fusion protein RLI, composed of the sushi+ domain of IL15Ra coupled via a linker to IL-15, has been suggested as an alternative approach to IL15 therapy (Bessard et al., 2009). It was found that administration of soluble IL-15/IL-15Rα complexes greatly enhanced IL-15 serum half-life and bioavailability in vivo (Stoklasek et al., 2010).

In addition to the effects on T and NK cells, IL-15 also has several effects on other components of the immune system. IL-15 protects neutrophils from apoptosis, modulates phagocytosis and stimulates the secretion of IL-8 and IL-1R antagonist. It functions through the activation of JAK2, p38 and ERK1/2 MAPK, Syk kinase and the NF-kB transcriptional factor (Pelletier et al., 2002). In mast cells, IL-15 can act as a growth factor and an inhibitor of apoptosis. In these cells IL-15 activates the JAK2/STAT5 pathway without the requirement of γc binding (Tagaya et al., 1996). IL-15 also induces B lymphocyte proliferation and differentiation, and increases immunoglobulin secretion (Armitage et al., 1995). It also prevents Fas-mediated apoptosis and allows induction of antibody responses partially independent of CD4-help (Demerci et al., 2004; Steel et al., 2010). Monocytes, macrophages and dendritic cells effectively transcribe and translate IL-15. They also respond to IL-15 stimulation. Macrophages respond by increasing phagocytosis, inducing IL-8, IL-12 and MCP-1 expression, and secreting IL-6, IL-8 and TNF α (Budagian et al., 2006). Dendritic cells incubated with IL-15 demonstrate maturation with increased CD83, CD86, CD40, and MHC class II expression, are also resistant to apoptosis, and show enhanced interferon-γ secretion (Anguille et al., 2009).

IL-15 has also been shown to have effects on non-hematological cells including myocytes, adipocytes, endothelial and neural cells. IL-15 has an anabolic effect on muscle and may support muscle cell differentiation (Quinn et al., 1995). It stimulates myocytes and muscle fibers to accumulate contractile protein and is able to slow muscle wasting in rats with cancer-related cachexia (Figueras et al., 2004). IL-15 has also been shown to stimulate angiogenesis (Angiolillo et al., 1997) and induce microglial growth and survival (Hanisch et al., 1997).

Interleukin-7 (IL-7), also of the IL-2/IL-15 family, is a well-characterized pleiotropic cytokine, and is expressed by stromal cells, epithelial cells, endothelial cells, fibroblasts, smooth muscle cells and keratinocytes, and following activation, by dendritic cells (Alpdogan et al., 2005). Although it was originally described as a growth and differentiation factor for precursor B lymphocytes, subsequent studies have shown that IL-7 is critically involved in T-lymphocyte development and differentiation. Interleukin-7 signaling is essential for optimal CD8 T-cell function, homeostasis and establishment of memory (Schluns et al., 2000); it is required for the survival of most T-cell subsets, and its expression has been proposed to be important for regulating T-cell numbers.

IL-7 binds to a dimeric receptor, including IL-7Rα and $\gamma_c$ to form a ternary complex that plays fundamental roles in extracellular matrix remodeling, development, and homeostasis of T and B cells (Mazzucchelli and Durum, 2007). IL-7 Ra also cross-reacts to form a ternary complex with thymic stromal lymphopoietin (TSLP) and its receptor (TSLPR), and activates the TSLP pathway, resulting in T and dendritic cell proliferation in humans and further B cell development in mice (Leonard, 2002). Tight regulation of the signaling cascades activated by the complexes are therefore crucial to normal cellular function. Under-stimulation of the IL-7 pathway caused by mutations in the IL-7Rα ectodomain inhibits T and B cell development, resulting in patients with a form of severe combined immunodeficiency (SCID) (Giliani et al., 2005; Puel et al., 1998).

IL-7 has a potential role in enhancing immune reconstitution in cancer patients following cytotoxic chemotherapy. IL-7 therapy enhances immune reconstitution and can augment even limited thymic function by facilitating peripheral expansion of even small numbers of recent thymic emigrants. Therefore, IL-7 therapy could potentially repair the immune system of patients who have been depleted by cytotoxic chemotherapy (Capitini et al., 2010).

Interleukin-12 (IL-12) is a disulfide-linked heterodimer of two separately encoded subunits (p35 and p40), which are linked covalently to give rise to the so-called bioactive heterodimeric (p70) molecule (Lieschke et al., 1997; Jana et al., 2014). Apart from forming heterodimers (IL-12 and IL-23), the p40 subunit is also secreted as a monomer (p40) and a homodimer ($p40_2$). It is known in the art that synthesis of the heterodimer as a single chain with a linker connecting the p35 to the p40 subunit preserves the full biological activity of the heterodimer. IL-12 plays a critical role in the early inflammatory response to infection and in the generation of Th1 cells, which favor cell-mediated immunity. It has been found that overproduction of IL-12 can be dangerous to the host because it is involved in the pathogenesis of a number of autoimmune inflammatory diseases (e.g. MS, arthritis, type 1 diabetes).

The IL-12 receptor (IL-12R) is a heterodimeric complex consisting of IL-12Rβ1 and IL-12Rβ2 chains expressed on the surface of activated T-cells and natural killer cells (Trinchieri et al., 2003). The IL-12Rβ1 chain binds to the IL-12p40 subunit, whereas IL-12p35 in association with IL-12Rβ2 confers an intracellular signaling ability (Benson et al., 2011). Signal transduction through IL-12R induces phosphorylation of Janus kinase (Jak2) and tyrosine kinase (Tyk2), that phosphorylate and activate signal transducer and activator of transcription (STAT)1, STAT3, STAT4, and STAT5. The specific cellular effects of IL-12 are due mainly to activation of STAT4. IL-12 induces natural killer and T-cells to produce cytokines, in particular interferon (IFN)γ, that mediate many of the proinflammatory activities of IL-12, including CD4+ T-cell differentiation toward the Th1 phenotype (Montepaone et al., 2014).

Regulatory T cells actively suppress activation of the immune system and prevent pathological self-reactivity and consequent autoimmune disease. Developing drugs and methods to selectively activate regulatory T cells for the treatment of autoimmune disease is the subject of intense research and, until the development of the present invention, which can selectively deliver active interleukins at the site of inflammation, has been largely unsuccessful. Regulatory T cells (Treg) are a class of CD4+CD25+ T cells that suppress the activity of other immune cells. Treg are central to immune system homeostasis, and play a major role in maintaining tolerance to self-antigens and in modulating the immune response to foreign antigens. Multiple autoimmune and inflammatory diseases, including Type 1 Diabetes (T1D), Systemic Lupus Erythematosus (SLE), and Graft-versus-Host Disease (GVHD) have been shown to have a deficiency of Treg cell numbers or Treg function.

Consequently, there is great interest in the development of therapies that boost the numbers and/or function of Treg cells. One treatment approach for autoimmune diseases being investigated is the transplantation of autologous, ex vivo-expanded Treg cells (Tang, Q., et al, 2013, Cold Spring Harb. Perspect. Med., 3:1-15). While this approach has shown promise in treating animal models of disease and in several early stage human clinical trials, it requires personalized treatment with the patient's own T cells, is invasive, and is technically complex. Another approach is treatment with low dose Interleukin-2 (IL-2). Treg cells characteristically express high constitutive levels of the high affinity IL-2 receptor, IL2Rαβγ, which is composed of the subunits IL2Rα (CD25), IL2Rβ (CD122), and IL2Rγ (CD132), and Treg cell growth has been shown to be dependent on IL-2 (Malek, T. R., et al., 2010, Immunity, 33:153-65).

Conversely, immune activation has also been achieved using IL-2, and recombinant IL-2 (Proleukin®) has been approved to treat certain cancers. High-dose IL-2 is used for the treatment of patients with metastatic melanoma and metastatic renal cell carcinoma with a long-term impact on overall survival.

Clinical trials of low-dose IL-2 treatment of chronic GVHD (Koreth, J., et al., 2011, N Engl J Med., 365:2055-66) and HCV-associated autoimmune vasculitis patients (Saadoun, D., et al., 2011, N Engl J Med., 365:2067-77) have demonstrated increased Treg levels and signs of clinical efficacy. New clinical trials investigating the efficacy of IL-2 in multiple other autoimmune and inflammatory diseases have been initiated. The rationale for using so-called low dose IL-2 was to exploit the high IL-2 affinity of the trimeric IL-2 receptor which is constitutively expressed on Tregs while leaving other T cells which do not express the high affinity receptor in the inactivated state. Aldesleukin (marketed as Proleukin® by Prometheus Laboratories, San Diego, CA), the recombinant form of IL-2 used in these trials, is associated with high toxicity. Aldesleukin, at high doses, is approved for the treatment of metastatic melanoma and metastatic renal cancer, but its side effects are so severe that its use is only recommended in a hospital setting with access to intensive care (Web address: www.proleukin.com/assets/pdf/proleukin.pdf).

The clinical trials of IL-2 in autoimmune diseases have employed lower doses of IL-2 in order to target Treg cells, because Treg cells respond to lower concentrations of IL-2 than many other immune cell types due to their expression of IL2R alpha (Klatzmann D, 2015 Nat Rev Immunol. 15:283-94). However, even these lower doses resulted in safety and tolerability issues, and the treatments used have employed daily subcutaneous injections, either chronically or in intermittent 5-day treatment courses. Therefore, there is a need for an autoimmune disease therapy that potentiates Treg cell numbers and function, that targets Treg cells more specifically than IL-2, that is safer and more tolerable, and that is administered less frequently.

One approach that has been suggested for improving the therapeutic index of IL-2-based therapy for autoimmune diseases is to use variants of IL-2 that are selective for Treg cells relative to other immune cells. IL-2 receptors are expressed on a variety of different immune cell types, including T cells, NK cells, eosinophils, and monocytes, and this broad expression pattern likely contributes to its pleiotropic effect on the immune system and high systemic toxicity. In particular, activated T effector cells express IL2Rαβγ, as do pulmonary epithelial cells. But, activating T effector cells runs directly counter to the goal of down-modulating and controlling an immune response, and activating pulmonary epithelial cells leads to known dose-limiting side effects of IL-2 including pulmonary edema. In fact, the major side effect of high-dose IL-2 immunotherapy is vascular leak syndrome (VLS), which leads to accumulation of intravascular fluid in organs such as lungs and liver with subsequent pulmonary edema and liver cell damage. There is no treatment of VLS other than withdrawal of IL-2. Low-dose IL-2 regimens have been tested in patients to avoid VLS, however, at the expense of suboptimal therapeutic results.

According to the literature, VLS is believed to be caused by the release of proinflammatory cytokines from IL-2-activated NK cells. However, there is some evidence that pulmonary edema results from direct binding of IL-2 to lung endothelial cells, which expressed low to intermediate levels of functional αβγ IL-2Rs. And, the pulmonary edema associated with interaction of IL-2 with lung endothelial cells was abrogated by blocking binding to CD25 with an anti-CD25 monoclonal antibody (mAb), in CD25-deficient host mice, or by the use of CD122-specific IL-2/anti-IL-2 mAb (IL-2/mAb) complexes, thus preventing VLS.

Treatment with interleukin cytokines other than IL-2 has been more limited. IL-15 displays immune cell stimulatory activity similar to that of IL-2 but without the same inhibitory effects, thus making it a promising immunotherapeutic candidate. Clinical trials of recombinant human IL-15 for the treatment of metastatic malignant melanoma or renal cell cancer demonstrated appreciable changes in immune cell distribution, proliferation, and activation and suggested potential antitumor activity (Conlon et. al., 2014). IL-15 is currently in clinical trials to treat various forms of cancer. However, IL-15 therapy is known to be associated with undesired and toxic effects, such as exacerbating certain leukemias, graft-versus-host disease, hypotension, thrombocytopenia, and liver injury. (Mishra A., et al., Cancer Cell, 2012, 22(5):645-55; Alpdogan O. et al., Blood, 2005, 105 (2):866-73; Conlon K C et al., J Clin Oncol, 2015, 33(1): 74-82.)

IL-7 promotes lymphocyte development in the thymus and maintains survival of naive and memory T cell homeostasis in the periphery. Moreover, it is important for the organogenesis of lymph nodes (LN) and for the maintenance of activated T cells recruited into the secondary lymphoid organs (SLOs) (Gao et. al., 2015). In clinical trials of IL-7, patients receiving IL-7 showed increases in both CD4+ and CD8+ T cells, with no significant increase in regulatory T cell numbers as monitored by FoxP3 expression (Sportes et al., 2008). In clinical trials reported in 2006, 2008 and 2010, patients with different kinds of cancers such as metastatic melanoma or sarcoma were injected subcutaneously with different doses of IL-7. Little toxicity was seen except for transient fevers and mild erythema. Circulating levels of both CD4+ and CD8+ T cells increased significantly and the number of Treg reduced. TCR repertoire diversity increased after IL-7 therapy. However, the anti-tumor activity of IL-7 was not well evaluated (Gao et. al., 2015). Results suggest that IL-7 therapy could enhance and broaden immune responses.

IL-12 is a pleiotropic cytokine, the actions of which create an interconnection between the innate and adaptive immunity. IL-12 was first described as a factor secreted from PMA-induced EBV-transformed B-cell lines. Based on its actions, IL-12 has been designated as cytotoxic lymphocyte maturation factor and natural killer cell stimulatory factor. Due to bridging the innate and adaptive immunity and potently stimulating the production of IFNγ, a cytokine coordinating natural mechanisms of anticancer defense, IL-12 seemed ideal candidate for tumor immunotherapy in humans. However, severe side effects associated with systemic administration of IL-12 in clinical investigations and the very narrow therapeutic index of this cytokine markedly tempered enthusiasm for the use of this cytokine in cancer patients (Lasek et. al., 2014). Approaches to IL-12 therapy in which delivery of the cytokine is tumor-targeted, which may diminish some of the previous issues with IL-12 therapy, are currently in clinical trials for cancers.

The direct use of IL-2 as an agonist to bind the IL-2R and modulate immune responses therapeutically has been problematic due its well-documented therapeutic risks, e.g., its short serum half-life and high toxicity. These risks have also limited the therapeutic development and use of other cytokines. New forms of cytokines that reduce these risks are needed. Disclosed herein are compositions and methods comprising IL-2 and IL-15 and other cytokines, functional fragments and muteins of cytokines, variants, and subunits of cytokines as well as conditionally active cytokines designed to address these risks and provide needed immunomodulatory therapeutics.

The present invention is designed to address the shortcomings of direct IL-2 therapy and therapy using other cytokines, for example using cytokine blocking moieties, e.g. steric blocking polypeptides, serum half-life extending polypeptides, targeting polypeptides, linking polypeptides, including protease cleavable linkers, and combinations thereof. Cytokines, including interleukins (e.g., IL-2, IL-7, IL-12, IL-15, IL-18, IL-21 IL-23), interferons (IFNs, including IFNalpha, IFNbeta and IFNgamma), tumor necrosis factors (e.g., TNFalpha, lymphotoxin), transforming growth factors (e.g., TGFbeta1, TGFbeta2, TGFbeta3), chemokines (C-X-C motif chemokine 10 (CXCL10), CCL19, CCL20, CCL21), and granulocyte macrophage-colony stimulating factor (GM-CS) are highly potent when administered to patients. As used herein, "chemokine" means a family of small cytokines with the ability to induce directed chemotaxis in nearby responsive cells Cytokines can provide powerful therapy, but are accompanied by undesired effects that are difficult to control clinically and which have limited the clinical use of cytokines. This disclosure relates to new forms of cytokines that can be used in patients with reduced or eliminated undesired effects. In particular, this disclosure relates to pharmaceutical compositions including chimeric polypeptides (fusion proteins), nucleic acids encoding fusion proteins and pharmaceutical formulations of the foregoing that contain cytokines or active fragments or muteins of cytokines that have decreased cytokine receptor activating activity in comparison to the corresponding cytokine. However, under selected conditions or in a selected biological environment the chimeric polypeptides activate their cognate receptors, often with the same or higher potency as the corresponding naturally occurring cytokine. As described herein, this is typically achieved using a cytokine blocking moiety that blocks or inhibits the receptor activating function of the cytokine, active fragment or mutein thereof under general conditions but not under selected conditions, such as those present at the desired site of cytokine activity (e.g., an inflammatory site or a tumor).

The chimeric polypeptides and nucleic acids encoding the chimeric polypeptides can be made using any suitable method. For example, nucleic acids encoding a chimeric polypeptide can be made using recombinant DNA techniques, synthetic chemistry or combinations of these techniques, and expressed in a suitable expression system, such as in CHO cells. Chimeric polypeptides can similarly be made, for example by expression of a suitable nucleic acid, using synthetic or semi-synthetic chemical techniques, and the like. In some embodiments, the blocking moiety can be attached to the cytokine polypeptide via sortase-mediated conjugation. "Sortases" are transpeptidases that modify proteins by recognizing and cleaving a carboxyl-terminal sorting signal embedded in or terminally attached to a target protein or peptide. Sortase A catalyzes the cleavage of the LPXTG motif (SEQ ID No.: 442) (where X is any standard amino acid) between the Thr and Gly residue on the target protein, with transient attachment of the Thr residue to the active site Cys residue on the enzyme, forming an enzyme-thioacyl intermediate. To complete transpeptidation and create the peptide-monomer conjugate, a biomolecule with an N-terminal nucleophilic group, typically an oligoglycine motif, attacks the intermediate, displacing Sortase A and joining the two molecules.

To form the cytokine-blocking moiety fusion protein, the cytokine polypeptide is first tagged at the N-terminus with a polyglycine sequence, or alternatively, with at the C-terminus with a LPXTG motif (SEQ ID NO.: 442). The blocking moiety or other element has respective peptides attached that serve as acceptor sites for the tagged polypeptides. For conjugation to domains carrying a LPXTG (SEQ ID NO.: 442) acceptor peptide attached via its N-terminus, the polypeptide will be tagged with an N-terminal poly-glycine stretch. For conjugation to domain carrying a poly-glycine peptide attached via its C-terminus, the polypeptide will be tagged at its C-terminus with a LPXTG (SEQ ID NO.: 442) sortase recognition sequence. Recognizing poly-glycine and LPXTG (SEQ ID NO.: 442) sequences, sortase will form a peptide bond between polymer-peptide and tagged polypeptides. The sortase reaction cleaves off glycine residues as intermediates and occurs at room temperature.

A variety of mechanisms can be exploited to remove or reduce the inhibition caused by the blocking moiety. For example, the pharmaceutical compositions can include a cytokine moiety and a blocking moiety, e.g. a steric blocking moiety, with a protease cleavable linker comprising a protease cleavage site located between the cytokine and cytokine blocking moiety or within the cytokine blocking moiety. When the protease cleavage site is cleaved, the blocking moiety can dissociate from cytokine, and the cytokine can then activate cytokine receptor. A cytokine moiety can also be blocked by a specific blocking moiety, such as an antibody, which binds an epitope found on the relevant cytokine.

Any suitable linker can be used. For example, the linker can comprise glycine-glycine, a sortase-recognition motif, or a sortase-recognition motif and a peptide sequence $(Gly_4Ser)_n$(SEQ ID NO.: 443) or $(Gly_3Ser)_n$, (SEQ ID NO.: 444) wherein n is 1, 2, 3, 4 or 5. Typically, the sortase-recognition motif comprises a peptide sequence LPXTG (SEQ ID NO.: 442), where X is any amino acid. In some embodiments, the covalent linkage is between a reactive lysine residue attached to the C-terminal of the cytokine polypeptide and a reactive aspartic acid attached to the N-terminal of the blocker or other domain. In other embodiments, the covalent linkage is between a reactive aspartic acid residue attached to the N-terminal of the cytokine polypeptide and a reactive lysine residue attached to the C-terminal of said blocker or other domain.

Accordingly, as described in detail herein, the cytokine blocking moieties used can be steric blockers. As used herein, a "steric blocker" refers to a polypeptide or polypeptide moiety that can be covalently bonded to a cytokine polypeptide directly or indirectly through other moieties such as linkers, for example in the form of a chimeric polypeptide (fusion protein), but otherwise does not covalently bond to the cytokine polypeptide. A steric blocker can non-covalently bond to the cytokine polypeptide, for example though electrostatic, hydrophobic, ionic or hydrogen bonding. A steric blocker typically inhibits or blocks the activity of the cytokine moiety due to its proximity to the cytokine moiety and comparative size. The steric inhibition of the cytokine moiety can be removed by spatially separating the cytokine moiety from the steric blocker, such as by enzymatically cleaving a fusion protein that contains a steric blocker and a cytokine polypeptide at a site between the steric blocker and the cytokine polypeptide.

As described in greater detail herein, the blocking function can be combined with or due to the presence of additional functional components in the pharmaceutical composition, such as a targeting domain, a serum half-life extension element, and protease-cleavable linking polypeptides. For example, a serum half-life extending polypeptide can also be a steric blocker.

In the interest of presenting a concise disclosure of the full scope of the invention, aspects of the invention are described in detail using the cytokine IL-2 as an exemplary cytokine. However, the invention and this disclosure are not limited to IL-2. It will be clear to a person of skill in the art that this disclosure, including the disclosed methods, polypeptides and nucleic acids, adequately describes and enables the use of other cytokines, fragments, variants, cytokine subunits, and muteins, such as IL-2, IL-7, IL-12, IL-15, IL-18, IL-21 IL-23, IFNalpha, IFNbeta, IFNgamma, TNFalpha, lymphotoxin, TGF-beta1, TGFbeta2, TGFbeta3, GM-CSF, CXCL10, CCL19, CCL20, CCL21 and functional fragments or muteins of any of the foregoing. Preferred cytokines for use in the fusion proteins disclosed herein are IL-2, IL-12, IFNalpha, IFNbeta, IFNgamma, muteins, functional variants, and functional fragments, or subunits of any of the foregoing. For example, the cytokine a IL-12 cytokine may be a p35 subunit, a p40 subunit, a heterodimer.

Various elements ensure the delivery and activity of IL-2 preferentially at the site of desired IL-2 activity and to severely limit systemic exposure to the interleukin via a blocking and/or a targeting strategy preferentially linked to a serum half-life extension strategy. In this serum half-life extension strategy, the blocked version of interleukin circulates for extended times (preferentially 1-2 or more weeks) but the activated version has the typical serum half-life of the interleukin.

By comparison to a serum half-life extended version, the serum half-life of IL-2 administered intravenously is only ~10 minutes due to distribution into the total body extracellular space, which is large, ~15 L in an average sized adult. Subsequently, IL-2 is metabolized by the kidneys with a half-life of ~2.5 hours. (Smith, K. "Interleukin 2 immunotherapy." *Therapeutic Immunology* 240 (2001)). By other measurements, IL-2 has a very short plasma half-life of 85 minutes for intravenous administration and 3.3 hours subcutaneous administration (Kirchner, G. I., et al., 1998, Br J Clin Pharmacol. 46:5-10). In some embodiments of this invention, the half-life extension element is linked to the interleukin via a linker which is cleaved at the site of action (e.g. by inflammation-specific or tumor-specific proteases) releasing the interleukin's full activity at the desired site and also separating it from the half-life extension of the uncleaved version. In such embodiments, the fully active and free interleukin would have very different pharmacokinetic (pK) properties—a half-life of hours instead of weeks. In addition, exposure to active cytokine is limited to the site of desired cytokine activity (e.g., an inflammatory site or tumor) and systemic exposure to active cytokine, and associated toxicity and side effects, are reduced.

Other cytokines envisioned in this invention have similar pharmacology (e.g. IL-15 as reported by Blood 2011 117: 4787-4795; doi: doi.org/10.1182/blood-2010-10-311456) as IL-2 and accordingly, the designs of this invention address the shortcomings of using these agents directly, and provide chimeric polypeptides that can have extended half-life and/or be targeted to a site of desired activity (e.g., a site of inflammation or a tumor).

If desired, IL-2 can be engineered to bind the IL-2R complex generally or one of the three IL-2R subunits specifically with an affinity that differs from that of the corresponding wild-type IL-2, for example toto selectively activate Tregs or Teff. For example, IL-2 polypeptides that are said to have higher affinity for the trimeric form of the IL-2 receptor relative to the dimeric beta/gamma form of the I1-2 receptor in comparison to wild type IL-2 can have an amino acid sequence that includes one of the following sets of mutations with respect to SEQ ID NO:1 (a mature IL-2 protein comprising amino acids 21-153 of human IL-2 having the Uniprot Accession No. P60568-1): (a) K64R, V69A, and Q74P; (b) V69A, Q74P, and T101A; (c) V69A, Q74P, and 1128T; (d) N30D, V69A, Q74P, and F103S; (e) K49E, V69A, A73V, and K76E; (f) V69A, Q74P, T101A, and T133N; (g) N30S, V69A, Q74P, and I128A; (h) V69A, Q74P, N88D, and S99P; (i) N30S, V69A, Q74P, and I128T; (j) K9T, Q11R, K35R, V69A, and Q74P; (k) A1T, M46L, K49R, E61D, V69A, and H79R; (1) K48E, E68D, N71T, N90H, F103S, and 1114V; (m) S4P, T10A, Q11R, V69A, Q74P, N88D, and T133A; (n) E15K, N30S Y31H, K35R, K48E, V69A, Q74P, and I92T; (o) N30S, E68D, V69A, N71A, Q74P, S75P, K76R, and N90H; (p) N30S, Y31C, T37A, V69A, A73V, Q74P, H79R, and I128T; (q) N26D, N29S, N30S, K54R, E67G, V69A, Q74P, and I92T; (r) K8R, Q13R, N26D, N30T, K35R, T37R, V69A, Q74P, and I92T; and (s) N29S, Y31H, K35R, T37A, K48E, V69A, N71R, Q74P, N88D, and 189V. This approach can also be applied to prepare muteins of other cytokines including interleukins (e.g., IL-2, IL-7, IL-12, IL-15, IL-18, IL-23), interferons (IFNs, including IFNalpha, IFNbeta and IFNgamma), tumor necrosis factors (e.g., TNFalpha, lymphotoxin), transforming growth factors (e.g., TGFbeta1, TGFbeta2, TGFbeta3) and granulocyte macrophage-colony stimulating factor (GM-CS). For example, muteins can be prepared that have desired binding affinity for a cognate receptor.

As noted above, any of the mutant IL-2 polypeptides disclosed herein can include the sequences described; they can also be limited to the sequences described and otherwise identical to SEQ ID NO:1. Moreover, any of the mutant IL-2 polypeptides disclosed herein can optionally include a substitution of the cysteine residue at position 125 with another residue (e.g., serine) and/or can optionally include a deletion of the alanine residue at position 1 of SEQ ID NO:1.

Another approach to improving the therapeutic index of an IL-2 based therapy is to optimize the pharmacokinetics of the molecule to maximally activate Treg cells. Early studies of IL-2 action demonstrated that IL-2 stimulation of human T cell proliferation in vitro required a minimum of 5-6 hours exposure to effective concentrations of IL-2 (Cantrell, D. A., et. al., 1984, Science, 224: 1312-1316). When administered to human patients, IL-2 has a very short plasma half-life of 85 minutes for intravenous administration and 3.3 hours subcutaneous administration (Kirchner, G. I., et al., 1998, Br J Clin Pharmacol. 46:5-10). Because of its short half-life, maintaining circulating IL-2 at or above the level necessary to stimulate T cell proliferation for the necessary duration necessitates high doses that result in peak IL-2 levels significantly above the EC50 for Treg cells or will require frequent administration. These high IL-2 peak levels can activate IL2Rβγ receptors and have other unintended or adverse effects, for example VLS as noted above. An IL-2 analog, or a multifunctional protein with IL-2 attached to a domain that enables binding to the FcRn receptor, with a longer circulating half-life than IL-2 can achieve a target drug concentration for a specified period of time at a lower dose than IL-2, and with lower peak levels. Such an IL-2 analog will therefore require either lower doses or less frequent administration than IL-2 to effectively stimulate Treg cells. Less frequent subcutaneous administration of an IL-2 drug will also be more tolerable for patients. A therapeutic with these characteristics will translate clinically into improved pharmacological efficacy, reduced toxicity, and improved patient compliance with therapy. Alternatively, IL-2 or muteins of IL-2 (herein, "IL-2*") can be selectively targeted to the intended site of action (e.g. sites of inflammation or a tumor). This targeting can be achieved by one of several strategies, including the addition of domains to the administered agent that comprise blockers of the IL-2 (or muteins) that are cleaved away or by targeting domains or a combination of the two.

In some embodiments, IL-2* partial agonists can be tailored to bind with higher or lower affinity depending on the desired target; for example, an IL-2* can be engineered to bind with enhanced affinity to one of the receptor subunits and not the others. These types of partial agonists, unlike full agonists or complete antagonists, offer the ability to tune the signaling properties to an amplitude that elicits desired functional properties while not meeting thresholds for undesired properties. Given the differential activities of the partial agonists, a repertoire of IL-2 variants could be engineered to exhibit an even finer degree of distinctive signaling activities, ranging from almost full to partial agonism to complete antagonism.

In some embodiments, the IL-2* has altered affinity for IL-2Rα. In some embodiments, the IL-2* has a higher affinity for IL-2Rα than wild-type IL-2. In other embodiments, the IL-2* has altered affinity for IL-2Rβ. In one embodiment, IL-2* has enhanced binding affinity for IL-2Rβ, e.g., the N-terminus of IL-2Rβ, that eliminates the functional requirement for IL-2Rα. In another embodiment, an IL-2* is generated that has increased binding affinity for IL-2Rβ but that exhibited decreased binding to IL-2Rγ, and thereby is defective IL-2Rβγ heterodimerization and signaling.

Blocking moieties, described in further detail below, can also be used to favor binding to or activation of one or more receptors. In one embodiment, blocking moieties are added such that IL-2Rβγ binding or activation is blocked but IL-2Rα binding or activation is not changed. In another embodiment, blocking moieties are added such that IL-2Rα binding or activation is diminished. In another embodiment, blocking moieties are added such that binding to and or activation of all three receptors is inhibited. This blocking may be relievable by removal of the blocking moieties in a particular environment, for example by proteolytic cleavage of a linker linking one or more blocking moieties to the cytokine.

A similar approach can be applied to improve other cytokines, particularly for use as immunostimulatory agents, for example for treating cancer. For example, in this aspect, the pharmacokinetics and/or pharmacodynamics of the cytokine (e.g., IL-2, IL-7, IL-12, IL-15, IL-18, IL-21 IL-23, IFNalpha, IFNbeta and IFNgamma, TNFalpha, lymphotoxin, TGFbeta1, TGFbeta2, TGFbeta3 GM-CSF, CXCL10, CCL19, CCL20, and CCL21 can be tailored to maximally activate effector cells (e.g., effect T cells, NK cells) and/or cytotoxic immune response promoting cells (e.g., induce dendritic cell maturation) at a site of desired activity, such as in a tumor, but preferably not systemically.

Thus, provided herein are pharmaceutical compositions comprising at least one cytokine polypeptide, such as interleukins (e.g., IL-2, IL-7, IL-12, IL-15, IL-18, IL-21, IL-23), interferons (IFNs, including IFNalpha, IFNbeta and IFNgamma), tumor necrosis factors (e.g., TNFalpha, lymphotoxin), transforming growth factors (e.g., TGFbeta1, TGFbeta2, TGFbeta3), chemokines (e.g. CXCL10, CCL19, CCL20, CCL21) and granulocyte macrophage-colony stimulating factor (GM-CS) or a functional fragment or mutein of any of the foregoing. The polypeptide typically also includes at least one linker amino acid sequence, wherein the amino acid sequence is in certain embodiments capable of being cleaved by an endogenous protease. In one embodiment, the linker comprises an amino acid sequence comprising HSSKLQ (SEQ ID NO.: 25), GPLGVRG (SEQ ID NO.: 445), IPVSLRSG (SEQ ID NO.: 446), VPLSLYSG (SEQ ID NO. 447), or SGESPAYYTA (SEQ ID NO. 448). In other embodiments, the chimeric polypeptide further contains a blocking moiety, e.g. a steric blocking polypeptide moiety, capable of blocking the activity of the interleukin polypeptide. The blocking moiety, for example, can comprise a human serum albumin (HSA) binding domain or an optionally branched or multi-armed polyethylene glycol (PEG). Alternatively, the pharmaceutical composition comprises a first cytokine polypeptide or a fragment thereof, and blocking moiety, e.g. a steric blocking polypeptide moiety, wherein the blocking moiety blocks the activity of the cytokine polypeptide on the cytokine receptor, and wherein the blocking moiety in certain embodiments comprises a protease cleavable domain. In some embodiments, blockade and reduction of cytokine activity is achieved simply by attaching additional domains with very short linkers to the N or C terminus of the interleukin domain. In such embodiments, it is anticipated the blockade is relieved by protease digestion of the blocking moiety or of the short linker that tethers the blocker to the interleukin. Once the domain is clipped or is released, it will no longer be able to achieve blockade of cytokine activity.

The pharmaceutical composition e.g., chimeric polypeptide can comprise two or more cytokines, which can be the same cytokine polypeptide or different cytokine polypeptides. For example, the two or more different types of cytokines have complementary functions. In some examples, a first cytokine is IL-2 and a second cytokine is IL-12. In some embodiments, each of the two or more different types of cytokine polypeptides have activities that modulate the activity of the other cytokine polypeptides. In some examples of chimeric polypeptides that contain two cytokine polypeptides, a first cytokine polypeptide is T-cell activating, and a second cytokine polypeptide is non-T-cell-activating. In some examples of chimeric polypeptides that contain two cytokine polypeptides, a first cytokine is a chemoattractant, e.g. CXCL10, and a second cytokine is an immune cell activator.

Preferably, the cytokine polypeptides (including functional fragments) that are included in the fusion proteins disclosed herein are not mutated or engineered to alter the properties of the naturally occurring cytokine, including receptor binding affinity and specificity or serum half-life. However, changes in amino acid sequence from naturally occurring (including wild type) cytokine are acceptable to facilitate cloning and to achieve desired expression levels, for example.

Blocking Moiety

The blocking moiety can be any moiety that inhibits the ability of the cytokine to bind and/or activate its receptor. The blocking moiety can inhibit the ability of the cytokine to bind and/or activate its receptor sterically blocking and/or by noncovalently binding to the cytokine. Examples of suitable blocking moieties include the full length or a cytokine-binding fragment or mutein of the cognate receptor of the cytokine. Antibodies and fragments thereof including, a polyclonal antibody, a recombinant antibody, a human antibody, a humanized antibody a single chain variable fragment (scFv), single-domain antibody such as a heavy chain variable domain (VH), a light chain variable domain (VL) and a variable domain of camelid-type nanobody (VHH), a dAb and the like that bind the cytokine can also be used. Other suitable antigen-binding domain that bind the cytokine can also be used, include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocallin and CTLA4 scaffolds. Further examples of suitable blocking polypeptides include polypeptides that sterically inhibit or block binding of the cytokine to its cognate receptor. Advantageously, such moieties can also function as half-life extending elements. For example, a peptide that is modified by conjugation to a water-soluble polymer, such as PEG, can sterically inhibit or prevent binding of the cytokine to its receptor. Polypeptides, or fragments thereof, that have long serum half-lives can also be used, such as serum albumin (human serum albumin), immunoglobulin Fc, transferrin and the like, as well as fragments and muteins of such polypeptides. Antibodies and antigen-binding domains that bind to, for example, a protein with a long serum half-life such as HSA, immunoglobulin or transferrin, or to a receptor that is recycled to the plasma membrane, such as FcRn or transferrin receptor, can also inhibit the cytokine, particularly when bound to their antigen. Examples of such antigen-binding polypeptides include a single chain variable fragment (scFv), single-domain antibody such as a heavy chain variable domain (VH), a light chain variable domain (VL) and a variable domain of camelid-type nanobody (VHH), a dAb and the like. Other suitable antigen-binding domain that bind the cytokine can also be used, include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocallin and CTLA4 scaffolds.

In illustrative examples, when IL-2 is the cytokine in the chimeric polypeptide, the blocking moiety can be the full length or fragment or mutein of the alpha chain of IL-2 receptor (IL-2Rα) or beta (IL-2Rβ) or gamma chain of IL-2 receptor (IL-2Rγ), an anti-IL-2 single-domain antibody (dAb) or scFv, a Fab, an anti-CD25 antibody or fragment thereof, and anti-HSA dAb or scFv, and the like. As described further herein, when an antibody fragement is used to attenuate the activity of the cytokine polypeptide, the blocking moiety in the fusion protein can be a single chain antibody binding fragment, such as an scFv. The blocking moiety can also be half of a two chain antigen binding fragment such as a VH-CH1, which associates with a complementary VL-CL on a second polypeptide for form an antibody binding site the binds the cytokine polypeptide.

In vivo Half-life Extension Elements

Preferably, the chimeric polypeptides comprise an in vivo half-life extension element. Increasing the in vivo half-life of therapeutic molecules with naturally short half-lives allows for a more acceptable and manageable dosing regimen without sacrificing effectiveness. As used herein, a "half-life extension element" is a part of the chimeric polypeptide that increases the in vivo half-life and improve pK, for example, by altering its size (e.g., to be above the kidney filtration cutoff), shape, hydrodynamic radius, charge, or parameters of absorption, biodistribution, metabolism, and elimination. An exemplary way to improve the pK of a polypeptide is by expression of an element in the polypeptide chain that binds to receptors that are recycled to the plasma membrane of cells rather than degraded in the lysosomes, such as the FcRn receptor on endothelial cells and transferrin receptor. Three types of proteins, e.g., human IgGs, HSA (or fragments), and transferrin, persist for much longer in human serum than would be predicted just by their size, which is a function of their ability to bind to receptors that are recycled rather than degraded in the lysosome. These proteins, or fragments of them that retain the FcRn binding are routinely linked to other polypeptides to extend their serum half-life. In one embodiment, the half-life extension element is a human serum albumin (HSA) binding domain. HSA (SEQ ID NO: 2) may also be directly bound to the pharmaceutical compositions or bound via a short linker. Fragments of HSA may also be used. HSA and fragments thereof can function as both a blocking moiety and a half-life extension element. Human IgGs and Fc fragments can also carry out a similar function.

The serum half-life extension element can also be antigen-binding polypeptide that binds to a protein with a long serum half-life such as serum albumin, transferrin and the like. Examples of such polypeptides include antibodies and fragments thereof including, a polyclonal antibody, a recombinant antibody, a human antibody, a humanized antibody a single chain variable fragment (scFv), single-domain antibody such as a heavy chain variable domain (VH), a light chain variable domain (VL) and a variable domain of camelid-type nanobody (VHH), a dAb and the like. Other suitable antigen-binding domain include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocallin and CTLA4 scaffolds. Further examples of antigen-binding polypeptides include a ligand for a desired receptor, a ligand-binding portion of a receptor, a lectin, and peptides that binds to or associates with one or more target antigens.

Some preferred serum half-life extension elements are polypeptides that comprise complementarity determining regions (CDRs), and optionally non-CDR loops. Advantageously, such serum half-life extension elements can extend the serum half-life of the cytokine, and also function as inhibitors of the cytokine (e.g., via steric blocking, non-covalent interaction or combination thereof) and/or as targeting domains. In some instances, the serum half-life extension elements are domains derived from an immunoglobulin molecule (Ig molecule) or engineered protein scaffolds that mimic antibody structure and/or binding activity. The Ig may be of any class or subclass (IgG1, IgG2, IgG3, IgG4, IgA, IgE, IgM etc). A polypeptide chain of an Ig molecule folds into a series of parallel beta strands linked by loops. In the variable region, three of the loops constitute the "complementarity determining regions" (CDRs) which determine the antigen binding specificity of the molecule. An IgG molecule comprises at least two heavy (H) chains and two light (L) chains inter-connected by disulfide bonds, or an antigen binding fragment thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs) with are hypervariable in sequence and/or involved in antigen recognition and/or usually form structurally defined loops, interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In some embodiments of this disclosure, at least some or all of the amino acid sequences of FR1, FR2, FR3, and FR4 are part of the "non-CDR loop" of the binding moieties described herein. A variable domain of an immunoglobulin molecule has several beta strands that are arranged in two sheets. The variable domains of both light and heavy immunoglobulin chains contain three hypervariable loops, or complementarity-determining regions (CDRs). The three CDRs of a V domain (CDR1, CDR2, CDR3) cluster at one end of the beta barrel. The CDRs are the loops that connect beta strands B-C, C'-C", and F-G of the immunoglobulin fold, whereas the bottom loops that connect beta strands AB, CC', C"-D and E-F of the immunoglobulin fold, and the top loop that connects the D-E strands of the immunoglobulin fold are the non-CDR loops. In some embodiments of this disclosure, at least some amino acid residues of a constant domain, CH1, CH2, or CH3, are part of the "non-CDR loop" of the binding moieties described herein. Non-CDR loops comprise, in some embodiments, one or more of AB, CD, EF, and DE loops of a C1-set domain of an Ig or an Ig-like molecule; AB, CC', EF, FG, BC, and EC' loops of a C2-set domain of an Ig or an Ig-like molecule; DE, BD, GF, A(A1A2)B, and EF loops of I(Intermediate)-set domain of an Ig or Ig-like molecule.

Within the variable domain, the CDRs are believed to be responsible for antigen recognition and binding, while the FR residues are considered a scaffold for the CDRs. However, in certain cases, some of the FR residues play an important role in antigen recognition and binding. Framework region residues that affect Ag binding are divided into two categories. The first are FR residues that contact the antigen, thus are part of the binding-site, and some of these residues are close in sequence to the CDRs. Other residues are those that are far from the CDRs in sequence, but are in close proximity to it in the 3-D structure of the molecule, e.g., a loop in heavy chain.

The binding moieties are any kinds of polypeptides. For example, in certain instances the binding moieties are natural peptides, synthetic peptides, or fibronectin scaffolds, or engineered bulk serum proteins. The bulk serum protein comprises, for example, albumin, fibrinogen, or a globulin. In some embodiments, the binding moieties are engineered scaffolds. Engineered scaffolds comprise, for example, sdAb, a scFv, a Fab, a VHH, a fibronectin type III domain, immunoglobulin-like scaffold (as suggested in Halaby et al., 1999. Prot Eng 12(7):563-571), DARPin, cystine knot peptide, lipocalin, three-helix bundle scaffold, protein G-related albumin-binding module, or a DNA or RNA aptamer scaffold.

In some cases, the serum half-life extending element comprises a binding site for a bulk serum protein. In some embodiments, the CDRs provide the binding site for the bulk serum protein. The bulk serum protein is, in some examples, a globulin, albumin, transferrin, IgG1, IgG2, IgG4, IgG3, IgA monomer, Factor XIII, Fibrinogen, IgE, or pentameric IgM. In some embodiments, the CDR form a binding site for an immunoglobulin light chain, such as an Igκ free light chain or an Igλ free light chain.

The serum half-life extension element can be any type of binding domain, including but not limited to, domains from a monoclonal antibody, a polyclonal antibody, a recombinant antibody, a human antibody, a humanized antibody. In some embodiments, the binding moiety is a single chain variable fragment (scFv), single-domain antibody such as a heavy chain variable domain (VH), a light chain variable domain (VL) and a variable domain (VHH) of camelid derived nanobody. In other embodiments, the binding moieties are non-Ig binding domains, i.e., antibody mimetic, such as anticalins, affilins, affibody molecules, affimers, affitins, alphabodies, avimers, DARPins, fynomers, kunitz domain peptides, and monobodies.

In other embodiments, the serum half-life extension element can be a water-soluble polymer or a peptide that is conjugated to a water-soluble polymer, such as PEG. "PEG," "polyethylene glycol" and "poly(ethylene glycol)" as used herein, are interchangeable and encompass any nonpeptidic water-soluble poly(ethylene oxide). The term "PEG" also means a polymer that contains a majority, that is to say, greater than 50%, of $—OCH_2CH_2—$ repeating subunits. With respect to specific forms, the PEG can take any number of a variety of molecular weights, as well as structures or geometries such as "branched," "linear," "forked," "multifunctional," and the like, to be described in greater detail below. The PEG is not limited to a particular structure and can be linear (e.g., an end capped, e.g., alkoxy PEG or a bifunctional PEG), branched or multi-armed (e.g., forked PEG or PEG attached to a polyol core), a dendritic (or star) architecture, each with or without one or more degradable linkages. Moreover, the internal structure of the PEG can be organized in any number of different repeat patterns and can be selected from the group consisting of homopolymer, alternating copolymer, random copolymer, block copolymer, alternating tripolymer, random tripolymer, and block tripolymer. PEGs can be conjugated to polypeptide and peptides through any suitable method. Typically, a reactive PEG derivative, such as N-hydroxysuccinamidyl ester PEG, is reacted with a peptide or polypeptide that includes amino acids with a side chain that contains an amine, sulfhydryl, carboxylic acid or hydroxyl functional group, such as cysteine, lysine, asparagine, glutamine, theonine, tyrosine, serine, aspartic acid, and glutamic acid.

Targeting and Retention Domains

For certain applications, it may be desirable to maximize the amount of time the construct is present in its desired location in the body. This can be achieved by including one further domain in the chimeric polypeptide (fusion protein)

to influence its movements within the body. For example, the chimeric nucleic acids can encode a domain that directs the polypeptide to a location in the body, e.g., tumor cells or a site of inflammation; this domain is termed a "targeting domain" and/or encode a domain that retains the polypeptide in a location in the body, e.g., tumor cells or a site of inflammation; this domain is termed a "retention domain". In some embodiments a domain can function as both a targeting and a retention domain. In some embodiments, the targeting domain and/or retention domain are specific to a protease-rich environment. In some embodiments, the encoded targeting domain and/or retention domain are specific for regulatory T cells (Tregs), for example targeting the CCR4 or CD39 receptors. Other suitable targeting and/or retention domains comprise those that have a cognate ligand that is overexpressed in inflamed tissues, e.g., the IL-1 receptor, or the IL-6 receptor. In other embodiments, the suitable targeting and/or retention domains comprise those who have a cognate ligand that is overexpressed in tumor tissue, e.g., Epcam, CEA or mesothelin. In some embodiments, the targeting domain is linked to the interleukin via a linker which is cleaved at the site of action (e.g. by inflammation or cancer specific proteases) releasing the interleukin full activity at the desired site. In some embodiments, the targeting and/or retention domain is linked to the interleukin via a linker which is not cleaved at the site of action (e.g. by inflammation or cancer specific proteases), causing the cytokine to remain at the desired site.

Antigens of choice, in some cases, are expressed on the surface of a diseased cell or tissue, for example a tumor or a cancer cell. Antigens useful for tumor targeting and retention include but are not limited to EpCAM, EGFR, HER-2, HER-3, c-Met, FOLR1, and CEA. Pharmaceutical compositions disclosed herein, also include proteins comprising two targeting and/or retention domains that bind to two different target antigens known to be expressed on a diseased cell or tissue. Exemplary pairs of antigen binding domains include but are not limited to EGFR/CEA, EpCAM/CEA, and HER-2/HER-3.

Suitable targeting and/or retention domains include antigen-binding domains, such as antibodies and fragments thereof including, a polyclonal antibody, a recombinant antibody, a human antibody, a humanized antibody a single chain variable fragment (scFv), single-domain antibody such as a heavy chain variable domain (VH), a light chain variable domain (VL) and a variable domain of camelid-type nanobody (VHH), a dAb and the like. Other suitable antigen-binding domain include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocallin and CTLA4 scaffolds. Further examples of antigen-binding polypeptides include a ligand for a desired receptor, a ligand-binding portion of a receptor, a lectin, and peptides that binds to or associates with one or more target antigens.

In some embodiments, the targeting and/or retention domains specifically bind to a cell surface molecule. In some embodiments, the targeting and/or retention domains specifically bind to a tumor antigen. In some embodiments, the targeting polypeptides specifically and independently bind to a tumor antigen selected from at least one of Fibroblast activation protein alpha (FAPa), Trophoblast glycoprotein (5T4), Tumor-associated calcium signal transducer 2 (Trop2), Fibronectin EDB (EDB-FN), fibronectin EIIIB domain, CGS-2, EpCAM, EGFR, HER-2, HER-3, cMet, CEA, and FOLR1. In some embodiments, the targeting polypeptides specifically and independently bind to two different antigens, wherein at least one of the antigens is a tumor antigen selected from EpCAM, EGFR, HER-2, HER-3, cMet, CEA, and FOLR1.

The targeting and/or retention antigen can be a tumor antigen expressed on a tumor cell. Tumor antigens are well known in the art and include, for example, EpCAM, EGFR, HER-2, HER-3, c-Met, FOLR1, PSMA, CD38, BCMA, and CEA. 5T4, AFP, B7-H3, Cadherin-6, CAIX, CD117, CD123, CD138, CD166, CD19, CD20, CD205, CD22, CD30, CD33, CD352, CD37, CD44, CD52, CD56, CD70, CD71, CD74, CD79b, DLL3, EphA2, FAP, FGFR2, FGFR3, GPC3, gpA33, FLT-3, gpNMB, HPV-16 E6, HPV-16 E7, ITGA2, ITGA3, SLC39A6, MAGE, mesothelin, Muc1, Muc16, NaPi2b, Nectin-4, P-cadherin, NY-ESO-1, PRLR, PSCA, PTK7, ROR1, SLC44A4, SLTRK5, SLTRK6, STEAP1, TIM1, Trop2, WT1.

The targeting and/or retention antigen can be an immune checkpoint protein. Examples of immune checkpoint proteins include but are not limited to CD27, CD137, 2B4, TIGIT, CD155, ICOS, HVEM, CD40L, LIGHT, TIM-1, OX40, DNAM-1, PD-L1, PD1, PD-L2, CTLA-4, CD8, CD40, CEACAM1, CD48, CD70, A2AR, CD39, CD73, B7-H3, B7-H4, BTLA, IDO1, IDO2, TDO, KIR, LAG-3, TIM-3, or VISTA.

The targeting and/or retention antigen can be a cell surface molecule such as a protein, lipid or polysaccharide. In some embodiments, a targeting and/or retention antigen is a on a tumor cell, virally infected cell, bacterially infected cell, damaged red blood cell, arterial plaque cell, inflamed or fibrotic tissue cell. The targeting and/or retention antigen can comprise an immune response modulator. Examples of immune response modulator include but are not limited to granulocyte-macrophage colony stimulating factor (GM-CSF), macrophage colony stimulating factor (M-CSF), granulocyte colony stimulating factor (G-CSF), interleukin 2 (IL-2), interleukin 3 (IL-3), interleukin 12 (IL-12), interleukin 15 (IL-15), B7-1 (CD80), B7-2 (CD86), GITRL, CD3, or GITR.

The targeting and/or retention antigen can be a cytokine receptor. Examples, of cytokine receptors include but are not limited to Type I cytokine receptors, such as GM-CSF receptor, G-CSF receptor, Type I IL receptors, Epo receptor, LIF receptor, CNTF receptor, TPO receptor, Type II Cytokine receptors, such as IFN-alpha receptor (IFNAR1, IFNAR2), IFB-beta receptor, IFN-gamma receptor (IFNGR1, IFNGR2), Type II IL receptors; chemokine receptors, such as CC chemokine receptors, CXC chemokine receptors, CX3C chemokine receptors, XC chemokine receptors; tumor necrosis receptor superfamily receptors, such as TNFRSF5/CD40, TNFRSF8/CD30, TNFRSF7/CD27, TNFRSF1A/TNFR1/CD120a, TNFRSF1B/TNFR2/CD120b; TGF-beta receptors, such as TGF-beta receptor 1, TGF-beta receptor 2; Ig super family receptors, such as IL-1 receptors, CSF-1R, PDGFR (PDGFRA, PDGFRB), SCFR.

Linkers

As stated above, the pharmaceutical compositions comprise one or more linker sequences. A linker sequence serves to provide flexibility between polypeptides, such that, for example, the blocking moiety is capable of inhibiting the activity of the cytokine polypeptide. The linker sequence can be located between any or all of the cytokine polypeptide, the serum half-life extension element, and/or the blocking moiety. As described herein at least one of the linkers is protease cleavable, and contains a (one or more) cleavage site for a (one or more) desired protease. Preferably, the desired protease is enriched or selectively expressed at the desired site of cytokine activity (e.g., the tumor microenvironment). Thus, the fusion protein is preferentially or selectively cleaved at the site of desired cytokine activity.

Suitable linkers can be of different lengths, such as from 1 amino acid (e.g., Gly) to 20 amino acids, from 2 amino acids to 15 amino acids, from 3 amino acids to 12 amino acids, including 4 amino acids to 10 amino acids, amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids.

The orientation of the components of the pharmaceutical composition, are largely a matter of design choice and it is recognized that multiple orientations are possible and all are intended to be encompassed by this disclosure. For example, a blocking moiety can be located C-terminally or N-terminally to a cytokine polypeptide.

Proteases known to be associated with diseased cells or tissues include but are not limited to serine proteases, cysteine proteases, aspartate proteases, threonine proteases, glutamic acid proteases, metalloproteases, asparagine peptide lyases, serum proteases, cathepsins, Cathepsin B, Cathepsin C, Cathepsin D, Cathepsin E, Cathepsin K, Cathepsin L, kallikreins, hK1, hK10, hK15, plasmin, collagenase, Type IV collagenase, stromelysin, Factor Xa, chymotrypsin-like protease, trypsin-like protease, elastase-like protease, subtilisin-like protease, actinidain, bromelain, calpain, caspases, caspase-3, Mir-CP, papain, HIV-protease, HSV protease, CMV protease, chymosin, renin, pepsin, matriptase, legumain, plasmepsin, nepenthesin, metalloexopeptidases, metallendopeptidases, matrix metalloproteases (MMP), MMP1, MMP2, MMP3, MMP8, MMP9, MMP13, MMP11, MMP14, urokinase plasminogen activator (uPA), enterokinase, prostate-specific antigen (PSA, hK3), interleukin-10β converting enzyme, thrombin, FAP (FAP-a), dipeptidyl peptidase, meprins, granzymes and dipeptidyl peptidase IV (DPPIV/CD26). Proteases capable of cleaving amino acid sequences encoded by the chimeric nucleic acid sequences provided herein can, for example, be selected from the group consisting of a prostate specific antigen (PSA), a matrix metalloproteinase (MMP), an A Disintigrin and a Metalloproteinase (ADAM), a plasminogen activator, a cathepsin, a caspase, a tumor cell surface protease, and an elastase. The MMP can, for example, be matrix metalloproteinase 2 (MMP2) or matrix metalloproteinase 9 (MMP9).

Proteases useful in the methods disclosed herein are presented in Table 1, and exemplary proteases and their cleavage site are presented in Table 1a:

TABLE 1

Proteases relevant to inflammation and cancer

| Protease | Specificity | Other aspects |
|---|---|---|
| Secreted by killer T cells: | | |
| Granzyme B (grB) | Cleaves after Asp residues (asp-ase) | Type of serine protease; strongly implicated in inducing perforin-dependent target cell apoptosis |
| Granzyme A (grA) | trypsin-like, cleaves after basic residues | Type of serine protease; |
| Granzyme H (grH) | Unknown substrate specificity | Type of serine protease; Other granzymes are also secreted by killer T cells, but not all are present in humans |
| Caspase-8 | Cleaves after Asp residues | Type of cysteine protease; plays essential role in TCR-induced cellular expansion-exact molecular role unclear |
| Mucosa-associated lymphoid tissue (MALT1) | Cleaves after arginine residues | Type of cysteine protease; likely acts both as a scaffold and proteolytically active enzyme in the CBM-dependent signaling pathway |
| Tryptase | Targets: angiotensin I, fibrinogen, prourokinase, TGFβ; preferentially cleaves proteins after lysine or arginine residues | Type of mast cell-specific serine protease; trypsin-like; resistant to inhibition by macromolecular protease inhibitors expressed in mammals due to their tetrameric structure, with all sites facing narrow central pore; also associated with inflammation |
| Associated with inflammation: | | |
| Thrombin | Targets: FGF-2, HB-EGF, Osteo-pontin, PDGF, VEGF | Type of serine protease; modulates activity of vascular growth factors, chemokines and extracellular proteins; strengthens VEGF-induced proliferation; induces cell migration; angiogenic factor; regulates hemostasis |
| Chymase | Exhibit chymotrypsin-like specificity, cleaving proteins after aromatic amino acid residues | Type of mast cell-specific serine protease |
| Carboxypeptidase A (MC-CPA) | Cleaves amino acid residues from C-terminal end of peptides and proteins | Type of zinc-dependent metalloproteinase |

TABLE 1-continued

| Proteases relevant to inflammation and cancer | | |
|---|---|---|
| Protease | Specificity | Other aspects |
| Kallikreins | Targets: high molecular weight kininogen, pro-urokinase | Type of serine protease; modulate relaxation response; contribute to inflammatory response; fibrin degradation |
| Elastase | Targets: E-cadherin, GM-CSF, IL-1, IL-2, IL-6, IL8, $p38^{MAPK}$, TNFα, VE-cadherin | Type of neutrophil serine protease; degrades ECM components; regulates inflammatory response; activates pro-apoptotic signaling |
| Cathepsin G | Targets: EGF, ENA-78, IL-8, MCP-1, MMP-2, MT1-MMP, PAI-1, RANTES, TGFβ TNFα | Type of serine protease; degrades ECM components; chemo-attractant of leukocytes; regulates inflammatory response; promotes apoptosis |
| PR-3 | Targets: ENA-78, IL-8, IL-18, JNK, $p38^{MAPK}$, TNFα | Type of serine protease; promotes inflammatory response; activates pro-apoptotic signaling |
| Granzyme M (grM) | Cleaves after Met and other long, unbranched hydrophobic residues | Type of serine protease; only expressed in NK cells |
| Calpains | Cleave between Arg and Gly | Family of cysteine proteases; calcium-dependent; activation is involved in the process of numerous inflammation-associated diseases |

?TABLE 1a

| Exemplary Proteases and Protease Recognition Sequences | | |
|---|---|---|
| Protease | Cleavage Domain Sequence | SEQ ID NO: |
| MMP7 | KRALGLPG | 3 |
| MMP7 | (DE)8RPLALWRS(DR)8 | 4 |
| MMP9 | PR(S/T)(L/I)(S/T) | 5 |
| MMP9 | LEATA | 6 |
| MMP11 | GGAANLVRGG | 7 |
| MMP14 | SGRIGFLRTA | 8 |
| MMP | PLGLAG | 9 |
| MMP | PLGLAX | 10 |
| MMP | PLGC(me)AG | 11 |
| MMP | ESPAYYTA | 12 |
| MMP | RLQLICL | 13 |
| MMP | RLQLKAC | 14 |
| MMP2, MMP9, MMP14 | EP(Cit)G(Hof)YL | 15 |
| Urokinase plasminogen activator (uPA) | SGRSA | 16 |
| Urokinase plasminogen activator (uPA) | DAFK | 17 |
| Urokinase plasminogen activator (uPA) | GGGRR | 18 |
| Lysosomal Enzyme | GFLG | 19 |
| Lysosomal Enzyme | ALAL | 20 |
| Lysosomal Enzyme | FK | 21 |

?TABLE 1a-continued

| Exemplary Proteases and Protease Recognition Sequences | | |
|---|---|---|
| Protease | Cleavage Domain Sequence | SEQ ID NO: |
| Cathepsin B | NLL | 22 |
| Cathepsin D | PIC(Et)FF | 23 |
| Cathepsin K | GGPRGLPG | 24 |
| Prostate Specific Antigen | HSSKLQ | 25 |
| Prostate Specific Antigen | HSSKLQL | 26 |
| Prostate Specific Antigen | HSSICLQEDA | 27 |
| Herpes Simplex Virus Protease | LVLASSSFGY | 28 |
| HIV Protease | GVSQNYPIVG | 29 |
| CMV Protease | GVVQASCRLA | 30 |
| Thrombin | F(Pip)RS | 31 |
| Thrombin | DPRSFL | 32 |
| Thrombin | PPRSFL | 33 |
| Caspase-3 | DEVD | 34 |
| Caspase-3 | DEVDP | 35 |
| Caspase-3 | KGSGDVEG | 36 |
| Interleukin 1β converting enzyme | GWEHDG | 37 |
| Enterokinase | EDDDDKA | 38 |
| FAP | KQEQNPGST | 39 |

?TABLE 1a-continued

Exemplary Proteases and Protease Recognition Sequences

| Protease | Cleavage Domain Sequence | SEQ ID NO: |
|---|---|---|
| Kallikrein 2 | GKAFRR | 40 |
| Plasmin | DAFK | 41 |
| Plasmin | DVLK | 42 |
| Plasmin | DAFK | 43 |
| TOP | ALLLALL | 44 |

Provided herein are pharmaceutical compositions comprising polypeptide sequences. As with all peptides, polypeptides, and proteins, including fragments thereof, it is understood that additional modifications in the amino acid sequence of the chimeric polypeptides (amino acid sequence variants) can occur that do not alter the nature or function of the peptides, polypeptides, or proteins. Such modifications include conservative amino acid substitutions and are discussed in greater detail below.

The compositions provided herein have a desired function. The compositions are comprised of at least a cytokine polypeptide, such as IL-2, IL-7, IL-12, IL-15, IL-18, IL-21, IFNα, or IFNγ, or a chemokine, such as CXCL10, CCL19, CCL20, CCL21, a blocking moiety, e.g. a steric blocking polypeptide, and an optional serum half-life extension element, and an optional targeting polypeptide, with one or more linkers connecting each polypeptide in the composition. The first polypeptide, e.g., an IL-2 mutein, is provided to be an active agent. The blocking moiety is provided to block the activity of the interleukin. The linker polypeptide, e.g., a protease cleavable polypeptide, is provided to be cleaved by a protease that is specifically expressed at the intended target of the active agent. Optionally, the blocking moiety blocks the activity of the first polypeptide by binding the interleukin polypeptide. In some embodiments, the blocking moiety, e.g. a steric blocking peptide, is linked to the interleukin via a protease-cleavable linker which is cleaved at the site of action (e.g. by inflammation-specific or tumor-specific proteases) releasing the cytokine full activity at the desired site.

The protease cleavage site may be a naturally occurring protease cleavage site or an artificially engineered protease cleavage site. The artificially engineered protease cleavage site can be cleaved by more than one protease specific to the desired environment in which cleavage will occur, e.g. a tumor. The protease cleavage site may be cleavable by at least one protease, at least two proteases, at least three proteases, or at least four proteases.

In some embodiments, the linker comprises glycine-glycine, a sortase-recognition motif, or a sortase-recognition motif and a peptide sequence $(Gly_4Ser)_n$ (SEQ ID NO.: 443) or $(Gly_3Ser)_n$, (SEQ ID NO.: 444), wherein n is 1, 2, 3, 4 or 5. In one embodiment, the sortase-recognition motif comprises a peptide sequence LPXTG (SEQ ID NO.: 442), where X is any amino acid. In one embodiment, the covalent linkage is between a reactive lysine residue attached to the C-terminal of the cytokine polypeptide and a reactive aspartic acid attached to the N-terminal of the blocking or other moiety. In one embodiment, the covalent linkage is between a reactive aspartic acid residue attached to the N-terminal of the cytokine polypeptide and a reactive lysine residue attached to the C-terminal of the blocking or other moiety.

Cleavage and Inducibility

As described herein, the activity of the cytokine polypeptide the context of the fusion protein is attenuated, and protease cleavage at the desired site of activity, such as in a tumor microenvironment, releases a form of the cytokine from the fusion protein that is much more active as a cytokine receptor agonist than the fusion protein. For example, the cytokine-receptor activating (agonist) activity of the fusion polypeptide can be at least about 10×, at least about 50×, at least about 100×, at least about 250×, at least about 500×, or at least about 1000× less than the cytokine receptor activating activity of the cytokine polypeptide as a separate molecular entity. The cytokine polypeptide that is part of the fusion protein exists as a separate molecular entity when it contains an amino acid that is substantially identical to the cytokine polypeptide and does not substantially include additional amino acids and is not associated (by covalent or non-covalent bonds) with other molecules. If necessary, a cytokine polypeptide as a separate molecular entity may include some additional amino acid sequences, such as a tag or short sequence to aid in expression and/or purification.

In other examples, the cytokine-receptor activating (agonist) activity of the fusion polypeptide is at least about 10×, at least about 50×, at least about 100×, at least about 250×, at least about 500×, or about 1000× less than the cytokine receptor activating activity of the polypeptide that contains the cytokine polypeptide that is produced by cleavage of the protease cleavable linker in the fusion protein. In other words, the cytokine receptor activating (agonist) activity of the polypeptide that contains the cytokine polypeptide that is produced by cleavage of the protease cleavable linker in the fusion protein is at least about 10×, at least about 50×, at least about 100×, at least about 250×, at least about 500×, or at least about 1000× greater than the cytokine receptor activating activity of the fusion protein.

Polypeptide Variants and Amino Acid Substitutions

The polypeptides described herein can include components (e.g., the cytokine, the blocking moiety) that have the same amino acid sequence of the corresponding naturally occurring protein (e.g., IL-2, IL-15, HSA) or can have an amino acid sequence that differs from the naturally occurring protein so long as the desired function is maintained. It is understood that one way to define any known modifications and derivatives or those that might arise, of the disclosed proteins and nucleic acids that encode them is through defining the sequence variants in terms of identity to specific known reference sequences. Specifically disclosed are polypeptides and nucleic acids which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the chimeric polypeptides provided herein. For example, provided are polypeptides or nucleic acids that have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the sequence of any of the nucleic acids or polypeptides described herein. Those of skill in the art readily understand how to determine the identity of two polypeptides or two nucleic acids. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman Adv. Appl. Math. 2:482

(1981), by the identity alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-7710 (1989); Jaeger et al., Methods Enzymol. 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

Protein modifications include amino acid sequence modifications. Modifications in amino acid sequence may arise naturally as allelic variations (e.g., due to genetic polymorphism), may arise due to environmental influence (e.g., by exposure to ultraviolet light), or may be produced by human intervention (e.g., by mutagenesis of cloned DNA sequences), such as induced point, deletion, insertion and substitution mutants. These modifications can result in changes in the amino acid sequence, provide silent mutations, modify a restriction site, or provide other specific mutations. Amino acid sequence modifications typically fall into one or more of three classes: substitutional, insertional or deletional modifications. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue inserted in its place. Such substitutions generally are made in accordance with the following Table 2 and are referred to as conservative substitutions.

?TABLE 2

Exemplary amino acid substitutions

| Amino Acid | Exemplary Substitutions |
|---|---|
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Modifications, including the specific amino acid substitutions, are made by known methods. For example, modifications are made by site specific mutagenesis of nucleotides in the DNA encoding the polypeptide, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

Modifications can be selected to optimize binding. For example, affinity maturation techniques can be used to alter binding of the scFv by introducing random mutations inside the complementarity determining regions (CDRs). Such random mutations can be introduced using a variety of techniques, including radiation, chemical mutagens or error-prone PCR. Multiple rounds of mutation and selection can be performed using, for example, phage display.

The disclosure also relates to nucleic acids that encode the chimeric polypeptides described herein, and to the use of such nucleic acids to produce the chimeric polypeptides and for therapeutic purposes. For example, the invention includes DNA and RNA molecules (e.g., mRNA, self-replicating RNA) that encode a chimeric polypeptide and to the therapeutic use of such DNA and RNA molecules.

Exemplary Compositions

Exemplary fusion proteins of the invention combine the above described elements in a variety of orientations. The orientations described in this section are meant as examples and are not to be considered limiting.

In some embodiments, the fusion protein comprises a cytokine, a blocking moiety and a half-life extension element. In some embodiments, the cytokine is positioned between the half-life extension element and the blocking moiety. In some embodiments, the cytokine is N-terminal to the blocking moiety and the half-life extension element. In some such embodiments, the cytokine is proximal to the blocking moiety; in some such embodiments, the cytokine is proximal to the half-life extension element. At least one protease-cleavable linker must be included in all embodiments, such that the cytokine may be active upon cleavage. In some embodiments, the cytokine is C-terminal to the blocking moiety and the half-life extension element. Additional elements may be attached to one another by a cleavable linker, a non-cleavable linker, or by direct fusion.

In some embodiments, the blocking domains used are capable of extending half-life, and the cytokine is positioned between two such blocking domains. In some embodiments, the cytokine is positioned between two blocking domains, one of which is capable of extending half-life.

In some embodiments, two cytokines are included in the same construct. In some embodiments, the cytokines are connected to two blocking domains each (three in total in one molecule), with a blocking domain between the two cytokine domains. In some embodiments, one or more additional half-life extension domains may be included to optimize pharmacokinetic properties. In some cases, it is beneficial to include two of the same cytokine to facilitate dimerization. An example of a cytokine that works as a dimer is IFN.

In some embodiments, three cytokines are included in the same construct. In some embodiments, the third cytokine may function to block the other two in place of a blocking domain between the two cytokines.

Preferred half-life extension elements for use in the fusion proteins are human serum albumin (HSA), an antibody or antibody fragment (e.g., scFV, dAb) which binds serum albumin, a human or humanized IgG, or a fragment of any of the foregoing. In some preferred embodiments, the blocking moiety is human serum albumin (HSA), or an antibody or antibody fragment which binds serum albumin, an antibody which binds the cytokine and prevents activation of binding or activation of the cytokine receptor, another cytokine, or a fragment of any of the foregoing. In preferred embodiments comprising an additional targeting domain, the targeting domain is an antibody which binds a cell surface protein which is enriched on the surface of cancer cells, such as EpCAM, FOLR1, and Fibronectin.

In embodiments, the fusion protein can contain an IL-2 polypeptide. The fusion protein containing an IL-2 polypeptide can comprise or consist of the amino acid sequence of any one of SEQ ID NOs. 257-300, 302-317, 325-353, 355-365, 366, 372-381, 383-385, 388-420, 579-608 and 636-646. The fusion proteins disclosed as SEQ ID NOs. 257-300, 302-317, 325-353, 355-365, 366, 372-381, 383-385, 388-420, 579-608, and 636-646 are also referred to herein as ACP289-ACP292, ACP296-ACP302, WW0301, ACP304-ACP306, ACP309-ACP313, WW0353, ACP414, ACP336-ACP398, WW0472-WW0477, ACP406-ACP426, ACP439-ACP447, ACP451-ACP471, WW0729, WW0734-WW0792, ACP101, ACP293-ACP295, ACP316-ACP335, ACP427-ACP438, and ACP448-ACP450. For example, the fusion protein can comprise the amino acid sequence of SEQ ID NO: 272. The fusion protein can comprise the amino acid sequence of SEQ ID NO: 286. The fusion protein can comprise the amino acid sequence of SEQ ID NO:362. The fusion protein can comprise the amino acid sequence of SEQ ID NO:336. The fusion protein can comprise the amino acid sequence of SEQ ID NO: 348. The fusion protein can comprise the amino acid sequence of SEQ ID NO: 363. The fusion protein can comprise the amino acid sequence of SEQ ID NO: 580.

In embodiments, the fusion protein can contain an IL-12 polypeptide. The fusion protein containing an IL-12 polypeptide can comprise or consist of the amino acid sequence of any one of SEQ ID NOs. 368-371, 434-440, 453-519, or 523-538. The fusion proteins disclosed as SEQ ID NOs. 368-371, 434-440, 453-519, or 523-538 are referred to herein as ACP240-ACP245, ACP247, ACP285-ACP288, WW0641, WW0649-WW0652, WW0662-WW0725, WW0765-WW0772, and WW0796-WW0803. For example, the fusion protein can comprise the amino acid sequence of SEQ ID NO:459. The fusion protein can comprise the amino acid sequence of SEQ ID NO: 466. The fusion protein can comprise the amino acid sequence of SEQ ID NO: 484. The fusion protein can comprise the amino acid sequence of SEQ ID NO: 506.

In embodiments, the fusion protein contains an IFN (e.g., IFNgamma, IFNalpha, IFNbeta) polypeptide. In some examples the IFN polypeptide is an IFNalpha or an IFNbeta. The fusion protein containing an IFN polypeptide can comprise or consist of the amino acid sequence of SEQ ID NOs. 421-430, and 539-578. The fusion proteins disclosed as SEQ ID NOs. 421-430, and 539-578 can be referred to herein as ACP200-ACP209, WW0644-WW0648, WW0781-WW0786, WW0815-WW0822, WW0831-WW0834, WW0737-WW0748, and WW0787-WW0790. For example, the fusion protein can comprise the amino acid sequence of SEQ ID NO: 421. The fusion protein can comprise the amino acid sequence of SEQ ID NO: 428. The fusion protein can comprise the amino acid sequence of 541. The fusion protein can comprise the amino acid sequence of SEQ IND NO: 558. The fusion protein can comprise the amino acid sequence of SEQ ID NO: 577.

In some aspects, the fusion polypeptide disclosed herein can be covalently or non-covalently bonded to a second polypeptide chain. For example, a fusion polypeptide can dimerize (i.e. form a dimer) or a portion of a fusion polypeptide may associate with another polypeptide, for example, to form a functional binding site for a cytokine polypeptide or serum albumin. In certain embodiments, the second polypeptide chain and the blocking moiety on the fusion polypeptide are complementary and together form a functional binding site that has specificity for the cytokine polypeptide contained in the fusion polypeptide. Exemplary functional binding sites that can be formed by the blocking moiety of the fusion polypeptide and a complimentary second polypeptide include antigen binding sites of antibodies, such as a Fab fragment of an antibody or a portion thereof. For example, one chain of a Fab that binds the cytokine can be the blocking moiety of the fusion polypeptide, e.g., a VH-CH1, and the complementary VL-CL can be part of the second polypeptide. In such situations, the blocking moiety of the fusion protein i.e., VH-CH1 and the second polypeptide that comprises the complementary VL-CL, can associate to form a functional binding site with specificity for the cytokine polypeptide contained within the fusion protein (e.g., IL-2, IL-12, IFNalpha, IFNbeta) and attenuates cytokine polypeptide activity. At least a portion of the blocking moiety can be on the second polypeptide chain can comprise at least a portion of the blocking moiety that associates with the blocking moiety on the fusion polypeptide.

In embodiments, the fusion protein containing an IL-2 cytokine polypeptide can be bonded covalently or noncovalently to a second polypeptide chain. The second polypeptide chain can contain an antibody light chain VL-CL that comprises or consist of the amino acid sequence of SEQ ID NO: 263, 264, or 333. Such a second polypeptide can bond with a complimentary VH-CH1 polypeptide contained within the fusion protein, e.g., as contained within SEQ ID NOS: 362, 363, 325, 286, 579, 581, or 582. The second polypeptide chain disclosed as SEQ ID NOs. 263, 264, and 333 can be referred herein as WW0523 (ACP381), WW0524 (ACP382), or WW0556 (ACP414).

In embodiments, the fusion polypeptide can comprise or consist of the amino acid sequence of SEQ ID NOs. 362, 363, 325, 286, 579, 581, or 582 and the second polypeptide chain can comprise or consist of the amino acid sequence of SEQ ID NOs: 263, 264, or 333. The fusion polypeptide disclosed as SEQ ID NOs. 362, 363, 325, 286, 579, 581, or 582 can be referred to as WW0520 (ACP378), WW0521 (ACP379), WW0548 (ACP406), WW0621 (ACP457), WW0729, WW0735, or WW0736, and the second polypeptide chain disclosed as SEQ ID NOs. 263, 264, and 333 can be referred herein as WW0523 (ACP381), WW0524 (ACP382), or WW0556 (ACP414).

For example, the fusion protein can comprise or consist the amino acid sequence of SEQ ID NO: 362 and the second polypeptide chain can comprise or consist the amino acid sequence of SEQ ID NO: 263. For example, the fusion protein can comprise or consist the amino acid sequence of SEQ ID NO: 362 and the second polypeptide chain can comprise or consist the amino acid sequence of SEQ ID NO: 264. For example, the fusion protein can comprise or consist the amino acid sequence of SEQ ID NO: 362 and the second polypeptide chain can comprise or consist the amino acid sequence of SEQ ID NO: 333. For example, the fusion protein can comprise or consist of an amino acid sequence of SEQ ID NO: 363 and the second polypeptide chain can comprise or consist of an amino acid sequence of SEQ ID NO: 263. For example, the fusion protein can comprise or consist of an amino acid sequence of SEQ ID No. 363 and the second polypeptide chain can comprise or consist of an amino acid sequence of SEQ ID NO: 264. For example, the fusion protein can comprise or consist of an amino acid sequence of SEQ ID NO: 363 and the second polypeptide chain can comprise or consist of an amino acid sequence of SEQ ID NO: 333. For example, the fusion protein can comprise or consist of an amino acid sequence of SEQ ID NO: 325 and the second polypeptide chain can comprise or consist of an amino acid sequence of SEQ ID NO: 264. For example, the fusion protein can comprise or consist of an amino acid sequence of SEQ ID NO: 325 and the second polypeptide chain can comprise or consist of an amino acid sequence of SEQ ID NO: 333. For example, the fusion protein can comprise or consist of an amino acid sequence of SEQ ID NO: 325 and the second polypeptide chain can comprise or consist of an amino acid sequence of SEQ ID NO: 263. For example, the fusion protein can comprise or consist of an amino acid sequence of SEQ ID NO: 286 and the second polypeptide chain can comprise or consist of an amino acid sequence of SEQ ID NO: 263. For example, the fusion protein can comprise or consist of an amino acid sequence of SEQ ID NO: 286 and the second polypeptide chain can comprise or consist of an amino acid sequence of SEQ ID NO: 264. For example, the fusion protein can comprise or consist of an amino acid sequence of SEQ ID NO: 286, and the second polypeptide can comprise or consist of an amino acid sequence of SEW ID NO: 333. For example, the fusion protein can comprise or consist of an amino acid sequence of SEQ ID NO: 579 and the second polypeptide chain can comprise or consist of an amino acid sequence of SEQ ID NO: 263. For example, the fusion protein can comprise or consist of an amino acid sequence of SEQ ID NO: 579 and the second polypeptide chain can comprise or consist of an amino acid sequence of SEQ ID NO: 264. For example, the fusion protein can comprise or consist of an amino acid sequence of SEQ ID NO: 579 and the second polypeptide chain can comprise or consist of an amino acid sequence of SEQ ID NO: 233. For example, the fusion protein can comprise or consist of SEQ ID NO: 581 and the second polypeptide chain can comprise or consist of SEQ ID NO.: 263. For example, the fusion protein can comprise or consist of SEQ ID NO: 581 and the second polypeptide chain can comprise or consist of SEQ ID NO.: 264. For example, the fusion protein can comprise or consist of SEQ ID NO: 581 and the second polypeptide chain can comprise or consist of SEQ ID NO.: 333. For example, the fusion protein can comprise or consist of SEQ ID NO: 582 and the second polypeptide chain can comprise or consist of SEQ ID NO: 263. For example, the fusion protein can comprise or consist of SEQ ID NO: 582 and the second polypeptide chain can comprise or consist of SEQ ID NO: 264. For example, the fusion protein can comprise or consist of SEQ ID NO: 582 and the second polypeptide chain can comprise or consist of SEQ ID NO: 333.

Methods of Treatment and Pharmaceutical Compositions

This disclosure also relates to pharmaceutical compositions that comprise one or more fusion proteins as disclosed herein, optionally in combination with another therapeutic agent, which are preferably immunomodulators or anti-cancer agents. The disclosure also relates to the use of such pharmaceutical compositions, and one or more fusion proteins, optionally in combination with another therapeutic agent in treatment of cancers.

The therapeutic combinations disclosed herein can comprise, for example, a fusion protein containing an IL-2 polypeptide, a fusion protein containing an IL-12 polypeptide, or a fusion protein containing an IFN polypeptide. Therapy can be provided using two or more fusion proteins. For example, the therapeutic combination can comprise a fusion protein containing an IL-2 polypeptide and a fusion protein containing an IL-12 polypeptide, a fusion protein containing an IL-2 polypeptide and a fusion protein containing an IFN polypeptide, a fusion protein containing an IL-12 polypeptide and a fusion protein containing an IFN polypeptide.

The therapeutic combinations disclosed herein can comprise a fusion polypeptide cytokine polypeptide [A], a blocking moiety [D], optionally a half-life extension moiety [H], and a protease-cleavable polypeptide linker, wherein the cytokine polypeptide and the blocking moiety and the optional half-life extension element when present are operably linked by the protease-cleavable polypeptide linker and the fusion polypeptide has attenuated cytokine receptor activating activity, wherein the cytokine-receptor activating activity of the fusion polypeptide is at least about 10× less than the cytokine receptor activating activity of the polypeptide that contains the cytokine polypeptide that is produced by cleavage of the protease cleavable linker. the fusion polypeptide has the formula:

[A]-[L1]-[H]-[L2]-[D] (I);

[D]-[L2]-[H]-[L1]-[A] (II);

[A]-[L1]-[D]-[L2]-[H] (III);

[H]-[L2]-[D]-[L1]-[A] (IV);

[H]-[L1]-[A]-[L2']-[D] (V);

[D]-[L1]-[A]-[L2']-[H] (VI);

wherein [A] is a cytokine polypeptide, [D] is a blocking moiety, [H] is a half-life extension moiety, [L1] is a protease-cleavable polypeptide linker, [L2] is an polypeptide linker that is optionally protease-cleavable, and [L2'] is a protease-cleavable polypeptide linker.

The therapeutic compositions can comprise a second fusion polypeptide comprising at least one of each of: a second cytokine polypeptide [A], a blocking moiety [D]optionally a half-life extension element [H]; and a protease-cleavable polypeptide linker [L]; wherein the cytokine polypeptide and the cytokine blocking moiety and the optional half-life extension element when present are operably linked by the protease-cleavable polypeptide linker and the fusion polypeptide has attenuated cytokine receptor activating activity, wherein the cytokine-receptor activating activity of the fusion polypeptide is at least about 10× less than the cytokine receptor activating activity of the polypeptide that contains the cytokine polypeptide that is produced by cleavage of the protease cleavable linker. The second fusion polypeptide can have the formula:

[A]-[L1]-[H]-[L2]-[D] (I);

[D]-[L2]-[H]-[L1]-[A] (II);

[A]-[L1]-[D]-[L2]-[H] (III);

[H]-[L2]-[D]-[L1]-[A] (IV);

[H]-[L1]-[A]-[L2']-[D] (V);

[D]-[L1]-[A]-[L2']-[H] (VI);

wherein [A] is a cytokine polypeptide, [D] is a blocking moiety, [H] is a half-life extension moiety, [L1] is a protease-cleavable polypeptide linker, [L2] is an polypeptide linker that is optionally protease-cleavable, and [L2'] is a protease-cleavable polypeptide linker.

The therapeutic combinations disclosed herein can comprise a first fusion protein comprising an amino acid selected from the group consisting of SEQ ID NOs. 257-300, 302-317, 325-353, 355-365, 366, 372-381, 383-385, 388-420, 579-608, 636-646, 368-371, 434-440, 453-519, 523-538, 421-430, and 539-578 and a second fusion protein comprising an amino acid sequence selected from the group consisting of selected from the group consisting of SEQ ID NOs. 257-300,302-317, 325-353, 355-365, 366, 372-381, 383-385, 388-420, 579-608, 636-646, 368-371, 434-440, 453-519, 523-538, 421-430, and 539-578. It is preferred that the first fusion protein and the second fusion protein are different. In some preferred embodiments, the therapeutic combination comprises a first fusion protein comprising an amino acid sequence selected from SEQ ID NO: 257-300, 302-317, 325-353, 355-365, 366, 372-381, 383-385, 388-420, 579-608, 636-646 and a second fusion protein comprising an amino acid sequence selected from SEQ ID NO: 368-371, 434-440, 453-519, 523-538, 421-430, and 539-578. In some preferred embodiments, the therapeutic combination comprises a first fusion proteins comprising an amino acid sequence selected from SEQ ID NO: 368-371, 434-440, 453-519, or 523-538 and a second fusion protein comprising an amino acid sequence selected from SEQ ID NO: 257-300, 302-317, 325-353, 355-365, 366, 372-381, 383-385, 388-420, 636-646, 579-608, 421-430, and 539-578. In some preferred embodiments, the therapeutic combination comprises a first fusion protein comprising an amino acid sequence selected from SEQ ID NO: 421-430, and 539-578 and a second fusion protein comprising an amino acid sequence selected from SEQ ID NOs. 257-300, 302-317, 325-353, 355-365, 366, 372-381, 383-385, 388-420, 579-608, 636-646, 368-371, 434-440, 453-519, 523-538, or combinations thereof.

The therapeutic combination disclosed herein can comprise a first fusion protein that is covalently or non-covalently bonded to a second polypeptide chain and a therapeutic agent. The therapeutic combination can comprise (i) a fusion polypeptide comprising an amino acid sequence selected from SEQ ID NOs. 362, 363, 325, 286, 579, 581, or 582 and a second polypeptide chain comprising the amino acid sequence of SEQ ID NOs: 263, 264, or 333, and (ii) a second therapeutic agent, wherein the second therapeutic agent is a second fusion polypeptide comprising an amino acid sequence selected from the group consisting of SEQ ID NOs. 257-300,302-317, 325-353, 355-365, 366, 372-381, 383-385, 388-420, 579-608, 636-646, 368-371, 434-440, 453-519, 523-538, 421-430, 539-578, or combinations thereof. It is preferred that the first fusion protein and the second fusion protein are not the same.

In embodiments, the therapeutic combination can comprise an additional therapeutic agent (e.g., one, two, three, four, five, or more therapeutic agents). In embodiments, the therapeutic combination can comprise 2 or more fusion proteins and one or more therapeutic agents, preferably agents for treating cancer.

Other exemplary therapeutic agents include, but are not limited to chemotherapeutic agents (e.g., Adriamycin, Cerubidine, Bleomycin, Alkeran, Velban, Oncovin, Fluorouracil, Thiotepa, Methotrexate, Bisantrene, Noantrone, Thiguanine, Cytaribine, Procarabizine), immuno-oncology agents (e.g., anti-PD-L1, anti-CTLA4, anti-PD-1, anti-CD47, anti-GD2, VEGF inhibitor), antibody-drug conjugates, cellular therapies (e.g, CAR-T, T-cell therapy), oncolytic viruses, radiation therapy and/or small molecules.

Non-limiting examples of anti-cancer agents that can be used include acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer, carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1 interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur, talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinzolidine sulfate; vinzolidine sulfate; vorozole; zeniplatin; zinostatin; zorubicin hydrochloride.

Accordingly, this disclosure relates to a therapeutic combination of any of the fusions proteins disclosed herein (e.g., fusion proteins that comprise an IL-2 polypeptide, and IL-12 polypeptide or an IFN polypeptide) in combination with a chemotherapeutic agent, such as Adriamycin, Cerubidine, Bleomycin, Alkeran, Velban, Oncovin, Fluorouracil, Thiotepa, Methotrexate, Bisantrene, Noantrone, Thiguanine, Cytaribine, Procarabizine. This disclosure relates to a therapeutic combination of any of the fusions proteins disclosed herein (e.g., fusion proteins that comprise an IL-2 polypeptide, and IL-12 polypeptide or an IFN polypeptide) in combination with an antibody-drug conjugate. A variety of antibody drug conjugates that are suitable for use in cancer therapy are well known and typically include an antibody that binds to a cellular antigen that is preferentially express or expressed at high levels on tumor cells, and a cytotoxic drug. This disclosure relates to a therapeutic combination of any of the fusion proteins disclosed herein (e.g., fusion proteins that comprise an IL-2 polypeptide, and IL-12 polypeptide, or an IFN polypeptide) in combination with a cellular therapy, such as CAR-T or T-cell therapy. The disclosure relates to a therapeutic combination of the fusion proteins disclosed herein (e.g., fusion proteins that comprise an IL-2 polypeptide, and IL-12 polypeptide, or an IFN polypeptide) in combination with an oncolytic virus. Exemplary oncolytic viruses include, oncolytic adenoviruses, type 1 herpes simplex virus (HSV), polioviruses, measles virus (MV), Newcastle disease virus (NDV), reoviruses, vesicular stomatitis virus (VSV), and Zika virus. This disclosure relates to a therapeutic combination of any of the fusion proteins disclosed herein (e.g., fusion proteins that comprise an IL-2 polypeptide, and IL-12 polypeptide, or an IFN polypeptide) in combination with radiation therapy, such an external beam radiation or internal therapy radiation therapy.

This disclosure relates to a therapeutic combination of any of the fusion proteins disclosed herein (e.g., fusion proteins that comprise an IL-2 polypeptide, and IL-12 polypeptide, or an IFN polypeptide) in combination with cytokines (e.g., IL-2, IL-15), signal induction inhibitors (e.g., BRAF inhibitors or MEK inhibitors), checkpoint inhibitors (e.g., PDL-1, PD-1, CTLA-4), c-met inhibitors, kinase inhibitors (e.g., VGEF inhibitors), a proteasome inhibitor, mTOR inhibitor, angiogenesis inhibitor. In embodiments, any one of the fusion proteins disclosed herein (e.g., fusion proteins that comprise an IL-2 polypeptide, and IL-12 polypeptide, or an IFN polypeptide) can be combined with an anti-PD-L1 agent or an anti-PD-1 agent. Exemplary PD-1 and/or PD-L1 inhibitors include, but are not limited to Spartalizumab, Camrelizumab, Sintilimab, Tislelizumab, Toripalimab, Dostarlimab, INCMGA00012, AMP-224, and AMP-514). In embodiments, a fusion protein comprising the amino acid sequence selected from SEQ ID NO: 257-300, 302-317, 325-353, 355-365, 366, 372-381, 383-385, 388-420, 579-608, 636-646, 368-371, 434-440, 453-519, 523-538, 421-430, and 539-578 can be combined with a check-point inhibitor, such as PDL-1, PD-1, or CTL-4.

Further provided are methods of treating a subject with or at risk of developing an of a disease or disorder, such as proliferative disease, a tumorous disease, an inflammatory disease, an immunological disorder, an autoimmune disease, an infectious disease, a viral disease, an allergic reaction, a parasitic reaction, or graft-versus-host disease. The methods disclosed herein are preferably used to treat a subject having cancer. The methods administering to a subject in need thereof an effective amount of a fusion protein as disclosed herein that is typically administered as a pharmaceutical composition. In some embodiments, the method further comprises selecting a subject with or at risk of developing such a disease or disorder. The pharmaceutical composition preferably comprises a blocked cytokine, fragment, variant, subunit, or mutein thereof that is activated at a site of inflammation or a tumor. In one embodiment, the chimeric polypeptide comprises a cytokine polypeptide, fragment or mutein thereof and a serum half-life extension element. In another embodiment, the chimeric polypeptide comprises a cytokine polypeptide, variant, subunit, fragment or mutein thereof and a blocking moiety, e.g. a steric blocking polypeptide, wherein the steric blocking polypeptide is capable of sterically blocking the activity of the cytokine polypeptide, fragment or mutein thereof. In another embodiment, the chimeric polypeptide comprises a cytokine polypeptide, fragment or mutein thereof, a blocking moiety, and a serum half-life extension element.

Inflammation is part of the complex biological response of body tissues to harmful stimuli, such as pathogens, damaged cells, or irritants, and is a protective response involving immune cells, blood vessels, and molecular mediators. The function of inflammation is to eliminate the initial cause of cell injury, clear out necrotic cells and tissues damaged from the original insult and the inflammatory process, and to initiate tissue repair. Inflammation can occur from infection, as a symptom or a disease, e.g., cancer, atherosclerosis, allergies, myopathies, HIV, obesity, or an autoimmune disease. An autoimmune disease is a chronic condition arising from an abnormal immune response to a self-antigen. Autoimmune diseases that may be treated with the polypeptides disclosed herein include but are not limited to lupus, celiac disease, diabetes mellitus type 1, Graves disease, inflammatory bowel disease, multiple sclerosis, psoriasis, rheumatoid arthritis, and systemic lupus erythematosus.

The pharmaceutical composition can comprise one or more protease-cleavable linker sequences. The linker sequence serves to provide flexibility between polypeptides, such that each polypeptide is capable of inhibiting the activity of the first polypeptide. The linker sequence can be located between any or all of the cytokine polypeptide, fragment or mutein thereof, the blocking moiety, and serum half-life extension element. Optionally, the composition comprises, two, three, four, or five linker sequences. The linker sequence, two, three, or four linker sequences can be the same or different linker sequences. In one embodiment, the linker sequence comprises GGGGS (SEQ ID NO.: 449), GSGSGS (SEQ ID NO.: 450), or $G(SGGG)_2SGGT$ (SEQ ID NO.: 451). In another embodiment, the linker comprises a protease-cleavable sequence selected from group consisting of HSSKLQ (SEQ ID NO.: 25), GPLGVRG (SEQ ID NO.: 445), IPVSLRSG (SEQ ID NO.: 446), VPLSLYSG (SEQ ID NO.: 447), and SGESPAYYTA (SEQ ID NO.: 448).

In some embodiments, the linker is cleaved by a protease selected from the group consisting of a kallikrein, thrombin, chymase, carboxypeptidase A, cathepsin G, an elastase, PR-3, granzyme M, a calpain, a matrix metalloproteinase (MMP), a plasminogen activator, a cathepsin, a caspase, a tryptase, or a tumor cell surface protease.

Suitable linkers can be of different lengths, such as from 1 amino acid (e.g., Gly) to 20 amino acids, from 2 amino acids to 15 amino acids, from 3 amino acids to 12 amino acids, including 4 amino acids to 10 amino acids, amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids.

Further provided are methods of treating a subject with or at risk of developing cancer. The methods comprise administering to the subject in need thereof an effective amount of a chimeric polypeptide (a fusion protein) as disclosed herein that is typically administered as a pharmaceutical composition. In some embodiments, the method further comprises selecting a subject with or at risk of developing cancer. The pharmaceutical composition preferably comprises a blocked cytokine, fragment or mutein thereof that is activated at a tumor site.

The methods disclosed herein can be used for any suitable cancer including, hematological malignancy, solid tumors, sarcomas, carcinomas, and other solid and non-solid tumors. Illustrative suitable cancers include, for example, acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, carcinoma of unknown primary origin, cardiac tumor, cervical cancer, chordoma, colon cancer, colorectal cancer, craniopharyngioma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, lip and oral cavity cancer, liver cancer, lobular carcinoma in situ, lung cancer, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fingoides, myelodysplastic syndrome, myelodysplastic/myeloproliferative neoplasm, nasal cavity and par nasal sinus cancer, nasopharyngeal cancer, neuroblastoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms tumor.

Preferably, the tumor is a solid tumor. Colon cancer, lung cancer, melanoma, sarcoma, renal cell carcinoma, and breast cancer are of particular interest.

The method can further involve the administration of one or more additional agents to treat cancer, such as one or more cytokine fusion proteins described herein, chemotherapeutic agents (e.g., Adriamycin, Cerubidine, Bleomycin, Alkeran, Velban, Oncovin, Fluorouracil, Thiotepa, Methotrexate, Bisantrene, Noantrone, Thiguanine, Cytaribine, Procarabizine), immuno-oncology agents (e.g., anti-PD-L1, anti-CTLA4, anti-PD-1, anti-CD47, anti-GD2, VEGF inhibitor), cellular therapies (e.g, CAR-T, T-cell therapy), oncolytic viruses, radiation therapy and the like.

In embodiments, the fusion proteins described herein, can be administered with one or more additional cytokine fusion proteins that are inducible. For example, a fusion protein containing an IL-2 polypeptide, as described herein, may be administered with fusion protein containing an IL-12 polypeptide, an IFN polypeptide, a different IL-2 polypeptide or a combinations thereof. A fusion protein containing an IL-12 polypeptide, as described herein, may be administered with a fusion protein containing an IL-2 polypeptide, an IFN polypeptide, a different IL-12 polypeptide or a combinations thereof. A fusion protein containing an IFN polypeptide, as described herein, may be administered with a fusion protein containing anIL-2 polypeptide, an IL-12 polypeptide, an different IFN polypeptide, or a combinations thereof.

In some preferred embodiments, a first fusion protein comprising the amino acid sequence of any one of SEQ ID NOS: 257-300, 302-317, 325-353, 355-365, 366, 372-381, 383-385, 388-420, 579-608, and 636-646 can be administered with a second different fusion protein comprising an amino acid sequence of any one of SEQ ID NOs. 368-371, 434-440, 453-519, 523-538, 421-430, and 539-578. In some preferred embodiments, a first fusion proteins comprising the amino acid sequence of any one of 368-371, 434-440, 453-519, or 523-538 can be administered with a second different fusion protein comprising an amino acid sequence of any one of SEQ ID NOs. 257-300, 302-317, 325-353, 355-365, 366, 372-381, 383-385, 388-420, 579-608, 636-646, 421-430, and 539-578. In some preferred embodiments, a first fusion protein comprising the amino acid sequence of any one of SEQ ID NOs. 421-430, and 539-578 can be administered with a second different fusion protein comprising the amino acid sequence of any one of SEQ ID NOs. 257-300, 302-317, 325-353, 355-365, 366, 372-381, 383-385, 388-420, 579-608, 636-646, 368-371, 434-440, 453-519, 523-538, or combinations thereof.

Further exemplary agents that can be administered in combination with one or more inducible cytokine fusion proteins described herein include, but are not limited to cytokines (e.g., IL-2, IL-15), signal induction inhibitors (e.g., BRAF inhibitors or MEK inhibitors), checkpoint inhibitors (e.g., PDL-1, PD-1, CTLA-4), c-met inhibitors, kinase inhibitors (e.g., VGEF inhibitors), a proteasome inhibitor, mTOR inhibitor, angiogenesis inhibitor.

A preferred immuno-oncology agent is an anti-PD-L1 agent or an anti-PD-1. Exemplary PD-1 and/or PD-L1 inhibitors include, but are not limited to Spartalizumab, Camrelizumab, Sintilimab, Tislelizumab, Toripalimab, Dostarlimab, INCMGA00012, AMP-224, and AMP-514). In embodiments, a fusion protein disclosed as 257-300, 302-317, 325-353, 355-365, 366, 372-381, 383-385, 388-420, 579-608, 636-646, 368-371, 434-440, 453-519, 523-538, 421-430, and 539-578 can be administered in combination with a check-point inhibitor, such as PDL-1, PD-1, or CTL-4.

Provided herein are pharmaceutical formulations or compositions containing the chimeric polypeptides and a pharmaceutically acceptable carrier. The herein provided compositions are suitable for administration in vitro or in vivo. By pharmaceutically acceptable carrier is meant a material that is not biologically or otherwise undesirable, i.e., the material is administered to a subject without causing undesirable biological effects or interacting in a deleterious manner with the other components of the pharmaceutical formulation or composition in which it is contained. The carrier is selected to minimize degradation of the active ingredient and to minimize adverse side effects in the subject.

Suitable carriers and their formulations are described in *Remington: The Science and Practice of Pharmacy,* 21$^{st}$ Edition, David B. Troy, ed., Lippicott Williams & Wilkins (2005). Typically, an appropriate amount of a pharmaceutically-acceptable salt is used in the formulation to render the formulation isotonic, although the formulate can be hypertonic or hypotonic if desired. Examples of the pharmaceutically-acceptable carriers include, but are not limited to, sterile water, saline, buffered solutions like Ringers solution, and dextrose solution. The pH of the solution is generally about 5 to about 8 or from about 7 to 7.5. Other carriers include sustained release preparations such as semipermeable matrices of solid hydrophobic polymers containing the immunogenic polypeptides. Matrices are in the form of shaped articles, e.g., films, liposomes, or microparticles. Certain carriers may be more preferable depending upon, for instance, the route of administration and concentration of composition being administered. Carriers are those suitable for administration of the chimeric polypeptides or nucleic acid sequences encoding the chimeric polypeptides to humans or other subjects.

The pharmaceutical formulations or compositions are administered in a number of ways depending on whether local or systemic treatment is desired and on the area to be treated. The compositions are administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy. In some embodiments, the compositions are administered locally (non-systemically), including intratumorally, intra-articularly, intrathecally, etc.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, anti-oxidants, chelating agents, and inert gases and the like.

Formulations for topical administration include ointments, lotions, creams, gels, drops, suppositories, sprays, liquids, and powders. Conventional pharmaceutical carriers, aqueous, powder, or oily bases, thickeners and the like are optionally necessary or desirable.

Compositions for oral administration include powders or granules, suspension or solutions in water or non-aqueous media, capsules, sachets, or tables. Thickeners, flavorings, diluents, emulsifiers, dispersing aids or binders are optionally desirable.

Optionally, the chimeric polypeptides or nucleic acid sequences encoding the chimeric polypeptides are administered by a vector. There are a number of compositions and methods which can be used to deliver the nucleic acid molecules and/or polypeptides to cells, either in vitro or in vivo via, for example, expression vectors. These methods and compositions can largely be broken down into two classes: viral based delivery systems and non-viral based delivery systems. Such methods are well known in the art and readily adaptable for use with the compositions and methods described herein. Such compositions and methods can be used to transfect or transduce cells in vitro or in vivo, for example, to produce cell lines that express and preferably secrete the encoded chimeric polypeptide or to therapeutically deliver nucleic acids to a subject. The components of the chimeric nucleic acids disclosed herein typically are operably linked in frame to encode a fusion protein.

As used herein, plasmid or viral vectors are agents that transport the disclosed nucleic acids into the cell without degradation and include a promoter yielding expression of the nucleic acid molecule and/or polypeptide in the cells into which it is delivered. Viral vectors are, for example, Adenovirus, Adeno-associated virus, herpes virus, Vaccinia virus, Polio virus, Sindbis, and other RNA viruses, including these viruses with the HIV backbone. Also preferred are any viral families which share the properties of these viruses which make them suitable for use as vectors. Retroviral vectors, in general are described by Coffin et al., Retroviruses, Cold Spring Harbor Laboratory Press (1997), which is incorporated by reference herein for the vectors and methods of making them. The construction of replication-defective adenoviruses has been described (Berkner et al., J. Virol. 61:1213-20 (1987); Massie et al., Mol. Cell. Biol. 6:2872-83 (1986); Haj-Ahmad et al., J. Virol. 57:267-74 (1986); Davidson et al., J. Virol. 61:1226-39 (1987); Zhang et al., BioTechniques 15:868-72 (1993)). The benefit and the use of these viruses as vectors is that they are limited in the extent to which they can spread to other cell types, since they can replicate within an initial infected cell, but are unable to form new infectious viral particles. Recombinant adenoviruses have been shown to achieve high efficiency after direct, in vivo delivery to airway epithelium, hepatocytes, vascular endothelium, CNS parenchyma, and a number of other tissue sites. Other useful systems include, for example, replicating and host-restricted non-replicating vaccinia virus vectors.

The provided polypeptides and/or nucleic acid molecules can be delivered via virus like particles. Virus like particles (VLPs) consist of viral protein(s) derived from the structural proteins of a virus. Methods for making and using virus like particles are described in, for example, Garcea and Gissmann, Current Opinion in Biotechnology 15:513-7 (2004).

The provided polypeptides can be delivered by subviral dense bodies (DBs). DBs transport proteins into target cells by membrane fusion. Methods for making and using DBs are described in, for example, Pepperl-Klindworth et al., Gene Therapy 10:278-84 (2003).

The provided polypeptides can be delivered by tegument aggregates. Methods for making and using tegument aggregates are described in International Publication No. WO 2006/110728.

Non-viral based delivery methods, can include expression vectors comprising nucleic acid molecules and nucleic acid sequences encoding polypeptides, wherein the nucleic acids are operably linked to an expression control sequence. Suitable vector backbones include, for example, those routinely used in the art such as plasmids, artificial chromosomes, BACs, YACs, or PACs. Numerous vectors and expression systems are commercially available from such corporations as Novagen (Madison, Wis.), Clonetech (Pal Alto, Calif.), Stratagene (La Jolla, Calif.), and Invitrogen/Life Technologies (Carlsbad, Calif.). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Such vectors can also be used to make the chimeric polypeptides by expression is a suitable host cell, such as CHO cells.

Preferred promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters, e.g. β-actin promoter or EF1α promoter, or from hybrid or chimeric promoters (e.g., CMV promoter fused to the β-actin promoter). Of course, promoters from the host cell or related species are also useful herein.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs (bp) in length, and they function in cis. Enhancers usually function to increase transcription from nearby promoters. Enhancers can also contain response elements that mediate the regulation of transcription. While many enhancer sequences are known from mammalian genes (globin, elastase, albumin, fetoprotein, and insulin), typically one will use an enhancer from a eukaryotic cell virus for general expression. Preferred examples are the SV40 enhancer on the late side of the replication origin, the cytomegalovirus early promoter enhancer, the polyoma enhancer on the late side of the replication origin, and adenovirus enhancers.

The promoter and/or the enhancer can be inducible (e.g. chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Preferred promoters of this type are the CMV promoter, the SV40 promoter, the β-actin promoter, the EF1α promoter, and the retroviral long terminal repeat (LTR).

The vectors also can include, for example, origins of replication and/or markers. A marker gene can confer a selectable phenotype, e.g., antibiotic resistance, on a cell. The marker product is used to determine if the vector has been delivered to the cell and once delivered is being expressed. Examples of selectable markers for mammalian cells are dihydrofolate reductase (DHFR), thymidine kinase, neomycin, neomycin analog G418, hygromycin, puromycin, and blasticidin. When such selectable markers are successfully transferred into a mammalian host cell, the transformed mammalian host cell can survive if placed under selective pressure. Examples of other markers include, for example, the *E. coli* lacZ gene, green fluorescent protein (GFP), and luciferase. In addition, an expression vector can include a tag sequence designed to facilitate manipulation or detection (e.g., purification or localization) of the expressed polypeptide. Tag sequences, such as GFP, glutathione S-transferase (GST), polyhistidine, c-myc, hemagglutinin, or FLAG™ tag (Kodak; New Haven, Conn.) sequences typically are expressed as a fusion with the encoded polypeptide. Such tags can be inserted anywhere within the polypeptide including at either the carboxyl or amino terminus.

As used herein, the terms peptide, polypeptide, or protein are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more. As used throughout, subject can be a vertebrate, more specifically a mammal (e.g. a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a disease or disorder (e.g. cancer). The term patient or subject includes human and veterinary subjects.

A subject at risk of developing a disease or disorder can be genetically predisposed to the disease or disorder, e.g., have a family history or have a mutation in a gene that causes the disease or disorder, or show early signs or symptoms of the disease or disorder. A subject currently with a disease or disorder has one or more than one symptom of the disease or disorder and may have been diagnosed with the disease or disorder.

The methods and agents as described herein are useful for both prophylactic and therapeutic treatment. For prophylactic use, a therapeutically effective amount of the chimeric polypeptides or chimeric nucleic acid sequences encoding the chimeric polypeptides described herein are administered to a subject prior to onset (e.g., before obvious signs of cancer or inflammation) or during early onset (e.g., upon initial signs and symptoms of cancer or inflammation). Prophylactic administration can occur for several days to years prior to the manifestation of symptoms of cancer or inflammation. Prophylactic administration can be used, for example, in the preventative treatment of subjects diagnosed with a genetic predisposition to cancer. Therapeutic treatment involves administering to a subject a therapeutically effective amount of the chimeric polypeptides or nucleic acid sequences encoding the chimeric polypeptides described herein after diagnosis or development of cancer or inflammation (e.g., an autoimmune disease). Prophylactic use may also apply when a patient is undergoing a treatment, e.g., a chemotherapy, in which inflammation is expected.

According to the methods taught herein, the subject is administered an effective amount of the agent (e.g., a chimeric polypeptide). The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products.

As used herein the terms treatment, treat, or treating refers to a method of reducing the effects of a disease or condition or symptom of the disease or condition. Thus, in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus, the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of the chimeric polypeptide or nucleic acid sequence encoding the chimeric polypeptide, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

IL-2 variants have been developed that are selective for IL2Rαβγ relative to IL2Rβγ (Shanafelt, A. B., et al., 2000, Nat Biotechnol. 18:1197-202; Cassell, D. J., et. al., 2002, Curr Pharm Des., 8:2171-83). These variants have amino acid substitutions which reduce their affinity for IL2RB. Because IL-2 has undetectable affinity for IL2RG, these variants consequently have reduced affinity for the IL2Rβγ receptor complex and reduced ability to activate IL2Rβγ-expressing cells, but retain the ability to bind IL2RA and the ability to bind and activate the IL2Rαβγ receptor complex.

One of these variants, IL2/N88R (Bay 50-4798), was clinically tested as a low-toxicity version of IL-2 as an immune system stimulator, based on the hypothesis that IL2Rβγ-expressing NK cells are a major contributor to toxicity. Bay 50-4798 was shown to selectively stimulate the proliferation of activated T cells relative to NK cells, and was evaluated in phase I/II clinical trials in cancer patients (Margolin, K., et. al., 2007, Clin Cancer Res., 13:3312-9) and HIV patients (Davey, R. T., et. al., 2008, J Interferon Cytokine Res., 28:89-100). These clinical trials showed that Bay 50-4798 was considerably safer and more tolerable than aldesleukin, and also showed that it increased the levels of CD4+CD25+ T cells, a cell population enriched in Treg cells. Subsequent to these trials, research in the field more fully established the identity of Treg cells and demonstrated that Treg cells selectively express IL2Rαβγ (reviewed in Malek, T. R., et al., 2010, Immunity, 33:153-65).

In addition, mutants can be made that selectively alter the affinity for the CD25 chain relative to native I1-2.

IL-2 can be engineered to produce mutants that bind the IL-2R complex generally or the IL-2Ra subunit specifically with an affinity that differs from that of the corresponding wild-type IL-2 or of a presently available mutant (referred to as C125S, as the cysteine residue at position 125 is replaced with a serine residue).

Accordingly, the present invention features mutant interleukin-2 (IL-2*) polypeptides that include an amino acid sequence that is at least 80% identical to wild-type IL-2 (e.g., 85, 87, 90, 95, 97, 98, or 99% identical) and that bind, as compared to WT IL-2, with higher to the IL-2 trimeric receptor relative to the dimeric IL-2 receptor. Typically, the muteins will also bind an IL-2 receptor α subunit (IL-2Rα) with an affinity that is greater than the affinity with which wild type IL-2 binds the IL-2Rα. The amino acid sequence within mutant IL-2 polypeptides can vary from SEQ ID NO:1 (UniProtKB accession number P60568) by virtue of containing (or only containing) one or more amino acid substitutions, which may be considered conservative or non-conservative substitutions. Non-naturally occurring amino acids can also be incorporated. Alternatively, or in addition, the amino acid sequence can vary from SEQ ID NO:1 (which may be considered the "reference" sequence) by virtue of containing and addition and/or deletion of one or more amino acid residues. More specifically, the amino acid sequence can differ from that of SEQ ID NO:1 by virtue of a mutation at least one of the following positions of SEQ ID NO:1: 1, 4, 8, 9, 10, 11, 13, 15, 26, 29, 30, 31, 35, 37, 46, 48, 49, 54, 61, 64, 67, 68, 69, 71, 73, 74, 75, 76, 79, 88, 89, 90, 92, 99, 101, 103, 114, 125, 128, or 133 (or combinations thereof). As noted, as few as one of these positions may be altered, as may two, three, four, five, six, seven, eight, nine, ten, or 11 or more (including up to all) of the positions. For example, the amino acid sequence can differ from SEQ ID NO:1 at positions 69 and 74 and further at one or more of positions 30, 35, and 128. The amino acid sequence can also differ from SEQ ID NO:2 (as disclosed in U.S. Pat. No. 7,569,215, incorporated herein by reference) at one of the following sets of positions: (a) positions 64, 69, and 74; (b) positions 69, 74, and 101; (c) positions 69, 74, and 128; (d) positions 30, 69, 74, and 103; (e) positions 49, 69, 73, and 76; (f) positions 69, 74, 101, and 133; (g) positions 30, 69, 74, and 128; (h) positions 69, 74, 88, and 99; (i) positions 30, 69, 74, and 128; (j) positions 9, 11, 35, 69, and 74; (k) positions 1, 46, 49, 61, 69, and 79; (l) positions 48, 68, 71, 90, 103, and 114; (m) positions 4, 10, 11, 69, 74, 88, and 133; (n) positions 15, 30 31, 35, 48, 69, 74, and 92; (O) positions 30, 68, 69, 71, 74, 75, 76, and 90; (p) positions 30, 31, 37, 69, 73, 74, 79, and 128; (q) positions 26, 29, 30, 54, 67, 69, 74, and 92; (r) positions 8, 13, 26, 30, 35, 37, 69, 74, and 92; and (s) positions 29, 31, 35, 37, 48, 69, 71, 74, 88, and 89. Aside from mutations at these positions, the amino acid sequence of the mutant IL-2 polypeptide can otherwise be identical to SEQ ID NO:1. With respect to specific substitutions, the amino acid sequence can differ from SEQ ID NO:1 by virtue of having one or more of the following mutations: A1T, S4P, K8R, K9T, T10A, Q11R, Q13R, E15K, N26D, N29S, N30S, N30D, N30T, Y31H, Y31C, K35R, T37A, T37R, M46L, K48E, K49R, K49E, K54R, E61D, K64R, E67G, E68D, V69A, N71T, N71A, N71R, A73V, Q74P, S75P, K76E, K76R, H79R, N88D, I89V, N90H, I92T, S99P, T101A, F103S, I114V, I128T, I128A, T133A, or T133N. Our nomenclature is consistent with that of the scientific literature, where the single letter code of the amino acid in the wild-type or reference sequence is followed by its position within the sequence and then by the single letter code of the amino acid with which it is replaced. Thus, A1T designates a substitution of the alanine residue a position 1 with threonine. Other mutant polypeptides within the scope of the invention include those that include a mutant of SEQ ID NO:2 having substitutions at V69 (e.g. A) and Q74 (e.g., P). For example, the amino acid sequence can include one of the following sets of mutations with respect to SEQ ID NO:2: (a) K64R, V69A, and Q74P; (b) V69A, Q74P, and T101A; (c) V69A, Q74P, and I128T; (d) N30D, V69A, Q74P, and F103S; (e) K49E, V69A, A73V, and K76E; (f) V69A, Q74P, T101A, and T133N; (g) N30S, V69A, Q74P, and I128A; (h) V69A, Q74P, N88D, and S99P; (i) N30S, V69A, Q74P, and I128T; (j) K9T, Q11R, K35R, V69A, and Q74P; (k) A1T, M46L, K49R, E61D, V69A, and H79R; (1) K48E, E68D, N71T, N90H, F103S, and I114V; (m) S4P, T10A, Q11R, V69A, Q74P, N88D, and T133A; (n) E15K, N30S Y31H, K35R, K48E, V69A, Q74P, and I92T; (o) N30S, E68D, V69A, N71A, Q74P, S75P, K76R, and N90H; (p) N30S, Y31C, T37A, V69A, A73V, Q74P, H79R, and I128T; (q) N26D, N29S, N30S, K54R, E67G, V69A, Q74P, and I92T; (r) K8R, Q13R, N26D, N30T, K35R, T37R, V69A, Q74P, and I92T; and (s) N29S, Y31H, K35R, T37A, K48E, V69A, N71R, Q74P, N88D, and I89V. SEQ ID NO:2 is disclosed in U.S. Pat. No. 7,569,215, which is incorporated herein by reference as an exemplary IL-2 polypeptide sequence that can be used in the invention.

As noted above, any of the mutant IL-2 polypeptides disclosed herein can include the sequences described; they can also be limited to the sequences described and otherwise identical to SEQ ID NO:1. Moreover, any of the mutant IL-2 polypeptides described herein can optionally include a substitution of the cysteine residue at position 125 with another residue (e.g., serine) and/or can optionally include a deletion of the alanine residue at position 1 of SEQ ID NO:1.

The mutant IL-2 polypeptides disclosed herein can bind to the IL-2Rα subunit with a $K_d$ of less than about 28 nM (e.g., less than about 25 nM; less than about 5 nM; about 1 nM; less than about 500 pM; or less than about 100 pM). More specifically, a mutant IL-2 polypeptide can have an affinity equilibrium constant less than 1.0 nM (e.g., about 0.8, 0.6, 0.4, or 0.2 nM). Affinity can also be expressed as a relative rate of dissociation from an IL-2Rα subunit or from an IL-2 receptor complex (e.g., a complex expressed on the surface of a cell or otherwise membrane bound). For example, the mutant IL-2 polypeptides can dissociate from, e.g., IL-2Rα, at a decreased rate relative to a wild-type polypeptide or to an IL-2 based therapeutic, e.g., IL-2*. Alternatively, affinity can be characterized as the time, or average time, an IL-2* polypeptide persists on, for example, the surface of a cell expressing an IL-2R. For example, an IL-2*polypeptide can persist on the receptor for at least about 2, 5, 10, 50, 100, or 250 times (or more).

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

The following are examples of methods and compositions of the invention. It is understood that various other embodiments may be practiced, given the general description provided herein.

Example 1: Detection of IL-2, IL-2 Mutein, IL-2Rα and IL-2$R_7$ in Fusion Proteins by ELISA IL-2 mutein is detected with a commercially available antibody, e.g., the anti-IL-2 monoclonal (JES6-1A12) (BD Pharmingen; San Jose, Calif.). A positive control is used to show whether the monoclonal antibody recognizes the cytokine or mutein. Antibodies against IL-2Rα and IL-2Rγ chain are also used. Wells of a 96-well plate are coated with an antibody (2.5 μg/ml) in PBS. Wells are blocked with 5% non-fat milk in PBS with 0.2% Tween®20 (PBS-M-Tw) and fusion proteins are added for 1-2 hours at 37° C. After washing, an anti-IL-2 biotin-labeled antibody, e.g., JES5H4 (BD Pharmingen) is added and binding is detected using Strepavidin HRP (Southern Biotechnology Associates; Birmingham, Ala.). The ELISA plate is developed by adding 50 μl O-phenylenediamine (OPD) (Sigma-Aldrich) in 0.1M Citrate pH 4.5 and 0.04% $H_2O_2$, stopped by adding 50 μl/well 2N $H_2SO_4$ and the absorbance was read at 490 nm.

Example 2: Protease Cleavage of Fusion Protein by MMP9 Protease

One of skill in the art would be familiar with methods of setting up protein cleavage assay. 100 ug of protein in 1×PBS pH 7.4 were cleaved with 1 μg active MMP9 (Sigma catalog #SAE0078-50 or Enzo catalog BML-SE360) and incubated at room temperature for up to 16 hours. Digested protein is subsequently used in functional assays or stored at −80° C. prior to testing. Extent of cleavage was monitored by SDS PAGE using methods well known in the art. As shown in FIGS. 10, 13, 18A, 18B, 24B, 24C, and 27A full cleavage of the fusion proteins by MMP9 protease is seen.

Example 3: CTLL-2 Assay

CTLL2 cells (ATCC) were plated in suspension at a concentration of 500,000 cells/well in culture media with or without 40 mg/ml human serum albumin (HSA) and stimulated with a dilution series of recombinant hIL2 or activatable hIL2 for 72 hours at 37° C. and 5% $CO_2$. Activity of uncleaved and cleaved activatable hIL2 was tested. Cleaved activatable hIL2 was generated by incubation with active MMP9. Cell activity was assessed using a CellTiter-Glo (Promega) luminescence-based cell viability assay.

Example 4: Protease Cleavage of the IL-2/IL-2Rα/IL-2Rγ Chimeric Polypeptide Results in Increased Accessibility to Antibodies and Biologically Active IL-2 Mutein The IL-2 mutein fusion proteins are biochemically characterized before and after cleavage with a protease, e.g., PSA. Immunoblot analyses will show that the fusion proteins can be cleaved by PSA and that there is an increase in intensity of the predicted low molecular weight cleavage product of approximately 20 kDa reactive with an anti-IL-2 antibody after treatment of the samples with PSA. The degree of cleavage is dependent upon the amount of PSA as well as the time of incubation. Interestingly, when the fusion protein is analyzed before and after PSA treatment by ELISA, it was found that the apparent amount of IL-2 is increased after PSA cleavage. In this experiment, there is an approximately 2 or 4-fold increase in the apparent amount of IL-2 detected using this sandwich ELISA depending on the construct, suggesting that the antibody binding is partially hindered in the intact fusion protein. Aliquots of the same samples are also analyzed after PSA treatment using the CTLL-2 cell line that requires IL-2 for growth and survival and the viability of cells can be ascertained using the colorimetric MTT assay. In this assay, the more a supernatant can be diluted, the more biologically active IL-2 it contains, and there is an increase in the amount of biologically active IL-2 after PSA cleavage. The amount of IL-2 mutein increase will suggest that after PSA cleavage there is an increase in the predicted low molecular weight cleavage fragment of approximately 20 kDa reactive with an anti-IL-2 antibody, an increase in antibody accessibility, and most importantly, an increase in the amount of biologically active IL-2 mutein.

Example 5. In Vivo Delivery of a Protease Activated Fusion Protein Results in Decreased Tumor Growth The chimeric polypeptide is examined to determine if it could have biological effects in vivo. For these experiments a system is used in which tumor cells injected intraperitoneally rapidly and preferentially attach and grow initially on the milky spots, a series of organized immune aggregates found on the omentum (Gerber et al., Am. J. Pathol. 169: 1739-52 (2006)). This system offers a convenient way to examine the effects of fusion protein treatment on tumor growth since fusion proteins can be delivered intraperitoneally multiple times and tumor growth can be analyzed by examining the dissociated omental cells. For these experiments, the Colon 38 cell line, a rapidly growing tumor cell line that expresses both MMP2 and MMP9 in vitro, may be used. The omental tissue normally expresses a relatively small amount of MMP2 and MMP9, but, when Colon 38 tumor is present on the omentum, MMP levels increase. Using this tumor model, the ability of IL-2 mutein fusion proteins to affect tumor growth is examined. Colon 38 cells are injected intraperitoneally, allowed to attach and grow for 1 day, and then treated daily with fusion protein interaperitoneally. At day 7, the animals are sacrificed and the omenta examined for tumor growth using flow cytometry and by a colony-forming assay.

Example 6: Construction of an Exemplary Activatable IL2 Protein Targeting CD20

Generation of an Activatable IL2 Domain

An IL-2 polypeptide capable of binding to CD20 polypeptide present in a tumor or on a tumor cell is produced as follows. A nucleic acid is produced that contains nucleic acid sequences: (1) encoding an IFNγ polypeptide sequence and (2) one or more polypeptide linkers. Activatable interleukin plasmid constructs can have optional Flag, His or other affinity tags, and are electroporated into HEK293 or other suitable human or mammalian cell lines and purified. Validation assays include T cell activation assays using T cells responsive to IFNγ stimulation in the presence of a protease.

Generation of a scFv CD20 Binding Domain

CD20 is one of the cell surface proteins present on B-lymphocytes. CD20 antigen is found in normal and malignant pre-B and mature B lymphocytes, including those in over 90% of B-cell non-Hodgkin's lymphomas (NHL). The antigen is absent in hematopoietic stem cells, activated B lymphocytes (plasma cells) and normal tissue. As such, several antibodies mostly of murine origin have been described: 1FS, 2B8/C2B8, 2H7, and 1H4.

Human or humanized anti-CD20 antibodies are therefore used to generate scFv sequences for CD20 binding domains of an activatable interleukin protein. DNA sequences coding for human or humanized VL and VH domains are obtained, and the codons for the constructs are, optionally, optimized for expression in cells from *Homo sapiens*. The order in which the VL and VH domains appear in the scFv is varied (i.e., VL-VH, or VH-VL orientation), and three copies of the "G4S" (SEQ ID NO.: 449) or "G4S" (SEQ ID NO.: 449) subunit $(G_4S)_3$ (SEQ ID NO.: 452) connect the variable domains to create the scFv domain. Anti-CD20 scFv plasmid constructs can have optional Flag, His or other affinity tags, and are electroporated into HEK293 or other suitable human or mammalian cell lines and purified. Validation assays include binding analysis by FACS, kinetic analysis using Proteon, and staining of CD20-expressing cells.

Cloning of DNA Expression Constructs Encoding the Activatable IL2 Protein

The activatable IL2 construct with protease cleavage site domains are used to construct an activatable interleukin protein in combination with an anti-CD20 scFv domain and a serum half-life extension element (e.g., a HSA binding peptide or VH domain). For expression of an activatable interleukin protein in CHO cells, coding sequences of all protein domains are cloned into a mammalian expression vector system. In brief, gene sequences encoding the activatable interleukin domain, serum half-life extension element, and CD20 binding domain along with peptide linkers L1 and L2 are separately synthesized and subcloned. The resulting constructs are then ligated together in the order of CD20 binding domain—L1-IL2 subunit 1-L2-protease cleavage domain—L3-IL2 subunit 2-L4-anti-CD20 scFv-L5-serum half-life extension element to yield a final construct. All expression constructs are designed to contain coding sequences for an N-terminal signal peptide and a C-terminal hexahistidine (6×His)-tag (SEQ ID NO. 354) to facilitate protein secretion and purification, respectively.

Expression of Activatable IL2 Proteins in Stably Transfected CHO Cells

A CHO cell expression system (Flp-In®, Life Technologies), a derivative of CHO-K1 Chinese Hamster ovary cells (ATCC, CCL-61) (Kao and Puck, Proc. Natl. Acad Sci USA 1968; 60(4):1275-81), is used. Adherent cells are subcultured according to standard cell culture protocols provided by Life Technologies.

For adaption to growth in suspension, cells are detached from tissue culture flasks and placed in serum-free medium. Suspension-adapted cells are cryopreserved in medium with 10% DMSO.

Recombinant CHO cell lines stably expressing secreted activatable interleukin proteins are generated by transfection of suspension-adapted cells. During selection with the antibiotic Hygromycin B viable cell densities are measured twice a week, and cells are centrifuged and resuspended in fresh selection medium at a maximal density of $0.1\times10^6$ viable cells/mL. Cell pools stably expressing activatable interleukin proteins are recovered after 2-3 weeks of selection at which point cells are transferred to standard culture medium in shake flasks. Expression of recombinant secreted proteins is confirmed by performing protein gel electrophoresis or flow cytometry. Stable cell pools are cryopreserved in DMSO containing medium.

Activatable IL2 proteins are produced in 10-day fed-batch cultures of stably transfected CHO cell lines by secretion into the cell culture supernatant. Cell culture supernatants are harvested after 10 days at culture viabilities of typically >75%. Samples are collected from the production cultures every other day and cell density and viability are assessed. On day of harvest, cell culture supernatants are cleared by centrifugation and vacuum filtration before further use.

Protein expression titers and product integrity in cell culture supernatants are analyzed by SDS-PAGE.

Purification of Activatable IL2 Proteins

Activatable IL2 proteins are purified from CHO cell culture supernatants in a two-step procedure. The constructs are subjected to affinity chromatography in a first step followed by preparative size exclusion chromatography (SEC) on Superdex 200 in a second step. Samples are buffer-exchanged and concentrated by ultrafiltration to a typical concentration of >1 mg/mL. Purity and homogeneity (typically >90%) of final samples are assessed by SDS PAGE under reducing and non-reducing conditions, followed by immunoblotting using an anti-HSA or anti idiotype antibody as well as by analytical SEC, respectively. Purified proteins are stored at aliquots at −80° C. until use.

Example 7: Determination of Antigen Affinity by Flow Cytometry

The activatable interleukin proteins of Example 6 are tested for their binding affinities to human $CD20^+$ cells and cynomolgus $CD20^+$ cells.

$CD20^+$ cells are incubated with 100 μL of serial dilutions of the activatable interleukin proteins of Example 1 and at least one protease. After washing three times with FACS buffer the cells are incubated with 0.1 mL of 10 μg/mL mouse monoclonal anti-idiotype antibody in the same buffer for 45 min on ice. After a second washing cycle, the cells are incubated with 0.1 mL of 15 μg/mL FITC-conjugated goat anti-mouse IgG antibodies under the same conditions as before. As a control, cells are incubated with the anti-His IgG followed by the FITC-conjugated goat anti-mouse IgG antibodies without the activatable IL2 proteins. The cells were then washed again and resuspended in 0.2 mL of FACS buffer containing 2 μg/mL propidium iodide (PI) in order to exclude dead cells. The fluorescence of $1\times10^4$ living cells is measured using a Beckman-Coulter FC500 MPL flow cytometer using the MXP software (Beckman-Coulter, Krefeld, Germany) or a Millipore Guava EasyCyte flow cytometer using the Incyte software (Merck Millipore, Schwalbach, Germany). Mean fluorescence intensities of the cell samples are calculated using CXP software (Beckman-Coulter, Krefeld, Germany) or Incyte software (Merck Millipore, Schwalbach, Germany). After subtracting the fluorescence intensity values of the cells stained with the secondary and tertiary reagents alone the values are then used for calculation of the $K_D$ values with the equation for one-site binding (hyperbola) of the GraphPad Prism (version 6.00 for Windows, GraphPad Software, La Jolla California USA).

CD20 binding and crossreactivity are assessed on the human CD20+ tumor cell lines. The $K_D$ ratio of crossreactivity is calculated using the $K_D$ values determined on the CHO cell lines expressing either recombinant human or recombinant cynomolgus antigens.

Example 8: Cytotoxicity Assay

The activatable interleukin protein of Example 6 is evaluated in vitro on its mediation of immune response to CD20+ target cells.

Fluorescence labeled CD20+ REC-1 cells (a Mantle cell lymphoma cell line, ATCC CRL-3004) are incubated with isolated PBMC of random donors or CB15 T-cells (standardized T-cell line) as effector cells in the presence of the activatable IL2 protein of Example 5 and at least one protease. After incubation for 4 h at 37° C. in a humidified incubator, the release of the fluorescent dye from the target cells into the supernatant is determined in a spectrofluorimeter. Target cells incubated without the activatable IL2 protein of Example land target cells totally lysed by the addition of saponin at the end of the incubation serve as negative and positive controls, respectively.

Based on the measured remaining living target cells, the percentage of specific cell lysis is calculated according to the following formula: [1−(number of living $targets_{(sample)}$/number of living $targets_{(spontaneous)}$)]×100%. Sigmoidal dose response curves and $EC_{50}$ values are calculated by non-linear regression/4-parameter logistic fit using the GraphPad Software. The lysis values obtained for a given antibody concentration are used to calculate sigmoidal dose-response curves by 4 parameter logistic fit analysis using the Prism software.

Example 9: Pharmacokinetics of Activatable Interleukin Proteins

The activatable interleukin protein of Example 6 is evaluated for half-time elimination in animal studies.

The activatable IL2 protein is administered to cynomolgus monkeys as a 0.5 mg/kg bolus injection into the saphenous vein. Another cynomolgus monkey group receives a comparable IL2 construct in size, but lacking a serum half-life extension element. A third and fourth group receive an IL2 construct with serum half-life extension element and a cytokine with CD20 and serum half-life extension elements respectively, and both comparable in size to the activatable interleukin protein. Each test group consists of 5 monkeys. Serum samples are taken at indicated time points, serially diluted, and the concentration of the proteins is determined using a binding ELISA to CD20.

Pharmacokinetic analysis is performed using the test article plasma concentrations. Group mean plasma data for each test article conforms to a multi-exponential profile when plotted against the time post-dosing. The data are fit by a standard two-compartment model with bolus input and first-order rate constants for distribution and elimination phases. The general equation for the best fit of the data for i.v. administration is: $c(t)=Ae^{-\alpha t}+Be^{-\beta t}$, where c(t) is the plasma concentration at time t, A and B are intercepts on the Y-axis, and α and β are the apparent first-order rate constants for the distribution and elimination phases, respectively. The α-phase is the initial phase of the clearance and reflects distribution of the protein into all extracellular fluid of the animal, whereas the second or β-phase portion of the decay curve represents true plasma clearance. Methods for fitting such equations are well known in the art. For example, $A=DN(\alpha-k21)/(\alpha-\beta)$, $B=DN(\beta-k21)/(\alpha-\beta)$, and α and β (for $\alpha>\beta$) are roots of the quadratic equation: $r^2+(k12+k21+k10)r+k21k10=0$ using estimated parameters of V=volume of distribution, k10=elimination rate, k12=transfer rate from compartment 1 to compartment 2 and k21=transfer rate from compartment 2 to compartment 1, and D=the administered dose.

Data analysis: Graphs of concentration versus time profiles are made using KaleidaGraph (KaleidaGraph™ V. 3.09 Copyright 1986-1997. Synergy Software. Reading, Pa.). Values reported as less than reportable (LTR) are not included in the PK analysis and are not represented graphically. Pharmacokinetic parameters are determined by compartmental analysis using WinNonlin software (WinNonlin® Professional V. 3.1 WinNonlin™ Copyright 1998-1999. Pharsight Corporation. Mountain View, Calif.). Pharmacokinetic parameters are computed as described in Ritschel W A and Kearns G L, 1999, IN: *Handbook Of Basic Pharmacokinetics Including Clinical Applications,* 5th edition, American Pharmaceutical Assoc., Washington, D.C.

It is expected that the activatable interleukin protein of Example 5 has improved pharmacokinetic parameters such as an increase in elimination half-time as compared to proteins lacking a serum half-life extension element.

Example 10: Xenograft Tumor Model

The activatable IL2 protein of Example 6 is evaluated in a xenograft model.

Female immune-deficient NOD/scid mice are sub-lethally irradiated (2 Gy) and subcutaneously inoculated with $4\times10^6$ Ramos RA1 cells into the right dorsal flank. When tumors reach 100 to 200 $mm^3$, animals are allocated into 3 treatment groups. Groups 2 and 3 (8 animals each) are intraperitoneally injected with $1.5\times10^7$ activated human T-cells. Three days later, animals from Group 3 are subsequently treated with a total of 9 intravenous doses of 50 sg activatable interleukin protein of Example 1 (qd×9d). Groups 1 and 2 are only treated with vehicle. Body weight and tumor volume are determined for 30 days.

It is expected that animals treated with the activatable interleukin protein of Example 5 have a statistically significant delay in tumor growth in comparison to the respective vehicle-treated control group.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 11: Mouse IFNγ WEHI Cell Survival Assay

WEHI279 cells (ATCC) were plated in suspension at a concentration of 25,000 cells/well in culture media with or without 1.5% human serum albumin (HSA) and stimulated with a dilution series of recombinant mIFNγ or inducible mIFNγ for 72 hours at 37° C. and 5% $CO_2$. Activity of uncleaved and cleaved inducible mIFNγ was tested. Cleaved inducible mIFNg was generated by incubation with active MMP9. Cell survival was assessed using a CellTiter-Glo (Promega) luminescence-based cell viability assay. The EC50 values for cleaved inducible mIFNg molecules were at least 100× more potent than un-cleaved inducible mIFNg molecules. As shown in FIGS. 16A-16F, greater inducibility was seen in assays wherein the culture media contained human serum albumin.

Example 12: Mouse IFNγ B16 Reporter and Mouse IFNα/β B16 Reporter Cell Assays B16-Blue IFNγ cells (InvivoGen) were plated at a concentration of 75,000 cells/well in culture media with or without 1.5% human serum albumin (HSA) and stimulated with a dilution series of recombinant mIFNγ or inducible mIFNγ for 24 hours at 37° C. and 5% $CO_2$. Activity of uncleaved and cleaved inducible mIFNγ was tested. Cleaved inducible mIFNγ was generated by incubation with active MMP9. Supernatants were harvested, and SEAP activation was assessed by adding QUANTI-Blue Reagent (InvivoGen), incubating at 37° C. for 2 hours, and measuring absorbance at 620 nm. Results are shown in FIGS. 17A-17F, 19A, 19B, 22A, 22B, 23A, 23B, and 28A-28N. This experiment was repeated with for IFNα fusion proteins using B16-Blue IFNα/β cells. The EC50 values for cleaved inducible mIFNα molecules were at least 100× more potent than un-cleaved inducible mIFNα molecules.

B16-Blue IFN-α/p cells (InvivoGen) were plated in suspension at a density of 75,000 cells/well in culture media with or without 15 mg/ml mouse serum albumin (HSA) and stimulated with a dilution series of recombinant mouse IFNα (or IFNβ) and activatable mouse IFNα (or IFNβ) for 20-24 hours at 37° C. and 5% $CO_2$. Activity of uncleaved and cleaved activatable IFNα (or IFNβ) was tested. Cleaved inducible IFNα (or IFNβ) was generated by incubation with active recombinant protease. Stimulation of B16-Blue IFN-α/β cells with IFNα (or IFNβ) induces expression of Secreted Alkaline Phosphatase (SEAP) from an ISRE- ISG54-SEAP reporter. IFNα (or IFNβ) activity was assessed by quantification of SEAP activity using the reagent QUANTI-Blue (InvivoGen), a colorimetric based assay. Results are shown in FIGS. 10A-10J.

Example 13. In Vivo Delivery of a Protease Activated Fusion Protein Results in Decreased Tumor Growth The chimeric polypeptide is examined to determine if it could have biological effects in vivo. For these experiments a system is used in which tumor cells injected intraperitoneally rapidly and preferentially attach and grow initially on the milky spots, a series of organized immune aggregates found on the omentum (Gerber et al., Am. J. Pathol. 169: 1739-52 (2006)). This system offers a convenient way to examine the effects of fusion protein treatment on tumor growth since fusion proteins can be delivered intraperitoneally multiple times and tumor growth can be analyzed by examining the dissociated omental cells. For these experiments, the Colon 38 cell line, a rapidly growing tumor cell line that expresses both MMP2 and MMP9 in vitro, may be used. The omental tissue normally expresses a relatively small amount of MMP2 and MMP9, but, when Colon 38 tumor is present on the omentum, MMP levels increase. Using this tumor model, the ability of IFN fusion proteins to affect tumor growth is examined. Colon 38 cells are injected intraperitoneally, allowed to attach and grow for 1 day, and then treated daily with fusion protein interaperitoneally. At day 7, the animals are sacrificed and the omenta examined for tumor growth using flow cytometry and by a colony-forming assay.

Example 13b: The Chimeric Polypeptide was Examined to Determine its Biological Effects In Vivo The MC38 cell line, a rapidly growing colon adenocarcinoma cell line that expresses MMP9 in vitro, was used. Using this tumor model, the ability of IFNγ fusion proteins to affect tumor growth was examined. MC38 cells were injected subcutaneously, allowed to grow for 10-14 days, and then treated with fusion protein twice weekly intraperitoneally for a total of four doses, at the levels shown in FIG. 21A-21C. As a comparator, wild-type mIFNγ was administered at the dose levels indicated, twice daily for 2 weeks on a 5 day on/2 day off schedule (10 total doses). Tumor growth and body weight were monitored approximately twice per week for two weeks.

Example 14: Construction of an Exemplary IFNγ Protein Targeting CD20

Generation of an Activatable Cytokine Domain

An IFNγ polypeptide capable of binding to CD20 polypeptide present in a tumor or on a tumor cell is produced as follows. A nucleic acid is produced that contains nucleic acid sequences: (1) encoding an IFNγ polypeptide sequence and (2) one or more polypeptide linkers. Activatable IFNγ plasmid constructs can have optional Flag, His or other affinity tags, and are electroporated into HEK293 or other suitable human or mammalian cell lines and purified. Validation assays include T cell activation assays using T cells responsive to IFNγ stimulation in the presence of a protease.

Generation of a scFv CD20 Binding Domain

CD20 is one of the cell surface proteins present on B-lymphocytes. CD20 antigen is found in normal and malignant pre-B and mature B lymphocytes, including those in over 90% of B-cell non-Hodgkin's lymphomas (NHL). The antigen is absent in hematopoietic stem cells, activated B lymphocytes (plasma cells) and normal tissue. As such, several antibodies mostly of murine origin have been described: 1F5, 2B8/C2B8, 2H7, and 1H4.

Human or humanized anti-CD20 antibodies are therefore used to generate scFv sequences for CD20 binding domains of an activatable IFNγ protein. DNA sequences coding for human or humanized VL and VH domains are obtained, and the codons for the constructs are, optionally, optimized for expression in cells from *Homo sapiens*. The order in which the VL and VH domains appear in the scFv is varied (i.e., VL-VH, or VH-VL orientation), and three copies of the "G4S" (SEQ ID NO.: 449) or "$G_4S$" (SEQ ID NO.: 449) subunit $(G_4S)_3$ (SEQ ID NO.: 452) connect the variable domains to create the scFv domain. Anti-CD20 scFv plasmid constructs can have optional Flag, His or other affinity tags, and are electroporated into HEK293 or other suitable human or mammalian cell lines and purified. Validation assays include binding analysis by FACS, kinetic analysis using Proteon, and staining of CD20-expressing cells.

Cloning of DNA Expression Constructs Encoding the Activatable IFNγ Protein

The activatable IFNγ construct with protease cleavage site domains are used to construct an activatable IFNγ protein in combination with an anti-CD20 scFv domain and a serum half-life extension element (e.g., a HSA binding peptide or VH domain), with the domains organized. For expression of an activatable IFNγ protein in CHO cells, coding sequences of all protein domains are cloned into a mammalian expression vector system. In brief, gene sequences encoding the activatable IFNγ domain, serum half-life extension element, and CD20 binding domain along with peptide linkers L1 and L2 are separately synthesized and subcloned. The resulting constructs are then ligated together in the order of CD20 binding domain—L1-IFNγ subunit 1-L2-protease cleavage domain—L3-IFNγ subunit2-L4-anti-CD20 scFv-L5-serum half-life extension element to yield a final construct. All expression constructs are designed to contain coding sequences for an N-terminal signal peptide and a C-terminal hexahistidine (6×His)-tag (SEQ ID NO.: 354) to facilitate protein secretion and purification, respectively.

Expression of Activatable IFNγ Proteins in Stably Transfected CHO Cells

A CHO cell expression system (Flp-In®, Life Technologies), a derivative of CHO-K1 Chinese Hamster ovary cells (ATCC, CCL-61) (Kao and Puck, Proc. Natl. Acad Sci USA 1968; 60(4):1275-81), is used. Adherent cells are subcultured according to standard cell culture protocols provided by Life Technologies.

For adaption to growth in suspension, cells are detached from tissue culture flasks and placed in serum-free medium. Suspension-adapted cells are cryopreserved in medium with 10% DMSO.

Recombinant CHO cell lines stably expressing secreted activatable IFNγ proteins are generated by transfection of suspension-adapted cells. During selection with the antibiotic Hygromycin B viable cell densities are measured twice a week, and cells are centrifuged and resuspended in fresh selection medium at a maximal density of $0.1\times10^6$ viable cells/mL. Cell pools stably expressing activatable IFNγ proteins are recovered after 2-3 weeks of selection at which point cells are transferred to standard culture medium in shake flasks. Expression of recombinant secreted proteins is confirmed by performing protein gel electrophoresis or flow cytometry. Stable cell pools are cryopreserved in DMSO containing medium.

Activatable IFNγ proteins are produced in 10-day fed-batch cultures of stably transfected CHO cell lines by secretion into the cell culture supernatant. Cell culture supernatants are harvested after 10 days at culture viabilities of typically >75%. Samples are collected from the production cultures every other day and cell density and viability are assessed. On day of harvest, cell culture supernatants are cleared by centrifugation and vacuum filtration before further use.

Protein expression titers and product integrity in cell culture supernatants are analyzed by SDS-PAGE.

Purification of Activatable IFNγ Proteins

Activatable IFNγ proteins are purified from CHO cell culture supernatants in a two-step procedure. The constructs are subjected to affinity chromatography in a first step followed by preparative size exclusion chromatography (SEC) on Superdex 200 in a second step. Samples are buffer-exchanged and concentrated by ultrafiltration to a typical concentration of >1 mg/mL. Purity and homogeneity (typically >90%) of final samples are assessed by SDS PAGE under reducing and non-reducing conditions, followed by immunoblotting using an anti-HSA or anti idiotype antibody as well as by analytical SEC, respectively. Purified proteins are stored at aliquots at −80° C. until use.

Example 15: Determination of Antigen Affinity by Flow Cytometry

The activatable IFNγ proteins of Example 1 are tested for their binding affinities to human $CD20^+$ cells and cynomolgus $CD20^+$ cells.

$CD20^+$ cells are incubated with 100 μL of serial dilutions of the activatable IFNγ proteins of Example 1 and at least one protease. After washing three times with FACS buffer the cells are incubated with 0.1 mL of 10 μg/mL mouse monoclonal anti-idiotype antibody in the same buffer for 45 min on ice. After a second washing cycle, the cells are incubated with 0.1 mL of 15 μg/mL FITC-conjugated goat anti-mouse IgG antibodies under the same conditions as before. As a control, cells are incubated with the anti-His IgG followed by the FITC-conjugated goat anti-mouse IgG antibodies without the activatable IFNγ proteins. The cells were then washed again and resuspended in 0.2 mL of FACS buffer containing 2 μg/mL propidium iodide (PI) in order to exclude dead cells. The fluorescence of $1\times10^4$ living cells is measured using a Beckman-Coulter FC500 MPL flow cytometer using the MXP software (Beckman-Coulter, Krefeld, Germany) or a Millipore Guava EasyCyte flow cytometer using the Incyte software (Merck Millipore, Schwalbach, Germany). Mean fluorescence intensities of the cell samples are calculated using CXP software (Beckman-Coulter, Krefeld, Germany) or Incyte software (Merck Millipore, Schwalbach, Germany). After subtracting the fluorescence intensity values of the cells stained with the secondary and tertiary reagents alone the values are then used for calculation of the $K_D$ values with the equation for one-site binding (hyperbola) of the GraphPad Prism (version 6.00 for Windows, GraphPad Software, La Jolla California USA).

CD20 binding and crossreactivity are assessed on the human $CD20^+$ tumor cell lines. The $K_D$ ratio of crossreactivity is calculated using the $K_D$ values determined on the CHO cell lines expressing either recombinant human or recombinant cynomolgus antigens.

Example 16: Cytotoxicity Assay

The activatable IFNγ protein of Example 5 is evaluated in vitro on its mediation of immune response to $CD20^+$ target cells.

Fluorescence labeled $CD20^+$ REC-1 cells (a Mantle cell lymphoma cell line, ATCC CRL-3004) are incubated with isolated PBMC of random donors or CB15 T-cells (standardized T-cell line) as effector cells in the presence of the activatable IFNγ protein of Example 5 and at least one protease. After incubation for 4 h at 37° C. in a humidified incubator, the release of the fluorescent dye from the target cells into the supernatant is determined in a spectrofluorimeter. Target cells incubated without the activatable IFNγ protein of Example 5 and target cells totally lysed by the addition of saponin at the end of the incubation serve as negative and positive controls, respectively.

Based on the measured remaining living target cells, the percentage of specific cell lysis is calculated according to the following formula: $[1-(\text{number of living targets}_{(sample)}/\text{number of living targets}_{(spontaneous)})]\times100\%$. Sigmoidal dose response curves and $EC_{50}$ values are calculated by non-linear regression/4-parameter logistic fit using the GraphPad Software. The lysis values obtained for a given antibody concentration are used to calculate sigmoidal dose-response curves by 4 parameter logistic fit analysis using the Prism software.

Example 17: Pharmacokinetics of Activatable IFNγ Proteins

The activatable IFNγ protein of Example 5 is evaluated for half-time elimination in animal studies.

The activatable IFNγ protein is administered to cynomolgus monkeys as a 0.5 mg/kg bolus injection into the saphenous vein. Another cynomolgus monkey group receives a comparable cytokine in size, but lacking a serum half-life extension element. A third and fourth group receive a cytokine with serum half-life extension elements and a cytokine with CD20 and serum half-life extension elements respectively, and both comparable in size to the activatable IFNγ protein. Each test group consists of 5 monkeys. Serum samples are taken at indicated time points, serially diluted, and the concentration of the proteins is determined using a binding ELISA to CD20.

Pharmacokinetic analysis is performed using the test article plasma concentrations. Group mean plasma data for each test article conforms to a multi-exponential profile when plotted against the time post-dosing. The data are fit by a standard two-compartment model with bolus input and first-order rate constants for distribution and elimination phases. The general equation for the best fit of the data for i.v. administration is: $c(t)=Ae^{-\alpha t}+Be^{-\beta t}$, where c(t) is the plasma concentration at time t, A and B are intercepts on the Y-axis, and α and β are the apparent first-order rate constants for the distribution and elimination phases, respectively. The α-phase is the initial phase of the clearance and reflects distribution of the protein into all extracellular fluid of the animal, whereas the second or β-phase portion of the decay curve represents true plasma clearance. Methods for fitting such equations are well known in the art. For example, $A=DN(\alpha-k21)/(\alpha-\beta)$, $B=DN(\beta-k21)/(\alpha-\beta)$, and α and β (for α>β) are roots of the quadratic equation: $r2+(k12+k21+k10)r+k21k10=0$ using estimated parameters of V=volume of distribution, k10=elimination rate, k12=transfer rate from compartment 1 to compartment 2 and k21=transfer rate from compartment 2 to compartment 1, and D=the administered dose.

Data analysis: Graphs of concentration versus time profiles are made using KaleidaGraph (KaleidaGraph™ V. 3.09 Copyright 1986-1997. Synergy Software. Reading, Pa.). Values reported as less than reportable (LTR) are not included in the PK analysis and are not represented graphically. Pharmacokinetic parameters are determined by compartmental analysis using WinNonlin software (WinNonlin® Professional V. 3.1 WinNonlin™ Copyright 1998-1999. Pharsight Corporation. Mountain View, Calif.). Pharmacokinetic parameters are computed as described in Ritschel W A and Kearns G L, 1999, IN: *Handbook Of Basic Pharmacokinetics Including Clinical Applications,* 5th edition, American Pharmaceutical Assoc., Washington, D.C.

It is expected that the activatable IFNγ protein of Example 5 has improved pharmacokinetic parameters such as an increase in elimination half-time as compared to proteins lacking a serum half-life extension element.

Example 18: Xenograft Tumor Model

The activatable IFNγ protein of Example 5 is evaluated in a xenograft model.

Female immune-deficient NOD/scid mice are sub-lethally irradiated (2 Gy) and subcutaneously inoculated with $4\times10^6$ Ramos RA1 cells into the right dorsal flank. When tumors reach 100 to 200 $mm^3$, animals are allocated into 3 treatment groups. Groups 2 and 3 (8 animals each) are intraperitoneally injected with $1.5\times10^7$ activated human T-cells. Three days later, animals from Group 3 are subsequently treated with a total of 9 intravenous doses of 50 sg activatable IFNγ protein of Example 5 (qdx9d). Groups 1 and 2 are only treated with vehicle. Body weight and tumor volume are determined for 30 days.

It is expected that animals treated with the activatable IFNγ protein of Example 5 have a statistically significant delay in tumor growth in comparison to the respective vehicle-treated control group.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 19: HEK-Blue Assay

HEK-Blue IL12 cells (InvivoGen) were plated in suspension at a concentration of 50,000 cells/well in culture media with or without 15 or 40 mg/ml human serum albumin (HSA) and stimulated with a dilution series of recombinant hIL12, chimeric IL12 (mouse p35/human p40) or activatable hIL12 for 20-24 hours at 37° C. and 5% $CO_2$. Activity of uncleaved and cleaved activatable hIL12 was tested. Cleaved inducible hIL12 was generated by incubation with active MMP9. IL12 activity was assessed by quantification of Secreted Alkaline Phosphatase (SEAP) activity using the reagent QUANTI-Blue (InvivoGen), a colorimetric based assay. Results are shown in FIGS. 7A-7Q, 11A-11B, 12A-12F, 15A-15D, and 26A-26D.

HEK-Blue IL2 cells (InvivoGen) were plated in suspension at a concentration of 50,000 cells/well in culture media with or without 15-40 mg/ml human serum albumin (HSA) and stimulated with a dilution series of recombinant hIL2 or activatable hIL2 for 24 hours at 37° C. and 5% $CO_2$. Activity of uncleaved and cleaved activatable hIL2 was tested. Cleaved inducible hIL2 was generated by incubation with active MMP9. IL12 activity was assessed by quantification of Secreted Alkaline Phosphatase (SEAP) activity using the reagent QUANTI-Blue (InvivoGen), a colorimetric based assay. Exemplary results are shown in FIGS. 1A-1F and FIGS. 24A-24D.

HEK-Blue IFN-α/b cells (InvivoGen) were plated in suspension at a density of 50,000 cells/well in culture media with or without 15 mg/ml human serum albumin (HSA) and stimulated with a dilution series of recombinant human IFNa (or IFNb) and activatable human IFNa (or IFNb) for 20-24 hours at 37° C. and 5% $CO_2$. Activity of uncleaved and cleaved activatable IFNa (or IFNb) was tested. Cleaved inducible IFNa (or IFNb) was generated by incubation with active recombinant protease. Stimulation of HEK-Blue IFN-α/β cells with IFNα (or IFNβ) induces expression of Secreted Alkaline Phosphatase (SEAP) from an ISG54-SEAP reporter. IFNα (or IFNβ) activity was assessed by quantification of SEAP activity using the reagent QUANTI-Blue (InvivoGen), a colorimetric based assay. Results are shown in FIGS. 36A-36H.

Example 20: Splenocyte T-Blast Assay

T-Blasts were induced from murine splenocytes with a 6-day incubation with PHA and a 24 hr incubation with recombinant hIL12. Tblasts were then plated in suspension at a concentration of 200,000 cells/well in culture media with or without 40 mg/ml human serum albumin (HSA) and stimulated with a dilution series of recombinant hIL12 or chimeric IL12 (mouse p35/human p40) or mouse IL12 for 72 hours at 37° C. and 5% $CO_2$. Activity of uncleaved and cleaved IL12 fusion proteins was tested. Cleaved inducible hIL12 was generated by incubation with active MMP9. IL12 activity was assessed by downstream quantification of IFNγ production using a mIFNγ alpha ELISA.

Example 21: In Vivo Delivery of a Protease Activated Fusion Protein Results in Decreased Tumor Growth The chimeric polypeptide is examined to determine if it could have biological effects in vivo. For these experiments a system is used in which tumor cells injected intraperitoneally rapidly and preferentially attach and grow initially on the milky spots, a series of organized immune aggregates found on the omentum (Gerber et al., Am. J. Pathol. 169: 1739-52 (2006)). This system offers a convenient way to examine the effects of fusion protein treatment on tumor growth since fusion proteins can be delivered intraperitoneally multiple times and tumor growth can be analyzed by examining the dissociated omental cells. For these experiments, the Colon 38 cell line, a rapidly growing tumor cell line that expresses both MMP2 and MMP9 in vitro, may be used. The omental tissue normally expresses a relatively small amount of MMP2 and MMP9, but, when Colon 38 tumor is present on the omentum, MMP levels increase. Using this tumor model, the ability of IL-2 mutein fusion proteins to affect tumor growth is examined. Colon 38 cells are injected intraperitoneally, allowed to attach and grow for 1 day, and then treated daily with fusion protein interaperitoneally. At day 7, the animals are sacrificed and the omenta examined for tumor growth using flow cytometry and by a colony-forming assay.

Example 22: Construction of an Exemplary Activatable Interleukin Protein Targeting CD20

Generation of an Activatable Interleukin Domain

The human IL-12p35 chain canonical sequence is Uniprot Accession No. P29459. The human IL-12p40 chain canonical sequence is Uniprot Accession No. P29460. IL-12p35 and IL-12p40 are cloned into an expression construct. A protease cleavage site is included between the IL-12p35 and IL-12p40 domains. An IL-12 polypeptide capable of binding to CD20 polypeptide present in a tumor or on a tumor cell is produced as follows. A nucleic acid is produced that contains nucleic acid sequences: (1) encoding an IFNγ polypeptide sequence and (2) one or more polypeptide linkers. Activatable interleukin plasmid constructs can have optional Flag, His or other affinity tags, and are electroporated into HEK293 or other suitable human or mammalian cell lines and purified. Validation assays include T cell activation assays using T cells responsive to IL-12 stimulation in the presence of a protease.

Generation of a scFv CD20 Binding Domain

CD20 is one of the cell surface proteins present on B-lymphocytes. CD20 antigen is found in normal and malignant pre-B and mature B lymphocytes, including those in over 90% of B-cell non-Hodgkin's lymphomas (NHL). The antigen is absent in hematopoietic stem cells, activated B lymphocytes (plasma cells) and normal tissue. As such, several antibodies mostly of murine origin have been described: 1F5, 2B8/C2B8, 2H7, and 1H4.

Human or humanized anti-CD20 antibodies are therefore used to generate scFv sequences for CD20 binding domains of an activatable interleukin protein. DNA sequences coding for human or humanized VL and VH domains are obtained, and the codons for the constructs are, optionally, optimized for expression in cells from *Homo sapiens*. The order in which the VL and VH domains appear in the scFv is varied (i.e., VL-VH, or VH-VL orientation), and three copies of the "G4S" (SEQ ID NO.: 449) or "$G_4S$" (SEQ ID NO.: 449) subunit $(G_4S)_3$ (SEQ ID NO.: 452) connect the variable domains to create the scFv domain. Anti-CD20 scFv plasmid constructs can have optional Flag, His or other affinity tags, and are electroporated into HEK293 or other suitable human or mammalian cell lines and purified. Validation assays include binding analysis by FACS, kinetic analysis using Proteon, and staining of CD20-expressing cells.

Cloning of DNA Expression Constructs Encoding the Activatable Interleukin Protein The activatable interleukin construct with protease cleavage site domains are used to construct an activatable interleukin protein in combination with an anti-CD20 scFv domain and a serum half-life extension element (e.g., a HSA binding peptide or VH domain). For expression of an activatable interleukin protein in CHO cells, coding sequences of all protein domains are cloned into a mammalian expression vector system. In brief, gene sequences encoding the activatable interleukin domain, serum half-life extension element, and CD20 binding domain along with peptide linkers L1 and L2 are separately synthesized and subcloned. The resulting constructs are then ligated together in the order of CD20 binding domain—L1-IL-12p35-L2-protease cleavage domain—L3-IL-12p40-L4-anti-CD20 scFv-L5-serum half-life extension element to yield a final construct. All expression constructs are designed to contain coding sequences for an N-terminal signal peptide and a C-terminal hexahistidine (6×His)-tag (SEQ ID NO.: 354) to facilitate protein secretion and purification, respectively.

Expression of Activatable Interleukin Proteins in Stably Transfected CHO Cells

A CHO cell expression system (Flp-In®, Life Technologies), a derivative of CHO-K1 Chinese Hamster ovary cells (ATCC, CCL-61) (Kao and Puck, Proc. Natl. Acad Sci USA 1968; 60(4):1275-81), is used. Adherent cells are subcultured according to standard cell culture protocols provided by Life Technologies.

For adaption to growth in suspension, cells are detached from tissue culture flasks and placed in serum-free medium. Suspension-adapted cells are cryopreserved in medium with 10% DMSO.

Recombinant CHO cell lines stably expressing secreted activatable interleukin proteins are generated by transfection of suspension-adapted cells. During selection with the antibiotic Hygromycin B viable cell densities are measured twice a week, and cells are centrifuged and resuspended in fresh selection medium at a maximal density of $0.1\times10^6$ viable cells/mL. Cell pools stably expressing activatable interleukin proteins are recovered after 2-3 weeks of selection at which point cells are transferred to standard culture medium in shake flasks. Expression of recombinant secreted proteins is confirmed by performing protein gel electrophoresis or flow cytometry. Stable cell pools are cryopreserved in DMSO containing medium.

Activatable interleukin proteins are produced in 10-day fed-batch cultures of stably transfected CHO cell lines by secretion into the cell culture supernatant. Cell culture supernatants are harvested after 10 days at culture viabilities of typically >75%. Samples are collected from the production cultures every other day and cell density and viability are assessed. On day of harvest, cell culture supernatants are cleared by centrifugation and vacuum filtration before further use.

Protein expression titers and product integrity in cell culture supernatants are analyzed by SDS-PAGE.

Purification of Activatable Interleukin Proteins

Activatable interleukin proteins are purified from CHO cell culture supernatants in a two-step procedure. The constructs are subjected to affinity chromatography in a first step followed by preparative size exclusion chromatography (SEC) on Superdex 200 in a second step. Samples are buffer-exchanged and concentrated by ultrafiltration to a typical concentration of >1 mg/mL. Purity and homogeneity (typically >90%) of final samples are assessed by SDS PAGE under reducing and non-reducing conditions, followed by immunoblotting using an anti-HSA or anti idiotype antibody as well as by analytical SEC, respectively. Purified proteins are stored at aliquots at −80° C. until use.

Example 23: Determination of Antigen Affinity by Flow Cytometry

The activatable interleukin proteins of Example 5 are tested for their binding affinities to human $CD20^+$ cells and cynomolgus $CD20^+$ cells.

$CD20^+$ cells are incubated with 100 μL of serial dilutions of the activatable interleukin proteins of Example 5 and at least one protease. After washing three times with FACS buffer the cells are incubated with 0.1 mL of 10 μg/mL mouse monoclonal anti-idiotype antibody in the same buffer for 45 min on ice. After a second washing cycle, the cells are incubated with 0.1 mL of 15 μg/mL FITC-conjugated goat anti-mouse IgG antibodies under the same conditions as before. As a control, cells are incubated with the anti-His IgG followed by the FITC-conjugated goat anti-mouse IgG antibodies without the activatable interleukin proteins. The cells were then washed again and resuspended in 0.2 mL of FACS buffer containing 2 μg/mL propidium iodide (PI) in order to exclude dead cells. The fluorescence of $1\times10^4$ living cells is measured using a Beckman-Coulter FC500 MPL flow cytometer using the MXP software (Beckman-Coulter, Krefeld, Germany) or a Millipore Guava EasyCyte flow cytometer using the Incyte software (Merck Millipore, Schwalbach, Germany). Mean fluorescence intensities of the cell samples are calculated using CXP software (Beckman-Coulter, Krefeld, Germany) or Incyte software (Merck Millipore, Schwalbach, Germany). After subtracting the fluorescence intensity values of the cells stained with the secondary and tertiary reagents alone the values are then used for calculation of the $K_D$ values with the equation for one-site binding (hyperbola) of the GraphPad Prism (version 6.00 for Windows, GraphPad Software, La Jolla California USA).

CD20 binding and crossreactivity are assessed on the human $CD20^+$ tumor cell lines. The $K_D$ ratio of crossreactivity is calculated using the $K_D$ values determined on the CHO cell lines expressing either recombinant human or recombinant cynomolgus antigens.

Example 24: Cytotoxicity Assay

The activatable interleukin protein of Example 5 is evaluated in vitro on its mediation of immune response to $CD20^+$ target cells.

Fluorescence labeled $CD20^+$ REC-1 cells (a Mantle cell lymphoma cell line, ATCC CRL-3004) are incubated with isolated PBMC of random donors or CB15 T-cells (standardized T-cell line) as effector cells in the presence of the activatable interleukin protein of Example 5 and at least one protease. After incubation for 4 h at 37° C. in a humidified incubator, the release of the fluorescent dye from the target cells into the supernatant is determined in a spectrofluorimeter. Target cells incubated without the activatable interleukin protein of Example 5 and target cells totally lysed by the addition of saponin at the end of the incubation serve as negative and positive controls, respectively.

Based on the measured remaining living target cells, the percentage of specific cell lysis is calculated according to the following formula: $[1-(\text{number of living targets}_{(sample)}/\text{number of living targets}_{(spontaneous)})]\times100\%$. Sigmoidal dose response curves and $EC_{50}$ values are calculated by non-linear regression/4-parameter logistic fit using the GraphPad Software. The lysis values obtained for a given antibody concentration are used to calculate sigmoidal dose-response curves by 4 parameter logistic fit analysis using the Prism software.

Example 25: Pharmacokinetics of Activatable Interleukin Proteins

The activatable interleukin protein of Example 5 is evaluated for half-time elimination in animal studies.

The activatable interleukin protein is administered to cynomolgus monkeys as a 0.5 mg/kg bolus injection into the saphenous vein. Another cynomolgus monkey group receives a comparable cytokine in size, but lacking a serum half-life extension element. A third and fourth group receive a cytokine with serum half-life extension elements and a cytokine with CD20 and serum half-life extension elements respectively, and both comparable in size to the activatable interleukin protein. Each test group consists of 5 monkeys. Serum samples are taken at indicated time points, serially diluted, and the concentration of the proteins is determined using a binding ELISA to CD20.

Pharmacokinetic analysis is performed using the test article plasma concentrations. Group mean plasma data for each test article conforms to a multi-exponential profile when plotted against the time post-dosing. The data are fit by a standard two-compartment model with bolus input and first-order rate constants for distribution and elimination phases. The general equation for the best fit of the data for i.v. administration is: $c(t)=Ae^{-\alpha t}+Be^{-\beta t}$, where c(t) is the plasma concentration at time t, A and B are intercepts on the Y-axis, and α and β are the apparent first-order rate constants for the distribution and elimination phases, respectively. The α-phase is the initial phase of the clearance and reflects distribution of the protein into all extracellular fluid of the animal, whereas the second or β-phase portion of the decay curve represents true plasma clearance. Methods for fitting such equations are well known in the art. For example, $A=DN(\alpha-k21)/(\alpha-\beta)$, $B=DN(\beta-k21)/(\alpha-\beta)$, and α and β (for $\alpha>\beta$) are roots of the quadratic equation: $r2+(k12+k21+k10)r+k21k10=0$ using estimated parameters of V=volume of distribution, k10=elimination rate, k12=transfer rate from compartment 1 to compartment 2 and k21=transfer rate from compartment 2 to compartment 1, and D=the administered dose.

Data analysis: Graphs of concentration versus time profiles are made using KaleidaGraph (KaleidaGraph™ V. 3.09 Copyright 1986-1997. Synergy Software. Reading, Pa.). Values reported as less than reportable (LTR) are not included in the PK analysis and are not represented graphically. Pharmacokinetic parameters are determined by compartmental analysis using WinNonlin software (WinNonlin® Professional V. 3.1 WinNonlin™ Copyright 1998-1999. Pharsight Corporation. Mountain View, Calif.). Pharmacokinetic parameters are computed as described in Ritschel W A and Kearns G L, 1999, IN: *Handbook Of Basic Pharmacokinetics Including Clinical Applications,* 5th edition, American Pharmaceutical Assoc., Washington, D.C.

It is expected that the activatable interleukin protein of Example 5 has improved pharmacokinetic parameters such as an increase in elimination half-time as compared to proteins lacking a serum half-life extension element.

Example 26: Xenograft Tumor Model

The activatable interleukin protein of Example 5 is evaluated in a xenograft model.

Female immune-deficient NOD/scid mice are sub-lethally irradiated (2 Gy) and subcutaneously inoculated with $4\times10^6$ Ramos RA1 cells into the right dorsal flank. When tumors reach 100 to 200 $mm^3$, animals are allocated into 3 treatment groups. Groups 2 and 3 (8 animals each) are intraperitoneally injected with $1.5\times10^7$ activated human T-cells. Three days later, animals from Group 3 are subsequently treated with a total of 9 intravenous doses of 50 μg activatable interleukin protein of Example 5 (qdx9d). Groups 1 and 2 are only treated with vehicle. Body weight and tumor volume are determined for 30 days.

It is expected that animals treated with the activatable interleukin protein of Example 5 have a statistically significant delay in tumor growth in comparison to the respective vehicle-treated control group.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 27: MC38 Experiments

The MC38 cell line, a rapidly growing colon adenocarcinoma cell line that expresses MMP9 in vitro, was used. Using this tumor model, the ability of fusion proteins to affect tumor growth was examined.

Example 27a: MC38 IL-2POC

| Agents and Treatment: | | | | | |
|---|---|---|---|---|---|
| Gr. | N | Agent | Formulation dose | Route | Schedule |
| 1# | 10 | Vehicle | — | ip | biwk × 3 |
| 2 | 7 | ACP16 | 700 μg/animal | ip | biwk × 3 |
| 3 | 7 | ACP16 | 230 μg/animal | ip | biwk × 3 |
| 4 | 7 | ACP16 | 70 μg/animal | ip | biwk × 3 |
| 5 | 7 | ACP16 | 55 ug/animal | ip | biwk × 3 |
| 6 | 7 | ACP16 | 17 μg/animal | ip | biwk × 3 |
| 7 | 7 | ACP132 | 361 μg/animal | ip | biwk × 3 |
| 8 | 7 | ACP132 | 119 μg/animal | ip | biwk × 3 |
| 9 | 7 | ACP132 | 36 μg/animal | ip | biwk × 3 |
| 10 | 7 | ACP132 | 28 μg/animal | ip | biwk × 3 |
| 11 | 7 | ACP132 | 9 μg/animal | ip | biwk × 3 |
| 12 | 7 | ACP21 | 540 μg/animal | ip | biwk × 3 |
| 13 | 7 | ACP21 | 177 μg/animal | ip | biwk × 3 |
| 14 | 7 | ACP21 | 54 μg/animal | ip | biwk × 3 |
| 15 | 7 | ACP21 | 42 μg/animal | ip | biwk × 3 |
| 16 | 7 | ACP21 | 13 μg/animal | ip | biwk × 3 |

#ControlGroup

Procedures:

Mice were anaesthetized with isoflurane for implant of cells to reduce the ulcerations. 308 CR female C57Bl/6 mice were set up with $5\times10^5$ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 $mm^3$ and begin treatment. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 $mm^3$ or 45 days, whichever comes first. Responders were followed longer. When the endpoint was reached, the animals are to be euthanized.

Results are shown in FIG. 35.

Example 27b: MC38 IL-2 POC. Treatment with ACP16, ACP124 and ACP130

| Agents and Treatment: | | | | | |
|---|---|---|---|---|---|
| Gr. | N | Agent | Formulation dose | Route | Schedule |
| 1# | 12 | Vehicle | — | ip | biwk × 2 |
| 2 | 8 | ACP16 | 4.4 μg/animal | ip | biwk × 2 |
| 3 | 8 | ACP16 | 17 μg/animal | ip | biwk × 2 |
| 4 | 8 | ACP16 | 70 μg/animal | ip | biwk × 2 |
| 5 | 8 | ACP16 | 232 μg/animal | ip | biwk × 2 |
| 6 | 8 | ACP130 | 19 μg/animal | ip | biwk × 2 |
| 7 | 8 | ACP130 | 45 μg/animal | ip | biwk × 2 |
| 8 | 8 | ACP130 | 180 μg/animal | ip | biwk × 2 |
| 9 | 8 | ACP130 | 600 μg/animal | ip | biwk × 1 |
| 12 | 8 | ACP124 | 17 μg/animal | ip | biwk × 2 |
| 13 | 8 | ACP124 | 70 μg/animal | ip | biwk × 2 |
| 14 | 8 | ACP124 | 230 μg/animal | ip | biwk × 2 |
| 15 | 8 | ACP124 | 700 μg/animal | ip | biwk × 2 |
| 16 | 8 | IL-2-WTI | 12 μg/animal | ip | bid × 5 then 2-day pause then bid × 5 then 2-day pause |
| 17 | 8 | IL-2-WTI | 36 μg/animal | ip | bid × 5 then 2-day pause then bid × 5 then 2-day pause |

#ControlGroup

Procedures:

Mice were anaesthetized with isoflurane for implant of cells to reduce the ulcerations. 308 CR female C57BL/6 mice were set up with $5\times10^5$ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 $mm^3$ and begin treatment. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 $mm^3$ or 45 days, whichever comes first. Responders were followed longer. When the endpoint was reached, the animals are to be euthanized.

Results are shown in FIGS. 31A-31C and FIGS. 32B-32C. Survival curves are shown in FIGS. 34A-34D.

Example 27c: MC38 IFNa and IL-12

| Agents and Treatment: | | | | | |
|---|---|---|---|---|---|
| Gr. | N | Agent | Formulation dose | Route | Schedule |
| 1# | 12 | Vehicle | — | ip | biwk × 3 |
| 2 | 8 | ACP11 | 17.5 μg/animal | ip | biwk × 3 |
| 3 | 8 | ACP11 | 175 μg/animal | ip | biwk × 3 |
| 4 | 8 | ACP11 | 525 μg/animal | ip | biwk × 3 |
| 5 | 8 | ACP31 | 33 μg/animal | ip | biwk × 3 |
| 6 | 8 | ACP31 | 110 μg/animal | ip | biwk × 3 |
| 7 | 8 | ACP31 | 330 μg/animal | ip | biwk × 3 |
| 8 | 8 | ACP131 | 1 μg/animal | ip | bid × 5 then 2-day pause then bid × 5 then 2-day pause |
| 9 | 8 | ACP131 | 10 μg/animal | ip | bid × 5 then 2-day pause then bid × 5 then 2-day pause |
| 10 | 8 | ACP131 | 30 μg/animal | ip | bid × 5 then 2-day pause then bid × 5 then 2-day pause |
| 11 | 8 | mIFNa1-WTI | 1 μg/animal | ip | bid × 5 then 2-day pause then bid × 5 then 2-day pause |
| 12 | 8 | mIFNa1-WTI | 10 μg/animal | ip | bid × 5 then 2-day pause then bid × 5 then 2-day pause |
| 13 | 8 | IL-12-HM-WTI | 2 μg/animal | ip | bid × 5 then 2-day pause then bid × 5 then 2-day pause |
| 14 | 8 | IL-12-HM-WTI | 10 μg/animal | ip | bid × 5 then 2-day pause then bid × 5 then 2-day pause |
| 15 | 8 | ACP131 | 5 μg/animal | itu | bid × 5 then 2-day pause then bid × 5 then 2-day pause |

#ControlGroup

Procedures:

Mice were anaesthetized with isoflurane for implant of cells to reduce the ulcerations. 308 CR female C57BL6 mice were set up with $5\times10^5$ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 $mm^3$ and begin treatment. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 $mm^3$ or 45 days, whichever comes first. Responders were followed longer. When the endpoint was reached, the animals are to be euthanized. Results are show in in FIGS. 29A-29B, and 30.

Example 27d: Treatment with ACP16, ACP132, and ACP21

| Agents and Treatment: | | | | | |
|---|---|---|---|---|---|
| Gr. | N | Agent | Formulation dose | Route | Schedule |
| 1# | 10 | Vehicle | — | ip | biwk × 2 |
| 2 | 7 | ACP16 | 17 μg/animal | ip | biwk × 2 |
| 3 | 7 | ACP16 | 55 μg/animal | ip | biwk × 2 |
| 4 | 7 | ACP16 | 70 μg/animal | ip | biwk × 2 |
| 5 | 7 | ACP16 | 230 μg/animal | ip | biwk × 2 |
| 6 | 7 | ACP132 | 9 μg/animal | ip | biwk × 2 |
| 7 | 7 | ACP132 | 28 μg/animal | ip | biwk × 1 |
| 8 | 7 | ACP132 | 36 μg/animal | ip | biwk × 1 |
| 9 | 7 | ACP132 | 119 μg/animal | ip | biwk × 1 |
| 10 | 7 | ACP21 | 13 μg/animal | ip | biwk × 2 |
| 11 | 7 | ACP21 | 42 μg/animal | ip | biwk × 2 |
| 12 | 7 | ACP21 | 54 μg/animal | ip | biwk × 2 |
| 13 | 7 | ACP21 | 177 μg/animal | ip | biwk × 2 |

Procedure

Mice were anaesthetized with isoflurane for implant of cells to reduce the ulcerations. CR female C57BL/6 mice were set up with $5\times10^5$ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 $mm^3$ and begin treatment. ACP16 was dosed at 17, 55, 70, or 230 μg/animal; ACP132 was dosed at 9, 28, 36, or 119 ug/animal; ACP21 was dosed at 13, 42, 54, or 177 μg/animal. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 $mm^3$ or 45 days, whichever comes first. Responders were followed longer. When the endpoint was reached, the animals are to be euthanized. Results are shown in FIG. 35.

Example 27e: MC38 Rechallenge

Cured mice (ACP16-treated) from Example 27b were rechallenged with tumor implantation to determine whether anti-tumor memory had been established from the initial treatments.

| Agents and Treatment: | | | | | |
|---|---|---|---|---|---|
| Gr. | N | Agent | Formulation dose | Route | Schedule |
| 1# | 33 | No Treatment | — | — | — |
| 2 | 7 | ACP16 | 70 μg/animal | ip | (ACP16 biwk × 2) |
| 3 | 8 | ACP16 | 232 μg/animal | ip | (ACP16 biwk × 2) |
| 5 | 5 | IL-2-WTI | 12 μg/animal | ip | (IL-2-WTI bid × 5 then 2-day pause then bid × 5 then 2-day pause) |
| 6 | 7 | IL-2-WTI | 36 μg/animal | ip | (IL-2-WTI bid × 5 then 2-day pause then bid × 5 then 2-day pause) |

#ControlGroup

Procedures:

Mice were anaesthetized with isoflurane for implant of cells to reduce the ulcerations. This portion of the study began on the day of implant (Day 1). Group 1 consisted of 33 CR female C57BL6 mice set up with $5\times10^5$ MC38 tumor cells in 0% Matrigel subcutaneously in the flank. Groups 2-6 consisted of 33 CR female C57Bl/6 mice set up with $5\times10^5$ MC38 tumor cells in 0% Matrigel sc in the left flank. The tumors from the previous MC38 experiment (Example 27b) were implanted in the right flank of each animal. Cell Injection Volume was 0.1 mL/mouse. Age of control mice at initiation was 14 to 17 weeks. These mice were age matched to mice from the previous MC38 experiment (Example 27b). No dosing of active agent occurred during rechallenge. Body Weights were take biweekly until end, as were caliper measurements. Any adverse reactions or death were reported immediately. Any individual animal with a single observation of >than 30% body weight loss or three consecutive measurements of >25% body weight loss was euthanized. Endpoint was tumor growth delay (TGD). Animals were monitored individually. The endpoint of the experiment was a tumor volume of 1000 $mm^3$ or 45 days, whichever comes first. Responders were followed longer when possible. When the endpoint is reached, the animals were euthanized. Results are shown in FIG. 33.

Example 27f: Treatment with ACP10, ACP11

| Agents and Treatment: | | | | | |
|---|---|---|---|---|---|
| Gr. | N | Agent | Formulation dose | Route | Schedule |
| 1# | 12 | Vehicle | — | ip | biwk × 2 |
| 2 | 8 | ACP11 | 175 μg/animal | ip | biwk × 2 |
| 3 | 8 | ACP11 | 300 μg/animal | ip | biwk × 2 |
| 4 | 8 | ACP10 | 5 μg/animal | ip | biwk × 2 |
| 5 | 8 | ACP10 | 10 μg/animal | ip | biwk × 2 |
| 6 | 8 | ACP10 | 43 μg/animal | ip | biwk × 2 |
| 7 | 8 | ACP10 | 43 μg/animal | ip | qwk × 2 |
| 8 | 8 | ACP10 | 172 μg/animal | ip | biwk × 2 |
| 9 | 8 | IL-12-HM-WTI | 5 μg/animal | ip | bid for 5 days first day 1 dose then 2-day pause then bid for 5 days first day 1 dose then 2-day pause |
| 10 | 8 | IL-12-HM-WTI | 20 μg/animal | ip | bid for 5 days first day 1 dose then 2-day pause then bid for 5 days first day 1 dose then 2-day pause |

Procedures

Mice were anaesthetized with isoflurane for implant of cells to reduce the ulcerations. CR female C57BL/6 mice were set up with $5\times10^5$ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 $mm^3$ and begin treatment. ACP11 was dosed at 175 or 300 μg/animal; ACP10 was dosed at 5, 10, 43, or 172 ug/animal; IL-12-HM-WTI was dosed at 5 or 20 ug/animal. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 $mm^3$ or 45 days, whichever comes first. Responders were followed longer. When the endpoint was reached, the animals are to be euthanized. Results are shown in FIG. 45 and FIGS. 46A-46D.

Example 27g: Treatment with ACP16, APC153, ACP155, ACP156 and ACP292

| Agents and Treatment: | | | | | |
|---|---|---|---|---|---|
| Gr. | N | Agent | Formulation dose | Route | Schedule |
| 1# | 12 | Vehicle | — | ip | biwk × 2 |
| 2 | 8 | ACP16 | 17 μg/animal | ip | biwk × 2 |
| 3 | 8 | ACP16 | 55 μg/animal | ip | biwk × 2 |
| 4 | 8 | ACP16 | 230 μg/animal | ip | biwk × 2 |
| 5 | 8 | ACP155 | 55 μg/animal | ip | biwk × 2 |
| 6 | 8 | ACP155 | 230 μg/animal | ip | biwk × 2 |
| 7 | 8 | ACP153 | 55 μg/animal | ip | biwk × 2 |
| 8 | 8 | ACP153 | 230 μg/animal | ip | biwk × 2 |
| 9 | 8 | ACP156 | 55 μg/animal | ip | biwk × 2 |
| 10 | 8 | ACP156 | 230 μg/animal | ip | biwk × 2 |
| 11 | 8 | ACP292 | 45 μg/animal | ip | biwk × 2 |
| 12 | 8 | ACP292 | 186 μg/animal | ip | biwk × 2 |

Procedures:

Mice were anaesthetized with isoflurane for implant of cells to reduce the ulcerations. CR female C57BL/6 mice were set up with $5\times10^5$ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 $mm^3$ and begin treatment. ACP16 was dosed at 17, 55 or 230 μg/animal; ACP153, ACP155 and ACP156 were dosed at 55 or 230 μg/animal; ACP292 was dosed at 45 or 186 μg/animal. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 $mm^3$ or 45 days, whichever comes first. Responders were followed longer. When the endpoint was reached, the animals are to be euthanized. Results are shown in FIGS. 49A-49I.

Example 27h: Treatment with ACP16, APC302 and ACP314

Agents and Treatment:

| Gr. | N | Agent | Formulation dose | Route | Schedule |
|---|---|---|---|---|---|
| 1# | 12 | Vehicle | — | ip | biwk × 2 |
| 2 | 9 | ACP16 | 55 μg/animal | ip | biwk × 2 |
| 3 | 9 | ACP16 | 230 μg/animal | ip | biwk × 2 |
| 4 | 9 | ACP302 | 33 μg/animal | ip | biwk × 2 |
| 5 | 9 | ACP302 | 106 μg/animal | ip | biwk × 2 |
| 6 | 9 | ACP302 | 442 μg/animal | ip | biwk × 2 |
| 7 | 9 | ACP302 | 1,344 μg/animal | ip | biwk × 2 |
| 8 | 9 | ACP314 | 21 μg/animal | ip | biwk × 2 |
| 9 | 9 | ACP314 | 68 μg/animal | ip | biwk × 2 |
| 10 | 9 | ACP314 | 283 μg/animal | ip | biwk × 2 |
| 11 | 9 | ACP314 | 861 μg/animal | ip | biwk × 2 |

Figure 50A:
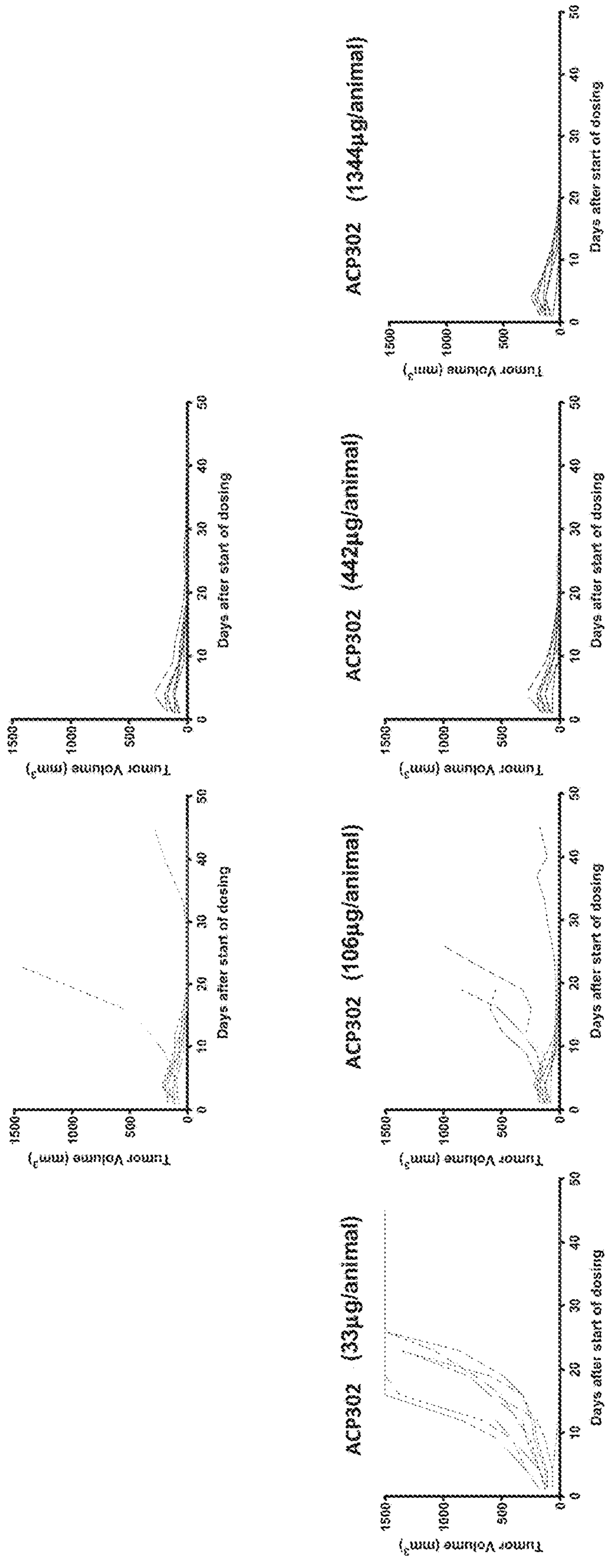
Figure 50B:
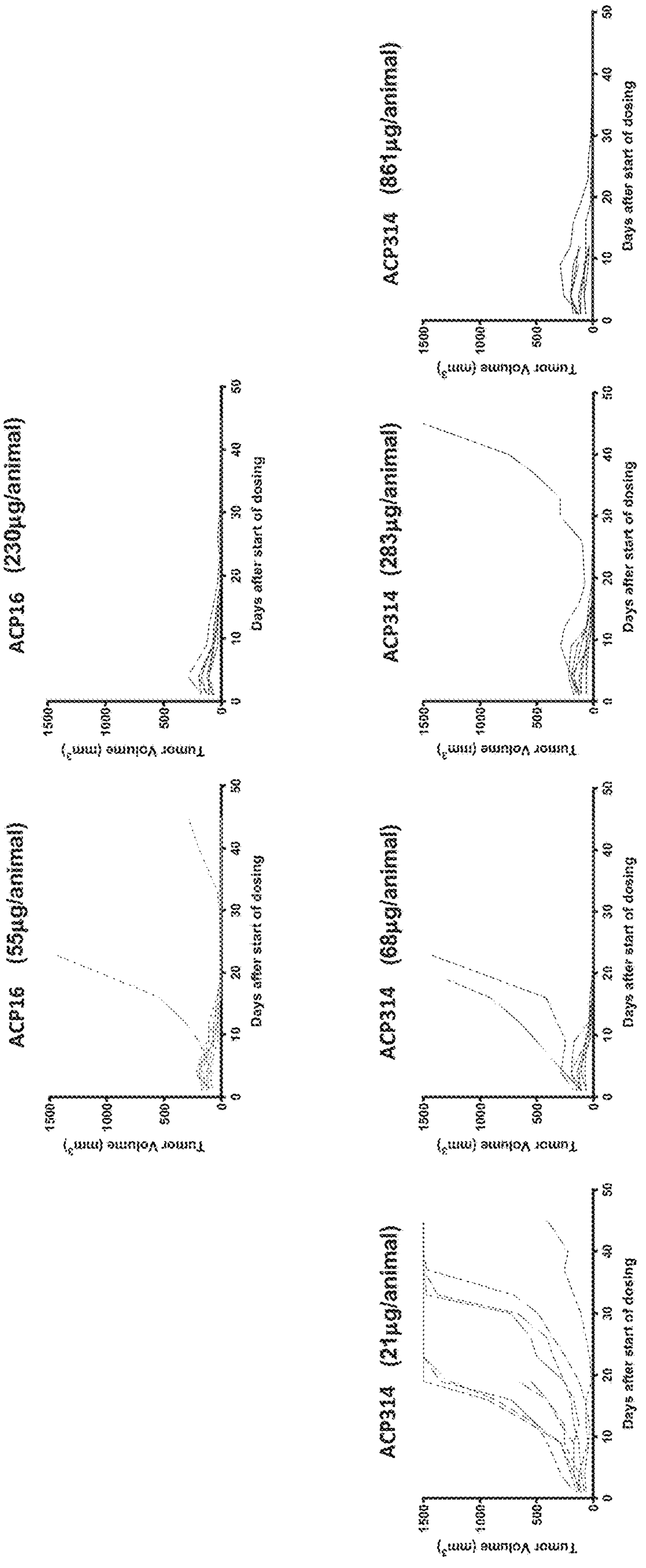

Procedures:

Mice were anaesthetized with isoflurane for implant of cells to reduce the ulcerations. CR female C57BL/6 mice were set up with $5\times10^5$ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 $mm^3$ and begin treatment. ACP16 was dosed at 55 or 230 μg/animal; ACP302 was dosed at 33, 106, 442 or 1344 ug/animal; ACP314 was dosed at 21, 68, 283 or 861 μg/animal. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 $mm^3$ or 45 days, whichever comes first. Responders were followed longer. When the endpoint was reached, the animals are to be euthanized. Results are shown in FIG. 50A-50B.

Example 27i: Treatment with ACP339

Agents and Treatment:

| Gr. | N | Agent | Formulation dose | Route | Schedule |
|---|---|---|---|---|---|
| 1# | 12 | Vehicle | — | ip | biwk × 2 |
| 2 | 9 | ACP339 | 55 μg/animal | ip | biwk × 2 |
| 3 | 9 | ACP339 | 230 μg/animal | ip | biwk × 2 |
| 4 | 9 | ACP339 | 700 μg/animal | ip | biwk × 2 |

Figure 51A:
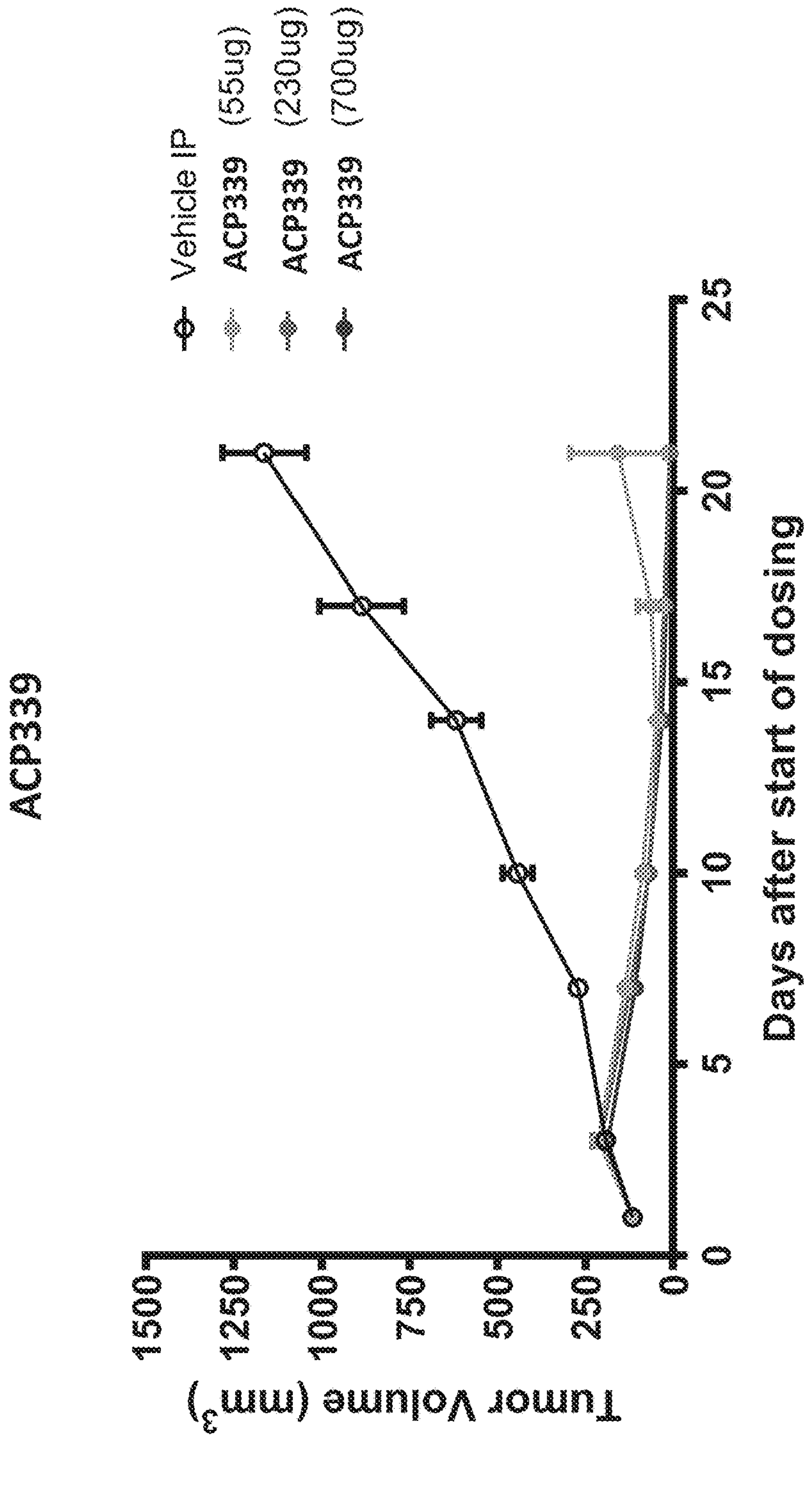
Figure 51B:
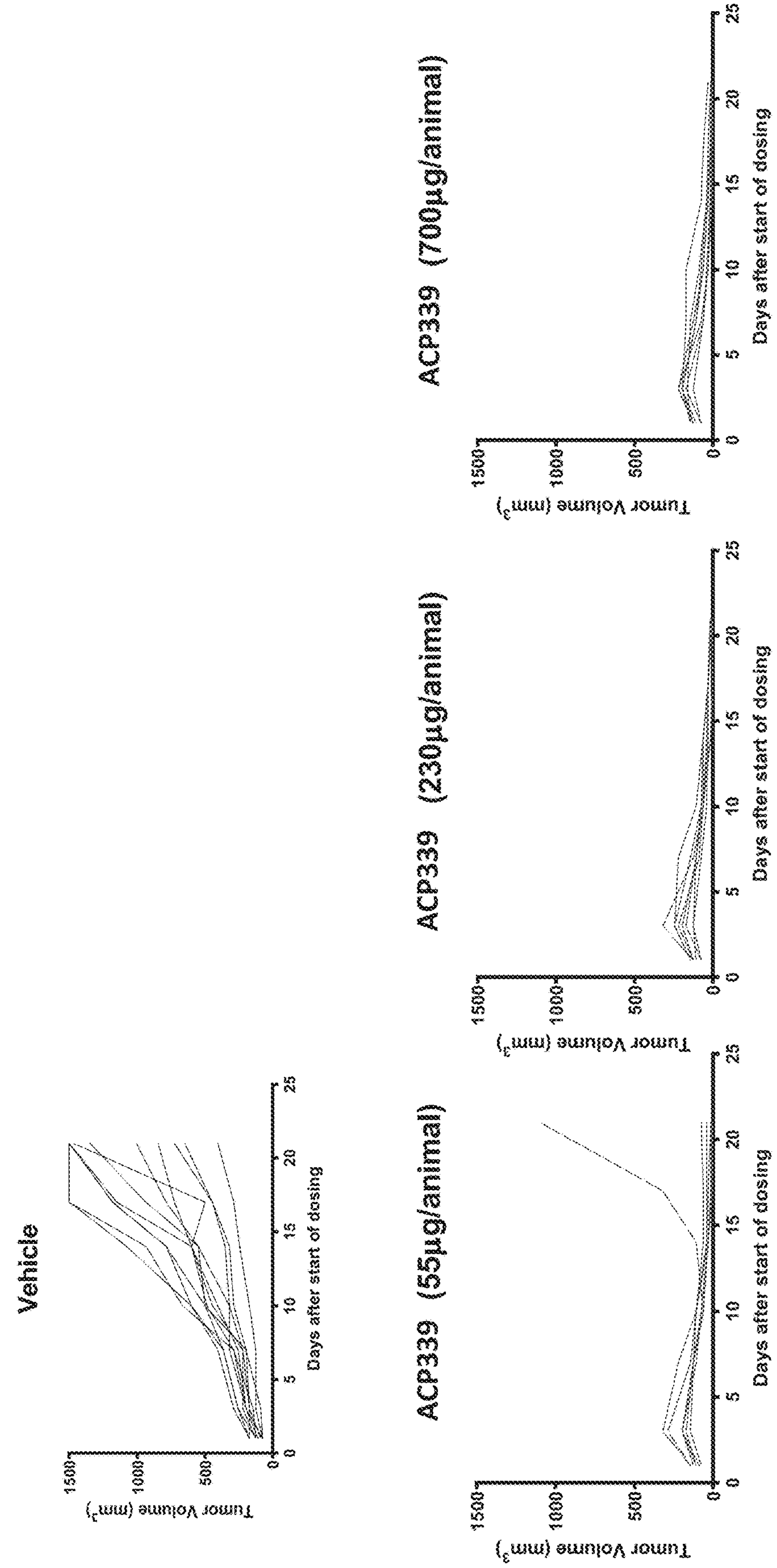
Figure 51C:
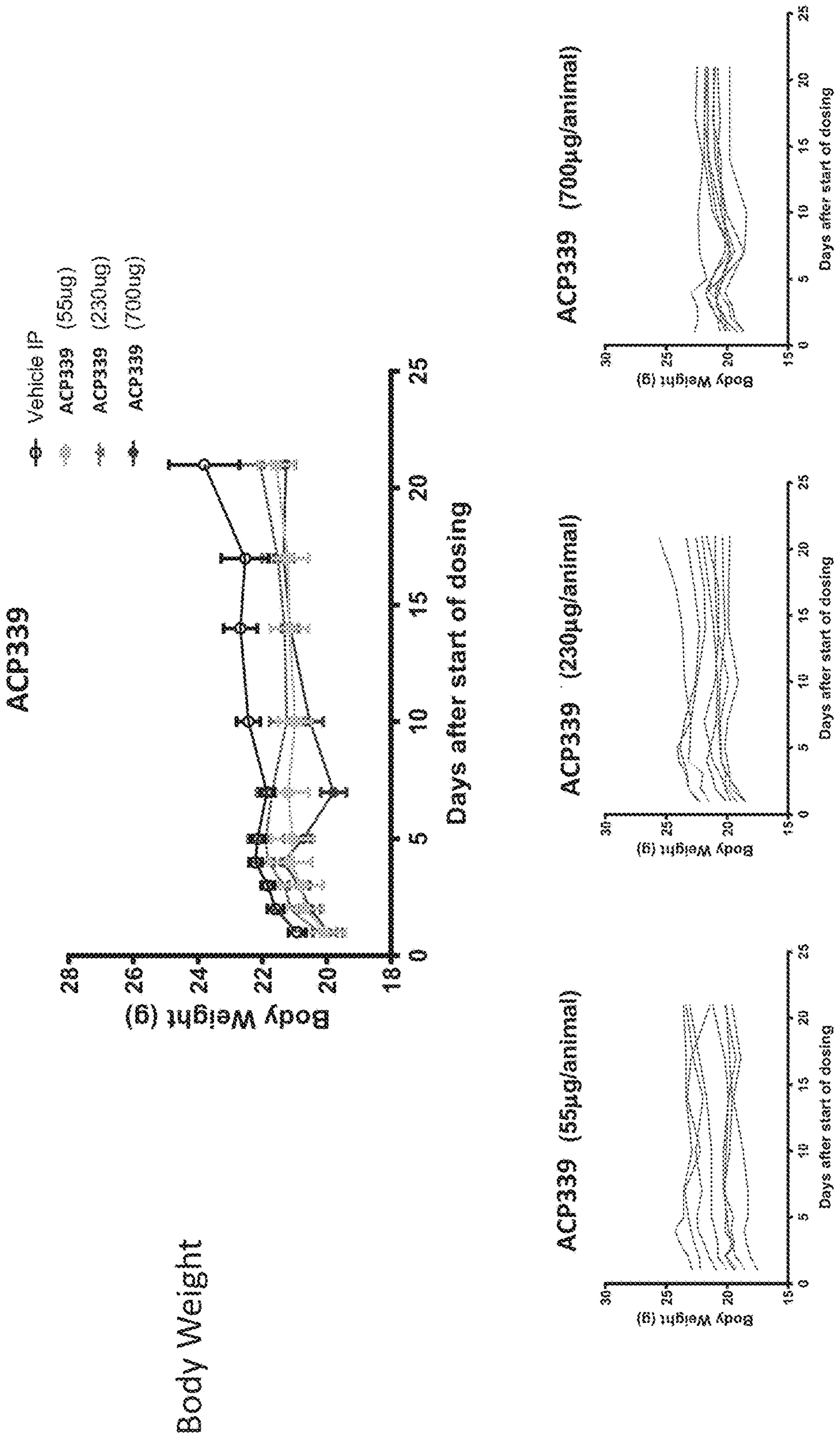
Figure 52A:
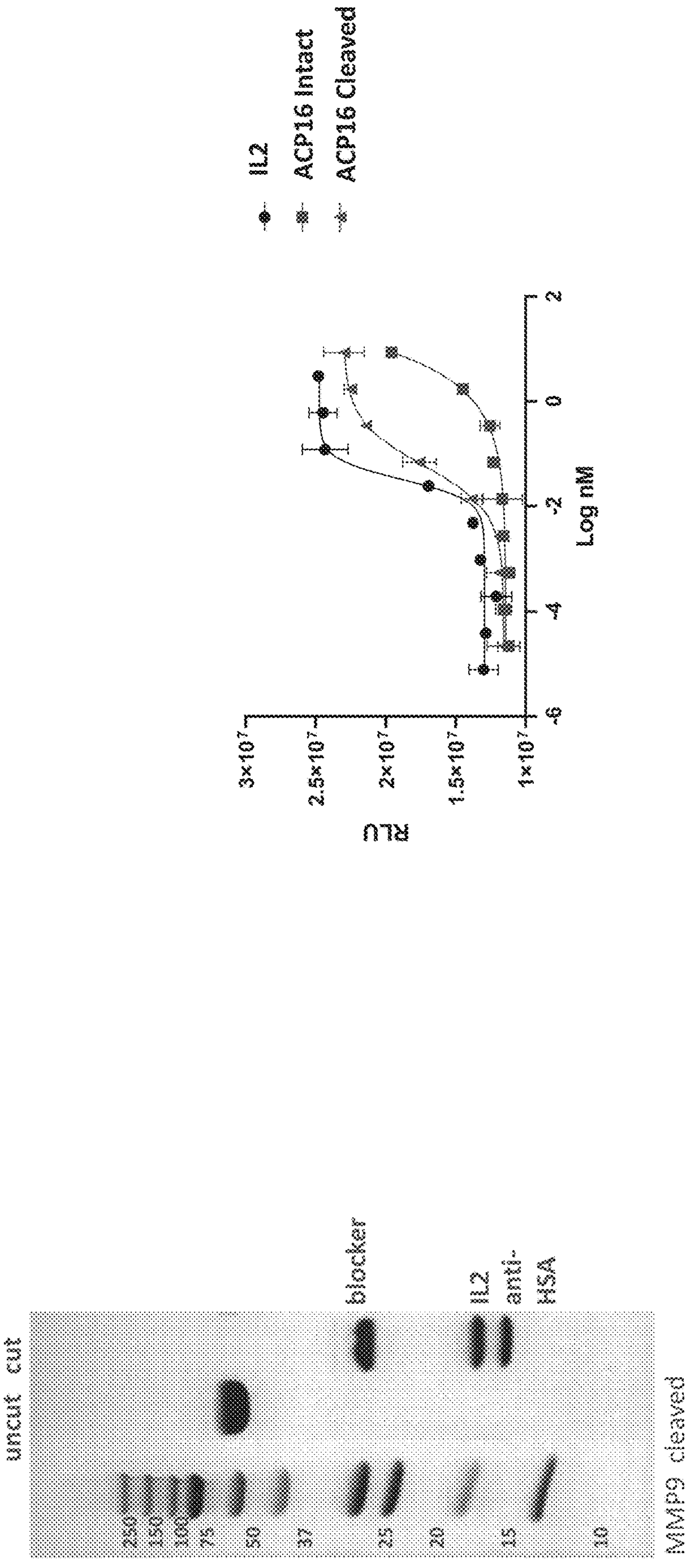
Figure 52B:
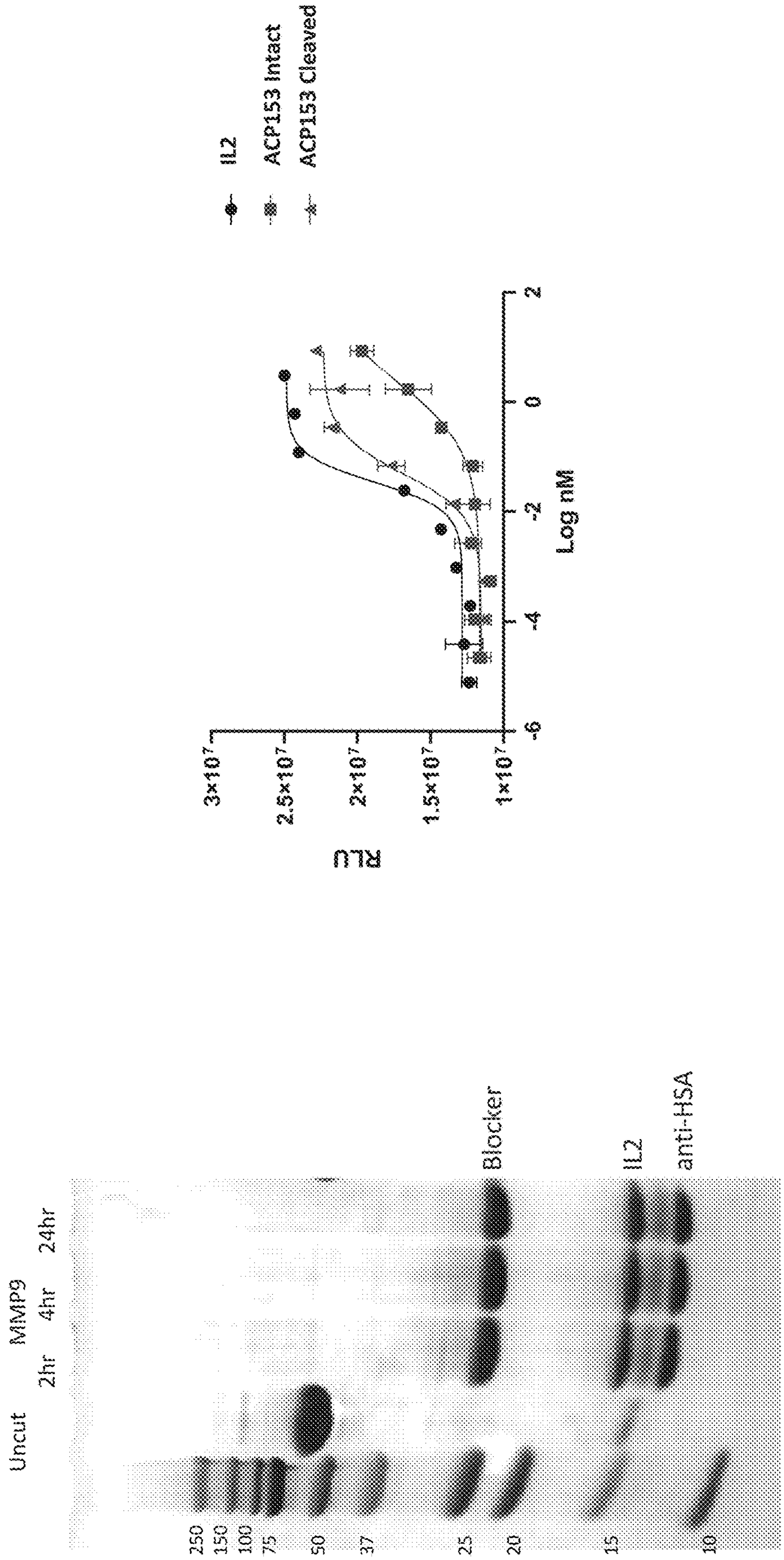
Figure 52C:
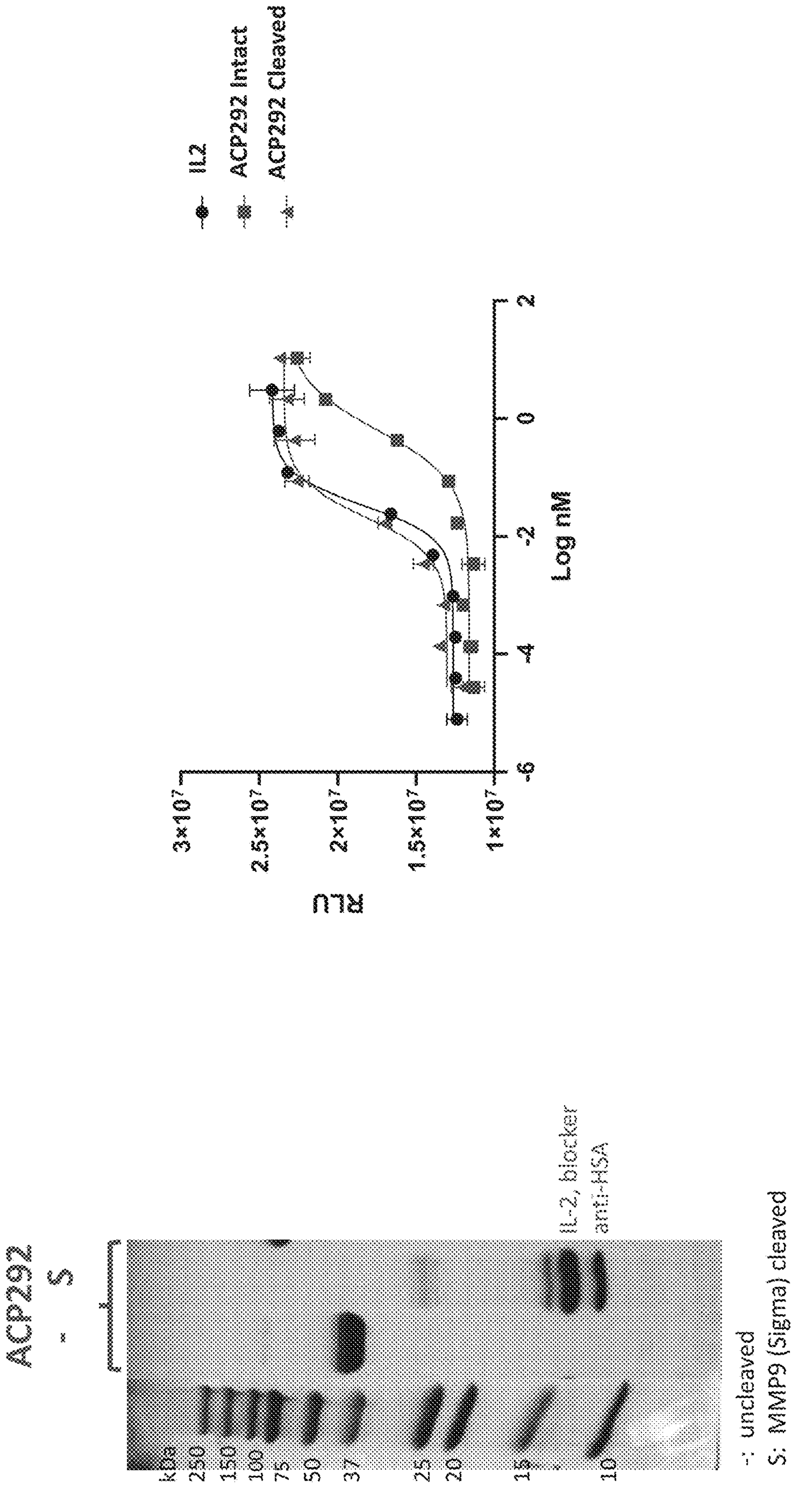
Figure 52D:
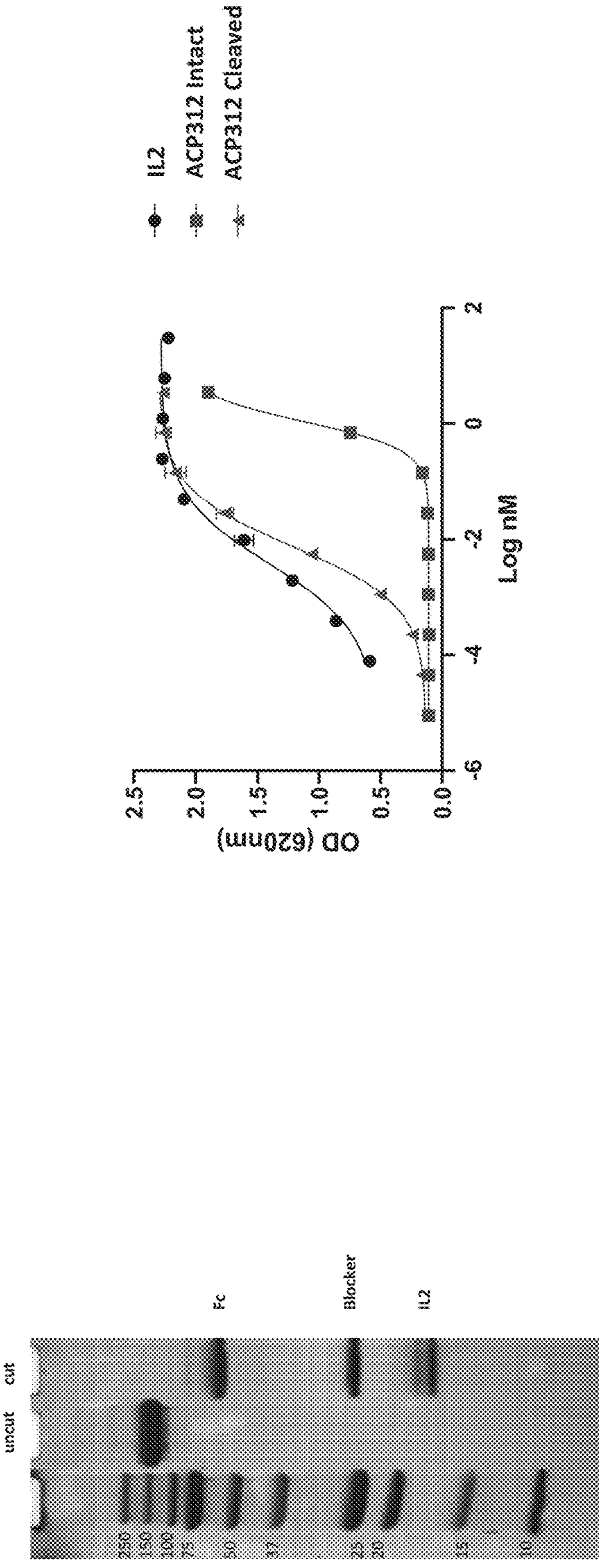
Figure 52E:
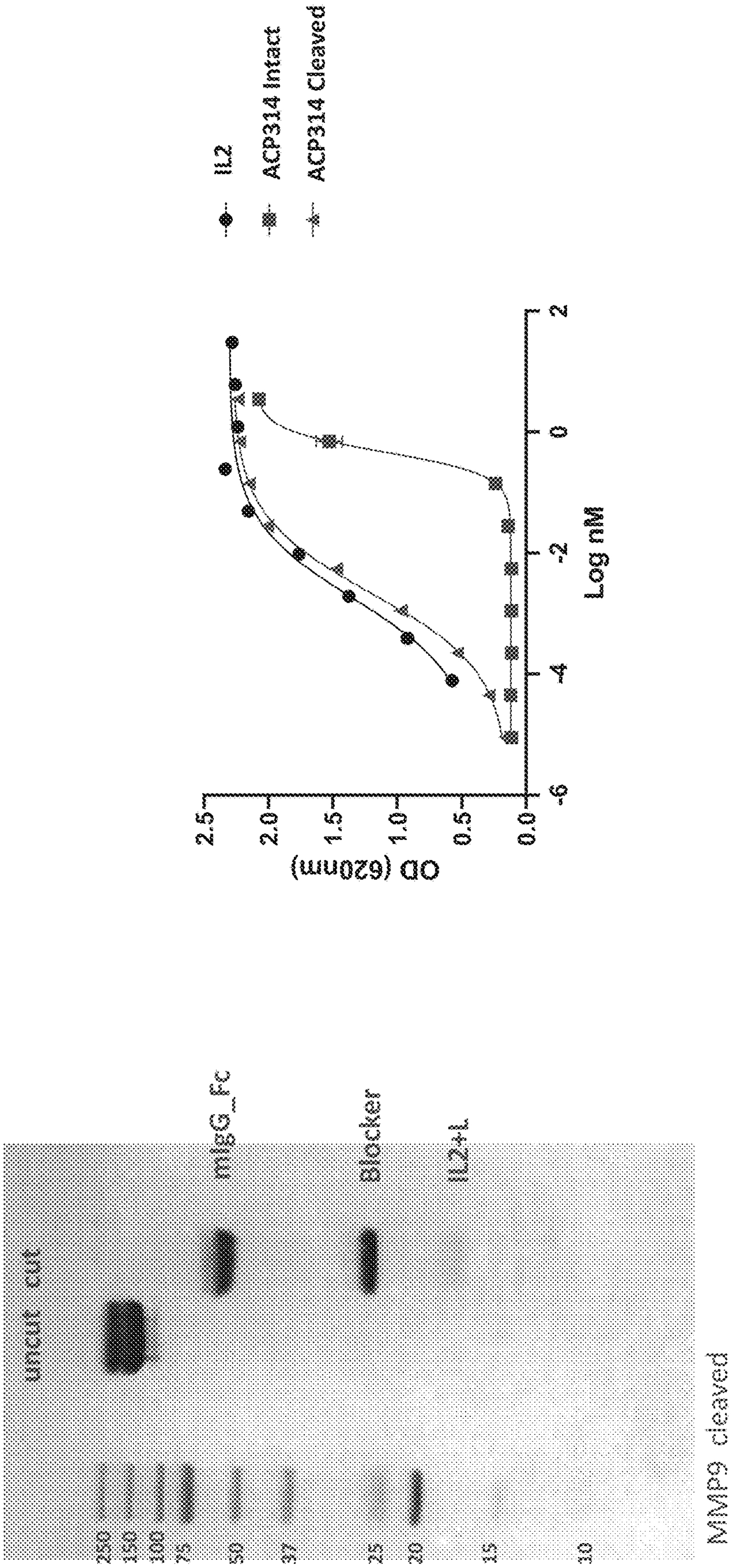
Figure 52F:
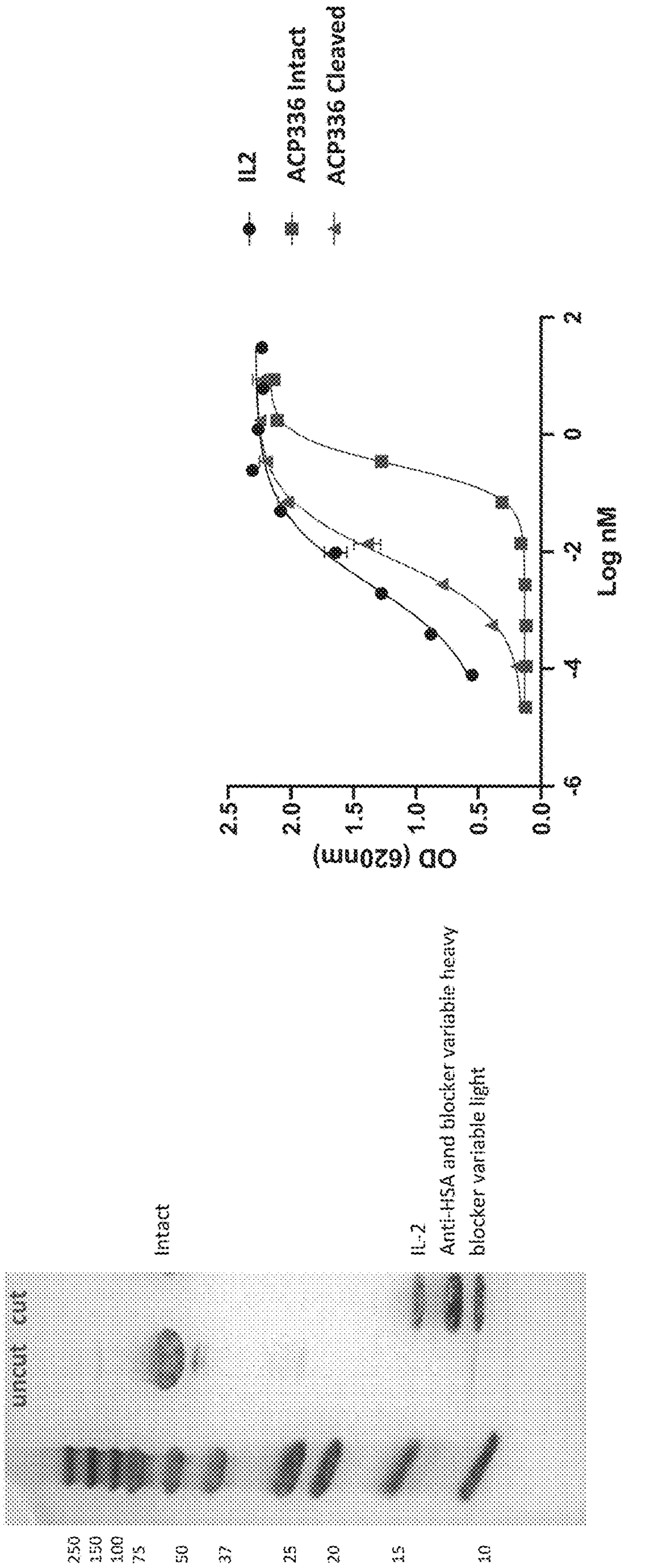
Figure 52G:
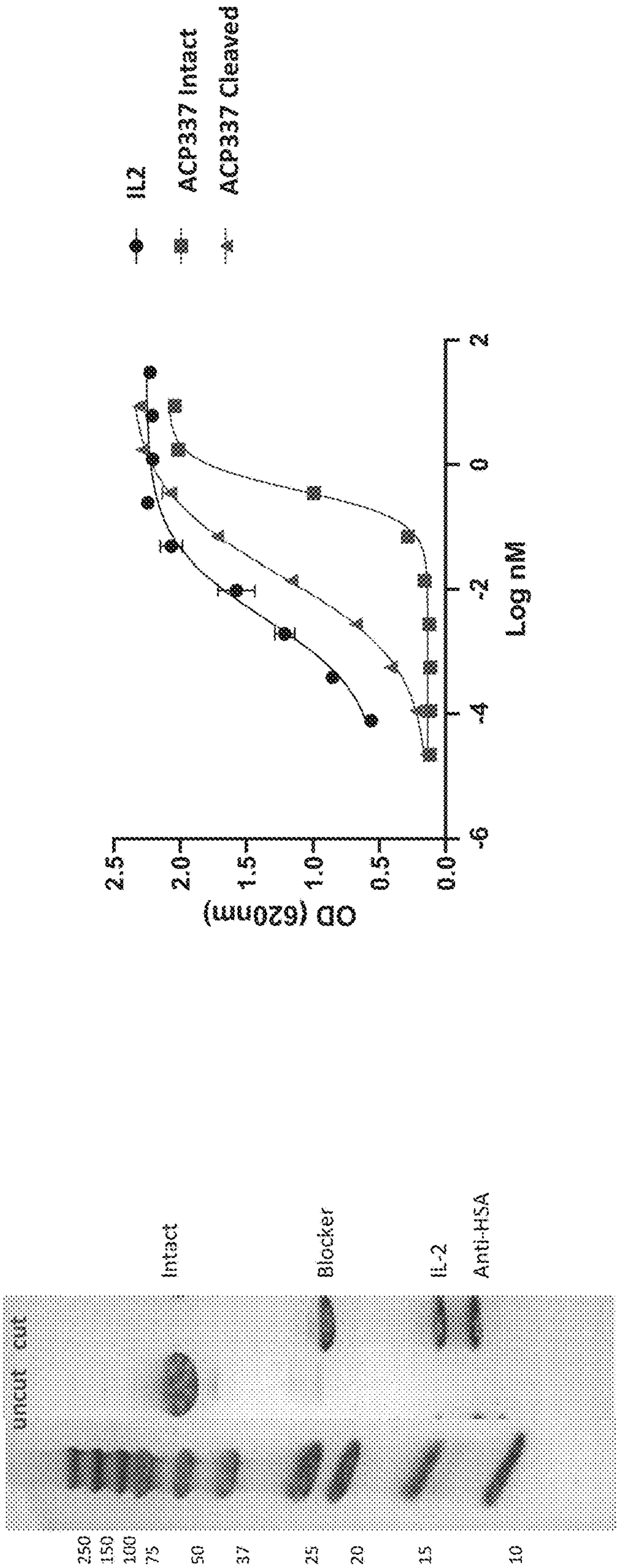
Figure 52H:
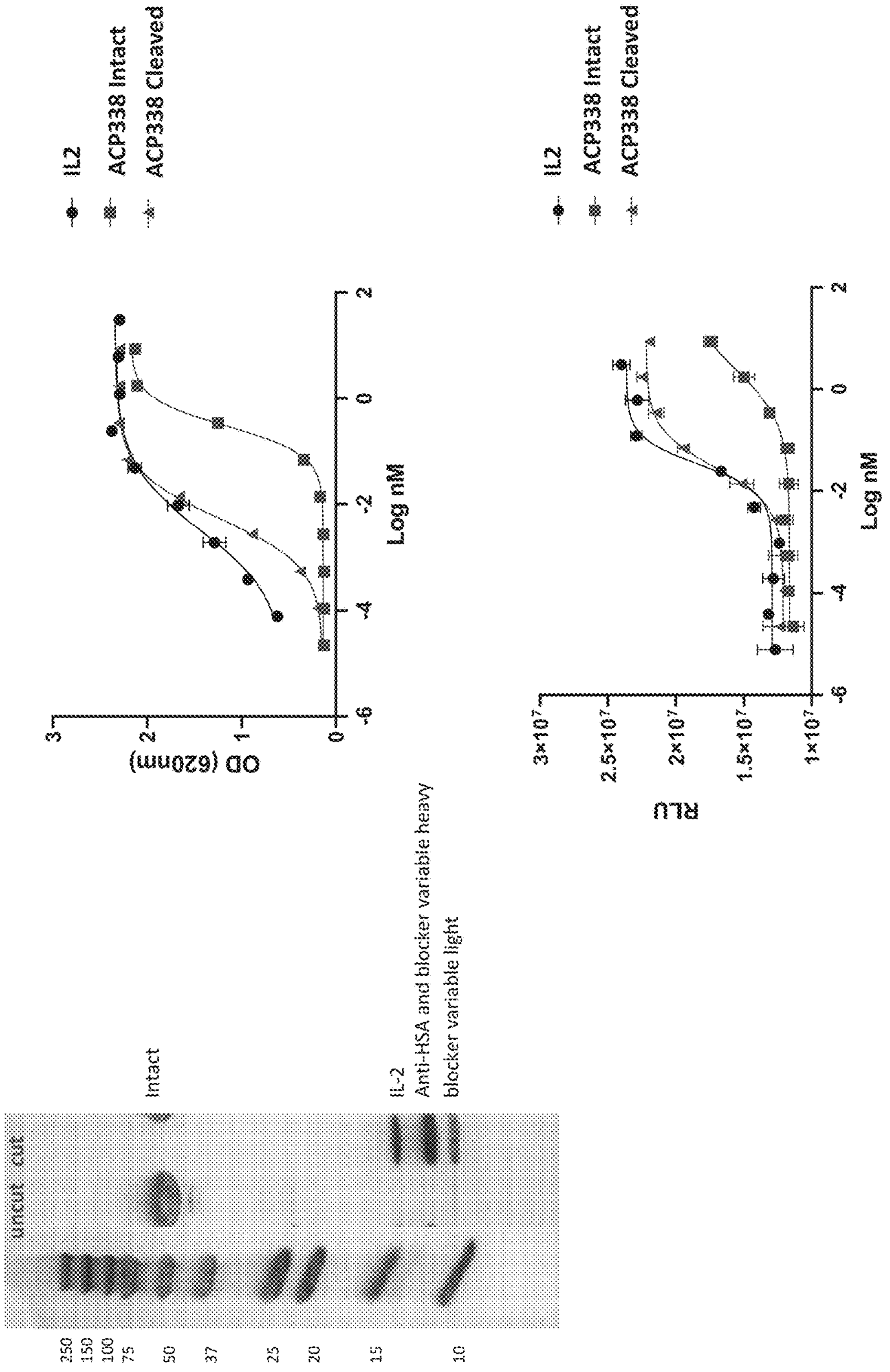
Figure 52I:
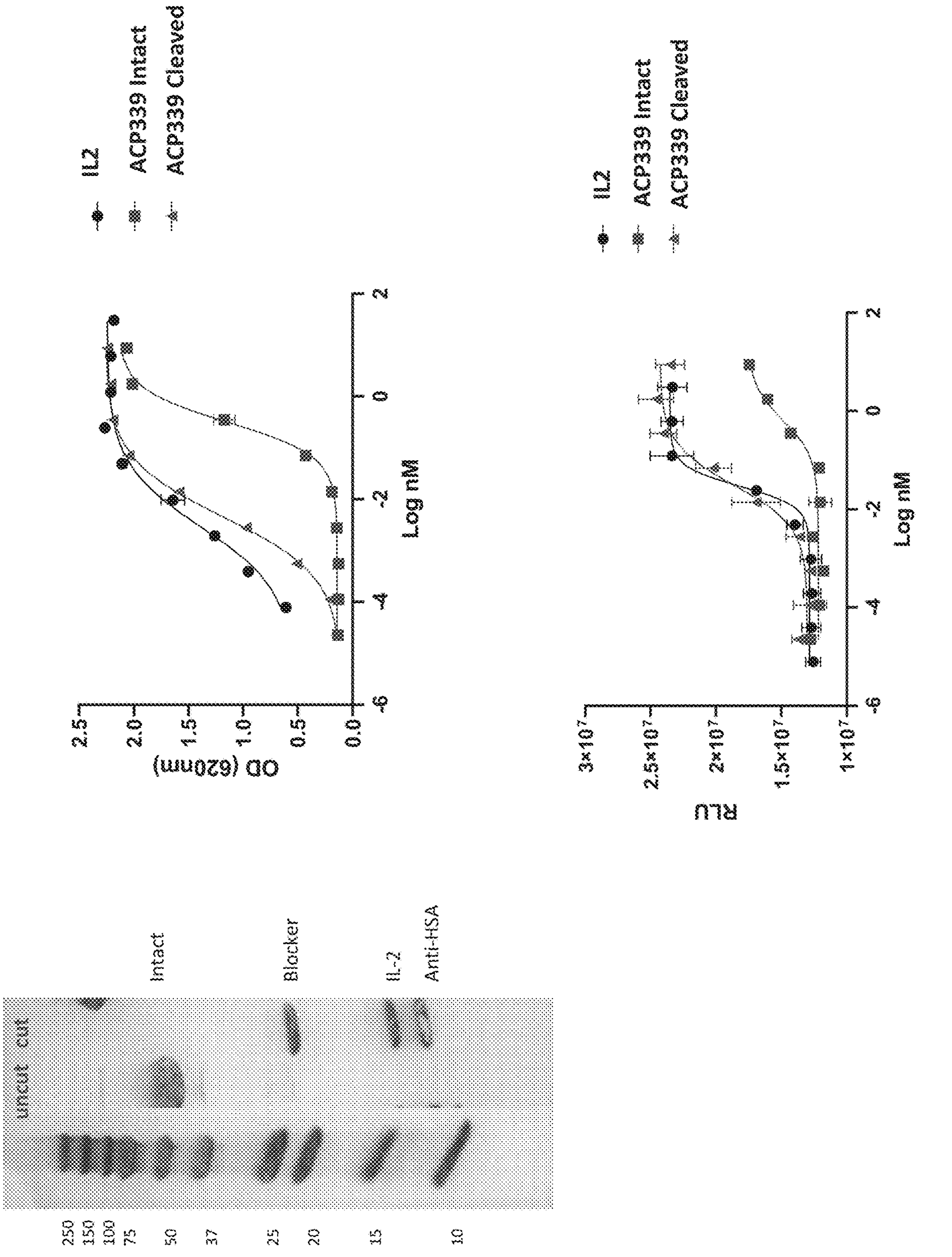
Figure 52J:
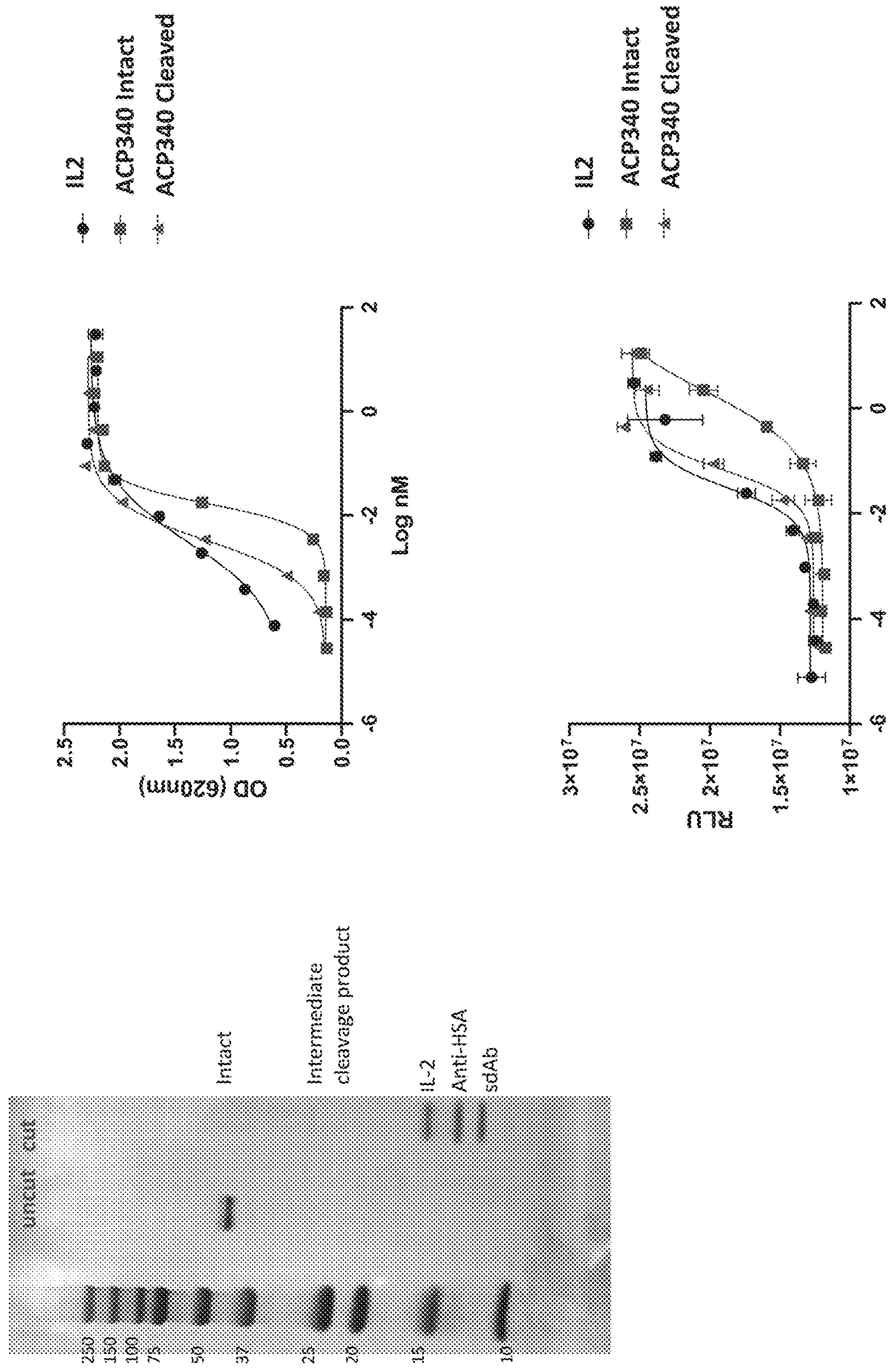
Figure 52K:
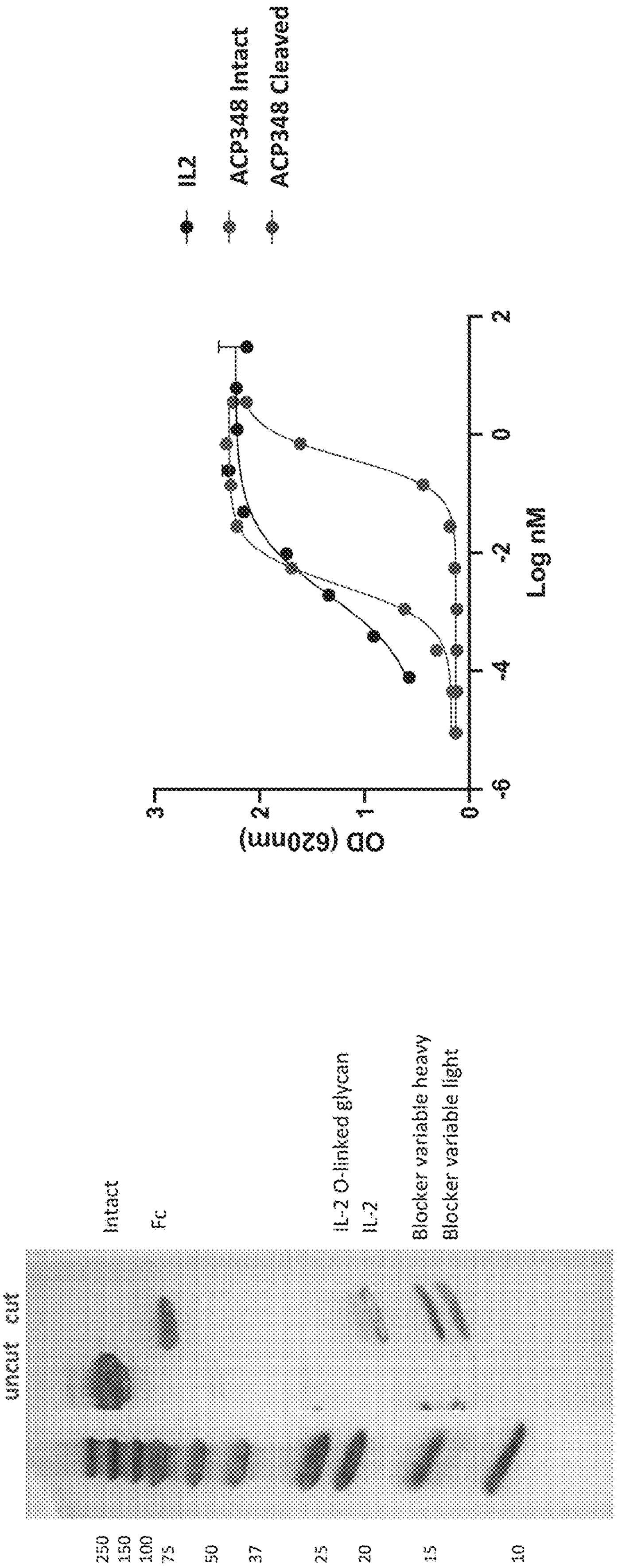
Figure 52L:
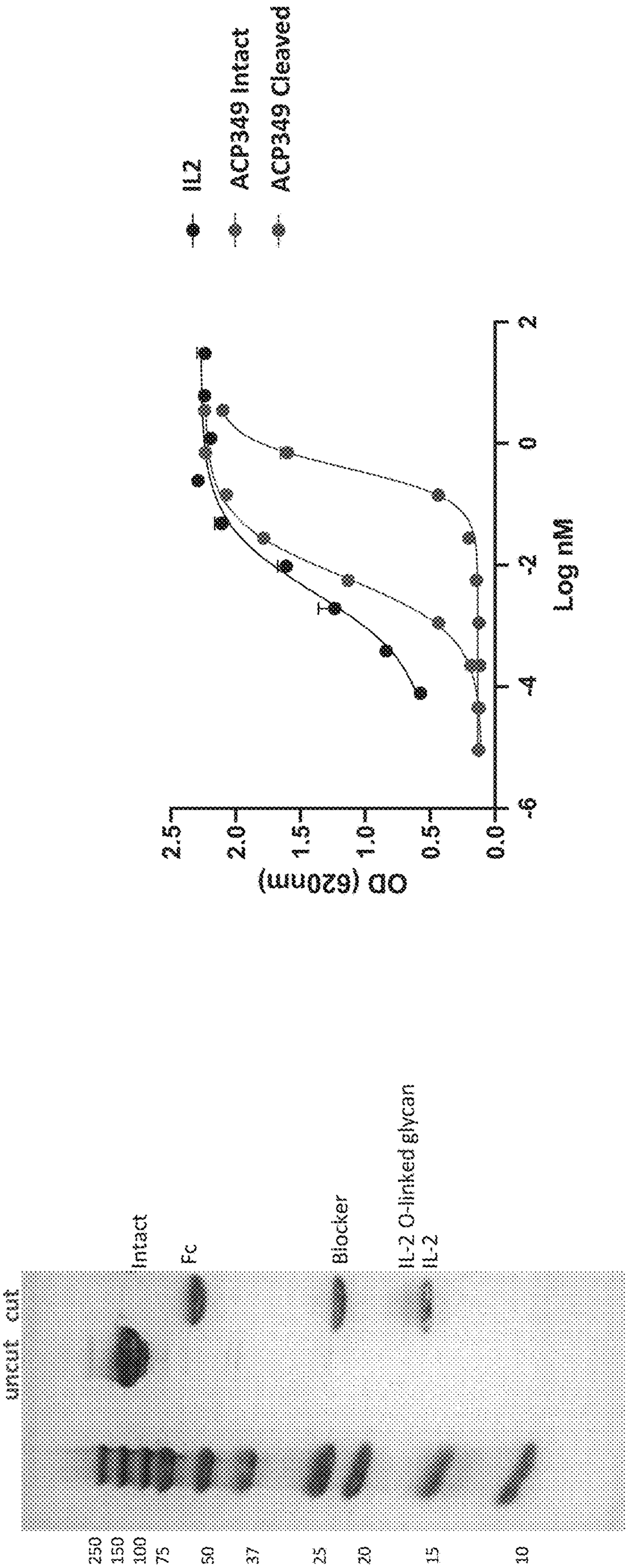
Figure 52M:
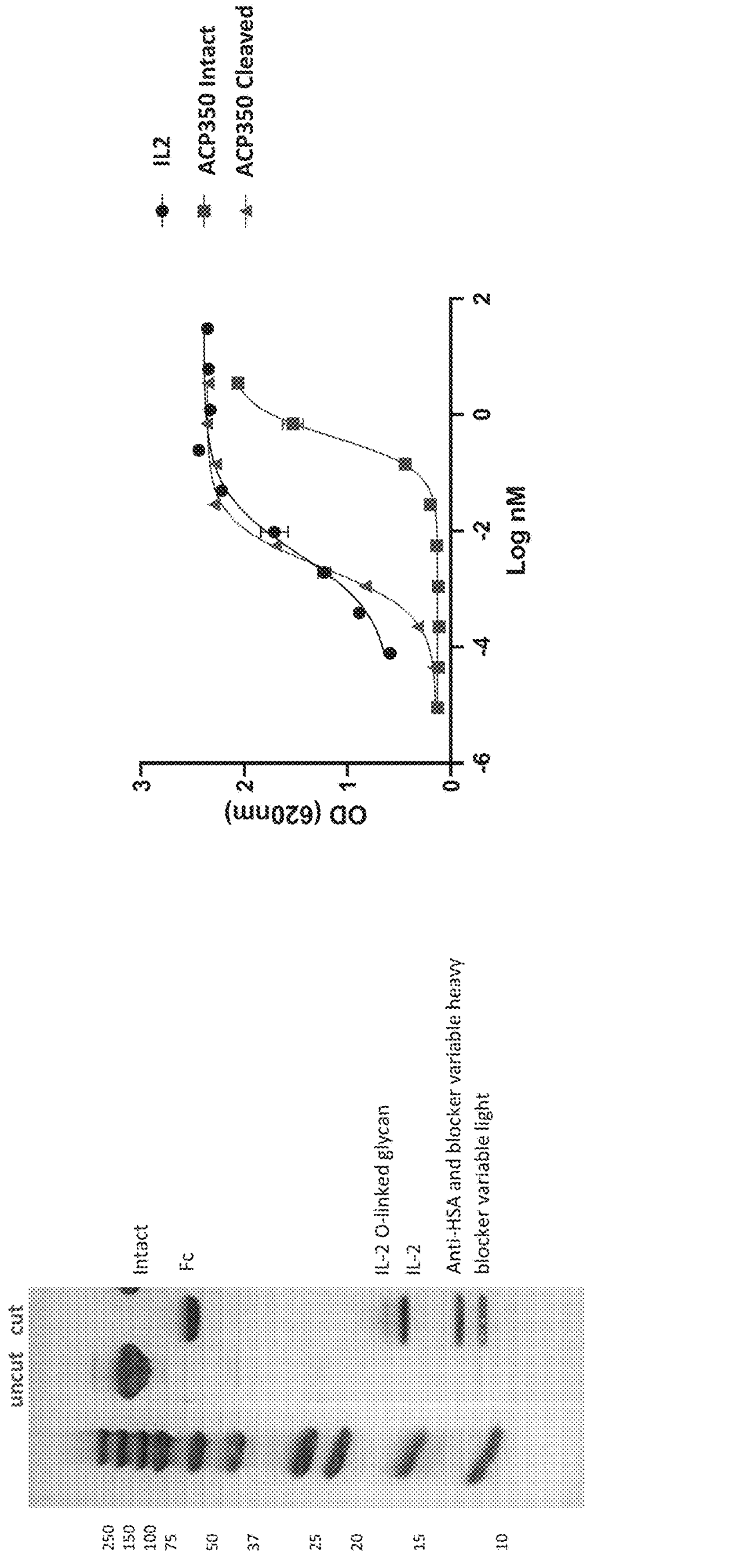
Figure 52N:
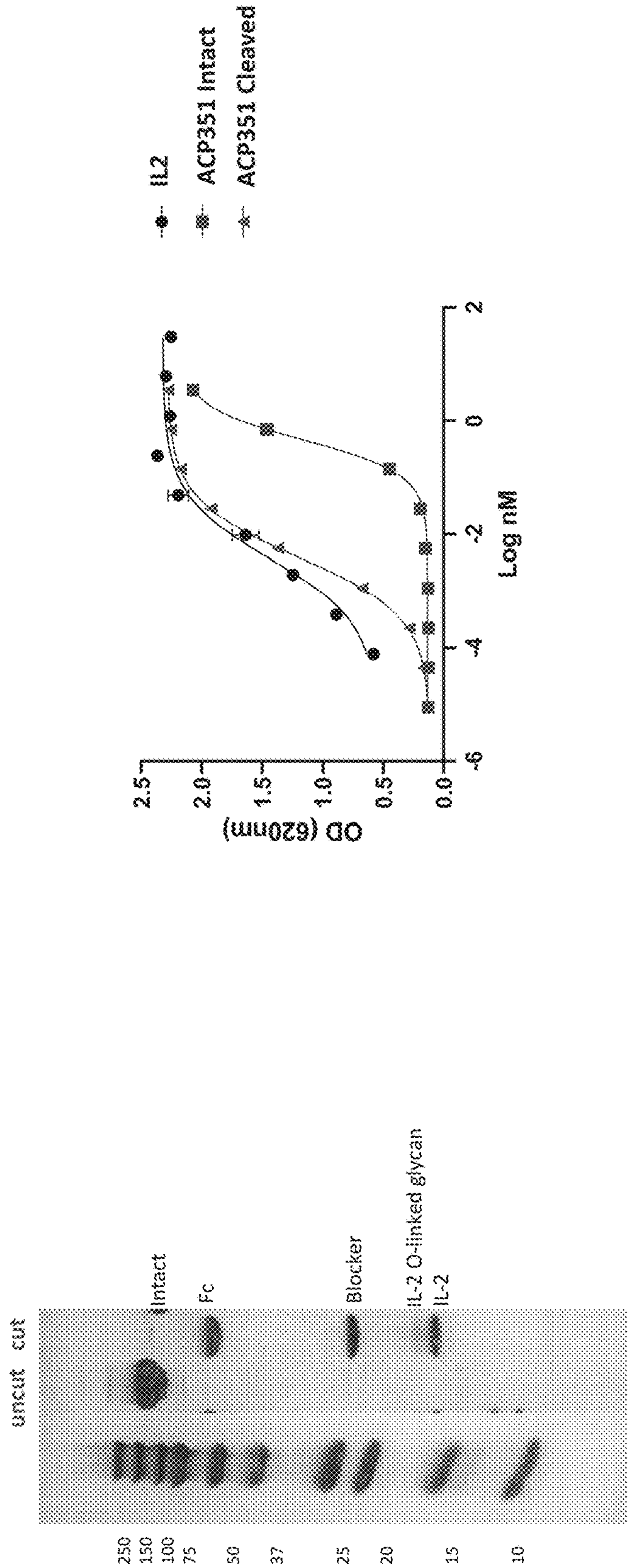
Figure 53A:
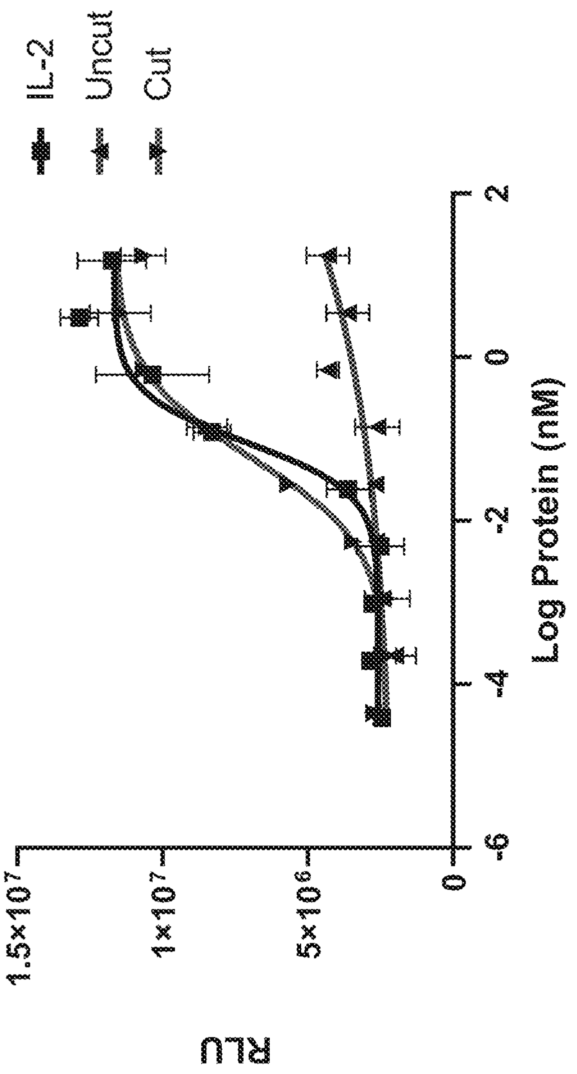
Figure 53B:
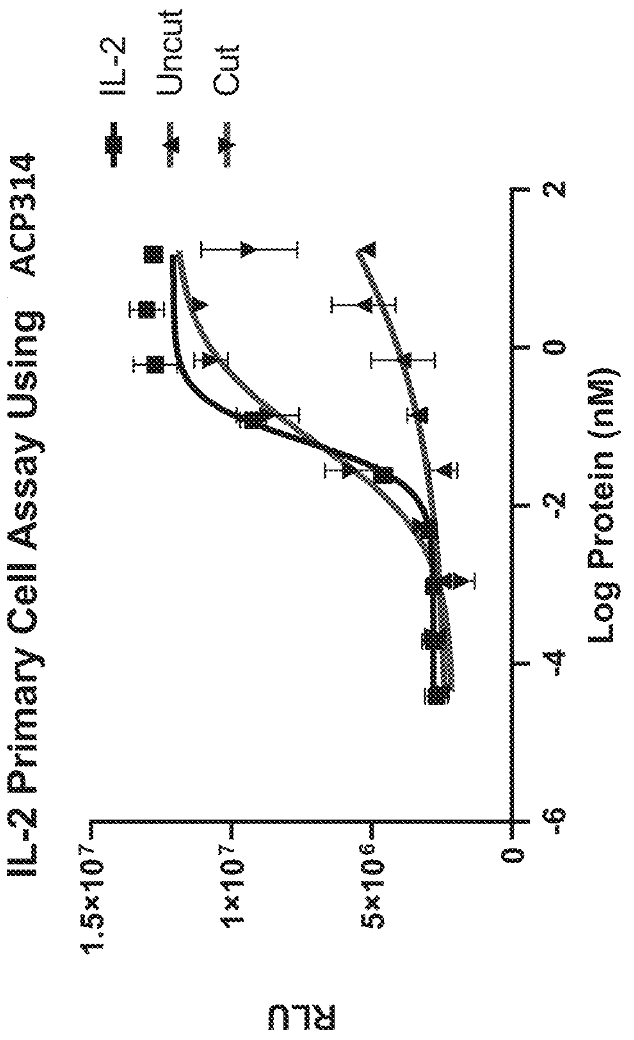

Procedures:

Mice were anaesthetized with isoflurane for implant of cells to reduce the ulcerations. CR female C57BL/6 mice were set up with $5\times10^5$ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 $mm^3$ and begin treatment. ACP339 was dosed at 55, 230 or 700 μg/animal. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 $mm^3$ or 45 days, whichever comes first. Responders were followed longer. When the endpoint was reached, the animals are to be euthanized. Results are shown in FIGS. 51A-51C.

Example 28: CT26 Experiments

The CT26 cell line, a rapidly growing colon adenocarcinomacell line that expresses MMP9 in vitro, was used. Using this tumor model, the ability of fusion proteins to affect tumor growth was examined.

Example 28a: Treatment with ACP16 Alone or in Combination with Anti-PD1 Antibody Agents and Treatment:

| Gr. | N | Agent | Formulation dose | Route | Schedule |
|---|---|---|---|---|---|
| 1# | 12 | vehicle 1 // vehicle 2 | na // na | ip // ip | days 1, 4, 8, 11 // days 3, 6, 10, 13 |
| 2 | 10 | vehicle 1 // ACP16 | na // 70 μg/animal | ip // ip | days 1, 4, 8, 11 // days 3, 6, 10, 13 |
| 3 | 10 | vehicle 1 // ACP16 | na // 232 μg/animal | ip // ip | days 1, 4, 8, 11 // days 3, 6, 10, 13 |
| 4 | 10 | vehicle 1 // ACP16 | na // 500 μg/animal | ip // ip | days 1, 4, 8, 11 // days 3, 6, 10, 13 |
| 5 | 10 | anti-PD-1 RMP1-14 // vehicle 2 | 200 μg/animal // na | ip // ip | days 1, 4, 8, 11 // days 3, 6, 10, 13 |
| 6 | 10 | anti-PD-1 RMP1-14 // ACP16 | 200 μg/animal // 70 μg/animal | ip // ip | days 1, 4, 8, 11 // days 3, 6, 10, 13 |
| 7 | 10 | anti-PD-1 RMP1-14 // ACP16 | 200 μg/animal // 232 μg/animal | ip // ip | days 1, 4, 8, 11 // days 3, 6, 10, 13 |
| 8 | 10 | anti-PD-1 RMP1-14 // ACP16 | 200 μg/animal // 500 μg/animal | ip // ip | days 1, 4, 8, 11 // days 3, 6, 10, 13 |
| 9 | 10 | vehicle 1 // IL-2 | na // 12 μg/animal | ip // ip | days 1, 4, 8, 11 // bid × 5 first day 1 dose per week × 2 |
| 10 | 10 | anti-PD-1 RMP1-14 // IL-2 | 200 μg/animal // 12 μg/animal | ip // ip | days 1, 4, 8, 11 // bid × 5 first day 1 dose per week × 2 |

Procedures:

Mice were anaesthetized with isoflurane for implant of cells to reduce the ulcerations. CR female BALB/c mice were set up with $3\times10^5$ CT26 tumor cells in 0% Matrigel sc in flank. Cell Injection Volume was 0.1 mL/mouse. Mouse age at start date was 8 to 12 weeks. Pair matches were performed when tumors reach an average size of 100-150 $mm^3$ and begin treatment. ACP 16 was dosed at 70, 230 or 500 μg/animal with or without anti-PD-1 antibody (RMP1-14) at 200 μg/animal. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 $mm^3$ or 45 days, whichever comes first. Responders were followed longer. When the endpoint was reached, the animals are to be euthanized. Results are shown in FIGS. 47A-47D and FIGS. 48A-48B.

Example 29. Human Tblast Assay

IL-2 T-Blast Assay. Pre-stimulated T cells (T-blasts) were used to assess the activity of inducible IL-2 fusion proteins.

T-Blasts were induced from human PBMCs with a 3-day incubation with PHA. Tblasts were then plated in suspension at a concentration of 50,000 or 75,000 cells/well in X-VIVO culture media (containing human serum albumin) and stimulated with a dilution series of recombinant IL-2 fusion proteins or human IL-2 for 72 hours at 37° C. and 5% $CO_2$. Activity of uncleaved and cleaved IL-2 fusion proteins was tested. Cleaved inducible IL-2 was generated by incubation with active MMP9. IL-2 activity was assessed measuring proliferation with CellTiter-Glo. Exemplary results are shown in FIG. 3A-3I.

IL-12 T-Blast Assay. T-Blasts were induced from human PBMCs through PHA stimulation for 72 hours. T-blasts were then washed and frozen prior use. For the assay, T-Blasts were thaw and plated in suspension at 100,000 cells/well in culture media containing human albumin and stimulated with a dilution series of recombinant hIL12 or chimeric IL12 (mouse p35/human p40) indukines or hIL12 indukines for 72 hours at 37° C. and 5% $CO_2$. Activity of uncleaved and cleaved IL12 fusion proteins was tested. Cleaved inducible hIL12 was generated by incubation with active MMP9 enzyme. IL12 activity was assessed by quantification of IFNγ production in supernatants using a hIFNγ Alpha-LISA kit. Exemplary results are shown in FIGS. 8A-8D.

Example 30. Luciferase Reporter Assay

IL-2 luciferase reporter cells (Promega), purchased from the manufacturer in a "Thaw and Use" format, were plated according to the manufacturer's directions and stimulated with a dilution series of recombinant hIL-2 or activatable hIL-2 for 6 hours at 37° C. and 5% $CO_2$. Activity of uncleaved and cleaved activatable IL-2 was tested. Cleaved inducible IL-2 was generated by incubation with active MMP9. IL-2 activity was assessed by quantification of luciferase activity using Bio-Glo™ Reagent (Promega), which allows for the measurement of luciferase activity by luminescence readout. Results are shown in FIGS. 2A-2J.

IL12 luciferase reporter cells (Promega), purchased from the manufacturer in a "Thaw and Use" format, were plated according to the manufacturer's directions and stimulated with a dilution series of recombinant hIL12 or activatable hIL12 for 6 hours at 37° C. and 5% $CO_2$. Activity of uncleaved and cleaved activatable IL12 was tested. Cleaved inducible IL12 was generated by incubation with active MMP9. IL12 activity was assessed by quantification of luciferase activity using Bio-Glo™ Reagent (Promega), which allows for the measurement of luciferase activity by luminescence readout. Results are shown in FIGS. 9A-9C.

Example 31. MC38 Experiments

Agents and Treatment:

| Group | N | Agent | Dose | Route | Schedule |
|---|---|---|---|---|---|
| 1 | 12 | vehicle | — | ip | biwk × 2 |
| 2 | 8 | WW0417 | 55 μg/animal | ip | biwk × 2 |
| 3 | 8 | WW0517 | 55 μg/animal | ip | biwk × 2 |
| 4 | 8 | WW0517 | 230 μg/animal | ip | biwk × 2 |
| 5 | 8 | WW0517 | 700 μg/animal | ip | biwk × 2 |
| 6 | 8 | WWW0520/0523 | 76 μg/animal | ip | biwk × 2 |
| 7 | 8 | WWW0520/0523 | 315 μg/animal | ip | biwk × 2 |
| 8 | 8 | WWW0520/0523 | 959 μg/animal | ip | biwk × 2 |
| 9 | 8 | WWW0548/0524 | 88 μg/animal | ip | biwk × 2 |
| 10 | 8 | WWW0548/0524 | 368 μg/animal | ip | biwk × 2 |

-continued

| Agents and Treatment: | | | | | |
|---|---|---|---|---|---|
| Group | N | Agent | Dose | Route | Schedule |
| 11 | 8 | WWW0548/0524 | 1,120 μg/animal | ip | biwk × 2 |
| 12 | 8 | WWW0548/0556 | 113 μg/animal | ip | biwk × 2 |
| 13 | 8 | WWW0548/0556 | 474 μg/animal | ip | biwk × 2 |
| 14 | 8 | WWW0548/0556 | 1,442 μg/animal | ip | biwk × 2 |
| 15 | 8 | WW0475 | 68 μg/animal | ip | biwk × 2 |
| 16 | 8 | WW0475 | 283 μg/animal | ip | biwk × 2 |
| 17 | 8 | WW0475 | 861 μg/animal | ip | biwk × 2 |
| 10 | 8 | WW0619 | 17 μg/animal | ip | biwk × 2 |
| 11 | 8 | WW0619 | 35 μg/animal | ip | biwk × 2 |
| 12 | 8 | WW0619 | 70 μg/animal | ip | biwk × 2 |
| 13 | 8 | WW0619 | 700 μg/animal | ip | biwk × 2 |
| 14 | 8 | WW0621/0523 | 24 μg/animal | ip | biwk × 2 |
| 15 | 8 | WW0621/0523 | 48 μg/animal | ip | biwk × 2 |
| 16 | 8 | WW0621/0523 | 96 μg/animal | ip | biwk × 2 |
| 17 | 8 | WW0621/0523 | 960 μg/animal | ip | biwk × 2 |

Figure 1A:
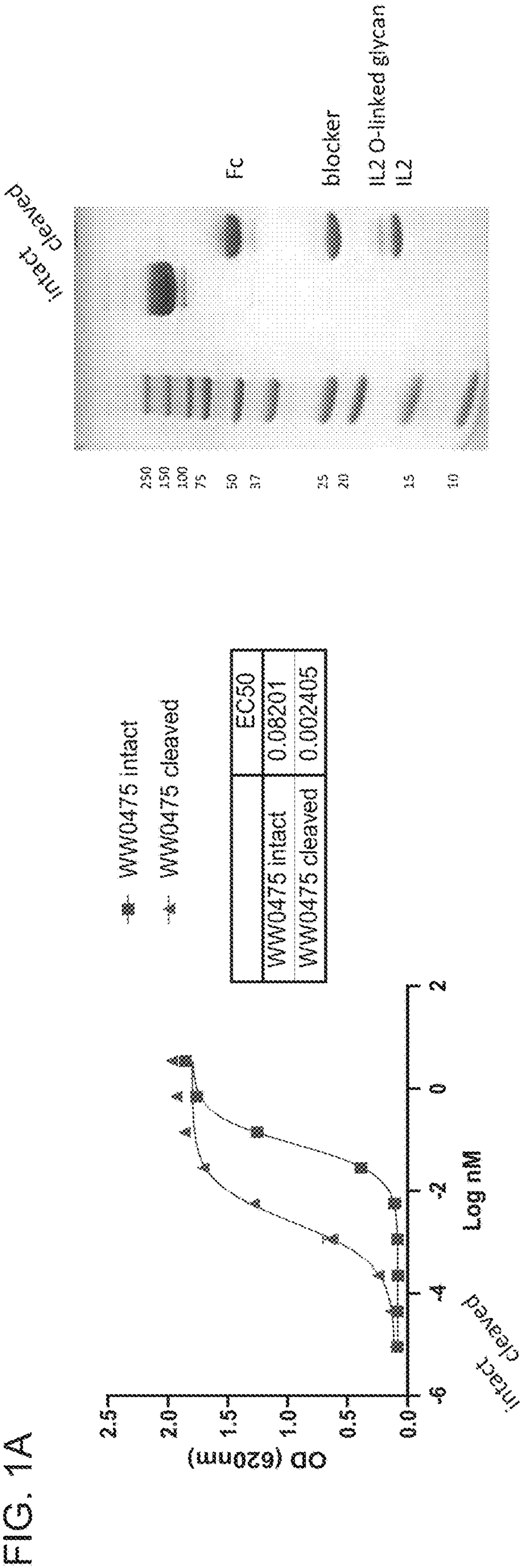
FIGS. 1A-1E are a series of graphs showing activity of IL-2 fusion proteins in a HEKBlue IL-2 reporter assay in the presence of HSA. Squares depict activity of the uncut IL-2 polypeptide (intact) and triangles depict the activity of the cut polypeptide (cleaved). Circles depict activity of control IL-2. EC50 for each IL-12. EC50 values for each are shown in the table.
Figure 1B:
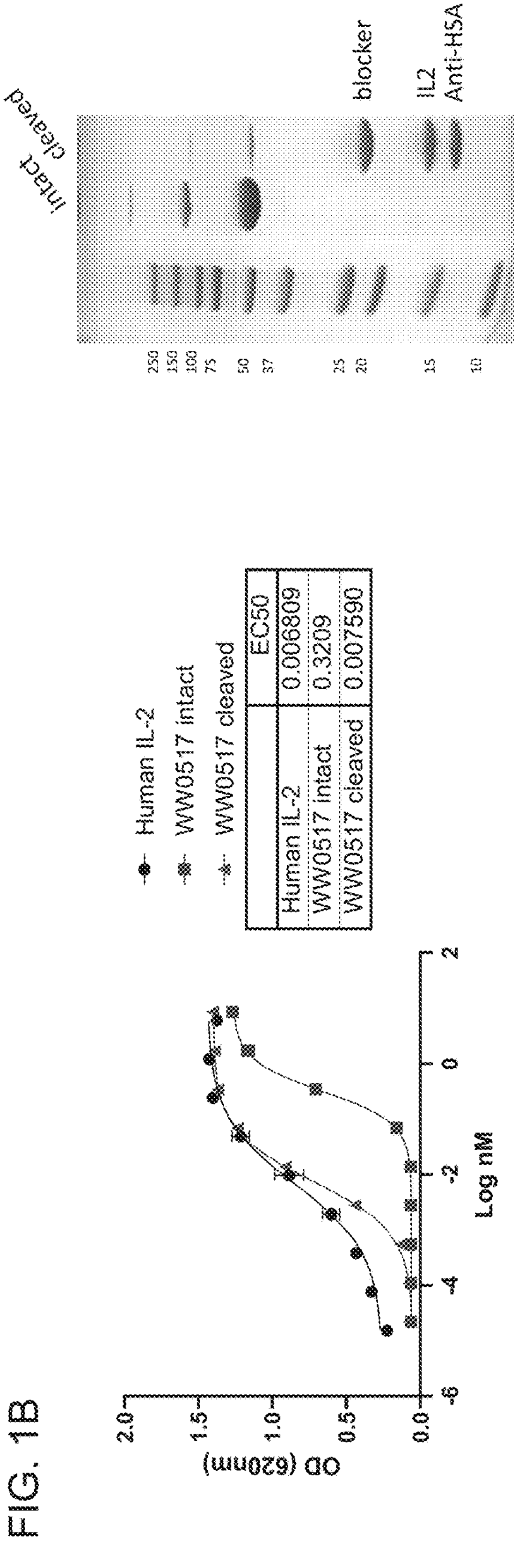
Figure 1C:
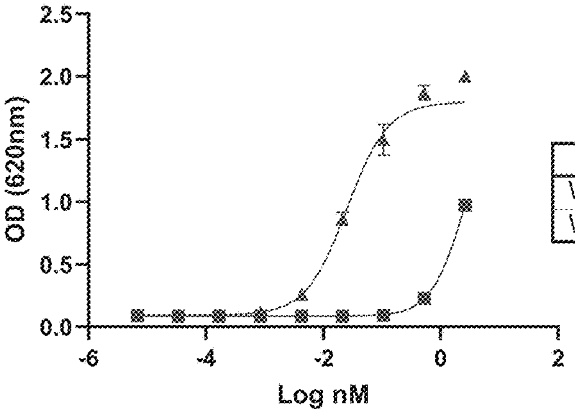
Figure 1C:
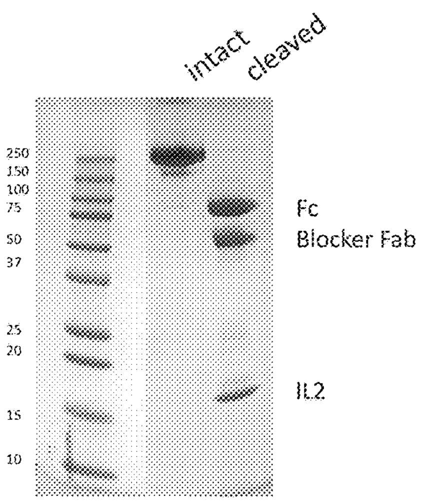
Figure 1D:
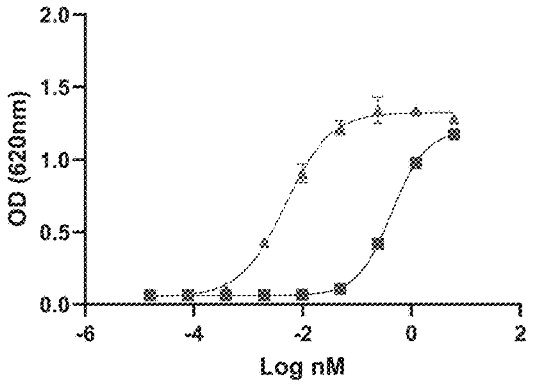
Figure 1D:
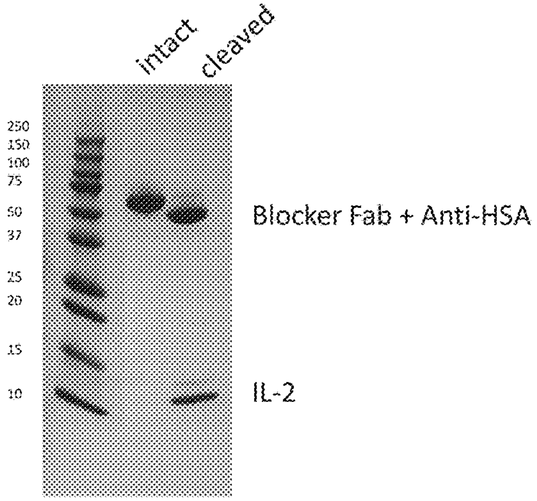
Figure 1E:
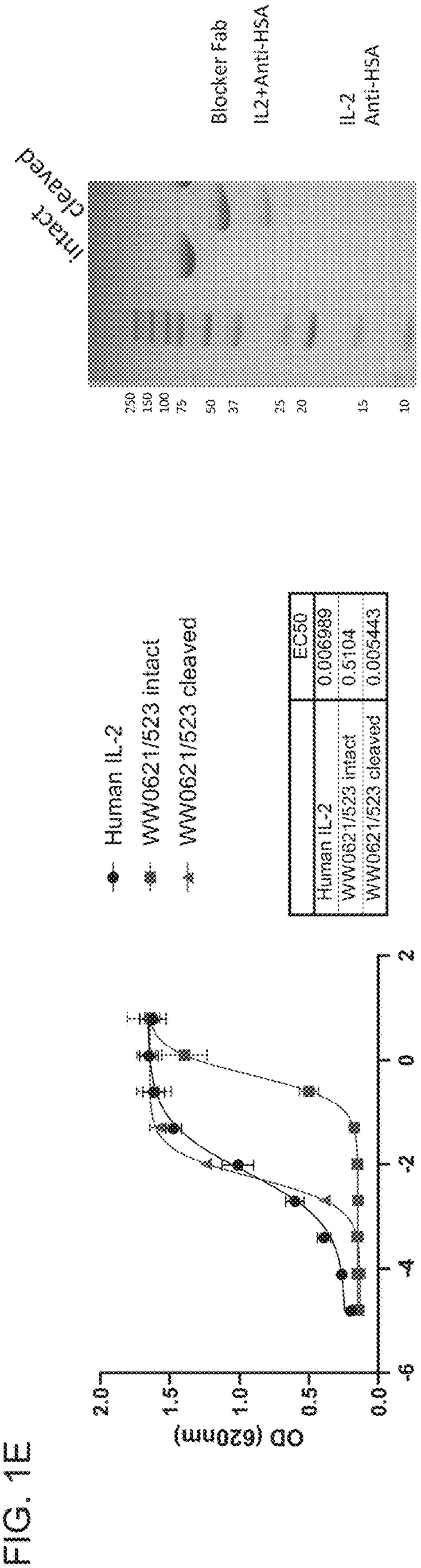
Figure 1F:
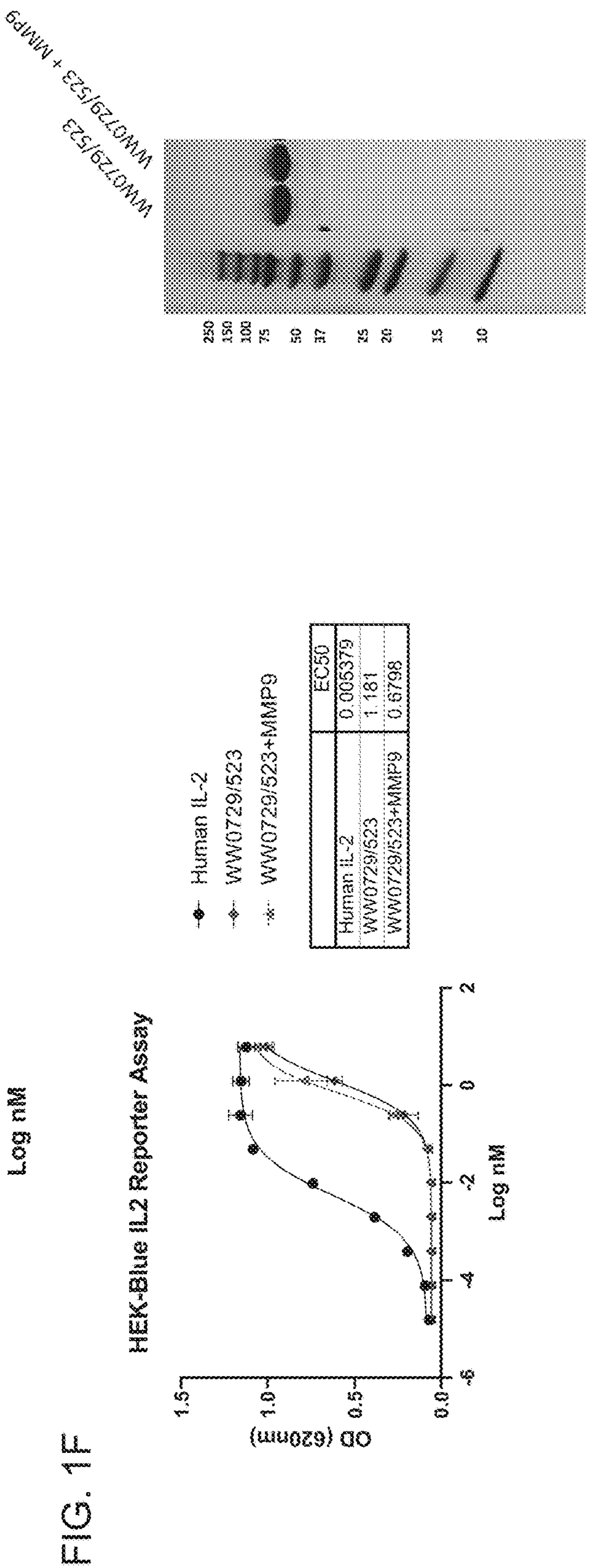
FIG. 1F is a graph showing activity of a non-cleavable control, WW0729/523.
Figure 2A:
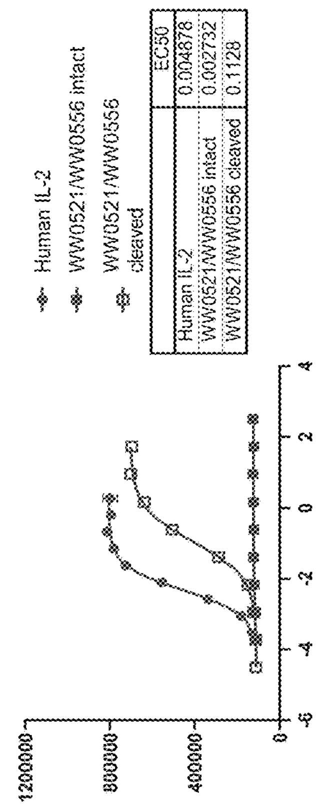
FIGS. 2A-2L are a series of graphs showing activity of fusion proteins in an IL-2 luciferase reporter assay. Closed squares depict activity of the uncut IL-2 polypeptide (intact) and open squares depict the activity of the cut IL-2 polypeptide (cleaved). Circles depict activity of the control (human IL-2). EC50 values for each are shown in the table (human IL-2). EC50 values for each are shown in the table. Constructs tested and depicted include WW0521/WW0556 (FIG. 2A), WW0521/WW0524 (FIG. 2B), WW0521/WW0523 (FIG. 2C), WW0520/WW0524 (FIG. 2D), WW0517 (FIG. 2E), WW0516 (FIG. 2F), WW0417 (FIG. 2G), WW0317 (FIG. 2H), WW0317 (FIG. 2I), and WW0520/WW0523 (FIG. 2J), WW0621/WW0523 (FIG. 2K), WW0048 (FIG. 2L).
Figure 2B:
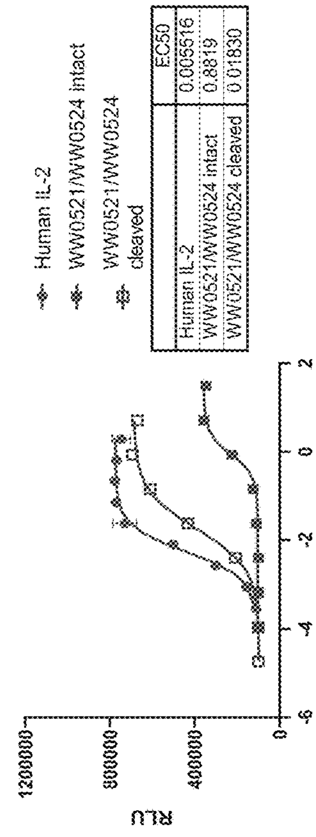
Figure 2C:
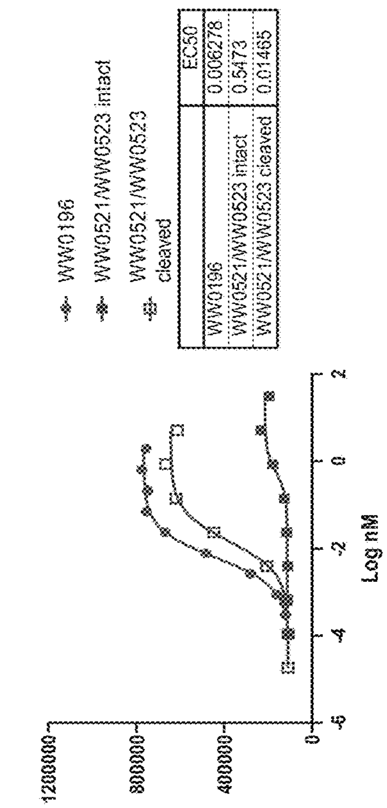
Figure 2D:
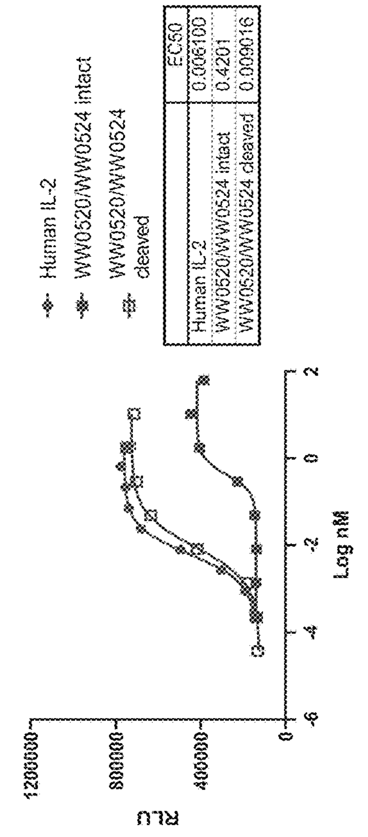
Figure 2E:
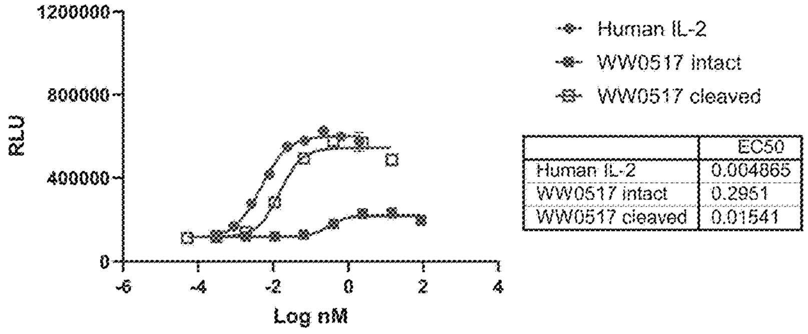
Figure 2F:
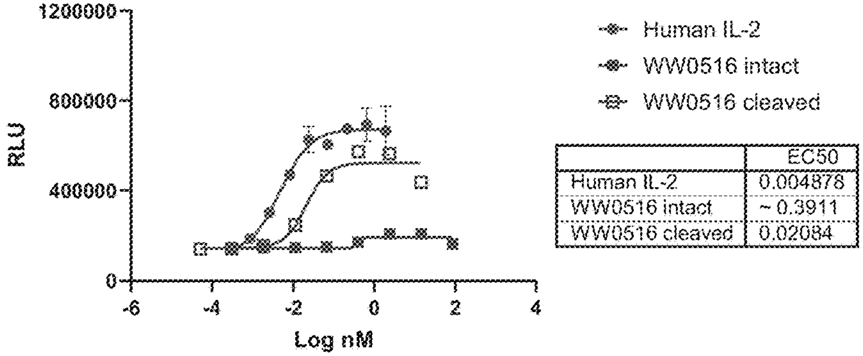
Figure 2G:
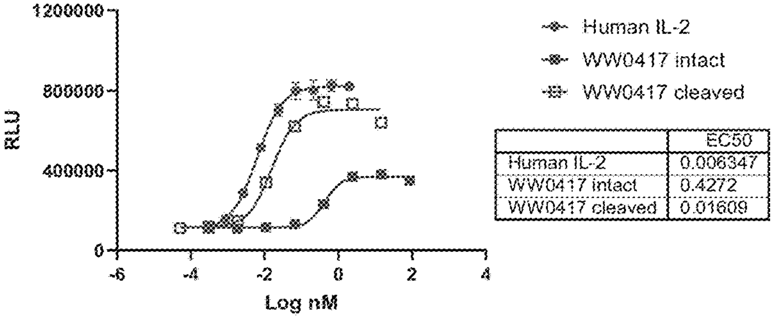
Figure 2H:
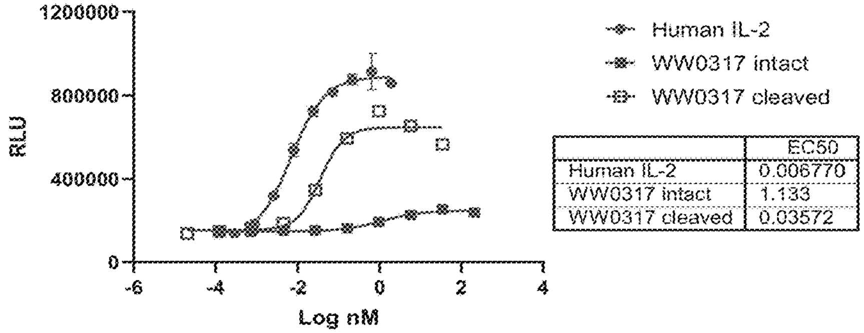
Figure 2I:
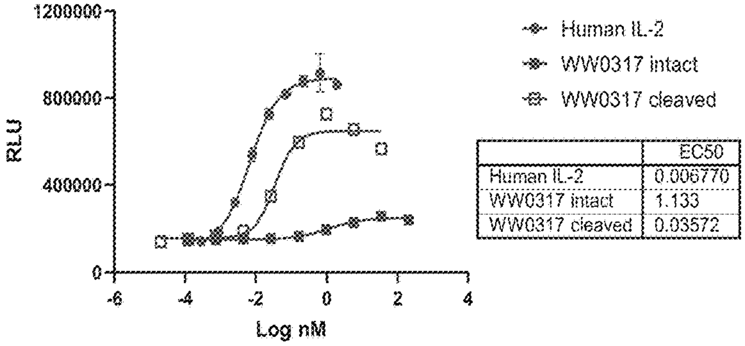
Figure 2J:
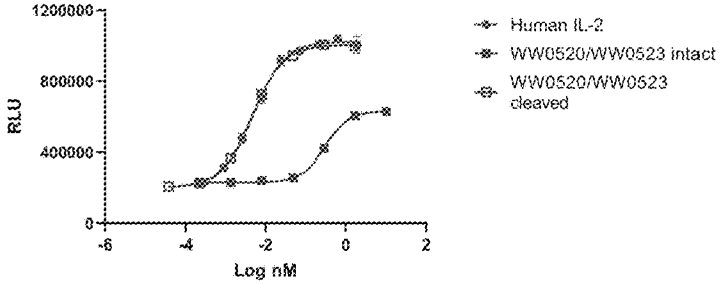
Figure 2K:
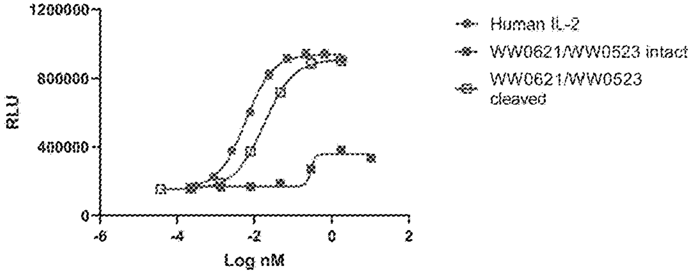
Figure 2L:
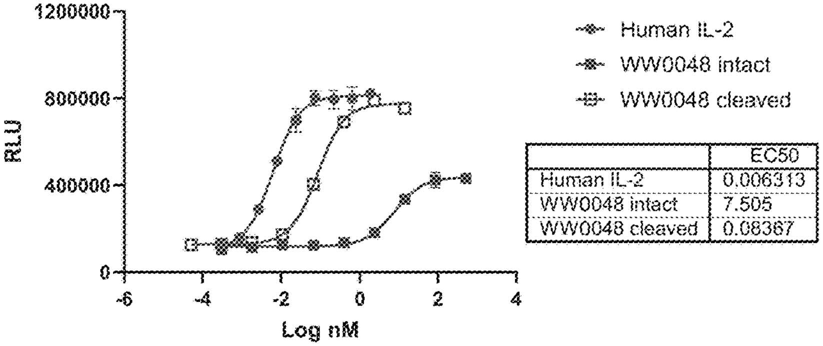
Figure 3B:
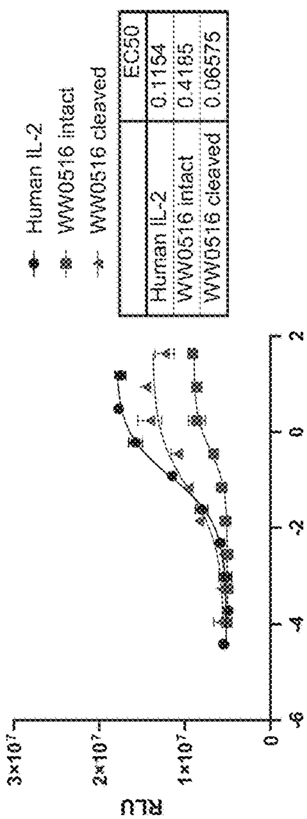
FIGS. 3A-3J are a series of graphs showing activity of fusion proteins in an IL-2 T-Blast assay.
Figure 3D:
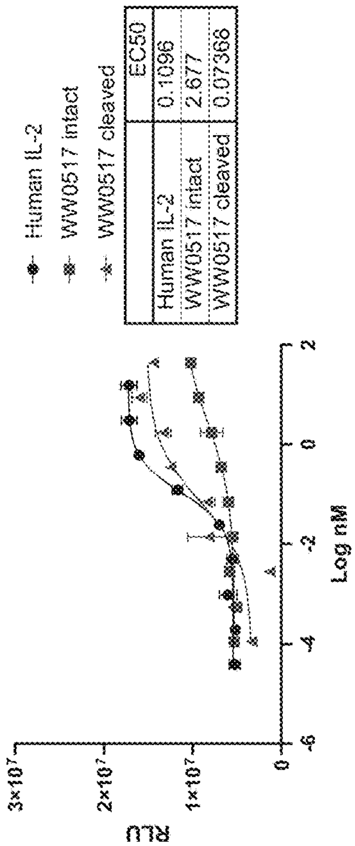
Figure 3A:
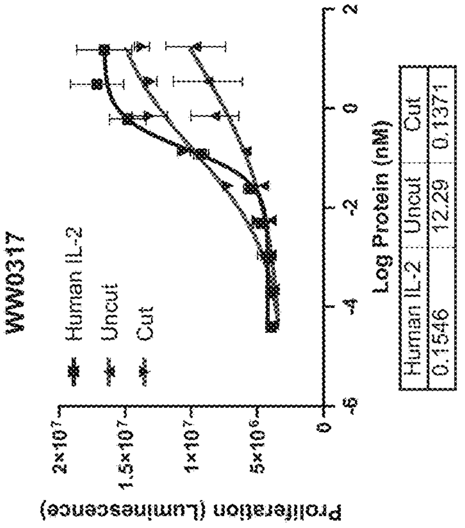
Figure 3C:
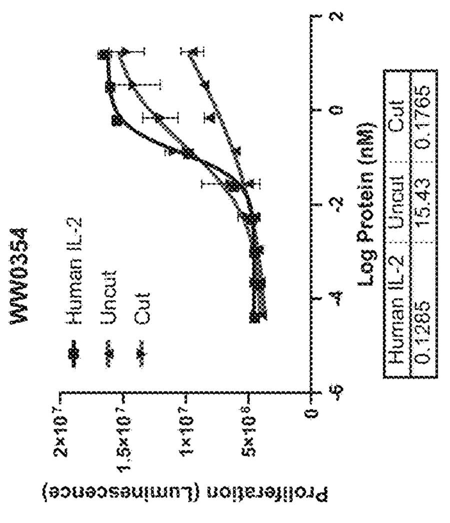
Figure 3F:
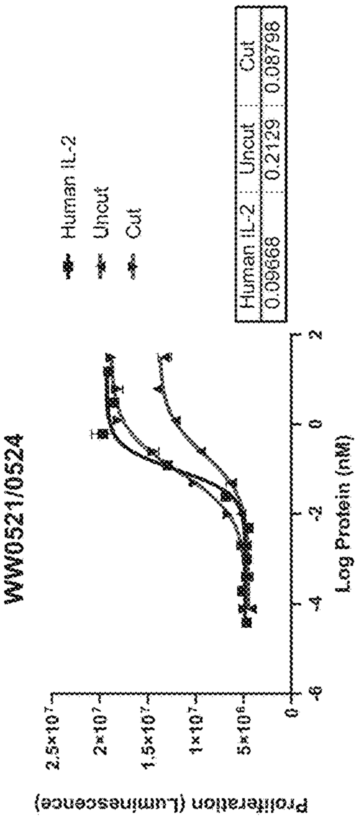
Figure 3E:
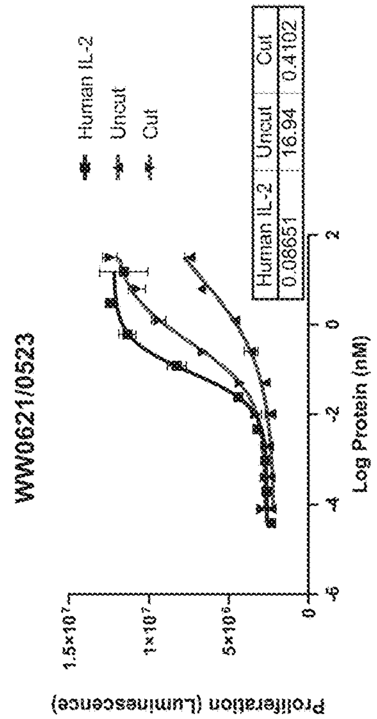
Figure 3G:
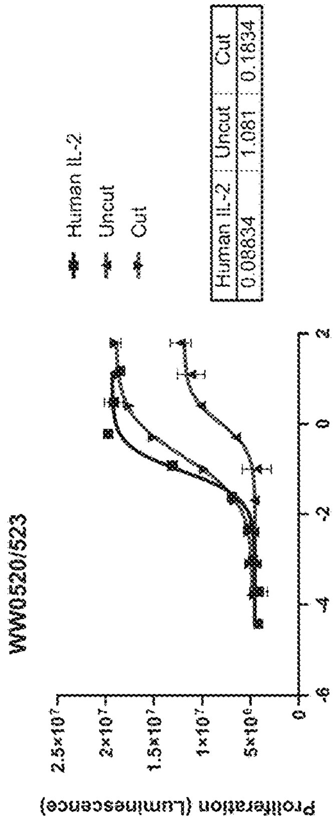
Figure 3H:
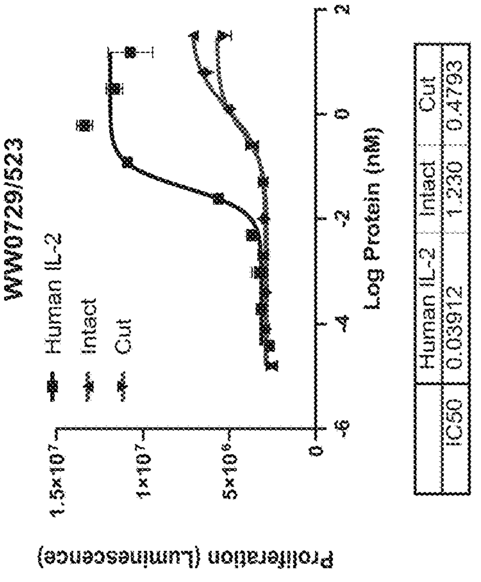
Figure 3J:
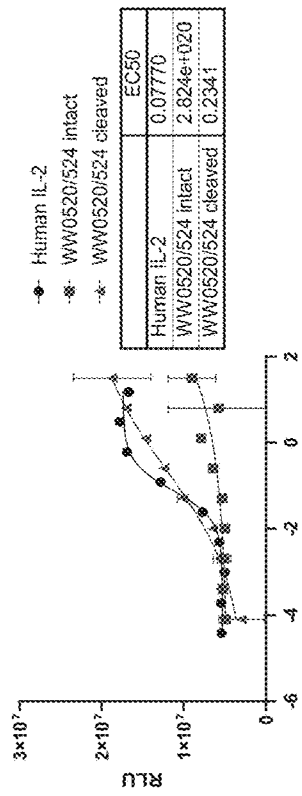
Figure 3I:
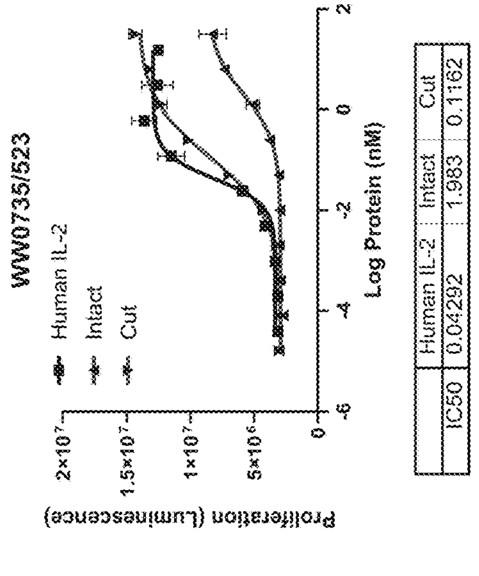
Figure 4A:
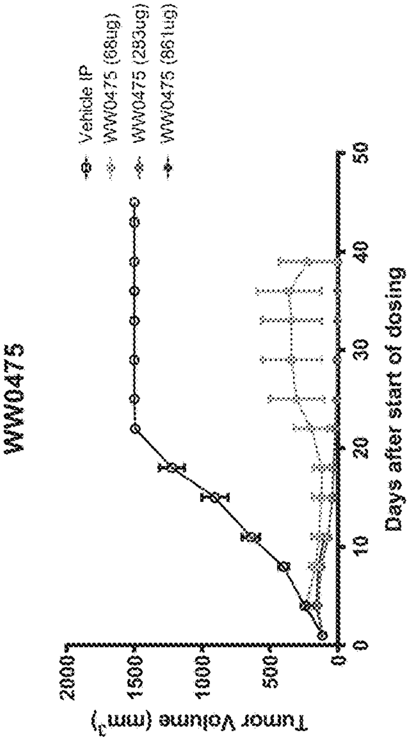
FIGS. 4A-4G are graphs that show results of analyzing WW0475, WW0520/0523, WW0548/0524, WW0548/0556, WW0517, WW0621/0523, and WW0619 IL-2 fusion proteins in a syngeneic MC38 mouse tumor model. Each graph shows average tumor volume (Mean+/−SEM) over time in mice treated with different doses of each of the fusion proteins as indicated. The data show tumor volume decreasing over time in a dose-dependent manner.
Figure 4B:
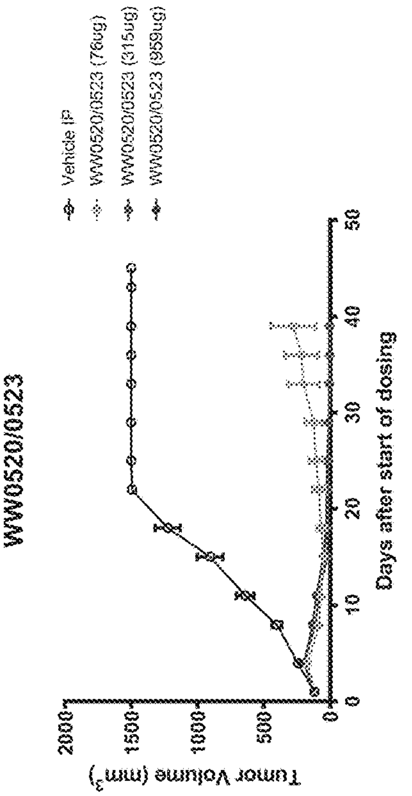
Figure 4C:
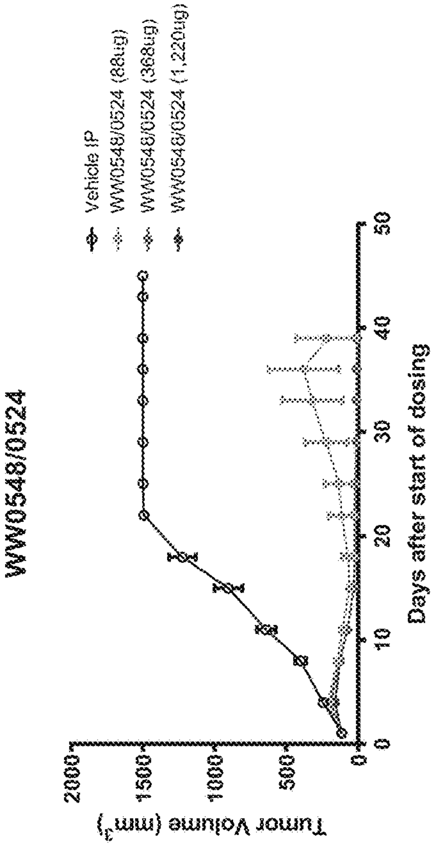
Figure 4D:
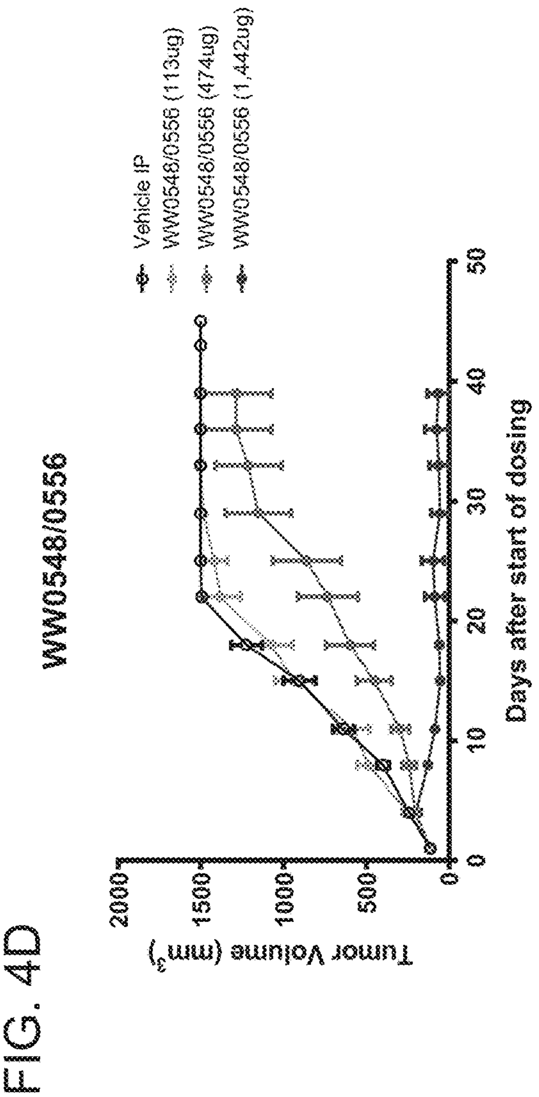
Figure 4E:
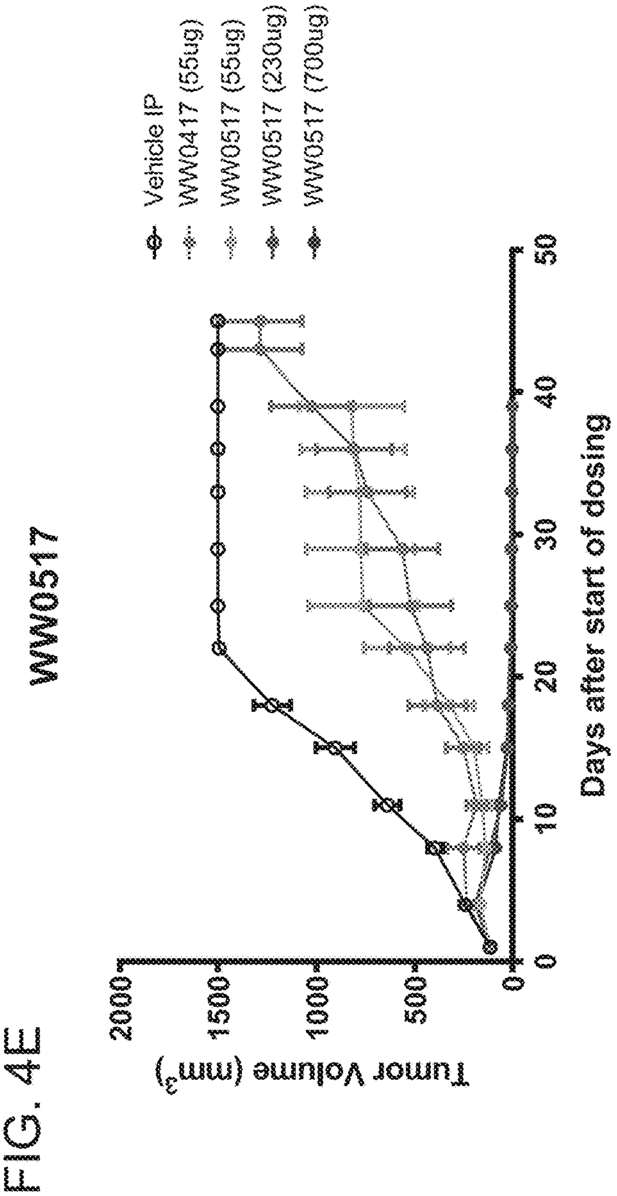
Figure 4F:
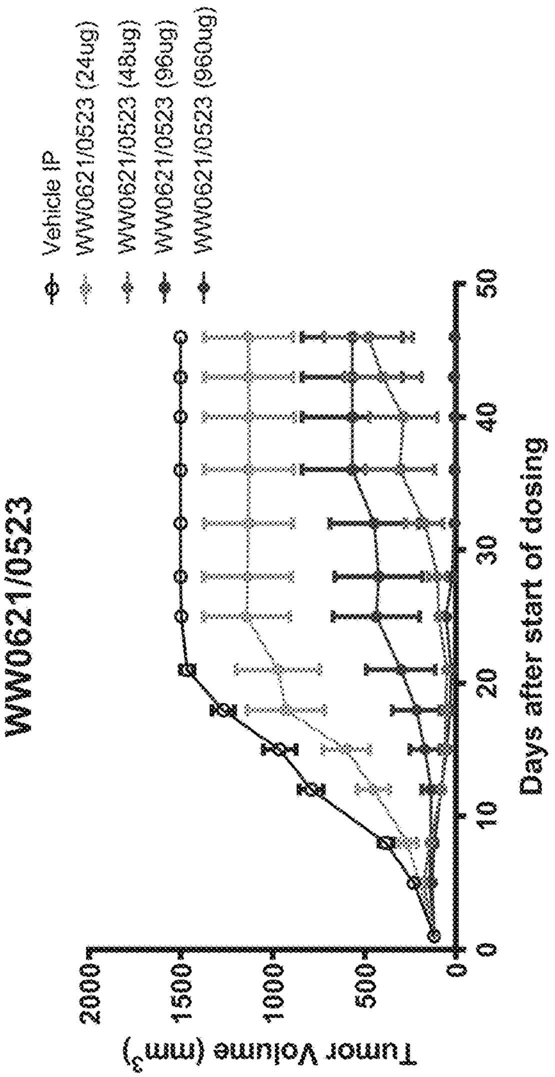
Figure 4G:
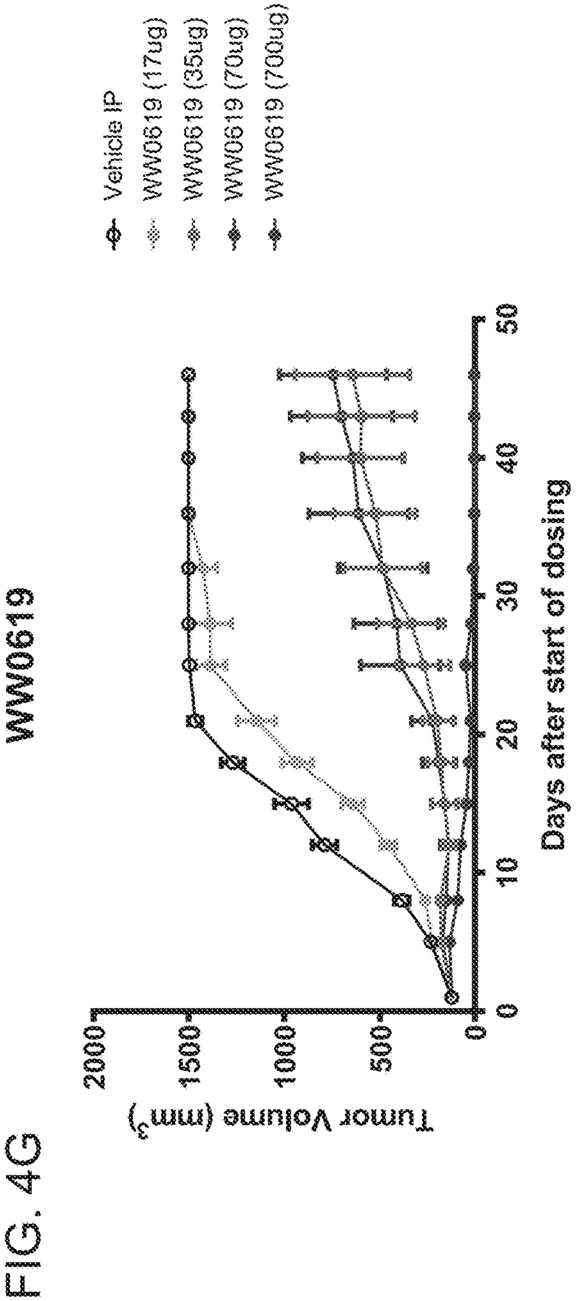
Figure 5A:
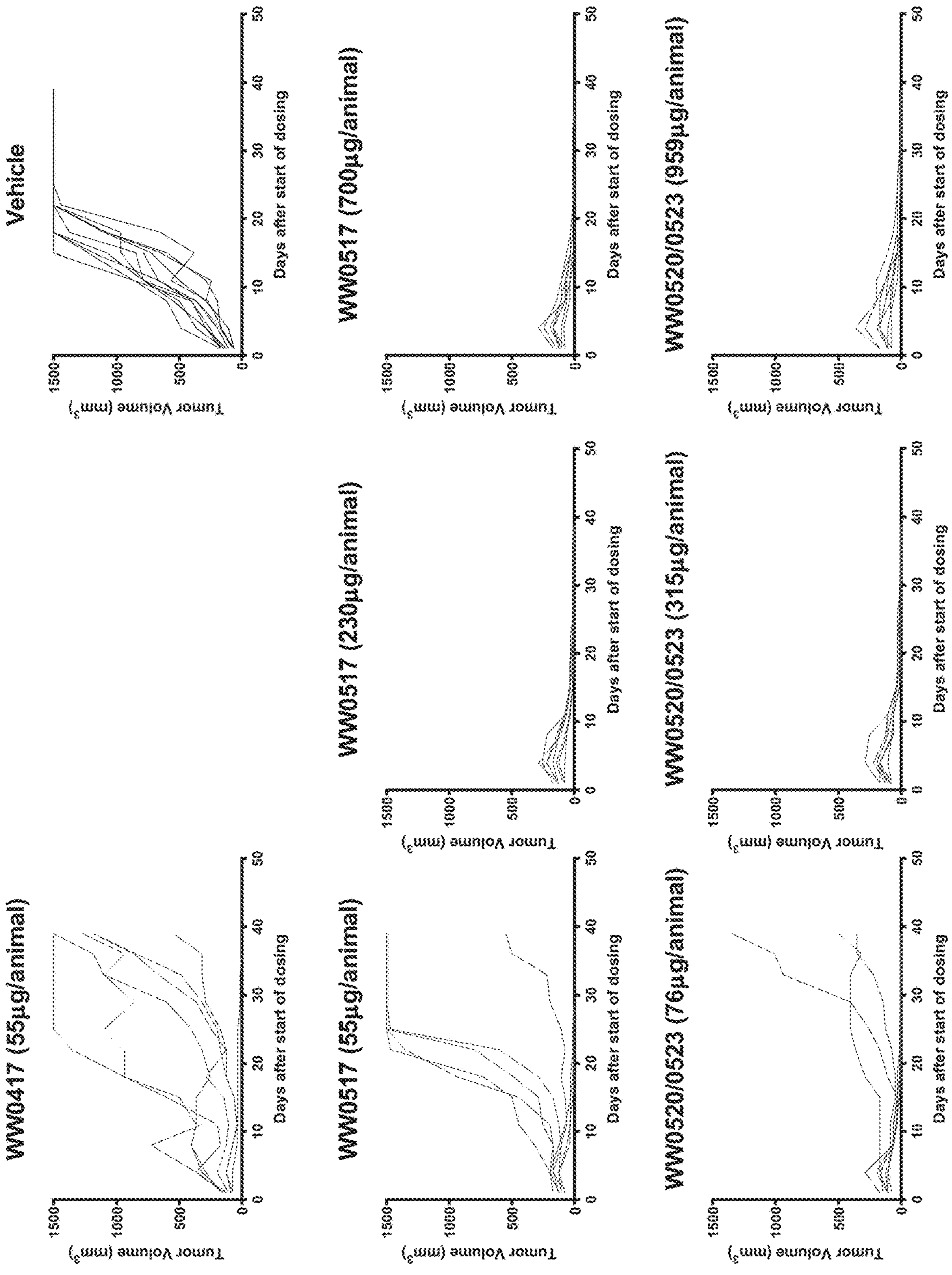
FIGS. 5A-5C are a series of spider plots showing activity of fusion proteins in the MC38 mouse syngeneic model corresponding to the data shown in FIG. 4A-4G. Each line in the plots is the tumor volume over time for a single mouse.
Figure 5B:
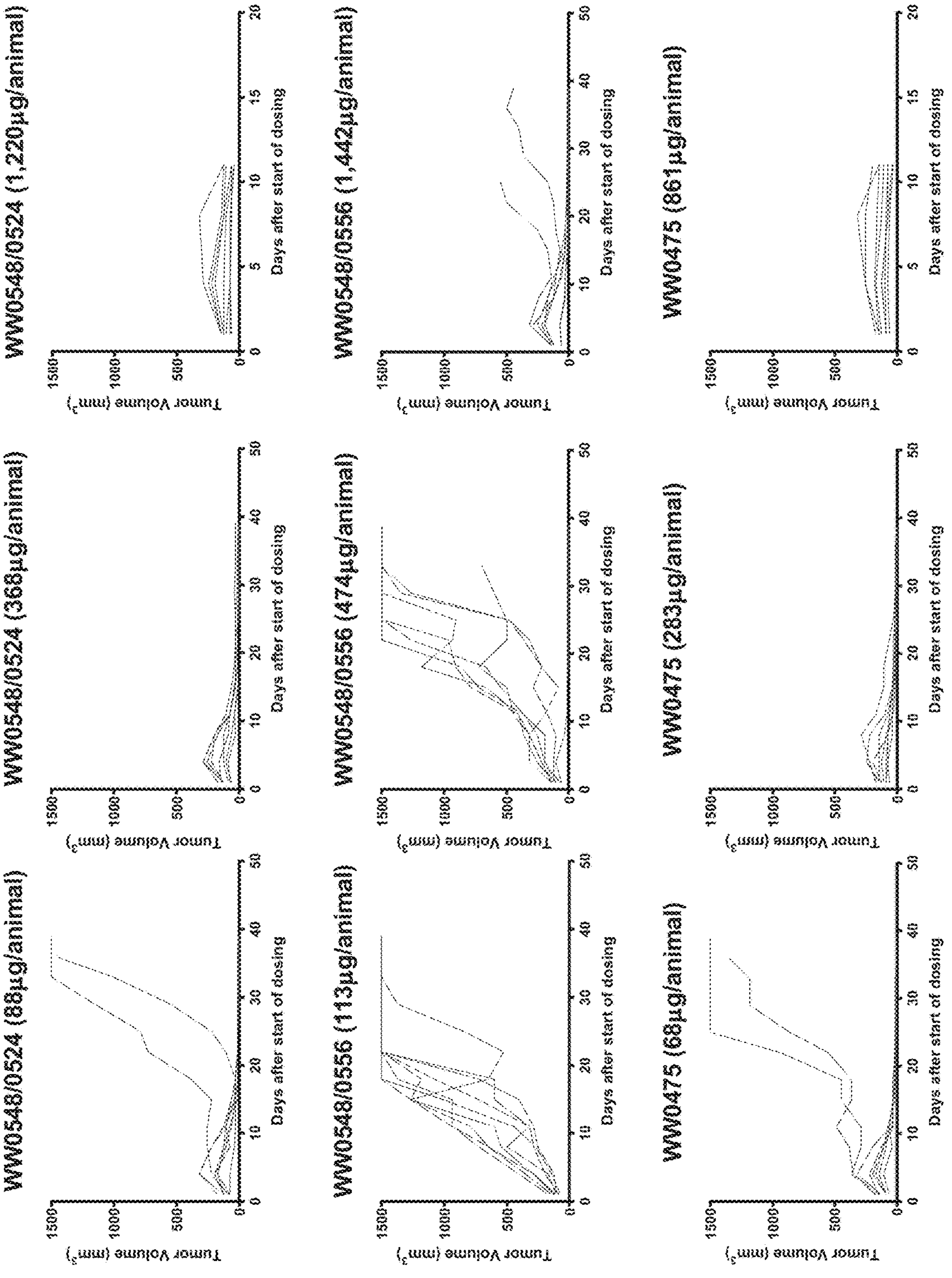
Figure 5C:
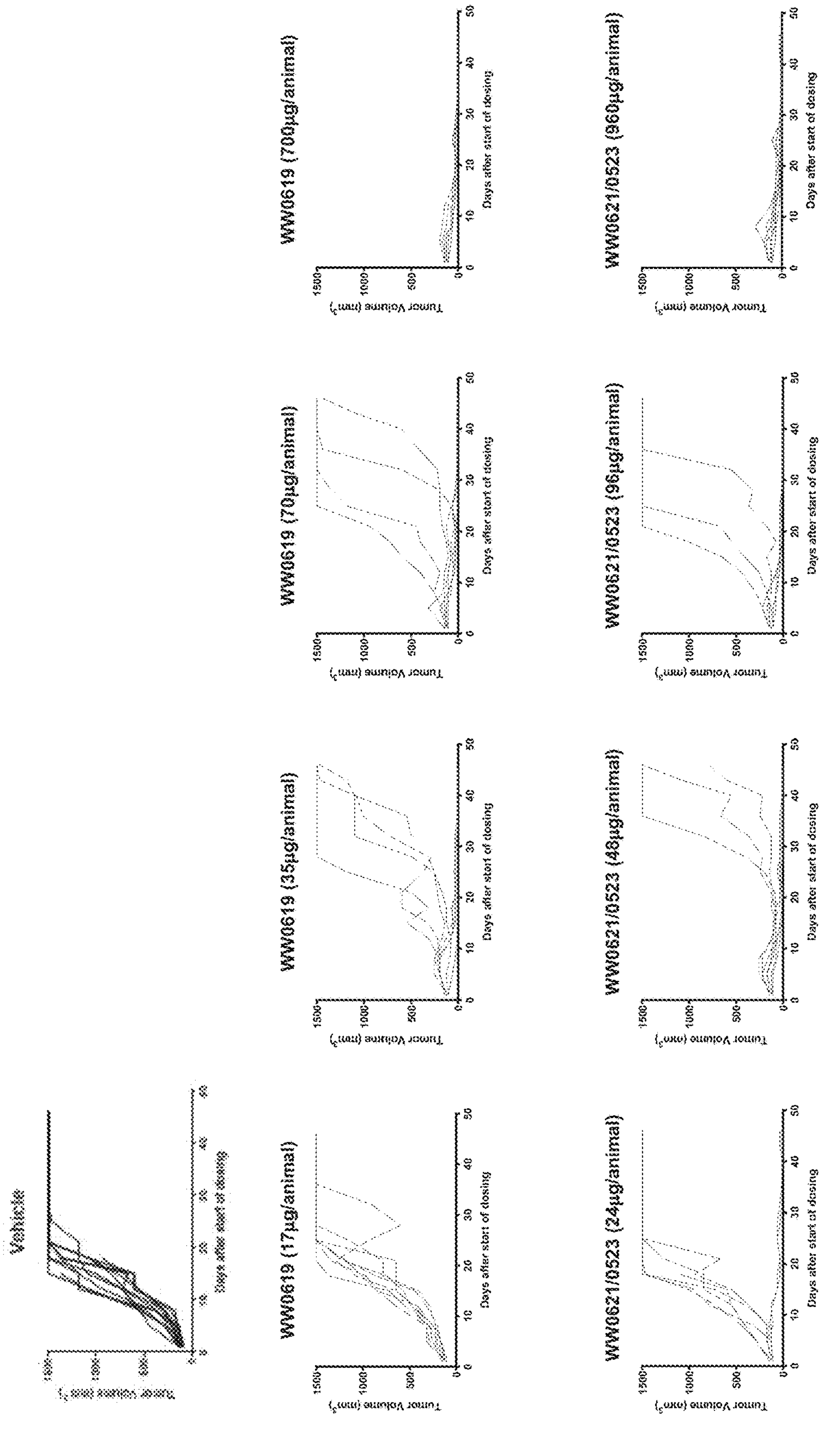
Figure 6A:
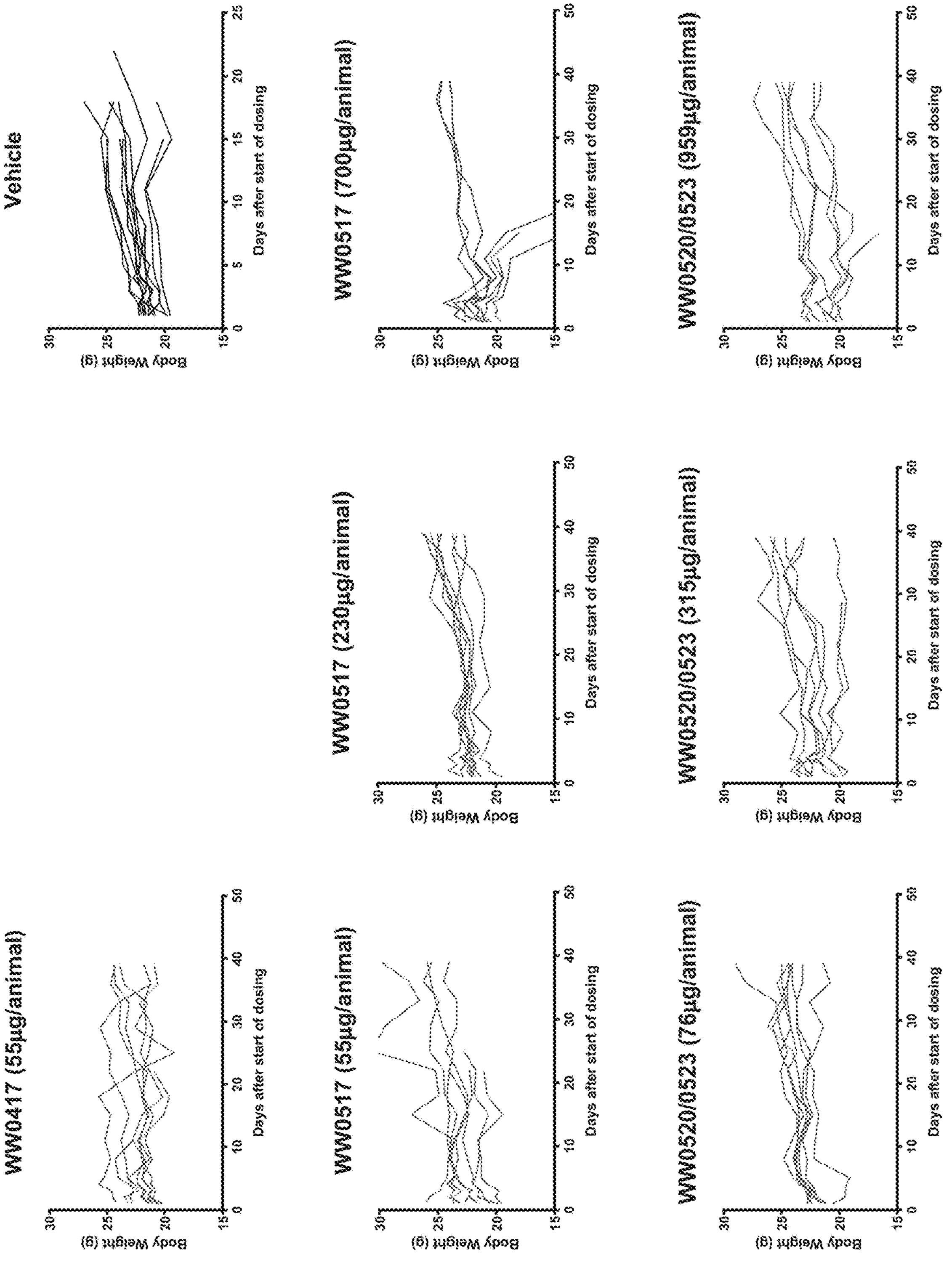
FIGS. 6A-6C are a series of spider plots showing the impact of fusion proteins on body weight in an MC38 mouse syngeneic model corresponding to the data shown in FIGS. 5A-5C. Each line in the plots is the body weight over time for a single mouse.
Figure 6B:
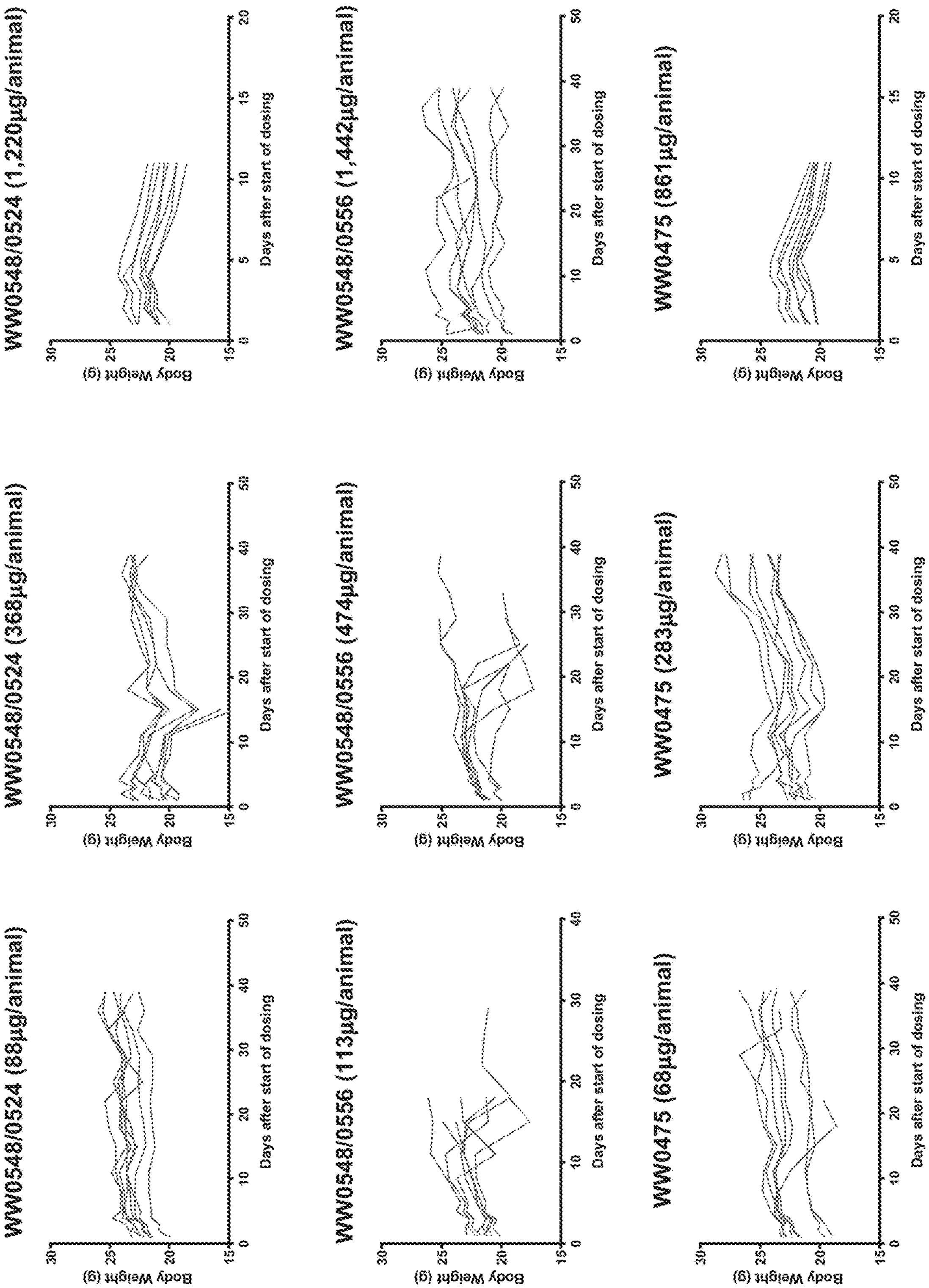
Figure 6C:
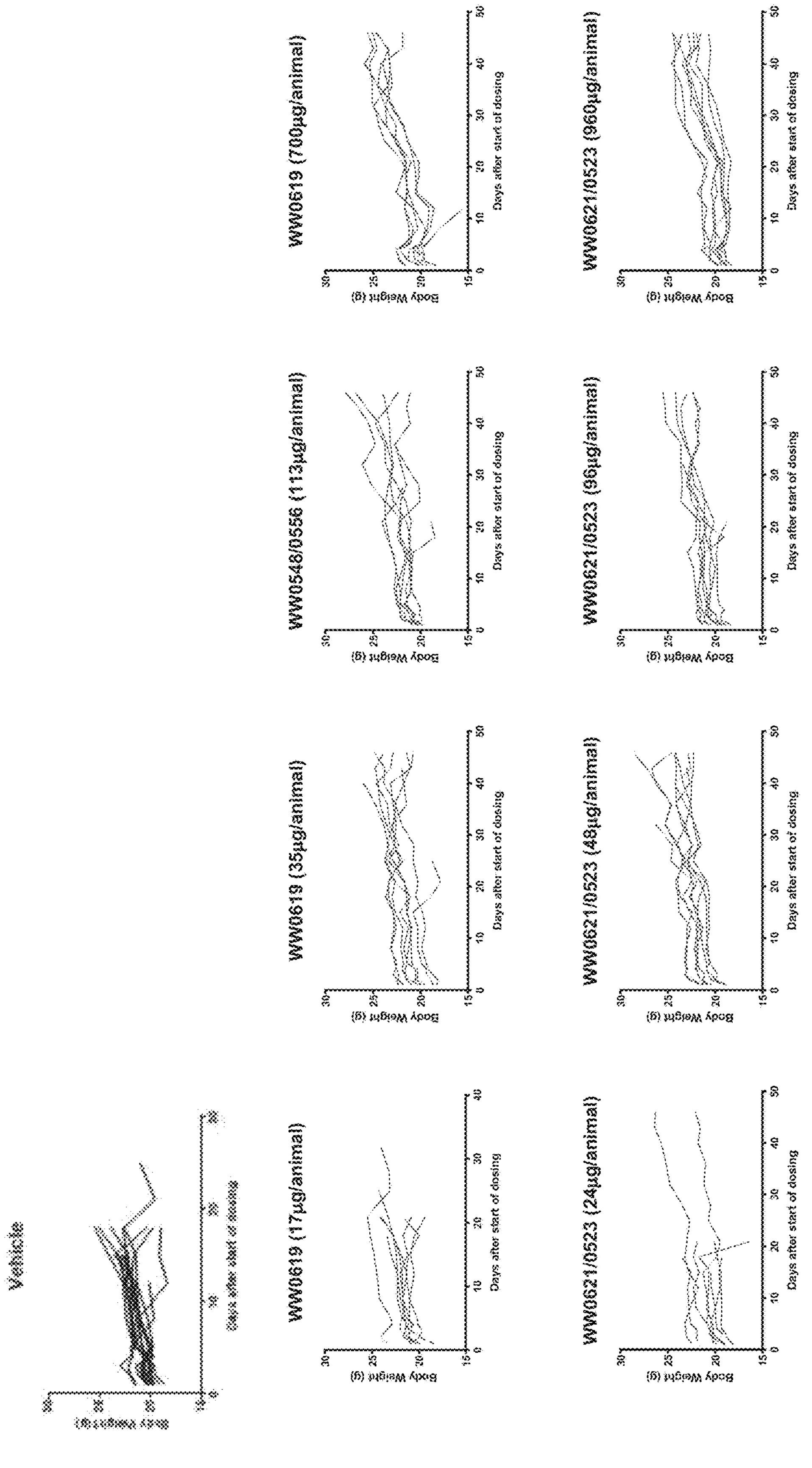
Figure 7A:
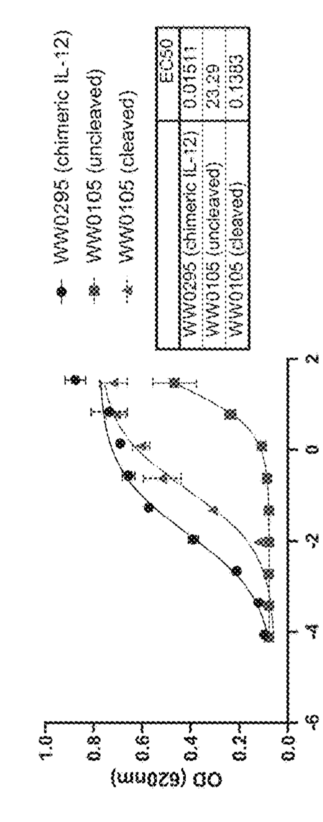
FIGS. 7A-7Q are a series of graphs showing activity of fusion proteins in an HEKBlue IL-12 reporter assay. FIGS.
Figure 7B:
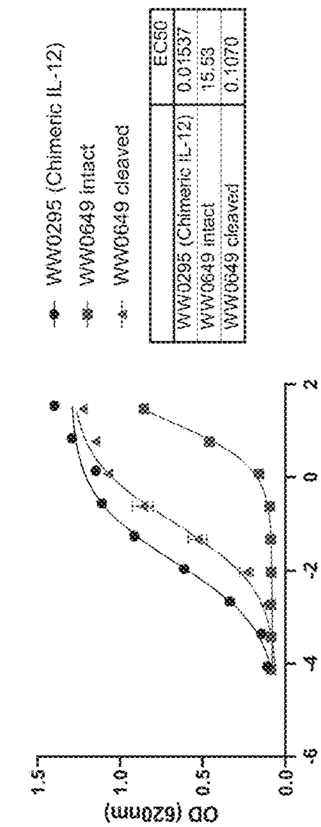
Figure 7C:
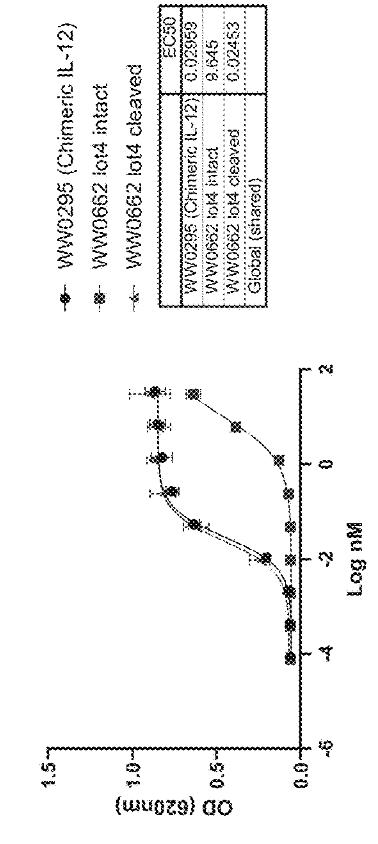
Figure 7D:
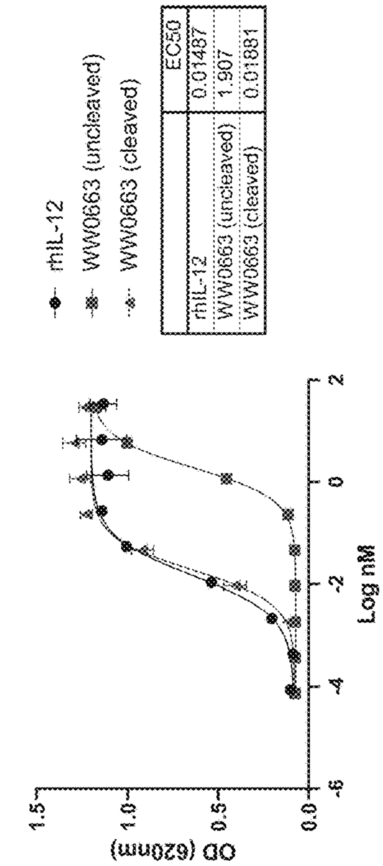
Figure 7F:
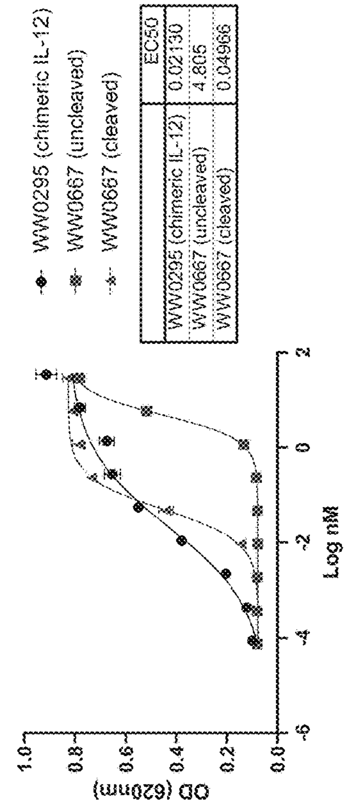
Figure 7E:
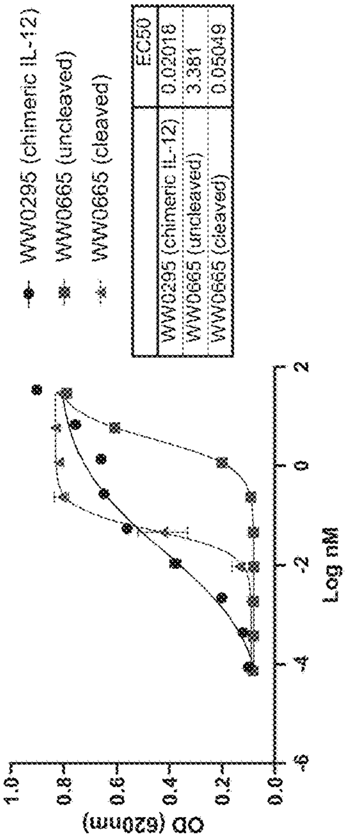
Figure 7G:
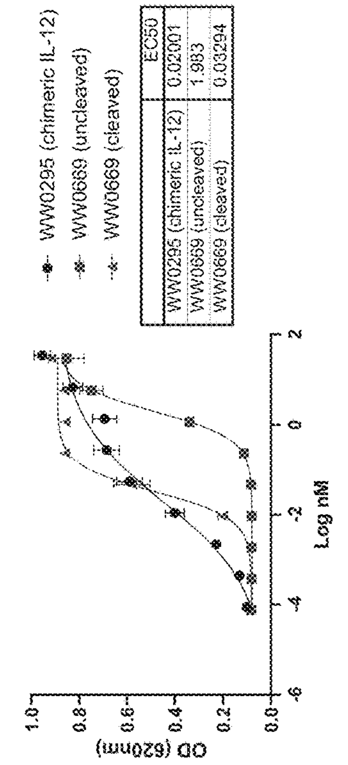
Figure 7H:
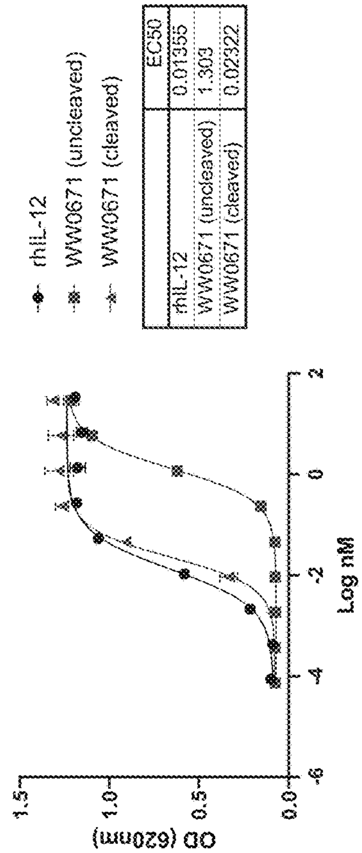
Figure 7I:
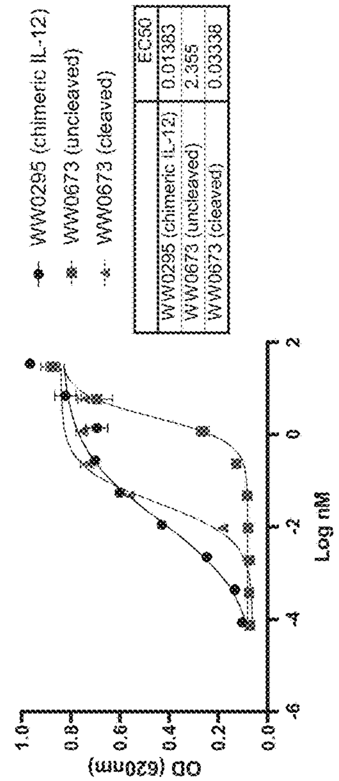
Figure 7J:
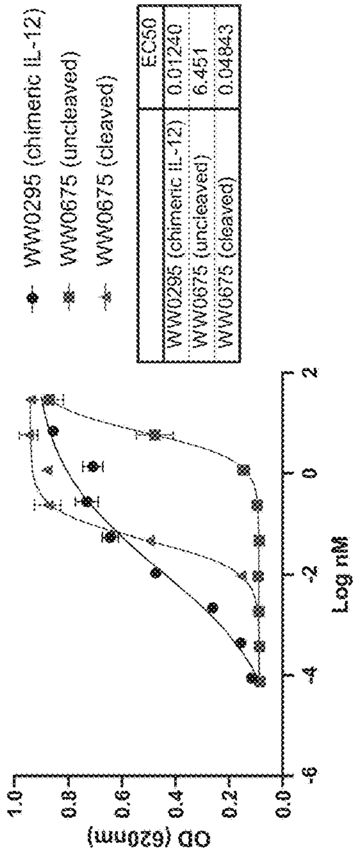
Figure 7K:
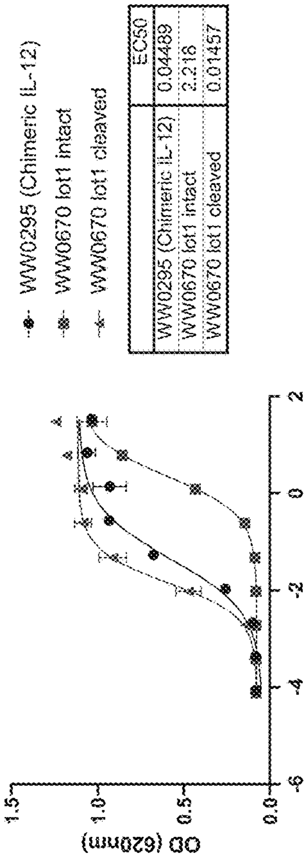
Figure 7L:
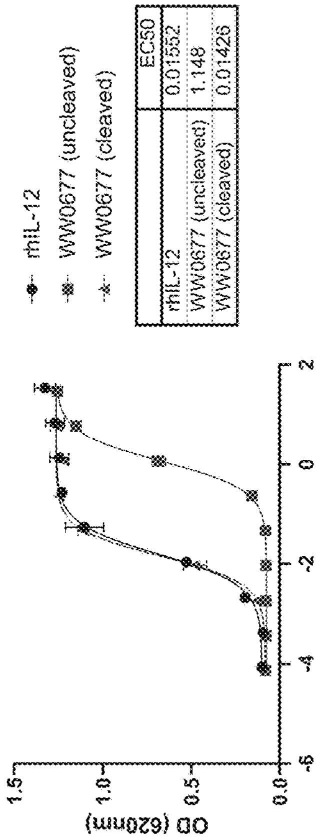
Figure 7M:
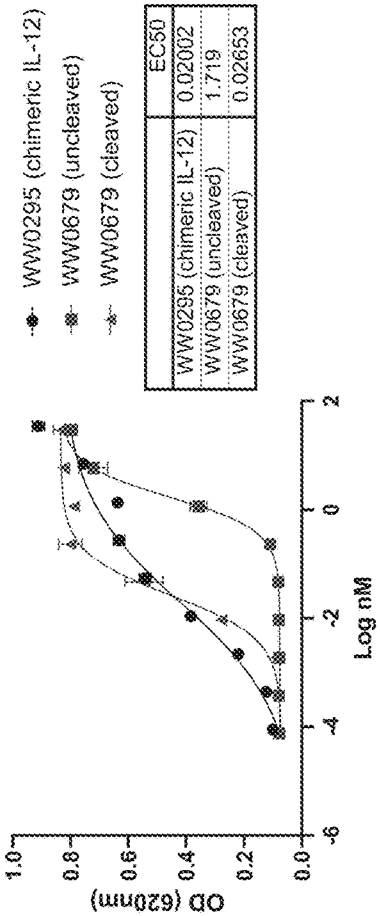
Figure 7N:
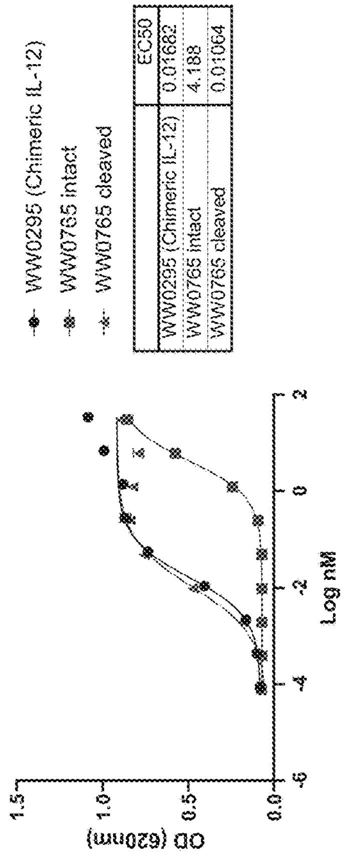
Figure 7O:
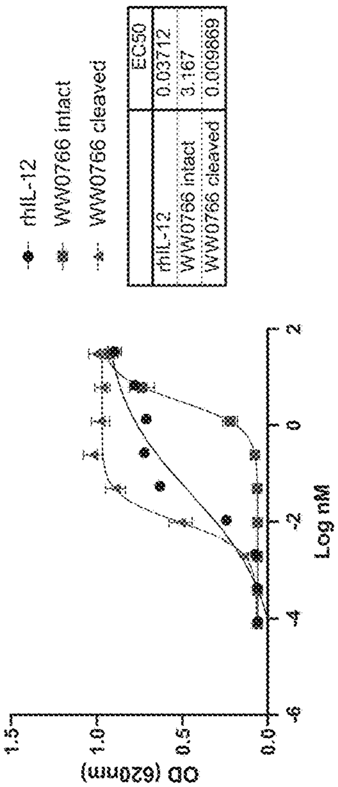
Figure 7P:
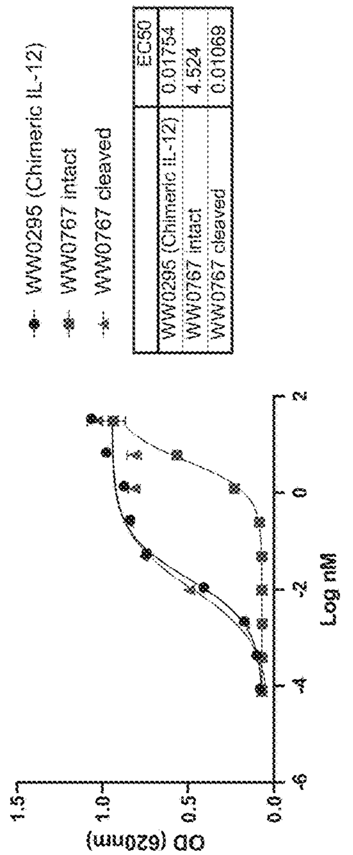
Figure 7Q:
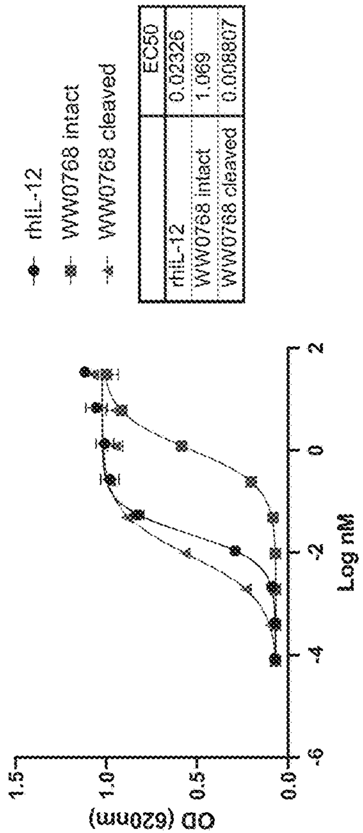
Figure 8A:
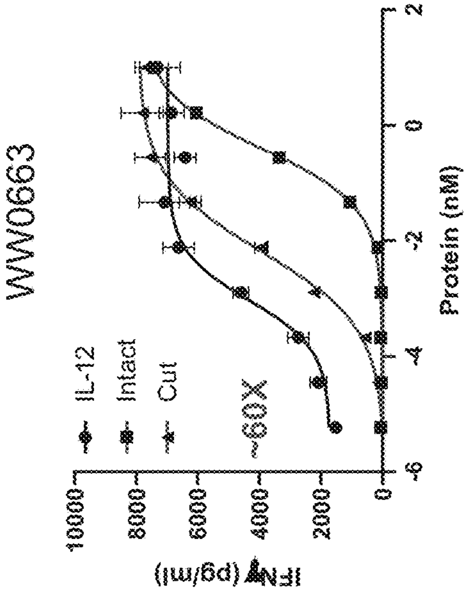
Figure 8B:
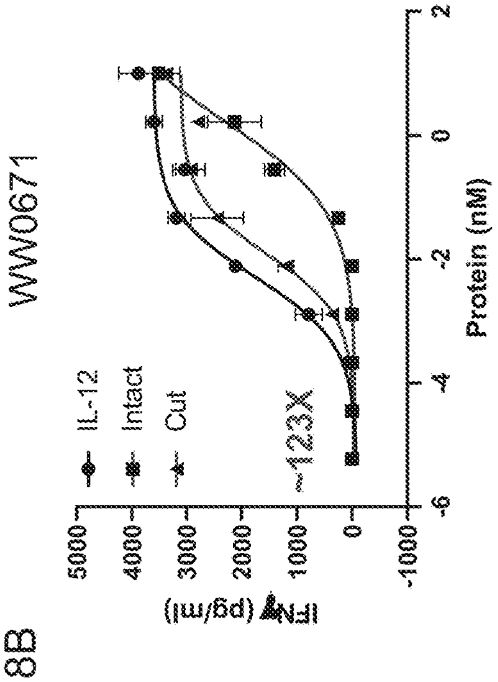
Figure 8C:
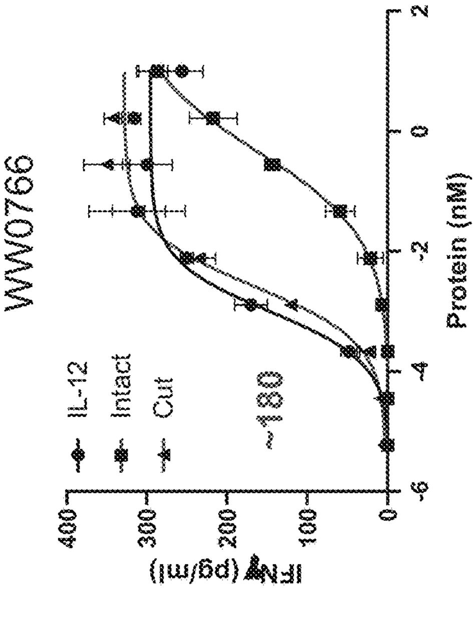
Figure 8D:
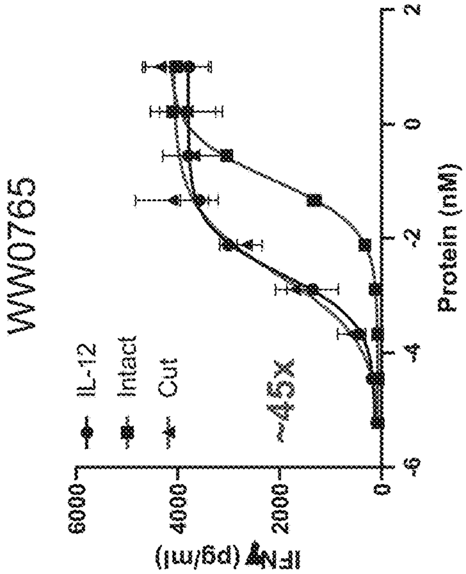

Procedures:

Mice were anaesthetized with isoflurane for implant of cells to reduce the ulcerations. 308 CR female C57BL/6 mice were set up with 5×10 MC38 tumor cells in 0% Matrigel sc in flank. Cell Injection Volume was 0.1 mL/mouse. Mouse age at start date was 8 to 12 weeks. Pair matches were performed when tumors reach an average size of 100-150 $mm^3$ and begin treatment. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized, and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 $mm^3$ or 45 days, whichever comes first. Responders were followed longer. When the endpoint was reached, the animals are to be euthanized. Results are shown in FIGS. 4-6.

Sample fusion protein constructs are detailed in Table 3. In table 3, "L" is an abbreviation of "linker", and "cleav. link." is an abbreviation of "cleavable linker". Other abbreviations "mIFNg" indicates mouse interferon gamma (IFNg); "hAlbumin" indicates human serum albumin (HSA); "mAlbumin" indicates mouse serum albumin.

Example 32. Human Interferon PBMC Assay

Human PBMCs were isolated form blood obtained from healthy donors. After isolation, PBMCs were cryopreserved until the assay was performed. For the assay, PBMCs were thawed and plated in suspension at 100,000 cells/well in X-Vivo media supplemented with 1.5% of human serum albumin. % well round bottom plates were used for the assay. Cells were stimulated with a dilution series of recombinant human IFNα and activatable human IFNα for 48 hours at 37° C. and 5% $CO_2$. Activity of uncleaved and cleaved activatable IFNα was tested. Cleaved inducible IFNα was generated by incubation with active recombinant protease. PBMC supernatants were collected and amounts of CXCL-10 (IP-10) produced were quantified using AlphaLISA as a measure of response. Results are shown in FIGS. 38A-38C.

TABLE 3

| CONSTRUCT PERMUTATION TABLE ("6xHis" disclosed as SEQ ID NO: 354) | |
|---|---|
| Construct Name | Construct Description |
| ACP01 | (anti-HSA)-(cleav. link.)-mouse IFNg-(cleav. link.)-(anti-HSA)-6xHis |
| ACP02 | (anti-HSA)-(cleav. link.)-mouse IFNg-(cleav. link.)-mouse IFNg-(cleav. link.)-(anti-HSA)-6xHis |
| ACP03 | (anti-HSA)-(cleav. link.)-mouse IFNg-mouse IFNg-(cleav. link.)-(anti-HSA)-6xHis |
| ACP50 | (anti-EpCAM)-(anti-HSA)-(cleav. link.)-mouse IFNg-mouse IFNg-(cleav. link.)-(anti-HSA)-6xHis |
| ACP51 | (anti-EpCAM)-Linker-(anti-HSA)-(cleav. link.)-mIFNg-(cleav. link.)-(anti-HSA)-6xHis |
| ACP52 | (anti-HSA)-(cleav. link.)-mIFNg-(cleav. link.)-(anti-HSA)-Linker-(anti-EpCAM)-6xHis |
| ACP53 | mAlbumin-(cleav. link.)-mIFNg-(cleav. link.)-mAlbumin-6xHis |
| ACP54 | mAlbumin-(cleav. link.)-mIFNg-Linker-mIFNg-(cleav. link.)-mAlbumin-6xHis |
| ACP30 | (anti-HSA)-(cleav. link.)-mouse IFNg-(cleav. link.)-(anti-HSA)-(cleav. link.)-mouse IFNg-(cleav. link.)-(anti-HSA)-6xHis |
| ACP55 | (anti-HSA)-(cleav. link.)-mouse IFNg-(cleav. link.)-(anti-HSA)-(cleav. link.)-mouse IFNg-(cleav. link.)-(anti-HSA)-6xHis-C-tag |
| ACP56 | (anti-FOLR1)-Linker-(anti-HSA)-(cleav. link.)-mIFNg-(cleav. link.)-(anti-HSA)-6xHis |
| ACP57 | (anti-HSA)-(cleav. link.)-mIFNg-(cleav. link.)-(anti-HSA)-Linker-(anti-FOLR1)-6xHis |
| ACP58 | (anti-HSA)-(cleav. link.)-mIFNg-(cleav. link.)-mIFNg-(cleav. link.)-(anti-HSA)-Linker-(anti-EpCAM)-6xHis |
| ACP59 | (anti-FOLR1)-Linker-(anti-HSA)-(cleav. link.)-mIFNg-(cleav. link.)-mIFNg-(cleav. link.)-(anti-HSA)-6xHis |
| ACP60 | (anti-HSA)-(cleav. link.)-mIFNg-(cleav. link.)-mIFNg-(cleav. link.)-(anti-HSA)-Linker-(anti-FOLR1)-6xHis |
| ACP61 | (anti-HSA)-(cleav. link.)-mIFNg-(cleav. link.)-mIFNg-(cleav. link.)-(anti-HSA)-Linker-FN(CGS-2)-6xHis |
| ACP63 | anti-FN CGS-2 scFv (Vh/Vl)-6xHis |
| ACP69 | (anti-HSA)-(cleav. link.)-mouse IFNg-(cleav. link.)-(anti-HSA)-(cleav. link.)-mouse IFNg |
| ACP70 | mouse IFNg-(cleav. link.)-(anti-HSA)-(cleav. link.)-mouse IFNg-(cleav. link.)-(anti-HSA) |
| ACP71 | mouse IFNg-(cleav. link.)-mAlbumin-(cleav. link.)-mouse IFNg-(cleav. link.)-mAlbumin |
| ACP72 | mAlbumin-(cleav. link.)-mouse IFNg-(cleav. link.)-mAlbumin-(cleav. link.)-mouse IFNg |

TABLE 3-continued

CONSTRUCT PERMUTATION TABLE ("6xHis" disclosed as SEQ ID NO: 354)

| Construct Name | Construct Description |
| --- | --- |
| ACP73 | mAlbumin-(cleav. link.)-mouse IFNg-(cleav. link.)-mAlbumin-(cleav. link.)-mouse IFNg-(cleav. link.)-mAlbumin |
| ACP74 | mAlbumin-(cleav. link.)-mouse IFNg-(cleav. link.)-5mer linker-mAlbumin-5mer linker-(cleav. link.)-mouse IFNg-(cleav. link.)-mAlbumin |
| ACP75 | mAlbumin-(cleav. link.)-mouse IFNg-(cleav. link.)-10mer linker-mAlbumin-10mer linker-(cleav. link.)-mouse IFNg-(cleav. link.)-mAlbumin |
| ACP78 | (anti-HSA)-Linker-mouse__IFNg-Linker-(anti-HSA)-Linker-mouse__IFNg-Linker-(anti-HSA)__(non-cleavable__control) |
| ACP134 | Anti-HSA-(cleav. link.)-mouse__IFNg-(cleav. link.)-anti-HSA-(cleav. link.)-mouse__IFNg-(cleav. link.)-anti-HSA-L-anti-FOLR1 |
| ACP135 | Anti-FOLR1-L-HSA-(cleav. link.)-mouse__IFNg-(cleav. link.)-HSA-(cleav. link.)-mouse__IFNg-(cleav. link.)-HSA |
| ACP04 | human p40-murine p35-6xHis |
| ACP05 | human p40-human p35-6xHis |
| ACP34 | mouse p35-(cleav. link.)-mouse p40-6xHis |
| ACP35 | mouse p35-GS-(cleav. link.)-GS-mouse p40-6xHis |
| ACP36 | (anti-HSA)-(Cleav. Linker)-mouse p40-mouse p35-(Cleav. Linker)-(anti-HSA)-6xHis |
| ACP37 | (anti-EpCAM)-(anti-HSA)-(Cleav. Linker)-mouse p40-mouse p35-(Cleav. Linker)-(anti-HSA)-6xHis |
| ACP79 | (anti-EpCAM)-Linker-(anti-HSA)-(cleav. link.)-mIL12-(cleav. link.)-(Anti-HSA)-6xHis |
| ACP80 | (anti-HSA)-(cleav. link.)-mIL12-(cleav. link.)-(anti-HSA)-Linker-(anti-EpCAM)-6xHis |
| ACP06 | Blocker12-Linker-(cleav. link.)-human p40-Linker-mouse p35-(cleav. link.)-(anti-HSA)-6xHis |
| ACP07 | Blocker12-Linker-(cleav. link.)-human p40-Linker-mouse p35-(cleav. link.)-(anti-HSA)-Linker-(anti-FOLR1)-6xHis |
| ACP08 | (anti-FOLR1)-Linker-Blocker12-Linker-(cleav. link.)-human p40-Linker-mouse p35-(cleav. link.)-(anti-HSA)-6xHis |
| ACP09 | (anti-HSA)-Linker-Blocker12-Linker-(cleav. link.)-human p40-Linker-mouse p35-6xHis |
| ACP10 | (anti-HSA)-(cleav. link.)-human p40-L-mouse p35-(cleav. link.)-Linker-Blocker12-6xHis |
| ACP11 | Human__p40-Linker-mouse__p35-(cleav. link.)-Linker-Blocker12-Linker-(anti-HSA)-6xHis |
| ACP91 | human__p40-Linker-mouse__p35-Linker-Linker-Blocker-Linker-(anti-HSA)__(non-cleavable__control) |
| ACP136 | human p40-L-mouse p35-(cleav. link.)-Blocker |
| ACP138 | human__p40-L-mouse__p35-(cleav. link.)-Blocker-L-(anti-HSA)-L-FOLR1 |
| ACP139 | Anti-FOLR1-L-human__p40-L-mouse__p35-(cleav. link.)-Blocker12-L-(anti-HSA) |
| ACP140 | Anti-FOLR1-(cleav. link.)-human__p40-L-mouse__p35-(cleav. link.)-Blocker12-L-(anti-HSA) |
| ACP12 | (anti-EpCAM)-IL2-(cleav. link.)-(anti-HSA)-blocker2-6xHis |
| ACP13 | (anti-EpCAM)-Blocker2-(anti-HSA)-(cleav. link.)-IL2-6xHis |
| ACP14 (WW0045) | Blocker2-Linker-(cleav. link.)-IL2- (cleav. link.)-(anti-HSA)-6xHis |
| ACP15 (WW0047) | Blocker2-Linker-(anti-HSA)-Linker-(cleav. link.)- IL2 -6xHis |
| ACP16 (WW0048) | IL2-(cleav. link.)-(anti-HSA)-Linker-(cleav. link.)-Blocker2-6xHis |
| ACP17 | (anti-EpCAM)-Linker-IL2-(cleav. link.)-(anti-HSA)-Linker-(cleav. link.)-Blocker2-6xHis |
| ACP18 | (anti-EpCAM)-Linker-IL2-(cleav. link.)-(anti-HSA)-Linker-vh(cleav. link.)vl-6xHis |
| ACP19 | IL2-(cleav. link.)-Linker-Blocker2-Linker-(anti-HSA)-Linker-(anti-EpCAM) -6xHis |
| ACP20 (WW0056) | IL2-(cleav. link.)-Blocker2-6xHis |
| ACP21 (WW0057) | IL2-(cleav. link.)-Linker-Blocker2-6xHis |
| ACP22 | IL2-(cleav. link.)-Linker-blocker-(cleav. link.)-(anti-HSA)-Linker-(anti-EpCAM)-6xHis |
| ACP23 | (anti-FOLR1)-(cleav. link.)-Blocker2-Linker-(cleav. link.)-(anti-HSA)-(cleav. link.)- IL2-6xHis |
| ACP24 (WW0074) | (Blocker2)-(cleav. link.)-(IL2)-6xHis |
| ACP25 (WW0075) | Blocker2-Linker-(cleav. link.)-IL2-6xHis |
| ACP26 | (anti-EpCAM)-Linker-IL2-(cleav. link.)-(anti-HSA)-Linker-blocker(NARA1 Vh/Vl) |
| ACP27 | (anti-EpCAM)-Linker-IL2-(cleav. link.)-(anti-HSA)-Linker-blocker(NARA1 Vl/Vh) |
| ACP28 | IL2-(cleav. link.)-Linker-Blocker2-(NARA1 Vh/Vl)-Linker-(anti-HSA)-Linker-(anti-EpCAM) |
| ACP29 | IL2-(cleav. link.)-Linker-Blocker2-(NARA1 Vl/Vh)-Linker-(anti-HSA)-Linker-(anti-EpCAM) |
| ACP38 | IL2-(cleav. link.)-blocker-(anti-HSA)-(anti-EpCAM)-6xHis |
| ACP39 | (anti-EpCAM)-(cleav. link.)-(anti-HSA)-(cleav. link.)-Blocker2-(cleav. link.)-IL-2-6xHis |
| ACP40 (WW0076) | CD25ecd-Linker-(cleav. link.)-IL2-6xHis |
| ACP41 (WW0077) | IL2-(cleav. link.)-Linker-CD25ecd-6xHis |
| ACP42 (WW0078) | (anti-HSA)-Linker-CD25ecd-Linker-(cleav. link.)-IL2-6xHis |
| ACP43 (WW0079) | IL2-(cleav. link.)-Linker-CD25ecd-Linker-(anti-HSA)-6xHis |
| ACP44 (WW0080) | IL2-(cleav. link.)-Linker-CD25ecd-(cleav. link.)-(anti-HSA)-6xHis |
| ACP45 (WW0046) | (anti-HSA)-(cleav. link.)-Blocker2-Linker-(cleav. link.)-IL2-6xHis |
| ACP46 | IL2-(cleav. link.)-linkerL-vh(cleav. link.)vl-Linker-(anti-HSA)-L-(anti-EpCAM)-6xHis |

TABLE 3-continued

CONSTRUCT PERMUTATION TABLE ("6xHis" disclosed as SEQ ID NO: 354)

| Construct Name | Construct Description |
|---|---|
| ACP47 | (anti-EpCAM)-Linker-IL2-(Cleavable Linker)-(anti-HSA)-Linker-Blocker2-6xHis |
| ACP48 (WW0054) | IL2-(cleav. link.)-Blocker2-Linker-(anti-HSA)-6xHis |
| ACP49 (WW0055) | IL2-(cleav. link.)-Linker-Blocker2-Linker-(anti-HSA)-6xHis |
| ACP92 | (anti-HSA)-(16mer Cleav. Link.)-IL2-(16mer Cleav. Link.)-(anti-HSA)-6XHis |
| ACP93 | (anti-EpCAM)-(anti-HSA)-(anti-EpCAM)-Blocker2-(cleav. link.)-IL2-6xHis |
| ACP94 | (anti-EpCAM)-(anti-HSA)-Blocker2-(cleav. link.)-IL2-6xHis |
| ACP95 | (anti-EpCAM)-(anti-HSA)-(cleav. link.)-IL2-6xHis |
| ACP96 | (anti-EpCAM)-(16mer cleav. link.)-IL2-(16mer cleav. link.)-(anti-HSA) |
| ACP97 | (anti-EpCAM)-(anti-HSA)-(cleav. link.)-IL2-(cleav. link.)-(anti-HSA)-6xHis |
| ACP99 | (anti-EpCAM)-Linker-IL2-(cleav. link.)-(anti-HSA)-6xHis |
| ACP100 | (anti-EpCAM)-Linker-IL2-6xHis |
| ACP101 (WW0061) | IL2-(cleav. link.)-(anti-HSA)-6xHis |
| ACP102 | (anti-EpCAM)-(cleav. link.)-IL2-(cleav. link.)-(anti-HSA)-Linker-blocker-6xHis |
| ACP103 | IL2-(cleav. link.)-Linker-Blocker2-Linker-(anti-HSA)-Linker-(antiI-FOLR1)-6xHis |
| ACP104 | (anti-FOLR1)-IL2-(cleav. link.)-(anti-HSA)-Linker-Blocker2-6xHis |
| ACP105 | Blocker2-Linker-(cleav. link.)-IL2-(cleav. link.)-(anti-HSA)-Linker-(anti-FOLR1)-6xHis |
| ACP106 | (anti-FOLR1)-Linker-(anti-HSA)-(cleav. link.)-blocker-Linker-(cleav. link.)-IL2 -6xHis |
| ACP107 | Blocker2-Linker-(anti-HSA)-(cleav. link.)-IL2-Linker-(anti-FOLR1)-6xHis |
| ACP108 | (anti-EpCAM)-IL2-(Dually cleav. link.)-(anti-HSA)-Linker-blocker-6xHis |
| ACP117 | anti-FN CGS-2 scFv (Vh/Vl)-6xHis |
| ACP118 | NARA1 Vh/Vl non-cleavable |
| ACP119 | NARA1 Vh/Vl cleavable |
| ACP120 | NARA1 Vl/Vh non-cleavable |
| ACP121 | NARA1 Vl/Vh cleavable |
| ACP124 (WW0159) | IL2-Linker-(anti-HSA)-Linker-Linker-blocker__(non-cleavable__control) |
| ACP132 (WW0177) | IL2-L-HSA |
| ACP141 (WW0178) | IL2-L-human__Albumin |
| ACP142 (WW0179) | IL2-(cleav. link.)-human__Albumin |
| ACP144 | IL2-(cleav. link.)-HSA-(cleav.-link.)blocker-L-(anti-FOLR1) |
| ACP145 | Anti-FOLR1-L-IL2-(cleav. link.)-HSA-Linker-(cleav. link.)-blocker2 |
| ACP146 | Anti-FOLR1-(cleav. link)-IL2-(cleav. link.)-HSA-Linker-(cleav. link.)-blocker2 |
| ACP133 (WW0196) | IL2-6x His |
| ACP147 | IL2-(cleav. Linker)-(anti-HSA)-Linker-(cleav. link.)-blocker2-L-(anti-EpCAM) |
| ACP148 | (anti-EpCAM)-L-IL2-(cleav. link.)-(anti-HSA)-L-(cleav. Linker)-blocker2 |
| ACP149 | (anti-EpCAM)-(cleav. link.)-IL2-(cleav. Linker)-(anti-HSA)-L-(cleav. Linker)-blocker2 |
| ACP31 | (anti-HSA)-(cleav. link.)-mIFNa1-(cleav. link.)-(anti-HSA) |
| ACP32 | (anti-HSA)-(cleav. link.)-mIFNa1(N + C trunc)-(cleav. link.)-(anti-HSA) |
| ACP33 | (anti-HSA)-(cleav. link.)-mIFNa1(C trunc)-(cleav. link.)-(anti-HSA) |
| ACP131 | mIFNa1 |
| ACP125 | Anti-HSA-(cleav. link.)-mIFNa1 |
| ACP126 | mIFNa1-(cleav. link.)-(anti-HSA) |
| ACP127 | Mouse__Albumin-(cleav. Link.)-mIFNa1-(cleav link)-mouse__Albumin |
| ACP128 | Mouse__Albumin-(cleav. link.)-mIFNa1 |
| ACP129 | mIFNa1-(cleav. link.)-mAlb |
| ACP150 | (Anti-FOLR1)-L-(anti-HSA)-(cleav. Link.)-mIFNa1-(cleav. Link.)-(anti-HSA) |
| ACP151 | Anti-FOLR1-L-(anti-HSA)-(cleav. Link.)-mIFNa1-(cleav. Link.)-(anti-HSA)-L-(anti-FOLR1) |
| ACP152 | (anti-HSA)-L-mIFNa1-L-(anti-HSA)__(non-cleavable__control) |
| ACP153 (WW0201) | IL2-(cleav. link.)-(anti-HSA)-linker(cleav. link.)-blocker2 |
| ACP154 (WW0202) | IL2-(cleav. link.)-(anti-HSA)-linker(cleav. link.)-blocker2 |
| ACP155 (WW0203) | IL2-(cleav. link.)-(anti-HSA)-linker(cleav. link.)-blocker2 |
| ACP156 (WW0204) | IL2-X-anti-HSA-LX-blocker__(X = Linker4__Blocker = Vh-Vl) |
| ACP157 (WW0205) | IL2-X-anti-HSA-LX-blocker__(X = Linker5__Blocker = Vh-Vl) |
| ACP200 | mAlb(D3)-X-mouse-IFNa-X-mAlb(D3)__(X = Linker 1) |
| ACP201 | mAlb(D1-L-D3)-X-mouse-IFNa-X-mAlb(D1-L-D3)__(X = Linker 1) |
| ACP202 | HSA-X-mIFNa1-X-HSA__(X = Linker 1 + 17aa) |
| ACP203 | HSA-X-mIFNa1-X-HSA__(X = Linker 2) |
| ACP204 | HSA-X-mIFNa1-X-HSA__(X = Linker 3) |
| ACP205 | HSA-X-mIFNa1-X-HSA__(X = Linker 4) |
| ACP206 | HSA-X-Human__IFNA2b-X-HSA__(X = Linker 2) |
| ACP207 | HSA-X-Human__IFNA2b-X-HSA__(X = Linker 3) |
| ACP208 | HSA-X-Human__IFNA2b-X-HSA__(X = Linker 4) |
| ACP211 | HSA-X-mouse-IFNg-X-IFNa-X-mouse-IFNg-X-HSA__(X = Linker 1) |

TABLE 3-continued

CONSTRUCT PERMUTATION TABLE ("6xHis" disclosed as SEQ ID NO: 354)

| Construct Name | Construct Description |
|---|---|
| ACP213 | mAlb(D3)-X-mouse-IFNg-X-mAlb(D3)-X-mouse-IFNg-X-mAlb(D3)__(X = Linker 1) |
| ACP214 | mAlb(D1-L-D3)-X-mouse-IFNg-X-mAlb(D1-L-D3)-X-mouse-IFNg-X-mAlb(D1-L-D3)__(X = Linker 1) |
| ACP215 | HSA-X-mouse-IFNg-X-HSA-X-mouse-IFNg-X-HSA__(X = Linker 1 + 17aa) |
| ACP240 | HSA-L-human__p40-L-mouse__p35-LL-Blocker__(non-cleavable; Blocker = Vl/Vh) |
| ACP241 | mAlb-X-human__p40-L-mouse__p35-XL-Blocker__(X = Linker 1; Blocker = Vl/Vh) |
| ACP242 | human__p40-L-mouse__p35-XL-Blocker-X-mAlb__(X = Linker 1; Blocker = Vl/Vh) |
| ACP243 | mIgG1__Fc-X-human__p40-L-mouse__p35-XL-Blocker__(X = Linker 1; Blocker = Vl/Vh) |
| ACP244 | human__p40-L-mouse__p35-XL-Blocker-X-mIgG1__Fc__(X = Linker 1; Blocker = Vl/Vh) |
| ACP245 | HSA-X-human__p40-L-mouse__p35-XL-Blocker(cleavable)__(X = Linker 1; Blocker = Vl-X-Vh) |
| ACP247 | HSA-X-human__p40-L-mouse__p35-XL-Blocker__(Blocker = 3CYT5; X = Linker 1) |
| ACP284 | HSA-X-mouse__p35-XL-Blocker__(Blocker = Vl/Vh; X = Linker 1) |
| ACP285 | HSA-X-human__p40__C199S-L-mouse__p35__C92S-XL-Blocker__(Blocker = __Vl/Vh; X = Linker 1) |
| ACP286 | HSA-X-human p40-L(4xG4S (SEQ ID NO: 453))-mouse p35-XL-Blocker__(Blocker = Vl/Vh; X = Linker 1) |
| ACP287 | HSA-X-human__p40__mouse__p35-XL-Blocker__(Blocker = Vl/Vh__VH44-VL100 disulfide; X = Linker 1) |
| ACP288 | HSA-X-human__p40__mouse__p35-XL-Blocker__(Blocker = Vl/Vh__VH105-VL43__disulfide; X = Linker 1) |
| ACP289 (WW0233) | Geneart__WW0048__IL2-X-HSA-LX-blocker__Fusion__protein-6xHis |
| ACP290 (WW0234) | IL2-X-HSA-LX-blocker__(X = Linker 1; Blocker = 3TOW69) |
| ACP291 (WW0235) | IL2-X-HSA-LX-blocker__(X = Linker 1; Blocker = 3TOW85) |
| ACP292 (WW0236) | IL2-X-HSA-LX-blocker__(X = Linker 1; Blocker = 2TOW91) |
| ACP296 (WW0250) | IL2-X-HSA-LX-blocker(cleavable)__(X = Linker 1; Blocker = Vh-X-Vl) |
| ACP297 (WW0251) | IL2-X-HSA-LX-blocker(A46L)__(X = Linker 1; Blocker = Vh/Vl) |
| ACP298 (WW0252) | IL2-X-HSA-LX-blocker(A46G)__(X = Linker 1; Blocker = Vh/Vl) |
| ACP299 (WW0253) | IL2(Cys145Ser)-X-HSA-LX-blocker__(X = Linker 1; Blocker = Vh/Vl) |
| ACP300 (WW0255) | IL2-X-hAlb-LX-blocker__(X = Linker 1; Blocker = Vh/Vl) |
| ACP302 (WW0296) | IL2-X-mAlb-LX-blocker__(X = Linker 1; Blocker = Vh/Vl) |
| ACP303 | mAlb-X-IL2(Nterm-41)-X-mALB__(X = Linker 1) |
| ACP304 (WW0302) | IL2-X-HSA-LX-blocker-XL-CD25ecd__(X = Linker 1; Blocker = Vh/Vl) |
| ACP305 (WW0303) | CD25ecd-LX-IL2-X-HSA-LX-blocker__(X = Linker 1; Blocker = Vh/Vl) |
| ACP306 (WW0304) | IL2-XL-CD25ecd-X-HSA-LX-blocker__(X = Linker 1; Blocker = Vh/Vl) |
| ACP309 (WW0307) | IL2-X-HSA-LX-blocker(A46S)__(X = Linker 1; Blocker = Vh/Vl) |
| ACP310 (WW0308) | IL2-X-HSA-LX-blocker(QAPRL__FR2)__(X = Linker 1; Blocker = Vh/Vl) |
| ACP311 (WW0316) | IL2-X-IgG4__Fc(S228P)-LX-Blocker__(X = Linker 1; Blocker = Vh/Vl) |
| ACP312 (WW0317) | IgG4__Fc(S228P)-X-IL2-LX-Blocker__(X = Linker 1; Blocker = Vh/Vl) |
| ACP313 (WW0318) | IL2-XL-Blocker-X-IgG4__Fc(S228P)__(X = Linker 1; Blocker = Vh/Vl) |
| ACP314 (WW0354) | mIgG1__Fc-X-IL2-LX-Blocker__(X = Linker 1; Blocker = Vh/Vl) |
| ACP336 (WW0414) | IL2-X-anti-HSA-LX-blocker__(Blocker = VHVL.F2.high.A02__Vh-X-Vl__A46S; X = Linker 2) |
| ACP337 (WW0415) | IL2-X-anti-HSA-LX-blocker__(Blocker = VHVL.F2.high.A02__Vh/Vl__A46S; X = Linker 2) |
| ACP338 (WW0416) | IL2-X-anti-HSA-LX-blocker__(Blocker = VHVL.F2.high.F03__Vh-X-Vl; X = Linker 2) |
| ACP339 (WW0417) | IL2-X-anti-HSA-LX-blocker__(Blocker = VHVL.F2.high.F03__Vh/Vl; X = Linker 2) |
| ACP340 (WW0418) | IL2-X-anti-HSA-LX-blocker__(Blocker = Hu2TOW91__B; X = Linker 2) |
| ACP341 (WW0419) | IL2-X-anti-HSA-LX-blocker__(Blocker = Hu3TOW85__A; X = Linker 2) |
| ACP342 (WW0420) | CD25ecd__C213S-LX-IL2-X-anti-HSA-LX-blocker__(Blocker = VHVL.F2.high.A02__Vh-X-Vl__A46S; X = Linker 2) |
| ACP343 (WW0421) | CD25ecd__C213S-LX-IL2-X-anti-HSA-LX-blocker__(Blocker = VHVL.F2.high.A02__Vh/Vl__A46S; X = Linker 2) |
| ACP344 | CD25ecd__C213S-LX-IL2-X-anti-HSA-LX-blocker__(Blocker = VHVL.F2.high.F03__Vh-X- |

TABLE 3-continued

| CONSTRUCT PERMUTATION TABLE ("6xHis" disclosed as SEQ ID NO: 354) | |
|---|---|
| Construct Name | Construct Description |
| (WW0422) | Vl; X = Linker 2) |
| ACP345 (WW0423) | CD25ecd__C213S-LX-IL2-X-anti-HSA-LX-blocker__(Blocker = VHVL.F2.high.F03__Vh/Vl; X = Linker 2) |
| ACP346 (WW0424) | CD25ecd__C213S-LX-IL2-X-anti-HSA-LX-blocker__(Blocker = Hu2TOW91__B; X = Linker 2) |
| ACP347 (WW0425) | CD25ecd__C213S-LX-IL2-X-anti-HSA-LX-blocker__(Blocker = Hu3TOW85__A; X = Linker 2) |
| ACP348 (WW0426) | IgG4__Fc(S228P)-X-IL2-LX-Blocker__(Blocker = VHVL.F2.high.A02__Vh-X-Vl__A46S; X = Linker 2) |
| ACP349 (WW0427) | IgG4__Fc(S228P)-X-IL2-LX-Blocker__(Blocker = VHVL.F2.high.A02__Vh\Vl__A46S; X = Linker 2) |
| ACP350 (WW0428) | IgG4__Fc(S228P)-X-IL2-LX-Blocker__(Blocker = VHVL.F2.high.F03__Vh-X-Vl; X = Linker 2) |
| ACP351 (WW0429) | IgG4__Fc(S228P)-X-IL2-LX-Blocker__(Blocker = VHVL.F2.high.F03__Vh\Vl; X = Linker 2) |
| ACP352 (WW0430) | IgG4__Fc(S228P)-X-IL2-LX-Blocker__(Blocker = Hu2TOW91__B; X = Linker 2) |
| ACP353 (WW0431) | IgG4__Fc(S228P)-X-IL2-LX-Blocker__(Blocker = Hu3TOW85__A; X = Linker 2) |
| ACP354 (WW0432) | IgG4__Fc(S228P)-X-CD25ecd__C213S-LX-IL2-LX-Blocker__(Blocker = VHVL.F2.high.A02__Vh-X-Vl__A46S; X = Linker 2) |
| ACP355 (WW0433) | IgG4__Fc(S228P)-X-CD25ecd__C213S-LX-IL2-LX-Blocker__(Blocker = VHVL.F2.high.A02__Vh\Vl__A46S; X = Linker 2) |
| ACP356 (WW0434) | IgG4__Fc(S228P)-X-CD25ecd__C213S-LX-IL2-LX-Blocker__(Blocker = VHVL.F2.high.F03__Vh-X-Vl; X = Linker 2) |
| ACP357 (WW0435) | IgG4__Fc(S228P)-X-CD25ecd__C213S-LX-IL2-LX-Blocker__(Blocker = VHVL.F2.high.F03__Vh\Vl; X = Linker 2) |
| ACP358 (WW0436) | IgG4__Fc(S228P)-X-CD25ecd__C213S-LX-IL2-LX-Blocker__(Blocker = Hu2TOW91__B; X = Linker 2) |
| ACP359 (WW0437) | IgG4__Fc(S228P)-X-CD25ecd__C213S-LX-IL2-LX-Blocker__(Blocker = Hu3TOW85__A; X = Linker 2) |
| ACP371 (WW0513) | IL2-X-anti-HSA-LX-blocker__(Blocker = Vh/Vl__VH44-VL100__disulfide; X = Linker 2) |
| ACP372 (WW0514) | IL2-X-anti-HSA-LX-blocker__(Blocker = Vh/Vl__VH105-VL43__disulfide; X = Linker 2) |
| ACP373 (WW0515) | IL2-X-anti-HSA-LX-blocker__(Blocker = VHVL.F2.high.A02__Vh/Vl__VH44-VL100__disulfide; X = Linker 2) |
| ACP374 (WW0516) | IL2-X-anti-HSA-LX-blocker__(Blocker = VHVL.F2.high.A02__Vh/Vl__VH105-VL43__disulfide; X = Linker 2) |
| ACP375 (WW0517) | IL2-X-anti-HSA-LX-blocker__(Blocker = VHVL.F2.high.F03__Vh/Vl__VH44-VL100__disulfide; X = Linker 2) |
| ACP376 (WW0521) | IL2-X-anti-HSA-LX-blocker__(Blocker = VHVL.F2.high.F03__Vh/Vl__VH105-VL43__disulfide X = Linker 2) |
| ACP377 (WW0519) | IL2-X-anti-HSA-LX-blocker__(Blocker = Hu2TOW91__A; X = Linker 2) |
| ACP378 (WW0520) | IL2-X-anti-HSA-LX-Heavy__blocker__Fab__(Blocker = VH-CH1; X = Linker 2) |
| ACP379 (WW0521) | IgG4__Fc(S228P)-X-IL2-LX-Heavy__blocker__Fab__(Blocker = VH-CH1; X = Linker 2) |
| ACP383 (WW0525) | IgG4__Fc(S228P)-X-IL2-LX-blocker__(Blocker = Vh/Vl__VH44-VL100__disulfide; X = LINKER 2) |
| ACP38 (WW05264) | IgG4__Fc(S228P)-X-IL2-LX-blocker__(Blocker = Vh/Vl__VH105-VL43__disulfide; X = MMP14-1) |
| ACP385 (WW0527) | IgG4__Fc(S228P)-X-IL2-LX-blocker__(Blocker = VHVL.F2.high.A02__Vh/Vl__VH44-VL100__disulfide; X = LINKER 2) |
| ACP386 (WW0528) | IgG4__Fc(S228P)-X-IL2-LX-blocker__(Blocker = VHVL.F2.high.A02__Vh/Vl__VH105-VL43__disulfide; X = Linker 2) |
| ACP387 (WW0529) | IgG4__Fc(S228P)-X-IL2-LX-blocker__(Blocker = VHVL.F2.high.F03__Vh/Vl__VH44-VL100__disulfide; X = Linker 2) |
| ACP388 (WW0530) | IgG4__Fc(S228P)-X-IL2-LX-blocker__(Blocker = VHVL.F2.high.F03__Vh/Vl__VH105-VL43__disulfide; X = Linker 2) |
| ACP389 (WW0531) | IgG4__Fc(S228P)-X-IL2-LX-blocker__(Blocker = Hu2TOW91__A; X = Linker 2) |
| ACP390 (WW0532) | IL2-X-anti-HSA-LX-blocker__(Blocker = VHVL.F2.high.A02__Vh/Vl__A46S__VH44-VL100__disulfide; X = Linker 2) |
| ACP391 (WW0533) | IgG4__Fc(S228P)-X-IL2-LX-blocker__(Blocker = VHVL.F2.high.A02__Vh/Vl__A46S__VH44-VL100__disulfide; X = Linker 2) |
| ACP392 (WW0534) | IL2-XL-CD25ecd__C213S-X-HSA-LX-blocker__(Blocker = VHVL.F2.high.A02__Vh__G44C__Vl__A46S__G100C; X = Linker 2) |
| ACP393 (WW0535) | IL2-XL-CD25ecd__C213S-X-HSA-LX-blocker__(Blocker = VHVL.F2.high.A02__Vh__Q105C__Vl__A43C; X = Linker 2) |
| ACP394 (WW0536) | IL2-XL-CD25ecd__C213S-X-HSA-LX-blocker__(Blocker = VHVL.F2.high.F03__Vh__G44C__Vl__G100C; X = Linker 2) |
| ACP395 (WW0537) | IL2-XL-CD25ecd__C213S-X-HSA-LX-blocker__(Blocker = VHVL.F2.high.F03__Vh__Q105C__Vl__A43C; X = Linker 2) |

TABLE 3-continued

| CONSTRUCT PERMUTATION TABLE (“6xHis” disclosed as SEQ ID NO: 354) | |
|---|---|
| Construct Name | Construct Description |
| ACP396 (WW0538) | IL2-XL-CD25ecd__C213S-X-HSA-LX-blocker__(Blocker = Hu2TOW91__A; X = Linker 2) |
| ACP397 (WW0539) | IL2-XL-CD25ecd__C213S-X-HSA-LX-blocker__(Blocker = Hu2TOW91__B; X = Linker 2) |
| ACP398 (WW0540) | IL2-XL-CD25ecd__C213S-X-HSA-LX-Heavy__blocker__Fab__(Blocker = VH-CH1; X = Linker 2) |
| ACP399 | Blocker-XL-HSA-X-IL2(Nterm-41)-X-HSA__(Blocker = VHVL.F2.high.A02__Vh__G44C__Vl__A46S__G100C; X = Linker 2) |
| ACP400 | Blocker-XL-HSA-X-IL2(Nterm-41)-X-HSA__(Blocker = VHVL.F2.high.A02__Vh__Q105C__Vl__A43C; X = Linker 2) |
| ACP401 | Blocker-XL-HSA-X-IL2(Nterm-41)-X-HSA__(Blocker = VHVL.F2.high.F03__Vh__G44C__Vl__G100C; X = Linker 2) |
| ACP402 | Blocker-XL-HSA-X-IL2(Nterm-41)-X-HSA__(Blocker = VHVL.F2.high.F03__Vh__Q105C__Vl__A43C; X = Linker 2) |
| ACP403 | Blocker-XL-HSA-X-IL2(Nterm-41)-X-HSA__(Blocker = Hu2TOW91__A; X = Linker 2) |
| ACP404 | Blocker-XL-HSA-X-IL2(Nterm-41)-X-HSA__(Blocker = Hu2TOW91__B; X = Linker 2) |
| ACP405 | Heavy__Blocker__Fab-XL-HSA-X-IL2(Ntenn-41)-X-HSA__(Blocker = VH-CH1; X = Linker 2) |
| ACP406 (WW0548) | mIgG1__Fc(S228P)-X-IL2-LX-Heavy__blocker__Fab__(Blocker = VH-CH1; X = Linker 2) |
| ACP407 (WW0549) | mIgG1__Fc(S228P)-X-IL2-LX-blocker__(Blocker = VHVL.F2.high.A02__Vh/Vl__VH44-VL100__disulfide; X = Linker 2) |
| ACP408 (WW0550) | mIgG1__Fc(S228P)-X-IL2-LX-blocker__(Blocker = VHVL.F2.high.A02__Vh/Vl__A46S__VH44-VL100__disulfide; X = Linker 2) |
| ACP409 (WW0551) | mIgG1__Fc(S228P)-X-IL2-LX-blocker__(Blocker = VHVL.F2.high.A02__Vh/Vl__VH105-VL43__disulfidel; X = Linker 2) |
| ACP410 (WW0552) | mIgG1__Fc(S228P)-X-IL2-LX-blocker__(Blocker = VHVL.F2.high.F03__Vh/Vl__VH44-VL100__disulfidel; X = Linker 2) |
| ACP411 (WW0553) | mIgG1__Fc(S228P)-X-IL2-LX-blocker__(Blocker = VHVL.F2.high.F03__Vh/Vl__VH105-VL43__disulfidel; X = Linker 2) |
| ACP412 (WW0554) | mIgG1__Fc(S228P)-X-IL2-LX-blocker__(Blocker = Hu2TOW91__A; X = Linker 2) |
| ACP413 (WW0555) | CD25__213S-L-Kappa__blocker__Fab__(Blocker = VHVL.F2.high.A02__A46S__Kappa) |
| ACP414 (WW0556) | CD25__213S-L-Kappa__blocker__Fab__(Blocker = VHVL.F2.high.F03__Kappa) |
| ACP415 (WW0557) | IL2-XL-blocker-L-CD25__213S-X-HSA__Blocker = VHVL.F2.high.A02__Vh__G44C__Vl__A46S__G100C; X = Linker 2) |
| ACP416 (WW0558) | IL2-XL-blocker-L-CD25__213S-X-HSA__(Blocker = VHVL.F2.high.A02__Vh__Q105C__Vl__A43C; X = Linker 2) |
| ACP417 (WW0559) | IL2-XL-blocker-L-CD25__213S-X-HSA__(Blocker = VHVL.F2.high.F03__Vh__G44C__Vl__G100C; X = Linker 2) |
| ACP418 (WW0560) | IL2-XL-blocker-L-CD25__213S-X-HSA__(Blocker = VHVL.F2.high.F03__Vh__Q105C__Vl__A43C; X = Linker 2) |
| ACP419 (WW0561) | IL2-XL-blocker-L-CD25__213S-X-HSA__(Blocker = Hu2TOW91__A; X = Linker 2) |
| ACP420 (WW0562) | IL2-XL-blocker-L-CD25__213S-X-HSA__(Blocker = Hu2TOW91__B; X = Linker 2) |
| ACP421 (WW0563) | HSA-X-blocker-L-CD25__213S-LX-IL2__(Blocker = VHVL.F2.high.A02__Vh__G44C__Vl__A46S__G100C; X = Linker 2) |
| ACP422 (WW0564) | HSA-X-blocker-L-CD25__213S-LX-IL2__(Blocker = VHVL.F2.high.A02__Vh__Q105C__Vl__A43C; X = Linker 2) |
| ACP423 (WW0565) | HSA-X-blocker-L-CD25__213S-LX-IL2__(Blocker = VHVL.F2.high.F03__Vh__G44C__Vl__G100C; X = Linker 2) |
| ACP424 (WW0566) | HSA-X-blocker-L-CD25__213S-LX-IL2__(Blocker = VHVL.F2.high.F03__Vh__Q105C__Vl__A43C; X = Linker 2) |
| ACP425 (WW0567) | HSA-X-blocker-L-CD25__213S-LX-IL2__(Blocker = Hu2TOW91__A; X = Linker 2) |
| ACP426 (WW0568) | HSA-X-blocker-L-CD25__213S-LX-IL2__(Blocker = Hu2TOW91__B; X = Linker 2) |
| ACP427 (WW0569) | IL2-X-anti-HSA-LX-Blocker1-L-Blocker2__(Blocker1 = VHVL.F2.high.A02__Vh__G44C__Vl__A46S__G100C, Blocker2 = Hu2TOW91__A; X = Linker 2) |
| ACP428 (WW0570) | IL2-X-anti-HSA-LX-Blocker1-L-Blocker2__(Blocker1 = VHVL.F2.high.A02__Vh__Q105C__Vl__A43C, Blocker2 = Hu2TOW91__A; X = Linker 2) |
| ACP429 (WW0571) | IL2-X-anti-HSA-LX-Blocker1-L-Blocker2__(Blocker1 = VHVL.F2.high.F03__Vh__G44C__Vl__G100C, Blocker2 = Hu2TOW91__A; X = Linker 2) |
| ACP430 (WW0572) | IL2-X-anti-HSA-LX-Blocker1-L-Blocker2__(Blocker1 = VHVL.F2.high.F03__Vh__Q105C__Vl__A43C, Blocker2 = Hu2TOW91__A; X = Linker 2) |
| ACP431 (WW0573) | IL2-X-anti-HSA-LX-Blocker1-L-Blocker2__(Blocker1 = VHVL.F2.high.A02__Vh__G44C__Vl__A46S__G100C, Blocker2 = Hu2TOW91__B; X = Linker 2) |
| ACP432 | IL2-X-anti-HSA-LX-Blocker1-L- |

TABLE 3-continued

CONSTRUCT PERMUTATION TABLE ("6xHis" disclosed as SEQ ID NO: 354)

| Construct Name | Construct Description |
|---|---|
| (WW0574) | Blocker2__(Blocker1 = VHVL.F2.high.A02__Vh__Q105C__Vl__A43C, Blocker2 = Hu2TOW91__B; X = Linker 2) |
| ACP433 (WW0575) | IL2-X-anti-HSA-LX-Blocker1-L-Blocker2__(Blocker1 = VHVL.F2.high.F03__Vh__G44C__Vl__G100C, Blocker2 = Hu2TOW91__B; X = Linker 2) |
| ACP434 (WW0576) | IL2-X-anti-HSA-LX-Blocker1-L-Blocker2__(Blocker1 = VHVL.F2.high.F03__Vh__Q105C__Vl__A43C, Blocker2 = Hu2TOW91__B; X = Linker 2) |
| ACP439 (WW0581) | IL2-X-anti-HSA-LX-blocker__(Blocker = VHVL.F2.high.C07__Vh/Vl; X = Linker 2) |
| ACP440 (WW0582) | IL2-X-anti-HSA-LX-blocker__(Blocker = VHVL.F2.high.C07__Vh/Vl__A46S; X = Linker 2) |
| ACP441 (WW0583) | IL2-X-anti-HSA-LX-blocker__(Blocker = VHVL.F2.high.C07__Vh/Vl__A46L; X = Linker 2) |
| ACP442 (WW0584) | IL2-X-anti-HSA-LX-blocker__(Blocker = VHVL.F2.high.C07__Vh/Vl__A46S__VH44-VL100__disulfide; X = Linker 2) |
| ACP443 (WW0585) | IL2-X-anti-HSA-LX-blocker__(Blocker = VHVL.F2.high.C07__Vh/Vl__A46L__VH44-VL100__disulfide; X = Linker 2) |
| ACP444 (WW0586) | IL2-X-anti-HSA-LX-blocker__(Blocker = VHVL.F2.high.C07__Vh/Vl__VH105-VL43__disulfide; X = Linker 2) |
| ACP445 (WW0587) | IL2-X-anti-HSA-LX-blocker__(Blocker = VHVL.F2.high.A02__Vh-X-Vl__A46L; X = Linker 2) |
| ACP446 (WW0588) | IL2-X-anti-HSA-LX-blocker__(Blocker = VHVL.F2.high.A02__Vh/Vl__A46L; X = Linker 2) |
| ACP447 (WW0589) | IL2-X-anti-HSA-LX-blocker__(Blocker = VHVL.F2.high.A02__Vh/Vl__A46L__VH44-VL100__disulfide; X = Linker 2) |
| ACP451 (WW0615) | IL2-X-anti-HSA-LX-blocker__(Blocker = VHVL.F2.high.A02__Vh/Vl__A46S; X = Linker 3) |
| ACP452 (WW0616) | IL2-X-anti-HSA-LX-blocker__(Blocker = VHVL.F2.high.F03__Vh/Vl; X = Linker 3) |
| ACP453 (WW0617) | IL2-X-anti-HSA-LX-blocker__(Blocker = VHVL.F2.high.A02__Vh/Vl__A46S__VH44-VL100__disulfide; X = Linker 3) |
| ACP454 (WW0618) | IL2-X-anti-HSA-LX-blocker__(Blocker = VHVL.F2.high.A02__Vh/Vl__VH105-VL43__disulfidel; X = Linker 3) |
| ACP455 (WW0619) | IL2-X-anti-HSA-LX-blocker__(Blocker = VHVL.F2.high.F03__Vh/Vl__VH44-VL100__disulfide; X = Linker 3) |
| ACP456 (WW0620) | IL2-X-anti-HSA-LX-blocker__(Blocker = VHVL.F2.high.F03__Vh/Vl__VH105-VL43__disulfideX = Linker 3) |
| ACP457 (WW0621) | IL2-X-anti-HSA-LX-Heavy__blocker__Fab__(Blocker = VH-CH1; X = Linker 3) |
| ACP458 (WW0622) | IgG4__Fc(S228P)-X-IL2-LX-Heavy__blocker__Fab__(Blocker = VH-CH1; X = Linker 3) |
| ACP459 (WW0623) | IgG4__Fc(S228P)-X-IL2-LX-Blocker__(Blocker = VHVL.F2.high.A02__Vh\Vl__A46S; X = Linker 3) |
| ACP460 (WW0624) | IgG4__Fc(S228P)-X-IL2-LX-Blocker__(Blocker = VHVL.F2.high.F03__Vh\Vl; X = Linker 3) |
| ACP461 (WW0625) | IgG4__Fc(S228P)-X-IL2-LX-blocker__(Blocker = VHVL.F2.high.A02__Vh/Vl__A46S__VH44-VL100__disulfide; X = Linker 3) |
| ACP462 (WW0626) | IgG4__Fc(S228P)-X-IL2-LX-blocker__(Blocker = VHVL.F2.high.A02__Vh/Vl__VH105-VL43__disulfidel; X = Linker 3) |
| ACP463 (WW0627) | IgG4__Fc(S228P)-X-IL2-LX-blocker__(Blocker = VHVL.F2.high.F03__Vh/Vl__VH44-VL100__disulfidel; X = Linker 3) |
| ACP464 (WW0628) | IgG4__Fc(S228P)-X-IL2-LX-blocker__(Blocker = VHVL.F2.high.F03__Vh/Vl__VH105-VL43__disulfidel; X = Linker 3) |
| ACP465 (WW0629) | mIgG1__Fc-X-IL2-LX-Blocker__(Blocker = VHVL.F2.high.A02__Vh\Vl__A46S; X = Linker 3) |
| ACP466 (WW0630) | mIgG1__Fc-X-IL2-LX-Blocker__(Blocker = VHVL.F2.high.F03__Vh\Vl; X = Linker 3) |
| ACP467 (WW0631) | mIgG1__Fc-X-IL2-LX-blocker__(Blocker = VHVL.F2.high.A02__Vh/Vl__A46S__VH44-VL100__disulfide; X = Linker 3) |
| ACP468 (WW0632) | mIgG1__Fc-X-IL2-LX-blocker__(Blocker = VHVL.F2.high.A02__Vh/Vl__VH105-VL43__disulfidel; X = Linker 3) |
| ACP469 (WW0633) | mIgG1__Fc-X-IL2-LX-blocker__(Blocker = VHVL.F2.high.F03__Vh/Vl__VH44-VL100__disulfidel; X = Linker 3) |
| ACP470 (WW0634) | mIgG1__Fc-X-IL2-LX-blocker__(Blocker = VHVL.F2.high.F03__Vh/Vl__VH105-VL43__disulfidel; X = Linker 3) |
| ACP471 (WW0642) | mIgG1__Fc-X-IL2-LX-Heavy__blocker__Fab__(Blocker = VH-CH1; X = Linker 3) |
| WW0301 | IL2-X-anti-HSA-LL-blocker__(X = Linker1__Blocker = Vh-Vl) |
| WW0353 | IL2-X-mIgG1__Fc-LX-Blocker__(X = Linker1__Blocker = Vh-Vl) |
| WW0355 | IL2-XL-Blocker-X-mIgG1__Fc__(X = Linker1__Blocker = Vh-Vl) |
| WW0365 | IL-2-L-anti-HSA-LX-Blocker__(instead__of__WW0048__IL2-X-anti-HSA-LX-blocker)__(X = Linker1) |
| WW0366 | IL-2-X-anti-HSA__(GeneArt__version__of__WW0061)__(X = Linker1) |
| WW0472 | mIgG1__Fc-X-IL2-LX-Blocker__(Blocker = VHVL.F2.high.A02__Vh-X-Vl__A46S__X = Linker2) |

TABLE 3-continued

| CONSTRUCT PERMUTATION TABLE ("6xHis" disclosed as SEQ ID NO: 354) | |
|---|---|
| Construct Name | Construct Description |
| WW0473 | mIgG1__Fc-X-IL2-LX-Blocker__(Blocker = VHVL.F2.high.A02__Vh-Vl__A46S__X = Linker2) |
| WW0474 | mIgG1__Fc-X-IL2-LX-Blocker__(Blocker = VHVL.F2.high.F03__Vh-X-Vl__X = Linker2) |
| WW0475 | mIgG1__Fc-X-IL2-LX-Blocker__(Blocker = VHVL.F2.high.F03__Vh-Vl__X = Linker2) |
| WW0476 | mIgG1__Fc-X-IL2-LX-Blocker__(Blocker = Hu2TOW91__B__X = Linker2) |
| WW0477 | mIgG1__Fc-X-IL2-LX-Blocker__(Blocker = Hu3TOW85__A__X = Linker2) |
| WW0641 | anti-HSA-X-human__p40__mouse__p35-XL-Blocker__(Blocker = Vl/Vh__VH105-VL43__disulfide; X = Linker1) |
| WW0649 | anti-HSA-X-human__p40-L-mouse__p35-XL-Blocker__(Blocker = Vl/Vh__X = Linker2) |
| WW0650 | anti-HSA-X-human__p40-L-Human__p35-XL-Blocker__(Blocker = Vl/Vh__X = Linker2) |
| WW0651 | anti-HSA-X-human__p40-L-mouse__p35-XL-Blocker__(Blocker = Vl/Vh__X = Linker3) |
| WW0652 | anti-HSA-X-human__p40-L-Human__p35-XL-Blocker__(Blocker = Vl/Vh__X = Linker3) |
| WW0662 | anti-HSA-X-human__p40-L-mouse__p35-XL-Blocker__(Blocker = Opt1__Hv__D53E__D61E__Vl/Vh__X = Linker2) |
| WW0663 | anti-HSA-X-human__p40-L-human__p35-XL-Blocker__(Blocker = Opt1__Hv__D53E__D61E__Vl/Vh__X = Linker2) |
| WW0664 | anti-HSA-X-human__p40-L-mouse__p35-XL-Blocker__(Blocker = Opt2__Lv__N31E-Hv__D53E__D61E__Vl/Vh__X = Linker2) |
| WW0665 | anti-HSA-X-human__p40-L-human__p35-XL-Blocker__(Blocker = Opt2__Lv__N31E-Hv__D53E__D61E__Vl/Vh__X = Linker2) |
| WW0666 | anti-HSA-X-human__p40-L-mouse__p35-XL-Blocker__(Blocker = Opt3__LV__S30D-Hv__D53E__D61E__Vl/Vh__X = Linker2) |
| WW0667 | anti-HSA-X-human__p40-L-human__p35-XL-Blocker__(Blocker = Opt3__LV__S30D-Hv__D53E__D61E__Vl/Vh__X = Linker2) |
| WW0668 | anti-HSA-X-human__p40-L-mouse__p35-XL-Blocker__(Blocker = Opt4__LV__S30D__N31E__Vl/Vh__X = Linker2) |
| WW0669 | anti-HSA-X-human__p40-L-human__p35-XL-Blocker__(Blocker = Opt4__LV__S30D__N31E__Vl/Vh__X = Linker2) |
| WW0670 | anti-HSA-X-human__p40-L-mouse__p35-XL-Blocker__(Blocker = Opt5__Lv__S30D__N31E-Hv__D53E__D61E__Vl/Vh__X = Linker2) |
| WW0672 | anti-HSA-X-human__p40-L-mouse__p35-XL-Blocker__(Blocker = Opt6__Lv__R27E__T32D(LCharge__16(combo2))__Vl/Vh__X = Linker2) |
| WW0673 | anti-HSA-X-human__p40-L-human__p35-XL-Blocker__(Blocker = Opt6__Lv__R27E__T32D(LCharge__16(combo2))__Vl/Vh__X = Linker2) |
| WW0674 | anti-HSA-X-human__p40-L-mouse__p35-XL-Blocker__(Blocker = Opt7__Lv__S30E-Hv__D53E__D61E__Vl/Vh__X = Linker2) |
| WW0675 | anti-HSA-X-human__p40-L-human__p35-XL-Blocker__(Blocker = Opt7__Lv__S30E-Hv__D53E__D61E__Vl/Vh__X = Linker2) |
| WW0676 | anti-HSA-X-human__p40-L-mouse__p35-XL-Blocker__(Blocker = Opt8__Lv__S30E N31E__Vl/Vh__X = Linker2) |
| WW0677 | anti-HSA-X-human__p40-L-human__p35-XL-Blocker__(Blocker = Opt8__Lv__S30E N31E__Vl/Vh__X = Linker2) |
| WW0678 | anti-HSA-X-human__p40-L-mouse__p35-XL-Blocker__(Blocker = Opt9__Lv__N31E-Hv__D53E__Vl/Vh__X = Linker2) |
| WW0679 | anti-HSA-X-human__p40-L-human__p35-XL-Blocker__(Blocker = Opt9__Lv__N31E-Hv__D53E__Vl/Vh__X = Linker2) |
| WW0680 | anti-HSA-X-human__p40-L-mouse__p35-XL-Blocker__(Blocker = Opt1__Hv__D53E__D61E__Vl/Vh__X = Linker3 |
| WW0681 | anti-HSA-X-human__p40-L-human__p35-XL-Blocker__(Blocker = Opt1__Hv__D53E__D61E__Vl/Vh__X = Linker3) |
| WW0682 | anti-HSA-X-human__p40-L-mouse__p35-XL-Blocker__(Blocker = Opt2__Lv__N31E-Hv__D53E__D61E__Vl/Vh__X = Linker3 |
| WW0683 | anti-HSA-X-human__p40-L-human__p35-XL-Blocker__(Blocker = Opt2__Lv__N31E-Hv__D53E__D61E__Vl/Vh__X = Linker3) |
| WW0684 | anti-HSA-X-human__p40-L-mouse__p35-XL-Blocker__(Blocker = Opt3__LV__S30D-Hv__D53E__D61E__Vl/Vh__X = Linker3 |
| WW0685 | anti-HSA-X-human__p40-L-human__p35-XL-Blocker__(Blocker = Opt3__LV__S30D-Hv__D53E__D61E__Vl/Vh__X = Linker3) |
| WW0686 | anti-HSA-X-human__p40-L-mouse__p35-XL-Blocker__(Blocker = Opt4__LV__S30D__N31E__Vl/Vh__X = Linker3 |
| WW0687 | anti-HSA-X-human__p40-L-human__p35-XL-Blocker__(Blocker = Opt4__LV__S30D__N31E__Vl/Vh__X = Linker3) |
| WW0688 | anti-HSA-X-human__p40-L-mouse__p35-XL-Blocker__(Blocker = Opt5__Lv__S30D__N31E-Hv__D53E__D61E__Vl/Vh__X = Linker3 |
| WW0689 | anti-HSA-X-human__p40-L-human__p35-XL-Blocker__(Blocker = Opt5__Lv__S30D__N31E-Hv__D53E__D61E__Vl/Vh__X = Linker3) |
| WW0690 | anti-HSA-X-human__p40-L-mouse__p35-XL-Blocker__(Blocker = Opt6__Lv__R27E__T32D(LCharge__16(combo2))__Vl/Vh__X = Linker3 |
| WW0691 | anti-HSA-X-human__p40-L-human__p35-XL-Blocker__(Blocker = Opt6__Lv__R27E__T32D(LCharge__16(combo2))__Vl/Vh__X = Linker3) |
| WW0692 | anti-HSA-X-human__p40-L-mouse__p35-XL-Blocker__(Blocker = Opt7__Lv__S30E-Hv__D53E__D61E__Vl/Vh__X = Linker3 |
| WW0693 | anti-HSA-X-human__p40-L-human__p35-XL-Blocker__(Blocker = Opt7__Lv__S30E-Hv__D53E__D61E__Vl/Vh__X = Linker3) |
| WW0694 | anti-HSA-X-human__p40-L-mouse__p35-XL-Blocker__(Blocker = Opt8__Lv__S30E__N31E__Vl/Vh__X = Linker3 |

TABLE 3-continued

| CONSTRUCT PERMUTATION TABLE ("6xHis" disclosed as SEQ ID NO: 354) | |
|---|---|
| Construct Name | Construct Description |
| WW0695 | anti-HSA-X-human_p40-L-human_p35-XL-Blocker_(Blocker = Opt8_Lv_S30E_N31E_Vl/Vh_X = Linker3) |
| WW0698 | anti-HSA-X-human_p40-L-mouse_p35-XL-Fab_Lambda_Blocker_(Blocker = Lambda_Fab_IGLC2-01_X = Linker2) |
| WW0699 | anti-HSA-X-human_p40-L-human_p35-XL-Fab_Lambda_Blocker_(Blocker = Lambda_Fab_IGLC2-01_X = Linker2) |
| WW0700 | anti-HSA-X-human_p40-L-mouse_p35-XL-Fab_Lambda_Blocker_(Blocker = Lambda_Fab_N31E_IGLC2-01_X = Linker2) |
| WW0701 | anti-HSA-X-human_p40-L-human_p35-XL-Fab_Lambda_Blocker_(Blocker = Lambda_Fab_N31E_IGLC2-01_X = Linker2) |
| WW0702 | anti-HSA-X-human_p40-L-mouse_p35-XL-Fab_Lambda_Blocker_(Blocker = Lambda_Fab_S30D_IGLC2-01_X = Linker2) |
| WW0703 | anti-HSA-X-human_p40-L-human_p35-XL-Fab_Lambda_Blocker_(Blocker = Lambda_Fab_S30D_IGLC2-01_X = Linker2) |
| WW0704 | anti-HSA-X-human_p40-L-mouse_p35-XL-Fab_Lambda_Blocker_(Blocker = Lambda_Fab_S30D_N31E_IGLC2-01_X = Linker2) |
| WW0705 | anti-HSA-X-human_p40-L-human_p35-XL-Fab_Lambda_Blocker_(Blocker = Lambda_Fab_S30D_N31E_IGLC2-01_X = Linker2) |
| WW0706 | anti-HSA-X-human_p40-L-mouse_p35-XL-Fab_Lambda_Blocker_(Blocker = Lambda_Fab_R27E_T32D_IGLC2-01_X = Linker2) |
| WW0707 | anti-HSA-X-human_p40-L-human_p35-XL-Fab_Lambda_Blocker_(Blocker = Lambda_Fab_R27E_T32D_IGLC2-01_X = Linker2) |
| WW0708 | anti-HSA-X-human_p40-L-mouse_p35-XL-Fab_Lambda_Blocker_(Blocker = Lambda_Fab_S30E_IGLC2-01_X = Linker2) |
| WW0709 | anti-HSA-X-human_p40-L-human_p35-XL-Fab_Lambda_Blocker_(Blocker = Lambda_Fab_S30E_IGLC2-01_X = Linker2) |
| WW0710 | anti-HSA-X-human_p40-L-mouse_p35-XL-Fab_Lambda_Blocker_(Blocker = Lambda_Fab_S30E_N31E_IGLC2-01_X = Linker2) |
| WW0711 | anti-HSA-X-human_p40-L-human_p35-XL-Fab_Lambda_Blocker_(Blocker = Lambda_Fab_S30E_N31E_IGLC2-01_X = Linker2) |
| WW0712 | anti-HSA-X-human_p40-L-mouse_p35-XL-Fab_Lambda_Blocker_(Blocker = Lambda_Fab_IGLC2-01_X = Linker3) |
| WW0713 | anti-HSA-X-human_p40-L-human_p35-XL-Fab_Lambda_Blocker_(Blocker = Lambda_Fab_IGLC2-01_X = Linker3) |
| WW0714 | anti-HSA-X-human_p40-L-mouse_p35-XL-Fab_Lambda_Blocker_(Blocker = Lambda_Fab_N31E_IGLC2-01_X = Linker3) |
| WW0715 | anti-HSA-X-human_p40-L-human_p35-XL-Fab_Lambda_Blocker_(Blocker = Lambda_Fab_N31E_IGLC2-01_X = Linker3) |
| WW0716 | anti-HSA-X-human_p40-L-mouse_p35-XL-Fab_Lambda_Blocker_(Blocker = Lambda_Fab_S30D_IGLC2-01_X = Linker3) |
| WW0717 | anti-HSA-X-human_p40-L-human_p35-XL-Fab_Lambda_Blocker_(Blocker = Lambda_Fab_S30D_IGLC2-01_X = Linker3) |
| WW0718 | anti-HSA-X-human_p40-L-mouse_p35-XL-Fab_Lambda_Blocker_(Blocker = Lambda_Fab_S30D_N31E_IGLC2-01_X = Linker3) |
| WW0719 | anti-HSA-X-human_p40-L-human_p35-XL-Fab_Lambda_Blocker_(Blocker = Lambda_Fab_S30D_N31E_IGLC2-01_X = Linker3) |
| WW0720 | anti-HSA-X-human_p40-L-mouse_p35-XL-Fab_Lambda_Blocker_(Blocker = Lambda_Fab_R27E_T32D_IGLC2-01_X = Linker3) |
| WW0721 | anti-HSA-X-human_p40-L-human_p35-XL-Fab_Lambda_Blocker_(Blocker = Lambda_Fab_R27E_T32D_IGLC2-01_X = Linker3) |
| WW0722 | anti-HSA-X-human_p40-L-mouse_p35-XL-Fab_Lambda_Blocker_(Blocker = Lambda_Fab_S30E_IGLC2-01_X = Linker3) |
| WW0723 | anti-HSA-X-human_p40-L-human_p35-XL-Fab_Lambda_Blocker_(Blocker = Lambda_Fab_S30E_IGLC2-01_X = Linker3) |
| WW0724 | anti-HSA-X-human_p40-L-mouse_p35-XL-Fab_Lambda_Blocker_(Blocker = Lambda_Fab_S30E_N31E_IGLC2-01_X = Linker3) |
| WW0725 | anti-HSA-X-human_p40-L-human_p35-XL-Fab_Lambda_Blocker_(Blocker = Lambda_Fab_S30E_N31E_IGLC2-01_X = Linker3) |
| WW0726 | Fab_Heavy_Blocker_(Blocker = IL-12_Heavy_Fab_IgG1_Fab) |
| WW0727 | Fab_Heavy_Blocker_(Blocker = IL-12_Heavy_Fab_D53E_D61E_IgG1_Fab) |
| WW0728 | Fab_Heavy_Blocker_(Blocker = IL-12_Heavy_Fab_D53E_IgG1_Fab) |
| WW0765 | human_p40-L-mouse_p35-X-anti-HSA-L-Blocker_(Blocker = Opt1_Hv_D53E_D61E_Vl/Vh_X = Linker2) |
| WW0766 | human_p40-L-human_p35-X-anti-HSA-L-Blocker_(Blocker = Opt1_Hv_D53E_D61E_Vl/Vh_X = Linker2) |
| WW0767 | human_p40-L-mouse_p35-X-anti-HSA-L-Blocker_(Blocker = Opt5_Lv_S30D_N31E-Hv_D53E_D61E_Vl/Vh_X = Linker2) |
| WW0768 | human_p40-L-human_p35-X-anti-HSA-L-Blocker_(Blocker = Opt5_Lv_S30D_N31E-Hv_D53E_D61E_Vl/Vh_X = Linker2) |
| WW0769 | human_p40-L-mouse_p35-X-anti-HSA-L-Fab_Lambda_Blocker_(Blocker = Lambda_Fab_IGLC2-01_X = Linker2) |
| WW0770 | human_p40-L-human_p35-X-anti-HSA-L-Fab_Lambda_Blocker_(Blocker = Lambda_Fab_IGLC2-01_X = Linker2) |
| WW0771 | human_p40-L-mouse_p35-X-anti-HSA-L-Fab_Lambda_Blocker_(Blocker = Lambda_Fab_S30D_N31E_IGLC2-01_X = Linker2) |

TABLE 3-continued

| CONSTRUCT PERMUTATION TABLE ("6xHis" disclosed as SEQ ID NO: 354) | |
|---|---|
| Construct Name | Construct Description |
| WW0772 | human__p40-L-human__p35-X-anti-HSA-L-Fab__Lambda__Blocker__(Blocker = Lambda__Fab__S30D__N31E__IGLC2-01__X = Linker2) |
| WW0796 | human__p40-L-mouse__p35-X-anti-HSA-L-Blocker__(Blocker = Opt1__Hv__D53E__D61E__Vl-Vh__X = Linker3) |
| WW0797 | human__p40-L-human__p35-X-anti-HSA-L-Blocker__(Blocker = Opt1__Hv__D53E__D61E__Vl-Vh__X = Linker3) |
| WW0798 | human__p40-L-mouse__p35-X-anti-HSA-L-Blocker__(Blocker = Opt5__Lv__S30D__N31E-Hv__D53E__D61E__Vl-Vh__X = Linker3) |
| WW0799 | human__p40-L-human__p35-X-anti-HSA-L-Blocker__(Blocker = Opt5__Lv__S30D__N31E-Hv__D53E__D61E__Vl-Vh__X = Linker3) |
| WW0800 | human__p40-L-mouse__p35-X-anti-HSA-L-Fab__Lambda__Blocker__(Blocker = Lambda__Fab__IGLC2-01__X = Linker3) |
| WW0801 | human__p40-L-human__p35-X-anti-HSA-L-Fab__Lambda__Blocker__(Blocker = Lambda__Fab__IGLC2-01__X = Linker3) |
| WW0802 | human__p40-L-mouse__p35-X-anti-HSA-L-Fab__Lambda__Blocker__(Blocker = Lambda__Fab__S30D__N31E__IGLC2-01__X = Linker3) |
| WW0803 | human__p40-L-human__p35-X-anti-HSA-L-Fab__Lambda__Blocker__(Blocker = Lambda__Fab__S30D__N31E__IGLC2-01__X = Linker3) |
| WW0643 | HSA-X-mIFNa11-X-HSA__(X = Linker2) |
| WW0644 | HSA-X-mIFNa11-X-HSA__(X = Linker3) |
| WW0645 | HSA-X-Human__IFNA14-X-HSA__(X = Linker2) |
| WW0646 | HSA-X-Human__IFNA14-X-HSA__(X = Linker3) |
| WW0647 | Mouse__IFNA11 |
| WW0648 | Human__IFNA14 |
| WW0781 | HSA-X-Human__IFNA2b__T129E-X-HSA__(X = Linker2) |
| WW0782 | HSA-X-Human__IFNA14__N95D-X-HSA__(X = Linker2) |
| WW0783 | HSA-X-Human__IFNA14__N25D__S27P__N95D-X-HSA__(X = Linker2) |
| WW0784 | Human__IFNA2b__T129E |
| WW0785 | Human__IFNA14__N95D |
| WW0786 | Human__IFNA14__N25D__S27P__N95D |
| WW0815 | mAlb-X-mIFNa1-X-mAlb__(X = Linker3) |
| WW0816 | mAlb-X-mIFNa11-X-mAlb__(X = Linker3) |
| WW0817 | anti-HSA-X-mIFNa1-X-mAlb__(X = Linker3) |
| WW0818 | anti-HSA-X-mIFNa11-mAlb__(X = Linker3) |
| WW0819 | mAlb-X-mIFNa1-X-anti-HSA__(X = Linker3) |
| WW0820 | mAlb-X-mIFNa11-anti-HSA__(X = Linker3) |
| WW0821 | Alb-X-Human__IFNA2b-X-Alb__(X = Linker3) |
| WW0822 | Alb-X-Human__IFNA14-X-Alb__(X = Linker3) |
| WW0831 | Alb-X-IFNa8-X-Alb__(X = Linker3) |
| WW0832 | Alb-X-IFNa16-Alb__(X = Linker3) |
| WW0833 | Anti-HSA-X-IFNa8-X-anti-HSA__(X = Linker3) |
| WW0834 | Anti-HSA-X-IFNa16-X-anti-HSA__(X = Linker3) |
| WW0737 | HSA-X-mIFNb-X-HSA__(X = Linker2) |
| WW0738 | HSA-X-mIFNb-X-HSA__(X = Linker3) |
| WW0739 | HSA-X-mIFNb__C38S-X-HSA__(X = Linker2) |
| WW0740 | HSA-X-mIFNb__C38S-X-HSA__(X = Linker3) |
| WW0741 | HSA-X-Human__IFNB-X-HSA__(X = Linker2) |
| WW0742 | HSA-X-Human__IFNB-X-HSA__(X = Linker3) |
| WW0743 | HSA-X-Human__IFNB__C38S-X-HSA__(X = Linker2) |
| WW0744 | HSA-X-Human__IFNB__C38S-X-HSA__(X = Linker3) |
| WW0745 | Mouse__IFNb |
| WW0746 | Mouse__IFNb__C38S |
| WW0747 | Human__IFNB |
| WW0748 | Human__IFNAB__C38S |
| WW0787 | HSA-X-Human__IFNB__N101Q-X-HSA__(X = Linker2) |
| WW0788 | HSA-X-Human__IFNB__N101Q__C38S-X-HSA__(X = Linker2) |
| WW0789 | Human__IFNB__N101Q |
| WW0790 | Human__IFNB__C38S__N101Q |
| WW0729 | IL2-L-anti-HSA-LL-Heavy__blocker__Fab__(Blocker = VH-CH1__non-cleavable) |
| WW0734 | IL2-X-anti-HSA-LL-Heavy__blocker__Fab__(Blocker = VH-CH1__X = Linker1) |
| WW0735 | IL2-X-anti-HSA-LL-Heavy__blocker__Fab__(Blocker = VH-CH1__X = Linker2) |
| WW0736 | IL2-X-anti-HSA-LL-Heavy__blocker__Fab__(Blocker = VH-CH1__X = Linker3) |
| WW0792 | Anti-IL-2__Fab__Heavy__IgG1__Blocker__His__tag |
| WW0061 | IL2-X-anti-HSA__Fusion__(X = Linker1) |
| ACP293 (WW0237) | 3TOW69sdAb |
| ACP294 (WW0238) | 3TOW85sdAb |
| ACP295 (WW0239) | 2TOW91sdAb |
| ACP315 (WW0368) | Hu2TOW91__A |
| ACP316 (WW0369) | Hu2TOW91__B |

TABLE 3-continued

CONSTRUCT PERMUTATION TABLE ("6xHis" disclosed as SEQ ID NO: 354)

| Construct Name | Construct Description |
|---|---|
| ACP317 (WW0370) | Hu2TOW91__C |
| ACP318 (WW0371) | Hu2TOW91__D |
| ACP319 (WW0372) | HE__LM__2TOW91 |
| ACP320 (WW0373) | HE__L__2TOW91 |
| ACP321 (WW0374) | Hu3TOW85__A |
| ACP322 (WW0375) | Hu3TOW85__B |
| ACP323 (WW0376) | Hu3TOW85__C |
| ACP324 (WW0377) | Hu3TOW85__D |
| ACP325 (WW0378) | HE__LM__3TOW85 |
| ACP326 (WW0379) | HE__L__3TOW85 |
| ACP327 (WW0380) | HE__LM__R45L__3TOW85 |
| ACP328 (WW0381) | Hu3TOW69__A |
| ACP329 (WW0382) | Hu3TOW69__B |
| ACP330 (WW0383) | Hu3TOW69__C |
| ACP331 (WW0384) | Hu3TOW69__D |
| ACP332 (WW0385) | Hu3TOW69__E |
| ACP333 (WW0386) | HE__LM__3TOW69 |
| ACP334 (WW0387) | HE__L__3TOW69 |
| ACP335 (WW0388__ | HE__LM__R45L__3TOW69 |
| ACP360 (WW0438) | Vh-Vl__3xG4S__A46S ("3xG4S" is disclosed as SEQ ID NO: 452) |
| ACP361 (WW0439) | Vh-Vl__3xG4S__A46S ("3xG4S" is disclosed as SEQ ID NO: 452) |
| ACP362 (WW0440) | Vh-X-Vl__X = Linker2 |
| ACP363 (WW0441) | Vh-X-Vl__X = Linker2__A46S |
| ACP364 (WW0442) | VHVL.F2.high.A02__Vh-Vl__3xG4S ("3xG4S" is disclosed as SEQ ID NO: 452) |
| ACP365 (WW0443) | VHVL.F2.high.A02__Vh-Vl__3xG4S__A46S ("3xG4S" is disclosed as SEQ ID NO: 452) |
| ACP366 (WW0444) | VHVL.F2.high.A02__Vh-X-Vl__X = Linker2 |
| ACP367 (WW0445) | VHVL.F2.high.A02__Vh-X-Vl__X = Linker2__A46S |
| ACP368 (WW0446) | VHVL.F2.high.F03__Vh-Vl__3xG4S ("3xG4S" is disclosed as SEQ ID NO: 452) |
| ACP369 (WW0449) | VHVL.F2.high.F03__Vh-X-Vl__X = Linker2 |
| ACP370 (WW0450) | VHVL.F2.high.C07__Vh-Vl__3xG4S ("3xG4S" is disclosed as SEQ ID NO: 452) |
| ACP380 (WW0522) | Kappa__blocker__Fab__(Blocker = Kappa) |
| ACP381 (WW0523) | Kappa__blocker__Fab__(Blocker = VHVL.F2.high.A02__A46S__Kappa) |
| ACP382 (WW0524) | Kappa__blocker__Fab__(Blocker = VHVL.F2.high.F03__Kappa) |
| ACP434 (WW0576) | IL2-X-anti-HSA-LX-Blocker1-L-Blocker2__(Blocker1 = VHVL.F2.high.F03__Vh__Q105C__Vl__A43C__Blocker2 = Hu2TOW91__B__X = Linker2) |
| ACP435 (WW0577) | Kappa__blocker1__Fab-L-blocker2__(Blocker1 = VHVL.F2.high.A02__A46S__Kappa__Blocker2 = Hu2TOW91__A) |
| ACP436 (WW0578) | Kappa__blocker1__Fab-L-blocker2__(Blocker1 = VHVL.F2.high.A02__A46S__Kappa__Blocker2 = Hu2TOW91__B) |
| ACP437 (WW0579) | Kappa__blocker1__Fab-L-blocked__(Blocker1 = VHVL.F2.high.F03__Kappa__Blocker2 = Hu2TOW91__A) |

TABLE 3-continued

CONSTRUCT PERMUTATION TABLE ("6xHis" disclosed as SEQ ID NO: 354)

| Construct Name | Construct Description |
|---|---|
| ACP438 (WW0580) | Kappa__blocker1__Fab-L-blocker2__(Blocker1 = VHVL.F2.high.F03__Kappa__Blocker2 = Hu2TOW91__B) |
| ACP448 (WW0590) | Kappa__blocker__Fab__(Blocker = VHVL.F2.high.C07__A46S__Kappa) |
| ACP449 (WW0591) | Kappa__blocker__Fab__(Blocker = VHVL.F2.high.C07__A46L__Kappa) |
| ACP450 (WW0592) | Kappa__blocker__Fab__(Blocker = VHVL.F2.high.A02__A46L__Kappa) |

Sequence table

| SEQ ID NO. | Name | Sequence |
|---|---|---|
| 1 | Human IL-2 | MYRMQLLSCI ALSLALVTNS APTSSSTKKT QLQLEHLLLD LQMILNGINN<br>YKNPKLTRML TFKFYMPKKA TELKHLQCLE EELKPLEEVL NLAQSKNFHL<br>RPRDLISNIN VIVLELKGSE TTFMCEYADE TATIVEFLNR WITFCQSIISTLT |
| 2 | Human serum albumin | MKWVTFISLL FLFSSAYSRG VFRRDAHKSE VAHRFKDLGE ENFKALVLIA<br>FAQYLQQCPF EDHVKLVNEV TEFAKTCVAD ESAENCDKSL HTLFGDKLCT<br>VATLRETYGE MADCCAKQEP ERNECFLQHK DDNPNLPRLV RPEVDVMCTA<br>FHDNEETFLK KYLYEIARRH PYFYAPELLF FAKRYKAAFT ECCQAADKAA<br>CLLPKLDELR DEGKASSAKQ GLKCASLQKF GERAFKAWAV ARLSQRFPKA<br>EFAEVSKLVT DLTKVHTECC HGDLLECADD RADLAKYICE NQDSISSKLK<br>ECCEKPLLEK SHCIAEVEND EMPADLPSLA ADFVGSKDVC KNYAEAKDVF<br>LGMFLYEYAR RHPDYSVVLL LRLAKTYETT LEKCCAAADP HECYAKVFDE<br>FKPLVEEPQN LIKQNCELFE QLGEYKFQNA LLVRYTKKVP QVSTPTLVEV<br>SRNLGKVGSK CCKHPEAKRM PCAEDCLSVF LNQLCVLHEK TPVSDRVTKC<br>CTESLVNGRPCFSALEVDETYVPKEFNAETFTFHADICTL SEKERQIKKQTALV<br>ELVKHK PKATKEQLKAVMDDFAAFVEKCCKADDKET<br>CFAEEGKKLVAASQAALGL |
| 45 | ACP12 (IL2 fusion protein) | QVQLQESGGGLVQAGGSLRLSCAASGRIFSIDIMSWYRQAPGKQRELVARITR<br>GGTISYDDSVKGRFTISRDNAKNTVYLQMNSLKPEDTGVYYCNALYGTDYW<br>GKGTQVTVSSggggsggggsggggsaptsssticktqlqlehllldlqmilnginnyknpkltrmlfficfympkk<br>atellchlqcleeelkpleevinlaqsknfhlrprdlisninvivlelkgsettfmceyadetative<br>flnrwitfcqsiistltSGGPGPAGMKGLPGSEVQLVESGGGLVQPGNSLRLSCAASGFTFSKFGMSWVRQ<br>APGKGLEWVSSISGSGRDTLYAESVKGRFTISRDNAKTTLYLQMNSLRPEDTA<br>VYYCTIGGSLSVSSQGTLVTVSSggggsggggsggggsEVQLVESGGGLVQPGGSLR<br>LSCAASGFTFSSYTLAWVRQAPGKGLEWVAAIDSSSYTYSPDTVRGRFTISRD<br>NAKNSLYLQMNSLRAEDTAVYYCARDSNWDALDYWGQGTTVTVSSGGGGS<br>GGGGSGGGGSDIQMTQSPSSLSASVGDRVTITCKASQNVGTNVGWYQQKPGK<br>APKALIYSASFRYSGVPSRFSGSGSGTDFTLTISSLQPEDFATYYCQQYYTYPYT<br>FGGGTKVEIKHHHHHH |
| 46 | ACP13 (IL2 fusion protein) | QVQLQESGGGLVQAGGSLRLSCAASGRIFSIDIMSWYRQAPGKQRELVARITR<br>GGTISYDDSVKGRFTISRDNAKNTVYLQMNSLKPEDTGVYYCNALYGTDYW<br>GKGTQVTVSSggggsggggsggggsEVQLVESGGGLVQPGGSLRLSCAASGFTFSSY<br>TLAWVRQAPGKGLEWVAAIDSSSYTYSPDTVRGRFTISRDNAKNSLYLQMNS<br>LRAEDTAVYYCARDSNWDALDYWGQGTTVTVSSGGGGSGGGGSGGGGSDI<br>QMTQSPSSLSASVGDRVTITCKASQNVGTNVGWYQQKPGKAPKALIYSASFR<br>YSGVPSRFSGSGSGTDFTLTISSLQPEDFATYYCQQYYTYPYTFGGGTKVEIKgg<br>ggsggggsggggsEVQLVESGGGLVQPGNSLRLSCAASGFTFSKFGMSWVRQAPGK<br>GLEWVSSISGSGRDTLYAESVKGRFTISRDNAKTTLYLQMNSLRPEDTAVYYC<br>TIGGSLSVSSQGTLVTVSSSGGPGPAGMKGLPGSaptsssticktqlqlehllldlqmilnginny<br>knpkltrmlfficfympkkatellchlqcleeelkpleevinlaqsknfblrprdlisninvivlelk<br>gsettfmceyadetativeflnrwitfcqsiistltHHHHHH |
| 47 | ACP14 (IL2 fusion protein) | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSGGGGSGGGGSGGGGSDIQMTQSPSSLSASVGDRVTITCK<br>ASQNVGTNVGWYQQKPGKAPKALIYSASFRYSGVPSRFSGSGSGTDFTLTISSL<br>WW0045QPEDFATYYCQQYYTYPYTFGGGTKVEIKggggsggggsggggsggggsggggsggggsSG<br>GPGPAGMKGLPGSaptsssticktqlqlehllldlqmilnginnyknpkltrmifficfympkkatelkhlqcleee<br>lkpleevinlaqsknfhlrprdlisninvivlelkgsettfmceyadetativeflnrwitfcqsiistltSGGPGPAGM<br>KGLPGSEVQLVESGGGLVQPGNSLRLSCAASGFTFSKFGMSWVRQAPGKGLE<br>WVSSISGSGRDTLYAESVKGRFTISRDNAKTTLYLQMNSLRPEDTAVYYCTIG<br>GSLSVSSQGTLVTVSSHHHHHH |

-continued

Sequence table

| SEQ ID NO. | Name | Sequence |
|---|---|---|
| 48 | ACP15<br>(IL2 fusion<br>protein)<br>(WW0047) | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSGGGGSGGGGSGGGGSDIQMTQSPSSLSASVGDRVTITCK<br>ASQNVGTNVGWYQQKPGKAPKALIYSASFRYSGVPSRFSGSGSGTDFTLTISSL<br>QPEDFATYYCQQYYTYPYTFGGGTKVEIKggggsggggsggggsggggsggggsggggsEV<br>QLVESGGGLVQPGNSLRLSCAASGFTFSKFGMSWVRQAPGKGLEWVSSISGS<br>GRDTLYAESVKGRFTISRDNAKTTLYLQMNSLRPEDTAVYYCTIGGSLSVSSQ<br>GTLVTVSSggggsggggsggggsSGGPGPAGMKGLPGSaptssstkktqlqlehllldlqmilnginn<br>yknpkltrinlifkfympkkatelkhlqcleeelkpleevinlaqsknfhlrprdlisninvivlelkgsettfmceyadetat<br>iveflnrwitfcqsiistltHHHHHH |
| 49 | ACP16<br>(IL2 fusion<br>protein)<br>(WW0048) | aptssstkktqlqlehllldlqmilnginnyknpkltrmltfkfympkkatelkhlqcleeelkpleevinlaqsknfhlrpr<br>dlisninvivlelkgsetlfmceyadetativeflnrwitfcqsiistltSGGPGPAGMKGLPGSEVQLVES<br>GGGLVQPGNSLRLSCAASGFTFSKFGMSWVRQAPGKGLEWVSSISGSGRDTL<br>YAESVKGRFTISRDNAKTTLYLQMNSLRPEDTAVYYCTIGGSLSVSSQGTLVT<br>VSSggggsggggsggggsggggsggggsggggsSGGPGPAGMKGLPGSEVQLVESGGGLV<br>QPGGSLRLSCAASGFTFSSYTLAWVRQAPGKGLEWVAAIDSSSYTYSPDTVRG<br>RFTISRDNAKNSLYLQMNSLRAEDTAVYYCARDSNWDALDYWGQGTTVTVS<br>SGGGGSGGGGSGGGGSDIQMTQSPSSLSASVGDRVTITCKASQNVGTNVGWY<br>QQKPGKAPKALIYSASFRYSGVPSRFSGSGSGTDFTLTISSLQPEDFATYYCQQ<br>YYTYPYTFGGGTKVEIKHHHHHH |
| 50 | ACP17<br>(IL2 fusion<br>protein) | QVQLQESGGGLVQAGGSLRLSCAASGRIFSIDIMSWYRQAPGKQRELVARITR<br>GGTISYDDSVKGRFTISRDNAKNTVYLQMNSLKPEDTGVYYCNALYGTDYW<br>GKGTQVTVSSggggsggggsggggsaptssstkktqlqlehllldlqmilnginnyknpkltrmilfklympkk<br>atelkhlqcleeelkpleevinlaqsknfhlrprdlisninvivlelkgsettfmceyadetativeflnrwitfc<br>qsiistltSGGPGPAGMKGLPGSEVQLVESGGGLVQPGNSLRLSCAASGFTFSKFGMSWVRQ<br>APGKGLEWVSSISGSGRDTLYAESVKGRFTISRDNAKTTLYLQMNSLRPEDTA<br>VYYCTIGGSLSVSSQGTLVTVSSggggsggggsggggsggggsggggsggggsSGGPGPAG<br>MKGLPGSEVQLVESGGGLVQPGGSLRLSCAASGFTFSSYTLAWVRQAPGKGL<br>EWVAAIDSSSYTYSPDTVRGRFTISRDNAKNSLYLQMNSLRAEDTAVYYCAR<br>DSNWDALDYWGQGTTVTVSSGGGGSGGGGSGGGGSDIQMTQSPSSLSASVG<br>DRVTITCKASQNVGTNVGWYQQKPGKAPKALIYSASFRYSGVPSRFSGSGSGT<br>DFTLTISSLQPEDFATYYCQQYYTYPYTFGGGTKVEIKHHHHHH |
| 51 | ACP18<br>(IL2 fusion<br>protein) | QVQLQESGGGLVQAGGSLRLSCAASGRIFSIDIMSWYRQAPGKQRELVARITR<br>GGTISYDDSVKGRFTISRDNAKNTVYLQMNSLKPEDTGVYYCNALYGTDYW<br>GKGTQVTVSSggggsggggsggggsaptssstkktqlqlehllldlqmilnginnyknpkltrmilfklympkk<br>atelkhlqcleeelkpleevinlaqsknfhlrprdlisninvivlelkgsettfmceyadetativeflnrwitf<br>cqsiistltSGGPGPAGMKGLPGSEVQLVESGGGLVQPGNSLRLSCAASGFTFSKFGMSWVRQ<br>APGKGLEWVSSISGSGRDTLYAESVKGRFTISRDNAKTTLYLQMNSLRPEDTA<br>VYYCTIGGSLSVSSQGTLVTVSSggggsggggsggggsggggsggggsggggsEVQLVESG<br>GGLVQPGGSLRLSCAASGFTFSSYTLAWVRQAPGKGLEWVAAIDSSSYTYSPD<br>TVRGRFTISRDNAKNSLYLQMNSLRAEDTAVYYCARDSNWDALDYWGQGTT<br>VTVSSsggpgpagmkglpgsDIQMTQSPSSLSASVGDRVTITCKASQNVGTNVGWY<br>QQKPGKAPKALIYSASFRYSGVPSRFSGSGSGTDFTLTISSLQPEDFATYYCQQ<br>YYTYPYTFGGGTKVEIKHHHHHH |
| 52 | ACP19<br>(IL2 fusion<br>protein) | aptssstkktqlqlehllldlqmilnginnyknpkltrmltfkfympkkatelkhlqcleeelkpleevi<br>nlaqsknfhlrprdlisninvivlelkgsettfmceyadetativeflnrwitfcqsiistltSGGPGPAG<br>MKGLPGSggggsggggsggggsggggsggggsggggsEVQLVESGGGLVQPGGSLRLSCAASGFTFSSYTLAWVR<br>QAPGKGLEWVAAIDSSSYTYSPDTVRGRFTISRDNAKNSLYLQMNSLRAEDTA<br>VYYCARDSNWDALDYWGQGTTVTVSSGGGGSGGGGSGGGGSDIQMTQSPSS<br>LSASVGDRVTITCKASQNVGTNVGWYQQKPGKAPKALIYSASFRYSGVPSRFS<br>GSGSGTDFTLTISSLQPEDFATYYCQQYYTYPYTFGGGTKVEIKggggsggggsggg<br>gsEVQLVESGGGLVQPGNSLRLSCAASGFTFSKFGMSWVRQAPGKGLEWVSSI<br>SGSGRDTLYAESVKGRFTISRDNAKTTLYLQMNSLRPEDTAVYYCTIGGSLSV<br>SSQGTLVTVSSggggsggggsggggsQVQLQESGGGLVQAGGSLRLSCAASGRIFSID<br>IMSWYRQAPGKQRELVARITRGGTISYDDSVKGRFTISRDNAKNTVYLQMNSL<br>KPEDTGVYYCNALYGTDYWGKGTQVTVSSHHHHHH** |
| 53 | ACP20<br>(IL2 fusion<br>protein)<br>(WW0056) | aptssstkktqlqlehllldlqmilnginnyknpkltrmltfkfympkkatelkhlqcleeelkpleev<br>dinlaqsknfhlrprlisninvivlelkgsetifmceyadetativeflnrwitfcqsiistltSGGPGPA<br>GGGLVQPGGSLRLSCAASGFTFSSYTLAWVRQAPGKGLEWVAAIDSSSYTYSP<br>GMKGLPGSEVQLVESDTVRGRFTISRDNAKNSLYLQMNSLRAEDTAVYYCARDSNWDALDYWGQGT<br>TVTVSSGGGGSGGGGSGGGGSDIQMTQSPSSLSASVGDRVTITCKASQNVGTN<br>VGWYQQKPGKAPKALIYSASFRYSGVPSRFSGSGSGTDFTLTISSLQPEDFATY<br>YCQQYYTYPYTFGGGTKVEIKHHHHHH |
| 54 | ACP21<br><br>(IL2 fusion | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltSGGPGPAGMKGLPGSggggsggggs<br>ggggsggggsggggsggggsEVQLVESGGGLVQPGGSLRLSCAASGFTFSSYTLAWVR |

-continued

Sequence table

| SEQ ID NO. | Name | Sequence |
|---|---|---|
| | protein) (WW0057) | QAPGKGLEWVAAIDSSSYTYSPDTVRGRFTISRDNAKNSLYLQMNSLRAEDTA<br>VYYCARDSNWDALDYWGQGTTVTVSSGGGGSGGGGSGGGGSDIQMTQSPSS<br>LSASVGDRVTITCKASQNVGTNVGWYQQKPGKAPKALIYSASFRYSGVPSRFS<br>GSGSGTDFTLTISSLQPEDFATYYCQQYYTYPYTFGGGTKVEIKHHHHHH |
| 55 | ACP22 (IL2 fusion protein) | aptsssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltSGGPGPAGMKGLPGSggggsggggs<br>ggggsggggsggggsggggsEVQLVESGGGLVQPGGSLRLSCAASGFTFSSYTLAWVR<br>QAPGKGLEWVAAIDSSSYTYSPDTVRGRFTISRDNAKNSLYLQMNSLRAEDTA<br>VYYCARDSNWDALDYWGQGTTVTVSSGGGGSGGGGSGGGGSDIQMTQSPSS<br>LSASVGDRVTITCKASQNVGTNVGWYQQKPGKAPKALIYSASFRYSGVPSRFS<br>GSGSGTDFTLTISSLQPEDFATYYCQQYYTYPYTFGGGTKVEIKSGGPGPAGM<br>KGLPGSEVQLVESGGGLVQPGNSLRLSCAASGFTFSKFGMSWVRQAPGKGLE<br>WVSSISGSGRDTLYAESVKGRFTISRDNAKTTLYLQMNSLRPEDTAVYYCTIG<br>GSLSVSSQGTLVTVSSggggsggggsggggsQVQLQESGGGLVQAGGSLRLSCAASG<br>RIFSIDIMSWYRQAPGKQRELVARITRGGTISYDDSVKGRFTISRDNAKNTVYL<br>QMNSLKPEDTGVYYCNALYGTDYWGKGTQVTVSSHHHHHH |
| 56 | ACP23 (IL2 fusion protein) | QVQLQESGGGLAQAGGSLSLSCAASGFTVSNSVMAWYRQTPGKQREFVAIIN<br>SVGSTNYADSVKGRFTISRDNAKNTVYLQMNNLKPEDTAVYVCNRNFDRIY<br>WGQGTQVTVSSSGGPGPAGMKGLPGSEVQLVESGGGLVQPGGSLRLSCAASG<br>FTFSSYTLAWVRQAPGKGLEWVAAIDSSSYTYSPDTVRGRFTISRDNAKNSLY<br>LQMNSLRAEDTAVYYCARDSNWDALDYWGQGTTVTVSSGGGGSGGGGSGG<br>GGSDIQMTQSPSSLSASVGDRVTITCKASQNVGTNVGWYQQKPGKAPKALIYS<br>ASFRYSGVPSRFSGSGSGTDFTLTISSLQPEDFATYYCQQYYTYPYTFGGGTKV<br>EIKggggsggggsggggsggggsggggsggggsSGGPGPAGMKGLPGSEVQLVESGGGLVQ<br>PGNSLRLSCAASGFTFSKFGMSWVRQAPGKGLEWVSSISGSGRDTLYAESVKG<br>RFTISRDNAKTTLYLQMNSLRPEDTAVYYCTIGGSLSVSSQGTLVTVSSSGGPGPAGMKG<br>LPGSaptssstldctqlqlehllldlqmilnginnyknpkltrmltfkfympkkatelkhlqcleeelkple<br>evinlaqsknfhlrprdlisninvivlelkgsettfmceyadetativeflnrwitfcqsiistltHHHHHH |
| 57 | ACP24 (IL2 fusion protein) (WW0074) | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSGGGGSGGGGSGGGGSDIQMTQSPSSLSASVGDRVTITCK<br>ASQNVGTNVGWYQQKPGKAPKALIYSASFRYSGVPSRFSGSGSGTDFTLTISSL<br>QPEDFATYYCQQYYTYPYTFGGGTKVEIKSGGPGPAGMKGLPGSaptssstIcktqlql<br>ehllldlqmilnginnyknpkltrmlfficfympldcatelkittqcleeelkpleevinlaqsknf<br>ittrprdlisninvivlelkgsettfmceyadetativeflnrwitfcqsiistltHHHHHH |
| 58 | ACP25 (IL2 fusion protein) (WW0075) | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSGGGGSGGGGSGGGGSDIQMTQSPSSLSASVGDRVTITCK<br>ASQNVGTNVGWYQQKPGKAPKALIYSASFRYSGVPSRFSGSGSGTDFTLTISSL<br>QPEDFATYYCQQYYTYPYTFGGGTKVEIKggggsggggsggggsggggsggggsggggsSG<br>GPGPAGMKGLPGSaptssstIcktqlqlehllldlqmilnginnyknpkftrmltfkfympkkatelkhlqcleee<br>lkpleevinlaqsknflilmrdlisninvivlelkgsettfmceyadetativeflnrwitfcqsiistltHHHHHH |
| 59 | ACP26 (IL2 fusion protein) | QVQLQESGGGLVQAGGSLRLSCAASGRIFSIDIMSWYRQAPGKQRELVARITR<br>GGTISYDDSVKGRFTISRDNAKNTVYLQMNSLKPEDTGVYYCNALYGTDYW<br>GKGTQVTVSSggggsggggsggggsaptssstIcktqlqlehllldlqmilnginnyknpkltrmltficfympkk<br>atelkittqcleeelkpleevinlaqsknfittrprdlisninvivlelkgsettfmceyadetativeflnrwi<br>tfcqsiistltSGGPGPAGMKGLPGSEVQLVESGGGLVQPGNSLRLSCAASGFTFSKFGMSWVRQ<br>APGKGLEWVSSISGSGRDTLYAESVKGRFTISRDNAKTTLYLQMNSLRPEDTA<br>VYYCTIGGSLSVSSQGTLVTVSSggggsggggsggggsggggsQVQLQQSGAELVRPGT<br>SVKVSCKASGYAFTNYLIEWVKQRPGQGLEWIGVINPGSGGTNYNEKFKGKA<br>TLTADKSSSTAYMQLSSLTSDDSAVYFCARWRGDGYYAYFDVWGAGTTVTV<br>SSggggsggggsggggsDIVLTQSPASLAVSLGQRATISCKASQSVDYDGDSYMNWY<br>QQKPGQPPKLLIYAASNLESGIPARFSGSGSGTDFTLNIHPVEEEDAATYYCQQ<br>SNEDPYTFGGGTKLEIKHHHHHHEPEA |
| 60 | ACP27 (IL2 fusion protein) | QVQLQESGGGLVQAGGSLRLSCAASGRIFSIDIMSWYRQAPGKQRELVARITR<br>GGTISYDDSVKGRFTISRDNAKNTVYLQMNSLKPEDTGVYYCNALYGTDYW<br>GKGTQVTVSSggggsggggsggggsaptssstkktqlqlehllldlqmilnginnyknpkltrmltfklympkk<br>atelkhlqcleeelkpleevinlaqsknfhlrprdlisninvivlelkgsettfmceyadetativeflnrwitfc<br>qsiistltSGGPGPAGMKGLPGSEVQLVESGGGLVQPGNSLRLSCAASGFTFSKFGMSWVRQ<br>APGKGLEWVSSISGSGRDTLYAESVKGRFTISRDNAKTTLYLQMNSLRPEDTA<br>VYYCTIGGSLSVSSQGTLVTVSSggggsggggsggggsggggsDIVLTQSPASLAVSLG<br>QRATISCKASQSVDYDGDSYMNWYQQKPGQPPKLLIYAASNLESGIPARFSGS<br>GSGTDFTLNIHPVEEEDAATYYCQQSNEDPYTFGGGTKLElKggggsggggsggggs<br>QVQLQQSGAELVRPGTSVKVSCKASGYAFTNYLIEWVKQRPGQGLEWIGVIN<br>PGSGGTNYNEKFKGKATLTADKSSSTAYMQLSSLTSDDSAVYFCARWRGDG<br>YYAYFDVWGAGTTVTVSSHHHHHHEPEA |

-continued

Sequence table

| SEQ ID NO. | Name | Sequence |
|---|---|---|
| 61 | ACP28 (IL2 fusion protein) | aptssstkktqlqlehllldlqmilnginnyknpkltrmltfkfympkkatelkhlqcleeelkpleevinlaqsk nfhlrprdlisninvivlelkgsettfmceyadetativeflnrwitfcqsiistltSGGPGPAGMKGLPGSggg gsggggsggggsggggsggggsggggsQVQLQQSGAELVRPGTSVKVSCKASGYAFTNYLIEWVKQRP GQGLEWIGVINPGSGGTNYNEKFKGKATLTADKSSSTAYMQLSSLTSDDSAV YFCARWRGDGYYAYFDVWGAGTTVTVSSggggsggggsggggsDIVLTQSPASLAV SLGQRATISCKASQSVDYDGDSYMNWYQQKPGQPPKLLIYAASNLESGIPARF SGSGSGTDFTLNIHPVEEEDAATYYCQQSNEDPYTFGGGTKLEIKggggsggggsgg ggsEVQLVESGGGLVQPGNSLRLSCAASGFTFSKFGMSWVRQAPGKGLEWVSS ISGSGRDTLYAESVKGRFTISRDNAKTTLYLQMNSLRPEDTAVYYCTIGGSLSV SSQGTLVTVSSggggsggggsggggsQVQLQESGGGLVQAGGSLRLSCAASGRIFSID IMSWYRQAPGKQRELVARITRGGTISYDDSVKGRFTISRDNAKNTVYLQMNSL KPEDTGVYYCNALYGTDYWGKGTQVTVSSHHHHHHEPEA |
| 62 | ACP29 (IL2 fusion protein) | aptssstkktqlqlehllldlqmilnginnyknpkltrmltfkfympkkatelkhlqcleeelkpleevinla qsknfhlrprdlisninvivlelkgsettfmceyadetativeflnrwitfcqsiistltSGGPGPAGMKGLP GSggggsggggsggggsggggsggggsDIVLTQSPASLAVSLGQRATISCKASQSVDYDGDSYMNWYQ QKPGQPPKLLIYAASNLESGIPARFSGSGSGTDFTLNIHPVEEEDAATYYCQQS NEDPYTFGGGTKLEIKggggsggggsggggsQVQLQQSGAELVRPGTSVKVSCKASG YAFTNYLIEWVKQRPGQGLEWIGVINPGSGGTNYNEKFKGKATLTADKSSST AYMQLSSLTSDDSAVYFCARWRGDGYYAYFDVWGAGTTVTVSSggggsggggsg gggsEVQLVESGGGLVQPGNSLRLSCAASGFTFSKFGMSWVRQAPGKGLEWVS SISGSGRDTLYAESVKGRFTISRDNAKTTLYLQMNSLRPEDTAVYYCTIGGSLS VSSQGTLVTVSSggggsggggsggggsQVQLQESGGGLVQAGGSLRLSCAASGRIFSI DIMSWYRQAPGKQRELVARITRGGTISYDDSVKGRFTISRDNAKNTVYLQMN SLKPEDTGVYYCNALYGTDYWGKGTQVTVSSHHHHHHEPEA |
| 63 | IL2Ra | 10 20 30 40 50<br>MDSYLLMWGL LTFIMVPGCQ AELCDDDPPE IPHATFKAMA YKEGTMLNCE<br>60 70 80 90 100<br>CKRGFRRIKS GSLYMLCTGN SSHSSWDNQC QCTSSATRNT TKQVTPQPEE<br>110 120 130 140 150<br>QKERKTTEMQ SPMQPVDQAS LPGHCREPPP WENEATERIY HFVVGQMVYY<br>160 170 180 190 200<br>QCVQGYRALH RGPAESVCKM THGKTRWTQP QLICTGEMET SQFPGEEKPQ<br>210 220 230 240 250<br>ASPEGRPESE TSCLVTTTDF QIQTEMAATM ETSIFTTEYQ VAVAGCVFLL<br>260 270<br>ISVLLLSGLT WQRRQRKSRR TI |
| 64 | IL2Rb | 10 20 30 40 50<br>MAAPALSWRL PLLILLLPLA TSWASAAVNG TSQFTCFYNS RANISCVWSQ<br>60 70 80 90 100<br>DGALQDTSCQ VHAWPDRRRW NQTCELLPVS QASWACNLIL GAPDSQKLTT<br>110 120 130 140 150<br>VDIVTLRVLC REGVRWRVMA IQDFKPFENL RLMAPISLQV VHVETHRCNI<br>160 170 180 190 200<br>SWEISQASHY FERHLEFEAR TLSPGHTWEE APLLTLKQKQ EWICLETLTP<br>210 220 230 240 250<br>DTQYEFQVRV KPLQGEFTTW SPWSQPLAFR TKPAALGKDT IPWLGHLLVG<br>260 270 280 290 300<br>LSGAFGFIIL VYLLINCRNT GPWLKKVLKC NTPDPSKFFS QLSSEHGGDV<br>310 320 330 340 350<br>QKWLSSPFPS SSFSPGGLAP EISPLEVLER DKVTQLLLQQ DKVPEPASLS<br>360 370 380 390 400<br>SNHSLTSCFT NQGYFFFHLP DALEIEACQV YFTYDPYSEE DPDEGVAGAP<br>410 420 430 440 450<br>TGSSPQPLQP LSGEDDAYCT FPSRDDLLLF SPSLLGGPSP PSTAPGGSGA<br>460 470 480 490 500<br>GEERMPPSLQ ERVPRDWDPQ PLGPPTPGVP DLVDFQPPPE LVLREAGEEV<br>510 520 530 540 550<br>PDAGPREGVS FPWSRPPGQG EFRALNARLP LNTDAYLSLQ ELQGQDPTHL<br>V |
| 65 | IL2Rg | 10 20 30 40 50<br>MLKPSLPFTS LLFLQLPLLG VGLNTTILTP NGNEDTTADF FLTTMPTDSL<br>60 70 80 90 100<br>SVSTLPLPEV QCFVFNVEYM NCTWNSSSEP QPTNLTLHYW YKNSDNDKVQ<br>110 120 130 140 150<br>KCSHYLFSEE ITSGCQLQKK EIHLYQTFVV QLQDPREPRR QATQMLKLQN<br>160 170 180 190 200<br>LVIPWAPENL TLHKLSESQL ELNWNNRFLN HCLEHLVQYR TDWDHSWTEQ<br>210 220 230 240 250<br>SVDYRHKFSL PSVDGQKRYT FRVRSRFNPL CGSAQHWSEW SHPIHWGSNT |

-continued

Sequence table

| SEQ ID NO. | Name | Sequence |
|---|---|---|
| | | 260 270 280 290 300<br>SKENPFLFAL EAVVISVGSM GLIISLLCVY FWLERTMPRI PTLKNLEDLV<br>310 320 330 340 350<br>TEYHGNFSAW SGVSKGLAES LQPDYSERLC LVSEIPPKGG ALGEGPGASP<br>360<br>CNQHSPYWAP PCYTLKPET |
| 66 | ACP04 (human p40/murine p35 IL12 fusion protein) | iwelkkdvyvveldwypdapgemvvitcdtpeedgitwadqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfsltfcvqvqgkskrekkdwftdktsatvicrknasisvraqthyyssswsewasvpcsggggsggggsggggs<br>rvipvsgparclsqsrnllkttddmvktareklkhysctaedidheditrdqtstlktclplelhknesclatretssttrgs<br>clppqktslmmticlgsiyedlkmyqtefqainaalqnhnhqqiildkgmlvaidelmqslnhngetlrqkppvgead<br>pyrvkmklcillhafstrvvtinrvmgylssaHHHHHH |
| 67 | ACP05 (human p40/murine p35 IL12 fusion protein) | iwelkkdvyvveldwypdapgemvvitcdtpeedgitwadqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfsltfcvqvqgkskrekkdwftdktsatvicrknasisvraqthyyssswsewasvpcsggggsggggsgg<br>ggsrnlpvatpdpgmfpclhhsqnllraysnmlqkarqtlefypctseeidheditkdktstveaclpleltknesclnsre<br>tsfitngsclasrktsfmmalclssiyedlkmyqvefktmnakllmdpkrqifldqnmlavidelmqalnfnsetvpqk<br>ssleepdfyktkiklcillhafriravtidrvmsylnasHHHHHH |
| 68 | ACP06 (human p40/murine p35 IL12 fusion protein) | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTVSSggggsggggsggggsggggsggggsggggsSGG<br>PGPAGMKGLPGSiwelkkdvyvveldwypdapgemvvitcdtpeedgitwtldqssevlgsgktltiqvkef<br>gdagqytchkggevlshsllllhkkedgiwstdilkdqkepknktflrceaknysgrftcwwlttistdltfsvkssrgssd<br>pqgvtcgaatlsaervrgdnkeyeysvecqedsacpaaeeslpievmvdavhklkyenytssffirdiikpdppknlql<br>kplknsrqvevsweypdtwstphsyfsltfcvqvqgkskrekkdrvftdktsatvicrknasisvraqthyyssswsew<br>asvpcsggggsggggsggggsrvipvsgparclsqsrnllkttddmvktareklkhysctaedidheditrdqtstlktcl<br>plelhknesclatretssttrgsclppqktslmmticlgsiyedlkmyqtefqainaalqnhnhqqiildkgmlvaidelm<br>qslnhngetlrqkppvgeadpyrvkmklcillhafstrvvtinrvmgylssaSGGPGPAGMKGLPGSEVQ<br>LVESGGGLVQPGNSLRLSCAASGFTFSKFGMSWVRQAPGKGLEWVSSISGSGR<br>DTLYAESVKGRFTISRDNAKTTLYLQMNSLRPEDTAVYYCTIGGSLSVSSQGT<br>LVTVSSHHHHHHEPEA |
| 69 | ACP07 (human p40/murine p35 IL12 fusion protein) | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTVSSggggsggggsggggsggggsggggsggggsSGG<br>PGPAGMKGLPGSiwelkkdvyvveldwypdapgemvvitcdtpeedgitwtldqssevlgsgktltiqvkef<br>gdagqytchkggevlshsllllhkkedgiwstdilkdqkepknktflrceaknysgrftcwwlttistdltfsvkssrgssd<br>pqgvtcgaatlsaervrgdnkeyeysvecqedsacpaaeeslpievmvdavificlkyenytssffirdiikpdppknlql<br>kplknsrqvevsweypdtwstphsyfshfcvqvqgkskrekkdrvftdktsatvicrknasisvraqchyyssswsew<br>asvpcsggggsggggsggggsrvipvsgparclsqsrnllkttddmvktareklkhysctaedidheditrdqtstlktcl<br>plelhknesclatretssttrgsclppqktslmmticlgsiyedlkmyqtefqainaalqnhnhqqiildkgmlvaidelm<br>qslnhngetlrqkppvgeadpyrvkmlcicillhafstrvvtinrvmgylssaSGGPGPAGMKGLPGSEVQ<br>LVESGGGLVQPGNSLRLSCAASGFTFSKFGMSWVRQAPGKGLEWVSSISGSGR<br>DTLYAESVKGRFTISRDNAKTTLYLQMNSLRPEDTAVYYCTIGGSLSVSSQGT<br>LVTVSSggggsggggsggggsQVQLQESGGGLAQAGGSLSLSCAASGFTVSNSVMA<br>WYRQTPGKQREFVAIINSVGSTNYADSVKGRFTISRDNAKNTVYLQMNNLKP<br>EDTAVYVCNRNFDRIYWGQGTQVTVSSHHHHHHEPEA |
| 70 | ACP08 (human p40/murine p35 IL12 fusion protein) | QVQLQESGGGLAQAGGSLSLSCAASGFTVSNSVMAWYRQTPGKQREFVAIIN<br>SVGSTNYADSVKGRFTISRDNAKNTVYLQMNNLKPEDTAVYVCNRNFDRIY<br>WGQGTQVTVSSggggsggggsggggsQSVLTQPPSVSGAPGQRVTISCSGSRSNIGSN<br>TVKWYQQLPGTAPKLLIYYNDQRPSGVPDRFSGSKSGTSASLAITGLQAEDEA<br>DYYCQSYDRYTHPALLFGTGTKVTVLggggsggggsggggsQVQLVESGGGVVQPG<br>RSLRLSCAASGFTFSSYGMHWVRQAPGKGLEWVAFIRYDGSNKYYADSVKG<br>RFTISRDNSKNTLYLQMNSLRAEDTAVYYCKTHGSHDNWGQGTMVTVSSggg<br>gsggggsggggsggggsggggsggggsSGGPGPAGMKGLPGSiwelkkdvyvveldwypdapgemv<br>vltcdtpeedgitwtldqssevlgsgktltiqvkefgdagqytchkggevlshsllllhkkedgiwstdilkdqkepknktf<br>liceaknysgrftcwwlttistdiffsvkssrgssdpqgvtcgaatlsaervrgdnkeyeysvecqedsacpaaeeslpiev<br>mvdavhklkyenytssffirdiikpdppknlqlkplknsrqvevsweypdtwstphsyfshfcvqvqgkskrekkdr<br>vftdktsatvicrknasisvraqchyyssswsewasvpcsggggsggggsggggsrvipvsgparclsqsrnllkttdd<br>mvktareklkhysctaedidheditrdqtstlktclplelhknesclatretssttrgsclppqktslmmticlgsiyedlkm<br>yqtefclainaalqnhnhqqiildkgmlvaidelmqslnhngetlrqkppvgeadpyrvkmklcillhafstrvvtinry<br>mgylssaSGGPGPAGMKGLPGSEVQLVESGGGLVQPGNSLRLSCAASGFTFSKFG |

-continued

Sequence table

| SEQ ID NO. | Name | Sequence |
|---|---|---|
| | | MSWVRQAPGKGLEWVSSISGSGRDTLYAESVKGRFTISRDNAKTTLYLQMNS<br>LRPEDTAVYYCTIGGSLSVSSQGTLVTVSSHHHHHHEPEA |
| 71 | ACP09 (human p40/murine p35 IL12 fusion protein) | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSggggsggggsggggsQSVLTQPPSVSGAPGQRVTISCSGSRSNIGSNTV<br>KWYQQLPGTAPKLLIYYNDQRPSGVPDRFSGSKSGTSASLAITGLQAEDEADY<br>YCQSYDRYTHPALLFGTGTKVTVLggggsggggsggggsQVQLVESGGGVVQPGRS<br>LRLSCAASGFTFSSYGMHWVRQAPGKGLEWVAFIRYDGSNKYYADSVKGRF<br>TISRDNSKNTLYLQMNSLRAEDTAVYYCKTHGSHDNWGQGTMVTVSSggggsg<br>gggsggggsggggsggggsggggsSGGPGPAGMKGLPGSiwelkkdvyvveldwypdapgemvvitc<br>dtpeedgitwadqssevlgsgktltiqvkefgdagqytchkggevlshslllhldcedgiwstdilkdqkepknktflice<br>aknysgrftcwwlttistdiffsvkssrgssdpqgvtcgaatlsaervrgdnkeyeysvecqedsacpaaeeslpievmv<br>davhklkyenytssffirdiikpdppknlqlkplknsrqvevsweypdtwstphsyfslifcvqvqgkskrekkdrvftd<br>ktsatvicrknasisvraqthyysssweewasvpcsggggsggggsggggsrvipvsgparclsqsrnllkttddmvkt<br>areklkhysctaedidheditrdqtstlktclplelhknesclatretssttrgsclppqktslmmticlgsiyedlkmyqtef<br>qainaalqnhnhqqiildkgmlvaidelmqslnhngetlrqkppvgeadpyrvkmklcillhafstrvvtinrvmgyls<br>saHHHHHHEPEA |
| 72 | ACP10 (human p40/murine p35 IL12 fusion protein) | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGSiwelkkdvyvveldwypdapgemvvitcdtpeedgitwtl<br>dqssevlgsgktltiqvkefgdagqytchkggevlshslllhkkedgiwstdilkdqkepknktflrceaknysgrftcw<br>wittistdlifsvkssrgssdpqgvtcgaatlsaervrgdnkeyeysvecqedsacpaaeeslpievmvdavhklkyeny<br>tssffirdiikpdppknlqlkplknsrqvevsweypdtwstphsyfsltfcvqvqgkskrekkdrvftdktsatvicrkna<br>sisvraqthyysssweewasvpcsggggsggggsggggsrvipvsgparclsqsrnllkttddmvktareklkhyscta<br>edidheditrdqtstlktclplelhknesclatretssttrgsclppqktslmmticlgsiyedlkmyqtefqainaalqnhnh<br>qqiildkgmlvaidelmqslnhngetlrqkppvgeadpyrvkmklcillhafstrvvtinrvmgylssaSGGPGPA<br>GMKGLPGSggggsggggsggggsggggsggggsggggsQSVLTQPPSVSGAPGQRVTISCS<br>GSRSNIGSNTVKWYQQLPGTAPKLLIYYNDQRPSGVPDRFSGSKSGTSASLAIT<br>GLQAEDEADYYCQSYDRYTHPALLFGTGTKVTVLggggsggggsggggsQVQLVES<br>GGGVVQPGRSLRLSCAASGFTFSSYGMHWVRQAPGKGLEWVAFIRYDGSNK<br>YYADSVKGRFTISRDNSKNTLYLQMNSLRAEDTAVYYCKTHGSHDNWGQGT<br>MVTVSSHHHHHHEPEA |
| 73 | ACP11 (human p40/murine p35 IL12 fusion protein) | iwelkkdvyvveldwypdapgemvvitcdtpeedgitwadqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfsltfcvqvqgkskrekkdivfldktsatvicrknasisvraqthyysssweewasvpcsggggsggggsggggsr<br>vipvsgparclsqsrnllkttddmvktareklkhysctaedidheditrdqtstlktclplelhknesclatretssttrgs<br>clppqktslmmticlgsiyedlkmyqtefqainaalqnhnhqqiildkgmlvaidelmqslnhngetlrqkppvgead<br>pyrvkmklcillhafstrvvtinrvmgylssaSGGPGPAGMKGLPGSggggsggggsggggsggggsggg<br>gsggggsQSVLTQPPSVSGAPGQRVTISCSGSRSNIGSNTVKWYQQLPGTAPKLLI<br>YYNDQRPSGVPDRFSGSKSGTSASLAITGLQAEDEADYYCQSYDRYTHPALLF<br>GTGTKVTVLggggsggggsggggsQVQLVESGGGVVQPGRSLRLSCAASGFTFSSYG<br>MHWVRQAPGKGLEWVAFIRYDGSNKYYADSVKGRFTISRDNSKNTLYLQMN<br>SLRAEDTAVYYCKTHGSHDNWGQGTMVTVSSggggsggggsggggsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>HHHHHHEPEA |
| 74 | IL12 p40 human (Uniprot (Accession No. P29460 | 10 20 30 40 50<br>MCHQQLVISW FSLVFLASPL VAIWELKKDV YVVELDWYPD APGEMVVLTC<br>60 70 80 90 100<br>DTPEEDGITH TLDQSSEVLG SGKTLTIQVK EFGDAGQYTC HYGGEYLSHS<br>110 120 130 140 150<br>LLLHSKKEDG IWSTDILKDQ KEPKNKTFLR CEAKNYSGRF TCWWLTTIST<br>160 170 180 190 200<br>DLTFSVKSSR GSSDPQGVTC GAATLSAERV RGDMKEYEYS VECQEDSACP<br>210 220 230 240 250<br>AAEESLPIEV MVDAVHKLKY ENYTSSFFIR DIIKPDPPKN LQLKPLKNSR<br>260 270 280 290 300<br>QVEVSWEVPD TWSTPHSYFS LTFCVQVQGK SKRSKKDRVF TDKTSATVIC<br>310 320<br>RKNASISVRA QDRYYSSSWS EWASVPCS |
| 75 | IL12p35 mouse (Uniprot Accession No. P43430 | 10 20 30 40 50<br>MCQSRYLLFL ATLALLNHLS LARVIPVSGP ARCLSQSRNL LKTTDDMVKT<br>60 70 80 90 100<br>AREKLKHYSC TAEDIIHEDI TRDQTSTLKT CLPLELHKNE SCLATRETSS<br>110 120 130 140 150<br>TIRGSCLPPQ KTSLMNTLCL GSIYEDLKMY QTEFQAINAA LQNHNHQQII<br>160 170 180 190 200 |

-continued

| Sequence table | | |
|---|---|---|
| SEQ ID NO. | Name | Sequence |
| | | LDKGMLVAID ELMQSLNHNG ETLRQKPPVG EADPYRVKMK LCILLHAFST<br>210<br>RVVTINRVMG YLSSA |
| 76 | IL12Rb-2 | [illegible] |
| 77 | IL-12Rb1 | 10 20 30 40 50<br>MEPLVTWVVP LLFLFLLSRQ GAACRTSECC FQDPPYPDAD SGSASGPRDL<br>60 70 80 90 100<br>RCYRISSDRY ECSWQYEGPT AGVSHFLRCC LSSGRCCYFA AGSATRLQFS<br>110 120 130 140 150<br>DQAGVSVLYT VTLWVESWAR MQTEKSPEVT LQLYNSVKYE PPLGDIKVSK<br>160 170 180 190 200<br>LAGQLRMEWE TPDNQVGAEV QFRHRTPSSP WKLGDCGPQD DDIESCLCPL<br>210 220 230 240 250<br>EMNVAQKFQL PRRQLGSQGS SWSKWSSPVC VPPENPPQPQ VRESVEQLGQ<br>260 270 280 290 300<br>DGRRRLTLKE QPTQLELPEG CQGLAPGIEV TYRLQLHMLS CPCKAKATRT<br>310 320 330 340 350<br>LHLGKMPYLS GAAYNVAVIS SNQFGPGLNQ TWHIPADTHT EPVALNISVG<br>360 370 380 390 400<br>TNGTTMYWPA RAQSMTYCIE WQPVGQDGGL ATCSLTAPQD PDPAGMATYS<br>410 420 430 440 450<br>WSRESGAMGQ EKCYYITIFA SAHPEKLTLW STVLSTYKFG GNASAAGTPH<br>460 470 480 490 500<br>HVSVKNHSLD SVSVDWAPSL LSTCPGVLKE YVVRCRDEDS KQVSEHPVQP<br>510 520 530 540 550<br>TETQVTLSGL RAGVAYTVQV RADTAWLRGV WSQPQRFSIE VQVSDWLIFF<br>560 570 580 590 600<br>ASLGSFLSIL LVGVLGYLGL MRAARHLCPP LPIPCASSAI EEPGGKETWQ<br>610 620 630 640 650<br>WINPVDFQEE ASLQEALVVE MSWDKGERTE PLEKTELPEG APELALDTEL<br>660<br>SLEDGDRCKA KM |
| 78 | IL-12p35 human (Uniprot accession no. P29459) | 10 20 30 40 50<br>MCHQQLVISW FSLVFLASPL VAINELKKDV YVVEVDWTYD APGEMVVLTC<br>60 70 80 90 100<br>DTPEEDDITW TLDQSSEVLG SGKTLTIQVK EFGDAGQYTC HKGGEVLSHS<br>110 120 130 140 150<br>LLLLHKKEDG IWSTDILKDQ KEPKNKTFLR CEAKNYSGRF TCWWLTTIST<br>160 170 180 190 200<br>DLTFSVKSSR GSSDPQGVTC GAATLSAERV RDGNKEYEYS VECQEDSACP<br>210 220 230 240 250<br>AAEESLPIEV MVDAVHKLYK ENYTSSFFIR DIIKPDPPKN LQLKPLKNSR<br>260 270 280 290 300<br>QVEVSWEYPD TWSTPHSYFS LTFCVQVQGK SKREKKDRVF TDKTSATVIC<br>310 320<br>RKNASISVRA QDRYYSSSWS EWASVPCS |
| 79 | IL-12p40 mouse (Uniprot accession no. P43432) | 10 20 30 40 50<br>MCPQKLTISW FAIVLLVSPL MAMWELEKDV YVVEVDWTPD APGETVNLTC<br>60 70 80 90 100<br>DTPEEDDITW TSDQRHGVIG SGKTLTITVK ELFDAGQYTC HKGGETLSKS<br>110 120 130 140 150<br>HLLLHKKENG IWSTEILKNF KNKTFLKCEA PNYSGRFTCS WLVQRNMDLK |

-continued

Sequence table

| SEQ ID NO. | Name | Sequence |
|---|---|---|
| | | 160 170 180 190 200<br>FNIKSSSSSP DSRAVTCGMA SLSAEKVTLD QRDYEKYSVS CQEDVTCPTA<br>210 220 230 240 250<br>EETLPIELAL EARQQNKYEN YSTSFFIRDI IKPDPPKNLQ MKPLKNSQVE<br>260 270 280 290 300<br>VSWEYPDSWS TPHSYFSLKF FVRIQRKKEK MKETEEGCNQ KGAFLVEKTS<br>310 320 330<br>TEVQCKGGNV CVQAQDRYYN SSCSKWACVP CRVRS |
| 80 | ACP01 (mouse IFNg fusion protein) | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGShgtviesleslnnyfnssgidveekslfldiwrnwqkdgdm<br>kilqsqiisfylrlfevlkdnqaisnnisvieshlittffsnskakkdafmsiakfevnnpqvqrqafnelirvvh<br>celpessIrkrkrsrcSGGPGPAGMKGLPGSEVQLVESGGGLVQPGNSLRLSCAASGFTFSKFG<br>MSWVRQAPGKGLEWVSSISGSGRDTLYAESVKGRFTISRDNAKTTLYLQMNS<br>LRPEDTAVYYCTIGGSLSVSSQGTLVTVSSHHHHHH |
| 81 | ACP02 (mouse IFNg fusion protein) | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGShgtviesleslnnyfnssgidveekslfldiwrnwqkdgdmkilqsqiis<br>fylrlfevlkdnqaisnnisvieshlittffsnskakkdafmsiakfevnnpqvqrqafnelirvvhqllpesslr<br>krkrsrcSGGPGPAGMKGLPGShgtviesleslnnyfnssgidveekslfldiwrnwqkdgdmkilqsqiisf<br>ylrlfevlkdnqaisnnisvieshlittffsnskakkdafmsiakfevnnpqvqrqafnelirvvhqllpess<br>likrkrsrcSGGPGPAGMKGLPGSEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSHHHHHH |
| 82 | ACP03 (mouse IFNg fusion protein) | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGShgtviesleslnnyfnssgidveekslfldiwrnwqkdgdmilqsqiis<br>kfylrlfevlkdnqaisnnisvieshlittffsnskaldcdafmsiakfevnnpqvqrqafnelirvvhqllpesslr<br>krkrsrcggggsggggsggggshgtviesleslnnyfnssgidveekslfldiwrnwqkdgdmkilqsqiisfylrlfevl<br>kdnqaisnnisvieshlittffsnskaldcdafmsiakfevnnpqvqrqafnelirvvhqllpesslrkrkrsrcSGGPGP<br>AGMKGLPGSEVQLVESGGGLVQPGNSLRLSCAASGFTFSKFGMSWVRQAPGK<br>GLEWVSSISGSGRDTLYAESVKGRFTISRDNAKTTLYLQMNSLRPEDTAVYYC<br>TIGGSLSVSSQGTLVTVSSHHHHHH |
| 83 | Human IFN-g (Uniprot 60Accession No. P01579) | 10 20 30 40 50<br>MKYTSYILAF QLCIVLGSLG CYCQDPYVKE AENLKKYFNA GHSDVADNGT<br>60 70 80 90 100<br>LFLGILKNWK EESDRKIMQS QIVSFYFKLF KNFKDDQSIQ KSVETIKEDM<br>110 120 130 140 150<br>NVKFFNSNKK KRDDFEKLTN YSVTDLNVQR KAIHELIQVM AELSPAAKTG<br>160<br>KRKRSQMLFR GRRASQ |
| 84 | Mouse IFNg (Uniprot Accession No. P01580) | 10 20 30 40 50<br>MNATHCILAL QLFLMAVSGC YCHGTVIESL ESLNNYFNSS GIDVEEKSLF<br>60 70 80 90 100<br>LDIWRNQQKD GDMKILQSQI ISFYLRLFEV LKDNQAISNN ISVIESHLIT<br>110 120 130 140 150<br>TFFSNSKAKK DAFMSIAKFE VNNPQVQRQA FNELIRVVHQ LLPESSLRKR<br>KRSRC |
| 85 | ACP30 (mouse IFNg fusion protein) | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGShgtviesleslnnyfnssgidv<br>eekslfldiwrnwqkdgdmkilqsqiisfylrlfevlkdnqaisnnisvieshlittffsnskaldcdafmsiakfevnnpq<br>vqrqafnelirvvhqllpesslrkrkrsrcSGGPGPAGMKGLPGSEVQLVESGGGLVQPGNSLR<br>LSCAASGFTFSKFGMSWVRQAPGKGLEWVSSISGSGRDTLYAESVKGRFTISR<br>DNAKTTLYLQMNSLRPEDTAVYYCTIGGSLSVSSQGTLVTVSSSGGPGPAGM<br>KGLPGShgtviesleslnnyfnssgidveekslfldiwrnwqkdgdmkilqsqiisfylrlfevlkdnqaisnnisvie<br>shlittffsnskakkdafmsiakfevnnpqvqrqafnelirvvhcillpesslikrkrsrcSGGPGPAGMKGLPG<br>SEVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSHHHHHH |
| 86 | ACP31 (mouse IFNal fusion protein) | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGScdlpqthnlinkraltlkqmrrlsplsclkdrkdfgfpqekvd<br>aqqikkagaipvlseltqqilniftskdssaawnttlldsfendlhqqlndlqgclmqqvgvqefpltqedallavrkyfhri<br>tvylrekkhspcawevvraevwralsssanvlgrlreekSGGPGPAGMKGLPGSEVQLVESGGGL<br>VQPGNSLRLSCAASGFTFSKFGMSWVRQAPGKGLEWVSSISGSGRDTLYAESV |

-continued

Sequence table

| SEQ ID NO. | Name | Sequence |
|---|---|---|
| | | KGRFTISRDNAKTTLYLQMNSLRPEDTAVYYCTIGGSLSVSSQGTLVTVSSHH<br>HHHHEPEA |
| 87 | ACP32 (mouse IFNal fusion protein) | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGScdlpqthnlinkraltlkqmrrlsplsclkdrkdfgfpqekvd<br>aqqikkagaipvlseltqqilniftskdssaawnttlldsfendlhqqlndlqgclmqqvgvqefpltqedallavrkyfhri<br>tvylrekkhspcawevvraevwralsssanvSGGPGPAGMKGLPGSEVQLVESGGGLVQPGN<br>SLRLSCAASGFTFSKFGMSWVRQAPGKGLEWVSSISGSGRDTLYAESVKGRFT<br>ISRDNAKTTLYLQMNSLRPEDTAVYYCTIGGSLSVSSQGTLVTVSSHHHHHHE<br>PEA |
| 88 | IFNgR1 | 10 20 30 40 50<br>MALLFLLPLV MQGVSRAEMG TADLGPSSVP IPTNVTIESY NMNPIVYWEY<br>60 70 80 90 100<br>QIMPQVPVFT VEVKNYGVKN SEWIDACINI SHYYCNISDH VGDPSNSLWV<br>110 120 130 140 150<br>RVKARVGQKE SAYAKSEEFA VCRDGKIGPP KLDIRKEEKQ IMIDIFHPSV<br>160 170 180 190 200<br>FVNGDEQEVD YDPETTCYIR VYNVYVRMNG SEIQYKILTQ KEDDCDEIQC<br>210 220 230 240 250<br>QLAIPVSSLN SQYCVSAEGV LHVWGVTTEK SKEVCITIFN SSIKGSLWIP<br>260 270 280 290 300<br>VVAALLLFLV LSLVFICFYI KKINPLKEKS IILPKSLISV VRSAILETKP<br>310 320 330 340 350<br>ESKYVSLITS YQPFSLEKEV VCEEPLSPAT VPGMHTEDNP QKVEHTEELS<br>360 370 380 390 400<br>SITEVVTTEE NIPDVVPGSH LTPIERESSS PLSSNQSEPG SIALMSYHSR<br>410 420 430 440 450<br>MCSESDHSRN GFDTDSSCLE SHSSLSDSEF PPNNKGEIKT EGQELITVIK<br>460 470 480 490 500<br>APTSFGYDKP HVLVDLLVDD SGKESLTGYR PTEDSKEFS |
| 89 | IFNgR2 | 10 20 30 40 50<br>MRPTLLWSLL LLLGVFAAAA AAPPDPLSQL PAPQHPKIRL YNAEQVLSWE<br>60 70 80 90 100<br>PVALSNSTRP VVYQVQFKYI DSKWFTADIM SIGVNCTQIT ATECDFTAAS<br>110 120 130 140 150<br>PSAGFPMDFN VTLRLRAELG ALHSAWVTMP WFQHYRNVTV GPPENIEVTP<br>160 170 180 190 200<br>GEGSLIIRFS SPFDIADTST AFFCYYVHYW EKGGIQQVKG PFRSNSISLD<br>210 220 230 240 250<br>NLKPSRVYCL QVQAQLLWNK SNIFRVGHLS NISCYEIMAD ASTELQQVIL<br>260 270 280 290 300<br>ISVGTFSLLS VLAGACFFLV LKYRGLIKYW FHTPPSIPLQ IEEYLKDPTQ<br>310 320 330 340 350<br>FILEALDKDS SPKDDVWDGV SIISFPEKEQ EDVLQTL |
| 90 | ACP51 Mouse IFG fusion protein | QVQLQESGGGLVQAGGSLRLSCAASGRIFSIDIMSWYRQAPGKQRELVARITR<br>GGTISYDDSVKGRFTISRDNAKNTVYLQMNSLKPEDTGVYYCNALYGTDYW<br>GKGTQVTVSSggggsggggsggggsEVQLVESGGGLVQPGNSLRLSCAASGFTFSKF<br>GMSWVRQAPGKGLEWVSSISGSGRDTLYAESVKGRFTISRDNAKTTLYLQMN<br>SLRPEDTAVYYCTIGGSLSVSSQGTLVTVSSSGGPGPAGMKGLPGShgtviesplesln<br>nyfnssgidveekslfldiwrnwqkdgdmkilqsqiisfylrlfevlkdnqaisnnisvieshlittffsnskakkdafmsi<br>akfevnnpqvqrqafnelirvvhqllpessIrkrkrsrcSGGPGPAGMKGLPGSEVQLVESGGGLV<br>QPGNSLRLSCAASGFTFSKFGMSWVRQAPGKGLEWVSSISGSGRDTLYAESVK<br>GRFTISRDNAKTTLYLQMNSLRPEDTAVYYCTIGGSLSVSSQGTLVTVSSHHH<br>HHH |
| 91 | ACP52 Mouse IFG fusion protein | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGShgtviesleslnnyfnssgidveekslfldiwrnwqkdgdm<br>kilqsqiisfylrlfevlkdnqaisnnisvieshlittffsnskakkdafmsiakfevnnpqvqrqafnelirvvhq<br>llpessIrkrkrsrcSGGPGPAGMKGLPGSEVQLVESGGGLVQPGNSLRLSCAASGFTFSKFG<br>MSWVRQAPGKGLEWVSSISGSGRDTLYAESVKGRFTISRDNAKTTLYLQMNS<br>LRPEDTAVYYCTIGGSLSVSSQGTLVTVSSSGGPGPAGMKGLPGSEVQLVESG<br>GGLVQPGNSLRLSCAASGFTFSKFGMSWVRQAPGKGLEWVSSISGSGRDTLY<br>AESVKGRFTISRDNAKTTLYLQMNSLRPEDTAVYYCTIGGSLSVSSQGTLVTV<br>SSggggsggggsggggsQVQLQESGGGLVQAGGSLRLSCAASGRIFSIDIMSWYRQA<br>PGKQRELVARITRGGTISYDDSVKGRFTISRDNAKNTVYLQMNSLKPEDTGVY<br>YCNALYGTDYWGKGTQVTVSSHHHHHH |

-continued

Sequence table

| SEQ ID NO. | Name | Sequence |
|---|---|---|
| 92 | ACP53 Mouse IFG fusion protein | eahkseiahryndlgeqhfkglvliafsqylqkcsydehaklvqevtdfaktcvadesaancdkslhtlfgdklcaipnlr<br>enygeladcctkqepemecflqlikddnpslppferpeaeamctsfkenpttfmghylhevarrlipyfyapellyyaeq<br>yneiltqccaeadkescltpkldgvkekalvssvrqrmkcssmqkfgerafkawavarlsqtfpnadfaeitklatdltkv<br>nkecchgdllecaddraelakymcenqatissklqtccdkpllkkahclsevehdtmpadlpaiaadfVedqevckny<br>aeakdvflgtflyeysrrhpdysvslllrlakkyeatlekccaeanppacygtvlaefqplveepknlvktncdlyeklgey<br>gfqnailvrytqkapqvstpUveaamlgrvgtkcctlpedqrlpcvedylsailnrvcllhektpvsehvtkccsgslver<br>rpcfsaltvdetyvpkefkaetftflisdictlpekekqikkqtalaelvkhkpkataeqlktvmddfaqfldtcckaadkdt<br>cfstegpnlvtrckdalaSGGPGPAGMKGLPGShgtviesleshmyfiissgidveekslfldiwrnwqkdgdmkilqsq<br>iisfylrlfevlkdiiqaismiisvieshlittffsiiskakkdafmsiakfevmipqvqrqafnelirvvliqllpes<br>slrkrkrsrcSGGPGPAGMKGLPGSeahkseiahiyndlgeqhfkglvliafsqylqkcsydehaklvqevtd<br>faktcvadesaancdkslhtlfgdklcaipnlrenygeladcctkqepemecflqhkddnpslppferpeaeamctslk<br>enpttfmghylhevarrhpyiyapellyyaeqyneiltqccaeadkescltpkldgvkekalvssvrqrmkcssmqkf<br>gcrafkawavarlsqtfpnadfaeitklatdltkvnkecchgdllecaddrackikymccnqatissklqtccdkpllkka<br>hclsevehdtmpadlpaiaadfVedqevcknyaeakdvflgtflyeysrrhpdysvslllrlakkyeatlekccaeanpp<br>acygtvlaefqplveepknlvktncdlyeklgeygfqnailvrytqkapqvstpUveaamlgrvgtkcctlpedqrlpcv<br>edylsailnrvcllhcktpvsehvtkccsgslverrpcfsaltvdetyvpkefkaetftnisdictlpekekqikkqtalaelv<br>klikpkalaeqlktvmddfaqfldtcckaadkdtcfstegpulvtrckdalaHHHHHH |
| 93 | ACP54 Mouse IFG fusion protein | eahkseiahiyndlgeqhfkglvliafsqylqkcsydehaklvqevtdfaktcvadesaancdkslhtlfgdklcaipnlr<br>enygeladcctkqepemecflqhkddnpslppferpeaeamctsfkenpttfmghylhevarrhpyfyapellyyaeq<br>yneiltqccaeadkescltpkldgvkekalvssviqrmkcssmqkfgerafkawavarlsqtfpnadfaeitklatdltkv<br>nkecchgdllecaddraelakymcenqatissklqtccdkpllkkahclsevehdtmpadlpaiaadfVedqevckny<br>aeakdvflgtflyeysrrhpdysvslllrlakkyeatlekccaeanppacygtvlaefqplveepkiilvktncdlyeklgey<br>gfqnailviytqkapqvstptiveaarnlgrvgtkcctlpedqrlpcvedylsailmvcllhektpvsehvtkccsgslver<br>rpcfsaltvdetyvpkefkaetftfhsdictlpekekqikkqtalaelvkhkpkataeqlktvmddfaqfldtcckaadkdt<br>cfstegpnlvtrckdalaSGGPGPAGMKGLPGShgtviesleslіinyfussgidveekslfldiwrnwqkdgd<br>mkilqsqiisfylrlfevlkdnqaismiisvieshlittffsnskakkdafnisiakfevmipqvqrqafnelirvvhqllpes<br>slrkrkrsrcggggsggggsggggshgtviesleslnnyfnssgidveekslfldiwmwqkdgdmkilqsqiisfylrlf<br>evlkdnqaisnnisvieshlittffsnskakkdafmsiakfevnnpqvqrqafnelirvvhqllpesslrkrkrsrcSGGP<br>GPAGMKGLPGSeahkseiahiyndlgeqhfkglvliafsqylqkcsydehaklvqevtdfaktcvadesaanc<br>dkslhtlfgdklcaipiilrenygeladcclkqepeniecflqhkddnpslppferpeaeamctsfkenpttfmghylhev<br>arrhpyfyapellyyaeqyneiltqccaeadkescltpkldgvkekalvssvrqnnkcssmqkfgerafkawavarlsq<br>tfpnadfaeitklatdltkvnkecchgdllecaddraelakymcenqatissklqtccdkpllkkahclsevehdtmpadl<br>paiaadfvedqevckiiyaeakdvflgtflyeysrrhpdysvslllrlakkyeatlekccaeanppacygtvlaefqplvee<br>pknlvktncdlyeklgeygfqnailviytqkapqvstptlveaamlgrvgtkcctlpedqrlpcvedylsailnrvcllhe<br>ktpvsehvtkccsgslverrpcfsaltvdetyvpkefkaetftfhsdictlpekekqikkqtalaelvkhkpkataeqlktv<br>mddfaqfldtcckaadkdtcfstegpnlvtrckdalaHHHHHH |
| 94 | ACP50 Mouse IFG fusion protein | mdmrvpaqllglllwlrgarcQVQLQESGGGLVQAGGSLRLSCAASGRIFSIDIMSWYR<br>QAPGKQRELVARITRGGTISYDDSVKGRFTISRDNAKNTVYLQMNSLKPEDTG<br>VYYCNALYGTDYWGKGTQVTVSSggggsggggsggggsEVQLVESGGGLVQPGNS<br>LRLSCAASGFTFSKFGMSWVRQAPGKGLEWVSSISGSGRDTLYAESVKGRFTI<br>SRDNAKTTLYLQMNSLRPEDTAVYYCTIGGSLSVSSQGTLVTVSSSGGPGPAG<br>MKGLPGShgtviesleslnnyfrissgidveekslfldiwrnwqkdgdmkilqsqiisfylrlfevlkdnqaisnnisvies<br>hlittffsnskaldcdafmsiakfevnnpqvqrqafnelirvvhqllpesslitcrlcrsreggggsggggsggggshgtv<br>iesleslnnyfussgidveekslfldiwrnwqkdgdmkilqsqiisfylrlfevlkdnqaisnnisvieshlittffsnskak<br>lulafmsiakfevnnpqvqrqafnelirvvhqllpesslrkrkrsrcSGGPGPAGMKGLPGSEVQLVES<br>GGGLVQPGNSLRLSCAASGFTFSKFGMSWVRQAPGKGLEWVSSISGSGRDTL<br>YAESVKGRFTISRDNAKTTLYLQMNSLRPEDTAVYYCTIGGSLSVSSQGTLVT<br>VSSHHHHHH |
| 95 | ACP55 Mouse IFG fusion protein | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGShgtviesleslnnyfnssgidv<br>eekslfldiwrnwqkdgdmkilqsqiisfylrlfevlkdnqaisnnisvieshlittffsnskaldcdafmsiakfevnnpq<br>vqrqafnelirvvhqllpesslrkrkrsrcSGGPGPAGMKGLPGSEVQLVESGGGLVQPGNSLR<br>LSCAASGFTFSKFGMSWVRQAPGKGLEWVSSISGSGRDTLYAESVKGRFTISR<br>DNAKTTLYLQMNSLRPEDTAVYYCTIGGSLSVSSQGTLVTVSSSGGPGPAGM<br>KGLPGShgtviesleslnnyfrissgidveekslfldiwrnwqkdgdmkilqsqiisfylrlfevlkdnqaisnnisvie<br>shlittffsnskakkdafmsiakfevnnpqvqrqafnelirvvhqllpesslrkrkrsrcSGGPGPAGMKGLPG<br>SEVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSHHHHHH |
| 96 | ACP56 Mouse IFG fusion protein | mclmrvpaqllglllwlrgarcQVQLQESGGGLAQAGGSLSLSCAASGFTVSNSVMAWY<br>RQTPGKQREFVAIINSVGSTNYADSVKGRFTISRDNAKNTVYLQMNNLKPEDT<br>AVYVCNRNFDRIYWGQGTQVTVSSggggsggggsggggsEVQLVESGGGLVQPGNS<br>LRLSCAASGFTFSKFGMSWVRQAPGKGLEWVSSISGSGRDTLYAESVKGRFTI<br>SRDNAKTTLYLQMNSLRPEDTAVYYCTIGGSLSVSSQGTLVTVSSSGGPGPAG<br>MKGLPGShgtviesleslnnyfrissgidveekslfldiwrnwqkdgdmkilqsqiisfylrlfevlkdnqaisnnisv<br>ieshlittffsnskakkdafmsiakfevnnpqvqrqafnelirvvhqllpesslrkrkrsrcSGGPGPAGMKGLP<br>GSEVQLVESGGGLVQPGNSLRLSCAASGFTFSKFGMSWVRQAPGKGLEWVSS |

-continued

Sequence table

| SEQ ID NO. | Name | Sequence |
|---|---|---|
| | | ISGSGRDTLYAESVKGRFTISRDNAKTTLYLQMNSLRPEDTAVYYCTIGGSLSV<br>SSQGTLVTVSSHHHHHHEPEA |
| 97 | ACP57 Mouse IFG fusion protein | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGShgtviesleslnnyfnssgidv<br>eekslfldiwrnwqkdgdmkilqsqiisfylrlfevlkdnqaisnnisvieshlittffsnskaldcdafmsiakfevnnpq<br>vqrqafnelirvvhqllpesslrkrkrsrcSGGPGPAGMKGLPGSEVQLVESGGGLVQPGNSLR<br>LSCAASGFTFSKFGMSWVRQAPGKGLEWVSSISGSGRDTLYAESVKGRFTISR<br>DNAKTTLYLQMNSLRPEDTAVYYCTIGGSLSVSSQGTLVTVSSggggsggggsgggg<br>sQVQLQESGGGLAQAGGSLSLSCAASGFTVSNSVMAWYRQTPGKQREFVAIIN<br>SVGSTNYADSVKGRFTISRDNAKNTVYLQMNNLKPEDTAVYVCNRNFDRIY<br>WGQGTQVTVSSHHHHHHEPEA |
| 98 | ACP58 Mouse fusion protein | mdmrvpaqllglllwlrgarcEVQLVESGGGLVQPGNSLRLSCAASGFTFSKFGMSWVR<br>IFGQAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGShgtviesleslnnyfnssgidv<br>eekslfldiwrnwqkdgdmkilqsqiisfylrlfevlkdnqaisnnisvieshlittffsnskaldcdafmsiakfevnnpq<br>vqrqafnelirvvhqllpesshicrkrsrcSGGPGPAGMKGLPGShgtviesleslnnyfrissgidveekslfldi<br>wrnwqkdgdmkilqsqiisfylrlfevlkdnqaisnnisvieshlittffsnskaldcdafmsiakfevnnpqvqrqafnel<br>irvvhqllpesslrkrkrsrcSGGPGPAGMKGLPGSEVQLVESGGGLVQPGNSLRLSCAAS<br>GFTFSKFGMSWVRQAPGKGLEWVSSISGSGRDTLYAESVKGRFTISRDNAKTT<br>LYLQMNSLRPEDTAVYYCTIGGSLSVSSQGTLVTVSSggggsggggsggggsQVQLQ<br>ESGGGLVQAGGSLRLSCAASGRIFSIDIMSWYRQAPGKQRELVARITRGGTISY<br>DDSVKGRFTISRDNAKNTVYLQMNSLKPEDTGVYYCNALYGTDYWGKGTQV<br>TVSSHHHHHHEPEA |
| 99 | ACP59 Mouse IFG fusion protein | mclmrvpaqllglllwlrgarcQVQLQESGGGLAQAGGSLSLSCAASGFTVSNSVMAWY<br>RQTPGKQREFVAIINSVGSTNYADSVKGRFTISRDNAKNTVYLQMNNLKPEDT<br>AVYVCNRNFDRIYWGQGTQVTVSSggggsggggsggggsEVQLVESGGGLVQPGNS<br>LRLSCAASGFTFSKFGMSWVRQAPGKGLEWVSSISGSGRDTLYAESVKGRFTI<br>SRDNAKTTLYLQMNSLRPEDTAVYYCTIGGSLSVSSQGTLVTVSSSGGPGPAG<br>MKGLPGShgtviesleslnnyfrissgidveekslfldiwrnwqkdgdmkilqsqiisfylrlfevlkdnqaisnnisv<br>ieshlittffsnskakkdafmsiakfevnnpqvqrqafnelirvvhqllpesslrkrkrsrcSGGPGPAGMKGLP<br>GShgtviesleslnnyfrissgidveekslfldiwrnwqkdgdmkilqsqiisfylrlfevlkdnqaisnnisviesh<br>littffsnskakkdafmsiakfevnnpqvqrqafnelirvvhqllpesslikrkrsrcSGGPGPAGMKGLPGSEVQ<br>LVESGGGLVQPGNSLRLSCAASGFTFSKFGMSWVRQAPGKGLEWVSSISGSGR<br>DTLYAESVKGRFTISRDNAKTTLYLQMNSLRPEDTAVYYCTIGGSLSVSSQGT<br>LVTVSSHHHHHHEPEA |
| 100 | ACP60 Mouse IFG fusion protein | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGShgtviesleslnnyfnssgidv<br>eekslfldiwrnwqkdgdmkilqsqiisfylrlfevlkdnqaisnnisvieshlittffsnskaldcdafmsiakfevnnpq<br>vqrqafnelirvvhqllpesshicrkrsrcSGGPGPAGMKGLPGShgtviesleslnnyfrissgidveekslfldi<br>wrnwqkdgdmkilqsqiisfylrlfevlkdnqaisnnisvieshlittffsnskaldcdafmsiakfevnnpqvqrqafnel<br>irvvhqllpesslikrkrsrcSGGPGPAGMKGLPGSEVQLVESGGGLVQPGNSLRLSCAAS<br>GFTFSKFGMSWVRQAPGKGLEWVSSISGSGRDTLYAESVKGRFTISRDNAKTT<br>LYLQMNSLRPEDTAVYYCTIGGSLSVSSQGTLVTVSSggggsggggsggggsQVQLQ<br>ESGGGLAQAGGSLSLSCAASGFTVSNSVMAWYRQTPGKQREFVAIINSVGSTN<br>YADSVKGRFTISRDNAKNTVYLQMNNLKPEDTAVYVCNRNFDRIYWGQGTQ<br>VTVSSHHHHHHEPEA |
| 101 | ACP61 Mouse IFG fusion protein | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGShgtviesleslnnyfnssgidv<br>eekslfldiwrnwqkdgdmkilqsqiisfylrlfevlkdnqaisnnisvieshlittffsnskaldcdafmsiakfevnnpq<br>vqrqafnelirvvhqllpesslikrkrsrcSGGPGPAGMKGLPGShgtviesleslnnyfnssgidveekslfldi<br>wrnwqkdgdmkilqsqiisfylrlfevlkdnqaisnnisvieshlittffsnskaldcdafmsiakfevnnpqvqrqafnel<br>irvvhqllpesslikrkrsrcSGGPGPAGMKGLPGSEVQLVESGGGLVQPGNSLRLSCAAS<br>VGFTFSKFGMSWVRQAPGKGLEWVSSISGSGRDTLYAESVKGRFTISRDNAKTT<br>LYLQMNSLRPEDTAVYYCTIGGSLSVSSQGTLVTVSSggggsggggsggggsEVQLV<br>ESGGGLVQPGGSLRLSCAASGFTFSSYAMSWVRQAPGKGLEWVSAISGSGGS<br>TYYADSVKGRFTISRDNSKNTLYLQMNSLRAEDTAVYYCARGVGAFRPYRKH<br>EWGQGTLVTVSRggggsggggsggggsSSELTQDPAVSVALGQTVRITCQGDSLRSY<br>YASWYQQKPGQAPVLVIYGKNNRPSGIPDRFSGSSSGNTASLTTTGAQAEDEA<br>DYYCNSSPFEENLVVFGGGTKLTVLHHHHHHEPEA |
| 102 | ACP63 Anti-FN CGS-2 scFv | mdmrvpaqllglllwlrgarcEVQLVESGGGLVQPGGSLRLSCAASGFTFSSYAMSWVR<br>QAPGKGLEWVSAISGSGGSTYYADSVKGRFTISRDNSKNTLYLQMNSLRAED<br>TAVYYCARGVGAFRPYRKHEWGQGTLVTVSRggggsggggsggggsSSELTQDPAV<br>SVALGQTVRITCQGDSLRSYYASWYQQKPGQAPVLVIYGKNNRPSGIPDRFSG |

-continued

Sequence table

| SEQ ID NO. | Name | Sequence |
|---|---|---|
| | | SSSGNTASLTTTGAQAEDEADYYCNSSPFEHNLVVFGGGTKLTVLHHHHHHE<br>PEA |
| 103 | ACP69 Mouse IFG fusion protein | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGShgtviesleslnnyfnssgidv<br>eekslfldiwrnwqkdgdmkilqsqiisfylrlfevlkdnqaisnnisvieshlittffsnskaldcdafmsiakfevnnpq<br>vqrqafnelirvvhqllpesslikrkrsrcSGGPGPAGMKGLPGSEVQLVESGGGLVQPGNSLR<br>LSCAASGFTFSKFGMSWVRQAPGKGLEWVSSISGSGRDTLYAESVKGRFTISR<br>DNAKTTLYLQMNSLRPEDTAVYYCTIGGSLSVSSQGTLVTVSSSGGPGPAGM<br>KGLPGShgtviesleslnnyfnssgidveekslfldiwrnwqkdgdmkilqsqiisfylrlfevlkdnqaisnnisvie<br>shlittffsnskakkdafmsiakfevnnpqvqrqafnelirvvhqllpesshkrkrsrcHHHHHHEPEA |
| 104 | ACP70 Mouse IFG fusion protein | mdmrvpaqllglllwlrgarchgtviesleslnnyfnssgidveekslfkliwrnwqkdgdmkilqsqiisfylrlfevlk<br>dnqaisnnisvieshlittffsnskakkdafmsiakfevnnpqvqrqafnelirvvhqllpesshkrkrsrcSGGPGP<br>AGMKGLPGSEVQLVESGGGLVQPGNSLRLSCAASGFTFSKFGMSWVRQAPGK<br>GLEWVSSISGSGRDTLYAESVKGRFTISRDNAKTTLYLQMNSLRPEDTAVYYC<br>TIGGSLSVSSQGTLVTVSSSGGPGPAGMKGLPGShgtviesleslnnyfnssgidveekslfldi<br>wrnwqkdgdmkilqsqiisfylrlfevlkdnqaisnnisvieshlittffsnskaldcdafmsiakfevnnpqvqrqafnel<br>irvvhqllpesslikrkrsrcSGGPGPAGMKGLPGSEVQLVESGGGLVQPGNSLRLSCAAS<br>GFTFSKFGMSWVRQAPGKGLEWVSSISGSGRDTLYAESVKGRFTISRDNAKTT<br>LYLQMNSLRPEDTAVYYCTIGGSLSVSSQGTLVTVSSHHHHHHEPEA |
| 105 | ACP71 Mouse IFG fusion protein | mdmrvpaqllglllwlrgarchgtviesleslnnyfnssgidveekslfldiwrnwqkdgdmkilqsqiisfylrlfevlk<br>dnqaisnnisvieshlittffsnskakkdafmsiakfevnnpqvqrqafnelirvvhqllpesshkrkrsrcSGGPGP<br>AGMKGLPGSEAHKSEIAHRYNDLGEQHFKGLVLIAFSQYLQKCSYDEHAKLV<br>QEVTDFAKTCVADESAANCDKSLHTLFGDKLCAIPNLRENYGELADCCTKQE<br>PERNECFLQHKDDNPSLPPFERPEAEAMCTSFKENPTTFMGHYLHEVARRHPY<br>FYAPELLYYAEQYNEILTQCCAEADKESCLTPKLDGVKEKALVSSVRQRMKC<br>SSMQKFGERAFKAWAVARLSQTFPNADFAEITKLATDLTKVNKECCHGDLLE<br>CADDRAELAKYMCENQATISSKLQTCCDKPLLKKAHCLSEVEHDTMPADLPA<br>IAADFVEDQEVCKNYAEAKDVFLGlFLYEYSRRHPDYSVSLLLRLAKKYEAT<br>LEKCCAEANPPACYGTVLAEFQPLVEEPKNLVKTNCDLYEKLGEYGFQNAILV<br>RYTQKAPQVSTPTLVEAARNLGRVGTKCCTLPEDQRLPCVEDYLSAILNRVCL<br>LHEKTPVSEHVIKCCSGSLVERRPCFSALTVDETYVPKEFKAETFTFHSDICTL<br>PEKEKQIKKQTALAELVKHKPKATAEQLKTVMDDFAQFLDTCCKAADKDTCF<br>STEGPNLVTRCKDALASGGPGPAGMKGLPGShgtviesleslnnyfassgidveekslfldiwrn<br>wqkdgdmkilqsqiisfylrlfevlkdnqaisnnisvieshlittffsnskaldcdafmsiakfevnnpqvqr<br>qafneliryvhqllpesslrkrkrsrcSGGPGPAGMKGLPGSEAHKSEIAHRYNDLGEQHFKGLVLIAF<br>SQYLQKCSYDEHAKLVQEVTDFAKTCVADESAANCDKSLHTLFGDKLCAIPN<br>LRENYGELADCCTKQEPERNECFLQHKDDNPSLPPFERPEAEAMCTSFKENPT<br>TFMGHYLHEVARRHPYFYAPELLYYAEQYNEILTQCCAEADKESCLTPKLDG<br>VKEKALVSSVRQRMKCSSMQKFGERAFKAWAVARLSQTFPNADFAEITKLAT<br>DLTKVNKECCHGDLLECADDRAELAKYMCENQATISSKLQTCCDKPLLKKAH<br>CLSEVEHDTMPADLPAIAADFVEDQEVCKNYAEAKDVFLGTFLYEYSRRHPD<br>YSVSLLLRLAKKYEATLEKCCAEANPPACYGTVLAEFQPLVEEPKNLVKTNC<br>DLYEKLGEYGFQNAILVRYTQKAPQVSTPTLVEAARNLGRVGTKCCTLPEDQ<br>RLPCVEDYLSAILNRVCLLHEKTPVSEHVTKCCSGSLVERRPCFSALTVDETYV<br>PKEFKAETFTFHSDICTLPEKEKQIKKQTALAELVKHKPKATAEQLKTVMDDF<br>AQFLDTCCKAADKDTCFSTEGPNLVTRCKDALAHHHHHHEPEA |
| 106 | ACP72 Mouse IFG fusion protein | mdmrvpaqllglllwlrgarcEAHKSEIAHRYNDLGEQHFKGLVLIAFSQYLQKCSYDE<br>HAKLVQEVTDFAKTCVADESAANCDKSLHTLFGDKLCAIPNLRENYGELADC<br>CTKQEPERNECFLQHKDDNPSLPPFERPEAEAMCTSFKENPTTFMGHYLHEVA<br>RRHPYFYAPELLYYAEQYNEILTQCCAEADKESCLTPKLDGVKEKALVSSVRQ<br>RMKCSSMQKFGERAFKAWAVARLSQTFPNADFAEITKLATDLTKVNKECCH<br>GDLLECADDRAELAKYMCENQATISSKLQTCCDKPLLKKAHCLSEVEHDTMP<br>ADLPAIAADFVEDQEVCKNYAEAKDVFLGTFLYEYSRRHPDYSVSLLLRLAK<br>KYEATLEKCCAEANPPACYGTVLAEFQPLVEEPKNLVKTNCDLYEKLGEYGF<br>QNAILVRYTQKAPQVSTPTLVEAARNLGRVGTKCCTLPEDQRLPCVEDYLSAI<br>LNRVCLLHEKTPVSEHVTKCCSGSLVERRPCFSALTVDETYVPKEFKAETFTFH<br>SDICTLPEKEKQIKKQTALAELVKHKPKATAEQLKTVMDDFAQFLDTCCKAA<br>DKDTCFSTEGPNLVTRCKDALASGGPGPAGMKGLPGShgtviesleslnnythssgidveekslfld<br>iwrnwqkdgdmkilqsqiisfylrlfevlkdnqaisnnisvieshlittffsnskakkdafmsiakfevnnpqvq<br>rqafnelirvvhqllpesslitcrkrsrcSGGPGPAGMKGLPGSEAHKSEIAHRYNDLGEQHFK<br>GLVLIAFSQYLQKCSYDEHAKLVQEVTDFAKTCVADESAANCDKSLHTLFGD<br>KLCAIPNLRENYGELADCCTKQEPERNECFLQHKDDNPSLPPFERPEAEAMCT<br>SFKENPTTFMGHYLHEVARRHPYFYAPELLYYAEQYNEILTQCCAEADKESCL<br>TPKLDGVKEKALVSSVRQRMKCSSMQKFGERAFKAWAVARLSQTFPNADFA<br>EITKLATDLTKVNKECCHGDLLECADDRAELAKYMCENQATISSKLQTCCDK<br>PLLKKAHCLSEVEHDTMPADLPAIAADFVEDQEVCKNYAEAKDVFLGTFLYE<br>YSRRHPDYSVSLLLRLAKKYEATLEKCCAEANPPACYGTVLAEFQPLVEEPKN<br>LVKTNCDLYEKLGEYGFQNAILVRYTQKAPQVSTPTLVEAARNLGRVGTKCC |

-continued

Sequence table

| SEQ ID NO. | Name | Sequence |
|---|---|---|
| | | TLPEDQRLPCVEDYLSAILNRVCLLHEKTPVSEHVTKCCSGSLVERRPCFSALT VDETYVPKEFKAETFTFHSDICTLPEKEKQIKKQTALAELVKHKPKATAEQLK TVMDDFAQFLDTCCKAADKDTCFSTEGPNLVTRCKDALASGGPGPAGMKGLPGShgtvie sleslnnyfassgidveekslfldiwrnwqkdgdmkilqsqiisfylrlfevlkdnqaisnnisvieshlitt ffsnskakkdafmsiakfevnnpqvqrqafnelirvvhqllpesslrkrkrsrcHHHHHHEPEA |
| 107 | ACP73 Mouse IFG fusion protein | mdmrvpaqllglllwlrgarcEAHKSEIAHRYNDLGEQHFKGLVLIAFSQYLQKCSYDE HAKLVQEVTDFAKTCVADESAANCDKSLHTLFGDKLCAIPNLRENYGELADC CTKQEPERNECFLQHKDDNPSLPPFERPEAEAMCTSFKENPTTFMGHYLHEVA RRHPYFYAPELLYYAEQYNEILTQCCAEADKESCLTPKLDGVKEKALVSSVRQ RMKCSSMQKFGERAFKAWAVARLSQTFPNADFAEITKLATDLTKVNKECCH GDLLECADDRAELAKYMCENQATISSKLQTCCDKPLLKKAHCLSEVEHDTMP ADLPAIAADFVEDQEVCKNYAEAKDVFLGTFLYEYSRRHPDYSVSLLLRLAK KYEATLEKCCAEANPPACYGTVLAEFQPLVEEPKNLVKTNCDLYEKLGEYGF QNAILVRYTQKAPQVSTPTLVEAARNLGRVGTKCCTLPEDQRLPCVEDYLSAI LNRVCLLHEKTPVSEHVTKCCSGSLVERRPCFSALTVDETYVPKEFKAETFTFH SDICTLPEKEKQIKKQTALAELVKHKPKATAEQLKTVMDDFAQFLDTCCKAA DKDTCFSTEGPNLVTRCKDALASGGPGPAGMKGLPGShgtviesleslnnythssgidvee kslfldiwrnwqkdgdmkilqsqiisfylrlfevlkdnqaisnnisvieshlittffsnskakkdafms iakfevnnpqvqrqafnelirvvhqllpesslitcrkrsrcSGGPGPAGMKGLPGSEAHKSEIAHRYNDLGEQHFK GLVLIAFSQYLQKCSYDEHAKLVQEVTDFAKTCVADESAANCDKSLHTLFGD KLCAIPNLRENYGELADCCTKQEPERNECFLQHKDDNPSLPPFERPEAEAMCT SFKENPTTFMGHYLHEVARRHPYFYAPELLYYAEQYNEILTQCCAEADKESCL TPKLDGVKEKALVSSVRQRMKCSSMQKFGERAFKAWAVARLSQTFPNADFA EITKLATDLTKVNKECCHGDLLECADDRAELAKYMCENQATISSKLQTCCDK PLLKKAHCLSEVEHDTMPADLPAIAADFVEDQEVCKNYAEAKDVFLGTFLYE YSRRHPDYSVSLLLRLAKKYEATLEKCCAEANPPACYGTVLAEFQPLVEEPKN LVKTNCDLYEKLGEYGFQNAILVRYTQKAPQVSTPTLVEAARNLGRVGTKCC TLPEDQRLPCVEDYLSAILNRVCLLHEKTPVSEHVTKCCSGSLVERRPCFSALT VDETYVPKEFKAETFTFHSDICTLPEKEKQIKKQTALAELVKHKPKATAEQLK TVMDDFAQFLDTCCKAADKDTCFSTEGPNLVTRCKDALASGGPGPAGMKGL PGShgtviesleslnnyfrissgidveekslfldiwrnwqkdgdmkilqsqiisfylrlfevlkdnqaisnnisvieshlitt ffsnskaldcdafmsiakfevnnpqvqrqafnelirvvhqllpesslrkrkrsrcSGGPGPAGMKGLPGSEA HKSEIAHRYNDLGEQHFKGLVLIAFSQYLQKCSYDEHAKLVQEVTDFAKTCV ADESAANCDKSLHTLFGDKLCAIPNLRENYGELADCCTKQEPERNECFLQHK DDNPSLPPFERPEAEAMCTSFKENPTTFMGHYLHEVARRHPYFYAPELLYYAE QYNEILTQCCAEADKESCLTPKLDGVKEKALVSSVRQRMKCSSMQKFGERAF KAWAVARLSQIFPNADFAEITKLATDLTKVNKECCHGDLLECADDRAELAKY MCENQATISSKLQTCCDKPLLKKAHCLSEVEHDTMPADLPAIAADFVEDQEV CKNYAEAKDVFLGTFLYEYSRRHPDYSVSLLLRLAKKYEATLEKCCAEANPP ACYGTVLAEFQPLVEEPKNLVKTNCDLYEKLGEYGFQNAILVRYTQKAPQVS TPTLVEAARNLGRVGTKCCTLPEDQRLPCVEDYLSAILNRVCLLHEKTPVSEH VTKCCSGSLVERRPCFSALTVDETYVPKEFKAETFTFHSDICTLPEKEKQIKKQ TALAELVKHKPKATAEQLKTVMDDFAQFLDTCCKAADKDTCFSTEGPNLVTR CKDALAHHHHHHEPEA |
| 108 | ACP74 Mouse IFG fusion protein | mdmrvpaqllglllwlrgarcEAHKSEIAHRYNDLGEQHFKGLVLIAFSQYLQKCSYDE HAKLVQEVTDFAKTCVADESAANCDKSLHTLFGDKLCAIPNLRENYGELADC CTKQEPERNECFLQHKDDNPSLPPFERPEAEAMCTSFKENPTTFMGHYLHEVA RRHPYFYAPELLYYAEQYNEILTQCCAEADKESCLTPKLDGVKEKALVSSVRQ RMKCSSMQKFGERAFKAWAVARLSQTFPNADFAEITKLATDLTKVNKECCH GDLLECADDRAELAKYMCENQATISSKLQTCCDKPLLKKAHCLSEVEHDTMP ADLPAIAADFVEDQEVCKNYAEAKDVFLGTFLYEYSRRHPDYSVSLLLRLAK KYEATLEKCCAEANPPACYGTVLAEFQPLVEEPKNLVKTNCDLYEKLGEYGF QNAILVRYTQKAPQVSTPTLVEAARNLGRVGTKCCTLPEDQRLPCVEDYLSAI LNRVCLLHEKTPVSEHVTKCCSGSLVERRPCFSALTVDETYVPKEFKAETFTFH SDICTLPEKEKQIKKQTALAELVKHKPKATAEQLKTVMDDFAQFLDTCCKAA DKDTCFSTEGPNLVTRCKDALASGGPGPAGMKGLPGShgtviesleslnnythssgidvee kslfldiwrnwqkdgdmkilqsqiisfylrlfevlkdnqaisnnisvieshlittffsnskakkdafmsiakfevnnpqvq rqafnelirvvhqllpesslitcrkrsrcSGGPGPAGMKGLPGSggggsEAHKSEIAHRYNDLGEQ HFKGLVLIAFSQYLQKCSYDEHAKLVQEVTDFAKTCVADESAANCDKSLHTL FGDKLCAIPNLRENYGELADCCTKQEPERNECFLQHKDDNPSLPPFERPEAEA MCTSFKENPTTFMGHYLHEVARRHPYFYAPELLYYAEQYNEILTQCCAEADK ESCLTPKLDGVKEKALVSSVRQRMKCSSMQKFGERAFKAWAVARLSQTFPN ADFAEITKLATDLTKVNKECCHGDLLECADDRAELAKYMCENQATISSKLQT CCDKPLLKKAHCLSEVEHDTMPADLPAIAADFVEDQEVCKNYAEAKDVFLGT FLYEYSRRHPDYSVSLLLRLAKKYEATLEKCCAEANPPACYGTVLAEFQPLVE EPKNLVKTNCDLYEKLGEYGFQNAILVRYTQKAPQVSTPTLVEAARNLGRVG TKCCTLPEDQRLPCVEDYLSAILNRVCLLHEKTPVSEHVTKCCSGSLVERRPCF SALTVDETYVPKEFKAETFTFHSDICTLPEKEKQIKKQTALAELVKHKPKATAE QLKTVMDDFAQFLDTCCKAADKDTCFSTEGPNLVTRCKDALAggggsSGGPGP AGMKGLPGShgtviesleslnnythssgidveekslfldiwrnwqk dgdmkilqsqiisfylrlfevlkdnqaisn |

-continued

Sequence table

| SEQ ID NO. | Name | Sequence |
|---|---|---|
| | | nisvieshlittffsnslcaldcdafmsiakfevnnpqvqrqafne<br>lirvvhqllpesslrkrkrsrcSGGPGPAGMK<br>GLPGSEAHKSEIAHRYNDLGEQHFKGLVLIAFSQYLQKCSYDEHAKLVQEVTD<br>FAKTCVADESAANCDKSLHTLFGDKLCAIPNLRENYGELADCCTKQEPERNEC<br>FLQHKDDNPSLPPFERPEAEAMCTSFKENPTTFMGHYLHEVARRHPYFYAPEL<br>LYYAEQYNEILTQCCAEADKESCLTPKLDGVKEKALVSSVRQRMKCSSMQKF<br>GERAFKAWAVARLSQTFPNADFAEITKLATDLTKVNKECCHGDLLECADDRA<br>ELAKYMCENQATISSKLQTCCDKPLLKKAHCLSEVEHDTMPADLPAIAADFVE<br>DQEVCKNYAEAKDVFLGTFLYEYSRRHPDYSVSLLLRLAKKYEATLEKCCAE<br>ANPPACYGTVLAEFQPLVEEPKNLVKTNCDLYEKLGEYGFQNAILVRYTQKA<br>PQVSTPTLVEAARNLGRVGTKCCTLPEDQRLPCVEDYLSAILNRVCLLHEKTP<br>VSEHVTKCCSGSLVERRPCFSALTVDETYVPKEFKAETFTFHSDICTLPEKEKQI<br>KKQTALAELVKHKPKATAEQLKTVMDDFAQFLDTCCKAADKDTCFSTEGPN<br>LVTRCKDALAHHHHHHEPEA |
| 109 | ACP75<br>Mouse IFG<br>fusion | mdmrvpaqllglllwlrgarcEAHKSEIAHRYNDLGEQHFKGLVLIAFSQYLQKCSYDE<br>HAKLVQEVTDFAKTCVADESAANCDKSLHTLFGDKLCAIPNLRENYGELADC<br>CTKQEPERNECFLQHKDDNPSLPPFERPEAEAMCTSFKENPTTFMGHYLHEVA<br>RRHPYFYAPELLYYAEQYNEILTQCCAEADKESCLTPKLDGVKEKALVSSVRQ<br>RMKCSSMQKFGERAFKAWAVARLSQTFPNADFAEITKLATDLTKVNKECCH<br>proteinGDLLECADDRAELAKYMCENQATISSKLQTCCDKPLLKKAHCLSEVEHDTMP<br>ADLPAIAADFVEDQEVCKNYAEAKDVFLGTFLYEYSRRHPDYSVSLLLRLAK<br>KYEATLEKCCAEANPPACYGTVLAEFQPLVEEPKNLVKTNCDLYEKLGEYGF<br>QNAILVRYTQKAPQVSTPTLVEAARNLGRVGTKCCTLPEDQRLPCVEDYLSAI<br>LNRVCLLHEKTPVSEHVTKCCSGSLVERRPCFSALTVDETYVPKEFKAETFTFH<br>SDICTLPEKEKQIKKQTALAELVKHKPKATAEQLKTVMDDFAQFLDTCCKAA<br>DKDTCFSTEGPNLVTRCKDALASGGPGPAGMKGLPGShgtviesleslnnyth<br>ssgidveekslfldiwrnwqkdgdmkilqsqiisfylrlfevlkdnqaisnni<br>svieshlittffsnskakkdafmsiakfevnnpqvqrqafnelirvvhq<br>llpesshicrkrsrcSGGPGPAGMKGLPGSggggsggggsEAHKSEIAHRYND<br>LGEQHFKGLVLIAFSQYLQKCSYDEHAKLVQEVTDFAKTCVADESAANCDKS<br>LHTLFGDKLCAIPNLRENYGELADCCTKQEPERNECFLQHKDDNPSLPPFERPE<br>AEAMCTSFKENPTTFMGHYLHEVARRHPYFYAPELLYYAEQYNEILTQCCAE<br>ADKESCLTPKLDGVKEKALVSSVRQRMKCSSMQKFGERAFKAWAVARLSQT<br>FPNADFAEITKLATDLTKVNKECCHGDLLECADDRAELAKYMCENQATISSKL<br>QTCCDKPLLKKAHCLSEVEHDTMPADLPAIAADFVEDQEVCKNYAEAKDVFL<br>GTFLYEYSRRHPDYSVSLLLRLAKKYEATLEKCCAEANPPACYGTVLAEFQPL<br>VEEPKNLVKTNCDLYEKLGEYGFQNAILVRYTQKAPQVSTPTLVEAARNLGR<br>VGTKCCTLPEDQRLPCVEDYLSAILNRVCLLHEKTPVSEHVTKCCSGSLVERR<br>PCFSALTVDETYVPKEFKAETFTFHSDICTLPEKEKQIKKQTALAELVKHKPKA<br>TAEQLKTVMDDFAQFLDTCCKAADKDTCFSTEGPNLVTRCKDALAggggsgggg<br>sSGGPGPAGMKGLPGShgtviesleslnnythssgidveekslfldiwrnwq<br>kdgdmkilqsqiisfylrlfe<br>vlkdnqaisnnisvieshlittffsnskakkdafmsiakfevnnpqvqrqaf<br>nelirvvhqllpesslikrkrsrcSGGP<br>GPAGMKGLPGSEAHKSEIAHRYNDLGEQHFKGLVLIAFSQYLQKCSYDEHAK<br>LVQEVTDFAKTCVADESAANCDKSLHTLFGDKLCAIPNLRENYGELADCCTK<br>QEPERNECFLQHKDDNPSLPPFERPEAEAMCTSFKENPTTFMGHYLHEVARRH<br>PYFYAPELLYYAEQYNEILTQCCAEADKESCLTPKLDGVKEKALVSSVRQRM<br>KCSSMQKFGERAFKAWAVARLSQIFPNADFAEITKLATDLTKVNKECCHGDL<br>LECADDRAELAKYMCENQATISSKLQTCCDKPLLKKAHCLSEVEHDTMPADL<br>PAIAADFVEDQEVCKNYAEAKDVFLGIFLYEYSRRHPDYSVSLLLRLAKKYE<br>ATLEKCCAEANPPACYGTVLAEFQPLVEEPKNLVKTNCDLYEKLGEYGFQNAI<br>LVRYTQKAPQVSTPTLVEAARNLGRVGTKCCTLPEDQRLPCVEDYLSAILNRV<br>CLLHEKTPVSEHVTKCCSGSLVERRPCFSALTVDETYVPKEFKAETFTFHSDIC<br>TLPEKEKQIKKQTALAELVKHKPKATAEQLKTVMDDFAQFLDTCCKAADKDT<br>CFSTEGPNLVTRCKDALAHHHHHHEPEA |
| 110 | ACP78<br>Mouse IFG<br>fusion<br>protein | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSggggsggggsgggg<br>shgtviesleslnnythssgidveekslfld<br>iwrnwqkdgdmkilqsqiisfylrlfevlkdnqaisnnisv<br>ieshlittffsnskaldcdafmsiakfevnnpqvqrqafne<br>lirvvhqllpesslrkrkrsreggggsggggsggggsEVQLVESGGGLVQPGNSLRLSCAASGFTF<br>SKFGMSWVRQAPGKGLEWVSSISGSGRDTLYAESVKGRFTISRDNAKTTLYL<br>QMNSLRPEDTAVYYCTIGGSLSVSSQGTLVTVSSggggsggggsggggshgtviesleslnn<br>ythssgidveekslildiwrnwqkdgdmkilqsqiisfylrlfevlkd<br>nqaisnnisvieshlittffsnskakkdafmsia<br>kfevnnpqvqrqafnelirvvhqllpesslrkrkrsreggggsggggsggggsEVQLVESGGGLVQPGNS<br>LRLSCAASGFTFSKFGMSWVRQAPGKGLEWVSSISGSGRDTLYAESVKGRFTI<br>SRDNAKTTLYLQMNSLRPEDTAVYYCTIGGSLSVSSQGTLVTVSSHHHHHHEP<br>EA |

-continued

Sequence table

| SEQ ID NO. | Name | Sequence |
|---|---|---|
| 111 | ACP 134 Mouse IFG fusion protein | mdmrvpaqllglllwlrgarcEVQLVESGGGLVQPGNSLRLSCAASGFTFSKFGMSWVR QAPGKGLEWVSSISGSGRDTLYAESVKGRFTISRDNAKTTLYLQMNSLRPEDT AVYYCTIGGSLSVSSQGTLVTVSSSGGPGPAGMKGLPGShgtviesleslnnyfnssgidv eekslfldiwrnwqkdgdmkilqsqiisfylrlfevlkdnqaisn nisvieshlittffsnskaldcdafmsiakfevnnpq vqrqafnelirvvhqllpesshkrkrsrcSGGPGPAGMKGLPGSEVQLVESGGGLVQPGNSLR LSCAASGFTFSKFGMSWVRQAPGKGLEWVSSISGSGRDTLYAESVKGRFTISR DNAKTTLYLQMNSLRPEDTAVYYCTIGGSLSVSSQGTLVTVSSSGGPGPAGM KGLPGShgtviesleslnnyfnssgidveekslfldiwrnwqkdgdmkilqsqiisfylrlfevlkdnqaisnnisvie shlittffsnskakkdafmsiakfevnnpqvqrqafnelirvvhqllpesshkrkrsrcSGGPGPAGMKGLPG SEVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSggggsggggsggggsQVQLQESGGGLAQAGGSLSLSCAASGFTVSNS VMAWYRQTPGKQREFVAIINSVGSTNYADSVKGRFTISRDNAKNTVYLQMNN LKPEDTAVYVCNRNFDRIYWGQGTQVTVSSHHHHHHEPEA |
| 112 | ACP135 Mouse IFG fusion protein | mdmrvpaqllglllwlrgarcQVQLQESGGGLAQAGGSLSLSCAASGFTVSNSVMAWY RQTPGKQREFVAIINSVGSTNYADSVKGRFTISRDNAKNTVYLQMNNLKPEDT AVYVCNRNFDRIYWGQGTQVTVSSggggsggggsggggsEVQLVESGGGLVQPGNS LRLSCAASGFTFSKFGMSWVRQAPGKGLEWVSSISGSGRDTLYAESVKGRFTI SRDNAKTTLYLQMNSLRPEDTAVYYCTIGGSLSVSSQGTLVTVSSSGGPGPAG MKGLPGShgtviesleslnnyfnssgidveekslfldiwrnwqkdgdmkilqsqiisfylrlfevlkdnqaisnnisv ieshlittffsnskakkdafmsiakfevnnpqvqrqafnelirvvhqllpesshkrkrsrcSGGPGPAGMKGLP GSEVQLVESGGGLVQPGNSLRLSCAASGFTFSKFGMSWVRQAPGKGLEWVSS ISGSGRDTLYAESVKGRFTISRDNAKTTLYLQMNSLRPEDTAVYYCTIGGSLSV SSQGTLVTVSSSGGPGPAGMKGLPGShgtviesleslnnyfnssgidveekslfldiwrnwqkdgd mkilqsqiisfylrlfevlkdnqaisnnisvieshlittffsnskakkda fmsiakfevnnpqvqrqafnelirvvhqllpes shkrkrsrcSGGPGPAGMKGLPGSEVQLVESGGGLVQPGNSLRLSCAASGFTFSKF GMSWVRQAPGKGLEWVSSISGSGRDTLYAESVKGRFTISRDNAKTTLYLQMN SLRPEDTAVYYCTIGGSLSVSSQGTLVTVSSHHHHHHEPEA |
| 113 | ACP34 Mouse IL-12 fusion protein | mdmrvpaqllglllwlrgarcrvipvsgparclsqsrnllkttddmvktareklkhysctaedidheditrdqtstlktclp lelhknesclatretssttrgsclppqktslmmticlgsiyedlkmyqtefqainaalqnhnhqqiildkgmlvaidelmq slnhngetlrqkppvgeadpyrvkmklcillhafstryvtinrvmgylssaSGGPGPAGMKGLPGSmwele kdvyvvevdwtpdapgetvnitcdtpeedditwtsdqrhgvigsgktltitykefldagqytchkggetlshshlllhkke ngiwsteilknfknktflkceapnysgrftcswlvqrnmdlkfniksssssspdsravtcgmaslsaekvtldqrdyekys vscqedvtcptaeetlpielalearqqnkyenystsffirdiikpdppknlqmkplknsqvevsweypdswstphsyfsl kffvriqrkkekmketeegcnqkgaflvektstevqckggnvcvqaqchyynsscskwacvpervrsHHHHHH |
| 114 | ACP35 Mouse IL-12 fusion protein | mdmrvpaqllglllwlrgarcrvipvsgparclsqsrnllkttddmvktareklkhysctaedidheditrdqtstlktclp lelhknesclatretssttrgsclppqktslmmticlgsiyedlkmyqtefqainaalqnhnhqqiildkgmlvaidelmq slnhngetlrqkppvgeadpyrvkmklcillhafstryvtinrvmgylssaggggsggggsggggsSGGPGPAG MKGLPGSggggsggggsggggsmwelekdvyvvevdwtpdapgetvnitcdtpeedditwtsdqrhgvigsg ktltitykefldagqytchkggetlshshlllhkkengiwsteilknfkatflkceapnysgrftcswlvqrnmdlkfnik sssssspdsravtcgmaslsaekvtldqrdyekysyscqedvtcptaeetlpielalearqqnkyenystsffirdiikpdpp knlqmkplknsqvevsweypdswstphsyfslkffvriqrkkekmketeegcnqkgaflvektstevqckggnvcv qaqdryynsscskwacvpervrsHHHHHH |
| 115 | ACP36 Mouse IL-12 fusion protein | mdmrvpaqllglllwlrgarcEVQLVESGGGLVQPGNSLRLSCAASGFTFSKFGMSWVR QAPGKGLEWVSSISGSGRDTLYAESVKGRFTISRDNAKTTLYLQMNSLRPEDT AVYYCTIGGSLSVSSQGTLVTVSSSGGPGPAGMKGLPGSmwelekdvyvvevdwtpd apgetvnhcdtpeedditwtsdqrhgvigsgktltitykefldagqytchkggetlshshlllhkkengiwsteilknfkn kffikceapnysgrftcswlvqrnmdlkfniksssssspdsravtcgmaslsaekvtldqrdyekysyscqedvtcptaee tlpielalearqqnkyenystsffirdiikpdppknlqmkplknsqvevsweypdswstphsyfslkffvriqrkkekm keteegcnqkgaflvektstevqckggnvcvqaqchyynsscskwacvpervrsggggsggggsggggsrvipvsgparcl sqsrifilkttddmvktareklkhysctaedidheditrdqtstlktclplelhknesclatretssttrgsclppqktsl mmticlgsiyedlkmyqtefciainaalqnhnhqqiildkgmlvaidelmqslnhngetlrqkppvgeadpyrvkmkl cillhafstryvtinrvmgylssaSGGPGPAGMKGLPGSEVQLVESGGGLVQPGNSLRLSC AASGFTFSKFGMSWVRQAPGKGLEWVSSISGSGRDTLYAESVKGRFTISRDNA KTTLYLQMNSLRPEDTAVYYCTIGGSLSVSSQGTLVTVSSHHHHHH |
| 116 | ACP37 Mouse IL-12 fusion protein | mdmrvpaqllglllwlrgarcQVQLQESGGGLVQAGGSLRLSCAASGRIFSIDIMSWYR QAPGKQRELVARITRGGTISYDDSVKGRFTISRDNAKNTVYLQMNSLKPEDTG VYYCNALYGTDYWGKGTQVTVSSggggsggggsggggsEVQLVESGGGLVQPGNS LRLSCAASGFTFSKFGMSWVRQAPGKGLEWVSSISGSGRDTLYAESVKGRFTI SRDNAKTTLYLQMNSLRPEDTAVYYCTIGGSLSVSSQGTLVTVSSSGGPGPAG MKGLPGSmwelekdvyvvevdwtpdapgetvnitcdtpeedditwtsdqrhgvigsgktltitykefldagqytc hkggetlshshlllhkkengiwsteilknfknktflkceapnysgrftcswlvqrnmdlkfniksssssspdsravtcgmas Vlsaekvtldqrdyekysyscqedvtcptaeetlpielalearqqnkyenystsffirdiikpdppknlqmkplknsqvevs weypdswstphsyfslkffvriqrkkekmketeegcnqkgaflvektstevqckggnvcvqaqchyynsscskwac vpervrsggggsggggsggggsrvipvsgparclsqsnillkttddmvktareklkhysctaedidheditrdqtstlktcl |

-continued

Sequence table

| SEQ ID NO. | Name | Sequence |
|---|---|---|
| | | plelhknesclatretssttrgsclppqktslmmticlgsiyedlkmyqtefciainaalqnhnhqqiildkgmlvaidelm<br>qslnhngetlrqkppvgeadpyrvkmklcillhafstrvvtinrvmgylssaSGGPGPAGMKGLPGSEVQ<br>LVESGGGLVQPGNSLRLSCAASGFTFSKFGMSWVRQAPGKGLEWVSSISGSGR<br>DTLYAESVKGRFTISRDNAKTTLYLQMNSLRPEDTAVYYCTIGGSLSVSSQGT<br>LVTVSSHHHHHH |
| 117 | ACP79<br>Mouse IL-<br>12 fusion<br>protein | mdmrvpaqllglllwlrgarcQVQLQESGGGLVQAGGSLRLSCAASGRIFSIDIMSWYR<br>QAPGKQRELVARITRGGTISYDDSVKGRFTISRDNAKNTVYLQMNSLKPEDTG<br>VYYCNALYGTDYWGKGTQVTVSSggggsggggsggggsEVQLVESGGGLVQPGNS<br>LRLSCAASGFTFSKFGMSWVRQAPGKGLEWVSSISGSGRDTLYAESVKGRFTI<br>SRDNAKTTLYLQMNSLRPEDTAVYYCTIGGSLSVSSQGTLVTVSSSGGPGPAG<br>MKGLPGSmwelekdvyvvevdwtpdapgetvnitcdtpeedditwtsdqrhgvigsgktltitykefldagqytc<br>hkggetlshshlllhkkengiwsteilknfknktflkceapnysgrftcswlvqrnmdlkfniksssssspdsravtcgmas<br>lsaekvtldqrdyekysyscqedvtcptaeetlpielalearqqnkyenystsffirdiikpdppknlqmkplknsqvevs<br>weypdswstphsyfslkffvriqrkkekmketeegcnqkgaflvektstevqckggnvcvqaqchyynsscskwac<br>vpervrsggggsggggsggggsrvipvsgparclsqsnillkttddmvktareklkhysctaedidheditrdqtstlktcl<br>plelhknesclatretssttrgsclppqktslmmticlgsiyedlkmyqtefciainaalqnhnhqqiildkgmlvaidelm<br>qslnhngetlrqkppvgeadpyrvkmlcicillhafstrvvtinrvmgylssaSGGPGPAGMKGLPGSEVQ<br>LVESGGGLVQPGNSLRLSCAASGFTFSKFGMSWVRQAPGKGLEWVSSISGSGR<br>DTLYAESVKGRFTISRDNAKTTLYLQMNSLRPEDTAVYYCTIGGSLSVSSQGT<br>LVTVSSHHHHHH |
| 118 | ACP80<br>Mouse IL-<br>12 fusion<br>protein | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGSmwelekdvyvvevdwtpd<br>apgetvnhcdtpeedditwtsdqrhgvigsgktltitykefldagqytchkggetlshshlllhkkengiwsteilknfkn<br>kffikceapnysgrftcswlvqrnmdlkfniksssssspdsravtcgmaslsaekvtldqrdyekysyscqedvtcptaee<br>tlpielalearqqnkyenystsffirdiikpdppknlqmkplknsqvevsweypdswstphsyfslkffvriqrkkekm<br>keteegcnqkgaflvektstevqckggnvcvqaqdwynsscskwacvpervrsggggsggggsggggsrvipvsgparc<br>lsqsnillkttddmvktareklkhysctaedidheditrdqtstlktclplelhknesclatretssttrgsclppqktsl<br>mmticlgsiyedlkmyqtefciainaalqnhnhqqiildkgmlvaidelmqslnhngetlrqkppvgeadpyrvkmkl<br>cillhafstrvvtinrvmgylssaSGGPGPAGMKGLPGSEVQLVESGGGLVQPGNSLRLSC<br>AASGFTFSKFGMSWVRQAPGKGLEWVSSISGSGRDTLYAESVKGRFTISRDNA<br>KTTLYLQMNSLRPEDTAVYYCTIGGSLSVSSQGTLVTVSSggggsggggsggggsQV<br>QLQESGGGLVQAGGSLRLSCAASGRIFSIDIMSWYRQAPGKQRELVARITRGG<br>TISYDDSVKGRFTISRDNAKNTVYLQMNSLKPEDTGVYYCNALYGTDYWGK<br>GTQVTVSSHHHHHH |
| 119 | ACP91<br>Chimeric<br>IL-12<br>fusion<br>protein | mdmrvpaqllglllwlrgarciwelkkdvyvveldwypdapgemvvitcdtpeedgitwildqssevlgsgkfltiqv<br>kefgdagqytchkggevlshsllllhkkedgiwstdilkdqkepknktflrceaknysgrftcwwlttistditfsvkssrg<br>ssdpqgvtcgaatlsaervrgdnkeyeysvecqedsacpaaeeslpievmvdavhklkyenytssffirdiikpdppkn<br>lqlkplknsrqvevsweypdtwstphsyfsltfcvqvqgkskrekkdrvftdktsatvicrknasisvraqchyysssws<br>ewasvpcsggggsggggsggggsrvipvsgparclsqsnillkttddmvktareklkhysctaedidheditrdqtstlkt<br>clplelhknesclatretssttrgsclppqktslmmticlgsiyedlkmyqtefqainaalqnhnhqqiildkgmlvaidel<br>mqslnhngetlrqkppvgeadpyrvkmklcillhafstivvtinrvmgylssaggggsggggsggggsggggsgggg<br>sggggsggggsggggsggggsQSVLTQPPSVSGAPGQRVTISCSGSRSNIGSNTVKWYQ<br>QLPGTAPKLLIYYNDQRPSGVPDRFSGSKSGTSASLAITGLQAEDEADYYCQS<br>YDRYTHPALLFGTGTKVTVLggggsggggsggggsQVQLVESGGGVVQPGRSLRLS<br>CAASGFTFSSYGMHWVRQAPGKGLEWVAFIRYDGSNKYYADSVKGRFTISRD<br>NSKNTLYLQMNSLRAEDTAVYYCKTHGSHDNWGQGTMVTVSSggggsggggsgg<br>ggsEVQLVESGGGLVQPGNSLRLSCAASGFTFSKFGMSWVRQAPGKGLEWVSS<br>ISGSGRDTLYAESVKGRFTISRDNAKTTLYLQMNSLRPEDTAVYYCTIGGSLSV<br>SSQGTLVTVSSHHHHHHEPEA |
| 120 | ACP136<br>Chimeric<br>IL-12<br>fusion<br>protein | mdmrvpaqllglllwlrgarciwelkkdvyvveldwypdapgemvvitcdtpeedgitwtldqssevlgsgkfltiqv<br>kefgdagqytchkggevlshsllllhkkedgiwstdilkdqkepknktflrceaknysgrftcwwlttistditfsvkssrg<br>ssdpqgvtcgaatlsaervrgdnkeyeysvecqedsacpaaeeslpievmvdavhklIcyenytssffirdiikpdppkn<br>lqlkplknsrqvevsweypdtwstphsyfshfcvqvqgkskrekkdrvftdktsatvicrknasisvraqchyysssws<br>ewasvpcsggggsggggsggggsrvipvsgparclsqsnillkttddmvktareklkhysctaedidheditrdqtstlkt<br>clplelhIcnesclatretssttrgsclppqktslmmticlgsiyedlkmyqtefqainaalqnhnhqqiildkgmlvaidel<br>mqslnhngetlrqkppvgeadpyrvkmklcillhafstrvvtinrvmgylssaSGGPGPAGMKGLPGSggg<br>gsggggsggggsggggsggggsggggsQSVLTQPPSVSGAPGQRVTISCSGSRSNIGSNTVK<br>WYQQLPGTAPKLLIYYNDQRPSGVPDRFSGSKSGTSASLAITGLQAEDEADYY<br>CQSYDRYTHPALLFGTGTKVTVLggggsggggsggggsQVQLVESGGGVVQPGRSL<br>RLSCAASGFTFSSYGMHWVRQAPGKGLEWVAFIRYDGSNKYYADSVKGRFTI<br>SRDNSKNTLYLQMNSLRAEDTAVYYCKTHGSHDNWGQGTMVTVSSHHHHH<br>HEPEA |
| 121 | ACP138<br>Chimeric<br>IL-12<br>fusion<br>protein | mdmrvpaqllglllwlrgarciwelkkdvyvveldwypdapgemvvlicdtpeedgitwtldqssevlgsgktltiqv<br>kefgdagqytchkggevlshsllllhIckedgiwstdilkdqkepknktflrceaknysgrftcwwlttistditfsvkssrg<br>ssdpqgvtcgaatlsaervrgdnkeyeysvecqedsacpaaeeslpievmvdavhklIcyenytssffirdiikpdppkn<br>lqlkplknsrqvevsweypdtwstphsyfshfcvqvqgkskrekkdrvftdktsatvicrknasisvraqchyysssws<br>ewasvpcsggggsggggsggggsrvipvsgparclsqsnillkttddmvktareklkhysctaedidheditrdqtstlkt |

-continued

Sequence table

| SEQ ID NO. | Name | Sequence |
|---|---|---|
| | | clplelhIcnesclatretssttrgsclppqktslmmticlgsiyedlkmyqtefqainaalqnhnhqqiildkgmlvaidel<br>mqslnhngetlrqkppvgeadpyrvkmklcillhafstrvvtinrvmgylssaSGGPGPAGMKGLPGSggg<br>gsggggsggggsggggsggggsggggsQSVLTQPPSVSGAPGQRVTISCSGSRSNIGSNTVK<br>WYQQLPGTAPKLLIYYNDQRPSGVPDRFSGSKSGTSASLAITGLQAEDEADYY<br>CQSYDRYTHPALLFGTGTKVTVLggggsggggsggggsQVQLVESGGGVVQPGRSL<br>RLSCAASGFTFSSYGMHWVRQAPGKGLEWVAFIRYDGSNKYYADSVKGRFTI<br>SRDNSKNTLYLQMNSLRAEDTAVYYCKTHGSHDNWGQGTMVTVSSggggsggg<br>gsggggsEVQLVESGGGLVQPGNSLRLSCAASGFTFSKFGMSWVRQAPGKGLEW<br>VSSISGSGRDTLYAESVKGRFTISRDNAKTTLYLQMNSLRPEDTAVYYCTIGGS<br>LSVSSQGTLVTVSSggggsggggsggggsQVQLQESGGGLAQAGGSLSLSCAASGFT<br>VSNSVMAWYRQTPGKQREFVAIINSVGSTNYADSVKGRFTISRDNAKNTVYL<br>QMNNLKPEDTAVYVCNRNFDRIYWGQGTQVTVSSHHHHHHEPEA |
| 122 | ACP139 Chimeric IL-12 fusion protein | mdmrvpaqllglllwlrgarcQVQLQESGGGLAQAGGSLSLSCAASGFTVSNSVMAWY<br>RQTPGKQREFVAIINSVGSTNYADSVKGRFTISRDNAKNTVYLQMNNLKPEDT<br>AVYVCNRNFDRIYWGQGTQVTVSSggggsggggsggggsiwelIckdvyvveldwypdapgem<br>vvitcdtpeedgitwadqssevlgsgktltiqvkefgdagqytchkggevlshsllllhldcedgiwstdilkdqkepknk<br>tflrceaknysgrftcwwlttistclitfsvkssrgssdpqgvtcgaatlsaervrgdnkeyeysvecqedsacpaaeeslpie<br>vmvdavhklIcyenytssffirdiikpdppknlqlkplknsrqvevsweypdtwstphsyfsltfcvqvqgkskrekkd<br>rvftdktsatvicrknasisvraqdryyssswsewasvpcsggggsggggsggggsrvipvsgparclsqsrnllkttdd<br>mvktareklkhysctaedidheditrdqtstlktclplelhknesclatretssttrgsclppqktslmmticlgsiyedlkm<br>yqtefgainaalqnhnhqqiildkgmlvaidelmqslnhngetlrqkppvgeadpyrvkmklcillhafstrvvtinry<br>mgylssaSGGPGPAGMKGLPGSggggsggggsggggsggggsggggsggggsQSVLTQPPSVS<br>GAPGQRVTISCSGSRSNIGSNTVKWYQQLPGTAPKLLIYYNDQRPSGVPDRFS<br>GSKSGTSASLAITGLQAEDEADYYCQSYDRYTHPALLFGTGTKVTVLggggsggg<br>gsggggsQVQLVESGGGVVQPGRSLRLSCAASGFTFSSYGMHWVRQAPGKGLE<br>WVAFIRYDGSNKYYADSVKGRFTISRDNSKNTLYLQMNSLRAEDTAVYYCKT<br>HGSHDNWGQGTMVTVSSggggsggggsggggsEVQLVESGGGLVQPGNSLRLSCA<br>ASGFTFSKFGMSWVRQAPGKGLEWVSSISGSGRDTLYAESVKGRFTISRDNAK<br>TTLYLQMNSLRPEDTAVYYCTIGGSLSVSSQGTLVTVSSHHHHHHEPEA |
| 123 | ACP140 Chimeric IL- 12 fusion protein | mdmrvpaqllglllwlrgarcQVQLQESGGGLAQAGGSLSLSCAASGFTVSNSVMAWY<br>RQTPGKQREFVAIINSVGSTNYADSVKGRFTISRDNAKNTVYLQMNNLKPEDT<br>AVYVCNRNFDRIYWGQGTQVTVSSSGGPGPAGMKGLPGSiwelkkcIvyvveldwyp<br>dapgemvvitcdtpeedgitwtldqssevlgsgktltiqvkefgdagqytchkggevlshsllllhIckedgiwstdilkdq<br>kepknkttflrceaknysgrftcwwlttistdiffsvkssrgssdpqgvtcgaatlsaervrgdnkeyeysvecqedsacpa<br>aeeslpievmvdavhklIcyenytssffirdiikpdppknlqlkplknsrqvevsweypdtwstphsyfsltfcvqvqgk<br>skrekkdrvftdktsatvicrknasisvraqchyyssswsewasvpcsggggsggggsggggsrvipvsgparclsqsr<br>nllkttddmvktareklkhysctaedidheditrdqtstlktclplelhIcnesclatretssttrgsclppqktslmmticlgsi<br>yedlkmyqtefgainaalqnhnhqqiildkgmlvaidelmqslnhngetlrqkppvgeadpyrvkmklcillhafstry<br>vtinrvmgylssaSGGPGPAGMKGLPGSggggsggggsggggsggggsggggsggggsQSVLTQP<br>PSVSGAPGQRVTISCSGSRSNIGSNTVKWYQQLPGTAPKLLIYYNDQRPSGVPD<br>RFSGSKSGTSASLAITGLQAEDEADYYCQSYDRYTHPALLFGTGTKVTVLgggg<br>sggggsggggsQVQLVESGGGVVQPGRSLRLSCAASGFTFSSYGMHWVRQAPGKG<br>LEWVAFIRYDGSNKYYADSVKGRFTISRDNSKNTLYLQMNSLRAEDTAVYYC<br>KTHGSHDNWGQGTMVTVSSggggsggggsggggsEVQLVESGGGLVQPGNSLRLSC<br>AASGFTFSKFGMSWVRQAPGKGLEWVSSISGSGRDTLYAESVKGRFTISRDNA<br>KTTLYLQMNSLRPEDTAVYYCTIGGSLSVSSQGTLVTVSSHHHHHHEPEA |
| 124 | ACP38 IL-2 fusion protein | mclmrvpaqllglllwlrgarcaptssstkktqlqlehllldlqmilnginnyknpkltrmltfkfympkkatelkhlqcle<br>eelkpleevinlaqsknfhlrprdlisninvivlelkgsetlfmceyadetativeflnrwitfcqsiistltSGGPGPAG<br>MKGLPGSEVQLVESGGGLVQPGGSLRLSCAASGFTFSSYTLAWVRQAPGKGL<br>EWVAAIDSSSYTYSPDTVRGRFTISRDNAKNSLYLQMNSLRAEDTAVYYCAR<br>DSNWDALDYWGQGTTVTVSSGGGGSGGGGSGGGGSDIQMTQSPSSLSASVG<br>DRVTITCKASQNVGTNVGWYQQKPGKAPKALIYSASFRYSGVPSRFSGSGSGT<br>DFTLTISSLQPEDFATYYCQQYYTYPYTFGGGTKVEIKggggsggggsggggsEVQLV<br>ESGGGLVQPGNSLRLSCAASGFTFSKFGMSWVRQAPGKGLEWVSSISGSGRDT<br>LYAESVKGRFTISRDNAKTTLYLQMNSLRPEDTAVYYCTIGGSLSVSSQGTLV<br>TVSSggggsggggsggggsQVQLQESGGGLVQAGGSLRLSCAASGRlFSIDIMSWYR<br>QAPGKQRELVARITRGGTISYDDSVKGRFTISRDNAKNTVYLQMNSLKPEDTG<br>VYYCNALYGTDYWGKGTQVTVSSHHHHHH |
| 125 | ACP39 IL-2 fusion protein | mdmrvpaqllglllwlrgarcQVQLQESGGGLVQAGGSLRLSCAASGRIFSIDIMSWYR<br>QAPGKQRELVARITRGGTISYDDSVKGRFTISRDNAKNTVYLQMNSLKPEDTG<br>VYYCNALYGTDYWGKGTQVTVSSSGGPGPAGMKGLPGSEVQLVESGGGLVQ<br>PGNSLRLSCAASGFTFSKFGMSWVRQAPGKGLEWVSSISGSGRDTLYAESVKG<br>RFTISRDNAKTTLYLQMNSLRPEDTAVYYCTIGGSLSVSSQGTLVTVSSSGGPG<br>PAGMKGLPGSEVQLVESGGGLVQPGGSLRLSCAASGFTFSSYTLAWVRQAPG<br>KGLEWVAAIDSSSYTYSPDTVRGRFTISRDNAKNSLYLQMNSLRAEDTAVYY<br>CARDSNWDALDYWGQGTTVTVSSGGGGSGGGGSGGGGSDIQMTQSPSSLSA<br>SVGDRVTITCKASQNVGTNVGWYQQKPGKAPKALIYSASFRYSGVPSRFSGSG<br>SGTDFTLTISSLQPEDFATYYCQQYYTYPYTFGGGTKVEIKSGGPGPAGMKGL |

-continued

Sequence table

| SEQ ID NO. | Name | Sequence |
|---|---|---|
| | | PGSaptssstkktqlqlehllldlqmilnginnyknpkltrmltfklympkkatelkhlqcleeelkpleevinlaqsknf<br>hlrprdlisninvivlelkgsetlfmceyadetativeflnrwitfcqsiistltHHHHHH** |
| 126 | ACP40<br>IL-2 fusion | mdmrvpaqllglllwlrgarcelcdddppeiphatfkamaykegtmlnceckrgfrriksgslymktgnsshsswd<br>nqcqctssatrnttkqvtpqpeeqkerkttemqspmqpvdqaslpghcrepppweneateriyhfvvgqmvyyqcv<br>qgyralhrgpaesvckmthgktrwtqpqlictgemetsqfpgeekpqaspegrpesetsclvtddfqiqtemaatmets<br>proteinifttteyqggggsggggsggggsggggsggggsggggsSGGPGPAGMKGLPGSaptssstkktqlqlehllld<br>lqmilnginnyknpkltrmlffidympldcatelkhlqcleeelkpleevinlaqsknfhlrprdlisninvivlelkgsettf<br>mceyadetativeflnrwitfcqsiistltHHHHHH |
| 127 | ACP41<br>IL-2 fusion<br>protein<br>(WW0076) | mclmrvpaqllglllwlrgarcaptssstkktqlqlehllldlqmilnginnyknpkltrmltfkfympkkatelkhlqcle<br>eelkpleevinlaqsknfhlrprdlisninvivlelkgsetlfmceyadetativeflnrwitfcqsiistltSGGPGPAG<br>MKGLPGSggggsggggsggggsggggsggggsggggselcdddppeiphallkamaykegtmlnceckrgfr<br>riksgslymlctgnsshsswdnqcqctssatrnttkqvtpqpeeqkerkttemqspmqpvdqaslpghcrepppwen<br>eateriyhfvvgqmvyyqcvqgyralhrgpaesvclunthgktrwtqpqlictgemetsqfpgeekpqaspegrpese<br>tsclvtdclfqiqtemaatmetsiftteyqHHHHHH |
| 128 | ACP42<br>IL-2<br>fusion<br>protein<br>(WW0078) | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSggggsggggsggggselcdddppeiphatfkamaykegtmln<br>ceckrgfrriksgslymktgnsshsswdnqcqctssatrnttkqvtpqpeeqkerkttemqspmqpvdqaslpghcre<br>pppweneateriyhfvvgqmvyyqcvqgyralhrgpaesvckmthgktrwtqpqlictgemetsqfpgeekpqasp<br>egrpesetsclvtdclfqiqtemaatmetsiftteyqggggsggggsggggsggggsggggsggggsSGGPGPAG<br>MKGLPGSaptssstkktqlqlehllldlqmilnginnyknpkltrmltfkfympkkatelkhlqcleeelkpleevinl<br>aqsknfblrprdlisninvivlelkgsetlfmceyadetativeflnrwitfcqsiistltHHHHHH |
| 129 | ACP43<br>IL-2 fusion<br>protein<br>(WW0079) | mclmrvpaqllglllwlrgarcaptssstkktqlqlehllldlqmilnginnyknpkltrmltfkfympkkatelkhlqcle<br>eelkpleevinlaqsknfhlrprdlisninvivlelkgsetlfmceyadetativeflnrwitfcqsiistltSGGPGPAG<br>MKGLPGSggggsggggsggggsggggsggggsggggselcdddppeiphallkamaykegtmlnceckrgfr<br>riksgslymlctgnsshsswdnqcqctssatrnttkqvtpqpeeqkerkttemqspmqpvdqaslpghcrepppwen<br>eateriyhfvvgqmvyyqcvqgyralhrgpaesvclunthgktrwtqpqlictgemetsqfpgeekpqaspegrpese<br>tsclvtddfqiqtemaatmetsiftteyqggggsggggsggggsEVQLVESGGGLVQPGNSLRLSCA<br>ASGFTFSKFGMSWVRQAPGKGLEWVSSISGSGRDTLYAESVKGRFTISRDNAK<br>TTLYLQMNSLRPEDTAVYYCTIGGSLSVSSQGTLVTVSSHHHHHH |
| 130 | ACP44<br>IL-2 fusion<br>protein<br>(WW0080) | mclmrvpaqllglllwlrgarcaptssstkktqlqlehllldlqmilnginnyknpkltrmltfkfympkkatelkhlqcle<br>eelkpleevinlaqsknfhlrprdlisninvivlelkgsettfmceyadetativeflnrwitfcqsiistltSGGPGPAG<br>MKGLPGSggggsggggsggggsggggsggggsggggselcdddppeiphatikamaykegtmlnceckrgfr<br>riksgslymlctgnsshsswdnqcqctssatrnttkqvtpqpeeqkerkttemqspmqpvdqaslpghcrepppwen<br>eateriyhfvvgqmvyyqcvqgyralhrgpaesvckmthgktrwtqpqlictgemetsqfpgeekpqaspegrpese<br>tsclvtddfqiqtemaatmetsiftteyqSGGPGPAGMKGLPGSEVQLVESGGGLVQPGNSLR<br>LSCAASGFTFSKFGMSWVRQAPGKGLEWVSSISGSGRDTLYAESVKGRFTISR<br>DNAKTTLYLQMNSLRPEDTAVYYCTIGGSLSVSSQGTLVTVSSHHHHHH |
| 131 | ACP45<br>IL-2<br>fusion<br>(WW0046) | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGSEVQLVESGGGLVQP<br>proteinGGSLRLSCAASGFTFSSYTLAWVRQAPGKGLEWVAAIDSSSYTYSPDTVRGRF<br>TISRDNAKNSLYLQMNSLRAEDTAVYYCARDSNWDALDYWGQGTTVTVSSG<br>GGGSGGGGSGGGGSDIQMTQSPSSLSASVGDRVTITCKASQNVGTNVGWYQQ<br>KPGKAPKALIYSASFRYSGVPSRFSGSGSGTDFTLTISSLQPEDFATYYCQQYY<br>TYPYTFGGGTKVEIKggggsggggsggggsggggsggggsggggsSGGPGPAGMKGLPGSa<br>ptssstkktqlqlehllldlqmilnginnyknpkihmltfkfympkkatelkhlqcleeelkpleevinlaqsknfhlrprd<br>lisninvivlelkgsettfmceyadetativeflnrwitfcqsiistltHHHHHH |
| 132 | ACP46<br>IL-2 fusion<br>protein | mclmrvpaqllglllwlrgarcaptssstkktqlqlehllldlqmilnginnyknpkltrmltfkfympkkatelkhlqcle<br>eelkpleevinlaqsknfhlrprdlisninvivlelkgsettfmceyadetativeflnrwitfcqsiistltSGGPGPAG<br>MKGLPGSggggsggggsggggsggggsggggsggggsEVQLVESGGGLVQPGGSLRLSCA<br>ASGFTFSSYTLAWVRQAPGKGLEWVAAIDSSSYTYSPDTVRGRFTISRDNAKN<br>SLYLQMNSLRAEDTAVYYCARDSNWDALDYWGQGTTVTVSSsggpgpagmkglp<br>gsDIQMTQSPSSLSASVGDRVTITCKASQNVGTNVGWYQQKPGKAPKALIYSA<br>SFRYSGVPSRFSGSGSGTDFTLTISSLQPEDFATYYCQQYYTYPYTFGGGTKVEI<br>KggggsggggsggggsEVQLVESGGGLVQPGNSLRLSCAASGFTFSKFGMSWVRQA<br>PGKGLEWVSSISGSGRDTLYAESVKGRFTISRDNAKTTLYLQMNSLRPEDTAV<br>YYCTIGGSLSVSSQGTLVTVSSggggsggggsggggsQVQLQESGGGLVQAGGSLRL<br>SCAASGRIFSIDIMSWYRQAPGKQRELVARITRGGTISYDDSVKGRFTISRDNA<br>KNTVYLQMNSLKPEDTGVYYCNALYGTDYWGKGTQVTVSSHHHHHH |
| 133 | ACP47<br>IL-2<br>fusion | mdmrvpaqllglllwlrgarcQVQLQESGGGLVQAGGSLRLSCAASGRIFSIDIMSWYR<br>QAPGKQRELVARITRGGTISYDDSVKGRFTISRDNAKNTVYLQMNSLKPEDTG<br>VYYCNALYGTDYWGKGTQVTVSSggggsggggsggggsaptssstkktqlqlehllldlqmilngin<br>proteinnyknpkltrmltfklympldcatelkhlqcleeelkpleevinlaqsknfhlrprd<br>lisninvivlelkgsettfmceyadet |

-continued

Sequence table

| SEQ ID NO. | Name | Sequence |
|---|---|---|
| | | ativeflnrwitfcqsiistltSGGPGPAGMKGLPGSEVQLVESGGGLVQPGNSLRLSCAAS<br>GFTFSKFGMSWVRQAPGKGLEWVSSISGSGRDTLYAESVKGRFTISRDNAKTT<br>LYLQMNSLRPEDTAVYYCTIGGSLSVSSQGTLVTVSSggggsggggsggggsggggsgg<br>ggsggggsEVQLVESGGGLVQPGGSLRLSCAASGFTFSSYTLAWVRQAPGKGLE<br>WVAAIDSSSYTYSPDTVRGRFTISRDNAKNSLYLQMNSLRAEDTAVYYCARD<br>SNWDALDYWGQGTTVTVSSGGGGSGGGGSGGGGSDIQMTQSPSSLSASVGD<br>RVTITCKASQNVGTNVGWYQQKPGKAPKALIYSASFRYSGVPSRFSGSGSGTD<br>FTLTISSLQPEDFATYYCQQYYTYPYTFGGGTKVEIKHHHHHH |
| 134 | ACP48<br>IL-2 fusion<br>protein<br>(WW0054) | mclmrvpaqllglllwlrgarcaptssstkktqlqlehllldlqmilnginnyknpkltrmltfkfympkkatelkhlqcle<br>eelkpleevinlaqsknfhlrprdlisninvivlelkgsettfmceyadetativeflnrwitfcqsiistltSGGPGPAG<br>MKGLPGSEVQLVESGGGLVQPGGSLRLSCAASGFTFSSYTLAWVRQAPGKGL<br>EWVAAIDSSSYTYSPDTVRGRFTISRDNAKNSLYLQMNSLRAEDTAVYYCAR<br>DSNWDALDYWGQGTTVTVSSGGGGSGGGGSGGGGSDIQMTQSPSSLSASVG<br>DRVTITCKASQNVGTNVGWYQQKPGKAPKALIYSASFRYSGVPSRFSGSGSGT<br>DFTLTISSLQPEDFATYYCQQYYTYPYTFGGGTKVEIKggggsggggsggggsEVQLV<br>ESGGGLVQPGNSLRLSCAASGFTFSKFGMSWVRQAPGKGLEWVSSISGSGRDT<br>LYAESVKGRFTISRDNAKTTLYLQMNSLRPEDTAVYYCTIGGSLSVSSQGTLV<br>TVSSHHHHHH |
| 135 | ACP49<br>IL-2 fusion<br>protein<br>(WW0055) | mclmrvpaqllglllwlrgarcaptssstkktqlqlehllldlqmilnginnyknpkltrmltfkfympkkatelkhlqcle<br>eelkpleevinlaqsknfhlrprdlisninvivlelkgsettfmceyadetativeflnrwitfcqsiistltSGGPGPAG<br>MKGLPGSggggsggggsggggsggggsggggsggggsEVQLVESGGGLVQPGGSLRLSCA<br>ASGFTFSSYTLAWVRQAPGKGLEWVAAIDSSSYTYSPDTVRGRFTISRDNAKN<br>SLYLQMNSLRAEDTAVYYCARDSNWDALDYWGQGTTVTVSSGGGGSGGGG<br>SGGGGSDIQMTQSPSSLSASVGDRVTITCKASQNVGTNVGWYQQKPGKAPKA<br>LIYSASFRYSGVPSRFSGSGSGTDFTLTISSLQPEDFATYYCQQYYTYPYTFGGG<br>TKVEIKggggsggggsggggsEVQLVESGGGLVQPGNSLRLSCAASGFTFSKFGMSW<br>VRQAPGKGLEWVSSISGSGRDTLYAESVKGRFTISRDNAKTTLYLQMNSLRPE<br>DTAVYYCTIGGSLSVSSQGTLVTVSSHHHHHH |
| 136 | ACP92<br>IL-2 fusion<br>protein | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGSaptssstkktqlqlehllldlqm<br>ilnginnyknpkltrmltfkfympkkatelkhlqcleeelkpleevinlaqsknfhlrprdlisninvivlelkgsettfmce<br>yadetativeflnrwitfcqsiistltSGGPGPAGMKGLPGSEVQLVESGGGLVQPGNSLRLSC<br>AASGFTFSKFGMSWVRQAPGKGLEWVSSISGSGRDTLYAESVKGRFTISRDNA<br>KTTLYLQMNSLRPEDTAVYYCTIGGSLSVSSQGTLVTVSSHHHHHH |
| 137 | ACP93<br>IL-2 fusion<br>protein | mdmrvpaqllglllwlrgarcQVQLQESGGGLVQAGGSLRLSCAASGRIFSIDIMSWYR<br>QAPGKQRELVARITRGGTISYDDSVKGRFTISRDNAKNTVYLQMNSLKPEDTG<br>VYYCNALYGTDYWGKGTQVTVSSgsgsgsgsgsgsgsgsEVQLVESGGGLVQPGNS<br>LRLSCAASGFTFSKFGMSWVRQAPGKGLEWVSSISGSGRDTLYAESVKGRFTI<br>SRDNAKTTLYLQMNSLRPEDTAVYYCTIGGSLSVSSQGTLVTVSSgsgsgsgsgsgs<br>gsgsQVQLQESGGGLVQAGGSLRLSCAASGRIFSIDIMSWYRQAPGKQRELVAR<br>ITRGGTISYDDSVKGRFTISRDNAKNTVYLQMNSLKPEDTGVYYCNALYGTD<br>YWGKGTQVTVSSgsgsgsgsgsgsgsgsEVQLVESGGGLVQPGGSLRLSCAASGFTFS<br>SYTLAWVRQAPGKGLEWVAAIDSSSYTYSPDTVRGRFTISRDNAKNSLYLQM<br>NSLRAEDTAVYYCARDSNWDALDYWGQGTTVTVSSGGGGSGGGGSGGGGS<br>DIQMTQSPSSLSASVGDRVTITCKASQNVGTNVGWYQQKPGKAPKALIYSASF<br>RYSGVPSRFSGSGSGTDFTLTISSLQPEDFATYYCQQYYTYPYTFGGGTKVEIK<br>SGGPGPAGMKGLPGSaptssstkktqlqlehllldlqmilnginnyknpklirmltfkfympkkatelkhlqcl<br>eeelkpleevinlaqsknfhlrprdlisninvivlelkgsettfmceyadetativeflnrwilfcqsiistltHHHHHH |
| 138 | ACP94<br>IL-2 fusion<br>protein | mdmrvpaqllglllwlrgarcQVQLQESGGGLVQAGGSLRLSCAASGRIFSIDIMSWYR<br>QAPGKQRELVARITRGGTISYDDSVKGRFTISRDNAKNTVYLQMNSLKPEDTG<br>VYYCNALYGTDYWGKGTQVTVSSgsgsgsgsgsgsgsgsEVQLVESGGGLVQPGNS<br>LRLSCAASGFTFSKFGMSWVRQAPGKGLEWVSSISGSGRDTLYAESVKGRFTI<br>SRDNAKTTLYLQMNSLRPEDTAVYYCTIGGSLSVSSQGTLVTVSSgsgsgsgsgsgs<br>gsgsEVQLVESGGGLVQPGGSLRLSCAASGFTFSSYTLAWVRQAPGKGLEWVA<br>AIDSSSYTYSPDTVRGRFTISRDNAKNSLYLQMNSLRAEDTAVYYCARDSNW<br>DALDYWGQGTTVTVSSGGGGSGGGGSGGGGSDIQMTQSPSSLSASVGDRVTI<br>TCKASQNVGTNVGWYQQKPGKAPKALIYSASFRYSGVPSRFSGSGSGTDFTLT<br>ISSLQPEDFATYYCQQYYTYPYTFGGGTKVEIKSGGPGPAGMKGLPGSaptssstk<br>ktqlqlehllldlqmilnginnyknpkltrmltfkfympkkatelkhlqcleeelkpleevinlaqsknfblrprdlisninv<br>ivlelkgsettfmceyadetativeflnrwitfcqsiistltHHHHHH |
| 139 | ACP95<br>IL-2 fusion<br>protein | mdmrvpaqllglllwlrgarcQVQLQESGGGLVQAGGSLRLSCAASGRIFSIDIMSWYR<br>QAPGKQRELVARITRGGTISYDDSVKGRFTISRDNAKNTVYLQMNSLKPEDTG<br>VYYCNALYGTDYWGKGTQVTVSSgsgsgsgsgsgsgsgsEVQLVESGGGLVQPGNS<br>LRLSCAASGFTFSKFGMSWVRQAPGKGLEWVSSISGSGRDTLYAESVKGRFTI<br>SRDNAKTTLYLQMNSLRPEDTAVYYCTIGGSLSVSSQGTLVTVSSSGGPGPAG<br>MKGLPGSaptssstkktqlqlehllldlqmilnginnyknpkltrmltfkfympkkatelkhlqcleeelkpleevinl<br>aqsknfblrprdlisninvivlelkgsettfmceyadetativeflnrwitfcqsiistltHHHHHH |

-continued

Sequence table

| SEQ ID NO. | Name | Sequence |
| --- | --- | --- |
| 140 | ACP96 IL-2 fusion protein | mdmrvpaqllglllwlrgarcQVQLQESGGGLVQAGGSLRLSCAASGRIFSIDIMSWYR<br>QAPGKQRELVARITRGGTISYDDSVKGRFTISRDNAKNTVYLQMNSLKPEDTG<br>VYYCNALYGTDYWGKGTQVTVSSSGGPGPAGMKGLPGSaptssstkktqlqlehllldlq<br>milnginnyknpklirmltfkfympkkatelkhlqcleeelkpleevinlaqsknfhlrprdlisninvivlelkgsettfm<br>ceyadetativeflnrwitfcqsiistltSGGPGPAGMKGLPGSEVQLVESGGGLVQPGNSLRL<br>SCAASGFTFSKFGMSWVRQAPGKGLEWVSSISGSGRDTLYAESVKGRFTISRD<br>NAKTTLYLQMNSLRPEDTAVYYCTIGGSLSVSSQGTLVTVSSHHHHHH |
| 141 | ACP97 IL-2 fusion protein | mdmrvpaqllglllwlrgarcQVQLQESGGGLVQAGGSLRLSCAASGRIFSIDIMSWYR<br>QAPGKQRELVARITRGGTISYDDSVKGRFTISRDNAKNTVYLQMNSLKPEDTG<br>VYYCNALYGTDYWGKGTQVTVSSggggsggggsggggsEVQLVESGGGLVQPGNS<br>LRLSCAASGFTFSKFGMSWVRQAPGKGLEWVSSISGSGRDTLYAESVKGRFTI<br>SRDNAKTTLYLQMNSLRPEDTAVYYCTIGGSLSVSSQGTLVTVSSSGGPGPAG<br>MKGLPGSaptsssticktqlqlehllldlqmilnginnyknpkltrmltfkfympkkatelklilqcleeelkpleevinl<br>aqsknfhlrprdlisninvivlelkgsettfmceyadetativeflnrwitfcqsiistltSGGPGPAGMKGLPGS<br>EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSHHHHHH |
| 142 | ACP99 IL-2 fusion protein | mdmrvpaqllglllwlrgarcQVQLQESGGGLVQAGGSLRLSCAASGRIFSIDIMSWYR<br>QAPGKQRELVARITRGGTISYDDSVKGRFTISRDNAKNTVYLQMNSLKPEDTG<br>VYYCNALYGTDYWGKGTQVTVSSggggsggggsggggsaptsssticktqlqlehllldlqmilngin<br>nyknpkltrmltficfympkkatelkhlqcleeelkpleevinlaqsknfhlrprdlisninvivlelkgsettfmceyadet<br>ativeflnrwitfcqsiistltSGGPGPAGMKGLPGSEVQLVESGGGLVQPGNSLRLSCAAS<br>GFTFSKFGMSWVRQAPGKGLEWVSSISGSGRDTLYAESVKGRFTISRDNAKTT<br>LYLQMNSLRPEDTAVYYCTIGGSLSVSSQGTLVTVSSHHHHHH |
| 143 | ACP100 IL-2 fusion protein | mdmrvpaqllglllwlrgarcQVQLQESGGGLVQAGGSLRLSCAASGRIFSIDIMSWYR<br>QAPGKQRELVARITRGGTISYDDSVKGRFTISRDNAKNTVYLQMNSLKPEDTG<br>VYYCNALYGTDYWGKGTQVTVSSggggsggggsggggsaptsssticktqlqlehllldlqmilngin<br>nyknpkltriniffficfympldcatelkhlqcleeelkpleevinlaqsknfhlrprdlisninvivlelkgset<br>tfmceyadetativeflnrwitfcqsiistltHHHHHH |
| 144 | ACP101 (WW0061) IL-2 fusion protein | mdmrvpaqllglllwlrgarcaptsssticktqlqlehllldlqmilnginnyknpkltrmlafympkkatelkhlqcle<br>eelkpleevinlaqsknfhlrprdlisninvivlelkgsettfmceyadetativeflnrwitfcqsiistltSGGPGPAG<br>MKGLPGSEVQLVESGGGLVQPGNSLRLSCAASGFTFSKFGMSWVRQAPGKGL<br>EWVSSISGSGRDTLYAESVKGRFTISRDNAKTTLYLQMNSLRPEDTAVYYCTI<br>GGSLSVSSQGTLVTVSSHHHHHH |
| 145 | ACP102 IL-2 fusion protein | mdmrvpaqllglllwlrgarcQVQLQESGGGLVQAGGSLRLSCAASGRIFSIDIMSWYR<br>QAPGKQRELVARITRGGTISYDDSVKGRFTISRDNAKNTVYLQMNSLKPEDTG<br>VYYCNALYGTDYWGKGTQVTVSSSGGPGPAGMKGLPGSaptsssticktqlqlehllldlq<br>milnginnyknpkltrmlafympkkatelkhlqcleeelkpleevinlaqsknfhliprdlisninvivlelkgsettfm<br>ceyadetativeflnrwitfcqsiistltSGGPGPAGMKGLPGSEVQLVESGGGLVQPGNSLRL<br>SCAASGFTFSKFGMSWVRQAPGKGLEWVSSISGSGRDTLYAESVKGRFTISRD<br>NAKTTLYLQMNSLRPEDTAVYYCTIGGSLSVSSQGTLVTVSSggggsggggsggggs<br>ggggsggggsggggsEVQLVESGGGLVQPGGSLRLSCAASGFTFSSYTLAWVRQAPG<br>KGLEWVAAIDSSSYTYSPDTVRGRFTISRDNAKNSLYLQMNSLRAEDTAVYY<br>CARDSNWDALDYWGQGTTVTVSSGGGGSGGGGSGGGGSDIQMTQSPSSLSA<br>SVGDRVTITCKASQNVGTNVGWYQQKPGKAPKALIYSASFRYSGVPSRFSGSG<br>SGTDFTLTISSLQPEDFATYYCQQYYTYPYTFGGGTKVEIKHHHHHH |
| 146 | ACP103 IL-2 fusion protein | mdmrvpaqllglllwlrgarcaptsssticktqlqlehllldlqmilnginnyknpkltrmla<br>fympkkatelkhlqcleeelkpleevinlaqsknfhlrprdlisninvivlelkgsettfmcey<br>adetativeflnrwitfcqsiistltSGGPGPAGMKGLPGSggggsggggsggggsggggsggggsg<br>gggsEVQLVESGGGLVQPGGSLRLSCAASGFTFSSYTLAWVRQAPGKGLEWVAAIDSSSYTYSPDTVR<br>GRFTISRDNAKNSLYLQMNSLRAEDTAVYYCARDSNWDALDYWGQGTTVTVSSGGGGSGGGG<br>SGGGGSDIQMTQSPSSLSASVGDRVTITCKASQNVGTNVGWYQQKPGKAPKA<br>LIYSASFRYSGVPSRFSGSGSGTDFTLTISSLQPEDFATYYCQQYYTYPYTFGGG<br>TKVEIKggggsggggsggggsEVQLVESGGGLVQPGNSLRLSCAASGFTFSKFGMSW<br>VRQAPGKGLEWVSSISGSGRDTLYAESVKGRFTISRDNAKTTLYLQMNSLRPE<br>DTAVYYCTIGGSLSVSSQGTLVTVSSggggsggggsggggsQVQLQESGGGLAQAGG<br>SLSLSCAASGFTVSNSVMAWYRQTPGKQREFVAIINSVGSTNYADSVKGRFTIS<br>RDNAKNTVYLQMNNLKPEDTAVYVCNRNFDRIYWGQGTQVTVSSHHHHHH |
| 147 | ACP104 IL-2 fusion protein | mdmrvpaqllglllwlrgarcQVQLQESGGGLAQAGGSLSLSCAASGFTVSNSVMAWY<br>RQTPGKQREFVAIINSVGSTNYADSVKGRFTISRDNAKNTVYLQMNNLKPEDT<br>AVYVCNRNFDRIYWGQGTQVTVSSaptsssticktqlqlehllldlqmilnginnyknpkltrmltfkfy<br>mpkkatelklilqcleeelkpleevlnlaqsknflilrprdlisninvivlelkgsettfmceyadetati<br>veflnrvvitfcqsiieflnrwitfcqsiistltSGGPGPAGMKGLPGSEVQLVESGGGLVQPGNSLRLSC<br>AASGFTFSKFGMSWVRQAPGKGLEWVSSISGSGRDTLYAESVKGRFTISRDNAKTTLYLQMNSLR<br>PEDTAVYYCTIGGSLSVSSQGTLVTVSSggggsggggsggggsggggsggggsggggsEVQL |

-continued

Sequence table

| SEQ ID NO. | Name | Sequence |
|---|---|---|
| | | VESGGGLVQPGGSLRLSCAASGFTFSSYTLAWVRQAPGKGLEWVAAIDSSSYT<br>YSPDTVRGRFTISRDNAKNSLYLQMNSLRAEDTAVYYCARDSNWDALDYWG<br>QGTTVTVSSGGGGSGGGGSGGGGSDIQMTQSPSSLSASVGDRVTITCKASQNV<br>GTNVGWYQQKPGKAPKALIYSASFRYSGVPSRFSGSGSGTDFTLTISSLQPEDF<br>ATYYCQQYYTYPYTFGGGTKVEIKHHHHHH |
| 148 | ACP105 IL-2 fusion protein | mdmrvpaqllglllwlrgarcEVQLVESGGGLVQPGGSLRLSCAASGFTFSSYTLAWVR<br>QAPGKGLEWVAAIDSSSYTYSPDTVRGRFTISRDNAKNSLYLQMNSLRAEDTA<br>VYYCARDSNWDALDYWGQGTTVTVSSGGGGSGGGGSGGGGSDIQMTQSPSS<br>LSASVGDRVTITCKASQNVGTNVGWYQQKPGKAPKALIYSASFRYSGVPSRFS<br>GSGSGTDFTLTISSLQPEDFATYYCQQYYTYPYTFGGGTKVEIKggggsggggsggg<br>gsggggsggggsggggsSGGPGPAGMKGLPGSaptssstkktqlqlehllldlqmilnginnyknpkltrml<br>tflcfympkkatelkhlqcleeelkpleevinlaqsknfhlrprdlisninvivlelkgsettfmceyadeta<br>tiveflnrwitfcqsiistltSGGPGPAGMKGLPGSEVQLVESGGGLVQPGNSLRLSCAASGFTFSKFG<br>MSWVRQAPGKGLEWVSSISGSGRDTLYAESVKGRFTISRDNAKTTLYLQMNS<br>LRPEDTAVYYCTIGGSLSVSSQGTLVTVSSggggsggggsggggsQVQLQESGGGLA<br>QAGGSLSLSCAASGFTVSNSVMAWYRQTPGKQREFVAIINSVGSTNYADSVK<br>GRFTISRDNAKNTVYLQMNNLKPEDTAVYVCNRNFDRIYWGQGTQVTVSSH<br>HHHHH |
| 149 | ACP106 IL-2 fusion protein | mdmrvpaqllglllwlrgarcQVQLQESGGGLAQAGGSLSLSCAASGFTVSNSVMAWY<br>RQTPGKQREFVAIINSVGSTNYADSVKGRFTISRDNAKNTVYLQMNNLKPEDT<br>AVYVCNRNFDRIYWGQGTQVTVSSggggsggggsggggsEVQLVESGGGLVQPGNS<br>LRLSCAASGFTFSKFGMSWVRQAPGKGLEWVSSISGSGRDTLYAESVKGRFTI<br>SRDNAKTTLYLQMNSLRPEDTAVYYCTIGGSLSVSSQGTLVTVSSSGGPGPAG<br>MKGLPGSEVQLVESGGGLVQPGGSLRLSCAASGFTFSSYTLAWVRQAPGKGL<br>EWVAAIDSSSYTYSPDTVRGRFTISRDNAKNSLYLQMNSLRAEDTAVYYCAR<br>DSNWDALDYWGQGTTVTVSSGGGGSGGGGSGGGGSDIQMTQSPSSLSASVG<br>DRVTITCKASQNVGTNVGWYQQKPGKAPKALIYSASFRYSGVPSRFSGSGSGT<br>DFTLTISSLQPEDFATYYCQQYYTYPYTFGGGTKVEIKggggsggggsggggsggggsgg<br>ggsggggsSGGPGPAGMKGLPGSaptssstkktqlqlehllldlqmilnginnyknpkltrmltfkfympkk<br>atelkhlqcleeelkpleevinlaqsknfhlrprdlisninvivlelkgsettfmceyadetativeflnrwil<br>fcqsiistltHHHHHH |
| 150 | ACP107 IL-2 fusion protein | mdmrvpaqllglllwlrgarcEVQLVESGGGLVQPGGSLRLSCAASGFTFSSYTLAWVR<br>QAPGKGLEWVAAIDSSSYTYSPDTVRGRFTISRDNAKNSLYLQMNSLRAEDTA<br>VYYCARDSNWDALDYWGQGTTVTVSSGGGGSGGGGSGGGGSDIQMTQSPSS<br>LSASVGDRVTITCKASQNVGTNVGWYQQKPGKAPKALIYSASFRYSGVPSRFS<br>GSGSGTDFTLTISSLQPEDFATYYCQQYYTYPYTFGGGTKVEIKggggsggggsggg<br>gsggggsggggsggggsEVQLVESGGGLVQPGNSLRLSCAASGFTFSKFGMSWVRQA<br>PGKGLEWVSSISGSGRDTLYAESVKGRFTISRDNAKTTLYLQMNSLRPEDTAV<br>YYCTIGGSLSVSSQGTLVTVSSSGGPGPAGMKGLPGSaptssstkktqlqlehllldlqmilng<br>innyknpkltrmltfkfympkkatelkhlqcleeelkpleevinlaqsknfhliprdlisninvivlelkgse<br>ettfmceyadtativeflnrwitfcqsiistltggggsggggsggggsQVQLQESGGGLAQAGGSLSLSCAASGFT<br>VSNSVMAWYRQTPGKQREFVAIINSVGSTNYADSVKGRFTISRDNAKNTVYL<br>QMNNLKPEDTAVYVCNRNFDRIYWGQGTQVTVSSHHHHHH |
| 151 | ACP108 IL-2 fusion protein | mdmrvpaqllglllwlrgarcQVQLQESGGGLVQAGGSLRLSCAASGRIFSIDIMSWYR<br>QAPGKQRELVARITRGGTISYDDSVKGRFTISRDNAKNTVYLQMNSLKPEDTG<br>VYYCNALYGTDYWGKGTQVTVSSggggsggggsggggsaptssstkktqlqlehllldlqmilngin<br>nyknpkltrmltfklympldcatelkhlqcleeelkpleevinlaqsknfhlrprdlisninvivlelkgsett<br>fmceyadetativeflnrwitfcqsiistltSGGPGPAGMKGLPGSrgetgpaaPGSEVQLVESGGGLVQPGNS<br>LRLSCAASGFTFSKFGMSWVRQAPGKGLEWVSSISGSGRDTLYAESVKGRFTI<br>SRDNAKTTLYLQMNSLRPEDTAVYYCTIGGSLSVSSQGTLVTVSSggggsggggsg<br>gggsggggsggggsggggsEVQLVESGGGLVQPGGSLRLSCAASGFTFSSYTLAWVRQ<br>APGKGLEWVAAIDSSSYTYSPDTVRGRFTISRDNAKNSLYLQMNSLRAEDTAV<br>YYCARDSNWDALDYWGQGTTVTVSSGGGGSGGGGSGGGGSDIQMTQSPSSL<br>SASVGDRVTITCKASQNVGTNVGWYQQKPGKAPKALIYSASFRYSGVPSRFSG<br>SGSGTDFTLTISSLQPEDFATYYCQQYYTYPYTFGGGTKVEIKHHHHHH |
| 152 | ACP117 Anti-FN CGS-2 scFv | mdmrvpaqllglllwlrgarcEVQLVESGGGLVQPGGSLRLSCAASGFTFSSYAMSWVR<br>QAPGKGLEWVSAISGSGGSTYYADSVKGRFTISRDNSKNTLYLQMNSLRAED<br>PEATAVYYCARGVGAFRPYRKHEWGQGTLVTVSRggggsggggsggggsSSELTQDPAV<br>SVALGQTVRITCQGDSLRSYYASWYQQKPGQAPVLVIYGKNNRPSGIPDRFSG<br>SSSGNTASLTTTGAQAEDEADYYCNSSPFEHNLVVFGGGTKLTVLHHHHHHE |
| 153 | ACP118 NARA1 Vh/Vl non-cleavable | mdmrvpaqllglllwlrgarcQVQLQQSGAELVRPGTSVKVSCKASGYAFTNYLIEWV<br>KQRPGQGLEWIGVINPGSGGTNYNEKFKGKATLTADKSSSTAYMQLSSLTSD<br>DSAVYFCARWRGDGYYAYFDVWGAGTTVTVSSggggsggggsggggsDIVLTQSP<br>ASLAVSLGQRATISCKASQSVDYDGDSYMNWYQQKPGQPPKLLIYAASNLES<br>GIPARFSGSGSGTDFTLNIHPVEEEDAATYYCQQSNEDPYTFGGGTKLEIKHHH<br>HHHEPEA |

-continued

Sequence table

| SEQ ID NO. | Name | Sequence |
|---|---|---|
| 154 | ACP119 NARA1 Vh/Vl cleavable | mdmrvpaqllglllwlrgarcQVQLQQSGAELVRPGTSVKVSCKASGYAFTNYLIEWV<br>KQRPGQGLEWIGVINPGSGGTNYNEKFKGKATLTADKSSSTAYMQLSSLTSD<br>DSAVYFCARWRGDGYYAYFDVWGAGTTVTVSSSGGPGPAGMKGLPGSDIVL<br>TQSPASLAVSLGQRATISCKASQSVDYDGDSYMNWYQQKPGQPPKLLIYAAS<br>NLESGIPARFSGSGSGTDFTLNIHPVEEEDAATYYCQQSNEDPYTFGGGTKLEI<br>KHHHHHHEPEA |
| 155 | ACP120 NARA1 Vl/Vh non-cleavable | mdmrvpaqllglllwlrgarcDIVLTQSPASLAVSLGQRATISCKASQSVDYDGDSYMN<br>WYQQKPGQPPKLLIYAASNLESGIPARFSGSGSGTDFTLNIHPVEEEDAATYYC<br>QQSNEDPYTFGGGTKLEIKggggsggggsggggsQVQLQQSGAELVRPGTSVKVSCK<br>ASGYAFTNYLIEWVKQRPGQGLEWIGVINPGSGGTNYNEKFKGKATLTADKS<br>SSTAYMQLSSLTSDDSAVYFCARWRGDGYYAYFDVWGAGTTVTVSSHHHHH<br>HEPEA |
| 156 | ACP121 NARA1 Vl/Vh cleavable | mdmrvpaqllglllwlrgarcDIVLTQSPASLAVSLGQRATISCKASQSVDYDGDSYMN<br>WYQQKPGQPPKLLIYAASNLESGIPARFSGSGSGTDFTLNIHPVEEEDAATYYC<br>QQSNEDPYTFGGGTKLEIKSGGPGPAGMKGLPGSQVQLQQSGAELVRPGTSV<br>KVSCKASGYAFTNYLIEWVKQRPGQGLEWIGVINPGSGGTNYNEKFKGKATL<br>TADKSSSTAYMQLSSLTSDDSAVYFCARWRGDGYYAYFDVWGAGTTVTVSS<br>HHHHHHEPEA |
| 157 | ACP124 IL-2 fusion protein (WW0159) | mdmrvpaqllglllwlrgarcaptssstkktqlqlehllldlqmilnginnyknpkltrmilfkfympkkatelkhlqcle<br>eelkpleevinlaqsknfhlrprdlisninvivlelkgsetlfmceyadetativeflnrwitfcqsiistliggggsggggsg<br>gggsEVQLVESGGGLVQPGNSLRLSCAASGFTFSKFGMSWVRQAPGKGLEWVS<br>SISGSGRDTLYAESVKGRFTISRDNAKTTLYLQMNSLRPEDTAVYYCTIGGSLS<br>VSSQGTLVTVSSHHHHHHEPEA |
| 158 | ACP132 IL-2 fusion protein (WW0177) | mdmrvpaqllglllwlrgarcaptssstkktqlqlehllldlqmilnginnyknpkltrmilfkfympkkatelkhlqcle<br>eelkpleevinlaqsknfhlrprdlisninvivlelkgsetlfmceyadetativeflnrwitfcqsiistliggggsggggsg<br>gggsdahksevahrfkdlgeenfkalvliafaqylqqcpfedhvklvnevtefaktcvadesaencdkslhtlfgdklctv<br>atlretygemadccakqepernecflqhkddnpnlprlvrpevdvmctafhdneeffildcylyeiarrhpyfyapellff<br>akrykaafteccqaadkaacllpkldelrdegkassakqrlkcaslqkfgerafkawavarlsqrfpkaefaevsklvtdlt<br>kyhtecchgdllecaddradlakyicenqdsissklkeccekpllekshciaevendempadlpslaadfveskdvckn<br>yaeakdvflgmflyeyarrhpdysvvillrlaktyettlekccaaadphecyakvfdefkplveepqnlikqncelfeqlg<br>eykfqnallviytldwpqvstptivevsrnlgkvgskcckhpeakrmpcaedylsvvinqlcvlhektpvsdrvtkcct<br>esknrrpcfsalevdetyvpkefnaetflfhadictlsekerqildcqtalvelvldikpkatkeqlkavmddfaafvekcc<br>kaddketcfaeegkklvaasqaalglHHHHHHEPEA |
| 159 | ACP141 IL-2 fusion protein (WW0178) | mdmrvpaqllglllwlrgarcaptssstkktqlqlehllldlqmilnginnyknpkltrmilfkfympkkatelkhlqcle<br>eelkpleevinlaqsknfhlrprdlisninvivlelkgsetlfmceyadetativeflnrwitfcqsiistliggggsggggsg<br>gggsdahksevahrfkdlgeenfkalvliafaqylqqcpfedhvklvnevtefaktcvadesaencdkslhtlfgdklctv<br>atlretygemadccakqepernecflqhkddnpnlprlvrpevdvmctafhdneeffildcylyeiarrhpyfyapellff<br>akrykaafteccqaadkaacllpkldelrdegkassakqrlkcaslqkfgerafkawavarlsqrfpkaefaevsklvtdlt<br>kyhtecchgdllecaddradlakyicenqdsissklkeccekpllekshciaevendempadlpslaadfveskdvckn<br>yaeakdvflgmflyeyarrhpdysvvillrlaktyettlekccaaadphecyakvfdefkplveepqnlikqncelfeqlg<br>eykfqnallviytldwpqvstptivevsrnlgkvgskcckhpeakrmpcaedylsvvinqlcvlhektpvsdrvtkcct<br>esknrrpcfsalevdetyvpkefnaetflfhadictlsekerqildcqtalvelvldikpkatkeqlkavmddfaafvekcc<br>kaddketcfaeegkklvaasqaalglHHHHHHEPEA |
| 160 | ACP142 IL-2 fusion protein (WW0179) | mdmrvpaqllglllwlrgarcaptssstIcktqlqlehllldlqmilnginnyknpkltrmilflcfympkkatelkhlqcle<br>eelkpleevinlaqsknfhlrprdlisninvivlelkgsetlfmceyadetativeflnrwitfcqsiistltSGGPGPAG<br>MKGLPGSdaliksevahrfkdlgeenfkalvliafaqylqqcpfedhvklvnevtefaktcvadesaencdkslhtlf<br>gdkletvatlretygemadccakqepernecflqhkddnpnlprlvrpevdvmctafhdneeffildcylyeiarrhpyf<br>yapellffakrykaafteccqaadkaacllpkldelrdegkassakqrlkcaslqkfgerafkawavarlsqrfpkaefaev<br>sklvtdltkvhtecchgdllecaddradlakyicenqdsissklkeccekpllekshciaevendempadlpslaadfves<br>kdvcknyaeakdvflgmflyeyarrhpdysvvillrlaktyettlekccaaadphecyakvfdefkplveepqnlikqn<br>celfeqlgeykfqnallviytkkvpqvstptivevsrnlgIcvgskcckhpeakrmpcaedylsvvinqlcvlhektpvs<br>drytkcctesknripcfsalevdetyvpkefnaelftfhadictlsekerqildcqtalvelvkhkpkatkeqlkavmdclfa<br>afvekcckaddketcfaeegIcklvaasqaalglHHHHHHEPEA |
| 161 | ACP144 IL-2 fusion protein | mdmrvpaqllglllwlrgarcaptssstIcktqlqlehllldlqmilnginnyknpkltrmilflcfympkkatelkhlqcle<br>eelkpleevinlaqsknfhlrprdlisninvivlelkgsetlfmceyadetativeflnrwitfcqsiistltSGGPGPAG<br>MKGLPGSEVQLVESGGGLVQPGNSLRLSCAASGFTFSKFGMSWVRQAPGKGL<br>EWVSSISGSGRDTLYAESVKGRFTISRDNAKTTLYLQMNSLRPEDTAVYYCTI<br>GGSLSVSSQGTLVTVSSggggsggggsggggsggggsggggsggggsSGGPGPAGMKGLPG<br>SEVQLVESGGGLVQPGGSLRLSCAASGFTFSSYTLAWVRQAPGKGLEWVAAI<br>DSSSYTYSPDTVRGRFTISRDNAKNSLYLQMNSLRAEDTAVYYCARDSNWDA<br>LDYWGQGTTVTVSSGGGGSGGGGSGGGGSDIQMTQSPSSLSASVGDRVTITC<br>KASQNVGTNVGWYQQKPGKAPKALIYSASFRYSGVPSRFSGSGSGTDFTLTIS<br>SLQPEDFATYYCQQYYTYPYTFGGGTKVEIKggggsggggsggggsQVQLQESGGG<br>LAQAGGSLSLSCAASGFTVSNSVMAWYRQTPGKQREFVAIINSVGSTNYADS<br>VKGRFTISRDNAKNTVYLQMNNLKPEDTAVYVCNRNFDRIYWGQGTQVTVS<br>SHHHHHHEPEA |

-continued

Sequence table

| SEQ ID NO. | Name | Sequence |
|---|---|---|
| 162 | ACP145 IL-2 fusion protein | mdmrvpaqllglllwlrgarcQVQLQESGGGLAQAGGSLSLSCAASGFTVSNSVMAWYRQTPGKQREFVAIINSVGSTNYADSVKGRFTISRDNAKNTVYLQMNNLKPEDTAVYVCNRNFDRIYWGQGTQVTVSSggggsggggsggggsaptssstldctqlqlehllldlqmilngInnyknpkltrmltfkfympldcatelkhlqcleeelkpleevinlaqsknflilrprdlisninvivlelkgsetlfmceyadetativeflnrwitfcqsiistltSGGPGPAGMKGLPGSEVQLVESGGGLVQPGNSLRLSCAASGFTFSKFGMSWVRQAPGKGLEWVSSISGSGRDTLYAESVKGRFTISRDNAKTTLYLQMNSLRPEDTAVYYCTIGGSLSVSSQGTLVTVSSggggsggggsggggsggggsggggsggggsSGGPGPAGMKGLPGSEVQLVESGGGLVQPGGSLRLSCAASGFTFSSYTLAWVRQAPGKGLEWVAAIDSSSYTYSPDTVRGRFTISRDNAKNSLYLQMNSLRAEDTAVYYCARDSNWDALDYWGQGTTVTVSSGGGGSGGGGSGGGGSDIQMTQSPSSLSASVGDRVTITCKASQNVGTNVGWYQQKPGKAPKALIYSASFRYSGVPSRFSGSGSGTDFTLTISSLQPEDFATYYCQQYYTYPYTFGGGTKVEIKHHHHHEPEA |
| 163 | ACP146 IL-2 fusion protein | mdmrvpaqllglllwlrgarcQVQLQESGGGLAQAGGSLSLSCAASGFTVSNSVMAWYRQTPGKQREFVAIINSVGSTNYADSVKGRFTISRDNAKNTVYLQMNNLKPEDTAVYVCNRNFDRIYWGQGTQVTVSSSGGPGPAGMKGLPGSaptssstIcktqlqlehllldlqmilngimiykiipkltrmltfkfSmpkkatelklilqcleeelkpleevlnlaqsknflilrprdlisninvivlelkgsettfmceyadetativeflnrwitfcqsiistltSGGPGPAGMKGLPGSEVQLVESGGGLVQPGNSLRLSCAASGFTFSKFGMSWVRQAPGKGLEWVSSISGSGRDTLYAESVKGRFTISRDNAKTTLYLQMNSLRPEDTAVYYCTIGGSLSVSSQGTLVTVSSggggsggggsggggsggggsggggsggggsSGGPGPAGMKGLPGSEVQLVESGGGLVQPGGSLRLSCAASGFTFSSYTLAWVRQAPGKGLEWVAAIDSSSYTYSPDTVRGRFTISRDNAKNSLYLQMNSLRAEDTAVYYCARDSNWDALDYWGQGTTVTVSSGGGGSGGGGSGGGGSDIQMTQSPSSLSASVGDRVTITCKASQNVGTNVGWYQQKPGKAPKALIYSASFRYSGVPSRFSGSGSGTDFTLTISSLQPEDFATYYCQQYYTYPYTFGGGTKVEIKHHHHHHEPEA |
| 164 | ACP133 (WW0196) IL-2-6xHis ("6xHis" disclosed as SEQ ID NO.: 354) | mdmrvpaqllglllwlrgarcaptssstIcktqlqlehllldlqmilnginnyknpkltrmilfkfympkkatelkhlqcleeelkpleevinlaqsknfhlrprdlisninvivlelkgsetlfmceyadetativeflnrwitfcqsiistltHHHHHH |
| 165 | ACP147 IL-2 fusion protein | mdmrvpaqllglllwlrgarcaptssstkktqlqlehllldlqmilnginnyknpkltrmltfkfympkkatelkhlqcleeelkpleevinlaqsknfhlrprdlisninvivlelkgsettfmceyadetativeflnrwitfcqsiistltSGGPGPAGMKGLPGSEVQLVESGGGLVQPGNSLRLSCAASGFTFSKFGMSWVRQAPGKGLEWVSSISGSGRDTLYAESVKGRFTISRDNAKTTLYLQMNSLRPEDTAVYYCTIGGSLSVSSQGTLVTVSSggggsggggsggggsggggsggggsggggsSGGPGPAGMKGLPGSEVQLVESGGGLVQPGGSLRLSCAASGFTFSSYTLAWVRQAPGKGLEWVAAIDSSSYTYSPDTVRGRFTISRDNAKNSLYLQMNSLRAEDTAVYYCARDSNWDALDYWGQGTTVTVSSGGGGSGGGGSGGGGSDIQMTQSPSSLSASVGDRVTITCKASQNVGTNVGWYQQKPGKAPKALIYSASFRYSGVPSRFSGSGSGTDFTLTISSLQPEDFATYYCQQYYTYPYTFGGGTKVEIKggggsggggsggggsQVQLQESGGGLVQAGGSLRLSCAASGRIFSIDIMSWYRQAPGKQRELVARITRGGTISYDDSVKGRFTISRDNAKNTVYLQMNSLKPEDTGVYYCNALYGTDYWGKGTQVTVSSHHHHHEPEA |
| 166 | ACP148 IL-2 fusion protein | mdmrvpaqllglllwlrgarcQVQLQESGGGLVQAGGSLRLSCAASGRIFSIDIMSWYRQAPGKQRELVARITRGGTISYDDSVKGRFTISRDNAKNTVYLQMNSLKPEDTGVYYCNALYGTDYWGKGTQVTVSSggggsggggsggggsaptsssticktqlqlehllldlqmilnginnyknpkltrmlificlympldcatelkhlqcleeelkpleevinlaqsknfhlrprdlisninvivlelkgsettfmceyadetativeflnrwitfcqsiistltSGGPGPAGMKGLPGSEVQLVESGGGLVQPGNSLRLSCAASGFTFSKFGMSWVRQAPGKGLEWVSSISGSGRDTLYAESVKGRFTISRDNAKTTLYLQMNSLRPEDTAVYYCTIGGSLSVSSQGTLVTVSSggggsggggsggggsggggsggggsggggsSGGPGPAGMKGLPGSEVQLVESGGGLVQPGGSLRLSCAASGFTFSSYTLAWVRQAPGKGLEWVAAIDSSSYTYSPDTVRGRFTISRDNAKNSLYLQMNSLRAEDTAVYYCARDSNWDALDYWGQGTTVTVSSGGGGSGGGGSGGGGSDIQMTQSPSSLSASVGDRVTITCKASQNVGTNVGWYQQKPGKAPKALIYSASFRYSGVPSRFSGSGSGTDFTLTISSLQPEDFATYYCQQYYTYPYTFGGGTKVEIKHHHHHEPEA |
| 167 | ACP149 IL-2 fusion | mdmrvpaqllglllwlrgarcQVQLQESGGGLVQAGGSLRLSCAASGRIFSIDIMSWYRQAPGKQRELVARITRGGTISYDDSVKGRFTISRDNAKNTVYLQMNSLKPEDTGproteinVYYCNALYGTDYWGKGTQVTVSSSGGPGPAGMKGLPGSaptsssticktqlqlehllldlqmilnginnyknpkltrmlafympkkatelkhlqcleeelkpleevinlaqsknfhlrprdlisninvivlelkgsettfmceyadetativeflnrwitfcqsiistltSGGPGPAGMKGLPGSEVQLVESGGGLVQPGNSLRLSCAASGFTFSKFGMSWVRQAPGKGLEWVSSISGSGRDTLYAESVKGRFTISRDNAKTTLYLQMNSLRPEDTAVYYCTIGGSLSVSSQGTLVTVSSggggsggggsggggsggggsggggsggggsSGGPGPAGMKGLPGSEVQLVESGGGLVQPGGSLRLSCAASG |

-continued

Sequence table

| SEQ ID NO. | Name | Sequence |
|---|---|---|
| | | FTFSSYTLAWVRQAPGKGLEWVAAIDSSSYTYSPDTVRGRFTISRDNAKNSLY<br>LQMNSLRAEDTAVYYCARDSNWDALDYWGQGTTVTVSSGGGGSGGGGSGG<br>GGSDIQMTQSPSSLSASVGDRVTITCKASQNVGTNVGWYQQKPGKAPKALIYS<br>ASFRYSGVPSRFSGSGSGTDFTLTISSLQPEDFATYYCQQYYTYPYTFGGGTKV<br>EIKHHHHHHEPEA |
| 168 | ACP33 Mouse IFNa-fusion protein | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGScdlpqthnlrnkraltllvqmrr<br>lsplsclkdrkdfgfpqekvdaqqildcaqaipvlseltqqilniftskdssaawnttlldsfendlhqqlndlqgclmqqvg<br>vqefpltqedallavrkythritvylrekkhspcawevvraevwralsssanvSGGPGPAGMKGLPGSEV<br>QLVESGGGLVQPGNSLRLSCAASGFTFSKFGMSWVRQAPGKGLEWVSSISGS<br>GRDTLYAESVKGRFTISRDNAKTTLYLQMNSLRPEDTAVYYCTIGGSLSVSSQ<br>GTLVTVSSHHHHHHEPEA |
| 169 | ACP131 Mouse IFNa | mdmrvpaqllglllwlrgarcallpqthnlinkralfilvqmrrlsplsclkdrkcifgfpqekvdaqqildcaqaipvlsel<br>tqqilniftskdssaawnttlldsfendlhqqlndlqgclmqqvgvqefpltqedallavrkyfhritvylrekkhspcawe<br>vvraevwralsssanvlgrlreekHHHHHHEPEA |
| 170 | ACP125 Mouse IFNa-fusion protein | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGScdlpqthnlrnkraltllvqmrr<br>lsplsclkdrkdfgfpqekvdaqqikkactaipvlseltqqilniftskdssaawnttlldsfcndlhqqlndlqgclmqqvg<br>vqefpltqedallavrIcyfhritvylrekkhspcawevvraevwralsssamIgrlreekHHHHHHEPEA |
| 171 | ACP126 Mouse IFNa-fusion protein | mdmrvpaqllginiwlrgarccdlpqthnlrnkraltllvqmrrlsplsclkdrkdfgfpqekvdaqqikkaqaipvlel<br>tqqilniftskdssaawnttlldsfcndlhqqlndlqgclmqqvgvqefpltqedallavrIcyfhritvylrekkhspcawe<br>vvraevwralsssamIgrlreekSGGPGPAGMKGLPGSEVQLVESGGGLVQPGNSLRLSC<br>AASGFTFSKFGMSWVRQAPGKGLEWVSSISGSGRDTLYAESVKGRFTISRDNA<br>KTTLYLQMNSLRPEDTAVYYCTIGGSLSVSSQGTLVTVSSHHHHHHEPEA |
| 172 | ACP127 Mouse IFNa-fusion protein | mdmrvpaqllglllwlrgarcEAHKSEIAHRYNDLGEQHFKGLVLIAFSQYLQKCSYDE<br>HAKLVQEVTDFAKTCVADESAANCDKSLHTLFGDKLCAIPNLRENYGELADC<br>CTKQEPERNECFLQHKDDNPSLPPFERPEAEAMCTSFKENPTTFMGHYLHEVA<br>RRHPYFYAPELLYYAEQYNEILTQCCAEADKESCLTPKLDGVKEKALVSSVRQ<br>RMKCSSMQKFGERAFKAWAVARLSQTFPNADFAEITKLATDLTKVNKECCH<br>GDLLECADDRAELAKYMCENQATISSKLQTCCDKPLLKKAHCLSEVEHDTMP<br>ADLPAIAADFVEDQEVCKNYAEAKDVFLGTFLYEYSRRHPDYSVSLLLRLAK<br>KYEATLEKCCAEANPPACYGTVLAEFQPLVEEPKNLVKTNCDLYEKLGEYGF<br>QNAILVRYTQKAPQVSTPTLVEAARNLGRVGTKCCTLPEDQRLPCVEDYLSAI<br>LNRVCLLHEKTPVSEHVTKCCSGSLVERRPCFSALTVDETYVPKEFKAETFTFH<br>SDICTLPEKEKQIKKQTALAELVKHKPKATAEQLKTVMDDFAQFLDTCCKAA<br>DKDTCFSTEGPNLVTRCKDALASGGPGPAGMKGLPGScdlpqthnlinkraltllvqmrrls<br>plsclkdrkcifgfpqekvdaqqikkactaipvlseltqqilniftskdssaawnttlldsfcndlhqqlndlqgclmqqvgv<br>qefpltqedallavrIcythritvylrekkhspcawevvraevwralsssamIgrlreekSGGPGPAGMKGLP<br>GSEAHKSEIAHRYNDLGEQHFKGLVLIAFSQYLQKCSYDEHAKLVQEVTDFA<br>KTCVADESAANCDKSLHTLFGDKLCAIPNLRENYGELADCCTKQEPERNECFL<br>QHKDDNPSLPPFERPEAEAMCTSFKENPTTFMGHYLHEVARRHPYFYAPELLY<br>YAEQYNEILTQCCAEADKESCLTPKLDGVKEKALVSSVRQRMKCSSMQKFGE<br>RAFKAWAVARLSQTFPNADFAEITKLATDLTKVNKECCHGDLLECADDRAEL<br>AKYMCENQATISSKLQTCCDKPLLKKAHCLSEVEHDTMPADLPAIAADFVED<br>QEVCKNYAEAKDVFLGTFLYEYSRRHPDYSVSLLLRLAKKYEATLEKCCAEA<br>NPPACYGTVLAEFQPLVEEPKNLVKTNCDLYEKLGEYGFQNAILVRYTQKAP<br>QVSTPTLVEAARNLGRVGTKCCTLPEDQRLPCVEDYLSAILNRVCLLHEKTPV<br>SEHVTKCCSGSLVERRPCFSALTVDETYVPKEFKAETFTFHSDICTLPEKEKQIK<br>KQTALAELVKHKPKATAEQLKTVMDDFAQFLDTCCKAADKDTCFSTEGPNL<br>VTRCKDALAHHHHHHEPEA |
| 173 | ACP128 Mouse IFNa-fusion protein | mdmrvpaqllglllwlrgarcEAHKSEIAHRYNDLGEQHFKGLVLIAFSQYLQKCSYDE<br>HAKLVQEVTDFAKTCVADESAANCDKSLHTLFGDKLCAIPNLRENYGELADC<br>CTKQEPERNECFLQHKDDNPSLPPFERPEAEAMCTSFKENPTTFMGHYLHEVA<br>RRHPYFYAPELLYYAEQYNEILTQCCAEADKESCLTPKLDGVKEKALVSSVRQ<br>RMKCSSMQKFGERAFKAWAVARLSQTFPNADFAEITKLATDLTKVNKECCH<br>GDLLECADDRAELAKYMCENQATISSKLQTCCDKPLLKKAHCLSEVEHDTMP<br>ADLPAIAADFVEDQEVCKNYAEAKDVFLGTFLYEYSRRHPDYSVSLLLRLAK<br>KYEATLEKCCAEANPPACYGTVLAEFQPLVEEPKNLVKTNCDLYEKLGEYGF<br>QNAILVRYTQKAPQVSTPTLVEAARNLGRVGTKCCTLPEDQRLPCVEDYLSAI<br>LNRVCLLHEKTPVSEHVTKCCSGSLVERRPCFSALTVDETYVPKEFKAETFTFH<br>SDICTLPEKEKQIKKQTALAELVKHKPKATAEQLKTVMDDFAQFLDTCCKAA<br>DKDTCFSTEGPNLVTRCKDALASGGPGPAGMKGLPGScdlpqthnlinkraltllvqmrrls<br>plsclkdrkcifgfpqekvdaqqikkactaipvlseltqqilniftskdssaawnttlldsfcndlhqqlndlqgclmqqvgv<br>qefpltqedallavrIcythritvylrekkhspcawevvraevwralsssamIgrlreekHHHHHHEPEA |

-continued

Sequence table

| SEQ ID NO. | Name | Sequence |
|---|---|---|
| 174 | ACP129 Mouse IFNa-fusion protein | mdmrvpaqllglllwlrgarccdlpqtlmlmkraltllvqmrrlsplsclkdrkdfgfpqekvdaqqikkactaipvlsel<br>tqqilniftskdssaawnttlldsfcndlhqqlndlqgclmqqvgvqefpltqedallavrIcyfhritvylrekkhspcawe<br>vvraevwralsssamIgrlreekSGGPGPAGMKGLPGSEAHKSEIAHRYNDLGEQHFKGL<br>VLIAFSQYLQKCSYDEHAKLVQEVTDFAKTCVADESAANCDKSLHTLFGDKL<br>CAIPNLRENYGELADCCTKQEPERNECFLQHKDDNPSLPPFERPEAEAMCTSF<br>KENPTTFMGHYLHEVARRHPYFYAPELLYYAEQYNEILTQCCAEADKESCLTP<br>KLDGVKEKALVSSVRQRMKCSSMQKFGERAFKAWAVARLSQTFPNADFAEIT<br>KLATDLTKVNKECCHGDLLECADDRAELAKYMCENQATISSKLQTCCDKPLL<br>KKAHCLSEVEHDTMPADLPAIAADFVEDQEVCKNYAEAKDVFLGTFLYEYSR<br>RHPDYSVSLLLRLAKKYEATLEKCCAEANPPACYGTVLAEFQPLVEEPKNLVK<br>TNCDLYEKLGEYGFQNAILVRYTQKAPQVSTPTLVEAARNLGRVGTKCCTLP<br>EDQRLPCVEDYLSAILNRVCLLHEKTPVSEHVTKCCSGSLVERRPCFSALTVDE<br>TYVPKEFKAETFTFHSDICTLPEKEKQIKKQTALAELVKHKPKATAEQLKTVM<br>DDFAQFLDTCCKAADKDTCFSTEGPNLVTRCKDALAHHHHHHEPEA |
| 175 | ACP150 Mouse IFNa-fusion protein | mdmrvpaqllglllwlrgarcQVQLQESGGGLAQAGGSLSLSCAASGFTVSNSVMAWY<br>RQTPGKQREFVAIINSVGSTNYADSVKGRFTISRDNAKNTVYLQMNNLKPEDT<br>AVYVCNRNFDRIYWGQGTQVTVSSggggsggggsggggsEVQLVESGGGLVQPGNS<br>LRLSCAASGFTFSKFGMSWVRQAPGKGLEWVSSISGSGRDTLYAESVKGRFTI<br>SRDNAKTTLYLQMNSLRPEDTAVYYCTIGGSLSVSSQGTLVTVSSSGGPGPAG<br>MKGLPGScdlpqthnlinkraltllvqmrrlsplsclkdrkclfgfpqekvdaqqikkapipvlseltqqilniftskd<br>ssaawnttlldsfcndlhqqlndlqgclmqqvgvqefpltqedallavrkythritvylrekichspcawevvraevwral<br>sssanylgrlreekSGGPGPAGMKGLPGSEVQLVESGGGLVQPGNSLRLSCAASGFTF<br>SKFGMSWVRQAPGKGLEWVSSISGSGRDTLYAESVKGRFTISRDNAKTTLYL<br>QMNSLRPEDTAVYYCTIGGSLSVSSQGTLVTVSSHHHHHHEPEA |
| 176 | ACP151 Mouse IFNa-fusion protein | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGScdlpqthnlinkraltllvqmrr<br>lsplsclkdrkdfgfpqekvdaqqikkaqaipvlseltqqilniftskdssaawnttlldsfcndlhqqlndlqgclmqqvg<br>vqefpltqedallavrkyfhritvylrekkhspcawevvraevwralsssanylgrlreekSGGPGPAGMKGLP<br>GSEVQLVESGGGLVQPGNSLRLSCAASGFTFSKFGMSWVRQAPGKGLEWVSS<br>ISGSGRDTLYAESVKGRFTISRDNAKTTLYLQMNSLRPEDTAVYYCTIGGSLSV<br>SSQGTLVTVSSggggsggggsggggsQVQLQESGGGLAQAGGSLSLSCAASGFTVSN<br>SVMAWYRQTPGKQREFVAIINSVGSTNYADSVKGRFTISRDNAKNTVYLQMN<br>NLKPEDTAVYVCNRNFDRIYWGQGTQVTVSSHHHHHHEPEA |
| 177 | ACP152 Mouse IFNa-fusion protein | mdmrvpaqllglllwlrgarcEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSggggsggggsggggscdlpqthnlinkraltllvqmrrlsplscl<br>kdrkdfgfpqekvdaqqikkacjaipvlseltqqilniftskdssaawnttlldsfcndlhqqlndlqgclmqqvgvqefpl<br>tqedallavrkyfhritvylrekkhspcawevvraevwralsssanylgrlreekggggsggggsggggsEVQLVE<br>SGGGLVQPGNSLRLSCAASGFTFSKFGMSWVRQAPGKGLEWVSSISGSGRDTL<br>YAESVKGRFTISRDNAKTTLYLQMNSLRPEDTAVYYCTIGGSLSVSSQGTLVT<br>VSSHHHHHHEPEA |
| 178 | ACP153 (WW0201) (IL-2 Conju-gate) | mdmrvpaqllglllwlrgarcaptsssildctqlqlehllldlqmilnginnyknpkltrmltfkfympkkatelkhlqcle<br>eelkpleevinlaqsknfhlrprdlisninvivlelkgsetifmceyadetativeflnrwitfcqsiistltsgGPAGL<br>YAQpgsEVQLVESGGGLVQPGNSLRLSCAASGFTFSKFGMSWVRQAPGKGLE<br>WVSSISGSGRDTLYAESVKGRFTISRDNAKTTLYLQMNSLRPEDTAVYYCTIG<br>GSLSVSSQGTLVTVSSggggsggggsggggsggggsggggsggggssggpGPAGLYAQpgsEV<br>QLVESGGGLVQPGGSLRLSCAASGFTFSSYTLAWVRQAPGKGLEWVAAIDSSS<br>YTYSPDTVRGRFTISRDNAKNSLYLQMNSLRAEDTAVYYCARDSNWDALDY<br>WGQGTTVTVSSGGGGSGGGGSGGGGSDIQMTQSPSSLSASVGDRVTITCKAS<br>QNVGTNVGWYQQKPGKAPKALIYSASFRYSGVPSRFSGSGSGTDFTLTISSLQP<br>EDFATYYCQQYYTYPYTFGGGTKVEIKHHHHHHEPEA |
| 179 | ACP154 (WW0202) (IL-2 Conju-g ate) | mdmrvpaqllglllwlrgarcaptsssildctqlqlehllldlqmilnginnyknpkltrmltfkfympkkatelkhlqcle<br>eelkpleevinlaqsknfhlrprdlisninvivlelkgsetifmceyadetativeflnrwitfcqsiistltsggpPGGPA<br>GIGpgsEVQLVESGGGLVQPGNSLRLSCAASGFTFSKFGMSWVRQAPGKGLEW<br>VSSISGSGRDTLYAESVKGRFTISRDNAKTTLYLQMNSLRPEDTAVYYCTIGGS<br>LSVSSQGTLVTVSSggggsggggsggggsggggsggggsggggssggpPGGPAGIGpgsEVQLV<br>ESGGGLVQPGGSLRLSCAASGFTFSSYTLAWVRQAPGKGLEWVAAIDSSSYTY<br>SPDTVRGRFTISRDNAKNSLYLQMNSLRAEDTAVYYCARDSNWDALDYWGQ<br>GTTVTVSSGGGGSGGGGSGGGGSDIQMTQSPSSLSASVGDRVTITCKASQNVG<br>TNVGWYQQKPGKAPKALIYSASFRYSGVPSRFSGSGSGTDFTLTISSLQPEDFA<br>TYYCQQYYTYPYTFGGGTKVEIKHHHHHHEPEA |
| 180 | ACP155 (WW0203) (IL-2 Conju-gate) | mdmrvpaqllglllwlrgarcaptssstkktqlqlehllldlqmilnginnyknpkltrmilfkfympkkatelkhlqcle<br>eelkpleevinlaqsknfhlrprdlisninvivlelkgsettfmceyadetativeflnrwitfcqsiistltsggpALFKSS<br>FPpgsEVQLVESGGGLVQPGNSLRLSCAASGFTFSKFGMSWVRQAPGKGLEWV<br>SSISGSGRDTLYAESVKGRFTISRDNAKTTLYLQMNSLRPEDTAVYYCTIGGSL<br>SVSSQGTLVTVSSggggsggggsggggsggggsggggsggggssggpALFKSSFPpgsEVQLVE |

-continued

Sequence table

| SEQ ID NO. | Name | Sequence |
|---|---|---|
| | | SGGGLVQPGGSLRLSCAASGFTFSSYTLAWVRQAPGKGLEWVAAIDSSSYTYS<br>PDTVRGRFTISRDNAKNSLYLQMNSLRAEDTAVYYCARDSNWDALDYWGQG<br>TTVTVSSGGGGSGGGGSGGGGSDIQMTQSPSSLSASVGDRVTITCKASQNVGT<br>NVGWYQQKPGKAPKALIYSASFRYSGVPSRFSGSGSGTDFTLTISSLQPEDFAT<br>YYCQQYYTYPYTFGGGTKVEIKHHHHHHEPEA |
| 181 | ACP156 (WW0204) (IL-2 Conju-gate) | mdmrvpaqllglllwlrgarcaptssstkktqlqlehllldlqmilnginnyknpkltrmilfkfympkkatelkhlqcle<br>eelkpleevinlaqsknfhlrprdlisninvivlelkgsettfmceyadetativeflnrwitfcqsiistltsggpPLAQK<br>LKSSpgsEVQLVESGGGLVQPGNSLRLSCAASGFTFSKFGMSWVRQAPGKGLE<br>WVSSISGSGRDTLYAESVKGRFTISRDNAKTTLYLQMNSLRPEDTAVYYCTIG<br>GSLSVSSQGTLVTVSSggggsggggsggggsggggsggggsggggssggpPLAQKLKSSpgsEV<br>QLVESGGGLVQPGGSLRLSCAASGFTFSSYTLAWVRQAPGKGLEWVAAIDSSS<br>YTYSPDTVRGRFTISRDNAKNSLYLQMNSLRAEDTAVYYCARDSNWDALDY<br>WGQGTTVTVSSGGGGSGGGGSGGGGSDIQMTQSPSSLSASVGDRVTITCKAS<br>QNVGTNVGWYQQKPGKAPKALIYSASFRYSGVPSRFSGSGSGTDFTLTISSLQP<br>EDFATYYCQQYYTYPYTFGGGTKVEIKHHHHHHEPEA |
| 182 | ACP157 (WW0205) (IL-2 Conju-gate) | mdmrvpaqllglllwlrgarcaptssstkktqlqlehllldlqmilnginnyknpkltrmilfkfympkkatelkhlqcle<br>eelkpleevinlaqsknfhlrprdlisninvivlelkgsettfmceyadetativeflnrwitfcqsiistltsggpPGGPA<br>GIGalfkssfpPLAQKLKSSpgsEVQLVESGGGLVQPGNSLRLSCAASGFTFSKFGM<br>SWVRQAPGKGLEWVSSISGSGRDTLYAESVKGRFTISRDNAKTTLYLQMNSL<br>RPEDTAVYYCTIGGSLSVSSQGTLVTVSSggggsggggsggggsggggsggggsggggssggp<br>PGGPAGIGalfkssfpPLAQKLKSSpgsEVQLVESGGGLVQPGGSLRLSCAASGFTFS<br>SYTLAWVRQAPGKGLEWVAAIDSSSYTYSPDTVRGRFTISRDNAKNSLYLQM<br>NSLRAEDTAVYYCARDSNWDALDYWGQGTTVTVSSGGGGSGGGGSGGGGS<br>DIQMTQSPSSLSASVGDRVTITCKASQNVGTNVGWYQQKPGKAPKALIYSASF<br>RYSGVPSRFSGSGSGTDFTLTISSLQPEDFATYYCQQYYTYPYTFGGGTKVEIK<br>HHHHHHEPEA |
| 183 | Not assigned | |
| 184 | Not assigned | |
| 185 | Not assigned | |
| 186 | Not assigned | |
| 187 | Not assigned | |
| 188 | Not assigned | |
| 189 | Not assigned | |
| 190 | Not assigned | |
| 191 | Blocker 2 (IL2 blocker) | mdmrvpaqllglllwlrgarcEVQLVESGGGLVQPGGSLRLSCAASGFTFSSYTLAWVR<br>QAPGKGLEWVAAIDSSSYTYSPDTVRGRFTISRDNAKNSLYLQMNSLRAEDTA<br>VYYCARDSNWDALDYWGQGTTVTVSSggggsggggsggggsDIQMTQSPSSLSASV<br>GDRVTITCKASQNVGTNVGWYQQKPGKAPKALIYSASFRYSGVPSRFSGSGSG<br>TDFTLTISSLQPEDFATYYCQQYYTYPYTFGGGTKVEIKHHHHHH<br>mdmrvpaqllglllwlrgarcQSVLTQPPSVSGAPGQRVTISCSGSRSNIGSNTVKWYQQ |
| 192 | Blocker 12 (IL-12 blocker) | LPGTAPKLLIYYNDQRPSGVPDRFSGSKSGTSASLAITGLQAEDEADYYCQSY<br>DRYTHPALLFGTGTKVTVLggggsggggsggggsQVQLVESGGGVVQPGRSLRLSC<br>AASGFTFSSYGMHWVRQAPGKGLEWVAFIRYDGSNKYYADSVKGRFTISRDN<br>SKNTLYLQMNSLRAEDTAVYYCKTHGSHDNWGQGTMVTVSSHHHHHH |
| 193 | Human IF NA2b | cdlpqthslgsrrtlmllaqmrrislfsclkdrhdfgfpqeefgnqfqkaetipvlhemiqqifhlfstkdssaawdetlldk<br>fytelyqqlndleacviqgvgvtetplmkedsilavrkyfqritlylkekkyspcawevvraeimrsfslstnlqesliske<br>HHHHHH** |
| 194 | ACP239-geneart | iwelkkdvyvveldwypdapgemvvltcdtpeedgitwtldqssevlgsgktltiqvkefgdagqytchkggevlshs<br>llllhkkedgiwstdilkdqkepknkffirceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfshfcvqvqgkskrekkdwftdktsatvicrknasisvraqdryysswsewasvpcsggggsggggsggggsr<br>vipvsgparclsqsrnllkttddmvktareklkhysctaedidheditrdqtstlktclplelhknesclatretssttrgs<br>clppqktslmmticlgsiyedlkmyqtefqainaalqnhnhqqiildkgmlvaidelmqslnhngetlrqkppvgead<br>pyrvkmklcillhafstrvvtinrvmgylssahhhhhh |
| 195 | 3CYT5_sd | QVQLQESGGGLVQAGGSLRLSCAASGRTFSSVYDMGWFRQAPGKDREFVARI<br>AbTESARNTRYADSVRGRFTISRDNAKNTVYLQMNNLELEDAAVYYCAADPQT<br>VVVGTPDYWGQGTQVTVSSAAAYPYDVPDYGSHHHHHH |

-continued

Sequence table

| SEQ ID NO. | Name | Sequence |
|---|---|---|
| 196 | ACP248 | QSVLTQPPSVSGAPGQRVTISCtGSsSNIGSNTVKWYQQLPGTAPKLLIYgNDQR PSGVPDRFSGSKSGTSASLAITGLQAEDEADYYCQSYDRYTHPAyvFGTGTKVT VLggggsggggsggggsQVQLVESGGGVVQPGRSLRLSCAASGFTFSSYGMHWVRQ APGKGLEWVAFIRYDGSNKYYADSVKGRFTISRDNSKNTLYLQMNSLRAEDT AVYYCKTHGSHDNWGQGTMVTVSSHHHHHH |
| 197 | ACP249 | QSVLTQPPSVSGAPGQRVTISCtGSsSNIGSNTVKWYQQLPGTAPKLLIYYNDQ RPSGVPDRFSGSKSGTSASLAITGLQAEDEADYYCQSYDRYTHPAyvFGTGTK VTVLggggsggggsggggsQVQLVESGGGVVQPGRSLRLSCAASGFTFSSYGMHWV RQAPGKGLEWVAFIRYDGSNKYYADSVKGRFTISRDNSKNTLYLQMNSLRAE DTAVYYCKTHGSHDNWGQGTMVTVSSHHHHHH |
| 198 | ACP250 | QSVLTQPPSVSGAPGQRVTISCSGSRSNIGSNTVKWYQQLPGTAPKLLIYYNDQ RPSGVPDRFSGSKSGTSASLAITGLQAEDEADYYCQSYDRYTHPALLFGTGTK VTVLggggsggggsggggsQVQLVESGGGVVQPGRSLRLSCAASGFTFSSYaMHWV RQAPGKGLEWVAvIsYDGSNKYYADSVKGRFTISRDNSKNTLYLQMNSLRAE DTAVYYCarHGSHDNWGQGTMVTVSSHHHHHH |
| 199 | ACP251 | QSVLTQPPSVSGAPGQRVTISCSGSRSNIGSNTVKWYQQLPGTAPKLLIYYNDQ RPSGVPDRFSGSKSGTSASLAITGLQAEDEADYYCQSYDRYTHPALLFGTGTK VTVLggggsggggsggggsQVQLVESGGGVVQPGRSLRLSCAASGFTFSSYGMHWV RQAPGKGLEWVAFIRYeGSNKYYADSVKGRFTISRDNSKNTLYLQMNSLRAE DTAVYYCKTHGSHDNWGQGTMVTVSSHHHHHH |
| 200 | ACP252 | QSVLTQPPSVSGAPGQRVTISCSGSRSNIGSNTVKWYQQLPGTAPKLLIYYNDQ RPSGVPDRFSGSKSGTSASLAITGLQAEDEADYYCQSYDRYTHPALLFGTGTK VTVLggggsggggsggggsQVQLVESGGGVVQPGRSLRLSCAASGFTFSSYGMHWV RQAPGKGLEWVAFIRYDGSNKYYAeSVKGRFTISRDNSKNTLYLQMNSLRAE DTAVYYCKTHGSHDNWGQGTMVTVSSHHHHHH |
| 201 | ACP253 | QSVLTQPPSVSGAPGQRVTISCSGSRSNIGSqTVKWYQQLPGTAPKLLIYYNDQ RPSGVPDRFSGSKSGTSASLAITGLQAEDEADYYCQSYeRYTHPALLFGTGTKV TVLggggsggggsggggsQVQLVESGGGVVQPGRSLRLSCAASGFTFSSYGMHWVR QAPGKGLEWVAFIRYDGSNKYYADSVKGRFTISRDNSKNTLYLQMNSLRAED TAVYYCKTHGSHDNWGQGTMVTVSSHHHHHH |
| 202 | ACP254 | QSVLTQPPSVSGAPGQRVTISCSGSRSNIGSqTVKWYQQLPGTAPKLLIYYNDQ RPSGVPDRFSGSKSGTSASLAITGLQAEDEADYYCQSYsRYTHPALLFGTGTKV TVLggggsggggsggggsQVQLVESGGGVVQPGRSLRLSCAASGFTFSSYGMHWVR QAPGKGLEWVAFIRYDGSNKYYADSVKGRFTISRDNSKNTLYLQMNSLRAED TAVYYCKTHGSHDNWGQGTMVTVSSHHHHHH |
| 203 | ACP255 | QSVLTQPPSVSGAPGQRVTISCSGSeSNIGSNTVKWYQQLPGTAPKLLIYYNDQ RPSGVPDRFSGSKSGTSASLAITGLQAEDEADYYCQSYDRYTHPALLFGTGTK VTVLggggsggggsggggsQVQLVESGGGVVQPGRSLRLSCAASGFTFSSYGMHWV RQAPGKGLEWVAFIRYDGSNKYYADSVKGRFTISRDNSKNTLYLQMNSLRAE DTAVYYCKTHGSHDNWGQGTMVTVSSHHHHHH |
| 204 | ACP256 | QSVLTQPPSVSGAPGQRVTISCSGSsSNIGSNTVKWYQQLPGTAPKLLIYYNDQ RPSGVPDRFSGSKSGTSASLAITGLQAEDEADYYCQSYDRYTHPALLFGTGTK VTVLggggsggggsggggsQVQLVESGGGVVQPGRSLRLSCAASGFTFSSYGMHWV RQAPGKGLEWVAFIRYDGSNKYYADSVKGRFTISRDNSKNTLYLQMNSLRAE DTAVYYCKTHGSHDNWGQGTMVTVSSHHHHHH |
| 205 | ACP257 | QSVLTQPPSVSGAPGQRVTISCSGSRSNIGdNTVKWYQQLPGTAPKLLIYYNDQ RPSGVPDRFSGSKSGTSASLAITGLQAEDEADYYCQSYDRYTHPALLFGTGTK VTVLggggsggggsggggsQVQLVESGGGVVQPGRSLRLSCAASGFTFSSYGMHWV RQAPGKGLEWVAFIRYDGSNKYYADSVKGRFTISRDNSKNTLYLQMNSLRAE DTAVYYCKTHGSHDNWGQGTMVTVSSHHHHHH |
| 206 | ACP258 | QSVLTQPPSVSGAPGQRVTISCSGSRSNIGeNTVKWYQQLPGTAPKLLIYYNDQ RPSGVPDRFSGSKSGTSASLAITGLQAEDEADYYCQSYDRYTHPALLFGTGTK VTVLggggsggggsggggsQVQLVESGGGVVQPGRSLRLSCAASGFTFSSYGMHWV RQAPGKGLEWVAFIRYDGSNKYYADSVKGRFTISRDNSKNTLYLQMNSLRAE DTAVYYCKTHGSHDNWGQGTMVTVSSHHHHHH |
| 207 | ACP259 | QSVLTQPPSVSGAPGQRVTISCSGSRSNIGSdTVKWYQQLPGTAPKLLIYYNDQ RPSGVPDRFSGSKSGTSASLAITGLQAEDEADYYCQSYDRYTHPALLFGTGTK VTVLggggsggggsggggsQVQLVESGGGVVQPGRSLRLSCAASGFTFSSYGMHWV RQAPGKGLEWVAFIRYDGSNKYYADSVKGRFTISRDNSKNTLYLQMNSLRAE DTAVYYCKTHGSHDNWGQGTMVTVSSHHHHHH |

-continued

Sequence table

| SEQ ID NO. | Name | Sequence |
|---|---|---|
| 208 | ACP260 | QSVLTQPPSVSGAPGQRVTISCSGSRSNIGSeTVKWYQQLPGTAPKLLIYYNDQ RPSGVPDRFSGSKSGTSASLAITGLQAEDEADYYCQSYDRYTHPALLFGTGTK VTVLggggsggggsggggsQVQLVESGGGVVQPGRSLRLSCAASGFTFSSYGMHWV RQAPGKGLEWVAFIRYDGSNKYYADSVKGRFTISRDNSKNTLYLQMNSLRAE DTAVYYCKTHGSHDNWGQGTMVTVSSHHHHHH |
| 209 | ACP261 | QSVLTQPPSVSGAPGQRVTISCSGSRSNIGSNdVKWYQQLPGTAPKLLIYYNDQ RPSGVPDRFSGSKSGTSASLAITGLQAEDEADYYCQSYDRYTHPALLFGTGTK VTVLggggsggggsggggsQVQLVESGGGVVQPGRSLRLSCAASGFTFSSYGMHWV RQAPGKGLEWVAFIRYDGSNKYYADSVKGRFTISRDNSKNTLYLQMNSLRAE DTAVYYCKTHGSHDNWGQGTMVTVSSHHHHHH |
| 210 | ACP262 | QSVLTQPPSVSGAPGQRVTISCSGSRSNIGSNTVdWYQQLPGTAPKLLIYYNDQ RPSGVPDRFSGSKSGTSASLAITGLQAEDEADYYCQSYDRYTHPALLFGTGTK VTVLggggsggggsggggsQVQLVESGGGVVQPGRSLRLSCAASGFTFSSYGMHWV RQAPGKGLEWVAFIRYDGSNKYYADSVKGRFTISRDNSKNTLYLQMNSLRAE DTAVYYCKTHGSHDNWGQGTMVTVSSHHHHHH |
| 211 | ACP263 | QSVLTQPPSVSGAPGQRVTISCSGSRSNIGSNTVeWYQQLPGTAPKLLIYYNDQ RPSGVPDRFSGSKSGTSASLAITGLQAEDEADYYCQSYDRYTHPALLFGTGTK VTVLggggsggggsggggsQVQLVESGGGVVQPGRSLRLSCAASGFTFSSYGMHWV RQAPGKGLEWVAFIRYDGSNKYYADSVKGRFTISRDNSKNTLYLQMNSLRAE DTAVYYCKTHGSHDNWGQGTMVTVSSHHHHHH |
| 212 | ACP264 | QSVLTQPPSVSGAPGQRVTISCSGSRSNIGSNTVKWYQQLPGTAPKLLIYYNDQ dPSGVPDRFSGSKSGTSASLAITGLQAEDEADYYCQSYDRYTHPALLFGTGTK VTVLggggsggggsggggsQVQLVESGGGVVQPGRSLRLSCAASGFTFSSYGMHWV RQAPGKGLEWVAFIRYDGSNKYYADSVKGRFTISRDNSKNTLYLQMNSLRAE DTAVYYCKTHGSHDNWGQGTMVTVSSHHHHHH |
| 213 | ACP265 | QSVLTQPPSVSGAPGQRVTISCSGSRSNIGSNTVKWYQQLPGTAPKLLIYYNDQ ePSGVPDRFSGSKSGTSASLAITGLQAEDEADYYCQSYDRYTHPALLFGTGTK VTVLggggsggggsggggsQVQLVESGGGVVQPGRSLRLSCAASGFTFSSYGMHWV RQAPGKGLEWVAFIRYDGSNKYYADSVKGRFTISRDNSKNTLYLQMNSLRAE DTAVYYCKTHGSHDNWGQGTMVTVSSHHHHHH |
| 214 | ACP266 | QSVLTQPPSVSGAPGQRVTISCSGSRSNIGSNTVKWYQQLPGTAPKLLIYYNDQ RPdGVPDRFSGSKSGTSASLAITGLQAEDEADYYCQSYDRYTHPALLFGTGTK VTVLggggsggggsggggsQVQLVESGGGVVQPGRSLRLSCAASGFTFSSYGMHWV RQAPGKGLEWVAFIRYDGSNKYYADSVKGRFTISRDNSKNTLYLQMNSLRAE DTAVYYCKTHGSHDNWGQGTMVTVSSHHHHHH |
| 215 | ACP267 | QSVLTQPPSVSGAPGQRVTISCSGSRSNIGSNTVKWYQQLPGTAPKLLIYYNDQ RPSGVPDRFSGSKSGTSASLAITGLQAEDEADYYCQSYDeYTHPALLFGTGTK VTVLggggsggggsggggsQVQLVESGGGVVQPGRSLRLSCAASGFTFSSYGMHWV RQAPGKGLEWVAFIRYDGSNKYYADSVKGRFTISRDNSKNTLYLQMNSLRAE DTAVYYCKTHGSHDNWGQGTMVTVSSHHHHHH |
| 216 | ACP268 | QSVLTQPPSVSGAPGQRVTISCSGSRSNIGSNTVKWYQQLPGTAPKLLIYYNDQ RPSGVPDRFSGSKSGTSASLAITGLQAEDEADYYCQSYDRYTdPALLFGTGTK VTVLggggsggggsggggsQVQLVESGGGVVQPGRSLRLSCAASGFTFSSYGMHWV RQAPGKGLEWVAFIRYDGSNKYYADSVKGRFTISRDNSKNTLYLQMNSLRAE DTAVYYCKTHGSHDNWGQGTMVTVSSHHHHHH |
| 217 | ACP269 | QSVLTQPPSVSGAPGQRVTISCSGSeSNIGSNTVKWYQQLPGTAPKLLIYYNDQ ePSGVPDRFSGSKSGTSASLAITGLQAEDEADYYCQSYDeYTHPALLFGTGTKV TVLggggsggggsggggsQVQLVESGGGVVQPGRSLRLSCAASGFTFSSYGMHWVR QAPGKGLEWVAFIRYDGSNKYYADSVKGRFTISRDNSKNTLYLQMNSLRAED TAVYYCKTHGSHDNWGQGTMVTVSSHHHHHH |
| 218 | ACP270 | QSVLTQPPSVSGAPGQRVTISCSGSeSNIGSNdVKWYQQLPGTAPKLLIYYNDQ RPSGVPDRFSGSKSGTSASLAITGLQAEDEADYYCQSYDRYTHPALLFGTGTK VTVLggggsggggsggggsQVQLVESGGGVVQPGRSLRLSCAASGFTFSSYGMHWV RQAPGKGLEWVAFIRYDGSNKYYADSVKGRFTISRDNSKNTLYLQMNSLRAE DTAVYYCKTHGSHDNWGQGTMVTVSSHHHHHH |
| 219 | ACP271 | QSVLTQPPSVSGAPGQRVTISCSGSRSNIGSNTVKWYQQLPGTAPKLLIYYNDQ RPSGVPDRFSGSKSGTSASLAITGLQAEDEADYYCQSYDRYTHPALLFGTGTK VTVLggggsggggsggggsQVQLVESGGGVVQPGRSLRLSCAASGFTFeSYGMHWV RQAPGKGLEWVAFIRYDGSNKYYADSVKGRFTISRDNSKNTLYLQMNSLRAE DTAVYYCKTHGSHDNWGQGTMVTVSSHHHHHH |

-continued

Sequence table

| SEQ ID NO. | Name | Sequence |
|---|---|---|
| 220 | ACP272 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSeYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 221 | ACP273 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSdYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 222 | ACP274 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIeYDGSNKYYADSVKGRFTISRDNSKNTLYLQMNSLRAE<br>DTAVYYCKTHGSHDNWGQGTMVTVSSHHHHHH |
| 223 | ACP275 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIdYDGSNKYYADSVKGRFTISRDNSKNTLYLQMNSLRAE<br>DTAVYYCKTHGSHDNWGQGTMVTVSSHHHHHH |
| 224 | ACP276 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNdYYADSVKGRFTISRDNSKNTLYLQMNSLRAE<br>DTAVYYCKTHGSHDNWGQGTMVTVSSHHHHHH |
| 225 | ACP277 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNeYYADSVKGRFTISRDNSKNTLYLQMNSLRAE<br>DTAVYYCKTHGSHDNWGQGTMVTVSSHHHHHH |
| 226 | ACP278 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVeGRFTISRDNSKNTLYLQMNSLRAE<br>DTAVYYCKTHGSHDNWGQGTMVTVSSHHHHHH |
| 227 | ACP279 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSeDNWGQGTMVTVSSHHHHHH |
| 228 | ACP280 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIeYDGSNKYYADSVeGRFTISRDNSKNTLYLQMNSLRAED<br>TAVYYCKTHGSHDNWGQGTMVTVSSHHHHHH |
| 229 | ACP281 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIeYDGSNKYYADSVeGRFTISRDNSKNTLYLQMNSLRAED<br>TAVYYCKTHGSeDNWGQGTMVTVSSHHHHHH |
| 230 | ACP282 | QSVLTQPPSVSGAPGQRVTISCSGSRSNIGSNTVKWYQQLPGTAPKLLIYYNDQ<br>RPSGVPDRFSGSKSGTSASLAITGLQAEDEADYYCQSYDRYTHPALLFGTGTK<br>VTVLggggsggggsggggsQVQLVESGGGVVQPGRSLRLSCAASGFTFSSYGMHWV<br>RQAPGKGLEWVAFIRYDGSNKYYADSVKGRFTISRDNSKNTLYLQMNSLRAE<br>DTAVYYCKTHGSHDNWGQGTMVTVSSHHHHHH |
| 231 | ACP283 (WW0617) | iwelkkdvyvveldwypdapgemvvitcdtpeedgitwddqssevlgsgktltiqvkefgdagqytchkggevlshs<br>sgrftcwwlttistdltfsvkssrgssdpqgvtcgaatlsaervrgdllllhkkedgiwstdilkdqkepknktflrceakny<br>nkeyeysvecqedsacpaaeeslpievmvdavhklkyenytssffirdiikpdppknlqlkplknsrqvevsweypdt<br>wstphsyfshfcvqvqgkskrekkdrvftdktsatvicrknasisvraqMyyssswsewasvpcs |

-continued

Sequence table

| SEQ ID NO. | Name | Sequence |
|---|---|---|
| 232 | 3TOW69sd Ab | QVQLQESGGGLVQTGGSLRLSCTTSGTIFSGYTMGWYRQAPGEQRELVAVISG<br>GGDTNYADSVKGRFTISRDNTKDTMYLQMNSLKPEDTAVYYCYSREVTPPW<br>KLYWGQGTQVTVSSAAAYPYDVPDYGSHHHHHH |
| 233 | 3TOW85sd Ab | QVQLQESGGGLVQEGGSLRLSCAASERIFSTDVMGWYRQAAEKQRELVAVVS<br>ARGTTNYLDAVKGRFTISRDNARNTLTLQMNDLKPEDTASYYCYVRETTSPW<br>RIYWGQGTQVTVSSAAAYPYDVPDYGSHHHHHH |
| 234 | 2T0W91sd Ab | QVQLQESGGGLVQAGGSLRLSCAASGSlFSANAMGWYRQAPGKQRELVAVIS<br>SGGSTNYADSVKGRFTISRDNAKNTVYLQMNSLKPEDTAVYYCMYSGSYYY<br>TPNDYWGQGTQVTVSSAAAYPYDVPDYGSHHHHHH |
| 235 | ACP301 | evqlvesggglvqpggslrlscaasgftfssytlawvrqapgkglewvaaidsssytyspdtvrgrftisrdnaknslylq<br>mnslraedtavyycardsnwdaldywgqgttvtvssggggsggggsggggsdiqmtqspsslsasvgdrvtitckasq<br>nvgtnvgwyqqkpgkapkaliysasflysgvpsrfsgsgsgtdftltisslqpecifatyycqqyytypylfgggtkveik<br>hhhhhh |
| 236 | Hu2TOW9 1_A | evqllesggglvqpggslrlscaasGSIFSANAMGwYrqapgkQReLvAVISSGGSTNYADSVK<br>GrftisrdnskntVylqmnslraedtavyycMYSGSYYYTPNDYwgqgtivtvssAAAYPYDVPD<br>YGSHHHHHH** |
| 237 | Hu2TOW9 1_B | evqllesggglvqpggslrlscaasGSIFSANAMGwYrqapgkgleLvAVISSGGSTNYADSVKG<br>rftisrdnskntVylqmnslraedtavyycMYSGSYYYTPNDYwgqgtivtvssAAAYPYDVPDY<br>GSHHHHHH** |
| 238 | Hu2TOW9 1_C | evqllesggglvqpggslrlscaasGSIFSANAMGwvrqapgkglewvsVISSGGSTNYADSVKGrf<br>tisrdnskntlylqmnslraedtavyycMYSGSYYYTPNDYwgqgtivtvssAAAYPYDVPDYGS<br>HHHHHH** |
| 239 | Hu2TOW9 1_D | QvqllesggglvqpggslrlscaasGSIFSANAMGwYrqapgkQReLvAVISSGGSTNYADSVK<br>GrftisrdnskntVylqmnslraedtavyycMYSGSYYYTPNDYwgqgtivtvssAAAYPYDVPD<br>YGSHHHHHH** |
| 240 | HE_LM_2 TOW91 | evqllesggglvqpggslrlscaasgSIfsANamGwYrqapgkgReLvAVissggstNyadsvkgrftisrdns<br>kntVylqmnslraedtavyycMYSGSYYYTPNDYWgqgtivtvssAAAYPYDVPDYGSHHH<br>HHH** |
| 241 | HE_LM_2T OW91 | QvqllesggglvqAggslrlscaasgSIfsANamGwYrqapgkQReLvAVissggstNyadsvkgrftisrdn<br>skntVylqmnslraedtavyycMYSGSYYYTPNDYwgqgtivtvssAAAYPYDVPDYGSHHH<br>HHH** |
| 242 | Hu3TOW8 5_A | evqllesggglvqpggslrlscaasERIFSTDVMGwYrqapgkQReLvAVVSARGTTNYLDAV<br>KGrftisrdnskntlylqmnslraedtavyycYVRETTSPWRIYwgqgtivtvssAAAYPYDVPDYG<br>SHHHHHH** |
| 243 | Hu3TOW8 5_B | evqllesggglvqpggslrlscaasERIFSTDVMGwYrqapgkgleLvAVVSARGTTNYLDAVK<br>GrftisrdnskntlylqmnslraedtavyycYVRETTSPWRIYwgqgtivtvssAAAYPYDVPDYGS<br>HHHHHH** |
| 244 | Hu3TOW8 5_C | evqllesggglvqpggslrlscaasERIFSTDVMGwvrqapgkglewvsVVSARGTTNYLDAVKG<br>rftisrdnskntlylqmnslraedtavyycYVRETTSPWRIYwgqgtivtvssAAAYPYDVPDYGSH<br>HHHHH** |
| 245 | Hu3TOW8 5_D | QvqllesggglvqpggslrlscaasERIFSTDVMGwYrqapgkQReLvAVVSARGTTNYLDAV<br>KGrftisrdnskntlylqmnslraedtavyycYVRETTSPWRIYwgqgtivtvssAAAYPYDVPDYG<br>SHHHHHH** |
| 246 | HE_LM_3 TO1T85 | evqllesggglvqpggslrlscaasERIfsTDVmGwYrqapgkgReLvAVVsARgTtNyLdsvkgrftisr<br>dnskntlylqmnslraedtavyycYVRETTSPWRIywgqgtivtvssAAAYPYDVPDYGSHHHH<br>HH** |
| 247 | HE_L_3T OW85 | QvqllesggglvqEggslrlscaasERIfsTDVmGwYrqaAgkQReLvAVVsARgTtNyLdAvkgrf<br>tisrdnskntlylqmnslraedtaSyycYVRETTSPWRIywgqgtivtvssAAAYPYDVPDYGSHH<br>HHHH** |
| 248 | HE_LM_R 45L_3TO W85 | evqllesggglvqpggslrlscaasERIfsTDVmGwYrqapgkgleLvAVVsARgTtNyLdsvkgrftisr<br>dnskntlylqmnslraedtavyycYVRETTSPWRIywgqgtivtvssAAAYPYDVPDYGSHHHH<br>HH** |
| 249 | Hu3TOW6 9_A | evqllesggglvqpggslrlscaTsGTIFSGYTMGwYrqapgkQReLvAVISGGGDTNYADSV<br>KGrftisrdnskDtMylqmnslraedtavyycYSREVTPPWKLYwgqgtivtvssAAAYPYDVPD<br>YGSHHHHHH** |

-continued

Sequence table

| SEQ ID NO. | Name | Sequence |
|---|---|---|
| 250 | Hu3TOW69_B | evqllesggglvqpggslrlscaTsGTIFSGYTMGwYrqapgkgleLvAVISGGGDTNYADSVKGrftisrdnskDtMylqmnslraedtavyycYSREVTPPWKLYwgqgtivtvssAAAYPYDVPDYGSHHHHHH** |
| 251 | Hu3TOW69_C | evqllesggglvqpggslrlscaasGTIFSGYTMGwvrqapgkglewvsVISGGGDTNYADSVKGrftisrdnskntlylqmnslraedtavyycYSREVTPPWKLYwgqgtivtvssAAAYPYDVPDYGSHHHHHH** |
| 252 | Hu3TOW69_D | QvqllesggglvqpggslrlscaTsGTIFSGYTMGwYrqapgkQReLvAVISGGGDTNYADSVKGrftisrdnskDtMylqmnslraedtavyycYSREVTPPWKLYwgqgtivtvssAAAYPYDVPDYGSHHHHHH** |
| 253 | Hu3TOW69_E | evqllesggglvqpggslrlscaTsGTIFSGYTMGwYrqapgkQReLvAVISGGGDTNYADSVKGrftisrdnskntMylqmnslraedtavyycYSREVTPPWKLYwgqgtivtvssAAAYPYDVPDYGSHHHHHH** |
| 254 | HE_LM_3TO1T69 | evqllesggglvqpggslrlscaTsgTIfsGyTmGwYrqapgkgReLvAVisGggDtNyadsvkgrftisrdnskntMylqmnslraedtavyycYSREVTPPWKLywgqgtivtvssAAAYPYDVPDYGSHHHHHH** |
| 255 | HE_L_3TOW69 | QvqllesggglvqTggslrlscaTsgTIfsGyTmGwYrqapgkQReLvAVisGggDtNyadsvkgrftisrdnskDtMylqmnslraedtavyycYSREVTPPWKLywgqgtivtvssAAAYPYDVPDYGSHHHHHH** |
| 256 | HE_LM_R45L_3TOW69 | evqllesggglvqpggslrlscaTsgTIfsGyTmGwYrqapgkgleLvAVisGggDtNyadsvkgrftisrdnskntMylqmnslraedtavyycYSREVTPPWKLywgqgtivtvssAAAYPYDVPDYGSHHHHHH** |
| 257 | ACP363 (WW0441) | EVQLVESGGGLVQPGGSLRLSCAASGFTFSSYTLAWVRQAPGKGLEWVAAIDSSSYTYSPDTVRGRFTISRDNAKNSLYLQMNSLRAEDTAVYYCARDSNWDALDYWGQGTTVTVSSggggsggggsggggsDIQMTQSPSSLSASVGDRVTITCKAREKLWSAVAWYQQKPGKAPKALIYSASFRYSGVPSRFSGSGSGTDFTLTISSLQPEDFATYYCQQYYTYPYTFGGGTKVEIKHHHHHH |
| 258 | ACP364 (WW0442) | EVQLVESGGGLVQPGGSLRLSCAASGFTFSSYTLAWVRQAPGKGLEWVAAIDSSSYTYSPDTVRGRFTISRDNAKNSLYLQMNSLRAEDTAVYYCARDSNWDALDYWGQGTTVTVSSggggsggggsggggsDIQMTQSPSSLSASVGDRVTITCKAREKLWSAVAWYQQKPGKAPKsLIYSASFRYSGVPSRFSGSGSGTDFTLTISSLQPEDFATYYCQQYYTYPYTFGGGTKVEIKHHHHHH |
| 259 | ACP367 (WW0445) | EVQLVESGGGLVQPGGSLRLSCAASGFTFSSYTLAWVRQAPGKGLEWVAAIDSSSYTYSPDTVRGRFTISRDNAKNSLYLQMNSLRAEDTAVYYCARDSNWDALDYWGQGTTVTVSSggggsggggsggggsDIQMTQSPSSLSASVGDRVTITCKVTEKVWGNVAWYQQKPGKAPISLIYSPSLRKSGVPSRFSGSGSGTDFTLTISSLQPEDFATYYCQQYYTYPYTFGGGTKVEIKHHHHHH |
| 260 | ACP369 (WW0449) | EVQLVESGGGLVQPGGSLRLSCAASGFTFSSYTLAWVRQAPGKGLEWVAAIDSSSYTYSPDTVRGRFTISRDNAKNSLYLQMNSLRAEDTAVYYCARDSNWDALDYWGQGTTVTVSSggggsggggsggggsDIQMTQSPSSLSASVGDRVTITCKSSEKLWANVAWYQQKPGKAPKALIYSASFRYSGVPSRFSGSGSGTDFTLTISSLQPEDFATYYCQQYYTYPYTFGGGTKVEIKHHHHHH |
| 261 | ACP370 (WW0450) | EVQLVESGGGLVQPGGSLRLSCAASGFTFSSYTLAWVRQAPGKGLEWVAAIDSSSYTYSPDTVRGRFTISRDNAKNSLYLQMNSLRAEDTAVYYCARDSNWDALDYWGQGTTVTVSSggggsggggsggggsDIQMTQSPSSLSASVGDRVTITCKSSEKLWANVAWYQQKPGKAPKsLIYSASFRYSGVPSRFSGSGSGTDFTLTISSLQPEDFATYYCQQYYTYPYTFGGGTKVEIKHHHHHH |
| 262 | ACP380 (WW0522) | DIQMTQSPSSLSASVGDRVTITCKASQNVGTNVGWYQQKPGKAPKALIYSASFRYSGVPSRFSGSGSGTDFTLTISSLQPEDFATYYCQQYYTYPYTFGGGTKVEIKrtvaapsvfifppsdeqlksgtasvvcllnnfypreakvqwkvdnalqsgnsqesvteqdskdstyslsstltlskadyekhkvyacevthqglsspvtksfnrgec |
| 263 | ACP381 (WW0523) | DIQMTQSPSSLSASVGDRVTITCKAREKLWSAVAWYQQKPGKAPKsLIYSASFRYSGVPSRFSGSGSGTDFTLTISSLQPEDFATYYCQQYYTYPYTFGGGTKVEIKrtvaapsvfifppsdeqlksgtasvvcllnnfypreakvqwkvdnalqsgnsqesvteqdskdstyslsstltlskadyekhkvyacevthqglsspvtksfnrgec |
| 264 | ACP382 (WW0524) | DIQMTQSPSSLSASVGDRVTITCKVTEKVWGNVAWYQQKPGKAPISLIYSPSLRKSGVPSRFSGSGSGTDFTLTISSLQPEDFATYYCQQYYTYPYTFGGGTKVEIKrtvaapsvfifppsdeqlksgtasvvcllnnfypreakvqwkvdnalqsgnsqesvteqdskdstyslsstltlskadyekhkvyacevthqglsspvtksfnrgec |

-continued

Sequence table

| SEQ ID NO. | Name | Sequence |
|---|---|---|
| 265 | ACP435 | DIQMTQSPSSLSASVGDRVTITCKAREKLWSAVAWYQQKPGKAPKsLIYSASF<br>RYSGVPSRFSGSGSGTDFTLTISSLQPEDFATYYCQQYYTYPYTFGGGTKVEIKr<br>tvaapsvfifppsdeqlksgtasvvellnnfypreakvqwkvdnalqsgnsqesvteqdskdstyslsstltlskadyekh<br>kvyacevthqglsspvtksfnrgecggggsggggsggggsggggsggggsggggsevqllesggglvqpggslrlsca<br>asgsifsanamgwyrqapgkrirelvavissggstnyadsvkgrftisrdnskntvylqmnslraedtavyycmysgsy<br>yytpndywgqgtivtvss** |
| 266 | ACP436 (WW0578) | DIQMTQSPSSLSASVGDRVTITCKAREKLWSAVAWYQQKPGKAPKsLIYSASF<br>RYSGVPSRFSGSGSGTDFTLTISSLQPEDFATYYCQQYYTYPYTFGGGTKVEIKr<br>tvaapsvfifppsdeqlksgtasvvellnnfypreakvqwkvdnalqsgnsqesvteqdskdstyslsstltlskadyekh<br>kvyacevthqglsspvtksfnrgecggggsggggsggggsggggsggggsggggsevqllesggglvqpggslrlsca<br>asgsifsanamgwyrqapgkglelvavissggstnyadsvkgrftisrdnskntvylqmnslraedtavyycmysgsy<br>yytpndywgqgtivtvss** |
| 267 | ACP437 (WW0579) | DIQMTQSPSSLSASVGDRVTITCKVTEKVWGNVAWYQQKPGKAPISLIYSPSL<br>RKSGVPSRFSGSGSGTDFTLTISSLQPEDFATYYCQQYYTYPYTFGGGTKVEIKr<br>tvaapsvfifppsdeqlksgtasvvellnnfypreakvqwkvdnalqsgnsqesvteqdskdstyslsstltlskadyekh<br>kvyacevthqglsspvtksfnrgecggggsggggsggggsggggsggggsggggsevqllesggglvqpggslrlsca<br>asgsifsanamgwyrqapglairelvavissggstnyadsvkgrftisrdnskntvylqmnslraedtavyycmysgsy<br>yytpndywgqgtivtvss** |
| 268 | ACP438 (WW0580) | DIQMTQSPSSLSASVGDRVTITCKVTEKVWGNVAWYQQKPGKAPISLIYSPSL<br>RKSGVPSRFSGSGSGTDFTLTISSLQPEDFATYYCQQYYTYPYTFGGGTKVEIKr<br>tvaapsvfifppsdeqlksgtasvvellnnfypreakvqwkvdnalqsgnsqesvteqdskdstyslsstltlskadyekh<br>kvyacevthqglsspvtksfnrgecggggsggggsggggsggggsggggsggggsevqllesggglvqpggslrlsca<br>asgsifsanamgwyrqapgkglelvavissggstnyadsvkgrftisrdnskntvylqmnslraedtavyycmysgsy<br>yytpndywgqgtivtvss** |
| 269 | ACP448 (WW0590) | DIQMTQSPSSLSASVGDRVTITCKSSEKLWANVAWYQQKPGKAPKsLIYSASF<br>RYSGVPSRFSGSGSGTDFTLTISSLQPEDFATYYCQQYYTYPYTFGGGTKVEIKr<br>tvaapsvfifppsdeqlksgtasvvcllnnfypreakvqwkvdnalqsgnsqesvteqdskdstyslsstltlskadyekh<br>kvyacevthqglsspvtksfnrgec** |
| 270 | ACP449 (WW0591) | DIQMTQSPSSLSASVGDRVTITCKSSEKLWANVAWYQQKPGKAPKLLIYSASF<br>RYSGVPSRFSGSGSGTDFTLTISSLQPEDFATYYCQQYYTYPYTFGGGTKVEIKr<br>tvaapsvfifppsdeqlksgtasvvcllnnfypreakvqwkvdnalqsgnsqesvteqdskdstyslsstltlskadyekh<br>kvyacevthqglsspvtksfnrgec** |
| 271 | ACP450 (WW0592) | DIQMTQSPSSLSASVGDRVTITCKAREKLWSAVAWYQQKPGKAPKLLIYSASF<br>RYSGVPSRFSGSGSGTDFTLTISSLQPEDFATYYCQQYYTYPYTFGGGTKVEIKr<br>tvaapsvfifppsdeqlksgtasvvcllnnfypreakvqwkvdnalqsgnsqesvteqdskdstyslsstltlskadyekh<br>kvyacevthqglsspvtksfnrgec** |
| 272 | ACP439 (WW0581) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKSSEKLWANVAWYQQKPG<br>KAPKALIYSASFRYSGVPSRFSGSGSGTDFTLTISSLQPEDFATYYCQQYYTYP<br>YTFGGGTKVEIK |
| 273 | ACP440 (WW0582) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKSSEKLWANVAWYQQKPG<br>KAPKsLIYSASFRYSGVPSRFSGSGSGTDFTLTISSLQPEDFATYYCQQYYTYPY<br>TFGGGTKVEIK |
| 274 | ACP441 (WW0583) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGQGTTVTVSSGGGG |

-continued

Sequence table

| SEQ ID NO. | Name | Sequence |
|---|---|---|
| | | SGGGGSGGGGSDIQMTQSPSSLSASVGDRVTITCKSSEKLWANVAWYQQKPG<br>KAPKLLIYSASFRYSGVPSRFSGSGSGTDFTLTISSLQPEDFATYYCQQYYTYPY<br>TFGGGTKVEIK |
| 275 | ACP442<br>(WW0584) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKcLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKSSEKLWANVAWYQQKPG<br>KAPKsLIYSASFRYSGVPSRFSGSGSGTDFTLTISSLQPEDFATYYCQQYYTYPY<br>TFGcGTKVEIK |
| 276 | ACP443<br>(WW0585) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKcLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKSSEKLWANVAWYQQKPG<br>KAPKLLIYSASFRYSGVPSRFSGSGSGTDFTLTISSLQPEDFATYYCQQYYTYPY<br>TFGcGTKVEIK |
| 277 | ACP444 | aptsssticktqlqlehllldlqmilnginnyknpkltrmltfkfympkkatelkhlqcleeelkpleevinlaqsknfhlrpr<br>(WW0586)dlisninvivlelkgsettfmceyadetativeflnrwiticqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGcGTTVTVSSGGGG<br>SGGGGSGGGGSDIQMTQSPSSLSASVGDRVTITCKSSEKLWANVAWYQQKPG<br>KcPKALIYSASFRYSGVPSRFSGSGSGTDFTLTISSLQPEDFATYYCQQYYTYPY<br>TFGGGTKVEIK |
| 278 | ACP445<br>(WW0587) | aptsssticktqlqlehllldlqmilnginnyknpkltrmltfkfympkkatelkhlqcleeelkpleevinlaqsknfhlrpr<br>dlisninvivlelkgsettfmceyadetativeflnrwiticqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGQGTTVTVSSsggpG<br>PAGLYAQpgsDIQMTQSPSSLSASVGDRVTITCKAREKLWSAVAWYQQKPGKA<br>PKLLIYSASFRYSGVPSRFSGSGSGTDFTLTISSLQPEDFATYYCQQYYTYPYTF<br>GGGTKVEIK |
| 279 | ACP446<br>(WW0588) | aptsssticktqlqlehllldlqmilnginnyknpkltrmltfkfympkkatelkhlqcleeelkpleevinlaqsknfhlrpr<br>dlisninvivlelkgsettfmceyadetativeflnrwiticqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKAREKLWSAVAWYQQKPG<br>KAPKLLIYSASFRYSGVPSRFSGSGSGTDFTLTISSLQPEDFATYYCQQYYTYPY<br>TFGGGTKVEIK |
| 280 | ACP447<br>(WW0589) | aptsssticktqlqlehllldlqmilnginnyknpkltrmltfkfympkkatelkhlqcleeelkpleevinlaqsknfhlrpr<br>dlisninvivlelkgsettfmceyadetativeflnrwiticqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKcLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKAREKLWSAVAWYQQKPG<br>KAPKLLIYSASFRYSGVPSRFSGSGSGTDFTLTISSLQPEDFATYYCQQYYTYPY<br>TFGcGTKVEIK |
| 281 | ACP451<br>(WW0615) | aptsssticktqlqlehllldlqmilnginnyknpkltrmltfkfympkkatelkhlqcleeelkpleevinlaqsknfhlrpr<br>dlisninvivlelkgsettfmceyadetativeflnrwiticqsiistltsggpALFKSSFPpgsEVQLVESGGG<br>LVQPGNSLRLSCAASGFTFSKFGMSWVRQAPGKGLEWVSSISGSGRDTLYAES |

-continued

Sequence table

| SEQ ID NO. | Name | Sequence |
| --- | --- | --- |
| | | VKGRFTISRDNAKTTLYLQMNSLRPEDTAVYYCTIGGSLSVSSQGTLVTVSSgg ggsggggsggggsggggsggggsggggsggggssggpALFKSSFPpgsEVQLVESGGGLVQPGGSLRL SCAASGFTFSSYTLAWVRQAPGKGLEWVAAIDSSSYTYSPDTVRGRFTISRDN AKNSLYLQMNSLRAEDTAVYYCARDSNWDALDYWGQGTTVTVSSGGGGSG GGGSGGGGSDIQMTQSPSSLSASVGDRVTITCKAREKLWSAVAWYQQKPGKA PKsLIYSASFRYSGVPSRFSGSGSGTDFTLTISSLQPEDFATYYCQQYYTYPYTF GGGTKVEIK** |
| 282 | ACP452 (WW0616) | aptsssticktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpALFKSSFPpgsEVQLVESGGG LVQPGNSLRLSCAASGFTFSKFGMSWVRQAPGKGLEWVSSISGSGRDTLYAES VKGRFTISRDNAKTTLYLQMNSLRPEDTAVYYCTIGGSLSVSSQGTLVTVSSgg ggsggggsggggsggggsggggsggggssggpALFKSSFPpgsEVQLVESGGGLVQPGGSLRL SCAASGFTFSSYTLAWVRQAPGKGLEWVAAIDSSSYTYSPDTVRGRFTISRDN AKNSLYLQMNSLRAEDTAVYYCARDSNWDALDYWGQGTTVTVSSGGGGSG GGGSGGGGSDIQMTQSPSSLSASVGDRVTITCKVTEKVWGNVAWYQQKPGK APISLIYSPSLRKSGVPSRFSGSGSGTDFTLTISSLQPEDFATYYCQQYYTYPYTF GGGTKVEIK** |
| 283 | ACP453 (WW0617) | aptsssticktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpALFKSSFPpgsEVQLVESGGG LVQPGNSLRLSCAASGFTFSKFGMSWVRQAPGKGLEWVSSISGSGRDTLYAES VKGRFTISRDNAKTTLYLQMNSLRPEDTAVYYCTIGGSLSVSSQGTLVTVSSgg ggsggggsggggsggggsggggsggggssggpALFKSSFPpgsEVQLVESGGGLVQPGGSLRL SCAASGFTFSSYTLAWVRQAPGKcLEWVAAIDSSSYTYSPDTVRGRFTISRDNA KNSLYLQMNSLRAEDTAVYYCARDSNWDALDYWGQGTTVTVSSGGGGSGG GGSGGGGSDIQMTQSPSSLSASVGDRVTITCKAREKLWSAVAWYQQKPGKAP KsLIYSASFRYSGVPSRFSGSGSGTDFTLTISSLQPEDFATYYCQQYYTYPYTFG cGTKVEIK** |
| 284 | ACP454 (WW0618) | aptsssticktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpALFKSSFPpgsEVQLVESGGG LVQPGNSLRLSCAASGFTFSKFGMSWVRQAPGKGLEWVSSISGSGRDTLYAES VKGRFTISRDNAKTTLYLQMNSLRPEDTAVYYCTIGGSLSVSSQGTLVTVSSgg ggsggggsggggsggggsggggsggggssggpALFKSSFPpgsEVQLVESGGGLVQPGGSLRL SCAASGFTFSSYTLAWVRQAPGKGLEWVAAIDSSSYTYSPDTVRGRFTISRDN AKNSLYLQMNSLRAEDTAVYYCARDSNWDALDYWGcGTTVTVSSGGGGSG GGGSGGGGSDIQMTQSPSSLSASVGDRVTITCKAREKLWSAVAWYQQKPGKc PKALIYSASFRYSGVPSRFSGSGSGTDFTLTISSLQPEDFATYYCQQYYTYPYTF GGGTKVEIK** |
| 285 | ACP455 (WW0619) | aptsssticktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpALFKSSFPpgsEVQLVESGGG LVQPGNSLRLSCAASGFTFSKFGMSWVRQAPGKGLEWVSSISGSGRDTLYAES VKGRFTISRDNAKTTLYLQMNSLRPEDTAVYYCTIGGSLSVSSQGTLVTVSSgg ggsggggsggggsggggsggggsggggssggpALFKSSFPpgsEVQLVESGGGLVQPGGSLRL SCAASGFTFSSYTLAWVRQAPGKcLEWVAAIDSSSYTYSPDTVRGRFTISRDNA KNSLYLQMNSLRAEDTAVYYCARDSNWDALDYWGQGTTVTVSSGGGGSGG GGSGGGGSDIQMTQSPSSLSASVGDRVTITCKVTEKVWGNVAWYQQKPGKA PISLIYSPSLRKSGVPSRFSGSGSGTDFTLTISSLQPEDFATYYCQQYYTYPYTFG cGTKVEIK** |
| 441 | ACP456 (WW0620) | aptsssticktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpALFKSSFPpgsEVQLVESGGG LVQPGNSLRLSCAASGFTFSKFGMSWVRQAPGKGLEWVSSISGSGRDTLYAES VKGRFTISRDNAKTTLYLQMNSLRPEDTAVYYCTIGGSLSVSSQGTLVTVSSgg ggsggggsggggsggggsggggsggggssggpALFKSSFPpgsEVQLVESGGGLVQPGGSLRL SCAASGFTFSSYTLAWVRQAPGKGLEWVAAIDSSSYTYSPDTVRGRFTISRDN AKNSLYLQMNSLRAEDTAVYYCARDSNWDALDYWGcGTTVTVSSGGGGSG GGGSGGGGSDIQMTQSPSSLSASVGDRVTITCKVTEKVWGNVAWYQQKPGKc PISLIYSPSLRKSGVPSRFSGSGSGTDFTLTISSLQPEDFATYYCQQYYTYPYTFG GGTKVEIK** |
| 286 | ACP457 (WW0621) | aptsssticktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpALFKSSFPpgsEVQLVESGGG LVQPGNSLRLSCAASGFTFSKFGMSWVRQAPGKGLEWVSSISGSGRDTLYAES VKGRFTISRDNAKTTLYLQMNSLRPEDTAVYYCTIGGSLSVSSQGTLVTVSSgg ggsggggsggggsggggsggggsggggssggpALFKSSFPpgsEVQLVESGGGLVQPGGSLRL SCAASGFTFSSYTLAWVRQAPGKGLEWVAAIDSSSYTYSPDTVRGRFTISRDN AKNSLYLQMNSLRAEDTAVYYCARDSNWDALDYWGQGTTVTVSSastkgpsvfp lapsskstsggtaalgclvkdyfpepvtvswnsgaltsgvhtfpavlqssglyslssvvtvpssslgtqtyicnvnhkpsnt kvdkrvepksc** |

-continued

Sequence table

| SEQ ID NO. | Name | Sequence |
|---|---|---|
| 287 | ACP458 (WW0622) | eskygppcppcpapeflggpsvflfppkpkdtlmisrtpevtcvvvdvsqedpevqfnwyvdgvevhnaktkpree qfnstyrvvsyltvlhqdwhigkeykckvsnkglpssiektiskakgqprepqvytlppsqeemtlmqvsltclvkgfy psdiavewesngqpennykappvldsdgsfflysrltvdksrwqegnvfscsvmhealhnhytqkslslslgksggp ALFKSSFPpgsaptssstkktqlqlehllldlqmilnginnyknpkltrmltfklympkkatelkhlqcleeelkplee vinlaqsknfhlrprdlisninvivlelkgsettfmceyadetativeflnrwitfcqsiistltggggsggggsggggsggg gsggggsggggssggpALFKSSFPpgsEVQLVESGGGLVQPGGSLRLSCAASGFTFSSY TLAWVRQAPGKGLEWVAAIDSSSYTYSPDTVRGRFTISRDNAKNSLYLQMNS LRAEDTAVYYCARDSNWDALDYWGQGTTVTVSSastkgpsvfplapsskstsggtaalgclv kdyfpepvtvswnsgaltsgvhtfpavlqssglyslssvvtvpssslgtqtyicnvnhkpsntkvdkrvepksc** |
| 288 | ACP459 (WW0623) | eskygppcppcpapeflggpsvflfppkpkdtlmisrtpevtcvvvdvsqedpevqfnwyvdgvevhnaktkpree qfnstyrvvsyltvlhqdwlngkeykckvsnkglpssiektiskakgqprepqvytlppsqeemtknqvsltclvkgfy psdiavewesngqpennykappvldsdgsfflysrltvdksrwqegnvfscsvmhealhnhytqkslslslgksggp ALFKSSFPpgsaptssstkktqlqlehllldlqmilnginnyknpkltrmltfklympkkatelkhlqcleeelkplee vinlaqsknfhlrprdlisninvivlelkgsettfmceyadetativeflnrwitfcqsiistltggggsggggsggggsggg gsggggsggggssggpALFKSSFPpgsEVQLVESGGGLVQPGGSLRLSCAASGFTFSSY TLAWVRQAPGKGLEWVAAIDSSSYTYSPDTVRGRFTISRDNAKNSLYLQMNS LRAEDTAVYYCARDSNWDALDYWGQGTTVTVSSGGGGSGGGGSGGGGSDI QMTQSPSSLSASVGDRVTITCKAREKLWSAVAWYQQKPGKAPKsLIYSASFRY SGVPSRFSGSGSGTDFTLTISSLQPEDFATYYCQQYYTYPYTFGGGTKVEIK** |
| 289 | ACP460 (WW0624) | eskygppcppcpapeflggpsvflfppkpkdtlmisrtpevtcvvvdvsqedpevqfnwyvdgvevhnaktkpree qfnstyrvvsyltvlhqdwlngkeykckvsnkglpssiektiskakgqprepqvytlppsqeemtknqvsltclvkgfy psdiavewesngqpennykappvldsdgsfflysrltvdksrwqegnvfscsvmhealhnhytqkslslslgksggp ALFKSSFPpgsaptssstkktqlqlehllldlqmilnginnyknpkltrmltfklympkkatelkhlqcleeelkplee vinlaqsknfhlrprdlisninvivlelkgsettfmceyadetativeflnrwitfcqsiistltggggsggggsggggsggg gsggggsggggssggpALFKSSFPpgsEVQLVESGGGLVQPGGSLRLSCAASGFTFSSY TLAWVRQAPGKGLEWVAAIDSSSYTYSPDTVRGRFTISRDNAKNSLYLQMNS LRAEDTAVYYCARDSNWDALDYWGQGTTVTVSSGGGGSGGGGSGGGGSDI QMTQSPSSLSASVGDRVTITCKVTEKVWGNVAWYQQKPGKAPISLIYSPSLRK SGVPSRFSGSGSGTDFTLTISSLQPEDFATYYCQQYYTYPYTFGGGTKVEIK** |
| 290 | ACP461 (WW0625) | eskygppcppcpapeflggpsvflfppkpkdtlmisrtpevtcvvvdvsqedpevqfnwyvdgvevhnaktkpree qfnstyrvvsyltvlhqdwlngkeykckvsnkglpssiektiskakgqprepqvytlppsqeemtknqvsltclvkgfy psdiavewesngqpennykappvldsdgsfflysrltvdksrwqegnvfscsvmhealhnhytqkslslslgksggp ALFKSSFPpgsaptssstkktqlqlehllldlqmilnginnyknpkltrmltfklympkkatelkhlqcleeelkplee vinlaqsknfhlrprdlisninvivlelkgsettfmceyadetativeflnrwitfcqsiistltggggsggggsggggsggg gsggggsggggssggpALFKSSFPpgsEVQLVESGGGLVQPGGSLRLSCAASGFTFSSY TLAWVRQAPGKcLEWVAAIDSSSYTYSPDTVRGRFTISRDNAKNSLYLQMNSL RAEDTAVYYCARDSNWDALDYWGQGTTVTVSSGGGGSGGGGSGGGGSDIQ MTQSPSSLSASVGDRVTITCKAREKLWSAVAWYQQKPGKAPKsLIYSASFRYS GVPSRFSGSGSGTDFTLTISSLQPEDFATYYCQQYYTYPYTFGcGTKVEIK** |
| 291 | ACP462 (WW0626) | eskygppcppcpapeflggpsvflfppkpkdtlmisrtpevtcvvvdvsqedpevqfnwyvdgvevhnaktkpree qfnstyrvvsyltvlhqdwlngkeykckvsnkglpssiektiskakgqprepqvytlppsqeemtknqvsltclvkgfy psdiavewesngqpennykappvldsdgsfflysrltvdksrwqegnvfscsvmhealhnhytqkslslslgksggp ALFKSSFPpgsaptssstkktqlqlehllldlqmilnginnyknpkltrmltfklympkkatelkhlqcleeelkplee vinlaqsknfhlrprdlisninvivlelkgsettfmceyadetativeflnrwitfcqsiistltggggsggggsggggsggg gsggggsggggssggpALFKSSFPpgsEVQLVESGGGLVQPGGSLRLSCAASGFTFSSY TLAWVRQAPGKGLEWVAAIDSSSYTYSPDTVRGRFTISRDNAKNSLYLQMNS LRAEDTAVYYCARDSNWDALDYWGcGTTVTVSSGGGGSGGGGSGGGGSDIQ MTQSPSSLSASVGDRVTITCKAREKLWSAVAWYQQKPGKcPKALIYSASFRYS GVPSRFSGSGSGTDFTLTISSLQPEDFATYYCQQYYTYPYTFGGGTKVEIK** |
| 292 | ACP463 (WW0627) | eskygppcppcpapeflggpsvflfppkpkdtlmisrtpevtcvvvdvsqedpevqfnwyvdgvevhnaktkpree qfnstyrvvsyltvlhqdwlngkeykckvsnkglpssiektiskakgqprepqvytlppsqeemtknqvsltclvkgfy psdiavewesngqpennykappvldsdgsfflysrltvdksrwqegnvfscsvmhealhnhytqkslslslgksggp ALFKSSFPpgsaptssstkktqlqlehllldlqmilnginnyknpkltrmltfklympkkatelkhlqcleeelkplee vinlaqsknfhlrprdlisninvivlelkgsettfmceyadetativeflnrwitfcqsiistltggggsggggsggggsggg gsggggsggggssggpALFKSSFPpgsEVQLVESGGGLVQPGGSLRLSCAASGFTFSSY TLAWVRQAPGKcLEWVAAIDSSSYTYSPDTVRGRFTISRDNAKNSLYLQMNSL RAEDTAVYYCARDSNWDALDYWGQGTTVTVSSGGGGSGGGGSGGGGSDIQ MTQSPSSLSASVGDRVTITCKVTEKVWGNVAWYQQKPGKAPISLIYSPSLRKS GVPSRFSGSGSGTDFTLTISSLQPEDFATYYCQQYYTYPYTFGcGTKVEIK** |
| 293 | ACP464 (WW0628) | eskygppcppcpapeflggpsvflfppkpkdtlmisrtpevtcyvvdvsqedpevqfnwyydgvevhnaktkpree qfnstyrvvsyltvlhqdwingkeykcicvsnkglpssiektiskakgqprepqvytlppsqeemtlmqvsltclvkgfy psdiavewesngqpennykappvldsdgsfflysrltvdksrwqegnvfscsvmhealhnhytqkslslslgksggp ALFKSSFPpgsaptsssticktqlqlehllldlqmilnginnyknpkltrmlfficfympkkatelkhlqcleeelkplee vinlaqsknfhlrprdlisninvivlelkgsettfmceyadetativeflnrwilfcqsiistltggggsggggsggggsggg gsggggsggggssggpALFKSSFPpgsEVQLVESGGGLVQPGGSLRLSCAASGFTFSSY TLAWVRQAPGKGLEWVAAIDSSSYTYSPDTVRGRFTISRDNAKNSLYLQMNS LRAEDTAVYYCARDSNWDALDYWGcGTTVTVSSGGGGSGGGGSGGGGSDIQ |

-continued

Sequence table

| SEQ ID NO. | Name | Sequence |
|---|---|---|
| | | MTQSPSSLSASVGDRVTITCKVTEKVWGNVAWYQQKPGKcPISLIYSPSLRKS GVPSRFSGSGSGTDFTLTISSLQPEDFATYYCQQYYTYPYTFGGGTKVEIK** |
| 294 | ACP465 (WW0629) | vprdcgckpcictypevssvfifppkpkdvltitltpkvtcyvvdiskddpevqfswfvddvevhtaqtqpreeqfnsif rsyselpimhqdwingkefkcrynsaafpapiektisktkgrpkapqvytipppkeqmakdkvsltcmitcapeditv ewqwngqpaenykntqpimdtdgsyfvysklnvqksnweagniftcsvlheglhnhhtekslshspgksggpAL FKSSFPpgsaptssticktqlqlehllldlqmilnginnyknpklbnillfldympkkatelkhlqcleeelkpleevin laqsknfhlrprdlisninvivlelkgsettfmceyadetativeflnrwilfcqsiistltggggsggggsggggsggggsg gggsggggssggpALFKSSFPpgsEVQLVESGGGLVQPGGSLRLSCAASGFTFSSYTL AWVRQAPGKGLEWVAAIDSSSYTYSPDTVRGRFTISRDNAKNSLYLQMNSLR AEDTAVYYCARDSNWDALDYWGQGTTVTVSSGGGGSGGGGSGGGGSDIQM TQSPSSLSASVGDRVTITCKAREKLWSAVAWYQQKPGKAPKsLIYSASFRYSG VPSRFSGSGSGTDFTLTISSLQPEDFATYYCQQYYTYPYTFGGGTKVEIK** |
| 295 | ACP466 (WW0630) | vprdcgckpcictypevssvfifppkpkdvltitltpkvtcyvvdiskddpevqfswfvddvevhtaqtqpreeqfnsif rsyselpimhqdwingkefkcrynsaafpapiektisktkgrpkapqvytipppkeqmakdkvsltcmitcapeditv ewqwngqpaenykntqpimdtdgsyfvysklnvqksnweagniftcsvlheglhnhhtekslshspgksggpAL FKSSFPpgsaptssticktqlqlehllldlqmilnginnyknpklbnillfldympkkatelkhlqcleeelkpleevin laqsknfhlrprdlisninvivlelkgsettfmceyadetativeflnrwilfcqsiistltggggsggggsggggsggggsg gggsggggssggpALFKSSFPpgsEVQLVESGGGLVQPGGSLRLSCAASGFTFSSYTL AWVRQAPGKGLEWVAAIDSSSYTYSPDTVRGRFTISRDNAKNSLYLQMNSLR AEDTAVYYCARDSNWDALDYWGQGTTVTVSSGGGGSGGGGSGGGGSDIQM TQSPSSLSASVGDRVTITCKVTEKVWGNVAWYQQKPGKAPISLIYSPSLRKSG VPSRFSGSGSGTDFTLTISSLQPEDFATYYCQQYYTYPYTFGGGTKVEIK** |
| 296 | ACP467 (WW0631) | vprdcgckpcictypevssvfifppkpkdvltitltpkvtcyvvdiskddpevqfswfvddvevhtaqtqpreeqfnsif rsyselpimhqdwingkefkcrynsaafpapiektisktkgrpkapqvytipppkeqmakdkvsltcmitcapeditv ewqwngqpaenykntqpimdtdgsyfvysklnvqksnweagniftcsvlheglhnhhtekslshspgksggpAL FKSSFPpgsaptssticktqlqlehllldlqmilnginnyknpklbnillfldympkkatelkhlqcleeelkpleevin laqsknfhlrprdlisninvivlelkgsettfmceyadetativeflnrwilfcqsiistltggggsggggsggggsggggsg gggsggggssggpALFKSSFPpgsEVQLVESGGGLVQPGGSLRLSCAASGFTFSSYTL AWVRQAPGKcLEWVAAIDSSSYTYSPDTVRGRFTISRDNAKNSLYLQMNSLR AEDTAVYYCARDSNWDALDYWGQGTTVTVSSGGGGSGGGGSGGGGSDIQM TQSPSSLSASVGDRVTITCKAREKLWSAVAWYQQKPGKAPKsLIYSASFRYSG VPSRFSGSGSGTDFTLTISSLQPEDFATYYCQQYYTYPYTFGcGTKVEIK** |
| 297 | ACP468 (WW0632) | vprdcgckpcictypevssvfifppkpkdvltitltpkvtcyvvdiskddpevqfswfvddvevhtaqtqpreeqfnsif rsyselpimhqdwingkefkcrynsaafpapiektisktkgrpkapqvytipppkeqmakdkvsltcmitcapeditv ewqwngqpaenykntqpimdtdgsyfvysklnvqksnweagniftcsvlheglhnhhtekslshspgksggpAL FKSSFPpgsaptssticktqlqlehllldlqmilnginnyknpklbnillfldympkkatelkhlqcleeelkpleevin laqsknfhlrprdlisninvivlelkgsettfmceyadetativeflnrwilfcqsiistltggggsggggsggggsggggsg gggsggggssggpALFKSSFPpgsEVQLVESGGGLVQPGGSLRLSCAASGFTFSSYTL AWVRQAPGKGLEWVAAIDSSSYTYSPDTVRGRFTISRDNAKNSLYLQMNSLR AEDTAVYYCARDSNWDALDYWGcGTTVTVSSGGGGSGGGGSGGGGSDIQMT QSPSSLSASVGDRVTITCKAREKLWSAVAWYQQKPGKcPKALIYSASFRYSGV PSRFSGSGSGTDFTLTISSLQPEDFATYYCQQYYTYPYTFGGGTKVEIK** |
| 298 | ACP469 (WW0633) | vprdcgckpcictypevssvfifppkpkdvltitltpkvtcyvvdiskddpevqfswfvddvevhtaqtqpreeqfnsif rsyselpimhqdwingkefkcrynsaafpapiektisktkgrpkapqvytipppkeqmakdkvsltcmitcapeditv ewqwngqpaenykntqpimdtdgsyfvysklnvqksnweagniftcsvlheglhnhhtekslshspgksggpAL FKSSFPpgsaptssstkktqlqlehllldlqmilngiimyknpklliiiiiltfkfympkkatelkhlqcleeelkpleevin laqsknfhlrprdlisninvivlelkgsettfmceyadetativeflnrwilfcqsiistltggggsggggsggggsggggsg gggsggggssggpALFKSSFPpgsEVQLVESGGGLVQPGGSLRLSCAASGFTFSSYTL AWVRQAPGKcLEWVAAIDSSSYTYSPDTVRGRFTISRDNAKNSLYLQMNSLR AEDTAVYYCARDSNWDALDYWGQGTTVTVSSGGGGSGGGGSGGGGSDIQM TQSPSSLSASVGDRVTITCKVTEKVWGNVAWYQQKPGKAPISLIYSPSLRKSG VPSRFSGSGSGTDFTLTISSLQPEDFATYYCQQYYTYPYTFGcGTKVEIK** |
| 299 | ACP470 (WW0634) | vprdcgckpcictypevssvfifppkpkdvltitltpkvtcyvvdiskddpevqfswfvddvevhtaqtqpreeqfnslf rsyselpimhqdwingkefkcrynsaafpapiektisktkgrpkapqvytipppkeqmakdkvsltcmitcapeditv ewqwngqpaenykntqpimdtdgsyfvysklnvqksnweagntftcsvlheglhnhhtekslshspgksggpAL FKSSFPpgsaptssticktqlqlehllldlqmilnginnyknpklbnillfldympkkatelkhlqcleeelkpleevin laqsknfhlrprdlisninvivlelkgsettfmceyadetativeflnrwilfcqsiistltggggsggggsggggsggggsg gggsggggssggpALFKSSFPpgsEVQLVESGGGLVQPGGSLRLSCAASGFTFSSYTL AWVRQAPGKGLEWVAAIDSSSYTYSPDTVRGRFTISRDNAKNSLYLQMNSLR AEDTAVYYCARDSNWDALDYWGcGTTVTVSSGGGGSGGGGSGGGGSDIQMT QSPSSLSASVGDRVTITCKVTEKVWGNVAWYQQKPGKcPISLIYSPSLRKSGVP SRFSGSGSGTDFTLTISSLQPEDFATYYCQQYYTYPYTFGGGTKVEIK** |
| 300 | ACP471 (WW0642) | mdmrvpaqllglllwlrgarcvprdcgckpcictvpevssvfifppkpkdvltitltpkvtcvvvdiskddpevqfswf vddveyhtaqtqpreeqfnslfrsyselpimhqdwingkefkcrynsaafpapiektisktkgrpkapqvytipppkeq makdkvsltcmitdffpeditvewqwngqpaenykntqpimdtdgsyfvysklnvqknweagntftcsvlheglh nhhtekslshspgksggpALFKSSFPpgsaptssticktqlqlehllldlqmilnginnyknpkltrmllfldympk |

-continued

Sequence table

| SEQ ID NO. | Name | Sequence |
|---|---|---|
| | | katelkhlqcleeelkpleevinlaqsknfhlrprdlisninvivlelkgsettfmceyadetativeflnrwilfcqsiistltg<br>gggsggggsggggsggggsggggsggggssggpALFKSSFPpgsEVQLVESGGGLVQPGGSLR<br>LSCAASGFTFSSYTLAWVRQAPGKGLEWVAAIDSSSYTYSPDTVRGRFTISRD<br>NAKNSLYLQMNSLRAEDTAVYYCARDSNWDALDYWGQGTTVTVSSastkgpsv<br>fplapsskstsggtaalgclykdyfpepvtvswnsgaltsgvhtipavlqssglyslssvvtvpssslgtqtyicnvnhkps<br>nticvdkrvepksc** |
| 301 | ACP382<br>(WW0524) | DIQMTQSPSSLSASVGDRVTITCKVTEKVWGNVAWYQQKPGKAPISLIYSPSL<br>RKSGVPSRFSGSGSGTDFTLTISSLQPEDFATYYCQQYYTYPYTFGGGTKVEIKr<br>tvaapsvfifppsdeqlksgtasvvcllnaypreakvqwkvdnalqsgnsqesvteqdskdstyslsstltlskadyekh<br>kvyacevthqglsspvtksfnrgec** |
| 302 | ACP383<br>(WW0525) | eskygppcppcpapeflggpsvflfppkpkdtlmisrtpevtcyvvdvsqedpevqfnwyydgvevhnaktkpree<br>qfnstyrvvsyltvlhqdwingkeykcicvsnkglpssiektiskakgqprepqvytlppsqeemtlmqvsltclvkgfy<br>psdiavewesngqpennykappvldsdgsfflysrltvdksrwqegnvfscsvmhealhnhytqkslslslgksggp<br>GPAGLYAQpgsaptssticktqlqlehllldlqmilnginnyknpkltrmllfklympldcatelkhlqcleeelkpl<br>eevinlaqsknfhlrprdlisninvivlelkgsettfmceyadetativeflnrwilfcqsiistltggggsggggsggggsgg<br>ggsggggsggggssggpGPAGLYAQpgsEVQLVESGGGLVQPGGSLRLSCAASGFTFS<br>SYTLAWVRQAPGKcLEWVAAIDSSSYTYSPDTVRGRFTISRDNAKNSLYLQM<br>NSLRAEDTAVYYCARDSNWDALDYWGQGTTVTVSSGGGGSGGGGSGGGGS<br>DIQMTQSPSSLSASVGDRVTITCKASQNVGTNVGWYQQKPGKAPKALIYSASF<br>RYSGVPSRFSGSGSGTDFTLTISSLQPEDFATYYCQQYYTYPYTFGcGTKVEIK*<br>* |
| 303 | ACP384<br>(WW0526) | eskygppcppcpapeflggpsvflfppkpkdtlmisrtpevtcyvvdvsqedpevqfnwyydgvevhnaktkpree<br>qfnstyrvvsyltvlhqdwingkeykcicvsnkglpssiektiskakgqprepqvytlppsqeemtlmqvsltclvkgfy<br>psdiavewesngqpennykappvldsdgsfflysrltvdksrwqegnvfscsvmhealhnhytqkslslslgksggp<br>GPAGLYAQpgsaptssticktqlqlehllldlqmilnginnyknpkltrmltfkfympldcatelkhlqcleeelkpl<br>eevinlaqsknfhlrprdlisninvivlelkgsettfmceyadetativeflnrwilfcqsiistltggggsggggsggggsgg<br>ggsggggsggggssggpGPAGLYAQpgsEVQLVESGGGLVQPGGSLRLSCAASGFTFS<br>SYTLAWVRQAPGKGLEWVAAIDSSSYTYSPDTVRGRFTISRDNAKNSLYLQM<br>NSLRAEDTAVYYCARDSNWDALDYWGcGTTVTVSSGGGGSGGGGSGGGGSD<br>IQMTQSPSSLSASVGDRVTITCKASQNVGTNVGWYQQKPGKcPKALIYSASFR<br>YSGVPSRFSGSGSGTDFTLTISSLQPEDFATYYCQQYYTYPYTFGGGTKVEIK** |
| 304 | ACP385<br>(WW0527) | eskygppcppcpapeflggpsvflfppkpkdtlmisrtpevtcyvvdvsqedpevqfnwyydgvevhnaktkpree<br>qfnstyrvvsyltvlhqdwingkeykcicvsnkglpssiektiskakgqprepqvytlppsqeemtlmqvsltclvkgfy<br>psdiavewesngqpennykappvldsdgsfflysrltvdksrwqegnvfscsvmhealhnhytqkslslslgksggp<br>GPAGLYAQpgsaptssticktqlqlehllldlqmilnginnyknpkltrmltfkfympldcatelkhlqcleeelkpl<br>eevinlaqsknfhlrprdlisninvivlelkgsettfmceyadetativeflnrwilfcqsiistltggggsggggsggggsgg<br>ggsggggsggggssggpGPAGLYAQpgsEVQLVESGGGLVQPGGSLRLSCAASGFTFS<br>SYTLAWVRQAPGKcLEWVAAIDSSSYTYSPDTVRGRFTISRDNAKNSLYLQM<br>NSLRAEDTAVYYCARDSNWDALDYWGQGTTVTVSSGGGGSGGGGSGGGGS<br>DIQMTQSPSSLSASVGDRVTITCKAREKLWSAVAWYQQKPGKAPKALIYSASF<br>RYSGVPSRFSGSGSGTDFTLTISSLQPEDFATYYCQQYYTYPYTFGcGTKVEIK*<br>* |
| 305 | ACP386<br>(WW0528) | eskygppcppcpapeflggpsvflfppkpkdtlmisrtpevtcvvvdvsqedpevqfnwyvdgvevhnaktkpree<br>qfnstyrvvsyltvlhqdwingkeykckvsnkglpssiektiskakgqprepqvytlppsqeemtlmqvsltclvkgfy<br>psdiavewesngqpennykttppvldsdgsfflysrltvdksrwqegnvfscsvmhealhnhytqkslslslgksggp<br>GPAGLYAQpgsaptssstIcktqlqlehllldlqmilnginnyknpkltrmltfkfympldcatelkhlqcleeelkpl<br>eevinlaqsknfldrprdlisninvivlelkgsettfmceyadetativeflnrwitfcqsiistltggggsggggsggggsgg<br>ggsggggsggggssggpGPAGLYAQpgsEVQLVESGGGLVQPGGSLRLSCAASGFTFS<br>SYTLAWVRQAPGKGLEWVAAIDSSSYTYSPDTVRGRFTISRDNAKNSLYLQM<br>NSLRAEDTAVYYCARDSNWDALDYWGcGTTVTVSSGGGGSGGGGSGGGGSD<br>IQMTQSPSSLSASVGDRVTITCKAREKLWSAVAWYQQKPGKcPKALIYSASFR<br>YSGVPSRFSGSGSGTDFTLTISSLQPEDFATYYCQQYYTYPYTFGGGTKVEIK** |
| 306 | ACP387<br>(WW0529) | eskygppcppcpapeflggpsvflfppkpkdtlmisrtpevtcvvvdvsqedpevqfnwyvdgvevhnaktkpree<br>qfnstyrvvsyltvlhqdwingkeykckvsnkglpssiektiskakgqprepqvytlppsqeemtlmqvsltclvkgfy<br>psdiavewesngqpennykttppvldsdgsfflysrltvdksrwqegnvfscsvmhealhnhytqkslslslgksggp<br>GPAGLYAQpgsaptssstIcktqlqlehllldlqmilnginnyknpkltrmltfkfympldcatelkhlqcleeelkpl<br>eevinlaqsknfldrprdlisninvivlelkgsettfmceyadetativeflnrwitfcqsiistltggggsggggsggggsgg<br>ggsggggsggggssggpGPAGLYAQpgsEVQLVESGGGLVQPGGSLRLSCAASGFTFS<br>SYTLAWVRQAPGKcLEWVAAIDSSSYTYSPDTVRGRFTISRDNAKNSLYLQM<br>NSLRAEDTAVYYCARDSNWDALDYWGQGTTVTVSSGGGGSGGGGSGGGGS<br>DIQMTQSPSSLSASVGDRVTITCKVTEKVWGNVAWYQQKPGKAPISLIYSPSL<br>RKSGVPSRFSGSGSGTDFTLTISSLQPEDFATYYCQQYYTYPYTFGcGTKVEIK*<br>* |
| 307 | ACP388<br>(WW0530) | eskygppcppcpapeflggpsvflfppkpkdtlmisrtpevtcvvvdvsqedpevqfnwyvdgvevhnaktkpree<br>qfnstyrvvsyltvlhqdwingkeykckvsnkglpssiektiskakgqprepqvytlppsqeemtlmqvsltclvkgfy<br>psdiavewesngqpennykttppvldsdgsfflysrltvdksrwqegnvfscsvmhealhnhytqkslslslgksggp |

-continued

Sequence table

| SEQ ID NO. | Name | Sequence |
|---|---|---|
| | | GPAGLYAQpgsaptssstIcktqlqlehllldlqmilnginnyknpkltrmlfficfympldcatelkhlqcleeelkpl<br>eevinlaqsknfldrprdlisninvivlelkgsettfmceyadetativeflnrwitfcqsiistltggggsggggsggggsgg<br>ggsggggsggggssggpGPAGLYAQpgsEVQLVESGGGLVQPGGSLRLSCAASGFTFS<br>SYTLAWVRQAPGKGLEWVAAIDSSSYTYSPDTVRGRFTISRDNAKNSLYLQM<br>NSLRAEDTAVYYCARDSNWDALDYWGcGTTVTVSSGGGGSGGGGSGGGGSD<br>IQMTQSPSSLSASVGDRVTITCKVTEKVWGNVAWYQQKPGKcPISLIYSPSLRK<br>SGVPSRFSGSGSGTDFTLTISSLQPEDFATYYCQQYYTYPYTFGGGTKVEIK** |
| 308 | ACP389 (WW0531) | eskygppcppcpapeflggpsvflfppkpkdtlmisrtpevtcvvvdvsqedpevqfnwyvdgvevhnaktkpree<br>qfnstyrvvsyltvlhqdwingkeykckvsnkglpssiektiskakgqprepqvytlppsqeemtlmqvsltclvkgfy<br>psdiavewesngqpennykttppvldsdgsfflysrltvdksrwqegnvfscsvmhealhnhytqkslslslgksggp<br>GPAGLYAQpgsaptssstIcktqlqlehllldlqmilnginnyknpkltrmltfkfympldcatelkhlqcleeelkpl<br>eevinlaqsknfldrprdlisninvivlelkgsettfmceyadetativeflnrwitfcqsiistltggggsggggsggggsgg<br>ggsggggsggggssggpGPAGLYAQpgsevqllesggglvqpggslrlscaasgsifsanamgwyrqapgkqr<br>elvavissggstnyadsvkgrftisrdnskntvylqmnstraedtavyycmysgsyyytpndywgqgtivtvss** |
| 309 | ACP390 (WW0532) | aptssstIcktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKcLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKAREKLWSAVAWYQQKPG<br>KAPKsLIYSASFRYSGVPSRFSGSGSGTDFTLTISSLQPEDFATYYCQQYYTYPY<br>TFGcGTKVEIK** |
| 310 | ACP391 (WW0533) | eskygppcppcpapeflggpsvflfppkpkdtlmisrtpevtcvvvdvsqedpevqfnwyvdgvevhnaktkpree<br>qfnstyrvvsyltvlhqdwingkeykckvsnkglpssiektiskakgqprepqvytlppsqeemtlmqvsltclvkgfy<br>psdiavewesngqpennykttppvldsdgsfflysrltvdksrwqegnvfscsvmhealhnhytqkslslslgksggp<br>GPAGLYAQpgsaptssstkktqlqlehllldlqmilnginnyknpkltrmlfficfympldcatelkhlqcleeelkpl<br>eevinlaqsknfhlrprdlisninvivlelkgsettfmceyadetativeflnrwitfcqsiistliggggsggggsggggsgg<br>ggsggggsggggssggpGPAGLYAQpgsEVQLVESGGGLVQPGGSLRLSCAASGFTFS<br>SYTLAWVRQAPGKcLEWVAAIDSSSYTYSPDTVRGRFTISRDNAKNSLYLQM<br>NSLRAEDTAVYYCARDSNWDALDYWGQGTTVTVSSGGGGSGGGGSGGGGS<br>DIQMTQSPSSLSASVGDRVTITCKAREKLWSAVAWYQQKPGKAPKsLIYSASF<br>RYSGVPSRFSGSGSGTDFTLTISSLQPEDFATYYCQQYYTYPYTFGcGTKVEIK*<br>* |
| 311 | ACP392 (WW0534) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsggggsggggsggg<br>gsggggsggggsggggselcdddppeiphatfkamaykegtmlnceckrgfrriksgslymlctgnsshsswdnqc<br>qctssatrnttkqvtpqpeeqkerkttemqspmqpvdqaslpghcrepppweneateriyhfvvgqmvyyqcvqgy<br>ralhrgpaesvckmthgktrwtqpqlictgemetsqfpgeekpqaspegrpesetsSlvtncifqiqtemaatmetsiftt<br>eyqsggpGPAGLYAQpgsEVQLVESGGGLVQPGNSLRLSCAASGFTFSKFGMSWV<br>RQAPGKGLEWVSSISGSGRDTLYAESVKGRFTISRDNAKTTLYLQMNSLRPED<br>TAVYYCTIGGSLSVSSQGTLVTVSSggggsggggsggggsggggsggggsggggssggpGPAG<br>LYAQpgsEVQLVESGGGLVQPGGSLRLSCAASGFTFSSYTLAWVRQAPGKcLE<br>WVAAIDSSSYTYSPDTVRGRFTISRDNAKNSLYLQMNSLRAEDTAVYYCARD<br>SNWDALDYWGQGTTVTVSSGGGGSGGGGSGGGGSDIQMTQSPSSLSASVGD<br>RVTITCKAREKLWSAVAWYQQKPGKAPKsLIYSASFRYSGVPSRFSGSGSGTD<br>FTLTISSLQPEDFATYYCQQYYTYPYTFGcGTKVEIK** |
| 312 | ACP393 (WW0535) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsggggsggggsggg<br>gsggggsggggsggggselcdddppeiphatfkamaykegtmlnceckrgfrriksgslymlctgnsshsswdnqc<br>qctssatrnttkqvtpqpeeqkerkttemqspmqpvdqaslpghcrepppweneateriyhfvvgqmvyyqcvqgy<br>ralhrgpaesvckmthgktrwtqpqlictgemetsqfpgeekpqaspegrpesetsSlvtncifqiqtemaatmetsiftt<br>eyqsggpGPAGLYAQpgsEVQLVESGGGLVQPGNSLRLSCAASGFTFSKFGMSWV<br>RQAPGKGLEWVSSISGSGRDTLYAESVKGRFTISRDNAKTTLYLQMNSLRPED<br>TAVYYCTIGGSLSVSSQGTLVTVSSggggsggggsggggsggggsggggsggggssggpGPAG<br>LYAQpgsEVQLVESGGGLVQPGGSLRLSCAASGFTFSSYTLAWVRQAPGKGLE<br>WVAAIDSSSYTYSPDTVRGRFTISRDNAKNSLYLQMNSLRAEDTAVYYCARD<br>SNWDALDYWGcGTTVTVSSGGGGSGGGGSGGGGSDIQMTQSPSSLSASVGDR<br>VTITCKAREKLWSAVAWYQQKPGKcPKALIYSASFRYSGVPSRFSGSGSGTDF<br>TLTISSLQPEDFATYYCQQYYTYPYTFGGGTKVEIK** |
| 313 | ACP394 (WW0536) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsggggsggggsggg<br>gsggggsggggsggggselcdddppeiphatfkamaykegtmlnceckrgfrriksgslymlctgnsshsswdnqc<br>qctssatrnttkqvtpqpeeqkerkttemqspmqpvdqaslpghcrepppweneateriyhfvvgqmvyyqcvqgy<br>ralhrgpaesvckmthgktrwtqpqlictgemetsqfpgeekpqaspegrpesetsSlvtncifqiqtemaatmetsiftt<br>eyqsggpGPAGLYAQpgsEVQLVESGGGLVQPGNSLRLSCAASGFTFSKFGMSWV |

-continued

Sequence table

| SEQ ID NO. | Name | Sequence |
|---|---|---|
| | | RQAPGKGLEWVSSISGSGRDTLYAESVKGRFTISRDNAKTTLYLQMNSLRPED<br>TAVYYCTIGGSLSVSSQGTLVTVSSggggsggggsggggsggggsggggsggggssggpGPAG<br>LYAQpgsEVQLVESGGGLVQPGGSLRLSCAASGFTFSSYTLAWVRQAPGKcLE<br>WVAAIDSSSYTYSPDTVRGRFTISRDNAKNSLYLQMNSLRAEDTAVYYCARD<br>SNWDALDYWGQGTTVTVSSGGGGSGGGGSGGGGSDIQMTQSPSSLSASVGD<br>RVTITCKVTEKVWGNVAWYQQKPGKAPISLIYSPSLRKSGVPSRFSGSGSGTD<br>FTLTISSLQPEDFATYYCQQYYTYPYTFGcGTKVEIK** |
| 314 | ACP395 (WW0537) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsggggsggggsggg<br>gsggggsggggsggggselcdddppeiphatfkamaykegtmlnceckrgfrriksgslymlctgnsshsswdnqc<br>qctssatrnttkqvtpqpeeqkerkttemqspmqpvdqaslpghcrepppweneateriyhfvvgqmvyyqcvqgy<br>ralhrgpaesvckmthgktrwtqpqlictgemetsqfpgeekpqaspegrpesetsSlvtncifqiqtemaatmetsiftt<br>eyqsggpGPAGLYAQpgsEVQLVESGGGLVQPGNSLRLSCAASGFTFSKFGMSWV<br>RQAPGKGLEWVSSISGSGRDTLYAESVKGRFTISRDNAKTTLYLQMNSLRPED<br>TAVYYCTIGGSLSVSSQGTLVTVSSggggsggggsggggsggggsggggsggggssggpGPAG<br>LYAQpgsEVQLVESGGGLVQPGGSLRLSCAASGFTFSSYTLAWVRQAPGKGLE<br>WVAAIDSSSYTYSPDTVRGRFTISRDNAKNSLYLQMNSLRAEDTAVYYCARD<br>SNWDALDYWGcGTTVTVSSGGGGSGGGGSGGGGSDIQMTQSPSSLSASVGDR<br>VTITCKVTEKVWGNVAWYQQKPGKcPISLIYSPSLRKSGVPSRFSGSGSGTDFT<br>LTISSLQPEDFATYYCQQYYTYPYTFGGGTKVEIK** |
| 315 | ACP396 (WW0538) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsggggsggggsggg<br>gsggggsggggsggggselcdddppeiphatfkamaykegtmlnceckrgfrriksgslymlctgnsshsswdnqc<br>qctssatrnttkqvtpqpeeqkerkttemqspmqpvdqaslpghcrepppweneateriyhfvvgqmvyyqcvqgy<br>ralhrgpaesvckmthgktrwtqpqlictgemetsqfpgeekpqaspegrpesetsSlytttclfqiqtemaatmetsiftt<br>eyqsggpGPAGLYAQpgsEVQLVESGGGLVQPGNSLRLSCAASGFTFSKFGMSWV<br>RQAPGKGLEWVSSISGSGRDTLYAESVKGRFTISRDNAKTTLYLQMNSLRPED<br>TAVYYCTIGGSLSVSSQGTLVTVSSggggsggggsggggsggggsggggsggggssggpGPAG<br>LYAQpgsevqllesggglvqpggslrlscaasgsifsanamgwyrqapgkqrelvavissggstnyadsvkgrftisr<br>dnskntvylqmnslraedtavyycmysgsyyytpndywgqgtivtvss** |
| 316 | ACP397 (WW0539) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsggggsggggsggg<br>gsggggsggggsggggselcdddppeiphatfkamaykegtmlnceckrgfrriksgslymlctgnsshsswdnqc<br>qctssatrnttkqvtpqpeeqkerkttemqspmqpvdqaslpghcrepppweneateriyhfvvgqmvyyqcvqgy<br>ralhrgpaesvckmthgktrwtqpqlictgemetsqfpgeekpqaspegrpesetsSlytttclfqiqtemaatmetsiftt<br>eyqsggpGPAGLYAQpgsEVQLVESGGGLVQPGNSLRLSCAASGFTFSKFGMSWV<br>RQAPGKGLEWVSSISGSGRDTLYAESVKGRFTISRDNAKTTLYLQMNSLRPED<br>TAVYYCTIGGSLSVSSQGTLVTVSSggggsggggsggggsggggsggggsggggssggpGPAG<br>LYAQpgsevqllesggglvqpggslrlscaasgsifsanamgwyrqapgkglelvavissggstnyadsvkgrftisr<br>dnskntvylqmnslraedtavyycmysgsyyytpndywgqgtivtvss** |
| 317 | ACP398 (WW0540) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsggggsggggsggg<br>gsggggsggggsggggselcdddppeiphatfkamaykegtmlnceckrgfrriksgslymlctgnsshsswdnqc<br>qctssatrnttkqvtpqpeeqkerkttemqspmqpvdqaslpghcrepppweneateriyhfvvgqmvyyqcvqgy<br>ralhrgpaesvckmthgktrwtqpqlictgemetsqfpgeekpqaspegrpesetsSlytttclfqiqtemaatmetsiftt<br>eyqsggpGPAGLYAQpgsEVQLVESGGGLVQPGNSLRLSCAASGFTFSKFGMSWV<br>RQAPGKGLEWVSSISGSGRDTLYAESVKGRFTISRDNAKTTLYLQMNSLRPED<br>TAVYYCTIGGSLSVSSQGTLVTVSSggggsggggsggggsggggsggggsggggssggpGPAG<br>LYAQpgsEVQLVESGGGLVQPGGSLRLSCAASGFTFSSYTLAWVRQAPGKGLE<br>WVAAIDSSSYTYSPDTVRGRFTISRDNAKNSLYLQMNSLRAEDTAVYYCARD<br>SNWDALDYWGQGTTVTVSSastkgpsvfplapsskstsggtaalgclvkdyfpepvtvswnsgaltsgv<br>htfpavlqssglyslssvvtvpssslgtqtyicnvnhkpsntkvdkrvepksc** |
| 318 | ACP399 | EVQLVESGGGLVQPGGSLRLSCAASGFTFSSYTLAWVRQAPGKcLEWVAAIDS<br>SSYTYSPDTVRGRFTISRDNAKNSLYLQMNSLRAEDTAVYYCARDSNWDALD<br>YWGQGTTVTVSSGGGGSGGGGSGGGGSDIQMTQSPSSLSASVGDRVTITCKA<br>REKLWSAVAWYQQKPGKAPKsLIYSASFRYSGVPSRFSGSGSGTDFTLTISSLQ<br>PEDFATYYCQQYYTYPYTFGcGTKVEIKsggpGPAGLYAQpgsggggsggggsggggsg<br>gggsggggsggggsEVQLVESGGGLVQPGNSLRLSCAASGFTFSKFGMSWVRQAPG<br>KGLEWVSSISGSGRDTLYAESVKGRFTISRDNAKTTLYLQMNSLRPEDTAVYY<br>CTIGGSLSVSSQGTLVTVSSsggpGPAGLYAQpgsfficlympkkatelkhlqcleeelkpleevinl<br>aqsknfhlrprdlisninvivlelkgsetlfmceyadetativeflnrwitfcqsiistltGGssstldctqlqle<br>hllldlqmilnginnyknpkltrmlsggpGPAGLYAQpgsEVQLVESGGGLVQPGNSLRLSCAASGFTFS<br>KFGMSWVRQAPGKGLEWVSSISGSGRDTLYAESVKGRFTISRDNAKTTLYLQ<br>MNSLRPEDTAVYYCTIGGSLSVSSQGTLVTVSS** |
| 319 | ACP400 | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGcGTTVTVSSGGGGSGGGGSGGGGSDIQMTQSPSSLSASVGDRVTITCKA |

-continued

Sequence table

| SEQ ID NO. | Name | Sequence |
|---|---|---|
| | | REKLWSAVAWYQQKPGKcPKALIYSASFRYSGVPSRFSGSGSGTDFTLTISSLQ<br>PEDFATYYCQQYYTYPYTFGGGTKVEIKsggpGPAGLYAQpgsggggsggggsggggsg<br>gggsggggsggggsEVQLVESGGGLVQPGNSLRLSCAASGFTFSKFGMSWVRQAPG<br>KGLEWVSSISGSGRDTLYAESVKGRFTISRDNAKTTLYLQMNSLRPEDTAVYY<br>CTIGGSLSVSSQGTLVTVSSsggpGPAGLYAQpgsfficlympkkatelkhlqcleeelkpleevinl<br>aqsknfhlrprdlisninvivlelkgsetlfmceyadetativeflnrwitfcqsiistltGGssstldctqlq<br>lehllldlqmilnginnyknpkltrmlsggpGPAGLYAQpgsEVQLVESGGGLVQPGNSLRLSCAASGFTFS<br>KFGMSWVRQAPGKGLEWVSSISGSGRDTLYAESVKGRFTISRDNAKTTLYLQ<br>MNSLRPEDTAVYYCTIGGSLSVSSQGTLVTVSS** |
| 320 | ACP401 | EVQLVESGGGLVQPGGSLRLSCAASGFTFSSYTLAWVRQAPGKcLEWVAAIDS<br>SSYTYSPDTVRGRFTISRDNAKNSLYLQMNSLRAEDTAVYYCARDSNWDALD<br>YWGQGTTVTVSSGGGGSGGGGSGGGGSDIQMTQSPSSLSASVGDRVTITCKV<br>TEKVWGNVAWYQQKPGKAPISLIYSPSLRKSGVPSRFSGSGSGTDFTLTISSLQ<br>PEDFATYYCQQYYTYPYTFGcGTKVEIKsggpGPAGLYAQpgsggggsggggsggggsg<br>gggsggggsggggsEVQLVESGGGLVQPGNSLRLSCAASGFTFSKFGMSWVRQAPG<br>KGLEWVSSISGSGRDTLYAESVKGRFTISRDNAKTTLYLQMNSLRPEDTAVYY<br>CTIGGSLSVSSQGTLVTVSSsggpGPAGLYAQpgsdklympkkatelkhlqcleeelkpleevinl<br>aqsknfhlrprdlisninvivlelkgsetifmceyadetativeflnrwitfcqsiistltGGssstkktqlqlehll<br>ldlqmilnginnyknpkltrmlsggpGPAGLYAQpgsEVQLVESGGGLVQPGNSLRLSCAASGFTFS<br>KFGMSWVRQAPGKGLEWVSSISGSGRDTLYAESVKGRFTISRDNAKTTLYLQ<br>MNSLRPEDTAVYYCTIGGSLSVSSQGTLVTVSS** |
| 321 | ACP402 | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGcGTTVTVSSGGGGSGGGGSGGGGSDIQMTQSPSSLSASVGDRVTITCKV<br>TEKVWGNVAWYQQKPGKcPISLIYSPSLRKSGVPSRFSGSGSGTDFTLTISSLQP<br>EDFATYYCQQYYTYPYTFGGGTKVEIKsggpGPAGLYAQpgsggggsggggsggggsgg<br>ggsggggsggggsEVQLVESGGGLVQPGNSLRLSCAASGFTFSKFGMSWVRQAPGK<br>GLEWVSSISGSGRDTLYAESVKGRFTISRDNAKTTLYLQMNSLRPEDTAVYYC<br>TIGGSLSVSSQGTLVTVSSsggpGPAGLYAQpgstfklympkkatelkhlqcleeelkpleevinla<br>qsknfldrprdlisninvivlelkgsellfmceyadetativeflnrwitfcqsiistltGGssstkktqlqlehlll<br>dlqmilnginnyknpkltrmlsggpGPAGLYAQpgsEVQLVESGGGLVQPGNSLRLSCAASGFTFS<br>KFGMSWVRQAPGKGLEWVSSISGSGRDTLYAESVKGRFTISRDNAKTTLYLQ<br>MNSLRPEDTAVYYCTIGGSLSVSSQGTLVTVSS** |
| 322 | ACP403 | evqllesggglvqpggslrlscaasgsifsanamgwyrqapgkqrelvavissggstnyadsvkgrftisrdnskntvyl<br>qmnslraedtavyycmysgsyyytpndywgqgtivtvsssggpGPAGLYAQpgsggggsggggsggggsg<br>gggsggggsggggsEVQLVESGGGLVQPGNSLRLSCAASGFTFSKFGMSWVRQAPG<br>KGLEWVSSISGSGRDTLYAESVKGRFTISRDNAKTTLYLQMNSLRPEDTAVYY<br>CTIGGSLSVSSQGTLVTVSSsggpGPAGLYAQpgsdklympkkatelkhlqcleeelkpleevinl<br>aqsknfhlrprdlisninvivlelkgsetifmceyadetativeflnrwideqsiistltGGssstkktqlqlehllldlqmiln<br>ginnyknpkltrmlsggpGPAGLYAQpgsEVQLVESGGGLVQPGNSLRLSCAASGFTFS<br>KFGMSWVRQAPGKGLEWVSSISGSGRDTLYAESVKGRFTISRDNAKTTLYLQ<br>MNSLRPEDTAVYYCTIGGSLSVSSQGTLVTVSS** |
| 323 | ACP404 | evqllesggglvqpggslrlscaasgsifsanamgwyrqapgkglelvavissggstnyadsvkgrftisrdnskntvyl<br>qmnslraedtavyycmysgsyyytpndywgqgtivtvsssggpGPAGLYAQpgsggggsggggsggggsg<br>gggsggggsggggsEVQLVESGGGLVQPGNSLRLSCAASGFTFSKFGMSWVRQAPG<br>KGLEWVSSISGSGRDTLYAESVKGRFTISRDNAKTTLYLQMNSLRPEDTAVYY<br>CTIGGSLSVSSQGTLVTVSSsggpGPAGLYAQpgsdklympkkatelkhlqcleeelkpleevinl<br>aqsknfhlrprdlisninvivlelkgsetifmceyadetativeflnrwideqsiistltGGssstkktqlqlehllldlqmiln<br>ginnyknpkltrmlsggpGPAGLYAQpgsEVQLVESGGGLVQPGNSLRLSCAASGFTFS<br>KFGMSWVRQAPGKGLEWVSSISGSGRDTLYAESVKGRFTISRDNAKTTLYLQ<br>MNSLRPEDTAVYYCTIGGSLSVSSQGTLVTVSS** |
| 324 | ACP405 | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSastkgpsvfplapsskstsggtaalgclvkdyfpepvtvswnsgaltsgvhtfpavlqss<br>glyslssvvtvpssslgtqtyicnvnhkpsntkvdkrvepkscsggpGPAGLYAQpgsggggsggggsggggs<br>ggggsggggsggggsEVQLVESGGGLVQPGNSLRLSCAASGFTFSKFGMSWVRQAP<br>GKGLEWVSSISGSGRDTLYAESVKGRFTISRDNAKTTLYLQMNSLRPEDTAVY<br>YCTIGGSLSVSSQGTLVTVSSsggpGPAGLYAQpgstildympkkatelkhlqcleeelkpleevl<br>nlaqsknfhlrprdlisninvivlelkgsettfmceyadetativeflnrwitfcqsiistltGGssstkktqlq<br>lehllldlqmilnginnyknpkltrmlsggpGPAGLYAQpgsEVQLVESGGGLVQPGNSLRLSCAASGFTF<br>SKFGMSWVRQAPGKGLEWVSSISGSGRDTLYAESVKGRFTISRDNAKTTLYL<br>QMNSLRPEDTAVYYCTIGGSLSVSSQGTLVTVSS** |
| 325 | ACP406 (WW0548) | vprdcgckpcictypevssvfifppkpkdvltitltpkvtcwvdiskddpevqfswfvddvevhtaqtqpreeqfnstf<br>rsyselpimhqdwingkefkcrynsaafpapiektisktkgrpkapqvytipppkeqmakdkvsltcmitdffpeditv<br>ewqwngqpaenyknqpimdtdgsyfyysklnvqksnweagniftcsvlheglhnhhtekslshspgksggpGP<br>AGLYAQpgsaptssstickqlqlehllldlqmilnginnyknpkltrmifficfympkkatelkhlqcleeelkpleev<br>lnlaqsknfhlrprdlisninvivlelkgsettfmceyadetativeflnrwilfcqsiistltggggsggggsggggsggggs |

-continued

Sequence table

| SEQ ID NO. | Name | Sequence |
|---|---|---|
| | | ggggsggggssggpGPAGLYAQpgsEVQLVESGGGLVQPGGSLRLSCAASGFTFSSYT<br>LAWVRQAPGKGLEWVAAIDSSSYTYSPDTVRGRFTISRDNAKNSLYLQMNSL<br>RAEDTAVYYCARDSNWDALDYWGQGTTVTVSSastkgpsvfplapsskstsggtaalgclvk<br>dyfpepvtvswnsgaltsgvhdpavlqssglyslssvvtvpssslgtqtyicnvnhkpsnticvdlavepksc** |
| 326 | ACP407 (WW0549) | vprdcgckpcictypevssvfifppkpkdvltitltpkvtcwvdiskddpevqfswfvddvevhtaqtqpreeqfnsif<br>rsyselpimhqdwingkefkcrynsaafpapiektisktkgrpkapqvytipppkeqmakdkvsltcmitcapeditv<br>ewqwngqpaenykntqpimdtdgsyfyysklnvqksnweagniftcsvlheglhnhhtekslshspgksggpGP<br>AGLYAQpgsaptsssticktqlqlehllldlqmilnginnyknpkltrmifficfympkkatelkhlqcleeelkpleev<br>lnlaqsknfhlrprdlisninvivlelkgsettfmceyadetativeflnrwilfcqsiistltggggsggggsggggsggggs<br>ggggsggggssggpGPAGLYAQpgsEVQLVESGGGLVQPGGSLRLSCAASGFTFSSYT<br>LAWVRQAPGKcLEWVAAIDSSSYTYSPDTVRGRFTISRDNAKNSLYLQMNSLR<br>AEDTAVYYCARDSNWDALDYWGQGTTVTVSSGGGGSGGGGSGGGGSDIQM<br>TQSPSSLSASVGDRVTITCKAREKLWSAVAWYQQKPGKAPKALIYSASFRYSG<br>VPSRFSGSGSGTDFTLTISSLQPEDFATYYCQQYYTYPYTFGcGTKVEIK** |
| 327 | ACP408 (WW0550) | vprdcgckpcictypevssvfifppkpkdvltitltpkvtcwvdiskddpevqfswfvddvevhtaqtqpreeqfnsif<br>rsyselpimhqdwingkefkcrynsaafpapiektisktkgrpkapqvytipppkeqmakdkvsltcmitcapeditv<br>ewqwngqpaenykntqpimdtdgsyfyysklnvqksnweagniftcsvlheglhnhhtekslshspgksggpGP<br>AGLYAQpgsaptsssticktqlqlehllldlqmilnginnyknpkltrmifficfympkkatelkhlqcleeelkpleev<br>lnlaqsknfhlrprdlisninvivlelkgsettfmceyadetativeflnrwilfcqsiistltggggsggggsggggsggggs<br>ggggsggggssggpGPAGLYAQpgsEVQLVESGGGLVQPGGSLRLSCAASGFTFSSYT<br>LAWVRQAPGKcLEWVAAIDSSSYTYSPDTVRGRFTISRDNAKNSLYLQMNSLR<br>AEDTAVYYCARDSNWDALDYWGQGTTVTVSSGGGGSGGGGSGGGGSDIQM<br>TQSPSSLSASVGDRVTITCKAREKLWSAVAWYQQKPGKAPKsLIYSASFRYSG<br>VPSRFSGSGSGTDFTLTISSLQPEDFATYYCQQYYTYPYTFGcGTKVEIK** |
| 328 | ACP409 (WW0551) | vprdcgckpcictypevssvfifppkpkdvltitltpkvtcwvdiskddpevqfswfvddvevhtaqtqpreeqfnsif<br>rsyselpimhqdwingkefkcrynsaafpapiektisktkgrpkapqvytipppkeqmakdkvsltcmitcapeditv<br>ewqwngqpaenykntqpimdtdgsyfyysklnvqksnweagniftcsvlheglhnhhtekslshspgksggpGP<br>AGLYAQpgsaptsssticktqlqlehllldlqmilnginnyknpkltrmifficfympkkatelkhlqcleeelkpleev<br>lnlaqsknfhlrprdlisninvivlelkgsettfmceyadetativeflnrwilfcqsiistltggggsggggsggggsggggs<br>ggggsggggssggpGPAGLYAQpgsEVQLVESGGGLVQPGGSLRLSCAASGFTFSSYT<br>LAWVRQAPGKGLEWVAAIDSSSYTYSPDTVRGRFTISRDNAKNSLYLQMNSL<br>RAEDTAVYYCARDSNWDALDYWGcGTTVTVSSGGGGSGGGGSGGGGSDIQ<br>MTQSPSSLSASVGDRVTITCKAREKLWSAVAWYQQKPGKcPKALIYSASFRYS<br>GVPSRFSGSGSGTDFTLTISSLQPEDFATYYCQQYYTYPYTFGGGTKVEIK** |
| 329 | ACP410 (WW0552) | vprdcgckpcictypevssvfifppkpkdvltitltpkvtcwvdiskddpevqfswfvddvevhtaqtqpreeqfnsif<br>rsyselpimhqdwingkefkcrynsaafpapiektisktkgrpkapqvytipppkeqmakdkvsltcmitcapeditv<br>ewqwngqpaenykntqpimdtdgsyfyysklnvqksnweagniftcsvlheglhnhhtekslshspgksggpGP<br>AGLYAQpgsaptsssticktqlqlehllldlqmilnginnyknpkltrmifficfympkkatelkhlqcleeelkpleev<br>lnlaqsknfhlrprdlisninvivlelkgsettfmceyadetativeflnrwilfcqsiistltggggsggggsggggsggggs<br>ggggsggggssggpGPAGLYAQpgsEVQLVESGGGLVQPGGSLRLSCAASGFTFSSYT<br>LAWVRQAPGKcLEWVAAIDSSSYTYSPDTVRGRFTISRDNAKNSLYLQMNSLR<br>AEDTAVYYCARDSNWDALDYWGQGTTVTVSSGGGGSGGGGSGGGGSDIQM<br>TQSPSSLSASVGDRVTITCKVTEKVWGNVAWYQQKPGKAPISLIYSPSLRKSG<br>VPSRFSGSGSGTDFTLTISSLQPEDFATYYCQQYYTYPYTFGcGTKVEIK** |
| 330 | ACP411 (WW0553) | vprdcgckpcictypevssvfifppkpkdvltitltpkvtcwvdiskddpevqfswfvddvevhtaqtqpreeqfnsif<br>rsyselpimhqdwingkefkcrynsaafpapiektisktkgrpkapqvytipppkeqmakdkvsltcmitcapeditv<br>ewqwngqpaenykntqpimdtdgsyfyysklnvqksnweagniftcsvlheglhnhhtekslshspgksggpGP<br>AGLYAQpgsaptsssticktqlqlehllldlqmilnginnyknpkltrmifficfympkkatelkhlqcleeelkpleev<br>lnlaqsknfhlrprdlisninvivlelkgsettfmceyadetativeflnrwilfcqsiistltggggsggggsggggsggggs<br>ggggsggggssggpGPAGLYAQpgsEVQLVESGGGLVQPGGSLRLSCAASGFTFSSYT<br>LAWVRQAPGKGLEWVAAIDSSSYTYSPDTVRGRFTISRDNAKNSLYLQMNSL<br>RAEDTAVYYCARDSNWDALDYWGcGTTVTVSSGGGGSGGGGSGGGGSDIQ<br>MTQSPSSLSASVGDRVTITCKVTEKVWGNVAWYQQKPGKcPISLIYSPSLRKS<br>GVPSRFSGSGSGTDFTLTISSLQPEDFATYYCQQYYTYPYTFGGGTKVEIK** |
| 331 | ACP412 (WW0554) | vprdcgckpcictypevssvfifppkpkdvltitltpkvtcwvdiskddpevqfswfvddvevhtaqtqpreeqfnstf<br>rsyselpimhqdwhigkefkcrynsaafpapiektisktkgrpkapqvytipppkeqmakdkvsltcmitclffpeditv<br>ewqwngqpaenykntqpimdtdgsyfvysklnvqksnweagntftcsvlheglhnhhtekslshspgksggpGP<br>AGLYAQpgsaptsssticktqlqlehllldlqmilnginnyknpkltrmlafympkkatelkhlqcleeelkpleev<br>lnlaqsknfhlrprdlisninvivlelkgsettfmceyadetativeflnrwitfcqsiistltggggsggggsggggsggggs<br>ggggsggggssggpGPAGLYAQpgsevqllesggglvqpggslrlscaasgsifsanamgwyrqapgkqrelv<br>avissggstnyadsvkgrftisrdnskntvylqmnslraedtavyycmysgsyyytpndywgqgtivtvss** |
| 332 | ACP413 (WW0555) | elcdddppeiphafficamaykegtmlnceckrgfrriksgslymlctgnsshsswdnqcqctssatrnttkqvtpqpee<br>qkerkttemqspmqpvdqaslpghcrepppweneateriyhfvvgqmvyyqcvqgyralhrgpaesvckmthgk<br>trwtqpqlictgemetsqfpgeekpqaspegrpesetsSlvtttclfqiqtemaatmetsiftteyqggggsggggsgggg<br>sggggsggggsggggsDIQMTQSPSSLSASVGDRVTITCKAREKLWSAVAWYQQKPG<br>KAPKsLIYSASFRYSGVPSRFSGSGSGTDFTLTISSLQPEDFATYYCQQYYTYPY |

-continued

Sequence table

| SEQ ID NO. | Name | Sequence |
|---|---|---|
| | | TFGGGTKVEIKrtvaapsvfifppsdeqlksgtasvvcllnnfypreakvqwkvdnalqsgnsqesvteqdskd styslsstifiskadyekhkvyacevthqglsspvtksfnrgec** |
| 333 | ACP414 (WW0556) | elcdddppeiphatfkamaykegtmlnceckrgfrriksgslymlctgnsshsswdnqcqctssatrnttkqvtpqpee qkerkttemqspmqpvdqaslpghcrepppweneateriyhfvvgqmvyyqcvqgyralhrgpaesvckmthgk trwtqpqlictgemetsqfpgeekpqaspegrpesetsSlvtttclfqiqtemaatmetsiftteyqggggsggggsgggg sggggsggggsggggsDIQMTQSPSSLSASVGDRVTITCKVTEKVWGNVAWYQQKP GKAPISLIYSPSLRKSGVPSRFSGSGSGTDFTLTISSLQPEDFATYYCQQYYTYP YTFGGGTKVEIKrtvaapsvfifppsdeqlksgtasvvcllnaypreakvqwkvdnalqsgnsqesvteqds kdstyslsstltlskadyekhkvyacevthqglsspvtksfnrgec** |
| 334 | ACP415 (WW0557) | aptsssticktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsggggsggggsggg gsggggsggggsggggsEVQLVESGGGLVQPGGSLRLSCAASGFTFSSYTLAWVRQA PGKcLEWVAAIDSSSYTYSPDTVRGRFTISRDNAKNSLYLQMNSLRAEDTAVY YCARDSNWDALDYWGQGTTVTVSSGGGGSGGGGSGGGGSDIQMTQSPSSLS ASVGDRVTITCKAREKLWSAVAWYQQKPGKAPKsLIYSASFRYSGVPSRFSGS GSGTDFTLTISSLQPEDFATYYCQQYYTYPYTFGcGTKVEIKggggsggggsggggsgg ggsggggsggggsggggsggggsggggselcdddppeiphatfkamaykegtmlnceckrgfrriksgslymlctg nsshsswdnqcqctssatrnttkqvtpqpeeqkerkttemqspmqpvdqaslpghcrepppweneateriyhfvvgq mvyyqcvqgyralhrgpaesvckmthgktrwtqpqlictgemetsqfpgeekpqaspegrpesetsSlvMdfqiqte maatmetsiftteyqsggpGPAGLYAQpgsEVQLVESGGGLVQPGNSLRLSCAASGFTFS KFGMSWVRQAPGKGLEWVSSISGSGRDTLYAESVKGRFTISRDNAKTTLYLQ MNSLRPEDTAVYYCTIGGSLSVSSQGTLVTVSS** |
| 335 | ACP416 (WW0558) | aptsssticktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsggggsggggsggg gsggggsggggsggggsEVQLVESGGGLVQPGGSLRLSCAASGFTFSSYTLAWVRQA PGKGLEWVAAIDSSSYTYSPDTVRGRFTISRDNAKNSLYLQMNSLRAEDTAVY YCARDSNWDALDYWGcGTTVTVSSGGGGSGGGGSGGGGSDIQMTQSPSSLSA SVGDRVTITCKAREKLWSAVAWYQQKPGKcPKALIYSASFRYSGVPSRFSGSG SGTDFTLTISSLQPEDFATYYCQQYYTYPYTFGGGTKVEIKggggsggggsggggsggg gsggggsggggsggggsggggsggggselcdddppeiphatfkamaykegtmlnceckrgfrriksgslymlctgns shsswdnqcqctssatrnttkqvtpqpeeqkerkttemqspmqpvdqaslpghcrepppweneateriyhfvvgqm vyyqcvqgyralhrgpaesvckmthgktrwtqpqlictgemetsqfpgeekpqaspegrpesetsSlvtttdfqiqtem aatmetsiftteyqsggpGPAGLYAQpgsEVQLVESGGGLVQPGNSLRLSCAASGFTFSK FGMSWVRQAPGKGLEWVSSISGSGRDTLYAESVKGRFTISRDNAKTTLYLQM NSLRPEDTAVYYCTIGGSLSVSSQGTLVTVSS** |
| 336 | ACP417 (WW0559) | aptsssticktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsggggsggggsggg gsggggsggggsggggsEVQLVESGGGLVQPGGSLRLSCAASGFTFSSYTLAWVRQA PGKcLEWVAAIDSSSYTYSPDTVRGRFTISRDNAKNSLYLQMNSLRAEDTAVY YCARDSNWDALDYWGQGTTVTVSSGGGGSGGGGSGGGGSDIQMTQSPSSLS ASVGDRVTITCKVTEKVWGNVAWYQQKPGKAPISLIYSPSLRKSGVPSRFSGS GSGTDFTLTISSLQPEDFATYYCQQYYTYPYTFGcGTKVEIKggggsggggsggggsgg ggsggggsggggsggggsggggsggggselcdddppeiphatfkamaykegtmlnceckrgfrriksgslymlctg nsshsswdnqcqctssatrnttkqvtpqpeeqkerkttemqspmqpvdqaslpghcrepppweneateriyhfvvgq mvyyqcvqgyralhrgpaesvckmthgktrwtqpqlictgemetsqfpgeekpqaspegrpesetsSlvMdfqiqte maatmetsiftteyqsggpGPAGLYAQpgsEVQLVESGGGLVQPGNSLRLSCAASGFTFS KFGMSWVRQAPGKGLEWVSSISGSGRDTLYAESVKGRFTISRDNAKTTLYLQ MNSLRPEDTAVYYCTIGGSLSVSSQGTLVTVSS** |
| 337 | ACP418 (WW0560) | aptssstkktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsggggsggggsggg gsggggsggggsggggsEVQLVESGGGLVQPGGSLRLSCAASGFTFSSYTLAWVRQA PGKGLEWVAAIDSSSYTYSPDTVRGRFTISRDNAKNSLYLQMNSLRAEDTAVY YCARDSNWDALDYWGcGTTVTVSSGGGGSGGGGSGGGGSDIQMTQSPSSLSA SVGDRVTITCKVTEKVWGNVAWYQQKPGKcPISLIYSPSLRKSGVPSRFSGSGS GTDFTLTISSLQPEDFATYYCQQYYTYPYTFGGGTKVEIKggggsggggsggggsgggg sggggsggggsggggsggggsggggselcdddppeiphatikamaykegtmlnceckrgfrriksgslymlctgnss hsswdnqcqctssatrnttkqvtpqpeeqkerkttemqspmqpvdqaslpghcrepppweneateriyhfvvgqmv yyqcvqgyralhrgpaesvckmthgktrwtqpqlictgemetsqfpgeekpqaspegrpesetsSlvtddfqiqtema atmetsiftteyqsggpGPAGLYAQpgsEVQLVESGGGLVQPGNSLRLSCAASGFTFSKF GMSWVRQAPGKGLEWVSSISGSGRDTLYAESVKGRFTISRDNAKTTLYLQMN SLRPEDTAVYYCTIGGSLSVSSQGTLVTVSS** |
| 338 | ACP419 (WW0561) | aptssstkktqlqlehllldlqmilnginnyknpkltrmltfkfympkkatelkhlqcleeelkpleevinlaqsknfhlrpr dlisninvivlelkgsettfmceyadetativeflnrwitfcqsiistltsggpGPAGLYAQpgsggggsggggsggg gsggggsggggsggggsevqllesggglvqpggslrlscaasgsifsanamgwyrqapgkqrelvavissggstnyad svkgrftisrdnskntvylqmnslraedtavyycmysgsyyytpndywgqgtivtvssggggsggggsggggsggg gsggggsggggsggggsggggsggggselcdddppeiphatfkamaykegtmlnceckrgfrriksgslymlctgns shsswdnqcqctssatrnttkqvtpqpeeqkerkttemqspmqpvdqaslpghcrepppweneateriyhfvvgqm |

-continued

Sequence table

| SEQ ID NO. | Name | Sequence |
|---|---|---|
| | | vyyqcvqgyralhrgpaesvckmthgktrwtqpqlictgemetsqfpgeekpqaspegrpesetsSlvtddfqiqtem<br>aatmetsiftteyqsggpGPAGLYAQpgsEVQLVESGGGLVQPGNSLRLSCAASGFTFSK<br>FGMSWVRQAPGKGLEWVSSISGSGRDTLYAESVKGRFTISRDNAKTTLYLQM<br>NSLRPEDTAVYYCTIGGSLSVSSQGTLVTVSS** |
| 339 | ACP420 (WW0562) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsggggsggggsggg<br>gsggggsggggsggggsevqllesggglvqpggslrlscaasgsifsanamgwyrqapgkglelvavissggstnyad<br>svkgrftisrdnskntvylqmnslraedtavyycmysgsyyytpndywgqgtivtvssggggsggggsggggsggg<br>gsggggsggggsggggsggggsggggselcdddppeiphatfkamaykegtmlnceckrgfrriksgslymlctgns<br>shsswdnqcqctssatrnttkqvtpqpeeqkerkttemqspmqpvdqaslpghcrepppweneateriyhfvvgqm<br>vyyqcvqgyralhrgpaesvckmthgktrwtqpqlictgemetsqfpgeekpqaspegrpesetsSlvtddfqiqtem<br>aatmetsiftteyqsggpGPAGLYAQpgsEVQLVESGGGLVQPGNSLRLSCAASGFTFSK<br>FGMSWVRQAPGKGLEWVSSISGSGRDTLYAESVKGRFTISRDNAKTTLYLQM<br>NSLRPEDTAVYYCTIGGSLSVSSQGTLVTVSS** |
| 340 | ACP421 (WW0563) | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsEVQLVESGGGLVQPGGSLRLSCAASGFTFS<br>SYTLAWVRQAPGKcLEWVAAIDSSSYTYSPDTVRGRFTISRDNAKNSLYLQM<br>NSLRAEDTAVYYCARDSNWDALDYWGQGTTVTVSSGGGGSGGGGSGGGGS<br>DIQMTQSPSSLSASVGDRVTITCKAREKLWSAVAWYQQKPGKAPKsLIYSASF<br>RYSGVPSRFSGSGSGTDFTLTISSLQPEDFATYYCQQYYTYPYTFGcGTKVEIKg<br>gggsggggsggggsggggsggggsggggsggggsggggsggggselcdddppeiphatfkamaykegtmlncec<br>krgfrriksgslymlctgnsshsswdnqcqctssatrnttkqvtpqpeeqkerkttemqspmqpvdqaslpghcrepp<br>pweneateriyhfvvgqmvyyqcvqgyralhrgpaesvckmthgktrwtqpqlictgemetsqfpgeekpqaspeg<br>rpesetsSlvtddfqiqtemaatmetsiftteyqggggsggggsggggsggggsggggsggggssggpGPAGLY<br>AQpgsaptsssstkktqlqlehllldlqmilnginnyknpkltrmlafympkkatelkhlqcleeelkpleevinlaqsk<br>nfhlrprdlisninvivlelkgsettfmceyadetativeflnrwitieqsiistlt** |
| 341 | ACP422 (WW0564) | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsEVQLVESGGGLVQPGGSLRLSCAASGFTFS<br>SYTLAWVRQAPGKGLEWVAAIDSSSYTYSPDTVRGRFTISRDNAKNSLYLQM<br>NSLRAEDTAVYYCARDSNWDALDYWGcGTTVTVSSGGGGSGGGGSGGGGSD<br>IQMTQSPSSLSASVGDRVTITCKAREKLWSAVAWYQQKPGKcPKALIYSASFR<br>YSGVPSRFSGSGSGTDFTLTISSLQPEDFATYYCQQYYTYPYTFGGGTKVEIKgg<br>ggsggggsggggsggggsggggsggggsggggsggggsggggselcdddppeiphatfkamaykegtmlnceck<br>rgfrriksgslymlctgnsshsswdnqcqctssatrnttkqvtpqpeeqkerkttemqspmqpvdqaslpghcreppp<br>weneateriyhfvvgqmvyyqcvqgyralhrgpaesvckmthgktrwtqpqlictgemetsqfpgeekpqaspegr<br>pesetsSlytttclfqiqtemaatmetsiftteyqggggsggggsggggsggggsggggsggggssggpGPAGLYA<br>Qpgsaptsssstkktqlqlehllldlqmilnginnyknpkltrmlfficfympkkatelkhlqcleeelkpleevinlaqsknf<br>hlrprdlisninvivlelkgsetlfmceyadetativeflnrwitfcqsiistlt** |
| 342 | ACP423 (WW0565) | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsEVQLVESGGGLVQPGGSLRLSCAASGFTFS<br>SYTLAWVRQAPGKcLEWVAAIDSSSYTYSPDTVRGRFTISRDNAKNSLYLQM<br>NSLRAEDTAVYYCARDSNWDALDYWGQGTTVTVSSGGGGSGGGGSGGGGS<br>DIQMTQSPSSLSASVGDRVTITCKVTEKVWGNVAWYQQKPGKAPISLIYSPSL<br>RKSGVPSRFSGSGSGTDFTLTISSLQPEDFATYYCQQYYTYPYTFGcGTKVEIKg<br>gggsggggsggggsggggsggggsggggsggggsggggsggggselcdddppeiphatfkamaykegtmlncec<br>krgfrriksgslymktgnsshsswdnqcqctssatrnttkqvtpqpeeqkerkttemqspmqpvdqaslpghcrepp<br>pweneateriyhfvvgqmvyyqcvqgyralhrgpaesvckmthgktrwtqpqlictgemetsqfpgeekpqaspeg<br>rpesetsSlvMdfqiqtemaatmetsiftteyqggggsggggsggggsggggsggggsggggssggpGPAGLY<br>AQpgsaptsssstkktqlqlehllldlqmilnginnyknpkltrmltfkfympkkatelkhlqcleeelkpleevinlaqsk<br>nfhlrprdlisninvivlelkgsetlfmceyadetativeflnrwitfcqsiistlt** |
| 343 | ACP424 (WW0566) | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsEVQLVESGGGLVQPGGSLRLSCAASGFTFS<br>SYTLAWVRQAPGKGLEWVAAIDSSSYTYSPDTVRGRFTISRDNAKNSLYLQM<br>NSLRAEDTAVYYCARDSNWDALDYWGcGTTVTVSSGGGGSGGGGSGGGGSD<br>IQMTQSPSSLSASVGDRVTITCKVTEKVWGNVAWYQQKPGKcPISLIYSPSLRK<br>SGVPSRFSGSGSGTDFTLTISSLQPEDFATYYCQQYYTYPYTFGGGTKVEIKggg<br>gsggggsggggsggggsggggsggggsggggsggggsggggselcdddppeiphatikamaykegtmlnceckr<br>gfrriksgslymktgnsshsswdnqcqctssatrnttkqvtpqpeeqkerkttemqspmqpvdqaslpghcrepppw<br>eneateriyhfvvgqmvyyqcvqgyralhrgpaesvckmthgktrwtqpqlictgemetsqfpgeekpqaspegrpe<br>setsSlytttclfqiqtemaatmetsiftteyqggggsggggsggggsggggsggggsggggssggpGPAGLYAQ<br>pgsaptsssstkktqlqlehllldlqmilnginnyknpkltrmltfklympldcatelkhlqcleeelkpleevinlaqsknfh<br>lrprdlisninvivlelkgsetlfmceyadetativeflnrwitfcqsiistlt** |

-continued

Sequence table

| SEQ ID NO. | Name | Sequence |
|---|---|---|
| 344 | ACP425 (WW0567) | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsevqllesggglvqpggslrlscaasgsifsanamgwyrqapgkq<br>relvavissggstnyadsvkgrftisrdnskntvylqmnslraedtavyycmysgsyyytpndywgqgtivtvssggg<br>gsggggsggggsggggsggggsggggsggggsggggsggggselcdddppeiphatikamaykegtmlnceckr<br>gfrriksgslymlctgnsshsswdnqcqctssatrnttkqvtpqpeeqkerkttemqspmqpvdqaslpghcrepppw<br>eneateriyhfvvgqmvyyqcvqgyralhrgpaesvckmthgktrwtqpqlictgemetsqfpgeekpqaspegrpe<br>setsSlytttclfqiqtemaatmetsiftteyqggggsggggsggggsggggsggggsggggssggpGPAGLYAQ<br>pgsaptssstkktqlqlehllldlqmilnginnyknpkltrmltfklympldcatelkhlqcleeelkpleevinlaqsknfh<br>lrprdlisninvivlelkgsettfmceyadetativeflnrwitfcqsiistlt** |
| 345 | ACP426 (WW0568) | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsevqllesggglvqpggslrlscaasgsifsanamgwyrqapgkg<br>lelvavissggstnyadsvkgrftisrdnskntvylqmnslraedtavyycmysgsyyytpndywgqgtivtvssgggg<br>sggggsggggsggggsggggsggggsggggsggggsggggselcdddppeiphatfkamaykegtmlnceckrgf<br>rriksgslymlctgnsshsswdnqcqctssatrnttkqvtpqpeeqkerkttemqspmqpvdqaslpghcrepppwe<br>neateriyhfvvgqmvyyqcvqgyralhrgpaesvckmthgktrwtqpqlictgemetsqfpgeekpqaspegrpes<br>etsSlytttclfqiqtemaatmetsiftteyqggggsggggsggggsggggsggggsggggssggpGPAGLYAQp<br>gsaptssstkktqlqlehllldlqmilnginnyknpkltrmltfkfympkkatelkhlqcleeelkpleevinlaqsknfhlr<br>prdlisninvivlelkgsetlfmceyadetativeflnrwitfcqsiistlt** |
| 346 | ACP427 (WW0569) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKcLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKAREKLWSAVAWYQQKPG<br>KAPKsLIYSASFRYSGVPSRFSGSGSGTDFTLTISSLQPEDFATYYCQQYYTYPY<br>TFGcGTKVEIKggggsggggsggggsggggsggggsggggsevqllesggglvqpggslrlscaasgsifsana<br>mgwyrqapgkqrelvavissggstnyadsvkgrftisrdnskntvylqmnslraedtavyycmysgsyyytpndyw<br>gqgtivtvss** |
| 347 | ACP428 (WW0570) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGcGTTVTVSSGGGG<br>SGGGGSGGGGSDIQMTQSPSSLSASVGDRVTITCKAREKLWSAVAWYQQKPG<br>KcPKALIYSASFRYSGVPSRFSGSGSGTDFTLTISSLQPEDFATYYCQQYYTYPY<br>TFGGGTKVEIKggggsggggsggggsggggsggggsggggsevqllesggglvqpggslrlscaasgsifsan<br>amgwyrqapgkqrelvavissggstnyadsvkgrftisrdnskntvylqmnslraedtavyycmysgsyyytpndy<br>wgqgtivtvss** |
| 348 | ACP429 (WW0571) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKcLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKVTEKVWGNVAWYQQKP<br>GKAPISLIYSPSLRKSGVPSRFSGSGSGTDFTLTISSLQPEDFATYYCQQYYTYP<br>YTFGcGTKVEIKggggsggggsggggsggggsggggsggggsevqllesggglvqpggslrlscaasgsifsa<br>namgwyrqapgkqrelvavissggstnyadsvkgrftisrdnskntvylqmnslraedtavyycmysgsyyytpndy<br>wgqgtivtvss** |
| 349 | ACP430 (WW0572) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGcGTTVTVSSGGGG<br>SGGGGSGGGGSDIQMTQSPSSLSASVGDRVTITCKVTEKVWGNVAWYQQKP<br>GKcPISLIYSPSLRKSGVPSRFSGSGSGTDFTLTISSLQPEDFATYYCQQYYTYPY<br>TFGGGTKVEIKggggsggggsggggsggggsggggsggggsevqllesggglvqpggslrlscaasgsifsan |

-continued

Sequence table

| SEQ ID NO. | Name | Sequence |
|---|---|---|
| | | amgwyrqapgkqrelvavissggstnyadsvkgrftisrdnskntvylqmnslraedtavyycmysgsyyytpndy<br>wgqgtivtvss** |
| 350 | ACP431<br>(WW0573) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKcLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKAREKLWSAVAWYQQKPG<br>KAPKsLIYSASFRYSGVPSRFSGSGSGTDFTLTISSLQPEDFATYYCQQYYTYPY<br>TFGcGTKVEIKggggsggggsggggsggggsggggsggggsevqllesggglvqpggslrlscaasgsifsana<br>mgwyrqapgkglelvavissggstnyadsvkgrftisrdnskntvylqmnslraedtavyycmysgsyyytpndyw<br>gqgtivtvss** |
| 351 | ACP432<br>(WW0574) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGcGTTVTVSSGGGG<br>SGGGGSGGGGSDIQMTQSPSSLSASVGDRVTITCKAREKLWSAVAWYQQKPG<br>KcPKALIYSASFRYSGVPSRFSGSGSGTDFTLTISSLQPEDFATYYCQQYYTYPY<br>TFGGGTKVEIKggggsggggsggggsggggsggggsggggsevqllesggglvqpggslrlscaasgsifsan<br>amgwyrqapgkglelvavissggstnyadsvkgrftisrdnskntvylqmnslraedtavyycmysgsyyytpndy<br>wgqgtivtvss** |
| 352 | ACP433<br>(WW0575) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKcLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKVTEKVWGNVAWYQQKP<br>GKAPISLIYSPSLRKSGVPSRFSGSGSGTDFTLTISSLQPEDFATYYCQQYYTYP<br>YTFGcGTKVEIKggggsggggsggggsggggsggggsggggsevqllesggglvqpggslrlscaasgsifsa<br>namgwyrqapgkglelvavissggstnyadsvkgrftisrdnskntvylqmnslraedtavyycmysgsyyytpndy<br>wgqgtivtvss** |
| 353 | ACP434 | aptssstkktqlqlehllldlqmilnginnyknpkltrmltfkfympkkatelkhlqcleeelkpleevinlaqsknfhlrpr<br>(WW0576)dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGcGTTVTVSSGGGG<br>SGGGGSGGGGSDIQMTQSPSSLSASVGDRVTITCKVTEKVWGNVAWYQQKP<br>GKcPISLIYSPSLRKSGVPSRFSGSGSGTDFTLTISSLQPEDFATYYCQQYYTYPY<br>TFGGGTKVEIKggggsggggsggggsggggsggggsggggsevqllesggglvqpggslrlscaasgsifsan<br>amgwyrqapgkglelvavissggstnyadsvkgrftisrdnskntvylqmnslraedtavyycmysgsyyytpndy<br>wgqgtivtvss** |
| 265 | ACP435<br>(WW0577) | DIQMTQSPSSLSASVGDRVTITCKAREKLWSAVAWYQQKPGKAPKsLIYSASF<br>RYSGVPSRFSGSGSGTDFTLTISSLQPEDFATYYCQQYYTYPYTFGGGTKVEIKr<br>tvaapsvfifppsdeqlksgtasvvellnaypreakvqwkvdnalqsgnsqesvteqdskdstyslsstltlskadyekh<br>kvyacevthqglsspvtksfmgecggggsggggsggggsggggsggggsggggsevqllesggglvqpggslrlsca<br>asgsifsanamgwyrqapgkqrelvavissggstnyadsvkgrftisrdnskntvylqmnslraedtavyycmysgsy<br>yytpndywgqgtivtvss** |
| 355 | ACP371<br>(WW0513) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKcLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKASQNVGTNVGWYQQKPG<br>KAPKALIYSASFRYSGVPSRFSGSGSGTDFTLTISSLQPEDFATYYCQQYYTYP<br>YTFGcGTKVEIK** |

-continued

Sequence table

| SEQ ID NO. | Name | Sequence |
|---|---|---|
| 356 | ACP372 (WW0514) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGcGTTVTVSSGGGG<br>SGGGGSGGGGSDIQMTQSPSSLSASVGDRVTITCKASQNVGTNVGWYQQKPG<br>KcPKALIYSASFRYSGVPSRFSGSGSGTDFTLTISSLQPEDFATYYCQQYYTYPY<br>TFGGGTKVEIK** |
| 357 | ACP373 (WW0515) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKcLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKAREKLWSAVAWYQQKPG<br>KAPKALIYSASFRYSGVPSRFSGSGSGTDFTLTISSLQPEDFATYYCQQYYTYP<br>YTFGcGTKVEIK** |
| 358 | ACP374 (WW0516) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGcGTTVTVSSGGGG<br>SGGGGSGGGGSDIQMTQSPSSLSASVGDRVTITCKAREKLWSAVAWYQQKPG<br>KcPKALIYSASFRYSGVPSRFSGSGSGTDFTLTISSLQPEDFATYYCQQYYTYPY<br>TFGGGTKVEIK** |
| 359 | ACP375 (WW0517) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKcLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKVTEKVWGNVAWYQQKP<br>GKAPISLIYSPSLRKSGVPSRFSGSGSGTDFTLTISSLQPEDFATYYCQQYYTYP<br>YTFGcGTKVEIK** |
| 360 | ACP376 (WW0521) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGcGTTVTVSSGGGG<br>SGGGGSGGGGSDIQMTQSPSSLSASVGDRVTITCKVTEKVWGNVAWYQQKP<br>GKcPISLIYSPSLRKSGVPSRFSGSGSGTDFTLTISSLQPEDFATYYCQQYYTYPY<br>TFGGGTKVEIK** |
| 361 | ACP377 (WW0519) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsevqllesggglvqpggslrlscaasgsi<br>fsanamgwyrqapgkqrelvavissggstnyadsvkgrftisrdnskntvylqmnslraedtavyycmysgsyyytp<br>ndywgqgtivtvss** |
| 362 | ACP378 (WW0520) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGQGTTVTVSSastkgps<br>vfplapsskstsggtaalgclvkdyfpepvtvswnsgaltsgvhtfpavlqssglyslssvvtvpssslgtqtyicnvnhkp<br>sntkvdkrvepksc** |

-continued

Sequence table

| SEQ ID NO. | Name | Sequence |
|---|---|---|
| 363 | ACP379<br>(WW0521) | eskygppcppcpapeflggpsvflfppkpkdtlmisrtpevtcvvvdvsqedpevqfnwyvdgvevhnaktkpree<br>qfnstyrvvsyltvlhqdwingkeykckvsnkglpssiektiskakgqprepqvytlppsqeemtlmqvsltclvkgfy<br>psdiavewesngqpennykttppvldsdgsfflysrltvdksrwqegnvfscsvmhealhnhytqkslslslgksggp<br>GPAGLYAQpgsaptssstkktqlqlehllldlqmilnginnyknpkltrmlfficfympldcatelkhlqcleeelkpl<br>eevinlaqsknfhlrprdlisninvivlelkgsetlfmceyadetativeflnrwitfcqsiistltggggsggggsggggsgg<br>ggsggggsggggssggpGPAGLYAQpgsEVQLVESGGGLVQPGGSLRLSCAASGFTFS<br>SYTLAWVRQAPGKGLEWVAAIDSSSYTYSPDTVRGRFTISRDNAKNSLYLQM<br>NSLRAEDTAVYYCARDSNWDALDYWGQGTTVTVSSastkgpsvfplapsskstsggtaal<br>gclvkdyfpepvtvswnsgaltsgvhtfpavlqssglyslssvvtvpssslgtqtyicnvnhkpsntkvdkrvepksc** |
| 364 | ACP368 | EVQLVESGGGLVQPGGSLRLSCAASGFTFSSYTLAWVRQAPGKGLEWVAAID<br>(WW0446)SSSYTYSPDTVRGRFTISRDNAKNSLYLQMNSLRAEDTAVYYCARDSNWDAL<br>DYWGQGTTVTVSSsggpGPAGLYAQpgsDIQMTQSPSSLSASVGDRVTITCKVTE<br>KVWGNVAWYQQKPGKAPISLIYSPSLRKSGVPSRFSGSGSGTDFTLTISSLQPE<br>DFATYYCQQYYTYPYTFGGGTKVEIKHHHHHH |
| 365 | ACP365<br>(WW0443) | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSsggpGPAGLYAQpgsDIQMTQSPSSLSASVGDRVTITCKARE<br>KLWSAVAWYQQKPGKAPKALIYSASFRYSGVPSRFSGSGSGTDFTLTISSLQPE<br>DFATYYCQQYYTYPYTFGGGTKVEIKHHHHHH |
| 366 | ACP366<br>(WW0444) | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSsggpGPAGLYAQpgsDIQMTQSPSSLSASVGDRVTITCKARE<br>KLWSAVAWYQQKPGKAPKsLIYSASFRYSGVPSRFSGSGSGTDFTLTISSLQPE<br>DFATYYCQQYYTYPYTFGGGTKVEIKHHHHHH |
| 367 | ACP284 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGSwipvsgparclsquallkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslahngetlrqkppvgeadpyrvkmklcillhafstrvvtinrvmgylssaSGGPGPAG<br>MKGLPGSggggsggggsggggsggggsggggsggggsQSVLTQPPSVSGAPGQRVTISCSGS<br>RSNIGSNTVKWYQQLPGTAPKLLIYYNDQRPSGVPDRFSGSKSGTSASLAITGL<br>QAEDEADYYCQSYDRYTHPALLFGTGTKVTVLggggsggggsggggsQVQLVESGG<br>GVVQPGRSLRLSCAASGFTFSSYGMHWVRQAPGKGLEWVAFIRYDGSNKYY<br>ADSVKGRFTISRDNSKNTLYLQMNSLRAEDTAVYYCKTHGSHDNWGQGTMV<br>TVSS |
| 368 | ACP285 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGSiwelkkdvyvveldwypdapgemvvltcdtpeedgitwtl<br>dqssevlgsgktltiqvkefgdagqytchkggevlshsllllhkkedgiwstdilkdqkepknktflrcealmysgrftcw<br>wittistdilfsvkssrgssdpqgvtcgaatlsaervrgdnkeyeysvecqedsaSpaaeeslpievmvdavhklkyeny<br>tssffirdiikpdppknlqlkplknsrqvevsweypdtwstphsyfsltkvqvqgkskrekkdrvftdktsatvicrkna<br>sisvramthyyssswsewasvpcsggggsggggsggggsrvipvsgparclsquallkttddmvktareklkhyscta<br>edidheditrdqtstlktclplelhknesSlatretssttrgsclppqktslmmticlgsiyedllanyqtefgainaalqnhnh<br>qqiildkgmlvaidelmqslahngetlrqkppvgeadpyrvkmklcillhafstrvvtinrvmgylssaSGGPGPA<br>GMKGLPGSggggsggggsggggsggggsggggsggggsQSVLTQPPSVSGAPGQRVTISCS<br>GSRSNIGSNTVKWYQQLPGTAPKLLIYYNDQRPSGVPDRFSGSKSGTSASLAIT<br>GLQAEDEADYYCQSYDRYTHPALLFGTGTKVTVLggggsggggsggggsQVQLVES<br>GGGVVQPGRSLRLSCAASGFTFSSYGMHWVRQAPGKGLEWVAFIRYDGSNK<br>YYADSVKGRFTISRDNSKNTLYLQMNSLRAEDTAVYYCKTHGSHDNWGQGT<br>MVTVSS |
| 369 | ACP286 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGSiwelkkdvyvveldwypdapgemvvltcdtpeedgitwtl<br>dqssevlgsgktltiqvkefgdagqytchkggevlshsllllhkkedgiwstdilkdqkepknktflrcealmysgrftcw<br>wittistdlifsvkssrgssdpqgvtcgaatlsaervrgdnkeyeysvecqedsacpaaeeslpievmvdavhklkyeny<br>tssffirdiikpdppknlqlkplknsrqvevsweypdtwstphsyfsltfcvqvqgkskrekkdrvftdktsatvicrkna<br>sisvracichyyssswsewasvpcsggggsggggsggggsggggsrvipvsgparclsqsrffilkttddmvktareklk<br>hysctaedidheditrdqtstlktclplelhknesclatretssttrgsclppqktslmmticlgsiyedlkmyqtefclainaal<br>qnhnhqqiildkgmlvaidelmqslnhngetlrqkppvgeadpyrvkmklcillhafstrvvtinrvmgylssaSGG<br>PGPAGMKGLPGSggggsggggsggggsggggsggggsggggsQSVLTQPPSVSGAPGQRVT<br>ISCSGSRSNIGSNTVKWYQQLPGTAPKLLIYYNDQRPSGVPDRFSGSKSGTSAS<br>LAITGLQAEDEADYYCQSYDRYTHPALLFGTGTKVTVLggggsggggsggggsQVQ<br>LVESGGGVVQPGRSLRLSCAASGFTFSSYGMHWVRQAPGKGLEWVAFIRYDG<br>SNKYYADSVKGRFTISRDNSKNTLYLQMNSLRAEDTAVYYCKTHGSHDNWG<br>QGTMVTVSS |

-continued

Sequence table

| SEQ ID NO. | Name | Sequence |
|---|---|---|
| 370 | ACP287 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGSiwelkkdvyvveldwypdapgemvvltcdtpeedgitwtl<br>dqssevlgsgkiltiqvkefgdagqytchkggevlshsllllhkkedgiwstdilkdqkepknktflrcealmysgrftcw<br>wittistditfsvkssrgssdpqgvtcgaatlsaervrgdnkeyeysvecqedsacpaaeeslpievmvdavhklkyeny<br>tssffirdiikpdppknlqlkplknsrqvevsweypdtwstphsyfslffevqvqgkskrekkdrvftdktsatvicrkna<br>sisvracichyysssswsewasvpcsggggsggggsggggsrvipvsgparclsqsmllkttddmvktareklkhyscta<br>edidheditrdqtstlktclplelhknesclatretssttrgsclppqktslmmticlgsiyedlkmyqtefqainaalqnhnh<br>qqiildkgmlvaidelmqslnhngetlrqkppvgeadpyrvkmklcillhafstrvvtinrvmgylssaSGGPGPA<br>GMKGLPGSggggsggggsggggsggggsggggsggggsQSVLTQPPSVSGAPGQRVTISCS<br>GSRSNIGSNTVKWYQQLPGTAPKLLIYYNDQRPSGVPDRFSGSKSGTSASLAIT<br>GLQAEDEADYYCQSYDRYTHPALLFGcGTKVTVLggggsggggsggggsQVQLVES<br>GGGVVQPGRSLRLSCAASGFTFSSYGMHWVRQAPGKcLEWVAFIRYDGSNKY<br>YADSVKGRFTISRDNSKNTLYLQMNSLRAEDTAVYYCKTHGSHDNWGQGTM<br>VTVSS |
| 371 | ACP288 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGSiwelkkdvyvveldwypdapgemvvltcdtpeedgitwtl<br>dqssevlgsgkiltiqvkefgdagqytchkggevlshsllllhkkedgiwstdilkdqkepknktflrcealmysgrftcw<br>wittistdlifsvkssrgssdpqgvtcgaatlsaervrgdnkeyeysvecqedsacpaaeeslpievmvdavhklkyeny<br>tssffirdiikpdppknlqlkplknsrqvevsweypdtwstphsyfsltfcvqvqgkskrekkdrvftdktsatvicrkna<br>sisvracichyysssswsewasvpcsggggsggggsggggsrvipvsgparclsqsmllkttddmvktareklkhyscta<br>edidheditrdqtstlktclplelhknesclatretssttrgsclppqktslmmticlgsiyedlkmyqtefqainaalqnhnh<br>qqiildkgmlvaidelmqslnhngetlrqkppvgeadpyrvkmkillhafstrvvtinrvmgylssaSGGPGPA<br>GMKGLPGSggggsggggsggggsggggsggggsggggsQSVLTQPPSVSGAPGQRVTISCS<br>GSRSNIGSNTVKWYQQLPGTcPKLLIYYNDQRPSGVPDRFSGSKSGTSASLAIT<br>GLQAEDEADYYCQSYDRYTHPALLFGTGTKVTVLggggsggggsggggsQVQLVES<br>GGGVVQPGRSLRLSCAASGFTFSSYGMHWVRQAPGKGLEWVAFIRYDGSNK<br>YYADSVKGRFTISRDNSKNTLYLQMNSLRAEDTAVYYCKTHGSHDNWGcGT<br>MVTVSS |
| 372 | ACP289 (WW0233) | aptssstkktqlqlehllldlqmilnginnyknpkltrmltfkfympkkatelkhlqcleeelkpleevinlaqsknfhlrpr<br>dlisninvivlelkgsettfmceyadetativeflnrwirdeqsiistltsggpgpagmkglpgsevqlvesggglvqpgns<br>lrlscaasgftiskfgmswvrqapgkglewvssisgsgrdtlyaesvkgrftisrdnakttlylqmnslrpedtavyyctig<br>gslsyssqgtivtvssggggsggggsggggsggggsggggsggggssggpgpagmkglpgsevqlvesggglvqpg<br>gslrlscaasgftfssytlawvrqapgkglewvaaidsssytyspdtvrgrftisrdnaknslylqmnslraedtavyycar<br>dsnwdaldywgqgttvtvssggggsggggsggggsggggsdiqmtqspsslsasvgdrvtitckasqnvgtnvgwyqqkpg<br>kapkaliysasfrysgvpsrfsgsgsgtdftltisslqpedfatyycqqyytypyttggtkveikhhhhhh |
| 373 | ACP290 (WW0234) | aptssstkktqlqlehllldlqmilnginnyknpkltrmltfkfympkkatelkhlqcleeelkpleevinlaqsknfhlrpr<br>dlisninvivlelkgsettfmceyadetativeflnrwirdeqsiistltsggpgpagmkglpgsevqlvesggglvqpgns<br>lrlscaasgftiskfgmswvrqapgkglewvssisgsgrdtlyaesvkgrftisrdnakttlylqmnslrpedtavyyctig<br>gslsyssqgtivtvssggggsggggsggggsggggsggggsggggssggpgpagmkglpgQVQLQESGGG<br>LVQTGGSLRLSCTTSGTIFSGYTMGWYRQAPGEQRELVAVISGGGDTNYADS<br>VKGRFTISRDNTKDTMYLQMNSLKPEDTAVYYCYSREVTPPWKLYWGQGTQ<br>VTVSSAAAYPYDVPDYGSHHHHHH |
| 374 | ACP291 (WW0235) | aptssstkktqlqlehllldlqmilnginnyknpkltrmltfkfympkkatelkhlqcleeelkpleevinlaqskahlrpr<br>dlisninvivlelkgsettfmceyadetativeflnrwitieqsiistltsggpgpagmkglpgsevqlvesggglvqpgns<br>lrlscaasgitiskfgmswvrqapgkglewvssisgsgrdtlyaesvkgrftisrdnakttlylqmnslrpedtavyyctig<br>gslsyssqgtivtvssggggsggggsggggsggggsggggsggggssggpgpagmkglpgQVQLQESGGG<br>LVQEGGSLRLSCAASERIFSTDVMGWYRQAAEKQRELVAVVSARGTTNYLDA<br>VKGRFTISRDNARNTLTLQMNDLKPEDTASYYCYVRETTSPWRIYWGQGTQV<br>TVSSAAAYPYDVPDYGSHHHHHH |
| 375 | ACP292 (WW0236) | aptssstkktqlqlehllldlqmilnginnyknpkltrmltildympldcatelkhlqcleeelkpleevinlaqsknfhlrpr<br>dlisninvivlelkgsettfmceyadetativeflnrwiticqsiistltsggpgpagmkglpgsevqlvesggglvqpgns<br>lrlscaasgfifskfgmswvrqapgkglewvssisgsgrdtlyaesvkgrftisrdnakttlylqmnslrpedtavyyctig<br>gslsyssqgtivtvssggggsggggsggggsggggsggggsggggssggpgpagmkglpgQVQLQESGGG<br>LVQAGGSLRLSCAASGSIFSANAMGWYRQAPGKQRELVAVISSGGSTNYADS<br>VKGRFTISRDNAKNTVYLQMNSLKPEDTAVYYCMYSGSYYYTPNDYWGQGT<br>QVTVSSAAAYPYDVPDYGSHHHHHH |
| 376 | ACP296 (WW0250) | aptssstkktqlqlehllldlqmilnginnyknpkltrmltfkfympkkatelkhlqcleeelkpleevinlaqsknfhlrpr<br>dlisninvivlelkgsettfmceyadetativeflnrwiticqsiistltSGGPGPAGMKGLPGSEVQLVES<br>GGGLVQPGNSLRLSCAASGFTFSKFGMSWVRQAPGKGLEWVSSISGSGRDTL<br>YAESVKGRFTISRDNAKTTLYLQMNSLRPEDTAVYYCTIGGSLSVSSQGTLVT<br>VSSggggsggggsggggsggggsggggsggggsSGGPGPAGMKGLPGSEVQLVESGGGLV<br>QPGGSLRLSCAASGFTFSSYTLAWVRQAPGKGLEWVAAIDSSSYTYSPDTVRG<br>RFTISRDNAKNSLYLQMNSLRAEDTAVYYCARDSNWDALDYWGQGTTVTVS<br>SSGGPGPAGMKGLPGSDIQMTQSPSSLSASVGDRVTITCKASQNVGTNVGWY |

-continued

Sequence table

| SEQ ID NO. | Name | Sequence |
|---|---|---|
| | | QQKPGKAPKALIYSASFRYSGVPSRFSGSGSGTDFTLTISSLQPEDFATYYCQQ<br>YYTYPYTFGGGTKVEIKHHHHHHEPEA** |
| 377 | ACP297 (WW0251) | aptssstkktqlqlehllldlqmilnginnyknpkltrmltfkfympkkatelkhlqcleeelkpleevinlaqsknfhlrpr<br>dlisninvivlelkgsettfmceyadetativeflnrwiticqsiistltSGGPGPAGMKGLPGSEVQLVES<br>GGGLVQPGNSLRLSCAASGFTFSKFGMSWVRQAPGKGLEWVSSISGSGRDTL<br>YAESVKGRFTISRDNAKTTLYLQMNSLRPEDTAVYYCTIGGSLSVSSQGTLVT<br>VSSggggsggggsggggsggggsggggsggggsSGGPGPAGMKGLPGSEVQLVESGGGLV<br>QPGGSLRLSCAASGFTFSSYTLAWVRQAPGKGLEWVAAIDSSSYTYSPDTVRG<br>RFTISRDNAKNSLYLQMNSLRAEDTAVYYCARDSNWDALDYWGQGTTVTVS<br>SGGGGSGGGGSGGGGSDIQMTQSPSSLSASVGDRVTITCKASQNVGTNVGWY<br>QQKPGKAPKLLIYSASFRYSGVPSRFSGSGSGTDFTLTISSLQPEDFATYYCQQ<br>YYTYPYTFGGGTKVEIKHHHHHHEPEA** |
| 378 | ACP298 (WW0252) | aptssstkktqlqlehllldlqmilnginnyknpkltrmltfkfympkkatelkhlqcleeelkpleevinlaqsknfhlrpr<br>dlisninvivlelkgsettfmceyadetativeflnrwiticqsiistltSGGPGPAGMKGLPGSEVQLVES<br>GGGLVQPGNSLRLSCAASGFTFSKFGMSWVRQAPGKGLEWVSSISGSGRDTL<br>YAESVKGRFTISRDNAKTTLYLQMNSLRPEDTAVYYCTIGGSLSVSSQGTLVT<br>VSSggggsggggsggggsggggsggggsggggsSGGPGPAGMKGLPGSEVQLVESGGGLV<br>QPGGSLRLSCAASGFTFSSYTLAWVRQAPGKGLEWVAAIDSSSYTYSPDTVRG<br>RFTISRDNAKNSLYLQMNSLRAEDTAVYYCARDSNWDALDYWGQGTTVTVS<br>SGGGGSGGGGSGGGGSDIQMTQSPSSLSASVGDRVTITCKASQNVGTNVGWY<br>QQKPGKAPKGLIYSASFRYSGVPSRFSGSGSGTDFTLTISSLQPEDFATYYCQQ<br>YYTYPYTFGGGTKVEIKHHHHHHEPEA** |
| 379 | ACP299 (WW0253) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitiSqsiistltSGGPGPAGMKGLPGSEVQLVES<br>GGGLVQPGNSLRLSCAASGFTFSKFGMSWVRQAPGKGLEWVSSISGSGRDTL<br>YAESVKGRFTISRDNAKTTLYLQMNSLRPEDTAVYYCTIGGSLSVSSQGTLVT<br>VSSggggsggggsggggsggggsggggsggggsSGGPGPAGMKGLPGSEVQLVESGGGLV<br>QPGGSLRLSCAASGFTFSSYTLAWVRQAPGKGLEWVAAIDSSSYTYSPDTVRG<br>RFTISRDNAKNSLYLQMNSLRAEDTAVYYCARDSNWDALDYWGQGTTVTVS<br>SGGGGSGGGGSGGGGSDIQMTQSPSSLSASVGDRVTITCKASQNVGTNVGWY<br>QQKPGKAPKALIYSASFRYSGVPSRFSGSGSGTDFTLTISSLQPEDFATYYCQQ<br>YYTYPYTFGGGTKVEIKHHHHHHEPEA** |
| 380 | ACP300 (WW0255) | aptssstkktqlqlehllldlqmilnginnyknpkltrmltfkfympkkatelkhlqcleeelkpleevinlaqsknfhlrpr<br>dlisninvivlelkgsettfmceyadetativeflnrwiticqsiistltSGGPGPAGMKGLPGSdahksevahrf<br>kdlgeenfkalvliafaqylqqcpfedhvklvnevtefaktcvadesaencdkslhtlfgdklctvatlretygemadcca<br>kqepernecflqhkddnpnlprlvrpevdvmctafhdneeffildcylyeiarrhpyfyapellffakrykaafteccqaa<br>dkaacllpkldelrdegkassakqrlkcaslqkfgerafkawavarlsqrfpkaefaevsklvtdltkvhtecchgdlleca<br>ddradlakyicenqdsissklkeccekpllekshciaevendempadlpslaacIfveskdvcknyaeakdvflgmfly<br>eyarrhpdysvvlllrlaktyettlekccaaadphecyalcvfdefkplveepqnlikqncelfeqlgeykfqnallviyildc<br>vpqvstptivevsralglcvgskcckhpeakrmpcaedylsvvinqlcvlhektpvsdrytkcceslvarrpcfsalevd<br>etyvpkefnaaftfhadictlsekerqikkqtalvelvlchkpkatkeqlkavmddfaafvekcckaddketcfaeegldc<br>lvaasqaalglggggsggggsggggsggggsggggsggggsSGGPGPAGMKGLPGSEVQLVESGG<br>GLVQPGGSLRLSCAASGFTFSSYTLAWVRQAPGKGLEWVAAIDSSSYTYSPDT<br>VRGRFTISRDNAKNSLYLQMNSLRAEDTAVYYCARDSNWDALDYWGQGTTV<br>TVSSGGGGSGGGGSGGGGSDIQMTQSPSSLSASVGDRVTITCKASQNVGTNVG<br>WYQQKPGKAPKALIYSASFRYSGVPSRFSGSGSGTDFTLTISSLQPEDFATYYC<br>QQYYTYPYTFGGGTKVEIKHHHHHHEPEA** |
| 381 | ACP302 (WW0296) | aptsssildctqlqlehllldlqmilnginnyknpkltrmltfkfympkkatelkhlqcleeelkpleevinlaqsknfhlrpr<br>dlisninvivlelkgsettfmceyadetativeflnrwiticqsiistltSGGPGPAGMKGLPGSEAHKSEIA<br>HRYNDLGEQHFKGLVLIAFSQYLQKCSYDEHAKLVQEVTDFAKTCVADESAA<br>NCDKSLHTLFGDKLCAIPNLRENYGELADCCTKQEPERNECFLQHKDDNPSLP<br>PFERPEAEAMCTSFKENPTTFMGHYLHEVARRHPYFYAPELLYYAEQYNEILT<br>QCCAEADKESCLTPKLDGVKEKALVSSVRQRMKCSSMQKFGERAFKAWAVA<br>RLSQTFPNADFAEITKLATDLTKVNKECCHGDLLECADDRAELAKYMCENQA<br>TISSKLQTCCDKPLLKKAHCLSEVEHDTMPADLPAIAADFVEDQEVCKNYAEA<br>KDVFLGTFLYEYSRRHPDYSVSLLLRLAKKYEATLEKCCAEANPPACYGTVL<br>AEFQPLVEEPKNLVKTNCDLYEKLGEYGFQNAILVRYTQKAPQVSTPTLVEAA<br>RNLGRVGTKCCTLPEDQRLPCVEDYLSAILNRVCLLHEKTPVSEHVTKCCSGS<br>LVERRPCFSALTVDETYVPKEFKAETFTFHSDICTLPEKEKQIKKQTALAELVK<br>HKPKATAEQLKTVMDDFAQFLDTCCKAADKDTCFSTEGPNLVTRCKDALAgg<br>ggsggggsggggsggggsggggsggggsSGGPGPAGMKGLPGSEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKASQNVGTNVGWYQQKPG<br>KAPKALIYSASFRYSGVPSRFSGSGSGTDFTLTISSLQPEDFATYYCQQYYTYP<br>YTFGGGTKVEIKHHHHHH** |

-continued

Sequence table

| SEQ ID NO. | Name | Sequence |
|---|---|---|
| 382 | ACP303 | EAHKSEIAHRYNDLGEQHFKGLVLIAFSQYLQKCSYDEHAKLVQEVTDFAKT<br>CVADESAANCDKSLHTLFGDKLCAIPNLRENYGELADCCTKQEPERNECFLQH<br>KDDNPSLPPFERPEAEAMCTSFKENPTTFMGHYLHEVARRHPYFYAPELLYYA<br>EQYNEILTQCCAEADKESCLTPKLDGVKEKALVSSVRQRMKCSSMQKFGERA<br>FKAWAVARLSQTFPNADFAEITKLATDLTKVNKECCHGDLLECADDRAELAK<br>YMCENQATISSKLQTCCDKPLLKKAHCLSEVEHDTMPADLPAIAADFVEDQE<br>VCKNYAEAKDVFLGTFLYEYSRRHPDYSVSLLLRLAKKYEATLEKCCAEANP<br>PACYGTVLAEFQPLVEEPKNLVKTNCDLYEKLGEYGFQNAILVRYTQKAPQV<br>STPTLVEAARNLGRVGTKCCTLPEDQRLPCVEDYLSAILNRVCLLHEKTPVSE<br>HVTKCCSGSLVERRPCFSALTVDETYVPKEFKAETFTFHSDICTLPEKEKQIKK<br>QTALAELVKHKPKATAEQLKTVMDDFAQFLDTCCKAADKDTCFSTEGPNLVT<br>RCKDALASGGPGPAGMKGLPGSfficfympldcatelkhlqcleeelkpleevinlaqsknfhlrprdlis<br>ninvivlelkgsettfmceyadetativeflnrwilfcqsiistltGGssticktqlqlehllldlqmilnginnyknpkltrm<br>ISGGPGPAGMKGLPGSEAHKSEIAHRYNDLGEQHFKGLVLIAFSQYLQKCSYD<br>EHAKLVQEVTDFAKTCVADESAANCDKSLHTLFGDKLCAIPNLRENYGELAD<br>CCTKQEPERNECFLQHKDDNPSLPPFERPEAEAMCTSFKENPFITMGHYLHEV<br>ARRHPYFYAPELLYYAEQYNEILTQCCAEADKESCLTPKLDGVKEKALVSSVR<br>QRMKCSSMQKFGERAFKAWAVARLSQlFPNADFAEITKLATDLTKVNKECC<br>HGDLLECADDRAELAKYMCENQATISSKLQTCCDKPLLKKAHCLSEVEHDTM<br>PADLPAIAADFVEDQEVCKNYAEAKDVFLGlFLYEYSRRHPDYSVSLLLRLAK<br>KYEATLEKCCAEANPPACYGTVLAEFQPLVEEPKNLVKTNCDLYEKLGEYGF<br>QNAILVRYTQKAPQVSTPTLVEAARNLGRVGTKCCTLPEDQRLPCVEDYLSAI<br>LNRVCLLHEKTPVSEHVTKCCSGSLVERRPCFSALTVDETYVPKEFKAETFTFH<br>SDICTLPEKEKQIKKQTALAELVKHKPKATAEQLKTVMDDFAQFLDTCCKAA<br>DKDTCFSTEGPNLVTRCKDALAHHHHHH** |
| 383 | ACP304 (WW0302) | aptsssildctqlqlehllldlqmilnginnyknpkltrmltfkfympkkatelkhlqcleeelkpleevinlaqsknfhlrpr<br>dlisninvivlelkgsettfmceyadetativeflnrwiticqsiistltSGGPGPAGMKGLPGSEVQLVES<br>GGGLVQPGNSLRLSCAASGFTFSKFGMSWVRQAPGKGLEWVSSISGSGRDTL<br>YAESVKGRFTISRDNAKTTLYLQMNSLRPEDTAVYYCTIGGSLSVSSQGTLVT<br>VSSggggsggggsggggsggggsggggsggggsSGGPGPAGMKGLPGSEVQLVESGGGLV<br>QPGGSLRLSCAASGFTFSSYTLAWVRQAPGKGLEWVAAIDSSSYTYSPDTVRG<br>RFTISRDNAKNSLYLQMNSLRAEDTAVYYCARDSNWDALDYWGQGTTVTVS<br>SGGGGSGGGGSGGGGSDIQMTQSPSSLSASVGDRVTITCKASQNVGTNVGWY<br>QQKPGKAPKALIYSASFRYSGVPSRFSGSGSGTDFTLTISSLQPEDFATYYCQQ<br>YYTYPYTFGGGTKVEIKSGGPGPAGMKGLPGSggggsggggsggggsggggsggggsggg<br>gselcdddppeiphatfkamaykegtmlnceckrgfrriksgslymktgnsshsswdnqcqctssatrnttkqvtpqp<br>eeqkerkttemqspmqpvdqaslpghcrepppweneateriyhfvvgqmvyyqcvqgyralhrgpaesvclunth<br>gktrwtqpqlictgemetsqfpgeekpqaspegrpesetsclvtltdfqiqtemaatmetsiftteyqHHHHHH** |
| 384 | ACP305 (WW0303) | elcdddppeiphatfkamaykegtmlnceckrgfrriksgslymktgnsshsswdnqcqctssatrnttkqvtpqpee<br>qkerkttemqspmqpvdqaslpghcrepppweneateriyhfvvgqmvyyqcvqgyralhrgpaesvckmthgk<br>trwtqpqlictgemetsqfpgeekpqaspegrpesetsclvtttdfqiqtemaatmetsiftteyqggggsggggsgggg<br>sggggsggggsggggsSGGPGPAGMKGLPGSaptssstlthqlqlehllldlqmilnginnyknpkltrmlIf<br>kfympkkatelkhlqcleeelkpleevinlaqsknfhlrprdlisninvivlelkgsettfmceyadetativeflnrwitfc<br>qsiistltSGGPGPAGMKGLPGSEVQLVESGGGLVQPGNSLRLSCAASGFTFSKFG<br>MSWVRQAPGKGLEWVSSISGSGRDTLYAESVKGRFTISRDNAKTTLYLQMNS<br>LRPEDTAVYYCTIGGSLSVSSQGTLVTVSSggggsggggsggggsggggsggggsggggsSG<br>GPGPAGMKGLPGSEVQLVESGGGLVQPGGSLRLSCAASGFTFSSYTLAWVRQ<br>APGKGLEWVAAIDSSSYTYSPDTVRGRFTISRDNAKNSLYLQMNSLRAEDTAV<br>YYCARDSNWDALDYWGQGTTVTVSSGGGGSGGGGSGGGGSDIQMTQSPSSL<br>SASVGDRVTITCKASQNVGTNVGWYQQKPGKAPKALIYSASFRYSGVPSRFSG<br>SGSGTDFTLTISSLQPEDFATYYCQQYYTYPYTFGGGTKVEIKHHHHHH** |
| 385 | ACP306 (WW0304) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltSGGPGPAGMKGLPGSggggsggggs<br>ggggsggggsggggsggggselcdddppeiphatfkamaykegtmlnceckrgfrriksgslymktgnsshsswd<br>nqcqctssatrnttkqvtpqpeeqkerkttemqspmqpvdqaslpghcrepppweneateriyhfvvgqmvyyqcv<br>qgyralhrgpaesvckmthgktrwtqpqlictgemetsqfpgeekpqaspegrpesetsclvtttdfqiqtemaatmets<br>iftteyqSGGPGPAGMKGLPGSEVQLVESGGGLVQPGNSLRLSCAASGFTFSKFG<br>MSWVRQAPGKGLEWVSSISGSGRDTLYAESVKGRFTISRDNAKTTLYLQMNS<br>LRPEDTAVYYCTIGGSLSVSSQGTLVTVSSggggsggggsggggsggggsggggsggggsSG<br>GPGPAGMKGLPGSEVQLVESGGGLVQPGGSLRLSCAASGFTFSSYTLAWVRQ<br>APGKGLEWVAAIDSSSYTYSPDTVRGRFTISRDNAKNSLYLQMNSLRAEDTAV<br>YYCARDSNWDALDYWGQGTTVTVSSGGGGSGGGGSGGGGSDIQMTQSPSSL<br>SASVGDRVTITCKASQNVGTNVGWYQQKPGKAPKALIYSASFRYSGVPSRFSG<br>SGSGTDFTLTISSLQPEDFATYYCQQYYTYPYTFGGGTKVEIKHHHHHH**<br>386ACP307EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGSfficlympldcatelkhlqcleeelkpleevinlaqsknfhlrpr<br>dlisninvivlelkgsettfmceyadetativeflnrwitfcqsiistitGGssstkktqlqlehllldlqmilnginnyknpkl<br>trmlSGGPGPAGMKGLPGSEVQLVESGGGLVQPGNSLRLSCAASGFTFSKFGMS |

-continued

Sequence table

| SEQ ID NO. | Name | Sequence |
|---|---|---|
| | | WVRQAPGKGLEWVSSISGSGRDTLYAESVKGRFTISRDNAKTTLYLQMNSLR<br>PEDTAVYYCTIGGSLSVSSQGTLVTVSSggggsggggsggggsggggsggggsggggsSGGP<br>GPAGMKGLPGSEVQLVESGGGLVQPGGSLRLSCAASGFTFSSYTLAWVRQAP<br>GKGLEWVAAIDSSSYTYSPDTVRGRFTISRDNAKNSLYLQMNSLRAEDTAVY<br>YCARDSNWDALDYWGQGTTVTVSSGGGGSGGGGSGGGGSDIQMTQSPSSLS<br>ASVGDRVTITCKASQNVGTNVGWYQQKPGKAPKALIYSASFRYSGVPSRFSGS<br>GSGTDFTLTISSLQPEDFATYYCQQYYTYPYTFGGGTKVEIKHHHHHH** |
| 387 | ACP308 | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSGGGGSGGGGSGGGGSDIQMTQSPSSLSASVGDRVTITCK<br>ASQNVGTNVGWYQQKPGKAPKALIYSASFRYSGVPSRFSGSGSGTDFTLTISSL<br>QPEDFATYYCQQYYTYPYTFGGGTKVEIKSGGPGPAGMKGLPGSggggsggggsg<br>gggsggggsggggsggggsEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSSGGPGPAGMKGLPGStfkfympkkatelkhlqcleee<br>lkpleevinlaqsknfhlrprdlisninvivlelkgsettfmceyadetativeflnrwitfcqsiistltGGssstkktqlqle<br>hllldlqmilnginnyknpkltrmlSGGPGPAGMKGLPGSEVQLVESGGGLVQPGNSLRLS<br>CAASGFTFSKFGMSWVRQAPGKGLEWVSSISGSGRDTLYAESVKGRFTISRDN<br>AKTTLYLQMNSLRPEDTAVYYCTIGGSLSVSSQGTLVTVSSHHHHHH** |
| 388 | ACP309 (WW0307) | aptssstkktqlqlehllldlqmilnginnyknpkltrmltfkfympkkatelkhlqcleeelkpleevinlaqsknfhlrpr<br>dlisninvivlelkgsetlfmceyadetativeflnrwitfcqsiistltSGGPGPAGMKGLPGSEVQLVES<br>GGGLVQPGNSLRLSCAASGFTFSKFGMSWVRQAPGKGLEWVSSISGSGRDTL<br>YAESVKGRFTISRDNAKTTLYLQMNSLRPEDTAVYYCTIGGSLSVSSQGTLVT<br>VSSggggsggggsggggsggggsggggsggggsSGGPGPAGMKGLPGSEVQLVESGGGLV<br>QPGGSLRLSCAASGFTFSSYTLAWVRQAPGKGLEWVAAIDSSSYTYSPDTVRG<br>RFTISRDNAKNSLYLQMNSLRAEDTAVYYCARDSNWDALDYWGQGTTVTVS<br>SGGGGSGGGGSGGGGSDIQMTQSPSSLSASVGDRVTITCKASQNVGTNVGWY<br>QQKPGKAPKSLIYSASFRYSGVPSRFSGSGSGTDFTLTISSLQPEDFATYYCQQY<br>YTYPYTFGGGTKVEIKHHHHHH** |
| 389 | ACP310 (WW0308) | aptssstkktqlqlehllldlqmilnginnyknpkltrmltfkfympkkatelkhlqcleeelkpleevinlaqsknfhlrpr<br>dlisninvivlelkgsetlfmceyadetativeflnrwitfcqsiistltSGGPGPAGMKGLPGSEVQLVES<br>GGGLVQPGNSLRLSCAASGFTFSKFGMSWVRQAPGKGLEWVSSISGSGRDTL<br>YAESVKGRFTISRDNAKTTLYLQMNSLRPEDTAVYYCTIGGSLSVSSQGTLVT<br>VSSggggsggggsggggsggggsggggsggggsSGGPGPAGMKGLPGSEVQLVESGGGLV<br>QPGGSLRLSCAASGFTFSSYTLAWVRQAPGKGLEWVAAIDSSSYTYSPDTVRG<br>RFTISRDNAKNSLYLQMNSLRAEDTAVYYCARDSNWDALDYWGQGTTVTVS<br>SGGGGSGGGGSGGGGSDIQMTQSPSSLSASVGDRVTITCKASQNVGTNVGWY<br>QQKPGQAPRLLIYSASFRYSGVPSRFSGSGSGTDFTLTISSLQPEDFATYYCQQY<br>YTYPYTFGGGTKVEIKHHHHHH** |
| 390 | ACP311 (WW0316) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltSGGPGPAGMKGLPGSeskygppcpp<br>cpapeflggpsvflfppkpkdtlmisrtpevtcvvvdvsqedpevqfnwyvdgvevhnaktkpreeqfnstyrvvsvl<br>tvlhqdwingkeykckvsnkglpssiektiskakgqprepqvytlppsqeemtknqvsltclvkgfypsdiavewesn<br>gqpennykttppvldsdgsfflysrltvdksrwqegnvfscsvmhealhnhytqkslslslgkggggsggggsggggs<br>ggggsggggsggggsSGGPGPAGMKGLPGSEVQLVESGGGLVQPGGSLRLSCAASG<br>FTFSSYTLAWVRQAPGKGLEWVAAIDSSSYTYSPDTVRGRFTISRDNAKNSLY<br>LQMNSLRAEDTAVYYCARDSNWDALDYWGQGTTVTVSSGGGGSGGGGSGG<br>GGSDIQMTQSPSSLSASVGDRVTITCKASQNVGTNVGWYQQKPGKAPKALIYS<br>ASFRYSGVPSRFSGSGSGTDFTLTISSLQPEDFATYYCQQYYTYPYTFGGGTKV<br>EIKHHHHHH** |
| 391 | ACP312 (WW0317) | eskygppcppcpapeflggpsvflfppkpkdtlmisrtpevtcvvvdvsqedpevqfnwyvdgvevhnaktkpree<br>qfnstyrvvsyltvlhqdwhigkeykckvsnkglpssiektiskakgqprepqvytlppsqeemtknqvsltclvkgfy<br>psdiavewesngqpennyklippvldsdgsfflysrltvdksrwqegnvfscsvmhealhnhytqkslslslgkSGG<br>PGPAGMKGLPGSaptssstkktqlqlehllldlqmilnginnyknpkltrmltfklympkkatelkhlqcleeel<br>kpleevinlaqsknfblrprdlisninvivlelkgsellfmceyadetativeflnrwitfcqsiistliggggsggggsgggg<br>sggggsggggsggggsSGGPGPAGMKGLPGSEVQLVESGGGLVQPGGSLRLSCAASG<br>FTFSSYTLAWVRQAPGKGLEWVAAIDSSSYTYSPDTVRGRFTISRDNAKNSLY<br>LQMNSLRAEDTAVYYCARDSNWDALDYWGQGTTVTVSSGGGGSGGGGSGG<br>GGSDIQMTQSPSSLSASVGDRVTITCKASQNVGTNVGWYQQKPGKAPKALIYS<br>ASFRYSGVPSRFSGSGSGTDFTLTISSLQPEDFATYYCQQYYTYPYTFGGGTKV<br>EIKHHHHHH** |
| 392 | ACP313 (WW0318) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltSGGPGPAGMKGLPGSggggsggggs<br>ggggsggggsggggsggggsEVQLVESGGGLVQPGGSLRLSCAASGFTFSSYTLAWVR<br>QAPGKGLEWVAAIDSSSYTYSPDTVRGRFTISRDNAKNSLYLQMNSLRAEDTA<br>VYYCARDSNWDALDYWGQGTTVTVSSGGGGSGGGGSGGGGSDIQMTQSPSS<br>LSASVGDRVTITCKASQNVGTNVGWYQQKPGKAPKALIYSASFRYSGVPSRFS |

-continued

Sequence table

| SEQ ID NO. | Name | Sequence |
|---|---|---|
| | | GSGSGTDFTLTISSLQPEDFATYYCQQYYTYPYTFGGGTKVEIKSGGPGPAGM<br>KGLPGSeskygppcppcpapeflggpsvflfppkpkdtlmisrtpevtcvvdvsqedpevqfnwyvdgvevh<br>naktkpreeqfnstyrvvsyltvlhqdwhigkeykckvsnkglpssiektiskakgqprepqvytlppsqeemtknqv<br>sliclvkgypsdiavewesngqpennyklippvldsdgsfflysrltvdksrwqegnvfscsvmhealhnhytqkslsl<br>slgIcHHHHHH** |
| 393 | ACP314<br>(WW0354) | vprdcgckpcictypevssvfifppkpkdvltitltpkvtcwvdiskddpevqfswfvddvevhtaqtqpreeqfnslf<br>rsyselpimhqdwingkefkcrynsaafpapiektisktkgrpkapqvytipppkeqmakdkvsltcmitclffpeditv<br>ewqwngqpaenykntqpimdtdgsyfyysklnvqksnweagnIftcsvlheglhnhhtekslshspgkSGGPG<br>PAGMKGLPGSaptssstIcktqlqlehllldlqmilnginnyknpkltrmlffidympkkatelkhlqcleeelkple<br>evinlaqsknfhlrprdlisninvivlelkgsetlfmceyadetativeflnrwilfcqsiistltggggsggggsggggsgg<br>ggsggggsggggsSGGPGPAGMKGLPGSEVQLVESGGGLVQPGGSLRLSCAASGFT<br>FSSYTLAWVRQAPGKGLEWVAAIDSSSYTYSPDTVRGRFTISRDNAKNSLYLQ<br>MNSLRAEDTAVYYCARDSNWDALDYWGQGTTVTVSSGGGGSGGGGSGGGG<br>SDIQMTQSPSSLSASVGDRVTITCKASQNVGTNVGWYQQKPGKAPKALIYSAS<br>FRYSGVPSRFSGSGSGTDFTLTISSLQPEDFATYYCQQYYTYPYTFGGGTKVEI<br>KHHHHHH** |
| 394 | ACP336<br>(WW0414) | aptssstIcktqlqlehllldlqmilnginnyknpkltrmltfkfympkkatelkhlqcleeelkpleevinlaqsknfhlrpr<br>dlisninvivlelkgsetlfmceyadetativeflnrwilfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGQGTTVTVSSsggpG<br>PAGLYAQpgsDIQMTQSPSSLSASVGDRVTITCKAREKLWSAVAWYQQKPGKA<br>PKsLIYSASFRYSGVPSRFSGSGSGTDFTLTISSLQPEDFATYYCQQYYTYPYTF<br>GGGTKVEIK** |
| 395 | ACP337<br>(WW0415) | aptssstIcktqlqlehllldlqmilnginnyknpkltrmltfkfympkkatelkhlqcleeelkpleevinlaqsknfhlrpr<br>dlisninvivlelkgsetlfmceyadetativeflnrwilfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKAREKLWSAVAWYQQKPG<br>KAPKsLIYSASFRYSGVPSRFSGSGSGTDFTLTISSLQPEDFATYYCQQYYTYPY<br>TFGGGTKVEIK** |
| 396 | ACP338<br>(WW0416) | aptssstIcktqlqlehllldlqmilnginnyknpkltrmltfkfympkkatelkhlqcleeelkpleevinlaqsknfhlrpr<br>dlisninvivlelkgsetlfmceyadetativeflnrwilfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGQGTTVTVSSsggpG<br>PAGLYAQpgsDIQMTQSPSSLSASVGDRVTITCKVTEKVWGNVAWYQQKPGK<br>APISLIYSPSLRKSGVPSRFSGSGSGTDFTLTISSLQPEDFATYYCQQYYTYPYTF<br>GGGTKVEIK** |
| 397 | ACP339<br>(WW0417) | aptssstIcktqlqlehllldlqmilnginnyknpkltrmltfkfympkkatelkhlqcleeelkpleevinlaqsknfhlrpr<br>dlisninvivlelkgsetlfmceyadetativeflnrwilfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsEVQLVESGGGLVQPGGS<br>LRLSCAASGFTFSSYTLAWVRQAPGKGLEWVAAIDSSSYTYSPDTVRGRFTISR<br>DNAKNSLYLQMNSLRAEDTAVYYCARDSNWDALDYWGQGTTVTVSSGGGG<br>SGGGGSGGGGSDIQMTQSPSSLSASVGDRVTITCKVTEKVWGNVAWYQQKP<br>GKAPISLIYSPSLRKSGVPSRFSGSGSGTDFTLTISSLQPEDFATYYCQQYYTYP<br>YTFGGGTKVEIK** |
| 398 | ACP340<br>(WW0418) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSS<br>ggggsggggsggggsggggsggggsggggssggpGPAGLYAQpgsevqllesggglvqpggslrlscaasgsi<br>fsanamgwyrqapgkglelvavissggstnyadsvkgrftisrdnskntvylqmnslraedtavyycmysgsyyytp<br>ndywgqgtivtvss** |
| 399 | ACP341<br>(WW0419) | aptssstkktqlqlehllldlqmilnginnyknpkltrmltfkfympkkatelkhlqcleeelkpleevinlaqsknfhlrpr<br>dlisninvivlelkgsettfmceyadetativeflnrwitfcqsiistltsggpGPAGLYAQpgsEVQLVESGG<br>GLVQPGNSLRLSCAASGFTFSKFGMSWVRQAPGKGLEWVSSISGSGRDTLYA |

-continued

Sequence table

| SEQ ID NO. | Name | Sequence |
|---|---|---|
| | | ESVKGRFTISRDNAKTTLYLQMNSLRPEDTAVYYCTIGGSLSVSSQGTLVTVSS<br>ggggsggggsggggsggggsggggsggggssggpGPAGLYAQpgsevqllesggglvqpggslrlscaaseri<br>fstdvmgwyrqapgkqrelvavvsargttnyldavkgrftisrdnskntlylqmnslraedtavyycyvrettspwriy<br>wgqgtivtvss** |
| 400 | ACP342<br>(WW0420) | elcdddppeiphatfkamaykegtmlnceckrgfrriksgslymlctgnsshsswdnqcqctssatrnttkqvtpqpee<br>qkerkttemqspmqpvdqaslpghcrepppweneateriyhfvvgqmvyyqcvqgyralhrgpaesvckmthgk<br>trwtqpqlictgemetsqfpgeekpqaspegrpesetsSlvtdclfqiqtemaatmetsiftteyqggggsggggsgggg<br>sggggsggggsggggssggpGPAGLYAQpgsaptssstkktqlqlehllldlqmilnginnyknpkltrmltfkfy<br>mpkkatelkhlqcleeelkpleevinlaqsknfhlrprdlisninvivlelkgsetlfmceyadetativeflnrwitfcqsii<br>stltsggpGPAGLYAQpgsEVQLVESGGGLVQPGNSLRLSCAASGFTFSKFGMSWV<br>RQAPGKGLEWVSSISGSGRDTLYAESVKGRFTISRDNAKTTLYLQMNSLRPED<br>TAVYYCTIGGSLSVSSQGTLVTVSSggggsggggsggggsggggsggggsggggssggpGPAG<br>LYAQpgsEVQLVESGGGLVQPGGSLRLSCAASGFTFSSYTLAWVRQAPGKGLE<br>WVAAIDSSSYTYSPDTVRGRFTISRDNAKNSLYLQMNSLRAEDTAVYYCARD<br>SNWDALDYWGQGTTVTVSSsggpGPAGLYAQpgsDIQMTQSPSSLSASVGDRVT<br>ITCKAREKLWSAVAWYQQKPGKAPKsLIYSASFRYSGVPSRFSGSGSGTDFTLT<br>ISSLQPEDFATYYCQQYYTYPYTFGGGTKVEIK** |
| 401 | ACP343<br>(WW0421) | elcdddppeiphatfkamaykegtmlnceckrgfrriksgslymlctgnsshsswdnqcqctssatrnttkqvtpqpee<br>qkerkttemqspmqpvdqaslpghcrepppweneateriyhfvvgqmvyyqcvqgyralhrgpaesvckmthgk<br>trwtqpqlictgemetsqfpgeekpqaspegrpesetsSlvtdclfqiqtemaatmetsiftteyqggggsggggsgggg<br>sggggsggggsggggssggpGPAGLYAQpgsaptssstkktqlqlehllldlqmilnginnyknpkltrmltfkfy<br>mpkkatelkhlqcleeelkpleevinlaqsknfhlrprdlisninvivlelkgsetlfmceyadetativeflnrwitfcqsii<br>stltsggpGPAGLYAQpgsEVQLVESGGGLVQPGNSLRLSCAASGFTFSKFGMSWV<br>RQAPGKGLEWVSSISGSGRDTLYAESVKGRFTISRDNAKTTLYLQMNSLRPED<br>TAVYYCTIGGSLSVSSQGTLVTVSSggggsggggsggggsggggsggggsggggssggpGPAG<br>LYAQpgsEVQLVESGGGLVQPGGSLRLSCAASGFTFSSYTLAWVRQAPGKGLE<br>WVAAIDSSSYTYSPDTVRGRFTISRDNAKNSLYLQMNSLRAEDTAVYYCARD<br>SNWDALDYWGQGTTVTVSSGGGGSGGGGSGGGGSDIQMTQSPSSLSASVGD<br>RVTITCKAREKLWSAVAWYQQKPGKAPKsLIYSASFRYSGVPSRFSGSGSGTD<br>FTLTISSLQPEDFATYYCQQYYTYPYTFGGGTKVEIK** |
| 402 | ACP344<br>(WW0422) | elcdddppeiphatfkamaykegtmlnceckrgfrriksgslymlctgnsshsswdnqcqctssatrnttkqvtpqpee<br>qkerkttemqspmqpvdqaslpghcrepppweneateriyhfvvgqmvyyqcvqgyralhrgpaesvckmthgk<br>trwtqpqlictgemetsqfpgeekpqaspegrpesetsSlvtdclfqiqtemaatmetsiftteyqggggsggggsgggg<br>sggggsggggsggggssggpGPAGLYAQpgsaptssstkktqlqlehllldlqmilnginnyknpkltrmilfkfy<br>mpkkatelkhlqcleeelkpleevinlaqsknfhlrprdlisninvivlelkgsetlfmceyadetativeflnrwitfcqsii<br>stltsggpGPAGLYAQpgsEVQLVESGGGLVQPGNSLRLSCAASGFTFSKFGMSWV<br>RQAPGKGLEWVSSISGSGRDTLYAESVKGRFTISRDNAKTTLYLQMNSLRPED<br>TAVYYCTIGGSLSVSSQGTLVTVSSggggsggggsggggsggggsggggsggggssggpGPAG<br>LYAQpgsEVQLVESGGGLVQPGGSLRLSCAASGFTFSSYTLAWVRQAPGKGLE<br>WVAAIDSSSYTYSPDTVRGRFTISRDNAKNSLYLQMNSLRAEDTAVYYCARD<br>SNWDALDYWGQGTTVTVSSsggpGPAGLYAQpgsDIQMTQSPSSLSASVGDRVT<br>ITCKVTEKVWGNVAWYQQKPGKAPISLIYSPSLRKSGVPSRFSGSGSGTDFTLT<br>ISSLQPEDFATYYCQQYYTYPYTFGGGTKVEIK** |
| 403 | ACP345<br>(WW0423) | elcdddppeiphatfkamaykegtmlnceckrgfrriksgslymlctgnsshsswdnqcqctssatrnttkqvtpqpee<br>qkerkttemqspmqpvdqaslpghcrepppweneateriyhfvvgqmvyyqcvqgyralhrgpaesvckmthgk<br>trwtqpqlictgemetsqfpgeekpqaspegrpesetsSlvtdclfqiqtemaatmetsiftteyqggggsggggsgggg<br>sggggsggggsggggssggpGPAGLYAQpgsaptssstkktqlqlehllldlqmilnginnyknpkltrmltfkfy<br>mpkkatelkhlqcleeelkpleevinlaqsknfblrprdlisninvivlelkgsetlfmceyadetativeflnrwilleqsii<br>stltsggpGPAGLYAQpgsEVQLVESGGGLVQPGNSLRLSCAASGFTFSKFGMSWV<br>RQAPGKGLEWVSSISGSGRDTLYAESVKGRFTISRDNAKTTLYLQMNSLRPED<br>TAVYYCTIGGSLSVSSQGTLVTVSSggggsggggsggggsggggsggggsggggssggpGPAG<br>LYAQpgsEVQLVESGGGLVQPGGSLRLSCAASGFTFSSYTLAWVRQAPGKGLE<br>WVAAIDSSSYTYSPDTVRGRFTISRDNAKNSLYLQMNSLRAEDTAVYYCARD<br>SNWDALDYWGQGTTVTVSSGGGGSGGGGSGGGGSDIQMTQSPSSLSASVGD<br>RVTITCKVTEKVWGNVAWYQQKPGKAPISLIYSPSLRKSGVPSRFSGSGSGTD<br>FTLTISSLQPEDFATYYCQQYYTYPYTFGGGTKVEIK** |
| 404 | ACP346<br>(WW0424) | elcdddppeiphatflcamaykegtmlnceckrgfrriksgslymktgnsshsswdnqcqctssatrnttkqvtpqpee<br>qkerkttemqspmqpvdqaslpghcrepppweneateriyhfvvgqmvyyqcvqgyralhrgpaesvckmthgk<br>trwtqpqlictgemetsqfpgeekpqaspegrpesetsSlvtttclfqiqtemaatmetsiftteyqggggsggggsgggg<br>sggggsggggsggggssggpGPAGLYAQpgsaptssticktqlqlehllldlqmilnginnyknpkltrmilflcfy<br>mpkkatelkhlqcleeelkpleevinlaqsknfblrprdlisninvivlelkgsetlfmceyadetativeflnrwilleqsii<br>stltsggpGPAGLYAQpgsEVQLVESGGGLVQPGNSLRLSCAASGFTFSKFGMSWV<br>RQAPGKGLEWVSSISGSGRDTLYAESVKGRFTISRDNAKTTLYLQMNSLRPED<br>TAVYYCTIGGSLSVSSQGTLVTVSSggggsggggsggggsggggsggggsggggssggpGPAG<br>LYAQpgsevqllesggglvqpggslrlscaasgsifsanamgwyrqapgkglelvavissggstnyadsvkgrftisr<br>dnskntvylqmnslraedtavyycmysgsyyytpndywgqgtivtvss** |

-continued

Sequence table

| SEQ ID NO. | Name | Sequence |
|---|---|---|
| 405 | ACP347 (WW0425) | elcdddppeiphatflcamaykegtmlnceckrgfrriksgslymktgnsshsswdnqcqctssatrnttkqvtpqpee<br>qkerkttemqspmqpvdqaslpghcrepppweneateriyhfvvgqmvyyqcvqgyralhrgpaesvckmthgk<br>trwtqpqlictgemetsqfpgeekpqaspegrpesetsSlvtttclfqiqtemaatmetsiftteyqggggsggggsgggg<br>sggggsggggsggggsggggssggpGPAGLYAQpgsaptssstickktqlqlehllldlqmilnginnyknpkltrmilflcfy<br>mpkkatelkhlqcleeelkpleevinlaqsknfblrprdlisninvivlelkgsetlfmceyadetativeflnrwilleqsii<br>stltsggpGPAGLYAQpgsEVQLVESGGGLVQPGNSLRLSCAASGFTFSKFGMSWV<br>RQAPGKGLEWVSSISGSGRDTLYAESVKGRFTISRDNAKTTLYLQMNSLRPED<br>TAVYYCTIGGSLSVSSQGTLVTVSSggggsggggsggggsggggsggggsggggsggggssggpGPAG<br>LYAQpgsevqllesggglvqpggslrlscaaserifstdvmgwyrqapgkqrelvavvsargttnyldavkgrftisrd<br>nskntlylqmnslraedtavyycyvrettspwriywgqgilvtvss** |
| 406 | ACP348 (WW0426) | eskygppcppcpapeflggpsvflfppkpkdtlmisrtpevtcvvvdvsqedpevqfnwyvdgvevhnaktkpree<br>qfnstyrvvsyltvlhqdwhigkeykcicvsnkglpssiektiskakgqprepqvytlppsqeemilmqvsltclvkgfy<br>psdiavewesngqpennykappvldsdgsfflysrltvdksrwqegnvfscsvmhealhnhytqkslslslgksggp<br>GPAGLYAQpgsaptssstickktqlqlehllldlqmilnginnyknpkltrmltfkfympldcatelkhlqcleeelkpl<br>eevinlaqsknfhlrprdlisninvivlelkgsetlfmceyadetativeflnrwitfcqsiistligggggsggggsggggsgg<br>ggsggggsggggssggpGPAGLYAQpgsEVQLVESGGGLVQPGGSLRLSCAASGFTFS<br>SYTLAWVRQAPGKGLEWVAAIDSSSYTYSPDTVRGRFTISRDNAKNSLYLQM<br>NSLRAEDTAVYYCARDSNWDALDYWGQGTTVTVSSsggpGPAGLYAQpgsDIQ<br>MTQSPSSLSASVGDRVTITCKAREKLWSAVAWYQQKPGKAPKsLIYSASFRYS<br>GVPSRFSGSGSGTDFTLTISSLQPEDFATYYCQQYYTYPYTFGGGTKVEIK** |
| 407 | ACP349 (WW0427) | eskygppcppcpapeflggpsvflfppkpkdtlmisrtpevtcvvvdvsqedpevqfnwyvdgvevhnaktkpree<br>qfnstyrvvsyltvlhqdwhigkeykcicvsnkglpssiektiskakgqprepqvytlppsqeemilmqvsltclvkgfy<br>psdiavewesngqpennykappvldsdgsfflysrltvdksrwqegnvfscsvmhealhnhytqkslslslgksggp<br>GPAGLYAQpgsaptssstickktqlqlehllldlqmilnginnyknpkltrmilfklympldcatelkhlqcleeelkpl<br>eevinlaqsknfhlrprdlisninvivlelkgsetlfmceyadetativeflnrwitfcqsiistligggggsggggsggggsgg<br>ggsggggsggggssggpGPAGLYAQpgsEVQLVESGGGLVQPGGSLRLSCAASGFTFS<br>SYTLAWVRQAPGKGLEWVAAIDSSSYTYSPDTVRGRFTISRDNAKNSLYLQM<br>NSLRAEDTAVYYCARDSNWDALDYWGQGTTVTVSSGGGGSGGGGSGGGGS<br>DIQMTQSPSSLSASVGDRVTITCKAREKLWSAVAWYQQKPGKAPKsLIYSASF<br>RYSGVPSRFSGSGSGTDFTLTISSLQPEDFATYYCQQYYTYPYTFGGGTKVEIK<br>** |
| 408 | ACP350 (WW0428) | eskygppcppcpapeflggpsvflfppkpkdtlmisrtpevtcvvvdvsqedpevqfnwyvdgvevhnaktkpree<br>qfnstyrvvsyltvlhqdwhigkeykcicvsnkglpssiektiskakgqprepqvytlppsqeemilmqvsltclvkgfy<br>psdiavewesngqpennykappvldsdgsfflysrltvdksrwqegnvfscsvmhealhnhytqkslslslgksggp<br>GPAGLYAQpgsaptssstickktqlqlehllldlqmilnginnyknpkltrmltfkfympldcatelkhlqcleeelkpl<br>eevinlaqsknfhlrprdlisninvivlelkgsetlfmceyadetativeflnrwitfcqsiistligggggsggggsggggsgg<br>ggsggggsggggssggpGPAGLYAQpgsEVQLVESGGGLVQPGGSLRLSCAASGFTFS<br>SYTLAWVRQAPGKGLEWVAAIDSSSYTYSPDTVRGRFTISRDNAKNSLYLQM<br>NSLRAEDTAVYYCARDSNWDALDYWGQGTTVTVSSsggpGPAGLYAQpgsDIQ<br>MTQSPSSLSASVGDRVTITCKVTEKVWGNVAWYQQKPGKAPISLIYSPSLRKS<br>GVPSRFSGSGSGTDFTLTISSLQPEDFATYYCQQYYTYPYTFGGGTKVEIK** |
| 409 | ACP351 (WW0429) | eskygppcppcpapeflggpsvflfppkpkdtlmisrtpevtcvvvdvsqedpevqfnwyvdgvevhnaktkpree<br>qfnstyrvvsyltvlhqdwhigkeykckvsnkglpssiektiskakgqprepqvytlppsqeemilmqvsltclvkgfy<br>psdiavewesngqpennykttppvldsdgsfflysrltvdksrwqegnvfscsvmhealhnhytqkslslslgksggp<br>GPAGLYAQpgsaptssstkktqlqlehllldlqmilnginnyknpkltrmltfkfympldcatelkhlqcleeelkpl<br>eevinlaqsknfhlrprdlisninvivlelkgsettfmceyadetativeflnrwitfcqsiistligggggsggggsggggsgg<br>ggsggggsggggssggpGPAGLYAQpgsEVQLVESGGGLVQPGGSLRLSCAASGFTFS<br>SYTLAWVRQAPGKGLEWVAAIDSSSYTYSPDTVRGRFTISRDNAKNSLYLQM<br>NSLRAEDTAVYYCARDSNWDALDYWGQGTTVTVSSGGGGSGGGGSGGGGS<br>DIQMTQSPSSLSASVGDRVTITCKVTEKVWGNVAWYQQKPGKAPISLIYSPSL<br>RKSGVPSRFSGSGSGTDFTLTISSLQPEDFATYYCQQYYTYPYTFGGGTKVEIK<br>** |
| 410 | ACP352 (WW0430) | eskygppcppcpapeflggpsvflfppkpkdtlmisrtpevtcvvvdvsqedpevqfnwyvdgvevhnaktkpree<br>qfnstyrvvsyltvlhqdwhigkeykckvsnkglpssiektiskakgqprepqvytlppsqeemilmqvsltclvkgfy<br>psdiavewesngqpennykttppvldsdgsfflysrltvdksrwqegnvfscsvmhealhnhytqkslslslgksggp<br>GPAGLYAQpgsaptssstkktqlqlehllldlqmilnginnyknpkltrmltfklympldcatelkhlqcleeelkpl<br>eevinlaqsknfhlrprdlisninvivlelkgsettfmceyadetativeflnrwitfcqsiistligggggsggggsggggsgg<br>ggsggggsggggssggpGPAGLYAQpgsevqllesggglvqpggslrlscaasgsifsanamgwyrqapgkgl<br>elvavissggstnyadsvkgrftisrdnskntvylqmnslraedtavyycmysgsyyytpndywgqgtivtvss** |
| 411 | ACP353 (WW0431) | eskygppcppcpapeflggpsvflfppkpkdtlmisrtpevtcvvvdvsqedpevqfnwyvdgvevhnaktkpree<br>qfnstyrvvsyltvlhqdwhigkeykckvsnkglpssiektiskakgqprepqvytlppsqeemilmqvsltclvkgfy<br>psdiavewesngqpennykttppvldsdgsfflysrltvdksrwqegnvfscsvmhealhnhytqkslslslgksggp<br>GPAGLYAQpgsaptssstkktqlqlehllldlqmilnginnyknpkltrmltfkfympldcatelkhlqcleeelkpl<br>eevinlaqsknfhlrprdlisninvivlelkgsettfmceyadetativeflnrwitfcqsiistligggggsggggsggggsgg<br>ggsggggsggggssggpGPAGLYAQpgsevqllesggglvqpggslrlscaaserifstdvmgwyrqapgkqr<br>elvavvsargttnyldavkgrftisrdnskntlylqmnslraedtavyycyvrettspwriywgqgtivtvss** |

-continued

Sequence table

| SEQ ID NO. | Name | Sequence |
|---|---|---|
| 412 | ACP354 (WW0432) | eskygppcppcpapeflggpsvflfppkpkdtlmisrtpevtcvvvdvsqedpevqfnwyvdgvevhnaktkpree<br>qfnstyrvvsyltvlhqdwhigkeykckvsnkglpssiektiskakgqprepqvytlppsqeemilmqvsltclvkgfy<br>psdiavewesngqpennykttppvldsdgsfflysrltvdksrwqegnvfscsvmhealhnhytqkslslslgksggp<br>GPAGLYAQpgselcdddppeiphalfkamaykegtmlnceckrgfrriksgslymlctgnsshsswdnqcqcts<br>satrnttkqvtpqpeeqkerkttemqspmqpvdqaslpghcrepppweneateriyhfvvgqmvyyqcvqgyralh<br>rgpaesvckmthgktrwtqpqlictgemetsqfpgeekpqaspegrpesetsSlvtddfqiqtemaatmetsiftteyq<br>ggggsggggsggggsggggsggggsggggssggpGPAGLYAQpgsaptssstkktqlqlehllldlqmilngin<br>nyknpkltrmltfkfympkkatelkhlqcleeelkpleevinlaqsknfblrprdlisninvivlelkgsettfmceyadet<br>ativeflnrwitfcqsiistliggggsggggsggggsggggsggggsggggssggpGPAGLYAQpgsEVQLV<br>ESGGGLVQPGGSLRLSCAASGFTFSSYTLAWVRQAPGKGLEWVAAIDSSSYTY<br>SPDTVRGRFTISRDNAKNSLYLQMNSLRAEDTAVYYCARDSNWDALDYWGQ<br>GTTVTVSSsggpGPAGLYAQpgsDIQMTQSPSSLSASVGDRVTITCKAREKLWSA<br>VAWYQQKPGKAPKsLIYSASFRYSGVPSRFSGSGSGTDFTLTISSLQPEDFATY<br>YCQQYYTYPYTFGGGTKVEIK** |
| 413 | ACP355 (WW0433) | eskygppcppcpapeflggpsvflfppkpkdtlmisrtpevtcvvvdvsqedpevqfnwyvdgvevhnaktkpree<br>qfnstyrvvsyltvlhqdwhigkeykckvsnkglpssiektiskakgqprepqvytlppsqeemilmqvsltclvkgfy<br>psdiavewesngqpennykttppvldsdgsfflysrltvdksrwqegnvfscsvmhealhnhytqkslslslgksggp<br>GPAGLYAQpgselcdddppeiphalfkamaykegtmlnceckrgfrriksgslymlctgnsshsswdnqcqcts<br>satrnttkqvtpqpeeqkerkttemqspmqpvdqaslpghcrepppweneateriyhfvvgqmvyyqcvqgyralh<br>rgpaesvckmthgktrwtqpqlictgemetsqfpgeekpqaspegrpesetsSlvtddfqiqtemaatmetsiftteyq<br>ggggsggggsggggsggggsggggsggggssggpGPAGLYAQpgsaptssstkktqlqlehllldlqmilngin<br>nyknpkltrmltfkfympkkatelkhlqcleeelkpleevinlaqsknfhlrprdlisninvivlelkgsettfmceyadet<br>ativeflnrwitfcqsiistliggggsggggsggggsggggsggggsggggssggpGPAGLYAQpgsEVQLV<br>ESGGGLVQPGGSLRLSCAASGFTFSSYTLAWVRQAPGKGLEWVAAIDSSSYTY<br>SPDTVRGRFTISRDNAKNSLYLQMNSLRAEDTAVYYCARDSNWDALDYWGQ<br>GTTVTVSSGGGGSGGGGSGGGGSDIQMTQSPSSLSASVGDRVTITCKAREKLW<br>SAVAWYQQKPGKAPKsLIYSASFRYSGVPSRFSGSGSGTDFTLTISSLQPEDFAT<br>YYCQQYYTYPYTFGGGTKVEIK** |
| 414 | ACP356 (WW0434) | eskygppcppcpapeflggpsvflfppkpkdtlmisrtpevtcvvvdvsqedpevqfnwyvdgvevhnaktkpree<br>qfnstyrvvsyltvlhqdwhigkeykckvsnkglpssiektiskakgqprepqvytlppsqeemtknqvsltclvkgfy<br>psdiavewesngqpennykappvldsdgsfflysrltvdksrwqegnvfscsvmhealhnhytqkslslslgksggp<br>GPAGLYAQpgselcdddppeiphalfkamaykegtmlnceckrgfrriksgslymlctgnsshsswdnqcqcts<br>satrnttkqvtpqpeeqkerkttemqspmqpvdqaslpghcrepppweneateriyhfvvgqmvyyqcvqgyralh<br>rgpaesvclunthgktrwtqpqlictgemetsqfpgeekpqaspegrpesetsSlytttdfqiqtemaatmetsiftteyq<br>ggggsggggsggggsggggsggggsggggssggpGPAGLYAQpgsaptssstkktqlqlehllldlqmilngin<br>nyknpkltrmlfficfympldcatelkhlqcleeelkpleevinlaqsknfhlrprdlisninvivlelkgsettfmceyadet<br>ativeflnrwitfcqsiistltggggsggggsggggsggggsggggsggggssggpGPAGLYAQpgsEVQLV<br>ESGGGLVQPGGSLRLSCAASGFTFSSYTLAWVRQAPGKGLEWVAAIDSSSYTY<br>SPDTVRGRFTISRDNAKNSLYLQMNSLRAEDTAVYYCARDSNWDALDYWGQ<br>GTTVTVSSsggpGPAGLYAQpgsDIQMTQSPSSLSASVGDRVTITCKVTEKVWGN<br>VAWYQQKPGKAPISLIYSPSLRKSGVPSRFSGSGSGTDFTLTISSLQPEDFATYY<br>CQQYYTYPYTFGGGTKVEIK** |
| 415 | ACP357 (WW0435) | eskygppcppcpapeflggpsvflfppkpkdtlmisrtpevtcvvvdvsqedpevqfnwyvdgvevhnaktkpree<br>qfnstyrvvsyltvlhqdwhigkeykckvsnkglpssiektiskakgqprepqvytlppsqeemtknqvsltclvkgfy<br>psdiavewesngqpennykappvldsdgsfflysrltvdksrwqegnvfscsvmhealhnhytqkslslslgksggp<br>GPAGLYAQpgselcdddppeiphalfkamaykegtmlnceckrgfrriksgslymlctgnsshsswdnqcqcts<br>satrnttkqvtpqpeeqkerkttemqspmqpvdqaslpghcrepppweneateriyhfvvgqmvyyqcvqgyralh<br>rgpaesvclunthgktrwtqpqlictgemetsqfpgeekpqaspegrpesetsSlytttdfqiqtemaatmetsiftteyq<br>ggggsggggsggggsggggsggggsggggssggpGPAGLYAQpgsaptssstkktqlqlehllldlqmilngin<br>nyknpkltrmlfficfympkkatelkhlqcleeelkpleevinlaqsknfhlrprdlisninvivlelkgsettfmceyadet<br>ativeflnrwitfcqsiistltggggsggggsggggsggggsggggsggggssggpGPAGLYAQpgsEVQLV<br>ESGGGLVQPGGSLRLSCAASGFTFSSYTLAWVRQAPGKGLEWVAAIDSSSYTY<br>SPDTVRGRFTISRDNAKNSLYLQMNSLRAEDTAVYYCARDSNWDALDYWGQ<br>GTTVTVSSGGGGSGGGGSGGGGSDIQMTQSPSSLSASVGDRVTITCKVTEKV<br>WGNVAWYQQKPGKAPISLIYSPSLRKSGVPSRFSGSGSGTDFTLTISSLQPEDF<br>ATYYCQQYYTYPYTFGGGTKVEIK** |
| 416 | ACP358 (WW0436) | eskygppcppcpapeflggpsvflfppkpkdtlmisrtpevtcvvvdvsqedpevqfnwyvdgvevhnaktkpree<br>qfnstyrvvsyltvlhqdwhigkeykckvsnkglpssiektiskakgqprepqvytlppsqeemtknqvsltclvkgfy<br>psdiavewesngqpennykappvldsdgsfflysrltvdksrwqegnvfscsvmhealhnhytqkslslslgksggp<br>GPAGLYAQpgselcdddppeiphalfkamaykegtmlnceckrgfrriksgslymlctgnsshsswdnqcqcts<br>satrnttkqvtpqpeeqkerkttemqspmqpvdqaslpghcrepppweneateriyhfvvgqmvyyqcvqgyralh<br>rgpaesvclunthgktrwtqpqlictgemetsqfpgeekpqaspegrpesetsSlytttdfqiqtemaatmetsiftteyq<br>ggggsggggsggggsggggsggggsggggssggpGPAGLYAQpgsaptssstkktqlqlehllldlqmilngin<br>nyknpkltrmlfficfympldcatelkhlqcleeelkpleevinlaqsknfhlrprdlisninvivlelkgsettfmceyadet<br>ativeflnrwitfcqsiistltggggsggggsggggsggggsggggsggggssggpGPAGLYAQpgsevqllesg<br>gglvqpggslrlscaasgsifsanamgwyrqapgkglelvavissggstnyadsvkgrftisrdnskntvylqmnslrae<br>dtavyycmysgsyyytpndywgqgtivtvss** |

-continued

Sequence table

| SEQ ID NO. | Name | Sequence |
|---|---|---|
| 417 | ACP359 (WW0437) | eskygppcppcpapeflggpsvflfppkpkdtlmisrtpevtcvvvdvsqedpevqfnwyvdgvevhnaktkpree<br>qfnstyrvvsyltvlhqdwhigkeykckvsnkglpssiektiskakgqprepqvytlppsqeemtknqvsltclvkgfy<br>psdiavewesngqpennykappvldsdgsfflysrltvdksrwqegnvfscsvmhealhnhytqkslslslgksggp<br>GPAGLYAQpgselcdddppeiphatfkamaykegtmlnceckrgfrriksgslymlctgnsshsswdnqcqcts<br>satrnttkqvtpqpeeqkerkttemqspmqpvdqaslpghcrepppweneateriyhfvvgqmvyyqcvqgyralh<br>rgpaesvclunthgktrwtqpqlictgemetsqfpgeekpqaspegrpesetsSlytttdfqiqtemaatmetsiftteyq<br>ggggsggggsggggsggggsggggsggggssggpGPAGLYAQpgsaptssstkktqlqlehllldlqmilngin<br>nyknpkltrmlfficfympldcatelkhlqcleeelkpleevinlaqsknfhlrprdlisninvivlelkgsettfmceyadet<br>ativeflnrwitfcqsiistltggggsggggsggggsggggsggggsggggssggpGPAGLYAQpgsevqllesg<br>gglvqpggslrlscaaserifstdvmgwyrqapgkqrelvavvsargttnyldavkgrftisrdnskntlylqmnslraed<br>tavyycyvrettspwriywgqgtivtvss** |
| 418 | ACP360 (WW0438) | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSggggsggggsggggsDIQMTQSPSSLSASVGDRVTITCKASQNV<br>GTNVGWYQQKPGKAPKsLIYSASFRYSGVPSRFSGSGSGTDFTLTISSLQPEDF<br>ATYYCQQYYTYPYTFGGGTKVEIKHHHHHH** |
| 419 | ACP361 (WW0439) | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSsggpGPAGLYAQpgsDIQMTQSPSSLSASVGDRVTITCKASQ<br>NVGTNVGWYQQKPGKAPKALIYSASFRYSGVPSRFSGSGSGTDFTLTISSLQPE<br>DFATYYCQQYYTYPYTFGGGTKVEIKHHHHHH** |
| 420 | ACP362 (WW0440) | EVQLVESGGGLVQPGGSLRLSCAASGFTFSSYTLAWVRQAPGKGLEWVAAID<br>SSSYTYSPDTVRGRFTISRDNAKNSLYLQMNSLRAEDTAVYYCARDSNWDAL<br>DYWGQGTTVTVSSsggpGPAGLYAQpgsDIQMTQSPSSLSASVGDRVTITCKASQ<br>NVGTNVGWYQQKPGKAPKsLIYSASFRYSGVPSRFSGSGSGTDFTLTISSLQPE<br>DFATYYCQQYYTYPYTFGGGTKVEIKHHHHHH** |
| 421 | ACP200 | lveepknlyktncdlyeklgeygfqnailvlytqkapqvstptiveaarnlgrvgtkcctlpedqrlpcvedylsailnrycl<br>lhektpvsehytkccsgslverrpcfsaltvdetyvpkefkaaftfhsdictlpekekqikkqtalaelvkhkpkataeqlk<br>tvmdclfaqfldtcckaadkdtcfstegpnlvtrckdalaSGGPGPAGMKGLPGScdlpqthnlinkraltllyq<br>mrrlsplsclkdrkclfgfpqekvdaqqikkaqaipvlseltqqilniftskdssaawnttlldsfcndlhqqlndlqgclmq<br>qvgvqefpltqedallavrkyfhrityylrelcichspcawevvraevwralsssanylgrlreekSGGPGPAGMK<br>GLPGSlveepknlyktncdlyeklgeygfqnailvrytqkapqvstptiveaarnlgrvgtkcctlpedqrlpcvedyl<br>sailnrycllhektpvsehytkccsgslverrpcfsaltvdetyvpkefkaelftihsdictlpekekqikkqtalaelvklikp<br>kataeqlktvmddfaqfldtcckaadkdtcfstegpnlvtrckdalaHHHHHH** |
| 422 | ACP201 | eahkseialuyndlgeqhfkglvliafsqylqkcsydehaklvqevtdfaktcvadesaancdkslhtlfgdklcaipnlr<br>enygeladcctkqepernecflqhkddnpslppferpeaeamctsfkenptlfmghylhevarrhpyfyapellyyaeq<br>yneiltqccaeadkescltpkldgykekalvssvrqGGGGSGGGGSGGSlveepknlyktncdlyeklgeygf<br>qnailvlytqkapqvstptiveaarnlgrvgtkcctlpedqrlpcvedylsailnrycllhektpvsehytkccsgslverrp<br>cfsaltvdetyvpkefkaallfhsdictlpekekqikkqtalaelvklikpkataeqlktvmddfaqfldtcckaadkdtcf<br>stegpnlvtrckdalaSGGPGPAGMKGLPGScdlpqtlmlinkraltllvqmrrlsplsclkdrkdfgfpqekv<br>daqqikkagaipvlseltqqilniftskdssaawnifildsfcndlhqqlndlqgclmqqvgvqefpltqedallavrkyfh<br>rityylrekkhspcawevvraevwralsssanylgrlreekSGGPGPAGMKGLPGSeahkseialllyndlge<br>qhflcglvliafsqylqkcsydehaklvqevtclfaktcvadesaancdkslhtlfgdklcaipnlrenygeladcctkqepe<br>rnecflqhkddnpslppferpeaeamctsfkenptlfmghylhevarrhpyfyapellyyaeqyneiltqccaeadkes<br>cltpkldgykekalvssvrqGGGGSGGGGSGGSlveepknlyktncdlyeklgeygfqnailviytqkapqvs<br>tptiveaarnlgrvgtkcctlpedqrlpcvedylsailnrycllhektpvsehytkccsgslverrpcfsaltvdetyvpkefk<br>aelltihsdictlpekekqikkqtalaelvklikpkataeqlktvmddfaqfldtcckaadkdtcfstegpnlvtrckdalaH<br>HHHHH** |
| 423 | ACP202 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSggggsgggSGGPGPAGMKGLPGSggggsgggscdlpqamlinkraltllvqmrrls<br>plsclkdrkclfgfpqekvdaqqikkagaipvlseltqqilniftskdssaawnttlldsfcndlhqqlndlqgclmqqvgv<br>qefpltqedallavrkyfhrityylrelcichspcawevvraevwralsssanylgrlreekggggsgggSGGPGPAG<br>MKGLPGSggggsgggsEVQLVESGGGLVQPGNSLRLSCAASGFTFSKFGMSWVR<br>QAPGKGLEWVSSISGSGRDTLYAESVKGRFTISRDNAKTTLYLQMNSLRPEDT<br>AVYYCTIGGSLSVSSQGTLVTVSSHHHHHH** |
| 424 | ACP203 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgscdlpqtlmlinkraltllvqmrrlsplsclkdrkdfgfpqekvdaq<br>qikkagaipvlseltqqilniftskdssaawnifildsfcndlhqqlndlqgclmqqvgvqefpltqedallavrkyfhritv<br>ylrelcichspcawevvraevwralsssanylgrlreeksggpGPAGLYAQpgsEVQLVESGGGLVQP<br>GNSLRLSCAASGFTFSKFGMSWVRQAPGKGLEWVSSISGSGRDTLYAESVKG<br>RFTISRDNAKTTLYLQMNSLRPEDTAVYYCTIGGSLSVSSQGTLVTVSS** |
| 425 | ACP204 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS |

-continued

Sequence table

| SEQ ID NO. | Name | Sequence |
|---|---|---|
| | | SQGTLVTVSSsggpALFKSSFPpgscdlpqthnlinkraltllvqmrrlsplsclkdrkdfgfpqekvdaqqi<br>klcaqaipvlseltqqilniftskdssaawnttlldsfcndlhqqlndlqgclmqqvgvqefpltqedallavrkyfhrityyl<br>rekkhspcawevvraevwralsssanylgrlreeksggpALFKSSFPpgsEVQLVESGGGLVQPGNS<br>LRLSCAASGFTFSKFGMSWVRQAPGKGLEWVSSISGSGRDTLYAESVKGRFTI<br>SRDNAKTTLYLQMNSLRPEDTAVYYCTIGGSLSVSSQGTLVTVSS** |
| 426 | ACP205 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpPLAQKLKSSpgscdlpqthnlinkraltllvqmrrlsplsclkdrkdfgfpqekvdaq<br>qikkagaipvlseltqqilniftskdssaawnifildsfcndlhqqlndlqgclmqqvgvqefpltqedallavrkyfhritv<br>ylrelcichspcawevvraevwralsssanylgrlreeksggpPLAQKLKSSpgsEVQLVESGGGLVQP<br>GNSLRLSCAASGFTFSKFGMSWVRQAPGKGLEWVSSISGSGRDTLYAESVKG<br>RFTISRDNAKTTLYLQMNSLRPEDTAVYYCTIGGSLSVSSQGTLVTVSS** |
| 427 | ACP206 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgscdlpqthslgsrrtlmllaqmrrislfsclkdrhdfgfpqeefgnqf<br>qkaetipvlhemiqqifnlfstkdssaawdetlldkfytelyqqlndleacviqgvgvtetplmkedsilavrkyfqritlyl<br>kekkyspcawevvraeimrsfslstnlqesliskesggpGPAGLYAQpgsEVQLVESGGGLVQPGN<br>SLRLSCAASGFTFSKFGMSWVRQAPGKGLEWVSSISGSGRDTLYAESVKGRFT<br>ISRDNAKTTLYLQMNSLRPEDTAVYYCTIGGSLSVSSQGTLVTVSS** |
| 428 | ACP207 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgscdlpqthslgsrrtlmllaqmrrislfsclkdrhdfgfpqeefgnqfq<br>kaetipvlhemiqqifnlfstkdssaawdetlldkfytelyqqlndleacviqgvgvtetplmkedsilavrkyfqritlylk<br>ekkyspcawevvraeimrsfslstnlqesliskesggpALFKSSFPpgsEVQLVESGGGLVQPGNSL<br>RLSCAASGFTFSKFGMSWVRQAPGKGLEWVSSISGSGRDTLYAESVKGRFTIS<br>RDNAKTTLYLQMNSLRPEDTAVYYCTIGGSLSVSSQGTLVTVSS** |
| 429 | ACP208 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpPLAQKLKSSpgscdlpqthslgsrrtlmllaqmrrislfsclkdrhdfgfpqeefgnqf<br>qkaetipvlhemiqqifnlfstkdssaawdetlldkfytelyqqlndleacviqgvgvtetplmkedsilavrkyfqritlyl<br>kekkyspcawevvraeimrsfslstnlqesliskesggpPLAQKLKSSpgsEVQLVESGGGLVQPG<br>NSLRLSCAASGFTFSKFGMSWVRQAPGKGLEWVSSISGSGRDTLYAESVKGRF<br>TISRDNAKTTLYLQMNSLRPEDTAVYYCTIGGSLSVSSQGTLVTVSS** |
| 430 | ACP211 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGShgtviesleslnnyfnssgidveekslfldiwrnwqkdgdm<br>kilqsqiisfylrlfevlkdnqaisnnisvieshlittffsnskakkdafmsiakfevnnpqvqrqafnelirvvhqllpesslr<br>krkrsrcSGGPGPAGMKGLPGScdlpqthnlinkraltllvqmrrlsplsclkdrkclfgfpqekvdaqqikka<br>qaipvlseltqqilniftskdssaawnttlldsfcndlhqqlndlqgclmqqvgvqefpltqedallavrkyfhritvylrek<br>khspcawevvraevwralsssanvlgrlreekSGGPGPAGMKGLPGShgtviesleslnnyfnssgidveek<br>slfldiwrnwqkdgdmkilqsqiisfylrlfevlkdnqaisnnisvieshlittffsnskaldcdafmsiakfevnnpqvqr<br>qafnelirvvhqllpesshkrkrsrcSGGPGPAGMKGLPGSEVQLVESGGGLVQPGNSLRLS<br>CAASGFTFSKFGMSWVRQAPGKGLEWVSSISGSGRDTLYAESVKGRFTISRDN<br>AKTTLYLQMNSLRPEDTAVYYCTIGGSLSVSSQGTLVTVSSHHHHHH |
| 431 | ACP213 | lveepknlvktncdlyeklgeygfqnailviytqkapqvstptiveaarnlgrvgtkcctlpedqrlpcvedylsailnrvcl<br>lhektpvsehytkccsgslverrpcfsaltvdetyvpkefkaelftfhsdictlpekekqikkqtalaelvkhkpkataeqlk<br>tvmdclfaqfldtcckaadkdtcfstegpnlvtrckdalaSGGPGPAGMKGLPGShgtviesleslnnyfnssgi<br>dveekslfldiwrnwqkdgdmkilqsqiisfylrlfevlkdnqaisnnisvieshlittffsnskaldcdafmsiakfevnn<br>pqvqrqafnelirvvhqllpesshkrkrsrcSGGPGPAGMKGLPGSlveepknlvktncdlyeklgeygfqn<br>ailvlytqkapqvstptiveaarnlgrvgtkcctlpedqrlpcvedylsailnrycllhektpvsehvtkccsgslverrpcfs<br>altvdetyvpkefkaelft-fhsdictlpekekqikkqtalaelvklikpkataeqlktvmddfaqfldtcckaadkdtcfste<br>gpnlvtrckdalaSGGPGPAGMKGLPGShgtviesleslnnyfnssgidveekslfldiwrnwqkdgdmkil<br>qsqiisfylrlfevlkdnqaisnnisvieshlittffsnskakkdafmsiakfevnnpqvqrqafnelirvvhqllpesshkr<br>krsrcSGGPGPAGMKGLPGSlveepknlvktncdlyeklgeygfqnailviytqkapqvstptiveaarnlgr<br>vgtkcctlpedqrlpcvedylsailnrycllhektpvsehvtkccsgslverrpcfsaltvdetyvpkefkaelftfhsdictl<br>pekekqikkqtalaelvklikpkataeqlktvmddfaqfldtcckaadkdtcfstegpnlvtrckdalaHHHHHH** |
| 432 | ACP214 | eahkseialllyndlgeqhflcglvliafsqylqkcsydehaklvqevtdfaktcvadesaancdkslhtlfgdklcaipnlr<br>enygeladcctkqepernecflqhkddnpslppferpeaeamctsfkenpttfmghylhevarrhpyfyapellyyaeq<br>yneiltqccaeadkescltpkldgvkekalvssvrqGGGGSGGGGSGGSlveepknlvktncdlyeklgeygf<br>qnailvlytqkapqvstptiveaarnlgrvgtkcctlpedqrlpcvedylsailnrycllhektpvsehytkccsgslverrp<br>cfsaltvdetyvpkefkaetflfhsdictlpekekqikkqtalaelvkhkpkataeqlktvmddfaqfldtcckaadkdtcf<br>stegpnlvtrckdalaSGGPGPAGMKGLPGShgtviesleslnnyfnssgidveekslfldiwrnwqkdgdm<br>kilqsqiisfylrlfevlkdnqaisnnisvieshlittffsnskakkdafmsiakfevnnpqvqrqafnelirvvhqllpesslr<br>krkrsrcSGGPGPAGMKGLPGSeahkseialuyndlgeqhfkglvliafsqylqkcsydehaklvqevtdfa<br>ktcvadesaancdkslhtlfgdklcaipnlrenygeladcctkqepernecflqhkddnpslppferpeaeamctsfken<br>pttfmghylhevarrhpyfyapellyyaeqyneiltqccaeadkescltpkldgvkekalvssvrqGGGGSGGGG |

-continued

Sequence table

| SEQ ID NO. | Name | Sequence |
|---|---|---|
| | | SGGSlveepknlvktncdlyeklgeygfqnailviytqkapqvstptiveaarnlgrvgtkcctlpedqrlpcvedylsa<br>ilnrycllhektpvsehytkccsgslverrpcfsaltvdetyvpkefkaelftfhsdictlpekekqikkqtalaelvkhkpk<br>ataeqlktvmddfaqfldtcckaadkdtcfstegpnlvtrckdalaSGGPGPAGMKGLPGShgtviesleslnn<br>yfnssgidveekslfldiwrnwqkdgdmkilqsqiisfylrlfevlkdnqaisnnisvieshlittffsnskakkdafmsia<br>kfevnnpqvqrqafnelirvvhqllpesslrlukrsrcSGGPGPAGMKGLPGSeahkseiahryndlgeqhflc<br>glvliafsqylqkcsydehaklvqevtdfaktcvadesaancdkslhtlfgdklcaipnlrenygeladcctkqepernec<br>flqhkddnpslppferpeaeamctsfkenptlfmghylhevarrhpyfyapellyyaeqyneiltqccaeadkescltpk<br>ldukekalvssvrqGGGGSGGGGSGGSlveepknlvktncdlyeklgeygfqnailviytqkapqvstptiv<br>eaarnlgrvgtkcctlpedqrlpcvedylsailnrycllhektpvsehytkccsgslverrpcfsaltvdetyvpkefkaelft<br>fhsdictlpekekqikkqtalaelvkhkpkataeqlktvmddfaqfldtcckaadkdtcfstegpnlvtrckdalaHHH<br>HHH** |
| 433 | ACP215 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSggggsgggSGGPGPAGMKGLPGSggggsgggshgtviesleslnnyfnssgidvee<br>kslfldiwrnwqkdgdmkilqsqiisfylrlfevlkdnqaisnnisvieshlittffsnskakkdafmsiakfevnnpqvq<br>rqafnelirvvhqllpesshkrkrsrcggggsgggSGGPGPAGMKGLPGSggggsgggsEVQLVESG<br>GGLVQPGNSLRLSCAASGFTFSKFGMSWVRQAPGKGLEWVSSISGSGRDTLY<br>AESVKGRFTISRDNAKTTLYLQMNSLRPEDTAVYYCTIGGSLSVSSQGTLVTV<br>SSggggsgggSGGPGPAGMKGLPGSggggsgggshgtviesleslnnyfnssgidveekslfldiwrnwq<br>kdgdmkilqsqiisfylrlfevlkdnqaisnnisvieshlitlffsnskaldcdafmsiakfevnnpqvqrqafneffivvhq<br>llpesshkrkrsrcggggsgggSGGPGPAGMKGLPGSggggsgggsEVQLVESGGGLVQPGN<br>SLRLSCAASGFTFSKFGMSWVRQAPGKGLEWVSSISGSGRDTLYAESVKGRFT<br>ISRDNAKTTLYLQMNSLRPEDTAVYYCTIGGSLSVSSQGTLVTVSSHHHHHH*<br>* |
| 434 | ACP240 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSggggsggggsggggsiwelkkdvyvveldwypdapgemvvltcdtpeedgitwtldqssevl<br>gsgktltiqvkefgdagqytchkggevlshsllllhkkedgiwstdilkdqkepknktflrceaknysgrftcwwlttistd<br>llfsvkssrgssdpqgvtcgaatlsaervrgdnkeyeysvecqedsacpaaeeslpievmvdavhklkyenytssffirdi<br>ikpdppknlqlkplknsrqvevsweypdtwstphsyfsitfcvqvqgkskrekkdrvftdkisatvicrknasisvraqd<br>iyyssswsewasvpcsggggsggggsggggsrvipvsgparclsqsrnllkttddmvktareklkhysctaedidhedi<br>trdqtstlktclplelhknesclatretssttrgsclppqktslmmticlgsiyedlkmyqtefqainaalqnhnhqqiildkg<br>mlvaidelmqslnhngetlrqkppvgeadpyrvkmklcillhafstryvtimvmgylssaggggsggggsggggsg<br>gggsggggsggggsggggsggggsggggsQSVLTQPPSVSGAPGQRVTISCSGSRSNIGSNT<br>VKWYQQLPGTAPKLLIYYNDQRPSGVPDRFSGSKSGTSASLAITGLQAEDEAD<br>YYCQSYDRYTHPALLFGTGTKVTVLggggsggggsggggsQVQLVESGGGVVQPGR<br>SLRLSCAASGFTFSSYGMHWVRQAPGKGLEWVAFIRYDGSNKYYADSVKGR<br>FTISRDNSKNTLYLQMNSLRAEDTAVYYCKTHGSHDNWGQGTMVTVSSHHH<br>HHH |
| 435 | ACP241 | EAHKSEIAHRYNDLGEQHFKGLVLIAFSQYLQKCSYDEHAKLVQEVTDFAKT<br>CVADESAANCDKSLHTLFGDKLCAIPNLRENYGELADCCTKQEPERNECFLQH<br>KDDNPSLPPFERPEAEAMCTSFKENPTTFMGHYLHEVARRHPYFYAPELLYYA<br>EQYNEILTQCCAEADKESCLTPKLDGVKEKALVSSVRQRMKCSSMQKFGERA<br>FKAWAVARLSQTFPNADFAEITKLATDLTKVNKECCHGDLLECADDRAELAK<br>YMCENQATISSKLQTCCDKPLLKKAHCLSEVEHDTMPADLPAIAADFVEDQE<br>VCKNYAEAKDVFLGTFLYEYSRRHPDYSVSLLLRLAKKYEATLEKCCAEANP<br>PACYGTVLAEFQPLVEEPKNLVKTNCDLYEKLGEYGFQNAILVRYTQKAPQV<br>STPTLVEAARNLGRVGTKCCTLPEDQRLPCVEDYLSAILNRVCLLHEKTPVSE<br>HVTKCCSGSLVERRPCFSALTVDETYVPKEFKAETFTFHSDICTLPEKEKQIKK<br>QTALAELVKHKPKATAEQLKTVMDDFAQFLDTCCKAADKDTCFSTEGPNLVT<br>RCKDALASGGPGPAGMKGLPGSiwelkkdvyvveldwypdapgemvvitcdtpeedgitwadqs<br>sevlgsgktltiqvkefgdagqytchkggevlshsllllhkkedgiwstdilkdqkepknktflrceaknysgrftcwwltt<br>istdltfsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsltfcvqvqgkskrekkdrvftdktsatvicrknasisv<br>raqthyyssswsewasvpcsggggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstryvtinrvmgylssaSGGPGPAG<br>MKGLPGSggggsggggsggggsggggsggggsggggsQSVLTQPPSVSGAPGQRVTISCSGS<br>RSNIGSNTVKWYQQLPGTAPKLLIYYNDQRPSGVPDRFSGSKSGTSASLAITGL<br>QAEDEADYYCQSYDRYTHPALLFGTGTKVTVLggggsggggsggggsQVQLVESGG<br>GVVQPGRSLRLSCAASGFTFSSYGMHWVRQAPGKGLEWVAFIRYDGSNKYY<br>ADSVKGRFTISRDNSKNTLYLQMNSLRAEDTAVYYCKTHGSHDNWGQGTMV<br>TVSSHHHHHH** |
| 436 | ACP242 | iwelkkdvyvveldwypdapgemvvitcdtpeedgitwtldqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfsltkvqvqgkskrekkdivftdktsatvicrknasisvraqchyyssswsewasvpcsggggsggggsgg<br>ggsrvipvsgparclsqsrnllkttddmvktareklkhysctaedidheditrdqtstlktclplelhknesclatretss<br>ttrgsclppqktslmmticlgsiyedlkmyqtefqainaalqnhnhqqiildkgmlvaidelmqslnhngetlrqkppvgead |

-continued

Sequence table

| SEQ ID NO. | Name | Sequence |
|---|---|---|
| | | pyrvkmklcillhafstryvtinrvmgylssaSGGPGPAGMKGLPGSggggsggggsggggsggggsggg<br>gsggggsQSVLTQPPSVSGAPGQRVTISCSGSRSNIGSNTVKWYQQLPGTAPKLLI<br>YYNDQRPSGVPDRFSGSKSGTSASLAITGLQAEDEADYYCQSYDRYTHPALLF<br>GTGTKVTVLggggsggggsggggsQVQLVESGGGVVQPGRSLRLSCAASGFTFSSYG<br>MHWVRQAPGKGLEWVAFIRYDGSNKYYADSVKGRFTISRDNSKNTLYLQMN<br>SLRAEDTAVYYCKTHGSHDNWGQGTMVTVSSSGGPGPAGMKGLPGSEAHKS<br>EIAHRYNDLGEQHFKGLVLIAFSQYLQKCSYDEHAKLVQEVTDFAKTCVADE<br>SAANCDKSLHTLFGDKLCAIPNLRENYGELADCCTKQEPERNECFLQHKDDNP<br>SLPPFERPEAEAMCTSFKENPTTFMGHYLHEVARRHPYFYAPELLYYAEQYNE<br>ILTQCCAEADKESCLTPKLDGVKEKALVSSVRQRMKCSSMQKFGERAFKAWA<br>VARLSQTFPNADFAEITKLATDLTKVNKECCHGDLLECADDRAELAKYMCEN<br>QATISSKLQTCCDKPLLKKAHCLSEVEHDTMPADLPAIAADFVEDQEVCKNY<br>AEAKDVFLGTFLYEYSRRHPDYSVSLLLRLAKKYEATLEKCCAEANPPACYG<br>TVLAEFQPLVEEPKNLVKTNCDLYEKLGEYGFQNAILVRYTQKAPQVSTPTLV<br>EAARNLGRVGTKCCTLPEDQRLPCVEDYLSAILNRVCLLHEKTPVSEHVTKCC<br>SGSLVERRPCFSALTVDETYVPKEFKAETFTFHSDICTLPEKEKQIKKQTALAEL<br>VKHKPKATAEQLKTVMDDFAQFLDTCCKAADKDTCFSTEGPNLVTRCKDAL<br>AHHHHHH** |
| 437 | ACP243 | vprdcgckpcictypevssvfifppkpkdvititltpkvtcvvvdiskddpevqfswfvddvevhtaqtqpreeqfnstf<br>rsyselpimhqdwingkefkcrynsaafpapiektisktkgrpkapqvytipppkeqmakdkvsltcmitclffpeditv<br>ewqwngqpaenykntqpimdtdgsyfvyskinvqksnweagniftcsvlheglhnhhtekslshspgkSGGPG<br>PAGMKGLPGSiwellckdvyvveldwypdapgemvvitcdtpeedgitwtldqssevlgsgktltiqvkefgda<br>gqytchkggevlshsllllhkkedgiwstdilkdqkepknktflrceaknysgrftcwwlttistdltfsvkssrgssdpqg<br>vtcgaatlsaervrgdnkeyeysvecqedsacpaaeeslpievmvdavhklkyenytssffirdiikpdppknlqlkplk<br>nsrqvevsweypdtwstphsyfsltfcvqvqgkskrekkdrvftdktsatvicrknasisvraqthyyssswsewasvp<br>csggggsggggsggggsrvipvsgparclsqsrifilkttddmvktareklkhysctaedidheditrdqtstlktclplelh<br>knesclatretssttrgsclppqktslmmticlgsiyedlkmyqtefqainaalqnhnhqqiildkgmlvaidelmqslnh<br>ngetlrqkppvgeadpyrvkmklcillhafstrvvtinrvmgylssaSGGPGPAGMKGLPGSggggsgggg<br>sggggsggggsggggsggggsQSVLTQPPSVSGAPGQRVTISCSGSRSNIGSNTVKWYQ<br>QLPGTAPKLLIYYNDQRPSGVPDRFSGSKSGTSASLAITGLQAEDEADYYCQS<br>YDRYTHPALLFGTGTKVTVLggggsggggsggggsQVQLVESGGGVVQPGRSLRLS<br>CAASGFTFSSYGMHWVRQAPGKGLEWVAFIRYDGSNKYYADSVKGRFTISRD<br>NSKNTLYLQMNSLRAEDTAVYYCKTHGSHDNWGQGTMVTVSSHHHHHH** |
| 438 | ACP244 | iwelkkdvyvveldwypdapgemvvitcdtpeedgitwtldqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfsltkvqvqgkskrekkdwftdktsatvicrknasisvraqthyyssswsewasvpcsggggsggggsgg<br>ggsrvipvsgparclsqsrnllkttddmvktareklkhysctaedidheditrdqtstlktclplelhknesclatretsst<br>trgsclppqktslmmticlgsiyedlkmyqtefqainaalqnhnhqqiildkgmlvaidelmqslnhngetlrqkppvgead<br>pyrvkmklcillhafstrvvtinrvmgylssaSGGPGPAGMKGLPGSggggsggggsggggsggggsggg<br>gsggggsQSVLTQPPSVSGAPGQRVTISCSGSRSNIGSNTVKWYQQLPGTAPKLLI<br>YYNDQRPSGVPDRFSGSKSGTSASLAITGLQAEDEADYYCQSYDRYTHPALLF<br>GTGTKVTVLggggsggggsggggsQVQLVESGGGVVQPGRSLRLSCAASGFTFSSYG<br>MHWVRQAPGKGLEWVAFIRYDGSNKYYADSVKGRFTISRDNSKNTLYLQMN<br>SLRAEDTAVYYCKTHGSHDNWGQGTMVTVSSSGGPGPAGMKGLPGSvprdcgc<br>kpcictypevssvfifppkpkdvltitltpkvtcwvdiskddpevqfswfvddvevhtaqtqpreeqfnstfrsyselpi<br>mhqdwhigkefkcrynsaafpapiektisktkgrpkapqvytipppkeqmakdkvsltcmitdffpeditvewqwn<br>gqpaenykntqpimdtdgsyfvysklnvqksnweagntftcsvlheglhnhhtekslshspgkHHHHHH** |
| 439 | ACP245 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGSiwelkkdvyvveldwypdapgemvvltcdtpeedgitwtl<br>dqssevlgsgkiltiqvkefgdagqytchkggevlshsllllhkkedgiwstdilkdqkepknkffirceaknysgrftcw<br>wittistdiffsvkssrgssdpqgvtcgaatlsaervrgdnkeyeysvecqedsacpaaeeslpievmvdavhklkyeny<br>tssffirdiikpdppknlqlkplknsrqvevsweypdtwstphsyfsltkvqvqgkskrekkdrvftdktsatvicrkna<br>sisvraqthyyssswsewasvpcsggggsggggsggggsrvipvsgparclsqunllkttddmvktareklkhyscta<br>edidheditrdqtstlktclplelhknesclatretssttrgsclppqktslmmticlgsiyedlkmyqtefqainaalqnhnh<br>qqiildkgmlvaidelmqslnhngetlrqkppvgeadpyrvkmklcillhafstrvvtinrvmgylssaSGGPGPA<br>GMKGLPGSggggsggggsggggsggggsggggsggggsQSVLTQPPSVSGAPGQRVTISCS<br>GSRSNIGSNTVKWYQQLPGTAPKLLIYYNDQRPSGVPDRFSGSKSGTSASLAIT<br>GLQAEDEADYYCQSYDRYTHPALLFGTGTKVTVLSGGPGPAGMKGLPGSQV<br>QLVESGGGVVQPGRSLRLSCAASGFTFSSYGMHWVRQAPGKGLEWVAFIRYD<br>GSNKYYADSVKGRFTISRDNSKNTLYLQMNSLRAEDTAVYYCKTHGSHDNW<br>GQGTMVTVSSHHHHHH |
| 440 | ACP247 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPGPAGMKGLPGSiwelkkdvyvveldwypdapgemvvltcdtpeedgitwtl<br>dqssevlgsgkiltiqvkefgdagqytchkggevlshsllllhkkedgiwstdilkdqkepknkifirceaknysgrftcw<br>wittistdlifsvkssrgssdpqgvtcgaatlsaervrgdnkeyeysvecqedsacpaaeeslpievmvdavhklkyeny<br>tssffirdiikpdppknlqlkplknsrqvevsweypdtwstphsyfsltkvqvqgkskrekkdrvftdktsatvicrkna |

-continued

Sequence table

| SEQ ID NO. | Name | Sequence |
|---|---|---|
| | | sisvraqthyyssswsewasvpcsggggsggggsggggsrvipvsgparclsqsrnllkttddmvktareklkhyscta<br>edidheditrdqtstlktclplelhknesclatretssttrgsclppqktslmmticlgsiyedlkmyqtefqainaalqnhnh<br>qqiildkgmlvaidelmqslnhngetlrqkppvgeadpyrvkmklcillhafstrvvtinrvmgylssaSGGPGPA<br>GMKGLPGSggggsggggsggggsggggsggggsggggsQVQLQESGGGLVQAGGSLRLSC<br>AASGRTFSSVYDMGWFRQAPGKDREFVARITESARNTRYADSVRGRFTISRDN<br>AKNTVYLQMNNLELEDAAVYYCAADPQTVVVGTPDYWGQGTQVTVSSHHH<br>HHH |
| 636 | WW0301 | APTSSSTKKTQLQLEHLLLDLQMILNGINNYKNPKLTRMLTFKFYMPKKATEL<br>KHLQCLEEELKPLEEVLNLAQSKNFHLRPRDLISNINVIVLELKGSETTFMCEY<br>ADETATIVEFLNRWITFCQSIISTLTSGGPGPAGMKGLPGSEVQLVESGGGLVQ<br>PGNSLRLSCAASGFTFSKFGMSWVRQAPGKGLEWVSSISGSGRDTLYAESVKG<br>RFTISRDNAKTTLYLQMNSLRPEDTAVYYCTIGGSLSVSSQGTLVTVSSGGGGS<br>GGGGSGGGGSGGGGSGGGGSGGGGSGGGGSGGGGSGGGGSEVQLVESGGGL<br>VQPGGSLRLSCAASGFTFSSYTLAWVRQAPGKGLEWVAAIDSSSYTYSPDTVR<br>GRFTISRDNAKNSLYLQMNSLRAEDTAVYYCARDSNWDALDYWGQGTTVTV<br>SSGGGGSGGGGSGGGGSDIQMTQSPSSLSASVGDRVTITCKASQNVGTNVGW<br>YQQKPGKAPKALIYSASFRYSGVPSRFSGSGSGTDFTLTISSLQPEDFATYYCQ<br>QYYTYPYTFGGGTKVEIKHHHHHH |
| 637 | WW0353 | APTSSSTKKTQLQLEHLLLDLQMILNGINNYKNPKLTRMLTFKFYMPKKATEL<br>KHLQCLEEELKPLEEVLNLAQSKNFHLRPRDLISNINVIVLELKGSETTFMCEY<br>ADETATIVEFLNRWITFCQSIISTLTSGGPGPAGMKGLPGSVPRDCGCKPCICTV<br>PBVSSVFIFPPKPKDVLTITLTPKVTCVVVDISKDDPEVQFSWFVDDVEVHTAQ<br>TQPREEQFNSTFRSVSELPIMHQDWLNGKEFKCRVNSAAFPAPIEKTISKTKGR<br>PKAPQVYTIPPPKEQMAKDKVSLTCMITDFFPEDITVEWQWNGQPAENYKNT<br>QPIMDTDGSYFVYSKLNVQKSNWEAGNTFTCSVLHEGLHNHHTEKSLSHSPG<br>KGGGGSGGGGSGGGGSGGGGSGGGGSGGGGSSGGPGPAGMKGLPGSEVQLV<br>ESGGGLVQPGGSLRLSCAASGFTFSSYTLAWVRQAPGKGLEWVAAIDSSSYTY<br>SPDTVRGRFTISRDNAKNSLYLQMNSLRAEDTAVYYCARDSNWDALDYWGQ<br>GTTVTVSSGGGGSGGGGSGGGGSDIQMTQSPSSLSASVGDRVTITCKASQNVG<br>TNVGWYQQKPGKAPKALIYSASFRYSGVPSRFSGSGSGTDFTLTISSLQPEDFA<br>TYYCQQYYTYPYTFGGGTKVEIKHHHHHH |
| 638 | WW0355 | APTSSSTKKTQLQLEHLLLDLQMILNGINNYKNPKLTRMLTFKFYMPKKATEL<br>KHLQCLEEELKPLEEVLNLAQSKNFHLRPRDLISNINVIVLELKGSETTFMCEY<br>ADETATIVEFLNRWITFCQSIISTLTSGGPGPAGMKGLPGSGGGGSGGGGSGGG<br>GSGGGGSGGGGSGGGGSEVQLVESGGGLVQPGGSLRLSCAASGFTFSSYTLA<br>WVRQAPGKGLEWVAAIDSSSYTYSPDTVRGRFTISRDNAKNSLYLQMNSLRA<br>EDTAVYYCARDSNWDALDYWGQGTTVTVSSGGGGSGGGGSGGGGSDIQMT<br>QSPSSLSASVGDRVTITCKASQNVGTNVGWYQQKPGKAPKALIYSASFRYSGV<br>PSRFSGSGSGTDFTLTISSLQPEDFATYYCQQYYTYPYTFGGGTKVEIKSGGPG<br>PAGMKGLPGSVPRDCGCKPCICTVPEVSSVFIFPPKPKDVLTITLTPKVTCVVV<br>DISKDDPEVQFSWFVDDVEVHTAQTQPREEQFNSlFRSVSELPIMHQDWLNGK<br>EFKCRVNSAAFPAPIEKTISKTKGRPKAPQVYTIPPPKEQMAKDKVSLTCMITD<br>FFPEDITVEWQWNGQPAENYKNTQPIMDTDGSYFVYSKLNVQKSNWEAGNT<br>FTCSVLHEGLHNHHTEKSLSHSPGKHHHHHH |
| 639 | WW0365 | APTSSSTKKTQLQLEHLLLDLQMILNGINNYKNPKLTRMLTFKFYMPKKATEL<br>KHLQCLEEELKPLEEVLNLAQSKNFHLRPRDLISNINVIVLELKGSETTFMCEY<br>ADETATIVEFLNRWITFCQSIISTLTGGGSGGGSGGGSGGGSEVQLVESGGGLV<br>QPGNSLRLSCAASGFTFSKFGMSWVRQAPGKGLEWVSSISGSGRDTLYAESVK<br>GRFTISRDNAKTTLYLQMNSLRPEDTAVYYCTIGGSLSVSSQGTLVTVSSGGG<br>GSGGGGSGGGGSGGGGSGGGGSGGGGSSGGPGPAGMKGLPGSEVQLVESGG<br>GLVQPGGSLRLSCAASGFTFSSYTLAWVRQAPGKGLEWVAAIDSSSYTYSPDT<br>VRGRFTISRDNAKNSLYLQMNSLRAEDTAVYYCARDSNWDALDYWGQGTTV<br>TVSSGGGGSGGGGSGGGGSDIQMTQSPSSLSASVGDRVTITCKASQNVGTNVG<br>WYQQKPGKAPKALIYSASFRYSGVPSRFSGSGSGTDFTLTISSLQPEDFATYYC<br>QQYYTYPYTFGGGTKVEIKHHHHHHEPEA |
| 640 | WW0366 | APTSSSTKKTQLQLEHLLLDLQMILNGINNYKNPKLTRMLTFKFYMPKKATEL<br>KHLQCLEEELKPLEEVLNLAQSKNFHLRPRDLISNINVIVLELKGSETTFMCEY<br>ADETATIVEFLNRWITFCQSIISTLTSGGPGPAGMKGLPGSEVQLVESGGGLVQ<br>PGNSLRLSCAASGFTFSKFGMSWVRQAPGKGLEWVSSISGSGRDTLYAESVKG<br>RFTISRDNAKTTLYLQMNSLRPEDTAVYYCTIGGSLSVSSQGTLVTVSSHHHH<br>HHEPEA |
| 641 | WW0472 | VPRDCGCKPCICTVPEVSSVFIFPPKPKDVLTITLTPKVTCVVVDISKDDPEVQF<br>SWFVDDVEVHTAQTQPREEQFNSTFRSVSELPIMHQDWLNGKEFKCRVNSAA<br>FPAPIEKTISKTKGRPKAPQVYTIPPPKEQMAKDKVSLTCMITDFFPEDITVEWQ<br>WNGQPAENYKNTQPIMDTDGSYFVYSKLNVQKSNWEAGNTFTCSVLHEGLH<br>NHHTEKSLSHSPGKSGGPGPAGLYAQPGSAPTSSSTKKTQLQLEHLLLDLQMI<br>LNGINNYKNPKLTRMLTFKFYMPKKATELKHLQCLEEELKPLEEVLNLAQSK |

-continued

Sequence table

| SEQ ID NO. | Name | Sequence |
|---|---|---|
| | | NFHLRPRDLISNINVIVLELKGSETTFMCEYADETATIVEFLNRWITFCQSIISTL TGGGGSGGGGSGGGGSGGGGSGGGGSGGGGSSGGPGPAGLYAQPGSEVQLV ESGGGLVQPGGSLRLSCAASGFTFSSYTLAWVRQAPGKGLEWVAAIDSSSYTY SPDTVRGRFTISRDNAKNSLYLQMNSLRAEDTAVYYCARDSNWDALDYWGQ GTTVTVSSSGGPGPAGLYAQPGSDIQMTQSPSSLSASVGDRVTITCKAREKLW SAVAWYQQKPGKAPKSLIYSASFRYSGVPSRFSGSGSGTDFTLTISSLQPEDFA TYYCQQYYTYPYTFGGGTKVEIK |
| 642 | WW0473 | VPRDCGCKPCICTVPEVSSVFIFPPKPKDVLTITLTPKVTCVVVDISKDDPEVQF SWFVDDVEVHTAQTQPREEQFNSTFRSVSELPIMHQDWLNGKEFKCRVNSAA FPAPIEKTISKTKGRPKAPQVYTIPPPKEQMAKDKVSLTCMITDFFPEDITVEWQ WNGQPAENYKNTQPIMDTDGSYFVYSKLNVQKSNWEAGNTFTCSVLHEGLH NHHTEKSLSHSPGKSGGPGPAGLYAQPGSAPTSSSTKKTQLQLEHLLLDLQMI LNGINNYKNPKLTRMLTFKFYMPKKATELKHLQCLEEELKPLEEVLNLAQSK NFHLRPRDLISNINVIVLELKGSETTFMCEYADETATIVEFLNRWITFCQSIISTL TGGGGSGGGGSGGGGSGGGGSGGGGSGGGGSSGGPGPAGLYAQPGSEVQLV ESGGGLVQPGGSLRLSCAASGFTFSSYTLAWVRQAPGKGLEWVAAIDSSSYTY SPDTVRGRFTISRDNAKNSLYLQMNSLRAEDTAVYYCARDSNWDALDYWGQ GTTVTVSSGGGGSGGGGSGGGGSDIQMTQSPSSLSASVGDRVTITCKAREKLW SAVAWYQQKPGKAPKSLIYSASFRYSGVPSRFSGSGSGTDFTLTISSLQPEDFA TYYCQQYYTYPYTFGGGTKVEIK |
| 643 | WW0474 | VPRDCGCKPCICTVPEVSSVFIFPPKPKDVLTITLTPKVTCVVVDISKDDPEVQF SWFVDDVEVHTAQTQPREEQFNSTFRSVSELPIMHQDWLNGKEFKCRVNSAA FPAPIEKTISKTKGRPKAPQVYTIPPPKEQMAKDKVSLTCMITDFFPEDITVEWQ WNGQPAENYKNTQPIMDTDGSYFVYSKLNVQKSNWEAGNTFTCSVLHEGLH NHHTEKSLSHSPGKSGGPGPAGLYAQPGSAPTSSSTKKTQLQLEHLLLDLQMI LNGINNYKNPKLTRMLTFKFYMPKKATELKHLQCLEEELKPLEEVLNLAQSK NFHLRPRDLISNINVIVLELKGSETTFMCEYADETATIVEFLNRWITFCQSIISTL TGGGGSGGGGSGGGGSGGGGSGGGGSGGGGSSGGPGPAGLYAQPGSEVQLV ESGGGLVQPGGSLRLSCAASGFTFSSYTLAWVRQAPGKGLEWVAAIDSSSYTY SPDTVRGRFTISRDNAKNSLYLQMNSLRAEDTAVYYCARDSNWDALDYWGQ GTTVTVSSSGGPGPAGLYAQPGSDIQMTQSPSSLSASVGDRVTITCKVTEKVW GNVAWYQQKPGKAPISLIYSPSLRKSGVPSRFSGSGSGTDFTLTISSLQPEDFAT YYCQQYYTYPYTFGGGTKVEIK |
| 644 | WW0475 | VPRDCGCKPCICTVPEVSSVFIFPPKPKDVLTITLTPKVTCVVVDISKDDPEVQF SWFVDDVEVHTAQTQPREEQFNSTFRSVSELPIMHQDWLNGKEFKCRVNSAA FPAPIEKTISKTKGRPKAPQVYTIPPPKEQMAKDKVSLTCMITDFFPEDITVEWQ WNGQPAENYKNTQPIMDTDGSYFVYSKLNVQKSNWEAGNTFTCSVLHEGLH NHHTEKSLSHSPGKSGGPGPAGLYAQPGSAPTSSSTKKTQLQLEHLLLDLQMI LNGINNYKNPKLTRMLTFKFYMPKKATELKHLQCLEEELKPLEEVLNLAQSK NFHLRPRDLISNINVIVLELKGSETTFMCEYADETATIVEFLNRWITFCQSIISTL TGGGGSGGGGSGGGGSGGGGSGGGGSGGGGSSGGPGPAGLYAQPGSEVQLV ESGGGLVQPGGSLRLSCAASGFTFSSYTLAWVRQAPGKGLEWVAAIDSSSYTY SPDTVRGRFTISRDNAKNSLYLQMNSLRAEDTAVYYCARDSNWDALDYWGQ GTTVTVSSGGGGSGGGGSGGGGSDIQMTQSPSSLSASVGDRVTITCKVTEKV WGNVAWYQQKPGKAPISLIYSPSLRKSGVPSRFSGSGSGTDFTLTISSLQPEDF ATYYCQQYYTYPYTFGGGTKVEIK |
| 645 | WW0476 | VPRDCGCKPCICTVPEVSSVFIFPPKPKDVLTITLTPKVTCVVVDISKDDPEVQF SWFVDDVEVHTAQTQPREEQFNSTFRSVSELPIMHQDWLNGKEFKCRVNSAA FPAPIEKTISKTKGRPKAPQVYTIPPPKEQMAKDKVSLTCMITDFFPEDITVEWQ WNGQPAENYKNTQPIMDTDGSYFVYSKLNVQKSNWEAGNTFTCSVLHEGLH NHHTEKSLSHSPGKSGGPGPAGLYAQPGSAPTSSSTKKTQLQLEHLLLDLQMI LNGINNYKNPKLTRMLTFKFYMPKKATELKHLQCLEEELKPLEEVLNLAQSK NFHLRPRDLISNINVIVLELKGSETTFMCEYADETATIVEFLNRWITFCQSIISTL TGGGGSGGGGSGGGGSGGGGSGGGGSGGGGSSGGPGPAGLYAQPGSEVQLL ESGGGLVQPGGSLRLSCAASGSIFSANAMGWYRQAPGKGLELVAVISSGGSTN YADSVKGRFTISRDNSKNTVYLQMNSLRAEDTAVYYCMYSGSYYYTPNDYW GQGTLVTVSS |
| 646 | WW0477 | VPRDCGCKPCICTVPEVSSVFIFPPKPKDVLTITLTPKVTCVVVDISKDDPEVQF SWFVDDVEVHTAQTQPREEQFNSTFRSVSELPIMHQDWLNGKEFKCRVNSAA FPAPIEKTISKTKGRPKAPQVYTIPPPKEQMAKDKVSLTCMITDFFPEDITVEWQ WNGQPAENYKNTQPIMDTDGSYFVYSKLNVQKSNWEAGNTFTCSVLHEGLH NHHTEKSLSHSPGKSGGPGPAGLYAQPGSAPTSSSTKKTQLQLEHLLLDLQMI LNGINNYKNPKLTRMLTFKFYMPKKATELKHLQCLEEELKPLEEVLNLAQSK NFHLRPRDLISNINVIVLELKGSETTFMCEYADETATIVEFLNRWITFCQSIISTL TGGGGSGGGGSGGGGSGGGGSGGGGSGGGGSSGGPGPAGLYAQPGSEVQLL ESGGGLVQPGGSLRLSCAASERIFSTDVMGWYRQAPGKQRELVAVVSARGTT NYLDAVKGRFTISRDNSKNTLYLQMNSLRAEDTAVYYCYVRETTSPWRIYWG QGTLVTVSS |

-continued

Sequence table

| SEQ ID NO. | Name | Sequence |
| --- | --- | --- |
| 647 | WW0649 Monomeric IL-12 (chimeric) poly-peptide, anti-HSA sdAb, scFv Blocker, 2 cleavage sites | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsgGPAGLYAQpgsiwelkkdvyvveldwypdapgemvvltcdtpeedgitwildqs<br>sevlgsgktltiqvkefgdagqytchkggevlshslllhldcedgiwstdilkdqkepluildflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdiyysssswsewasvpcsggggsggggsggggsrvipvsgparclsqsrnllkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSRSN<br>IGSNTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYDGSNKYYADS<br>VKGRFTISRDNSKNTLYLQMNSLRAEDTAVYYCKTHGSHDNWGQGTMVTVS<br>S** |
| 454 | WW0650 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwildqs<br>sevlgsgktltiqvkefgdagqytchkggevlshslllhldcedgiwstdilkdqkepluildflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdiyysssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGSNTVKWYQQLPGTAPKLLIYYNDQRPSGVPDRFSGSKSGTSASLAITG<br>LQAEDEADYYCQSYDRYTHPALLFGTGTKVTVLggggsggggsggggsQVQLVESG<br>GGVVQPGRSLRLSCAASGFTFSSYGMHWVRQAPGKGLEWVAFIRYDGSNKY<br>YADSVKGRFTISRDNSKNTLYLQMNSLRAEDTAVYYCKTHGSHDNWGQGTM<br>VTVSS** |
| 455 | WW0651 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvitcdtpeedgitwildqss<br>evlgsglaltiqvkefgdagqytchkggevlshsllllhkkedgiwstdilkdqkepknktflrceaknysgrftcwwltti<br>stdiffsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsitfcvqvqgkskrekkdrvftdktsatvicrknasisvr<br>aqdiyysssswsewasvpcsggggsggggsggggsrvipvsgparclsqsrnllkttddmvktareklkhysctaedid<br>heditrdqtstlktclplelhknesclatretssttrgsclppqktslmmticlgsiyedlkmyqtefqainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsggggsQSVLTQPPSVSGAPGQRVTISCSGSRSNI<br>GSNTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYDGSNKYYADS<br>VKGRFTISRDNSKNTLYLQMNSLRAEDTAVYYCKTHGSHDNWGQGTMVTVS<br>S** |
| 456 | WW0652 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvitcdtpeedgitwildqss<br>evlgsglaltiqvkefgdagqytchkggevlshsllllhkkedgiwstdilkdqkepknktflrceaknysgrftcwwltti<br>stdiffsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsitfcvqvqgkskrekkdrvftdktsatvicrknasisvr<br>aqdiyysssswsewasvpcsggggsggggsggggsrnlpvatpdpgmfpclhhsqnllraysnmlqkarqtlefypct<br>seeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpALFK<br>SSFPpgsggggsggggsggggsggggsggggsggggsQSVLTQPPSVSGAPGQRVTISCSGSRS<br>NIGSNTVKWYQQLPGTAPKLLIYYNDQRPSGVPDRFSGSKSGTSASLAITGLQ<br>AEDEADYYCQSYDRYTHPALLFGTGTKVTVLggggsggggsggggsQVQLVESGGG<br>VVQPGRSLRLSCAASGFTFSSYGMHWVRQAPGKGLEWVAFIRYDGSNKYYA<br>DSVKGRFTISRDNSKNTLYLQMNSLRAEDTAVYYCKTHGSHDNWGQGTMVT<br>VSS** |
| 457 | WW0662 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvitcdtpeedgitwtldqs<br>sevlgsgktltiqvkefgdagqytchkggevlshsllllhIckedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsltfcvqvqgkskrekkdrvftdktsatvicrknasisv<br>raqchyysssswsewasvpcsggggsggggsggggsrvipvsgparclsqsrffilkttddmvktareklkhysctaedi<br>dheditrdqtstlktclplelhknesclatretssttrgsclppqktslmmticlgsiyedlkmyqtefqainaalqnhnhqqi |

-continued

Sequence table

| SEQ ID NO. | Name | Sequence |
| --- | --- | --- |
| | | ildkgmlvaidelmqslnhngethqkppvgeadpyrvkmklcillhafstryvtinrvmgylssasggpGPAGLY<br>AQpgsggggsggggsggggsggggsggggsggggsQSVLTQPPSVSGAPGQRVTISCSGSRSN<br>IGSNTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeGSNKYYAeSV<br>KGRFTISRDNSKNTLYLQMNSLRAEDTAVYYCKTHGSHDNWGQGTMVTVSS<br>** |
| 458 | WW0663 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvitcdtpeedgitwtldqs<br>sevlgsgktltiqvkefgdagqytchkggevlshslllhIckedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsltfcvqvqgkskrekkdrvftdktsatvicrknasisv<br>raqchyyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalcissiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGSNTVKWYQQLPGTAPKLLIYYNDQRPSGVPDRFSGSKSGTSASLAITG<br>LQAEDEADYYCQSYDRYTHPALLFGTGTKVTVLggggsggggsggggsQVQLVESG<br>GGVVQPGRSLRLSCAASGFTFSSYGMHWVRQAPGKGLEWVAFIRYeGSNKYY<br>AeSVKGRFTISRDNSKNTLYLQMNSLRAEDTAVYYCKTHGSHDNWGQGTMV<br>TVSS** |
| 459 | WW0664 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvitcdtpeedgitwtldqs<br>sevlgsgktltiqvkefgdagqytchkggevlshslllhIckedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsltfcvqvqgkskrekkdrvftdktsatvicrknasisv<br>raqchyyssswsewasvpcsggggsggggsggggsrvipvsgparclsqsrffilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngethqkppvgeadpyrvkmklcillhafstryvtinrvmgylssasggpGPAGLY<br>AQpgsggggsggggsggggsggggsggggsggggsQSVLTQPPSVSGAPGQRVTISCSGSRSN<br>IGSeTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeGSNKYYAeSV<br>KGRFTISRDNSKNTLYLQMNSLRAEDTAVYYCKTHGSHDNWGQGTMVTVSS<br>** |
| 460 | WW0665 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvitcdtpeedgitwtldqs<br>sevlgsgktltiqvkefgdagqytchkggevlshslllhIckedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsltfcvqvqgkskrekkdrvftdktsatvicrknasisv<br>raqchyyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalcissiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGSeTVKWYQQLPGTAPKLLIYYNDQRPSGVPDRFSGSKSGTSASLAITG<br>LQAEDEADYYCQSYDRYTHPALLFGTGTKVTVLggggsggggsggggsQVQLVESG<br>GGVVQPGRSLRLSCAASGFTFSSYGMHWVRQAPGKGLEWVAFIRYeGSNKYY<br>AeSVKGRFTISRDNSKNTLYLQMNSLRAEDTAVYYCKTHGSHDNWGQGTMV<br>TVSS** |
| 461 | WW0666 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSRSN<br>IGdNTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeGSNKYYAeSV<br>KGRFTISRDNSKNTLYLQMNSLRAEDTAVYYCKTHGSHDNWGQGTMVTVSS<br>** |

-continued

Sequence table

| SEQ ID NO. | Name | Sequence |
|---|---|---|
| 462 | WW0667 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGdNTVKWYQQLPGTAPKLLIYYNDQRPSGVPDRFSGSKSGTSASLAITG<br>LQAEDEADYYCQSYDRYTHPALLFGTGTKVTVLggggsggggsggggsQVQLVESG<br>GGVVQPGRSLRLSCAASGFTFSSYGMHWVRQAPGKGLEWVAFIRYeGSNKYY<br>AeSVKGRFTISRDNSKNTLYLQMNSLRAEDTAVYYCKTHGSHDNWGQGTMV<br>TVSS** |
| 463 | WW0668 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSRSN<br>IGdeTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYDGSNKYYADS<br>VKGRFTISRDNSKNTLYLQMNSLRAEDTAVYYCKTHGSHDNWGQGTMVTVS<br>S** |
| 464 | WW0669 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGdeTVKWYQQLPGTAPKLLIYYNDQRPSGVPDRFSGSKSGTSASLAITG<br>LQAEDEADYYCQSYDRYTHPALLFGTGTKVTVLggggsggggsggggsQVQLVESG<br>GGVVQPGRSLRLSCAASGFTFSSYGMHWVRQAPGKGLEWVAFIRYDGSNKY<br>YADSVKGRFTISRDNSKNTLYLQMNSLRAEDTAVYYCKTHGSHDNWGQGTM<br>VTVSS** |
| 465 | WW0670 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSRSN<br>IGdeTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeGSNKYYAeSV<br>KGRFTISRDNSKNTLYLQMNSLRAEDTAVYYCKTHGSHDNWGQGTMVTVSS<br>** |
| 466 | WW0671 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm |

-continued

Sequence table

| SEQ ID NO. | Name | Sequence |
|---|---|---|
| | | dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGdeTVKWYQQLPGTAPKLLIYYNDQRPSGVPDRFSGSKSGTSASLAITG<br>LQAEDEADYYCQSYDRYTHPALLFGTGTKVTVLggggsggggsggggsQVQLVESG<br>GGVVQPGRSLRLSCAASGFTFSSYGMHWVRQAPGKGLEWVAFIRYeGSNKYY<br>AeSVKGRFTISRDNSKNTLYLQMNSLRAEDTAVYYCKTHGSHDNWGQGTMV<br>TVSS** |
| 467 | WW0672 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryysssswsewasvpcsggggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSeSN<br>IGSNdVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYDGSNKYYADS<br>VKGRFTISRDNSKNTLYLQMNSLRAEDTAVYYCKTHGSHDNWGQGTMVTVS<br>S** |
| 468 | WW0673 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryysssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SeSNIGSNdVKWYQQLPGTAPKLLIYYNDQRPSGVPDRFSGSKSGTSASLAITG<br>LQAEDEADYYCQSYDRYTHPALLFGTGTKVTVLggggsggggsggggsQVQLVESG<br>GGVVQPGRSLRLSCAASGFTFSSYGMHWVRQAPGKGLEWVAFIRYDGSNKY<br>YADSVKGRFTISRDNSKNTLYLQMNSLRAEDTAVYYCKTHGSHDNWGQGTM<br>VTVSS** |
| 469 | WW0674 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryysssswsewasvpcsggggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSRSN<br>IGeNTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeGSNKYYAeSV<br>KGRFTISRDNSKNTLYLQMNSLRAEDTAVYYCKTHGSHDNWGQGTMVTVSS<br>** |
| 470 | WW0675 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryysssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGeNTVKWYQQLPGTAPKLLIYYNDQRPSGVPDRFSGSKSGTSASLAITG<br>LQAEDEADYYCQSYDRYTHPALLFGTGTKVTVLggggsggggsggggsQVQLVESG<br>GGVVQPGRSLRLSCAASGFTFSSYGMHWVRQAPGKGLEWVAFIRYeGSNKYY<br>AeSVKGRFTISRDNSKNTLYLQMNSLRAEDTAVYYCKTHGSHDNWGQGTMV<br>TVSS** |

-continued

Sequence table

| SEQ ID NO. | Name | Sequence |
|---|---|---|
| 471 | WW0676 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSRSN<br>IGeeTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYDGSNKYYADS<br>VKGRFTISRDNSKNTLYLQMNSLRAEDTAVYYCKTHGSHDNWGQGTMVTVS<br>S** |
| 472 | WW0677 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsltfcvqvqgkskrekkdrvftdktsatvicrknasisv<br>raqdryyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalcissiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGeeTVKWYQQLPGTAPKLLIYYNDQRPSGVPDRFSGSKSGTSASLAITGL<br>QAEDEADYYCQSYDRYTHPALLFGTGTKVTVLggggsggggsggggsQVQLVESGG<br>GVVQPGRSLRLSCAASGFTFSSYGMHWVRQAPGKGLEWVAFIRYDGSNKYY<br>ADSVKGRFTISRDNSKNTLYLQMNSLRAEDTAVYYCKTHGSHDNWGQGTMV<br>TVSS** |
| 473 | WW0678 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvitcdtpeedgitwtldqs<br>sevlgsgktltiqvkefgdagqytchkggevlshslllhIckedgiwstdilkdqkepknktflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsltfcvqvqgkskrekkdrvftdktsatvicrknasisv<br>raqdryyssswsewasvpcsggggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstryvtinrvmgylssasggpGPAGLY<br>AQpgsggggsggggsggggsggggsggggsggggsQSVLTQPPSVSGAPGQRVTISCSGSRSN<br>IGSeTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeGSNKYYADSV<br>KGRFTISRDNSKNTLYLQMNSLRAEDTAVYYCKTHGSHDNWGQGTMVTVSS<br>** |
| 474 | WW0679 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvitcdtpeedgitwtldqs<br>sevlgsgktltiqvkefgdagqytchkggevlshslllhIckedgiwstdilkdqkepknktflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsltfcvqvqgkskrekkdrvftdktsatvicrknasisv<br>raqdryyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalcissiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGSeTVKWYQQLPGTAPKLLIYYNDQRPSGVPDRFSGSKSGTSASLAITG<br>LQAEDEADYYCQSYDRYTHPALLFGTGTKVTVLggggsggggsggggsQVQLVESG<br>GGVVQPGRSLRLSCAASGFTFSSYGMHWVRQAPGKGLEWVAFIRYeGSNKYY<br>ADSVKGRFTISRDNSKNTLYLQMNSLRAEDTAVYYCKTHGSHDNWGQGTMV<br>TVSS** |
| 475 | WW0680 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvitcdtpeedgitwtldqss<br>evlgsgktltiqvkefgdagqytchkggevlshslllhkkedgiwstdilkdqkepknktflrceaknysgrftcwwltti<br>stdiffsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdryyssswsewasvpcsggggsggggsggggsrvipvsgparclsqsrnllkttddmvktareklkhysctaedid<br>heditrdqtstlktclplelhknesclatretssttrgsclppqktslmmticlgsiyedlkmyqtefqainaalqnhnhqqiil |

-continued

Sequence table

| SEQ ID NO. | Name | Sequence |
|---|---|---|
| | | dkgmlvaidelmqslnhngetlrqkppvgeadpyrvkmklcillhafstryvtinrvmgylssasggpALFKSSF<br>PpgsggggsggggsggggsggggsggggsggggsqsVLTQPPSVSGAPGQRVTISCSGSRSNI<br>GSNTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeGSNKYYAeSV<br>KGRFTISRDNSKNTLYLQMNSLRAEDTAVYYCKTHGSHDNWGQGTMVTVSS<br>** |
| 476 | WW0681 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshslllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqthyyssswsewasvpcsggggsggggsggggsrnlpvatpdpgmfpclhhsqnllraysnmlqkarqtlefypct<br>seeidheditkdktstveaclplelltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpALFK<br>SSFPpgsggggsggggsggggsggggsggggsggggsQSVLTQPPSVSGAPGQRVTISCSGSRS<br>NIGSNTVKWYQQLPGTAPKLLIYYNDQRPSGVPDRFSGSKSGTSASLAITGLQ<br>AEDEADYYCQSYDRYTHPALLFGTGTKVTVLggggsggggsggggsQVQLVESGGG<br>VVQPGRSLRLSCAASGFTFSSYGMHWVRQAPGKGLEWVAFIRYeGSNKYYAe<br>SVKGRFTISRDNSKNTLYLQMNSLRAEDTAVYYCKTHGSHDNWGQGTMVTV<br>ss** |
| 477 | WW0682 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshslllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqthyyssswsewasvpcsggggsggggsggggsrvipvsgparclsqsrnllkttddmvktareklkhysctaedid<br>heditrdqtstlktclplelhknesclatretssttrgsclppqktslmmticlgsiyedlkmyqtefciainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsggggsqsVLTQPPSVSGAPGQRVTISCSGSRSNI<br>GSeTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeGSNKYYAeSV<br>KGRFTISRDNSKNTLYLQMNSLRAEDTAVYYCKTHGSHDNWGQGTMVTVSS |
| ** | | |
| 635 | WW0683 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshslllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqthyyssswsewasvpcsggggsggggsggggsrnlpvatpdpgmfpclhhsqnllraysnmlqkarqtlefypct<br>seeidheditkdktstveaclplelltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpALFK<br>SSFPpgsggggsggggsggggsggggsggggsggggsQSVLTQPPSVSGAPGQRVTISCSGSRS<br>NIGSeTVKWYQQLPGTAPKLLIYYNDQRPSGVPDRFSGSKSGTSASLAITGLQA<br>EDEADYYCQSYDRYTHPALLFGTGTKVTVLggggsggggsggggsQVQLVESGGGV<br>VQPGRSLRLSCAASGFTFSSYGMHWVRQAPGKGLEWVAFIRYeGSNKYYAeS<br>VKGRFTISRDNSKNTLYLQMNSLRAEDTAVYYCKTHGSHDNWGQGTMVTVS<br>S** |
| 478 | WW0684 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshslllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqthyyssswsewasvpcsggggsggggsggggsrvipvsgparclsqsrnllkttddmvktareklkhysctaedid<br>heditrdqtstlktclplelhknesclatretssttrgsclppqktslmmticlgsiyedlkmyqtefciainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsggggsqsVLTQPPSVSGAPGQRVTISCSGSRSNI<br>GdNTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeGSNKYYAeSV<br>KGRFTISRDNSKNTLYLQMNSLRAEDTAVYYCKTHGSHDNWGQGTMVTVSS<br>** |

-continued

Sequence table

| SEQ ID NO. | Name | Sequence |
|---|---|---|
| 479 | WW0685 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshslllllhkkedgiwstdilkdqkepknktflrceaknysgrftcwwltti<br>stdllfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdlyyssswsewasvpcsggggsggggsggggsrnlpvatpdpgmfpclhhsqnllraysnmlqkarqtlefypct<br>seeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpALFK<br>SSFPpgsggggsggggsggggsggggsggggsggggsQSVLTQPPSVSGAPGQRVTISCSGSRS<br>NIGdNTVKWYQQLPGTAPKLLIYYNDQRPSGVPDRFSGSKSGTSASLAITGLQA<br>EDEADYYCQSYDRYTHPALLFGTGTKVTVLggggsggggsggggsQVQLVESGGGV<br>VQPGRSLRLSCAASGFTFSSYGMHWVRQAPGKGLEWVAFIRYeGSNKYYAeS<br>VKGRFTISRDNSKNTLYLQMNSLRAEDTAVYYCKTHGSHDNWGQGTMVTVS<br>S** |
| 480 | WW0686 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshslllllhkkedgiwstdilkdqkepknktflrceaknysgrftcwwltti<br>stdllfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdlyyssswsewasvpcsggggsggggsggggsrvipvsgparclsqsrnllkttddmvktareklkhysctaedid<br>heditrdqtstlktclplelhknesclatretssttrgsclppqktslmmticlgsiyedlkmyqtefqainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsggggsQSVLTQPPSVSGAPGQRVTISCSGSRSNI<br>GdeTVKWYQQLPGTAPKLLIYYNDQRPSGVPDRFSGSKSGTSASLAITGLQAED<br>EADYYCQSYDRYTHPALLFGTGTKVTVLggggsggggsggggsQVQLVESGGGVVQ<br>PGRSLRLSCAASGFTFSSYGMHWVRQAPGKGLEWVAFIRYDGSNKYYADSV<br>KGRFTISRDNSKNTLYLQMNSLRAEDTAVYYCKTHGSHDNWGQGTMVTVSS<br>** |
| 481 | WW0687 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshslllllhkkedgiwstdilkdqkepknktflrceaknysgrftcwwltti<br>stdllfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdlyyssswsewasvpcsggggsggggsggggsrnlpvatpdpgmfpclhhsqnllraysnmlqkarqtlefypct<br>seeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpALFK<br>SSFPpgsggggsggggsggggsggggsggggsggggsQSVLTQPPSVSGAPGQRVTISCSGSRS<br>NIGdeTVKWYQQLPGTAPKLLIYYNDQRPSGVPDRFSGSKSGTSASLAITGLQA<br>EDEADYYCQSYDRYTHPALLFGTGTKVTVLggggsggggsggggsQVQLVESGGGV<br>VQPGRSLRLSCAASGFTFSSYGMHWVRQAPGKGLEWVAFIRYDGSNKYYAD<br>SVKGRFTISRDNSKNTLYLQMNSLRAEDTAVYYCKTHGSHDNWGQGTMVTV<br>SS** |
| 482 | WW0688 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshslllllhkkedgiwstdilkdqkepknktflrceaknysgrftcwwltti<br>stdllfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdlyyssswsewasvpcsggggsggggsggggsrvipvsgparclsqsrnllkttddmvktareklkhysctaedid<br>heditrdqtstlktclplelhknesclatretssttrgsclppqktslmmticlgsiyedlkmyqtefqainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsggggsQSVLTQPPSVSGAPGQRVTISCSGSRSNI<br>GdeTVKWYQQLPGTAPKLLIYYNDQRPSGVPDRFSGSKSGTSASLAITGLQAED<br>EADYYCQSYDRYTHPALLFGTGTKVTVLggggsggggsggggsQVQLVESGGGVVQ<br>PGRSLRLSCAASGFTFSSYGMHWVRQAPGKGLEWVAFIRYeGSNKYYAeSVK<br>GRFTISRDNSKNTLYLQMNSLRAEDTAVYYCKTHGSHDNWGQGTMVTVSS** |
| 483 | WW0689 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvitcdtpeedgitwtldqss<br>evlgsgktltiqvkefgdagqytchkggevlshslllllhlckedgiwstdilkdqkepknklflrceaknysgrftcwwltti<br>stdiffsvkssrgssdpqgvtcgaatlsaervrgdnkeyeysvecqedsacpaaeeslpievmvdavhklkyenytssff<br>irdiikpdppknlqlkplknsrqvevsweypdtwstphsyfslIfcvqvqgkskrekkdryftdktsatvicrknasisvr<br>aqdwyssswsewasvpcsggggsggggsggggsrnlpvatpdpgmfpclhhsqnllraysnmlqkarqtlefypct<br>seeidheditkdktstveaclpleltknesclnsretsfitngsclasrktsfmmalclssiyedllunyqveflamnakllm<br>dpkrqindqnmlavidelmqalnfnsetvpqkssleepdfyktkiklcillhafriravtidrvmsylnassggpALFK |

-continued

Sequence table

| SEQ ID NO. | Name | Sequence |
|---|---|---|
| | | SSFPpgsggggsggggsggggsggggsggggsggggsQSVLTQPPSVSGAPGQRVTISCSGSRS<br>NIGdeTVKWYQQLPGTAPKLLIYYNDQRPSGVPDRFSGSKSGTSASLAITGLQA<br>EDEADYYCQSYDRYTHPALLFGTGTKVTVLggggsggggsggggsQVQLVESGGGV<br>VQPGRSLRLSCAASGFTFSSYGMHWVRQAPGKGLEWVAFIRYeGSNKYYAeS<br>VKGRFTISRDNSKNTLYLQMNSLRAEDTAVYYCKTHGSHDNWGQGTMVTVS<br>S** |
| 484 | WW0690 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvitcdtpeedgitwtldqss<br>evlgsgktltiqvkefgdagqytchkggevlshsllllhlckedgiwstdilkdqkepknklflrceaknysgrftcwwltti<br>stdiffsvkssrgssdpqgvtcgaatlsaervrgdnkeyeysvecqedsacpaaeeslpievmvdavhklkyenytssff<br>irdiikpdppknlqlkplknsrqvevsweypdtwstphsyfslIfcvqvqgkskrekkdryftdktsatvicrknasisvr<br>aqdwyssswsewasvpcsggggsggggsggggsrvipvsgparclsqsnillkttddmvktareklkhysctaedid<br>heditrdqtstlktclplelhknesclatretssttrgsclppqktslmmticlgsiyedlkmyqtefriainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsggggsQSVLTQPPSVSGAPGQRVTISCSGSeSNIG<br>SNdVKWYQQLPGTAPKLLIYYNDQRPSGVPDRFSGSKSGTSASLAITGLQAED<br>EADYYCQSYDRYTHPALLFGTGTKVTVLggggsggggsggggsQVQLVESGGGVVQ<br>PGRSLRLSCAASGFTFSSYGMHWVRQAPGKGLEWVAFIRYDGSNKYYADSV<br>KGRFTISRDNSKNTLYLQMNSLRAEDTAVYYCKTHGSHDNWGQGTMVTVSS<br>** |
| 485 | WW0691 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvitcdtpeedgitwtldqss<br>evlgsgktltiqvkefgdagqytchkggevlshsllllhlckedgiwstdilkdqkepknklflrceaknysgrftcwwltti<br>stdiffsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsiticvqvqgkskrekkdryftdktsatvicrknasisvr<br>aqdwyssswsewasvpcsggggsggggsggggsrnlpvatpdpgmfpclhhsqnllraysnmlqkarqtlefypct<br>seeidheditkdktstveaclpleltknesclnsretsfitngsclasrktsfmmalclssiyedllunyqveflamnakllm<br>dpkrqindqnmlavidelmqalnfnsetvpqkssleepdfyktkiklcillhafriravtidrvmsylnassggpALFK<br>SSFPpgsggggsggggsggggsggggsggggsggggsQSVLTQPPSVSGAPGQRVTISCSGSeS<br>NIGSNdVKWYQQLPGTAPKLLIYYNDQRPSGVPDRFSGSKSGTSASLAITGLQA<br>EDEADYYCQSYDRYTHPALLFGTGTKVTVLggggsggggsggggsQVQLVESGGGV<br>VQPGRSLRLSCAASGFTFSSYGMHWVRQAPGKGLEWVAFIRYDGSNKYYAD<br>SVKGRFTISRDNSKNTLYLQMNSLRAEDTAVYYCKTHGSHDNWGQGTMVTV<br>SS** |
| 486 | WW0692 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvitcdtpeedgitwtldqss<br>evlgsgktltiqvkefgdagqytchkggevlshsllllhlckedgiwstdilkdqkepknklflrceaknysgrftcwwltti<br>stdiffsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsiticvqvqgkskrekkdryftdktsatvicrknasisvr<br>aqdwyssswsewasvpcsggggsggggsggggsrvipvsgparclsqsnillkttddmvktareklkhysctaedid<br>heditrdqtstlktclplelhknesclatretssttrgsclppqktslmmticlgsiyedlkmyqtefriainaalqnhnhqqiil<br>dkgmlvaidelmqslnhngethqkppvgeadpyrvkmklcillhafstryvtinrvmgylssasggpALFKSSF<br>PpgsggggsggggsggggsggggsggggsggggsQSVLTQPPSVSGAPGQRVTISCSGSRSNI<br>GeNTVKWYQQLPGTAPKLLIYYNDQRPSGVPDRFSGSKSGTSASLAITGLQAE<br>DEADYYCQSYDRYTHPALLFGTGTKVTVLggggsggggsggggsQVQLVESGGGVV<br>QPGRSLRLSCAASGFTFSSYGMHWVRQAPGKGLEWVAFIRYeGSNKYYAeSV<br>KGRFTISRDNSKNTLYLQMNSLRAEDTAVYYCKTHGSHDNWGQGTMVTVSS<br>** |
| 487 | WW0693 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvitcdtpeedgitwtldqss<br>evlgsgktltiqvkefgdagqytchkggevlshsllllhkkedgiwstdilkdqkepknktflrceaknysgrftcwwltti<br>stcliffsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqchyyssswsewasvpcsggggsggggsggggsrnlpvatpdpgmfpclhhsqnllraysnmlqkarqtlefypct<br>seeidheditkdktstveaclpleltknesclnsretsfitngsclasrktsfmmalclssiyedllunyqveflamnakllm<br>dpkrqifldqnmlavidelmqalnfnsetvpqkssleepdfyktkiklcillhafriravtidrvmsylnassggpALFK<br>SSFPpgsggggsggggsggggsggggsggggsggggsQSVLTQPPSVSGAPGQRVTISCSGSRS<br>NIGeNTVKWYQQLPGTAPKLLIYYNDQRPSGVPDRFSGSKSGTSASLAITGLQA<br>EDEADYYCQSYDRYTHPALLFGTGTKVTVLggggsggggsggggsQVQLVESGGGV<br>VQPGRSLRLSCAASGFTFSSYGMHWVRQAPGKGLEWVAFIRYeGSNKYYAeS<br>VKGRFTISRDNSKNTLYLQMNSLRAEDTAVYYCKTHGSHDNWGQGTMVTVS<br>S** |
| 488 | WW0694 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS |

Sequence table

| SEQ ID NO. | Name | Sequence |
|---|---|---|
| | | SQGTLVTVSSsggpALFKSSFPpgsiwelkkdvyvveldwypdapgemvvitcdtpeedgitwtldqss evlgsgktltiqvkefgdagqytchkggevlshsllllhkkedgiwstdilkdqkepknktflrceaknysgrftcwwltti stcliffsvkssrgssdpqgvtcgaatlsaervrgdnkeyeysvecqedsacpaaeeslpievmvdavhklkyenytssff irdiikpdppknlqlkplknsrqvevsweypdtwstphsyfsltfcvqvqgkskrekkdrvftdktsatvicrknasisvr aqchyyssswsewasvpcsggggsggggsggggsrvipvsgparclsqsmllkttddmvktareklkhysctaedid heditrdqtstlktclplelhknesclatretssttrgsclppqktslmmticlgsiyedlkmyqtefqainaalqnhnhqqiil dkgmlvaidelmqslnhngethqkppvgeadpyrvkmklcillhafstryvtinrvmgylssasggpALFKSSF PpgsggggsggggsggggsggggsggggsQSVLTQPPSVSGAPGQRVTISCSGSRSNI GeeTVKWYQQLPGTAPKLLIYYNDQRPSGVPDRFSGSKSGTSASLAITGLQAED EADYYCQSYDRYTHPALLFGTGTKVTVLggggsggggsggggsQVQLVESGGGVVQ PGRSLRLSCAASGFTFSSYGMHWVRQAPGKGLEWVAFIRYDGSNKYYADSV KGRFTISRDNSKNTLYLQMNSLRAEDTAVYYCKTHGSHDNWGQGTMVTVSS \*\* |
| 489 | WW0695 | GSGRDTLYAESVKGRFTIEVQLVESGGGLVQPGNSLRLSCAASGFTFSKFGMSWVRQAPGKGLEWVSSIS SRDNAKTTLYLQMNSLRPEDTAVYYCTIGGSLSVS SQGTLVTVSSsggpALFKSSFPpgsiwelkkdvyvveldwypdapgemvvitcdtpeedgitwtldqss evlgsgktltiqvkefgdagqytchkggevlshsllllhkkedgiwstdilkdqkepknktflrceaknysgrftcwwltti stcliffsvkssrgssdpqgvtcgaatlsaervrgdnkeyeysvecqedsacpaaeeslpievmvdavhklkyenytssff irdiikpdppknlqlkplknsrqvevsweypdtwstphsyfsltfcvqvqgkskrekkdrvftdktsatvicrknasisvr aqchyyssswsewasvpcsggggsggggsggggsrnlpvatpdpgmfpclhhsqnllraysnmlqkarqtlefypct seeidheditkdktstveaclplelktknesclnsretsfitngsclasrktsfmmalclssiyedllunyqveflamnakllm dpkrqifldqnmlavidelmqalnfnsetvpqkssleepdfyktkiklcillhafriravtidrvmsylnassggpALFK SSFPpgsggggsggggsggggsggggsggggsggggsQSVLTQPPSVSGAPGQRVTISCSGSRS NIGeeTVKWYQQLPGTAPKLLIYYNDQRPSGVPDRFSGSKSGTSASLAITGLQA EDEADYYCQSYDRYTHPALLFGTGTKVTVLggggsggggsggggsQVQLVESGGGV VQPGRSLRLSCAASGFTFSSYGMHWVRQAPGKGLEWVAFIRYDGSNKYYAD SVKGRFTISRDNSKNTLYLQMNSLRAEDTAVYYCKTHGSHDNWGQGTMVTV SS\*\* |
| 490 | WW0696 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpALFKSSFPpgsiwelkkdvyvveldwypdapgemvvitcdtpeedgitwtldqss evlgsgktltiqvkefgdagqytchkggevlshsllllhkkedgiwstdilkdqkepknktflrceaknysgrftcwwltti stcliffsvkssrgssdpqgvtcgaatlsaervrgdnkeyeysvecqedsacpaaeeslpievmvdavhklkyenytssff irdiikpdppknlqlkplknsrqvevsweypdtwstphsyfsitfcvqvqgkskrekkdrvftdktsatvicrknasisvr aqdlyyssswsewasvpcsggggsggggsggggsrvipvsgparclsqsrnllkttddmvktareklkhysctaedid heditrdqtstlktclplelhknesclatretssttrgsclppqktslmmticlgsiyedlkmyqtefciainaalqnhnhqqiil dkgmlvaidelmqslnhngetlrqkppvgeadpyrvkmklcillhafstrvvtinrvmgylssasggpALFKSSF PpgsggggsggggsggggsggggsggggsggggsQSVLTQPPSVSGAPGQRVTISCSGSRSNI GSeTVKWYQQLPGTAPKLLIYYNDQRPSGVPDRFSGSKSGTSASLAITGLQAE DEADYYCQSYDRYTHPALLFGTGTKVTVLggggsggggsggggsQVQLVESGGGVV QPGRSLRLSCAASGFTFSSYGMHWVRQAPGKGLEWVAFIRYeGSNKYYADSV KGRFTISRDNSKNTLYLQMNSLRAEDTAVYYCKTHGSHDNWGQGTMVTVSS \*\* |
| 491 | WW0697 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpALFKSSFPpgsiwelkkdvyvveldwypdapgemvvlicdtpeedgitwtldqss evlgsgktltiqvkefgdagqytchkggevlshsllllhkkedgiwstdilkdqkepknktflrceaknysgrftcwwltti stdiffsvkssrgssdpqgvtcgaatlsaervrgdnkeyeysvecqedsacpaaeeslpievmvdavhklkyenytssff irdiikpdppknlqlkplknsrqvevsweypdtwstphsyfsitfcvqvqgkskrekkdrvftdktsatvicrknasisvr aqdlyyssswsewasvpcsggggsggggsggggsrnlpvatpdpgmfpclhhsqnllraysnmlqkarqtlefypct seeidheditkdktstveaclplelktknesclnsretsfitngsclasrktsfmmalclssiyedlkmyqvefktmnakllm dpkrqifldqnmlavidelmqalnfnsetvpqkssleepdfyktkiklcillhafriravtidrvmsylnassggpALFK SSFPpgsggggsggggsggggsggggsggggsggggsQSVLTQPPSVSGAPGQRVTISCSGSRS NIGSeTVKWYQQLPGTAPKLLIYYNDQRPSGVPDRFSGSKSGTSASLAITGLQA EDEADYYCQSYDRYTHPALLFGTGTKVTVLggggsggggsggggsQVQLVESGGGV VQPGRSLRLSCAASGFTFSSYGMHWVRQAPGKGLEWVAFIRYeGSNKYYADS VKGRFTISRDNSKNTLYLQMNSLRAEDTAVYYCKTHGSHDNWGQGTMVTVS S\*\* |
| 492 | WW0698 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSsggpGPAGLYAQpgsiwelkkdvyvveldwypdapgemvvltcdtpeedgitwtldqs sevlgsgktltiqvkefgdagqytchkggevlshsllllhkkedgiwstdilkdqkepknkiflrceaknysgrftcwwltt istdlifsvkssrgssdpqgvtcgaatlsaervrgdnkeyeysvecqedsacpaaeeslpievmvdavhklkyenytssf firdiikpdppknlqlkplknsrqvevsweypdtwstphsyfsitfcvqvqgkskrekkdrvftdktsatvicrknasisv raqdlyyssswsewasvpcsggggsggggsggggsrvipvsgparclsqsrifilkttddmvktareklkhysctaedi dheditrdqtstlktclplelhknesclatretssttrgsclppqktslmmticlgsiyedlkmyqtefqainaalqnhnhqqi ildkgmlvaidelmqslnhngetlrqkppvgeadpyrvkmklcillhafstrvvtinrvmgylssasggpGPAGLY AQpgsggggsggggsggggsggggsggggsggggsggggsQSVLTQPPSVSGAPGQRVTISCSGSRSN IGSNTVKWYQQLPGTAPKLLIYYNDQRPSGVPDRFSGSKSGTSASLAITGLQAE |

-continued

Sequence table

| SEQ ID NO. | Name | Sequence |
|---|---|---|
| | | DEADYYCQSYDRYTHPALLFGTGTKVTVLgqpkaapsvtlfppsseelqankatlyclisdfypg<br>avtvawkadsspvkagvettlpskqsnnkyaassylsltpeqwkshrsyscqvthegstvektvaptecs** |
| 493 | WW0699 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdlyyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGSNTVKWYQQLPGTAPKLLIYYNDQRPSGVPDRFSGSKSGTSASLAITG<br>LQAEDEADYYCQSYDRYTHPALLFGTGTKVTVLgqpkaapsvtlfppsseelqankatlycli<br>sdfypgavtvawkadsspvkagvettlpskqsnnkyaassylsltpeqwkshrsyscqvthegstvektvaptecs** |
| 494 | WW0700 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkiflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSRSN<br>IGSeTVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlyclisdfypg<br>avtvawkadsspvkagvettlpskqsnnkyaassylsltpeqwkshrsyscqvthegstvektvaptecs** |
| 495 | WW0701 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkffirceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGSeTVKWYQQLPGTAPKLLIYYNDQRPSGVPDRFSGSKSGTSASLAITG<br>LQAEDEADYYCQSYDRYTHPALLFGTGTKVTVLgqpkaapsvtlfppsseelqankatlycli<br>sdfypgavtvawkadsspvkagvettlpskqsnnkyaassylsltpeqwkshrsyscqvthegstvektvaptecs** |
| 496 | WW0702 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkffirceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSRSN<br>IGdNTVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlyclisdfypg<br>avtvawkadsspvkagvettlpskqsnnkyaassylsltpeqwkshrsyscqvthegstvektvaptecs** |
| 497 | WW0703 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkffirceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfslIfcvqvqgkskrekkdrvftdktsatvicrknasisv<br>raqdryyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGdNTVKWYQQLPGTAPKLLIYYNDQRPSGVPDRFSGSKSGTSASLAITG<br>LQAEDEADYYCQSYDRYTHPALLFGTGTKVTVLgqpkaapsvtlfppsseelqankatlycli<br>sdfypgavtvawkadsspvkagvettlpskqsnnkyaassylsltpeqwkshrsyscqvthegstvektvaptecs** |

-continued

Sequence table

| SEQ ID NO. | Name | Sequence |
|---|---|---|
| 498 | WW0704 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknkffirceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSRSN<br>IGdeTVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlyclisdfypg<br>avtvawkadsspvkagvettlpskqsnnkyaassylsltpeqwkshrsyscqvthegstvektvaptecs** |
| 499 | WW0705 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknktflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGdeTVKWYQQLPGTAPKLLIYYNDQRPSGVPDRFSGSKSGTSASLAITG<br>LQAEDEADYYCQSYDRYTHPALLFGTGTKVTVLgqpkaapsvtlfppsseelqankatlycli<br>sdfypgavtvawkadsspvkagvettlpskqsnnkyaassylsltpeqwkshrsyscqvthegstvektvaptecs** |
| 500 | WW0706 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknktflrceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSeSN<br>IGSNdVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlyclisclfypg<br>avtvawkadsspvkagvettlpskqsnnkyaassylsltpeqwkshrsyscqvthegstvektvaptecs** |
| 501 | WW0707 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknkffirceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SeSNIGSNdVKWYQQLPGTAPKLLIYYNDQRPSGVPDRFSGSKSGTSASLAITG<br>LQAEDEADYYCQSYDRYTHPALLFGTGTKVTVLgqpkaapsvtlfppsseelqankatlycli<br>sdfypgavtvawkadsspvkagvettlpskqsnnkyaassylsltpeqwkshrsyscqvthegstvektvaptecs** |
| 502 | WW0708 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshslllhkkedgiwstdilkdqkepknkffirceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqdryyssswsewasvpcsggggsggggsggggsrvipvsgparclsqsrifilkttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSRSN<br>IGeNTVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlyclisdfypg<br>avtvawkadsspvkagvettlpskqsnnkyaassylsltpeqwkshrsyscqvthegstvektvaptecs** |
| 503 | WW0709 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs |

Sequence table

| SEQ ID NO. | Name | Sequence |
|---|---|---|
| | | sevlgsgktltiqvkefgdagqytchkggevlshsllllhkkedgiwstdilkdqkepknkffirceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqthyyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGeNTVKWYQQLPGTAPKLLIYYNDQRPSGVPDRFSGSKSGTSASLAITG<br>LQAEDEADYYCQSYDRYTHPALLFGTGTKVTVLgqpkaapsvtlfppsseelqankatlycli<br>sdfypgavtvawkadsspvkagvettlpskqsnnkyaassylsltpeqwkshrsyscqvthegstvektvaptecs** |
| 504 | WW0710 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkffirceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqthyyssswsewasvpcsggggsggggsggggsrvipvsgparclsqsrnllktttddmvktareklkhysctaedi<br>dheditrdqtstlktclplelhknesclatretssttrgsclppqktslmmticlgsiyedlkmyqtefqainaalqnhnhqqi<br>ildkgmlvaidelmqslnhngetlrqkppvgeadpyrvkmklcillhafstrvvtinrvmgylssasggpGPAGLY<br>AQpgsggggsggggsggggsggggsggggsggggsQSVLTQPPSVSGAPGQRVTISCSGSRSN<br>IGeeTVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlycliscifypg<br>avtvawkadsspvkagvettlpskqsnnkyaassylsltpeqwkshrsyscqvthegstvektvaptecs** |
| 505 | WW0711 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpGPAGLYAQpgsiwelkkdvyvveldwypdapgemvvltcdtpeedgitwtldqs<br>sevlgsgktltiqvkefgdagqytchkggevlshsllllhkkedgiwstdilkdqkepknkffirceaknysgrftcwwltt<br>istdlifsvkssrgssdpqgvtcgaatlsaervrgdnkeyeysvecqedsacpaaeeslpievmvdavhklkyenytssf<br>firdiikpdppknlqlkplknsrqvevsweypdtwstphsyfsitfcvqvqgkskrekkdrvftdktsatvicrknasisv<br>raqthyyssswsewasvpcsggggsggggsggggsrnlpvatpdpgmfpclhhsqnllraysnmlqkarqtlefypc<br>tseeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpGPA<br>GLYAQpgsggggsggggsggggsggggsggggsggggsQSVLTQPPSVSGAPGQRVTISCSG<br>SRSNIGeeTVKWYQQLPGTAPKLLIYYNDQRPSGVPDRFSGSKSGTSASLAITGL<br>QAEDEADYYCQSYDRYTHPALLFGTGTKVTVLgqpkaapsvtlfppsseelqankatlyclis<br>dfypgavtvawkadsspvkagvettlpskqsnnkyaassylsltpeqwkshrsyscqvthegstvektvaptecs** |
| 506 | WW0712 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvltcdtpeedgitwtldqss<br>evlgsgktltiqvkefgdagqytchkggevlshsllllhkkedgiwstdilkdqkepknktflrceaknysgrftcwwltti<br>stdiffsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsitfcvqvqgkskrekkdrvftdktsatvicrknasisvr<br>aqthyyssswsewasvpcsggggsggggsggggsrvipvsgparclsqsrnllktttddmvktareklkhysctaedid<br>heditrdqtstlktclplelhknesclatretssttrgsclppqktslmmticlgsiyedlkmyqtefciainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsggggsgggggsQSVLTQPPSVSGAPGQRVTISCSGSRSNI<br>GSNTVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlycliscifypg<br>avtvawkadsspvkagvettlpskqsnnkyaassylsltpeqwkshrsyscqvthegstvektvaptecs** |
| 507 | WW0713 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshsllllhkkedgiwstdilkdqkepknktflrceaknysgrftcwwltti<br>stdllfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdfyyssswsewasvpcsggggsggggsggggsrnlpvatpdpgmfpclhhsqnllraysnmlqkarqtlefypct<br>seeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpALFK<br>SSFPpgsggggsggggsggggsggggsggggsggggsQSVLTQPPSVSGAPGQRVTISCSGSRS<br>NIGSNTVKWYQQLPGTAPKLLIYYNDQRPSGVPDRFSGSKSGTSASLAITGLQ<br>AEDEADYYCQSYDRYTHPALLFGTGTKVTVLgqpkaapsvtlfppsseelqankatlycliscif<br>ypgavtvawkadsspvkagvetttpskqsnnkyaassylsltpeqwkshrsyscqvthegstvektvaptecs** |
| 508 | WW0714 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshsllllhkkedgiwstdilkdqkepknktflrceaknysgrftcwwltti<br>stdllfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr |

-continued

Sequence table

| SEQ ID NO. | Name | Sequence |
| --- | --- | --- |
| | | aqdfyyssswsewasvpcsggggsggggsggggsrvipvsgparclsqsrfdlkttddmvktareklkhysctaedid<br>heditrdqtstlktclplelhknesclatretssttrgsclppqktslmmticlgsiyedlkmyqtefciainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsggggsQSVLTQPPSVSGAPGQRVTISCSGSRSNI<br>GSeTVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlycliscifypg<br>avtvawkadsspvkagvettlpskqsnnkyaassylsltpeqwkshrsyscqvthegstvektvaptecs** |
| 509 | WW0715 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshsllllhkkedgiwstdilkdqkepknktflrceaknysgrftcwwltti<br>stdllfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdfyyssswsewasvpcsggggsggggsggggsrnlpvatpdpgmfpclhhsqnllraysnmlqkarqtlefypct<br>seeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpALFK<br>SSFPpgsggggsggggsggggsggggsggggsggggsQSVLTQPPSVSGAPGQRVTISCSGSRS<br>NIGSeTVKWYQQLPGTAPKLLIYYNDQRPSGVPDRFSGSKSGTSASLAITGLQA<br>EDEADYYCQSYDRYTHPALLFGTGTKVTVLgqpkaapsvtlfppsseelqankatlyclisdfyp<br>gavtvawkadsspvkagvetttpskqsnnkyaassylsltpeqwkshrsyscqvthegstvektvaptecs** |
| 510 | WW0716 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshsllllhkkedgiwstdilkdqkepknktflrceaknysgrftcwwltti<br>stdllfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdfyyssswsewasvpcsggggsggggsggggsrvipvsgparclsqsrfdlkttddmvktareklkhysctaedid<br>heditrdqtstlktclplelhknesclatretssttrgsclppqktslmmticlgsiyedlkmyqtefciainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsggggsQSVLTQPPSVSGAPGQRVTISCSGSRSNI<br>GdNTVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlyclisdfypg<br>avtvawkadsspvkagvettlpskqsnnkyaassylsltpeqwkshrsyscqvthegstvektvaptecs** |
| 511 | WW0717 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshsllllhkkedgiwstdilkdqkepknktflrceaknysgrftcwwltti<br>stdllfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdlyyssswsewasvpcsggggsggggsggggsrnlpvatpdpgmfpclhhsqnllraysnmlqkarqtlefypct<br>seeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpALFK<br>SSFPpgsggggsggggsggggsggggsggggsggggsQSVLTQPPSVSGAPGQRVTISCSGSRS<br>NIGdNTVKWYQQLPGTAPKLLIYYNDQRPSGVPDRFSGSKSGTSASLAITGLQA<br>EDEADYYCQSYDRYTHPALLFGTGTKVTVLgqpkaapsvtlfppsseelqankatlyclisdfyp<br>gavtvawkadsspvkagvetttpskqsnnkyaassylsltpeqwkshrsyscqvthegstvektvaptecs** |
| 512 | WW0718 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshsllllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdlyyssswsewasvpcsggggsggggsggggsrvipvsgparclsqsrnllkttddmvktareklkhysctaedid<br>heditrdqtstlktclplelhknesclatretssttrgsclppqktslmmticlgsiyedlkmyqtefciainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsggggsQSVLTQPPSVSGAPGQRVTISCSGSRSNI<br>GdeTVKWYQQLPGTAPKLLIYYNDQRPSGVPDRFSGSKSGTSASLAITGLQAED<br>EADYYCQSYDRYTHPALLFGTGTKVTVLgqpkaapsvtlfppsseelqankativclisdfypga<br>vtvawkadsspvkagvetttpskqsnnkyaassylsltpeqwkshrsyscqvthegstvektvaptecs** |
| 513 | WW0719 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshsllllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdlyyssswsewasvpcsggggsggggsggggsrnlpvatpdpgmfpclhhsqnllraysnmlqkarqtlefypct<br>seeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpALFK |

-continued

Sequence table

| SEQ ID NO. | Name | Sequence |
|---|---|---|
| | | SSFPpgsggggsggggsggggsggggsggggsggggsQSVLTQPPSVSGAPGQRVTISCSGSRS<br>NIGdeTVKWYQQLPGTAPKLLIYYNDQRPSGVPDRFSGSKSGTSASLAITGLQA<br>EDEADYYCQSYDRYTHPALLFGTGTKVTVLgqpkaapsvtlfppsseelqankatlyclisdfyp<br>gavtvawkadsspvkagvetttpskqsnnkyaassylsltpeqwkshrsyscqvthegstvektvaptecs** |
| 514 | WW0720 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshslllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdlyyssswsewasvpcsggggsggggsggggsrvipvsgparclsqsrnllkttddmvktareklkhysctaedid<br>heditrdqtstlktclplelhknesclatretssttrgsclppqktslmmticlgsiyedlkmyqtefqainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsggggsQSVLTQPPSVSGAPGQRVTISCSGSeSNIG<br>SNdVKWYQQLPGTAPKLLIYYNDQRPSGVPDRFSGSKSGTSASLAITGLQAED<br>EADYYCQSYDRYTHPALLFGTGTKVTVLgqpkaapsvtlfppsseelqankativclisdfypga<br>vtvawkadsspvkagvetttpskqsnnkyaassylsltpeqwkshrsyscqvthegstvektvaptecs** |
| 515 | WW0721 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshslllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdlyyssswsewasvpcsggggsggggsggggsrnlpvatpdpgmfpclhhsqnllraysnmlqkarqtlefypct<br>seeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpALFK<br>SSFPpgsggggsggggsggggsggggsggggsggggsQSVLTQPPSVSGAPGQRVTISCSGSeS<br>NIGSNdVKWYQQLPGTAPKLLIYYNDQRPSGVPDRFSGSKSGTSASLAITGLQA<br>EDEADYYCQSYDRYTHPALLFGTGTKVTVLgqpkaapsvtlfppsseelqankatlyclisdfyp<br>gavtvawkadsspvkagvetttpskqsnnkyaassylsltpeqwkshrsyscqvthegstvektvaptecs** |
| 516 | WW0722 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsgALFKSSFPpgsiwelkkdvyvveldwypdapgemvvlicdtpeedgitwtldqss<br>evlgsgktltiqvkefgdagqytchkggevlshslllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdlyyssswsewasvpcsggggsggggsggggsrvipvsgparclsqsrnllkttddmvktareklkhysctaedid<br>heditrdqtstlktclplelhknesclatretssttrgsclppqktslmmticlgsiyedlkmyqtefciainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsggggsQSVLTQPPSVSGAPGQRVTISCSGSRSNI<br>GeNTVKWYQQLPGTAPKLLIYYNDQRPSGVPDRFSGSKSGTSASLAITGLQAE<br>DEADYYCQSYDRYTHPALLFGTGTKVTVLgqpkaapsvtlfppsseelqankatlyclisdfypg<br>avtvawkadsspvkagvettlpskqsnnkyaassylsltpeqwkshrsyscqvthegstvektvaptecs** |
| 517 | WW0723 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshslllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdlyyssswsewasvpcsggggsggggsggggsrnlpvatpdpgmfpclhhsqnllraysnmlqkarqtlefypct<br>seeidheditkdktstveaclpleltknesclnsretsfitngsclasrktsfmmalclssiyedlkmyqvefktmnakllm<br>dpkrqifldqnmlavidelmqalnfnsetvpqkssleepdfyktkiklcillhafriravtidrvmsylnassggpALFK<br>SSFPpgsggggsggggsggggsggggsggggsggggsQSVLTQPPSVSGAPGQRVTISCSGSRS<br>NIGeNTVKWYQQLPGTAPKLLIYYNDQRPSGVPDRFSGSKSGTSASLAITGLQA<br>EDEADYYCQSYDRYTHPALLFGTGTKVTVLgqpkaapsvtlfppsseelqankatlyclisdfyp<br>gavtvawkadsspvkagvetttpskqsnnkyaassylsltpeqwkshrsyscqvthegstvektvaptecs** |
| 518 | WW0724 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshslllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdlyyssswsewasvpcsggggsggggsggggsrvipvsgparclsqsrnllkttddmvktareklkhysctaedid<br>heditrdqtstlktclplelhknesclatretssttrgsclppqktslmmticlgsiyedlkmyqtefciainaalqnhnhqqiil<br>dkgmlvaidelmqslnhngetlrqkppvgeadpyrvkmklcillhafstrvvtinrvmgylssasggpALFKSSF<br>PpgsggggsggggsggggsggggsggggsggggsQSVLTQPPSVSGAPGQRVTISCSGSRSNI<br>GeeTVKWYQQLPGTAPKLLIYYNDQRPSGVPDRFSGSKSGTSASLAITGLQAED |

-continued

Sequence table

| SEQ ID NO. | Name | Sequence |
|---|---|---|
| | | EADYYCQSYDRYTHPALLFGTGTKVTVLgqpkaapsvtlfppsseelqankativclisdfypga<br>vtvawkadsspvkagvetttpskqsnnkyaassylsltpeqwkshrsyscqvthegstvektvaptecs** |
| 519 | WW0725 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSsggpALFKSSFPpgsiwelkkdvyvveldwypdapgemvvlicdtpeedgitwtldqss<br>evlgsgktltiqvkefgdagqytchkggevlshsllllhkkedgiwstdilkdqkepknktflrceaknysgrftcwwltti<br>stdltfsvkssrgssdpqgvtcgaatlsaervrgdnkeyeysvecqedsacpaaeeslpievmvdavhklkyenytssff<br>irdiikpdppknlqlkplknsrqvevsweypdtwstphsyfsltfcvqvqgkskrekkdrvftdktsatvicrknasisvr<br>aqdryyssswsewasvpcsggggsggggsggggsrnlpvatpdpgmfpclhhsqnllraysnmlqkarqtlefypct<br>seeidheditkdktstveaclpleltknesclnsretsfitngsclasrktsfmmalclssiyedlkmyqvefktmnakllm<br>dpkrqifldqnmlavidelmqalnfnsetvpqksslee pdfyktkiklcillhafriravtidrvmsylnassggpALFK<br>SSFPpgsggggsggggsggggsggggsggggsggggsQSVLTQPPSVSGAPGQRVTISCSGSRS<br>NIGeeTVKWYQQLPGTAPKLLIYYNDQRPSGVPDRFSGSKSGTSASLAITGLQA<br>EDEADYYCQSYDRYTHPALLFGTGTKVTVLgqpkaapsvtlfppsseelqankatlyclisdfyp<br>gavtvawkadsspvkagvetttpskqsnnkyaassylsltpeqwkshrsyscqvthegstvektvaptecs** |
| 520 | WW0726 | QVQLVESGGGVVQPGRSLRLSCAASGFTFSSYGMHWVRQAPGKGLEWVAFIR<br>YDGSNKYYADSVKGRFTISRDNSKNTLYLQMNSLRAEDTAVYYCKTHGSHD<br>NWGQGTMVTVSSastkgpsvfplapsskstsggtaalgclvkdyfpepvtvswnsgaltsgvhtfpavlqssgl<br>yslssvvtvpssslgtqtyicnvnhkpsntkvdkrvepksc** |
| 521 | WW0727 | QVQLVESGGGVVQPGRSLRLSCAASGFTFSSYGMHWVRQAPGKGLEWVAFIR<br>YeGSNKYYAeSVKGRFTISRDNSKNTLYLQMNSLRAEDTAVYYCKTHGSHDN<br>WGQGTMVTVSSastkgpsvfplapsskstsggtaalgclvkdyfpepvtvswnsgaltsgvhtfpavlqssgly<br>slssvvtvpssslgtqtyicnvnhkpsntkvdkrvepksc** |
| 522 | WW0728 | QVQLVESGGGVVQPGRSLRLSCAASGFTFSSYGMHWVRQAPGKGLEWVAFIR<br>YeGSNKYYADSVKGRFTISRDNSKNTLYLQMNSLRAEDTAVYYCKTHGSHDN<br>WGQGTMVTVSSastkgpsvfplapsskstsggtaalgclvkdyfpepvtvswnsgaltsgvhtfpavlqssgly<br>slssvvtvpssslgtqtyicnvnhkpsntkvdkrvepksc** |
| 523 | WW0765 | iwelkkdvyvveldwypdapgemvvlicdtpeedgitwildqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfshfcvqvqgkskrekkdivftdktsatvicrknasisvraqdryyssswsewasvpcsggggsggggsgg<br>ggsrvipvsgparclsqsrnllkttddmvktareklkhysctaedidheditrdqtstlktclplelhknesclatretssttrgs<br>clppqktslmmticlgsiyedlkmyqtefqainaalqnhnhqqiildkgmlvaidelmqslnhngetlrqkppvgead<br>pyrvkmklcillhafstryvtinrvmgylssasggpGPAGLYAQpgsEVQLVESGGGLVQPGNSL<br>RLSCAASGFTFSKFGMSWVRQAPGKGLEWVSSISGSGRDTLYAESVKGRFTIS<br>RDNAKTTLYLQMNSLRPEDTAVYYCTIGGSLSVSSQGTLVTVSSggggsggggsgg<br>ggsggggsggggsggggsQSVLTQPPSVSGAPGQRVTISCSGSRSNIGSNTVKWYQQLP<br>GTAPKLLIYYNDQRPSGVPDRFSGSKSGTSASLAITGLQAEDEADYYCQSYDR<br>YTHPALLFGTGTKVTVLggggsggggsggggsQVQLVESGGGVVQPGRSLRLSCAA<br>SGFTFSSYGMHWVRQAPGKGLEWVAFIRYeGSNKYYAeSVKGRFTlSRDNSKN<br>TLYLQMNSLRAEDTAVYYCKTHGSHDNWGQGTMVTVSS** |
| 524 | WW0766 | iwelkkdvyvveldwypdapgemvvitcdtpeedgitwtldqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfshfcvqvqgkskrekkchvftdktsatvicrknasisvraqdryyssswsewasvpcsggggsggggsgg<br>ggsrnlpvatpdpgmfpclhhsqnllraysnmlqkarqtlefypctseeidheditkdktstveaclpleltknesclnsre<br>tsfitngsclasrktsfmmalclssiyedlkmyqvefktmnakllmdpkrqifldqnmlavidelmqalnfnsetvpqk<br>ssleepdfyktkiklcillhafriravtidrvmsylnassggpGPAGLYAQpgsEVQLVESGGGLVQPG<br>NSLRLSCAASGFTFSKFGMSWVRQAPGKGLEWVSSISGSGRDTLYAESVKGRF<br>TISRDNAKTTLYLQMNSLRPEDTAVYYCTIGGSLSVSSQGTLVTVSSggggsgggg<br>sggggsggggsggggsggggsQSVLTQPPSVSGAPGQRVTISCSGSRSNIGSNTVKWYQ<br>QLPGTAPKLLIYYNDQRPSGVPDRFSGSKSGTSASLAITGLQAEDEADYYCQS<br>YDRYTHPALLFGTGTKVTVLggggsggggsggggsQVQLVESGGGVVQPGRSLRLS<br>CAASGFTFSSYGMHWVRQAPGKGLEWVAFIRYeGSNKYYAeSVKGRFTISRD<br>NSKNTLYLQMNSLRAEDTAVYYCKTHGSHDNWGQGTMVTVSS** |
| 525 | WW0767 | iwelkkdvyvveldwypdapgemvvitcdtpeedgitwildqssevlgsgktltiqvkefgdagqytchkggevlshs<br>llllhkkedgiwstdilkdqkepknktflrceaknysgrftcwwlttistdltfsvkssrgssdpqgvtcgaatlsaervrgd<br>nkeyeysvecqedsacpaaeeslpievmvdavhklkyenytssffirdiikpdppknlqlkplknsrqvevsweypdt<br>wstphsyfshfcvqvqgkskrekkchvftdktsatvicrknasisvraqdryyssswsewasvpcsggggsggggsgg<br>ggsrvipvsgparclsqsrnllkttddmvktareklkhysctaedidheditrdqtstlktclplelhknesclatretssttrgs<br>clppqktslmmticlgsiyedlkmyqtefqainaalqnhnhqqiildkgmlvaidelmqslnhngetlrqkppvgead<br>pyrvkmklcillhafstrvvtinrvmgylssasggpGPAGLYAQpgsEVQLVESGGGLVQPGNSL<br>RLSCAASGFTFSKFGMSWVRQAPGKGLEWVSSISGSGRDTLYAESVKGRFTIS<br>RDNAKTTLYLQMNSLRPEDTAVYYCTIGGSLSVSSQGTLVTVSSggggsggggsgg<br>ggsggggsggggsggggsQSVLTQPPSVSGAPGQRVTISCSGSRSNIGdeTVKWYQQLP<br>GTAPKLLIYYNDQRPSGVPDRFSGSKSGTSASLAITGLQAEDEADYYCQSYDR |

-continued

Sequence table

| SEQ ID NO. | Name | Sequence |
|---|---|---|
| | | YTHPALLFGTGTKVTVLggggsggggsggggsQVQLVESGGGVVQPGRSLRLSCAA SGFTFSSYGMHWVRQAPGKGLEWVAFIRYeGSNKYYAeSVKGRFTlSRDNSKN TLYLQMNSLRAEDTAVYYCKTHGSHDNWGQGTMVTVSS** |
| 526 | WW0768 | iwelkkdvyvveldwypdapgemvvitcdtpeedgitwtldqssevlgsgktltiqvkefgdagqytchkggevlshs llllhkkedgiwstdilkdqkepknktflrceaknysgrftcwwlttistdltfsvkssrgssdpqgvtcgaatlsaervrgd nkeyeysvecqedsacpaaeeslpievmvdavhklkyenytssffirdiikpdppknlqlkplknsrqvevsweypdt wstphsyfshfcvqvqgkskrekkchvftdktsatvicrknasisvraqdryysssswsewasvpcsggggsggggsgg ggsrnlpvatpdpgmfpclhhsqnllraysnmlqkarqtlefypctseeidheditkdktstveaclplelteknesclnsre tsfitngsclasrktsfmmalclssiyedlkmyqvefktmnakllmdpkrqifldqnmlavidelmqalnfnsetvpqk ssleepdfyktkiklcillhafriravtidrvmsylnassggpGPAGLYAQpgsEVQLVESGGGLVQPG NSLRLSCAASGFTFSKFGMSWVRQAPGKGLEWVSSISGSGRDTLYAESVKGRF TISRDNAKTTLYLQMNSLRPEDTAVYYCTIGGSLSVSSQGTLVTVSSggggsgggg sggggsggggsggggsggggsQSVLTQPPSVSGAPGQRVTISCSGSRSNIGdeTVKWYQQ LPGTAPKLLIYYNDQRPSGVPDRFSGSKSGTSASLAITGLQAEDEADYYCQSY DRYTHPALLFGTGTKVTVLggggsggggsggggsQVQLVESGGGVVQPGRSLRLSC AASGFTFSSYGMHWVRQAPGKGLEWVAFIRYeGSNKYYAeSVKGRFTISRDNS KNTLYLQMNSLRAEDTAVYYCKTHGSHDNWGQGTMVTVSS** |
| 527 | WW0769 | iwelkkdvyvveldwypdapgemvvitcdtpeedgitwildqssevlgsgktltiqvkefgdagqytchkggevlshs llllhkkedgiwstdilkdqkepknktflrceaknysgrftcwwlttistdltfsvkssrgssdpqgvtcgaatlsaervrgd nkeyeysvecqedsacpaaeeslpievmvdavhklkyenytssffirdiikpdppknlqlkplknsrqvevsweypdt wstphsyfshfcvqvqgkskrekkchvftdktsatvicrknasisvraqdryysssswsewasvpcsggggsggggsgg ggsrvipvsgparclsqsrnllkttddmvktareklkhysctaedidheditrdqtstlktclplelhknesclatretssttrgs clppqktslmmticlgsiyedlkmyqtefqainaalqnhnhqqiildkgmlvaidelmqslnhngetlrqkppvgead pyrvkmklcillhafstrvvtinrvmgylssasggpGPAGLYAQpgsEVQLVESGGGLVQPGNSL RLSCAASGFTFSKFGMSWVRQAPGKGLEWVSSISGSGRDTLYAESVKGRFTIS RDNAKTTLYLQMNSLRPEDTAVYYCTIGGSLSVSSQGTLVTVSSggggsggggsgg ggsggggsggggsggggsQSVLTQPPSVSGAPGQRVTISCSGSRSNIGSNTVKWYQQLP GTAPKLLIYYNDQRPSGVPDRFSGSKSGTSASLAITGLQAEDEADYYCQSYDR YTHPALLFGTGTKVTVLgqpkaapsvtlfppsseelqankatlyclisdfypgavtvawkadsspvkagv etttpskqsnnkyaassylsltpeqwkshrsyscqvthegstvektvaptecs** |
| 528 | WW0770 | iwelkkdvyvveldwypdapgemvvitcdtpeedgitwtldqssevlgsgktltiqvkefgdagqytchkggevlshs llllhkkedgiwstdilkdqkepknktflrceaknysgrftcwwlttistdltfsvkssrgssdpqgvtcgaatlsaervrgd nkeyeysvecqedsacpaaeeslpievmvdavhklkyenytssffirdiikpdppknlqlkplknsrqvevsweypdt wstphsyfshfcvqvqgkskrekkdwftdktsatvicrknasisvraqdryysssswsewasvpcsggggsggggsgg ggsrnlpvatpdpgmfpclhhsqnllraysnmlqkarqtlefypctseeidheditkdktstveaclplelteknesclnsre tsfitngsclasrktsfmmalclssiyedlkmyqvefktmnakllmdpkrqifldqnmlavidelmqalnfnsetvpqk ssleepdfyktkiklcillhafriravtidrvmsylnassggpGPAGLYAQpgsEVQLVESGGGLVQPG NSLRLSCAASGFTFSKFGMSWVRQAPGKGLEWVSSISGSGRDTLYAESVKGRF TISRDNAKTTLYLQMNSLRPEDTAVYYCTIGGSLSVSSQGTLVTVSSggggsgggg sggggsggggsggggsggggsQSVLTQPPSVSGAPGQRVTISCSGSRSNIGSNTVKWYQ QLPGTAPKLLIYYNDQRPSGVPDRFSGSKSGTSASLAITGLQAEDEADYYCQS YDRYTHPALLFGTGTKVTVLgqpkaapsvtlfppsseelqankatlyclisdfypgavtvawkadsspv kagvetttpskqsnnkyaassylsltpeqwkshrsyscqvthegstvektvaptecs** |
| 529 | WW0771 | iwelkkdvyvveldwypdapgemvvitcdtpeedgitwtldqssevlgsgktltiqvkefgdagqytchkggevlshs llllhkkedgiwstdilkdqkepknktflrceaknysgrftcwwlttistdltfsvkssrgssdpqgvtcgaatlsaervrgd nkeyeysvecqedsacpaaeeslpievmvdavhklkyenytssffirdiikpdppknlqlkplknsrqvevsweypdt wstphsyfshfcvqvqgkskrekkdwftdktsatvicrknasisvraqdryysssswsewasvpcsggggsggggsgg ggsrvipvsgparclsqsrnllkttddmvktareklkhysctaedidheditrdqtstlktclplelhknesclatretssttrgs clppqktslmmticlgsiyedlkmyqtefqainaalqnhnhqqiildkgmlvaidelmqslnhngetlrqkppvgead pyrvkmklcillhafstryvtinrvmgylssasggpGPAGLYAQpgsEVQLVESGGGLVQPGNSL RLSCAASGFTFSKFGMSWVRQAPGKGLEWVSSISGSGRDTLYAESVKGRFTIS RDNAKTTLYLQMNSLRPEDTAVYYCTIGGSLSVSSQGTLVTVSSggggsggggsgg ggsggggsggggsggggsQSVLTQPPSVSGAPGQRVTISCSGSRSNIGdeTVKWYQQLP GTAPKLLIYYNDQRPSGVPDRFSGSKSGTSASLAITGLQAEDEADYYCQSYDR YTHPALLFGTGTKVTVLgqpkaapsvtlfppsseelqankatlyclisdfypgavtvawkadsspvkagv etttpskqsnnkyaassylsltpeqwkshrsyscqvthegstvektvaptecs** |
| 530 | WW0772 | iwelkkdvyvveldwypdapgemvvitcdtpeedgitwtldqssevlgsgktltiqvkefgdagqytchkggevlshs llllhkkedgiwstdilkdqkepknktflrceaknysgrftcwwlttistdltfsvkssrgssdpqgvtcgaatlsaervrgd nkeyeysvecqedsacpaaeeslpievmvdavhklkyenytssffirdiikpdppknlqlkplknsrqvevsweypdt wstphsyfshfcvqvqgkskrekkdwftdktsatvicrknasisvraqdryysssswsewasvpcsggggsggggsgg ggsrnlpvatpdpgmfpclhhsqnllraysnmlqkarqtlefypctseeidheditkdktstveaclplelteknesclnsre tsfitngsclasrktsfmmalclssiyedlkmyqvefktmnakllmdpkrqifldqnmlavidelmqalnfnsetvpqk ssleepdfyktkiklcillhafriravtidrvmsylnassggpGPAGLYAQpgsEVQLVESGGGLVQPG NSLRLSCAASGFTFSKFGMSWVRQAPGKGLEWVSSISGSGRDTLYAESVKGRF TISRDNAKTTLYLQMNSLRPEDTAVYYCTIGGSLSVSSQGTLVTVSSggggsgggg sggggsggggsggggsggggsQSVLTQPPSVSGAPGQRVTISCSGSRSNIGdeTVKWYQQ LPGTAPKLLIYYNDQRPSGVPDRFSGSKSGTSASLAITGLQAEDEADYYCQSY |

-continued

Sequence table

| SEQ ID NO. | Name | Sequence |
|---|---|---|
| | | DRYTHPALLFGTGTKVTVLgqpkaapsvtlfppsseelqankatlyclisdfypgavtvawkadsspvka gvettlpskqsnnkyaassylsltpeqwkshrsyscqvthegstvektvaptecs** |
| 531 | WW0796 | iwelkkdvyvveldwypdapgemvvitcdtpeedgitwtldqssevlgsgktltiqvkefgdagqytchkggevlshs llllhkkedgiwstdilkdqkepknktflrceaknysgrftcwwlttistdltfsvkssrgssdpqgvtcgaatlsaervrgd nkeyeysvecqedsacpaaeeslpievmvdavhklkyenytssffirdiikpdppknlqlkplknsrqvevsweypdt wstphsyfshfcvqvqgkskrekkdwftdktsatvicrknasisvraqdryyssswsewasvpcsggggsggggsgg ggsrvipvsgparclsqsrnllkttddmvktareklkhysctaedidheditrdqtstlktclplelhknesclatretssttrgs clppqktslmmticlgsiyedlkmyqtefqainaalqnhnhqqiildkgmlvaidelmqslnhngetlrqkppvgead pyrvkmklcillhafstrvvtinrvmgylssasggpALFKSSFPpgsEVQLVESGGGLVQPGNSLR LSCAASGFTFSKFGMSWVRQAPGKGLEWVSSISGSGRDTLYAESVKGRFTISR DNAKTTLYLQMNSLRPEDTAVYYCTIGGSLSVSSQGTLVTVSSggggsggggsgggg sggggsggggsggggsQSVLTQPPSVSGAPGQRVTISCSGSRSNIGSNTVKWYQQLPG TAPKLLIYYNDQRPSGVPDRFSGSKSGTSASLAITGLQAEDEADYYCQSYDRY THPALLFGTGTKVTVLggggsggggsggggsQVQLVESGGGVVQPGRSLRLSCAAS GFTFSSYGMHWVRQAPGKGLEWVAFIRYeGSNKYYAeSVKGRFTISRDNSKN TLYLQMNSLRAEDTAVYYCKTHGSHDNWGQGTMVTVSS** |
| 532 | WW0797 | iwelkkdvyvveldwypdapgemvvItcdtpeedgitwildqssevIgsgktItiqvkefgdagqytchkggevIshs llllhkkedgiwstdilkdqkepknktflrceaknysgrftcwwIttistdIffsvkssrgssdpqgvtcgaatIsaervrgd nkeyeysvecqedsacpaaeeslpievmvdavhklkyenytssffirdiikpdppknIqlkplknsrqvevsweypdt wstphsyfshfcvqvqgkskrekkdwftdktsatvicrknasisvraqdryyssswsewasvpcsggggsggggsgg ggsrnIpvatpdpgmfpclhhsqnlIraysnmlqkarqtlefypctseeidheditkdktstveacIpleltknescInsre tsfitngsclasrktsfmmalcIssiyedlkmyqvefktmnakIlmdpkrqifldqnmlavidelmqaInfnsetvpqk ssleepdfyktkiklcillhafriravtidrvmsylnassggpALFKSSFPpgsEVQLVESGGGLVQPGN SLRLSCAASGFTFSKFGMSWVRQAPGKGLEWVSSISGSGRDTLYAESVKGRFT ISRDNAKTTLYLQMNSLRPEDTAVYYCTIGGSLSVSSQGTLVTVSSggggsggggsg gggsggggsggggsggggsQSVLTQPPSVSGAPGQRVTISCSGSRSNIGSNTVKWYQQL PGTAPKLLIYYNDQRPSGVPDRFSGSKSGTSASLAITGLQAEDEADYYCQSYD RYTHPALLFGTGTKVTVLggggsggggsggggsQVQLVESGGGVVQPGRSLRLSCA ASGFTFSSYGMHWVRQAPGKGLEWVAFIRYeGSNKYYAeSVKGRFTISRDNSK NTLYLQMNSLRAEDTAVYYCKTHGSHDNWGQGTMVTVSS** |
| 533 | WW0798 | iwelkkdvyvveldwypdapgemvvItcdtpeedgitwtldqssevIgsgktItiqvkefgdagqytchkggevIshs llllhkkedgiwstdilkdqkepknktflrceaknysgrftcwwIttistdIffsvkssrgssdpqgvtcgaatIsaervrgd nkeyeysvecqedsacpaaeeslpievmvdavhlayenytssffirdiikpdppknIqlkplknsrqvevsweypdt wstphsyfshfcvqvqgkskrekkdwftdktsatvicrknasisvraqdryyssswsewasvpcsggggsggggsgg ggsrvipvsgparcIsqsrnlIkttddmvktareklkhysctaedidheditrdqtstIktclplelhknesclatretssttrgs cIppqktsImmticlgsiyedlkmyqtefqainaalqnhnhqqiildkgmlvaidelmqslnhngetIrqkppvgead pyrvkmklcillhafstrvvtinrvmgylssasggpALFKSSFPpgsEVQLVESGGGLVQPGNSLR LSCAASGFTFSKFGMSWVRQAPGKGLEWVSSISGSGRDTLYAESVKGRFTISR DNAKTTLYLQMNSLRPEDTAVYYCTIGGSLSVSSQGTLVTVSSggggsggggsgggg sggggsggggsggggsQSVLTQPPSVSGAPGQRVTISCSGSRSNIGdeTVKWYQQLPGT APKLLIYYNDQRPSGVPDRFSGSKSGTSASLAITGLQAEDEADYYCQSYDRYT HPALLFGTGTKVTVLggggsggggsggggsQVQLVESGGGVVQPGRSLRLSCAASGF TFSSYGMHWVRQAPGKGLEWVAFIRYeGSNKYYAeSVKGRFTISRDNSKNTL YLQMNSLRAEDTAVYYCKTHGSHDNWGQGTMVTVSS** |
| 534 | WW0799 | iwelkkdvyvveldwypdapgemvvItcdtpeedgitwildqssevIgsgktItiqvkefgdagqytchkggevIshs llllhkkedgiwstdilkdqkepknktflrceaknysgrftcwwIttistdIffsvkssrgssdpqgvtcgaatIsaervrgd nkeyeysvecqedsacpaaeeslpievmvdavhlayenytssffirdiikpdppknIqlkplknsrqvevsweypdt wstphsyfshfcvqvqgkskrekkdwftdktsatvicrknasisvraqdryyssswsewasvpcsggggsggggsgg ggsrnIpvatpdpgmfpclhhsqnlIraysnmlqkarqtlefypctseeidheditkdktstveacIpleltknescInsre tsfitngsclasrktsfmmalcIssiyedlkmyqvefktmnakIlmdpkrqifldqnmlavidelmqaInfnsetvpqk ssleepdfyktkiklcillhafriravtidrvmsylnassggpALFKSSFPpgsEVQLVESGGGLVQPGN SLRLSCAASGFTFSKFGMSWVRQAPGKGLEWVSSISGSGRDTLYAESVKGRFT ISRDNAKTTLYLQMNSLRPEDTAVYYCTIGGSLSVSSQGTLVTVSSggggsggggsg gggsggggsggggsggggsQSVLTQPPSVSGAPGQRVTISCSGSRSNIGdeTVKWYQQL PGTAPKLLIYYNDQRPSGVPDRFSGSKSGTSASLAITGLQAEDEADYYCQSYD RYTHPALLFGTGTKVTVLggggsggggsggggsQVQLVESGGGVVQPGRSLRLSCA ASGFTFSSYGMHWVRQAPGKGLEWVAFIRYeGSNKYYAeSVKGRFTISRDNSK NTLYLQMNSLRAEDTAVYYCKTHGSHDNWGQGTMVTVSS** |
| 535 | WW0800 | iwelkkdvyvveldwypdapgemvvitcdtpeedgitwildqssevlgsgktltiqvkefgdagqytchkggevlshs llllhkkedgiwstdilkdqkepknkffirceaknysgrftcwwlttistdltfsvkssrgssdpqgvtcgaatlsaervrgd nkeyeysvecqedsacpaaeeslpievmvdavhklkyenytssffirdiikpdppknlqlkplknsrqvevsweypdt wstphsyfshfcvqvqgkskrekkdwftdktsatvicrknasisvraqdryyssswsewasvpcsggggsggggsgg ggsrvipvsgparclsqsrnllkttddmvktareklkhysctaedidheditrdqtstlktclplelhknesclatretssttrgs clppqktslmmticlgsiyedlkmyqtefqainaalqnhnhqqiildkgmlvaidelmqslnhngetlrqkppvgead pyrvkmklcillhafstrvvtinrvmgylssasggpALFKSSFPpgsEVQLVESGGGLVQPGNSLR LSCAASGFTFSKFGMSWVRQAPGKGLEWVSSISGSGRDTLYAESVKGRFTISR DNAKTTLYLQMNSLRPEDTAVYYCTIGGSLSVSSQGTLVTVSSggggsggggsgggg sggggsggggsggggsQSVLTQPPSVSGAPGQRVTISCSGSRSNIGSNTVKWYQQLPG |

-continued

Sequence table

| SEQ ID NO. | Name | Sequence |
|---|---|---|
| | | TAPKLLIYYNDQRPSGVPDRFSGSKSGTSASLAITGLQAEDEADYYCQSYDRY THPALLFGTGIKVTVLgqpkaapsvtlfppsseelqankatlycliscifypgavtvawkadsspvkagvett tpskqsnnkyaassylsltpeqwkshrsyscqvthegstvektvaptecs** |
| 536 | WW0801 | iwelkkdvyvveldwypdapgemvvitcdtpeedgitwildqssevlgsgktltiqvkefgdagqytchkggevlshs llllhkkedgiwstdilkdqkepknkifirceaknysgrftcwwlttistdltfsvkssrgssdpqgvtcgaatlsaervrgd nkeyeysvecqedsacpaaeeslpievmvdavhklkyenytssffirdiikpdppknlqlkplknsrqvevsweypdt wstphsyfshfcvqvqgkskrekkdwftdktsatvicrknasisvraqdryyssswsewasvpcsggggsggggsgg ggsrnlpvatpdpgmfpclhhsqnllraysnmlqkarqtlefypctseeidheditkdktstveaclpleltknesclnsre tsfitngsclasrktsfmmalclssiyedlkmyqvefktmnakllmdpkrqifldqnmlavidelmqalnfnsetvpqk ssleepdfyktkiklcillhafriravtidrvmsylnassggpALFKSSFPpgsEVQLVESGGGLVQPGN SLRLSCAASGFTFSKFGMSWVRQAPGKGLEWVSSISGSGRDTLYAESVKGRFT ISRDNAKTTLYLQMNSLRPEDTAVYYCTIGGSLSVSSQGTLVTVSSggggsggggsg gggsggggsggggsggggsQSVLTQPPSVSGAPGQRVTISCSGSRSNIGSNTVKWYQQL PGTAPKLLIYYNDQRPSGVPDRFSGSKSGTSASLAITGLQAEDEADYYCQSYD RYTHPALLFGTGIKVTVLgqpkaapsvtlfppsseelqankatlyclisdfypgavtvawkadsspvkag vettlpskqsnnkyaassylsltpeqwkshrsyscqvthegstvektvaptecs** |
| 537 | WW0802 | iwelkkdvyvveldwypdapgemvvitcdtpeedgitwildqssevlgsgktltiqvkefgdagqytchkggevlshs llllhkkedgiwstdilkdqkepknkffirceaknysgrftcwwlttistdltfsvkssrgssdpqgvtcgaatlsaervrgd nkeyeysvecqedsacpaaeeslpievmvdavhklkyenytssffirdiikpdppknlqlkplknsrqvevsweypdt wstphsyfshfcvqvqgkskrekkchvftdktsatvicrknasisvraqdryyssswsewasvpcsggggsggggsgg ggsrvipvsgparclsqsrnllkttddmvktareklkhysctaedidheditrdqtstlktclplelhknesclatretssttrgs clppqktslmmticlgsiyedlkmyqtefqainaalqnhnhqqiildkgmlvaidelmqslnhngetlrqkppvgead pyrvkmklcillhafstrvvtinrvmgylssasggpALFKSSFPpgsEVQLVESGGGLVQPGNSLR LSCAASGFTFSKFGMSWVRQAPGKGLEWVSSISGSGRDTLYAESVKGRFTISR DNAKTTLYLQMNSLRPEDTAVYYCTIGGSLSVSSQGTLVTVSSggggsggggsgggg sggggsggggsggggsQSVLTQPPSVSGAPGQRVTISCSGSRSNIGdeTVKWYQQLPGT APKLLIYYNDQRPSGVPDRFSGSKSGTSASLAITGLQAEDEADYYCQSYDRYT HPALLFGTGTKVTVLgqpkaapsvtlfppsseelqankativclisdfypgavtvawkadsspvkagvettt pskqsnnkyaassylsltpeqwkshrsyscqvthegstvektvaptecs** |
| 538 | WW0803 | iwelkkdvyvveldwypdapgemvvitcdtpeedgitwfldqssevlgsgktltiqvkefgdagqytchkggevlshs llllhkkedgiwstdilkdqkepknktflrceaknysgrftcwwlttistdltfsvkssrgssdpqgvtcgaatlsaervrgd nkeyeysvecqedsacpaaeeslpievmvdavhklkyenytssffirdiikpdppknlqlkplknsrqvevsweypdt wstphsyfshfcvqvqgkskrekkdwftdktsatvicrknasisvraqdryyssswsewasvpcsggggsggggsgg ggsrnlpvatpdpgmfpclhhsqnllraysnmlqkarqtlefypctseeidheditkdktstveaclpleltknesclnsre tsfitngsclasrktsfmmalclssiyedlkmyqvefktmnakllmdpkrqifldqnmlavidelmqalnfnsetvpqk ssleepdfyktkiklcillhafriravtidrvmsylnassggpALFKSSFPpgsEVQLVESGGGLVQPGN SLRLSCAASGFTFSKFGMSWVRQAPGKGLEWVSSISGSGRDTLYAESVKGRFT ISRDNAKTTLYLQMNSLRPEDTAVYYCTIGGSLSVSSQGTLVTVSSggggsggggsg gggsggggsggggsggggsQSVLTQPPSVSGAPGQRVTISCSGSRSNIGdeTVKWYQQL PGTAPKLLIYYNDQRPSGVPDRFSGSKSGTSASLAITGLQAEDEADYYCQSYD RYTHPALLFGTGTKVTVLgqpkaapsvtlfppsseelqankatlyclisdfypgavtvawkadsspvkag vettlpskqsnnkyaassylsltpeqwkshrsyscqvthegstvektvaptecs** |
| 539 | WW0643 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGLYAQPGSCDLPHTYNLRNKRALKVLAQMRRLTPL SCLKDRKDFGFPLEKVDAQQIQKAQSIPVLRDLTQQILNLFASKDSSAAWNAT LLDSFCNDLHQQLNDLQGCLMQQVGVQESPLTQEDSLLAVRIYFHRITVFLRE KKHSPCAWEVVRAEVWRALSSSANVLGRLREEKASGGPGPAGLYAQPGSEV QLVESGGGLVQPGNSLRLSCAASGFTFSKFGMSWVRQAPGKGLEWVSSISGS GRDTLYAESVKGRFTISRDNAKTTLYLQMNSLRPEDTAVYYCTIGGSLSVSSQ GTLVTVSS |
| 540 | WW0644 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPALFKSSFPPGSCDLPHTYNLRNKRALKVLAQMRRLTPLS CLKDRKDFGFPLEKVDAQQIQKAQSIPVLRDLTQQILNLFASKDSSAAWNATL LDSFCNDLHQQLNDLQGCLMQQVGVQESPLTQEDSLLAVRIYFHRITVFLREK KHSPCAWEVVRAEVWRALSSSANVLGRLREEKASGGPALFKSSFPPGSEVQL VESGGGLVQPGNSLRLSCAASGFTFSKFGMSWVRQAPGKGLEWVSSISGSGR DTLYAESVKGRFTISRDNAKTTLYLQMNSLRPEDTAVYYCTIGGSLSVSSQGT LVTVSS |
| 541 | WW0645 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGLYAQPGSCNLSQTHSLNNRRTLMLMAQMRRISPFS CLKDRHDFEFPQEEFDGNQFQKAQAISVLHEMMQQTFNLFSTKNSSAAWDET LLEKFYIELFQQMNDLEACVIQEVGVEETPLMNEDSILAVKKYFQRITLYLME KKYSPCAWEVVRAEIMRSLSFSTNLQKRLRRKDSGGPGPAGLYAQPGSEVQL VESGGGLVQPGNSLRLSCAASGFTFSKFGMSWVRQAPGKGLEWVSSISGSGR |

-continued

Sequence table

| SEQ ID NO. | Name | Sequence |
|---|---|---|
| | | DTLYAESVKGRFTISRDNAKTTLYLQMNSLRPEDTAVYYCTIGGSLSVSSQGT LVTVSS |
| 542 | WW0646 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPALFKSSFPPGSCNLSQTHSLNNRRTLMLMAQMRRISPFSC LKDRHDFEFPQEEFDGNQFQKAQAISVLHEMMQQTFNLFSTKNSSAAWDETL LEKFYIELFQQMNDLEACVIQEVGVEETPLMNEDSILAVKKYFQRITLYLMEK KYSPCAWEVVRAEIMRSLSFSTNLQKRLRRKDSGGPALFKSSFPPGSEVQLVES GGGLVQPGNSLRLSCAASGFTFSKFGMSWVRQAPGKGLEWVSSISGSGRDTL YAESVKGRFTISRDNAKTTLYLQMNSLRPEDTAVYYCTIGGSLSVSSQGTLVT VSS |
| 543 | WW0647 | CDLPHTYNLRNKRALKVLAQMRRLTPLSCLKDRKDFGFPLEKVDAQQIQKAQ SIPVLRDLTQQILNLFASKDSSAAWNATLLDSFCNDLHQQLNDLQGCLMQQV GVQESPLTQEDSLLAVRIYFHRITVFLREKKHSPCAWEVVRAEVWRALSSSAN VLGRLREEKAHHHHHH |
| 544 | WW0648 | CNLSQTHSLNNRRTLMLMAQMRRISPFSCLKDRHDFEFPQEEFDGNQFQKAQ AISVLHEMMQQTFNLFSTKNSSAAWDETLLEKFYIELFQQMNDLEACVIQEVG VEETPLMNEDSILAVKKYFQRITLYLMEKKYSPCAWEVVRAEIMRSLSFSTNL QKRLRRKDHHHHHH |
| 545 | WW0781 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGLYAQPGSCDLPQTHSLGSRRTLMLLAQMRRISLFS CLKDRHDFGFPQEEFGNQFQKAETIPVLHEMIQQIFNLFSTKDSSAAWDETLLD KFYTELYQQLNDLEACVIQGVGVEETPLMKEDSILAVRKYFQRITLYLKEKKY SPCAWEVVRAEIMRSFSLSTNLQESLRSKESGGPGPAGLYAQPGSEVQLVESG GGLVQPGNSLRLSCAASGFTFSKFGMSWVRQAPGKGLEWVSSISGSGRDTLY AESVKGRFTISRDNAKTTLYLQMNSLRPEDTAVYYCTIGGSLSVSSQGTLVTV SS |
| 546 | WW0782 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGLYAQPGSCNLSQTHSLNNRRTLMLMAQMRRISPFS CLKDRHDFEFPQEEFDGNQFQKAQAISVLHEMMQQTFNLFSTKDSSAAWDET LLEKFYIELFQQMNDLEACVIQEVGVEETPLMNEDSILAVKKYFQRITLYLME KKYSPCAWEVVRAEIMRSLSFSTNLQKRLRRKDSGGPGPAGLYAQPGSEVQL VESGGGLVQPGNSLRLSCAASGFTFSKFGMSWVRQAPGKGLEWVSSISGSGR DTLYAESVKGRFTISRDNAKTTLYLQMNSLRPEDTAVYYCTIGGSLSVSSQGT LVTVSS |
| 547 | WW0783 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGLYAQPGSCDLPQTHSLNNRRTLMLMAQMRRISPFS CLKDRHDFEFPQEEFDGNQFQKAQAISVLHEMMQQTFNLFSTKDSSAAWDET LLEKFYIELFQQMNDLEACVIQEVGVEETPLMNEDSILAVKKYFQRITLYLME KKYSPCAWEVVRAEIMRSLSFSTNLQKRLRRKDSGGPGPAGLYAQPGSEVQL VESGGGLVQPGNSLRLSCAASGFTFSKFGMSWVRQAPGKGLEWVSSISGSGR DTLYAESVKGRFTISRDNAKTTLYLQMNSLRPEDTAVYYCTIGGSLSVSSQGT LVTVSS |
| 548 | WW0784 | CDLPQTHSLGSRRTLMLLAQMRRISLFSCLKDRHDFGFPQEEFGNQFQKAETIP VLHEMIQQIFNLFSTKDSSAAWDETLLDKFYTELYQQLNDLEACVIQGVGVEE TPLMKEDSILAVRKYFQRITLYLKEKKYSPCAWEVVRAEIMRSFSLSTNLQESL RSKEHHHHHH |
| 549 | WW0785 | CNLSQTHSLNNRRTLMLMAQMRRISPFSCLKDRHDFEFPQEEFDGNQFQKAQ AISVLHEMMQQTFNLFSTKDSSAAWDETLLEKFYIELFQQMNDLEACVIQEVG VEETPLMNEDSILAVKKYFQRITLYLMEKKYSPCAWEVVRAEIMRSLSFSTNL QKRLRRKDHHHHHH |
| 550 | WW0786 | CDLPQTHSLNNRRTLMLMAQMRRISPFSCLKDRHDFEFPQEEFDGNQFQKAQ AISVLHEMMQQTFNLFSTKDSSAAWDETLLEKFYIELFQQMNDLEACVIQEVG VEETPLMNEDSILAVKKYFQRITLYLMEKKYSPCAWEVVRAEIMRSLSFSTNL QKRLRRKDHHHHHH |
| 551 | WW0815 | EAHKSEIAHRYNDLGEQHFKGLVLIAFSQYLQKCSYDEHAKLVQEVTDFAKT CVADESAANCDKSLHTLFGDKLCAIPNLRENYGELADCCTKQEPERNECFLQH KDDNPSLPPFERPEAEAMCTSFKENPTTFMGHYLHEVARRHPYFYAPELLYYA EQYNEILTQCCAEADKESCLTPKLDGVKEKALVSSVRQRMKCSSMQKFGERA FKAWAVARLSQTFPNADFAEITKLATDLTKVNKECCHGDLLECADDRAELAK |

-continued

Sequence table

| SEQ ID NO. | Name | Sequence |
| --- | --- | --- |
| | | YMCENQATISSKLQTCCDKPLLKKAHCLSEVEHDTMPADLPAIAADFVEDQE<br>VCKNYAEAKDVFLGTFLYEYSRRHPDYSVSLLLRLAKKYEATLEKCCAEANP<br>PACYGTVLAEFQPLVEEPKNLVKTNCDLYEKLGEYGFQNAILVRYTQKAPQV<br>STPTLVEAARNLGRVGTKCCTLPEDQRLPCVEDYLSAILNRVCLLHEKTPVSE<br>HVTKCCSGSLVERRPCFSALTVDETYVPKEFKAETFTFHSDICTLPEKEKQIKK<br>QTALAELVKHKPKATAEQLKTVMDDFAQFLDTCCKAADKDTCFSTEGPNLVT<br>RCKDALASGGPALFKSSFPPGSCDLPQTHNLRNKRALTLLVQMRRLSPLSCLK<br>DRKDFGFPQEKVDAQQIKKAQAIPVLSELTQQILNIFTSKDSSAAWNTTLLDSF<br>CNDLHQQLNDLQGCLMQQVGVQEFPLTQEDALLAVRKYFHRITVYLREKKH<br>SPCAWEVVRAEVWRALSSSANVLGRLREEKSGGPALFKSSFPPGSEAHKSEIA<br>HRYNDLGEQHFKGLVLIAFSQYLQKCSYDEHAKLVQEVTDFAKTCVADESAA<br>NCDKSLHTLFGDKLCAIPNLRENYGELADCCTKQEPERNECFLQHKDDNPSLP<br>PFERPEAEAMCTSFKENPTTFMGHYLHEVARRHPYFYAPELLYYAEQYNEILT<br>QCCAEADKESCLTPKLDGVKEKALVSSVRQRMKCSSMQKFGERAFKAWAVA<br>RLSQTFPNADFAEITKLATDLTKVNKECCHGDLLECADDRAELAKYMCENQA<br>TISSKLQTCCDKPLLKKAHCLSEVEHDTMPADLPAIAADFVEDQEVCKNYAEA<br>KDVFLGTFLYEYSRRHPDYSVSLLLRLAKKYEATLEKCCAEANPPACYGTVL<br>AEFQPLVEEPKNLVKTNCDLYEKLGEYGFQNAILVRYTQKAPQVSTPTLVEAA<br>RNLGRVGTKCCTLPEDQRLPCVEDYLSAILNRVCLLHEKTPVSEHVTKCCSGS<br>LVERRPCFSALTVDETYVPKEFKAETFTFHSDICTLPEKEKQIKKQTALAELVK<br>HKPKATAEQLKTVMDDFAQFLDTCCKAADKDTCFSTEGPNLVTRCKDALAH<br>HHHHH |
| 552 | WW0816 | EAHKSEIAHRYNDLGEQHFKGLVLIAFSQYLQKCSYDEHAKLVQEVTDFAKT<br>CVADESAANCDKSLHTLFGDKLCAIPNLRENYGELADCCTKQEPERNECFLQH<br>KDDNPSLPPFERPEAEAMCTSFKENPTTFMGHYLHEVARRHPYFYAPELLYYA<br>EQYNEILTQCCAEADKESCLTPKLDGVKEKALVSSVRQRMKCSSMQKFGERA<br>FKAWAVARLSQTFPNADFAEITKLATDLTKVNKECCHGDLLECADDRAELAK<br>YMCENQATISSKLQTCCDKPLLKKAHCLSEVEHDTMPADLPAIAADFVEDQE<br>VCKNYAEAKDVFLGTFLYEYSRRHPDYSVSLLLRLAKKYEATLEKCCAEANP<br>PACYGTVLAEFQPLVEEPKNLVKTNCDLYEKLGEYGFQNAILVRYTQKAPQV<br>STPTLVEAARNLGRVGTKCCTLPEDQRLPCVEDYLSAILNRVCLLHEKTPVSE<br>HVTKCCSGSLVERRPCFSALTVDETYVPKEFKAETFTFHSDICTLPEKEKQIKK<br>QTALAELVKHKPKATAEQLKTVMDDFAQFLDTCCKAADKDTCFSTEGPNLVT<br>RCKDALASGGPALFKSSFPPGSCDLPHTYNLRNKRALKVLAQMRRLTPLSCLK<br>DRKDFGFPLEKVDAQQIQKAQSIPVLRDLTQQILNLFASKDSSAAWNATLLDS<br>FCNDLHQQLNDLQGCLMQQVGVQESPLTQEDSLLAVRIYFHRITVFLREKKHS<br>PCAWEVVRAEVWRALSSSANVLGRLREEKASGGPALFKSSFPPGSEAHKSEIA<br>HRYNDLGEQHFKGLVLIAFSQYLQKCSYDEHAKLVQEVTDFAKTCVADESAA<br>NCDKSLHTLFGDKLCAIPNLRENYGELADCCTKQEPERNECFLQHKDDNPSLP<br>PFERPEAEAMCTSFKENPTTFMGHYLHEVARRHPYFYAPELLYYAEQYNEILT<br>QCCAEADKESCLTPKLDGVKEKALVSSVRQRMKCSSMQKFGERAFKAWAVA<br>RLSQTFPNADFAEITKLATDLTKVNKECCHGDLLECADDRAELAKYMCENQA<br>TISSKLQTCCDKPLLKKAHCLSEVEHDTMPADLPAIAADFVEDQEVCKNYAEA<br>KDVFLGTFLYEYSRRHPDYSVSLLLRLAKKYEATLEKCCAEANPPACYGTVL<br>AEFQPLVEEPKNLVKTNCDLYEKLGEYGFQNAILVRYTQKAPQVSTPTLVEAA<br>RNLGRVGTKCCTLPEDQRLPCVEDYLSAILNRVCLLHEKTPVSEHVTKCCSGS<br>LVERRPCFSALTVDETYVPKEFKAETFTFHSDICTLPEKEKQIKKQTALAELVK<br>HKPKATAEQLKTVMDDFAQFLDTCCKAADKDTCFSTEGPNLVTRCKDALAH<br>HHHHH |
| 553 | WW0817 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPALFKSSFPPGSCDLPQTHNLRNKRALTLLVQMRRLSPLSC<br>LKDRKDFGFPQEKVDAQQlKKAQAIPVLSELTQQILNIFTSKDSSAAWNTTLLD<br>SFCNDLHQQLNDLQGCLMQQVGVQEFPLTQEDALLAVRKYFHRITVYLREKK<br>HSPCAWEVVRAEVWRALSSSANVLGRLREEKSGGPALFKSSFPPGSEAHKSEI<br>AHRYNDLGEQHFKGLVLIAFSQYLQKCSYDEHAKLVQEVTDFAKTCVADESA<br>ANCDKSLHTLFGDKLCAIPNLRENYGELADCCTKQEPERNECFLQHKDDNPSL<br>PPFERPEAEAMCTSFKENPTTFMGHYLHEVARRHPYFYAPELLYYAEQYNEIL<br>TQCCAEADKESCLTPKLDGVKEKALVSSVRQRMKCSSMQKFGERAFKAWAV<br>ARLSQlFPNADFAEITKLATDLTKVNKECCHGDLLECADDRAELAKYMCENQ<br>ATISSKLQTCCDKPLLKKAHCLSEVEHDTMPADLPAIAADFVEDQEVCKNYAE<br>AKDVFLGIFLYEYSRRHPDYSVSLLLRLAKKYEATLEKCCAEANPPACYGTV<br>LAEFQPLVEEPKNLVKTNCDLYEKLGEYGFQNAILVRYTQKAPQVSTPTLVEA<br>ARNLGRVGTKCCTLPEDQRLPCVEDYLSAILNRVCLLHEKTPVSEHVTKCCSG<br>SLVERRPCFSALTVDETYVPKEFKAETFTFHSDICTLPEKEKQIKKQTALAELV<br>KHKPKATAEQLKTVMDDFAQFLDTCCKAADKDTCFSTEGPNLVTRCKDALA<br>HHHHHH |
| 554 | WW0818 | EVQLVESGGGLVQPGNSLRLSCAASGFTFSKFGMSWVRQAPGKGLEWVSSIS<br>GSGRDTLYAESVKGRFTISRDNAKTTLYLQMNSLRPEDTAVYYCTIGGSLSVS<br>SQGTLVTVSSSGGPALFKSSFPPGSCDLPHTYNLRNKRALKVLAQMRRLTPLS |

-continued

Sequence table

| SEQ ID NO. | Name | Sequence |
|---|---|---|
| | | CLKDRKDFGFPLEKVDAQQIQKAQSIPVLRDLTQQILNLFASKDSSAAWNATL<br>LDSFCNDLHQQLNDLQGCLMQQVGVQESPLTQEDSLLAVRIYFHRITVFLREK<br>KHSPCAWEVVRAEVWRALSSSANVLGRLREEKASGGPALFKSSFPPGSEAHK<br>SEIAHRYNDLGEQHFKGLVLIAFSQYLQKCSYDEHAKLVQEVTDFAKTCVAD<br>ESAANCDKSLHTLFGDKLCAIPNLRENYGELADCCTKQEPERNECFLQHKDD<br>NPSLPPFERPEAEAMCTSFKENPTTFMGHYLHEVARRHPYFYAPELLYYAEQY<br>NEILTQCCAEADKESCLTPKLDGVKEKALVSSVRQRMKCSSMQKFGERAFKA<br>WAVARLSQTFPNADFAEITKLATDLTKVNKECCHGDLLECADDRAELAKYM<br>CENQATISSKLQTCCDKPLLKKAHCLSEVEHDTMPADLPAIAADFVEDQEVCK<br>NYAEAKDVFLGTFLYEYSRRHPDYSVSLLLRLAKKYEATLEKCCAEANPPAC<br>YGTVLAEFQPLVEEPKNLVKTNCDLYEKLGEYGFQNAILVRYTQKAPQVSTPT<br>LVEAARNLGRVGTKCCTLPEDQRLPCVEDYLSAILNRVCLLHEKTPVSEHVTK<br>CCSGSLVERRPCFSALTVDETYVPKEFKAETFTFHSDICTLPEKEKQIKKQTAL<br>AELVKHKPKATAEQLKTVMDDFAQFLDTCCKAADKDTCFSTEGPNLVTRCK<br>DALAHHHHHH |
| 555 | WW0819 | EAHKSEIAHRYNDLGEQHFKGLVLIAFSQYLQKCSYDEHAKLVQEVTDFAKT<br>CVADESAANCDKSLHTLFGDKLCAIPNLRENYGELADCCTKQEPERNECFLQH<br>KDDNPSLPPFERPEAEAMCTSFKENPTTFMGHYLHEVARRHPYFYAPELLYYA<br>EQYNEILTQCCAEADKESCLTPKLDGVKEKALVSSVRQRMKCSSMQKFGERA<br>FKAWAVARLSQTFPNADFAEITKLATDLTKVNKECCHGDLLECADDRAELAK<br>YMCENQATISSKLQTCCDKPLLKKAHCLSEVEHDTMPADLPAIAADFVEDQE<br>VCKNYAEAKDVFLGTFLYEYSRRHPDYSVSLLLRLAKKYEATLEKCCAEANP<br>PACYGTVLAEFQPLVEEPKNLVKTNCDLYEKLGEYGFQNAILVRYTQKAPQV<br>STPTLVEAARNLGRVGTKCCTLPEDQRLPCVEDYLSAILNRVCLLHEKTPVSE<br>HVTKCCSGSLVERRPCFSALTVDETYVPKEFKAETFTFHSDICTLPEKEKQIKK<br>QTALAELVKHKPKATAEQLKTVMDDFAQFLDTCCKAADKDTCFSTEGPNLVT<br>RCKDALASGGPALFKSSFPPGSCDLPQTHNLRNKRALTLLVQMRRLSPLSCLK<br>DRKDFGFPQEKVDAQQIKKAQAIPVLSELTQQILNIFTSKDSSAAWNTTLLDSF<br>CNDLHQQLNDLQGCLMQQVGVQEFPLTQEDALLAVRKYFHRITVYLREKKH<br>SPCAWEVVRAEVWRALSSSANVLGRLREEKSGGPALFKSSFPPGSEVQLVESG<br>GGLVQPGNSLRLSCAASGFTFSKFGMSWVRQAPGKGLEWVSSISGSGRDTLY<br>AESVKGRFTISRDNAKTTLYLQMNSLRPEDTAVYYCTIGGSLSVSSQGTLVTV<br>SSHHHHHH |
| 556 | WW0820 | EAHKSEIAHRYNDLGEQHFKGLVLIAFSQYLQKCSYDEHAKLVQEVTDFAKT<br>CVADESAANCDKSLHTLFGDKLCAIPNLRENYGELADCCTKQEPERNECFLQH<br>KDDNPSLPPFERPEAEAMCTSFKENPTTFMGHYLHEVARRHPYFYAPELLYYA<br>EQYNEILTQCCAEADKESCLTPKLDGVKEKALVSSVRQRMKCSSMQKFGERA<br>FKAWAVARLSQTFPNADFAEITKLATDLTKVNKECCHGDLLECADDRAELAK<br>YMCENQATISSKLQTCCDKPLLKKAHCLSEVEHDTMPADLPAIAADFVEDQE<br>VCKNYAEAKDVFLGTFLYEYSRRHPDYSVSLLLRLAKKYEATLEKCCAEANP<br>PACYGTVLAEFQPLVEEPKNLVKTNCDLYEKLGEYGFQNAILVRYTQKAPQV<br>STPTLVEAARNLGRVGTKCCTLPEDQRLPCVEDYLSAILNRVCLLHEKTPVSE<br>HVTKCCSGSLVERRPCFSALTVDETYVPKEFKAETFTFHSDICTLPEKEKQIKK<br>QTALAELVKHKPKATAEQLKTVMDDFAQFLDTCCKAADKDTCFSTEGPNLVT<br>RCKDALASGGPALFKSSFPPGSCDLPHTYNLRNKRALKVLAQMRRLTPLSCLK<br>DRKDFGFPLEKVDAQQIQKAQSIPVLRDLTQQILNLFASKDSSAAWNATLLDS<br>FCNDLHQQLNDLQGCLMQQVGVQESPLTQEDSLLAVRIYFHRITVFLREKKHS<br>PCAWEVVRAEVWRALSSSANVLGRLREEKASGGPALFKSSFPPGSEVQLVESG<br>GGLVQPGNSLRLSCAASGFTFSKFGMSWVRQAPGKGLEWVSSISGSGRDTLY<br>AESVKGRFTISRDNAKTTLYLQMNSLRPEDTAVYYCTIGGSLSVSSQGTLVTV<br>SSHHHHHH |
| 557 | WW0821 | DAHKSEVAHRFKDLGEENFKALVLIAFAQYLQQCPFEDHVKLVNEVTEFAKT<br>CVADESAENCDKSLHTLFGDKLCTVATLRETYGEMADCCAKQEPERNECFLQ<br>HKDDNPNLPRLVRPEVDVMCTAFHDNEETFLKKYLYEIARRHPYFYAPELLFF<br>AKRYKAAFTECCQAADKAACLLPKLDELRDEGKASSAKQRLKCASLQKFGER<br>AFKAWAVARLSQRFPKAEFAEVSKLVTDLTKVHTECCHGDLLECADDRADL<br>AKYICENQDSISSKLKECCEKPLLEKSHCIAEVENDEMPADLPSLAADFVESKD<br>VCKNYAEAKDVFLGMFLYEYARRHPDYSVVLLLRLAKTYETTLEKCCAAAD<br>PHECYAKVFDEFKPLVEEPQNLIKQNCELFEQLGEYKFQNALLVRYTKKVPQV<br>STPTLVEVSRNLGKVGSKCCKHPEAKRMPCAEDYLSVVLNQLCVLHEKTPVS<br>DRVTKCCTESLVNRRPCFSALEVDETYVPKEFNAETFTFHADICTLSEKERQIK<br>KQTALVELVKHKPKATKEQLKAVMDDFAAFVEKCCKADDKETCFAEEGKKL<br>VAASQAALGLSGGPALFKSSFPPGSCDLPQTHSLGSRRTLMLLAQMRRISLFSC<br>LKDRHDFGFPQEEFGNQFQKAETIPVLHEMIQQIFNLFSTKDSSAAWDETLLDK<br>FYTELYQQLNDLEACVIQGVGVTETPLMKEDSILAVRKYFQRITLYLKEKKYS<br>PCAWEVVRAEIMRSFSLSTNLQESLRSKESGGPALFKSSFPPGSDAHKSEVAHR<br>FKDLGEENFKALVLIAFAQYLQQCPFEDHVKLVNEVTEFAKTCVADESAENC<br>DKSLHTLFGDKLCTVATLRETYGEMADCCAKQEPERNECFLQHKDDNPNLPR<br>LVRPEVDVMCTAFHDNEETFLKKYLYEIARRHPYFYAPELLFFAKRYKAAFTE<br>CCQAADKAACLLPKLDELRDEGKASSAKQRLKCASLQKFGERAFKAWAVAR |

-continued

Sequence table

| SEQ ID NO. | Name | Sequence |
| --- | --- | --- |
| | | LSQRFPKAEFAEVSKLVTDLTKVHTECCHGDLLECADDRADLAKYICENQDSI SSKLKECCEKPLLEKSHCIAEVENDEMPADLPSLAADFVESKDVCKNYAEAKD VFLGMFLYEYARRHPDYSVVLLLRLAKTYETTLEKCCAAADPHECYAKVFDE FKPLVEEPQNLIKQNCELFEQLGEYKFQNALLVRYTKKVPQVSTPTLVEVSRN LGKVGSKCCKHPEAKRMPCAEDYLSVVLNQLCVLHEKTPVSDRVTKCCTESL VNRRPCFSALEVDETYVPKEFNAETFTFHADICTLSEKERQIKKQTALVELVKH KPKATKEQLKAVMDDFAAFVEKCCKADDKETCFAEEGKKLVAASQAALGL |
| 558 | WW0822 | DAHKSEVAHRFKDLGEENFKALVLIAFAQYLQQCPFEDHVKLVNEVTEFAKT CVADESAENCDKSLHTLFGDKLCTVATLRETYGEMADCCAKQEPERNECFLQ HKDDNPNLPRLVRPEVDVMCTAFHDNEETFLKKYLYEIARRHPYFYAPELLFF AKRYKAAFTECCQAADKAACLLPKLDELRDEGKASSAKQRLKCASLQKFGER AFKAWAVARLSQRFPKAEFAEVSKLVTDLTKVHTECCHGDLLECADDRADL AKYICENQDSISSKLKECCEKPLLEKSHCIAEVENDEMPADLPSLAADFVESKD VCKNYAEAKDVFLGMFLYEYARRHPDYSVVLLLRLAKTYETTLEKCCAAAD PHECYAKVFDEFKPLVEEPQNLIKQNCELFEQLGEYKFQNALLVRYTKKVPQV STPTLVEVSRNLGKVGSKCCKHPEAKRMPCAEDYLSVVLNQLCVLHEKTPVS DRVTKCCTESLVNRRPCFSALEVDETYVPKEFNAETFTFHADICTLSEKERQIK KQTALVELVKHKPKATKEQLKAVMDDFAAFVEKCCKADDKETCFAEEGKKL VAASQAALGLSGGPALFKSSFPPGSCNLSQTHSLNNRRTLMLMAQMRRISPFS CLKDRHDFEFPQEEFDGNQFQKAQAISVLHEMMQQTFNLFSTKNSSAAWDET LLEKFYIELFQQMNDLEACVIQEVGVEETPLMNEDSILAVKKYFQRITLYLME KKYSPCAWEVVRAEIMRSLSFSTNLQKRLRRKDSGGPALFKSSFPPGSDAHKS EVAHRFKDLGEENFKALVLIAFAQYLQQCPFEDHVKLVNEVTEFAKTCVADE SAENCDKSLHTLFGDKLCTVATLRETYGEMADCCAKQEPERNECFLQHKDDN PNLPRLVRPEVDVMCTAFHDNEETFLKKYLYEIARRHPYFYAPELLFFAKRYK AAFTECCQAADKAACLLPKLDELRDEGKASSAKQRLKCASLQKFGERAFKA WAVARLSQRFPKAEFAEVSKLVTDLTKVHTECCHGDLLECADDRADLAKYIC ENQDSISSKLKECCEKPLLEKSHCIAEVENDEMPADLPSLAADFVESKDVCKN YAEAKDVFLGMFLYEYARRHPDYSVVLLLRLAKTYETTLEKCCAAADPHECY AKVFDEFKPLVEEPQNLIKQNCELFEQLGEYKFQNALLVRYTKKVPQVSTPTL VEVSRNLGKVGSKCCKHPEAKRMPCAEDYLSVVLNQLCVLHEKTPVSDRVT KCCTESLVNRRPCFSALEVDETYVPKEFNAETFTFHADICTLSEKERQIKKQTA LVELVKHKPKATKEQLKAVMDDFAAFVEKCCKADDKETCFAEEGKKLVAAS QAALGL |
| 559 | WW08 31 | DAHKSEVAHRFKDLGEENFKALVLIAFAQYLQQCPFEDHVKLVNEVTEFAKT CVADESAENCDKSLHTLFGDKLCTVATLRETYGEMADCCAKQEPERNECFLQ HKDDNPNLPRLVRPEVDVMCTAFHDNEETFLKKYLYEIARRHPYFYAPELLFF AKRYKAAFTECCQAADKAACLLPKLDELRDEGKASSAKQRLKCASLQKFGER AFKAWAVARLSQRFPKAEFAEVSKLVTDLTKVHTECCHGDLLECADDRADL AKYICENQDSISSKLKECCEKPLLEKSHCIAEVENDEMPADLPSLAADFVESKD VCKNYAEAKDVFLGMFLYEYARRHPDYSVVLLLRLAKTYETTLEKCCAAAD PHECYAKVFDEFKPLVEEPQNLIKQNCELFEQLGEYKFQNALLVRYTKKVPQV STPTLVEVSRNLGKVGSKCCKHPEAKRMPCAEDYLSVVLNQLCVLHEKTPVS DRVTKCCTESLVNRRPCFSALEVDETYVPKEFNAETFTFHADICTLSEKERQIK KQTALVELVKHKPKATKEQLKAVMDDFAAFVEKCCKADDKETCFAEEGKKL VAASQAALGLSGGPALFKSSFPPGSCDLPQTHSLGNRRALILLAQMRRISPFSC LKDRHDFEFPQEEFDDKQFQKAQAISVLHEMIQQTFNLFSTKDSSAALDETLL DEFYIELDQQLNDLESCVMQEVGVIESPLMYEDSILAVRKYFQRITLYLTEKKY SSCAWEVVRAEIMRSFSLSINLQKRLKSKESGGPALFKSSFPPGSDAHKSEVAH RFKDLGEENFKALVLIAFAQYLQQCPFEDHVKLVNEVTEFAKTCVADESAEN CDKSLHTLFGDKLCTVATLRETYGEMADCCAKQEPERNECFLQHKDDNPNLP RLVRPEVDVMCTAFHDNEETFLKKYLYEIARRHPYFYAPELLFFAKRYKAAFT ECCQAADKAACLLPKLDELRDEGKASSAKQRLKCASLQKFGERAFKAWAVA RLSQRFPKAEFAEVSKLVTDLTKVHTECCHGDLLECADDRADLAKYICENQD SISSKLKECCEKPLLEKSHCIAEVENDEMPADLPSLAADFVESKDVCKNYAEA KDVFLGMFLYEYARRHPDYSVVLLLRLAKTYETTLEKCCAAADPHECYAKVF DEFKPLVEEPQNLIKQNCELFEQLGEYKFQNALLVRYTKKVPQVSTPTLVEVS RNLGKVGSKCCKHPEAKRMPCAEDYLSVVLNQLCVLHEKTPVSDRVTKCCTE SLVNRRPCFSALEVDETYVPKEFNAETFTFHADICTLSEKERQIKKQTALVELV KHKPKATKEQLKAVMDDFAAFVEKCCKADDKETCFAEEGKKLVAASQAALG L |
| 560 | WW0832 | DAHKSEVAHRFKDLGEENFKALVLIAFAQYLQQCPFEDHVKLVNEVTEFAKT CVADESAENCDKSLHTLFGDKLCTVATLRETYGEMADCCAKQEPERNECFLQ HKDDNPNLPRLVRPEVDVMCTAFHDNEETFLKKYLYEIARRHPYFYAPELLFF AKRYKAAFTECCQAADKAACLLPKLDELRDEGKASSAKQRLKCASLQKFGER AFKAWAVARLSQRFPKAEFAEVSKLVTDLTKVHTECCHGDLLECADDRADL AKYICENQDSISSKLKECCEKPLLEKSHCIAEVENDEMPADLPSLAADFVESKD VCKNYAEAKDVFLGMFLYEYARRHPDYSVVLLLRLAKTYETTLEKCCAAAD PHECYAKVFDEFKPLVEEPQNLIKQNCELFEQLGEYKFQNALLVRYTKKVPQV STPTLVEVSRNLGKVGSKCCKHPEAKRMPCAEDYLSVVLNQLCVLHEKTPVS |

-continued

Sequence table

| SEQ ID NO. | Name | Sequence |
|---|---|---|
| | | DRVTKCCTESLVNRRPCFSALEVDETYVPKEFNAETFTFHADICTLSEKERQIK KQTALVELVKHKPKATKEQLKAVMDDFAAFVEKCCKADDKETCFAEEGKKL VAASQAALGLSGGPALFKSSFPPGSCDLPQTHSLGNRRALILLAQMGRISHFSC LKDRYDFGFPQEVFDGNQFQKAQAISAFHEMIQQTFNLFSTKDSSAAWDETLL DKFYIELFQQLNDLEACVTQEVGVEEIALMNEDSILAVRKYFQRITLYLMGKK YSPCAWEVVRAEIMRSFSFSTNLQKGLRRKDSGGPALFKSSFPPGSDAHKSEV AHRFKDLGEENFKALVLIAFAQYLQQCPFEDHVKLVNEVTEFAKTCVADESA ENCDKSLHTLFGDKLCTVATLRETYGEMADCCAKQEPERNECFLQHKDDNPN LPRLVRPEVDVMCTAFHDNEETFLKKYLYEIARRHPYFYAPELLFFAKRYKAA FTECCQAADKAACLLPKLDELRDEGKASSAKQRLKCASLQKFGERAFKAWA VARLSQRFPKAEFAEVSKLVTDLTKVHTECCHGDLLECADDRADLAKYICEN QDSISSKLKECCEKPLLEKSHCIAEVENDEMPADLPSLAADFVESKDVCKNYA EAKDVFLGMFLYEYARRHPDYSVVLLLRLAKTYETTLEKCCAAADPHECYAK VFDEFKPLVEEPQNLIKQNCELFEQLGEYKFQNALLVRYTKKVPQVSTPTLVE VSRNLGKVGSKCCKHPEAKRMPCAEDYLSVVLNQLCVLHEKTPVSDRVTKC CTESLVNRRPCFSALEVDETYVPKEFNAETFTFHADICTLSEKERQIKKQTALV ELVKHKPKATKEQLKAVMDDFAAFVEKCCKADDKETCFAEEGKKLVAASQA ALGL |
| 561 | WW0833 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPALFKSSFPPGSCDLPQTHSLGNRRALILLAQMRRISPFSCL KDRHDFEFPQEEFDDKQFQKAQAISVLHEMIQQTFNLFSTKDSSAALDETLLD EFYIELDQQLNDLESCVMQEVGVIESPLMYEDSILAVRKYFQRITLYLTEKKYS SCAWEVVRAEIMRSFSLSINLQKRLKSKESGGPALFKSSFPPGSEVQLVESGGG LVQPGNSLRLSCAASGFTFSKFGMSWVRQAPGKGLEWVSSISGSGRDTLYAES VKGRFTISRDNAKTTLYLQMNSLRPEDTAVYYCTIGGSLSVSSQGTLVTVSS |
| 562 | WW0834 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPALFKSSFPPGSCDLPQTHSLGNRRALILLAQMGRISHFSCL KDRYDFGFPQEVFDGNQFQKAQAISAFHEMIQQTFNLFSTKDSSAAWDETLLD KFYIELFQQLNDLEACVTQEVGVEEIALMNEDSILAVRKYFQRITLYLMGKKY SPCAWEVVRAEIMRSFSFSTNLQKGLRRKDSGGPALFKSSFPPGSEVQLVESGG GLVQPGNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGTLVTVSS |
| 563 | WW0737 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGLYAQPGSINYKQLQLQERTNIRKCQELLEQLNGKIN LTYRADFKIPMEMTEKMQKSYTAFAIQEMLQNVFLVFRNNFSSTGWNETIVV RLLDELHQQTVFLKTVLEEKQEERLTWEMSSTALHLKSYYWRVQRYLKLMK YNSYAWMVVRAEIFRNFLIIRRLTRNFQNSGGPGPAGLYAQPGSEVQLVESGG GLVQPGNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGTLVTVSS |
| 564 | WW0738 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPALFKSSFPPGSINYKQLQLQERTNIRKCQELLEQLNGKINL TYRADFKIPMEMTEKMQKSYTAFAIQEMLQNVFLVFRNNFSSTGWNETIVVR LLDELHQQTVFLKTVLEEKQEERLTWEMSSTALHLKSYYWRVQRYLKLMKY NSYAWMVVRAEIFRNFLIIRRLTRNFQNSGGPALFKSSFPPGSEVQLVESGGGL VQPGNSLRLSCAASGFTFSKFGMSWVRQAPGKGLEWVSSISGSGRDTLYAESV KGRFTISRDNAKTTLYLQMNSLRPEDTAVYYCTIGGSLSVSSQGTLVTVSS |
| 565 | WW0739 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGLYAQPGSINYKQLQLQERTNIRKSQELLEQLNGKIN LTYRADFKIPMEMTEKMQKSYTAFAIQEMLQNVFLVFRNNFSSTGWNETIVV RLLDELHQQTVFLKTVLEEKQEERLTWEMSSTALHLKSYYWRVQRYLKLMK YNSYAWMVVRAEIFRNFLIIRRLTRNFQNSGGPGPAGLYAQPGSEVQLVESGG GLVQPGNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGTLVTVSS |
| 566 | WW0740 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPALFKSSFPPGSINYKQLQLQERTNIRKSQELLEQLNGKINL TYRADFKIPMEMTEKMQKSYTAFAIQEMLQNVFLVFRNNFSSTGWNETIVVR LLDELHQQTVFLKTVLEEKQEERLTWEMSSTALHLKSYYWRVQRYLKLMKY NSYAWMVVRAEIFRNFLIIRRLTRNFQNSGGPALFKSSFPPGSEVQLVESGGGL VQPGNSLRLSCAASGFTFSKFGMSWVRQAPGKGLEWVSSISGSGRDTLYAESV KGRFTISRDNAKTTLYLQMNSLRPEDTAVYYCTIGGSLSVSSQGTLVTVSS |

-continued

Sequence table

| SEQ ID NO. | Name | Sequence |
| --- | --- | --- |
| 567 | WW0741 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGLYAQPGSMSYNLLGFLQRSSNFQCQKLLWQLNGR LEYCLKDRMNFDIPEEIKQLQQFQKEDAALTIYEMLQNIFAIFRQDSSSTGWNE TIVENLLANVYHQINHLKTVLEEKLEKEDFTRGKLMSSLHLKRYYGRILHYLK AKEYSHCAWTIVRVEILRNFYFINRLTGYLRNSGGPGPAGLYAQPGSEVQLVE SGGGLVQPGNSLRLSCAASGFTFSKFGMSWVRQAPGKGLEWVSSISGSGRDTL YAESVKGRFTISRDNAKTTLYLQMNSLRPEDTAVYYCTIGGSLSVSSQGTLVT VSS |
| 568 | WW0742 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPALFKSSFPPGSMSYNLLGFLQRSSNFQCQKLLWQLNGRL EYCLKDRMNFDIPEEIKQLQQFQKEDAALTIYEMLQNIFAIFRQDSSSTGWNET IVENLLANVYHQINHLKTVLEEKLEKEDFTRGKLMSSLHLKRYYGRILHYLKA KEYSHCAWTIVRVEILRNFYFINRLTGYLRNSGGPALFKSSFPPGSEVQLVESG GGLVQPGNSLRLSCAASGFTFSKFGMSWVRQAPGKGLEWVSSISGSGRDTLY AESVKGRFTISRDNAKTTLYLQMNSLRPEDTAVYYCTIGGSLSVSSQGTLVTV SS |
| 569 | WW0743 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGLYAQPGSMSYNLLGFLQRSSNFQSQKLLWQLNGR LEYCLKDRMNFDIPEEIKQLQQFQKEDAALTIYEMLQNIFAIFRQDSSSTGWNE TIVENLLANVYHQINHLKTVLEEKLEKEDFTRGKLMSSLHLKRYYGRILHYLK AKEYSHCAWTIVRVEILRNFYFINRLTGYLRNSGGPGPAGLYAQPGSEVQLVE SGGGLVQPGNSLRLSCAASGFTFSKFGMSWVRQAPGKGLEWVSSISGSGRDTL YAESVKGRFTISRDNAKTTLYLQMNSLRPEDTAVYYCTIGGSLSVSSQGTLVT VSS |
| 570 | WW0744 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPALFKSSFPPGSMSYNLLGFLQRSSNFQSQKLLWQLNGRL EYCLKDRMNFDIPEEIKQLQQFQKEDAALTIYEMLQNIFAIFRQDSSSTGWNET IVENLLANVYHQINHLKTVLEEKLEKEDFTRGKLMSSLHLKRYYGRILHYLKA KEYSHCAWTIVRVEILRNFYFINRLTGYLRNSGGPALFKSSFPPGSEVQLVESG GGLVQPGNSLRLSCAASGFTFSKFGMSWVRQAPGKGLEWVSSISGSGRDTLY AESVKGRFTISRDNAKTTLYLQMNSLRPEDTAVYYCTIGGSLSVSSQGTLVTV SS |
| 571 | WW0745 | INYKQLQLQERTNIRKCQELLEQLNGKINLTYRADFKIPMEMTEKMQKSYTAF AIQEMLQNVFLVFRNNFSSTGWNETIVVRLLDELHQQTVFLKTVLEEKQEERL TWEMSSTALHLKSYYWRVQRYLKLMKYNSYAWMVVRAEIFRNFLIIRRLTR NFQNHHHHHH |
| 572 | WW0746 | INYKQLQLQERTNIRKSQELLEQLNGKINLTYRADFKIPMEMTEKMQKSYTAF AIQEMLQNVFLVFRNNFSSTGWNETIVVRLLDELHQQTVFLKTVLEEKQEERL TWEMSSTALHLKSYYWRVQRYLKLMKYNSYAWMVVRAEIFRNFLIIRRLTR NFQNHHHHHH |
| 573 | WW0747 | MSYNLLGFLQRSSNFQCQKLLWQLNGRLEYCLKDRMNFDIPEEIKQLQQFQK EDAALTIYEMLQNIFAIFRQDSSSTGWNETIVENLLANVYHQINHLKTVLEEKL EKEDFTRGKLMSSLHLKRYYGRILHYLKAKEYSHCAWTIVRVEILRNFYFINR LTGYLRNHHHHHH |
| 574 | WW0748 | MSYNLLGFLQRSSNFQSQKLLWQLNGRLEYCLKDRMNFDIPEEIKQLQQFQKE DAALTIYEMLQNIFAIFRQDSSSTGWNETIVENLLANVYHQINHLKTVLEEKLE KEDFTRGKLMSSLHLKRYYGRILHYLKAKEYSHCAWTIVRVEILRNFYFINRL TGYLRNHHHHHH |
| 575 | WW0787 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGLYAQPGSMSYNLLGFLQRSSNFQCQKLLWQLNGR LEYCLKDRMNFDIPEEIKQLQQFQKEDAALTIYEMLQNIFAIFRQDSSSTGWQE TIVENLLANVYHQINHLKTVLEEKLEKEDFTRGKLMSSLHLKRYYGRILHYLK AKEYSHCAWTIVRVEILRNFYFINRLTGYLRNSGGPGPAGLYAQPGSEVQLVE SGGGLVQPGNSLRLSCAASGFTFSKFGMSWVRQAPGKGLEWVSSISGSGRDTL YAESVKGRFTISRDNAKTTLYLQMNSLRPEDTAVYYCTIGGSLSVSSQGTLVT VSS |
| 576 | WW0788 | EVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVS SQGTLVTVSSSGGPGPAGLYAQPGSMSYNLLGFLQRSSNFQSQKLLWQLNGR |

-continued

Sequence table

| SEQ ID NO. | Name | Sequence |
| --- | --- | --- |
| | | LEYCLKDRMNFDIPEEIKQLQQFQKEDAALTIYEMLQNIFAIFRQDSSSTGWQE TIVENLLANVYHQINHLKTVLEEKLEKEDFTRGKLMSSLHLKRYYGRILHYLK AKEYSHCAWTIVRVEILRNFYFINRLTGYLRNSGGPGPAGLYAQPGSEVQLVE SGGGLVQPGNSLRLSCAASGFTFSKFGMSWVRQAPGKGLEWVSSISGSGRDTL YAESVKGRFTISRDNAKTTLYLQMNSLRPEDTAVYYCTIGGSLSVSSQGTLVT VSS |
| 577 | WW0789 | MSYNLLGFLQRSSNFQCQKLLWQLNGRLEYCLKDRMNFDIPEEIKQLQQFQK EDAALTIYEMLQNIFAIFRQDSSSTGWQETIVENLLANVYHQINHLKTVLEEKL EKEDFTRGKLMSSLHLKRYYGRILHYLKAKEYSHCAWTIVRVEILRNFYFINR LTGYLRNHHHHHH |
| 578 | WW0790 | MSYNLLGFLQRSSNFQSQKLLWQLNGRLEYCLKDRMNFDIPEEIKQLQQFQKE DAALTIYEMLQNIFAIFRQDSSSTGWQETIVENLLANVYHQINHLKTVLEEKLE KEDFTRGKLMSSLHLKRYYGRILHYLKAKEYSHCAWTIVRVEILRNFYFINRL TGYLRNHHHHHH |
| 579 | WW0729 | APTSSSTKKTQLQLEHLLLDLQMILNGINNYKNPKLTRMLTFKFYMPKKATEL KHLQCLEEELKPLEEVLNLAQSKNFHLRPRDLISNINVIVLELKGSETTFMCEY ADETATIVEFLNRWITFCQSIISTLTSGGPGGGGSGGGPGSEVQLVESGGGLVQ PGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSGGGGS GGGGSGGGGSGGGGSGGGGSGGGGSSGGPGGGGSGGGPGSEVQLVESGGGL VQPGGSLRLSCAASGFTFSSYTLAWVRQAPGKGLEWVAAIDSSSYTYSPDTVR GRFTISRDNAKNSLYLQMNSLRAEDTAVYYCARDSNWDALDYWGQGTTVTV SSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKRVEPKSC |
| 580 | WW0734 | APTSSSTKKTQLQLEHLLLDLQMILNGINNYKNPKLTRMLTFKFYMPKKATEL KHLQCLEEELKPLEEVLNLAQSKNFHLRPRDLISNINVIVLELKGSETTFMCEY ADETATIVEFLNRWITFCQSIISTLTSGGPGPAGMKGLPGSEVQLVESGGGLVQ PGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSGGGGS GGGGSGGGGSGGGGSGGGGSGGGGSGGGGSGGGGSGGGGSEVQLVESGGGL VQPGGSLRLSCAASGFTFSSYTLAWVRQAPGKGLEWVAAIDSSSYTYSPDTVR GRFTISRDNAKNSLYLQMNSLRAEDTAVYYCARDSNWDALDYWGQGTTVTV SSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKRVEPKSC |
| 581 | WW0735 | APTSSSTKKTQLQLEHLLLDLQMILNGINNYKNPKLTRMLTFKFYMPKKATEL KHLQCLEEELKPLEEVLNLAQSKNFHLRPRDLISNINVIVLELKGSETTFMCEY ADETATIVEFLNRWITFCQSIISTLTSGGPGPAGLYAQPGSEVQLVESGGGLVQP GNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSGGGGS GGGGSGGGGSGGGGSGGGGSGGGGSGGGGSGGGGSGGGGSEVQLVESGGGL VQPGGSLRLSCAASGFTFSSYTLAWVRQAPGKGLEWVAAIDSSSYTYSPDTVR GRFTISRDNAKNSLYLQMNSLRAEDTAVYYCARDSNWDALDYWGQGTTVTV SSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKRVEPKSC |
| 582 | WW0736 | APTSSSTKKTQLQLEHLLLDLQMILNGINNYKNPKLTRMLTFKFYMPKKATEL KHLQCLEEELKPLEEVLNLAQSKNFHLRPRDLISNINVIVLELKGSETTFMCEY ADETATIVEFLNRWITFCQSIISTLTSGGPALFKSSFPPGSEVQLVESGGGLVQP GNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSGGGGS GGGGSGGGGSGGGGSGGGGSGGGGSGGGGSGGGGSGGGGSEVQLVESGGGL VQPGGSLRLSCAASGFTFSSYTLAWVRQAPGKGLEWVAAIDSSSYTYSPDTVR GRFTISRDNAKNSLYLQMNSLRAEDTAVYYCARDSNWDALDYWGQGTTVTV SSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKRVEPKSC |
| 583 | WW0792 | EVQLVESGGGLVQPGGSLRLSCAASGFTFSSYTLAWVRQAPGKGLEWVAAID SSSYTYSPDTVRGRFTISRDNAKNSLYLQMNSLRAEDTAVYYCARDSNWDAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCHHHHHH |
| 584 | WW0061 | APTSSSTKKTQLQLEHLLLDLQMILNGINNYKNPKLTRMLTFKFYMPKKATEL KHLQCLEEELKPLEEVLNLAQSKNFHLRPRDLISNINVIVLELKGSETTFMCEY ADETATIVEFLNRWITFCQSIISTLTSGGPGPAGMKGLPGSEVQLVESGGGLVQ PGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSHHHH HH |

-continued

Sequence table

| SEQ ID NO. | Name | Sequence |
|---|---|---|
| 585 | ACP293 (WW0237) | QVQLQESGGGLVQTGGSLRLSCTTSGTIFSGYTMGWYRQAPGEQRELVAVISG GGDTNYADSVKGRFTISRDNTKDTMYLQMNSLKPEDTAVYYCYSREVTPPW KLYWGQGTQVTVSSAAAYPYDVPDYGSHHHHHH |
| 586 | ACP294 (WW0238) | QVQLQESGGGLVQEGGSLRLSCAASERIFSTDVMGWYRQAAEKQRELVAVVS ARGTTNYLDAVKGRFTISRDNARNTLTLQMNDLKPEDTASYYCYVRETTSPW RIYWGQGTQVTVSSAAAYPYDVPDYGSHHHHHH |
| 587 | ACP295 (WW0239) | QVQLQESGGGLVQAGGSLRLSCAASGSlFSANAMGWYRQAPGKQRELVAVIS SGGSTNYADSVKGRFTISRDNAKNTVYLQMNSLKPEDTAVYYCMYSGSYYY TPNDYWGQGTQVTVSSAAAYPYDVPDYGSHHHHHH |
| 588 | ACP315 (WW0368) | EVQLLESGGGLVQPGGSLRLSCAASGSIFSANAMGWYRQAPGKQRELVAVISS GGSTNYADSVKGRFTISRDNSKNTVYLQMNSLRAEDTAVYYCMYSGSYYYTP NDYWGQGTLVTVSSAAAYPYDVPDYGSHHHHHH |
| 589 | ACP316 (WW0369) | EVQLLESGGGLVQPGGSLRLSCAASGSIFSANAMGWYRQAPGKGLELVAVISS GGSTNYADSVKGRFTISRDNSKNTVYLQMNSLRAEDTAVYYCMYSGSYYYTP NDYWGQGTLVTVSSAAAYPYDVPDYGSHHHHHH |
| 590 | ACP317 (WW0370) | EVQLLESGGGLVQPGGSLRLSCAASGSIFSANAMGWVRQAPGKGLEWVSVIS SGGSTNYADSVKGRFTISRDNSKNTLYLQMNSLRAEDTAVYYCMYSGSYYYT PNDYWGQGTLVTVSSAAAYPYDVPDYGSHHHHHH |
| 591 | ACP318 (WW0371) | QVQLLESGGGLVQPGGSLRLSCAASGSIFSANAMGWYRQAPGKQRELVAVIS SGGSTNYADSVKGRFTISRDNSKNTVYLQMNSLRAEDTAVYYCMYSGSYYYT PNDYWGQGTLVTVSSAAAYPYDVPDYGSHHHHHH |
| 592 | ACP319 (WW0372) | EVQLLESGGGLVQPGGSLRLSCAASGSIFSANAMGWYRQAPGKGRELVAVISS GGSTNYADSVKGRFTISRDNSKNTVYLQMNSLRAEDTAVYYCMYSGSYYYTP NDYWGQGTLVTVSSAAAYPYDVPDYGSHHHHHH |
| 593 | ACP320 (WW0373) | QVQLLESGGGLVQAGGSLRLSCAASGSIFSANAMGWYRQAPGKQRELVAVIS SGGSTNYADSVKGRFTISRDNSKNTVYLQMNSLRAEDTAVYYCMYSGSYYYT PNDYWGQGTLVTVSSAAAYPYDVPDYGSHHHHHH |
| 594 | ACP321 (WW0374) | EVQLLESGGGLVQPGGSLRLSCAASERIFSTDVMGWYRQAPGKQRELVAVVS ARGTTNYLDAVKGRFTISRDNSKNTLYLQMNSLRAEDTAVYYCYVRETTSPW RIYWGQGTLVTVSSAAAYPYDVPDYGSHHHHHH |
| 595 | ACP322 (WW0375) | EVQLLESGGGLVQPGGSLRLSCAASERIFSTDVMGWYRQAPGKGLELVAVVS ARGTTNYLDAVKGRFTISRDNSKNTLYLQMNSLRAEDTAVYYCYVRETTSPW RIYWGQGTLVTVSSAAAYPYDVPDYGSHHHHHH |
| 596 | ACP323 (WW0376) | EVQLLESGGGLVQPGGSLRLSCAASERIFSTDVMGWVRQAPGKGLEWVSVVS ARGTTNYLDAVKGRFTISRDNSKNTLYLQMNSLRAEDTAVYYCYVRETTSPW RIYWGQGTLVTVSSAAAYPYDVPDYGSHHHHHH |
| 597 | ACP324 (WW0377) | QVQLLESGGGLVQPGGSLRLSCAASERIFSTDVMGWYRQAPGKQRELVAVVS ARGTTNYLDAVKGRFTISRDNSKNTLYLQMNSLRAEDTAVYYCYVRETTSPW RIYWGQGTLVTVSSAAAYPYDVPDYGSHHHHHH |
| 598 | ACP325 (WW0378) | EVQLLESGGGLVQPGGSLRLSCAASERIFSTDVMGWYRQAPGKGRELVAVVS ARGTTNYLDSVKGRFTISRDNSKNTLYLQMNSLRAEDTAVYYCYVRETTSPW RIYWGQGTLVTVSSAAAYPYDVPDYGSHHHHHH |
| 599 | ACP326 (WW0379) | QVQLLESGGGLVQEGGSLRLSCAASERIFSTDVMGWYRQAAGKQRELVAVVS ARGTTNYLDAVKGRFTISRDNSKNTLYLQMNSLRAEDTASYYCYVRETTSPW RIYWGQGTLVTVSSAAAYPYDVPDYGSHHHHHH |
| 600 | ACP327 (WW0380) | EVQLLESGGGLVQPGGSLRLSCAASERIFSTDVMGWYRQAPGKGLELVAVVS ARGTTNYLDSVKGRFTISRDNSKNTLYLQMNSLRAEDTAVYYCYVRETTSPW RIYWGQGTLVTVSSAAAYPYDVPDYGSHHHHHH |
| 601 | ACP328 (WW0381) | EVQLLESGGGLVQPGGSLRLSCATSGTIFSGYTMGWYRQAPGKQRELVAVISG GGDTNYADSVKGRFTISRDNSKDTMYLQMNSLRAEDTAVYYCYSREVTPPW KLYWGQGTLVTVSSAAAYPYDVPDYGSHHHHHH |
| 602 | ACP329 (WW0382) | EVQLLESGGGLVQPGGSLRLSCATSGTIFSGYTMGWYRQAPGKGLELVAVISG GGDTNYADSVKGRFTISRDNSKDTMYLQMNSLRAEDTAVYYCYSREVTPPW KLYWGQGTLVTVSSAAAYPYDVPDYGSHHHHHH |

-continued

Sequence table

| SEQ ID NO. | Name | Sequence |
|---|---|---|
| 603 | ACP330 (WW0383) | EVQLLESGGGLVQPGGSLRLSCAASGTIFSGYTMGWVRQAPGKGLEWVSVIS GGGDTNYADSVKGRFTISRDNSKNTLYLQMNSLRAEDTAVYYCYSREVTPPW KLYWGQGTLVTVSSAAAYPYDVPDYGSHHHHHH |
| 604 | ACP331 (WW0384) | QVQLLESGGGLVQPGGSLRLSCATSGTIFSGYTMGWYRQAPGKQRELVAVIS GGGDTNYADSVKGRFTISRDNSKDTMYLQMNSLRAEDTAVYYCYSREVTPP WKLYWGQGTLVTVSSAAAYPYDVPDYGSHHHHHH |
| 605 | ACP332 (WW0385) | EVQLLESGGGLVQPGGSLRLSCATSGTIFSGYTMGWYRQAPGKQRELVAVISG GGDTNYADSVKGRFTISRDNSKNTMYLQMNSLRAEDTAVYYCYSREVTPPW KLYWGQGTLVTVSSAAAYPYDVPDYGSHHHHHH |
| 606 | ACP333 (WW0386) | EVQLLESGGGLVQPGGSLRLSCATSGTIFSGYTMGWYRQAPGKGRELVAVISG GGDTNYADSVKGRFTISRDNSKNTMYLQMNSLRAEDTAVYYCYSREVTPPW KLYWGQGTLVTVSSAAAYPYDVPDYGSHHHHHH |
| 607 | ACP334 (WW0387) | QVQLLESGGGLVQTGGSLRLSCATSGTIFSGYTMGWYRQAPGKQRELVAVIS GGGDTNYADSVKGRFTISRDNSKDTMYLQMNSLRAEDTAVYYCYSREVTPP WKLYWGQGTLVTVSSAAAYPYDVPDYGSHHHHHH |
| 608 | ACP335 (WW0388_ | EVQLLESGGGLVQPGGSLRLSCATSGTIFSGYTMGWYRQAPGKGLELVAVISG GGDTNYADSVKGRFTISRDNSKNTMYLQMNSLRAEDTAVYYCYSREVTPPW KLYWGQGTLVTVSSAAAYPYDVPDYGSHHHHHH |
| 609 | MMP14_1 | GPAGLYAQ |
| 610 | MMP9_1 | GPAGMKGL |
| 611 | FAPa_1 | PGGPAGIG |
| 612 | CTSL1_1 | ALFKSSFP |
| 613 | CTSL1_2 | ALFFSSPP |
| 614 | ADAM17_1 | LAQRLRSS |
| 615 | ADAM17_2 | LAQKLKSS |
| 616 | ALU30-1 | GALFKSSFPSGGGPAGLYAQGGSGKGGSGK |
| 617 | ALU30-2 | RGSGGGPAGLYAQGSGGGPAGLYAQGGSGK |
| 618 | ALU30-3 | KGGGPAGLYAQGPAGLYAQGPAGLYAQGSR |
| 619 | ALU30-4 | RGGPAGLYAQGGPAGLYAQGGGPAGLYAQK |
| 620 | ALU30-5 | KGGALFKSSFPGGPAGIGPLAQKLKSSGGS |
| 621 | ALU30-6 | SGGPGGPAGIGALFKSSFPLAQKLKSSGGG |
| 622 | ALU30-7 | RGPLAQKLKSSALFKSSFPGGPAGIGGGGK |
| 623 | ALU30-8 | GGGALFKSSFPLAQKLKSSPGGPAGIGGGR |
| 624 | ALU30-9 | RGPGGPAGIGPLAQKLKSSALFKSSFPGGG |
| 625 | ALU30-10 | RGGPLAQKLKSSPGGPAGIGALFKSSFPGK |
| 626 | ALU30-11 | RSGGPAGLYAQALFKSSFPLAQKLKSSGGG |
| 627 | ALU30-12 | GGPLAQKLKSSALFKSSFPGPAGLYAQGGR |
| 628 | ALU30-13 | GGALFKSSFPGPAGLYAQPLAQKLKSSGGK |
| 629 | ALU30-14 | RGGALFKSSFPLAQKLKSSGPAGLYAQGGK |
| 630 | ALU30-15 | RGGGPAGLYAQPLAQKLKSSALFKSSFPGG |
| 631 | ALU30-16 | SGPLAQKLKSSGPAGLYAQALFKSSFPGSK |
| 632 | ALU30-17 | KGGPGGPAGIGPLAQRLRSSALFKSSFPGR |

-continued

| Sequence table | | |
|---|---|---|
| SEQ ID NO. | Name | Sequence |
| 633 | ALU30-18 | KSGPGGPAGIGALFFSSPPLAQKLKSSGGR |
| 634 | ALU30-19 | SGGFPRSGGSFNPRTFGSKRKRRGSRGGGG |

INCORPORATION BY REFERENCE

The entire disclosures of all patent and non-patent publications cited herein are each incorporated by reference in their entireties for all purposes.

OTHER EMBODIMENTS

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

The invention claimed is:

1. A method of treating a cancer, in a human subject comprising administering to the subject in need thereof an effective amount of therapeutic combination comprising
   a) an inducible cytokine polypeptide, wherein the inducible cytokine polypeptide comprises a) a cytokine polypeptide; b) a cytokine blocking moiety that inhibits cytokine receptor activating activity of the cytokine polypeptide; and c) a half-life extension domain; wherein the cytokine polypeptide is operably linked to the cytokine blocking moiety through a first linker comprising a cleavable peptide and the cytokine blocking moiety is operably linked to the half-life extension domain through a second linker; and
   b) a cellular therapy.

2. The method of claim 1, where the cellular therapy comprises T-cell therapy.

3. The method of 2, wherein the T-cell therapy comprises activated T cells.

4. The method of claim 2, wherein the T-cell therapy comprises CAR-T cells.

5. The method of claim 1, where the cellular therapy comprises NK cells.

6. The method of claim 1, wherein cytokine polypeptide comprises IL-2, IL-7, IL-12, IL-15, IL-18, IL-21, IL-23, TGF, interferon alpha, interferon beta, interferon gamma, TNF, TGFbeta, CXCL10, CCL19, CCL20, CCL21, or a mutein, a variant, an active fragment, or a subunit of any of the foregoing.

7. The method of claim 1, wherein the inducible cytokine polypeptide comprises IL-2.

8. The method of claim 1, wherein the inducible cytokine polypeptide comprises IL-12.

9. The method of claim 1, wherein the inducible cytokine polypeptide comprises one polypeptide chain, or two or more polypeptide chains.

10. The method of claim 1, wherein the cytokine blocking moiety is a ligand-binding domain or fragment of a cognate receptor for the cytokine polypeptide or an antibody or antigen-binding fragment of an antibody that binds the cytokine polypeptide.

11. The method of claim 1, wherein half-life extension domain is an immunoglobulin Fc, human serum albumin or a fragment thereof that binds neonatal Fc receptor, or an antigen-binding portion of an antibody that binds to FcRn or to human serum albumin.

12. The method of claim 1, wherein a) the cytokine polypeptide is an IL-2 polypeptide; b) the cytokine blocking moiety is a IL-2-binding domain or fragment of an IL-2 receptor or an antibody or antigen-binding fragment of an antibody that binds IL-2; and c) the half-life extension domain is an immunoglobulin Fc, human serum albumin or a fragment thereof that binds neonatal Fc receptor, or an antigen-binding portion of an antibody that binds to FcRn or to human serum albumin.

13. The method of claim 10, wherein the cytokine blocking moiety is a IL-2-binding domain or fragment of an IL-2 receptor, and the IL-2 receptor comprises IL-2Rα (CD25), IL-2Rβ (CD122), IL-2Rγ (CD132) or combinations thereof.

14. The method of claim 10, wherein the cytokine blocking moiety is an antibody or antigen-binding fragment of an antibody that binds IL-2.

15. The method of claim 1, wherein a) the cytokine polypeptide is an IL-12 polypeptide; b) the cytokine blocking moiety is a IL-12-binding domain or fragment of an IL-12 receptor or an antibody or antigen-binding fragment of an antibody that binds IL-12; and c) the half-life extension domain is an immunoglobulin Fc, human serum albumin or a fragment thereof that binds neonatal Fc receptor, or an antigen-binding portion of an antibody that binds to FcRn or to human serum albumin.

16. The method of claim 15, wherein the cytokine blocking moiety is a IL-12-binding domain or fragment of an IL-12 receptor, and the IL-12 receptor comprises IL-12Rβ1, IL-12Rβ2 or combinations thereof.

17. The method of claim 15, wherein the cytokine blocking moiety is an antibody or antigen-binding fragment of an antibody that binds IL-12.

18. The method of claim 1, wherein the cancer is characterized by solid tumors.

19. The method of claim 1, wherein the inducible cytokine polypeptide comprises a substrate for a protease and has at least about 10× less cytokine receptor activating activity relative to the polypeptide that contains the cytokine that is produced by protease cleavage of the inducible cytokine polypeptide.

* * * * *